US007432261B2

(12) United States Patent
Cannizzaro et al.

(10) Patent No.: US 7,432,261 B2
(45) Date of Patent: Oct. 7, 2008

(54) ANTI-INFLAMMATORY PHOSPHONATE COMPOUNDS

(75) Inventors: Carina Cannizzaro, San Mateo, CA (US); James Chen, San Ramon, CA (US); Xiaowu Chen, San Mateo, CA (US); Aesop Cho, Mountain View, CA (US); Lee Chong, Newark, CA (US); Maria Fardis, San Carlos, CA (US); Craig Gibbs, Palo Alto, CA (US); Ralph F. Hirschmann, Philadelphia, PA (US); Thorsten Kirschberg, Belmont, CA (US); Christopher P. Lee, San Francisco, CA (US); Kuei-Ying Lin, Fremont, CA (US); Richard L. Mackman, Millbrae, CA (US); Peter H. Nelson, Los Altos, CA (US); David A. Oare, Belmont, CA (US); Hyung-Jung Pyun, Freemont, CA (US); Adrian S. Ray, San Mateo, CA (US); Rosemarie Sherlock, Palo Alto, CA (US); Sundaramoorthi Swaminathan, Burlingame, CA (US); William J. Watkins, Sunnyvale, CA (US); Jennifer R. Zhang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 267 days.

(21) Appl. No.: 10/833,294

(22) Filed: Apr. 26, 2004

(65) Prior Publication Data

US 2006/0199788 A1    Sep. 7, 2006

Related U.S. Application Data

(60) Provisional application No. 60/465,683, filed on Apr. 25, 2003, provisional application No. 60/465,682, filed on Apr. 25, 2003, provisional application No. 60/465,620, filed on Apr. 25, 2003, provisional application No. 60/465,452, filed on Apr. 25, 2003, provisional application No. 60/465,449, filed on Apr. 25, 2003, provisional application No. 60/465,335, filed on Apr. 25, 2003, provisional application No. 60/465,547, filed on Apr. 25, 2003, provisional application No. 60/465,695, filed on Apr. 25, 2003, provisional application No. 60/465,746, filed on Apr. 25, 2003, provisional application No. 60/465,406, filed on Apr. 25, 2003, provisional application No. 60/465,479, filed on Apr. 25, 2003, provisional application No. 60/465,480, filed on Apr. 25, 2003, provisional application No. 60/465,749, filed on Apr. 25, 2003, provisional application No. 60/465,638, filed on Apr. 25, 2003, provisional application No. 60/465,332, filed on Apr. 25, 2003, provisional application No. 60/465,560, filed on Apr. 25, 2003, provisional application No. 60/465,422, filed on Apr. 25, 2003, provisional application No. 60/465,342, filed on Apr. 25, 2003, provisional application No. 60/465,632, filed on Apr. 25, 2003, provisional application No. 60/465,640, filed on Apr. 25, (Continued)

(51) Int. Cl.
*A61K 31/60* (2006.01)
*C07D 237/00* (2006.01)
(52) U.S. Cl. .................... 514/247; 544/224
(58) Field of Classification Search ................. 544/232, 544/224; 514/247
See application file for complete search history.

(56) References Cited

U.S. PATENT DOCUMENTS 4,665,074 A * 5/1987 Amschler .................. 514/247
5,413,996 A   5/1995 Bodor (Continued)

FOREIGN PATENT DOCUMENTS

EP    0 267 050    5/1988
EP    0 441 192    1/1991

(Continued)

OTHER PUBLICATIONS

Allen, Lee F. et al., CI-1040 (PDI84352), a Targeted Signal Transduction Inhibitor of MEK (MAPKK),*Seminars in Oncology*, Oct. 2003, pp. 105-116, vol. 30, No. 5, Elsevier Inc.
Bantia, Shanta et al., Purine nucleoside phosphorylase inhibitor BCX-1777 (Immucillin-H)—a novel potent and orally active immunosuppressive agent, *International Immunopharmacology*, 2001, pp. 1199-1210, Elsevier Science B.V.
Beauchamp, Lilia M., et al., Guanine, Pyrazolo[3,4-d]pyrimidine, and Triazolo[4,5-d]pyrimidine(8-Azaguanine) Phosphonate Acyclic Derivatives as Inhibitors of Purine Nucleoside Phosphorylase, *Journal of Medicinal Chemistry*, 1996, pp. 949-956, American Chemical Society.
Bohani D. W. et al., A-420983: a potent, orally active inhibitor of Ick with efficacy in a model of transplant rejection, *Bioorganic & Medicinal Chemistry Letters*, 2004, vol. 14.
Bzowska, Agnieszka et al., Purine nucleoside phosphorylases: properties, functions, and clinical aspects, *Pharmacology & Therapeutics*, 2000, pp. 349-425, vol. 88, Elsevier Science Inc.
Chapman, H. et al., Practical Synthesis, Separation, and Stereochemical Assignment of the PMPA Pro-Drug GS-7340, Nucleosides, Nucleotides & Nucleic Acids, 2001, pp. 621-628, vol. 20, Nos. 4-7, Marcel Dekker, Inc.
Clark, Jeremy L. et al., Mycophenolic Acid Analogues as Potential Agents Against West Nile Virus Infection.

(Continued)

*Primary Examiner*—Rei-Tsang Shiao
(74) *Attorney, Agent, or Firm*—Viksnins, Harris & Padys PLLP

(57) ABSTRACT

The invention is related to phosphorus substituted anti-inflammatory compounds, compositions containing such compounds, and therapeutic methods that include the administration of such compounds, as well as to processes and intermediates useful for preparing such compounds.

20 Claims, No Drawings

Related U.S. Application Data

(60) 2003, provisional application No. 60/465,756, filed on Apr. 25, 2003, provisional application No. 60/465,424, filed on Apr. 25, 2003, provisional application No. 60/465,373, filed on Apr. 25, 2003, provisional application No. 60/465,420, filed on Apr. 25, 2003, provisional application No. 60/465,380, filed on Apr. 25, 2003, provisional application No. 60/465,433, filed on Apr. 25, 2003, provisional application No. 60/465,419, filed on Apr. 25, 2003, provisional application No. 60/465,481, filed on Apr. 25, 2003, provisional application No. 60/465,377, filed on Apr. 25, 2003, provisional application No. 60/465,844, filed on Apr. 25, 2003, provisional application No. 60/465,658, filed on Apr. 25, 2003, provisional application No. 60/465,581, filed on Apr. 25, 2003, provisional application No. 60/465,532, filed on Apr. 25, 2003, provisional application No. 60/465,531, filed on Apr. 25, 2003, provisional application No. 60/493,310, filed on Aug. 7, 2003, provisional application No. 60/493,309, filed on Aug. 7, 2003, provisional application No. 60/493,303, filed on Aug. 7, 2003, provisional application No. 60/493,302, filed on Aug. 7, 2003, provisional application No. 60/495,757, filed on Aug. 14, 2003, provisional application No. 60/495,427, filed on Aug. 15, 2003, provisional application No. 60/495,389, filed on Aug. 15, 2003, provisional application No. 60/495,366, filed on Aug. 15, 2003, provisional application No. 60/495,563, filed on Aug. 15, 2003, provisional application No. 60/495,295, filed on Aug. 15, 2003, provisional application No. 60/495,532, filed on Aug. 15, 2003, provisional application No. 60/495,414, filed on Aug. 15, 2003, provisional application No. 60/495,380, filed on Aug. 15, 2003, provisional application No. 60/495,680, filed on Aug. 15, 2003, provisional application No. 60/495,679, filed on Aug. 15, 2003, provisional application No. 60/495,749, filed on Aug. 15, 2003, provisional application No. 60/495,748, filed on Aug. 15, 2003, provisional application No. 60/495,597, filed on Aug. 15, 2003, provisional application No. 60/495,471, filed on Aug. 15, 2003, provisional application No. 60/495,691, filed on Aug. 15, 2003, provisional application No. 60/495,276, filed on Aug. 15, 2003, provisional application No. 60/495,754, filed on Aug. 15, 2003, provisional application No. 60/495,472, filed on Aug. 15, 2003, provisional application No. 60/495,530, filed on Aug. 15, 2003, provisional application No. 60/495,375, filed on Aug. 15, 2003, provisional application No. 60/495,274, filed on Aug. 15, 2003, provisional application No. 60/495,533, filed on Aug. 15, 2003, provisional application No. 60/495,529, filed on Aug. 15, 2003, provisional application No. 60/495,455, filed on Aug. 15, 2003, provisional application No. 60/495,537, filed on Aug. 15, 2003, provisional application No. 60/495,456, filed on Aug. 15, 2003, provisional application No. 60/495,660, filed on Aug. 15, 2003, provisional application No. 60/495,398, filed on Aug. 15, 2003, provisional application No. 60/495,425, filed on Aug. 15, 2003, provisional application No. 60/495,393, filed on Aug. 15, 2003, provisional application No. 60/495,460, filed on Aug. 15, 2003, provisional application No. 60/495,416, filed on Aug. 15, 2003, provisional application No. 60/495,614, filed on Aug. 15, 2003, provisional application No. 60/495,661, filed on Aug. 15, 2003, provisional application No. 60/513,951, filed on Oct. 23, 2003, provisional application No. 60/514,072, filed on Oct. 24, 2003, provisional application No. 60/514,054, filed on Oct. 24, 2003, provisional application No. 60/513,971, filed on Oct. 24, 2003, provisional application No. 60/514,394, filed on Oct. 24, 2003, provisional application No. 60/514,393, filed on Oct. 24, 2003, provisional application No. 60/513,950, filed on Oct. 24, 2003, provisional application No. 60/513,945, filed on Oct. 24, 2003, provisional application No. 60/513,944, filed on Oct. 24, 2003, provisional application No. 60/513,947, filed on Oct. 24, 2003, provisional application No. 60/513,975, filed on Oct. 24, 2003, provisional application No. 60/514,453, filed on Oct. 24, 2003, provisional application No. 60/514,464, filed on Oct. 24, 2003, provisional application No. 60/514,203, filed on Oct. 24, 2003, provisional application No. 60/513,953, filed on Oct. 24, 2003, provisional application No. 60/514,450, filed on Oct. 24, 2003, provisional application No. 60/514,244, filed on Oct. 24, 2003, provisional application No. 60/514,466, filed on Oct. 24, 2003, provisional application No. 60/513,973, filed on Oct. 24, 2003, provisional application No. 60/514,202, filed on Oct. 24, 2003, provisional application No. 60/514,424, filed on Oct. 24, 2003, provisional application No. 60/513,970, filed on Oct. 24, 2003, provisional application No. 60/514,324, filed on Oct. 24, 2003, provisional application No. 60/514,111, filed on Oct. 24, 2003, provisional application No. 60/514,110, filed on Oct. 24, 2003, provisional application No. 60/514,334, filed on Oct. 24, 2003, provisional application No. 60/514,085, filed on Oct. 24, 2003, provisional application No. 60/514,130, filed on Oct. 24, 2003, provisional application No. 60/513,961, filed on Oct. 24, 2003, provisional application No. 60/514,131, filed on Oct. 24, 2003, provisional application No. 60/514,200, filed on Oct. 24, 2003, provisional application No. 60/514,280, filed on Oct. 24, 2003, provisional application No. 60/514,098, filed on Oct. 24, 2003, provisional application No. 60/513,977, filed on Oct. 24, 2003, provisional application No. 60/514,174, filed on Oct. 24, 2003, provisional application No. 60/513,924, filed on Oct. 24, 2003, provisional application No. 60/514,143, filed on Oct. 24, 2003, provisional application No. 60/514,144, filed on Oct. 24, 2003, provisional application No. 60/514,206, filed on Oct. 24, 2003, provisional application No. 60/514,160, filed on Oct. 24, 2003, provisional application No. 60/514,326, filed on Oct. 24, 2003, provisional application No. 60/514,205, filed on Oct. 24, 2003, provisional application No. 60/513,979, filed on Oct. 24, 2003, provisional application No. 60/514,075, filed on Oct. 24, 2003, provisional application No. 60/513,946, filed on Oct. 24, 2003, provisional application No. 60/514,051, filed on Oct. 24, 2003, provisional application No. 60/514,161, filed on Oct. 24, 2003, provisional application No. 60/514,204, filed on Oct. 24, 2003, provisional application No. 60/514,325, filed on Oct. 24, 2003, provisional application No. 60/514,044, filed on Oct. 24, 2003, provisional application No. 60/514,201, filed on Oct. 24, 2003, provisional application No. 60/514,522, filed on Oct. 24, 2003, provisional application No. 60/514,175, filed on Oct. 24, 2003, provisional application No. 60/514,113, filed on Oct. 24, 2003, provisional application No. 60/514,097, filed on Oct. 24, 2003, provisional application No. 60/514,360, filed on Oct. 24, 2003, provisional application No. 60/513,976, filed on Oct. 24, 2003, provisional application No. 60/514,107, filed on Oct. 24, 2003, provisional application No. 60/513,982, filed on Oct. 24, 2003, provisional application No. 60/514,116, filed on Oct. 24, 2003, provisional application No. 60/513,562, filed on Oct. 24, 2003, provisional application No. 60/513,592, filed on Oct. 24, 2003, provisional application No. 60/513,563, filed on Oct. 24, 2003, provisional application No. 60/513,530, filed on Oct. 24, 2003, provisional application No. 60/513,579, filed on Oct. 24, 2003, provisional application No. 60/514,298, filed on Oct. 24, 2003, provisional application No. 60/513,531, filed on Oct. 24, 2003, provisional application No. 60/513,561, filed on Oct. 24, 2003, provisional application No. 60/513,589, filed on Oct. 24, 2003, provisional application No. 60/513,588, filed on Oct. 24, 2003, provisional application No. 60/514,258, filed on Oct. 24, 2003, provisional application No. 60/513,948, filed on Oct. 24, 2003, provisional application No. 60/514,140, filed on Oct. 24, 2003, provisional application No. 60/513,593, filed on Oct. 24, 2003, provisional application No. 60/514,021, filed on Oct. 24, 2003, provisional application No. 60/532,257, filed on Dec. 22, 2003, provisional application No. 60/532,230, filed on Dec. 22, 2003, provisional application No. 60/531,960, filed on Dec. 22, 2003, provisional application No. 60/532,160, filed on Dec. 22, 2003, provisional application No. 60/531,940, filed on Dec. 22, 2003, provisional application No. 60/532,591, filed on Dec. 23, 2003, provisional application No. 60/536,003, filed on Jan. 12, 2004, provisional application No. 60/536,027, filed on Jan. 12, 2004, provisional application No. 60/536,180, filed on Jan. 12, 2004, provisional application No. 60/536,005, filed on Jan. 12, 2004, provisional application No. 60/536,004, filed on Jan. 12, 2004, provisional application No. 60/536,009, filed on Jan. 12, 2004.

U.S. PATENT DOCUMENTS

| | | |
|---|---|---|
| 5,493,030 A | 2/1996 | Morgans et al. |
| 5,585,397 A | 12/1996 | Tung et al. |
| 5,633,279 A | 5/1997 | Morgans et al. |
| 5,654,286 A | 8/1997 | Hostetler |
| 5,670,497 A | 9/1997 | Bold et al. |
| 5,747,498 A | 5/1998 | Schnur et al. |
| 5,750,343 A | 5/1998 | Maag et al. |
| 5,750,493 A | 5/1998 | Schinazi et al. |
| 5,811,422 A | 9/1998 | Lam et al. |
| 5,874,577 A | 2/1999 | Chen et al. |
| 5,914,332 A | 6/1999 | Chen et al. |
| 6,072,053 A | 6/2000 | Vince et al. |
| 6,174,888 B1 | 1/2001 | McQuire et al. |
| 6,312,662 B1 | 11/2001 | Robinson et al. |
| 6,319,946 B1 | 11/2001 | Hale et al. |
| 6,395,763 B1 | 5/2002 | Stamos et al. |
| 6,608,027 B1 | 8/2003 | Tsantrizos et al. |
| 6,767,900 B2 | 7/2004 | Ubasawa et al. |
| 2001/0031773 A1 | 10/2001 | Camden |
| 2002/0119443 A1 | 8/2002 | Becker et al. |
| 2003/0109498 A1 | 6/2003 | Yuasa et al. |
| 2004/0121316 A1 | 6/2004 | Birkus et al. |
| 2004/0167096 A1 | 8/2004 | Cheng et al. |

FOREIGN PATENT DOCUMENTS

| | | |
|---|---|---|
| EP | 0 465 297 | 1/1992 |
| EP | 0 531 597 | 3/1993 |
| EP | 0 632 048 | 1/1995 |
| EP | 0 786 455 | 7/1997 |
| EP | 0 852 233 | 7/1998 |
| EP | 0 919 562 | 6/1999 |
| EP | 1 295 879 | 3/2003 |
| WO | WO 88/06158 | 8/1988 |
| WO | WO91/19721 | 12/1991 |
| WO | WO 92/00988 | 1/1992 |
| WO | WO 92/18520 | 10/1992 |
| WO | WO 93/12123 | 6/1993 |
| WO | WO 93/24510 | 12/1993 |
| WO | WO 96/14314 | 5/1996 |
| WO | WO 96/40156 | 12/1996 |
| WO | WO 97/01558 | 1/1997 |
| WO | WO 98/04569 | 2/1998 |
| WO | WO 98/11906 | 3/1998 |
| WO | WO 98/15563 | 4/1998 |
| WO | WO 99/33815 | 7/1999 |
| WO | WO 99/62921 | 12/1999 |
| WO | WO 00/04033 | 1/2000 |
| WO | WO 00/52015 A2 | 9/2000 |
| WO | WO 00/52015 A3 | 2/2001 |
| WO | WO 01/13957 | 3/2001 |
| WO | WO 01/17982 | 3/2001 |
| WO | WO 01/19320 | 3/2001 |
| WO | WO 01/39724 A2 | 6/2001 |
| WO | WO 01/46204 | 6/2001 |
| WO | WO 01/64693 | 9/2001 |
| WO | WO 01/39724 A3 | 10/2001 |
| WO | WO 01/96329 | 12/2001 |
| WO | WO 01/96354 | 12/2001 |
| WO | WO 02/03997 | 1/2002 |
| WO | WO 02/06292 | 1/2002 |
| WO | WO 02/08241 | 1/2002 |
| WO | WO 02/14344 | 2/2002 |
| WO | WO 02/48165 A2 | 6/2002 |
| WO | WO 02/057425 | 7/2002 |
| WO | WO 02/100415 | 12/2002 |
| WO | WO 02/103008 A2 | 12/2002 |
| WO | WO 03/028737 | 4/2003 |
| WO | WO 02/048165 A3 | 5/2003 |
| WO | WO 03/050129 | 6/2003 |
| WO | WO 03/059255 | 7/2003 |
| WO | WO 03/064383 | 8/2003 |
| WO | WO 03/066005 | 8/2003 |
| WO | WO 03/080078 | 10/2003 |
| WO | WO 02/103008 A3 | 11/2003 |
| WO | WO 03/090690 | 11/2003 |
| WO | WO 2004/096234 | 11/2004 |
| WO | WO 2004/096818 A2 | 11/2004 |
| WO | WO 2005/011709 | 2/2005 |
| WO | WO 2005/011709 A1 | 2/2005 |
| WO | WO 2004/096818 A3 | 4/2005 |

OTHER PUBLICATIONS

Conklyn, Maryrose et al., The JAK3 inhibitor CP-690550 selectively reduces NK and CD8+ cell numbers in cynomolgus monkey blood following chronic oral dosing, *Journal of Leukocyte Biology*, Dec. 2004, pp. 1-8, vol. 76, The Society for Leukocyte Biology.

De Clereq, E., Highlights in the Development of New Antiviral Agents, *Mini Reviews in Medicinal Chemistry*, 2002, 163-175, vol. 2, No. 2., Bentham Science Publishers, Ltd.

Evans, Gary B., Exploring Structure—Activity Relationships of Transition State Analogues of Human Purine Nucleoside Phosphorylase, *J. Med. Chem.*, 2003, 3412-3423, vol. 46, No. 15, American Chemical Society.

Gumina, Giuseppe et al., Advances in antiviral agents for hepatitis B virus, *Antiviral Chemistry & Chemotherapy*, 2001, 93-112, vol. 12, Suppl. 1, International Medical Press.

Gobec, S. et al., Phosphonate inhibitors of antiget 85C, a crucial enzyme involved in the biosynthesis of the mycobacterium tuberculosis cell wall, *Bioorganic and Medicinal Chemistry Letters*, 2004, vol. 14.

Hegedus, Louis S. et al., Synthesis of 4'-Methyl and 4'-cyano Carbocyclic 2',3'-Didehydro Nucleoside Analogues via 1,4-Addition to Substituted Cyclopentenones, *J. Org. Chem.*, 2004, 8492-8495, vol. 69, No. 24, American Chemical Society.

Herczegh P., et al., Osteoadsorptive bisphosphonate derivatives of fluoroquinolone antibacterials, *J. Med. Chem.*, 2002, vol. 45.

Hirabayashi, Hideki et al., Bone-Specific Drug Delivery Systems, *Clinical Pharacokinetics*, 2003, 1319-1330, vol. 42, No. 15.

Holy A. et al., Synthesis, *Cllect. Czech. Chem. Commun.*, 1989, vol. 54, pp. 2190-2210.

Jain, Jugnu et al., Characterization of Pharmacological Efficacy of VX-148, a New, Potent Immunosuppressive Inosine 5'-Monophosphate Dehydrogenase Inhibitor, *Journal of Pharmacology and Experimental Therapeutics*, 2002, 1272-1277, vol. 302, No. 3, The American Society for Pharmacology and Experimental Therapeutics.

Karpenko, Inna L. et al., Synthesis and Antiherpetic Activity of Acyclovir Phosphonates, *Nucleosides, Nucleotides & Nucleic Acids*, 2003, 319-328, vol. 22, No. 3, Marcel Dekker, Inc.

Kato, Keisuke et al., Stereoselective synthesis of 4'-.alpha.-alkyclcarbovir derivatives based on an asymmetric synthesis or chemo-enzymatic procedure, *Chemical & Pharmaceutical Bulletin*, 1999, 1256-1264, vol. 49, No. 9, Pharmaceutical Society of Japan.

Kato, Keisuke et al., Enantio- and diastereoselective syntheis of 4'-α-substituted carbocyclic nucleosides, Tetrahedron: *Asymmetry*, 1998, 911-914, vol. 9, Elsevier Science Ltd.

Kilpatrick, J. Michael, Intravenous and oral pharmacokinetic study of BCX-1777, a novel purine nucleoside phosphorylase transition-state inhibitor, In vivo effects on blood 2'-deoxyguanosine in primates, *International Immunopharmacology*, 2003, 541-548, vol. 3, Elsevier Science B.V.

Kim, Choung Un et al., Regiospecific and Highly Stereoselective Electrophilic Addition to Furanoid Glycals: Synthesis of Phosphonate Nucleotide Analogues with Potent Activity against HIV, J. Org. Chem., 1991, 2642-2647, vol. 56, No. 8, American Chemical Society.

Kinsky, Stephen C. et al., Inhibition of cell proliferation by putative metabolites and non-degradable analogs of methotrexate-.gama.-dimyristoylphosphatidylethanolamine, *Biochimica et Biphysica Acta*, 19878, 211-218, vol. 917, No. 2., Elsevier Science Publishers B.V.

Kinsky, Stephen C. et al., Effect of liposomes sentitized with methotrexate-γ-dimyristoylphosphatidylethanolamine on cells that are resistant to methotrexate, *Biochimica et Biophysica Acta*, 1986, 129-135, vol. 885, Elsevier Science Publishers B.V.

Kinsky, Stephen C. et al., Circumvention of the methotrexate transport system by methotrexate-phosphatidylethanolamine derivatives effect of fatty acid chain length, *Biochimica et Biophysica Acta*, 1987, 96-103, vol. 921, Elsevier Science Publishers B. V.

Ko, Ok Hyun et al., Efficient synthesis of novel carbocyclic nucleosides via sequential Claisen rearrangement and ring-closing metathesis, *Tetrahedron Letters*, 2002, 6399-6402, vol. 43, Elsevier Science Ltd.

Reed, Leff et al., Antidiabetic PPARγ Ligands: An update on Compounds in development, *Curr. Med. Chem.—Imun., Endoc. & Metab. Agents*, 2002, 33-47, vol. 2, No. 1, Bentham Science Publishers Ltd.

Lewandowicz, Andrzej et al., Achieving the Ultimate Physiological Goal in Transition State Analogue Inhibitors for Purine Nucleoside Phosphorylase, *The Journal of Biological Chemistry*, 2003, 31465-31468, vol. 278, No. 34, The American Society for Biochemistry and Molecular Biology, Inc.

Pankiewicz, Krzysztof W., Novel Mycophenolic Adenine Bis(phosphonate) Analogues As Potential Differentiation Agents against Human Leukemia, *J. Med. Chem.*, 2002 703-712, vol. 45, No. 3, American Chemical Society.

Ono-Nita, Suzane Kioko et al., Novel Nucleoside Analogue MCC-478 (LY582563) Is Effective against Wild-Type or Lamivudine-Resistant Hepatitis B Virus, *Antimicrobial Agents and Chemotherapy*, 2002, 2602-2605, vol. 46, No. 8, American Society for Microbiology.

Parang, Keykavous et al., Novel Approaches for Designing 5'-O-Ester Prodrugs of 3'-Azido-2', 3'-dideoxythymidine (AZT), *Current Medicinal Chemistry*, 2000, 995-1039, vol. 7, No. 10, Bentham Science Publishers Ltd.

Prashad, Mahavir et al., An Efficient and Large-Scale Enantioselective Synthesis of PNP405: A Purine Nucleoside Phosphorylase Inhibitor, *J. Org. Chem.*, 2002, 6612-6617, vol. 67, No. 19, American Chemical Society.

Ray, Adrian S. et al., Role of Purine Nucleoside Phosphorylase in Interactions between 2', 3'-Dideoxyinosine and Allopurinal, Ganciclovir, or Tenofovir, Antimicrobial Agents and Chemotherapy, 2004, 1089-1095, vol. 48, No. 4, American Society for Microbiology.

Roberts, Stanley M., Development of the route to the new anti-AIDS drug abacavir: A highlight of academic/industry laison, *IDrugs*, 1998, 896-899, vol. 1, No. 8, Current Drugs Ltd.

Rosowsky, Andre et al., Methotrexate Analogues—27, *Biochemical Pharmacology*, 1986, 3327-3333, vol. 35, No. 19, Pergamon Journals Ltd.

Rosowsky, Andre et al., Methotrexate Analogues, 32, Chain Extension, α-Carboxyl Replacement by Sulfonate and Phosphonate: Effect on Enzyme Binding and Cell-Growth Inhibition, *J. Med. Chem.*, 1988, 1326-1331, vol. 31, No. 7, American Chemical Society.

Schultz, C., Prodrugs of biologically active phosphate esters, *Bioorganic & Medicinal Chemistry*, 2003, 885-898, vol. 11, Elsevier Science Ltd., GB.

Sekiya, Kouichi et al., 2-Amino-6-arylthio-9-[2-(phosphonomethoxy) ethyl) purine Bis(2,2,2-trifluoroethyl) Esters as Novel HBV-Specific Antiviral Reagents, Journal of Medicinal Chemistry, 2002, 3138-3142, vol. 45, No. 14, American Chemical Society.

Shi, Wuxian et al., *Plasmodium falciparum* Purine Nucleoside Phosphorylase, The Journal of Biological Chemistry, 2004, 18103-18106, vol. 279, No. 18, The American Society of Biochemistry and Molecular Biology, Inc.

Sintchak, Michael D. et al., The structure of inosine 5'-monophosphate dehydrogenase and the design of novel inhibitors, Immunopharmachology, 2000, 163-184, vol. 47, Elsevier.

Srinivas, Ranga V. et al., Metabolism and In Vitro Antiretroviral Activities of Bis(Pivaloyloxymethyl) Prodrugs of Acyclic Nucleoside Phosphonates, Antimicrobial Agents and Chemotherapy, 1993, 2247-2250, vol. 37, No. 10, American Society for Microbiology.

Sturtz, Georges et al., Su rune nouvelle approche de pharmacomodulation du methotrexate: synthese d'analogues gem-diphosphoniques d'amethopterine et de la N-10 deaza amethopterine, Medicinal Chemistry, C. R. Acad. Sci. Paris, 1990, vol. 10, No. 2, 739-742, Academie des Sciences.

Sturtz, Georges et al., Analogues phosphonoglutamiques d'amethopterine (methotrexate), Eur. J. Med. Chem—Chim. Ther., 1984, 267-273, vol. 19, No. 3.

Sturtz, G. et al., Synthesis of gem-bisphosphonic methotrexate conjugates and their biological response towards Walker's osteosarcoma, *Eur. J. Med. Chem.*, 1993, 899-903, vol. 28, Elsevier.

Sturtz, G. et al., A study of the delivery-targeting concept applied to antineoplasic drugs active on human osteosarcoma, I. Synthesis and biological activity in nude mice carrying human osteosarcoma xenografts of gem-bisphosphonic methotrexate analogues, Eur J. Med. Chem., 1992, 825-833, vol. 27, No. 8, Elsevier.

Waegell W. et al. A420983, a novel, small molecule inhibitor of LCK prevents allograft rejection, Transplantation Proceedings, 2002, 1411-1417, vol. 34.

Wroblewski, Andrzej et al., Synthesis of (1R,2S)- and (1S,2S)-3-(4-carbamoyl-1,2,3-triazol-1-yl)-1,2-dihydroxypropylphosphonates, Tetrahedron: Asymmetry, 2004, 1457-1464, vol. 15, Elsevier.

Abdel-Meguid, Sherin S. et al., Inhibition of Human Immunodeficiency Virus-1 Protease by a $C_2$-Symmetric Phosphinate. Synthesis and Crystallographic Analysis, *Biochemistry*, 1993, 1543-1572, vol. 32, No. 31.

De Clercq, Erik, New Developments in Anti-HIV Chemotherapy, *Current Medicinal Chemistry*, 2001, 1543-1572, vol. 8, No. 13, Bentham Science Publishers Ltd.

Dvorakova, Hana et al., Synthesis of 2'-Aminomethyl Derivatives of N-(2-(Phosphonomethoxy)ethyl) Nucleotide Analogues as Potential Antiviral Agents, *J. Med. Chem.*, 1996, 3263-3268. vol. 38, No. 17.

Menendez-Arias, Luis et al. Targeting HIV: antiretroviral therapy and development of drug resistance, *TRENDS in Pharmacological Sciences*, 2002, 381-388, vol. 23, No. 8, Elsevier Science Ltd.

Vielhaber, Bernd, Bericht vom 3rd International Workshop on Salvage Therapy for HIV-Infection, *Deutsche Aids-Hilfe e.V. FaxReport zu HIV und AIDS*, 2000, 12-14.

Hostetier, CAS:127:185859 (1997).

Morgans et al., CAS:124:86709 (1995).

Sturtz et al., CAS:101:143560 (1984).

* cited by examiner

ANTI-INFLAMMATORY PHOSPHONATE COMPOUNDS

PRIORITY OF INVENTION

This application claims the benefit of priority under 35 U.S.C. § 119(e) to U.S. Provisional Patent Application Ser. Nos. 60/465,683, 60/465,682, 60/465,620, 60/465,452, 60/465,449, 60/465,335, 60/465,547, 60/465,695, 60/465,746, 60/465,406, 60/465,479, 60/465,480, 60/465,749, 60/465,638, 60/465,332, 60/465,560, 60/465,422, 60/465,342, 60/465,632, 60/465,640, 60/465,756, 60/465,424, 60/465,373, 60/465,420, 60/465,380, 60/465,433, 60/465,419, 60/465,481, 60/465,377, 60/465,844, 60/465,658, 60/465,581, 60/465,532, and 60/465,531, all filed Apr. 25, 2003; to U.S. Provisional Patent Application Ser. Nos. 60/493,310, 60/493,309, 60/493,303, and 60/493,302, all filed Aug. 7, 2003; to U.S. Provisional Patent Application Ser. Nos. 60/495,427, 60/495,389, 60/495,366, 60/495,563, 60/495,295, 60/495,532, 60/495,414, 60/495,380, 60/495,680, 60/495,679, 60/495,749, 60/495,748, 60/495,597, 60/495,471, 60/495,691, 60/495,276, 60/495,754, 60/495,472, 60/495,530, 60/495,375, 60/495,274, 60/495,533, 60/495,529, 60/495,455, 60/495,537, 60/495,456, 60/495,660, 60/495,398, 60/495,425, 60/495,393, 60/495,460, 60/495,416, and 60/495,614, all filed Aug. 15, 2003; and 60/495,757, filed Aug. 14, 2003 to U.S. Provisional Patent Application Ser. Nos. 60/514,072, 60/514,054, 60/513,971, 60/514,394, 60/514,393, 60/513,950, 60/513,945, 60/513,944, 60/513,947, 60/513,975, 60/514,453, 60/514,464, 60/514,203, 60/513,953, 60/514,450, 60/514,244, 60/514,466, 60/513,973, 60/514,202, 60/514,424, 60/513,970, 60/514,324, 60/514,111, 60/514,110, 60/514,334, 60/514,085, 60/514,130, 60/513,961, 60/514,131, 60/514,200, 60/514,280, 60/514,098, 60/513,977, 60/514,174, 60/513,924, 60/514,143, 60/514,144, 60/514,206, 60/514,160, 60/514,326, 60/514,205, 60/513,979, 60/514,075, 60/513,946, 60/514,051, 60/514,161, 60/514,204, 60/514,325, 60/514,044, 60/514,201, 60/514,522, 60/514,175, 60/514,113, 60/514,097, 60/514,360, 60/513,976, 60/514,107, 60/513,982, 60/514,116, 60/513,562, 60/513,592, 60/513,563, 60/513,530, 60/513,579, 60/514,298, 60/513,531, 60/513,561, 60/513,589, 60/513,588, 60/514,258, 60/513,948, 60/514,140, 60/513,593, and 60/514,021 all filed Oct. 24, 2003; and 60/513,951, filed Oct. 23, 2003 to U.S. Provisional Patent Application Ser. Nos. 60/532,257, 60/532,230, 60/531,960, 60/532,160, and 60/531,940, all filed Dec. 22, 2003; to U.S. Provisional Application Ser. No. 60/532,591, filed Dec. 23, 2003, and to U.S. Provisional Patent Application Ser. Nos. 60/536,003, 60/536,027, 60/536,180, 60/536,005, 60/536,004, and to 60/536,009, all filed Jan. 12, 2004. The entirety of each Provisional Application listed above is incorporated herein by reference. This application also claims priority to U.S. Provisional Patent Application Ser. No. 60/495,661 filed Aug. 15, 2003.

FIELD OF THE INVENTION

The invention relates generally to phosphonate containing compounds with anti-inflammatory activity.

BACKGROUND OF THE INVENTION

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g., to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., glucocorticoids and other anti-inflammatory drugs) that can be administered. By comparison, although oral administration of drugs is generally recognized as a convenient and economical method of administration, oral administration can result in either (a) uptake of the drug through the cellular and tissue barriers, e.g., blood/brain, epithelial, and cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells.

Inflammation is a major problem for many people. Thus, there is a need for novel anti-inflammatory agents, e.g. drugs, having improved anti-inflammation properties, pharmacokinetic properties, activity, oral bioavailability, potency, or effective half-lives in vivo. Such agents may also have distinct resistance profiles, fewer side effects, less complicated dosing schedules, or have increased oral activity.

There is also a need for assay methods capable of determining the presence, absence or amounts of inflammation. Such methods would be of practical utility in the search for inhibitors as well as for diagnosing the presence of inflammation.

SUMMARY OF THE INVENTION

Intracellular targeting may be achieved by methods and compositions that allow accumulation or retention of biologically active agents inside cells. The present invention provides novel phosphonate containing analogs of anti-inflammatory compounds. These compounds possess the utilities of the related anti-inflammatory compounds, but due to the presence of the phosphonate group(S) they typically provide cellular accumulation of the analog. Thus, compounds of the invention may demonstrate improved anti-inflammatory properties, pharmacokinetic properties, oral bioavailability, potency, or extended effective half-life in vivo, or a combination thereof. The compounds of the invention may also have distinct resistance profiles, fewer side effects, less complicated dosing schedules, or have increased oral activity.

The present invention relates generally to the accumulation or retention of therapeutic compounds inside cells. The invention is more particularly related to attaining high concentrations of phosphonate-containing molecules in target cells. Such effective targeting may be applicable to a variety of therapeutic formulations and procedures.

Accordingly, in one embodiment the invention provides a compound of the invention which is a conjugate comprising an anti-inflammatory compound linked to one or more phosphonate groups; or a pharmaceutically acceptable salt or solvate thereof.

In another embodiment the invention provides a compound of the invention, or a pharmaceutically acceptable salt or solvate thereof, that is a compound of any one of formulae 500-611:

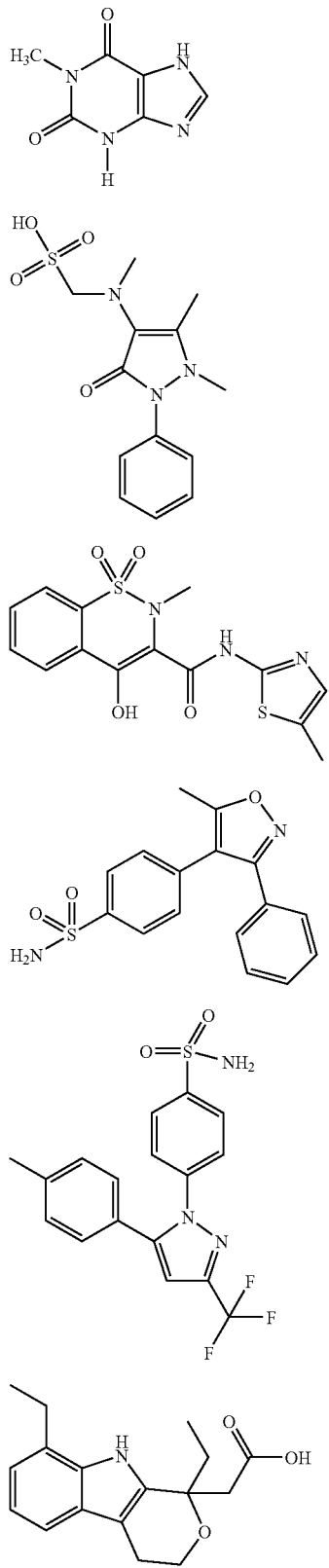

-continued
| | |
|---|---|
| 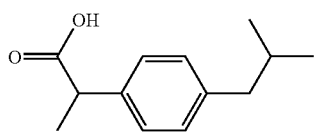 | 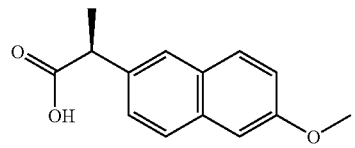 512, 513 |
| 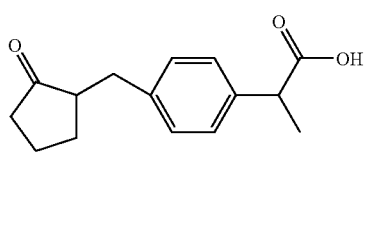 | 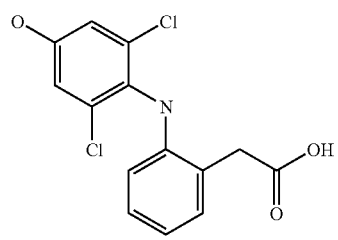 514, 515 |
| 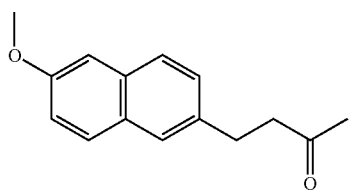 | 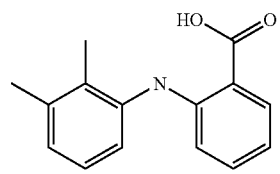 516, 517 |
| 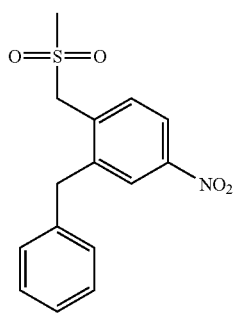 | 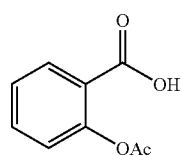 518, 519 |
| 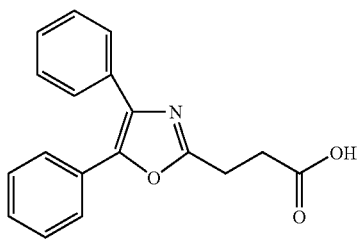 | 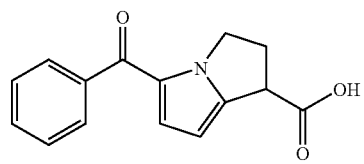 520, 521 |
| 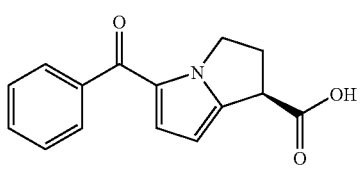 | 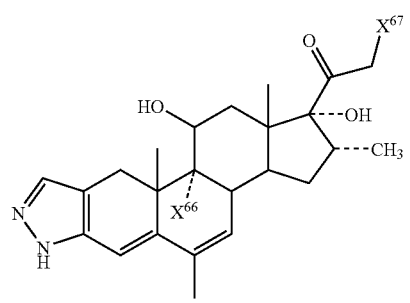 522, 523 |

-continued
524
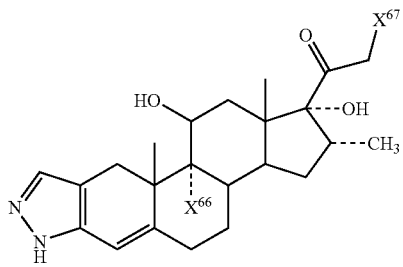
525
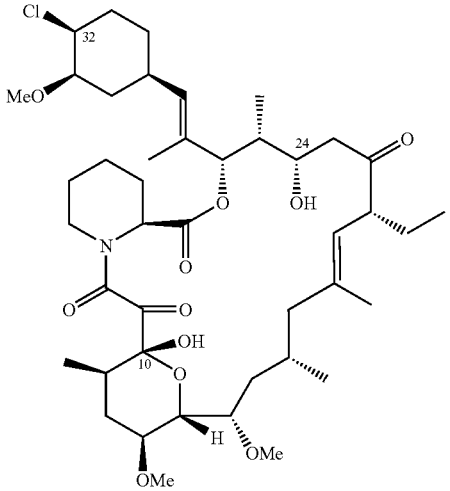
526
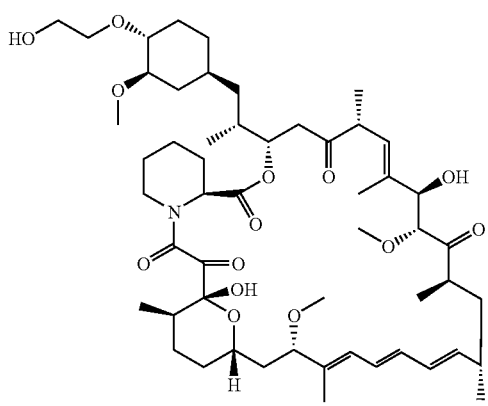
527
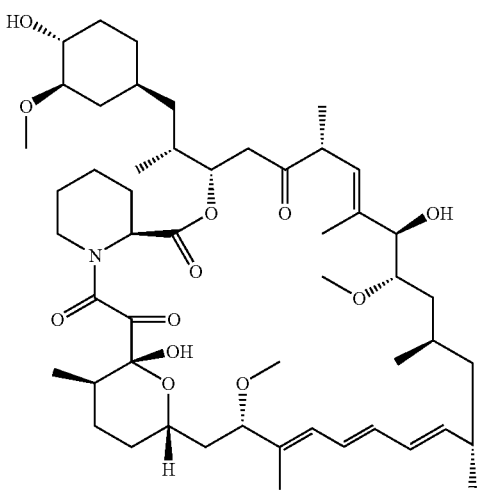
528
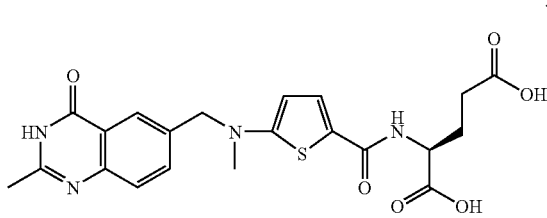
529
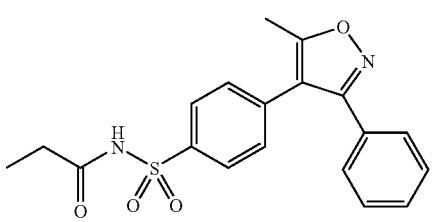
530
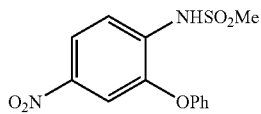
531
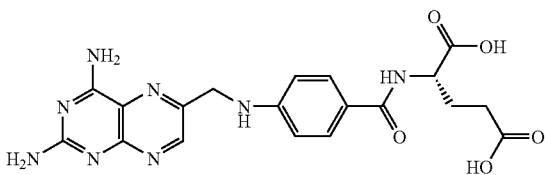

-continued
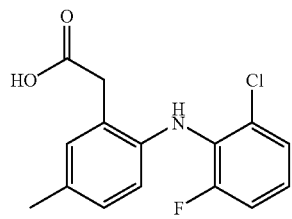
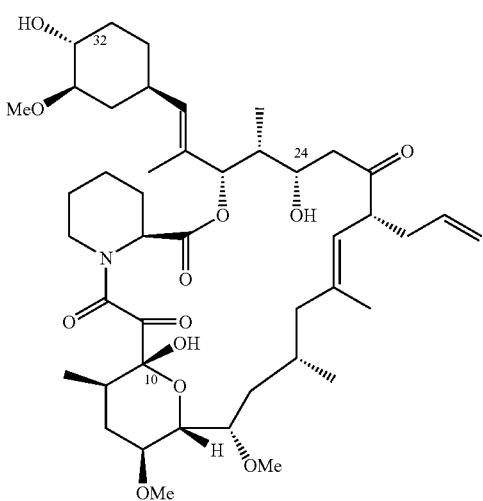
532
533
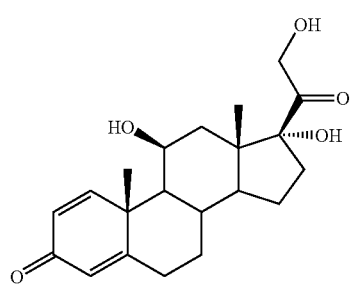
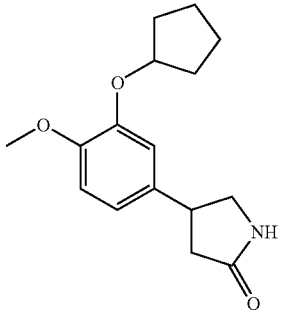
534
535
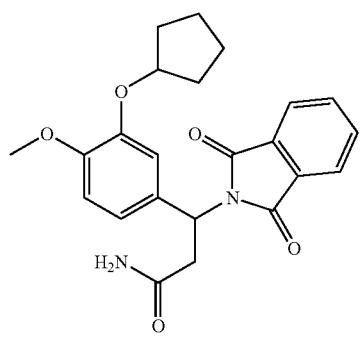
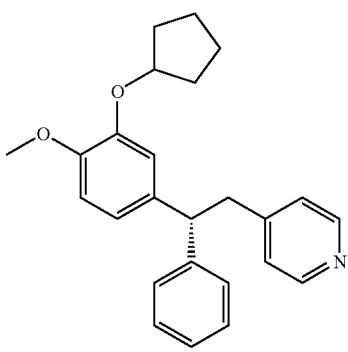
536
537
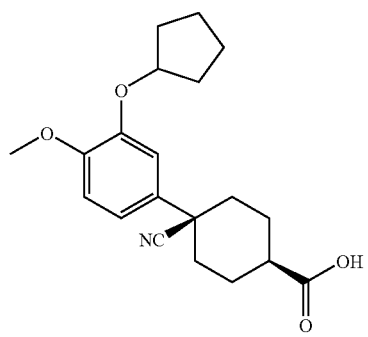
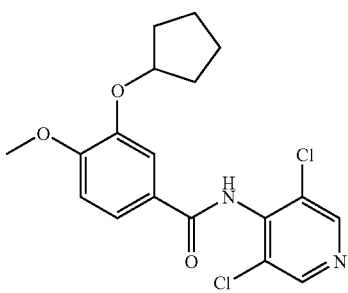
538
539

-continued
540
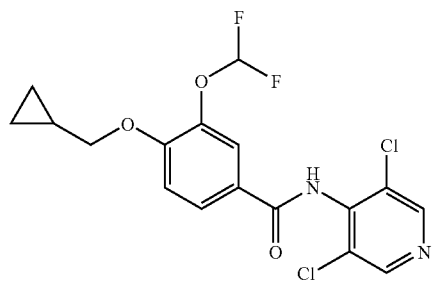
541
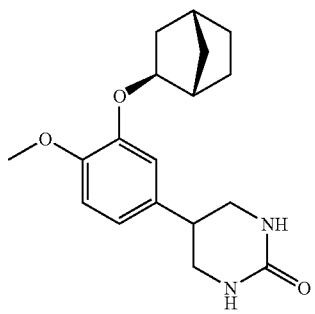
542
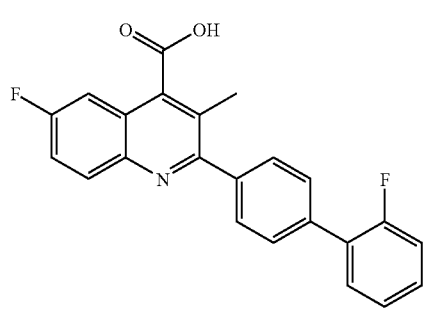
543
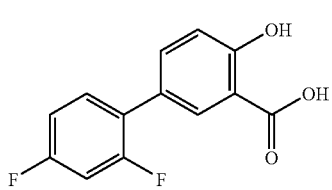
544
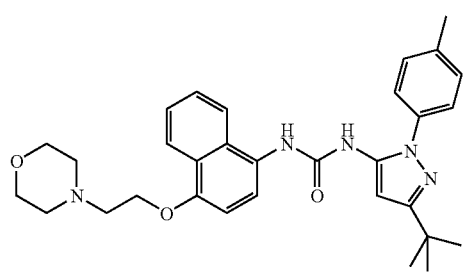
545
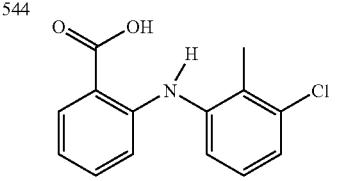
546
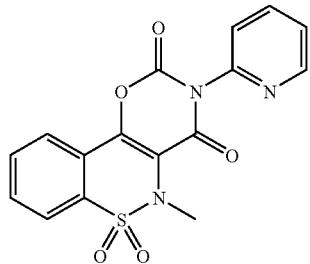
547
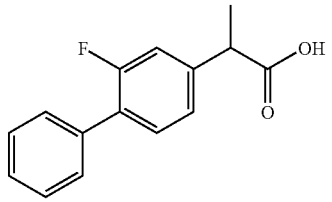
548
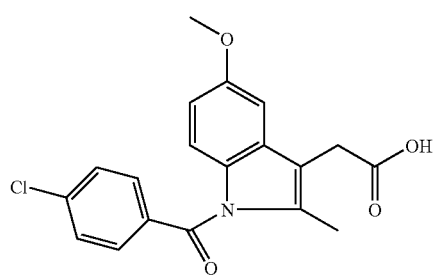
549
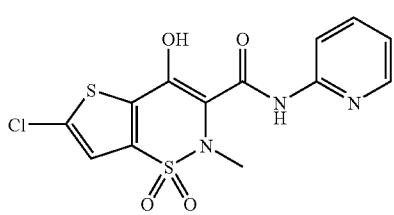
550
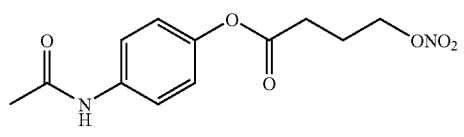
551
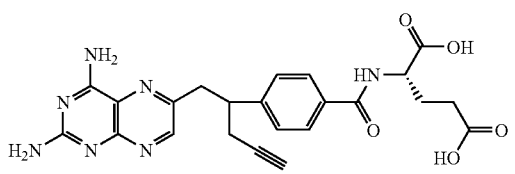

-continued
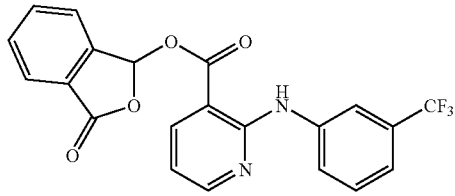 552
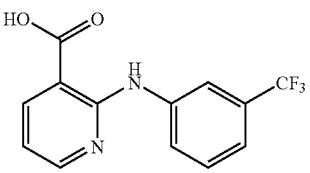 553
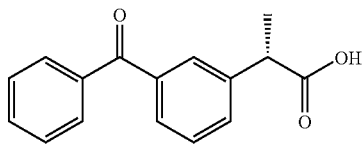 554
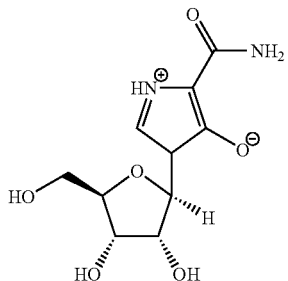 555
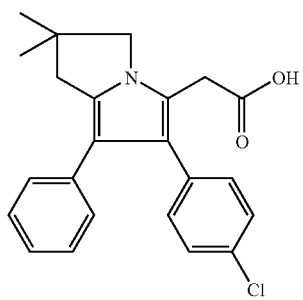 556
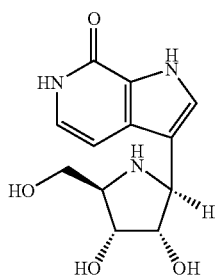 557
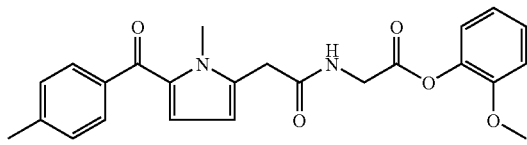 558
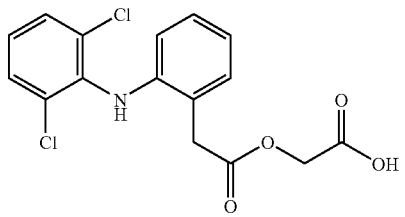 559
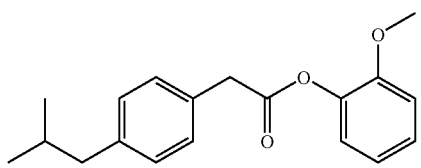 560
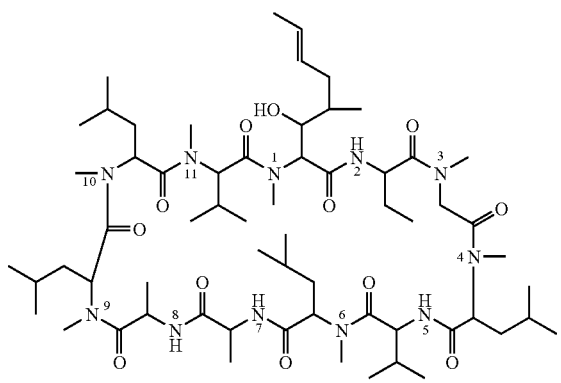 561
562
563

-continued
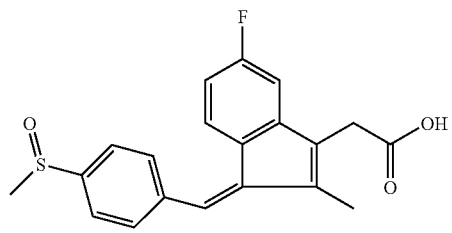
564
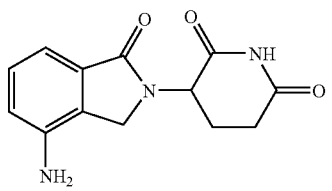
565
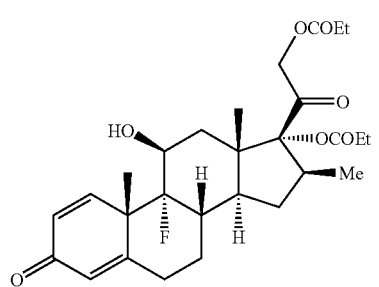
566
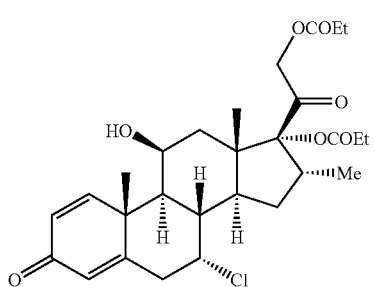
567
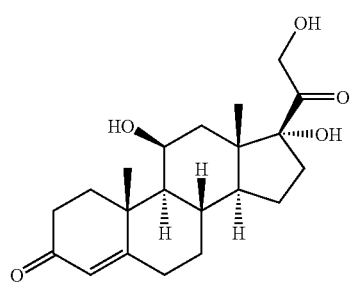
568
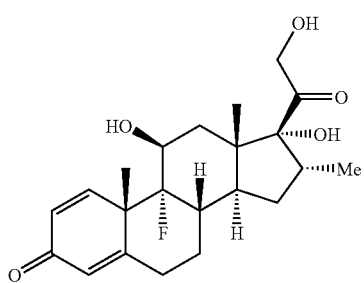
569
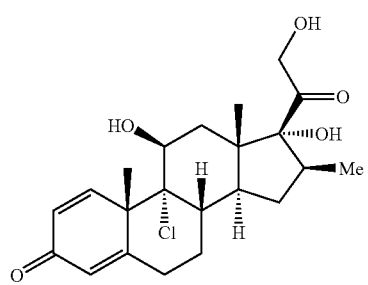
570
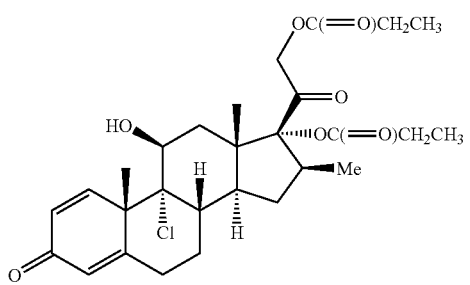
571
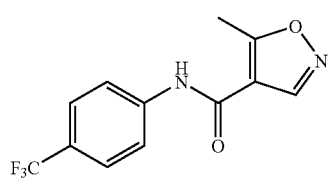
572
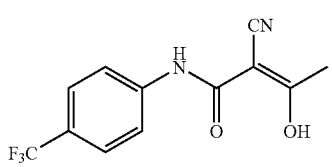
573
574
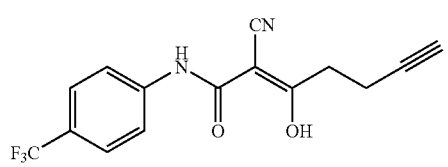
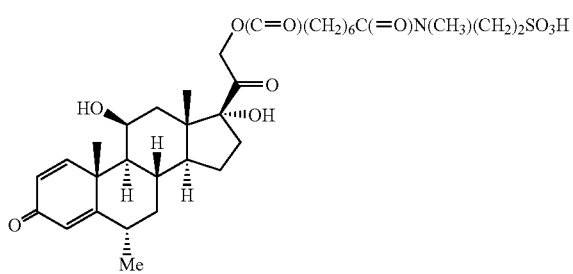
575

-continued
| 576 | 577 |
|---|---|
| 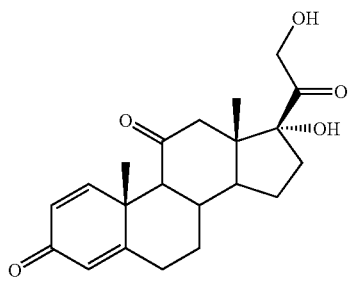 | 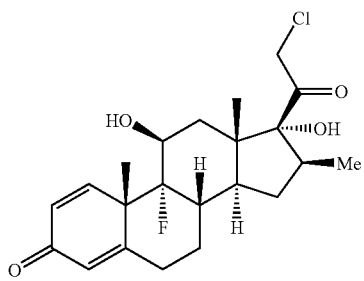 |
| 578 | 579 |
| 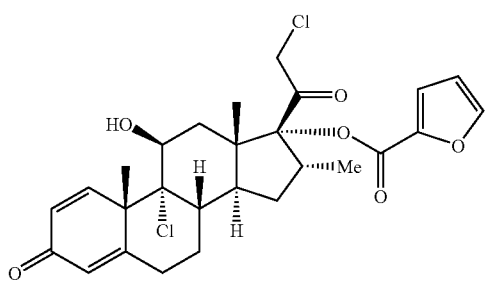 | 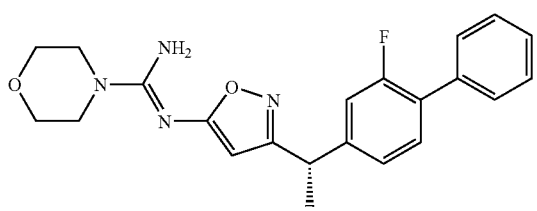 |
| 580 | 581 |
| 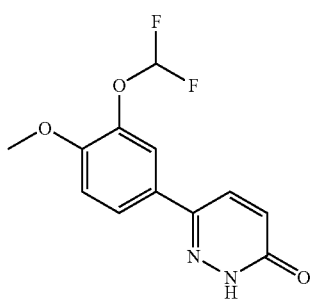 | 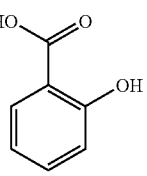 |
| 582 | 583 |
| 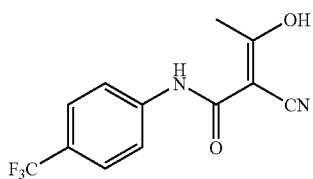 | 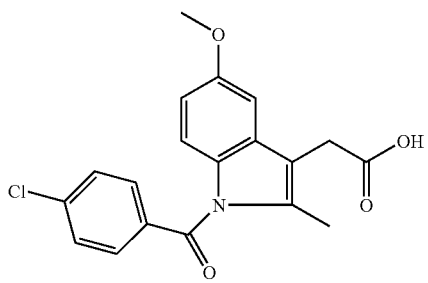 |
| 584 | 585 |
| 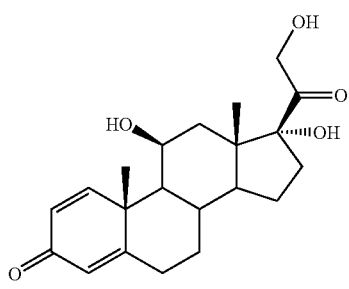 | 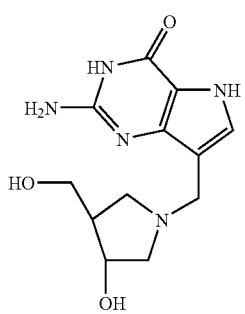 |

586 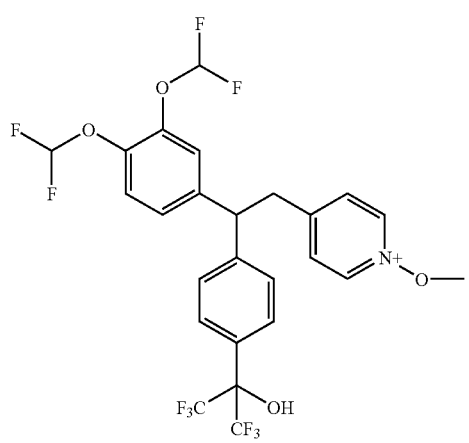
587 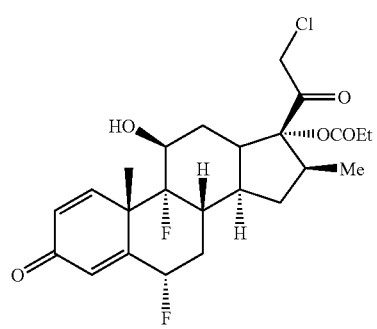
588 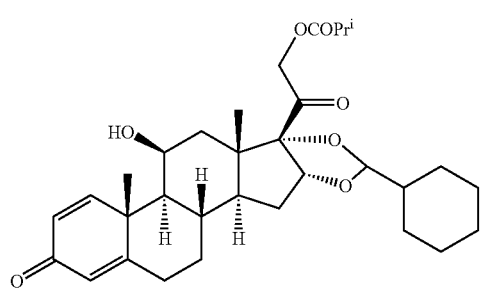
589 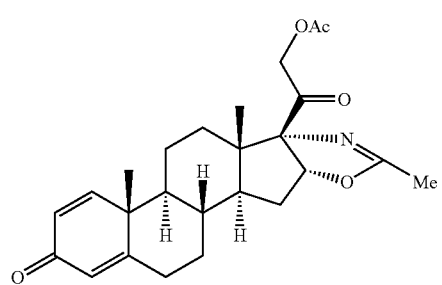
590 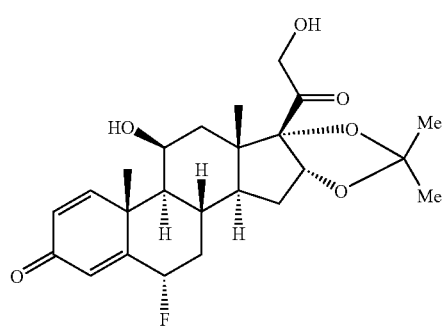
591 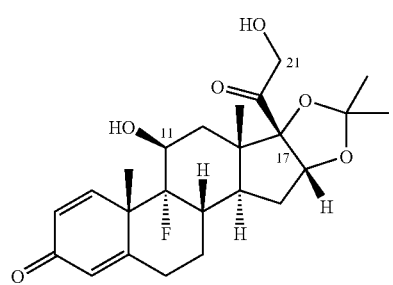
592 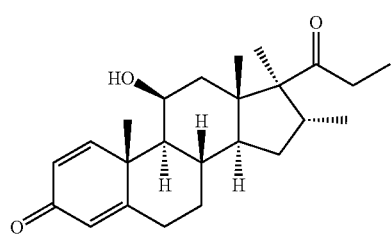
593 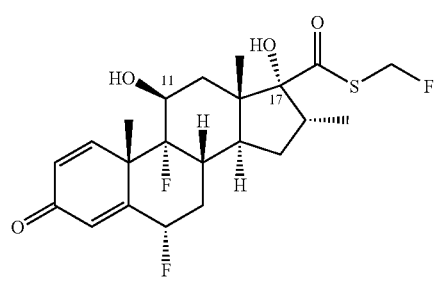

-continued
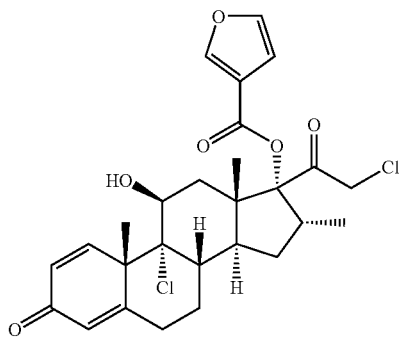
594
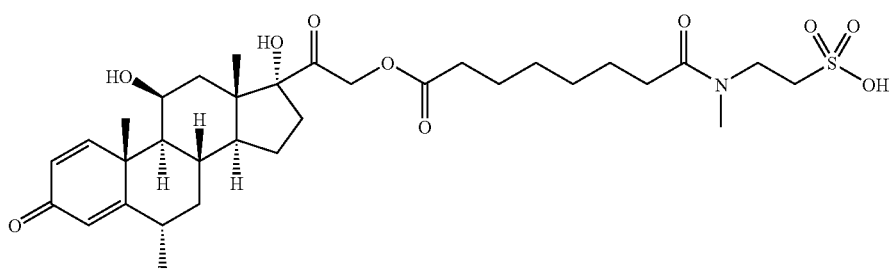
595
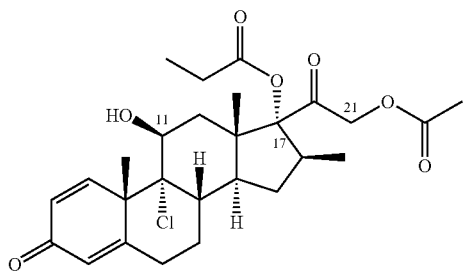
596
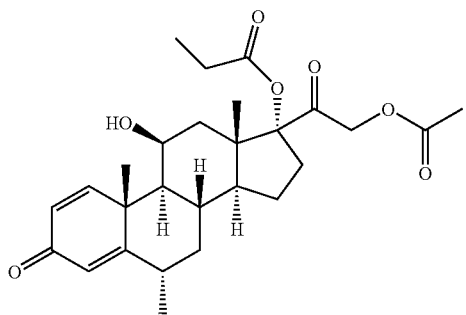
597
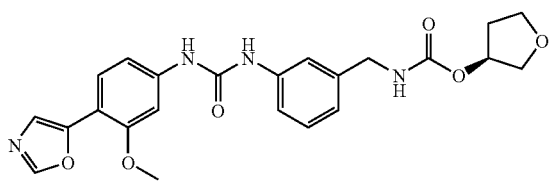
598
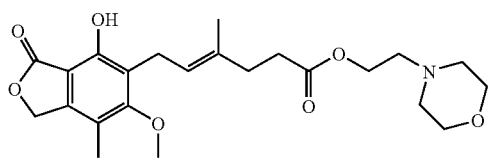
599
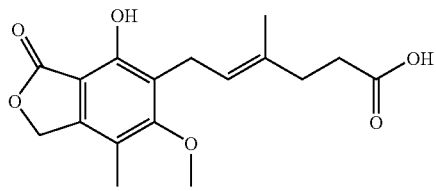
600
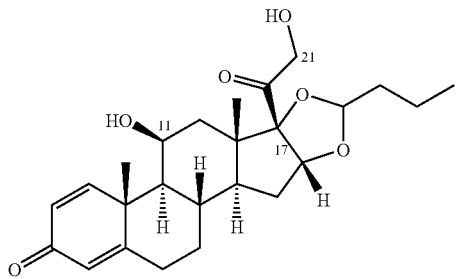
601

-continued
602
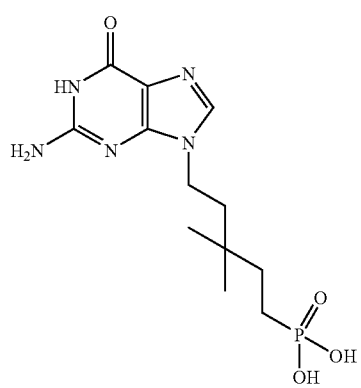
603
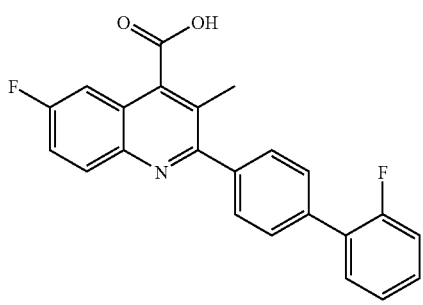
604
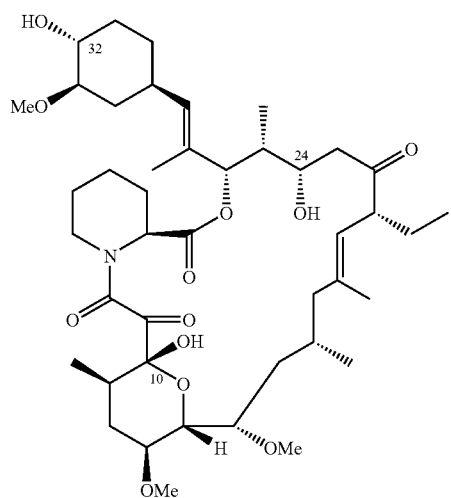
605
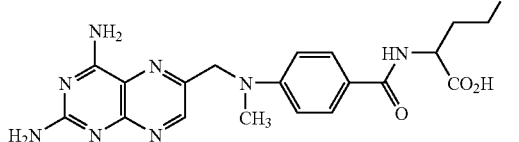
606
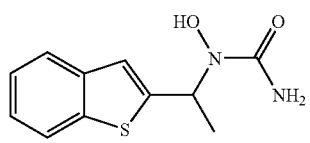
607
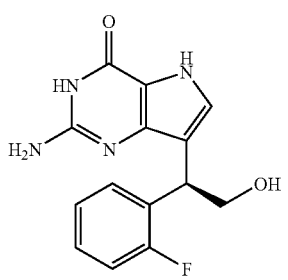
608
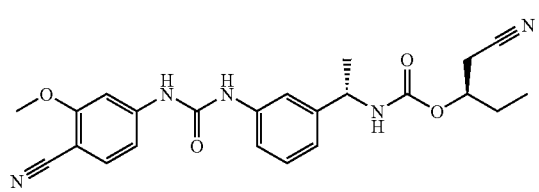
609
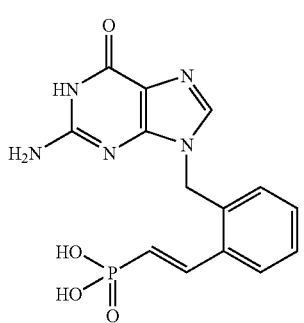

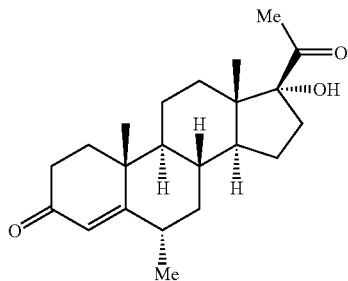
610

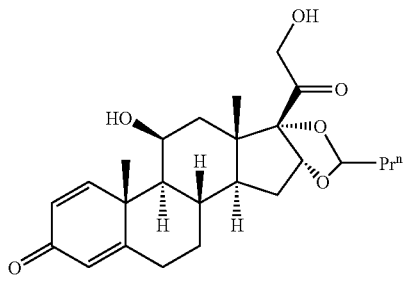
611 that is substituted with one or more groups $A^0$, wherein:
$A^0$ is $A^1$, $A^2$ or $W^3$, with the proviso that the conjugate includes at least one $A^1$;

$A^1$ is:

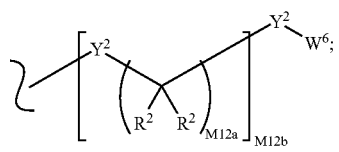

$A^2$ is:

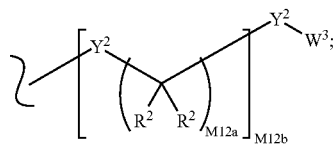

$A^3$ is:

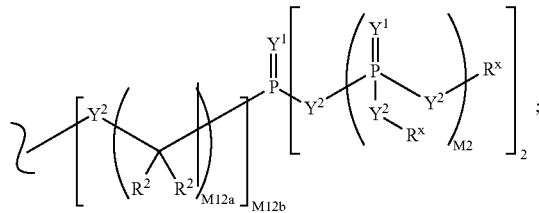

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$; and when $Y^2$ joins two phosphorous atoms $Y^2$ can also be $C(R^2)(R^2)$;

$R^x$ is independently H, $R^1$, $R^2$, $W^3$, a protecting group, or the formula:

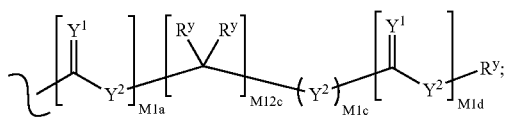

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $-C(Y^1)R^5$, $-C(Y^1)W^5$, $-SO_{M2}R^5$, or $-SO_{M2}W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1;
M12c is 0, 1, 2, 3, 4, 5, 6, 7, 8, 9, 10, 11 or 12;
$X^{66}$ is hydrogen or fluorine; and
$X^{67}$ is hydrogen, hydroxy, or acyloxy.

In another embodiment the invention provides a compound of the invention which is a compound of the formula:

[DRUG]-$(A^0)_{nn}$ or a pharmaceutically acceptable salt thereof wherein,
DRUG is a compound of any one of formulae 500-611:
nn is 1, 2, or 3;
$A^0$ is $A^1$, $A^2$ or $W^3$ with the proviso that the compound includes at least one $A^1$;

$A^1$ is:

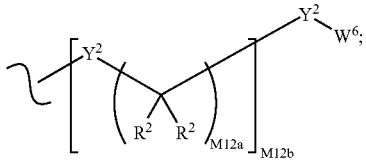

-continued

A² is:

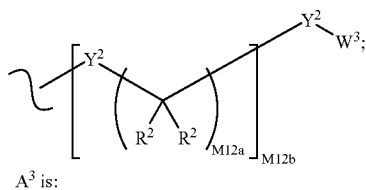

A³ is:

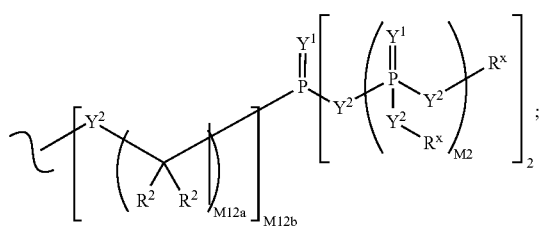

Y¹ is independently O, S, N(R$^x$), N(O)(R$^x$), N(OR$^x$), N(O)(OR$^x$), or N(N(R$^x$)(R$^x$));

Y² is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;

R$^x$ is independently H, R¹, W³, a protecting group, or the formula:

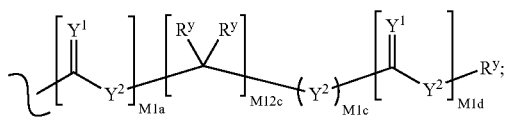

wherein:
R$^y$ is independently H, W³, R² or a protecting group;
R¹ is independently H or alkyl of 1 to 18 carbon atoms;

R² is independently H, R¹, R³ or R⁴ wherein each R⁴ is independently substituted with 0 to 3 R³ groups or taken together at a carbon atom, two R² groups form a ring of 3 to 8 carbons and the ring may be substituted with 0 to 3 R³ groups;

R³ is R$^{3a}$, R$^{3b}$, R$^{3c}$ or R$^{3d}$, provided that when R³ is bound to a heteroatom, then R³ is R$^{3c}$ or R$^{3d}$;

R$^{3a}$ is F, Cl, Br, I, —CN, N$_3$ or —NO$_2$;

R$^{3b}$ is Y¹;

R$^{3c}$ is —R$^x$, —N(R$^x$)(R$^x$), —SR$^x$, —S(O)R$^x$, —S(O)$_2$R$^x$, —S(O)(OR$^x$), —S(O)$_2$(OR$^x$), —OC(Y¹)R$^x$, —OC(Y¹)OR$^x$, —OC(Y¹)(N(R$^x$)(R$^x$)), —SC(Y¹)R$^x$, —SC(Y¹)OR$^x$, —SC(Y¹)(N(R$^x$)(R$^x$)), —N(R$^x$)C(Y¹)R$^x$, —N(R$^x$)C(Y¹)OR$^x$, or —N(R$^x$)C(Y¹)(N(R$^x$)R$^x$));

R$^{3d}$ is —C(Y¹)R$^x$, —C(Y¹)OR$^x$ or —C(Y¹)(N(R$^x$)(R$^x$));

R⁴ is an alkyl of 1 to 18 carbon atoms, alkenyl of 2 to 18 carbon atoms, or alkynyl of 2 to 18 carbon atoms;

R⁵ is R⁴ wherein each R⁴ is substituted with 0 to 3 R³ groups;

R$^{5a}$, is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 R³ groups;

W³ is W⁴ or W⁵;

W⁴ is R⁵, —C(Y¹)R⁵, —C(Y¹)W⁵, —SO$_2$R⁵, or —SO$_2$W⁵;

W⁵ is carbocycle or heterocycle wherein W⁵ is independently substituted with 0 to 3 R² groups;

W⁶ is W³ independently substituted with 1, 2, or 3 A³ groups;

M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1;
M12c is 0, 1, 2, 3, 4, 5, 6, 7, 8, 9, 10, 11 or 12;
X$^{66}$ is hydrogen or fluorine; and
X$^{67}$ is hydrogen, hydroxy, or acyloxy.

In another embodiment the invention provides a compound of the invention which is a compound of any one of formulae 1-296:

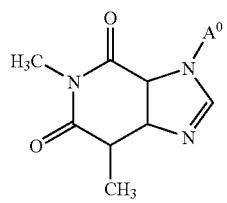

1

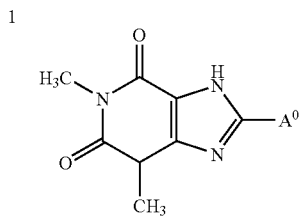

2

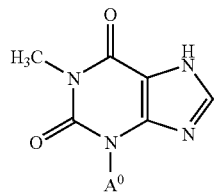

3

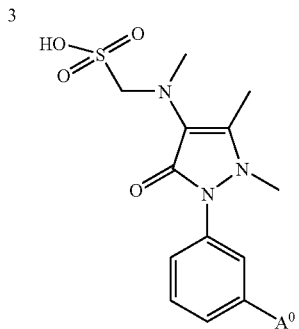

4

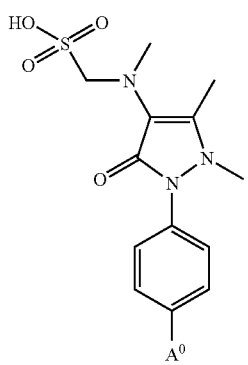
5
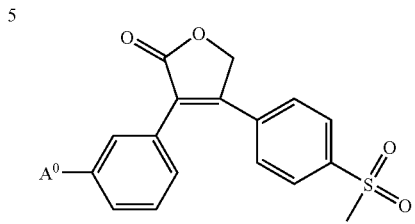
6
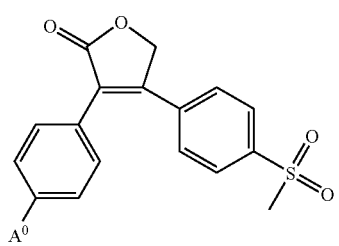
7
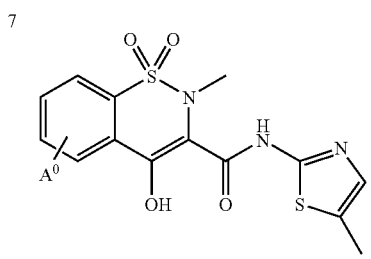
8
9
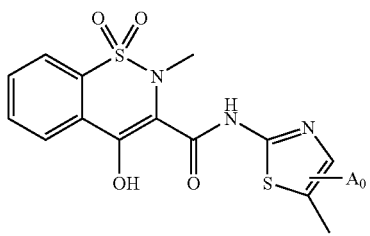
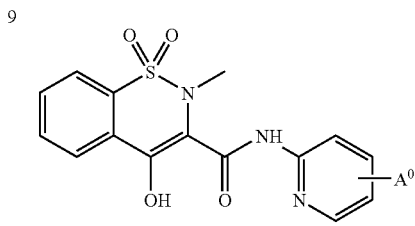
10
11
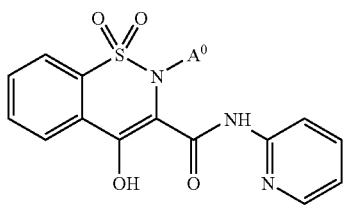
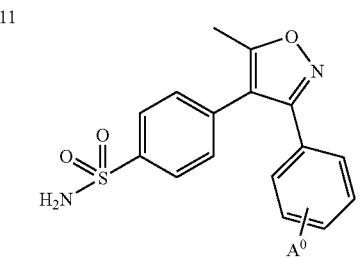
12
13
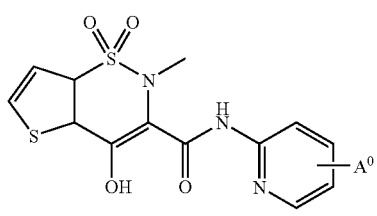
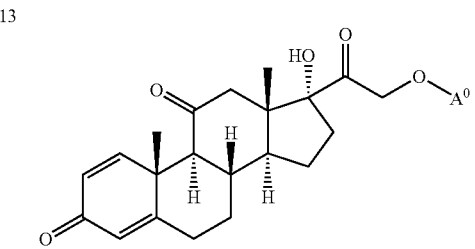
14

-continued
15
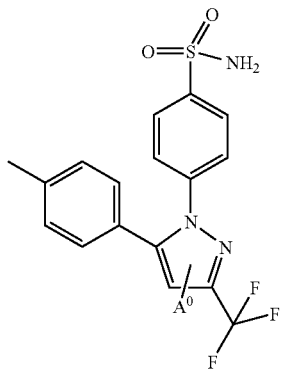
16
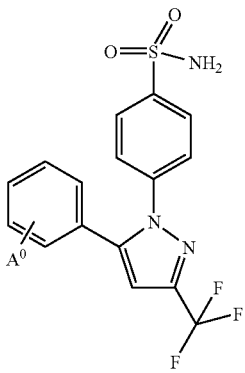
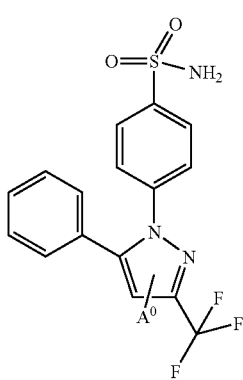
17
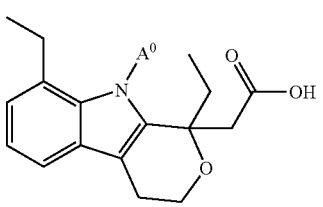
18
19
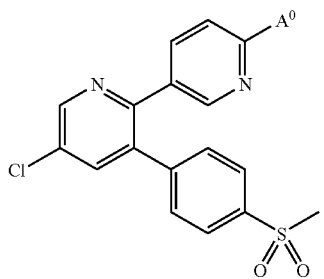
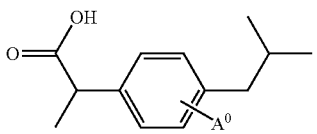
20
21
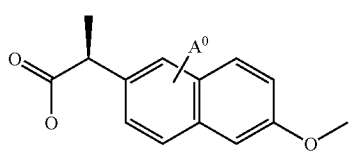
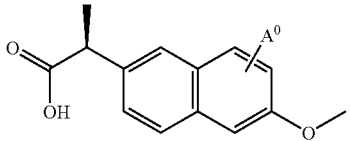
22
23
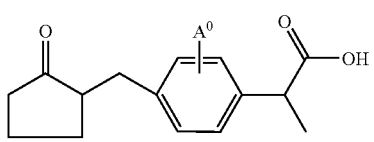
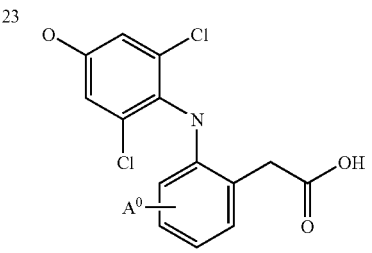
24

-continued
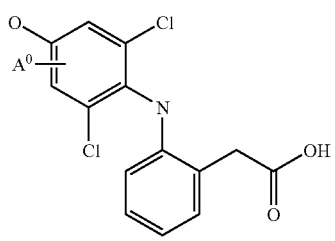
25
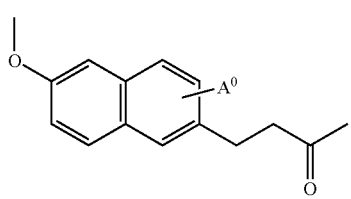
26
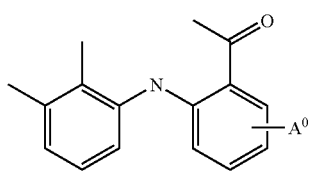
27
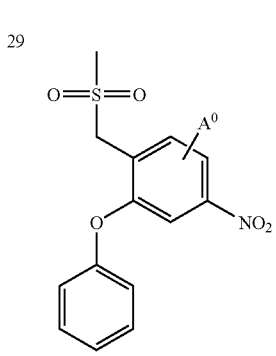
28
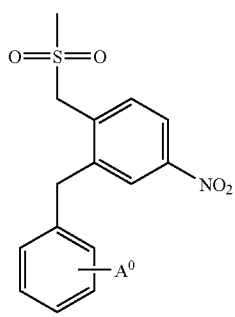
29
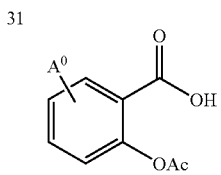
30
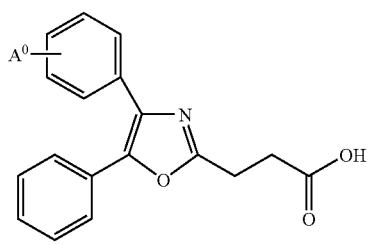
31
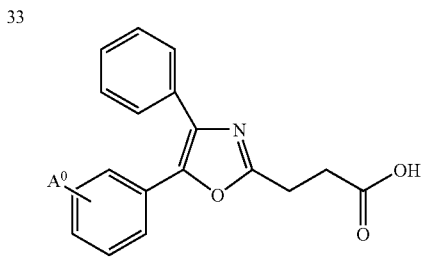
32
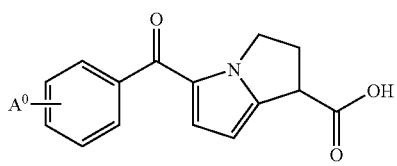
33
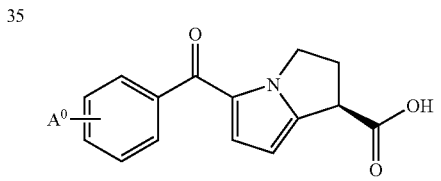
34
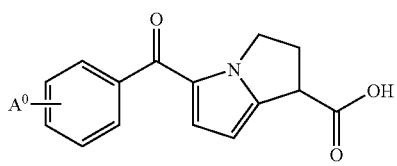
35
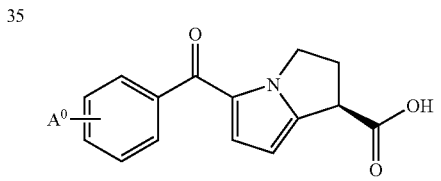
36

-continued
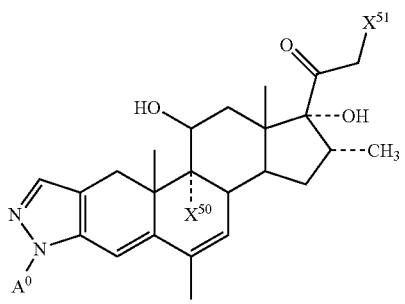 37
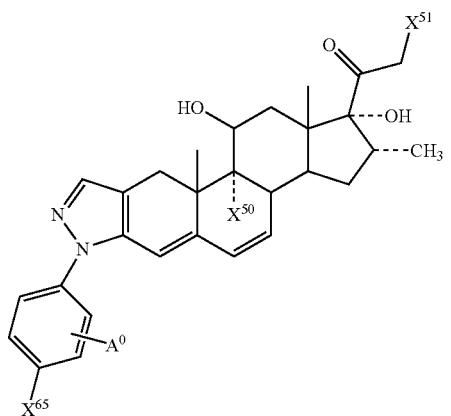 38
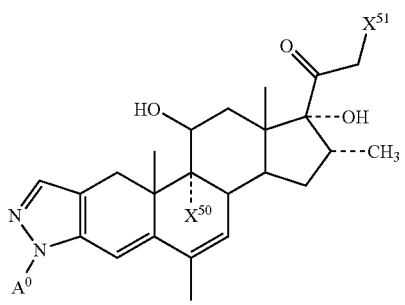 39
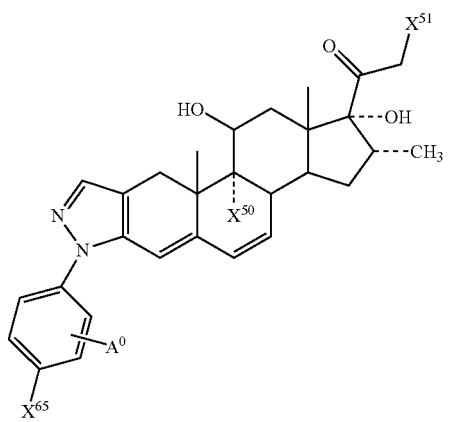 40
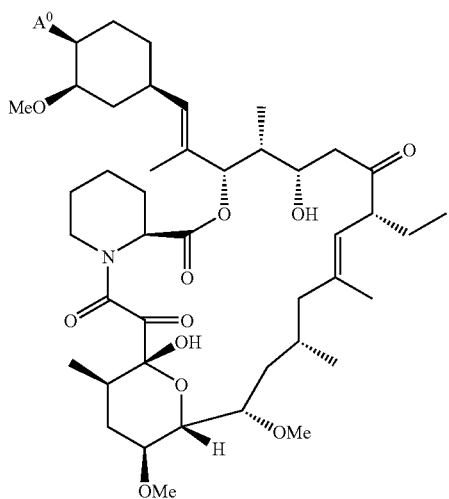 41
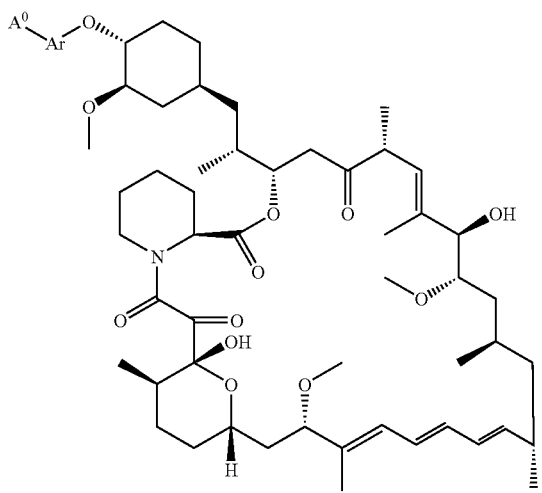 42

-continued
43
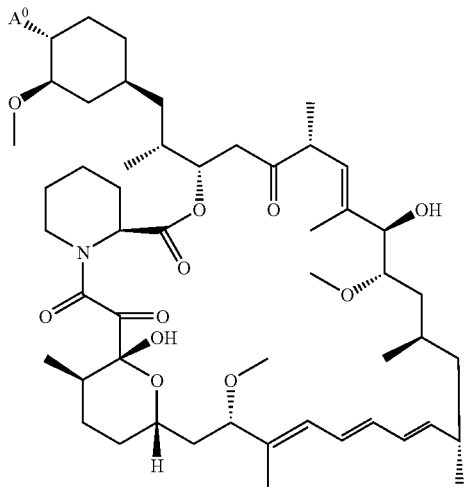
44
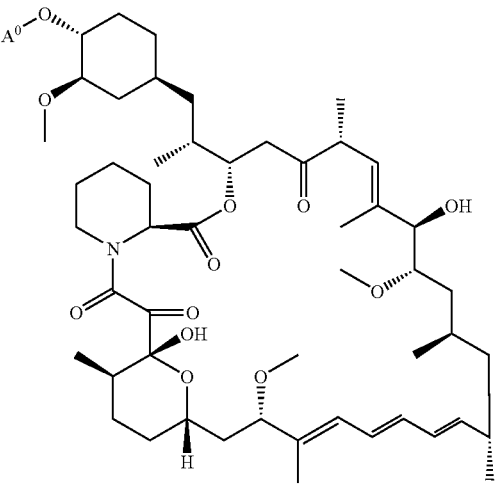
45
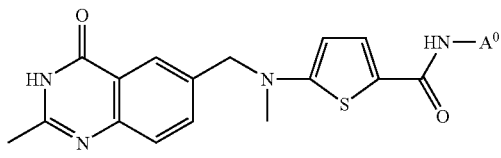
46
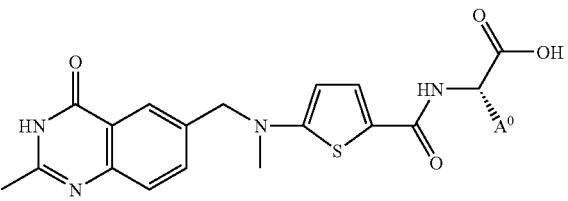
47
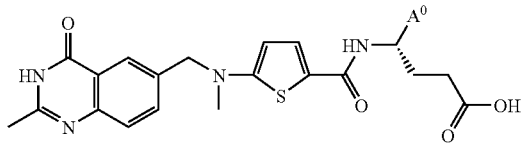
48
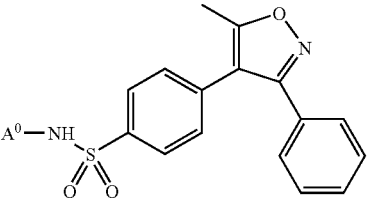
49
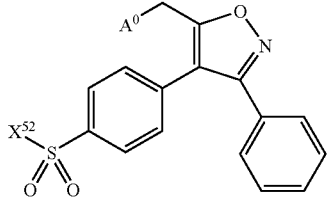
50
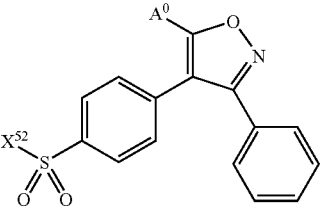
51
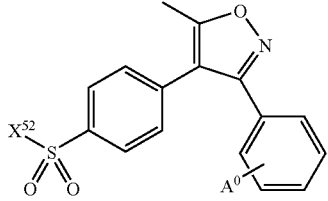
52
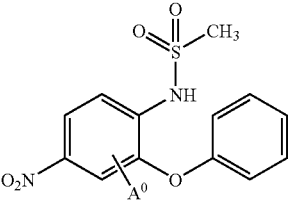
53
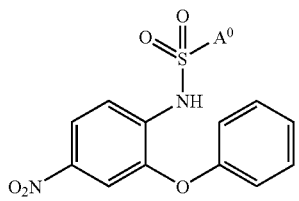
54
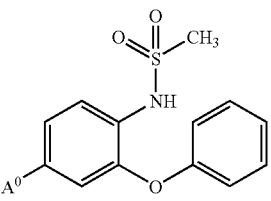

-continued
55
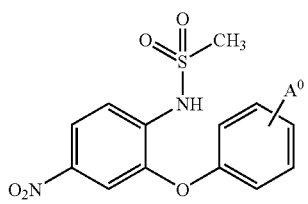
56
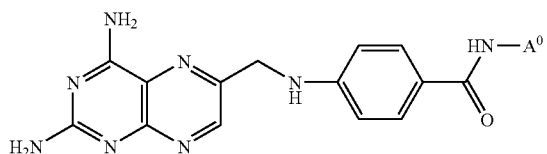
57
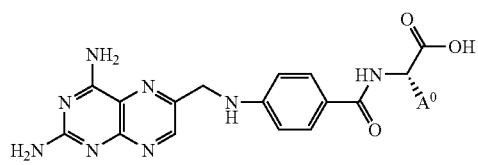
58
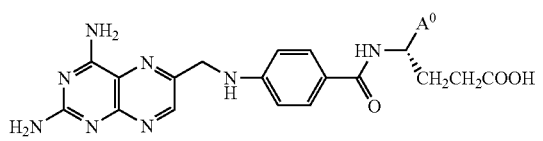
59
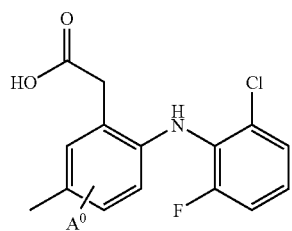
60
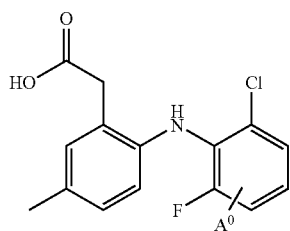
61
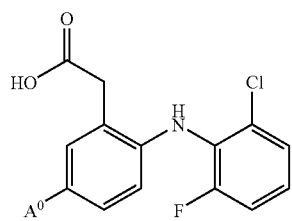
62
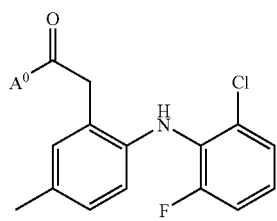
63
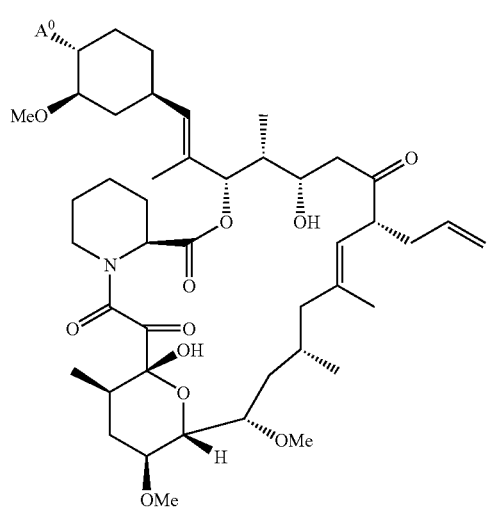
64
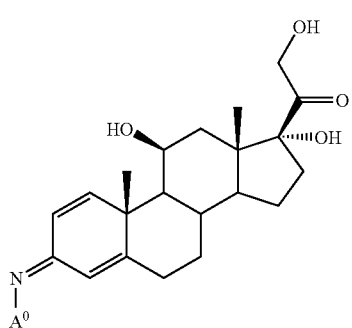

-continued
65
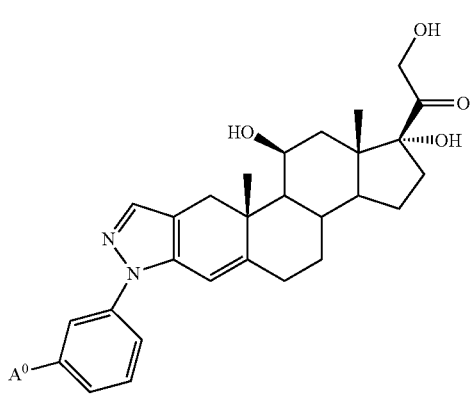
66
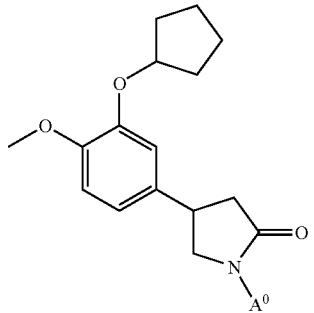
67
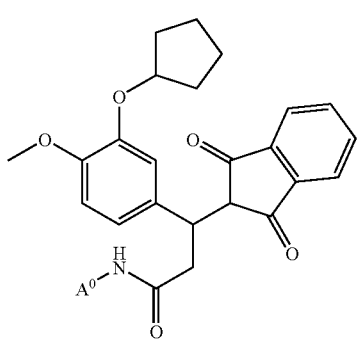
68
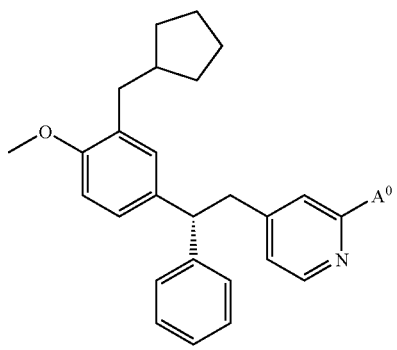
69
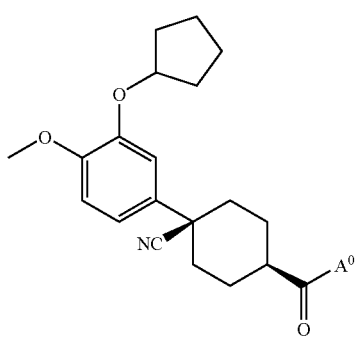
70
71
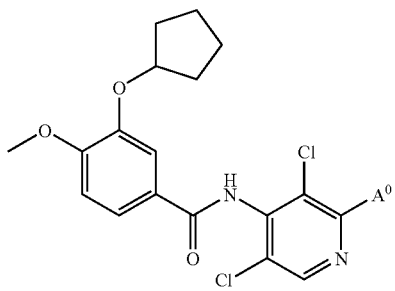
72
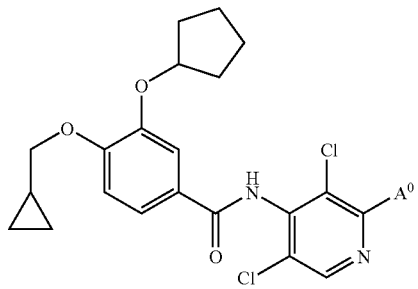

-continued
73
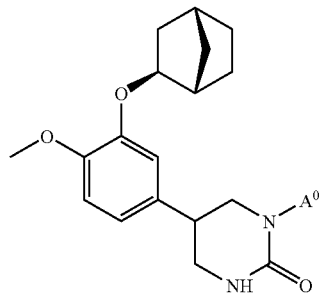
74
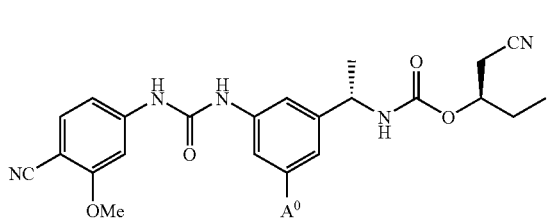
75
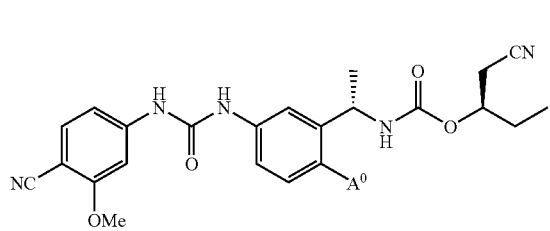
76
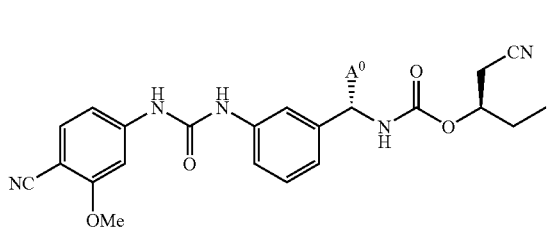
77
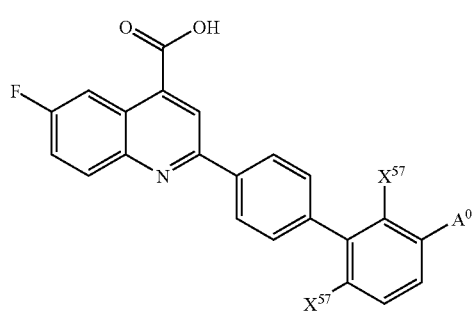
78
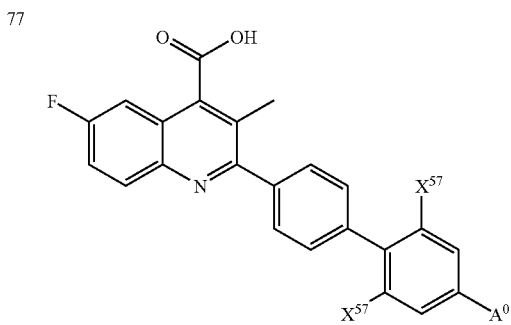
79
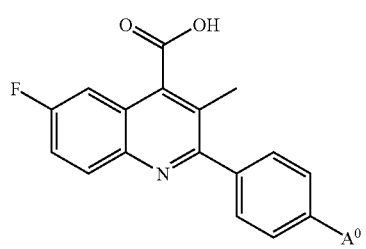
80
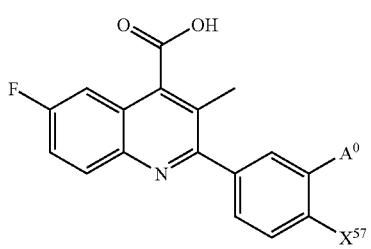
81
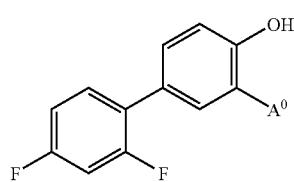
82
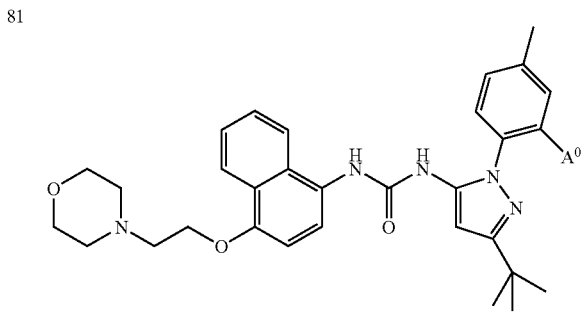

83
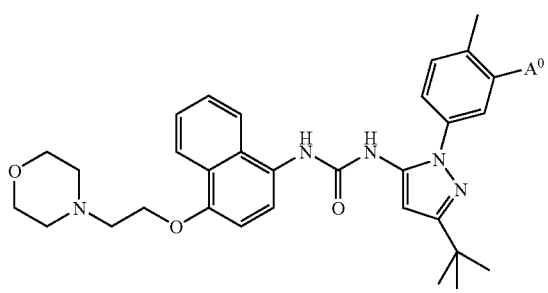
84
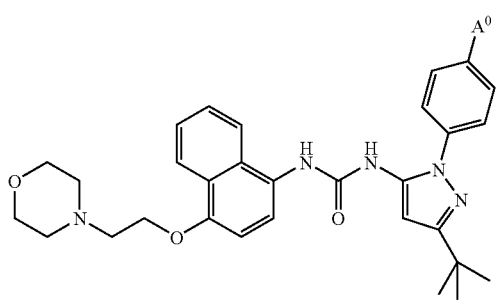
85
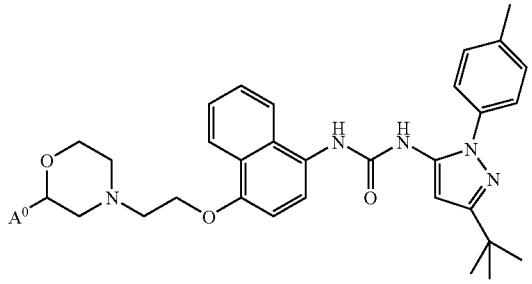
86
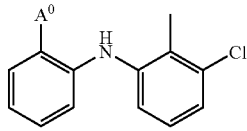
87
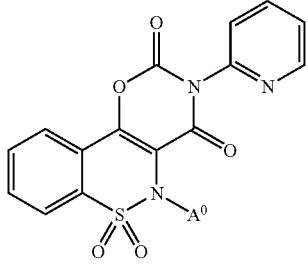
88
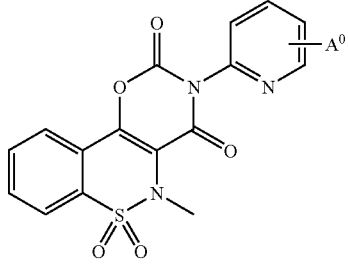
89
90
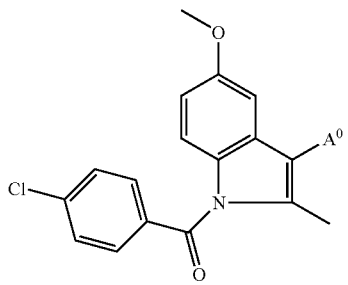
91
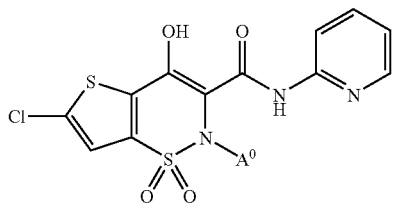
92
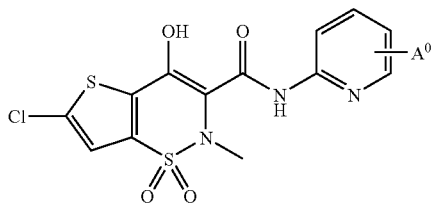
93
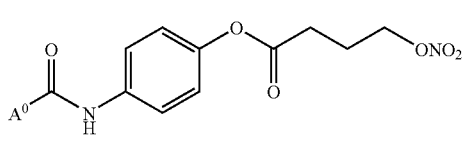
94
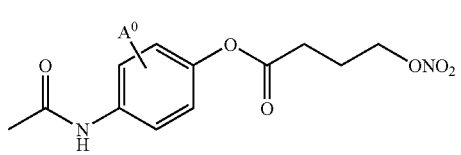

-continued
95
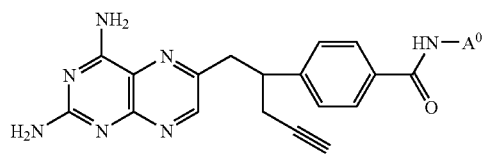
96
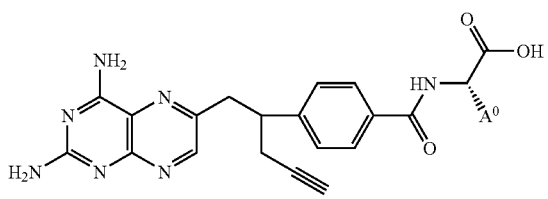
97
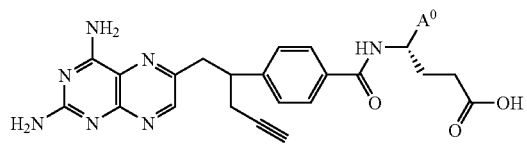
98
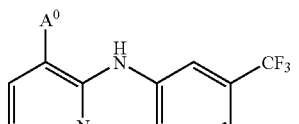
99
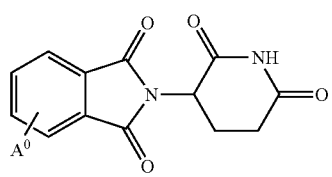
100
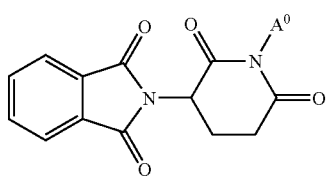
101
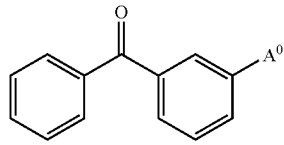
102
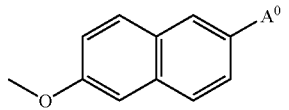
103
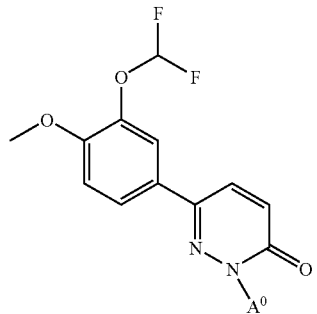
104
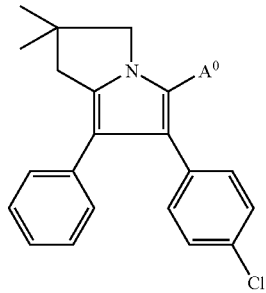
105
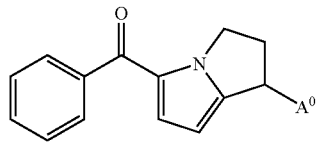
106
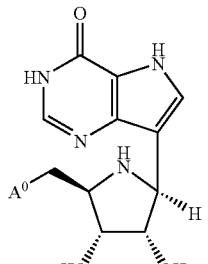
or
107
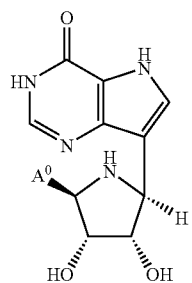
108
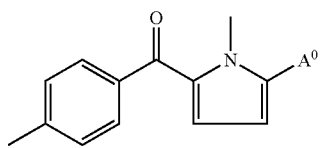

-continued
108 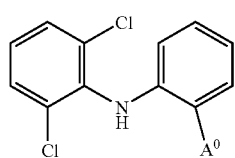 109 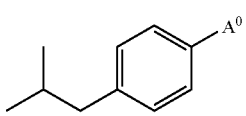 110
111 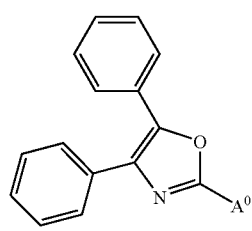 112 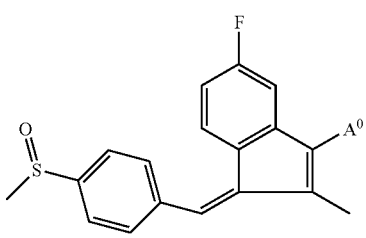
113 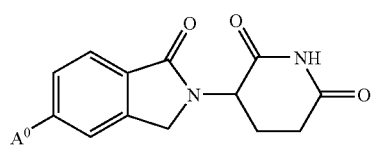 114 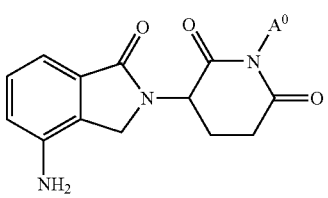
115 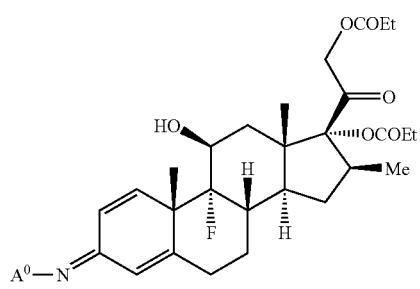 116 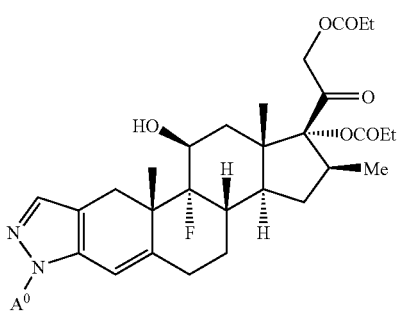
117 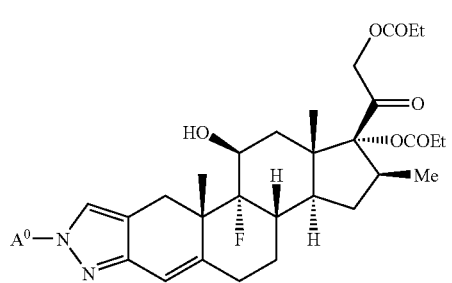 118 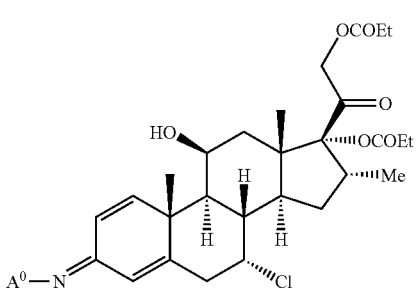
119 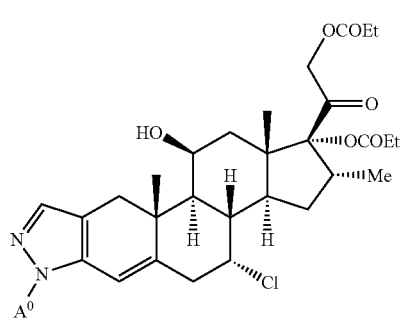 120 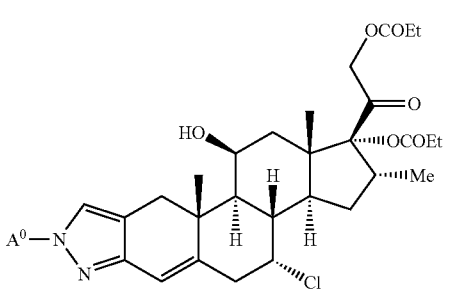

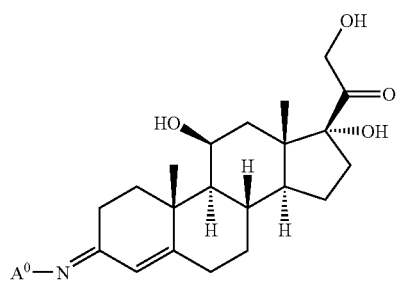
121
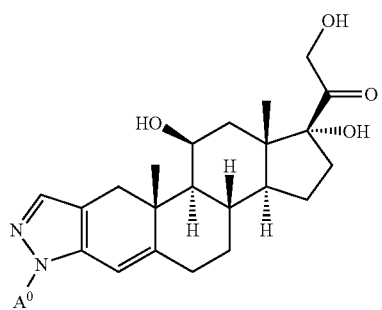
122
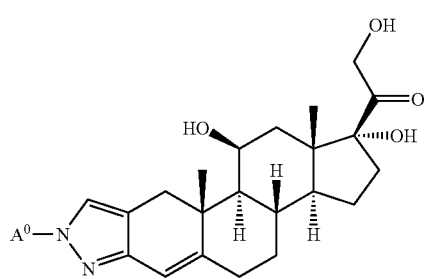
123
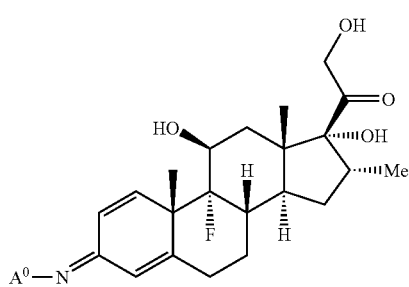
124
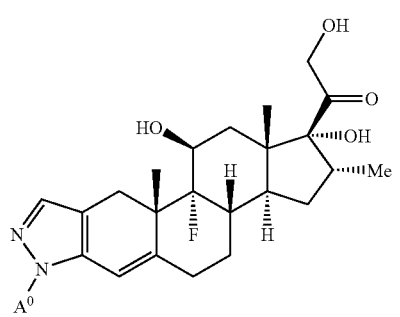
125
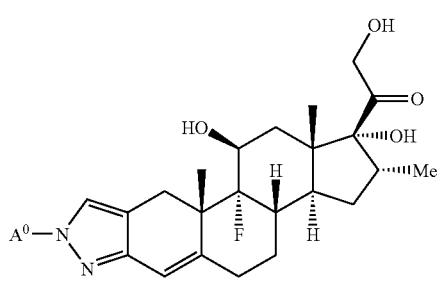
126
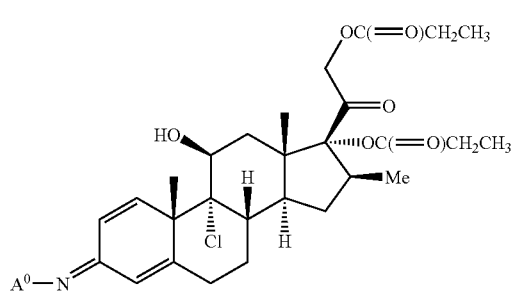
127
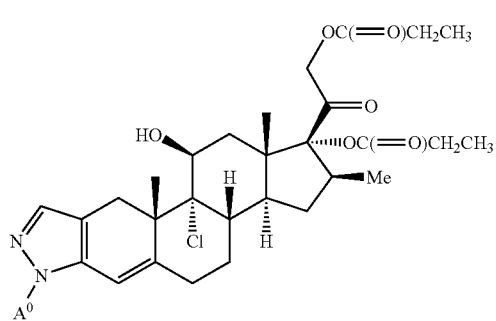
128
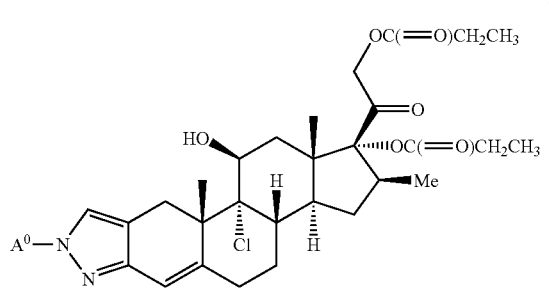
129
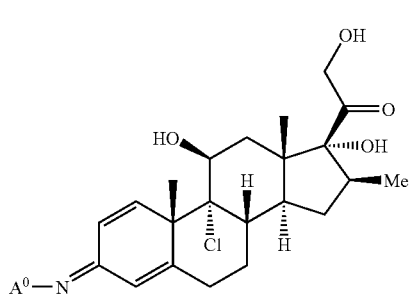
130

-continued
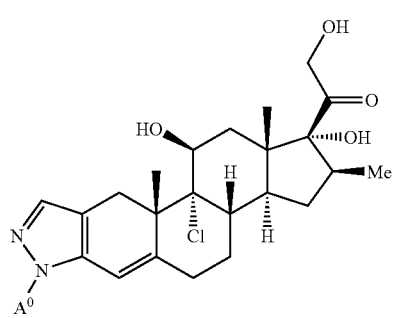 131
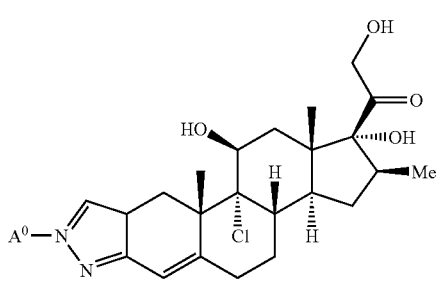 132
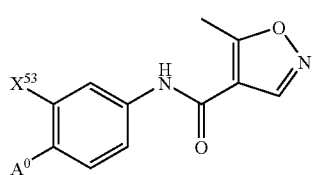 133
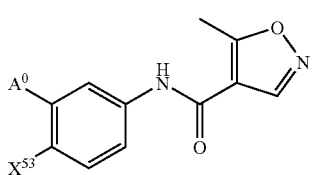 134
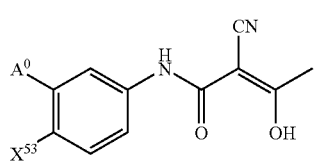 135
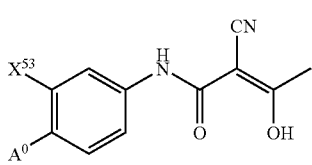 136
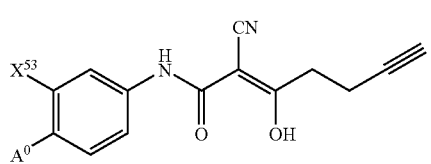 137
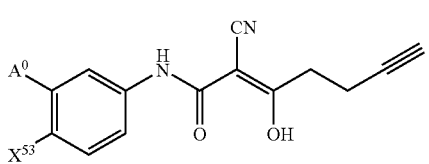 138
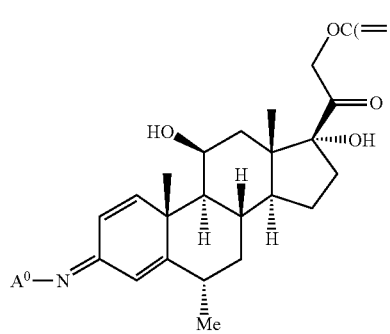 139
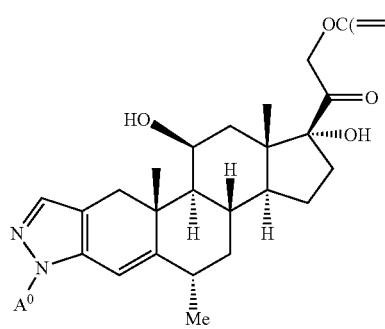 140

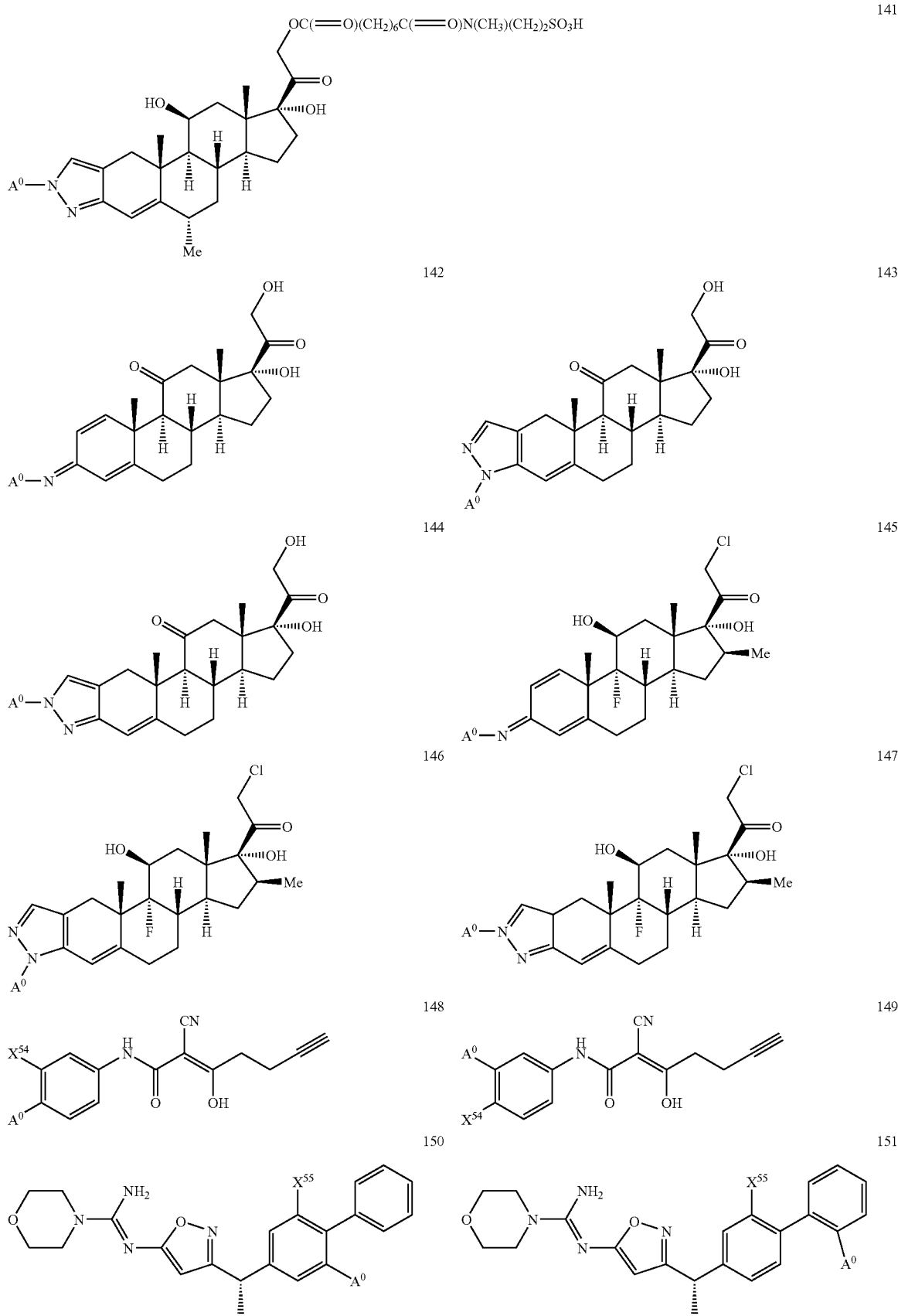

152 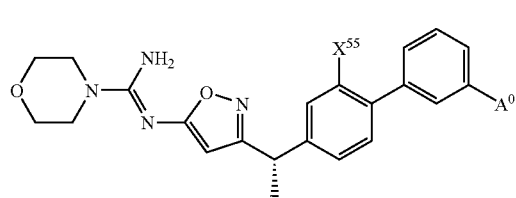
153 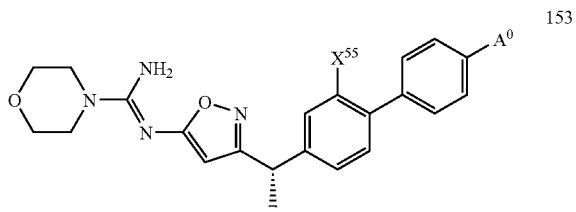
154 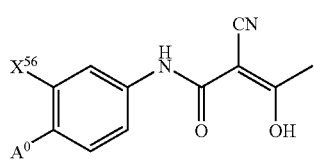
155 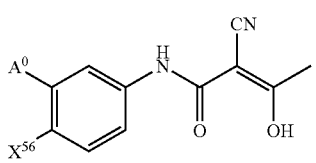
156 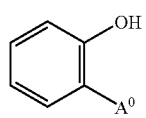
157 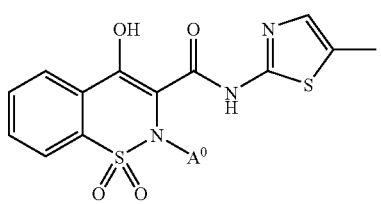
158 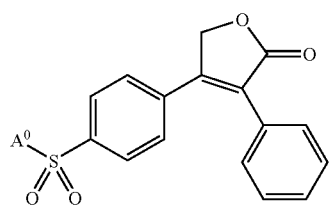
159 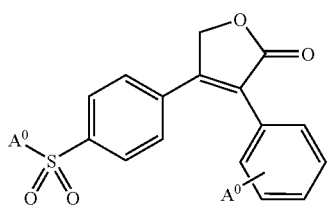
160 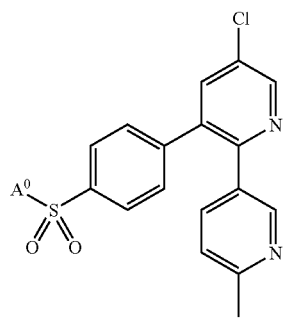
161 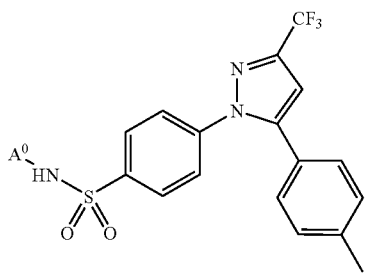
162 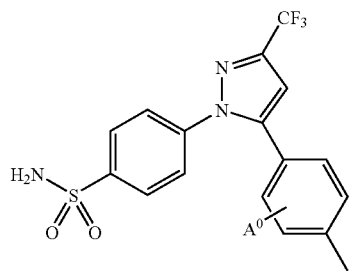
163 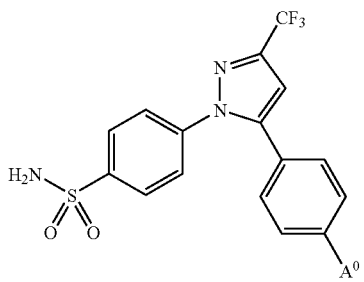

-continued
164
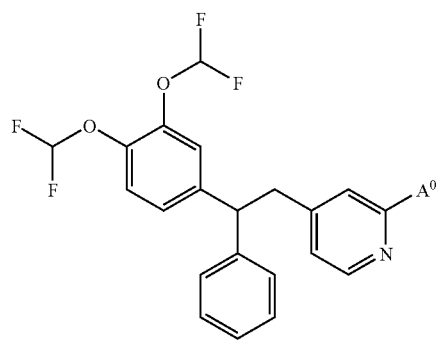
165
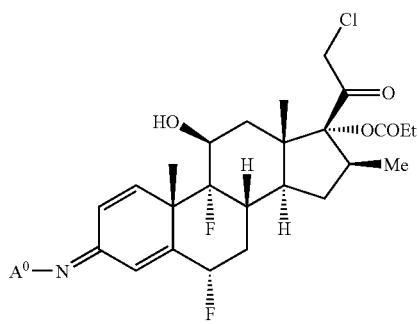
166
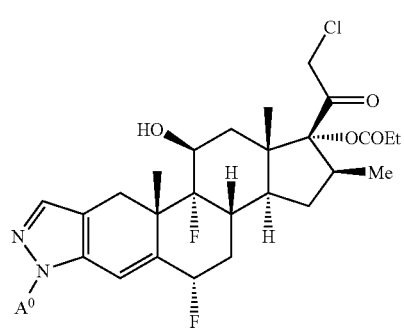
167
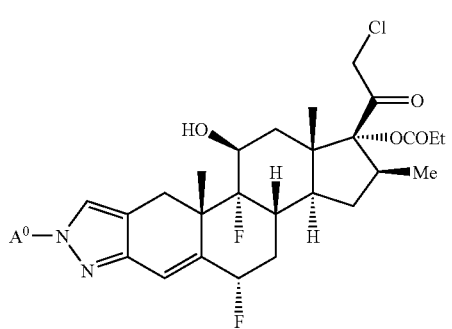
168
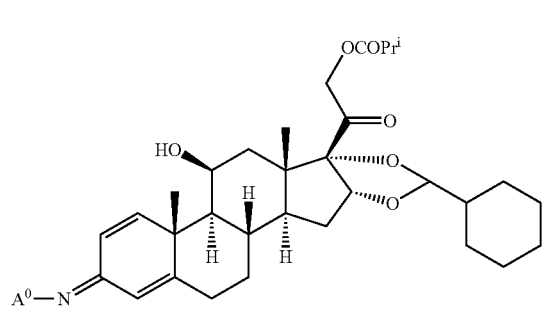
169
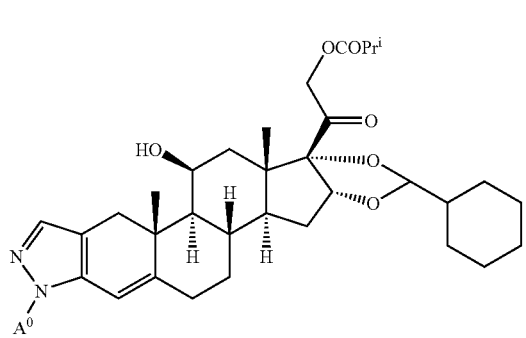
170
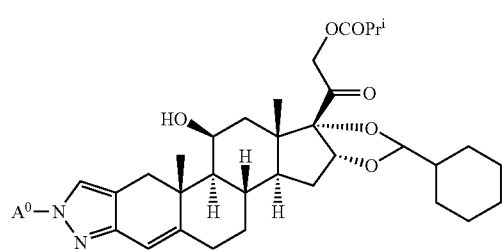
171
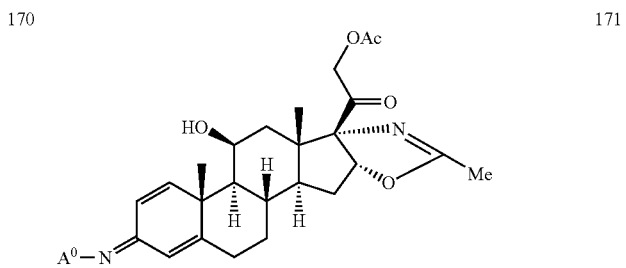
172
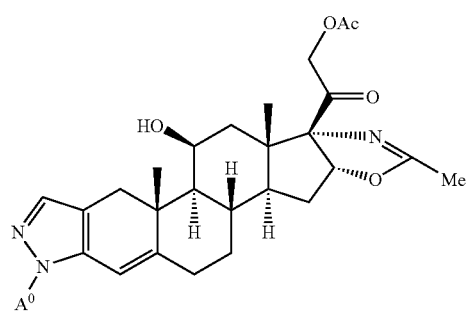
173
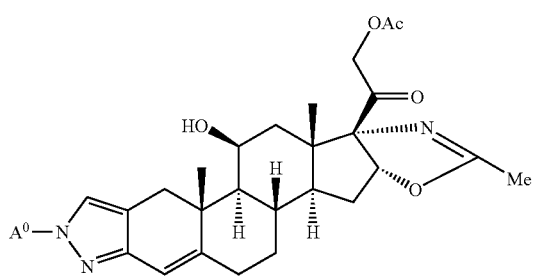

-continued
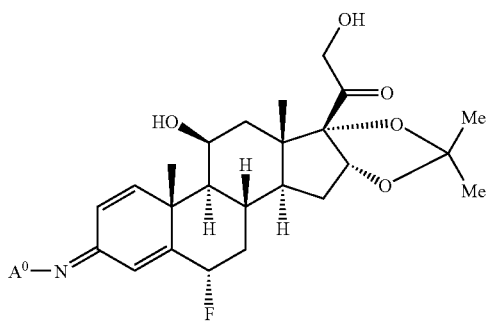 174
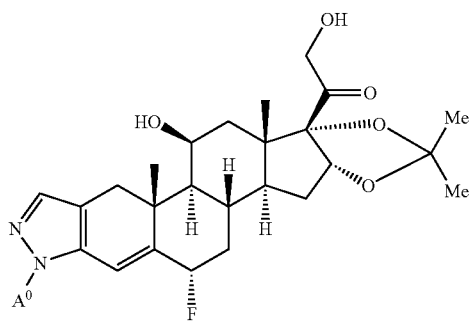 175
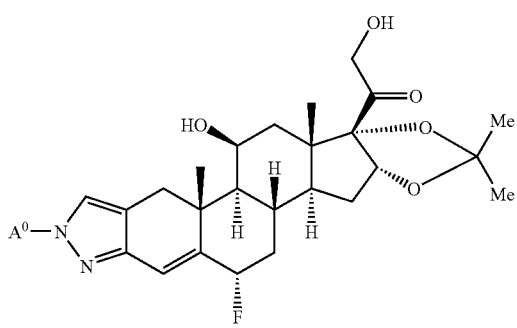 176
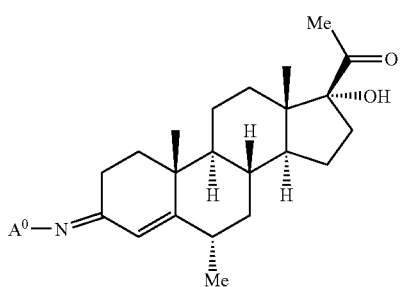 177
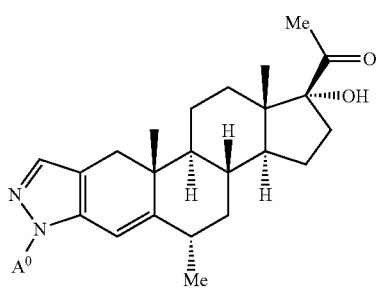 178
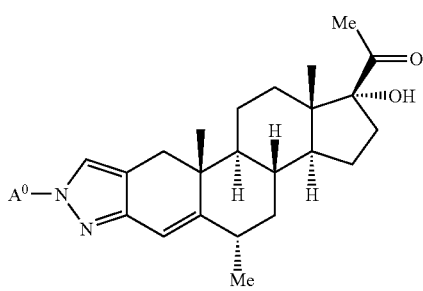 179
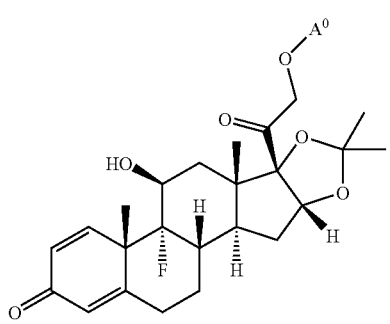 180
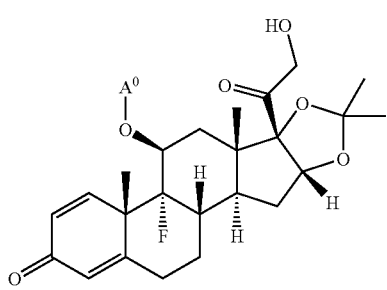 181
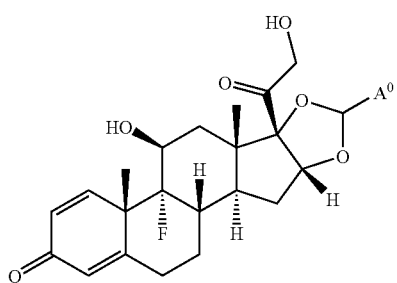 182
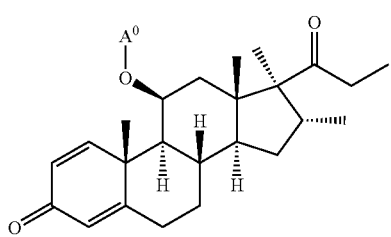 183

-continued
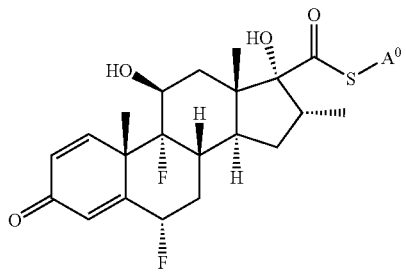
184
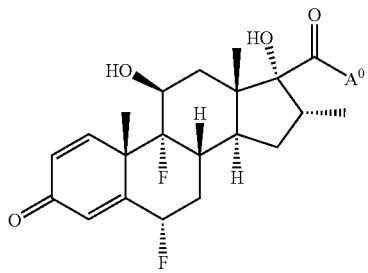
185
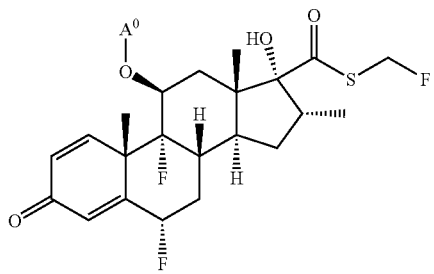
186
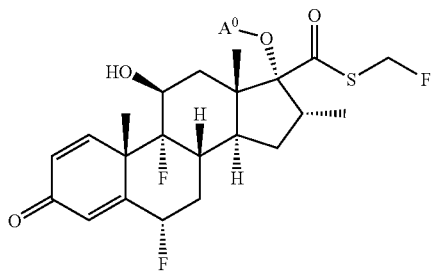
187
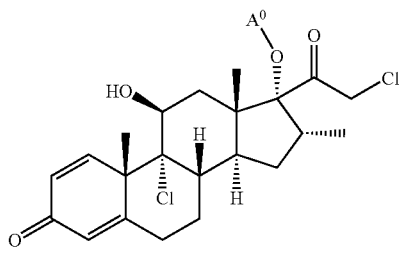
188
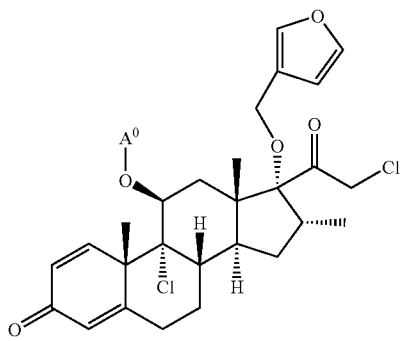
189
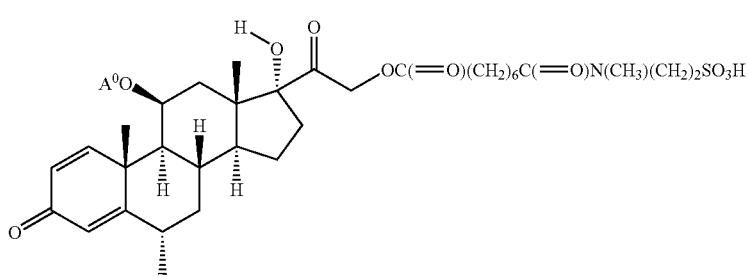
190
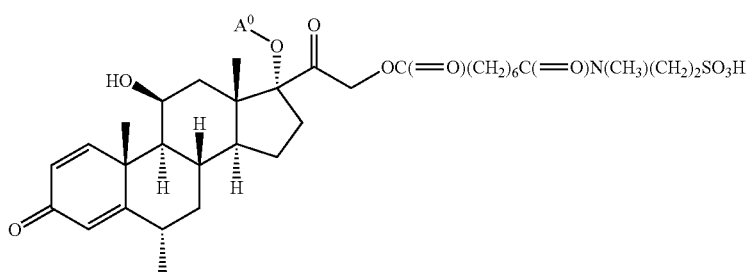
191

-continued
| | |
|---|---|
| 192 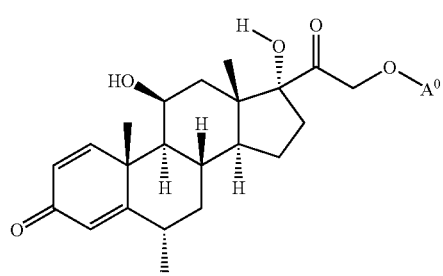 | 193 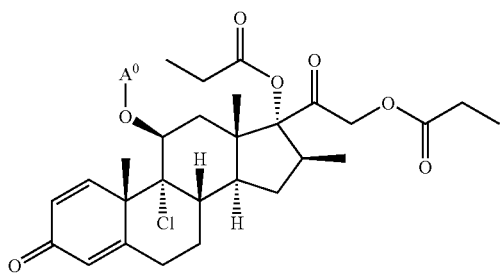 |
| 194 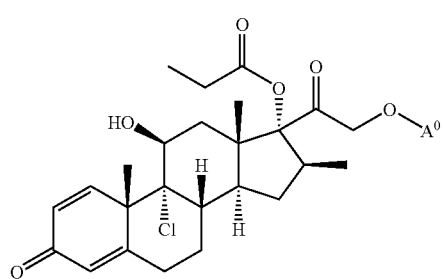 | 195 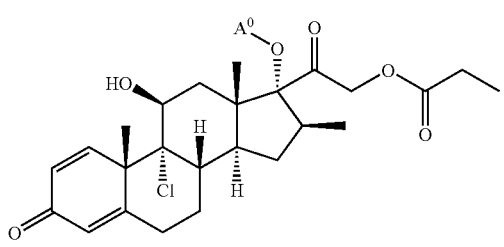 |
| 196 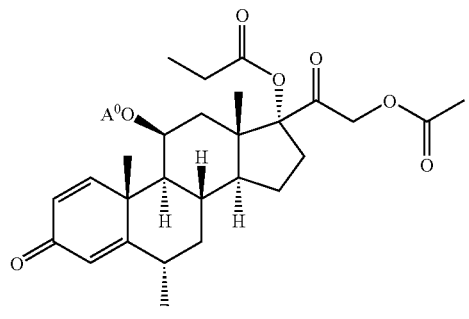 | 197 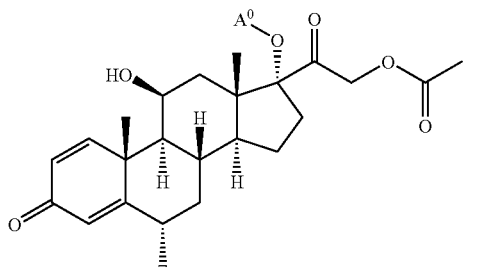 |
| 198 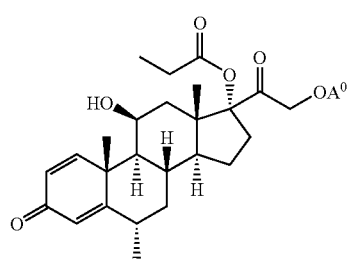 | 199 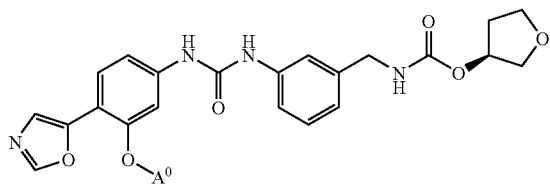 |
| 200 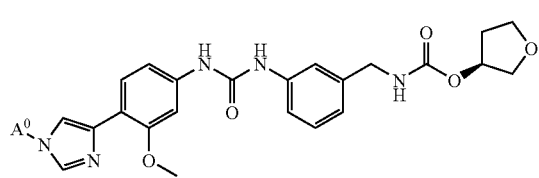 | 201 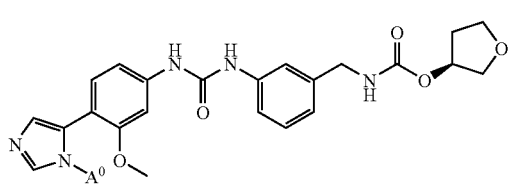 |
| 202 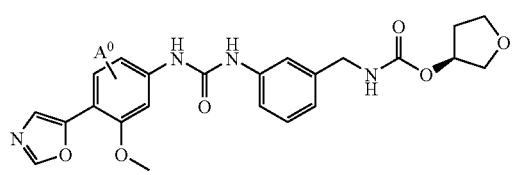 | 203 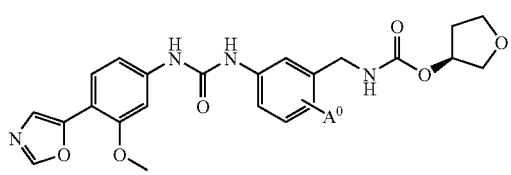 |

-continued
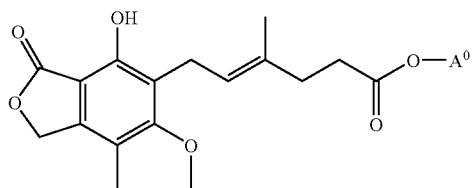
204
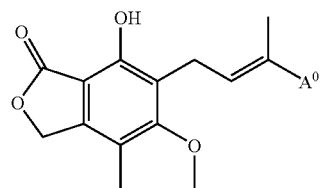
205
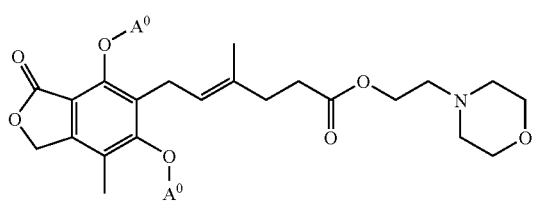
206
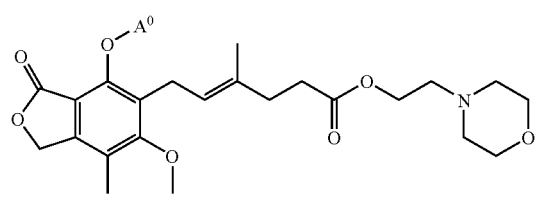
207
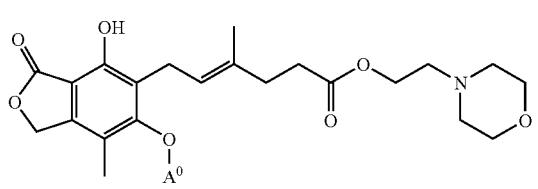
208
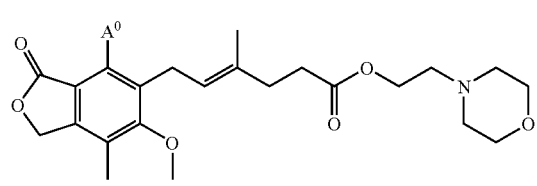
209
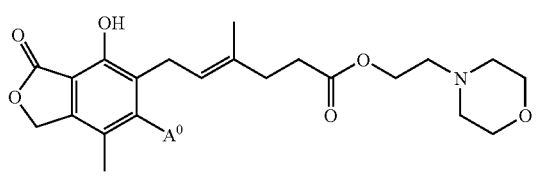
210
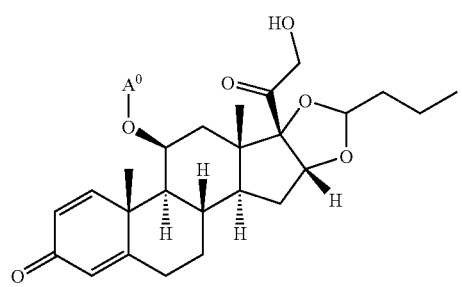
211
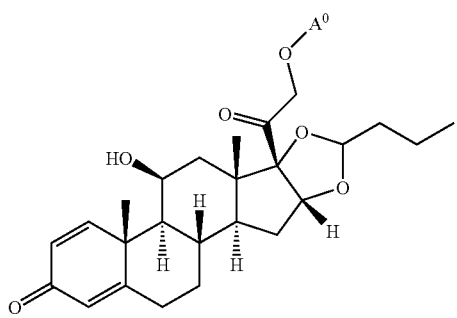
212
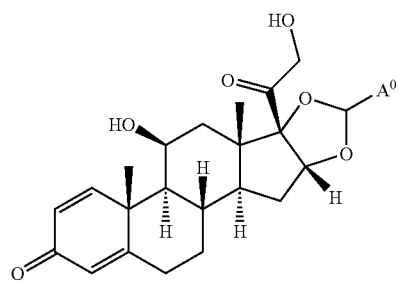
213
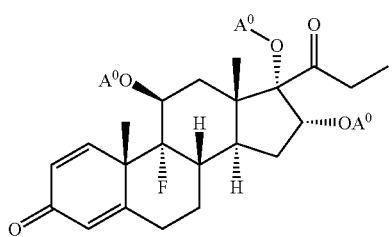
214
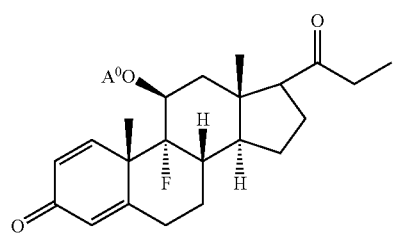
215

-continued
216 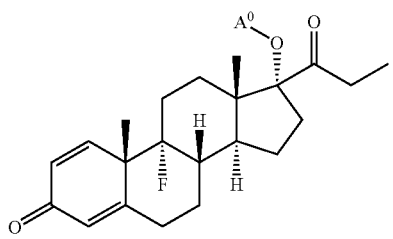 217 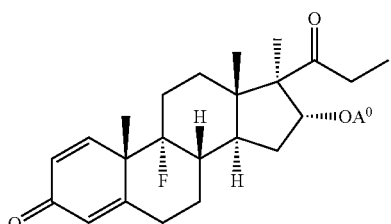
218 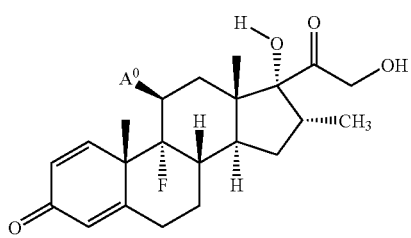 219 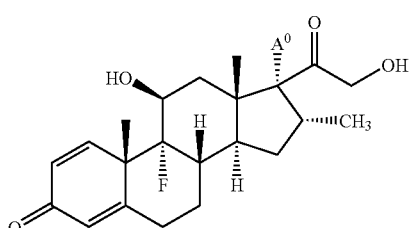
220 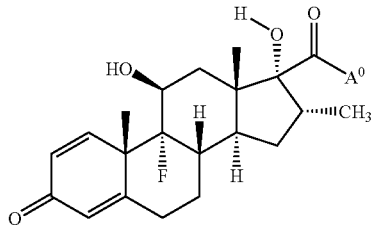 221 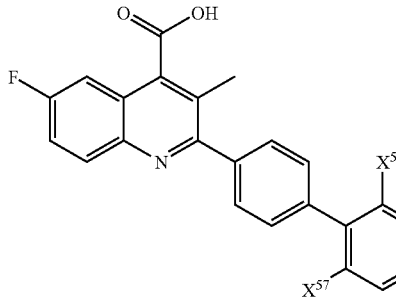
222 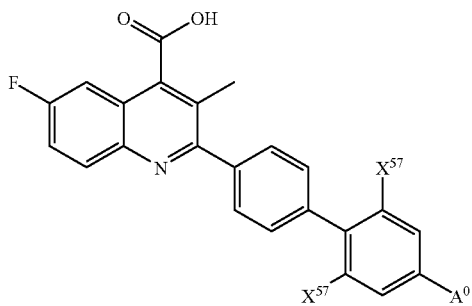 223 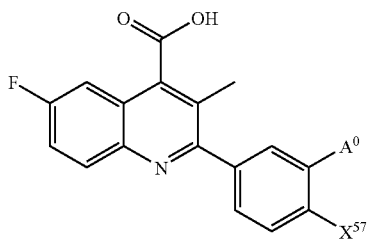
224 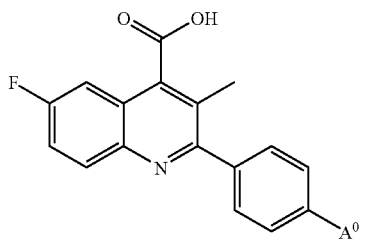 225 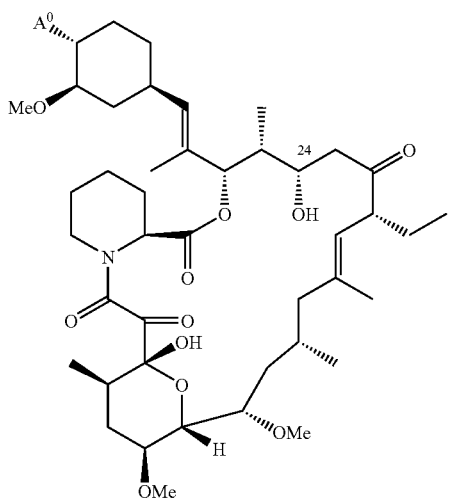

-continued
226 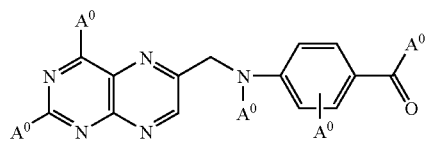
227 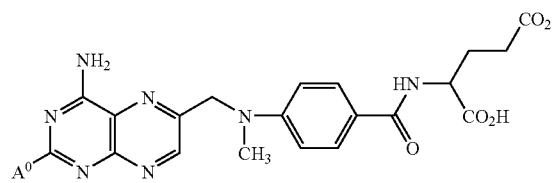
228 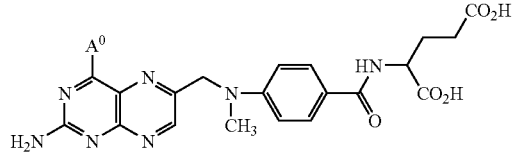
229 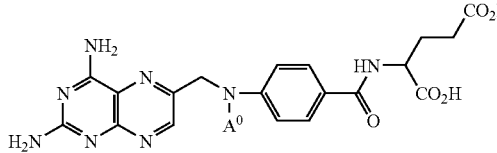
230 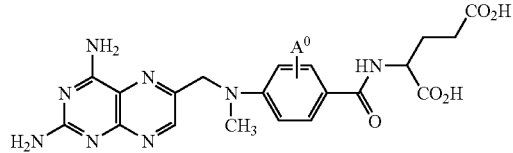
231 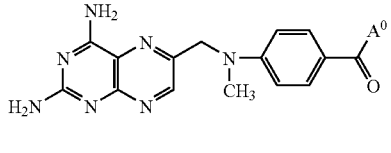
232 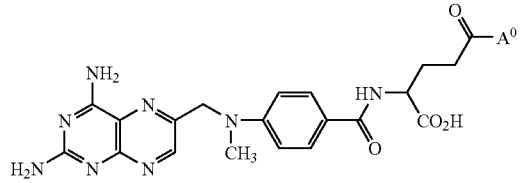
233 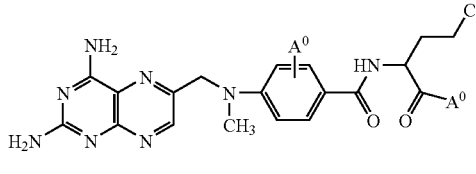
234 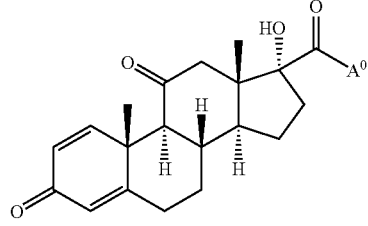
235 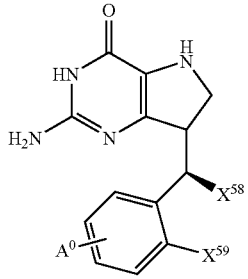
236 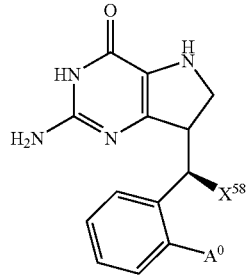
237 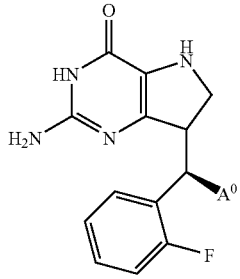
238 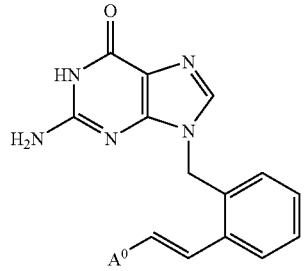
239 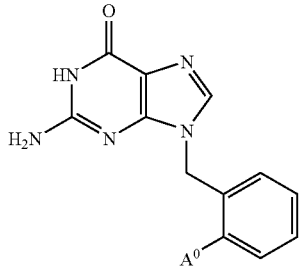

-continued
| | |
|---|---|
| 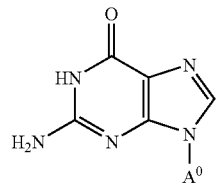 240 | 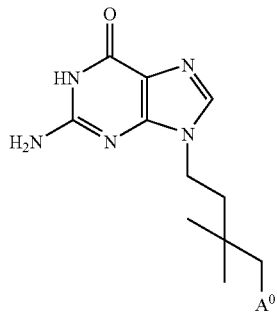 241 |
| 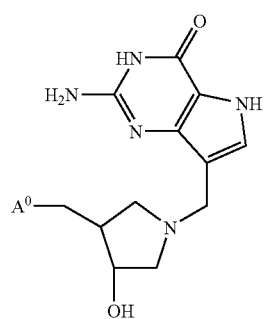 242 | 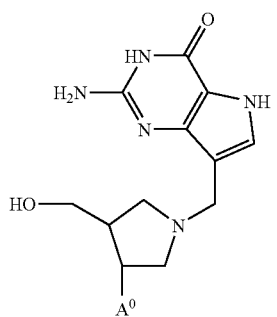 243 |
| 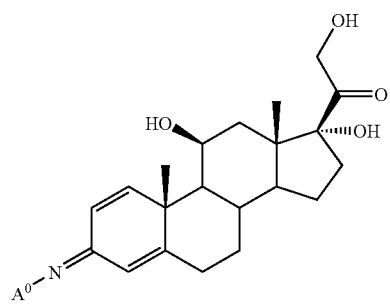 244 | 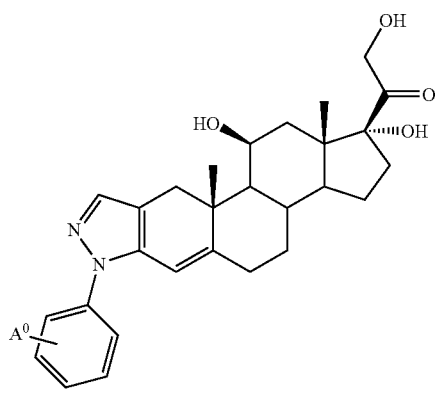 245 |
| 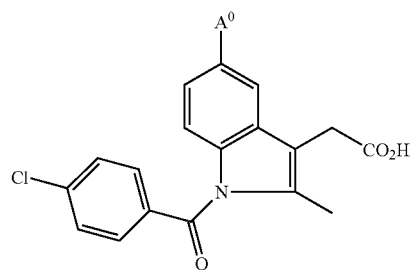 246 | 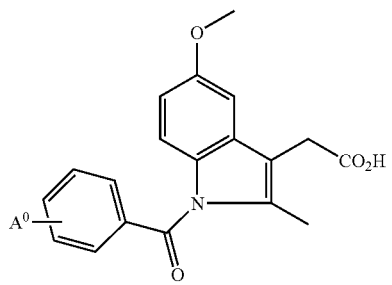 247 |
| 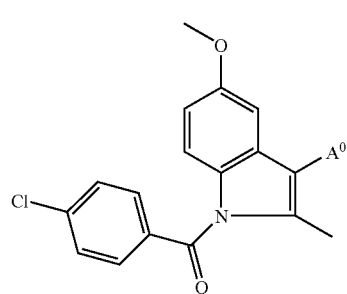 248 | 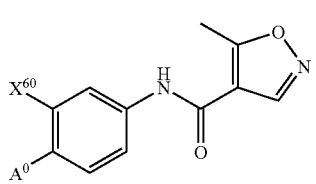 249 |

-continued
| 250 | 251 |
|---|---|
| 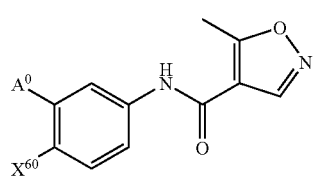 | 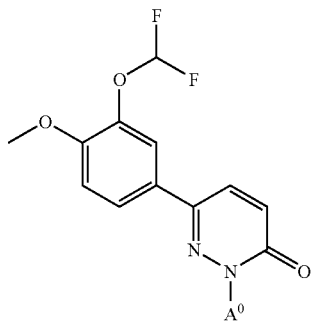 |
| 252 | 253 |
| 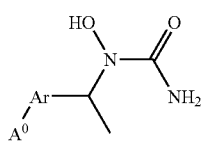 | 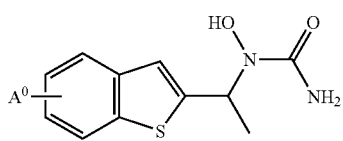 |
| 254 | 255 |
| 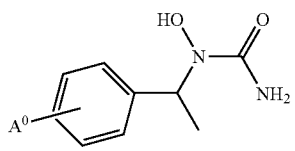 | 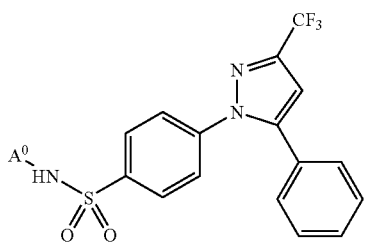 |
| 256 | 257 |
| 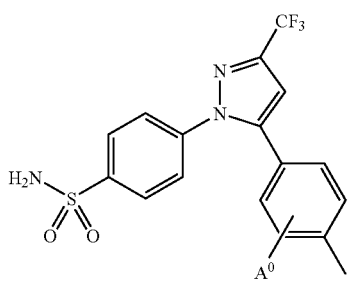 | 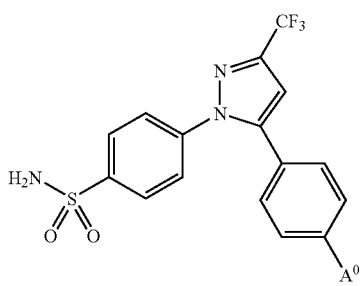 |
| 258 | 259 |
| 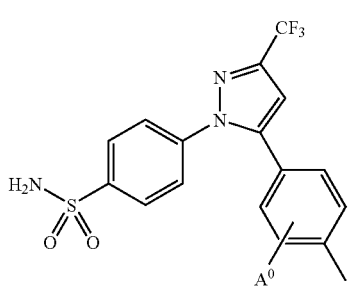 | 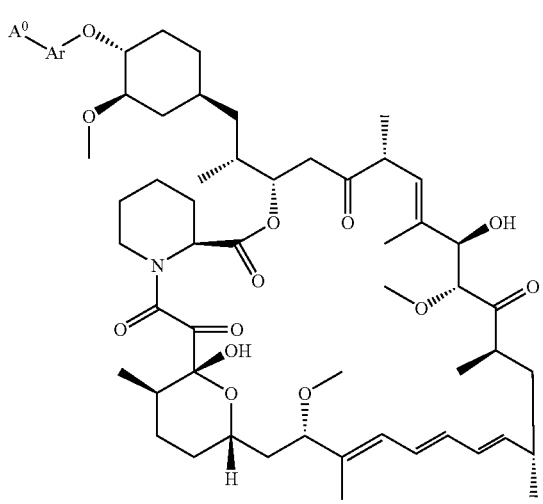 |

-continued
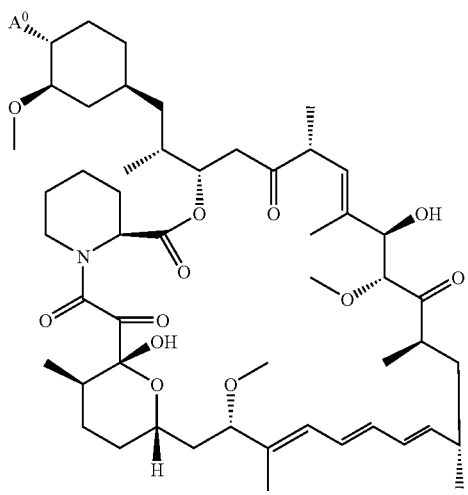
260
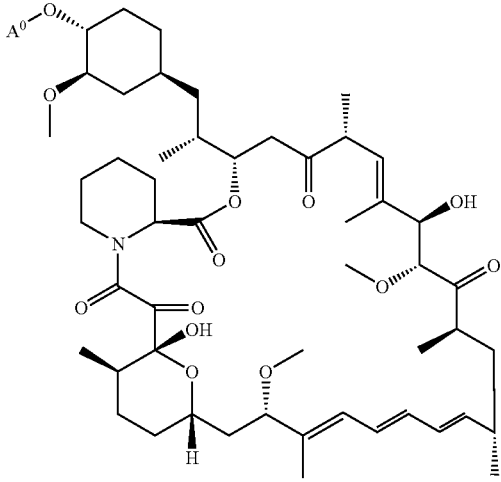
261
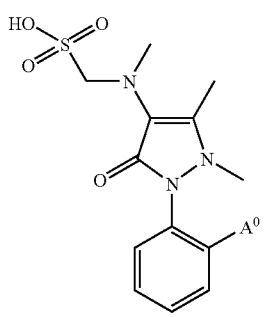
262
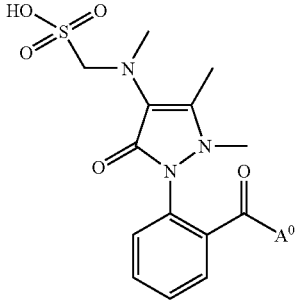
263
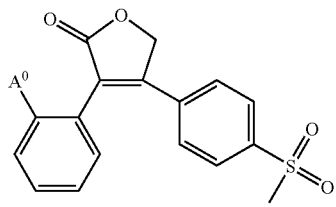
264
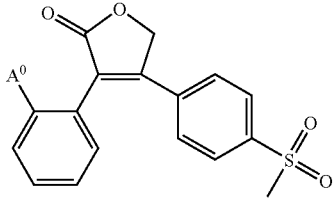
265
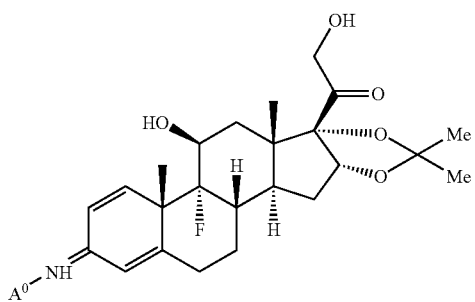
266
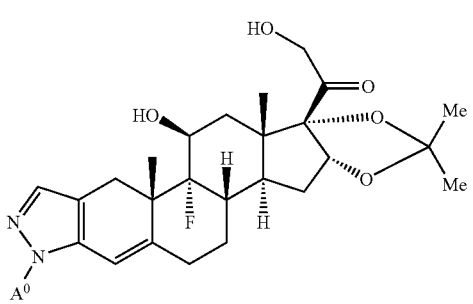
267
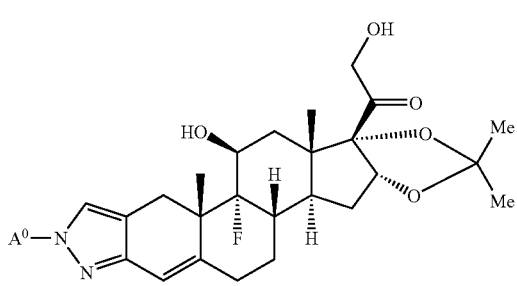
268
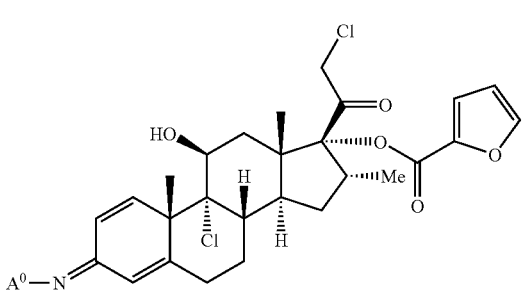
269

-continued
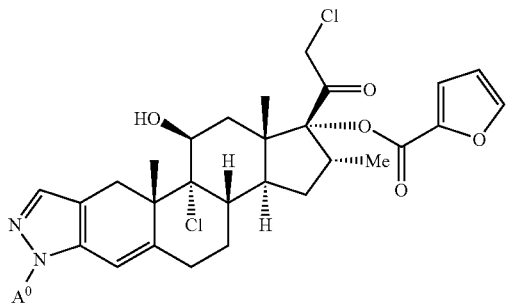
270
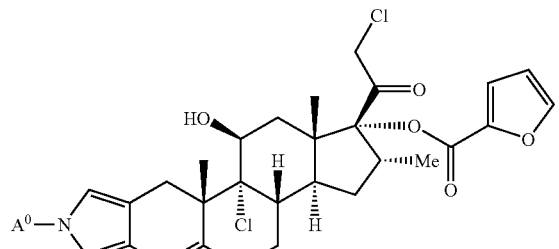
271
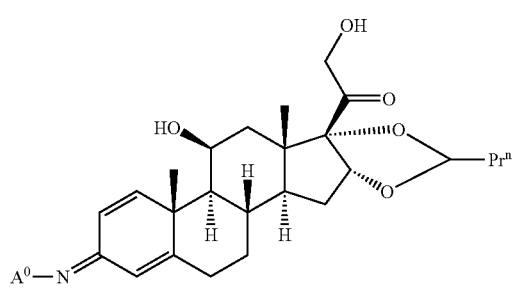
272
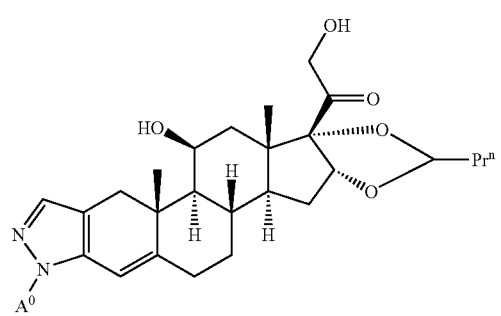
273
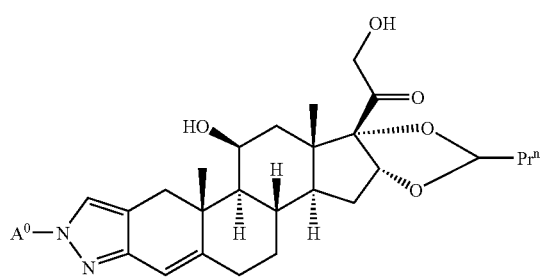
274
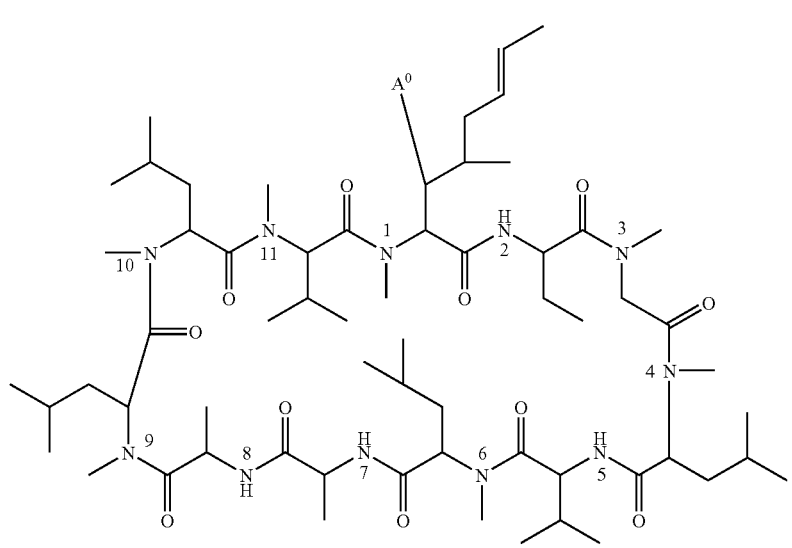
275

276
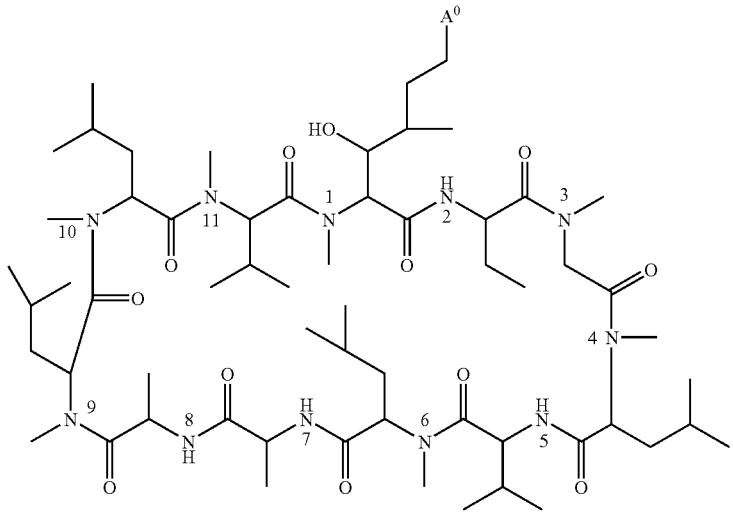
277
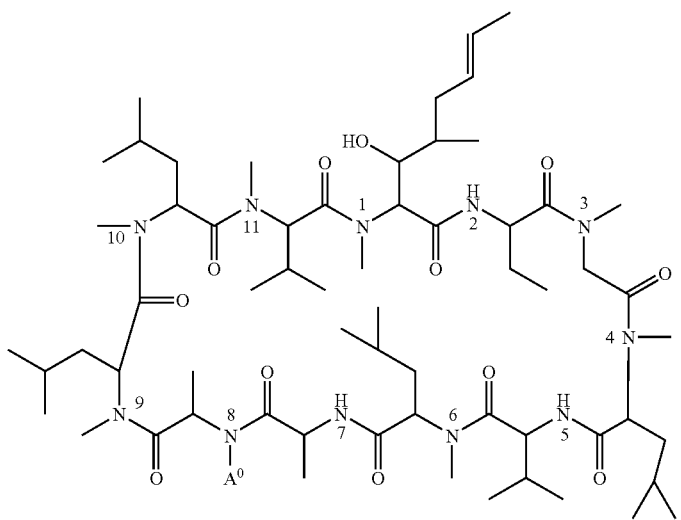
278
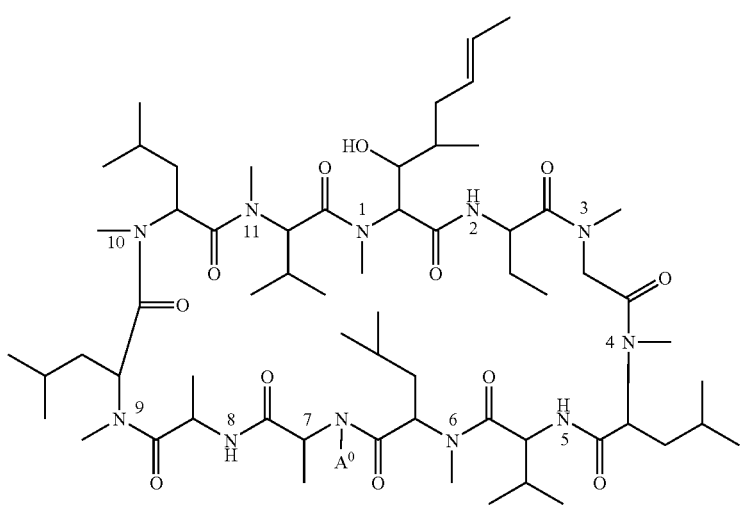

-continued
279
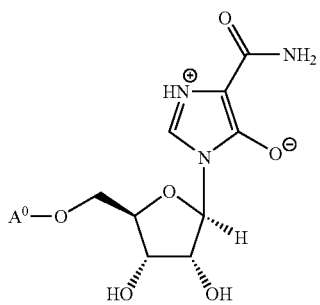
280
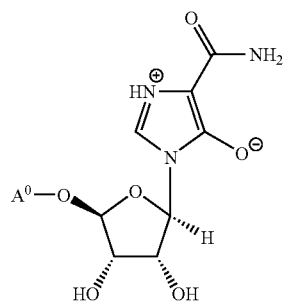
281
282
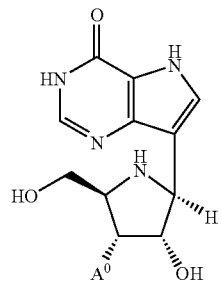
283
284
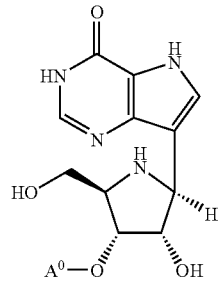
285
286
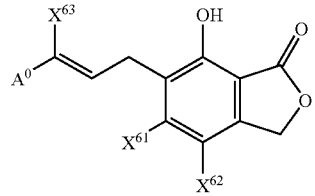
287
288
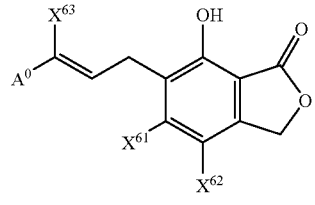
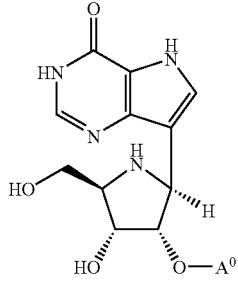
289
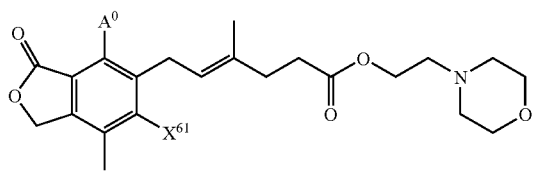
290
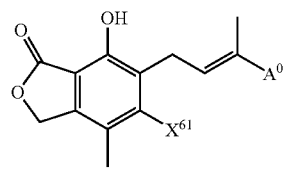

-continued

291

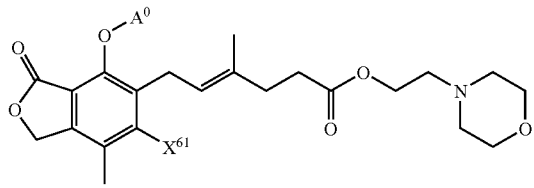

292

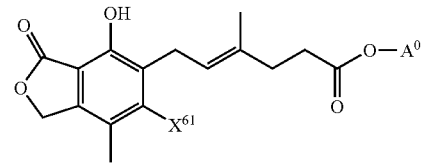

293

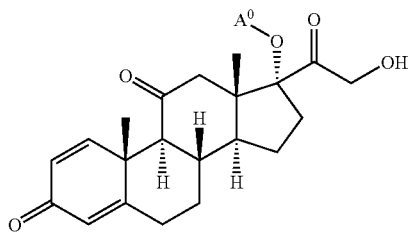

294

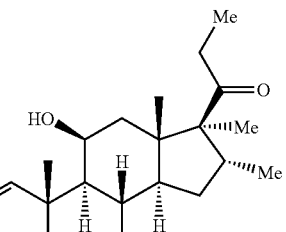

295

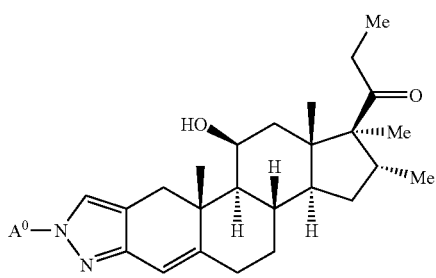

296

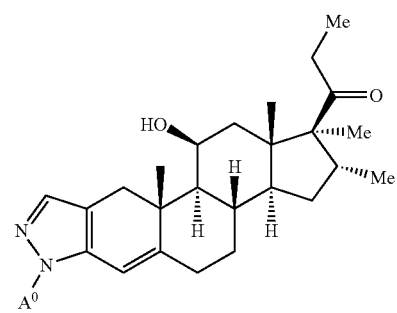

wherein:

$A^0$ is $A^1$, $A^2$ or $W^3$ with the proviso that one $A^0$ is $A^1$;

$A^1$ is:

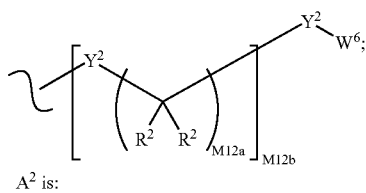

$A^2$ is:

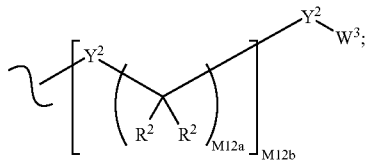

$A^3$ is:

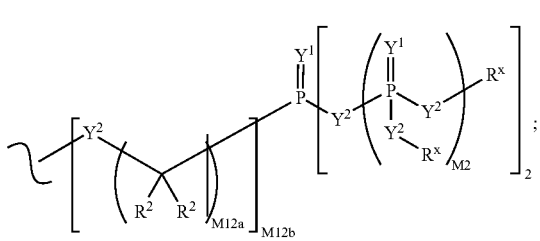

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $R^1$, $W^3$, a protecting group, or the formula:

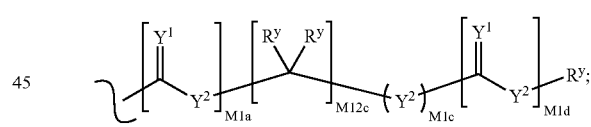

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —C(Y$^1$)R$^5$, —C(Y$^1$)W$^5$, —SO$_2$R$^5$, or —SO$_2$W$^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{50}$ is H or F;

$X^{51}$ is H, hydroxy, or acyloxy;

$X^{52}$ is NH$_2$ or EtC(O)N—Na+;

$X^{53}$ is H, methyl, CF$_3$, or halo;

$X^{54}$ is H, halo, trifluoromethyl, (C1-C3)alkyl, cyano, or (C$_1$-C$_3$)alkoxy;

$X^{55}$ is H, F, Cl, Br, methyl, or trifluoromethyl;

$X^{56}$ is hydrogen, halo, trifluoromethyl, cyano, methyl;

$X^{57}$ is H, F, Cl, CF$_3$, cyano, methyl, or t-butyl;

$X^{58}$ is H or CH$_2$OH;

$X^{59}$ is H or F;

$X^{60}$ is H, trifluoromethyl, or cyano;

$X^{61}$ is methoxy, ethoxy, propoxy, difluoromethoxy, trifluoromethoxy, vinyl, ethyl, methyl, propyl, butyl, cyclopropyl, N-methylamino, or N-formylamino;

$X^{62}$ is methyl, chloro, or trifluoromethyl;

$X^{63}$ is H, methyl, ethyl, cyclopropyl, vinyl, or trifluoromethyl;

$X^{64}$ is H, methyl, ethyl, cyclopropyl, chloro, vinyl, allyl, 3-methyl-1-buten-1-yl;

$X^{65}$ is H or F; and

Ar is aryl or heteroaryl.

The invention also provides a pharmaceutical composition comprising an effective amount of a compound of the invention, or a pharmaceutically acceptable salt thereof, in combination with a pharmaceutically acceptable diluent or carrier.

This invention also pertains to a method of increasing cellular accumulation and retention of an anti-inflammatory drug compound comprising linking the compound to one or more phosphonate groups.

The invention also provides a method of treating inflammation in a mammal, comprising administering a compound of the invention to the mammal.

The invention also provides a compound of the invention for use in medical therapy (preferably for use in treating inflammation, as well as the use of a compound of the invention for the manufacture of a medicament useful for the treatment of inflammation.

In another aspect the invention also provides a method for inhibiting inflammatory activity comprising contacting a sample in need of such treatment with a compound or composition of the invention.

The invention also provides processes and novel intermediates disclosed herein which are useful for preparing compounds of the invention. Some of the compounds of the invention are useful to prepare other compounds of the invention.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

When tradenames are used herein, applicants intend to independently include the tradename product and the active pharmaceutical ingredient(S) of the tradename product.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

The terms "phosphonate" and "phosphonate group" include functional groups or moieties within a molecule that comprises a phosphorous that is 1) single-bonded to a carbon, 2) double-bonded to a heteroatom, 3) single-bonded to a heteroatom, and 4) single-bonded to another heteroatom, wherein each heteroatom can be the same or different. The terms "phosphonate" and "phosphonate group" also include functional groups or moieties that comprise a phosphorous in the same oxidation state as the phosphorous described above, as well as functional groups or moieties that comprise a prodrug moiety that can separate from a compound so that the compound retains a phosphorous having the characteriatics described above. For example, the terms "phosphonate" and "phosphonate group" include phosphonic acid, phosphonic monoester, phosphonic diester, phosphonamidate, and phosphonthioate functional groups. In one specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen, and 4) single-bonded to another oxygen, as well as functional groups or moieties that comprise a prodrug moiety that can separate from a compound so that the compound retains a phosphorous having such characteriatics. In another specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen or nitrogen, and 4) single-bonded to another oxygen or nitrogen, as well as functional groups or moieties that comprise a prodrug moiety that can separate from a compound so that the compound retains a phosphorous having such characteristics.

The term "prodrug" as used herein refers to any compound that when administered to a biological system generates the drug substance, i.e. active ingredient, as a result of spontaneous chemical reaction(S), enzyme catalyzed chemical reaction(S), photolysis, and/or metabolic chemical reaction(S). A prodrug is thus a covalently modified analog or latent form of a therapeutically-active compound.

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2C(=O)R^9$ and acyloxymethyl carbonates —$CH_2C(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC)—$CH_2C(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate the phosphoric acid and the quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958). Cyclic phosphonate esters have also been described as prodrugs of phosphorus-containing compounds (Erion et al., U.S. Pat. No. 6,312,662).

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of a compound having an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound having a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH(CH₃)CH₂CH₃), 2-methyl-2-propyl (t-Bu, t-butyl, —C(CH₃)₃), 1-pentyl (n-pentyl, —CH₂CH₂CH₂CH₂CH₃), 2-pentyl (—CH(CH₃)CH₂CH₂CH₃), 3-pentyl (—CH(CH₂CH₃)₂), 2-methyl-2-butyl (—C(CH₃)₂CH₂CH₃), 3-methyl-2-butyl (—CH(CH₃)CH(CH₃)₂), 3-methyl-1-butyl (—CH₂CH₂CH(CH₃)₂), 2-methyl-1-butyl (—CH₂CH(CH₃)CH₂CH₃), 1-hexyl (—CH₂CH₂CH₂CH₂CH₂CH₃), 2-hexyl (—CH(CH₃)CH₂CH₂CH₂CH₃), 3-hexyl (—CH(CH₂CH₃)(CH₂CH₂CH₃)), 2-methyl-2-pentyl (—C(CH₃)₂CH₂CH₂CH₃), 3-methyl-2-pentyl (—CH(CH₃)CH(CH₃)CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C(CH₃)₂CH(CH₃)₂), 3,3-dimethyl-2-butyl (—CH(CH₃)C(CH₃)₃).

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl (—CH=CH₂), allyl (—CH₂CH=CH₂), cyclopentenyl (—C₅H₇), 5-hexenyl (—CH₂CH₂CH₂CH₂CH=CH₂), and 2,5-hexadienyl (—CH₂CH=CHCH₂CH=CH₂).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH), propargyl (—CH₂C≡CH), and 2,5-hexadiynyl (—CH₂C≡CH CH₂C≡CH)

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH₂—) 1,2-ethyl (—CH₂CH₂—), 1,3-propyl (—CH₂CH₂CH₂—), 1,4-butyl (—CH₂CH₂CH₂CH₂—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH₂C≡C—), and 4-pentynyl (—CH₂CH₂CH₂C—CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —O⁻, —OR, —SR, —S⁻, —NR₂, —NR₃, =NR, —CX₃, —CN, —OCN, —SCN, —N=C=O, —NCS, —NO, —NO₂, =N₂, —N₃, NC(=O)R, —C(=O)R, —C(=O)NRR—S(=O)₂O⁻, —S(=O)₂OH, —S(=O)₂R, —OS(=O)₂OR, —S(=O)₂NR, —S(=O)R, —OP(=O)O₂RR, —P(=O)O₂RR, —P(=O)(O⁻)₂, —P(=O)(OH)₂, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

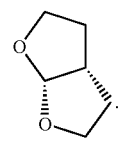

By way of example and not limitation, carbon bonded heterocycles can be bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having 3 to 7 carbon atoms as a monocycle, 7 to 12 carbon atoms as a bicycle, and up to about 20 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(S). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary phosphonate ester-forming group is the phenyl carbocycle in substructure $A_3$ having the formula:

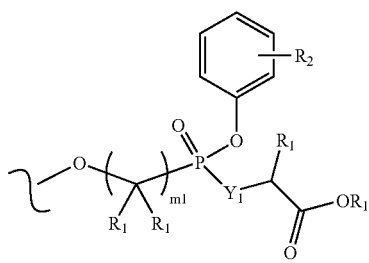

wherein $R_1$ may be H or $C_1$-$C_{12}$ alkyl; m1 is 1, 2, 3, 4, 5, 6, 7 or 8, and the phenyl carbocycle is substituted with 0 to 3 $R_2$ groups. Where $Y_1$ is O, a lactate ester is formed, and where $Y_1$ is $N(R_2)$, $N(OR_2)$ or $N(N(R_2)_2)$, a phosphonamidate ester results.

In its ester-forming role, a protecting group typically is bound to any acidic group such as, by way of example and not limitation, a —$CO_2H$ or —C(S)OH group, thereby resulting in —$CO_2R^x$ where $R^x$ is defined herein. Also, $R^x$ for example includes the enumerated ester groups of WO 95/07920.

Examples of protecting groups include:

$C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R_1$—O—$C_1$-$C_{12}$ alkylene, $C_1$-$C_{12}$ alkoxy, CN, $NO_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-,3- and 4-acetylphenyl, 1,8-dihydroxynaphthyl (—$C_{10}H_6$—OH) and aryloxy ethyl [$C_6$-$C_9$ aryl (including phenoxy ethyl)], 2,2'-dihydroxybiphenyl, 2-, 3- and 4-N,N-dialkylaminophenol, —$C_6H_4CH_2$—$N(CH_3)_2$, trimethoxybenzyl, triethoxybenzyl, 2-alkyl pyridinyl ($C_{1-4}$ alkyl);

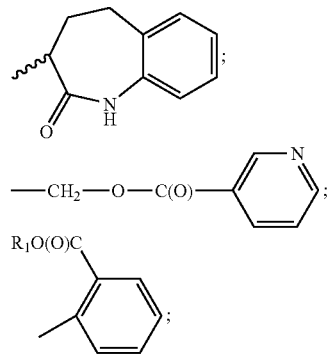

esters of 2-carboxyphenyl; and $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2CCl_3$), $C_1$-$C_{12}$ alkyl (including methyl and ethyl), $C_2$-$C_{12}$ alkenyl or $C_2$-$C_{12}$ alkynyl; alkoxy ethyl [$C_1$-$C_6$ alkyl including —$CH_2$—$CH_2$—O—$CH_3$ (methoxy ethyl)]; alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5CH_3$, —$CH_2CH_2F$, —$CH_2CH_2Cl$, —$CH_2CF_3$, and —$CH_2CCl_3$);

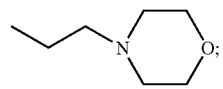

—N-2-propylmorpholino, 2,3-dihydro-6-hydroxyindene, sesamol, catechol monoester, —$CH_2$—C(O)—$N(R^1)_2$, —$CH_2$—$S(O)(R^1)$, —$CH_2$—$S(O)_2(R^1)$, —$CH_2$—CH(OC(O)$CH_2R^1$)—$CH_2(OC(O)CH_2R^1)$, cholesteryl, enolpyruvate (HOOC—C(=$CH_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo*. (1974) 5(6):670-671;

cyclic carbonates such as (5-$R_d$-2-oxo-1,3-dioxolen-4-yl) methyl esters (Sakamoto et al., *Chem. Pharm. Bull.* (1984) 32(6)2241-2248) where $R_d$ is $R_1$, $R^4$ or aryl; and

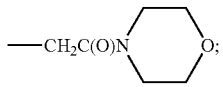

The hydroxyl groups of the compounds of this invention optionally are substituted with one of groups III, IV or V disclosed in WO 94/21604, or with isopropyl.

Table A lists examples of protecting group ester moieties that for example can be bonded via oxygen to —C(O)O— and —P(O)(O—)$_2$ groups. Several amidates also are shown, which are bound directly to —C(O)— or —P(O)$_2$. Esters of structures 1-5,8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, CsCO$_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| | |
|---|---|
| 1. | —CH$_2$—C(O)—N(R$_1$)$_2$* |
| 2. | —CH$_2$—S(O)(R$_1$) |
| 3. | —CH$_2$—S(O)$_2$(R$_1$) |
| 4. | —CH$_2$—O—C(O)—CH$_2$—C$_6$H$_5$ |
| 5. | 3-cholesteryl |
| 6. | 3-pyridyl |
| 7. | N-ethylmorpholino |
| 8. | —CH$_2$—O—C(O)—C$_6$H$_5$ |
| 9. | —CH$_2$—O—C(O)—CH$_2$CH$_3$ |
| 10. | —CH$_2$—O—C(O)—C(CH$_3$)$_3$ |
| 11. | —CH$_2$—CCl$_3$ |
| 12. | —C$_6$H$_5$ |
| 13. | —NH—CH$_2$—C(O)O—CH$_2$CH$_3$ |
| 14. | —N(CH$_3$)—CH$_2$—C(O)O—CH$_2$CH$_3$ |
| 15. | —NHR$_1$ |
| 16. | —CH$_2$—O—C(O)—C$_{10}$H$_{15}$ |
| 17. | —CH$_2$—O—C(O)—CH(CH$_3$)$_2$ |
| 18. | —CH$_2$—C#H(OC(O)CH$_2$R$_1$)—CH$_2$—(OC(O)CH$_2$R$_1$)* |
| 19. | 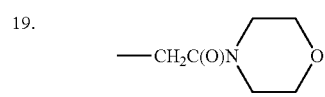 |
| 20. |  |
| 21. |  |

TABLE A-continued

| | |
|---|---|
| 22. | —CH$_2$—O—C(O)— (3-pyridyl) |
| 23. | —CH$_2$CH$_2$— (2-pyridyl) |
| 24. | CH$_3$O(O)C— (2-methylphenyl) |
| 25. | CH$_3$CH$_2$O(O)C— (2-methylphenyl) |
| 26. | —CH$_2$— (2,4,5-trimethoxyphenyl, OCH$_3$ groups) | chiral center is (R), (S) or racemate.

Other esters that are suitable for use herein are described in EP 632048.

Protecting groups also includes "double ester" forming profunctionalities such as —CH$_2$OC(O)OCH$_3$,

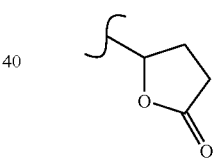

—CH$_2$SCOCH$_3$, —CH$_2$OCON(CH$_3$)$_2$, or alkyl- or aryl-acyloxyalkyl groups of the structure —CH(R$^1$ or W$^5$)O((CO)R$^{37}$) or —CH(R$^1$ or W$^5$)((CO)OR$^{38}$) (linked to oxygen of the acidic group) wherein R$^{37}$ and R$^{38}$ are alkyl, aryl, or alkylaryl groups (see U.S. Pat. No. 4,968,788). Frequently R$^{37}$ and R$^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including —CH(CH$_2$CH$_2$OCH$_3$)OC(O)C(CH$_3$)$_3$,

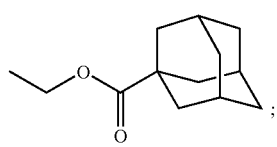

—$CH_2OC(O)C_{10}H_{15}$, —$CH_2OC(O)C(CH_3)_3$, —$CH(CH_2OCH_3)OC(O)C(CH_3)_3$, —$CH(CH(CH_3)_2)OC(O)C(CH_3)_3$, —$CH_2OC(O)CH_2CH(CH_3)_2$, —$CH_2OC(O)C_6H_{11}$, —$CH_2OC(O)C_6H_5$, —$CH_2OC(O)C_{10}H_{15}$, —$CH_2OC(O)CH_2CH_3$, —$CH_2OC(O)CH(CH_3)_2$, —$CH_2OC(O)C(CH_3)_3$ and —$CH_2OC(O)CH_2C_6H_5$.

In some claims the protected acidic group is an ester of the acidic group and is the residue of a hydroxyl-containing functionality. In other claims, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under $R^{31}$ or $R^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or $C_1$-$C_4$ alkylestercarboxyphenyl (salicylate $C_1$-$C_{12}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);

Substituted Methyl Ethers (Methoxymethyl, Methylthiomethyl, t-Butylthiomethyl, (Phenyldimethylsilyl) methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl) phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));

Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, p-Chlorophenyl, p-Methoxyphenyl, 2,4-Dinitrophenyl, Benzyl);

Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl) bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);

Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);

Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

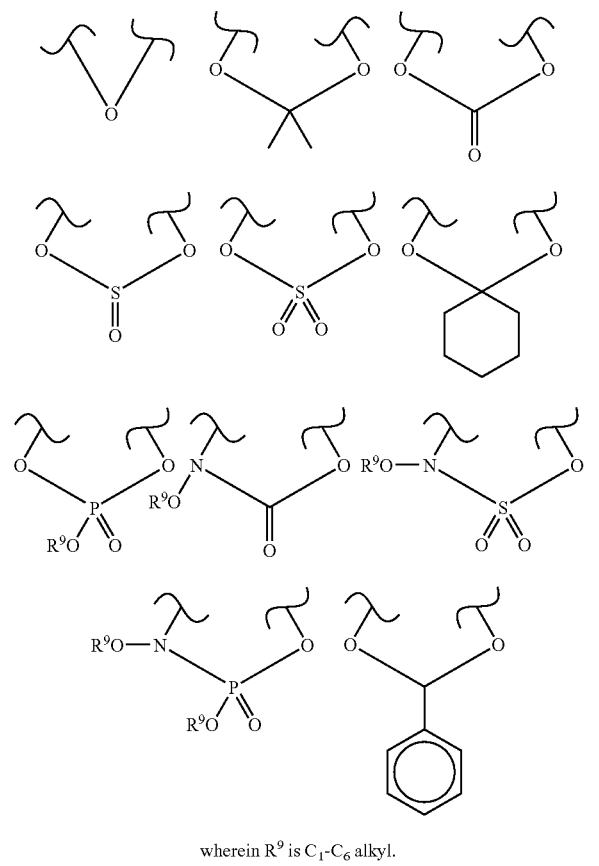

wherein $R^9$ is $C_1$-$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichoroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N-oxide);

Imine Derivatives: (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N-isopropylidene, N-p-nitrobenzylidene, N-salicylidene, N-5-chlorosalicylidene, N-(5-chloro-2-hydroxyphenyl)phenylmethylene, N-cyclohexylidene);

Enamine Derivatives: (N-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N—Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)$R^1$ or —N=C$R^1$N($R^1$)$_2$. Another protecting group, also useful as a prodrug for amino or —NH($R^5$), is:

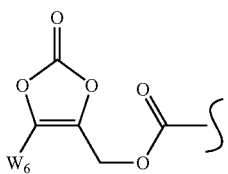

See for example Alexander, J. et al. (1996) *J. Med. Chem.* 39:480-486.

Amino Acid and Polypeptide Protecting Group and Conjugates

An amino acid or polypeptide protecting group of a compound of the invention has the structure $R^{15}$NHCH($R^{16}$)C(O)—, where $R^{15}$ is H, an amino acid or polypeptide residue, or $R^5$, and $R^{16}$ is defined below.

$R^{16}$ is lower alkyl or lower alkyl ($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. $R^{10}$ also is taken together with the amino acid $α_N^{10}$ to form a proline residue ($R^{10}$=—CH$_2$)$_3$—). However, $R^{10}$ is generally the side group of a naturally-occurring amino acid such as H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$—SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. $R^{10}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —NHSO$_2$R, NHC(O)R, —N(R)$_2$, NH$_2$ or —NH(R)(H), whereby for example a carboxylic acid is reacted, i.e. coupled, with the amine to form an amide, as in C(O)NR$_2$. A phosphonic acid may be reacted with the amine to form a phosphonamidate, as in —P(O)(OR)(NR$_2$).

In general, amino acids have the structure $R^{17}$C(O)CH($R^{16}$)NH—, where $R^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted at $R^3$ of substituents $A^1$, $A^2$ or $A^3$ in Formula I. These conjugates are produced by forming an amide bond between a carboxyl group of the amino acid (or C-terminal amino acid of a polypeptide for example). Similarly, conjugates are formed between $R^3$ (Formula I) and an amino group of an amino acid or polypeptide. Generally, only one of any site in the parental molecule is amidated with an amino acid as described herein, although it is within the scope of this invention to introduce amino acids at more than one permitted site. Usually, a carboxyl group of $R^3$ is amidated with an amino acid. In general, the α-amino or α-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino acids or polypeptides it will be understood that the carboxyl group optionally will be blocked, e.g., by $R^1$, esterified with $R^5$ or amidated. Similarly, the amino side chains $R^{16}$ optionally will be blocked with $R^1$ or substituted with $R^5$.

Such ester or amide bonds with side chain amino or carboxyl groups, like the esters or amides with the parental molecule, optionally are hydrolyzable in vivo or in vitro under acidic (pH <3) or basic (pH >10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine;

2-hexosaminic acids such as D-glucosaminic acid or D-galactosaminic acid;

α-Amino-δ-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains a peptidolytic enzyme cleavage site at the peptide bond between the first and second residues adjacent to the acidic heteroatom. Such cleavage sites are flanked by enzymatic recognition structures, e.g., a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In claims where $W_1$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence —$X^4$-pro-$X^5$— (where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) *Pharm Res.* 9:969-978). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Specific Embodiments of the Invention

Specific values described for radicals, substituents, and ranges, as well as specific embodiments of the invention described herein, are for illustration only; they do not exclude other defined values or other values within defined ranges.

In one specific embodiment of the invention, the conjugate is a compound that is substituted with one or more phosphonate groups either directly or indirectly through a linker; and that is optionally substituted with one or more groups $A^0$; or a pharmaceutically acceptable salt thereof, wherein:

$A^0$ is $A^1$, $A^2$ or $W^3$;

$A^1$ is:

$A^2$ is:

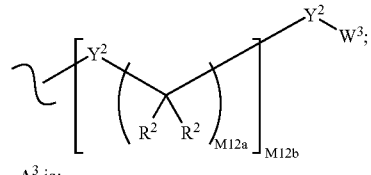

$A^3$ is:

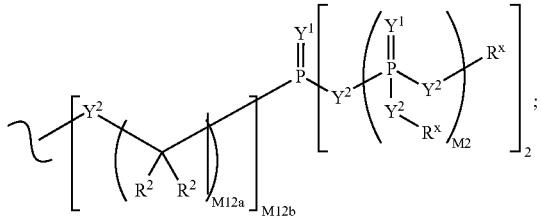

$Y^1$ is independently O, S, N($R^x$), N(O)($R^x$), N(O$R^x$), N(O)(O$R^x$), or N(N($R^x$)($R^x$));

$Y^2$ is independently a bond, O, N($R^x$), N(O)($R^x$), N(O$R^x$), N(O)(O$R^x$), N(N($R^x$)($R^x$)), —S(O)$_{M2}$—, or —S(O)$_{M2}$—S(O)$_{M2}$—;

$R^x$ is independently H, $R^1$, $W^3$, a protecting group, or the formula:

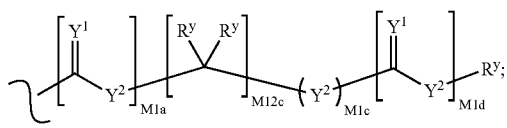

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is $R^x$, $N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;

$R^{3d}$ is —$C(Y^1)R^x$, —$C(Y^1)OR^x$ or —$C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In another specific embodiment of the invention $A^1$ is of the formula:

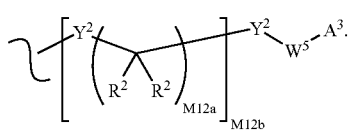

In another specific embodiment of the invention $A^1$ is of the formula:

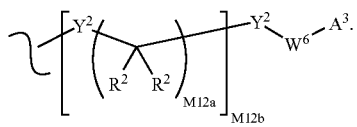

In another specific embodiment of the invention $A^1$ is of the formula:

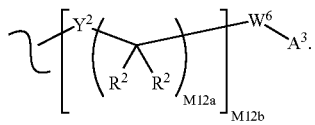

In another specific embodiment of the invention $A^1$ is of the formula:

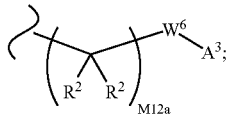

In another specific embodiment of the invention $A^1$ is of the formula:

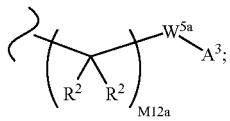

and $W^{5a}$ is a carbocycle or a heterocycle where $W^{5a}$ is independently substituted with 0 or 1 $R^2$ groups. A specific velue for M12a is 1.

In another specific embodiment of the invention $A^1$ is of the formula:

In another specific embodiment of the $A^1$ is of the formula:

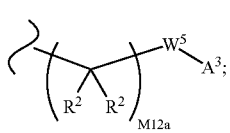

In another specific embodiment of the $A^1$ is of the formula:

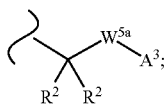

wherein $W^{5a}$ is a carbocycle independently substituted with 0 or 1 $R^2$ groups;

In another specific embodiment of the $A^1$ is of the formula:

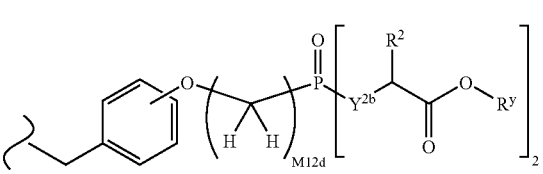

wherein $Y^{2b}$ is O or $N(R^2)$; and M12d is 1, 2, 3, 4, 5, 6, 7 or 8.

In another specific embodiment of the $A^1$ is of the formula:

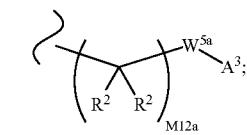

wherein $W^{5a}$ is a carbocycle independently substituted with 0 or 1 $R^2$ groups;

In another specific embodiment of the $A^1$ is of the formula:

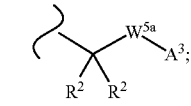

wherein $W^{5a}$ is a carbocycle or heterocycle where $W^{5a}$ is independently substituted with 0 or 1 $R^2$ groups.

In another specific embodiment of the invention $A^1$ is of the formula:

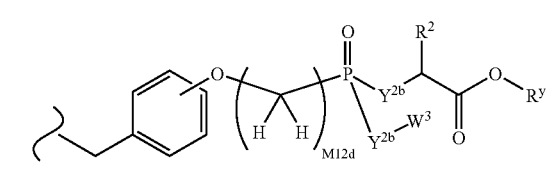

wherein $Y^{2b}$ is O or $N(R^2)$; and M12d is 1, 2, 3, 4, 5, 6, 7 or 8.

In a specific embodiment of the invention $A^2$ is of the formula:

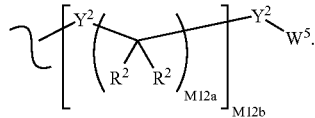

In another specific embodiment of the invention $A^2$ is of the formula:

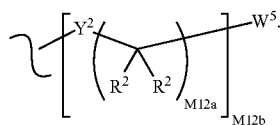

In another specific embodiment of the invention M12b is 1.
In another specific embodiment of the invention e M12b is 0, $Y^2$ is a bond and $W^5$ is a carbocycle or heterocycle where $W^5$ is optionally and independently substituted with 1, 2, or 3 $R^2$ groups.

In another specific embodiment of the invention $A^2$ is of the formula:

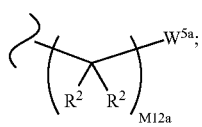

wherein $W^{5a}$ is a carbocycle or heterocycle where $W^{5a}$ is optionally and independently substituted with 1, 2, or 3 $R^2$ groups.

In another specific embodiment of the invention M12a is 1.
In another specific embodiment of the invention $A^2$ is selected from phenyl, substituted phenyl, benzyl, substituted benzyl, pyridyl and substituted pyridyl.

In another specific embodiment of the invention $A^2$ is of the formula:

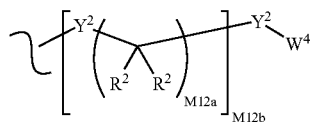

In another specific embodiment of the invention $A^2$ is of the formula:

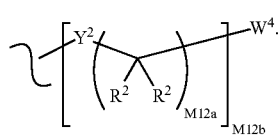

In another specific embodiment of the invention M12b is 1.

In a specific embodiment of the invention $A^3$ is of the formula:

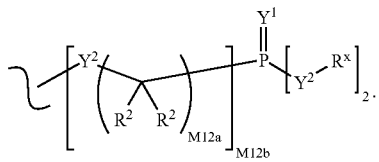

In another specific embodiment of the invention $A^3$ is of the formula:

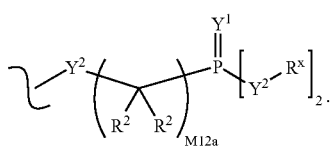

In another specific embodiment of the invention $A^3$ is of the formula:

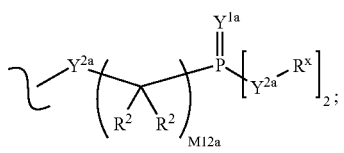

wherein $Y^{1a}$ is O or S; and $Y^{2a}$ is O, $N(R^x)$ or S.

In another specific embodiment of the invention $A^3$ is of the formula:

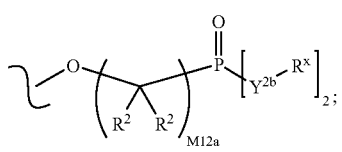

wherein $Y^{2b}$ is O or $N(R^x)$.

In another specific embodiment of the invention $A^3$ is of the formula:

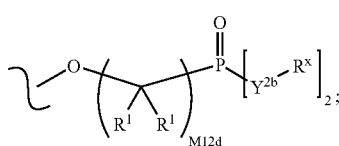

wherein $Y^{2b}$ is O or $N(R^x)$; and M12d is 1, 2, 3, 4, 5, 6, 7 or 8.

In another specific embodiment of the invention $A^3$ is of the formula:

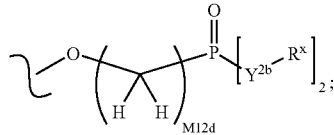

wherein $Y^{2b}$ is O or $N(R^x)$; and M12d is 1, 2, 3, 4, 5, 6, 7 or 8.

In another specific embodiment of the invention M12d is 1.

In another specific embodiment of the invention $A^3$ is of the formula:

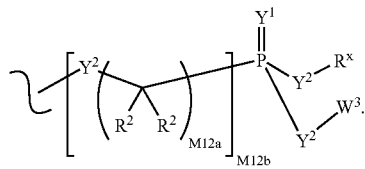

In another specific embodiment of the invention $A^3$ is of the formula:

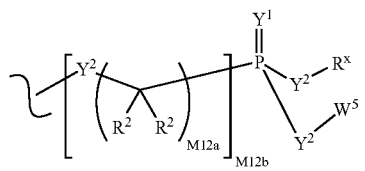

In another specific embodiment of the invention $W^5$ is a carbocycle.

In another specific embodiment of the invention $A^3$ is of the formula:

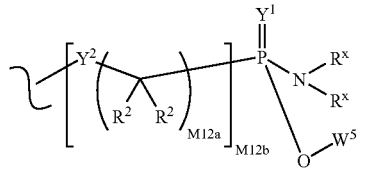

In another specific embodiment of the invention $W^5$ is phenyl.

In another specific embodiment of the invention $A^3$ is of the formula:

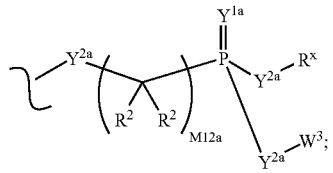

wherein $Y^{1a}$ is O or S; and $Y^{2a}$ is O, $N(R^x)$ or S.

In another specific embodiment of the invention A³ is of the formula:

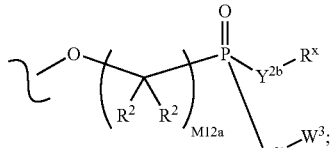

wherein Y$^{2b}$ is O or N(R$^x$).

In another specific embodiment of the invention A³ is of the formula:

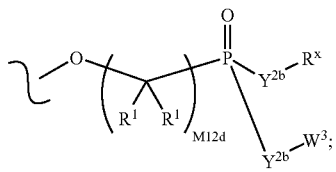

wherein Y$^{2b}$ is O or N(R$^x$); and M12d is 1, 2, 3, 4, 5, 6, 7 or 8.

In another specific embodiment of the invention R¹ is H.

In another specific embodiment of the invention A³ is of the formula:

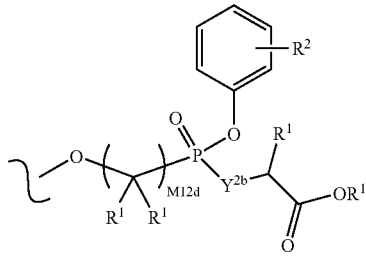

wherein the phenyl carbocycle is substituted with 0, 1, 2, or 3 R² groups.

In another specific embodiment of the invention A³ is of the formula:

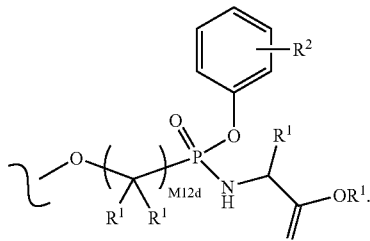

In another specific embodiment of the invention A³ is of the formula:

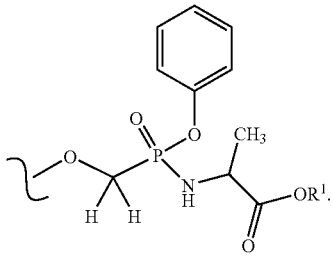

In another specific embodiment of the invention A³ is of the formula:

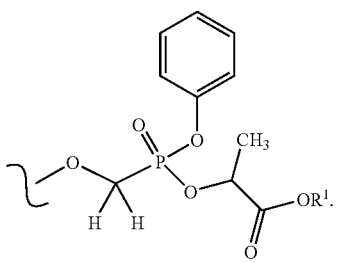

In another specific embodiment of the invention A³ is of the formula:

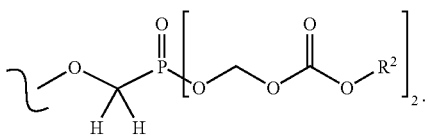

In another specific embodiment of the invention A³ is of the formula:

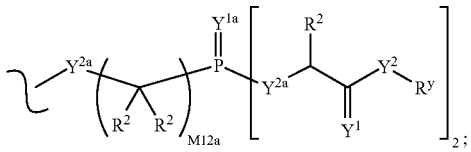

wherein Y$^{1a}$ is O or S; and Y$^{2a}$ is O, N(R²) or S.

In another specific embodiment of the invention A³ is of the formula:

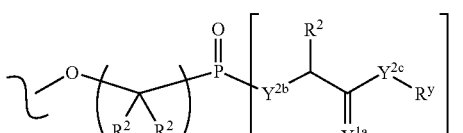

wherein Y$^{1a}$ is O or S; Y$^{2b}$ is O or N(R²); and Y$^{2c}$ is O, N(R$^y$) or S.

In another specific embodiment of the invention $A^3$ is of the formula:

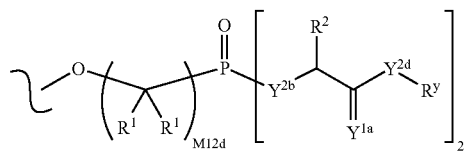

wheren $Y^{1a}$ is O or S; $Y^{2b}$ is O or $N(R^2)$; $Y^{2d}$ is O or $N(R^y)$; and M12d is 1, 2, 3, 4, 5, 6, 7 or 8.

In another specific embodiment of the invention $A^3$ is of the formula:

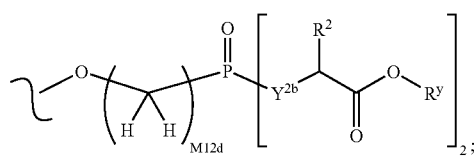

wherein $Y^{2b}$ is O or $N(R^2)$; and M12d is 1, 2, 3, 4, 5, 6, 7 or 8.

In another specific embodiment of the invention $A^3$ is of the formula:

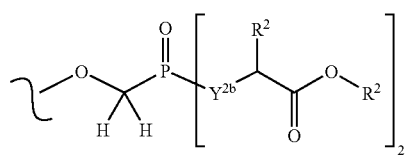

wherein $Y^{2b}$ is O or $N(R^2)$.

In another specific embodiment of the invention $A^3$ is of the formula:

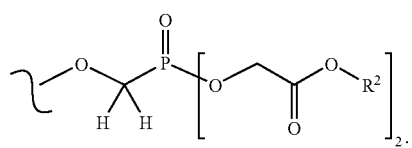

In another specific embodiment of the invention $A^3$ is of the formula:

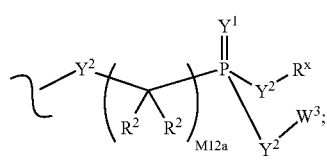

In another specific embodiment of the invention $A^3$ is of the formula:

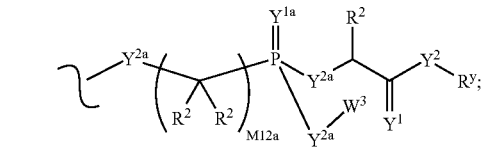

wherein $Y^{1a}$ is O or S; and $Y^{2a}$ is O, $N(R^2)$ or S.

In another specific embodiment of the invention $A^3$ is of the formula:

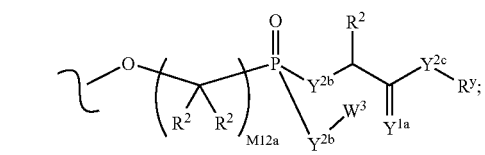

wherein $Y^{1a}$ is O or S; $Y^{2b}$ is O or $N(R^2)$; and $Y^{2c}$ is O, $N(R^y)$ or S.

In another specific embodiment of the invention $A^3$ is of the formula:

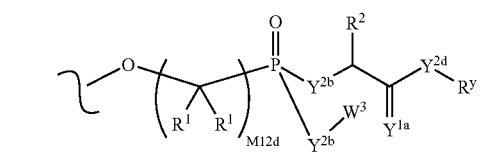

wherein $Y^{1a}$ is O or S; $Y^{2b}$ is O or $N(R^2)$; $Y^{2d}$ is O or $N(R^y)$; and M12d is 1, 2, 3, 4, 5, 6, 7 or 8.

In another specific embodiment of the invention $A^3$ is of the formula:

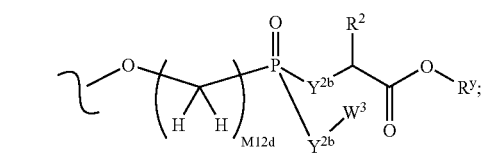

wherein $Y^{2b}$ is O or $N(R^2)$; and M12d is 1, 2, 3, 4, 5, 6, 7 or 8.

In another specific embodiment of the invention $A^3$ is of the formula:

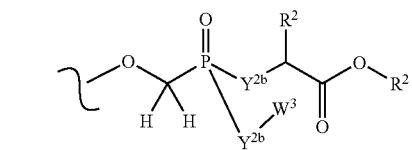

wherein $Y^{2b}$ is O or $N(R^2)$.

In another specific embodiment of the invention $A^3$ is of the formula:

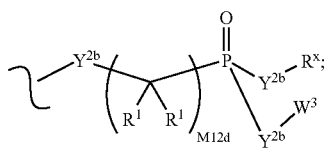

wherein: $Y^{2b}$ is O or N($R^x$); and M12d is 1, 2, 3, 4, 5, 6, 7 or 8.

In another specific embodiment of the invention $A^3$ is of the formula:

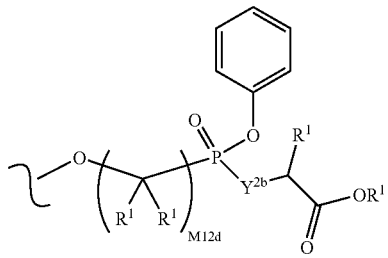

wherein the phenyl carbocycle is substituted with 0, 1, 2, or 3 $R^2$ groups.

In another specific embodiment of the invention $A^3$ is of the formula:

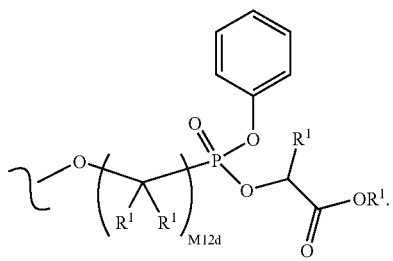

wherein the phenyl carbocycle is substituted with 0, 1, 2, or 3 $R^2$ groups.

In another specific embodiment of the invention $A^3$ is of the formula:

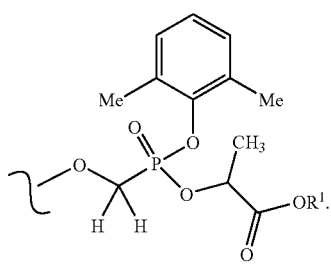

In a specific embodiment of the invention $A^0$ is of the formula:

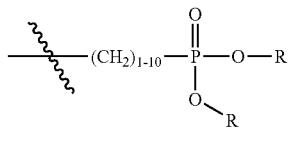

wherein each R is independently $(C_1-C_6)$alkyl.

In a specific embodiment of the invention $R^x$ is independently H, $R^1$, $W^3$, a protecting group, or the formula:

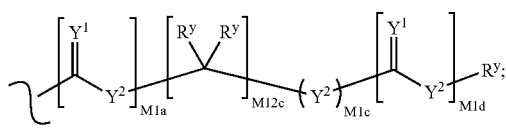

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

In a specific embodiment of the invention $R^x$ is of the formula:

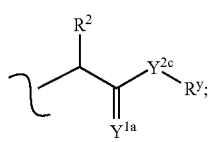

wherein $Y^{1a}$ is O or S; and $Y^{2c}$ is O, N($R^y$) or S.

In a specific embodiment of the invention $R^x$ is of the formula:

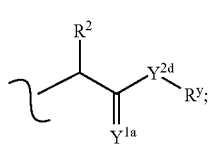

wherein $Y^{1a}$ is O or S; and $Y^{2d}$ is O or N($R^y$).

In a specific embodiment of the invention $R^x$ is of the formula:

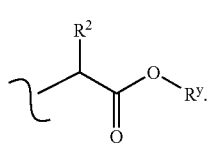

In a specific embodiment of the invention $R^y$ is hydrogen or alkyl of 1 to 10 carbons.

In a specific embodiment of the invention $R^x$ is of the formula:

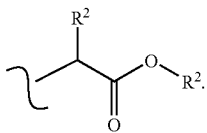

In a specific embodiment of the invention $R^x$ is of the formula:

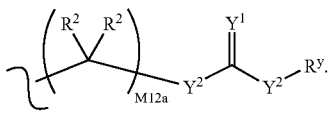

In a specific embodiment of the invention $R^x$ is of the formula:

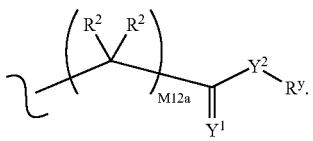

In a specific embodiment of the invention $Y^1$ is O or S

In a specific embodiment of the invention $Y^2$ is O, $N(R^y)$ or S.

In one specific embodiment of the invention $R^x$ is a group of the formula:

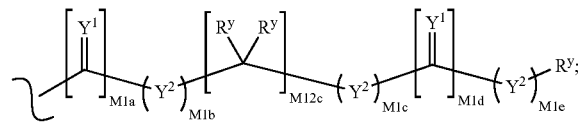

wherein:
m1a, m1b, m1c, m1d and m1e are independently 0 or 1;
m12c is 0, 1, 2, 3, 4, 5, 6, 7, 8, 9, 10, 11 or 12;
$R^y$ is H, $W^3$, $R^2$ or a protecting group; provided that:
if m1a, m12c, and m1d are 0, then m1b, m1c and m1e are 0;
if m1a and m12c are 0 and m1d is not 0, then m1b and m1c are 0;
if m1a and m1d are 0 and m12c is not 0, then m1b and at least one of m1c and m/e are 0;
if m1a is 0 and m12c and m1d are not 0, then m1b is 0;
if m12c and m1d are 0 and m1a is not 0, then at least two of m1b, m1c and m1e are 0;
if m12c is 0 and m1a and m1d are not 0, then at least one of m1b and m1c are 0; and
if m1d is 0 and m1a and m12c are not 0, then at least one of m1c and m1e are 0.

In another specific embodiment, the invention provides a compound of the formula:

[DRUG]-$(A^0)_{nn}$ or a pharmaceutically acceptable salt thereof wherein,
DRUG is a compound of any one of formulae 500-611
nn is 1, 2, or 3;

$A^0$ is $A^1$, $A^2$ or $W^3$ with the proviso that the compound includes at least one $A^1$;

$A^1$ is:

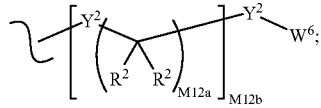

$A^2$ is:

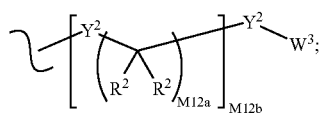

$A^3$ is:

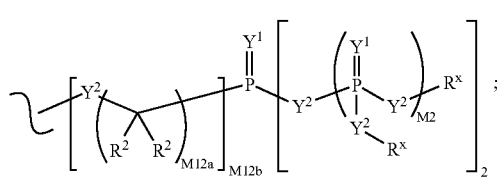

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$;

$R^x$ is independently H, $R^1$, $W^3$, a protecting group, or the formula:

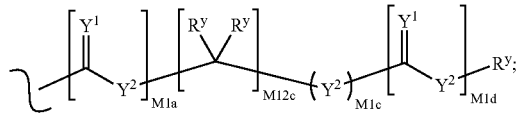

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, $-CN$, $N_3$ or $-NO_2$;
$R^{3b}$ is $Y^1$;
$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;
$R^{3d}$ is $-C(Y^1)R^x$, $-C(Y^1)OR^x$ or $-C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —C(Y$^1$)R$^5$, —C(Y$^1$)W$^5$, —SO$_2$R$^5$, or —SO$_2$W$^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{66}$ is hydrogen or fluorine; and $X^{67}$ is hydrogen, hydroxy, or acyloxy.

In another specific embodiment, the invention provides a compound of the formula 1-296;

or a pharmaceutically acceptable salt thereof wherein:

$A^0$ is $A^1$;

$A^1$ is:

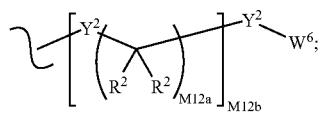

$A^3$ is:

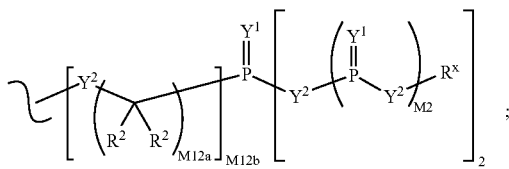

$Y^1$ is independently O, S, N(R$^x$), N(O)(R$^x$), N(OR$^x$), N(O)(OR$^x$), or N(N(R$^x$)(R$^x$));

$Y^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;

$R^x$ is independently H, $W^3$, a protecting group, or the formula:

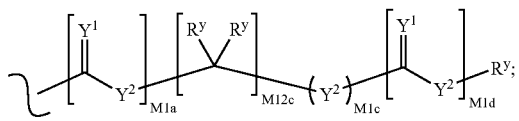

$R^y$ is independently H, $W^3$, $R^2$ or a protecting group;

$R^1$ is independently H or alkyl of 1 to 18 carbon atoms;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, N$_3$ or —NO$_2$;

$R^{3b}$ is $Y^1$;

$R^{3c}$ is R$^x$, N(R$^x$)(R$^x$), —SR$^x$, —S(O)R$^x$, —S(O)$_2$R$^x$, —S(O)(OR$^x$), —S(O)$_2$(OR$^x$), —OC(Y$^1$)R$^x$, —OC(Y$^1$)OR$^x$, —OC(Y$^1$)(N(R$^x$)(R$^x$)), —SC(Y$^1$)R$^x$, —SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$));

$R^{3d}$ is —C(Y$^1$)R$^x$, —C(Y$^1$)OR$^x$ or —C(Y$^1$)(N(R$^x$)(R$^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is R$^5$, —C(Y$^1$)R$^5$, —C(Y)W$^5$, —SO$_2$R$^5$, or —SO$_2$W$^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{50}$ is H or F;

$X^{51}$ is H, hydroxy, or acyloxy;

$X^{52}$ is NH$_2$ or EtC(O)N—Na+;

$X^{53}$ is H, methyl, CF$_3$, or halo;

$X^{54}$ is H, halo, trifluoromethyl, (C1-C3)alkyl, cyano, or (C$_1$-C$_3$)alkoxy;

$X^{55}$ is H, F, Cl, Br, methyl, or trifluoromethyl;

$X^{56}$ is hydrogen, halo, trifluoromethyl, cyano, methyl;

$X^{57}$ is H, F, Cl, CF$_3$, cyano, methyl, or t-butyl;

$X^{58}$ is H or CH$_2$OH;

$X^{59}$ is H or F;

$X^{60}$ is H, trifluoromethyl, or cyano;

$X^{61}$ is methoxy, ethoxy, vinyl, ethyl, methyl, cyclopropyl, N-methylamino, or N-formylamino;

$X^{62}$ is methyl, chloro, or trifluoromethyl;

$X^{63}$ is H, methyl, ethyl, cyclopropyl, vinyl, or trifluoromethyl;

$X^{64}$ is H, methyl, ethyl, cyclopropyl, chloro, vinyl, allyl, 3-methyl-1-buten-1yl;

$X^{65}$ is H or F; and

Ar is aryl or heteroaryl.

In another specific embodiment, the invention provides a compound of the formula:

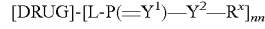

or a pharmaceutically acceptable salt thereof wherein,

DRUG is a compound of any one of 500-611;

$Y^1$ is independently O, S, N(R$^x$), N(O)(R$^x$), N(OR$^x$), N(O)(OR$^x$), or N(N(R$^x$)(R$^x$));

$Y^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;

$R^x$ is independently H, $W^3$, a protecting group, or the formula:

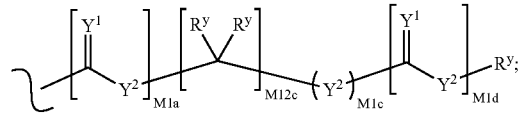

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, N$_3$ or —NO$_2$;

$R^{3b}$ is $Y^1$;

$R^{3c}$ is $R^x$, —N($R^x$)($R^x$), —S$R^x$, —S(O)$R^x$, —S(O)$_2R^x$, —S(O)(O$R^x$), —S(O)$_2$(O$R^x$), —OC($Y^1$)$R^x$, —OC($Y^1$)O$R^x$, —OC($Y^1$)(N($R^x$)($R^x$)), —SC($Y^1$)$R^x$, —SC($Y^1$)O$R^x$, —SC($Y^1$)(N($R^x$)($R^x$)), —N($R^x$)C($Y^1$)$R^x$, —N($R^x$)C($Y^1$)O$R^x$, or —N($R^x$)C($Y^1$)(N($R^x$)($R^x$));

$R^{3d}$ is —C($Y^1$)$R^x$, —C($Y^1$)O$R^x$ or —C($Y^1$)(N($R^x$)($R^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —C($Y^1$)$R^5$, —C($Y^1$)$W^5$, —SO$_2R^5$, or —SO$_2W^5$;

$W^5$ is carbocycle or heterocycle wherein $W^5$ is independently substituted with 0 to 3 $R^2$ groups;

M2 is 1, 2, or 3;

M1a, M1c, and M1d are independently 0 or 1;

M12c is 0, 1, 2, 3, 4, 5, 6, 7, 8, 9, 10, 11 or 12;

$X^{66}$ is hydrogen or fluorine; and $X^{67}$ is hydrogen, hydroxy, or acyloxy;

nn is 1, 2, or 3; and

L is a linking group.

In another specific embodiment, the invention provides a compound of which is a compound of the formula:

[DRUG]-($A^0$)$_{nn}$ or a pharmaceutically acceptable salt thereof wherein,

DRUG is a compound of any one of formulae 500-611;

nn is 1, 2, or 3;

$A^0$ is $A^1$, $A^2$, or $W^3$ with the proviso that the compound includes at least one $A^1$;

$A^1$ is:

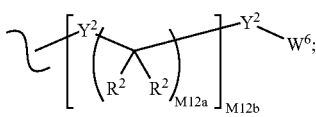

$A^2$ is:

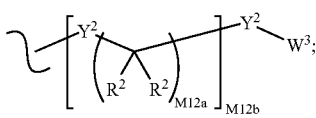

$A^3$ is:

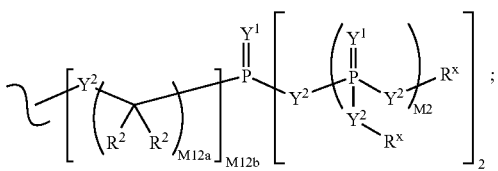

$Y^1$ is independently O, S, N($R^x$), N(O)($R^x$), N(O$R^x$), N(O)(O$R^x$), or N(N($R^x$)($R^x$));

$Y^2$ is independently a bond, O, N($R^x$), N(O)($R^x$), N(O$R^x$), N(O)(O$R^x$), N(N($R^x$)($R^x$)), —S(O)$_{M2}$—, or —S(O)$_{M2}$—S(O)$_{M2}$—;

$R^x$ is independently H, $W^3$, a protecting group, or the formula:

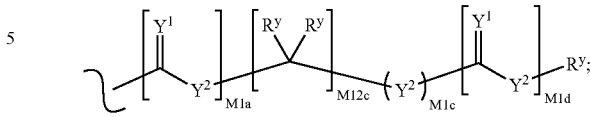

$R^y$ is independently H, $W^3$, $R^2$ or a protecting group;

$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —NO$_2$;

$R^{3b}$ is $Y^1$;

$R^{3c}$ is $R^x$, N($R^x$)($R^x$), —S$R^x$, —S(O)$R^x$, —S(O)$_2R^x$, —S(O)(O$R^x$), —S(O)$_2$(O$R^x$), —OC($Y^1$)$R^x$, —OC($Y^1$)O$R^x$, —OC($Y^1$)(N($R^x$)($R^x$)), —SC($Y^1$)$R^x$, —SC($Y^1$)O$R^x$, —SC($Y^1$)(N($R^x$)($R^x$)), —N($R^x$)C($Y^1$)$R^x$, N($R^x$)C($Y^1$)O$R^x$, or —N($R^x$)C($Y^1$)(N($R^x$)($R^x$));

$R^{3d}$ is —C($Y^1$)$R^x$, —C($Y^1$)O$R^x$ or —C($Y^1$)(N($R^x$)($R^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —C($Y^1$)$R^5$, —C($Y^1$)$W^5$, —SO$_2R^5$, or —SO$_2W^5$;

$W^5$ is carbocycle or heterocycle wherein $W^5$ is independently substituted with 0 to 3 $R^2$ groups;

$W^6$ is $W^3$ independently substituted with 1, 2, or 3 A groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

$X^{66}$ is hydrogen or fluorine; and $X^{67}$ is hydrogen, hydroxy, or acyloxy.

In one specific embodiment of the invention $X^{61}$ is methoxy, ethoxy, n-propoxy, difluoromethoxy, trifluoromethoxy, ethyl, methyl, propyl, or n-butyl)

In compounds of the invention $W^5$ carbocycles and $W^5$ heterocycles may be independently substituted with 0 to 3 $R^2$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

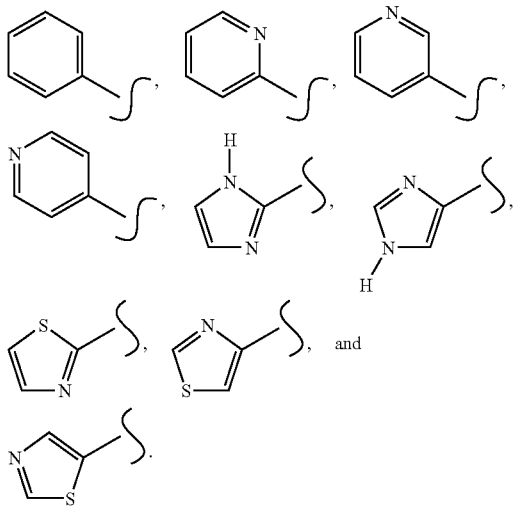

$W^5$ carbocycles and heterocycles may be independently substituted with 0 to 3 $R^2$ groups, as defined above. For example, substituted $W^5$ carbocycles include:

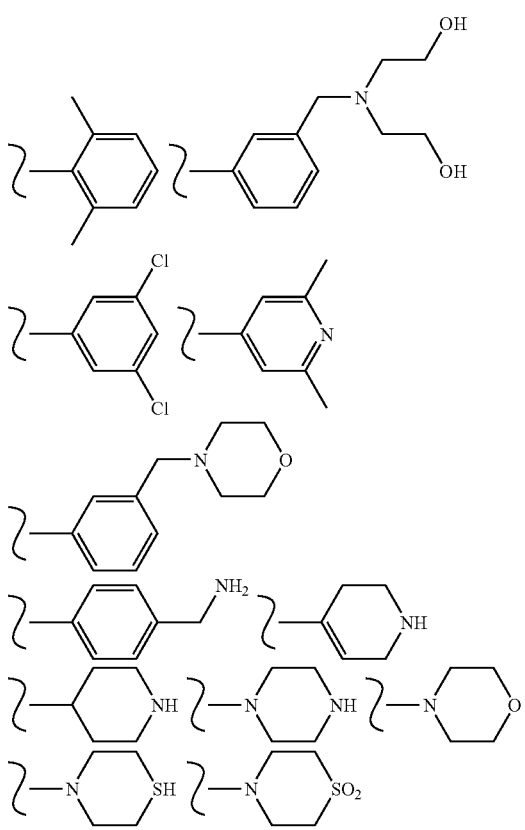

Examples of substituted phenyl carbocycles include:

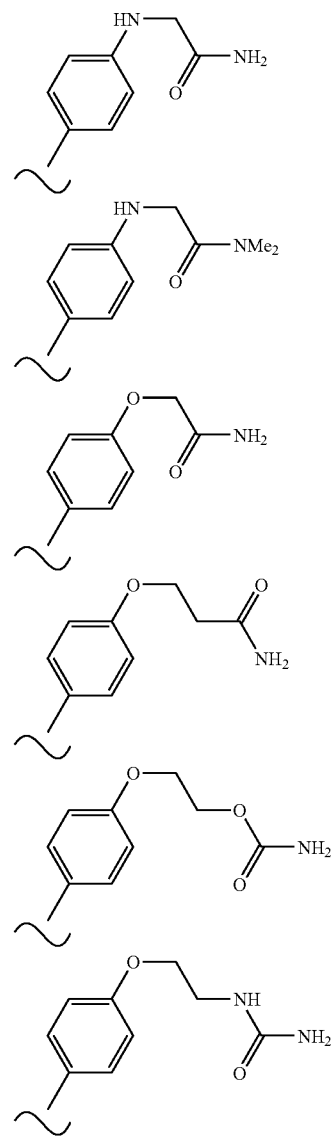

Linking Groups and Linkers

The invention provides conjugates that comprise an anti-inflammatory compound that is linked to one or more phosphonate groups either directly (e.g. through a covalent bond) or through a linking group (i.e. a linker). The nature of the linker is not critical provided it does not interfere with the ability of the phosphonate containing compound to function as a therapeutic agent. The phosphonate or the linker can be linked to the compound (e.g. a compound of 500-611) at any synthetically feasible position on the compound by removing a hydrogen or any portion of the compound to provide an open valence for attachment of the phosphonate or the linker.

In one embodiment of the invention the linking group or linker (which can be designated "L") can include all or a portions of the group $A^0, A^1, A^2, A^3,$ or $W^3$ described herein, such as for example, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

In another embodiment of the invention the linking group or linker has a molecular weight of from about 20 daltons to about 400 daltons.

In another embodiment of the invention the linking group or linker has a length of about 5 angstroms to about 300 angstroms.

In another embodiment of the invention the linking group or linker separates the DRUG and the phosphorous of the phosphonate group by about 5 angstroms to about 200 angstroms, inclusive, in length.

In another embodiment of the invention the linking group or linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, ($C_3$-$C_6$)Cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In another embodiment of the invention the linking group or linker is of the formula W-A wherein A is ($C_1$-$C_{24}$)alkyl, ($C_2$-$C_{24}$)alkenyl, ($C_2$-$C_{24}$)alkynyl, ($C_3$-$C_8$)Cycloalkyl, ($C_6$-$C_{10}$)aryl or a combination thereof, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or ($C_1$-$C_6$)alkyl.

In another embodiment of the invention the linking group or linker is a divalent radical formed from a peptide.

In another embodiment of the invention the linking group or linker is a divalent radical formed from an amino acid.

In another embodiment of the invention the linking group or linker is a divalent radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In another embodiment of the invention the linking group or linker is of the formula W—(CH$_2$)$_n$ wherein, n is between about 1 and about 10; and W is —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or ($C_1$-$C_6$)alkyl.

In another embodiment of the invention the linking group or linker is methylene, ethylene, or propylene.

In another embodiment of the invention the linking group or linker is attached to the phosphonate group through a carbon atom of the linker.

Intracellular Targeting

The phosphonate group of the compounds of the invention may cleave in vivo in stages after they have reached the desired site of action, i.e. inside a cell. One mechanism of action inside a cell may entail a first cleavage, e.g. by esterase, to provide a negatively-charged "locked-in" intermediate. Cleavage of a terminal ester grouping in a compound of the invention thus affords an unstable intermediate which releases a negatively charged "locked in" intermediate.

After passage inside a cell, intracellular enzymatic cleavage or modification of the phosphonate or prodrug compound may result in an intracellular accumulation of the cleaved or modified compound by a "trapping" mechanism. The cleaved or modified compound may then be "locked-in" the cell by a significant change in charge, polarity, or other physical property change which decreases the rate at which the cleaved or modified compound can exit the cell, relative to the rate at which it entered as the phosphonate prodrug. Other mechanisms by which a therapeutic effect are achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

From the foregoing, it will be apparent that many different drugs can be derivatized in accord with the present invention. Numerous such drugs are specifically mentioned herein. However, it should be understood that the discussion of drug families and their specific members for derivatization according to this invention is not intended to be exhaustive, but merely illustrative.

Anti-Inflammatory Compound

The compounds of the invention include those with anti-inflammatory activity. The compounds of the inventions bear one or more (e.g. 1, 2, 3, or 4) phosphonate groups, which may be or may include a prodrug moiety (e.g., a phosphonate diester, phosphonamidate-ester prodrug, or a phosphondiamidate-ester (Jiang et al., U.S. 2002/0173490 A1).

The term "anti-inflammatory compound" includes those compounds having anti-inflammatory activity that are described in *J. Org. Chem.* 64:1042-1044 (1999); *J. Org. Chem.* 64:1042-1044 (1999); U.S. Pat. No. 4,335,121; U.S. Pat. No. 4,472,393; *Tetrahedron*, 1999, 55, 3355-3364; *J. Pharm. Sci.* 1985, 74, 365-374; U.S. Pat. No. 4,472,392; *Drug Dev. Ind. Pharm.*, 1994, 20, 2479-2492; U.S. Pat. No. 3,312,590; *Eur. J. Clin. Pharmacol.* 1992, 43, 157-159; *J. Am. Acad. Dermatol.* 1993, 29, 576-580; U.S. Pat. No. 4,786,637; U.S. Pat. No. 4,753,935; Lee et al. *Pharm Res*, 1990, 7, 161; U.S. Pat. No. 3,929,768; U.S. Pat. No. 4,680,299; U.S. Pat. No. 5,032,597; EP00184162A2; EP00184162A2; U.S. Pat. No. 3,929,992; U.S. Pat. No. 3,993,749; U.S. Pat. No. 4,873,259; and *Biochemistry*, 2003, 42, 6057. The definition of anti-inflammatory compound includes not only the generic disclosures cited above but also each and every species set forth therein. The phosphonate group may be a phosphonate prodrug moiety. The prodrug moiety may be sensitive to hydrolysis, such as, but not limited to, a pivaloyloxymethyl carbonate (POC) or POM group. Alternatively, the prodrug moiety may be sensitive to enzymatic potentiated cleavage, such as a lactate ester or a phosphonamidate-ester group.

The term "anti-inflammatory compound" also includes theophylline, methylxanthine, metamizole, rofecoxib, meloxicam, piroxicam, valdecoxib, tenoxicam, celecoxib, etodolac, etoricoxib, ibuprofin, naproxen, loxoprofen, diclofenac, relafen, mefenamic acid, nimesulide, aspirin, oxaprozin, toradol, R ketorolac, steroid phosphonates, pimecrolimus, everolimus, sirolimus, raltitrexed (tomudex), parecoxib, nimesulide, aminopterin, lumiracoxib, tacrolimus, prednisolone, rolipram, CC-1088, CDP 840, cilomilast, piclamilast, roflumilast, atizoram, VX-148, brequinar, diflunisal, doramapimod, tolfenamic acid, droxicam, flurbiprofen, indomethacin, lornoxicam, NCX-701, 10-propargyl-10-deaza-aminopterin (PDX), talniflumate, thalidomide, dexketoprofen, zardaverine, nabumetone, licofelone, ketorolac, BCX-1777, amtolmetine guacil, aceclofenac, metoxibutropate, oxaprozin, sulindac, revimid, diprolene, aclometasone, hydrocortisone, vanceril, leflunomide, methylprednisolone suleptanate, prednisone, clobetasol, SMP-114, teriflunomide, salicylic acid, etoricoxib, L-791,943, halobetasol propionate, ciclesonide, deflazacort, flunisolide, medroxyprogesterone, triamcinolone acetonide, rimexolone, fluticasone, mometasone furoate, methylprednisolone suleptanate, beclometasone, methylprednisolone aceponate, merimepodib, mycophenolate, budesonide, dexamethasone, brequinar, immunosuppressive macrolide, methotrexate, zileuton, PNP-405, MDL-74428, prodrugs of 9-(3,3-dimethyl-5-phosphonopentyl) guanine, prodrugs of DADME-IMMG, leflunomide, zardaverine, cyclosporine A, and mizoribine.

Typically, compounds of the invention have a molecular weight of from about 400 amu to about 10,000 amu; in a specific embodiment of the invention, compounds have a molecular weight of less than about 5000 amu; in another specific embodiment of the invention, compounds have a molecular weight of less than about 2500 amu; in another specific embodiment of the invention, compounds have a molecular weight of less than about 1000 amu; in another specific embodiment of the invention, compounds have a molecular weight of less than about 800 amu; in another specific embodiment of the invention, compounds have a molecular weight of less than about 600 amu; and in another specific embodiment of the invention, compounds have a molecular weight of less than about 600 amu and a molecular weight of greater than about 400 amu.

The compounds of the invention also typically have a logD (polarity) less than about 5. In one embodiment the invention provides compounds having a logD less than about 4; in another one embodiment the invention provides compounds having a logD less than about 3; in another one embodiment the invention provides compounds having a logD greater than about −5; in another one embodiment the invention provides compounds having a logD greater than about −3; and in another one embodiment the invention provides compounds having a logD greater than about 0 and less than about 3.

Selected substituents within the compounds of the invention are present to a recursive degree. In this context, "recursive substituent" means that a substituent may recite another instance of itself. Because of the recursive nature of such substituents, theoretically, a large number may be present in any given claim. For example, $R^x$ contains a $R^y$ substituent. $R^y$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$, $R^y$ and $R^3$ are all recursive substituents in certain claims. Typically, each of these may independently occur 20, 19, 18, 17, 16, 15, 14, 13, 12, 11, 10, 9, 8, 7, 6, 5, 4, 3, 2, 1, or 0, times in a given claim. More typically, each of these may independently occur 12 or fewer times in a given claim. More typically yet, $W^3$ will occur 0 to 8 times, $R^y$ will occur 0 to 6 times and $R^3$ will occur 0 to 10 times in a given claim. Even more typically, $W^3$ will occur 0 to 6 times, $R^y$ will occur 0 to 4 times and $R^3$ will occur 0 to 8 times in a given claim.

Recursive substituents are an intended aspect of the invention. One of ordinary skill in the art of medicinal chemistry understands the versatility of such substituents. To the degree that recursive substituents are present in an claim of the invention, the total number will be determined as set forth above.

Whenever a compound described herein is substituted with more than one of the same designated group, e.g., "$R^1$" or "$R^{6a}$", then it will be understood that the groups may be the same or different, i.e., each group is independently selected.

Wavy lines indicate the site of covalent bond attachments to the adjoining groups, moieties, or atoms.

In one specific embodiment of the invention, the anti-inflammatory compound is a non-steroidal anti-inflammatory compound (e.g. a compound of formula 500-522, 525-565, 572-574, 579-583, 585-586, and 598-600 and 602-611).

In another specific embodiment of the invention, the anti-inflammatory compound is a steroidal anti-inflammatory compound. Steroidal anti-inflammatory compounds include those compounds that include the following fused ring system:

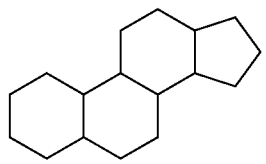

In one embodiment of the invention, the anti-inflammatory compound is a steroidal anti-inflammatory compound that includes the following fused ring system:

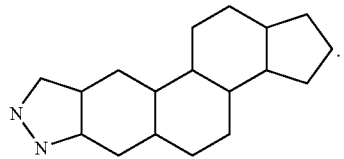

In another embodiment of the invention, the anti-inflammatory compound is a steroidal anti-inflammatory compound of any one of formulae 523-524, 566-571, 575-578, 584, and 587-597, and 601.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

In one embodiment of the invention, the compound is not a purine nucleoside phosphorylase inhibitor; in one embodiment the compound is not an anti-cancer agent; in one embodiment the compound is not active against immune-mediated conditions; in one embodiment the compound is not active against metabolic diseases the compound is not an antiviral agent; in one embodiment not a nucleoside; in one embodiment the compound is not a kinase inhibitor; in one embodiment the compound is not an antimetabolite; in one embodiment the compound is not an IMPDH inhibitor; in one embodiment the compound is not an anti-infective; in one embodiment the compound is not a compound of formula 242 or 243; in one embodiment the compound is not a compound of any one of formulae 74-76, 199-203, 279-280, 204-210, and 286-292; in one embodiment the compound is not a compound of any one of formulae 45-47, 56-58, 229, 95-97, and 226-233; in one embodiment the compound is not a compound of any one of formulae 82-85; in one embodiment the compound is not a compound of any one of formulae 106-107, 235-243, and 281-285; in one embodiment the compound is not a compound of any one of formulae 106-107 and 242-243; in one embodiment the compound is not a compound of any one of formulae 74-76, 199-203, 204-210, 281-285, and 286-292; in one embodiment the compound is not a compound of any one of formulae 14, 41-44, 63-65, 74-76, 79-80, 99-100, 106-107, 113-126, 204-210, 133-155, 165-173, 177-192, 196-210, 214-243, 249-250, 272-274, 269-271, 275-280, 286-292, and 293-296; in one embodiment the compound is not a compound of any one of formulae 43-47, 56-58, 229, 74-79, 95-97, 99-100, 106-107, 113-114, 124-126, 133-138, 154-155, 158-159, 165-167, 199-210, 214-224, 226-233, 235-243, 249-250, and 279-292; in one embodiment the compound is not a compound of any one of formulae 503, 526-528, 531, 542, 551, 554, 557, 559, 565, 569, 572-574, 577, 585, 587, 598-600, 602, 603, 605, 607, 608, and 609; in one embodiment the compound is not a compound of any one of formulae 525-527, 533, 534, 542, 554, 557, 559, 563, 565-567, 569, 572-579, 585, 587-589, 591-595, 597-600, 602, 604-605, and 607-611; in one embodiment the compound is not a compound of any one of formulae 598-600, 577, and 608; in one embodiment the compound is not a compound of formula 557 or 585; in one embodiment the compound is not a compound of any one of formulae 557, 577, 585, 602, 607, and 609; in one embodiment the compound is not a compound of formula 544; in one embodiment the compound is not a compound of any one of formulae 528, 531, 551, and 605; in one embodiment the compound is not a compound of any one of formulae 559, 598-600 and 608; and in one embodiment the compound is not a compound of formula 585.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the iinvention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of Inflammation

Another aspect of the invention relates to methods of inhibiting inflammation comprising the step of treating a sample or subject suspected of needing such inhibition with a composition of the invention.

Compositions of the invention may act as inhibitors of inflammation or as intermediates for such inhibitors or have other utilities as described below. The inhibitors may bind to locations on the surface or in a cavity of a cell having a geometry unique to the specific compound or a portion of the compound. Compositions binding a cell may bind with varying degrees of reversibility. Those compounds binding substantially irreversibly are ideal candidates for use in this method of the invention. Once labeled, the substantially irreversibly binding compositions are useful as probes for the detection of inflammation. Accordingly, the invention relates to methods of detecting inflammation in a sample or subject suspected of being inflamed or of including an inflammatory agent, comprising the steps of: treating such a sample or subject with a composition comprising a compound of the invention bound to (or comprising) a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention a "sample" suspected of being inflamed or including an inflammatory agent include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Samples can be contained in any medium including water and organic solvent\water mixtures. Samples include living organisms such as humans, and man made materials such as cell cultures.

The treating step of the invention comprises adding the compound of the invention to the sample or it comprises adding a precursor of the compound to the sample. The addition step comprises any method of administration as described herein.

If desired, the anti-inflammatory activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(S) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(S) in an amount of, for example, 0.075 to 20% w/w (including active ingredient(S) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(S) with or without stabilizer(S) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment of inflammation as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses) or against existing inflammation, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention can also be used in combination with other active ingredients. Such combinations are typically selected based on the condition to be treated, cross-reactivities of ingredients and pharmaco-properties of the combination. For example, when treating inflammation the compositions of the invention can be combined with other anti-inflammatory compounds.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" or a "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-inflammatory effect denotes an anti-inflammatory effect which is greater than the predicted purely additive effects of the individual compounds of the combination.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess noanti-inflammatory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

Exemplary Methods of Making the Compounds of the Invention.

The invention also relates to methods of making the compounds of the invention. The compounds are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry*. In 9 Volumes, Barry M. Trost, Editor-in-Chief (Pergamon Press, New York, 1993 printing).

Schemes and Examples

General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

Anti-Inflammatory Activity

Compositions of the invention are screened for anti-inflammatory activity by any of the conventional techniques for evaluating enzyme activity. Within the context of the invention, typically compositions are first screened for inhibitory activity in vitro and compositions showing inhibitory activity are then screened for activity in vivo. Compositions having in vitro Ki (inhibitory constants) of less then about $5 \times 10^{-6}$ M, typically less than about $1 \times 10^{-7}$ M and preferably less than about $5 \times 10^{-8}$ M are preferred for in vivo use. For example, the anti-inflammatory properties of the compounds of the invetion can be assessed using assays available to the art worker, e.g., using the methods described in *Brit. J. Pharmacol.*, 1997, 121, 171; *Anal. Biochem.*, 1995, 231, 354; *Pharmacol. Exp. Ther.*, 1992, 263, 1195; and/or *Eur. J. Pharmacol.*, 1995, 281, 107.

The anti-inflammatory properties of a compound may also be assessed by measuring the inhibition of IMPDH, e.g., using the following general method.

IMPDH Inhibition Assay Protocol

The following reagents are used to measure the IMPDH inhibitory activity: Tris-HCL pH=8.0 (Sigma #41K8411); KCl (Sigma # P-9541); EDTA (Sigma # E-7889); DTT (Sigma # D-9779); β-NAD+ (Sigma#N-6522); IMP (Sigma #I-4625); IMPDH II (Sigma #I-1782); Glycerol (Sigma# G-7757); and a 96 Well UV Transparent (BD Falcon #).

The following solutions are prepared, with all components diluted in de-ionized water: Solution #1 is 135 mM Tris, pH=8.0; Solution #2 is 625 mM KCl, 19 uM EDTA, 6.5 mM DTT, pH=8.0; Solution #3 is 13 mM β-NAD+; Solution #4 is 6 mM IMP; Solution #5 is 20 mM Tris, 0.5 mM EDTA, 1 mM DTT, 10% Glycerol.

To prepare the reagent cocktail, combine 11.5 mL of Solution #1, 2.5 mL of Solution #2, and 0.5 mL of Solution #3, and adjust the to pH=8.0. Dilute IMPDH II in Solution #5 to a final concentration of 11.5 nM.

To determine the IMPDH inhibition, first add 280 μL of the reagent cocktail and 10 uL of Solution #4 to each Reaction. Then, initiate the reaction by the addition of 10 μL of IMPDH II enzyme and read the plate at time=0 min at 340 nm. Then, incubate the plate at 37° C. for 5 hours. Finally, read the plate at 340 nM after 5 hrs.

The final assay concentrations, at 37° C., are: Tris, 100 mM, pH 8.0; potassium chloride, 100 mM; EDTA, 3.1 mM; DTT, 1.1 mM; glycerol, 0.33% (v/v); Beta-NAD, 0.42 mM; and IMP, 0.2 mM.

The anti-inflammatory properties of the compounds can also be assessed by measuring the inhibition of cell proliferation, e.g., using the following method.

Cell Proliferation Assay Protocol

Peripheral blood mononuclear cells ($1 \times 10^5$ cells/well) are cultured in microtiter plates with RPMI-1640 (Gibco) supplemented with 5% fetal calf serum, penicillin and streptomycin, with a final volume of 0.2 mL. Phytohemagglutinin (PHA-L) is used at a concentration of 10 μg/mL to stimulate cell proliferation. The cells are incubated at 37° C. in an atmosphere of air with 7% $CO_2$ and 100% humidity for 72 hrs. A pulse of 0.5 μCi/well tritiated thymidine is added for the final 6-16 h culture. Cells are harvested and the uptake of radioactivity measured by standard scintillation procedures.

Examples General Section

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention. For example, the interconversion of various phosphonate compounds of the invention is illustrated below.

Interconversions of the Phosphonates R-LINK-P(O)($^{OR1}$)$_2$, R-LINK-P(O)($^{OR1}$)(OH) AND R-LINK-P(O)(OH)$_2$.

The following schemes 32-38 described the preparation of phosphonate esters of the general structure R-link-P(O)($^{OR1}$)$_2$, in which the groups R$^1$ may be the same or different. The R$^1$ groups attached to a phosphonate ester, or to precursors thereto, may be changed using established chemical transformations. The interconversion reactions of phosphonates are illustrated in Scheme S32. The group R in Scheme 32 represents the substructure, i.e. the drug "scaffold, to which the substituent link-P(O)($^{OR1}$)$_2$ is attached, either in the compounds of the invention, or in precursors thereto. At the point in the synthetic route of conducting a phosphonate interconversion, certain functional groups in R may be protected. The methods employed for a given phosphonate transformation depend on the nature of the substituent R$^1$, and of the substrate to which the phosphonate group is attached. The preparation and hydrolysis of phosphonate esters is described in *Organic Phosphorus Compounds*, G. M. Kosolapoff, L. Maeir, eds, Wiley, 1976, p. 9ff.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med. Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I,* 1577). Chlorophosphonate species may also be generated in situ from corresponding cyclic phosphites (Silverburg, et al., (1996) *Tetrahedron lett.*, 37:771-774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron lett.*, 29:5763-66).

Phosphonate prodrugs of the present invention may also be prepared from the free acid by Mitsunobu reactions (Mitsunobu, (1981) Synthesis, 1; Campbell, (1992) *J. Org. Chem.* 57:6331), and other acid coupling reagents including, but not limited to, carbodiimides (Alexander, et al, (1994) *Collect. Czech. Chem. Commun.* 59:1853; Casara et al, (1992) *Bioorg. Med. Chem. Lett.* 2:145; Ohashi et al, (1988) *Tetrahedron Lett.*, 29:1189), and benzotriazolyloxytris-(dimethylamino) phosphonium salts (Campagne et al (1993) *Tetrahedron Lett.* 34:6743).

Aryl halides undergo Ni$^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis et al (1987) *J. Am. Chem. Soc.* 109:2831; Lu et al (1987) *Synthesis* 726). In another method, aryl phosphonate esters are prepared from aryl phosphates under anionic rearrangement conditions (Melvin (1981) *Tetrahedron Lett.* 22:3375; Casteel et al (1991) *Synthesis,* 691). N-Alkoxy aryl salts with alkali metal derivatives of cyclic alkyl phosphonate provide general synthesis for heteroaryl-2-phosphonate linkers (Redmore (1970) *J. Org. Chem.* 35:4114). These above mentioned methods can also be extended to compounds where the W$^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethyl-carbodiimide hydrochloride (EDCI) can also be utilized for the synthesis of cyclic phosphonate prodrugs.

The conversion of a phosphonate diester S32.1 into the corresponding phosphonate monoester S32.2 (Scheme 32, Reaction 1) is accomplished by a number of methods. For example, the ester S32.1 in which R$^1$ is an aralkyl group such as benzyl, is converted into the monoester compound S32.2 by reaction with a tertiary organic base such as diazabicyclooctane (DABCO) or quinuclidine, as described in *J. Org. Chem.* (1995) 60:2946. The reaction is performed in an inert hydrocarbon solvent such as toluene or xylene, at about 110° C. The conversion of the diester S32.1 in which R$^1$ is an aryl group such as phenyl, or an alkenyl group such as allyl, into the monoester S32.2 is effected by treatment of the ester S32.1 with a base such as aqueous sodium hydroxide in acetonitrile or lithium hydroxide in aqueous tetrahydrofuran. Phosphonate diesters S32.1 in which one of the groups R$^1$ is aralkyl, such as benzyl, and the other is alkyl, is converted into the monoesters S32.2 in which R$^1$ is alkyl by hydrogenation, for example using a palladium on carbon catalyst. Phosphonate diesters in which both of the groups R$^1$ are alkenyl, such as allyl, is converted into the monoester S32.2 in which R$^1$ is alkenyl, by treatment with chlorotris(triphenylphosphine) rhodium (Wilkinson's catalyst) in aqueous ethanol at reflux, optionally in the presence of diazabicyclooctane, for example by using the procedure described in *J. Org. Chem.* (1973) 38:3224, for the cleavage of allyl carboxylates.

The conversion of a phosphonate diester S32.1 or a phosphonate monoester S32.2 into the corresponding phosphonic acid S32.3 (Scheme 32, Reactions 2 and 3) can be effected by reaction of the diester or the monoester with trimethylsilyl bromide, as described in *J. Chem. Soc., Chem. Comm.*, (1979) 739. The reaction is conducted in an inert solvent such as, for example, dichloromethane, optionally in the presence of a silylating agent such as bis(trimethylsilyl)trifluoroacetamide, at ambient temperature. A phosphonate monoester S32.2 in which R$^1$ is aralkyl such as benzyl, is converted into the corresponding phosphonic acid S32.3 by hydrogenation over a palladium catalyst, or by treatment with hydrogen chloride in an ethereal solvent such as dioxane. A phosphonate monoester S32.2 in which R$^1$ is alkenyl such as, for example, allyl, is converted into the phosphonic acid S32.3 by reaction with Wilkinson's catalyst in an aqueous organic solvent, for example in 15% aqueous acetonitrile, or in aqueous ethanol, for example using the procedure described in *Helv. Chim. Acta.* (1985) 68:618. Palladium catalyzed hydrogenolysis of phosphonate esters S32.1 in which R$^1$ is benzyl is described in *J. Org. Chem.* (1959) 24:434. Platinum-catalyzed hydrogenolysis of phosphonate esters S32.1 in which R¹ is phenyl is described in *J. Am. Chem. Soc.* (1956) 78:2336.

The conversion of a phosphonate monoester S32.2 into a phosphonate diester S32.1 (Scheme 32, Reaction 4) in which the newly introduced R¹ group is alkyl, aralkyl, haloalkyl such as chloroethyl, or aralkyl is effected by a number of reactions in which the substrate S32.2 is reacted with a hydroxy compound R¹OH, in the presence of a coupling agent. Typically, the second phosphonate ester group is different than the first introduced phosphonate ester group, i.e. R¹ is followed by the introduction of R² where each of R¹ and R² is alkyl, aralkyl, haloalkyl such as chloroethyl, or aralkyl (Scheme 32, Reaction 4a) whereby S32.2 is converted to S32.1a. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester S32.2 to the diester S32.1 is effected by the use of the Mitsunobu reaction, as described above (Scheme 7). The substrate is reacted with the hydroxy compound R¹OH, in the presence of diethyl azodicarboxylate and a triarylphosphine such as triphenyl phosphine. Alternatively, the phosphonate monoester S32.2 is transformed into the phosphonate diester S32.1, in which the introduced R¹ group is alkenyl or aralkyl, by reaction of the monoester with the halide R¹Br, in which R¹ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester S32.2 is transformed into the chloro analog RP(O)($^{OR1}$)Cl by reaction with thionyl chloride or oxalyl chloride and the like, as described in *Organic Phosphorus Compounds*, G. M. Kosolapoff, L. Maeir, eds, Wiley, 1976, p. 17, and the thus-obtained product RP(O)($^{OR1}$)Cl is then reacted with the hydroxy compound R¹OH, in the presence of a base such as triethylamine, to afford the phosphonate diester S32.1.

A phosphonic acid R-link-P(O)(OH)₂ is transformed into a phosphonate monoester RP(O)($^{OR1}$)(OH) (Scheme 32, Reaction 5) by means of the methods described above of for the preparation of the phosphonate diester R-link-P(O)(OR¹)₂ S32.1, except that only one molar proportion of the component R¹OH or R¹Br is employed. Dialkyl phosphonates may be prepared according to the methods of: Quast et al (1974) *Synthesis* 490; Stowell et al (1990) *Tetrahedron Lett.* 3261; U.S. Pat. No. 5,663,159.

A phosphonic acid R-link-P(O)(OH)₂ S32.3 is transformed into a phosphonate diester R-link-P(O)($^{OR1}$)₂ S32.1 (Scheme 32, Reaction 6) by a coupling reaction with the hydroxy compound R¹OH, in the presence of a coupling agent such as Aldrithiol-2 (Aldrich) and triphenylphosphine. The reaction is conducted in a basic solvent such as pyridine. Alternatively, phosphonic acids S32.3 are transformed into phosphonic esters S32.1 in which R¹ is aryl, by means of a coupling reaction employing, for example, dicyclohexylcarbodiimide in pyridine at ca 70° C. Alternatively, phosphonic acids S32.3 are transformed into phosphonic esters S32.1 in which R¹ is alkenyl, by means of an alkylation reaction. The phosphonic acid is reacted with the alkenyl bromide R¹Br in a polar organic solvent such as acetonitrile solution at reflux temperature, the presence of a base such as cesium carbonate, to afford the phosphonic ester S32.1.

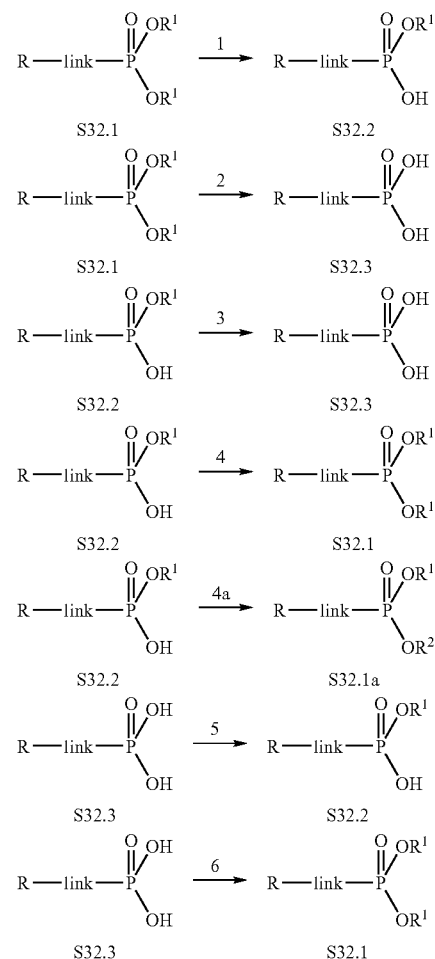

Scheme 32

Preparation of Phosphonate Carbamates.

Phosphonate esters may contain a carbamate linkage. The preparation of carbamates is described in *Comprehensive Organic Functional Group Transformations*, A. R. Katritzky, ed., Pergamon, 1995, Vol. 6, p. 416ff, and in *Organic Functional Group Preparations*, by S. R. Sandler and W. Karo, Academic Press, 1986, p. 260ff. The carbamoyl group may be formed by reaction of a hydroxy group according to the methods known in the art, including the teachings of Ellis, U.S. 2002/0103378 A1 and Hajima, U.S. Pat. No. 6,018,049.

Scheme 33 illustrates various methods by which the carbamate linkage is synthesized. As shown in Scheme 33, in the general reaction generating carbamates, an alcohol S33.1, is converted into the activated derivative S33.2 in which Lv is a leaving group such as halo, imidazolyl, benztriazolyl and the like, as described herein. The activated derivative S33.2 is then reacted with an amine S33.3, to afford the carbamate product S33.4. Examples 1-7 in Scheme 33 depict methods by which the general reaction is effected. Examples 8-10 illustrate alternative methods for the preparation of carbamates.

Scheme 33, Example 1 illustrates the preparation of carbamates employing a chloroformyl derivative of the alcohol S33.5. In this procedure, the alcohol S33.5 is reacted with phosgene, in an inert solvent such as toluene, at about 0° C., as described in *Org. Syn. Coll. Vol.* 3, 167, 1965, or with an equivalent reagent such as trichloromethoxy chloroformate, as described in *Org. Syn. Coll. Vol.* 6, 715, 1988, to afford the chloroformate S33.6. The latter compound is then reacted with the amine component S33.3, in the presence of an organic or inorganic base, to afford the carbamate S33.7. For example, the chloroformyl compound S33.6 is reacted with the amine S33.3 in a water-miscible solvent such as tetrahydrofuran, in the presence of aqueous sodium hydroxide, as described in *Org. Syn. Coll. Vol.* 3, 167, 1965, to yield the carbamate S33.7. Alternatively, the reaction is performed in dichloromethane in the presence of an organic base such as diisopropylethylamine or dimethylaminopyridine.

Scheme 33, Example 2 depicts the reaction of the chloroformate compound S33.6 with imidazole to produce the imidazolide S33.8. The imidazolide product is then reacted with the amine S33.3 to yield the carbamate S33.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in *J. Med. Chem.*, 1989, 32, 357.

Scheme 33 Example 3, depicts the reaction of the chloroformate S33.6 with an activated hydroxyl compound R"OH, to yield the mixed carbonate ester S33.10. The reaction is conducted in an inert organic solvent such as ether or dichloromethane, in the presence of a base such as dicyclohexylamine or triethylamine. The hydroxyl component R"OH is selected from the group of compounds S33.19-S33.24 shown in Scheme 33, and similar compounds. For example, if the component R"OH is hydroxybenztriazole S33.19, N-hydroxysuccinimide S33.20, or pentachlorophenol, S33.21, the mixed carbonate S33.10 is obtained by the reaction of the chloroformate with the hydroxyl compound in an ethereal solvent in the presence of dicyclohexylamine, as described in *Can. J. Chem.*, 1982, 60, 976. A similar reaction in which the component R"OH is pentafluorophenol S33.22 or 2-hydroxypyridine S33.23 is performed in an ethereal solvent in the presence of triethylamine, as described in *Syn.*, 1986, 303, and *Chem. Ber.* 118, 468, 1985.

Scheme 33 Example 4 illustrates the preparation of carbamates in which an alkyloxycarbonylimidazole S33.8 is employed. In this procedure, an alcohol S33.5 is reacted with an equimolar amount of carbonyl diimidazole S33.11 to prepare the intermediate S33.8. The reaction is conducted in an aprotic organic solvent such as dichloromethane or tetrahydrofuran. The acyloxyimidazole S33.8 is then reacted with an equimolar amount of the amine R'NH$_2$ to afford the carbamate S33.7. The reaction is performed in an aprotic organic solvent such as dichloromethane, as described in *Tet. Lett.*, 42, 2001, 5227, to afford the carbamate S33.7.

Scheme 33, Example 5 illustrates the preparation of carbamates by means of an intermediate alkoxycarbonylbenztriazole S33.13. In this procedure, an alcohol ROH is reacted at ambient temperature with an equimolar amount of benztriazole carbonyl chloride S33.12, to afford the alkoxycarbonyl product S33.13. The reaction is performed in an organic solvent such as benzene or toluene, in the presence of a tertiary organic amine such as triethylamine, as described in *Synthesis.*, 1977, 704. The product is then reacted with the amine R'NH$_2$ to afford the carbamate S33.7. The reaction is conducted in toluene or ethanol, at from ambient temperature to about 80° C. as described in *Synthesis.*, 1977, 704.

Scheme 33, Example 6 illustrates the preparation of carbamates in which a carbonate (R"O)$_2$CO, S33.14, is reacted with an alcohol S33.5 to afford the intermediate alkyloxycarbonyl intermediate S33.15. The latter reagent is then reacted with the amine R'NH$_2$ to afford the carbamate S33.7. The procedure in which the reagent S33.15 is derived from hydroxybenztriazole S33.19 is described in Synthesis, 1993, 908; the procedure in which the reagent S33.15 is derived from N-hydroxysuccinimide S33.20 is described in *Tet. Lett.*, 1992, 2781; the procedure in which the reagent S33.15 is derived from 2-hydroxypyridine S33.23 is described in *Tet. Lett.*, 1991, 4251; the procedure in which the reagent S33.15 is derived from 4-nitrophenol S33.24 is described in *Synthesis*. 1993, 103. The reaction between equimolar amounts of the alcohol ROH and the carbonate S33.14 is conducted in an inert organic solvent at ambient temperature.

Scheme 33, Example 7 illustrates the preparation of carbamates from alkoxycarbonyl azides S33.16. In this procedure, an alkyl chloroformate S33.6 is reacted with an azide, for example sodium azide, to afford the alkoxycarbonyl azide S33.16. The latter compound is then reacted with an equimolar amount of the amine R'NH$_2$ to afford the carbamate S33.7. The reaction is conducted at ambient temperature in a polar aprotic solvent such as dimethylsulfoxide, for example as described in *Synthesis.*, 1982, 404.

Scheme 33, Example 8 illustrates the preparation of carbamates by means of the reaction between an alcohol ROH and the chloroformyl derivative of an amine S33.17. In this procedure, which is described in *Synthetic Organic Chemistry*, R. B. Wagner, H. D. Zook, Wiley, 1953, p. 647, the reactants are combined at ambient temperature in an aprotic solvent such as acetonitrile, in the presence of a base such as triethylamine, to afford the carbamate S33.7.

Scheme 33, Example 9 illustrates the preparation of carbamates by means of the reaction between an alcohol ROH and an isocyanate S33.18. In this procedure, which is described in *Synthetic Organic Chemistry*, R. B. Wagner, H. D. Zook, Wiley, 1953, p. 645, the reactants are combined at ambient temperature in an aprotic solvent such as ether or dichloromethane and the like, to afford the carbamate S33.7.

Scheme 33, Example 10 illustrates the preparation of carbamates by means of the reaction between an alcohol ROH and an amine R'NH$_2$. In this procedure, which is described in *Chem. Lett.* 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate S33.7.

Scheme 33. Preparation of carbamates.

General reaction

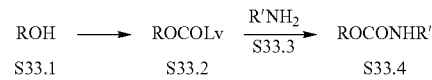

Examples

-continued (2)
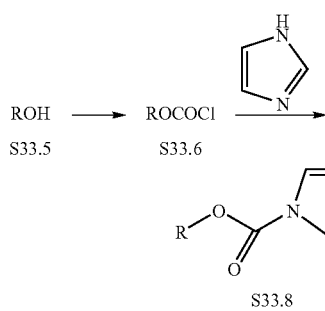

(3)
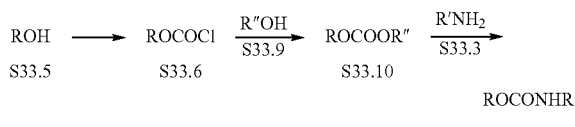

(4)
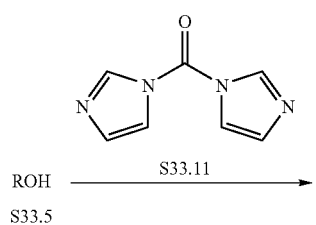

(5)
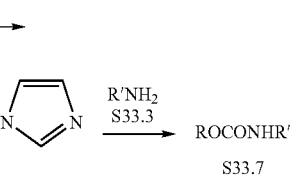

(6) ROH $\xrightarrow[\text{S33.14}]{(R^2O_2)C=O}$ ROCOR'' $\xrightarrow[\text{S33.3}]{R'NH_2}$ ROCONHR'
 S33.5                                  S33.15                          S33.7

(7) ROH $\longrightarrow$ ROCOCl $\longrightarrow$ ROCON$_3$ $\xrightarrow{R'NH_2 \; 33.3}$ ROCONHR'
 S33.5              S33.6                    S33.16                                       33.7

(8) ROH $\xrightarrow[\text{S33.17}]{R'NHCOCl}$ ROCONHR'
 S33.5                             33.7

(9) ROH $\xrightarrow[\text{S33.18}]{R'NCO}$ ROCONHR'
 S33.5                             33.7

(10) ROH $\xrightarrow[\text{S33.3}]{R'NH_2}$ ROCONHR'
 S33.5                             33.7

R''OH =

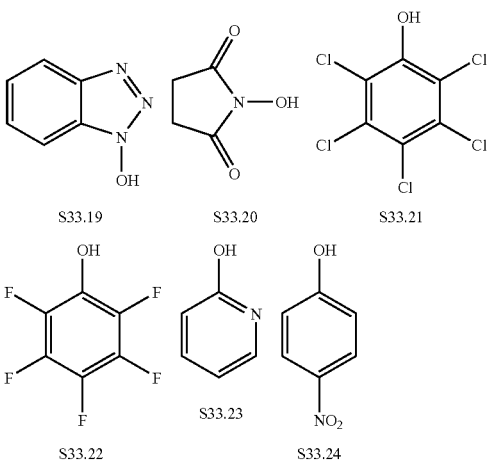

Preparation of Carboalkoxy-Substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in *J. Gen. Chem. USSR*, 1983, 53, 480, *Zh. Obschei Khim.*, 1958, 28, 1063, or *J. Org. Chem.*, 1994, 59, 6144, or by reaction with oxalyl chloride, as described in *J. Am. Chem. Soc.*, 1994, 116, 3251, or *J. Org. Chem.*, 1994, 59, 6144, or by reaction with phosphorus pentachloride, as described in *J. Org. Chem.*, 2001, 66, 329, or in *J. Med. Chem.*, 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in *J. Chem. Soc., Chem. Comm.* (1991) 312, or *Nucleosides & Nucleotides* (2000) 19:1885. Activated sulfonyloxy derivatives are obtained by the reaction of phosphonic acids with trichloromethylsulfonyl chloride or with triisopropylbenzenesulfonyl chloride, as described in *Tet. Lett.* (1996) 7857, or *Bioorg. Med. Chem. Lett.* (1998) 8:663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in *J. Chem. Soc., Chem. Comm.* (1991) 312 or *Coll. Czech. Chem. Comm.* (1987) 52:2792. The use of ethyl dimethylaminopropyl carbodiimide for activation and coupling of phosphonic acids is described in *Tet. Lett.*, (2001) 42:8841, or *Nucleosides & Nucleotides* (2000) 19:1885.

A number of additional coupling reagents have been described for the preparation of amidates and esters from phosphonic acids. The agents include Aldrithiol-2, and PYBOP and BOP, as described in *J. Org. Chem.*, 1995, 60, 5214, and *J. Med. Chem.* (1997) 40:3842, mesitylene-2-sulfonyl-3-nitro-1,2,4-triazole (MSNT), as described in *J. Med. Chem.* (1996) 39:4958, diphenylphosphoryl azide, as described in *J. Org. Chem.* (1984) 49:1158, 1-(2,4,6-triisopropylbenzenesulfonyl-3-nitro-1,2,4-triazole (TPSNT) as described in *Bioorg. Med. Chem. Lett.* (1998) 8:1013, bromotris(dimethylamino)phosphonium hexafluorophosphate (BroP), as described in *Tet. Lett.*, (1996) 37:3997, 2-chloro-5,5-dimethyl-2-oxo-1,3,2-dioxaphosphinane, as described in *Nucleosides Nucleotides* 1995, 14, 871, and diphenyl chlorophosphate, as described in *J. Med. Chem.*, 1988, 31, 1305.

Phosphonic acids are converted into amidates and esters by means of the Mitsunobu reaction, in which the phosphonic acid and the amine or hydroxy reactant are combined in the presence of a triaryl phosphine and a dialkyl azodicarboxylate. The procedure is described in *Org. Lett.*, 2001, 3, 643, or *J. Med. Chem.*, 1997, 40, 3842.

Phosphonic esters are also obtained by the reaction between phosphonic acids and halo compounds, in the presence of a suitable base. The method is described, for example, in *Anal. Chem.*, 1987, 59, 1056, or *J. Chem. Soc. Perkin Trans.*, 1,1993, 19, 2303, or *J. Med. Chem.*, 1995, 38, 1372, or *Tet. Lett.*, 2002, 43, 1161.

Schemes 34-37 illustrate the conversion of phosphonate esters and phosphonic acids into carboalkoxy-substituted phosphonbisamidates (Scheme 34), phosphonamidates (Scheme 35), phosphonate monoesters (Scheme 36) and phosphonate diesters, (Scheme 37). Scheme 38 illustrates synthesis of gem-dialkyl amino phosphonate reagents.

Scheme 34 illustrates various methods for the conversion of phosphonate diesters S34.1 into phosphonbisamidates S34.5. The diester S34.1, prepared as described previously, is hydrolyzed, either to the monoester S34.2 or to the phosphonic acid S34.6. The methods employed for these transformations are described above. The monoester S34.2 is converted into the monoamidate S34.3 by reaction with an aminoester S34.9, in which the group $R^2$ is H or alkyl; the group $R^{4b}$ is a divalent alkylene moiety such as, for example, $CHCH_3$, $CHCH_2CH_3$, $CH(CH(CH_3)_2)$, $CH(CH_2Ph)$, and the like, or a side chain group present in natural or modified aminoacids; and the group $R^{5b}$ is $C_1$-$C_{12}$ alkyl, such as methyl, ethyl, propyl, isopropyl, or isobutyl; $C_6$-$C_{20}$ aryl, such as phenyl or substituted phenyl; or $C_6$-$C_{20}$ arylalkyl, such as benzyl or benzhydryl. The reactants are combined in the presence of a coupling agent such as a carbodiimide, for example dicyclohexyl carbodiimide, as described in *J. Am. Chem. Soc.*, (1957) 79:3575, optionally in the presence of an activating agent such as hydroxybenztriazole, to yield the amidate product S34.3. The amidate-forming reaction is also effected in the presence of coupling agents such as BOP, as described in *J. Org. Chem.* (1995) 60:5214, Aldrithiol, PYBOP and similar coupling agents used for the preparation of amides and esters. Alternatively, the reactants S34.2 and S34.9 are transformed into the monoamidate S34.3 by means of a Mitsunobu reaction. The preparation of amidates by means of the Mitsunobu reaction is described in *J. Med. Chem.* (1995) 38:2742. Equimolar amounts of the reactants are combined in an inert solvent such as tetrahydrofuran in the presence of a triaryl phosphine and a dialkyl azodicarboxylate. The thus-obtained monoamidate ester S34.3 is then transformed into amidate phosphonic acid S34.4. The conditions used for the hydrolysis reaction depend on the nature of the $R^1$ group, as described previously. The phosphonic acid amidate S34.4 is then reacted with an aminoester S34.9, as described above, to yield the bisamidate product S34.5, in which the amino substituents are the same or different. Alternatively, the phosphonic acid S34.6 may be treated with two different amino ester reagents simultaneously, i.e. S34.9 where $R^2$, $R^{4b}$ or $R^{5b}$ are different. The resulting mixture of bisamidate products S34.5 may then be separable, e.g. by chromatography.

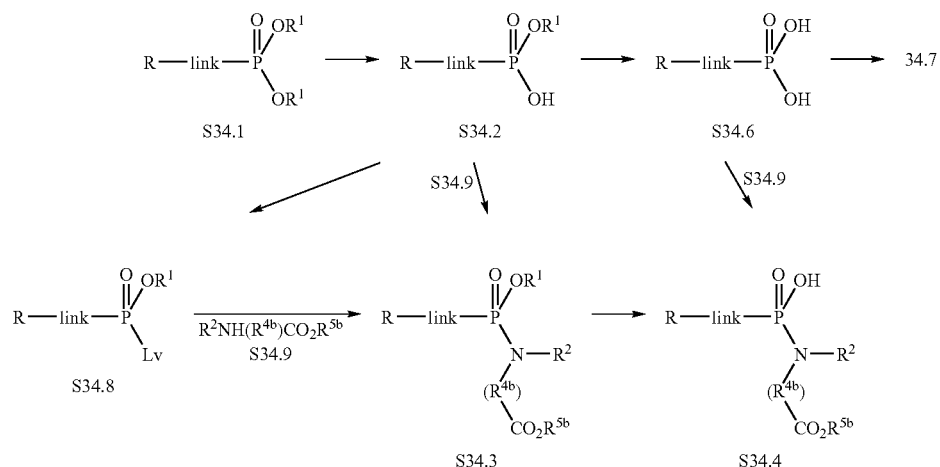

Scheme 34

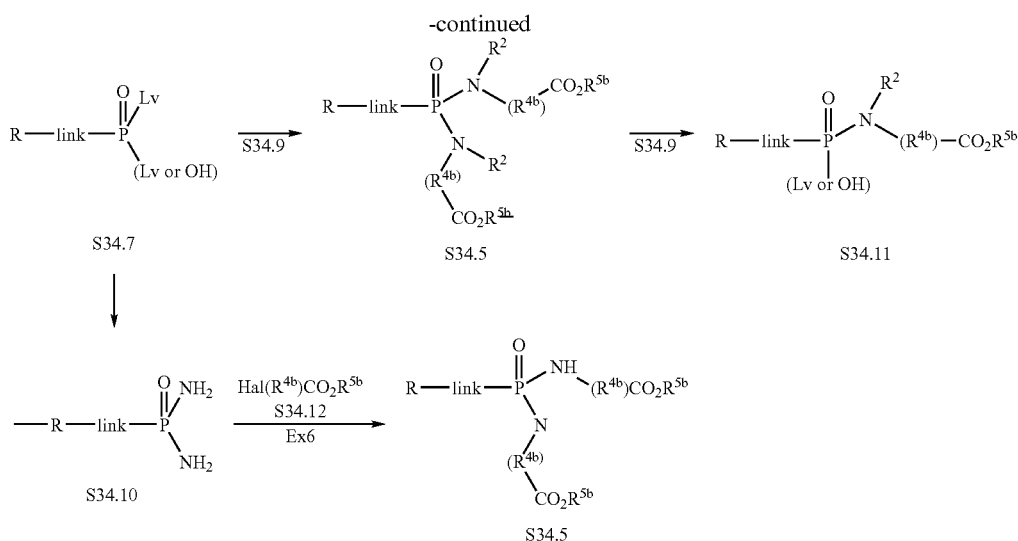

An example of this procedure is shown in Scheme 34, Example 1. In this procedure, a dibenzyl phosphonate S34.14 is reacted with diazabicyclooctane (DABCO) in toluene at reflux, as described in *J. Org. Chem.*, 1995, 60, 2946, to afford the monobenzyl phosphonate S34.15. The product is then reacted with equimolar amounts of ethyl alaninate S34.16 and dicyclohexyl carbodiimide in pyridine, to yield the amidate product S34.17. The benzyl group is then removed, for example by hydrogenolysis over a palladium catalyst, to give the monoacid product S34.18 which may be unstable according to *J. Med. Chem.* (1997) 40(23):3842. This compound S34.18 is then reacted in a Mitsunobu reaction with ethyl leucinate S34.19, triphenyl phosphine and diethylazodicarboxylate, as described in *J. Med. Chem.*, 1995, 38, 2742, to produce the bisamidate product S34.20.

Using the above procedures, but employing in place of ethyl leucinate S34.19 or ethyl alaninate S34.16, different aminoesters S34.9, the corresponding products S34.5 are obtained.

Alternatively, the phosphonic acid S34.6 is converted into the bisamidate S34.5 by use of the coupling reactions described above. The reaction is performed in one step, in which case the nitrogen-related substituents present in the product S34.5 are the same, or in two steps, in which case the nitrogen-related substituents can be different.

An example of the method is shown in Scheme 34, Example 2. In this procedure, a phosphonic acid S34.6 is reacted in pyridine solution with excess ethyl phenylalaninate S34.21 and dicyclohexylcarbodiimide, for example as described in *J. Chem. Soc., Chem. Comm.*, 1991, 1063, to give the bisamidate product S34.22.

Using the above procedures, but employing, in place of ethyl phenylalaninate, different aminoesters S34.9, the corresponding products S34.5 are obtained.

As a further alternative, the phosphonic acid S34.6 is converted into the mono or bis-activated derivative S34.7, in which Lv is a leaving group such as chloro, imidazolyl, triisopropylbenzenesulfonyloxy etc. The conversion of phosphonic acids into chlorides S34.7 (Lv=Cl) is effected by reaction with thionyl chloride or oxalyl chloride and the like, as described in *Organic Phosphorus Compounds*, G. M. Kosolapoff, L. Maeir, eds, Wiley, 1976, p. 17. The conversion of phosphonic acids into monoimidazolides S34.7 (Lv=imidazolyl) is described in *J. Med. Chem.*, 2002, 45, 1284 and in *J. Chem. Soc. Chem. Comm.*, 1991, 312. Alternatively, the phosphonic acid is activated by reaction with triisopropylbenzenesulfonyl chloride, as described in *Nucleosides and Nucleotides*, 2000, 10, 1885. The activated product is then reacted with the aminoester S34.9, in the presence of a base, to give the bisamidate S34.5. The reaction is performed in one step, in which case the nitrogen substituents present in the product S34.5 are the same, or in two steps, via the intermediate S34.11, in which case the nitrogen substituents can be different.

Examples of these methods are shown in Scheme 34, Examples 3 and 5. In the procedure illustrated in Scheme 34, Example 3, a phosphonic acid S34.6 is reacted with ten molar equivalents of thionyl chloride, as described in *Zh. Obschei Khim.*, 1958, 28, 1063, to give the dichloro compound S34.23. The product is then reacted at reflux temperature in a polar aprotic solvent such as acetonitrile, and in the presence of a base such as triethylamine, with butyl serinate S34.24 to afford the bisamidate product S34.25.

Using the above procedures, but employing, in place of butyl serinate S34.24, different aminoesters S34.9, the corresponding products S34.5 are obtained.

In the procedure illustrated in Scheme 34, Example 5, the phosphonic acid S34.6 is reacted, as described in *J. Chem. Soc. Chem. Comm.*, 1991, 312, with carbonyl diimidazole to give the imidazolide S34.S32. The product is then reacted in acetonitrile solution at ambient temperature, with one molar equivalent of ethyl alaninate S34.33 to yield the monodisplacement product S34.S34. The latter compound is then reacted with carbonyl diimidazole to produce the activated intermediate S34.35, and the product is then reacted, under the same conditions, with ethyl N-methylalaninate S34.33a to give the bisamidate product S34.36.

Using the above procedures, but employing, in place of ethyl alaninate S34.33 or ethyl N-methylalaninate S34.33a, different aminoesters S34.9, the corresponding products S34.5 are obtained.

The intermediate monoamidate S34.3 is also prepared from the monoester S34.2 by first converting the monoester into the activated derivative S34.8 in which Lv is a leaving group such as halo, imidazolyl etc, using the procedures described above. The product S34.8 is then reacted with an aminoester S34.9 in the presence of a base such as pyridine, to give an intermediate monoamidate product S34.3. The latter compound is then converted, by removal of the $R^1$ group and coupling of the product with the aminoester S34.9, as described above, into the bisamidate S34.5.

An example of this procedure, in which the phosphonic acid is activated by conversion to the chloro derivative S34.26, is shown in Scheme 34, Example 4. In this procedure, the phosphonic monobenzyl ester S34.15 is reacted, in dichloromethane, with thionyl chloride, as described in *Tet. Letters.*, 1994, 35, 4097, to afford the phosphoryl chloride S34.26. The product is then reacted in acetonitrile solution at ambient temperature with one molar equivalent of ethyl 3-amino-2-methylpropionate S34.27 to yield the monoamidate product S34.28. The latter compound is hydrogenated in ethylacetate over a 5% palladium on carbon catalyst to produce the monoacid product S34.29. The product is subjected to a Mitsunobu coupling procedure, with equimolar amounts of butyl alaninate S34.30, triphenyl phosphine, diethylazodicarboxylate and triethylamine in tetrahydrofuran, to give the bisamidate product S34.31.

Using the above procedures, but employing, in place of ethyl 3-amino-2-methylpropionate S34.27 or butyl alaninate S34.30, different aminoesters S34.9, the corresponding products S34.5 are obtained.

The activated phosphonic acid derivative S34.7 is also converted into the bisamidate S34.5 via the diamino compound S34.10. The conversion of activated phosphonic acid derivatives such as phosphoryl chlorides into the corresponding amino analogs S34.10, by reaction with ammonia, is described in *Organic Phosphorus Compounds*, G. M. Kosolapoff, L. Maeir, eds, Wiley, 1976. The bisamino compound S34.10 is then reacted at elevated temperature with a haloester S34.12 (Hal=halogen, i.e. F, Cl, Br, I), in a polar organic solvent such as dimethylformamide, in the presence of a base such as 4, 4-dimethylaminopyridine (DMAP) or potassium carbonate, to yield the bisamidate S34.5. Alternatively, S34.6 may be treated with two different amino ester reagents simulataneously, i.e. S34.12 where $R^{4b}$ or $R^{5b}$ are different. The resulting mixture of bisamidate products S34.5 may then be separable, e.g. by chromatography.

An example of this procedure is shown in Scheme 34, Example 6. In this method, a dichlorophosphonate S34.23 is reacted with ammonia to afford the diamide S34.37. The reaction is performed in aqueous, aqueous alcoholic or alcoholic solution, at reflux temperature. The resulting diamino compound is then reacted with two molar equivalents of ethyl 2-bromo-3-methylbutyrate S34.38, in a polar organic solvent such as N-methylpyrrolidinone at ca. 150° C., in the presence of a base such as potassium carbonate, and optionally in the presence of a catalytic amount of potassium iodide, to afford the bisamidate product S34.39.

Using the above procedures, but employing, in place of ethyl 2-bromo-3-methylbutyrate S34.38, different haloesters S34.12 the corresponding products S34.5 are obtained.

The procedures shown in Scheme 34 are also applicable to the preparation of bisamidates in which the aminoester moiety incorporates different functional groups. Scheme 34, Example 7 illustrates the preparation of bisamidates derived from tyrosine. In this procedure, the monoimidazolide S34.32 is reacted with propyl tyrosinate S34.40, as described in Example 5, to yield the monoamidate S34.41. The product is reacted with carbonyl diimidazole to give the imidazolide S34.42, and this material is reacted with a further molar equivalent of propyl tyrosinate to produce the bisamidate product S34.43.

Using the above procedures, but employing, in place of propyl tyrosinate S34.40, different aminoesters S34.9, the corresponding products S34.5 are obtained. The aminoesters employed in the two stages of the above procedure can be the same or different, so that bisamidates with the same or different amino substituents are prepared.

Scheme 35 illustrates methods for the preparation of phosphonate monoamidates.

In one procedure, a phosphonate monoester S34.1 is converted, as described in Scheme 34, into the activated derivative S34.8. This compound is then reacted, as described above, with an aminoester S34.9, in the presence of a base, to afford the monoamidate product S35.1.

The procedure is illustrated in Scheme 35, Example 1. In this method, a monophenyl phosphonate S35.7 is reacted with, for example, thionyl chloride, as described in *J. Gen. Chem.* USSR., 1983, 32, 367, to give the chloro product S35.8. The product is then reacted, as described in Scheme 34, with ethyl alaninate S3, to yield the amidate S35.10.

Using the above procedures, but employing, in place of ethyl alaninate S35.9, different aminoesters S34.9, the corresponding products S35.1 are obtained.

Alternatively, the phosphonate monoester S34.1 is coupled, as described in Scheme 34, with an aminoester S34.9 to produce the amidate S335.1. If necessary, the $R^1$ substituent is then altered, by initial cleavage to afford the phosphonic acid S35.2. The procedures for this transformation depend on the nature of the $R^1$ group, and are described above. The phosphonic acid is then transformed into the ester amidate product S35.3, by reaction with the hydroxy compound $R^3OH$, in which the group $R^3$ is aryl, heterocycle, alkyl, cycloalkyl, haloalkyl etc, using the same coupling procedures (carbodiimide, Aldrithiol-2, PYBOP, Mitsunobu reaction etc) described in Scheme 34 for the coupling of amines and phosphonic acids.

Scheme 34 Example 1

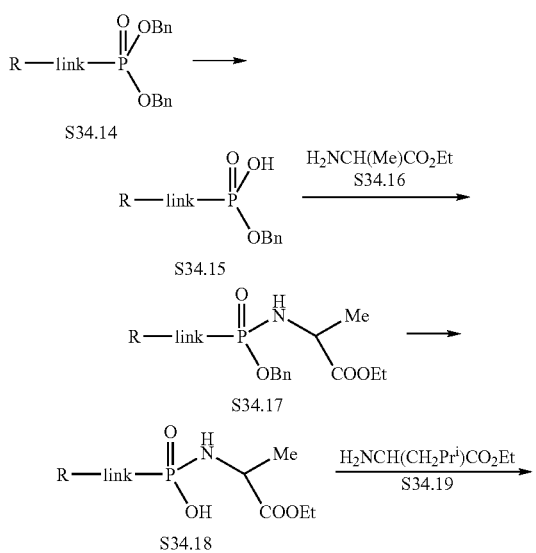

-continued
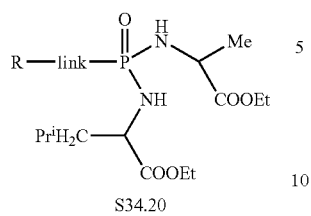
S34.20
Scheme 34 Example 2
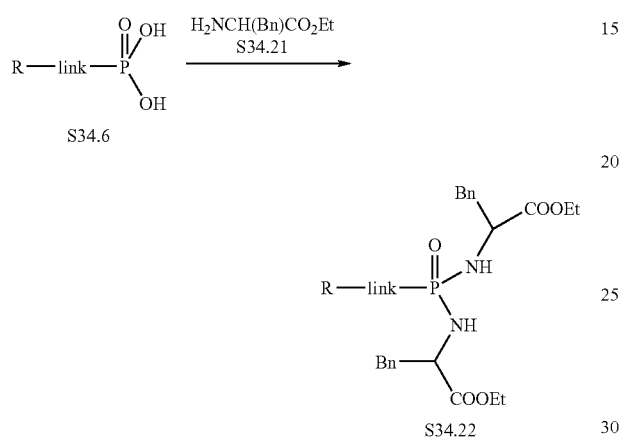
S34.22
Scheme 34 Example 3
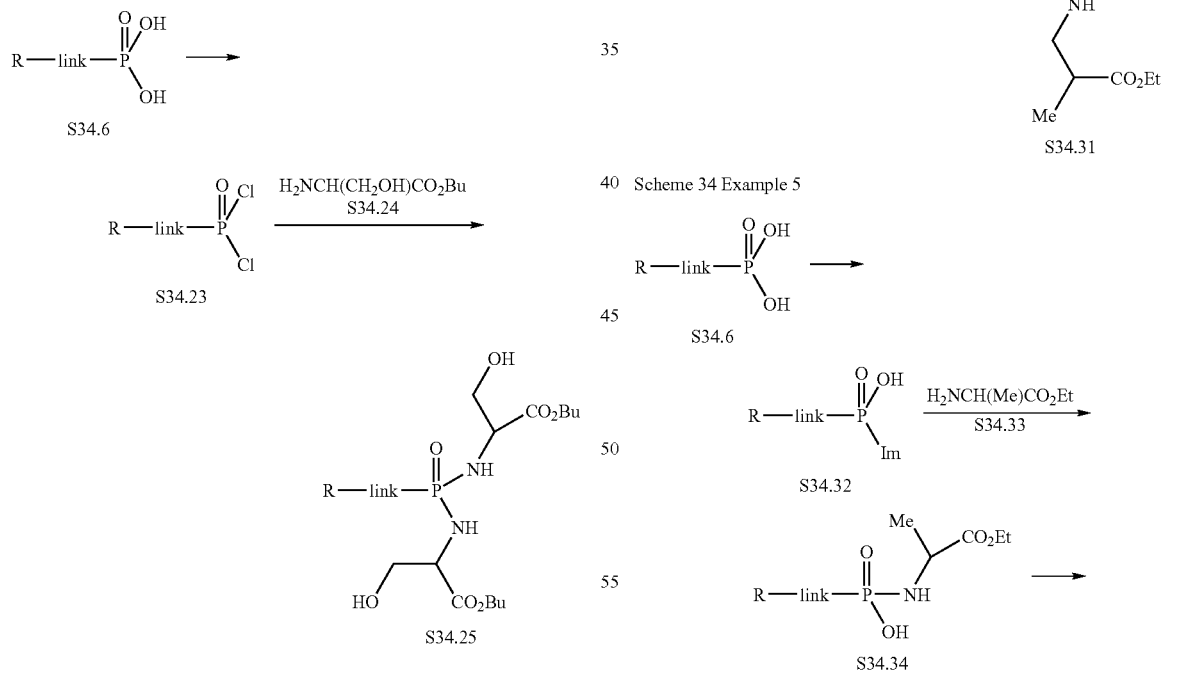
Scheme 34 Example 4
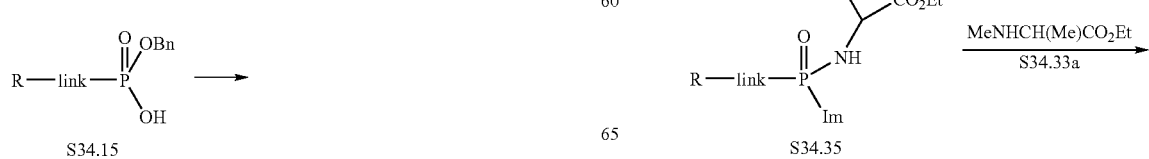
S34.15
-continued
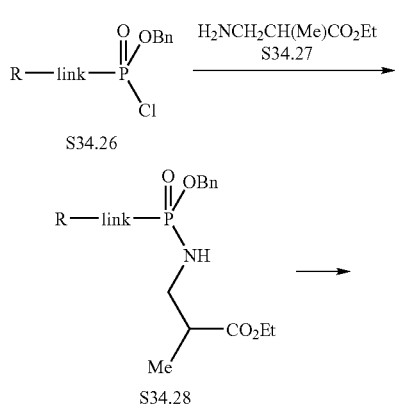
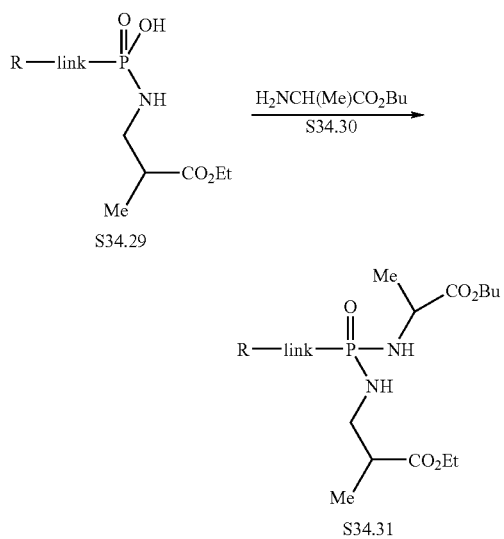
Scheme 34 Example 5

-continued

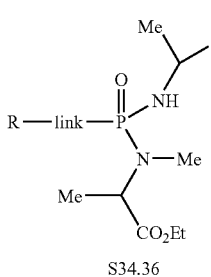
S34.36

Scheme 34 Example 5

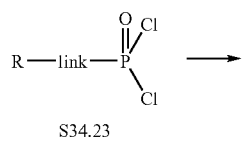
S34.23

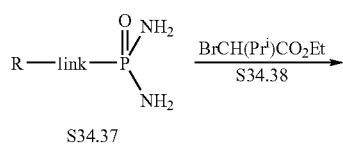
S34.37

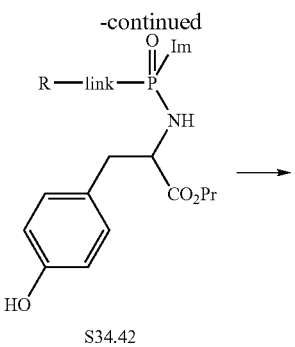
S34.42

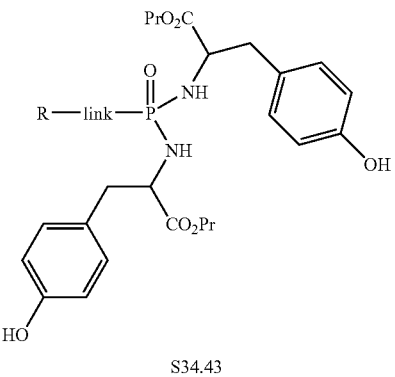
S34.43

Examples of this method are shown in Scheme 35, Examples and 2 and 3. In the sequence shown in Example 2, a monobenzyl phosphonate S35.11 is transformed by reaction with ethyl alaninate, using one of the methods described above, into the monoamide S35.12. The benzyl group is then removed by catalytic hydrogenation in ethylacetate solution over a 5% palladium on carbon catalyst, to afford the phosphonic acid amidate S35.13. The product is then reacted in dichloromethane solution at ambient temperature with equimolar amounts of 1-(dimethylaminopropyl)-3-ethylcarbodiimide and trifluoroethanol S35.14, for example as described in *Tet. Lett.*, 2001, 42, 8841, to yield the amidate ester S35.15.

In the sequence shown in Scheme 35, Example 3, the monoamidate S35.13 is coupled, in tetrahydrofuran solution at ambient temperature, with equimolar amounts of dicyclohexyl carbodiimide and 4-hydroxy-N-methylpiperidine S35.16, to produce the amidate ester product S35.17.

Using the above procedures, but employing, in place of the ethyl alaninate product S35.12 different monoacids S35.2, and in place of trifluoroethanol S35.14 or 4-hydroxy-N-methylpiperidine S35.16, different hydroxy compounds $R^3OH$, the corresponding products S35.3 are obtained.

Alternatively, the activated phosphonate ester S34.8 is reacted with ammonia to yield the amidate S35.4. The product is then reacted, as described in Scheme 34, with a haloester S35.5, in the presence of a base, to produce the amidate product S35.6. If appropriate, the nature of the $R^1$ group is changed, using the procedures described above, to give the product S35.3. The method is illustrated in Scheme 35, Example 4. In this sequence, the monophenyl phosphoryl chloride S35.18 is reacted, as described in Scheme 34, with ammonia, to yield the amino product S35.19. This material is then reacted in N-methylpyrrolidinone solution at 170° with butyl 2-bromo-3-phenylpropionate S35.20 and potassium carbonate, to afford the amidate product S35.21.

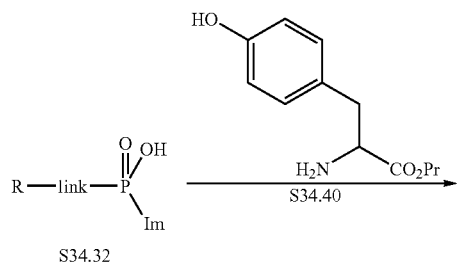
S34.39

Scheme 34 Example 7

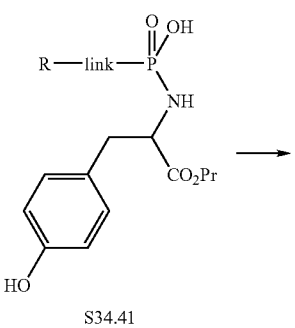
S34.32

S34.41

Using these procedures, but employing, in place of butyl 2-bromo-3-phenylpropionate S35.20, different haloesters S35.5, the corresponding products S35.6 are obtained.

The monoamidate products S35.3 are also prepared from the doubly activated phosphonate derivatives S34.7. In this procedure, examples of which are described in *Synlett.*, 1998, 1, 73, the intermediate S34.7 is reacted with a limited amount of the aminoester S34.9 to give the mono-displacement product S34.11. The latter compound is then reacted with the hydroxy compound $R^3OH$ in a polar organic solvent such as dimethylformamide, in the presence of a base such as diisopropylethylamine, to yield the monoamidate ester S35.3.

The method is illustrated in Scheme 35, Example 5. In this method, the phosphoryl dichloride S35.22 is reacted in dichloromethane solution with one molar equivalent of ethyl N-methyl tyrosinate S35.23 and dimethylaminopyridine, to generate the monoamidate S35.24. The product is then reacted with phenol S35.25 in dimethylformamide containing potassium carbonate, to yield the ester amidate product S35.26.

Using these procedures, but employing, in place of ethyl N-methyl tyrosinate S35.23 or phenol S35.25, the aminoesters 34.9 and/or the hydroxy compounds $R^3OH$, the corresponding products S35.3 are obtained.

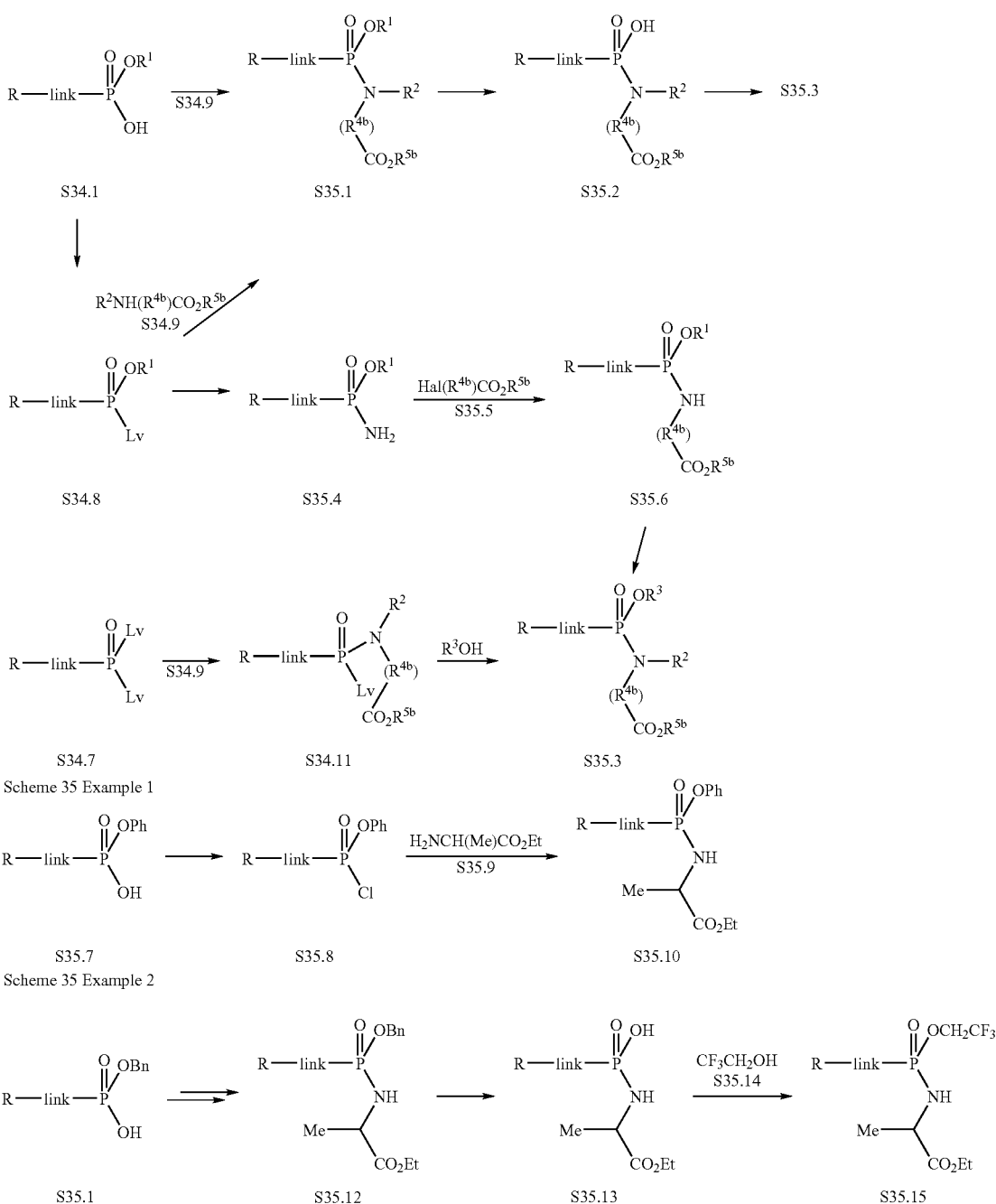

Scheme 35

Scheme 35 Example 3

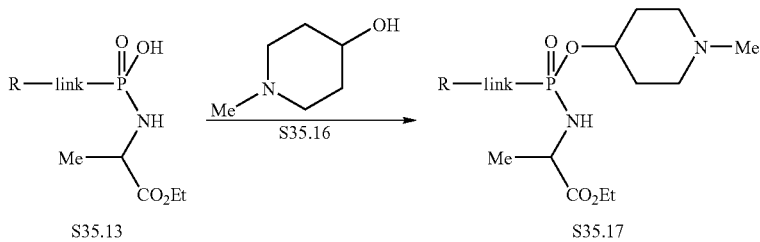

S35.13 → S35.17

Scheme 35 Example 4

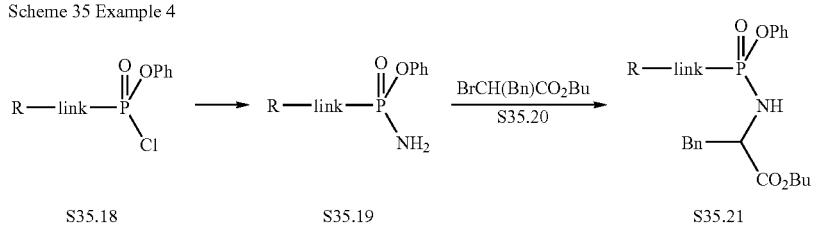

S35.18 → S35.19 → S35.21

Scheme 35 Example 5

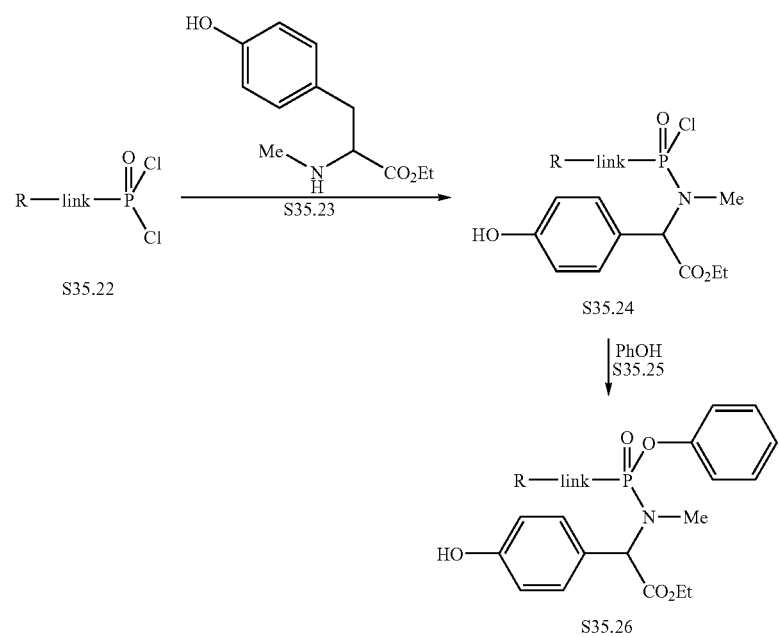

S35.22 → S35.24 → S35.26

Scheme 36 illustrates methods for the preparation of carboalkoxy-substituted phosphonate diesters in which one of the ester groups incorporates a carboalkoxy substituent.

In one procedure, a phosphonate monoester S34.1, prepared as described above, is coupled, using one of the methods described above, with a hydroxyester S36.1, in which the groups $R^{4b}$ and $R^{5b}$ are as described in Scheme 34. For example, equimolar amounts of the reactants are coupled in the presence of a carbodiimide such as dicyclohexyl carbodiimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 36, Example 1. In this method, a monophenyl phosphonate S36.9 is coupled, in dichloromethane solution in the presence of dicyclohexyl carbodiimide, with ethyl 3-hydroxy-2-methylpropionate S36.10 to yield the phosphonate mixed diester S36.11.

Using this procedure, but employing, in place of ethyl 3-hydroxy-2-methylpropionate S36.10, different hydroxyesters S33.1, the corresponding products S33.2 are obtained.

The conversion of a phosphonate monoester S34.1 into a mixed diester S36.2 is also accomplished by means of a Mitsunobu coupling reaction with the hydroxyester S36.1, as described in Org. Lett., 2001, 643. In this method, the reactants 34.1 and S36.1 are combined in a polar solvent such as tetrahydrofuran, in the presence of a triarylphosphine and a dialkyl azodicarboxylate, to give the mixed diester S36.2. The $R^1$ substituent is varied by cleavage, using the methods described previously, to afford the monoacid product S36.3. The product is then coupled, for example using methods described above, with the hydroxy compound $R^3OH$, to give the diester product S36.4.

The procedure is illustrated in Scheme 36, Example 2. In this method, a monoallyl phosphonate S36.12 is coupled in tetrahydrofuran solution, in the presence of triphenylphosphine and diethylazodicarboxylate, with ethyl lactate S36.13 to give the mixed diester S36.14. The product is reacted with tris(triphenylphosphine) rhodium chloride (Wilkinson catalyst) in acetonitrile, as described previously, to remove the allyl group and produce the monoacid product S36.15. The latter compound is then coupled, in pyridine solution at ambient temperature, in the presence of dicyclohexyl carbodiimide, with one molar equivalent of 3-hydroxypyridine S36.16 to yield the mixed diester S36.17.

Using the above procedures, but employing, in place of the ethyl lactate S36.13 or 3-hydroxypyridine, a different hydroxyester S36.1 and/or a different hydroxy compound $R^3OH$, the corresponding products S36.4 are obtained.

The mixed diesters S36.2 are also obtained from the monoesters S34.1 via the intermediacy of the activated monoesters S36.5. In this procedure, the monoester S34.1 is converted into the activated compound S36.5 by reaction with, for example, phosphorus pentachloride, as described in *J. Org. Chem.,* 2001, 66, 329, or with thionyl chloride or oxalyl chloride (Lv=Cl), or with triisopropylbenzenesulfonyl chloride in pyridine, as described in *Nucleosides and Nucleotides,* 2000, 19, 1885, or with carbonyl diimidazole, as described in *J. Med. Chem.,* 2002, 45, 1284. The resultant activated monoester is then reacted with the hydroxyester S36.1, as described above, to yield the mixed diester S36.2.

The procedure is illustrated in Scheme 36, Example 3. In this sequence, a monophenyl phosphonate S36.9 is reacted, in acetonitrile solution at 70° C., with ten equivalents of thionyl chloride, so as to produce the phosphoryl chloride S36.19. The product is then reacted with ethyl 4-carbamoyl-2-hydroxybutyrate S36.20 in dichloromethane containing triethylamine, to give the mixed diester S36.21.

Using the above procedures, but employing, in place of ethyl 4-carbamoyl-2-hydroxybutyrate S36.20, different hydroxyesters S36.1, the corresponding products S36.2 are obtained.

The mixed phosphonate diesters are also obtained by an alternative route for incorporation of the $R^3O$ group into intermediates S36.3 in which the hydroxyester moiety is already incorporated. In this procedure, the monoacid intermediate S36.3 is converted into the activated derivative S36.6 in which Lv is a leaving group such as chloro, imidazole, and the like, as previously described. The activated intermediate is then reacted with the hydroxy compound $R^3OH$, in the presence of a base, to yield the mixed diester product S36.4.

The method is illustrated in Scheme 36, Example 4. In this sequence, the phosphonate monoacid S36.22 is reacted with trichloromethanesulfonyl chloride in tetrahydrofuran containing collidine, as described in *J. Med. Chem.,* 1995, 38, 4648, to produce the trichloromethanesulfonyloxy product S36.23. This compound is reacted with 3-(morpholinomethyl)phenol S36.24 in dichloromethane containing triethylamine, to yield the mixed diester product S36.25.

Using the above procedures, but employing, in place of with 3-(morpholinomethyl)phenol S36.24, different alcohols $R^3OH$, the corresponding products S36.4 are obtained.

The phosphonate esters S36.4 are also obtained by means of alkylation reactions performed on the monoesters S34.1. The reaction between the monoacid S34.1 and the haloester S36.7 is performed in a polar solvent in the presence of a base such as diisopropylethylamine, as described in *Anal. Chem.,* 1987, 59, 1056, or triethylamine, as described in *J. Med. Chem.,* 1995, 38, 1372, or in a non-polar solvent such as benzene, in the presence of 18-crown-6, as described in *Syn. Comm.,* 1995, 25, 3565.

The method is illustrated in Scheme 36, Example 5. In this procedure, the monoacid S36.26 is reacted with ethyl 2-bromo-3-phenylpropionate S36.27 and diisopropylethylamine in dimethylformamide at 80° C. to afford the mixed diester product S36.28.

Using the above procedure, but employing, in place of ethyl 2-bromo-3-phenylpropionate S36.27, different haloesters S36.7, the corresponding products S36.4 are obtained.

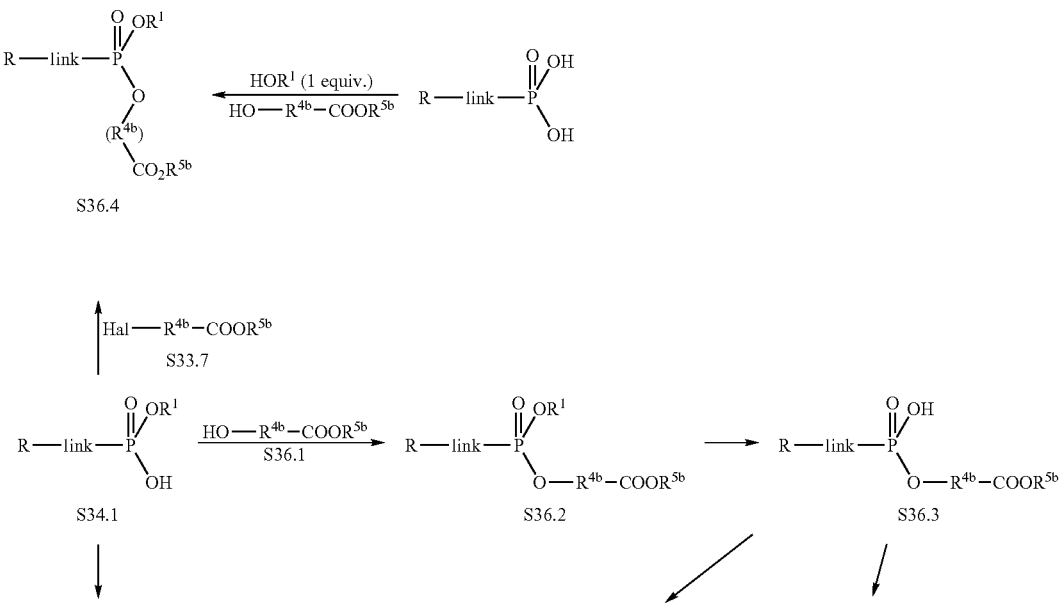

Scheme 36

-continued
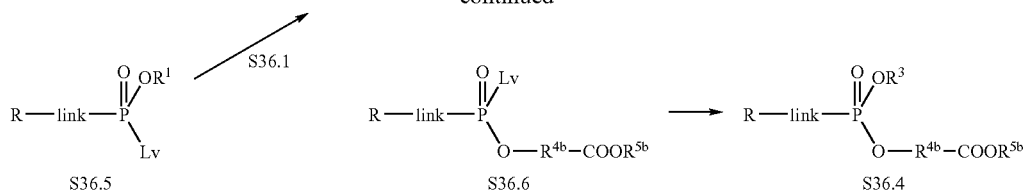
Scheme 36 Example 1
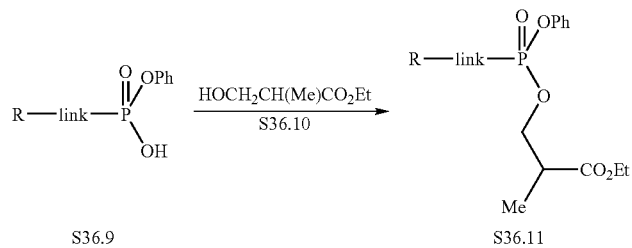
Scheme 36 Example 2
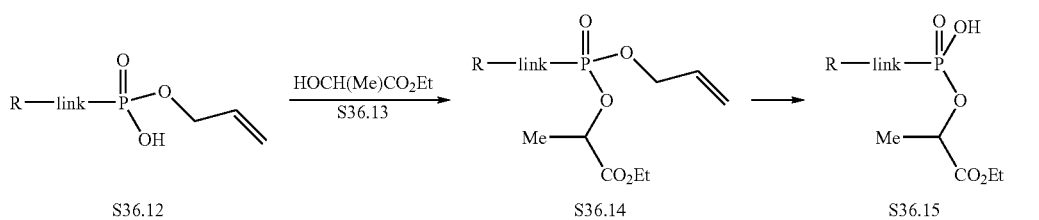
Scheme 36 Example 3
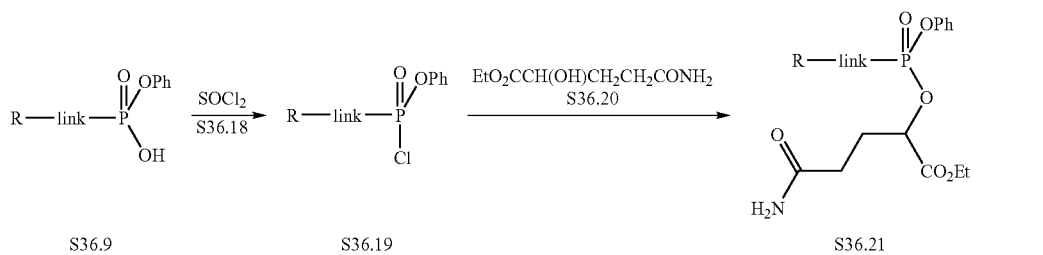
Scheme 36 Example 4
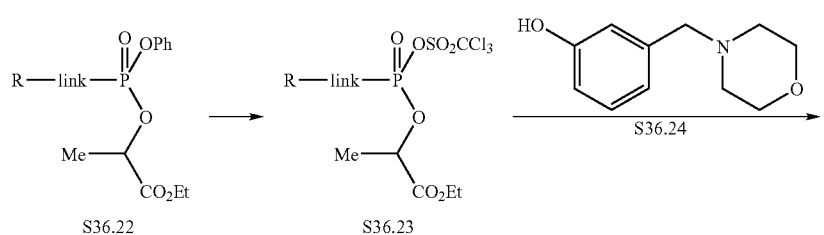

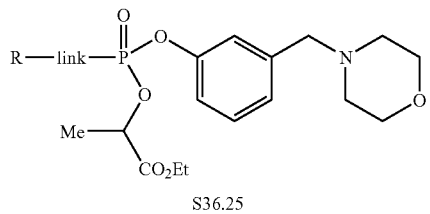

S36.25

Scheme 36 Example 5

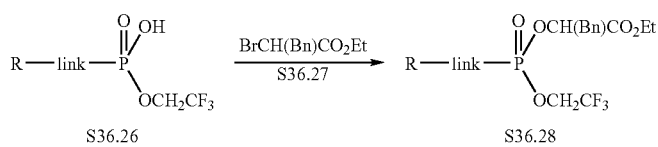

Scheme 37 illustrates methods for the preparation of phosphonate diesters in which both the ester substituents incorporate carboalkoxy groups.

The compounds are prepared directly or indirectly from the phosphonic acids S34.6. In one alternative, the phosphonic acid is coupled with the hydroxyester S37.2, using the conditions described previously in Schemes 34-36, such as coupling reactions using dicyclohexyl carbodiimide or similar reagents, or under the conditions of the Mitsunobu reaction, to afford the diester product S37.3 in which the ester substituents are identical.

This method is illustrated in Scheme 37, Example 1. In this procedure, the phosphonic acid S34.6 is reacted with three molar equivalents of butyl lactate S37.5 in the presence of Aldrithiol-2 and triphenyl phosphine in pyridine at ca. 70° C., to afford the diester S37.6.

Using the above procedure, but employing, in place of butyl lactate S37.5, different hydroxyesters S37.2, the corresponding products S37.3 are obtained.

Alternatively, the diesters S37.3 are obtained by alkylation of the phosphonic acid S34.6 with a haloester S37.1. The alkylation reaction is performed as described in Scheme 36 for the preparation of the esters S36.4.

This method is illustrated in Scheme 37, Example 2. In this procedure, the phosphonic acid S34.6 is reacted with excess ethyl 3-bromo-2-methylpropionate S37.7 and diisopropylethylamine in dimethylformamide at ca. 80° C., as described in *Anal. Chem.*, 1987, 59, 1056, to produce the diester S37.8.

Using the above procedure, but employing, in place of ethyl 3-bromo-2-methylpropionate S37.7, different haloesters S37.1, the corresponding products S37.3 are obtained.

The diesters S37.3 are also obtained by displacement reactions of activated derivatives S34.7 of the phosphonic acid with the hydroxyesters S37.2. The displacement reaction is performed in a polar solvent in the presence of a suitable base, as described in Scheme 36. The displacement reaction is performed in the presence of an excess of the hydroxyester, to afford the diester product S37.3 in which the ester substituents are identical, or sequentially with limited amounts of different hydroxyesters, to prepare diesters S37.3 in which the ester substituents are different.

The methods are illustrated in Scheme 37, Examples 3 and 4. As shown in Example 3, the phosphoryl dichloride S35.22 is reacted with three molar equivalents of ethyl 3-hydroxy-2-(hydroxymethyl)propionate S37.9 in tetrahydrofuran containing potassium carbonate, to obtain the diester product S37.10.

Using the above procedure, but employing, in place of ethyl 3-hydroxy-2-(hydroxymethyl)propionate S37.9, different hydroxyesters S37.2, the corresponding products S37.3 are obtained.

Scheme 37, Example 4 depicts the displacement reaction between equimolar amounts of the phosphoryl dichloride S35.22 and ethyl 2-methyl-3-hydroxypropionate S37.11, to yield the monoester product S37.12. The reaction is conducted in acetonitrile at 70° in the presence of diisopropylethylamine. The product S37.12 is then reacted, under the same conditions, with one molar equivalent of ethyl lactate S37.13, to give the diester product S37.14.

Using the above procedures, but employing, in place of ethyl 2-methyl-3-hydroxypropionate S37.11 and ethyl lactate S37.13, sequential reactions with different hydroxyesters S37.2, the corresponding products S37.3 are obtained.

Scheme 37

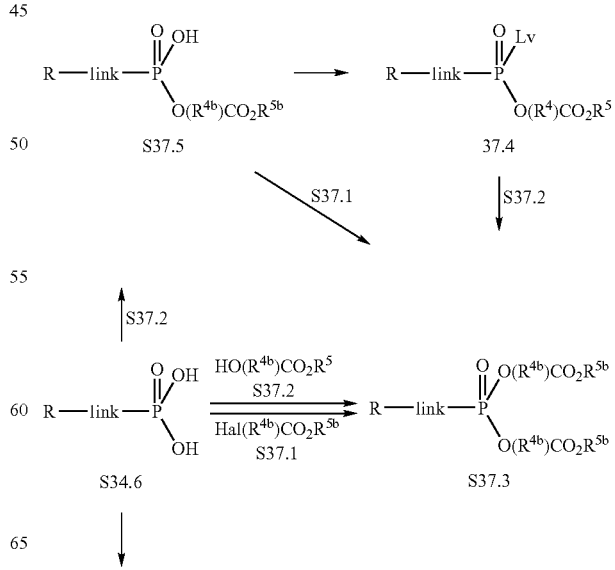

Scheme 37 Example 1

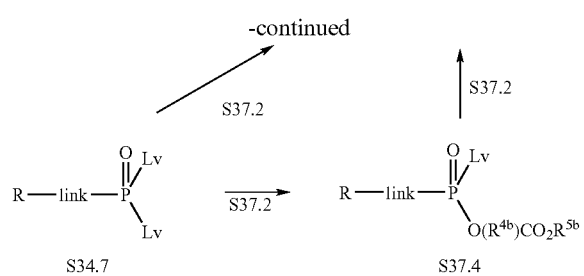

S34.7

Scheme 37 Example 2

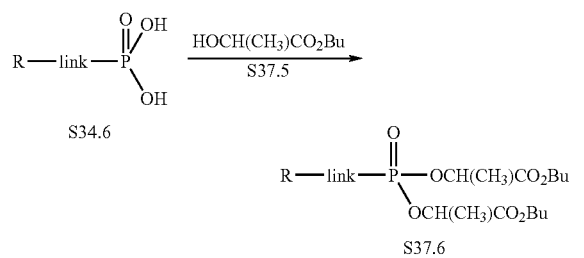

Scheme 37 Example 3

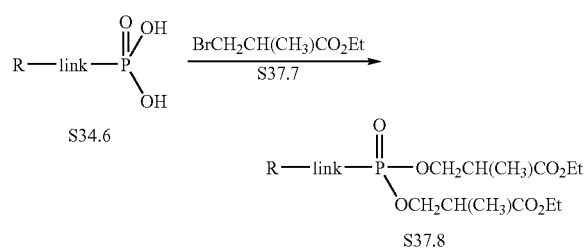

Scheme 37 Example 4

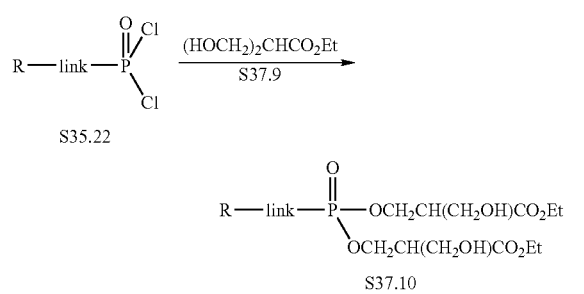

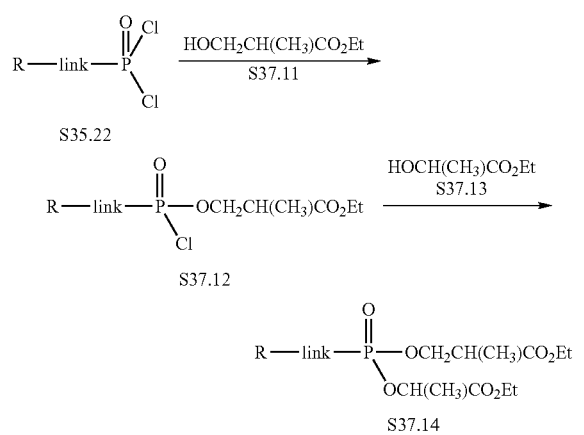

2,2-Dimethyl-2-aminoethylphosphonic acid intermediates can be prepared by the route in Scheme 5. Condensation of 2-methyl-2-propanesulfinamide with acetone give sulfinyl imine S38.11 (*J. Org. Chem.* 1999, 64, 12). Addition of dimethyl methylphosphonate lithium to S38.11 afford S38.12. Acidic methanolysis of S38.12 provide amine S38.13. Protection of amine with Cbz group and removal of methyl groups yield phosphonic acid S38.14, which can be converted to desired S38.15 (Scheme 38a) using methods reported earlier on. An alternative synthesis of compound S38.14 is also shown in Scheme 38b. Commercially available 2-amino-2-methyl-1-propanol is converted to aziridines S38.16 according to literature methods (*J. Org. Chem.* 1992, 57, 5813; Syn. Lett. 1997, 8, 893). Aziridine opening with phosphite give S38.17 (*Tetrahedron Lett.* 1980, 21, 1623). Reprotection) of S38.17 affords S38.14.

Scheme 38a

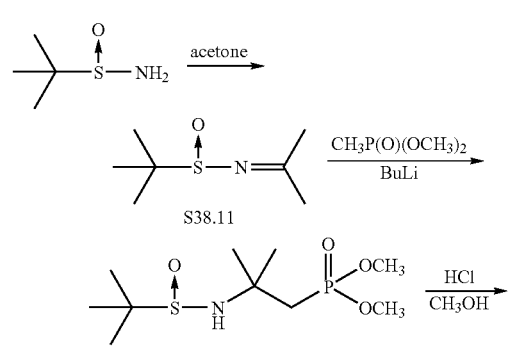

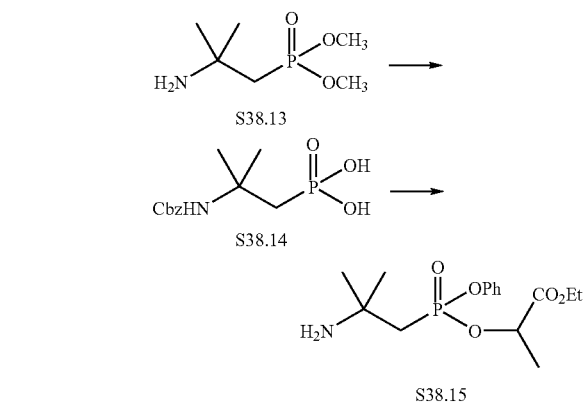

Scheme 38b

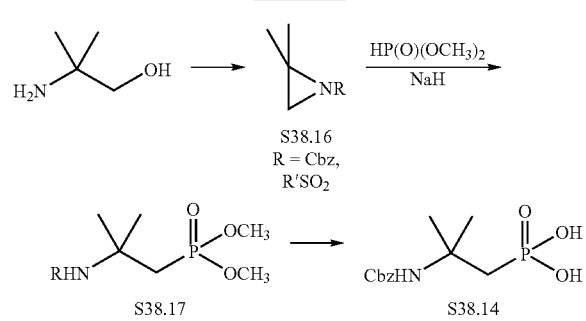

The invention will now be illustrated by the following non-limiting Examples.

EXAMPLE 1

Synthesis of Representative Compounds of Formula 1

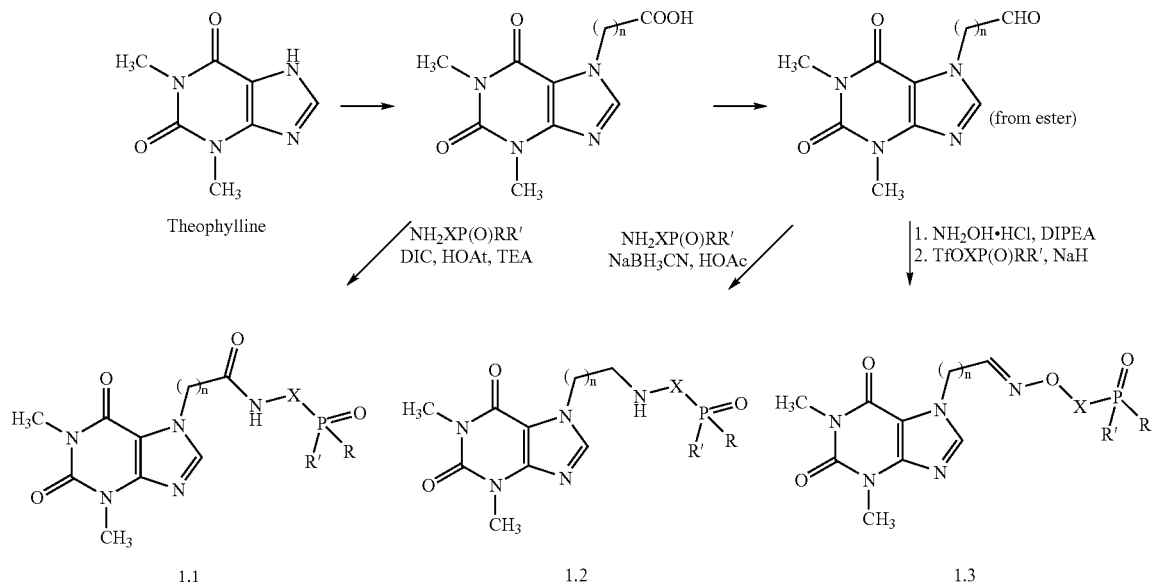

Theophylline is readily converted to N-7 carboxylyic esters by simply alkylation. The ester is first saponified to the corresponding acid derivative. The acid derivative is reacted with aminophosphonate, DIC, and HOAt to afford compounds of formula 1.1. The ester is reduced to aldehyde derivative, for example by reductive amination with an aminophosphonate, NaBH$_3$CN, and HOAc to provide compounds of formula 1.2. The aldehyde can also be reacted with hydroxylamine hydrocchloride, followed by a triflated phosphonate to give compounds of formula 1.3.

EXAMPLE 2

Synthesis of Representative Compounds of Formula 1

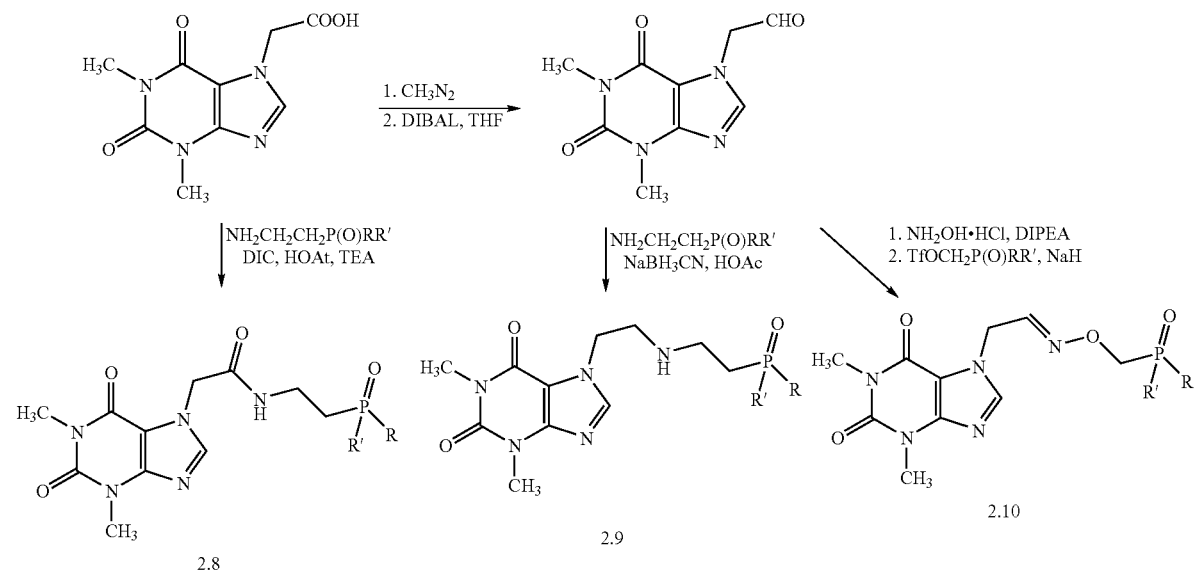

Compounds 2.8, 2.9, and 2.10, can be prepared as follows. Theophylline-7-acetic acid (J. Amer. Che. Soc. 1967, 89, 308) is reacted with aminoethyl phosphonate, DIC, HOAt to afford compound 2.8. Alternatively, the acid is converted to methyl ester by reaction with diazomethane, followed by the reduction with DIBAL in THF to give N-7-aldehyde derivate. This aldehyde is reacted with hydroxylamine hydrochloride in the presence of TEA, followed by treating with NaH and triflated phosphonate to furnish the desired product 2.10. The reductive amination of the aldehyde with aminoethyl phosphonate, NaBH$_3$CN, and HOAc gives compound 2.9.

EXAMPLE 3

Synthesis of Representative Compounds of Formula 2

Theophylline (J. Gen. Chem. USSR 1946, 16, 179; Chem. Ber. 1962, 95 403) is protected with adequate protecting group, followed by reaction with n-BuLi, DMF to generat the 6-formaldehyde derivative. This aldehyde is converted to analog 3.4 by the reductive amination with aminophosphonate followed by the removal of N-7 protecting group. Analog 3.5 is prepared from the aldehyde in 3 steps. First the aldehyde is reacted with hydroxylamine to give the corresponding oxime, followed by reaction with a triflated phosphonate and deprotection of N-7 protecting group to provide a compound of formula 3.5.

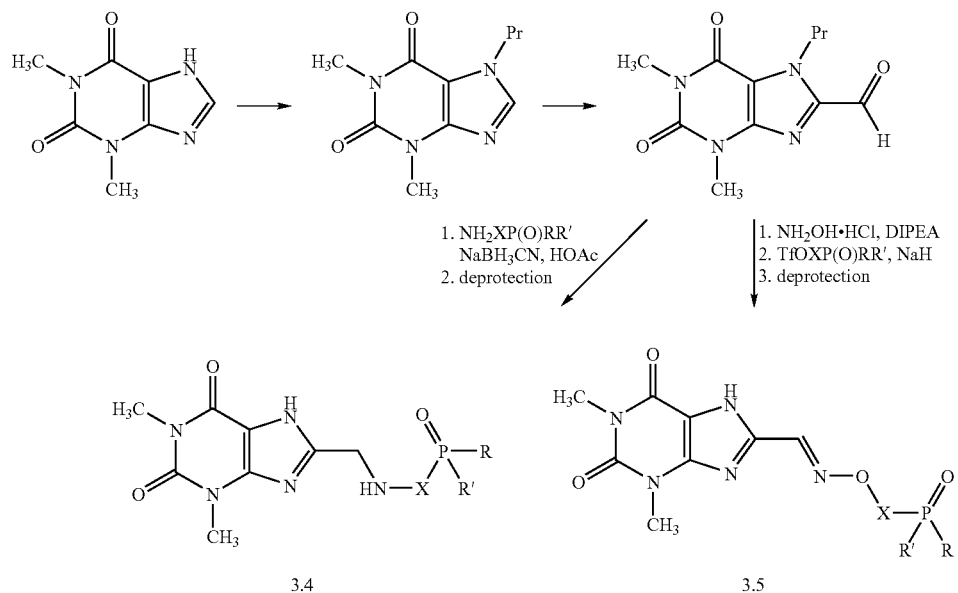

EXAMPLE 4

Synthesis of Representative Compounds of Formula 2

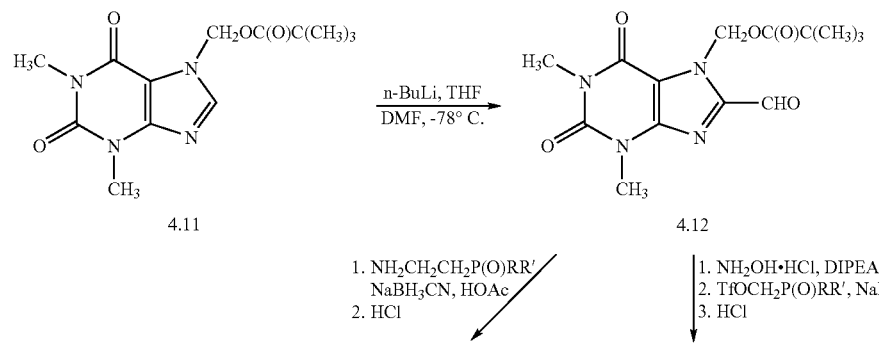

-continued

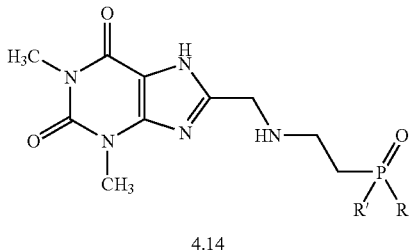

4.14

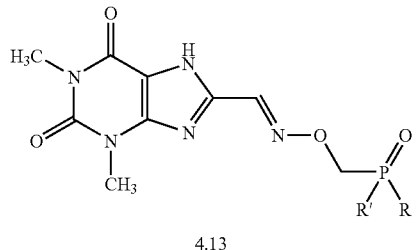

4.13

Theophylline is protected with acid labile group by treating with NaH and (pivaloyloxy)mehtyl chloride to give 4.11 (J. O. C. 1980, 45, 1711). Compound 4.11 is treated with n-BuLi at −78° C. in THF and reacted with DMF to give 4.12. The reductive amination of 4.12 with aminoethyl phosphonate, NaBH$_3$CN, and HOAc, followed by aqueous hydrochloric acid furnishes the product 4.14. Aldehyde 4.12 can also be reacted with hydroxylamine hydrochloride in the presence base, followed by reaction with NaH and a triflated phosphonate, and deprotection with aqueous HCl to give compound 4.13.

The synthesis of analogs 5.6, 5.7, and 5.8 is illustrated above. 1-Methylxanthine is selectly protected with pivaloyoxymethyl group followed by alkylation at N-4, tp provide a key intermediate for preparing 5.6-5.8. Hydrogenation to convert the benzyl ester to the acid followed by reaction with aminophosphonate gives compound 5.6. Reduction of the benzyl ester to the alcohol, followed by reductive amination with aminophosphonate and acid deprotection affords compound 5.7. Analog 5.8 is prepared from the aldehyde stepwise with hydroxylamine, triflated phosphonate, and deprotection of N-7.

EXAMPLE 5

Synthesis of Representative Compounds of Formula 3

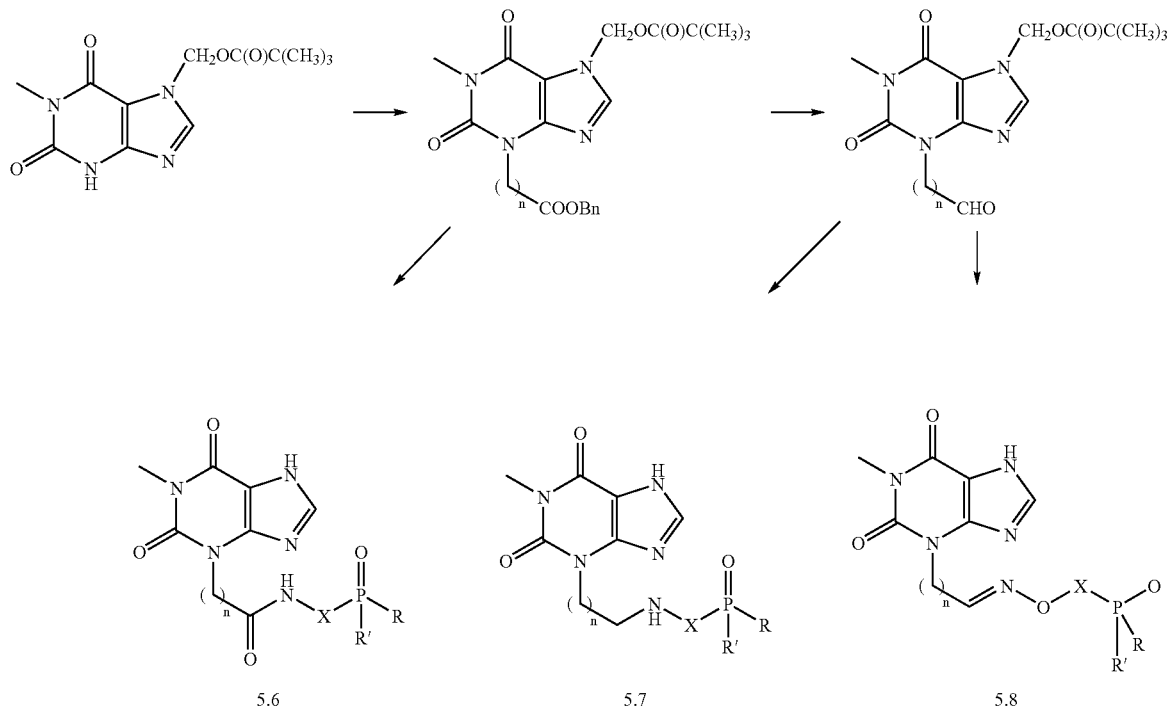

EXAMPLE 6

Synthesis of Representative Compounds of Formula 3

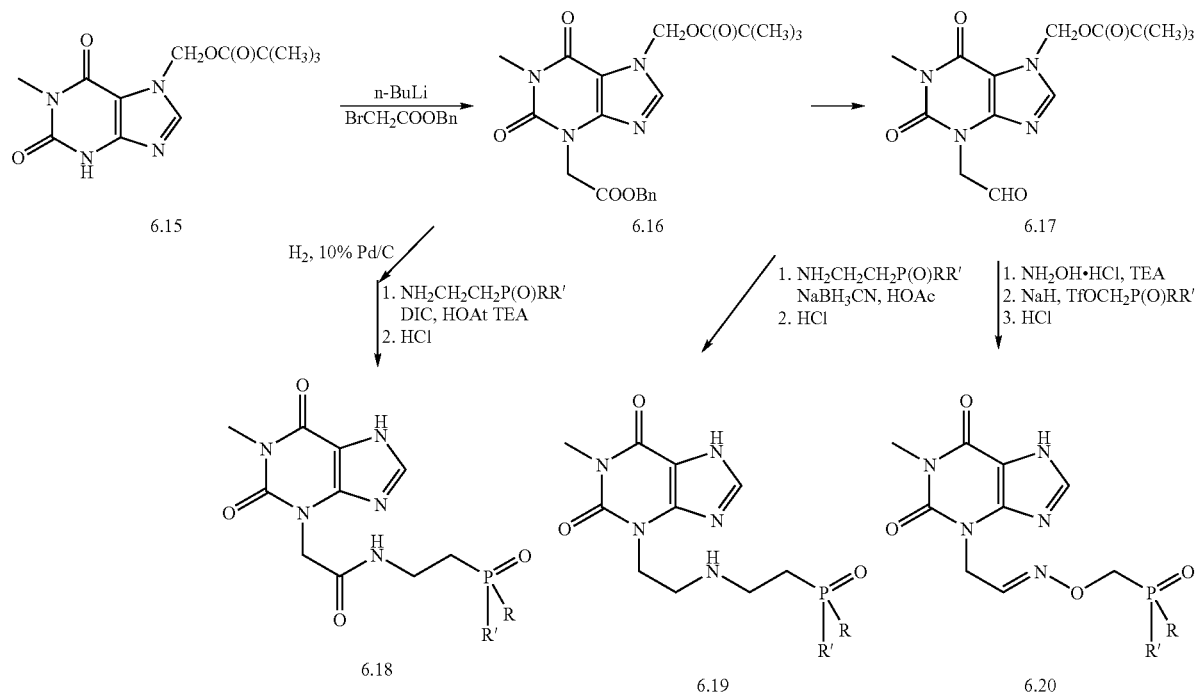

Compounds of formulae 6.18, 6.19, and 6.20 can be synthesized as outlined above. Compound 6.15 is prepared as previously reported (J. O. C. 1980, 45, 1711). N-7 protected 1-N-methylxanthine 6.15 is alkyated with benzyl bromoacetate to provide intermediate 6.16. The hydrogenation of 6.16 in the presence of 10% Pd/C gives the corresponding acid derivative. The acid derivative is reacted with aminoethyl phosphonate, DIC, and HOAt, and deprotected with aqueous HCl to furnish 6.18. Benzyl ester 6.16 can be reduced with DIBAL in THF to the corresponding aldehyde 6.17. Aldehyde 6.17 is reacted with hydroxylamine hydrochloride in the presence of base (e.g. TEA), followed by reaction with NaH and triflated phosphonate, and deprotection with aqueous HCl to give compound 6.20. The reductive amination of 6.17 with aminoethyl phosphonate, NaBH3CN, and HOAc, followed by deprotection with aqueous HCl furnishes the desired product 6.19.

EXAMPLE 7

Synthesis of Representative Compounds of Formulae 4 and 5

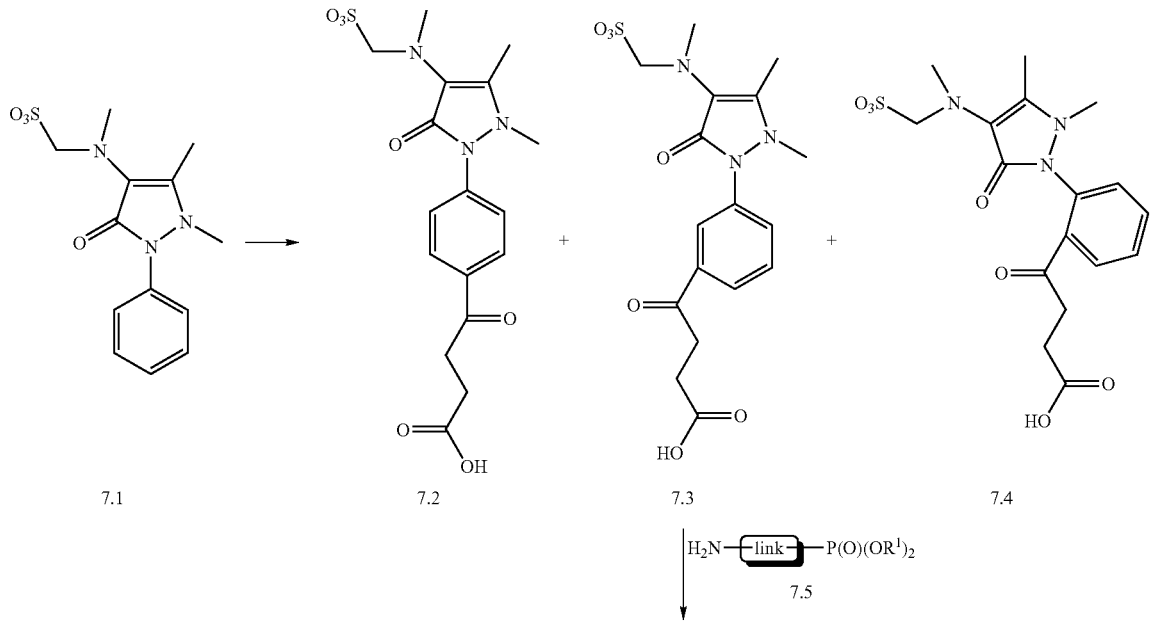

-continued

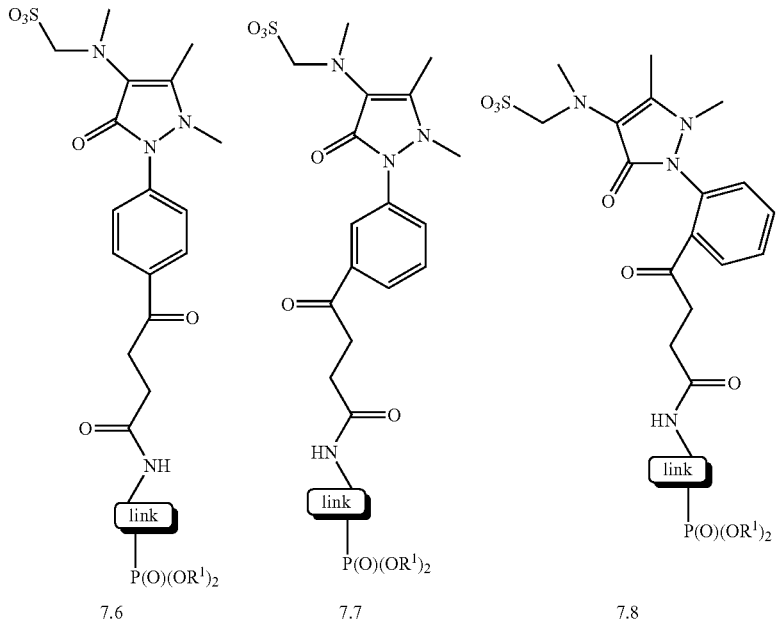

Metamizole 7.1 can be purchased from Sigma (Cat. No. D8890) or prepared as in DE 259577 and DE 254711. The preparation of the phosphonate linkage to 7.1 through the carboxylic acid derivatives 7.2, 7.3 and 7.4 to give compounds of formula 7.6, 7.7, and 7.8 is illustrated above. Compound 7.1 is dissolved in a suitable solvent such as, for example, DCM and is then treated with AlCl₃ and a suitable anhydride, for example, succinic anhydride as described in Tett. Lett 42 (2001) 1467-1469. The acylated products are purified using reverse phase HPLC or flash chromatography on silica gel to give carboxylic acid derivatives 7.2, 7.3 and 7.4. Metamizole derivatives 7.2, 7.3 and 7.4 are independently dissolved in a suitable solvent such as, for example, DMF and treated with an amine phosphonic acid ester of the general formula 7.5 in the presence of a suitable coupling reagant and tertiary organic base to afford the amides 7.6, 7.7, and 7.8.

EXAMPLE 8

Synthesis of Representative Compounds of Formulae 4 and 5

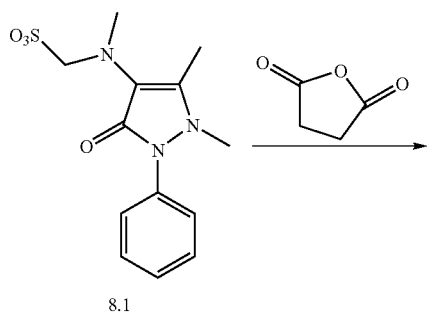

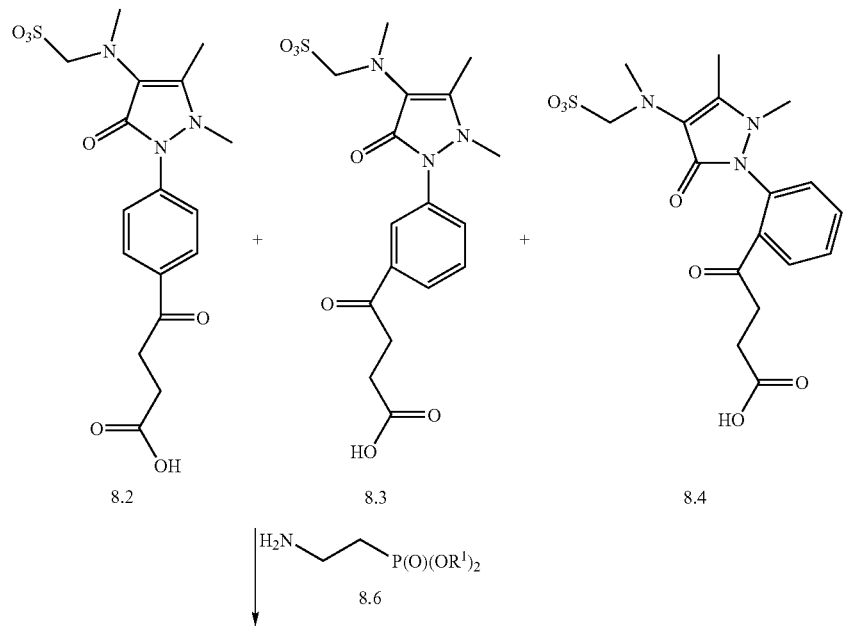

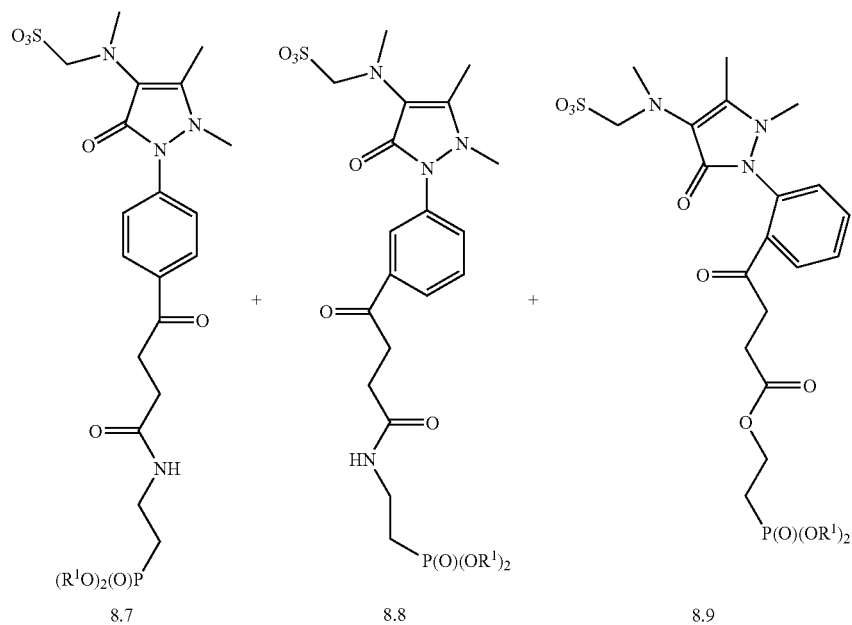

For example, 8.2, 8.3, or 8.4 is dissolved in DMF and treated with 3 equivalents of (benzotriazol-1-yloxy)tripyrrolidinophosphonium hexafluorophosphate (PYBOP, Sigma) and 6 equivalents of diisopropylamine. The activated esters of 8.2, 8.3 and 8.4 are then independently treated with 3 equivalents of the hydrochloride salt of diethyl 2-aminoethyl-1-phosphonate 8.6 which is prepared as described in J. Med. Chem 41 4439-4452. The final products are purified by reverse phase or flash chromatography on silica gel to give amides 8.7, 8.8 and 8.9. Using the above procedure but employing different phosphonate reagants in the place of 8.6 additional compounds of the invention can be prepared.

EXAMPLE 9
Synthesis of Representative Compounds of Formulae 6 and 7
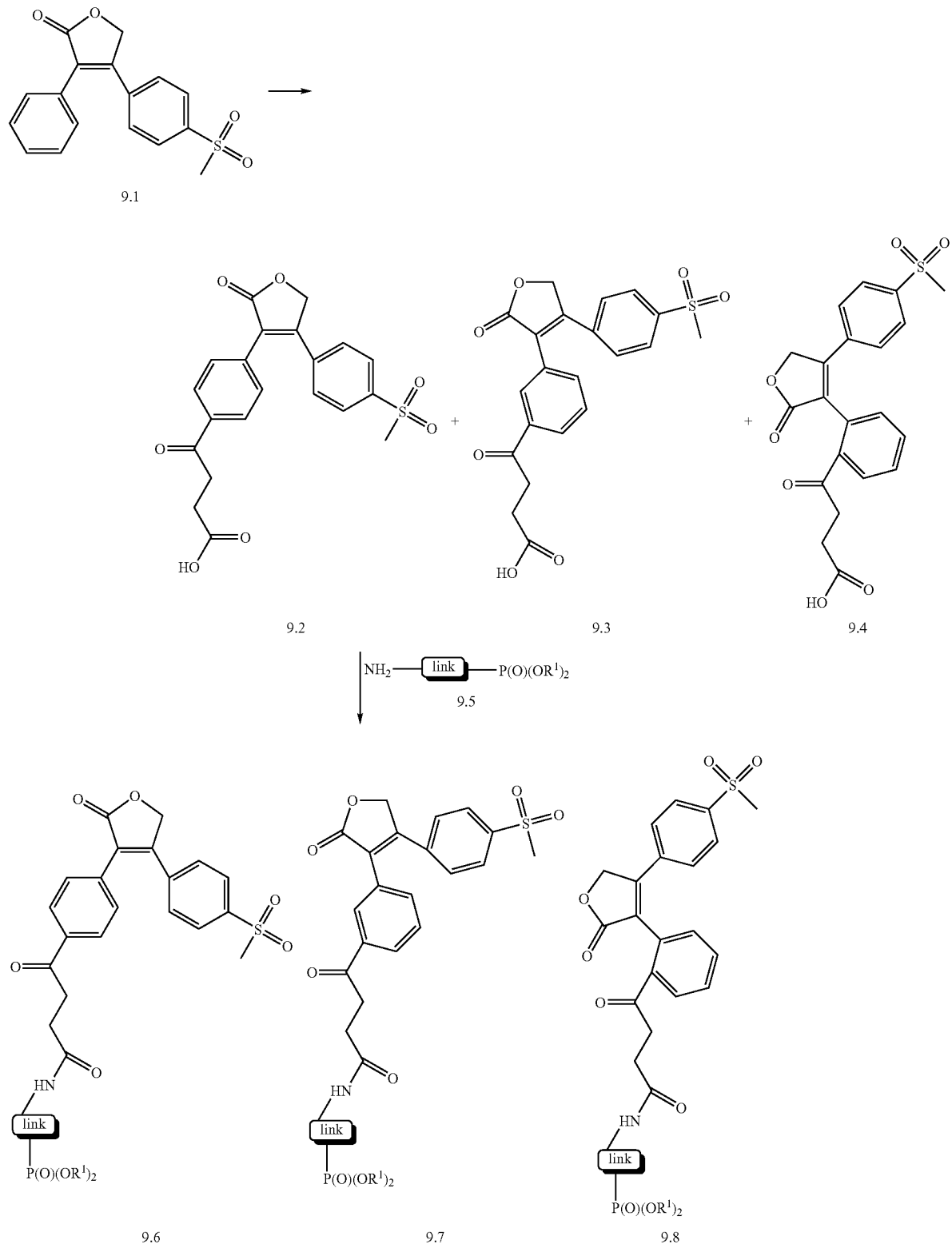

Rofecoxib derivative 9.1 can be obtained as described in U.S. Pat. No. 5,474,995 Example 24. Compound 1.1 is dissolved in a suitable solvent such as, for example, DCM and is then treated with AlCl$_3$ and a suitable anhydride, for example, succinic anhydride as described in Tett. Lett 42 (2001) 1467-1469. The acylated products are purified using reverse phase HPLC or flash chromatography on silica gel to give carboxylic acid derivatives 9.2, 9.3 and 9.4. Rofecoxib derivatives 9.2, 9.3 and 9.4 are independently dissolved in a suitable solvent such as, for example, DMF and is then treated with an amine phosphonic acid ester of the general formula 9.5 in the presence of a suitable coupling reagant and tertiary organic base to afford the amides 9.6, 9.7 and 9.8.

EXAMPLE 10

Synthesis of Representative Compounds of Formula 6 and 7

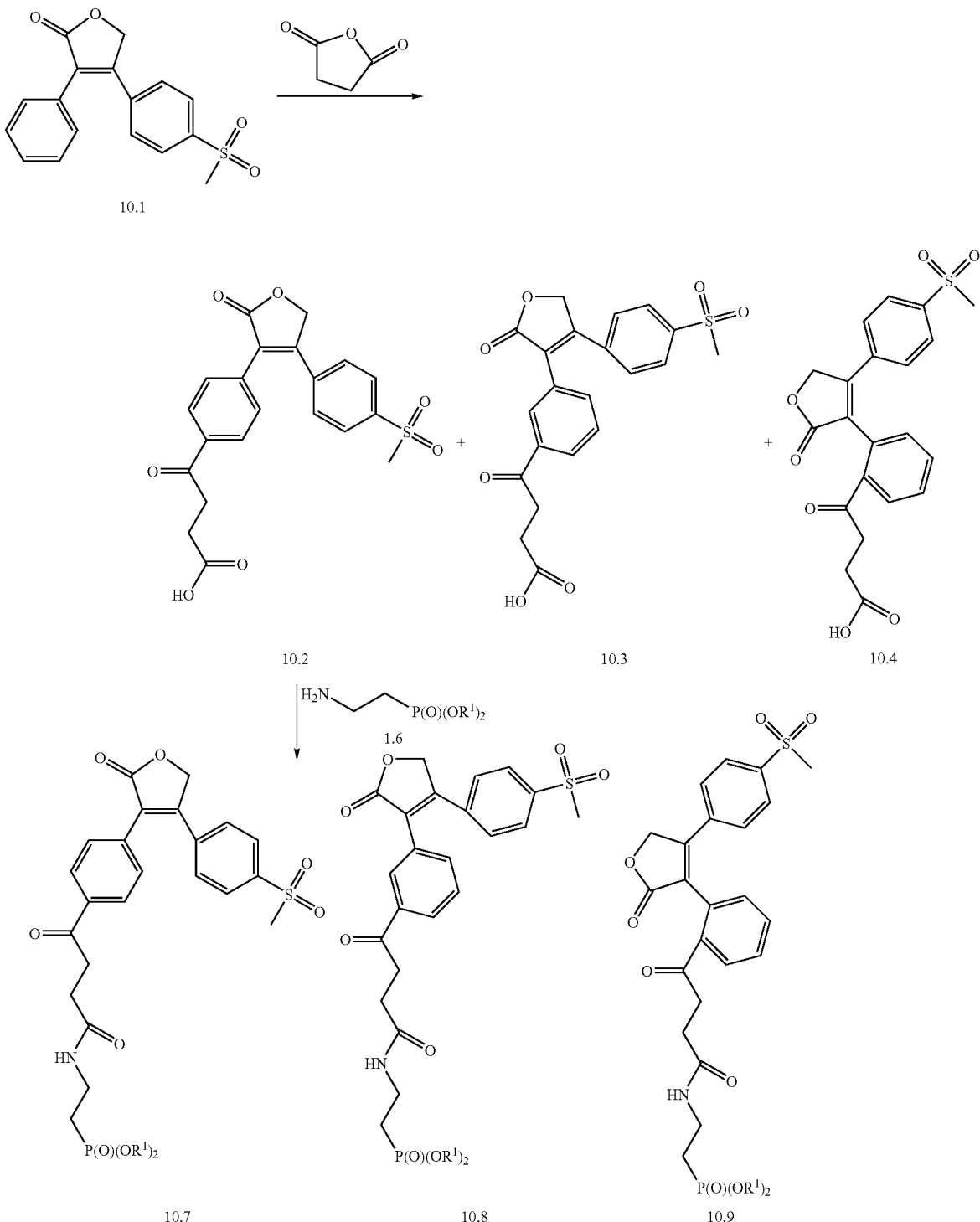

Compound 10.2, 10.3, or 10.4 dissolved in DMF, is treated with 3 equivalents of (benzotriazol-1-yloxy)tripyrrolidinophosphonium hexafluorophosphate (PYBOP, Sigma) and 6 equivalents of diisopropylamine. The activated esters of 10.2, 10.3 and 10.4 are then independently treated with 3 equivalents of the hydrochloride salt of diethyl 2-aminoethyl-1-phosphonate 10.6 which is prepared as described in J. Med. Chem 41 4439-4452. The final products are purified by reverse phase or flash chromatography on silica gel to give amides 10.7, 10.8 and 10.9. Using the above procedure but employing different phosphonate reagants in the place of compound 8.6 additional compounds of the invention can be prepared.

EXAMPLE 11

Synthesis of Representative Compounds of Formulae 8 and 9

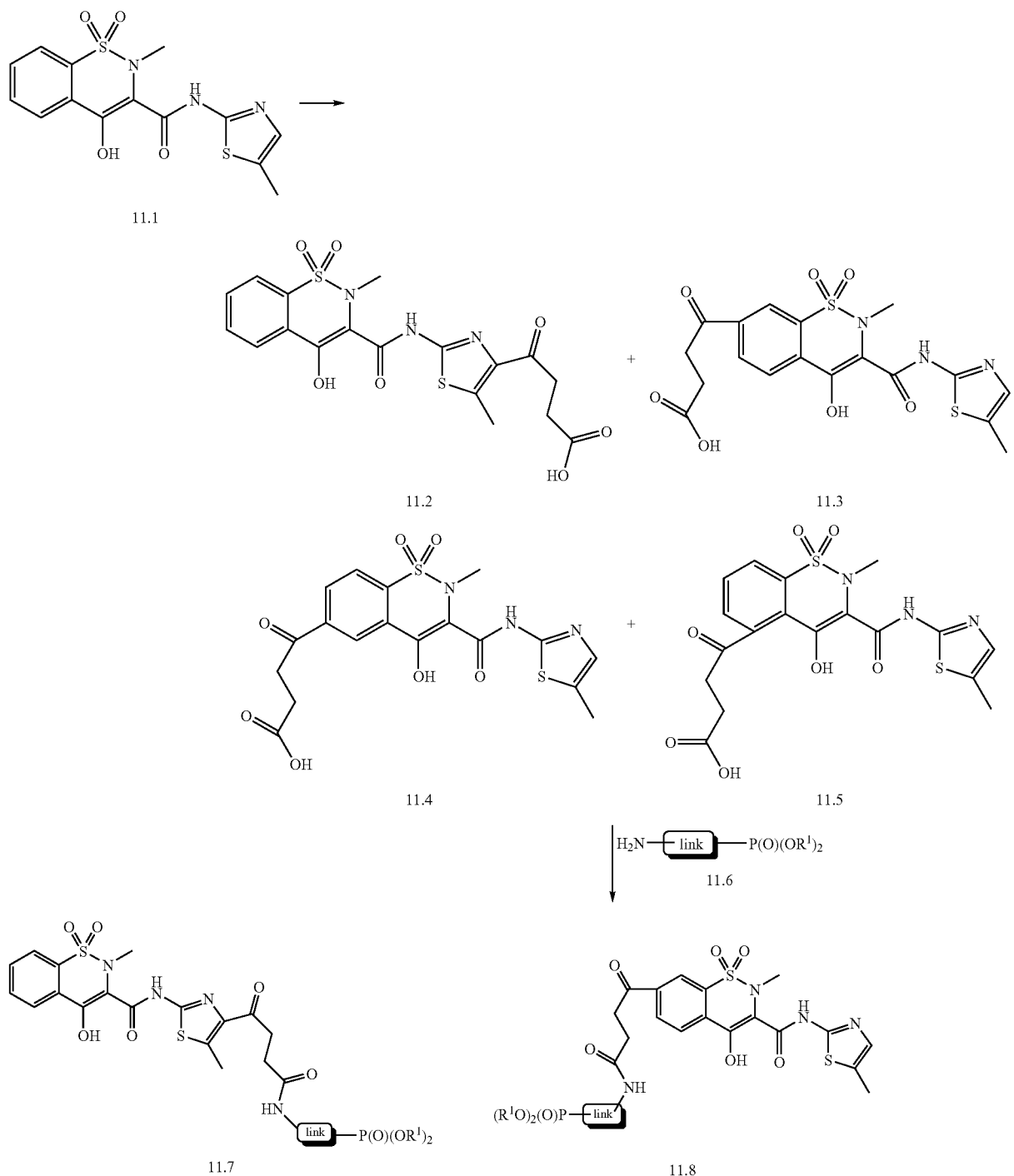

-continued

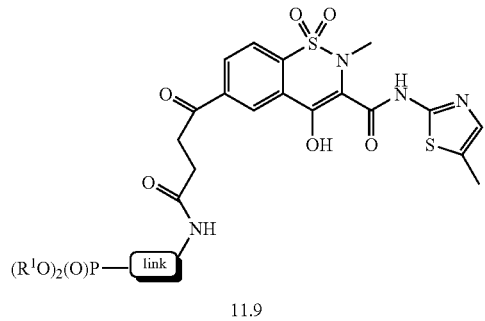
11.9

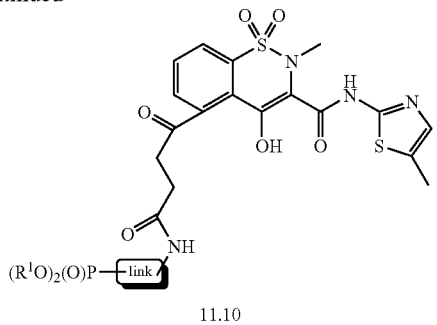
11.10

Compound 11.1 is dissolved in a suitable solvent such as, for example, DCM and is then treated with AlCl₃ and a suitable anhydride, for example, succinic anhydride as described in Tett. Lett 42 (2001) 1467-1469. The acylated products are purified using reverse phase HPLC or flash chromatography on silica gel to give carboxylic acid derivatives 11.2, 11.3, 11.4 and 11.5. Compounds 11.2, 11.3, 11.4 and 11.5 are independently dissolved in a suitable solvent such as, for example, DMF and is then treated with an amine phosphonic acid ester of the general formula 11.6 in the presence of a suitable coupling reagant and tertiary organic base to afford the amides 11.7, 11.8, 11.9, and 11.10.

EXAMPLE 12

Synthesis of Representative Compounds of Formulae 8 and 9

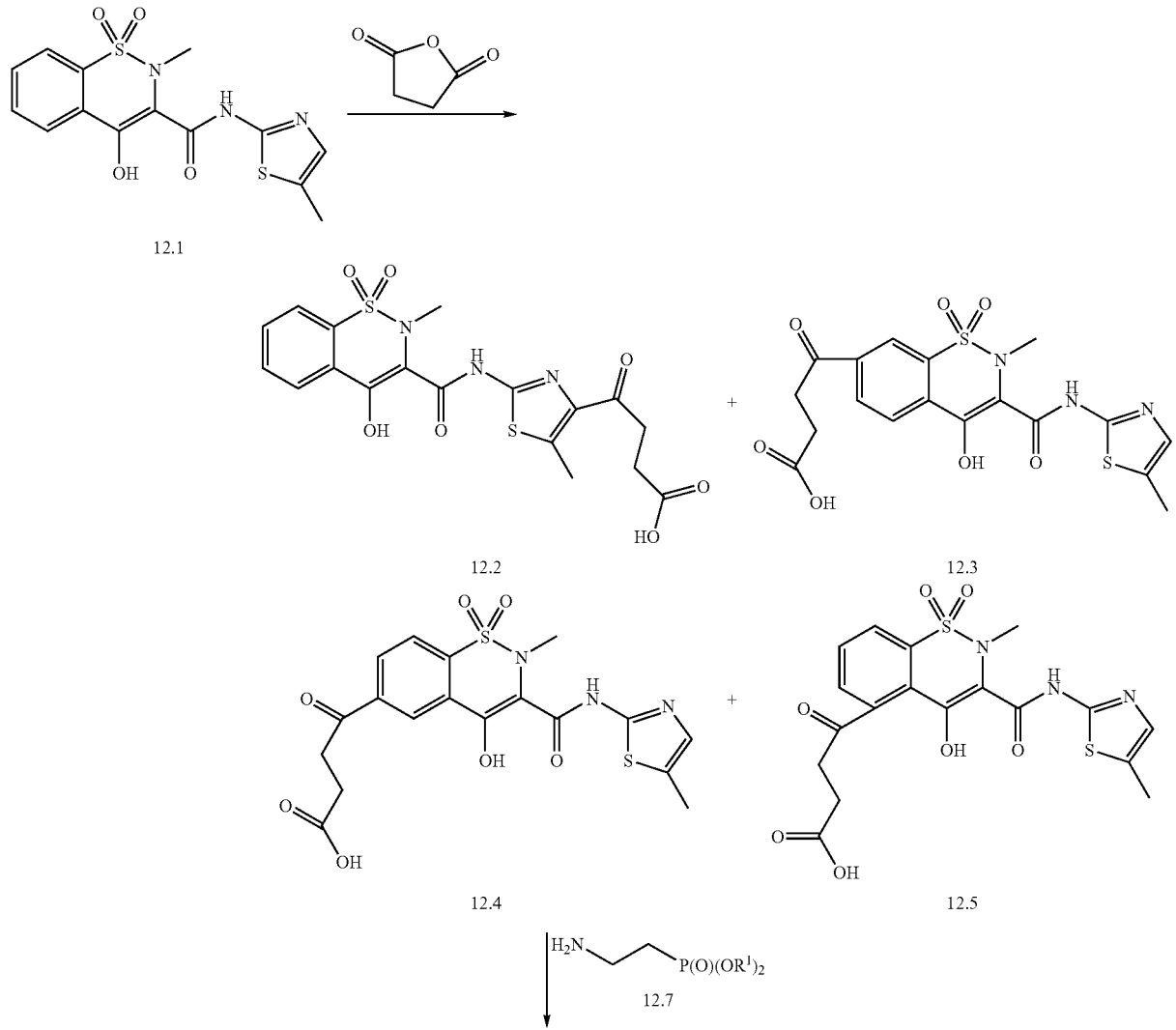

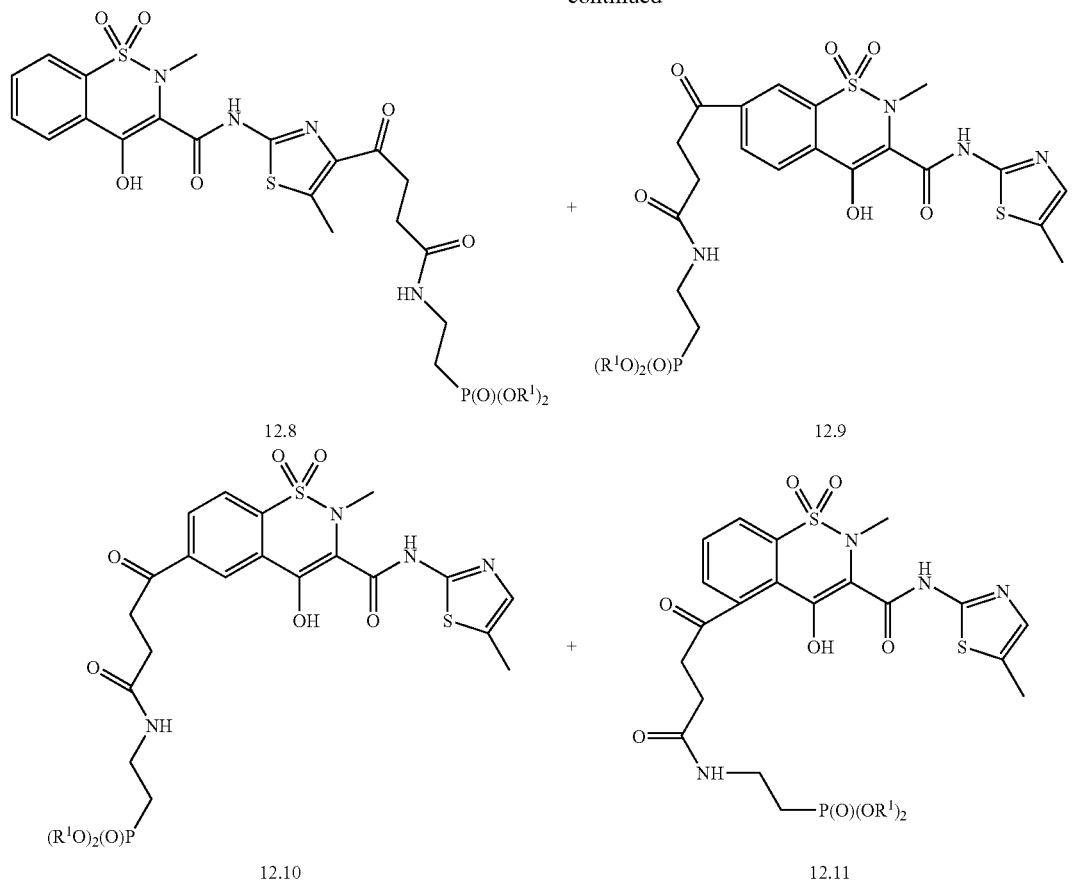

Compound 12.2 12.3, 12.4, or 12.5 is dissolved in DMF and treated with 3 equivalents of (benzotriazol-1-yloxy)tripyrrolidinophosphonium hexafluorophosphate (PYBOP, Sigma) and 6 equivalents of diisopropylamine. The activated esters of compounds 12.2, 12.3, 12.4 and 12.5 are then independently treated with 3 equivalents of the hydrochloride salt of diethyl 2-aminoethyl-1-phosphonate 12.7 which is prepared as described in J. Med. Chem 41 4439-4452. The final products are purified by reverse phase or flash chromatography on silica gel to give amides 12.8, 12.9, 12.10 and 12.11. Using the above procedure but employing different phosphonate reagants in the place of 12.7 additional compounds of the invention can be prepared.

EXAMPLE 13

Synthesis of Representative Compounds of Formula 10

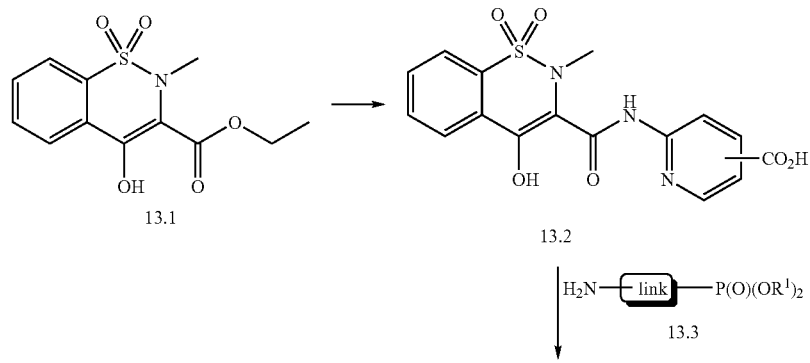

-continued

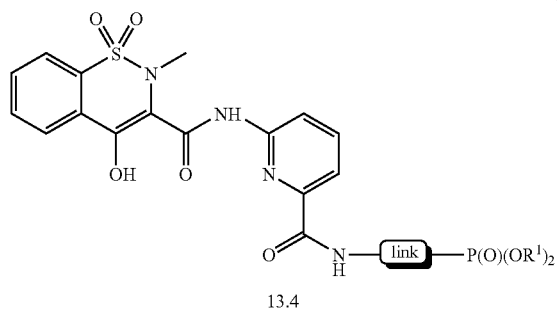
13.4

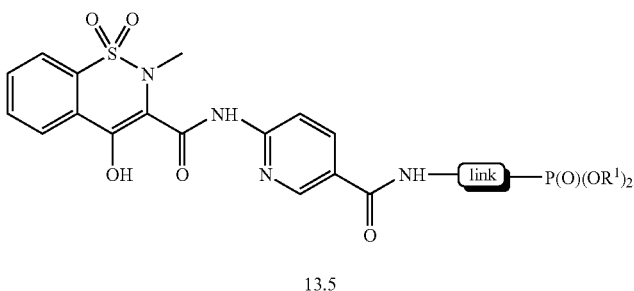
13.5

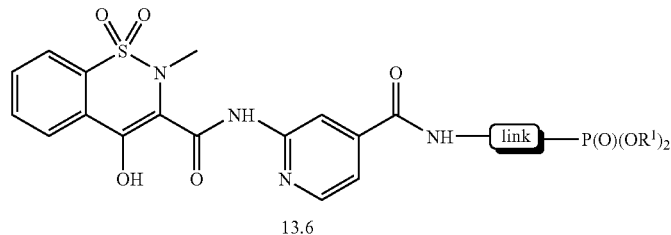
13.6

Intermediate 13.1 is available from Sigma or alternatively can be prepared as described in U.S. Pat. No. 3,591,584. Intermediate 13.2 can be prepared as described in U.S. Pat. No. 3,891,637 example XI or as describe in *J. Med. Chem.* 14 1171-1175 (1971) and coupled to the appropriately substituted aminonictonic acid using the procedure described in J. Med. Chem. 30 678-682 1987.

Piroxicam derivative 13.2 is treated with an amine phosphonic acid ester of the general formula 13.3 in the presence of a suitable coupling reagant and tertiary organic base to afford the amides 13.4, 13.5, and 13.6.

EXAMPLE 14

Synthesis of Representative Compounds of Formula 10

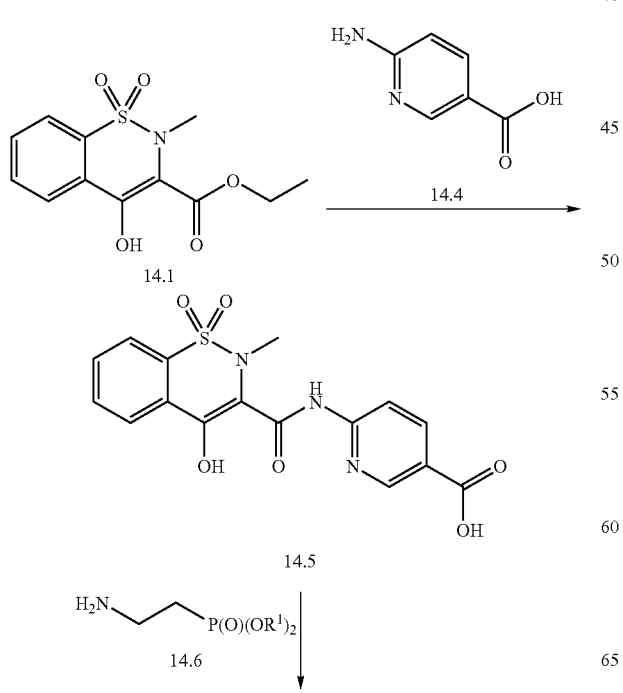

-continued

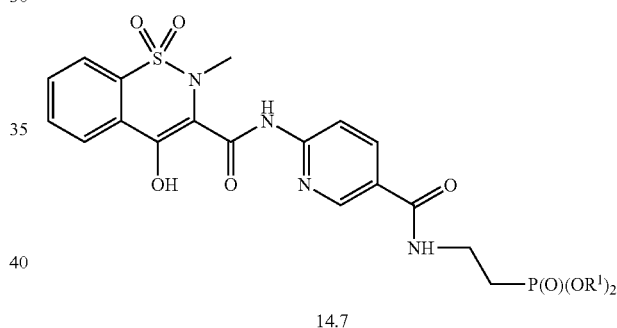
14.7

Compound 14.1 and 6-aminonictonic acid are dissolved in a suitable solvent such as xylene and refluxed with active carbon to give intermediate 14.5. Piroxicam derivative 14.5 is then dissolved in anhydrous DMF and treated with 3 equivalents of O-(7-azabenzotriazol-1-yl-N,N,N',N'-tetramethyluronium hexaflurophosphate (Sigma) and 6 equivalents of diisopropylethylamine. The activated ester of 14.5 is then treated with 3 equivalents of the hydrochloride salt of diethyl 2-aminoethyl-1-phosphonate 14.6 which is prepared as described in J. Med. Chem 41 4439-4452, to form the amide 14.7 which is purified by reverse phase or normal phase chromatography. Using the above procedure but employing different phosphonate reagants in the place of compound 14.6 additional compounds of the invention can be prepared.

EXAMPLE 15
Synthesis of Representative Compounds of Formula 12
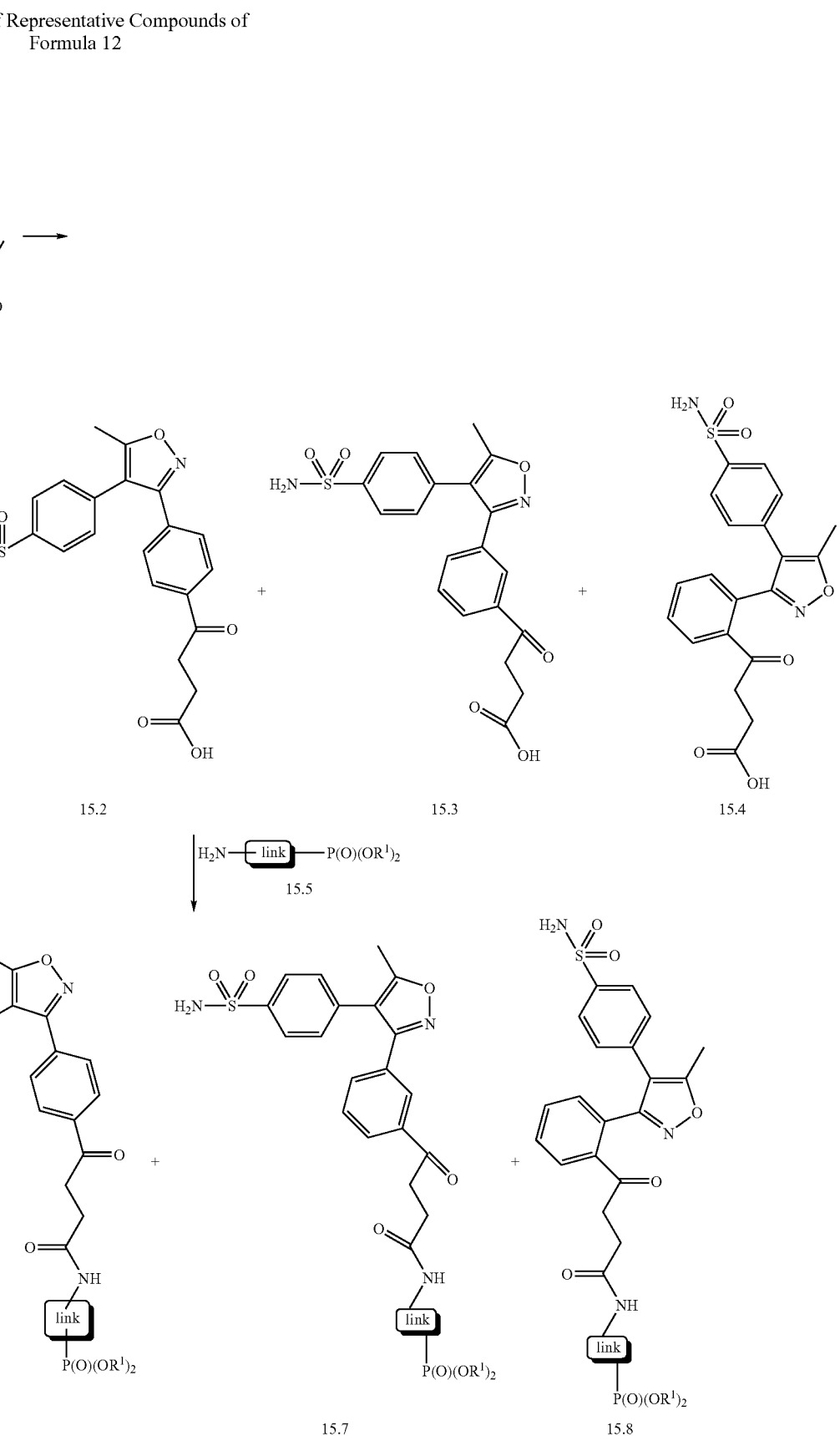

Valdecoxib derivative 15.1 can be obtained as described in U.S. Pat. No. 5,633,272 Example 1. Compound 15.1 is dissolved in a suitable solvent such as, for example, DCM and is treated with $AlCl_3$ and a suitable anhydride, for example, succinic anhydride as described in Tett. Lett 42 (2001) 1467-1469. The acylated products are purified using reverse phase HPLC or flash chromatography on silica gel to give carboxylic acid derivatives 15.2, 15.3 and 15.4. Valdecoxib derivatives 15.2, 15.3 and 15.4 are independently dissolved in a suitable solvent such as, for example, DMF and treated with an amine phosphonic acid ester of the general formula 15.5 in the presence of a suitable coupling reagant and tertiary organic base to afford the amides 15.6, 15.7, and 15.8.

EXAMPLE 16

Synthesis of Representative Compounds of Formula 12

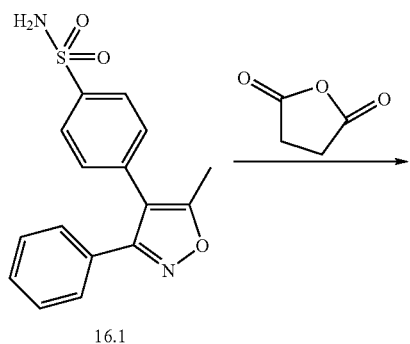

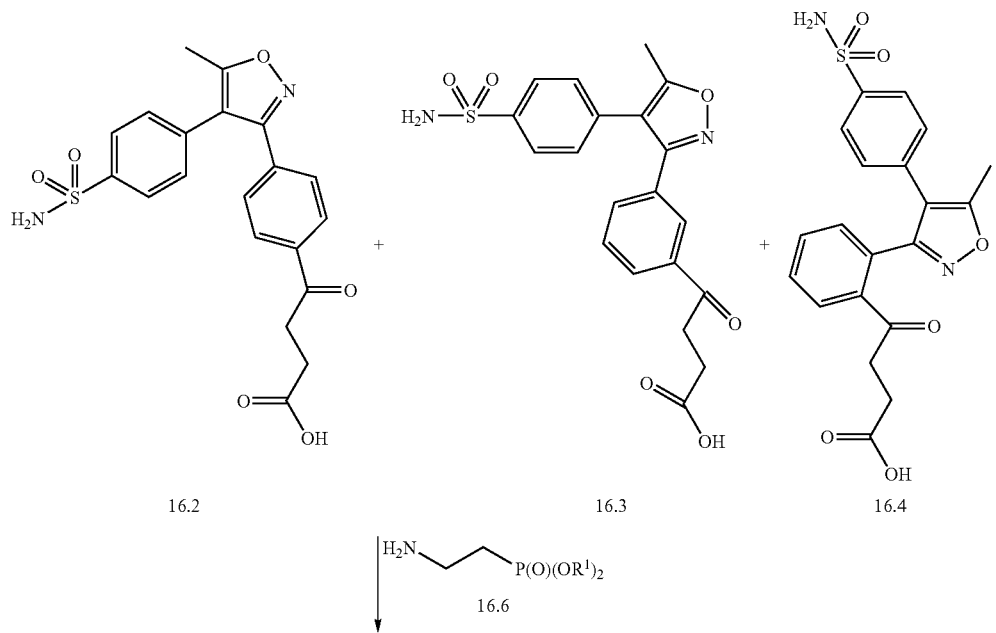

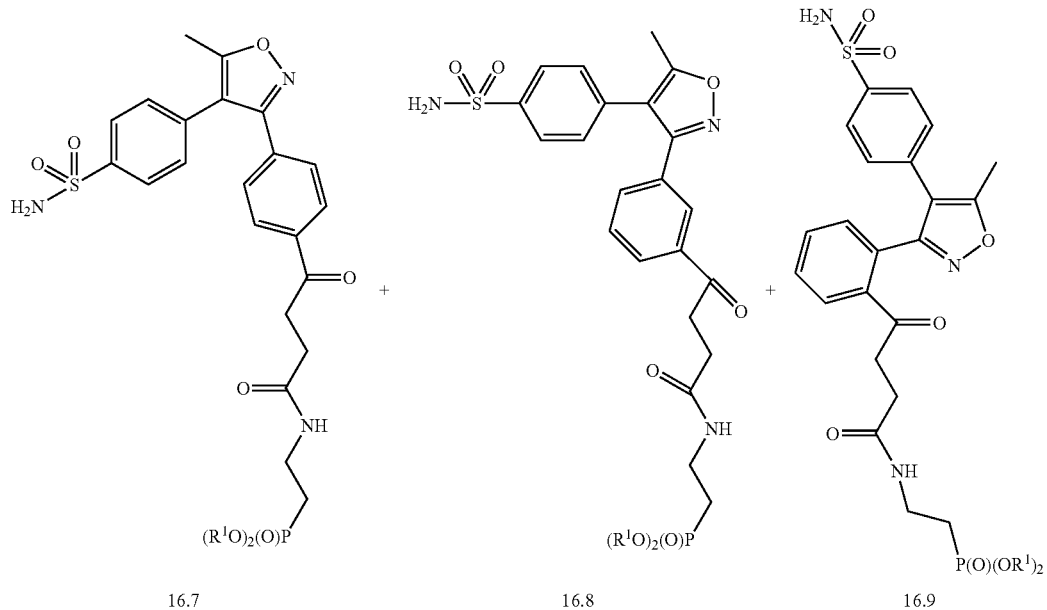

16.7    16.8    16.9

Compound 16.2, 16.3, or 16.4 dissolved in DMF, is treated with 3 equivalents of (benzotriazol-1-yloxy)tripyrrolidino-phosphonium hexafluorophosphate (PYBOP, Sigma) and 6 equivalents of diisopropylamine. The activated esters of 16.2, 16.3 and 16.4 are then independently treated with 3 equivalents of the hydrochloride salt of diethyl 2-aminoethyl-1-phosphonate 16.6 which is prepared as described in J. Med. Chem 41 4439-4452. The final products are purified by reverse phase or flash chromatography on silica gel to give amides 16.7, 16.8 and 16.9. Using the above procedure but employing different phosphonate reagants in the place of 16.6 additional compounds of the invention can be prepared.

EXAMPLE 17

Synthesis of Representative Compounds of Formula 13

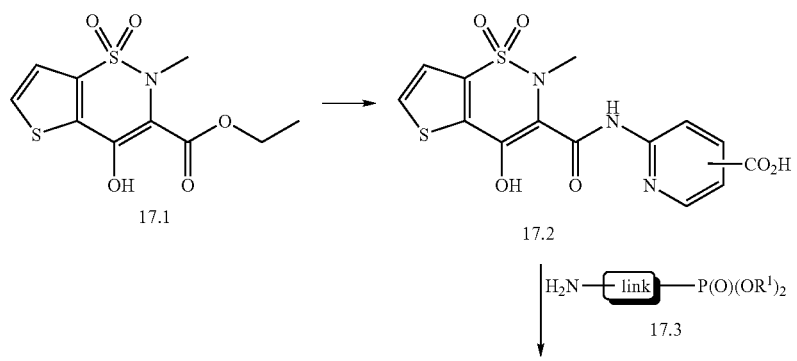

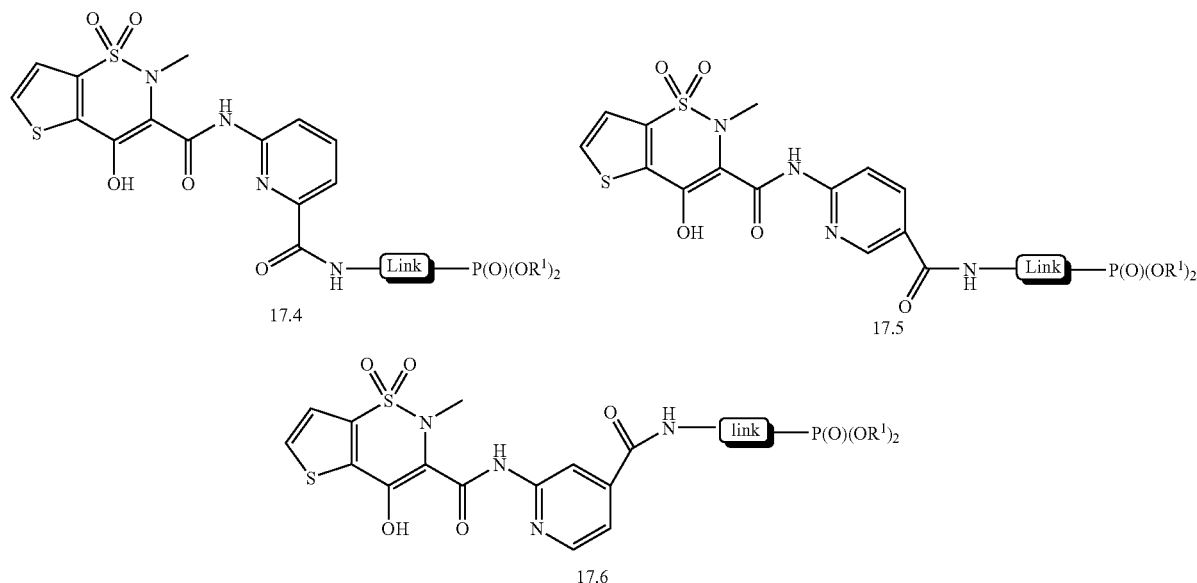

Intermediate 17.1 is prepared as described in U.S. Pat. No. 4,076,709 example 9 or as described in *J. Med. Chem.* 30 678-682 1987. Intermediate 17.1 is converted to intermediate 17.2 using the appropriately substituted aminonicotinic acid. Intermediate 17.2 is treated with an amine phosphonic acid ester of the general formula 17.3 in the presence of a suitable coupling reagant and tertiary organic base to afford the amides 17.4, 17.5 and 17.6.

EXAMPLE 18

Synthesis of Representative Compounds of Formula 13

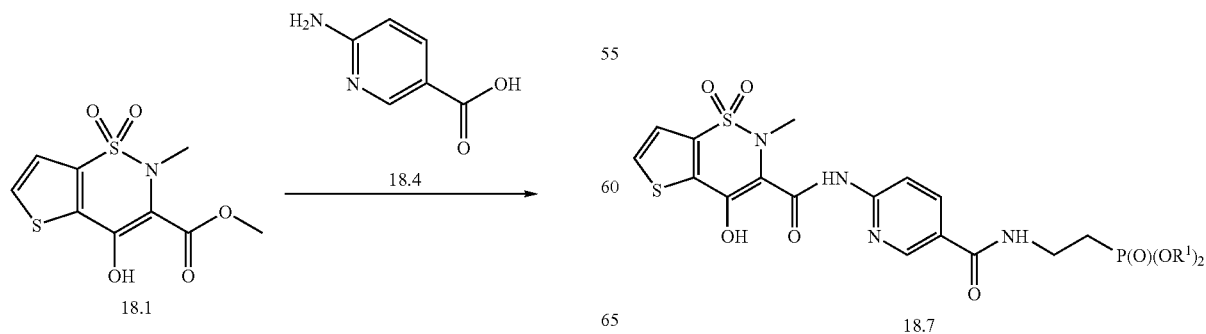

Compound 18.1 and 6-aminonictonic acid are dissolved in a suitable solvent such as xylene and refluxed with active carbon to give intermediate 18.5. which is purified by reverse phase or normal phase chromatography. Tenoxicam derivative 18.5 is then dissolved in anhydrous DMF and treated with 3 equivalents of O-(7-azabenzotriazol-1-yl-N,N,N',N'-tetramethyluronium hexaflurophosphate (Sigma) and 6 equivalents of diisopropylethylamine. The activated ester of 18.5 is then treated with 3 equivalents of the hydrochloride salt of diethyl 2-aminoethyl-1-phosphonate 18.6 which is prepared as described in *J. Med. Chem* 41 4439-4452 to give compound 18.7 which is purified by reverse phase or normal phase chromatography. Using the above procedure but employing different phosphonate reagants in the place of compound 18.6 additional compounds of the invention can be prepared.

EXAMPLE 19

Synthesis of Representative Compounds of Formula 16 ans 17

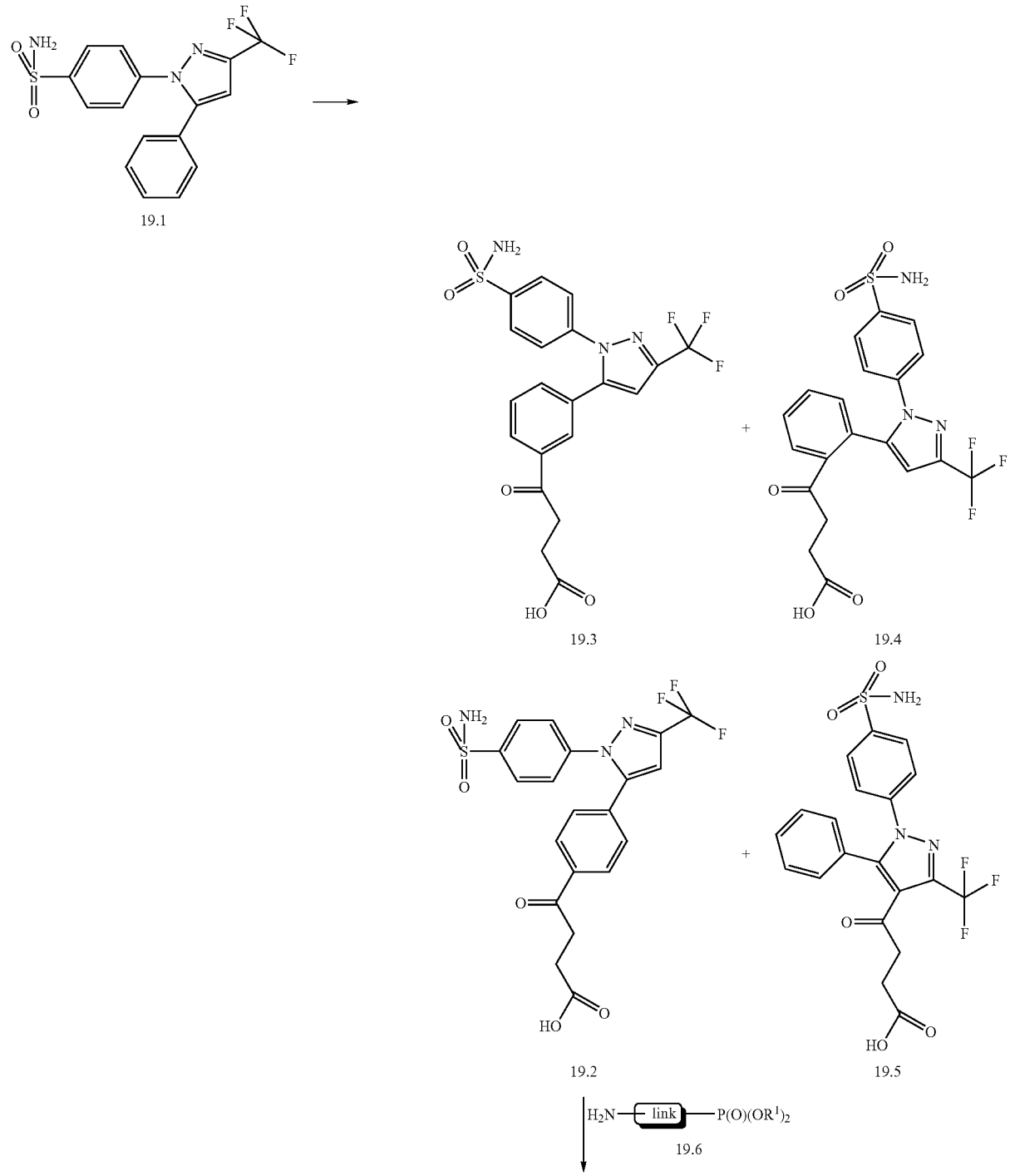

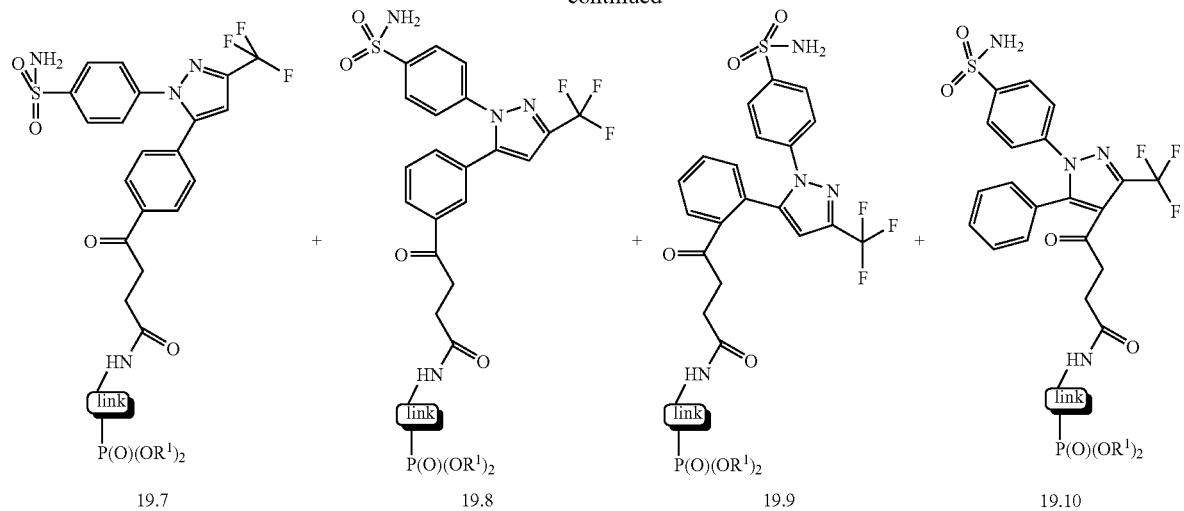

19.7      19.8      19.9      19.10

Celecoxib derivative 19.1 can be obtained as described in U.S. Pat. No. 5,466,823 Example (1 g). Compound 19.1 is dissolved in a suitable solvent such as, for example, DCM and is then treated with $AlCl_3$ and a suitable anhydride, for example, succinic anhydride as described in *Tett. Lett* 42 (2001) 1467-1469. The acylated products are purified using reverse phase HPLC or flash chromatography on silica gel to give carboxylic acid derivatives 19.2, 19.3, 19.4 and 19.5. Celecoxib derivatives 19.2, 19.3, 19.4 and 19.5 are independently dissolved in a suitable solvent such as, for example, DMF and treated with an amine phosphonic acid ester of the general formula 19.6 in the presence of a suitable coupling reagant and tertiary organic base to afford the amides 19.7, 19.8, 19.9 and 19.10.

EXAMPLE 20

Synthesis of Representative Compounds of Formulae 16 and 17

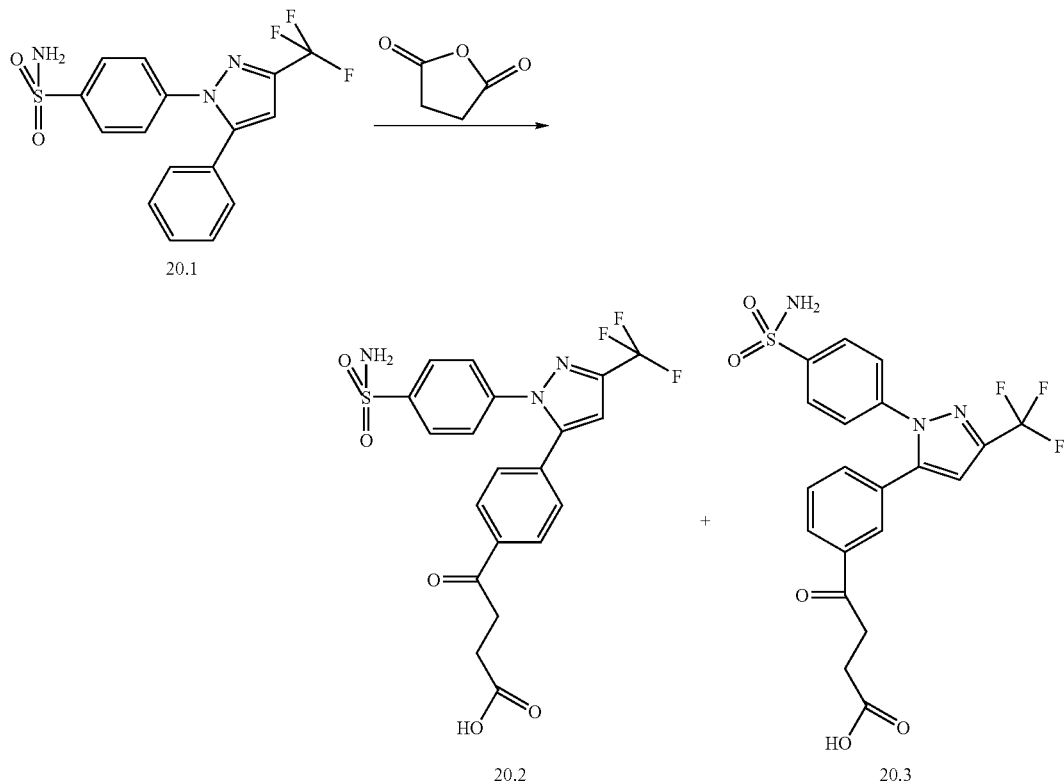

20.1

20.2      20.3

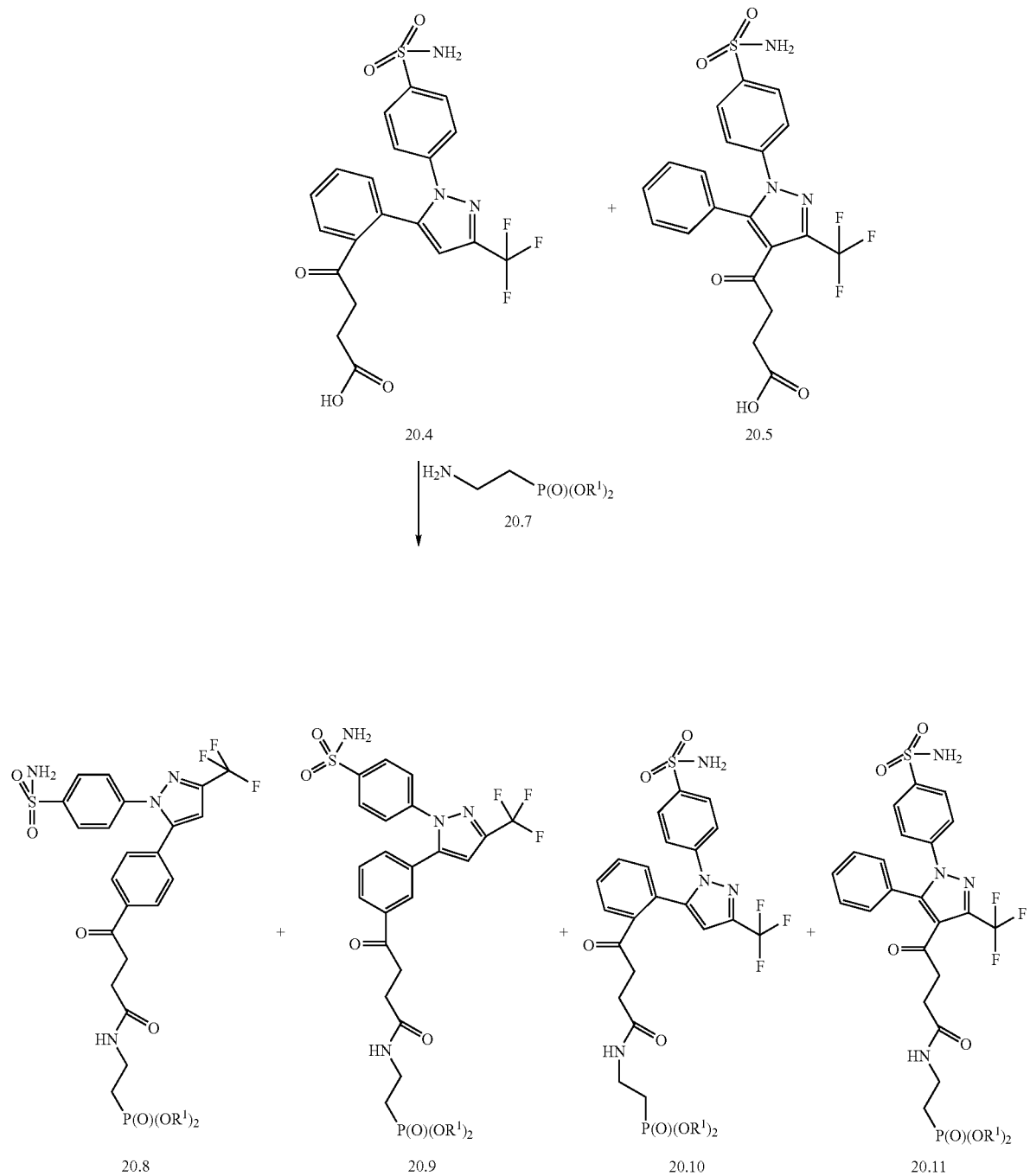

Compound 20.2, 20.3, 20.4, or 20.5 dissolved in DMF, is treated with 3 equivalents of (benzotriazol-1-yloxy)tripyrrolidinophosphonium hexafluorophosphate (PYBOP, Sigma) and 6 equivalents of diisopropylamine. The activated esters of 20.2, 20.3 20.4 and 20.5 are then independently treated with 3 equivalents of the hydrochloride salt of diethyl 2-aminoethyl-1-phosphonate 20.7 which is prepared as described in *J. Med. Chem* 41 4439-4452. The final products are purified by reverse phase or flash chromatography on silica gel to give amides 20.8, 20.9, 20.10 and 20.11. Using the above procedure but employing different phosphonate reagants in the place of 20.7 additional compounds of the invention can be prepared.

EXAMPLE 21

Synthesis of Representative Compounds of Formula 18

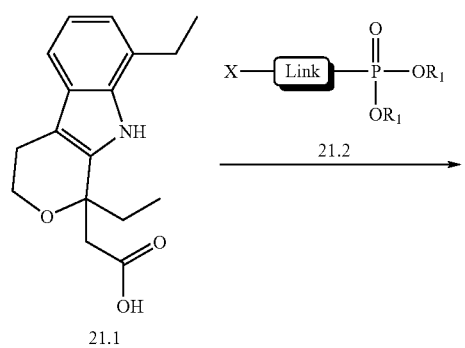

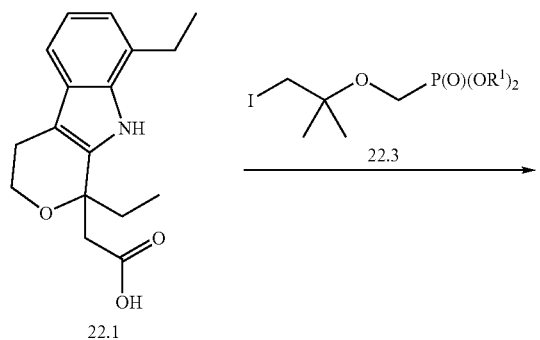

X = Cl, Br, I
$R^1$ = H, alkyl, aryl, haloalkyl, alkenyl, aralkyl, aryl

Etodolac 21.1 can be purchased from Sigma (Cat. No. E0156) or obtained as described in U.S. Pat. No. 3,939,178 Example 477. The indole 21.1 is deprotonated with a suitably strong base such as, for example, KOH or $K_2CO_3$ in DMSO or DMF as described in *J. Org. Chem* 64 6102-6105, followed by alkylation with a halide phosphonic acid ester of the general formula 21.2. The alkylated product is purified by reverse phase or flash chromatography on silica gel to give compound 21.3.

EXAMPLE 22

Synthesis of Representative Compounds of Formula 18

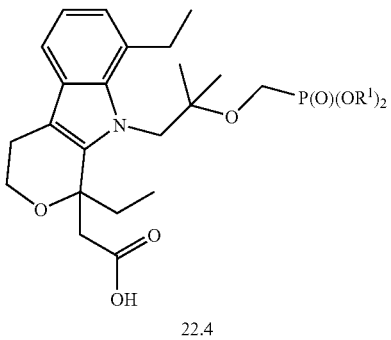

Compound 22.1 is dissolved in DMSO and treated with 6 equivalents of potassium hydroxide, followed by addition of 1.1 equivalents of 22.3 which is prepared as described in *J. Org. Chem*, 52 4427. The residue is purified using reverse-phase or normal phase chromatography to give 22.4 Using the above procedure but employing different phosphonate reagants in the place of compound 22.3 additional compounds of the invention can be prepared.

EXAMPLE 23

Synthesis of Representative Compounds of Formula 19

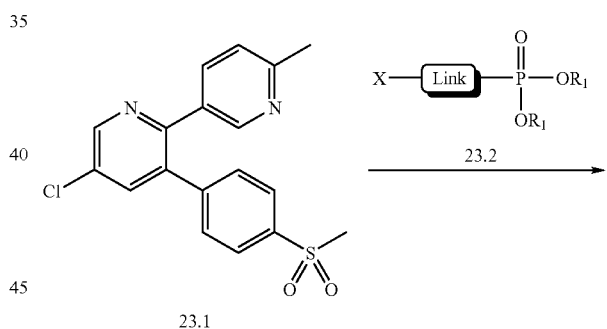

X = I, Br, Cl
$R^1$ = H, alkyl, aryl, haloalkyl, alkenyl, aralkyl, aryl

Etoricoxib derivative 23.1 can be obtained as described in U.S. Pat. No. 5,861,419 Example 59. Alternative syntheses for 23.1 are described in *J. Org. Chem* 2000, 65, 8415-8420. The 2-methyl group of the 5-pyridyl ring is deprotonated with a suitably strong base such as, for example, n-BuLi using the procedure described in *J. Org. Chem* 1987, 52, 4227 followed by alkylation of the newly formed carbanion with a halide phosphonic acid ester of the general formula 23.2. The alkylated product is purified by reverse phase or flash chromatography on silica gel to give compound 23.3.

EXAMPLE 24

Synthesis of Representative Compounds of Formula 19

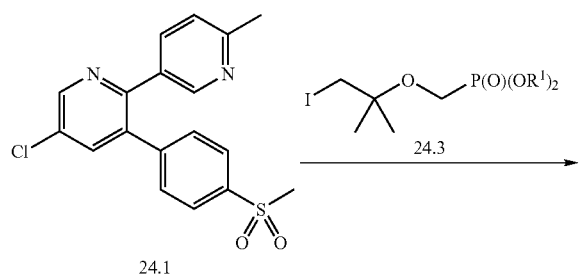

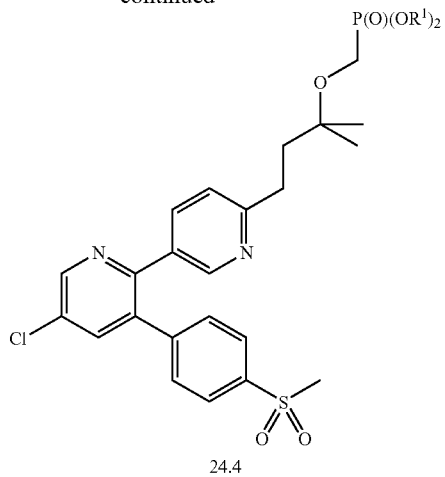

1.5 Equivalents of a 1.6 N solution of n-butyllithium in hexane is added to a solution of compound 24.1 in anhydrous ethyl ether at 0° C. The solution is treated with 4 equivalents of compound 24.3 which is prepared as described in *J. Org. Chem,* 52 4427. The residue is purified using reverse-phase or normal phase chromatography to give 24.4. Using the above procedure but employing different phosphonate reagants in the place of compound 24.3 additional compounds of the invention can be prepared.

EXAMPLE 25

Synthesis of Representative Compounds of Formula 20

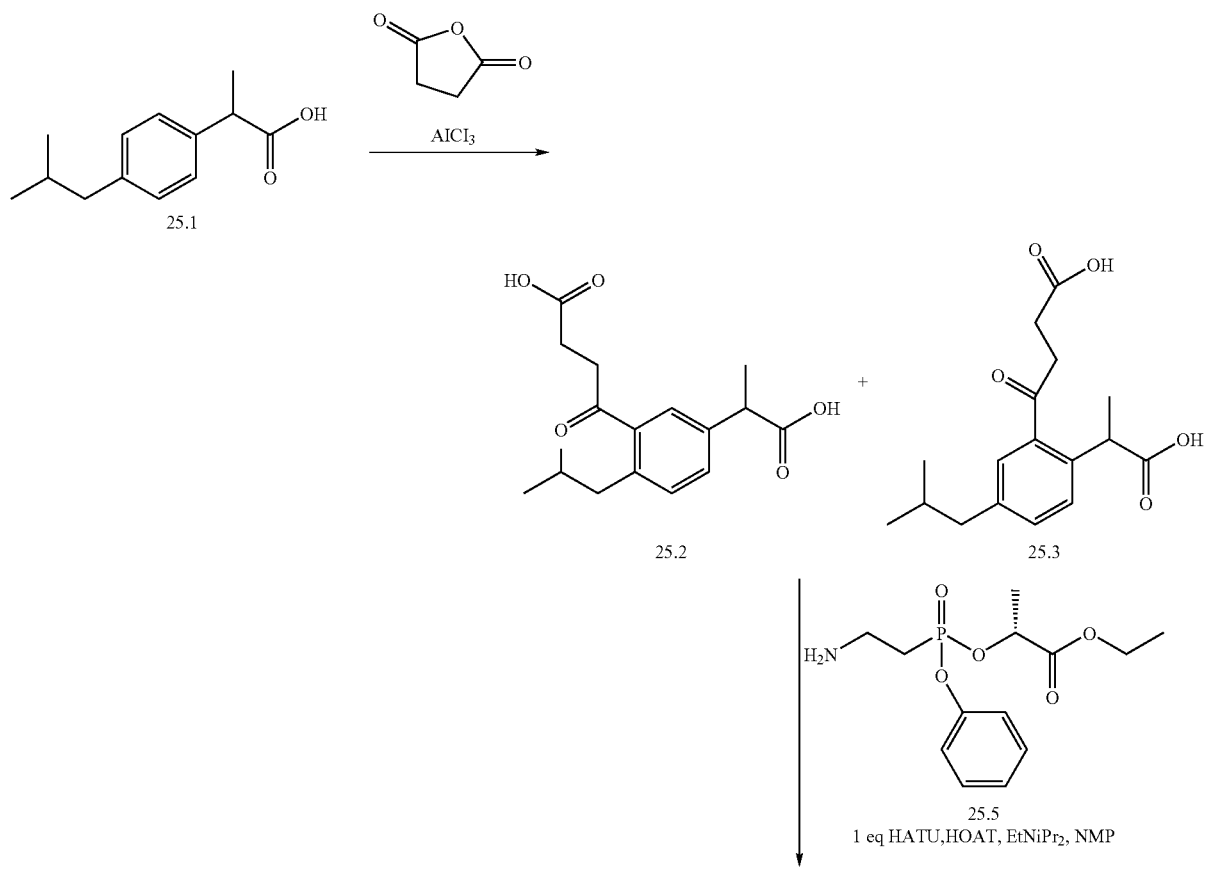

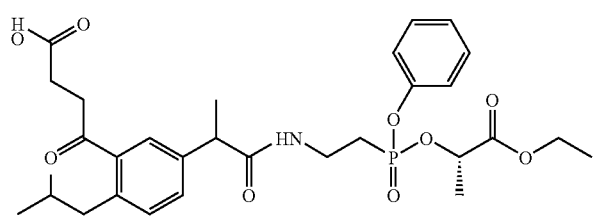

25.6

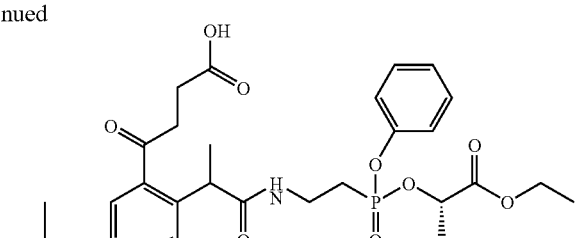

25.7

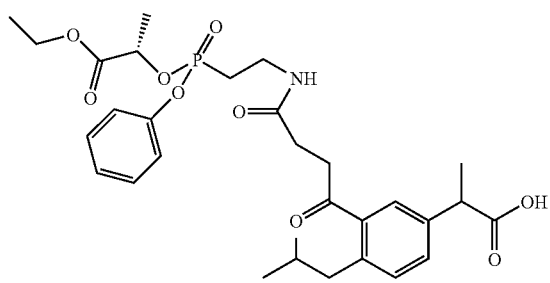

25.8

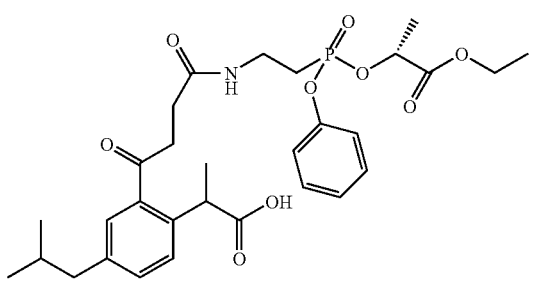

25.9

Ibuprofen (U.S. Pat. No. 3,385,886), commercially available from Sigm-Aldrich, is converted to dicaroxylic acids 25.2 and 25.3 by the action of succinic anhydride in the presence of aluminum trichloride in a suitable solvent (carbon disulfide, nitrobenzene, dichloroethane). Covnersion 25.2 and 25.3 to phosphonate prodrugs occurs by the addition of 1.5 equivalents HOAT, HATU, diisoproplylethylamine to 25.2 and 25.3 followed by the addition of 25.5 all in a suitable solvent such as NMP, DMF, THF, or dichloroethane. Separation of the final mixture leads to the desired materials 25.6 and 25.7, 25.8 and 25.9.

EXAMPLE 26

Synthesis of Representative Compounds of Formulae 21 and 22

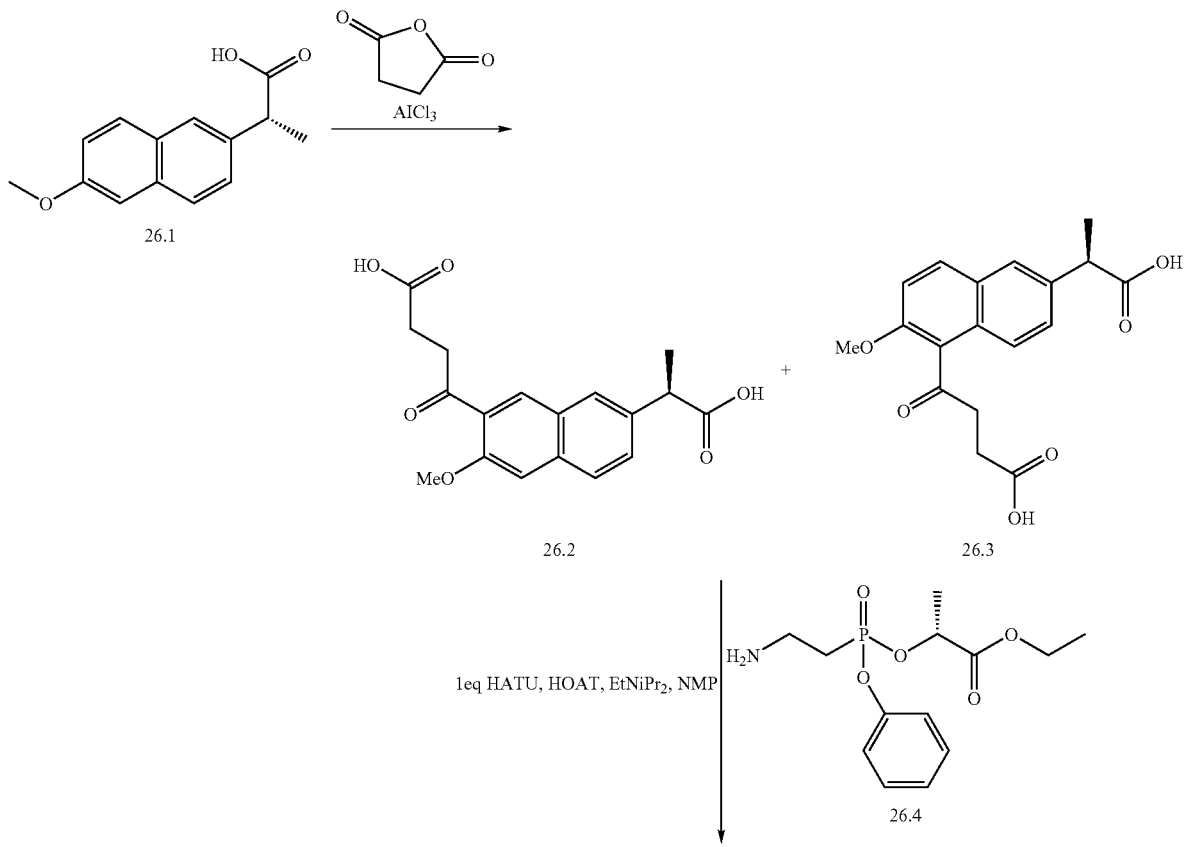

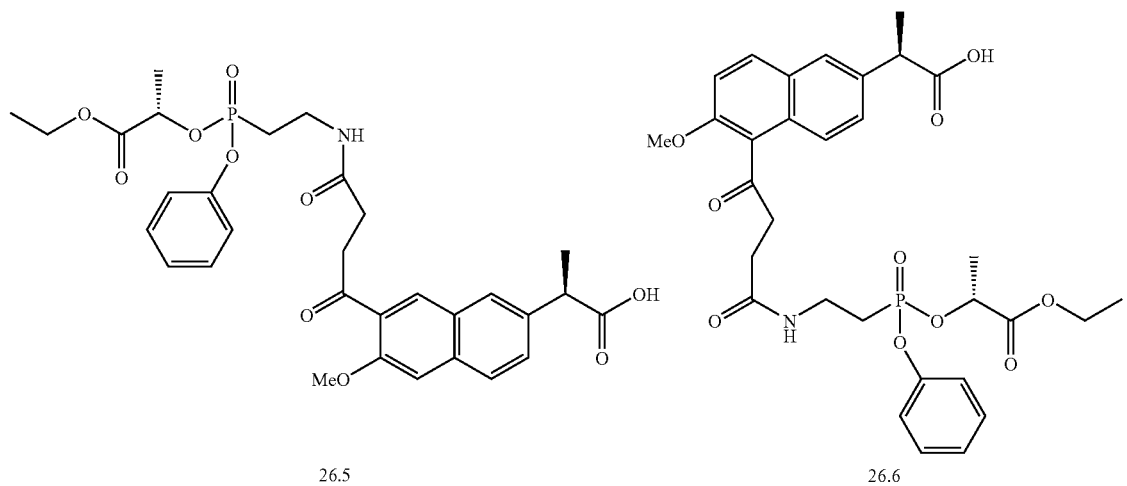

26.5  26.6

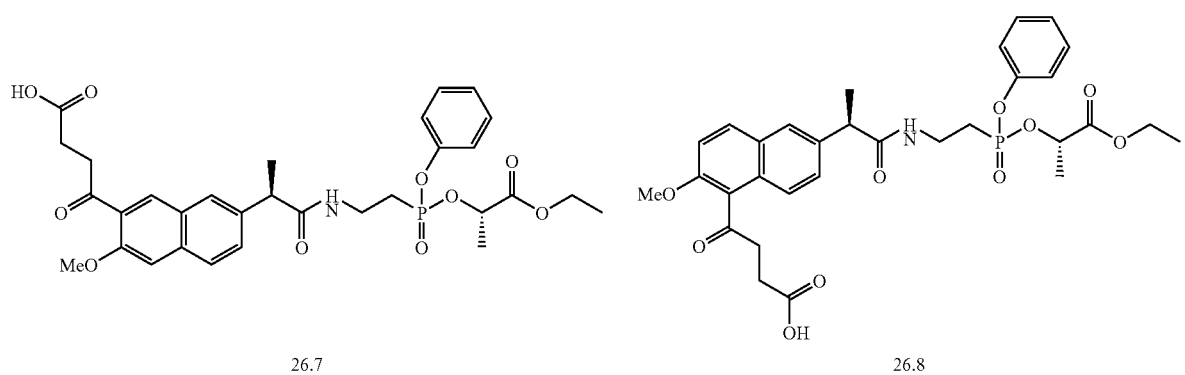

26.7  26.8

Naproxen (U.S. Pat. No. 3,904,683), commercially available from Sigm-Aldrich, is converted to dicaroxylic acids 26.2 and 26.3 by the action of succinic anhydride in the presence of aluminum trichloride in a suitable solvent such as carbon disulfide, nitrobenzene, and dichloroethane. Conversion of 26.2 and 26.3 to phosphonate prodrugs occurs by the addition of 1.5 equivalents HOAT, HATU, and diisoproplyl-ethylamine to 26.2 and 26.3 followed by the addition of 26.4 all in a suitable solvent such as NMP, DMF, THF, or dichloroethane. Separation of the final mixture leads to the desired materials 26.5, 26.6, 26.7, 26.8.

EXAMPLE 27

Synthesis of Representative Compounds of Formula 23

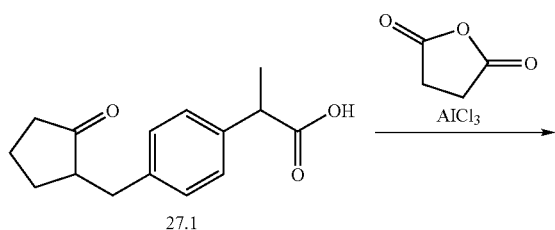

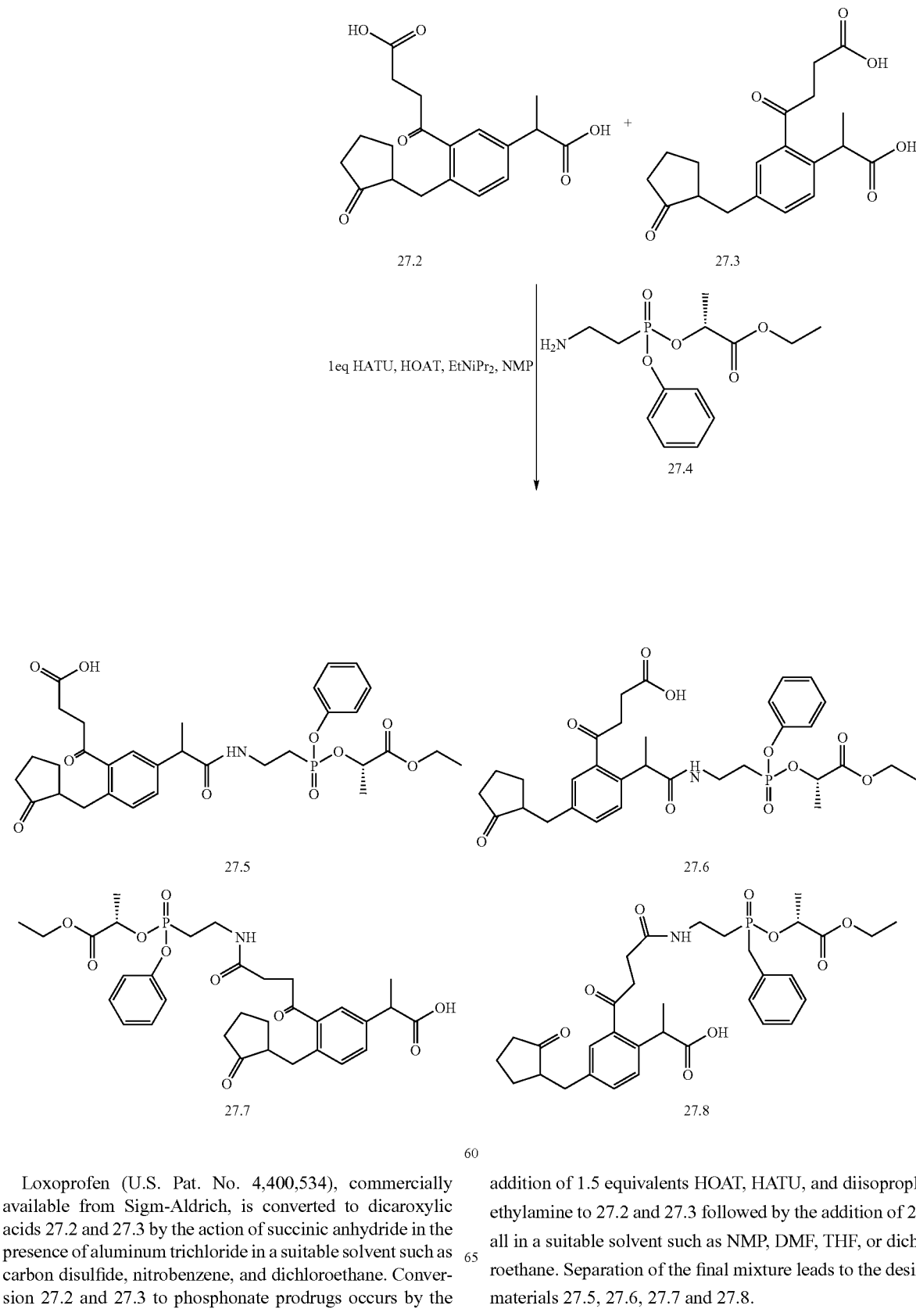

Loxoprofen (U.S. Pat. No. 4,400,534), commercially available from Sigm-Aldrich, is converted to dicaroxylic acids 27.2 and 27.3 by the action of succinic anhydride in the presence of aluminum trichloride in a suitable solvent such as carbon disulfide, nitrobenzene, and dichloroethane. Conversion 27.2 and 27.3 to phosphonate prodrugs occurs by the addition of 1.5 equivalents HOAT, HATU, and diisoproplyl-ethylamine to 27.2 and 27.3 followed by the addition of 27.4 all in a suitable solvent such as NMP, DMF, THF, or dichloroethane. Separation of the final mixture leads to the desired materials 27.5, 27.6, 27.7 and 27.8.

EXAMPLE 28

Synthesis of Representative Compounds of Formula 25

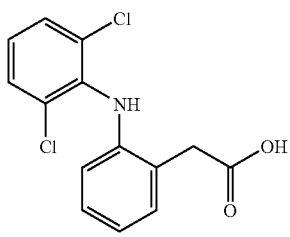

Diclofenac

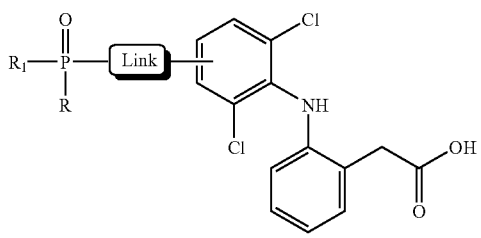

28.1 link = linkage group
R = OAryl, O-heteroaryl, amino acid ester
R$_1$ = lactate, amino acid ester Representative compounds of the invention (28.1) are illustrated above. A linkage group is a portion of the structure that links two substructures, one of which is Diclofenac having the general formula above, the other a phosphonate moiety bearing the appropriate R and R$_1$ groups. The linkage typically has at least one uninterrupted chain of atoms other than hydrogen. The R and R$_1$ groups can be both natural and un-natural amino acid esters linked through the amine nitrogen, or alternatively, one of the groups can be substituted for oxygen linked aryl, alkyl, aralkyl group. Alternatively one of the groups may be an oxygen linked aryl, alkyl, aralkyl group and the other lactate ester.

The preparation of a representative compound of the invention is illustrated below.

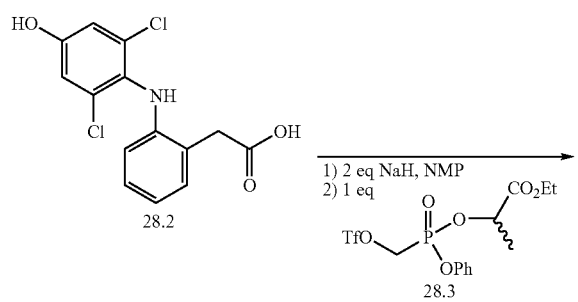

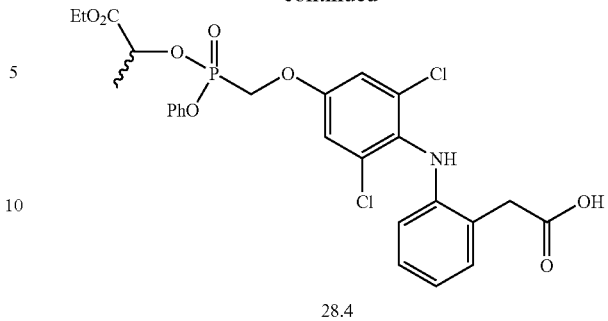

28.4

Compound 28.2 (available from Sigma-Aldrich) is reacted with 3 equivalents of a strong base (for example, NaH, KH, NaHMDS, KHMDS, LDA) in a polar aprotic solvent (DMF, DMSO, NMP, DMA, THF) for a period of 1 minute to 4 hours. To this mixture is added triflate 28.3. After standard work-up and purification, 28.4 is formed.

EXAMPLE 29

Synthesis of Representative Compounds of Formula 26

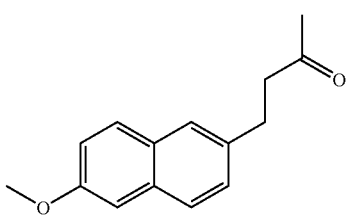

Relafen 29.1

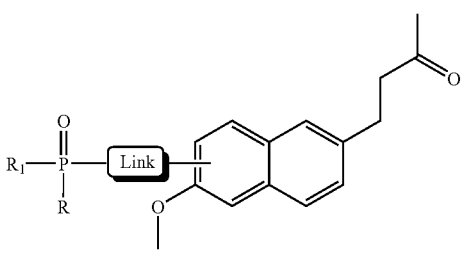

link = linkage group
R = OAryl, O-heteroaryl, amino acid ester
R$_1$ = lactate, amino acid ester Representative compounds of the invention (29.1) are illustrated above. A linkage group is a portion of the structure that links two substructures, one of which is Relafen having the general formula above, the other a phosphonate moiety bearing the appropriate R and R$_1$ groups. The linkage has at least one uninterrupted chain of atoms other than hydrogen. The R and R$_1$ groups can be both natural and un-natural amino acid esters linked through the amine nitrogen, or alternatively, one of the groups can be substituted for oxygen linked aryl, alkyl, aralkyl group. Alternatively one of the groups may be an oxygen linked aryl, alkyl, aralkyl group and the other lactate ester.

The preparation of a representative compound of the invention is illustrated below.
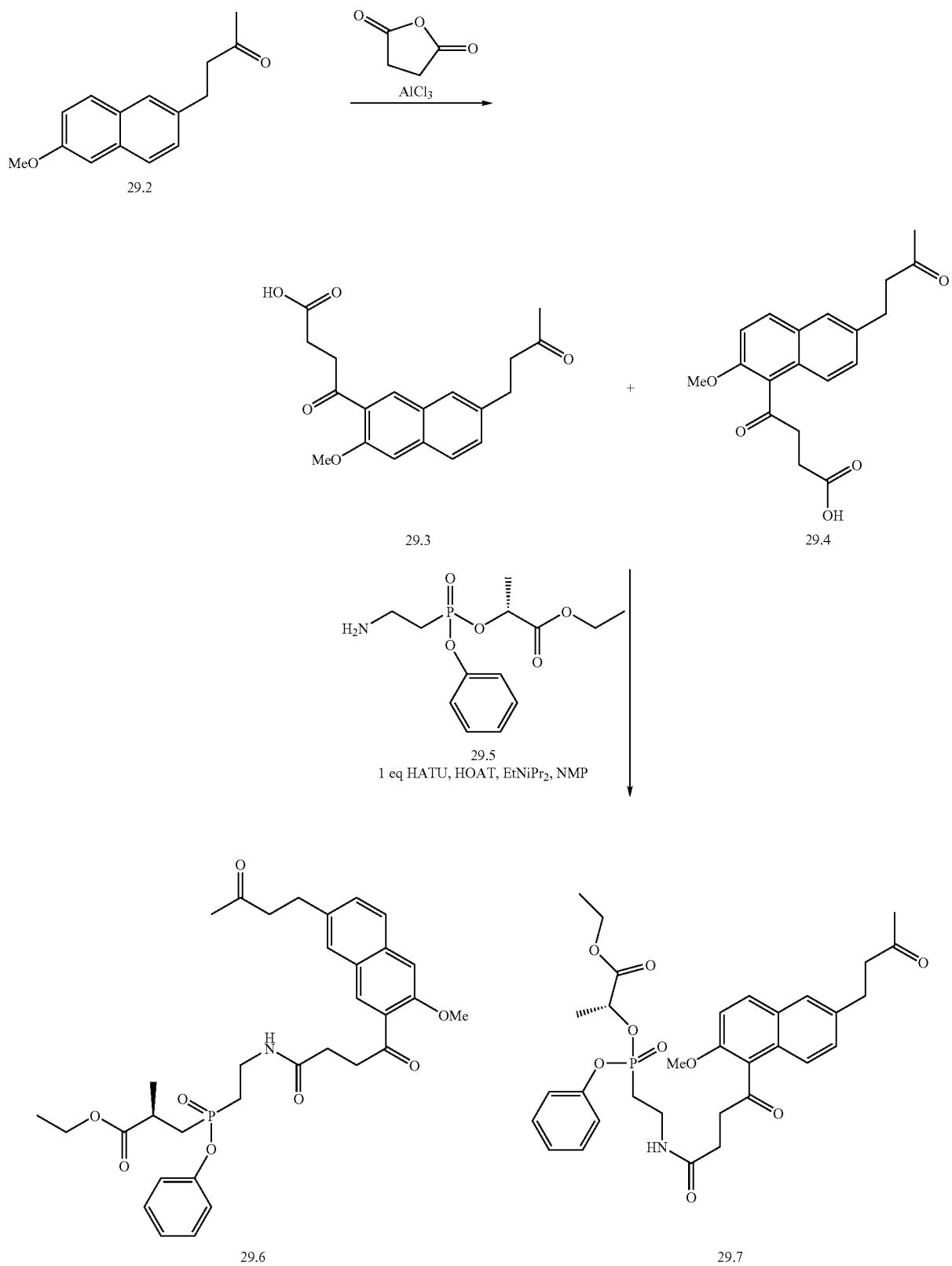

Relafen (29.2, U.S. Pat. No. 4,106,179), commercially available from Sigm-Aldrich, is converted to carboxylic acids 29.3 and 29.4 by the action of succinic anhydride in the presence of aluminum trichloride in a suitable solvent such as carbon disulfide, nitrobenzene, and dichloroethane. Conversion 29.3 and 29.4 to phosphonate prodrugs occurs by the addition of 1.5 equivalents HOAT, HATU, and diisoproplyl-ethylamine to 29.3 and 29.4 followed by the addition of 29.5 all in a suitable solvent such as NMP, DMF, THF, or, dichloroethane. This process can either occur after separation of 29.3 from 29.4 by standard means or on the mixture of products. Separation of the final mixture leads to the desired materials. 29.6 and 29.7.

-continued

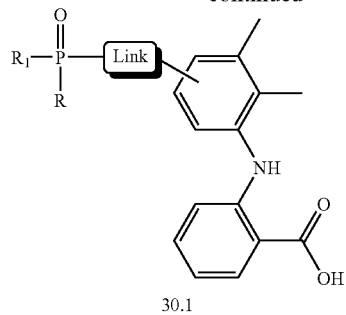

30.1 link = linkage group
R = OAryl, O-heteroaryl, amino acid ester
$R_1$ = lactate, amino acid ester Representative compounds of the invention (30.1) are illustrated above. A linkage group is a portion of the structure that links two substructures, one of which is Mefeamic Acid having the general formula above, the other a phosphonate moiety bearing the appropriate R and $R_1$ groups. The linkage has at least one uninterrupted chain of atoms other than hydrogen. The R and $R_1$ groups can be both natural and un-natural amino acid esters linked through the amine nitrogen, or alternatively, one of the groups can be substituted for oxygen linked aryl, alkyl, aralkyl group. Alternatively one of the groups may be an oxygen linked aryl, alkyl, aralkyl group and the other lactate ester.

The preparation of a representative compound of the invention is illustrated below.

EXAMPLE 30

Synthesis of Representative Compounds of Formula 28

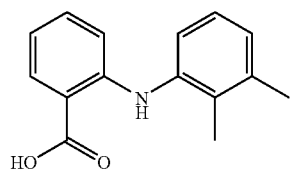

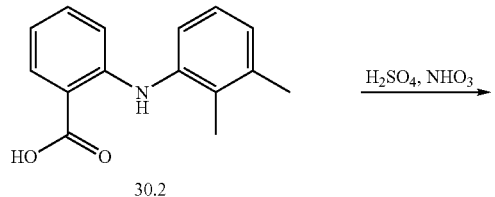

30.2

$\xrightarrow{H_2SO_4, NHO_3}$

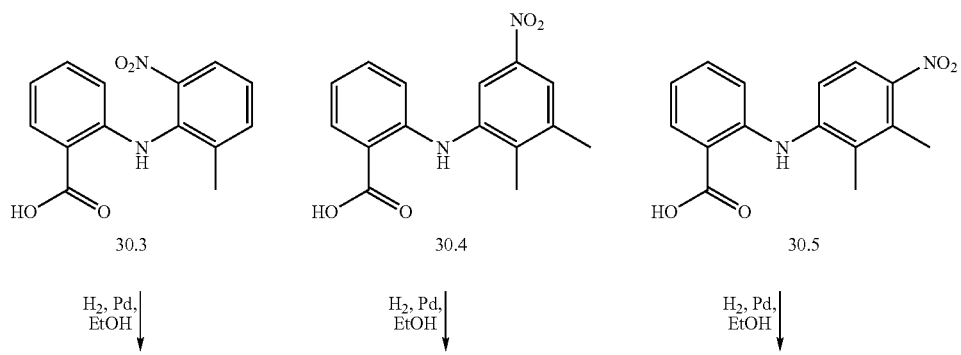

30.3  30.4  30.5

$H_2$, Pd, EtOH

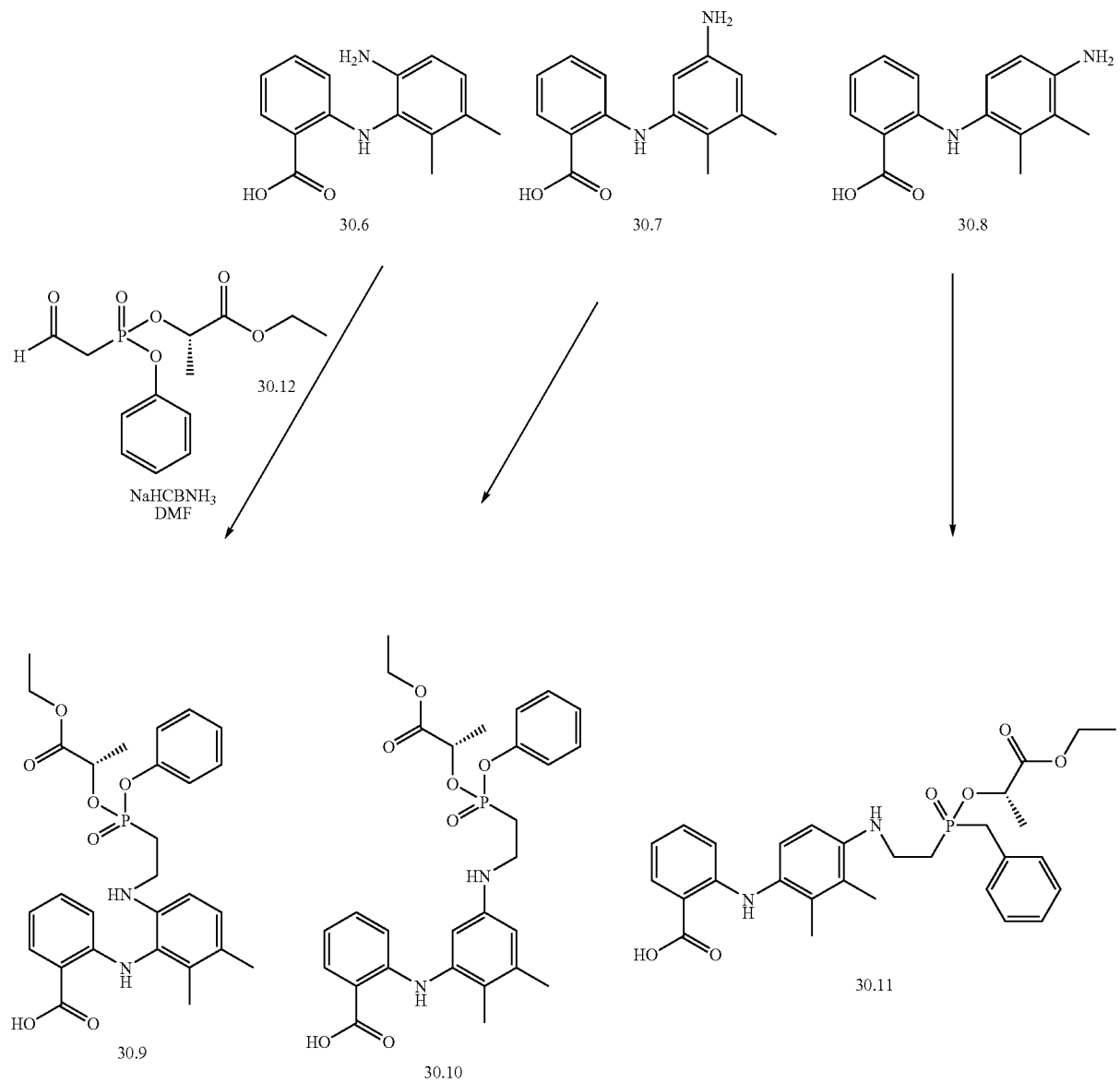

Mefeamic Acid (30.2, U.S. Pat. No. 3,138,636), available from Sigm-Aldrich, is converted to nitro derivatives 30.3, 30.4, and 30.5 by the action of nitric acid in the presence of fuming sulfuric acid. Conversion of 30.3, 30.4, and 30.5 to the corresponding anilines (30.6, 30.7, and 30.8) is performed by reductive amination with 30.12 under a variety of conditions (Zn/AcOH, SnCl2, H2/Pd/C) in the appropriate solvents. The anilines are converted to 30.9, 30.10, and 30.11 by the action of a suitable reducing agent (NaCNBH$_3$, NaHB(OAc)$_3$, or NaBH$_4$) all in a suitable solvents such as NMP, DMF, THF, EtOH or dichloroethane. The regioisomers can be separated using standard methods known in the art at the nitro, aniline, or phosphonate stages.

EXAMPLE 31

Synthesis of Representative Compounds of Formula 30 and 31

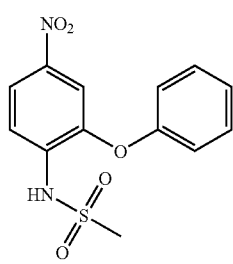

-continued

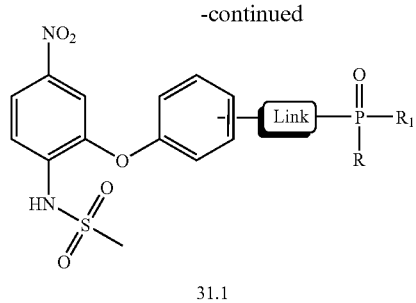

31.1 link = linkage group
R = OAryl, O-heteroaryl, amino acid ester
R₁ = lactate, amino acid ester Representative compounds of the invention (31.1) are illustrated above. A linkage group is a portion of the structure that links two substructures, one of which is Nimesulide having the general formula above, the other a phosphonate moiety bearing the appropriate R and R₁ groups. The linkage has at least one uninterrupted chain of atoms other than hydrogen. The R and R₁ groups can be both natural and un-natural amino acid esters linked through the amine nitrogen, or alternatively, one of the groups can be substituted for oxygen linked aryl, alkyl, aralkyl group. Alternatively one of the groups may be an oxygen linked aryl, alkyl, aralkyl group and the other lactate ester.

The preparation of a representative compound of the invention is illustrated below.

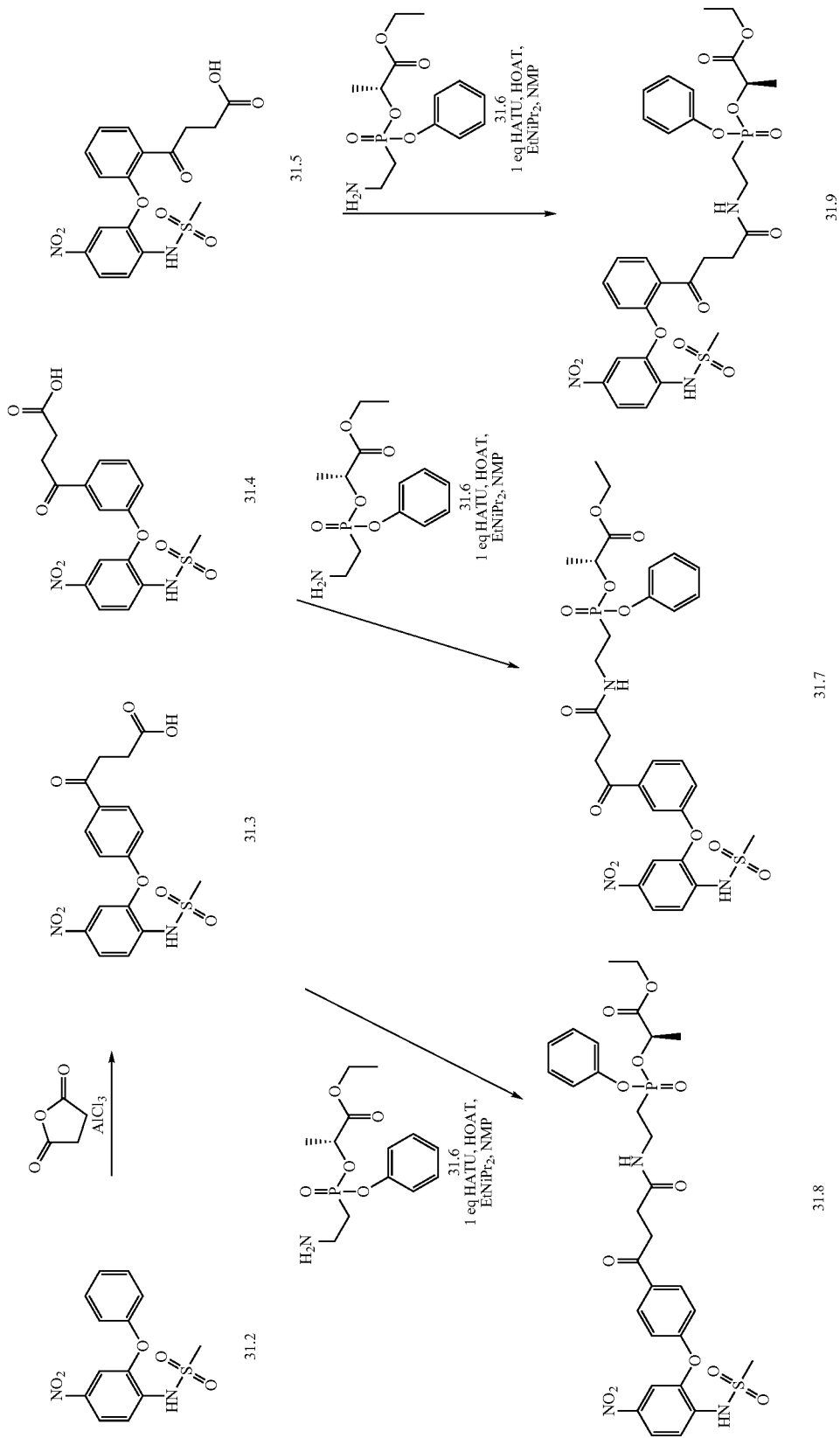

Nimesulide (31.2, U.S. Pat. No. 3,840,597), available from Sigm-Aldrich, is converted to dicaroxylic acids 31.3, 31.4, and 31.5 by the action of succinic anhydride in the presence of a Lewis acid such as aluminum trichloride in a suitable solvent such as carbon disulfide, nitrobenzene, and dichloroethane. The products are separated by standard methods or carried through to the next step after work-up. Conversion of 31.3, 31.4, and 31.5 to phosphonate prodrugs occurs by the addition of 1.5 equivalents HOAT, HATU, and diisoproplylethylamine to 31.3, 31.4, and 31.5 followed by the addition of 31.6 all in a suitable solvent such as NMP, DMF, THF, or dichloroethane. Separation and/or purification of the final mixture produces to the desired materials 31.7, 31.8, and 31.9.

EXAMPLE 32

Synthesis of Representative Compounds of Formula 32

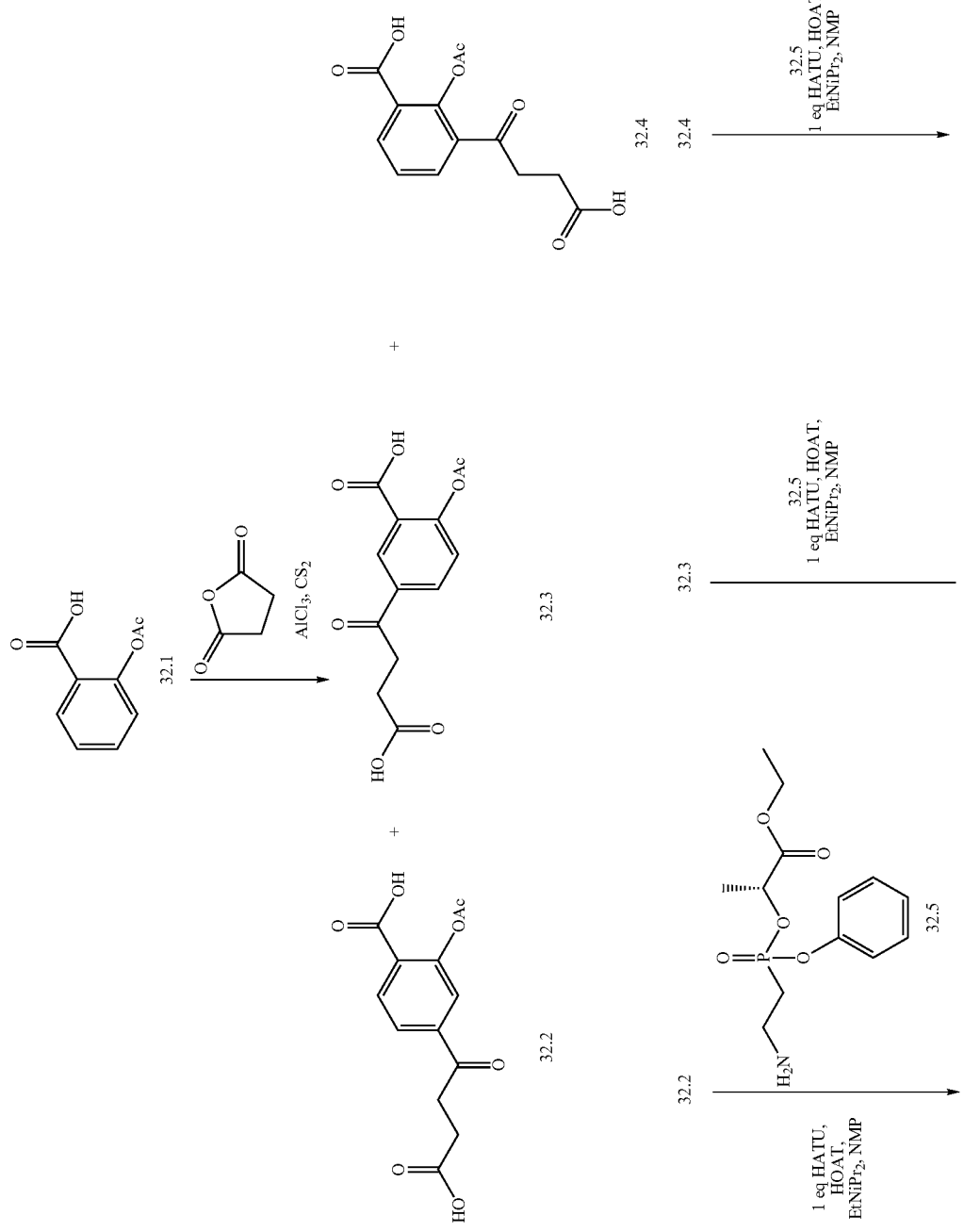

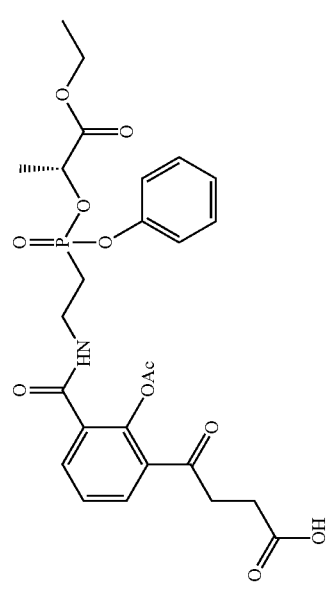
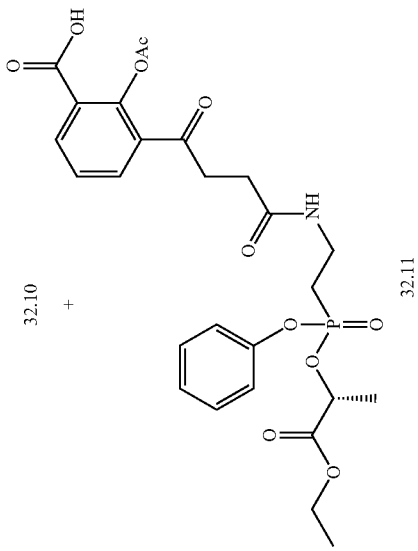
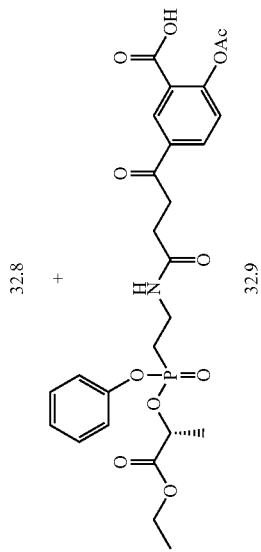
-continued
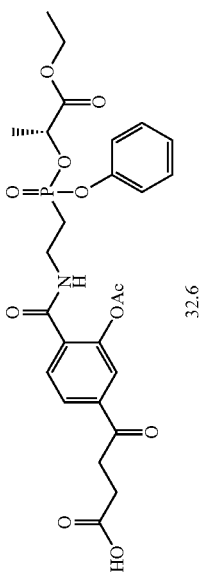
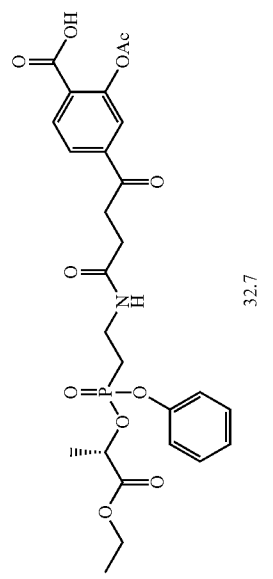

Aspirin (32.1), available from Sigma-Aldrich, is converted to dicarboxylic acids 32.2, 32.3, and 32.4 by the action of succinic anhydride in the presence of a Lewis acid such as aluminum trichloride in a suitable solvent (carbon disulfide, nitrobenzene, dichloroethane). Conversion 32.2, 32.3, and 32.4 to phosphonate prodrugs occurs by the addition of 1.5 equivalents HOAT, HATU, diisoproplylethylamine to 32.2, 32.3, and 32.4 followed by the addition of 32.5 all in a suitable solvent such as NMP, DMF, THF, or dichloroethane. Separation using standard methonds of the final mixture leads to the desired materials 32.6, 32.7, and 32.8, 32.9, 32.10, and 32.11. Alternatively, 3.1, 3.2, and 3.3 can be separated using standard methods and carried forward.

EXAMPLE 33

Synthesis of Representative Compounds of Formulae 33 and 34

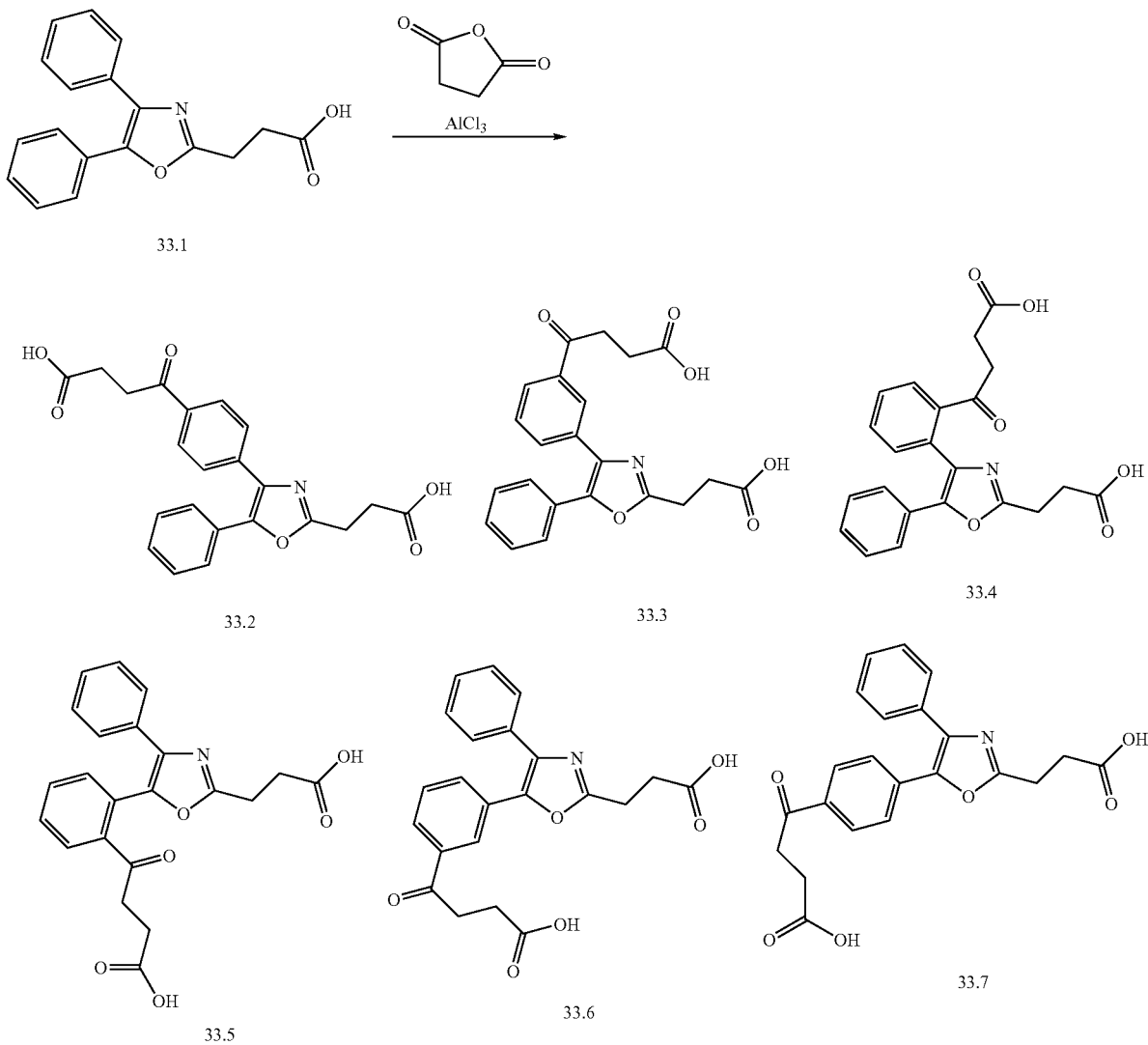

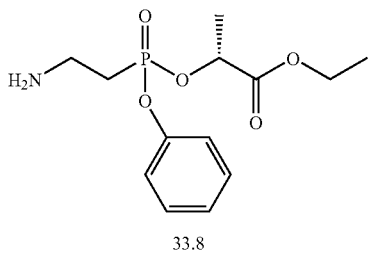

1.5 eq HATU, HOAT, EtNiPr₂, NMP

-continued

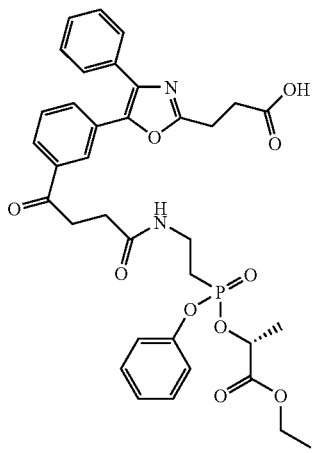

33.9

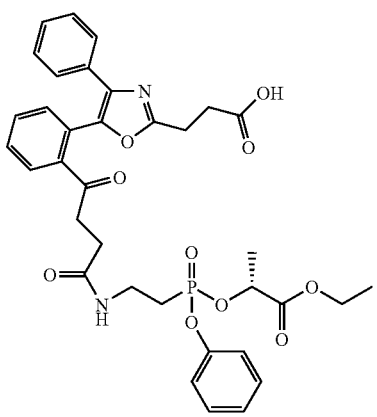

33.10

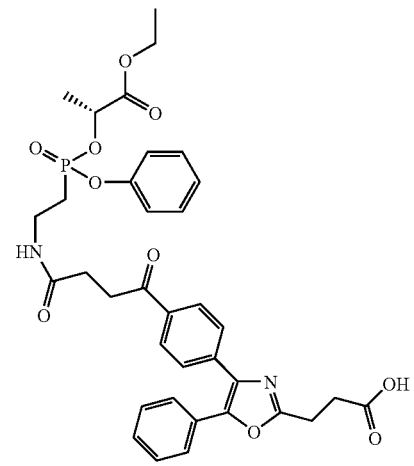

33.11

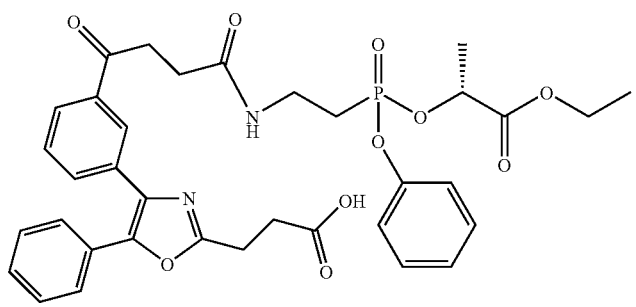

33.12

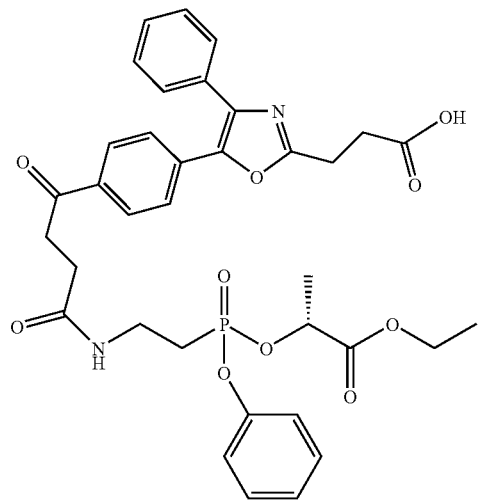

33.13

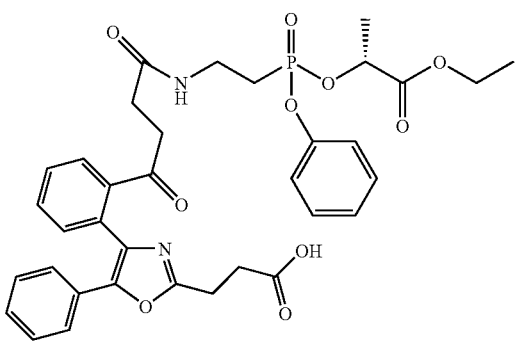

33.14

Oxaprozin (33.1, U.S. Pat. No. 3,578,671), available from Sigma-Aldrich, is converted to carboxylic acids 33.2, 33.3, 33.4, 33.5, 33.6, and 33.7 by the action of succinic anhydride in the presence of a Lewis acid such as aluminum trichloride in a suitable solvent such as carbon disulfide, nitrobenzene, or dichloroethane. Conversion 33.2, 33.3, 33.4, 33.5, 33.6, and 33.7 to phosphonate prodrugs occurs by the addition of 1.5 equivalents HOAT, HATU, and diisoproplylethylamine 33.2, 33.3, 33.4, 33.5, 33.6, and 33.7 followed by the addition of 33.8 all in a suitable solvent such as NMP, DMF, THF, or dichloroethane. This process can either occur after separation of 33.2, 33.3, 33.4, 33.5, 33.6, and 33.7 by standard means or

245 on the mixture of products. Separation of the final mixture leads to the desired materials 33.9, 33.10, 33.11, 33.12, 33.13, and 33.14.

EXAMPLE 34

Synthesis of Representative Compounds of Formulae 35 and 36

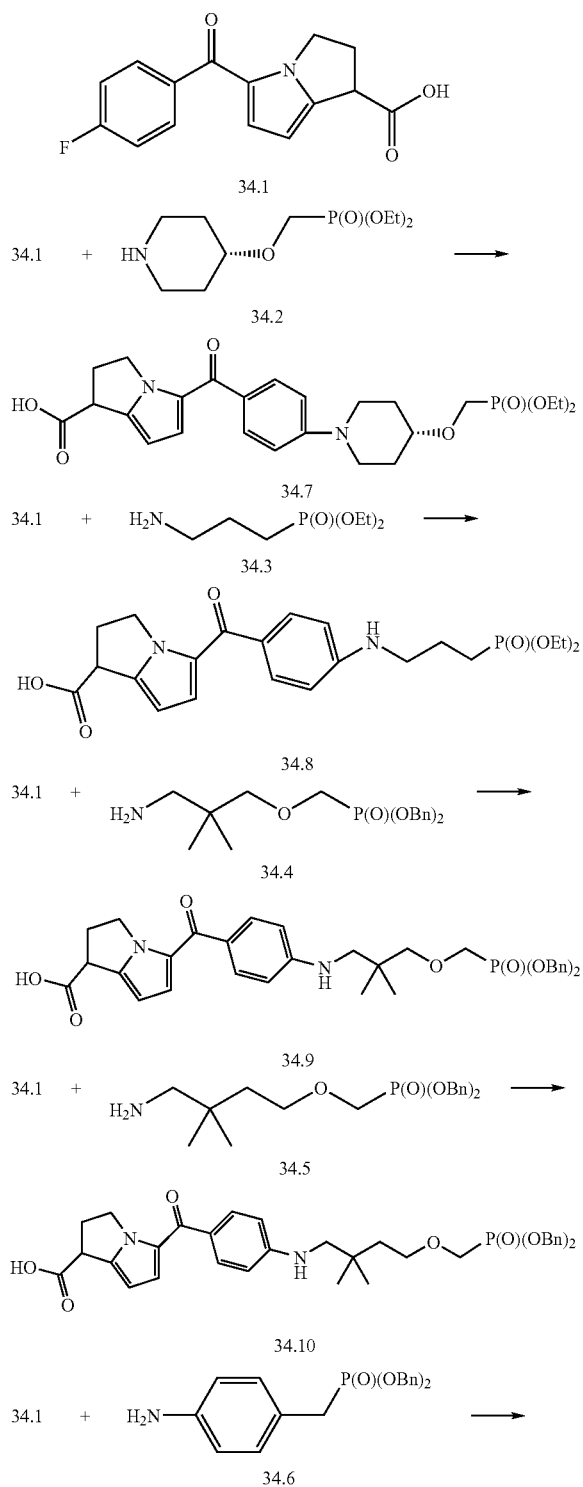

246

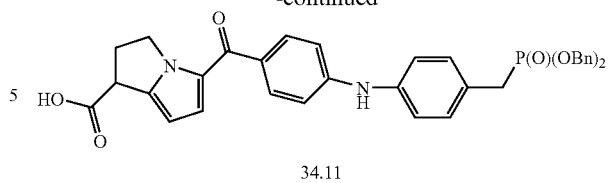

Starting material 34.1 (U.S. Pat. No. 4,347,186) is combined separately with amino phosphonates 34.2, 34.3, 34.4, 34.5, and 34.6 by the action a weak base (for example, diisopropyl ethyl amine, triethyl amine, potassium carbonate, sodium carbonate) in a suitable polar solvent such NMP, DMF, or DMSO and heated between 40 and 200° C. for a period between 30 minutes and 2 weeks. Products are isolated and purified using standard protocols. Single enantiomers of 34.7, 34.8, 34.9, 34.10, and 34.11 can be prepared as set out in U.S. Pat. No. 4,089,969, page 19 paragraph 10. These resolved intermediates can be carried through as with the linked Toradol compounds to form linked forms of (R)-Ketorolac. Alternatively, resolution of the enantiomers can occur at the 34.2, 34.3, 34.4, 34.4, 34.5, and 34.6 stage in analogy to U.S. Pat. No. 4,089,969.

EXAMPLE 35

Synthesis of Representative Compounds of Formulae 37-40

Representative phosphonate compounds of formulae 37-40 can be prepared from the compounds described by J. H. Fried et al., *J. Am. Chem. Soc.,* 1963, 85, 236-238 and R. Hirschmann et al., *J. Am. Chem. Soc.,* 1964, 86, 1521-1527 using techniques similar to those described herein.

EXAMPLE 36

Synthesis of Representative Pimecrolimus Analogs of Formula 41

In the following illustration the chloro substituted ring of pimecrolimus is replaced by the group

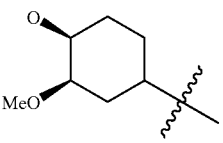

and the remainder of the molecule is not shown in the illustration, although it is understood that the remainder of the molecule is present.

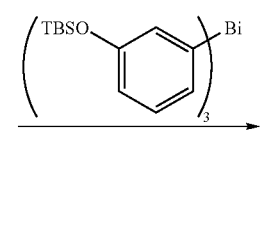

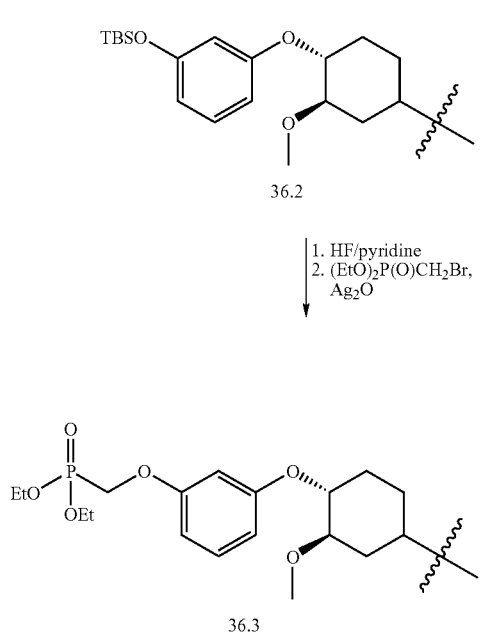

36.2

1. HF/pyridine
2. (EtO)₂P(O)CH₂Br, Ag₂O 36.3

Ascomycyn, a synthetic precursor of pimecrolimus, is O-arylated as shown above using an appropriate aryl bismuth reagent according to a procedure such as that reported in *Bioorg. Med. Chem. Lett,* 1995, 5, 1035. 3-(Dimethyl-t-butylsilyloxy)bromobenzene is treated either with magnesium in diethyl ether or with butyllithium in tetrahydrofuran, and the resulting organometallic reagent is reacted with bismuth trichloride to generate the triarybismuthine. After treating with 1-1.2 equivalents of peracetic acid, the bismuth(V) reagent is mixed with ascomycin and copper(II) acetate. The reaction is allowed to proceed for a day at room temperature or, if necessary, at reflux, affording the desired 3-(dimethyl-t-butylsilyoxy)phenyl ether. After removal of the dimethyl-t-butylsilyl protecting group, O-akylation is achieved with diethyl (bromomethyl)phosphonate in the presence of silver oxide, affording the desired pimecrolimus analog containing a diethylphosphonate 36.3. Silver ion-assisted reactions have been used to mediate O-alkylations of ascomycin: see *J. Med. Chem.,* 1998, 41, 1764.

EXAMPLE 37

Synthesis of Representative Pimecrolimus Analogs of Formula 41

In the following illustration the chloro substituted ring of pimecrolimus is replaced by the group

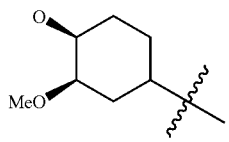

and the remainder of the molecule is not shown in the illustration, although it is understood that the remainder of the molecule is present.

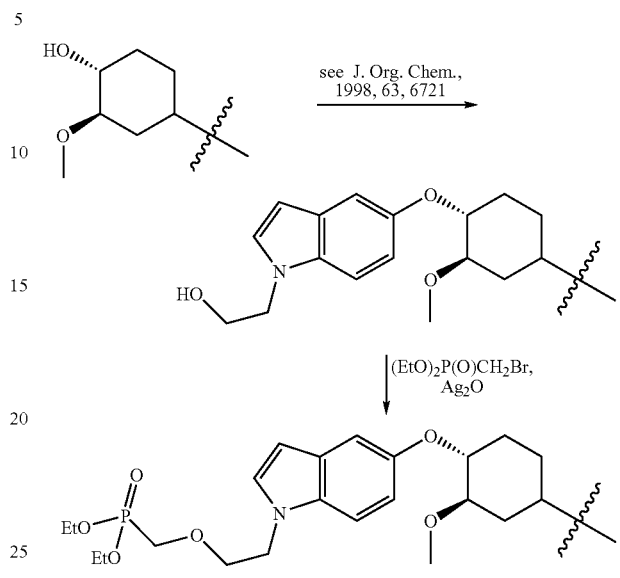

A phosphonate derivative of pimecrolimus indolyl ether is prepared as illustrated above, in a similar manner to that described in Example 36, with the exception that the key triindolylbismuthine intermediate is obtained from 5-bromoindole following the procedure described in *J. Org. Chem.* 1998, 63, 6721.

EXAMPLE 38

Synthesis of Representative Everolimus Analog of Formula 42

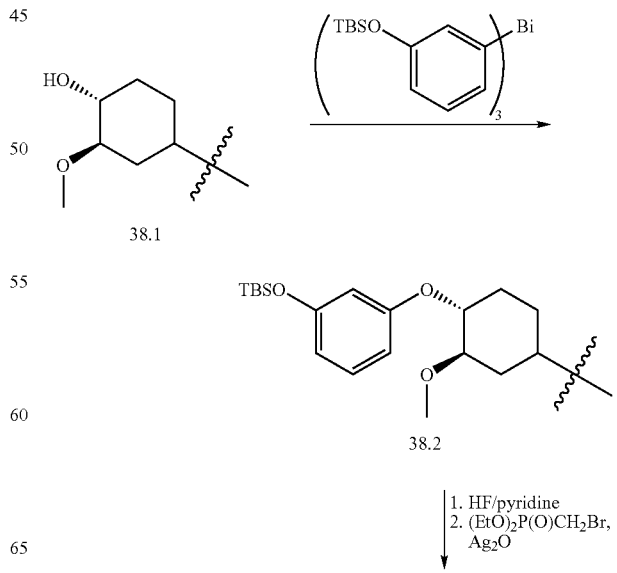

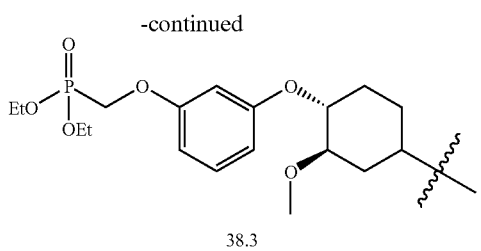

38.3

Rapamycin (compound 38.1 wherein the remaining portion of the rapamycin structure is not shown), a synthetic precursor of everolimus, is O-arylated as shown above using an appropriate aryl bismuth reagent according to a procedure such as that reported in *Bioorg. Med. Chem. Lett*, 1995, 5, 1035. 3-(Dimethyl-t-butylsilyloxy)bromobenzene is treated either with magnesium in diethyl ether or with butyl lithium in tetrahydrofuran, and the resulting organometallic reagent is reacted with bismuth trichloride to generate the triarybismuthine. After treating with 1-1.2 equivalents of peracetic acid, the bismuth(V) reagent is mixed with rapamycin and copper(II) acetate. The reaction is allowed to proceed for a day at room temperature or, if necessary, at reflux, affording the desired 3-(dimethyl-t-butylsilyloxy)phenyl ether 38.2. After removal of the dimethyl-t-butylsilyl protecting group, O-akylation is achieved with diethyl (bromomethyl)phosphonate in the presence of silver oxide, affording the desired everolimus analog containing the diethylphosphonate 38.3. Silver ion-assisted reactions have been used to mediate O-alkylations on an immunosuppresive macrolide structurally similar to rapamycin: see *J. Med. Chem.*, 1998, 41, 1764.

EXAMPLE 39

Synthesis of Representative Everolimus Analog of Formula 42

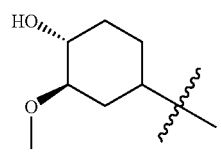

39.1 see J. Org. Chem., 1998, 63, 6721

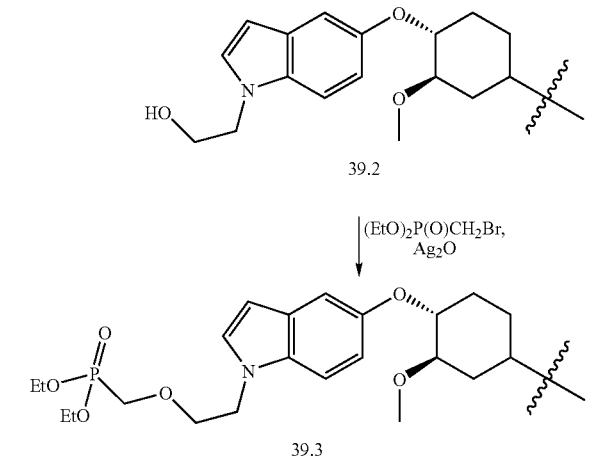

A phosphonate derivative of everolimus indolyl ether is prepared from rapamycin (formula 39.1 wherein the remaining portion of the rapamycin structure is not shown) in a similar manner to that described in Example 38, with the exception that the key triindolylbismuthine intermediate is obtained from 5-bromoindole following the procedure described in *J. Org. Chem.* 1998, 63, 6721.

EXAMPLE 40

Synthesis of Representative Sirolimus Analogs of Formula 42

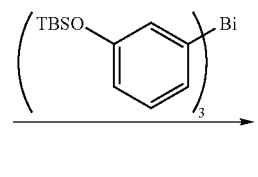

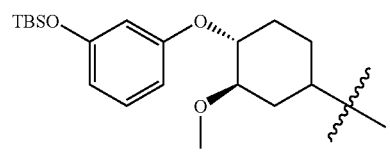

1. HF/pyridine
2. (EtO)$_2$P(O)CH$_2$Br, Ag$_2$O

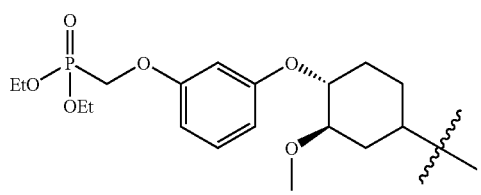

Sirolimus is O-arylated as shown above using an appropriate aryl bismuth reagent according to a procedure such as that reported in *Bioorg. Med. Chem. Lett*, 1995, 5, 1035. 3-(Dimethyl-t-butylsilyloxy)bromobenzene is treated either with magnesium in diethyl ether or with butyllithium in tetrahydrofuran, and the resulting organometallic reagent is reacted with bismuth trichloride to generate the triarybismuthine. After treating with 1-1.2 equivalents of peracetic acid, the bismuth(V) reagent is then mixed with sirolimus and copper (II) acetate. The reaction is allowed to proceed for a day at room temperature or, if necessary, at reflux, affording the desired 3-(dimethyl-t-butylsilyloxy)phenyl ether. After removal of the dimethyl-t-butylsilyl protecting group, O-akylation is achieved with diethyl (bromomethyl)phosphonate in the presence of silver oxide, affording the desired sirolimus analog containing the diethylphosphonate. Silver ion-assisted reactions have been used to mediate O-alkylations on an immunosuppresive macrolide structurally similar to sirolimus: see *J Med. Chem.*, 1998, 41, 1764.

EXAMPLE 41

Synthesis of Representative Sirolimus Analogs of Formula 42

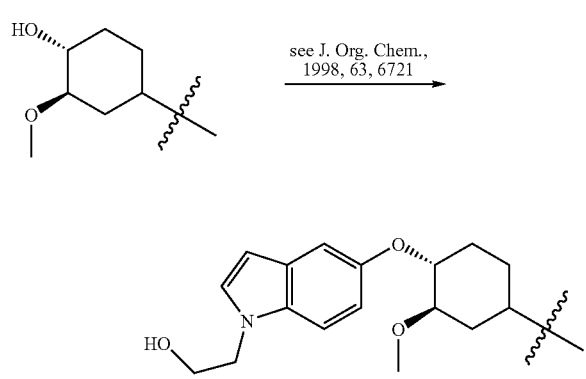

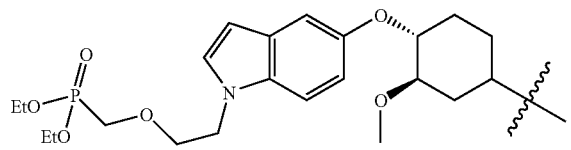

A sirolimus indolyl ether is prepared as illustrated above, in a similar manner to that described in Example 40, with the exception that the key triindolylbismuthine intermediate is obtained from 5-bromoindole following the procedure described in *J. Org. Chem.* 1998, 63, 6721.

EXAMPLE 42

Synthesis of Representative Compounds of Formula 45

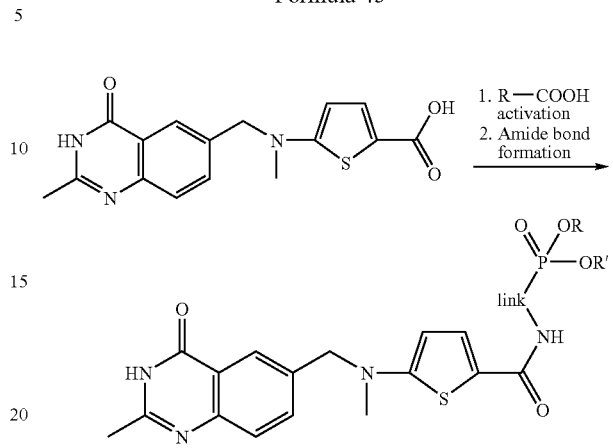

Representative compounds of the invention can be prepared as illustrated above. The preparation of a specific compound of the invention is described below.

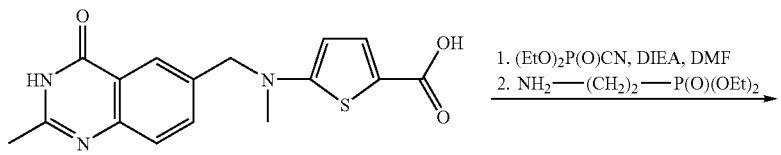

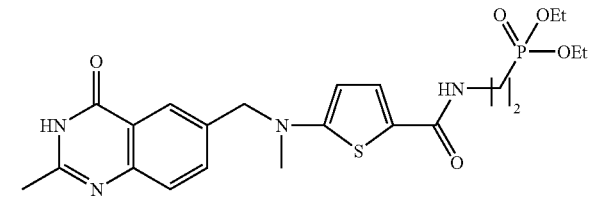

The starting carboxylic acid can be treated in a solvent such as dimethylformamide (DMF) or N-methylpyrrolidinone (NMP) with a coupling reagent such as diethyl cyanophosphonate or isobutyl chloroformate and a base such as diisopropylethylamine (DIEA) at room temperature (*J. Med. Chem.*, 1982, 25, 960-964 and *J. Med. Chem.*, 1984, 27, 600-604). When the activation is complete, 2-aminoethylphosphonic acid diethyl ester (commercially available) is added. After consumption of the activated species is observed the solvent is removed in vacuo and the product is isolated via chromatography. Alternatively, the product can be isolated through precipitation from the reaction solution with an organic solvent like diethyl ether or the like.

EXAMPLE 43

Synthesis of Representative Compounds of Formula 45

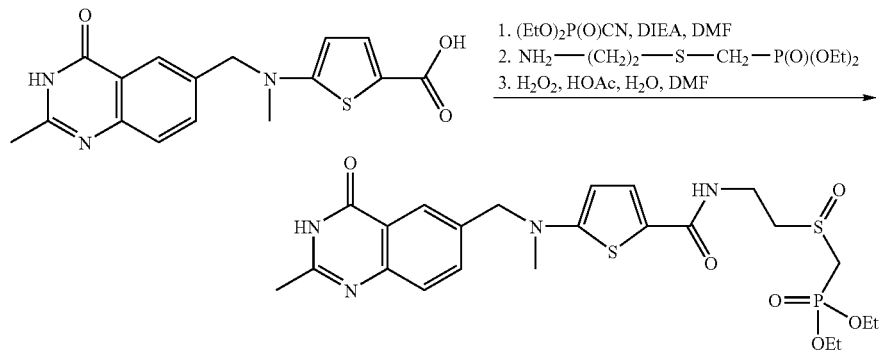

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, 1982, 25, 960-964 and *J. Med. Chem.*, 1984, 27, 600-604). When the activation is complete, (2-amino-ethylsulfanylmethyl)-phosphonic acid diethyl ester (made by base-catalyzed coupling of 2-aminoethanethiol with diethyl phosphonomethyltriflate, prepared according to *Tetrahedron Lett.*, 1986, 27, 1477) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The intermediate is then dissolved in a mixture of water, DMF, and acetic acid and is treated with hydrogen peroxide solution (excess). After removal of the solvents the product is isolated via chromatography. Alternatively, the product can be isolated through precipitation from the reaction solution with an organic solvent like diethyl ether or the like.

EXAMPLE 44

Synthesis of Representative Compounds of Formula 46

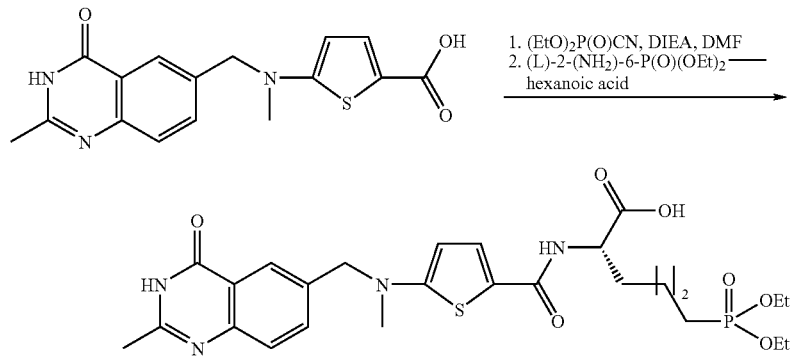

The starting carboxylic acid can be treated in a solvent such as DMF or NMP with a coupling reagent such as diethyl cyanophosphonate or isobutyl chloroformate and a base such as DIEA at room temperature (*J. Med. Chem.*, 1982, 25, 960-964 and *J. Med. Chem.*, 1984, 27, 600-604.). When the activation is complete, (L)-2-amino-6-(diethylphosphonato)-hexanoic acid is added. After consumption of the activated species is observed the solvent is removed in vacuo and the product is isolated via chromatography. Alternatively, the product can be isolated through precipitation from the reaction solution with an organic solvent like diethyl ether or the like.

EXAMPLE 45

Synthesis of Representative Compounds of Formula 47

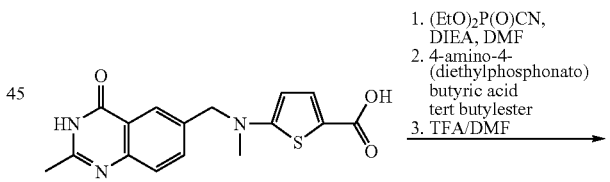

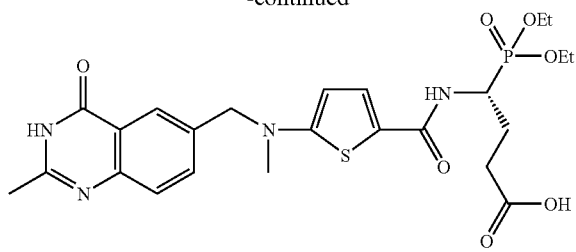

The starting carboxylic acid can be treated in a solvent such as DMF or NMP with a coupling reagent such as diethyl cyanophosphonate or isobutyl chloroformate and a base such as DIEA at room temperature (*J. Med. Chem.*, 1982, 25, 960-964 and *J. Med. Chem.*, 1984, 27, 600-604). When the activation is complete, 4-amino-4-(diethylphosphonato)-butyric acid tert butylester (*J. Am. Chem. Soc.*, 1995, 117, 10879-10888) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The crude intermediate is then dissolved in DMF and treated with trifluoroacetic acid (TFA). The product is isolated via chromatography after removal of the solvents. Alternatively, the product can be isolated through precipitation form the reaction solution with an organic solvent like diethyl ether or the like.

EXAMPLE 46

Synthesis of Representative Compounds of Formula 48

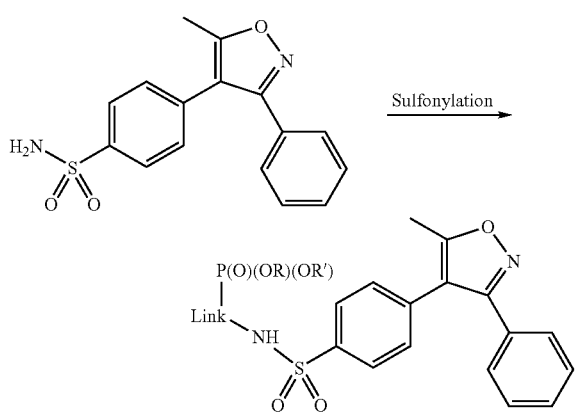

Representative compounds of the invention can be prepared as illustrated above. Sulfonylation is conveniently carried out by reaction of the aniline with a sulfonyl chloride in the presence of a base such as triethylamine (*J. Med. Chem.*, 1995, 38, 4897) in a solvent such as dichloromethane. Either one equivalent or an excess of the sulfonyl chloride may be used; in the latter case, the bis-sulfonamide may be formed, in which case hydrolysis to the monosulfonamide is achieved through reaction with sodium hydroxide.

A sulfonylating reagent that can be used in the above procedure can be prepared as follows.

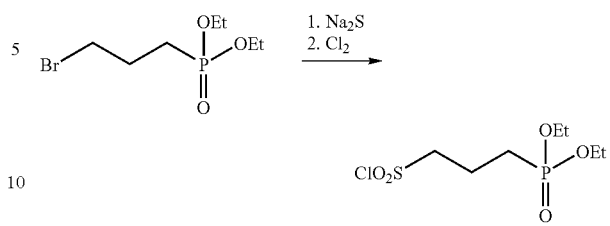

(3-Bromo-propyl)-phosphonic acid diethyl ester is treated with sodium sulfide in a solvent such as ethanol, and the thiol produced is oxidized with chlorine in an aqueous solvent system to give the sulfonyl chloride (see Gilbert, 'Sulfonylation and Related Reactions, Interscience, New York, 1965, pp 202-214).

EXAMPLE 47

Synthesis of Representative Compounds of Formula 49

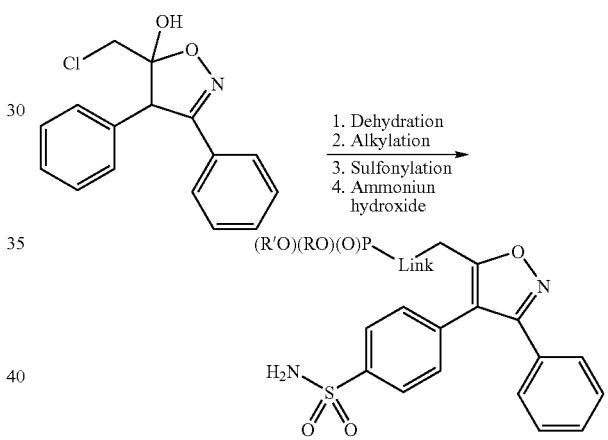

The starting chloromethyl compound (see *J. Med. Chem.*, 2000, 43, 775) serves as a useful intermediate for the introduction of a phosphonate moiety at the methyl substituent of the isoxazole. After this is achieved, the sulfonamide group is introduced by the same methods as for valdecoxib itself.

Optionally, the parecoxib-style prodrug may be formed by acylation of the sulfonamide using propionic anhydride and a base such as triethylamine, followed by formation of the sodium salt with sodium hydroxide (see *J. Med. Chem.*, 2000, 43, 1661).

A representative compound of the inveition can be prepared as follows.

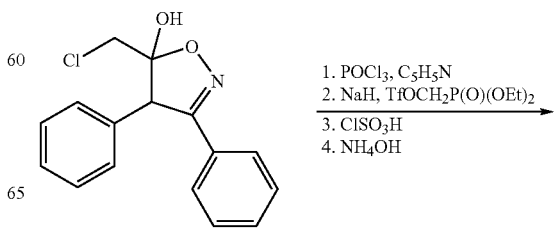

-continued

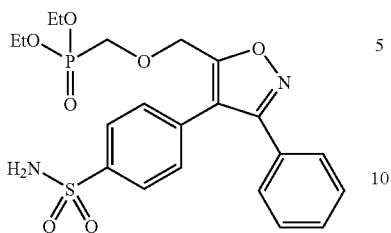

The chloromethyl compound (see *J. Med. Chem.*, 2000, 43, 775) is treated with a dehydrating reagent such as phosphorus oxychloride in the presence of a base such as pyridine, optionally in a solvent such as dichloromethane. The (5-chloromethyl)isoxazole so formed is then treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding the desired phosphonate diester. Sulfonylation with chlorosulfonic acid, quenching the resulting sulfonyl chloride with ammonium hydroxide (according to *J. Med. Chem.*, 2000, 43, 775) gives the desired product.

EXAMPLE 48

Synthesis of Representative Compounds of Formula 51

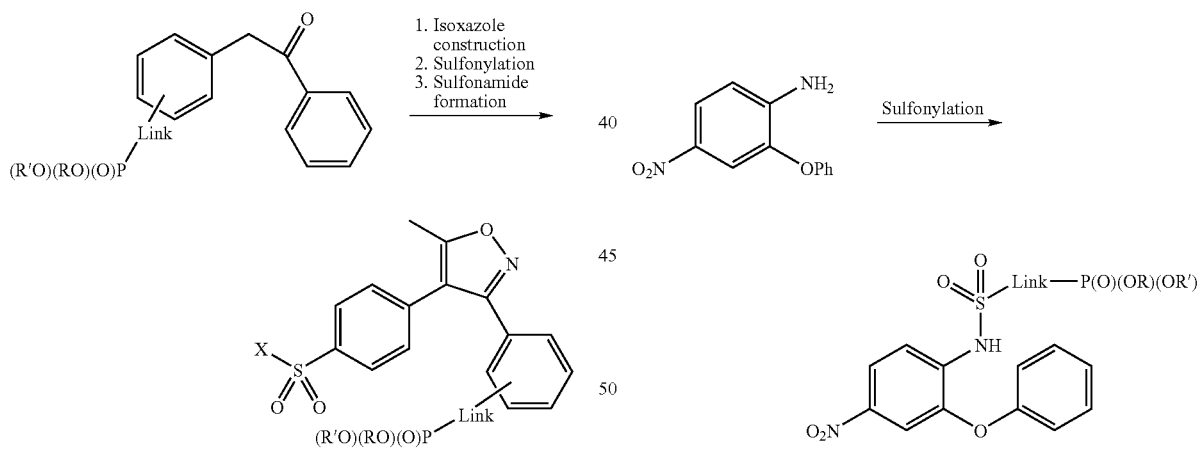

Repersentative compounds of the invention can also be prepared as illustrated above. For example, a specific compound of the invention can be prepared as follows.

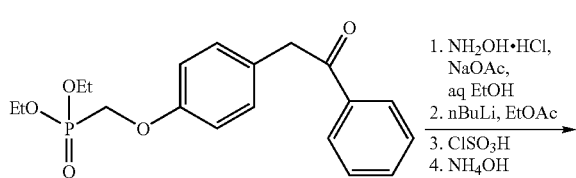

-continued

The deoxybenzoin derivative bearing a phosphonate moiety (formed from commercially available 2-(4-methoxyphenyl) acetophenone by demethylation with hydrobromic acid in acetic acid, and subsequent alkylation with diethyl phosphonomethyltriflate (prepared according to *Tetrahedron Lett.*, 1986, 27, 1477) in the presence of a base such as potassium carbonate in a solvent such as dimethylformamide) is subjected to the same transformations as those outlined in *J. Med. Chem.*, 2000, 43, 775 to provide the phosphonate compound of the invention.

EXAMPLE 49

Synthesis of Representative Compounds of Formula 53

Representative compounds of the invention can be prepared as illustrated above. Sulfonylation is conveniently carried out by reaction of the aniline with a sulfonyl chloride in the presence of a base such as triethylamine (*J. Med. Chem.*, 1995, 38, 4897) in a solvent such as dichloromethane. Either one equivalent or an excess of the sulfonyl chloride may be used; in the latter case, the bis-sulfonamide is formed, and hydrolysis to the monosulfonamide is achieved through reaction with sodium hydroxide. For example, a specific compound of the invention can be prepared as follows.

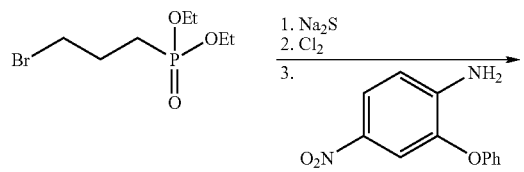

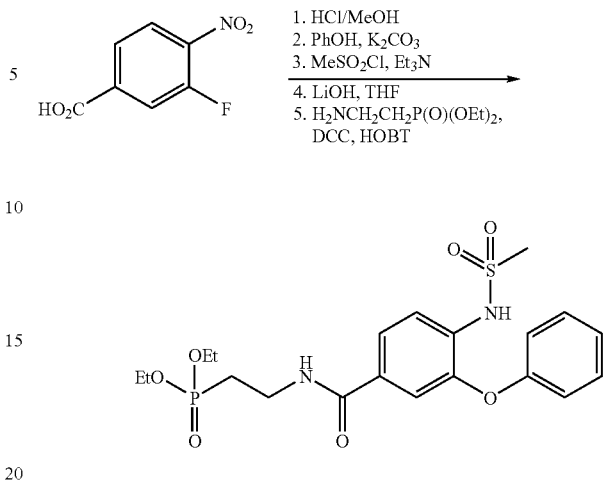

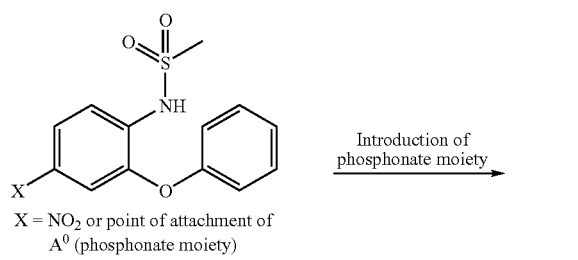

(3-Bromo-propyl)-phosphonic acid diethyl ester is treated with sodium sulfide in a solvent such as ethanol, and the thiol produced is oxidised with chlorine in an aqueous solvent system to give the sulfonyl chloride (see Gilbert, 'Sulfonylation and Related Reactions, Intrscience, New York, 1965, pp 202-214). This reagent is used in the sulfonylation reaction described above to provide the representative compound of the invention.

EXAMPLE 50

Synthesis of Representative Compounds of Formulae 52 and 54

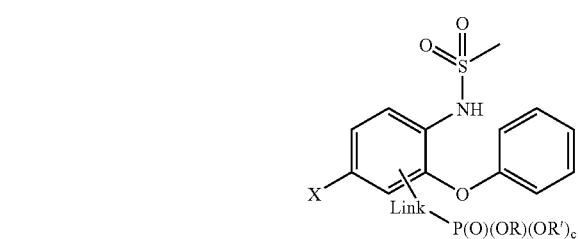

Representative compounds of the invention can be prepared as illustrated above. The phosphonate moiety may be attached to the central phenyl ring. If it is linked at the position para- to the sulfonylamide residue, the linker should optimally exert an electron-withdrawing effect to maximize the COX-2 inhibitory activity (see *J. Med. Chem.*, 1995, 38, 4897). For example, a specific compound of the invention can be prepared as follows.

3-Fluoro-4-nitrobenzoic acid is esterified by heating briefly in acidic methanol. Treatment with phenol in a solvent such as dimethylformamide in the presence of a base such as potassium carbonate causes displacement of the fluoride and generation of the bis-aryl ether. Subsequent saponification of the benzoate ester with lithium hydroxide in a solvent such as tetrahydrofuran gives the free acid, which is coupled with 2-aminoethylphosphonic acid diethyl ester (commercially available) using standard reagents for the formation of a secondary amide such as dicyclohexylcarbodiimide (DCC) and hydroxybenztriazole (HOBT), in a solvent such as dimethylformamide.

EXAMPLE 51

Synthesis of Representative Compounds of Formula 55

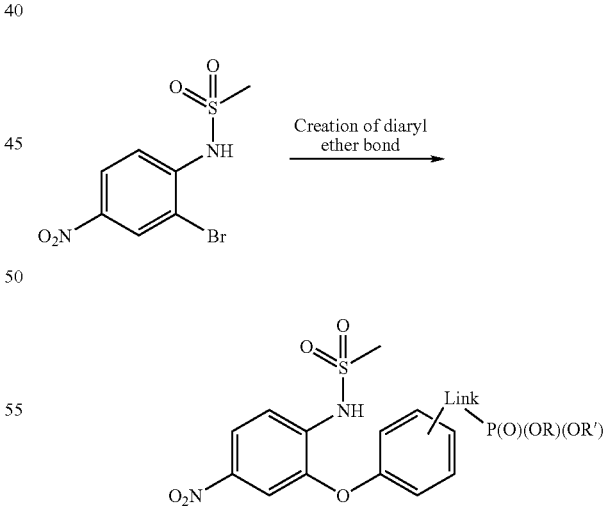

Representative compounds of the invention can be prepared as illustrated above. The diaryl ether is conveniently formed using the Ullman method (*Russ. Chem. Rev.*, 1974, 43, 679), catalyzed by copper(I) salts. Using this method, a phenol already bearing a phosphonate moiety may be used to generate the desired analog efficiently. For example, a specific compound of the invention can be prepared as follows.

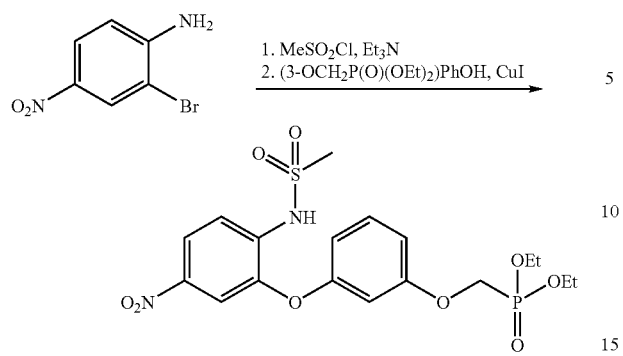

2-Bromo-4-nitroaniline is sulfonylated in a manner similar to that described in example 49. The subsequent Ullman ether synthesis using (3-hydroxy-phenoxymethyl)phosphonic acid diethyl ester (formed by the reaction of resorcinol and diethyl phosphonomethyltriflate (prepared according to *Tetrahedron Lett.*, 1986, 27, 1477) in the presence of a base such as magnesium t-butoxide gives the desired product.

EXAMPLE 52

Synthesis of Representative Compounds of Formula 56

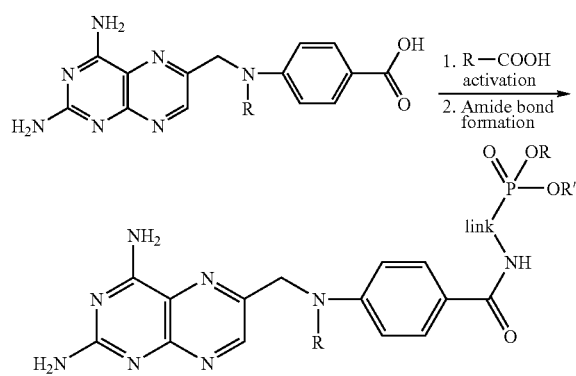

Representative compounds of the invention can be prepared as illustrated above. Final compounds, be they diastereoisomers or enantiomers, may typically be purified by chromatographic means. In case a direct coupling to aminopterin is hampered by the presence of a free secondary amine in the starting material (R=H), this entity is temporarily protected either with a tert.butoxycarbonyl group (R=Boc) or benzyloxycarbonyl (R=Cbz or Z) according to standard procedures (Green Wutts: Protective groups in organic chemistry)

EXAMPLE 53

Synthesis of Representative Compounds of Formula 56

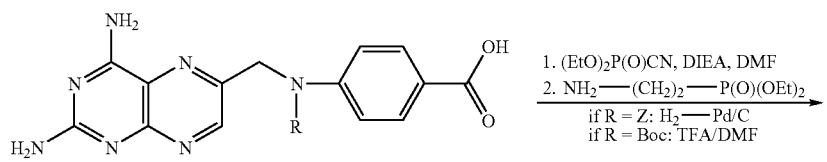

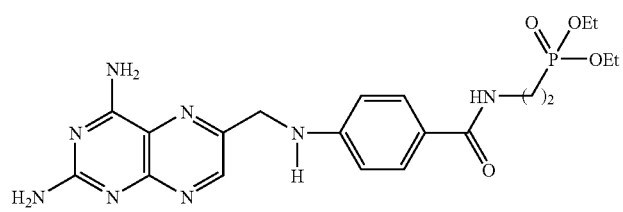

The starting carboxylic acid can be treated in a solvent such as dimethylformamide (DMF) or N-methylpyrrolidinone (NMP) with a coupling reagent such as diethyl cyanophosphonate or isobutyl chloroformate and a base such as diisopropylethylamine (DIEA) at room temperature (*J. Med. Chem.*, 1982, 25, 960-964 and *J. Med. Chem.*, 1984, 27, 600-604). When the activation is complete, 2-aminoethylphosphonic acid diethyl ester (commercially available) is added. After consumption of the activated species is observed the solvent is removed in vacuo and the product is isolated via chromatography. Alternatively, the product can be isolated through precipitation from the reaction solution with an organic solvent such as diethyl ether or the like.

In case R=Z: The compound is dissolved in an organic solvent like DMF or NMP and a catalytic amount of Pd/C is added. The reaction mixture is stirred under an atmosphere of hydrogen until the starting material is consumed. The Pd/C is removed by filtration and the solvent is evaporated in vacuo. The product is isolated via chromatography. Alternatively, the product can be isolated through precipitation from the reaction solution with an organic solvent such as diethyl ether or the like.

EXAMPLE 54

Synthesis of Representative Compounds of Formula 56

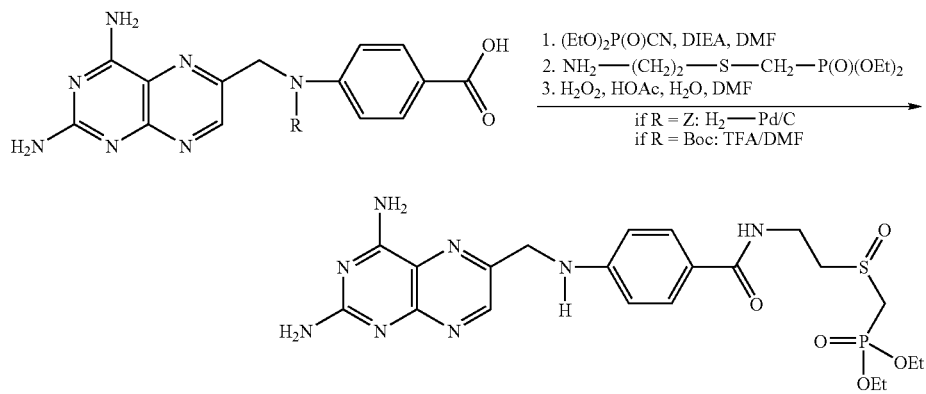

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, 1982, 25, 960-964 and *J. Med. Chem.*, 1984, 27, 600-604). When the activation is complete, (2-amino-ethyl-sulfanylmethyl)-phosphonic acid diethyl ester (made by base-catalyzed coupling of 2-aminoethanethiol with diethyl phosphonomethyltriflate, prepared according to *Tetrahedron Lett.*, 1986, 27, 1477) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The intermediate is then dissolved in a mixture of water, DMF, and acetic acid and is treated with hydrogen peroxide solution (excess). After removal of the solvents the product is isolated via chromatography. Alternatively, the product can be isolated through precipitation from the reaction solution with an organic solvent like diethyl ether or the like.

In case R=Z: The compound is dissolved in an organic solvent like DMF or NMP and a catalytic amount of Pd/C is added. The reaction mixture is stirred under an atmosphere of hydrogen until the starting material is consumed. The Pd/C is removed by filtration and the solvent is evaporated in vacuo. The product is isolated via chromatography. Alternatively, the product can be isolated through precipitation from the reaction solution with an organic solvent such as diethyl ether or the like.

EXAMPLE 55

Synthesis of Representative Compounds of Formula 57

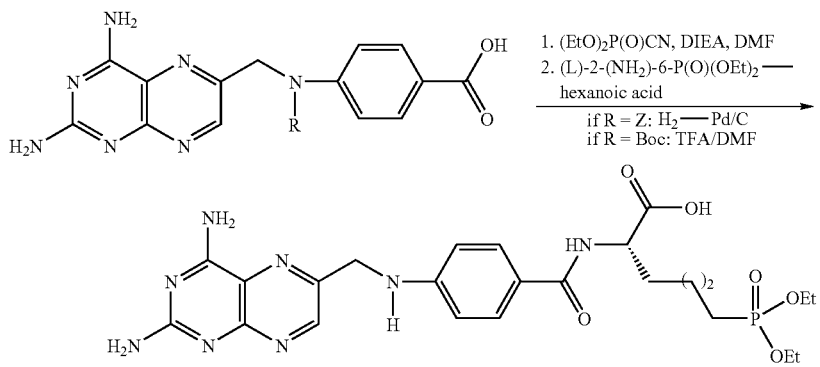

The starting carboxylic acid can be treated in a solvent such as DMF or NMP with a coupling reagent such as diethyl cyanophosphonate or isobutyl chloroformate and a base such as DIEA at room temperature (*J. Med. Chem.*, 1982, 25, 960-964 and *J. Med. Chem.*, 1984, 27, 600-604.). When the activation is complete, (L)-2-amino-6-(diethylphosphonato)-hexanoic acid is added. After consumption of the activated species is observed the solvent is removed in vacuo and the product is isolated via chromatography. Alternatively, the product can be isolated through precipitation from the reaction solution with an organic solvent such as diethyl ether or the like.

In case R=Z: The compound is dissolved in an organic solvent like DMF or NMP and a catalytic amount of Pd/C is added. The reaction mixture is stirred under an atmosphere of hydrogen until the starting material is consumed.

The Pd/C is removed by filtration and the solvent is evaporated in vacuo. The product is isolated via chromatography. Alternatively, the product can be isolated through precipitation from the reaction solution with an organic solvent such as diethyl ether or the like.

EXAMPLE 56

Synthesis of Representative Compounds of Formula 58

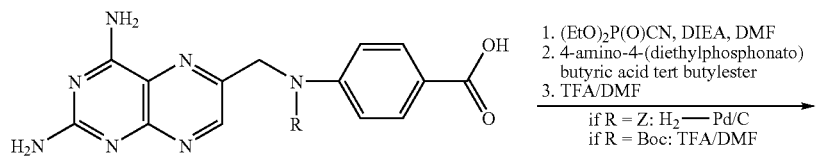

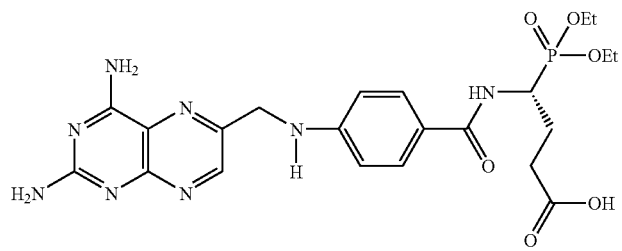

The starting carboxylic acid can be treated in a solvent such as DMF or NMP with a coupling reagent such as diethyl cyanophosphonate or isobutyl chloroformate and a base such as DIEA at room temperature (*J. Med. Chem.*, 1982, 25, 960-964 and *J. Med. Chem.*, 1984, 27, 600-604). When the activation is complete, 4-amino-4-(diethylphosphonato)-butyric acid tert butylester (*J. Am. Chem. Soc.*, 1995, 117, 10879-10888) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The crude intermediate is then dissolved in DMF and treated with TFA (excess). The product is isolated via chromatography after removal of the solvents. Alternatively, the product can be isolated through precipitation form the reaction solution with an organic solvent such as diethyl ether or the like.

In case R=Z: The compound is dissolved in an organic solvent like DMF or NMP and a catalytic amount of Pd/C is added. The reaction mixture is stirred under an atmosphere of hydrogen until the starting material is consumed. The Pd/C is removed and the solvent is evaporated in vacuo. The product is isolated via chromatography. Alternatively, the product can be isolated through precipitation from the reaction solution with an organic solvent such as diethyl ether or the like.

EXAMPLE 57

Synthesis of Representative Compounds of Formula 59

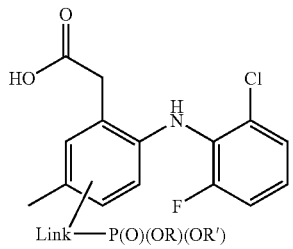

-continued

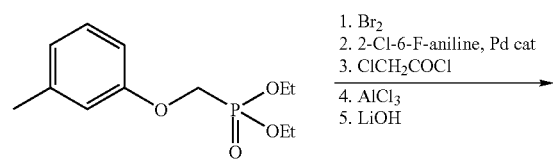

Representative compounds of the invention can be prepared as illustrated above. The construction of the lumiracoxib core proceeds according to the procedures described in WO-00123346. For example, a specific compound of the invention can be prepared as follows.

-continued

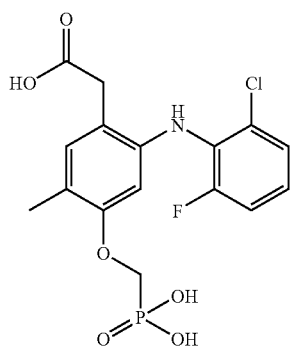

Bromination (by standard methods—see de la Mare, 'Electrophilic Halogenation', Cambridge University Press, London, 1976) of m-tolyloxymethylphosphonic acid diethyl ester (formed from commercially available 3-methylphenol by alkylation with diethyl phosphonomethyltriflate (prepared according to *Tetrahedron Lett.,* 1986, 27, 1477) in the presence of a base such as potassium carbonate) gives a mixture of isomers that are separated by chromatography, each of which is potentially useful in the synthesis of analogs containing phosphonate moieties linked to different positions of the phenyl ring in question. Subsequent steps proceed as described in WO-00123346, yielding ultimately a phosphonic acid analog of lumiracoxib. The key step is the coupling of the aryl bromide and 2-chloro-5-fluoroaniline, catalyzed by a palladium (II) salt, typically with sodium t-butoxide as base (see *Angew. Chem. Int. Ed.,* 1998, 37, 2046-2067).

EXAMPLE 58

Synthesis of Representative Compounds of Formula 60

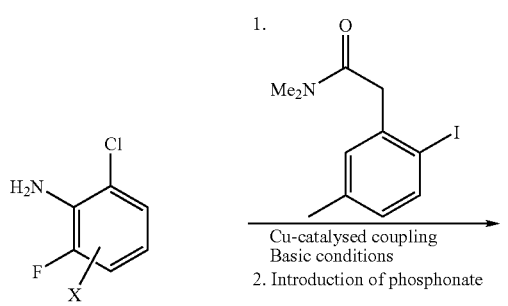

X = group suitable for transformation to phophonate moiety

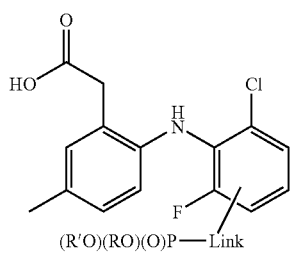

Representative compounds of the invention can be prepared as illustrated above. This route to lumiracoxib analogs is described in WO-09911605, and relies on a copper-catalyzed step for forming the bis-aryl amine with the phenyl acetic acid side chain already in place on one of the reagents. The phosphonate-bearing moity is conveniently introduced after this step, which typically requires heating (e.g. in xylenes). For example, a specific compound of the invention can be prepared as follows.

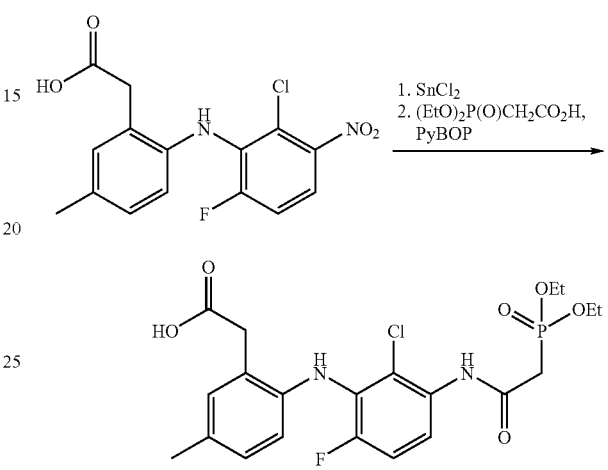

The product of coupling between N,N-dimethyl-5-methyl-2-iodophenylacetamide and 2-chloro-6-fluoro-5-nitroaniline is subjected to reduction under standard conditions such as treatment with tin(II) chloride or hydrogenation over palladium on charcoal. The resulting primary aniline is coupled with (diethoxy-phosphoryl)acetic acid (commercially available) in the presence of a reagent such as benzotriazole-1-yl-oxy-tris-pyrrolidino-phosphonium hexafluorophosphate (PyBOP®) to provide the compound of the invention.

EXAMPLE 59

Synthesis of Representative Compounds of Formula 61

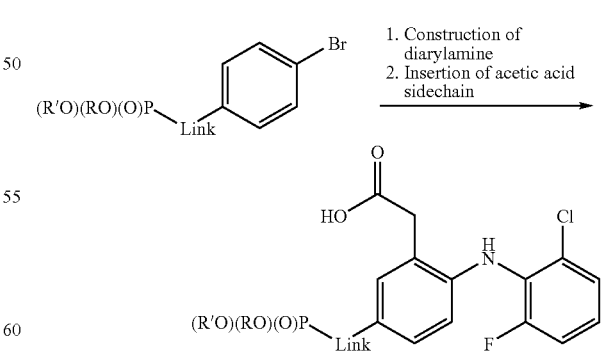

Representative compounds of the invention can be prepared as illustrated above. This route is analogous to that described in Example 57. A specific compound of the invention can be prepared as follows.

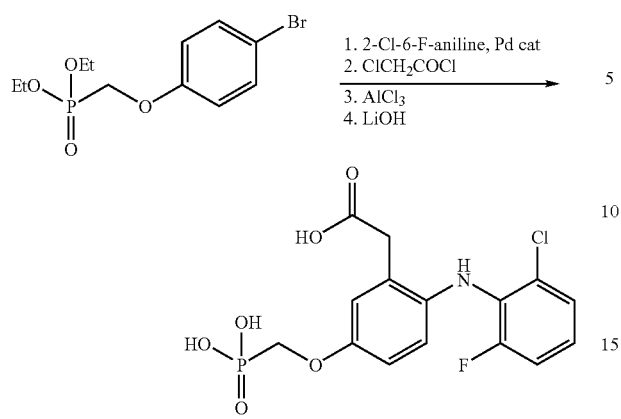

(4-Bromo-phenoxymethyl)phosphonic acid diethyl ester (formed from commercially available 4-bromophenol by alkylation with diethyl phosphonomethyltriflate (prepared according to *Tetrahedron Lett.*, 1986, 27, 1477) in the presence of a base such as potassium carbonate) serves a suitable starting material for an analog bearing a phosphonate linked at the position shown, using chemistry analagous to that described in Example 57 above.

EXAMPLE 60

Synthesis of Representative Compounds of Formula 62

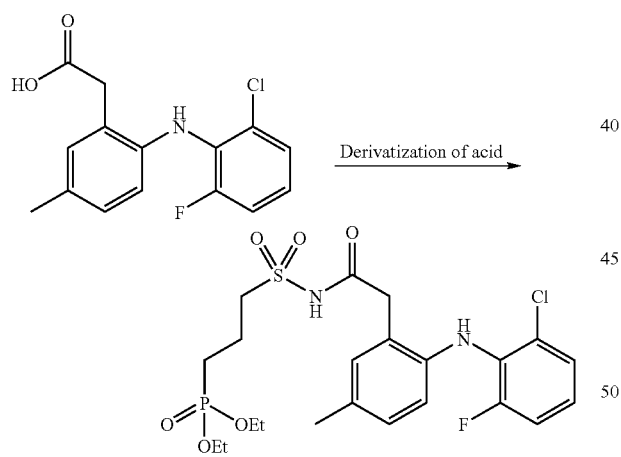

Representative compounds of the invention can be prepared as illustrated above. The phosphonate-bearing moity may be attached to the carboxylate residue of lumiracoxib using a derivative such as an acylsulfonamide to preserve the acidic nature of the group. For example, a specific compound of the invention can be prepared as follows.

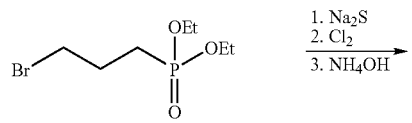

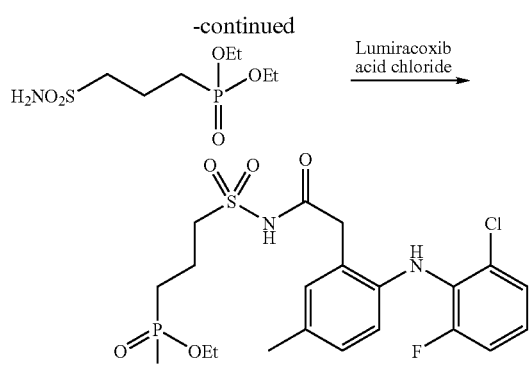

(3-Bromo-propyl)-phosphonic acid diethyl ester is treated with sodium sulfide in a solvent such as ethanol, and the thiol produced is oxidized with chlorine in an aqueous solvent system to give the sulfonyl chloride (see Gilbert, 'Sulfonylation and Related Reactions, Interscience, New York, 1965, pp 202-214). This reagent is treated briefly with ammonium hydroxide to generate the sulfonamide, which is condensed with the acid chloride of lumiracoxib (generated by treatment of lumiracoxib with thionyl chloride is a solvent such as diochloromethane), yielding the compound of the invention.

EXAMPLE 61

Synthesis of Representative Tacrolimus Analog of Formula 63

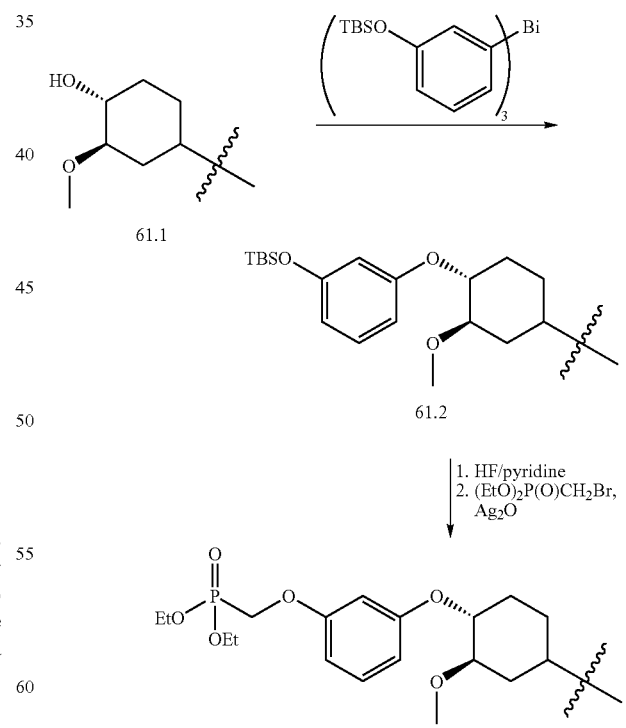

Tacrolimus (compound 61.1 wherein the remaining portion of the tacrolimus molecule is not shown) is O-arylated as shown above using an appropriate aryl bismuth reagent according to a procedure such as that reported in *Bioorg. Med. Chem. Lett,* 1995, 5, 1035. 3-(dimethyl-t-butylsilyloxy)bromobenzene is treated either with magnesium in diethyl ether or with butyllithium in tetrahydrofuran, and the resulting organometallic reagent is reacted with bismuth trichloride to generate the triarybismuthine. After treating with 1-1.2 equivalents of peracetic acid, the bismuth(V) reagent is mixed with tacrolimus 61.1 and copper(II) acetate. The reaction is allowed to proceed for a day at room temperature or, if necessary, at reflux, affording the desired 3-(dimethyl-t-butylsilyloxy)phenyl ether. After removal of the dimethyl-t-butylsilyl protecting group with HF, O-akylation is achieved with diethyl (bromomethyl)phosphonate in the presence of silver oxide, affording the desired tacrolimus analog containing the diethylphosphonate 61.3. Silver ion-assisted reactions have been used to mediate O-alkylations on an immunosuppresive macrolide structurally similar to tacrolimus: see *J. Med. Chem.,* 1998, 41, 1764.

EXAMPLE 62

Synthesis of representative Tacrolimus Analog of Formula 63 obtained from 5-bromoindole following the procedure described in J. Org. Chem. 1998, 63, 6721.

EXAMPLE 63

Synthesis of Representative Compounds of Formulae 64 and 65

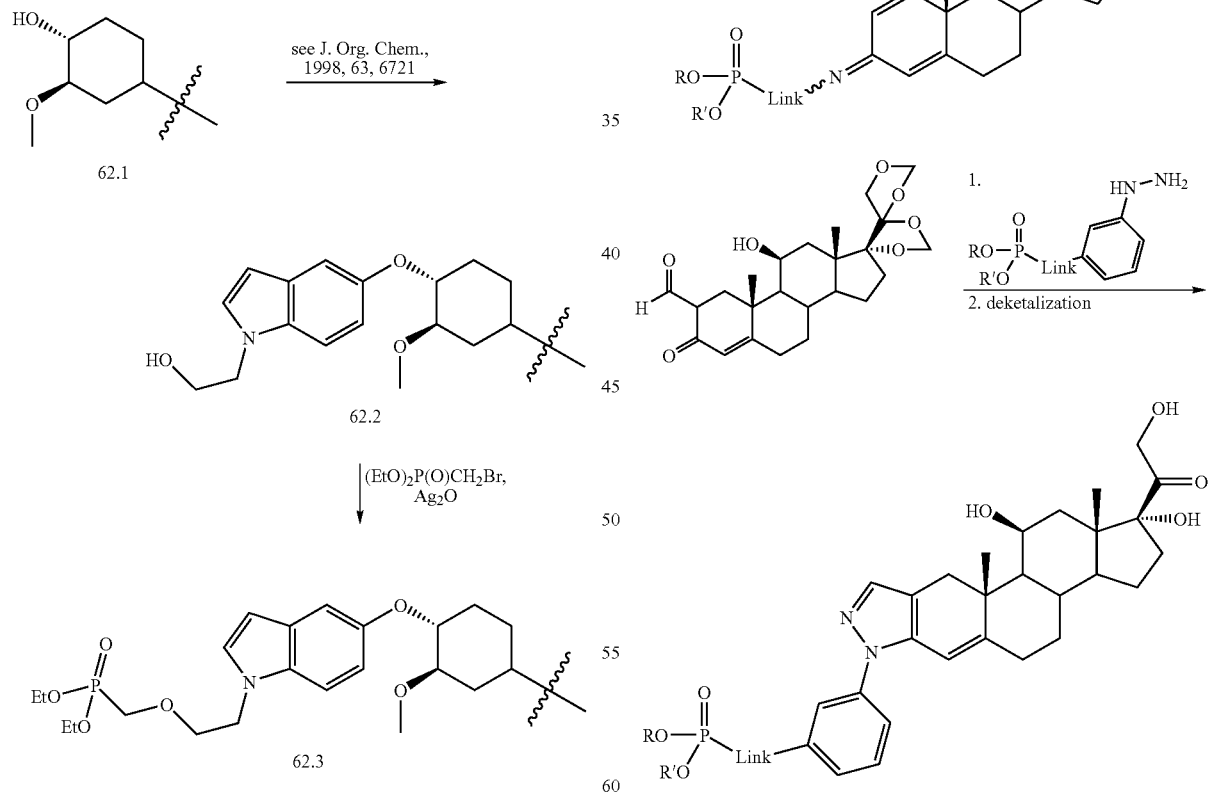

A phosphonate derivative of tacrolimus indolyl ether is prepared from tacrolimus (compound 62.1 wherein the remaining portion of the tacrolimus molecule is not shown) in a similar manner to that described in Example 61 with the exception that the key triindolylbismuthine intermediate is Representative compounds of the invention can be made by procedures such as those described by Boer, et al, *J. Mass Spectrom.* 1995, 30, 497-504 and Hoyte, et al, *J. Med. Chem.* 2002, 45, 5397-5405, or they can be made according to the general routes outlined above.

EXAMPLE 64

Synthesis of Representative Compounds of Formula 64

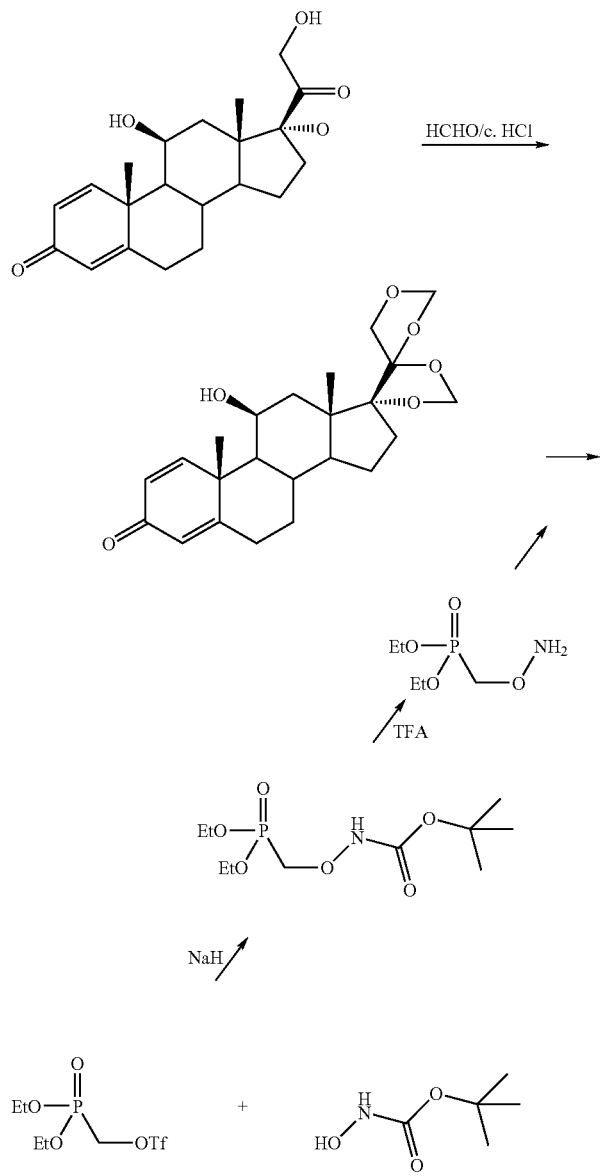

Prednisolone is treated in a solvent such as chloroform with formaldehyde in the presence of an acid such as concentrated hydrochloric acid. After stirring for several hours (preferably 7 to 10 hours) at room temperature, the layers are separated and the organic layer is concentrated to afford the bis-(methylenedioxy) intermediate (Hirschmann, R. et al, *J. Am. Chem. Soc.* 1964, 86, 1520-1527). This intermediate is treated with diethyl (aminooxymethyl)phosphonate in a solvent such as pyridine to afford the oxime, which is then treated with aqueous acid to remove the bis-(methylenedioxy) protecting group For example, the oxime is treated with 60% aqueous formic acid and heated at 90° C. for 10 min., cooled and concentrated using portions of ethanol to assist in removing formic acid. Chromatographic purification and/or crystallization of the residue yield the phosphonate oxime analog of prednisolone. A key precursor of this synthesis, diethyl (aminooxymethyl)-phosphonate, can be obtained from diethyl (trifluoromethylsulfonyloxymethyl)-phosphonate and N-(t-butoxycarbonyl)-hydroxylamine. Accordingly, N-(t-butoxycarbonyl)hydroxylamine is dissolved in a solvent such as THF and treated with sodium hydride. When bubbling ceases, diethyl (trifluoromethyl-sulfonyloxymethyl)phosphonate (prepared according to *Tetrahedron Lett.,* 1986, 27, 1477) is added. After quenching the reaction with aqueous ammonium chloride and extracting the product with an organic solvent such as ethyl acetate, the N-Boc protected diethyl (aminooxymethyl)phosphonate is isolated by chromatography. The N-Boc protecting group is then removed by treatment of trifluoroacetic acid, affording the desired diethyl (aminooxymethyl)phosphonate.

EXAMPLE 65

Synthesis of Representative Compounds of Formula 65

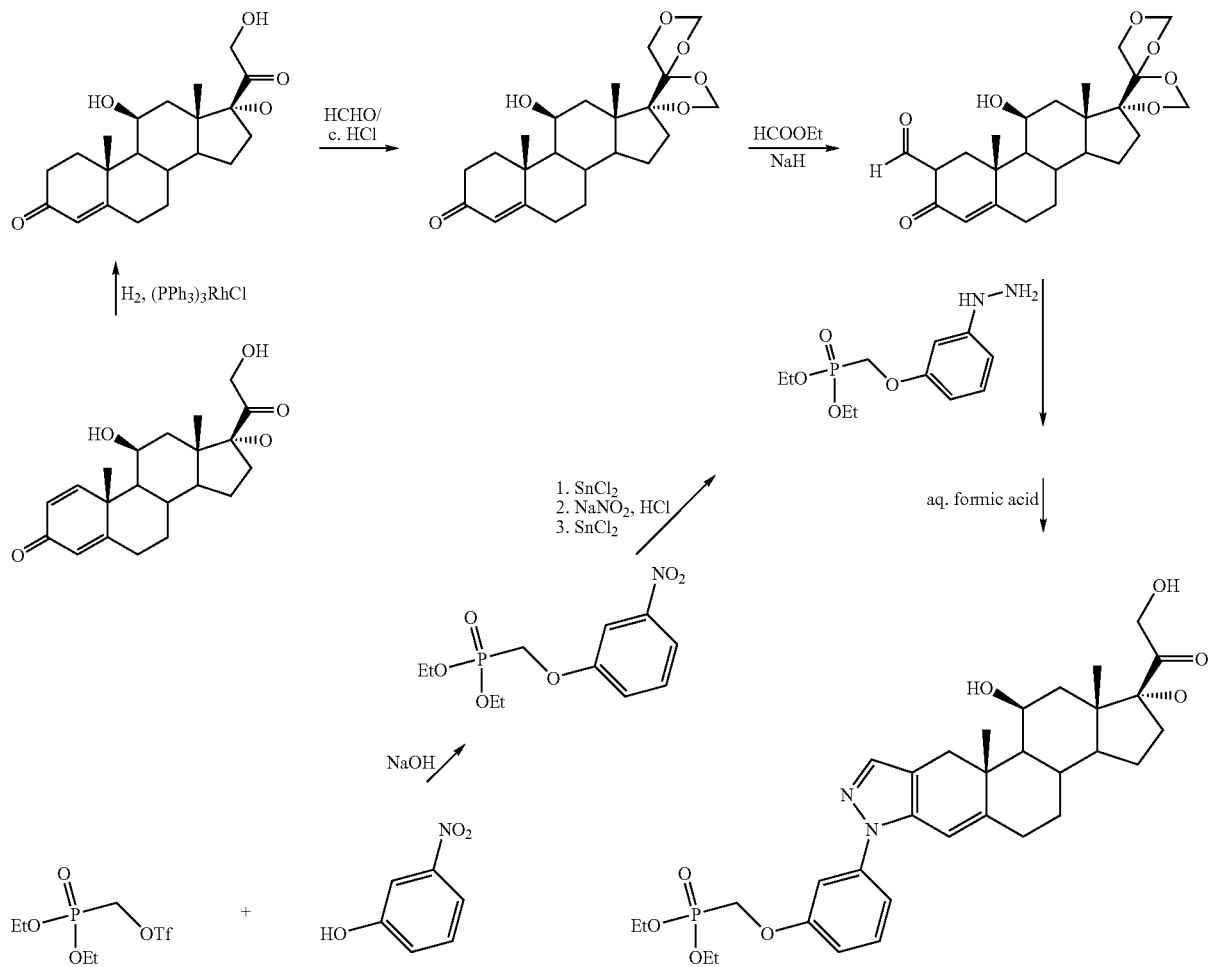

A phosphonate pyrazole analog of prednisolone can be prepared as illustrated above. Prednisolone is reduced to 1,2-dihydroprednisolone using a rhodium catalysis such as tris(triphenylphosphine)rhodium(I) chloride under hydrogen according to a procedure such as that reported by Procopiou, P. et al, *J. Med. Chem.* 2001, 44, 602-612. The dihydroxy ketone group on the D ring of the steroid is then protected using the method described in Example 64, before formylation at the C-2 position. For example, the bis-(methylenedioxy) intermediate is treated with freshly distilled ethyl formate and sodium hydride in a solvent such as toluene. The reaction is quenched with aqueous solution of a weak base such as potassium dihydrogen phosphate. The crude product is purified by a general method such as crystallization, affording the 2-formyl intermediate. This 2-formyl compound is condensed with a phosphonate-substituted phenylhydrazine to yield, after removal of the bis-(methylenedioxy) protecting group, the desired phosphonate pyrazole analog of prednisolone. A key precursor, 3-[(diethylphosphono)methoxy]phenylhydrazine, can be made starting from diethyl (trifluoromethylsulfonyloxymethyl)phosphonate and 3-nitrophenol. 3-Nitrophenol is treated with a base such as sodium hydroxide and then O-alkylated with diethyl (trifluoromethylsulfonyloxymethyl)phosphonate. The nitro group is reduced with tin(II) chloride and subsequently converted to the aryl hydrazine by diazotization and reduction with sodium sulfite (*Chem. Ber.*, 1960, 93, 540) or tin(II) chloride (*J. Med. Chem.*, 2001, 44, 4031).

EXAMPLE 66

Synthesis of Representative Compounds of Formula 67

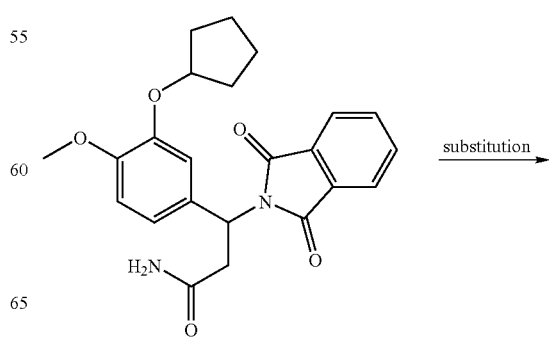

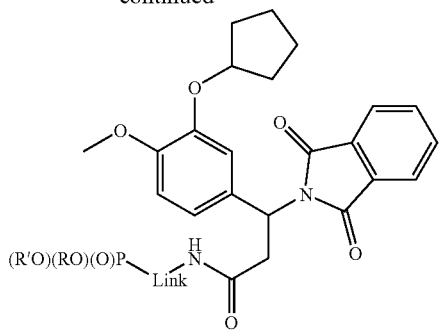

link includes 1 or more atoms; 2 or more is preferred

Representative compounds of the invention can be prepared as illustrated above. For example, a specific compound of Formula 67 can be prepared as follows.

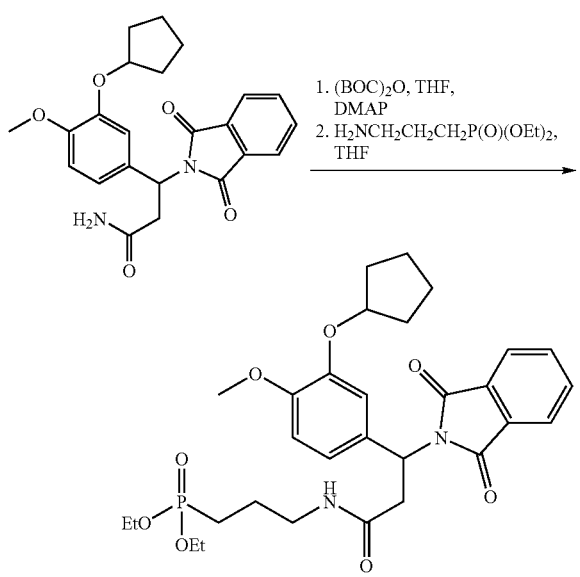

The primary amide in CC-1088 can be acylated with (BOC)$_2$O using N,N-dimethylaminopyridine as a base in a solvent such as tetrahydrofuran. Subsequent condensation with 3-aminopropylphosphonic acid diethyl ester in a solvent such as tetrahydrofuran gives the desired compound.

EXAMPLE 67

Synthesis of Representative Compounds of Formula 68

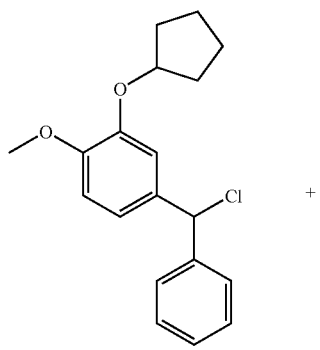

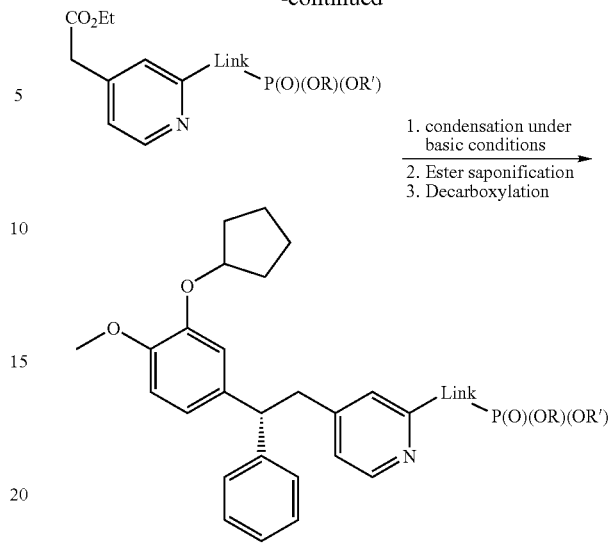

link includes 1 or more atoms; 2 or more is preferred

Representative compounds of the invention can be prepared as illustrated above. For example, a specific compound of Formula 68 can be prepared as follows.

The chloride is made from (3-cyclopentyloxy-4-methoxyphenyl)phenylketone (U.S. Pat. No. 5,622,977) by reduction with sodium borohydride in ethanol and treatment of the resulting alcohol with triphenylphosphine, carbon tetrachloride and diisopropyl azodicarboxylate in a solvent such as tetrahydrofuran. The condensation is achieved by treatment of the two reagents with sodium ethoxide in ethanol. The ethyl ester in the product is saponified by treatment with lithium hydroxide in ethanol, and the resulting acid is decarboxylated by heating under acidic conditions. The two enantiomers of the product may be separated by chromatography.

The synthesis of a pyridine intermediate is illustrated below.

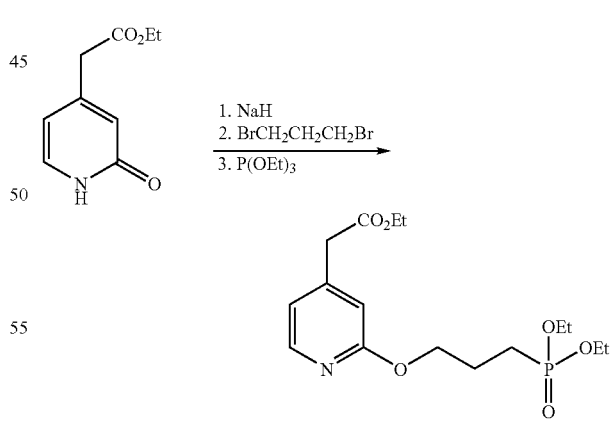

(2-Oxo-1,2-dihydro-pyridin-4-yl)-acetic acid ethyl ester is treated with a base such as sodium hydride in a solvent such as tetrahydrofuran. After bubbling ceases, an excess of 1,3-dibromopropane is added. After quenching the reaction with aqueous ammonium chloride and extracting the product with an organic solvent such as ethyl acetate, the mono-bromide is isolated by chromatography. The bromide is then heated with triethylphosphite in a solvent such as toluene to generate the diethyl ester of the desired phosphonic acid.

EXAMPLE 68

Synthesis of Representative Compounds of Formula 69

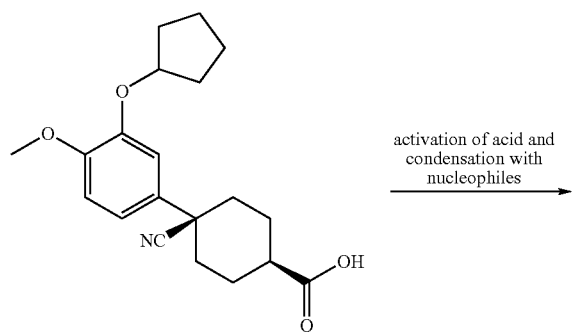

activation of acid and condensation with nucleophiles

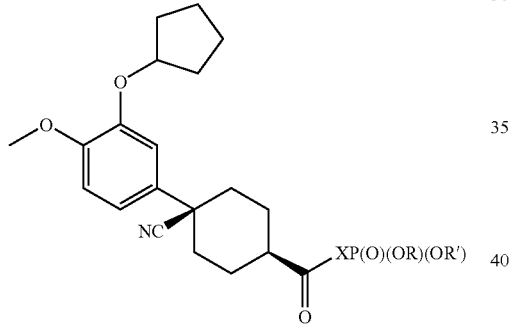

X = 1, 2, 3, or 4, or greater spacer atoms

Representative compounds of the invention can be prepared as illustrated above. For example, a specific compound of Formula 69 can be prepared as follows.

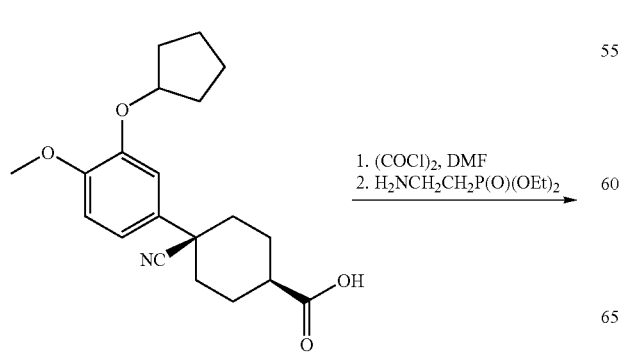

1. (COCl)$_2$, DMF
2. H$_2$NCH$_2$CH$_2$P(O)(OEt)$_2$

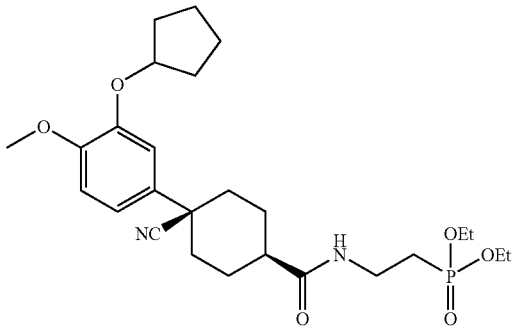

Cilomilast can be converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired compound.

EXAMPLE 69

Synthesis of Representative Compounds of Formula 70

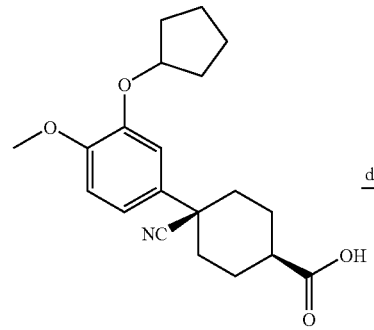

reduction of acid; activation of alcohol; displacement by phosphite

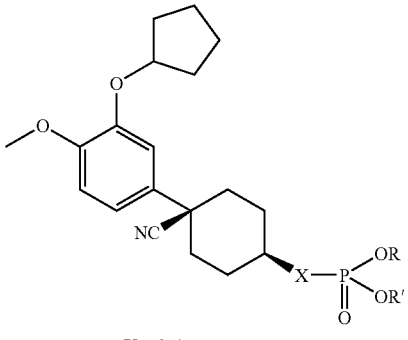

X = 0-4 spacer atoms

Representative compounds of the invention can be prepared as illustrated above. For example, a specific compound of Formula 70 can be prepared as follows.

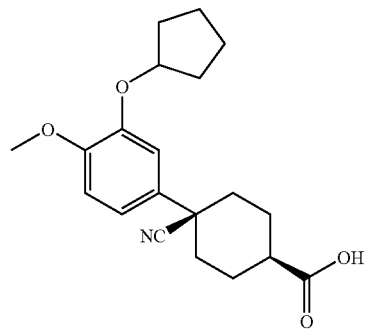

1. BH₃
2. CBr₄, PPh₃, THF
3. P(OEt)₃, heat

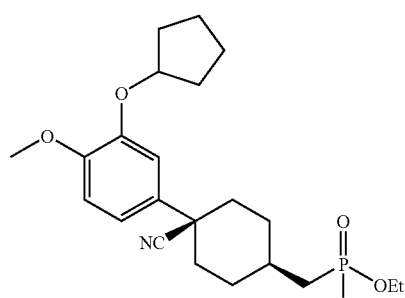

The carboxylic acid of cilomilast can be reduced to the alcohol by treatment with diborane in a solvent such as tetrahydrofuran. The alcohol is converted to the bromide by treatment with carbon tetrabromide and triphenylphosphine in a solvent such as tetrahydrofuran or dichloromethane. The bromide is then heated with triethylphosphite in a solvent such as toluene to generate the diethyl ester of the phosphonic acid.

EXAMPLE 70

Synthesis of Representative Compounds of Formula 71

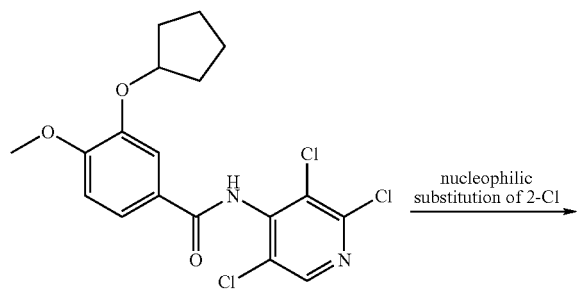

nucleophilic substitution of 2-Cl

-continued

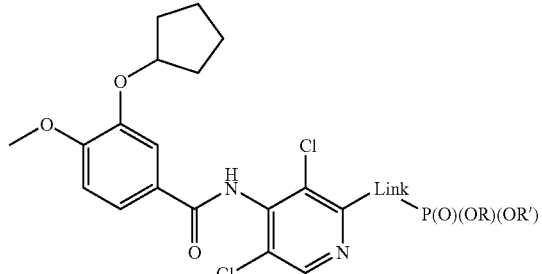

link includes 1 or more atoms; 2 or more is preferred

Representative compounds of the invention can be prepared as illustrated above. For example, a specific compound of Formula 71 can be prepared as follows.

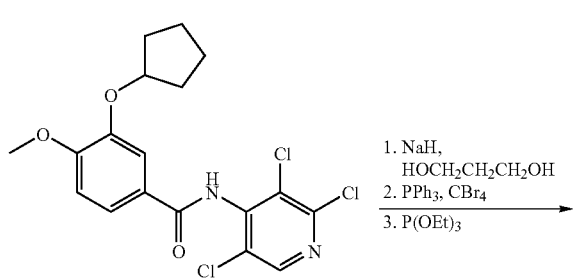

1. NaH, HOCH₂CH₂CH₂OH
2. PPh₃, CBr₄
3. P(OEt)₃

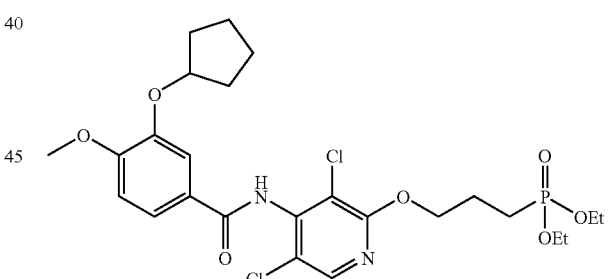

1,3-Dihydroxypropane is treated with a base such as sodium hydride in a solvent such as tetrahydrofuran. After bubbling ceases, the 2,3,5-trichloropyridyl analog of piclamilast (made by methods analogous to those described in U.S. Pat. No. 5,698,711) is added. After quenching the reaction with aqueous ammonium chloride and extracting the product with an organic solvent such as ethyl acetate, the monoalkylated alcohol is isolated by chromatography. The alcohol is converted to the bromide by treatment with carbon tetrabromide, triphenylphosphine and diisopropyl azodicarboxylate in a solvent such as tetrahydrofuran or dichloromethane. The bromide is then heated with triethylphosphite in a solvent such as toluene to generate the diethyl ester of the phosphonic acid.

EXAMPLE 71

Synthesis of Representative Compounds of Formula 72

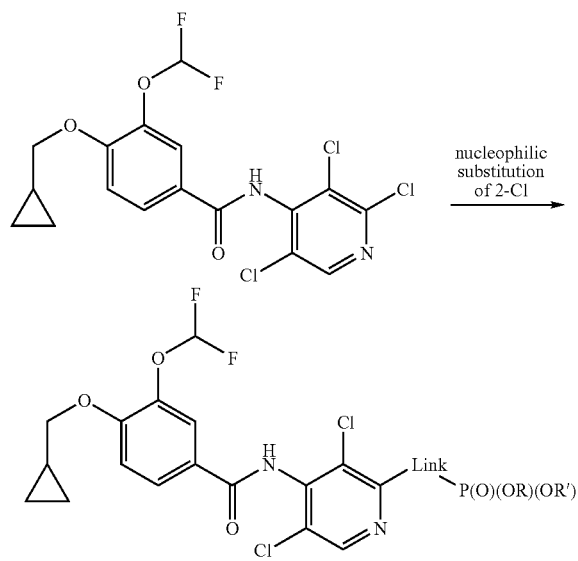

link includes 1 or more atoms; 2 or more is preferred

Representative compounds of the invention can be prepared as illustrated above. For example, a specific compound of Formula 72 can be prepared as follows.

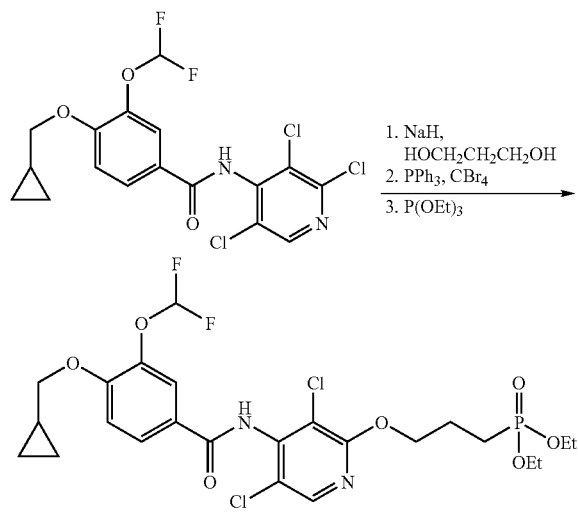

1,3-Dihydroxypropane is treated with a base such as sodium hydride in a solvent such as tetrahydrofuran. After bubbling ceases, the 2,3,5-trichloropyridyl analog of roflumilast (made by methods analogous to those described in U.S. Pat. No. 5,712,298) is added. After quenching the reaction with aqueous ammonium chloride and extracting the product with an organic solvent such as ethyl acetate, the mono-alkylated alcohol is isolated by chromatography. The alcohol is converted to the bromide by treatment with carbon tetrabromide, triphenylphosphine and diisopropyl azodicarboxylate in a solvent such as tetrahydrofuran or dichloromethane. The bromide is then heated with triethylphosphite in a solvent such as toluene to generate the diethyl ester of the phosphonic acid.

EXAMPLE 72

Synthesis of Representative Compounds of Formula 73

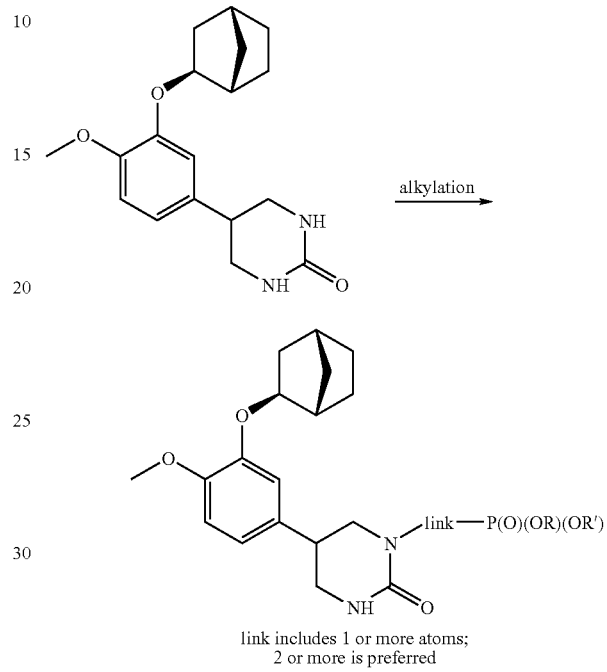

link includes 1 or more atoms; 2 or more is preferred

Representative compounds of the invention can be prepared as illustrated above. For example, a specific compound of Formula 73 can be prepared as follows.

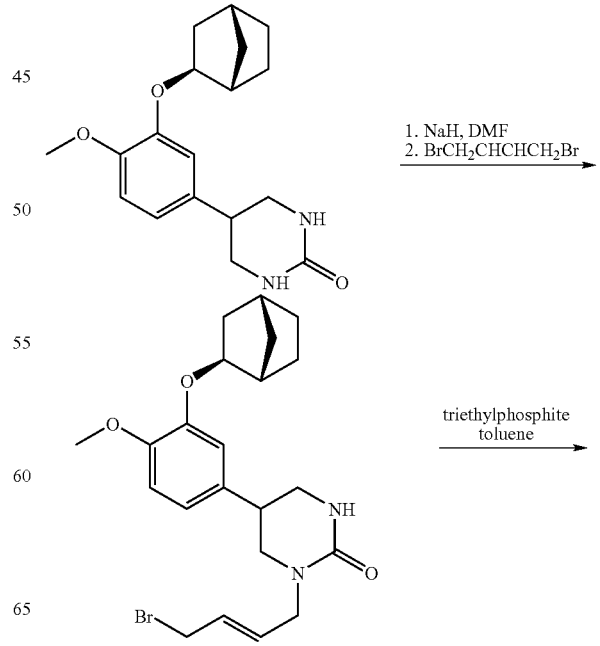

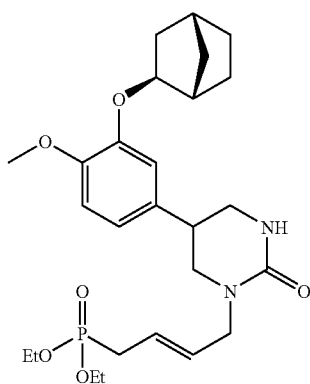

Atizoram can be treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the mono-alkylated product is isolated by chromatography. The allylic bromide is then heated with triethylphosphite in a solvent such as toluene to generate the diethyl ester of the phosphonic acid.

Synthetic methodologies and intermediate compounds that can be used to prepare VX-148 analogs of formulae A, B, or C are described in Examples 73-78. These compounds are representative examples of compounds of Formulae 74, 75, and 76.

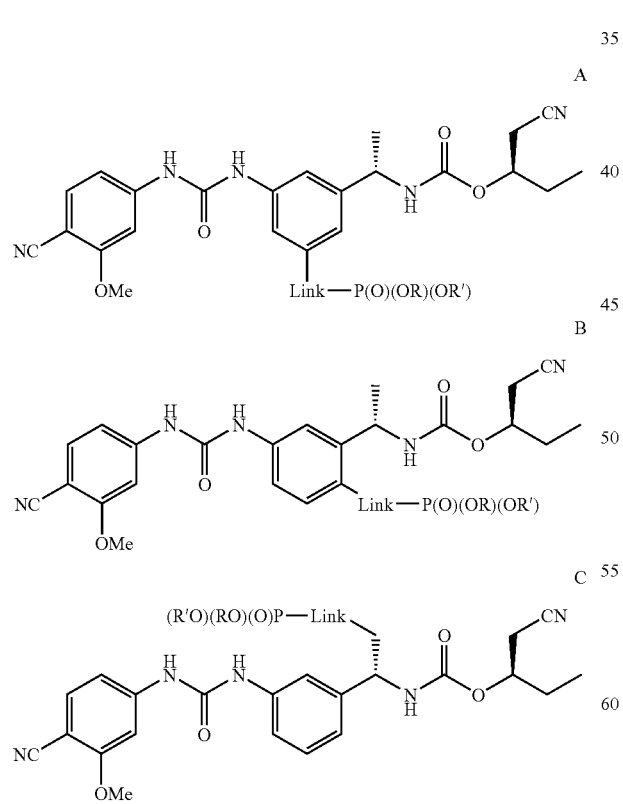

Link includes 0-8 atoms; 2-6 is preferred

EXAMPLE 73

General Synthesis of Aniline Intermediate Useful for Preparing VX-148 Analog of Formula A

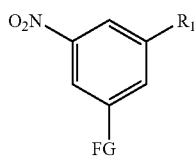

$R_1$ = 1-carbon substituent;
FG = functional group

1. Manipulation of FG to introduce phosphonate moiety
2. Manipulation of $R_1$ to protected primary amine
3. Reduction of nitro group

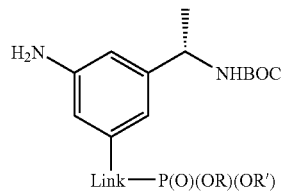

A general scheme that is useful for converting a 3,5-difunctionalized nitrobenzene derivative to an aniline that can be used to prepare a VX-148 analog of the invention is illustrated above.

EXAMPLE 74

Synthesis of Aniline Intermediate Useful for Preparing VX-148 Analog of Formula A

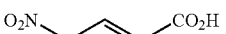

1. SOCl2
2. MeONH(Me)
3. MeLi
4. K2CO3, DMF BrCH2CH:CHCH2Br
5. P(OEt)3

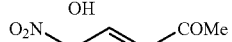

1. homochiral oxazaborolidine
3. DIAD/PPh3/NaN3
4. PPh3
5. (BOC)2O
6. SnCl2, EtOH

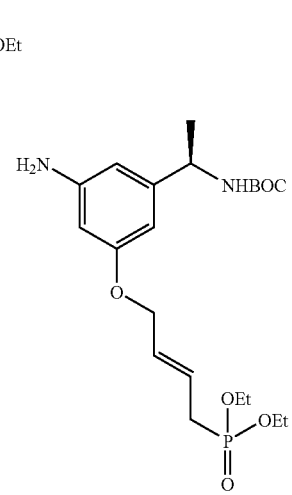

3-Hydroxy-5-nitro-benzoic acid is heated briefly in thionyl chloride to generate the acid chloride. This is then condensed with O,N-dimethyl-hydroxylaamine in the presence of a base such as triethylamine to produce the Weinreb amide which, upon reaction with methyl lithium, gives the acetophenone derivative. This is then treated with a base such as potassium carbonate in a dipolar aprotic solvent such as dimethyl-formamide, in the presence of an excess of E-1,4-dibromobutene. The monobromide is isolated by chromatography and then subjected to treatment with triethylphosphite in a solvent such as toluene (or other Arbuzov reaction conditions: see Engel, R., Synthesis of carbon-phosphorus bonds, CRC press, 1988) to generate the desired phosphonate diethyl ester. Thereafter, the carbonyl of the acetophenone is reduced enantioselectively using an appropriate homochiral oxazaborolidine such as that described by Corey (*J. Am. Chem. Soc.*, 1987, 109, 5551), and the resulting alcohol is displaced by azide using a method such as that described by Mitsunobu (*Bull. Chem. Soc. Japan.*, 1971, 44, 3427). The azide is reduced to the amine under Staudinger conditions (*Helv. Chim. Act.*, 1919, 2, 635) and protected as the t-butyl carbonate. Finally, the desired aniline intermediate is generated by tin(II)-mediated reduction of the nitrobenzene.

EXAMPLE 75

Synthesis of VX-148 Analog of formula B

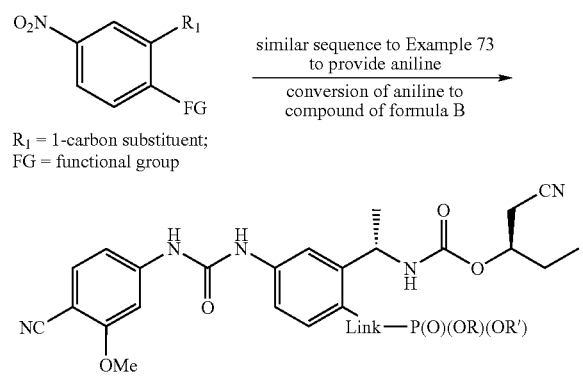

A general scheme that is useful for converting a 3,4-difunctionalized nitrobenzene derivative to an aniline, which can be converted to a compound of formula B using coupling reactions similar to those described in U.S. Pat. No. 6,054,472 and U.S. Pat. No. 6,344,465, is illustrated above.

EXAMPLE 76

General Route to Representative Compounds of Formula C

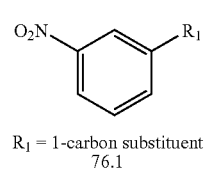

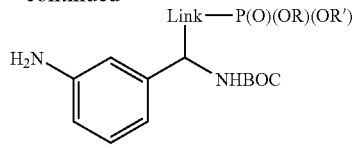

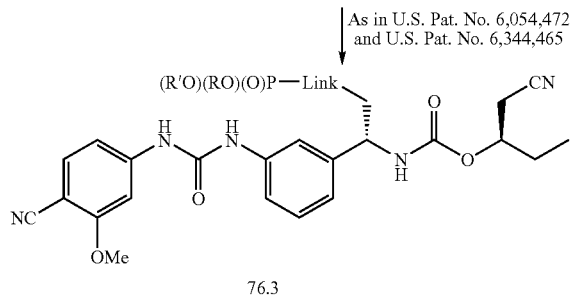

Manipulation of a 3-substituted nitrobenzene 76.1 provides aniline 76.2, which can be converted to a compound of formula C using coupling reactions similar to those described in U.S. Pat. No. 6,054,472 and U.S. Pat. No. 6,344,465.

EXAMPLE 77

General Route to Aniline Intermediate Useful For Preparing Representative Compounds of Formula C

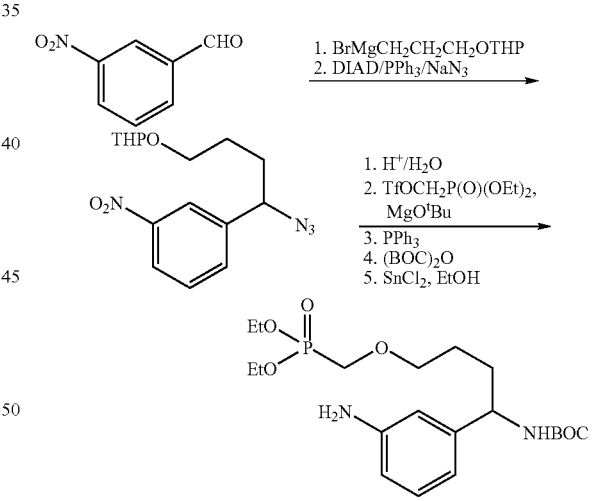

3-Nitrobenzaldehyde reacts with a Grignard reagent to introduce a tether bearing a protected alcohol and simultaneously to generate a benzylic alcohol, as shown. The alcohol is displaced by an azide in a manner similar to that described for Example 9. After deprotection, the liberated alcohol is alkylated with diethyl phosphonomethyltriflate (prepared according to *Tetrahedron Lett.*, 1986, 27, 1477) using a base such as magnesium tert-butoxide in a solvent such as tetrahydrofuran. Subsequent transformations of the azide and nitro groups proceed in a fashion similar to that described in Example 74. See Batt et al, *Bioorg. Med. Chem. Lett.*, 1995, 5, 1549.

EXAMPLE 78

General Route to Aniline Intermediate Useful For Preparing Representative Compounds of Formula C

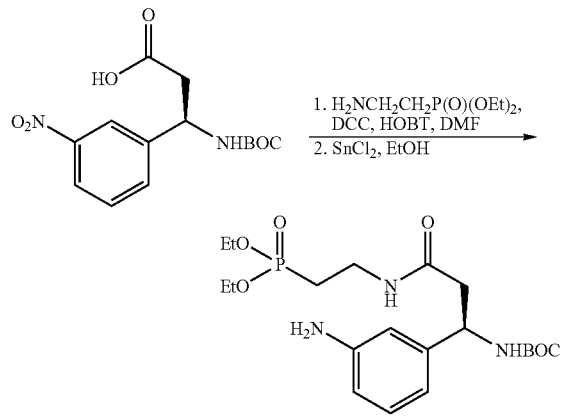

3-tert-Butoxycarbonylamino-3-(3-nitro-phenyl)-propionic acid (commercially available) is coupled with 2-aminoethylphosphonic acid diethyl ester (commercially available) using standard reagents for the formation of a secondary amide such as dicyclohexylcarbodiimide (DCC) and hydroxybenztriazole (HOBT), in a solvent such as dimethylformamide. Subsequent reduction of the nitro group proceeds in a fashion similar to that described in Example 74.

EXAMPLE 79

General Route to Representative Compounds of Formula 79

The following is a general route that can be used to prepare compounds of Formula 79.

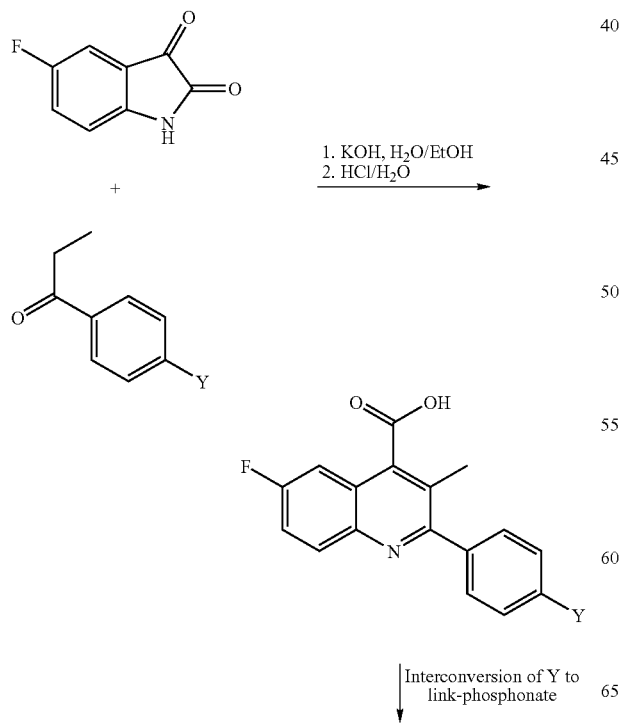

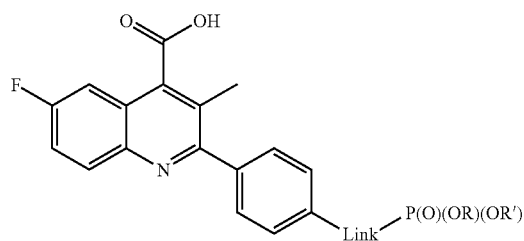

EXAMPLE 80

Preparation of a Representative Compound of Formula 77

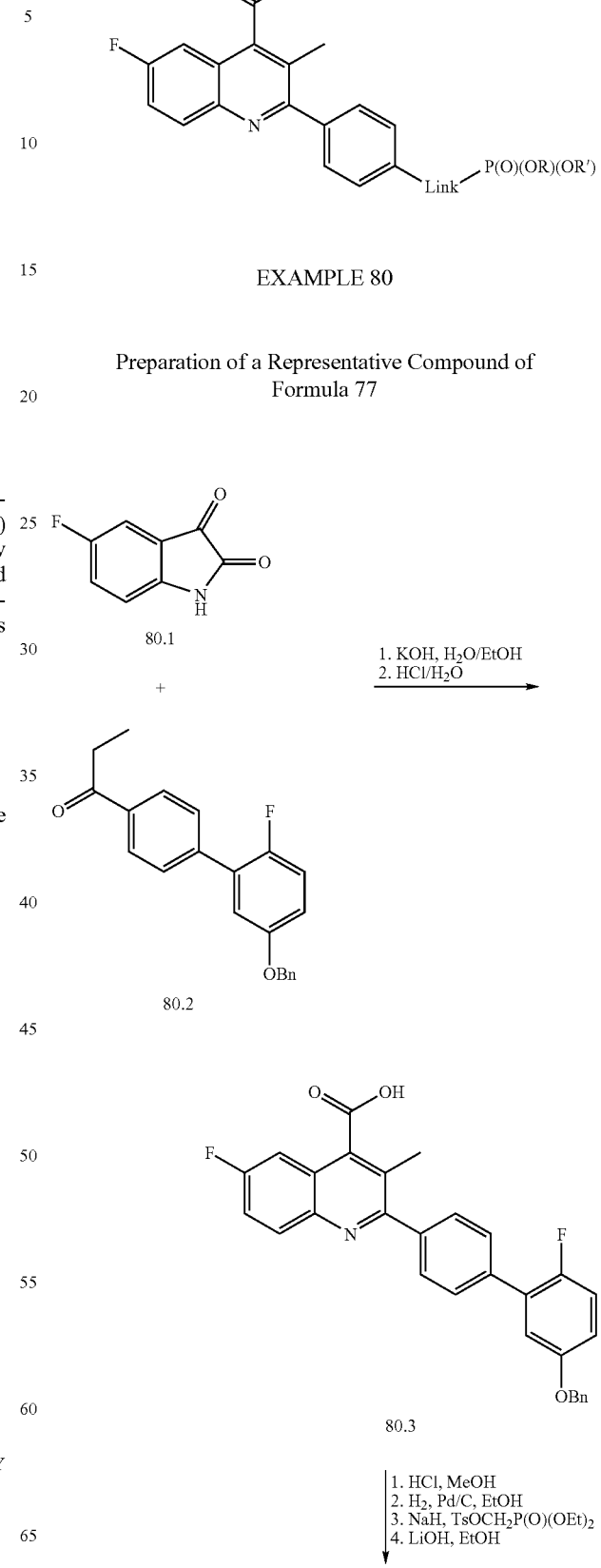

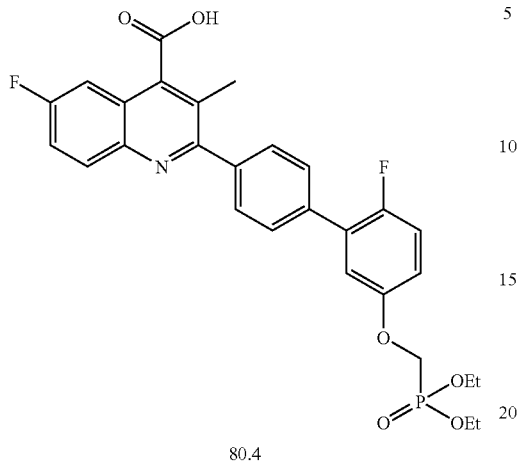

80.4

The initial Pfitzinger condensation of compound 80.1 and compound 80.2 is achieved in a single step using potassium hydroxide with acidic work-up, as shown. Alternatively, the initial aldol condensation may be performed using diethylamine in ethanol, and the quinoline ring may be formed as a second step mediated by an acid such as hydrochloric acid in a solvent such as 1,4-dioxane. Following removal of the benzyl protecting group via hydrogenation, the phenol can be treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding the desired phosphonate diester. The carboxylate is deprotected by treatment with lithium hydroxide in ethanol to provide the compound 80.4 (which is a compound of formula 78).

EXAMPLE 81

Preparation of a Representative Brequinar Phosphonate Analog of Formula 80

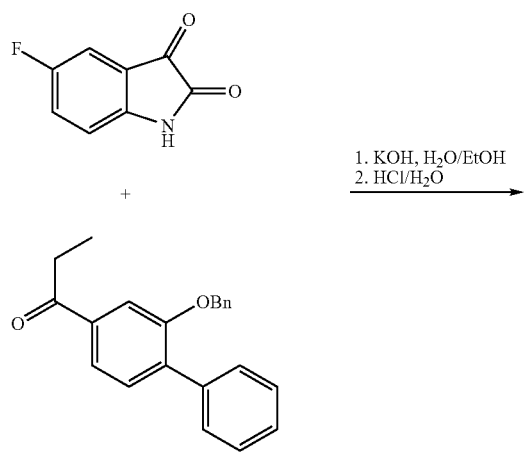

1. KOH, H$_2$O/EtOH
2. HCl/H$_2$O

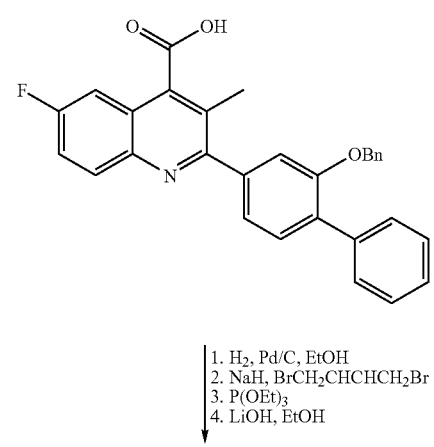

1. H$_2$, Pd/C, EtOH
2. NaH, BrCH$_2$CHCHCH$_2$Br
3. P(OEt)$_3$
4. LiOH, EtOH

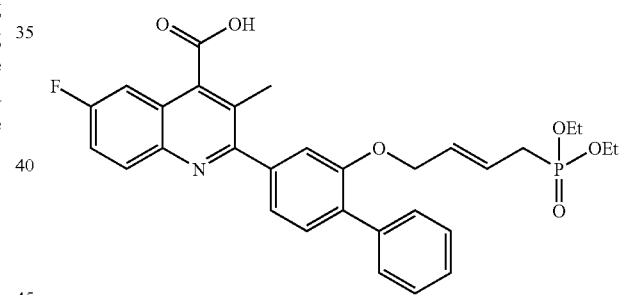

The synthesis is similar to that depicted in Example 80 except that, following deprotonation of the phenol, E-1,4-dibromobutene is added in excess. After quenching the reaction with aqueous ammonium chloride and extracting the product with an organic solvent such as ethyl acetate, the mono-alkylated product is isolated by chromatography. The resulting bromide is heated with triethylphosphite in a solvent such as toluene to generate the diethyl ester of the desired phosphonic acid, and the carboxylic acid is deprotected as before to provide a compound of formula 80.

EXAMPLE 82

Preparation of Representative Compound of Formula 81

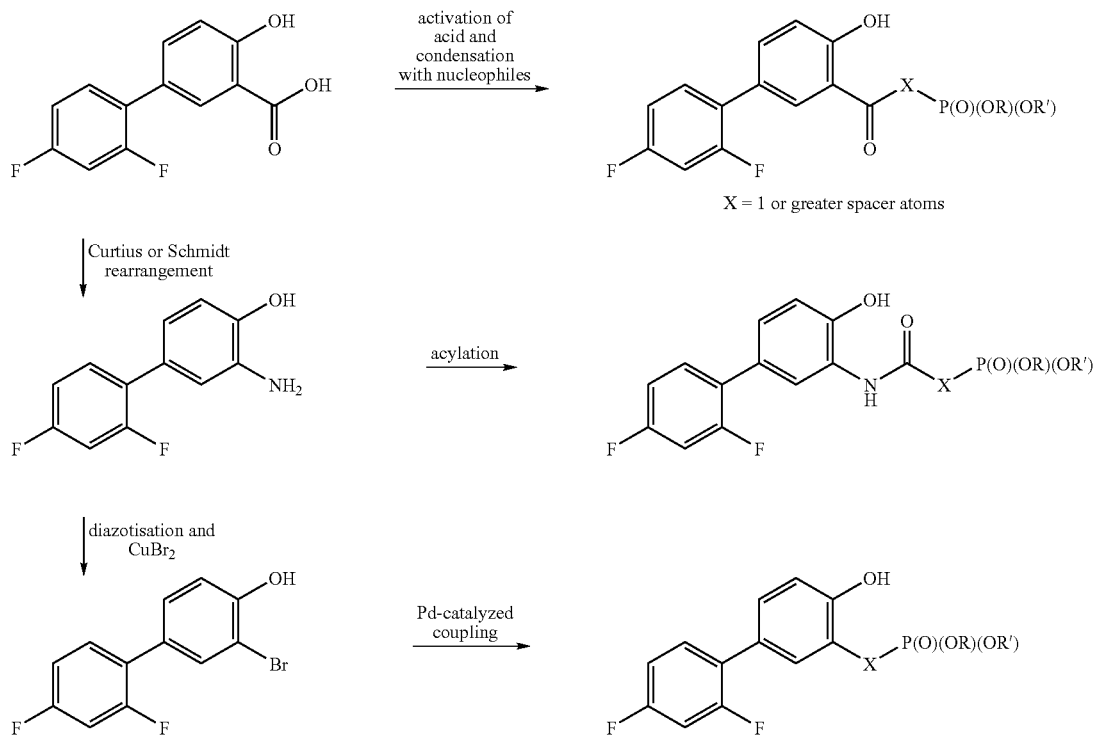

Representative compounds of the invention can be prepared as illustrated above. For example, specific compounds of Formula 81 can be prepared as follows.

Diflunisal is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Diflunisal is treated in a solvent such as acetonitrile with diphenylphosphoryl azide in the presence of a base such as triethylamine at room temperature or up to reflux temperature. After cooling, the mixture is treated with diluted hydrochloric acid to provide the aniline (J. Org. Chem., 2002, 67, 6260). The aniline is then acylated with an activated diethylphosphonoacetic acid to provide the desired amide linker compound, according to a procedure such as those reported in J. Med. Chem., 1982, 25, 960-964 and J. Med. Chem., 1984, 27, 600-604. The activated diethylphosphonoacetic acid is obtained by treatment in a solvent such as dimethylformamide with a coupling reagent such as diethyl cyanophosphonate and a base such as diisopropylethylamine at room temperature.

The aniline derived from diflunisal is converted to the aryl bromide using a variant of the Sandmeyer reaction (Bull. Chem. Soc. Jpn., 1980, 53, 1065). This is then coupled with pent-4-ynyl-phosphonic acid diethyl ester (generated from 5-chloro-1-pentyne and triethylphosphite in a solvent such as toluene, or other Arbuzov reaction conditions: see Engel, R., Synthesis of carbon-phosphorus bonds, CRC press, 1988) under conditions such as those pioneered by Sonagashira (Sonogashira, K.; Tohda, Y.; Hagihara, N. Tetrahedron Lett., 1975, 4467) to afford the desired diflunisal analog containing a phosphonate.

EXAMPLE 83

Preparation of Representative Compounds of Formula 82

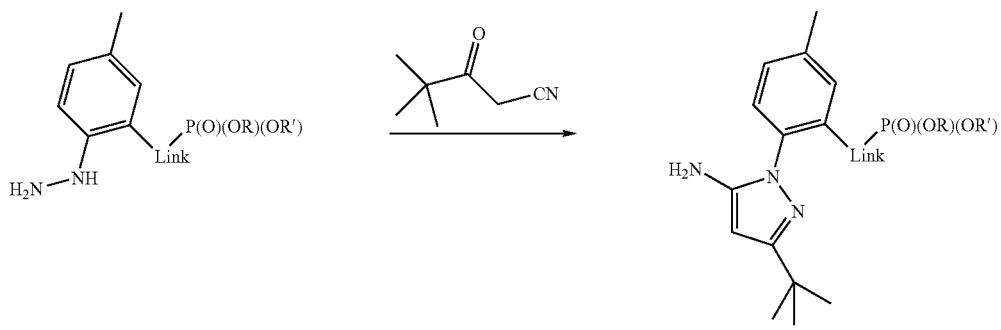

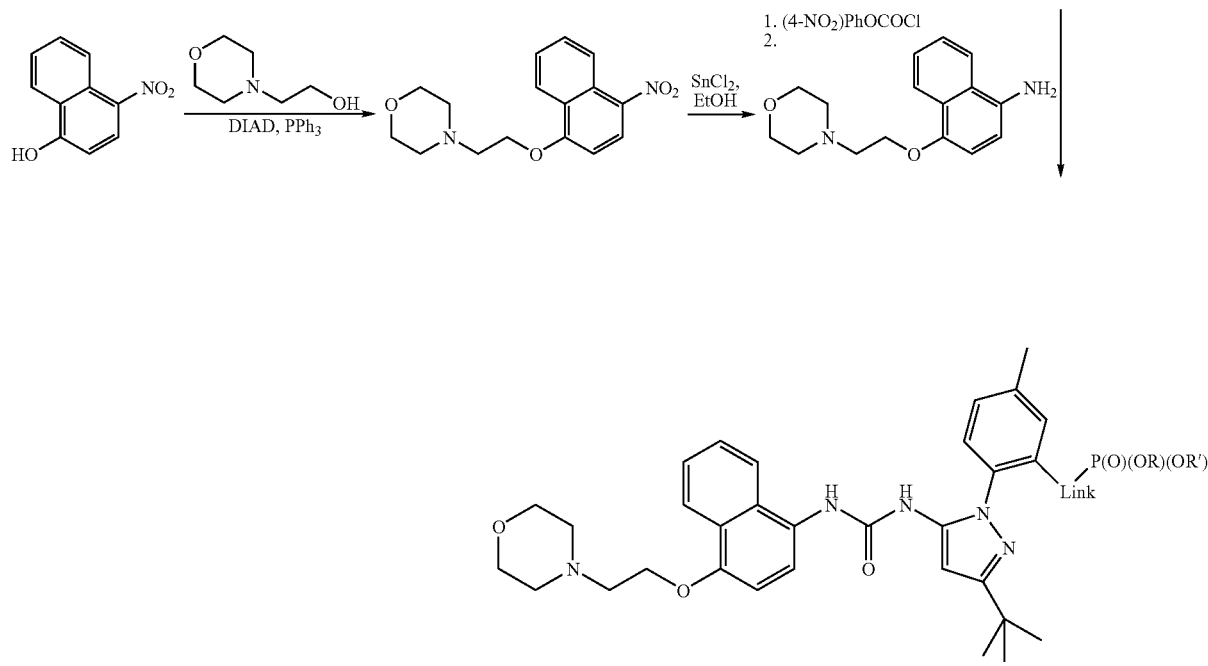

Representative compounds of the invention can be prepared as illustrated above. The aryl hydrazine is condensed with 4,4-dimethyl-3-oxo-pentanenitrile to form an aminopyrazole (as described in *J. Med. Chem.*, 2002, 45, 2994). Urea formation is accomplished by sequential condensation with 4-nitrophenyl chloroformate and the requisite aniline. The latter is generated from 4-nitro-naphthalen-1-ol by reaction with 2-morpholin-4-yl-ethanol using a method such as that described by Mitsunobu (*Bull. Chem. Soc. Japan*, 1971, 44, 3427), followed by tin(II)-mediated reduction of the nitro group to provide the aniline.

The synthesis of a suitable phosphonate-containing arylhydrazine intermediate is illustrated below.

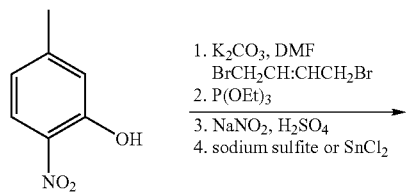

-continued

5-Methyl-2-nitrophenol is alkylated with E-1,4-dibromobutene. The resulting monobromide is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. The nitro group is converted to the aryl hydrazine by diazotization and reduction with sodium sulfite (*Chem. Ber.*, 1960, 93, 540) or tin(II) chloride (*J. Med. Chem.*, 2001, 44, 4031).

The syntheses of suitable phosphonate-containing aryl hydrazines in which link is attached to the 3- or 4-positions of the phenyl ring are analogous to that shown in Example 83, starting from 2-methyl-5-nitrophenol and 4-nitrophenol, respectively.

EXAMPLE 84

Preparation of Representative Compound of Formula 85

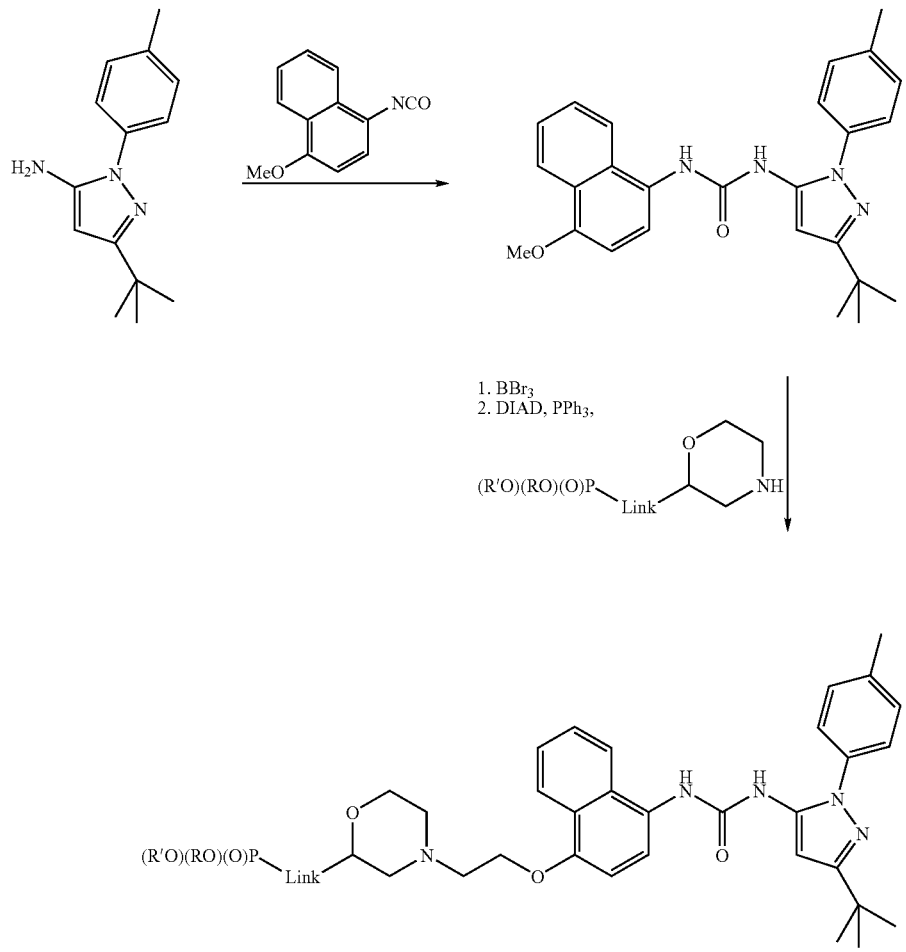

Representative compounds of the invention can be prepared as illustrated above. Following the synthesis of the urea through condensation of 5-tert-butyl-2-p-tolyl-2H-pyrazol-3-ylamine and 1-isocyanato-4-methoxy-naphthalene, the product is demethylated by treatment with a Lewis acid such as boron tribromide. The resulting phenol is coupled with a suitable morpholine derivative using a method such as that described by Mitsunobu (*Bull. Chem. Soc. Japan.*, 1971, 44, 3427).

The synthesis of a suitable phosphonate-containing morpholine intermediate is illustrated below.

Morpholine-2,4-dicarboxylic acid 4-benzyl ester (generated from morpholine-2,4-dicarboxylic acid by reaction with benzyl chloroformate under standard protection conditions (such as those described in Greene, T., Protective groups in organic synthesis, Wiley-interscience, 1999)) is coupled with 2-aminoethylphosphonic acid diethyl ester (commercially available) using standard reagents for the formation of a secondary amide such as dicyclohexylcarbodiimide (DCC) and hydroxybenztriazole (HOBT), in a solvent such as dimethylformamide. Removal of the benzyl carbamate protecting group by hydrogenation over palladium in a solvent such as methanol (as described in Greene, T. ibid.) provides the desired product.

EXAMPLE 85
Preparation of Representative Compounds of Formula 86
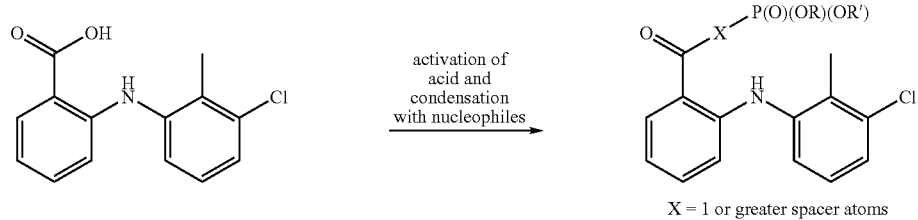
X = 1 or greater spacer atoms
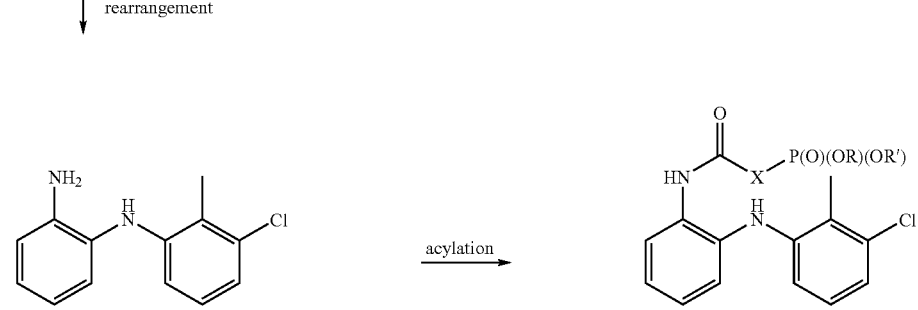
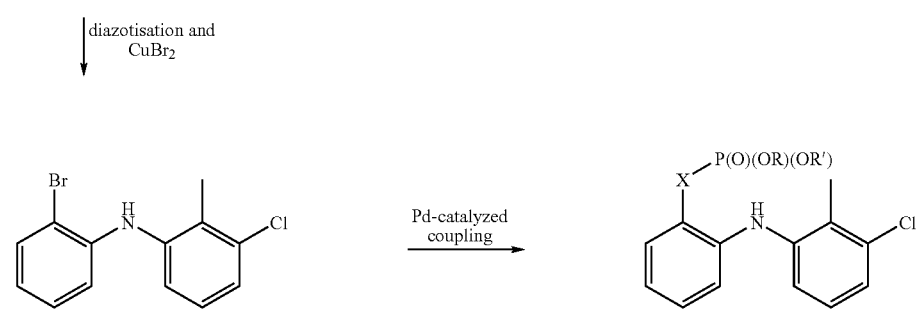
Representative compounds of the invention can be prepared as illustrated above. For example, specific compounds of Formula 86 can be prepared as follows.
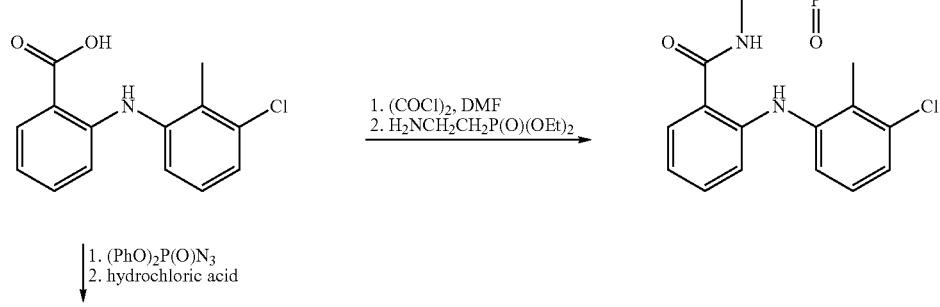

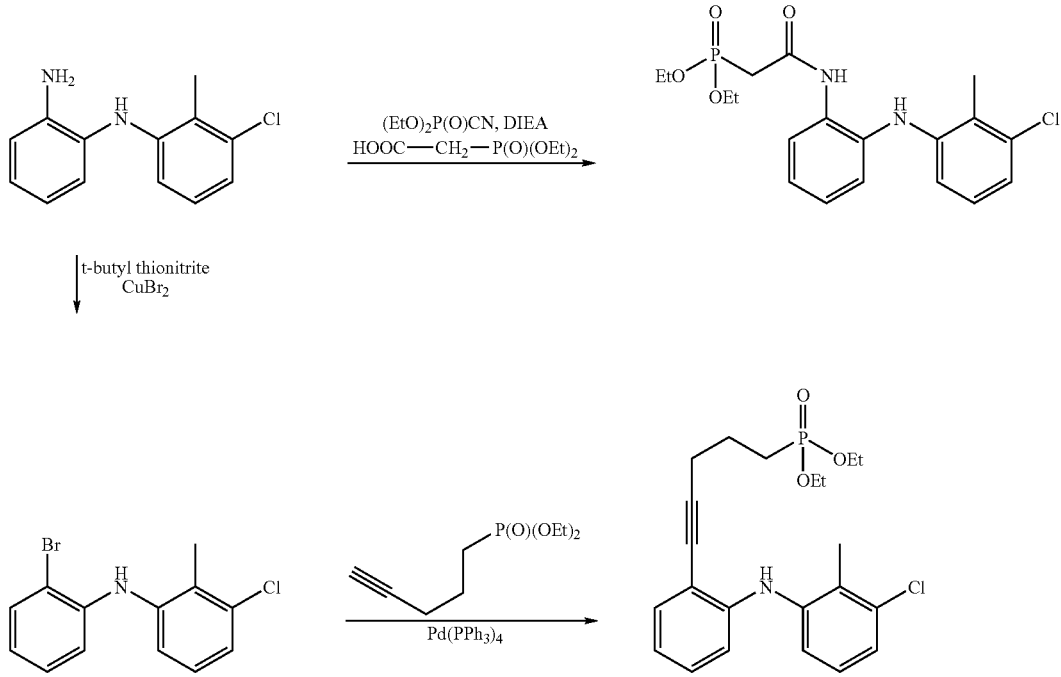

Tolfenamic acid is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Tolfenamic acid is treated in a solvent such as acetonitrile with diphenylphosphoryl azide in the presence of a base such as triethylamine at room temperature or up to reflux temperature. After cooling, the mixture is treated with diluted hydrochloric acid to provide the aniline (*J. Org. Chem.*, 2002, 67, 6260). The aniline is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid is obtained by treatment in a solvent such as dimethylformamide with a coupling reagent such as diethyl cyanophosphonate and a base such as diisopropylethylamine at room temperature.

The aniline derived from tolfenamic acid is converted to the aryl bromide using a variant of the Sandmeyer reaction (*Bull. Chem. Soc. Jpn.*, 1980, 53, 1065). This is then coupled with pent-4-ynyl-phosphonic acid diethyl ester (generated from 5-chloro-1-pentyne and triethylphosphite in a solvent such as toluene, or other Arbuzov reaction conditions: see Engel, R., Synthesis of carbon-phosphorus bonds, CRC press, 1988) under conditions such as those pioneered by Sonogashira (Sonogashira, K.; Tohda, Y.; Hagihara, N. *Tetrahedron Lett.*, 1975, 4467) to generate the desired phosphonate-containing analog of tolfenamic acid.

EXAMPLE 86

Preparation of Representative Compounds of Formula 87

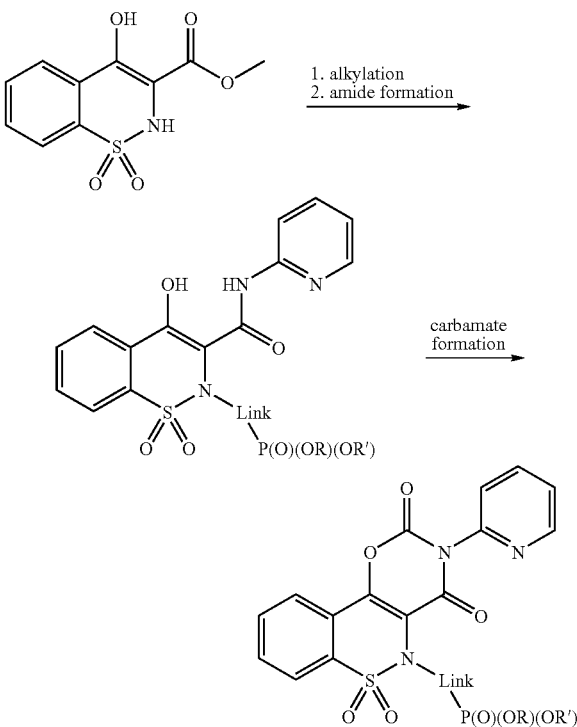

Representative compounds of the invention can be prepared as illustrated above. For example, a specific compound of Formula 87 can be prepared as follows.

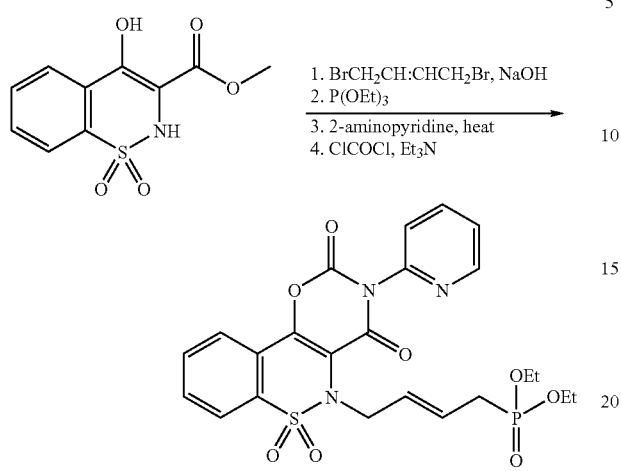

The methyl ester shown is treated in a solvent such as ethanol with excess E-1,4-dibromobutene in the presence of a base such as sodium hydroxide, as described in *J. Med. Chem.*, 1997, 40, 980. The monobromide so formed is then heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. Heating with 2-aminopyridine in solvents such as xylenes, as described in *J. Med. Chem.*, 1997, 40, 980, gives the desired piroxicam analogue, which is transformed to the corresponding droxicam-like prodrug by treatment with phosgene and a tertiary amine such as triethylamine in solvents such as tetrahydrofuran and/or benzene, as described in *J. Med. Chem.*, 1973, 16, 44.

EXAMPLE 87

Preparation of Representative Compounds of Formula 88

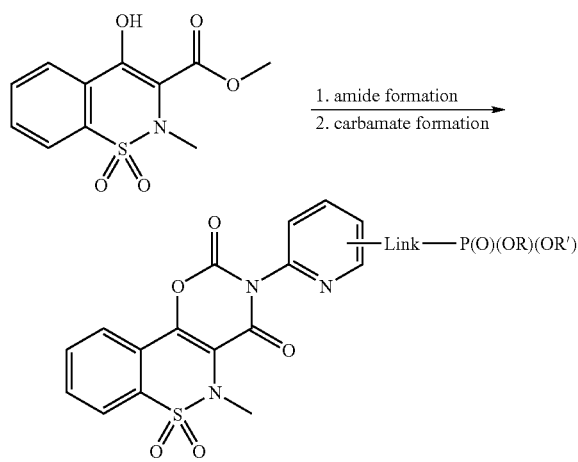

Representative compounds of the invention can be prepared as illustrated above. For example, a specific compound of Formula 88 can be prepared as follows.

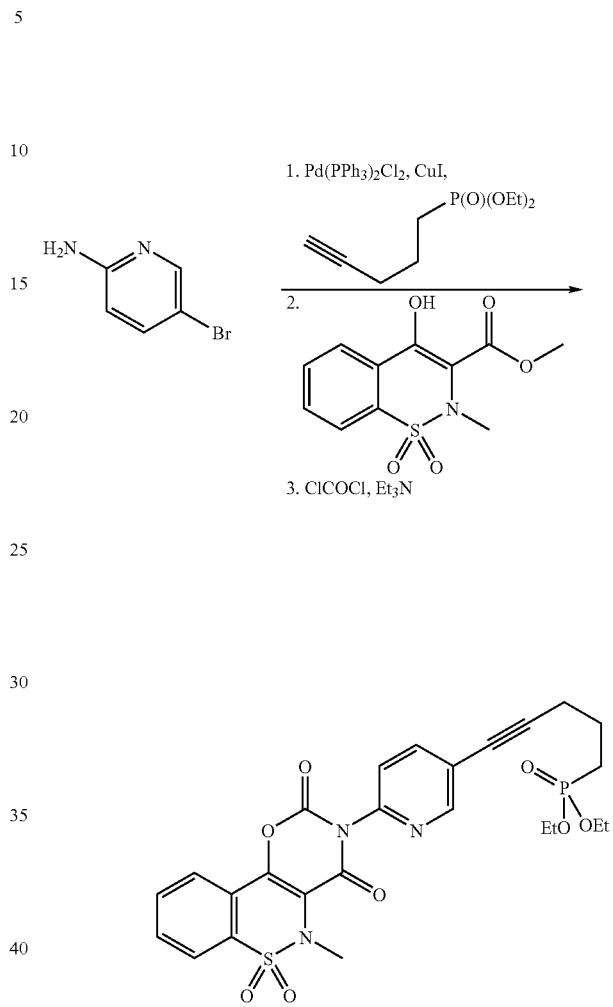

2-Amino-5-bromopyridine is coupled with pent-4-ynyl-phosphonic acid diethyl ester (generated from 5-chloro-1-pentyne and triethylphosphite in a solvent such as toluene, or other Arbuzov reaction conditions: see Engel, R., Synthesis of carbon-phosphorus bonds, CRC press, 1988) under conditions such as those pioneered by Sonagashira (Sonogashira, K.; Tohda, Y.; Hagihara, N. *Tetrahedron Lett.*, 1975, 4467) to afford the desired phosphonate-containing aminopyridine. This is then heated with the methyl ester shown in solvents such as xylenes, as described in *J. Med. Chem.*, 1997, 40, 980, to give the desired piroxicam analogue, which is transformed to the corresponding droxicam-like prodrug by treatment with phosgene and a tertiary amine such as triethylamine in solvents such as tetrahydrofuran and/or benzene, as described in *J. Med. Chem.*, 1973, 16, 44.

EXAMPLE 88
Preparation of Representative Compounds of Formula 89
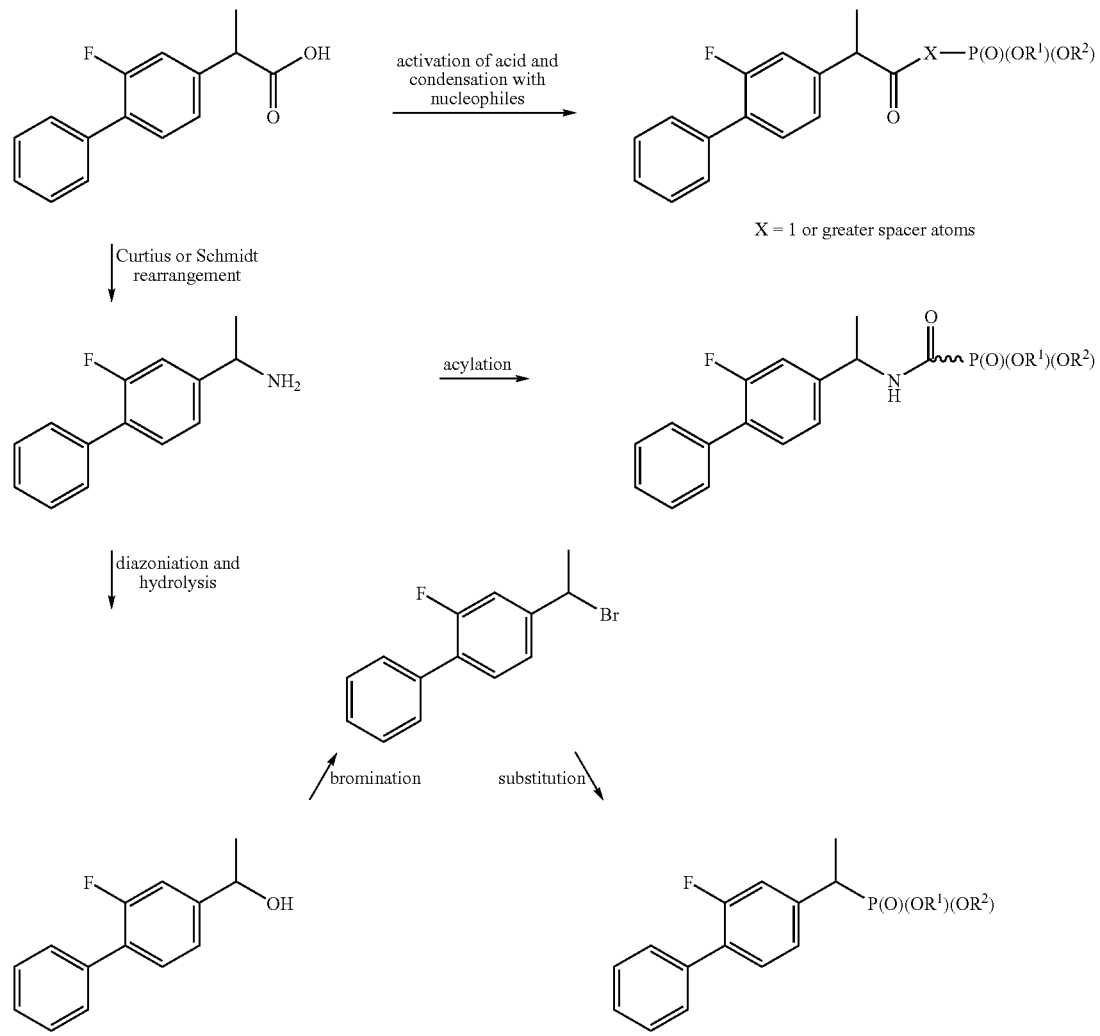
Representative compounds of the invention can be prepared as illustrated above. For example, specific compounds of Formula 89 can be prepared as follows.
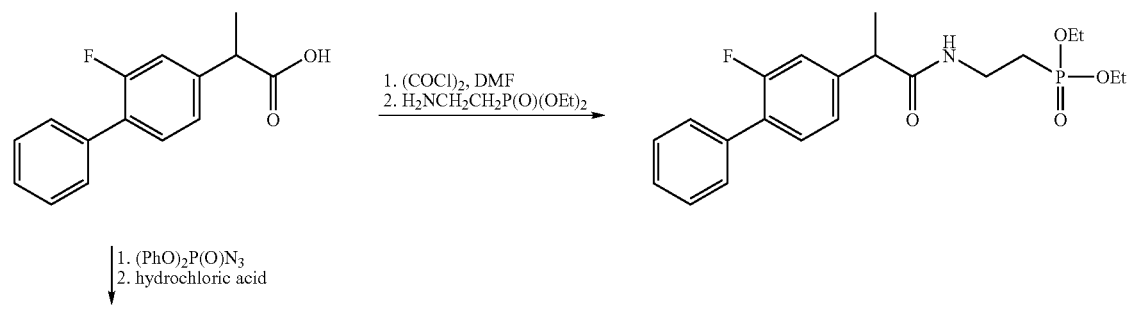

-continued

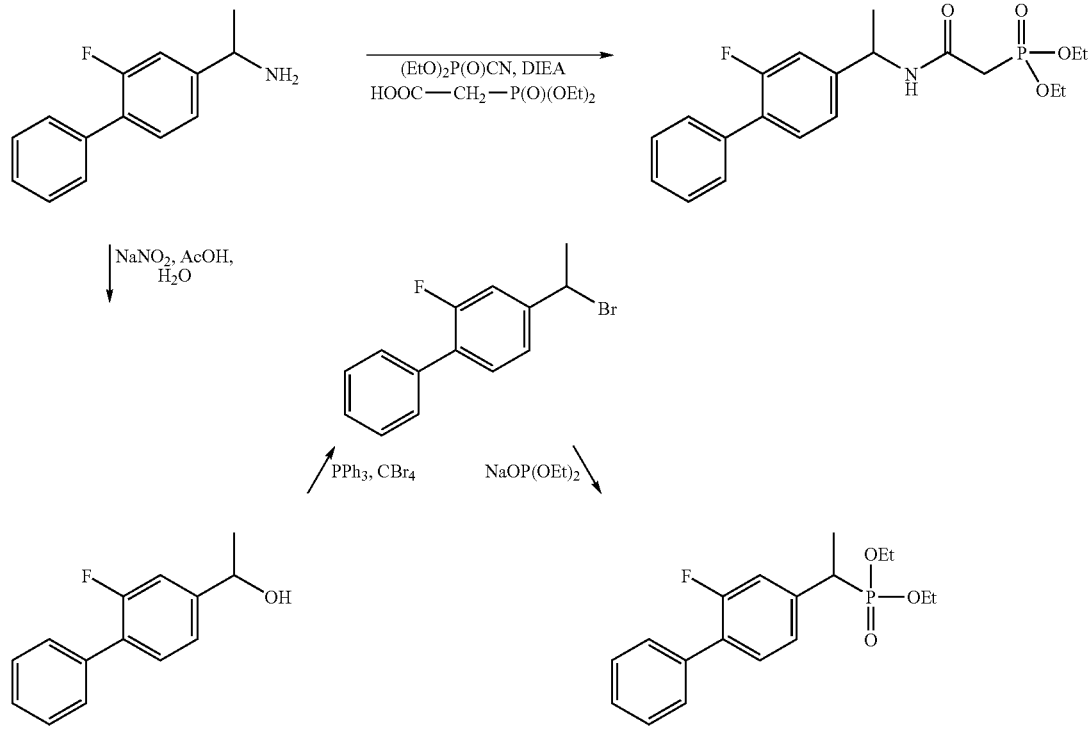

Flurbiprofen is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Flurbiprofen is treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.*, 2002, 67, 6260). The amine is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid is obtained by treatment in a solvent such as dimethylformamide with a coupling reagent such as diethyl cyanophosphonate and a base such as diisopropylethylamine at room temperature.

The amine derived from flurbiprofen can be converted to the alcohol, according to a procedure such as that reported in *J. Org. Chem.*, 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.*, 2002, 67, 7215. The bromide is treated in a solvent such as tetrahydrofuran with sodium salt of phosphonic acid diethyl ester to provide the desired phosphonate derivative of flurbiprofen, according to a procedure such as that reported in *Tetrahedron*, 1996, 52, 4411.

EXAMPLE 89

Preparation of Representative Compounds of Formula 90

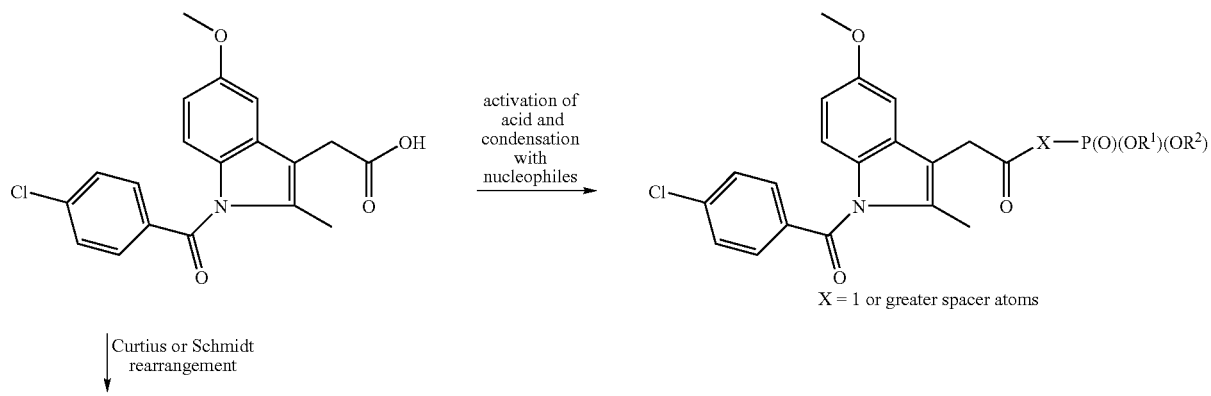

X = 1 or greater spacer atoms

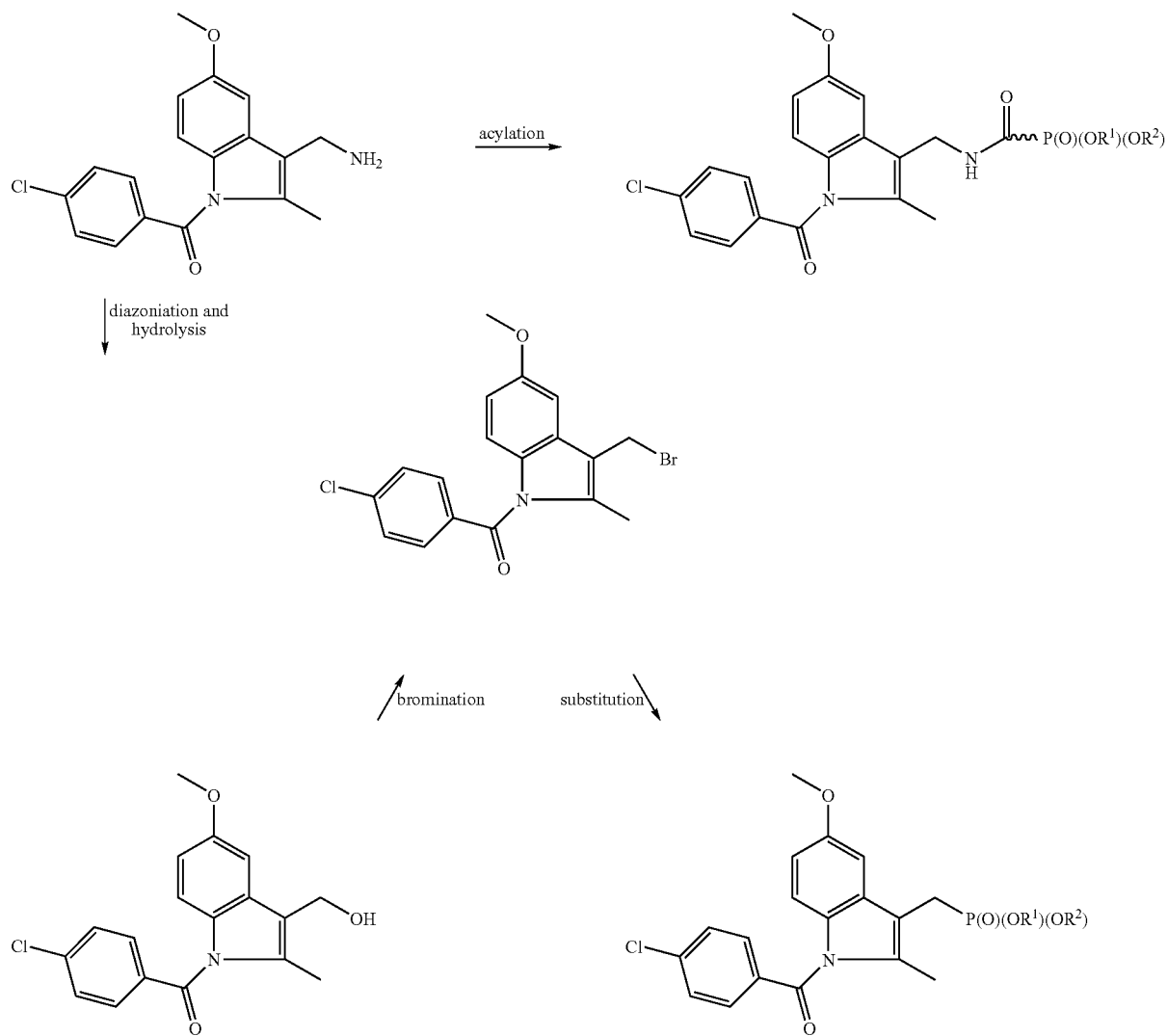
Representative compounds of the invention can be prepared as illustrated above. For example, specific compounds of Formula 90 can be prepared as follows.
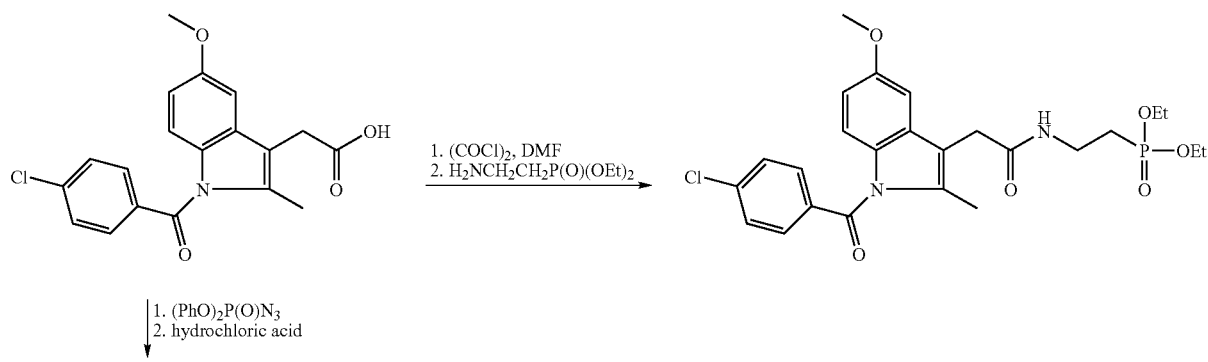

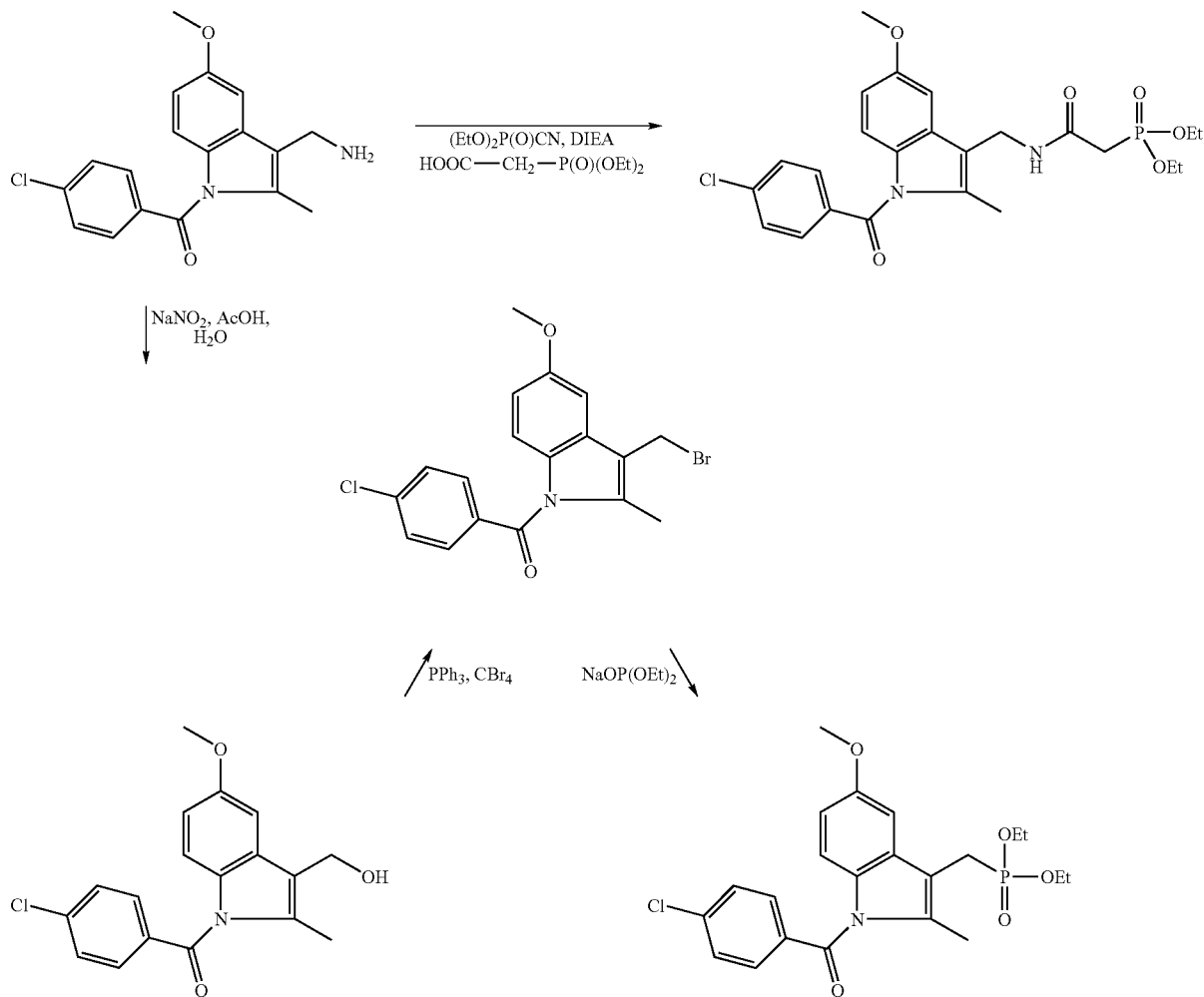

Indomethacin is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Indomethacin is treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.*, 2002, 67, 6260). The amine is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid can be obtained by treatment in a solvent such as dimethylformamide with a coupling reagent such as diethyl cyanophosphonate and a base such as diisopropylethylamine at room temperature.

The amine derived from indomethacin can be converted to the alcohol, according to a procedure such as that reported in *J. Org. Chem.*, 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.*, 2002, 67, 7215. The bromide is treated in a solvent such as tetrahydrofuran with sodium salt of phosphonic acid diethyl ester to provide the desired phosphonate derivative of indomethacin, according to a procedure such as that reported in *Tetrahedron*, 1996, 52, 4411.

EXAMPLE 90

Preparation of Representative Compounds of Formula 91

Compounds of the invention can be prepared as generally described in Schemes 1 and 2, with examples depicted in Examples 1 and 2.

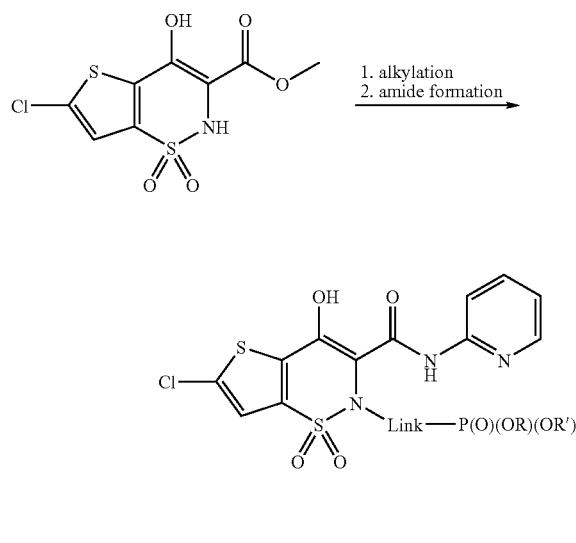

Representative compounds of the invention can be prepared as illustrated above. For example, specific compounds of Formula 91 can be prepared as follows.

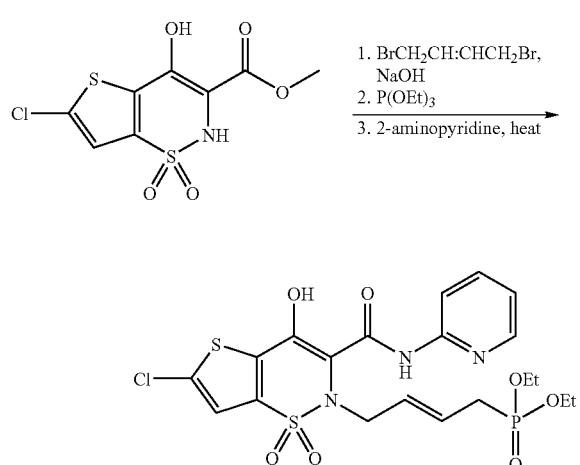

The methyl ester shown (made from the des-chloro compound (*J. Med. Chem.*, 1987, 30, 678) by treatment with N-chlorosuccinimide in a solvent such as dichloromethane) is treated in a solvent such as ethanol with excess E-1,4-dibromobutene in the presence of a base such as sodium hydroxide, as described in *J. Med. Chem.*, 1997, 40, 980. The monobromide so formed is then heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. Finally, heating with 2-aminopyridine in solvents such as xylenes, as described in *J. Med. Chem.*, 1997, 40, 980, gives the desired analogue.

EXAMPLE 91

Preparation of Representative Compounds of Formula 92

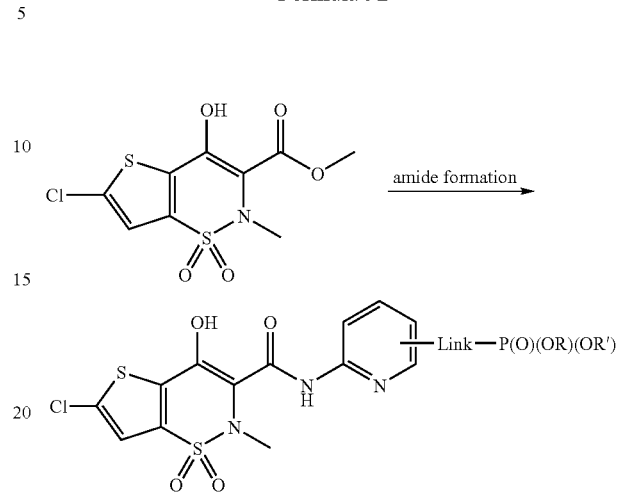

Representative compounds of the invention can be prepared as illustrated above. For example, specific compounds of Formula 92 can be prepared as follows.

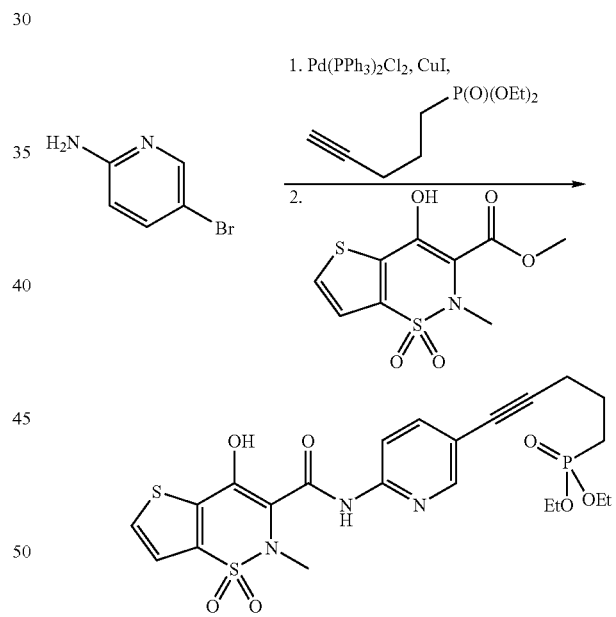

2-Amino-5-bromopyridine is coupled with pent-4-ynyl-phosphonic acid diethyl ester (generated from 5-chloro-1-pentyne and triethylphosphite in a solvent such as toluene, or other Arbuzov reaction conditions: see Engel, R., Synthesis of carbon-phosphorus bonds, CRC press, 1988) under conditions such as those pioneered by Sonagashira (Sonogashira, K.; Tohda, Y.; Hagihara, N. *Tetrahedron Lett.*, 1975, 4467) to afford the desired phosphonate-containing aminopyridine. This is then heated with the methyl ester shown in solvents such as xylenes, as described in *J. Med. Chem.*, 1997, 40, 980, to give the desired lomoxicam analogue.

EXAMPLE 92

Preparation of Representative Compounds of Formula 93

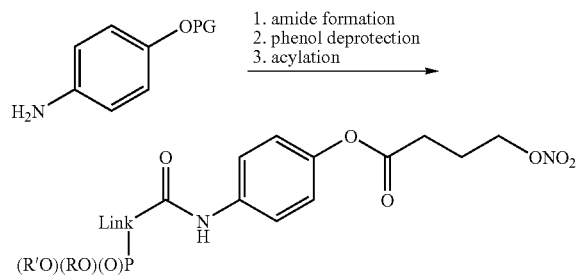

Representative compounds of the invention can be prepared as illustrated above. For example, specific compounds of Formula 93 can be prepared as follows.

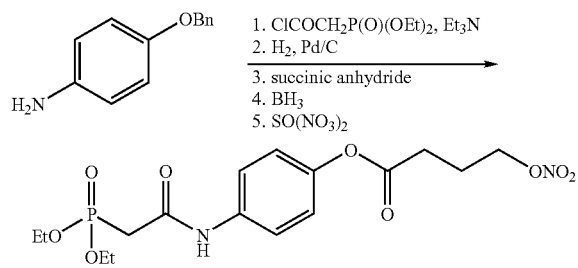

4-Benzyloxyaniline is condensed with diethyl phosphonoacetic acid chloride (formed from diethyl phosphonoacetic acid by treatment with oxalyl chloride, in the presence of a catalytic amount of dimethylformamide, in a solvent such as dichloromethane) in the presence of a base such as triethylamine. The phenol is liberated by hydrogenation over a catalyst of palladium on charcoal according to Greene, Protective Groups in Synthesis, Wiley, 1999. This is then condensed with succinic anhydride using a base such as sodium hydride in a solvent such as tetrahydrofuran (*Bioorg. Med. Chem. Lett.*, 2002, 12, 2545). The acid so formed is reduced with diborane in a solvent such as tetrahydrofuran, and the resulting primary alcohol is reacted with the nitrating reagent shown in a solvent such as tetrahydrofuran (*Helv. Chim. Act.*, 1984, 67, 906).

EXAMPLE 93

Preparation of Representative Compounds of Formula 94

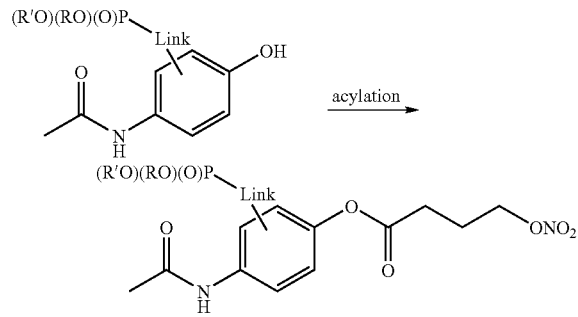

Representative compounds of the invention can be prepared as illustrated above. For example, specific compounds of Formula 94 can be prepared as follows.

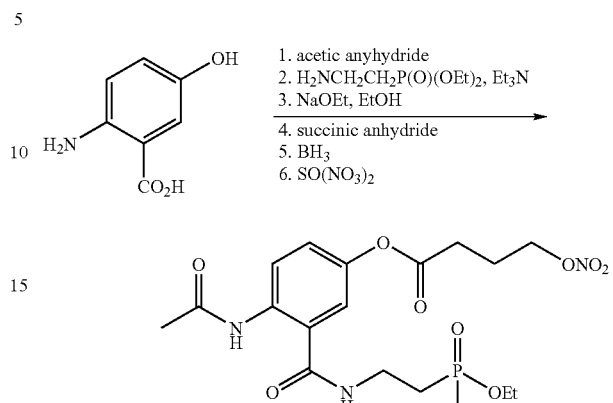

5-Hydroxyanthranilic acid is heated with acetic anhydride, generating the tri-acetylated species. This is then allowed to react with 2-aminoethylphosphonic acid diethyl ester in the presence of a base such as triethylamine in a solvent such as dichloromethane to generate the phosphonate-containing amide. Following deprotection of the phenol by treatment with sodium ethoxide, the nitrate-containing side-chain is constructed by initial condensation with succinic anhydride using a base such as sodium hydride in a solvent such as tetrahydrofuran (*Bioorg. Med. Chem. Lett.*, 2002, 12, 2545), reduction of the acid so formed with diborane in a solvent such as tetrahydrofuran, and finally reaction of the resulting primary alcohol with the nitrating reagent shown in a solvent such as tetrahydrofuran (*Helv. Chim. Act.*, 1984, 67, 906).

EXAMPLE 94

Preparation of Representative Compounds of Formula 95

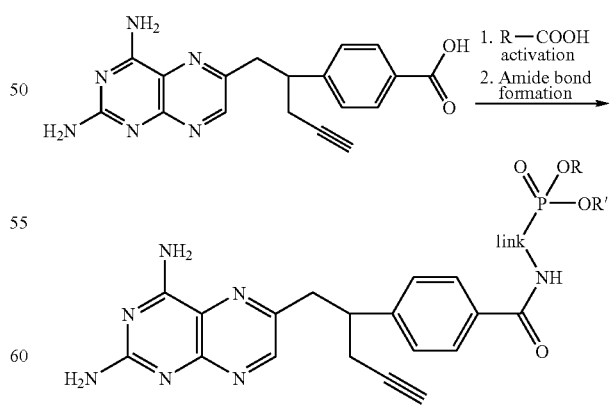

Representative compounds of the invention can be prepared as illustrated above. For example, a specific compound of Formula 95 can be prepared as follows.

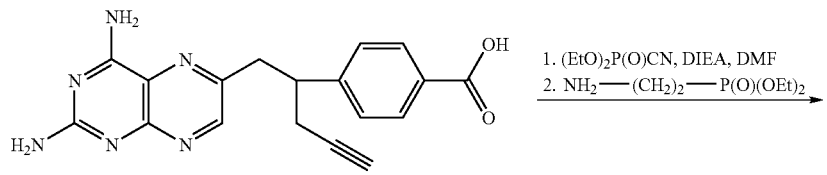

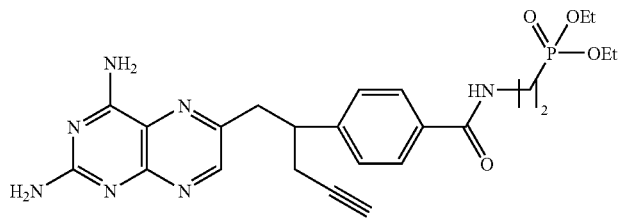

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, 1982, 25, 960-964 and *J. Med. Chem.*, 1984, 27, 600-604). When the activation is complete, 2-aminoethylphosphonic acid diethyl ester (commercially available) is added. After consumption of the activated species is observed the solvent is removed in vacuo and the product is isolated via chromatography. Alternatively, the product can be isolated through precipitation from the reaction solution with an organic solvent like diethyl ether or the like.

EXAMPLE 95

Preparation of Representative Compound of Formula 95

The starting carboxylic acid can be treated in a solvent such as DMF or NMP with a coupling reagent such as diethyl cyanophosphonate or isobutyl chloroformate and a base such as diisopropylethylamine (DIEA) at room temperature (*J. Med. Chem.*, 1982, 25, 960-964 and *J. Med. Chem.*, 1984, 27, 600-604). When the activation is complete, (2-amino-ethylsulfanylmethyl)-phosphonic acid diethyl ester (made by base-catalyzed coupling of 2-aminoethanethiol with diethyl phosphonomethyltriflate, prepared according to *Tetrahedron Lett.*, 1986, 27, 1477) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The intermediate is then dissolved in a mixture of water, DMF, and acetic acid and is treated with hydrogen peroxide solution (excess). After removal of the solvents the product is isolated via chromatography. Alternatively, the product can be isolated through precipitation from the reaction solution with an organic solvent like diethyl ether or the like.

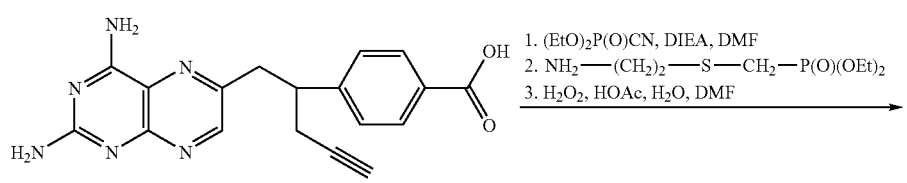

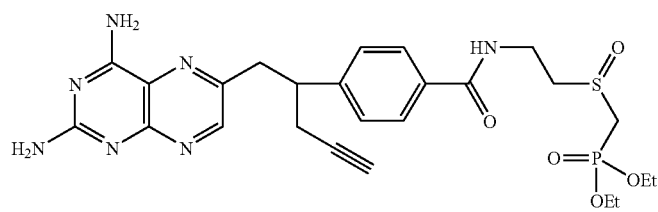

EXAMPLE 96

Preparation of Representative Compound of Formula 96

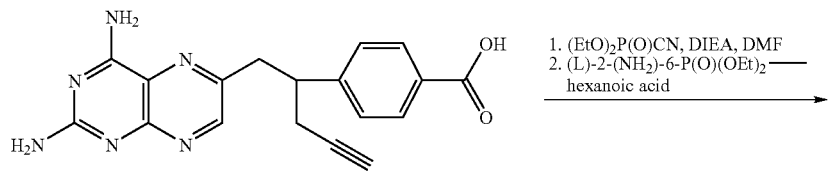

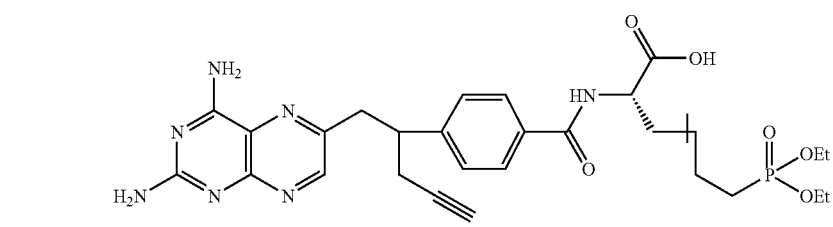

The starting carboxylic acid can be treated in a solvent such as DMF or NMP with a coupling reagent such as diethyl cyanophosphonate or isobutyl chloroformate and a base such as DIEA at room temperature (*J. Med. Chem.*, 1982, 25, 960-964 and *J. Med. Chem.*, 1984, 27, 600-604.). When the activation is complete, (L)-2-amino-6-(diethylphosphonato)-hexanoic acid is added. After consumption of the activated species is observed the solvent is removed in vacuo and the product is isolated via chromatography. Alternatively, the product can be isolated through precipitation from the reaction solution with an organic solvent like diethyl ether or the like.

EXAMPLE 97

Preparation of Representative Compound of Formula 97

The starting carboxylic acid can be treated in a solvent such as DMF or NMP with a coupling reagent such as diethyl cyanophosphonate or isobutyl chloroformate and a base such as DIEA at room temperature (*J. Med. Chem.*, 1982, 25, 960-964 and *J. Med. Chem.*, 1984, 27, 600-604). When the activation is complete, 4-amino-4-(diethylphosphonato)-butyric acid tert butylester (*J. Am. Chem. Soc.*, 1995, 117, 10879-10888) is added. After consumption of the activated species is observed the solvent is removed in vacuo and the intermediate is isolated via chromatography. Alternatively, the intermediate can be isolated through precipitation from the reaction solution with an organic solvent like diethyl ether or the like. The crude intermediate is then dissolved in DMF and treated with TFA (excess). The product is isolated via chromatography after removal of the solvents. Alternatively, the product can be isolated through precipitation form the reaction solution with an organic solvent like diethyl ether or the like

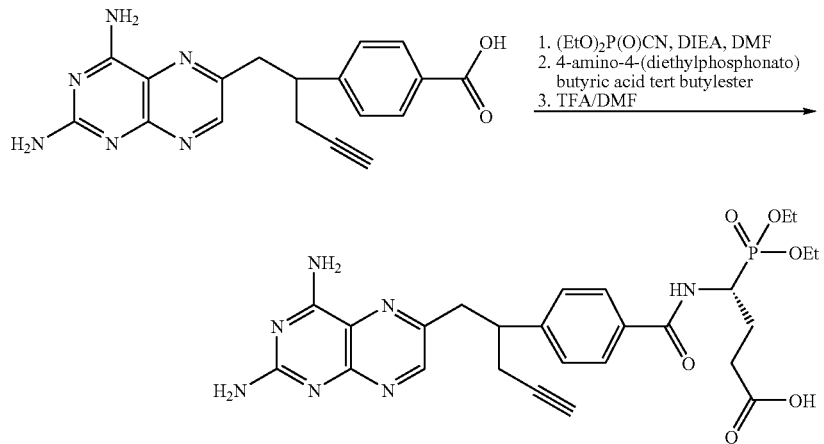

EXAMPLE 98
Preparation of Representative Compound of Formula 98
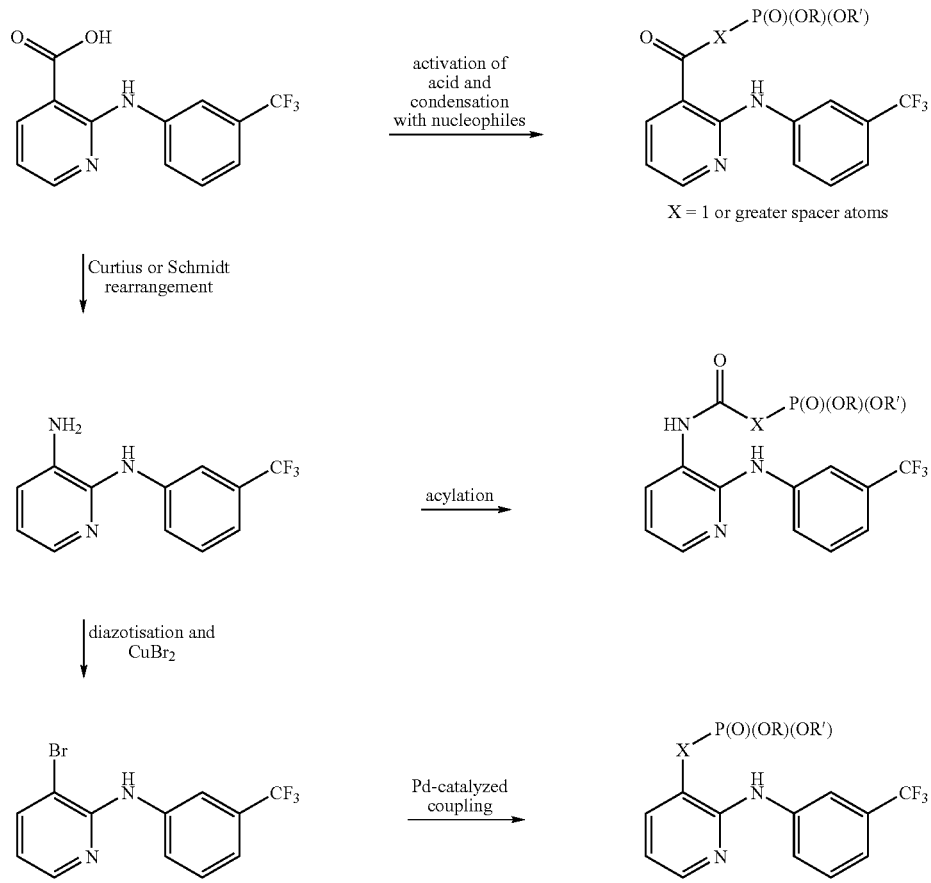
X = 1 or greater spacer atoms
Representative compounds of the invention can be prepared as illustrated above. For example, specific compounds of Formula 98 can be prepared as follows.
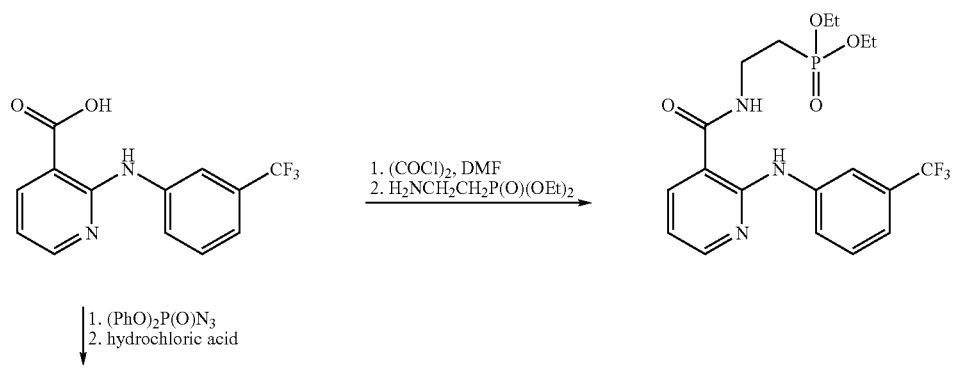

-continued

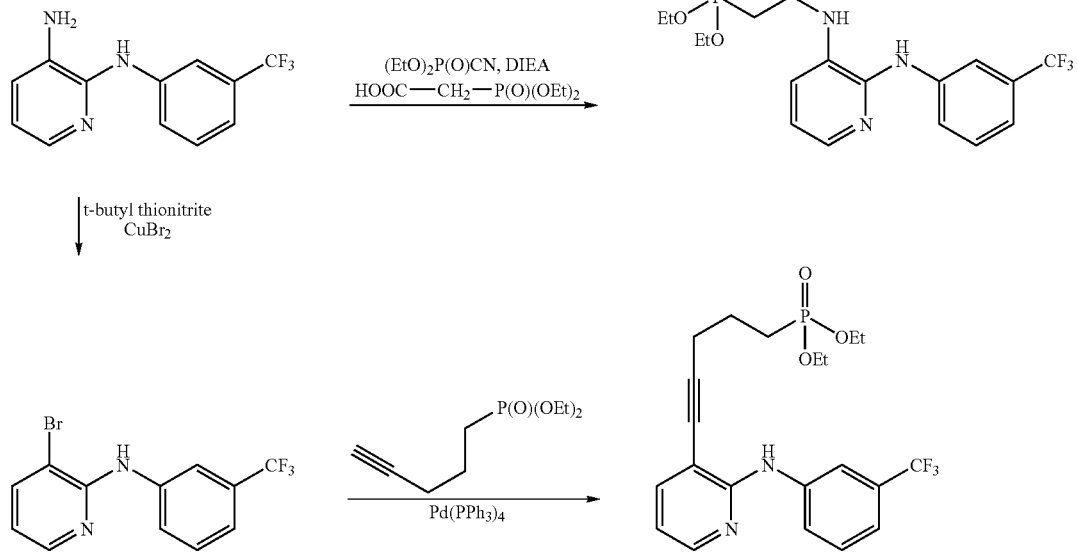

Niflumic acid is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Niflumic acid is treated in a solvent such as acetonitrile with diphenylphosphoryl azide in the presence of a base such as triethylamine at room temperature or up to reflux temperature. After cooling, the mixture is treated with diluted hydrochloric acid to provide the aniline (*J. Org. Chem.*, 2002, 67, 6260). The aniline is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid is obtained by treatment in a solvent such as dimethylformamide with a coupling reagent such as diethyl cyanophosphonate and a base such as diisopropylethylamine at room temperature.

The aniline derived from niflumic acid is converted to the aryl bromide using a variant of the Sandmeyer reaction (*Bull. Chem. Soc. Jpn.*, 1980, 53, 1065). This is then coupled with pent-4-ynyl-phosphonic acid diethyl ester (generated from 5-chloro-1-pentyne and triethylphosphite in a solvent such as toluene, or other Arbuzov reaction conditions: see Engel, R., Synthesis of carbon-phosphorus bonds, CRC press, 1988) under conditions such as those pioneered by Sonagashira (Sonogashira, K.; Tohda, Y.; Hagihara, N. *Tetrahedron Lett.*, 1975, 4467) to generate the desired phosphonate-containing analog of niflumic acid.

EXAMPLE 99

Preparation of Representative Compounds of Formulae 99 and 100

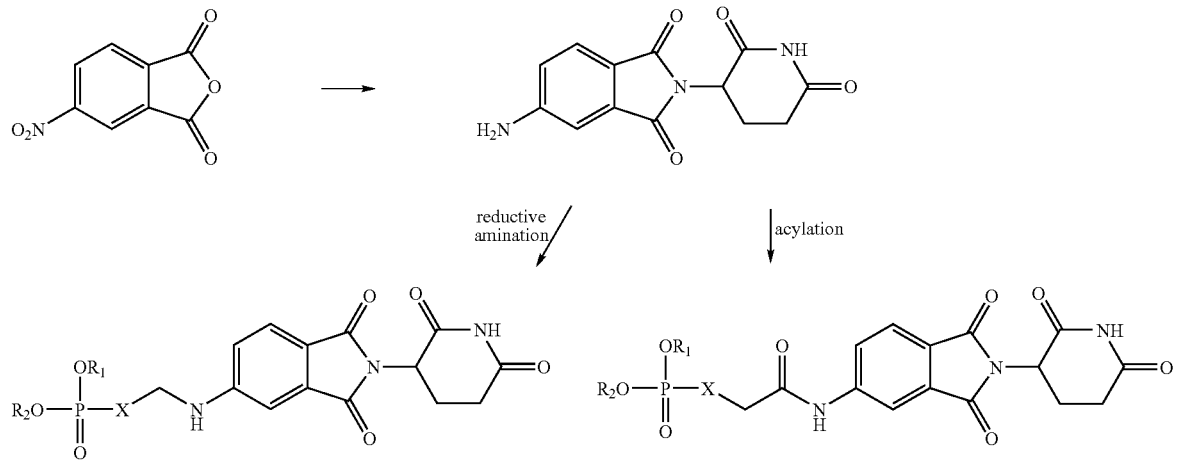

-continued

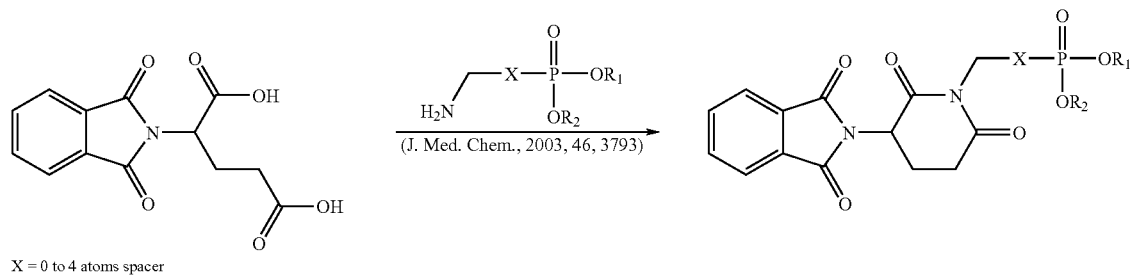

X = 0 to 4 atoms spacer

Representative compounds of the invention can be prepared as illustrated above. For example, specific compounds of Formula 99 and 100 can be prepared as follows.

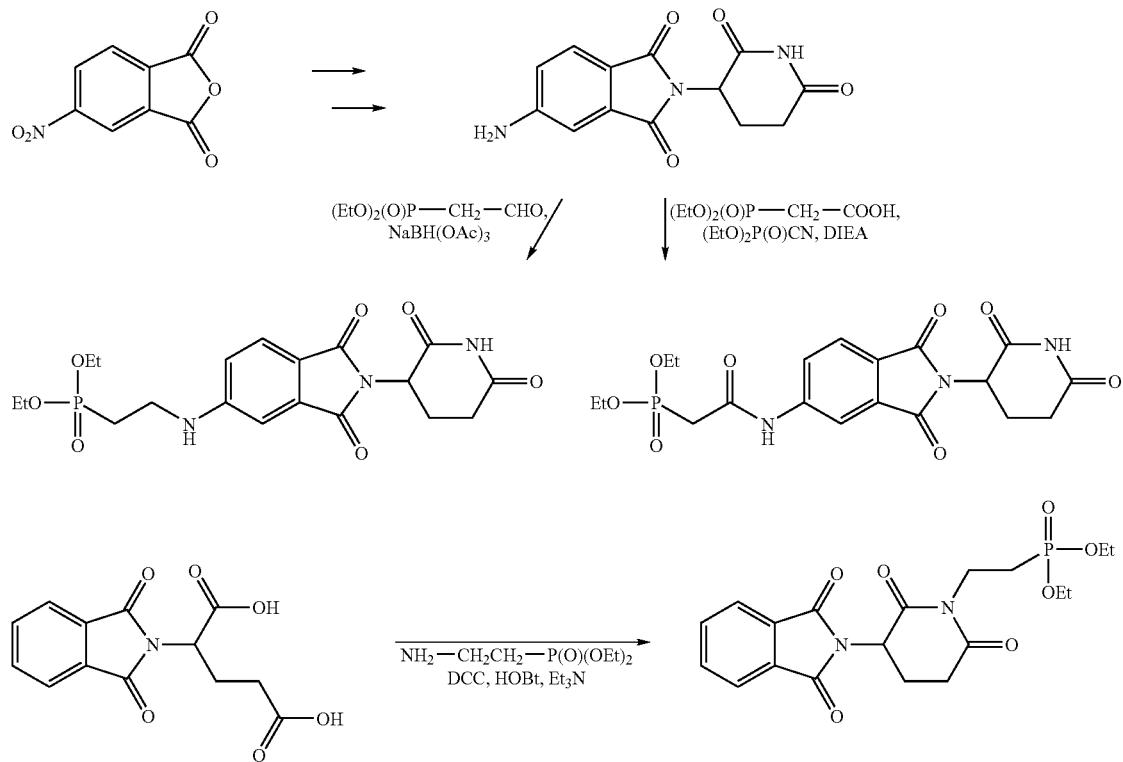

5-Nitro-isobenzofuran-1,3-dione (commercially available) is converted to 5-amino-2-(2,6-dioxo-piperidin-3-yl)-isoindole-1,3-dione following the procedures reported in *Bioorg. Med. Chem. Lett.*, 1999, 9, 1625. This amine intermediate is subjected to a reductive amination with diethylphosphonoacetaldehyde (obtained from ozonolysis of diethyl allyphosphonate) in the presence of a reducing agent such as sodium triacetoxyborohydride to generate the desired amine linker analog (*J. Org. Chem.*, 1996, 61, 3849). Alternatively, the amine is acylated with an activated diethylphosphonoacetic acid to provide the desired amide linker compound, according to a procedure such as those reported in *J. Med. Chem.*, 1982, 25, 960 and *J. Med. Chem.*, 1984, 27, 600. The activated diethylphosphonoacetic acid can be obtained by treatment in a solvent such as dimethylformamide with a coupling reagent such as diethyl cyanophosphonate and a base such as diisopropylethylamine at room temperature.

2-(1,3-Dioxo-1,3-dihydro-isoindol-2-yl)-pentanedioic acid (commercially available) is treated in a solvent such as acetonitrile with triethylamine, 1-hydroxybenzotriazole, 4-methoxybenzylamine, and 1,3-dicyclohexylcarbodiimide. After the reaction is complete, the solvent is removed and the residue is purified by chromatography to generate the desired analog, according to a procedure such as that reported in *J. Med. Chem.*, 2003, 46, 3793.

EXAMPLE 100
Preparation of Representative Compound of Formula 101
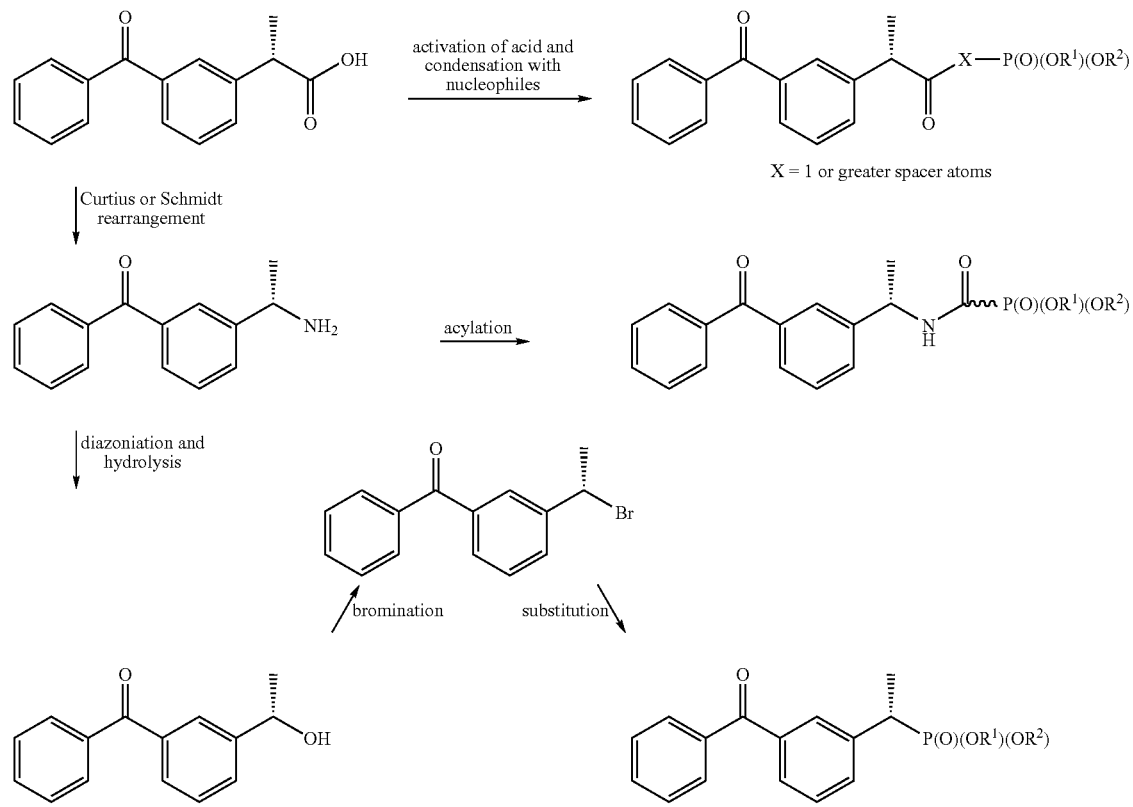
Representative compounds of the invention can be prepared as illustrated above. For example, specific compounds of Formula 101 can be prepared as follows.
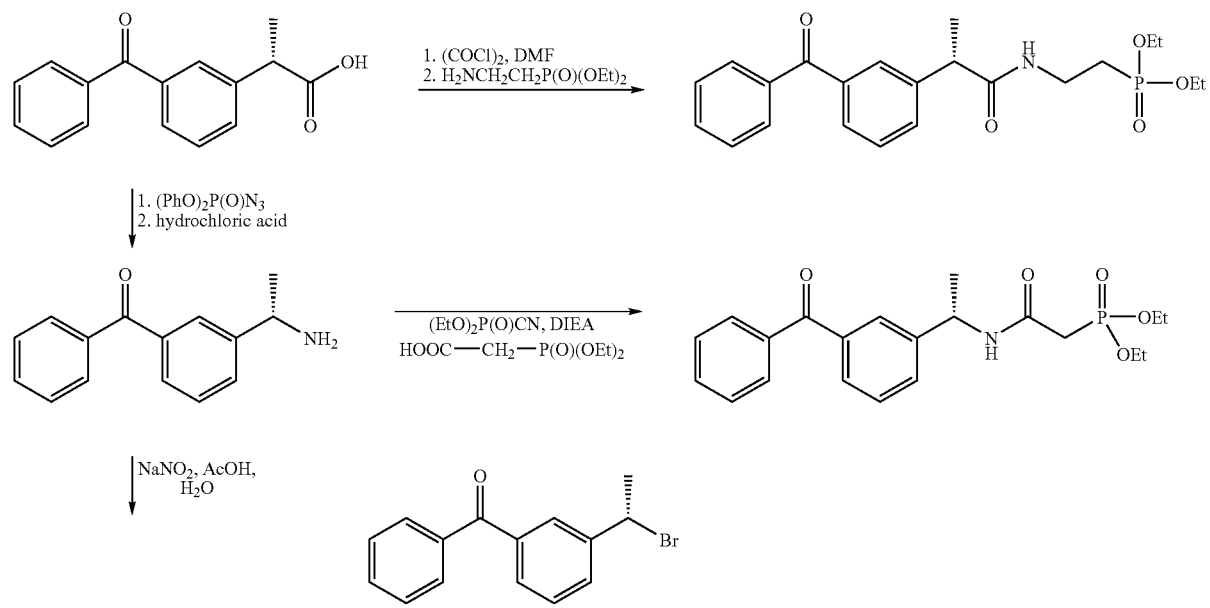

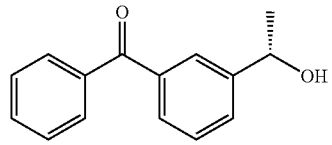 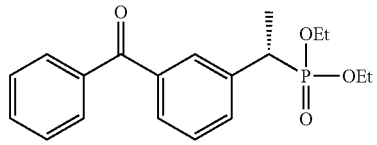

Dexketoprofen is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Dexketoprofen is treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.,* 2002, 67, 6260). The amine is then acylated with an activated diethylphosphonoacetic acid to provide the desired amide linker compound, according to a procedure such as those reported in *J. Med. Chem.,* 1982, 25, 960-964 and *J. Med. Chem.,* 1984, 27, 600-604. The activated diethylphosphonoacetic acid is obtained by treatment in a solvent such as dimethylformamide with a coupling reagent such as diethyl cyanophosphonate and a base such as diisopropylethylamine at room temperature.

The amine derived from dexketoprofen is converted to the alcohol, according to a procedure such as that reported in *J. Org. Chem.,* 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.,* 2002, 67, 7215. The bromide is treated in a solvent such as tetrahydrofuran with sodium salt of phosphonic acid diethyl ester to provide the desired phosphonate derivative of dexketoprofen, according to a procedure such as that reported in Tetrahedron, 1996, 52, 4411.

EXAMPLE 101

Preparation of Representative Compound of Formula 102

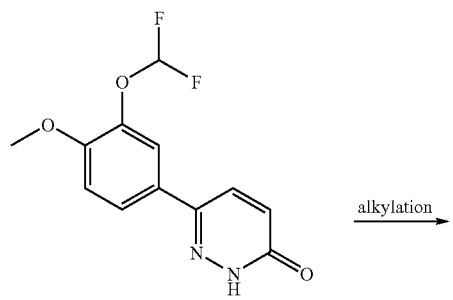

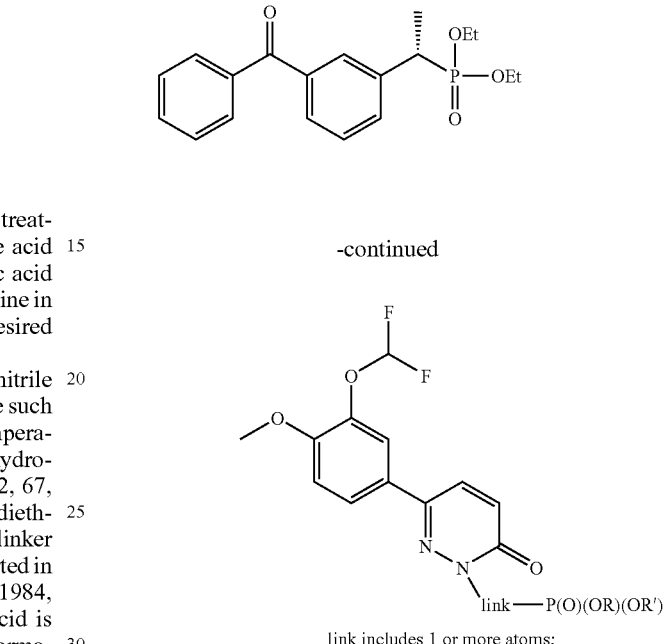

link includes 1 or more atoms;
2 or more is preferred

Representative compounds of the invention can be prepared as illustrated above. For example, a specific compound of Formula 102 can be prepared as follows.

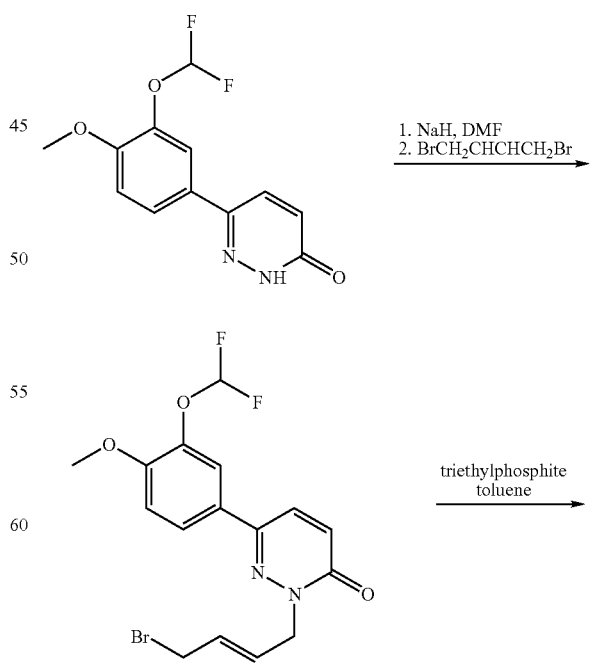

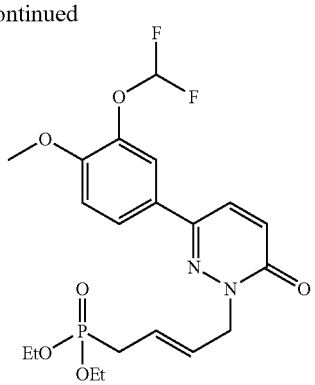

Zardaverine can be treated in a solvent such as DMF or THF with a base such as sodium hydride. When bubbling ceases, E-1,4-dibromobutene is added in excess. After quenching the reaction with aqueous ammonium chloride and extracting the product with an organic solvent such as ethyl acetate, the mono-alkylated product is isolated by chromatography. The allylic bromide is then heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid.

EXAMPLE 102

Preparation of Representative Compounds of Formula 102

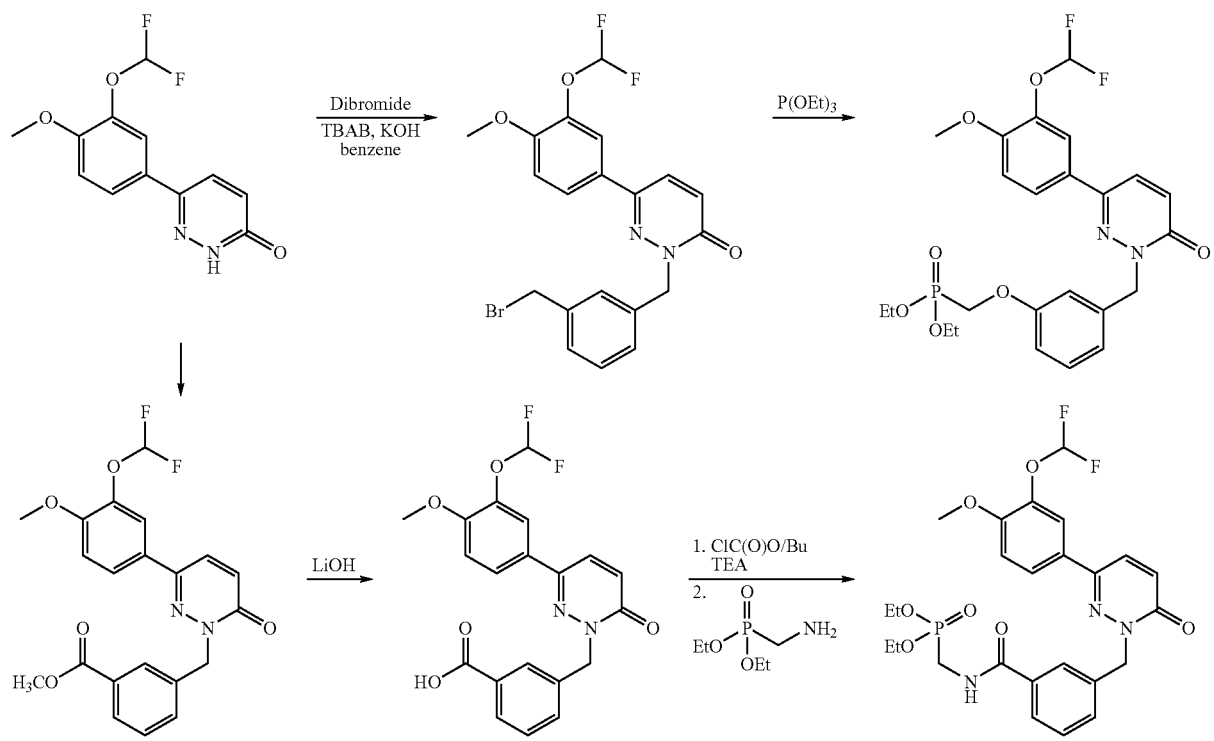

Other specific compounds of Formula 102 can be prepared as illustrated above.

EXAMPLE 103

Preparation of Representative Compounds of Formula 103

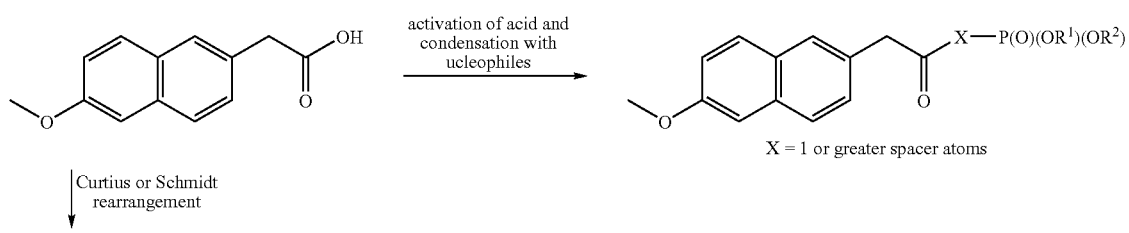

$X = 1$ or greater spacer atoms

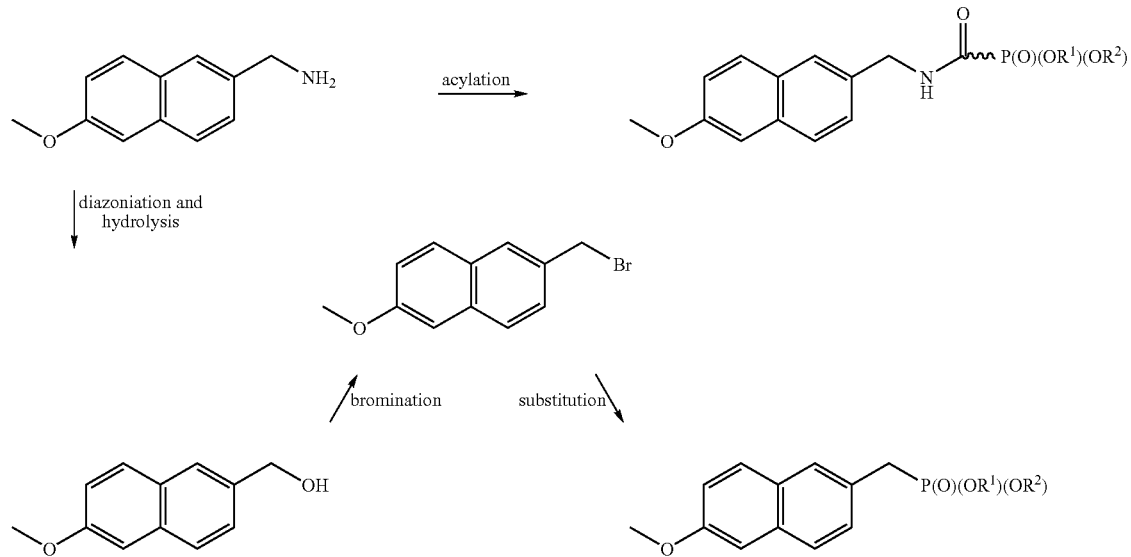
Representative compounds of the invention can be prepared as illustrated above. For example, specific compounds of Formula 103 can be prepared as follows.
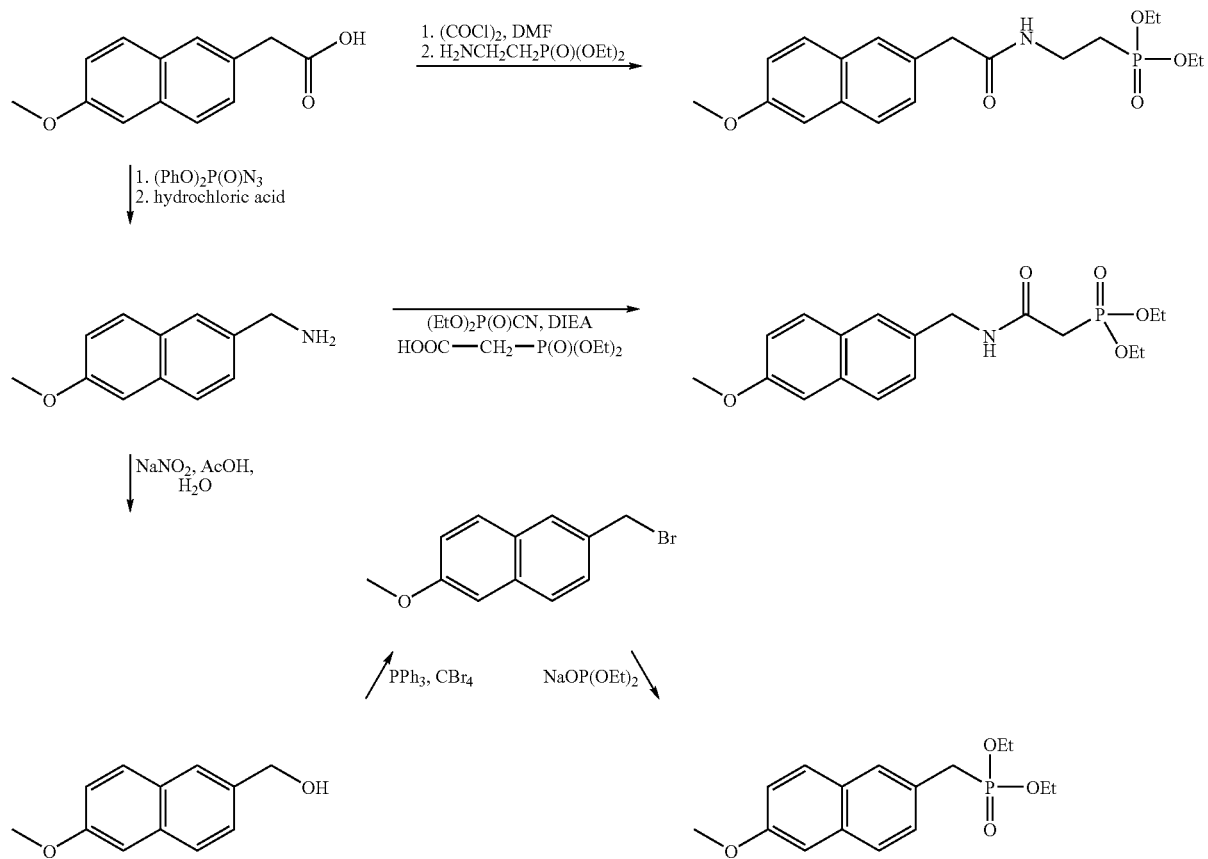

6-Methoxy-2-naphthylacetic acid, a major active metabolite of nabumetone (commercially available), can be converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

6-Methoxy-2-naphthylacetic acid can be treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.*, 2002, 67, 6260). The amine is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid can be obtained by treatment in a solvent such as dimethylformamide with a coupling reagent such as diethyl cyanophosphonate and a base such as diisopropylethylamine at room temperature.

The amine derived from 6-methoxy-2-naphthylacetic acid can be converted to the alcohol, according to a procedure such as that reported in *J. Org. Chem.*, 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.*, 2002, 67, 7215. The bromide is treated in a solvent such as tetrahydrofuran with sodium salt of phosphonic acid diethyl ester to provide the desired phosphonate derivative of nabumetone, according to a procedure such as that reported in *Tetrahedron*, 1996, 52, 4411.

EXAMPLE 104

Preparation of Representative Compounds of Formula 104

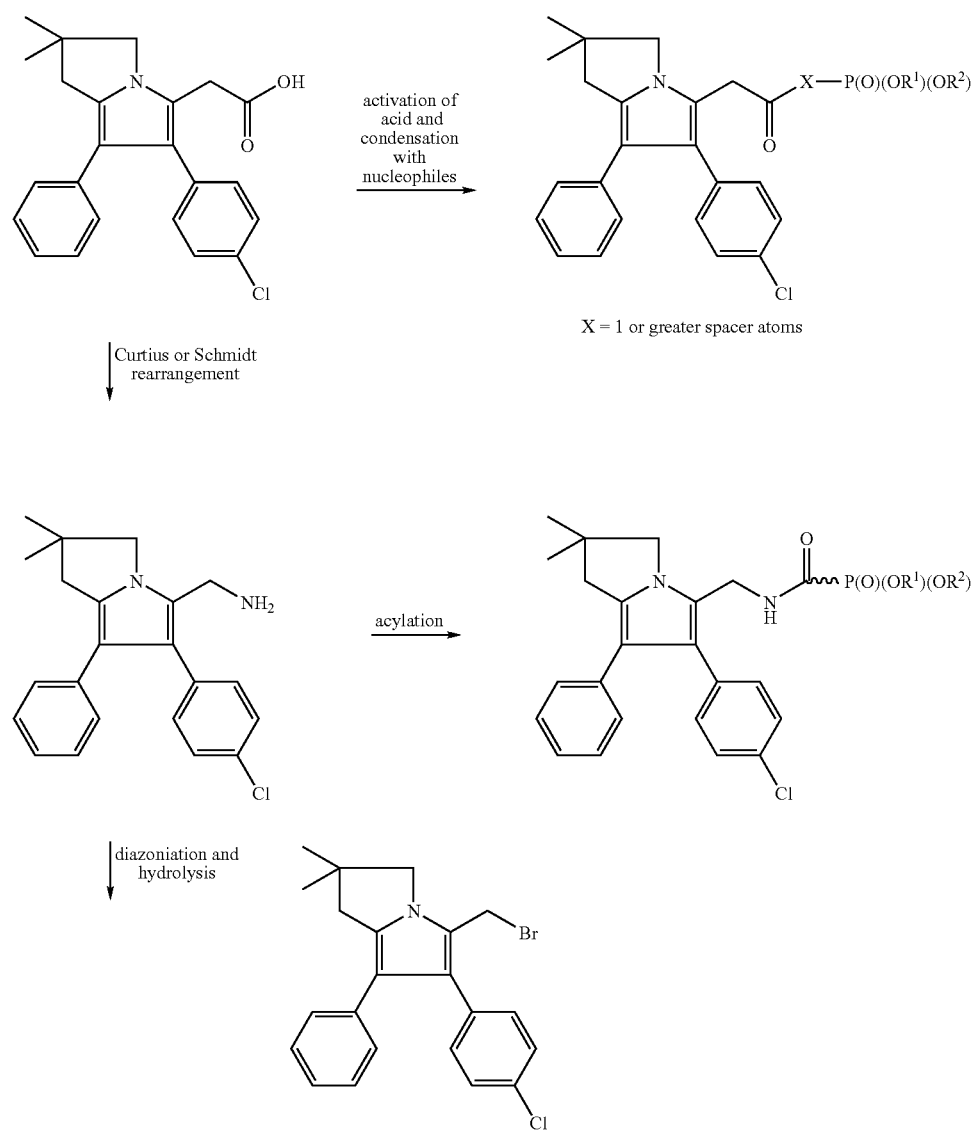

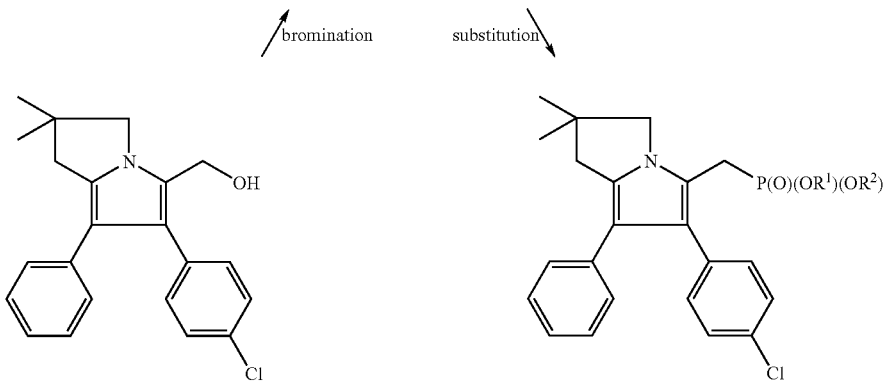
Representative compounds of the invention can be prepared as illustrated above. For example, specific compounds of Formula 104 can be prepared as follows.
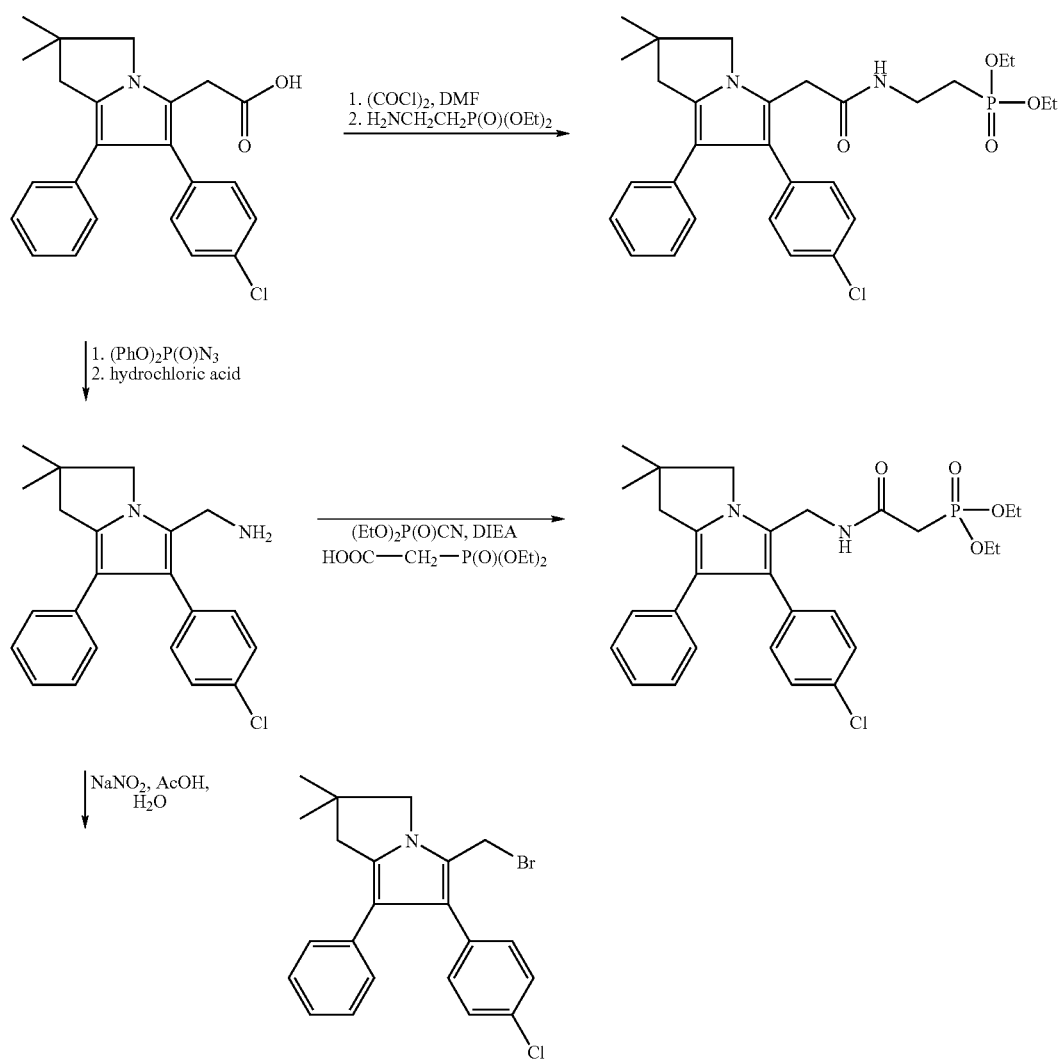

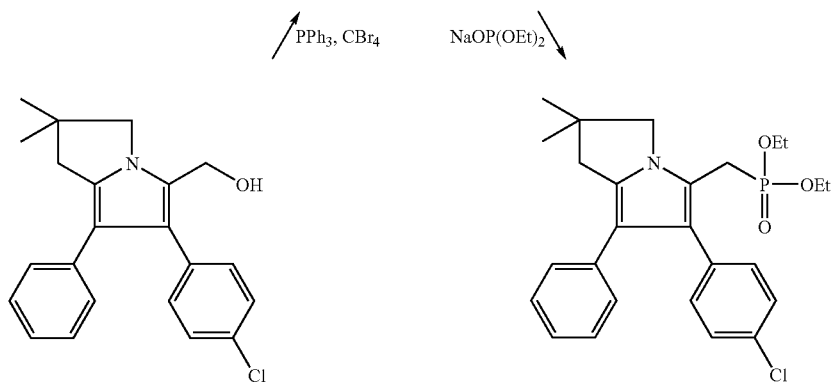

Licofelone is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Licofelone is treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.*, 2002, 67, 6260). The amine is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid can be obtained by treatment in a solvent such as dimethylformamide with a coupling reagent such as diethyl cyanophosphonate and a base such as diisopropylethylamine at room temperature.

The amine derived from licofelone can be converted to the alcohol, according to a procedure such as that reported in *J. Org. Chem.*, 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.*, 2002, 67, 7215. The bromide is treated in a solvent such as tetrahydrofuran with sodium salt of phosphonic acid diethyl ester to provide the desired phosphonate derivative of licofelone, according to a procedure such as that reported in *Tetrahedron*, 1996, 52, 4411.

EXAMPLE 105

Preparation of Representative Compounds of Formula 105

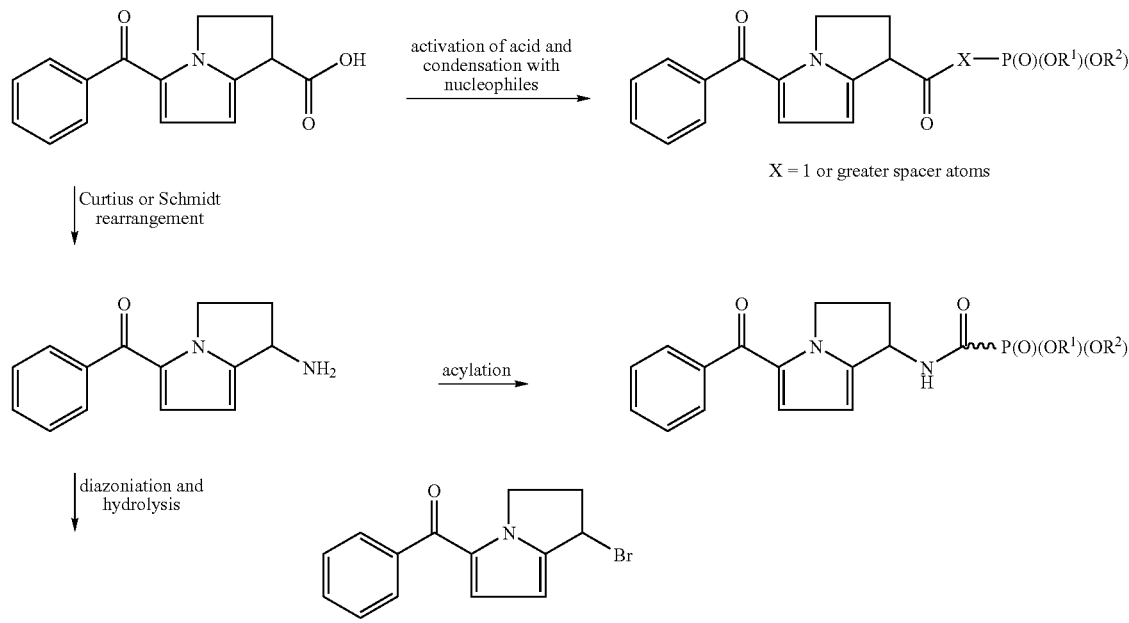

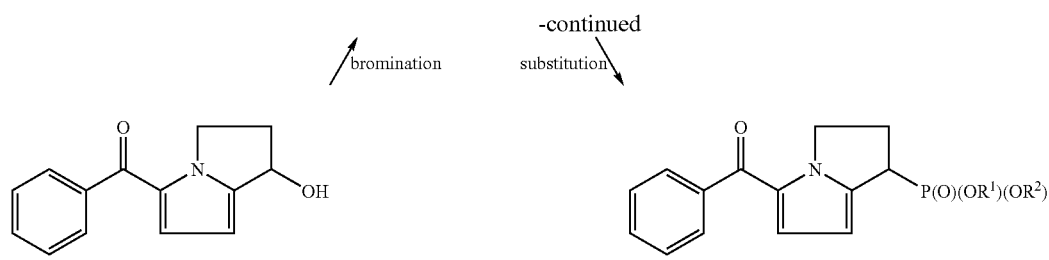

Representative compounds of the invention can be prepared as illustrated above. For example, specific compounds of Formula 105 can be prepared as follows.

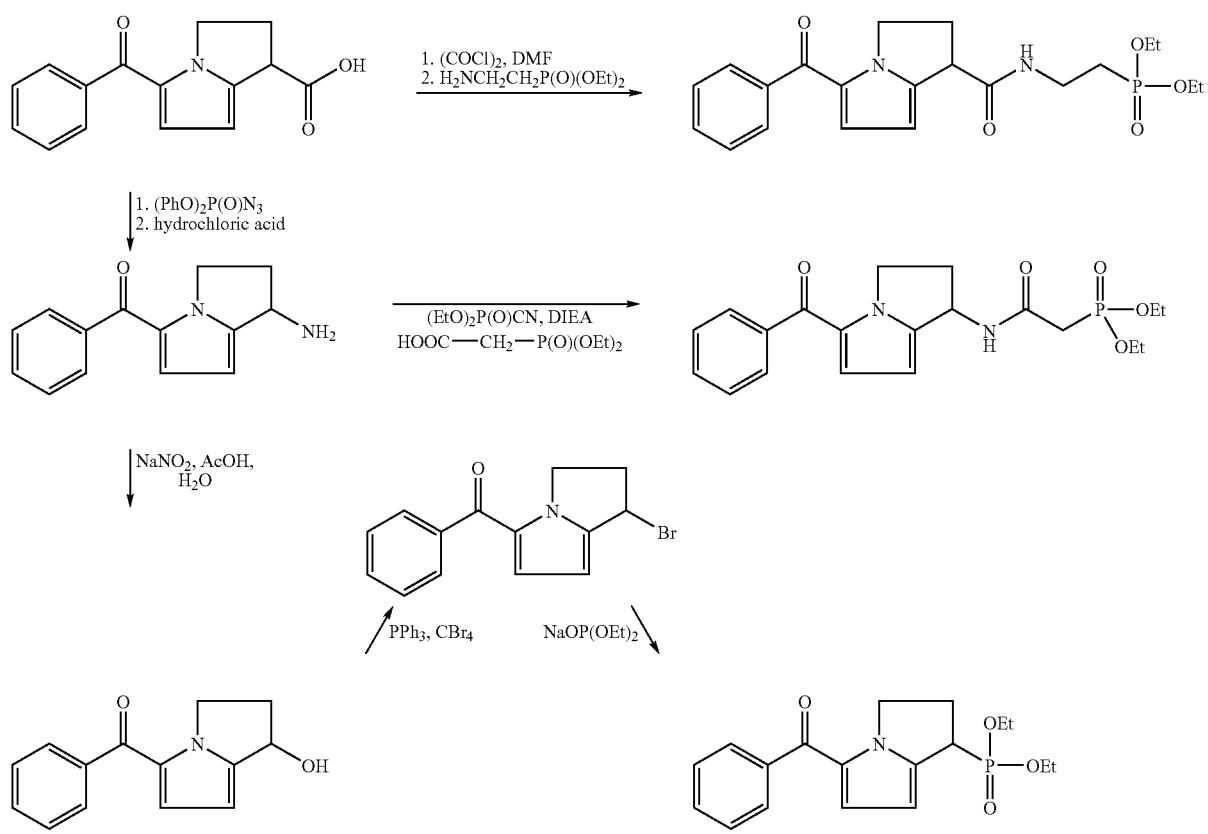

Ketorolac is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Ketorolac is treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.*, 2002, 67, 6260). The amine is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid can be obtained by treatment in a solvent such as dimethylformamide with a coupling reagent such as diethyl cyanophosphonate and a base such as diisopropylethylamine at room temperature.

The amine derived from ketorolac can be converted to the alcohol, according to a procedure such as that reported in *J. Org. Chem.*, 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.*, 2002, 67, 7215. The bromide is treated in a solvent such as tetrahydrofuran with sodium salt of phosphonic acid diethyl ester to provide the desired phosphonate derivative of ketorolac, according to a procedure such as that reported in *Tetrahedron,* 1996, 52, 4411.

EXAMPLE 106

Preparation of Representative Compounds of Formula 106

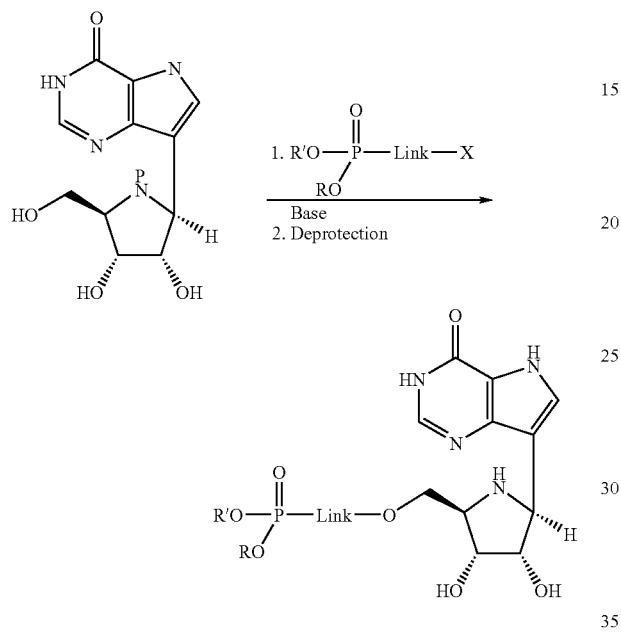

Representative compounds of the invention can be prepared as illustrated above. For example, a specific compound of Formula 106 can be prepared as follows.

The Boc-protected (1S)-1-(9-deazaguanin-9-yl)-1,4-dideoxy-1,4-imino-D-ribitol, compound 106.1, is prepared by stirring the (1S)-1-(9-deazaguanin-9-yl)-1,4-dideoxy-1,4-imino-D-ribitol (WO 9,919,338 and Evans, G. B. et al., *Tetrahedron,* 2000, 56, 3053, also reported in Evans, G. B. et al., *J. Med. Chem.* 2003, 46, 3412) with BOC anhydride as described in Greene, T., Protective groups in organic synthesis, Wiley-Interscience, 1999. Compound 106.1 is then treated in a solvent such as tetrahydrofuran or dimethylformamide with a base such as sodium hydride. When bubbling ceases, diethyl phosphonomethyltriflate (prepared according to *Tetrahedron Lett.,* 1986, 27, 1477) is added, yielding the desired phosphonate diester 106.2 after deprotection of the BOC group using trifluoroacetic acid (TFA).

EXAMPLE 107

Preparation of Representative Compounds of Formula 107

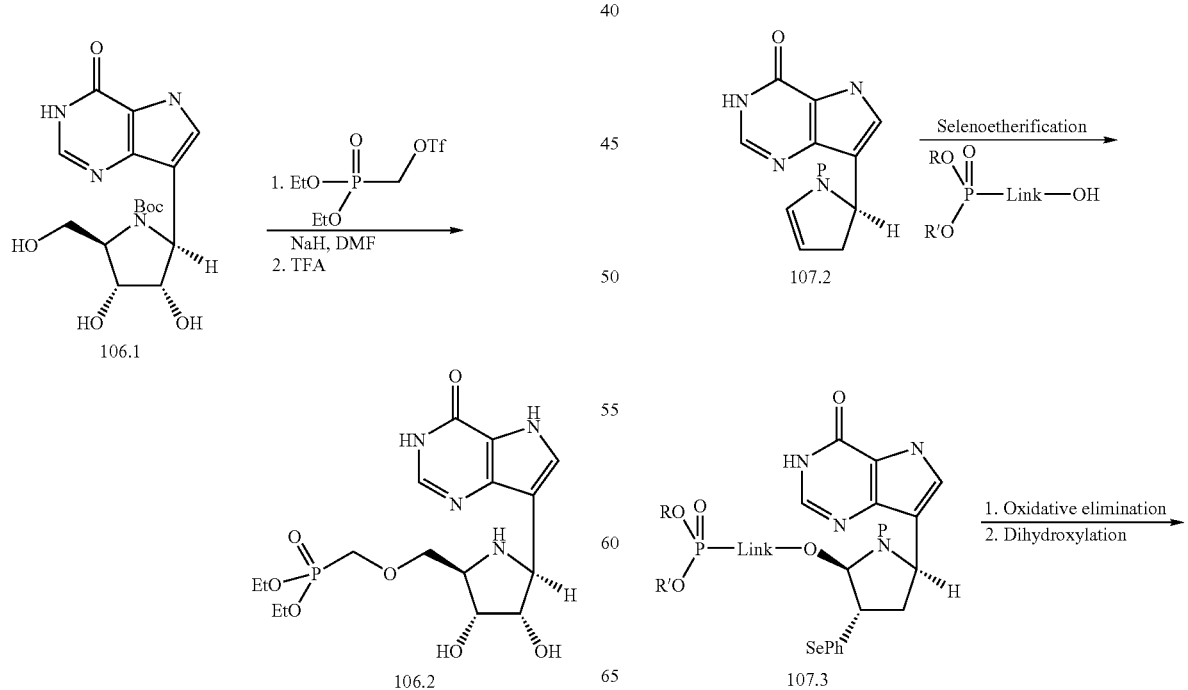

-continued

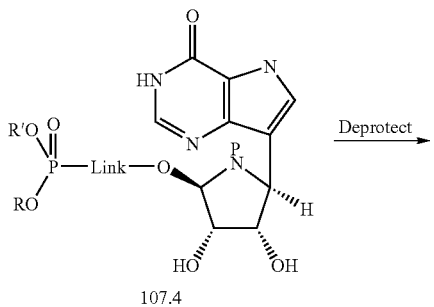
107.4

Deprotect →

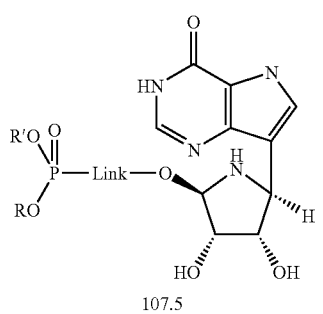
107.5

Representative compounds of the invention can be prepared as illustrated above. Deprotected compound 107.1 ((1R)-1-(9-deazahypoxanthin-9-yl)-1,2,4-trideoxy-1,4-imino-D-erythro-pentitol, as the hydrochloride salt) is prepared as described in Evans, G. B. et al., *Tetrahedron*, 2000, 56, 3053, using di-t-butyl dicarbonate in dichloromethane. Oxidation of the 5'-OH followed by elimination provides glycal 107.2 (see the procedure of Zemlicka J. et al., *J. Am. Chem. Soc.*, 1972, 94, 9, 3213). Selenoetherification provides the protected phosphonate 107.3 (Kim, C. et al., *J. Org. Chem.*, 1991, 56, 2642). Oxidative elimination of the phenylselenide (as described in Kim, C. et al., *J. Org. Chem.*, 1991, 56, 2642) followed by stereoselective dihydroxylation provides the desired diol 107.4. Finally, the protecting group is removed to provide compound 107.5.

A specific compound of Formula 107 can be prepared as follows.

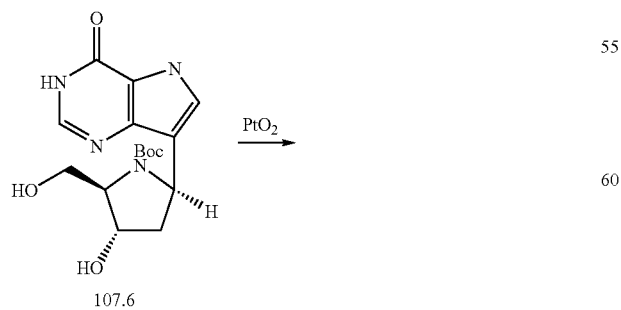
107.6

PtO₂ →

-continued

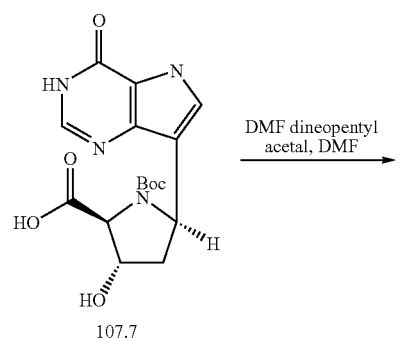
107.7

DMF dineopentyl acetal, DMF →

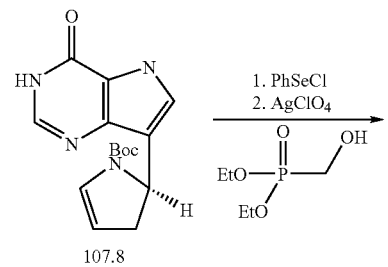
107.8

1. PhSeCl
2. AgClO₄
→

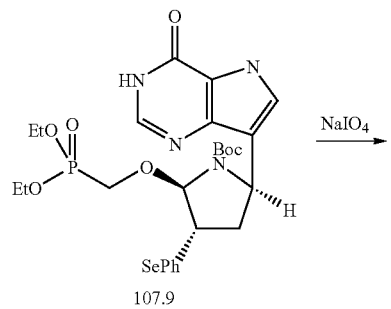
107.9

NaIO₄ →

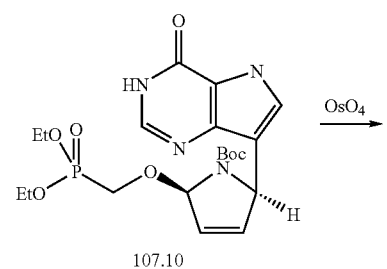
107.10

OsO₄ →

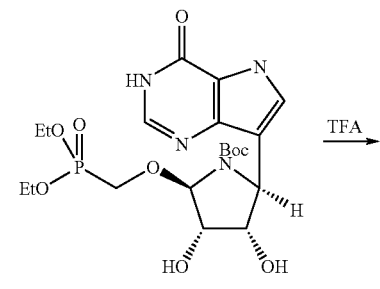
107.11

TFA →

-continued

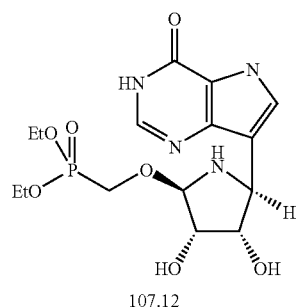

107.12

Specifically, (1R)-1-(9-deazahypoxanthin-9-yl)-1,2,4-trideoxy-1,4-imino-D-erythro-pentitol, prepared as the HCl salt as described in Evans, G. B. et al., *Tetrahedron*, 2000, 56, 3053, is first protected and then oxidized with $PtO_2$ to provide carboxylic acid 107.7. Decarboxylative elimination is achieved using dimethylformamide dineopentyl acetal in dimethylformamide at high temperature (Zemlicka J. et al., *J. Am. Chem. Soc.*, 1972, 94, 9, 3213). Selenoetherification followed by treatment of the protected glycal with silver perchlorate in the presence of diethyl(hydroxylmethyl)phosphonate (Phillion, D. et al., Tetrahedron Lett., 1986, 27, 1477) provides the phosphonate 107.9 (Kim, C. et al., *J. Org. Chem.*, 1991, 56, 2642). Oxidative elimination of the selenide followed by dihydroxylation using osmium tetraoxide provides diol 107.11. Removal of the amine protecting group, according to the procedure of Greene, T., Protective groups in organic synthesis, Wiley-Interscience, 1999, provides compound 107.12.

EXAMPLE 108

Preparation of Representative Compounds of Formula 108

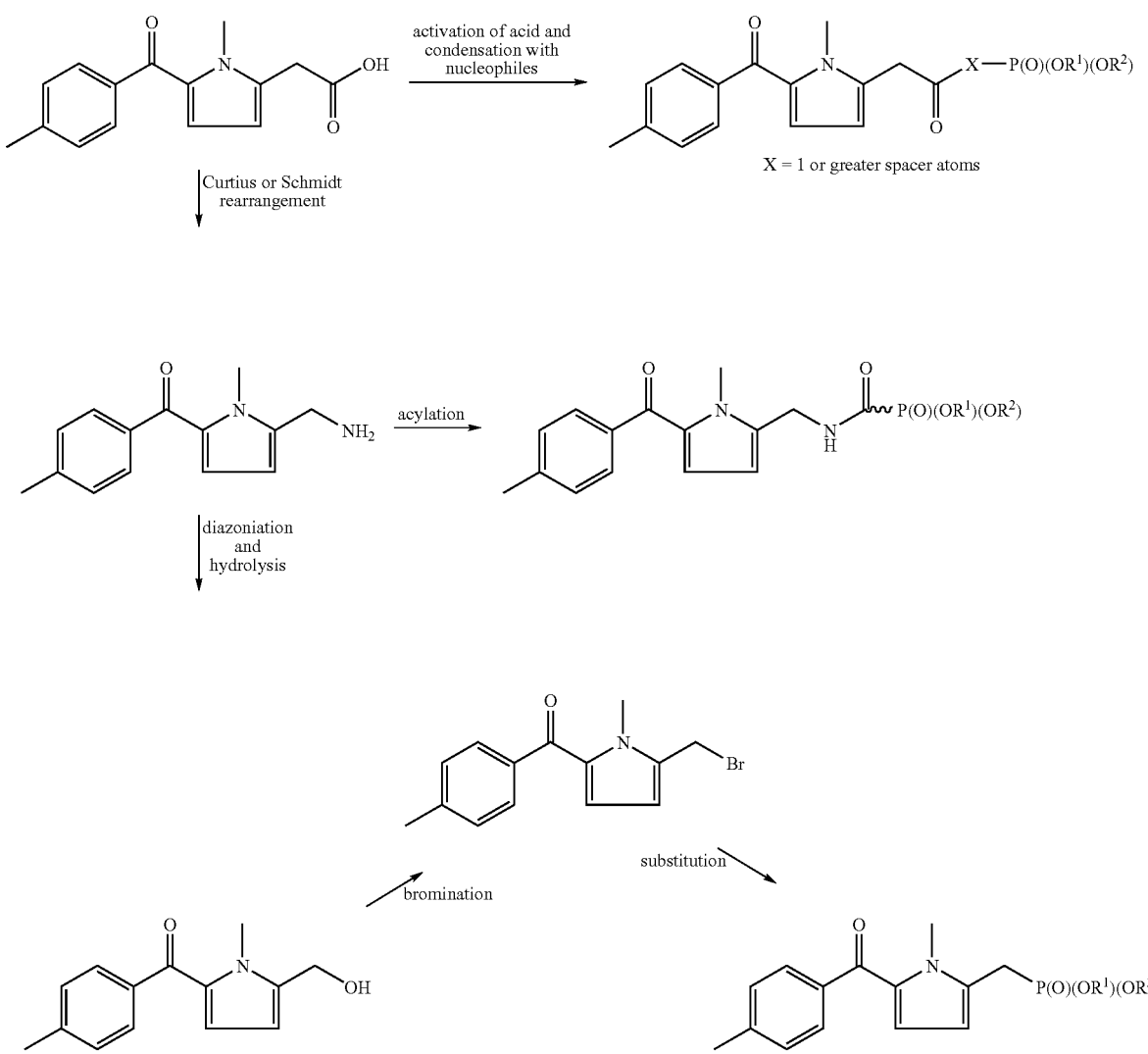

Representative compounds of the invention can be prepared as illustrated above. For example, specific compounds of Formula 108 can be prepared as follows.

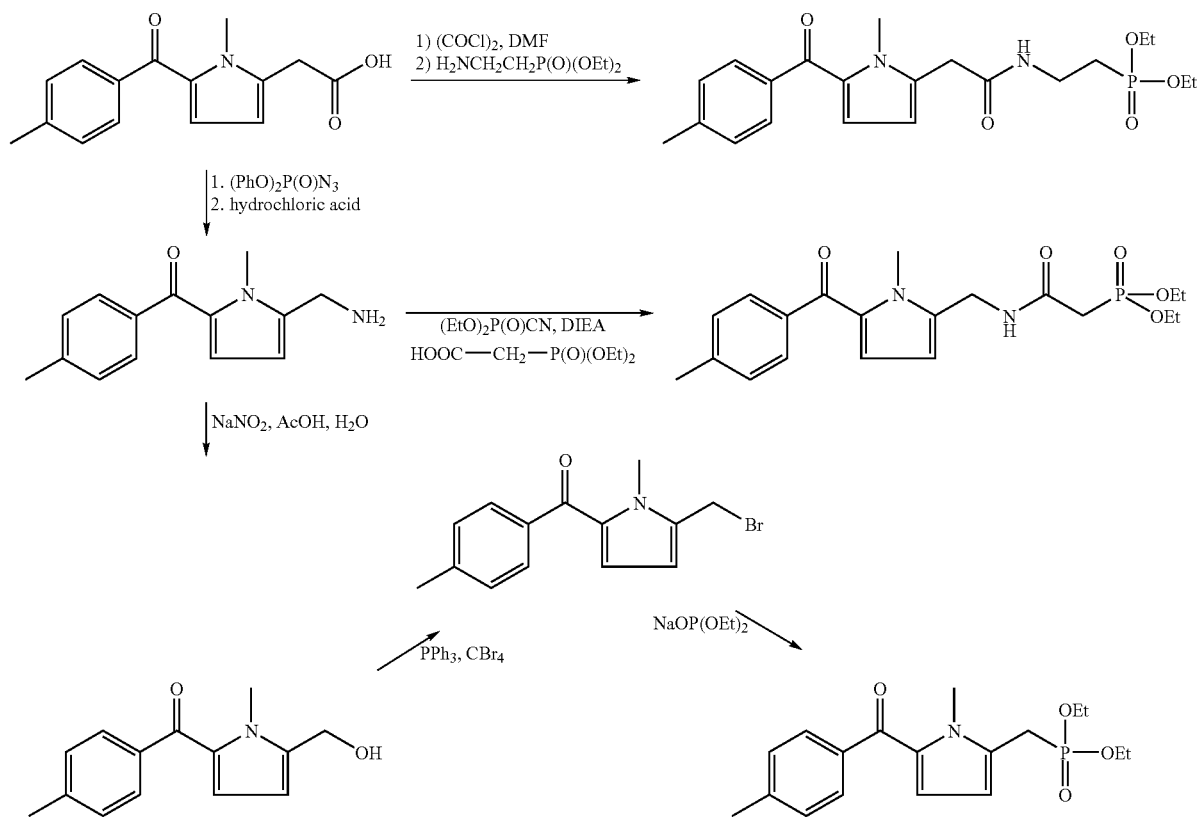

Tolmetine, an active metabolite of amtolmetine guacil, is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Tolmetine is treated in a solvent such as acetonitrile with diphenylphosphoryl azide in the presence of a base such as triethylamine at room temperature or up to reflux temperature. After cooling, the mixture is treated with diluted hydrochloric acid to provide the amine (J. Org. Chem., 2002, 67, 6260). The amine is then acylated with an activated diethylphosphonoacetic acid to provide the desired amide linker compound, according to a procedure such as those reported in J. Med. Chem., 1982, 25, 960-964 and J. Med. Chem., 1984, 27, 600-604. The activated diethylphosphonoacetic acid is obtained by treatment in a solvent such as dimethylformamide with a coupling reagent such as diethyl cyanophosphonate and a base such as diisopropylethylamine at room temperature.

The amine derived from tolmetine is converted to the alcohol according to the procedure reported in J. Org. Chem., 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in J. Org. Chem., 2002, 67, 7215. The bromide is treated in a solvent such as tetrahydrofuran with sodium salt of phosphonic acid diethyl ester to provide the desired phosphonate derivative of amtolmetine guacil, according to a procedure such as that reported in Tetrahedron, 1996, 52, 4411.

EXAMPLE 109

Preparation of Representative Compounds of Formula 109

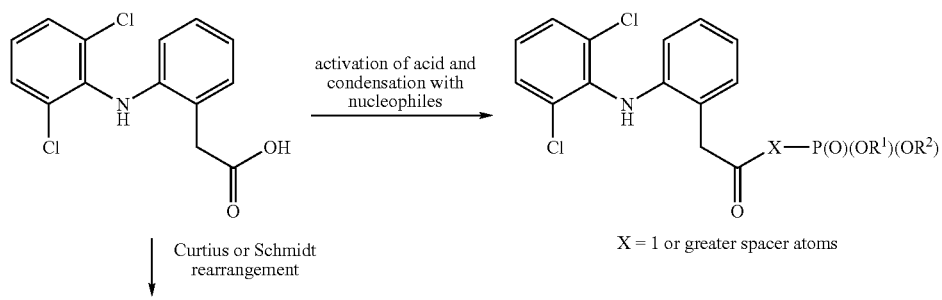

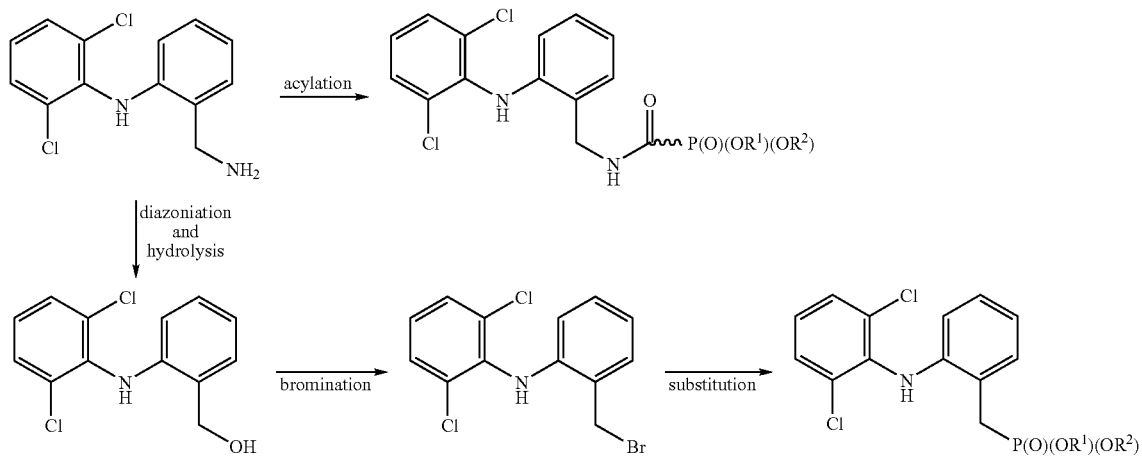

Representative compounds of the invention can be prepared as illustrated above. For example, specific compounds of Formula 109 can be prepared as follows.

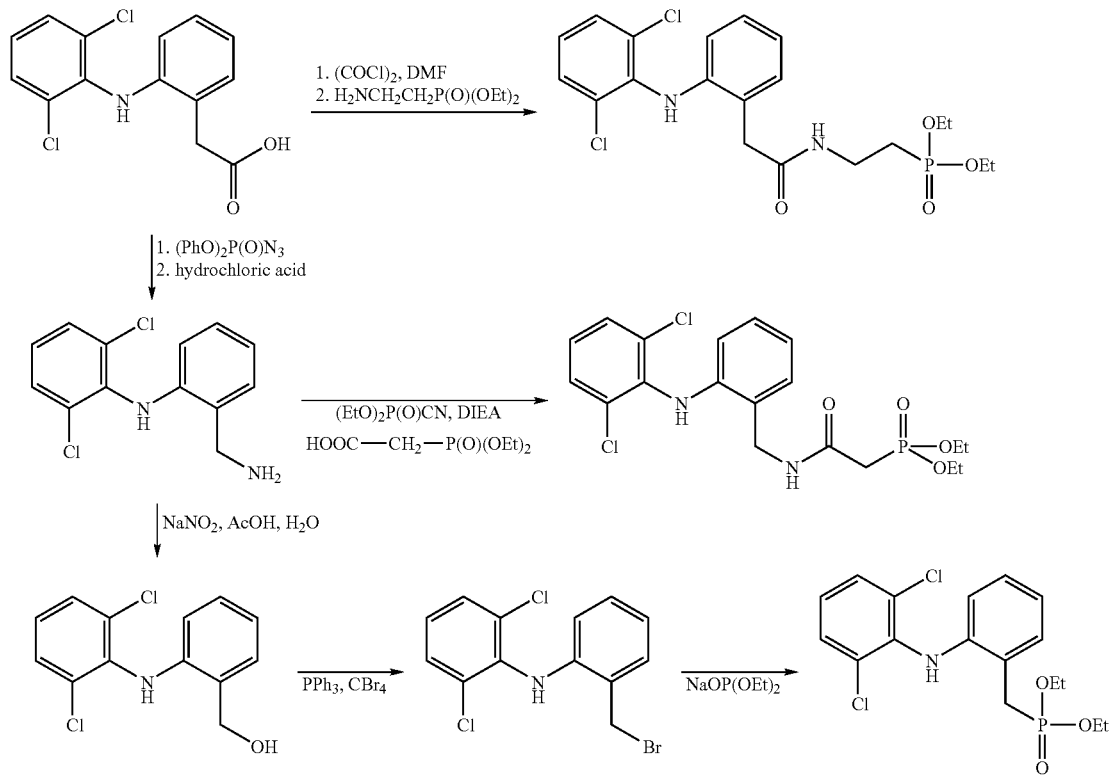

Diclofenac, a metabolite and a synthetic precursor of aceclofenac, can be converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired compound.

Diclofenac can be treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.*, 2002, 67, 6260). The amine is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid can be obtained by treatment in a solvent such as dimethylformamide with a coupling reagent such as diethyl cyanophosphonate and a base such as diisopropylethylamine at room temperature.

The amine derived from diclofenac can be converted to the alcohol, according to a procedure such as that reported in *J. Org. Chem.*, 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.*, 2002, 67, 7215. The bromide is treated in a solvent such as tetrahydrofuran with sodium salt of phosphonic acid diethyl ester to provide the desired phosphonate derivative of aceclofenac, according to a procedure such as that reported in *Tetrahedron*, 1996, 52, 4411.

EXAMPLE 110

Preparation of Representative Compounds of Formula 110

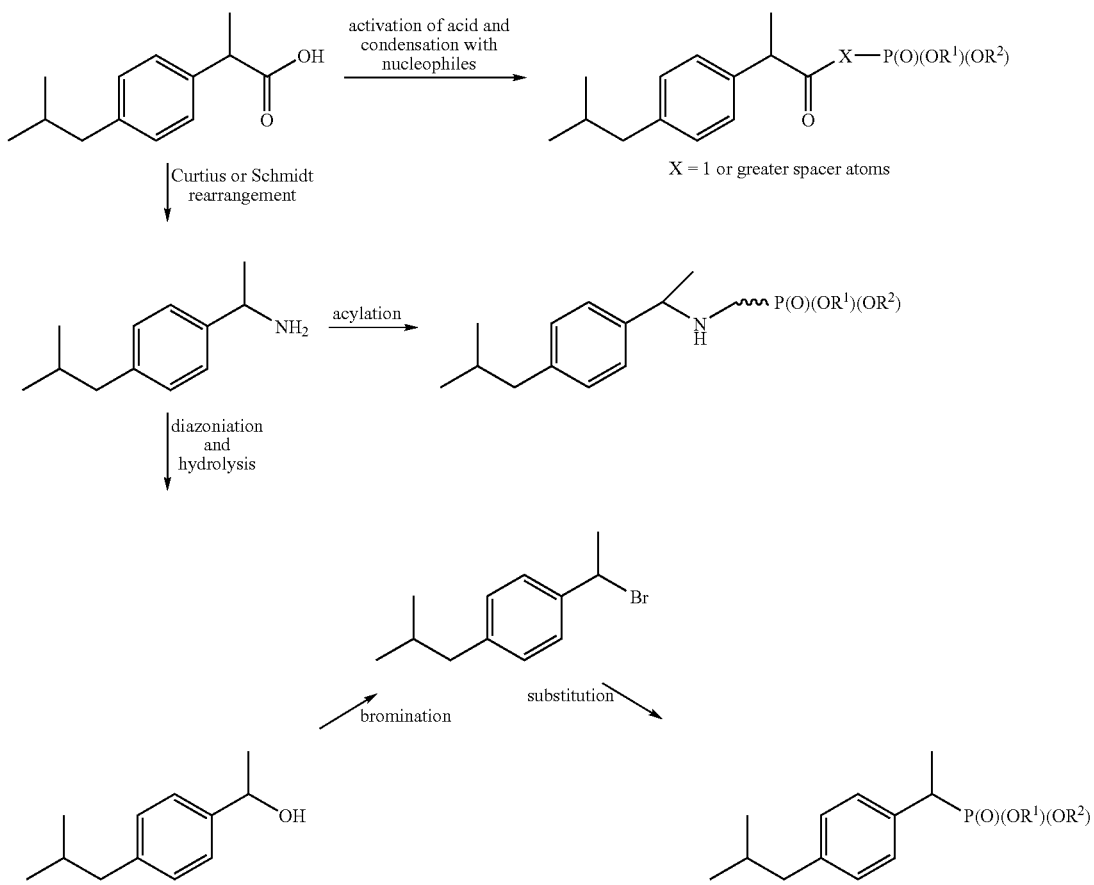

Representative compounds of the invention can be prepared as illustrated above. For example, specific compounds of Formula 110 can be prepared as follows.

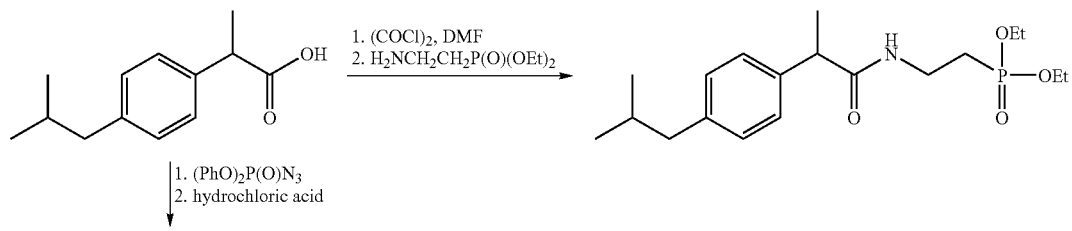

-continued

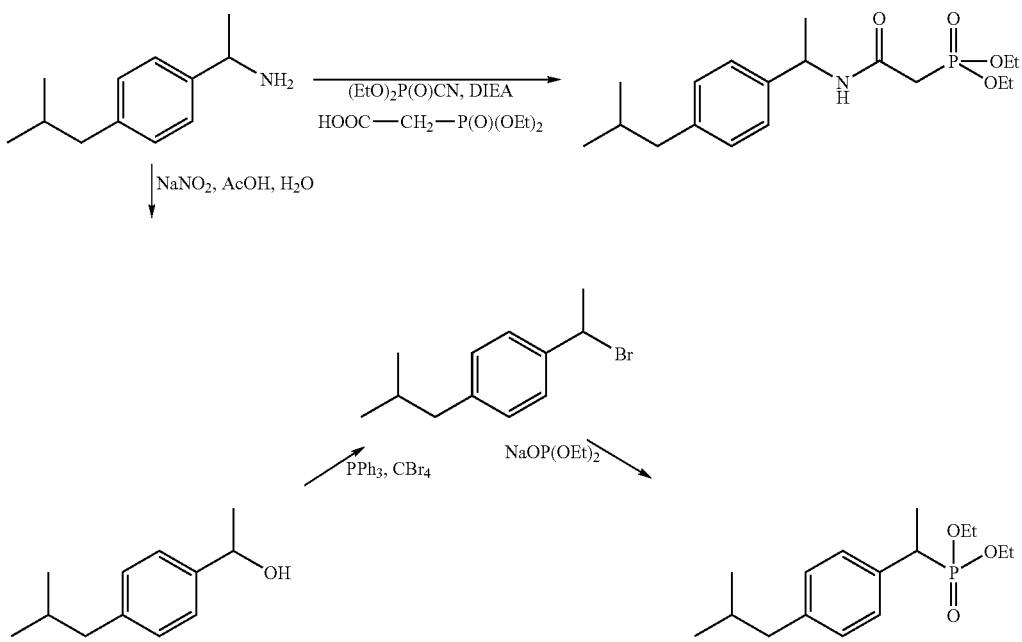

Ibuprofen, an active metabolite of metoxibutropate, can be converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Ibuprofen can be treated in a solvent such as acetonitrile with diphenylphosphoryl azide in the presence of a base such as triethylamine at room temperature or up to reflux temperature. After cooling, the mixture is treated with diluted hydrochloric acid to provide the amine (J. Org. Chem., 2002, 67, 6260). The amine is then acylated with an activated diethylphosphonoacetic acid to provide the desired amide linker compound, according to a procedure such as those reported in J. Med. Chem., 1982, 25, 960-964 and J. Med. Chem., 1984, 27, 600-604. The activated diethylphosphonoacetic acid can be obtained by treatment in a solvent such as dimethylformamide with a coupling reagent such as diethyl cyanophosphonate and a base such as diisopropylethylamine at room temperature.

The amine derived from ibuprofen can be converted to the alcohol, according to a procedure such as that reported in J. Org. Chem., 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in J. Org. Chem., 2002, 67, 7215. The bromide is treated in a solvent such as tetrahydrofuran with sodium salt of phosphonic acid diethyl ester to provide the desired phosphonate derivative of metoxibutropate, according to a procedure such as that reported in Tetrahedron, 1996, 52, 4411.

EXAMPLE 111

Preparation of Representative Compounds of Formula 111

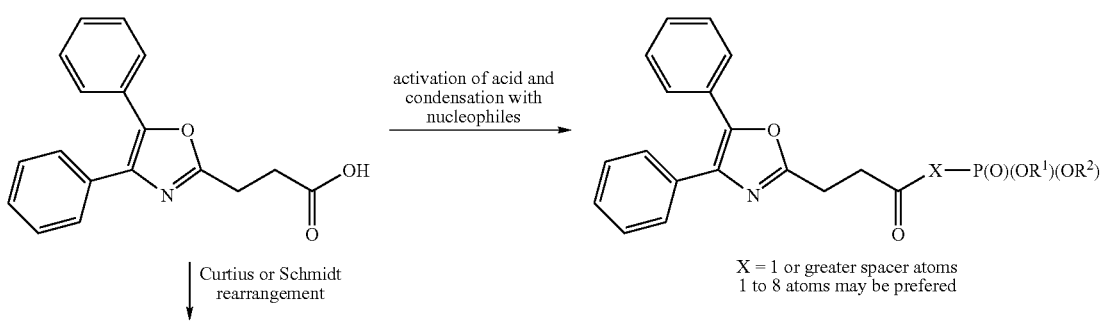

X = 1 or greater spacer atoms
1 to 8 atoms may be prefered

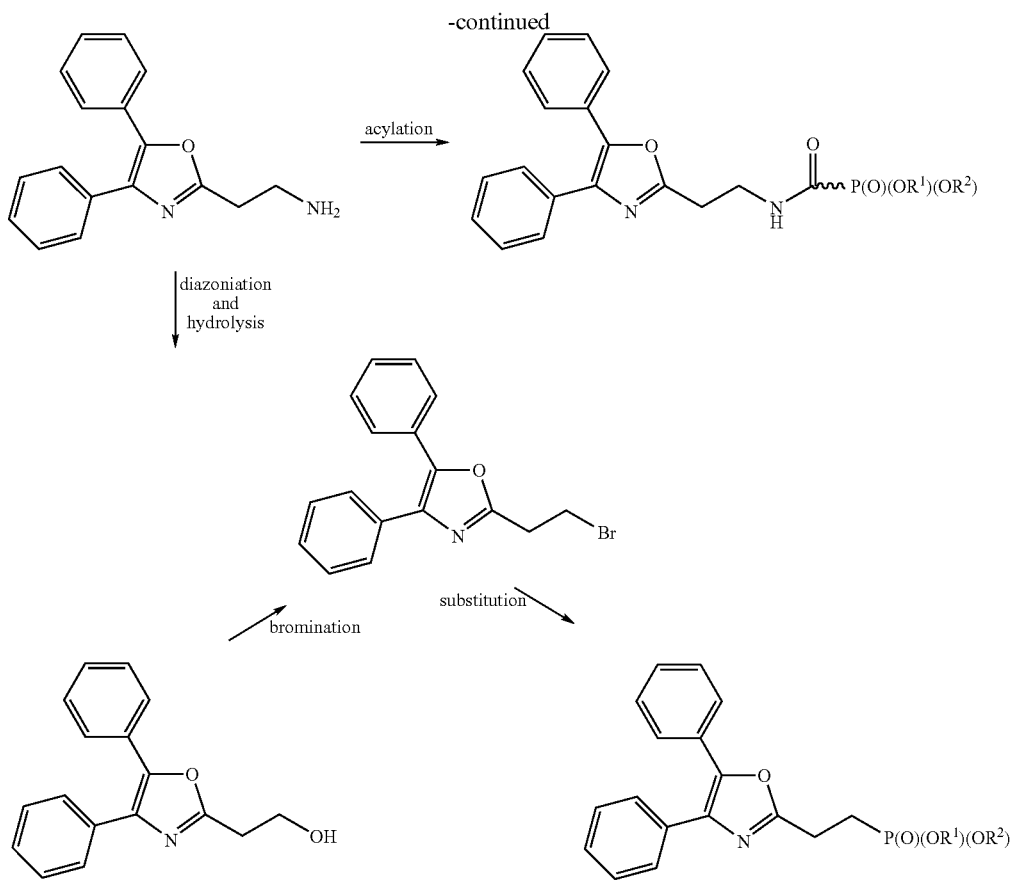
Representative compounds of the invention can be prepared as illustrated above. For example, specific compounds of Formula III can be prepared as follows.
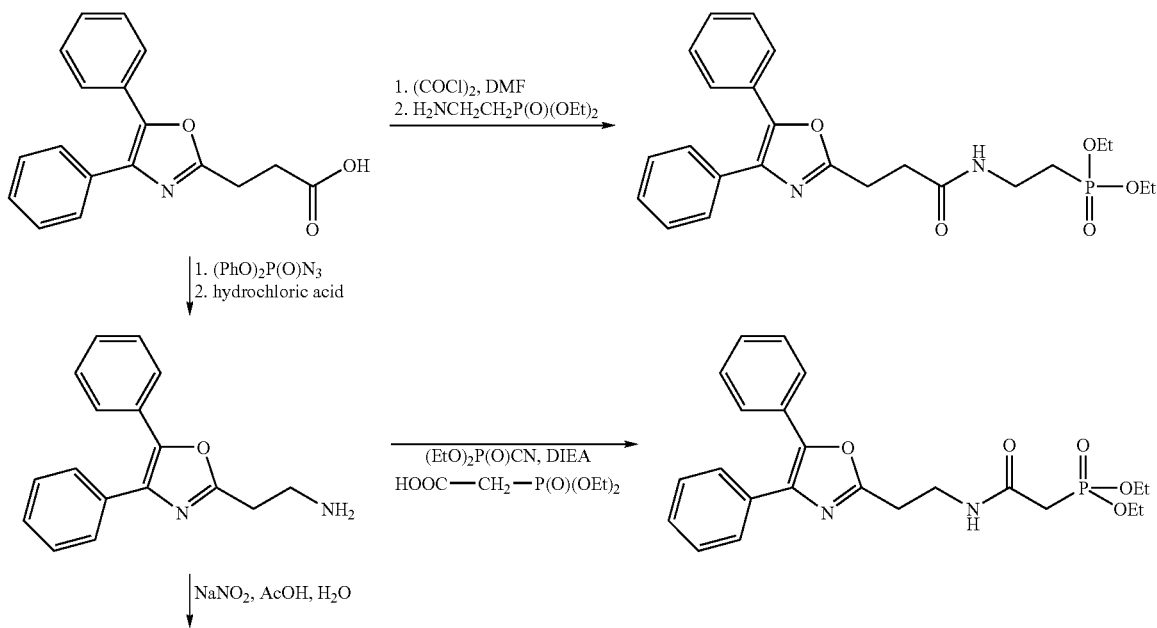

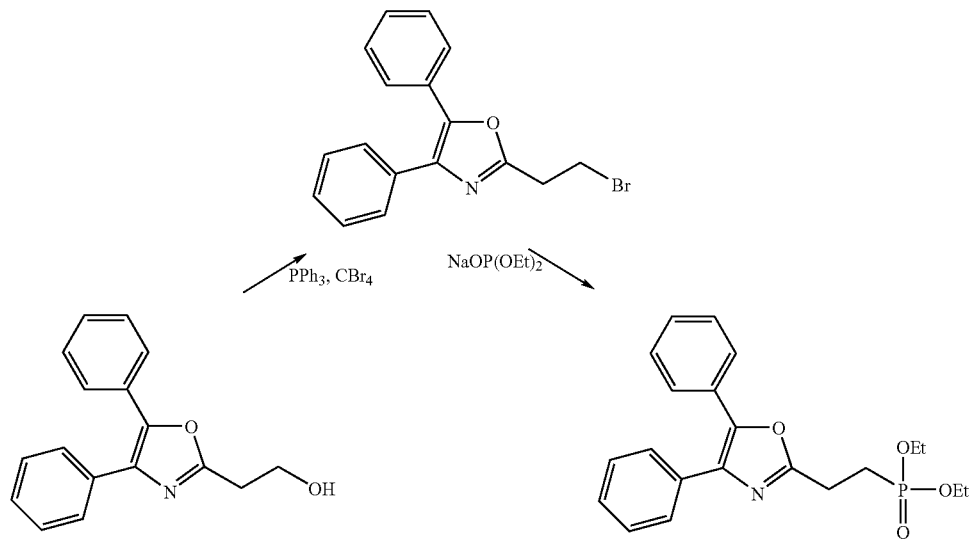

Oxaprozin can be converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Oxaprozin can be treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.*, 2002, 67, 6260). The amine is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid can be obtained by treatment in a solvent such as dimethylformamide with a coupling reagent such as diethyl cyanophosphonate and a base such as diisopropylethylamine at room temperature.

The amine derived from oxaprozin can be converted to the alcohol, according to a procedure such as that reported in *J. Org. Chem.*, 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.*, 2002, 67, 7215. The bromide is treated in a solvent such as tetrahydrofuran with sodium salt of phosphonic acid diethyl ester to provide the desired phosphonate derivative of oxaprozin, according to a procedure such as that reported in *Tetrahedron*, 1996, 52, 4411.

EXAMPLE 112

Preparation of Representative Compounds of Formula 112

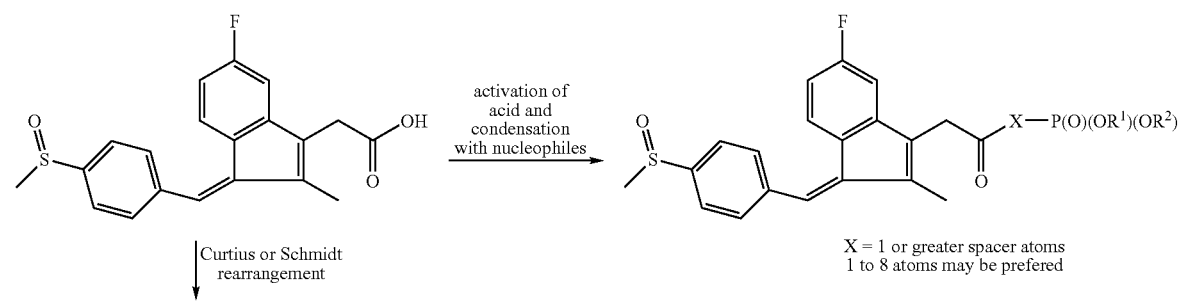

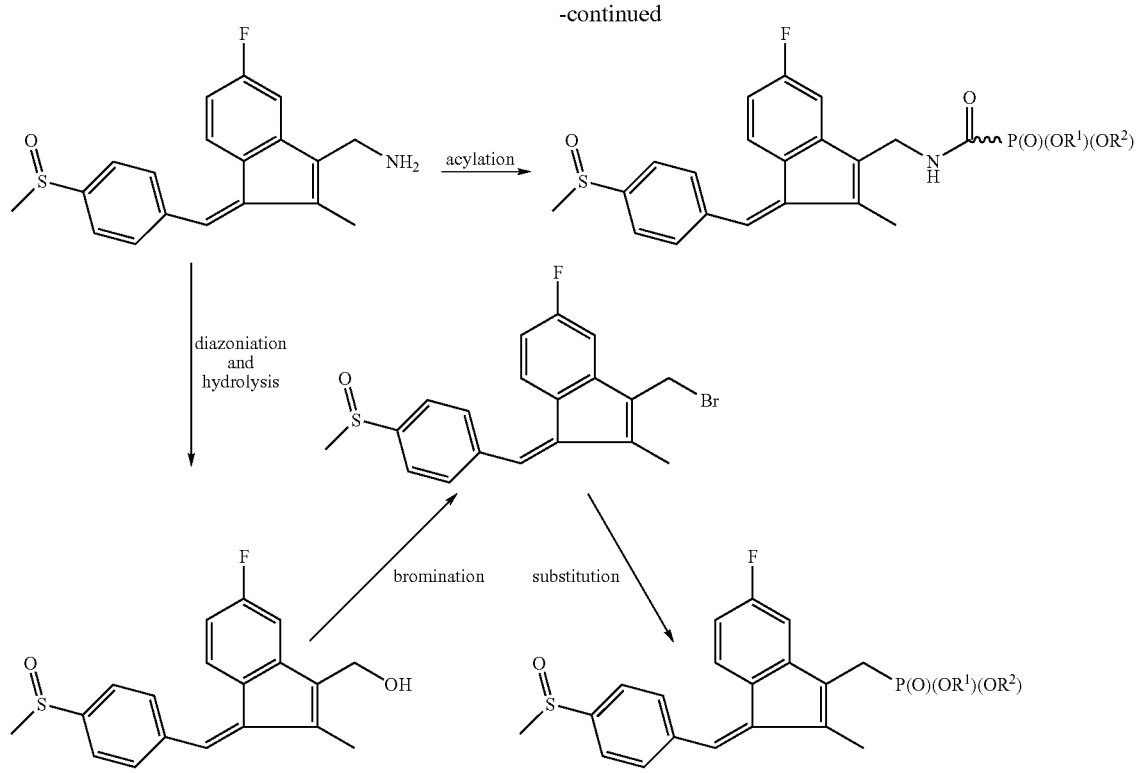
Representative compounds of the invention can be prepared as illustrated above. For example, specific compounds of Formula 112 can be prepared as follows.
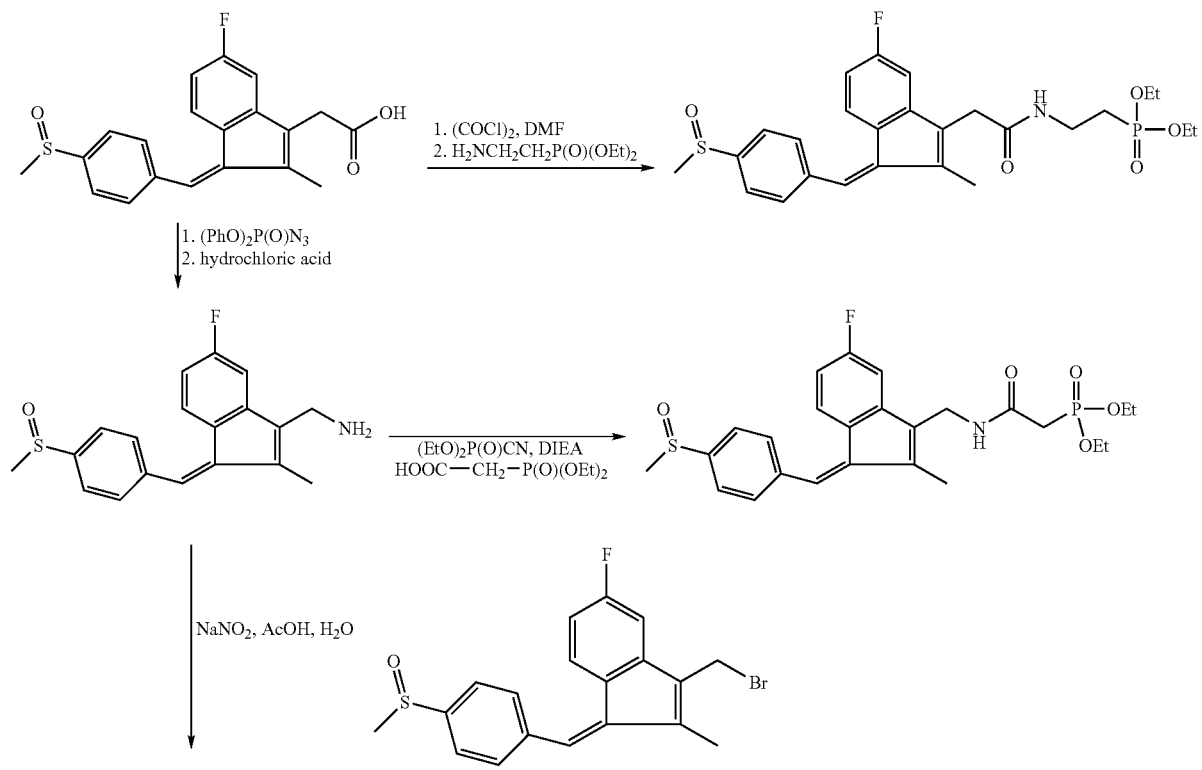

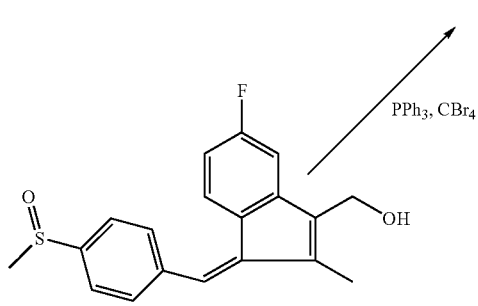
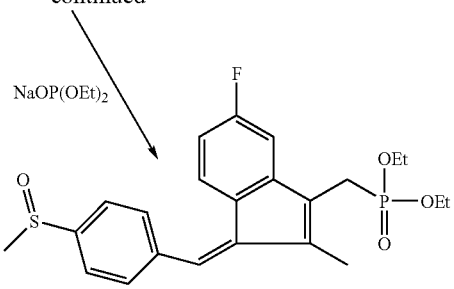

Sulindac can be converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

Sulindac can be treated in a solvent such as acetonitrile with diphenylphosphoryl azide in the presence of a base such as triethylamine at room temperature or up to reflux temperature. After cooling, the mixture is treated with diluted hydrochloric acid to provide the amine (*J. Org. Chem.*, 2002, 67, 6260). The amine is then acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid can be obtained by treatment in a solvent such as dimethylformamide with a coupling reagent such as diethyl cyanophosphonate and a base such as diisopropylethylamine at room temperature.

The amine derived from sulindac can be converted to the alcohol, according to a procedure such as that reported in *J. Org. Chem.*, 1999, 64, 4159. Accordingly, the amine is dissolved in a mixed solvent of acetic acid and water, to which sodium nitrite in water is added dropwise to afford the desired alcohol. The alcohol is then converted to the bromide by treatment with triphenylphosphine and tetrabromomethane, according to a procedure such as that described in *J. Org. Chem.*, 2002, 67, 7215. The bromide is treated in a solvent such as tetrahydrofuran with sodium salt of phosphonic acid diethyl ester to provide the desired phosphonate derivative of sulindac, according to a procedure such as that reported in *Tetrahedron*, 1996, 52, 4411.

EXAMPLE 113

Preparation of Representative Compounds of Formulae 113 and 114

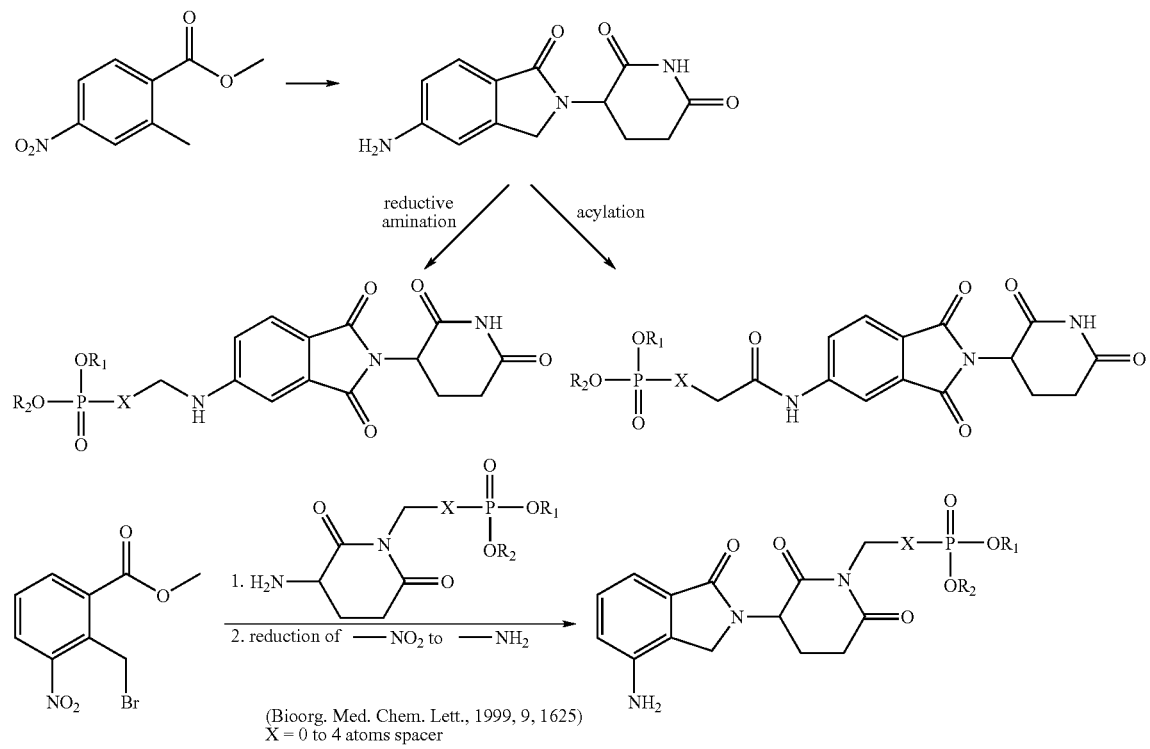

Representative compounds of the invention can be prepared as illustrated above. For example, specific compounds of Formula 113 and 114 can be prepared as follows.

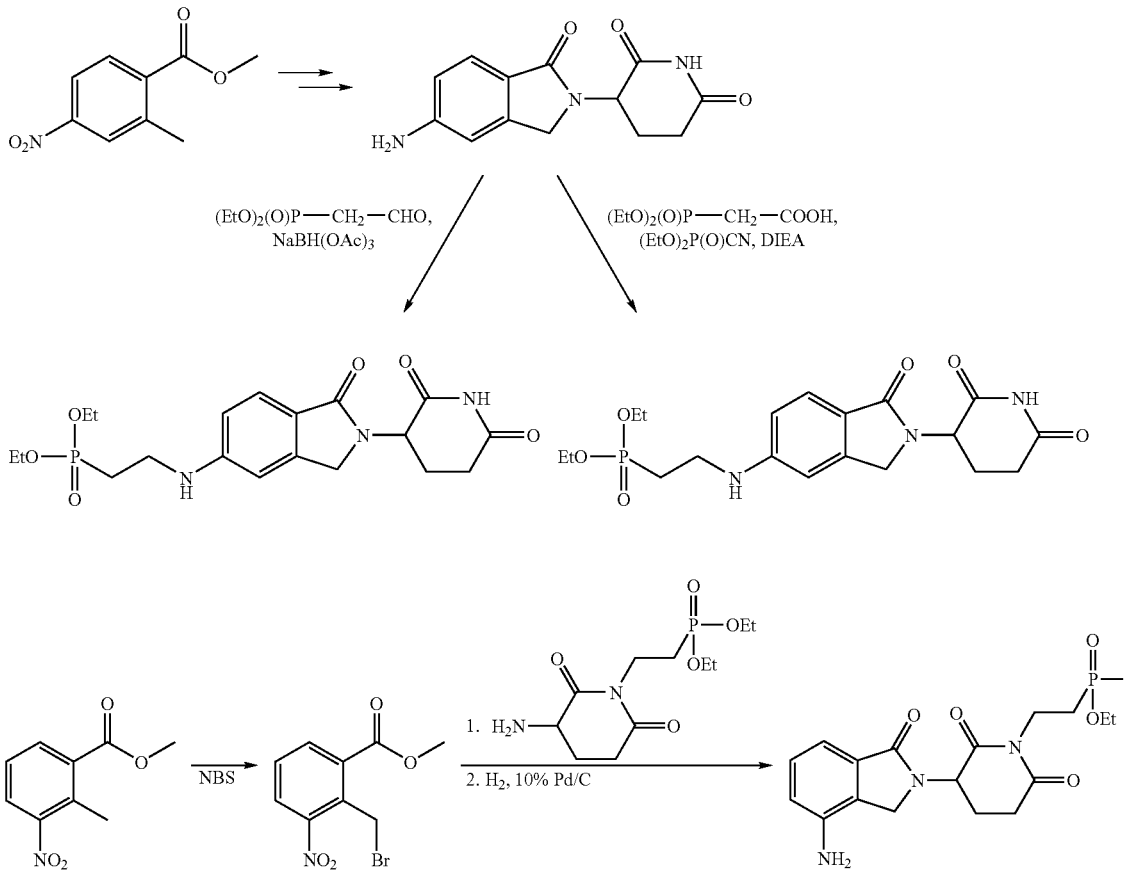

2-Methyl-4-nitrobenzoic acid methyl ester (commercially available) is converted to 3-(5-amino-1-oxo-1,3-dihydro-isoindol-2-yl)-piperidine-2,6-dione, following the procedures reported in *Bioorg. Med. Chem. Lett.*, 1999, 9, 1625. This amine intermediate is subjected to a reductive amination with diethylphosphonoacetaldehyde (obtained from ozonolysis of diethyl allyphosphonate) in the presence of a reducing agent such as sodium triacetoxyborohydride to generate the desired amine linker analog (*J. Org. Chem.*, 1996, 61, 3849). Alternatively, the amine is acylated with an activated diethylphosphonoacetic acid to provide the desired amide linker compound, according to a procedure such as those reported in *J. Med. Chem.*, 1982, 25, 960 and *J. Med. Chem.*, 1984, 27, 600. The activated diethylphosphonoacetic acid can be obtained by treatment in a solvent such as dimethylformamide with a coupling reagent such as diethyl cyanophosphonate and a base such as diisopropylethylamine at room temperature.

2-Methyl-3-nitrobenzoic acid methyl ester (commercially available) is treated in a solvent such as carbon tetrachloride with N-bromosuccinimide under light to produce 2-bromomethyl-3-nitrobenzoic acid methyl ester. This benzylic bromide is treated in a solvent such as dimethylformamide with [2-(3-amino-2,6-dioxo-piperidin-1-yl)-ethyl]-phosphonic acid diethyl ester (for the preparation of this compound, see below) in the presence of a base such as triethylamine. The coupled product is then reduced by hydrogenation (*Bioorg. Med. Chem. Lett.*, 1999, 9, 1625) to afford the desired analog.

[2-(3-Amino-2,6-dioxo-piperidin-1-yl)-ethyl]-phosphonic acid diethyl ester is obtained according to a procedure such as that reported in *J. Med. Chem.*, 2003, 46, 3793. Accordingly, benzyloxycarbonyl-protected glutaric acid is treated in a solvent such as acetonitrile with triethylamine, 1-hydroxy-benzotriazole, diethyl 2-aminoethyl-phosphonate and 1,3-dicyclohexyl-carbodiimide. After the reaction is complete, the solvent is removed and the residue is purified by chromatography to generate the cyclic product, which is subjected to hydrogen in the presence of palladium catalysis to afford the desired intermediate.

EXAMPLES 114-117

Diproline Derivatives

The structures of Diprolene (German Patent DE 2905674) and representative diproline phosphonate derivatives of the invention are shown below, in which the substituent $R^1$ is H, alkyl, alkenyl, aryl or aralkyl. The derivatives incorporate a phosphonate moiety $(R^1O)_2P(O)$ connected to the nucleus by means of a variable linking group, designated as "link" in the attached structures.

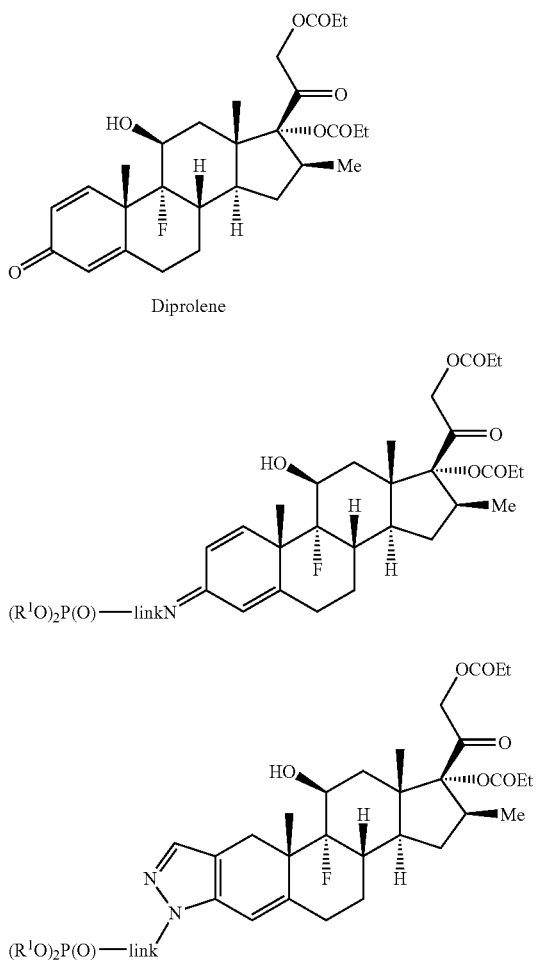

EXAMPLE 114

Preparation of Representative Diproline Derivatives

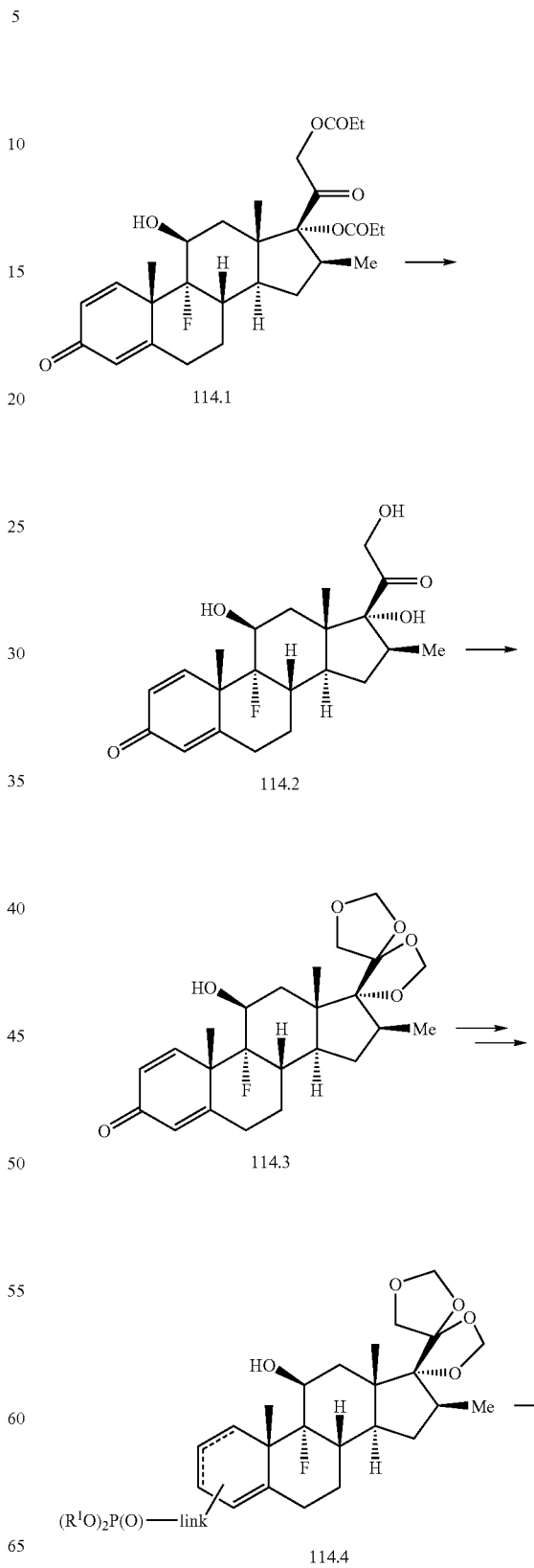

The synthesis of representative phosphonate derivatives of diproline is outlined in Examples 114-117. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

-continued

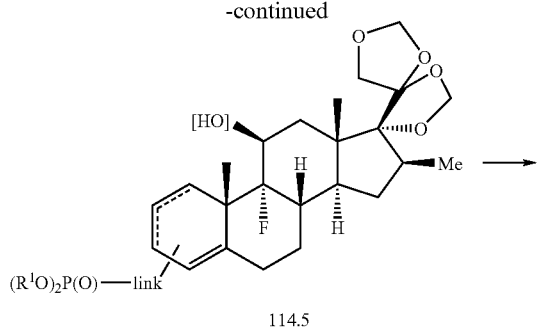

114.5

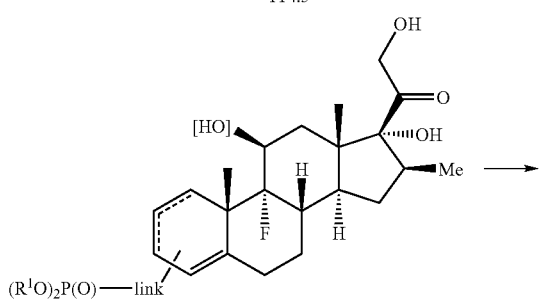

114.6

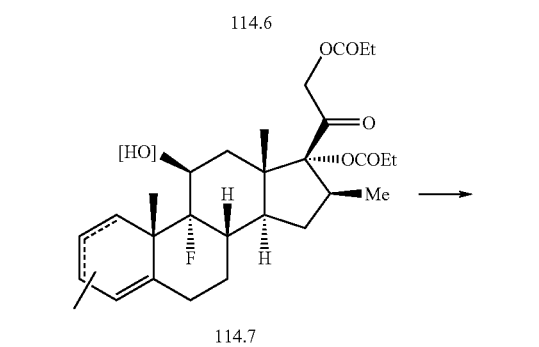

114.7

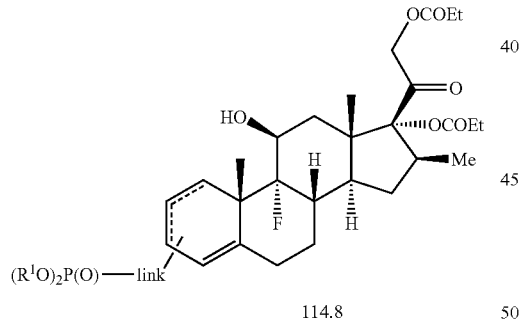

114.8

The steroid side-chain is protected as a bis-methylenedioxy (BMD) moiety. In this sequence, the propionate esters are hydrolyzed, for example by reaction with two molar equivalents of lithium hydroxide in aqueous dimethoxyethane solution at ambient temperature, to give the diol 114.2. The product is then reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 114.3. The phosphonate moiety is then introduced, using the procedures described below, to produce the phosphonate ester 114.4. Prior to hydrolysis of the BMD protecting group, the 11-hydroxyl group is protected. The protecting group is selected so that it is stable to the conditions required for removal of the BMD group, and so that it is removable without affecting the subsequently introduced 17, 21-diester moiety. For example, the 11-hydroxyl group is protected by conversion to the 4-azidobutyrate ester, by reaction with 4-azidobutyryl chloride in pyridine. The 11-azidobutyrate group is then removed from the diester 114.7 by reaction with triphenylphosphine, as described in Bull. Soc. Chem. Jpn., 59, 1296, 1986. Alternatively, the 11-hydroxyl group is protected by conversion to the 2-(trimethylsilyl)ethyl carbonate, by reaction with 2-(trimethylsilyl)ethyl carbonyl chloride and pyridine. The 2-(trimethylsilyl) carbonate is removed from the diester 114.7 by reaction with tetrabutylammonium fluoride in tetrahydrofuran at ambient temperature, as described in Tet. Lett., 22, 969, 1981.

Alternatively, the 11-hydroxyl group is protected by conversion to the trichloroacetyl ester, by reaction with trichloroacetyl chloride in dimethylformamide-pyridine. The trichloroacetyl ester is removed by reaction with ethanolic ammonia at ambient temperature, as described in Coll. Czech. Chem. Commun., 27, 2567, 1962.

The BMD moiety in the protected product 114.5 is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the diol 114.6; the latter compound is then acylated, for example by reaction with propionic acid and dicyclohexyl carbodiimide in dimethylformamide at ambient temperature, or by reaction with propionyl chloride and triethylamine in dichloromethane, to produce the dipropionate 114.7. Deprotection of the 11-hydroxyl group, as described above, then affords the diester 114.8.

Alternatively, the 20-ketone group is protected as the diethylamine adduct by reaction with titanium tetrakis(diethylamide), as described in Protective Groups in Organic Synthesis, by T. W. Greene and P. G. M Wuts, Wiley, Second Edition 1990, p. 219.

EXAMPLE 115

Preparation of Representative Diproline Derivatives

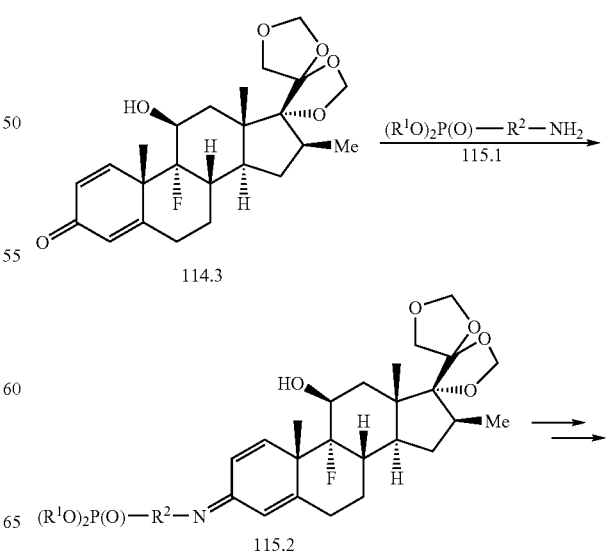

-continued

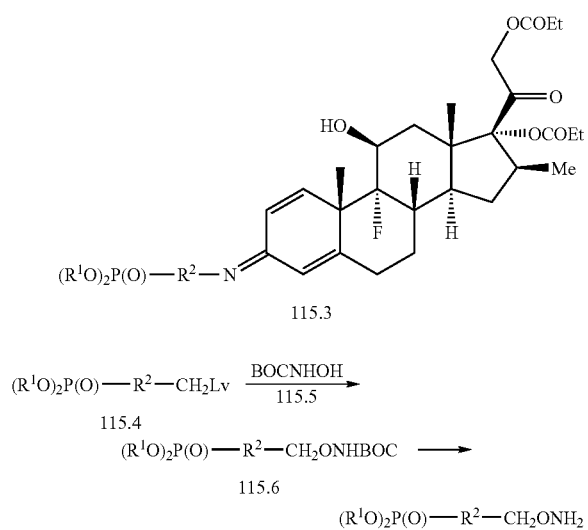

115.3

(R¹O)₂P(O)—R²—CH₂Lv $\xrightarrow{\text{BOCNHOH}}$
115.5
115.4

(R¹O)₂P(O)—R²—CH₂ONHBOC ⟶
115.6

(R¹O)₂P(O)—R²—CH₂ONH₂
115.7

The preparation of phosphonate derivatives of diproline in which the phosphonate is attached by means of an imino or iminoxy group and a variable carbon chain is illustrated above. In this procedure, the BMD-protected derivative 114.3 is reacted with an amine or hydroxylamine 115.1, in which R² is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, to afford the imine or iminoxy product 115.2. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in Anal. Bioch., 1978, 86, 133. and in J. Mass. Spectrom., 1995, 30, 497. The BMD-protected compound 115.2 is then converted, as described in example 114 into the diester 115.3.

The preparation of hydroxylamine ethers incorporating a phosphonate group is also illustrated above. In this procedure, a phosphonate 115.4, in which Lv is a leaving group such as bromo or trifluoromethylsulfonyloxy, is reacted with BOC-hydroxylamine 115.5 (Aldrich) to produce the ether 115.6. The reaction is conducted between equimolar amounts of the reactants in a polar solvent such as dimethylformamide or tetrahydrofuran, in the presence of a base such as potassium hydroxide or dimethylaminopyridine, to give the product 115.6. Deprotection, for example by treatment with trifluoroacetic acid, then gives the hydroxylamine ether 115.7.

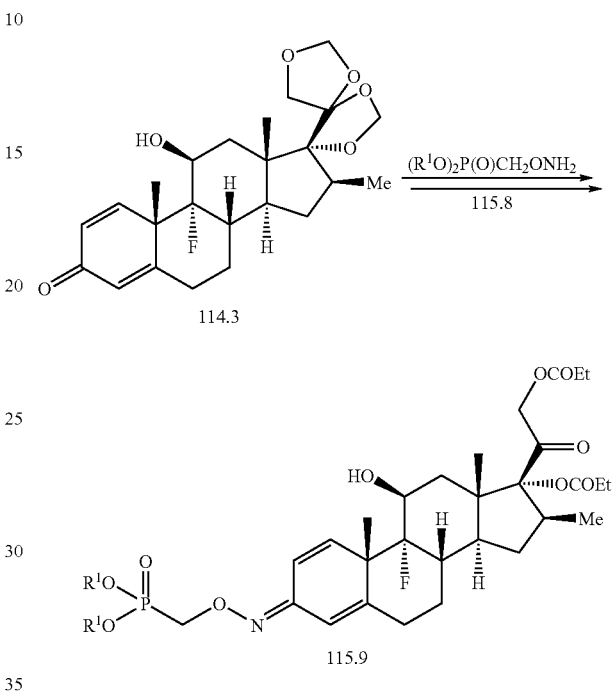

The preparation of phosphonate derivatives of diproline in which the phosphonate is attached by means of an iminoxy group is illustrated above. In this procedure, the substrate 114.3 is reacted with a dialkyl phosphonomethyl hydroxylamine 115.8, prepared as described above from a dialkyl trifluoromethylsulfonyloxymethyl phosphonate (Tet. Lett., 1986, 27, 1477) and BOC-hydroxylamine, to afford, after deprotection and side chain acylation, the oxime ether 115.9. The oxime forming reaction is performed at ambient temperature in pyridine solution between equimolar amounts of the reactants. Using the above procedures, but employing, in place of the oxime ether 115.8, different oxime ethers 115.7, the corresponding products 115.3 are obtained.

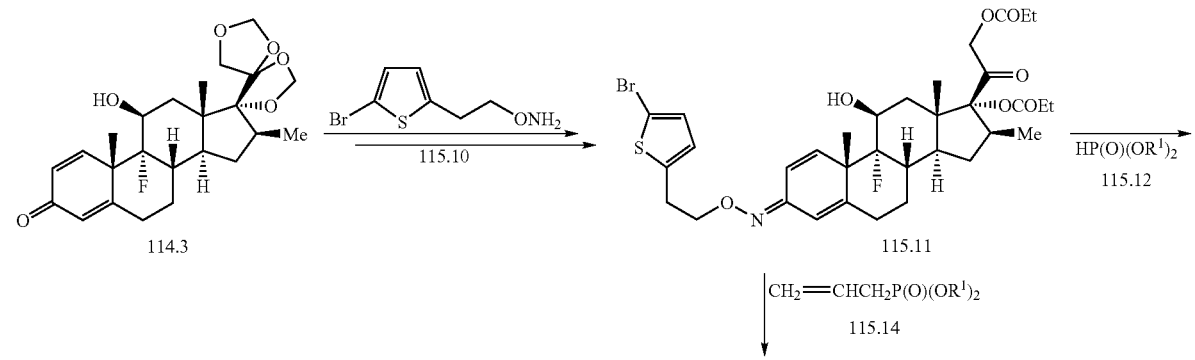

-continued

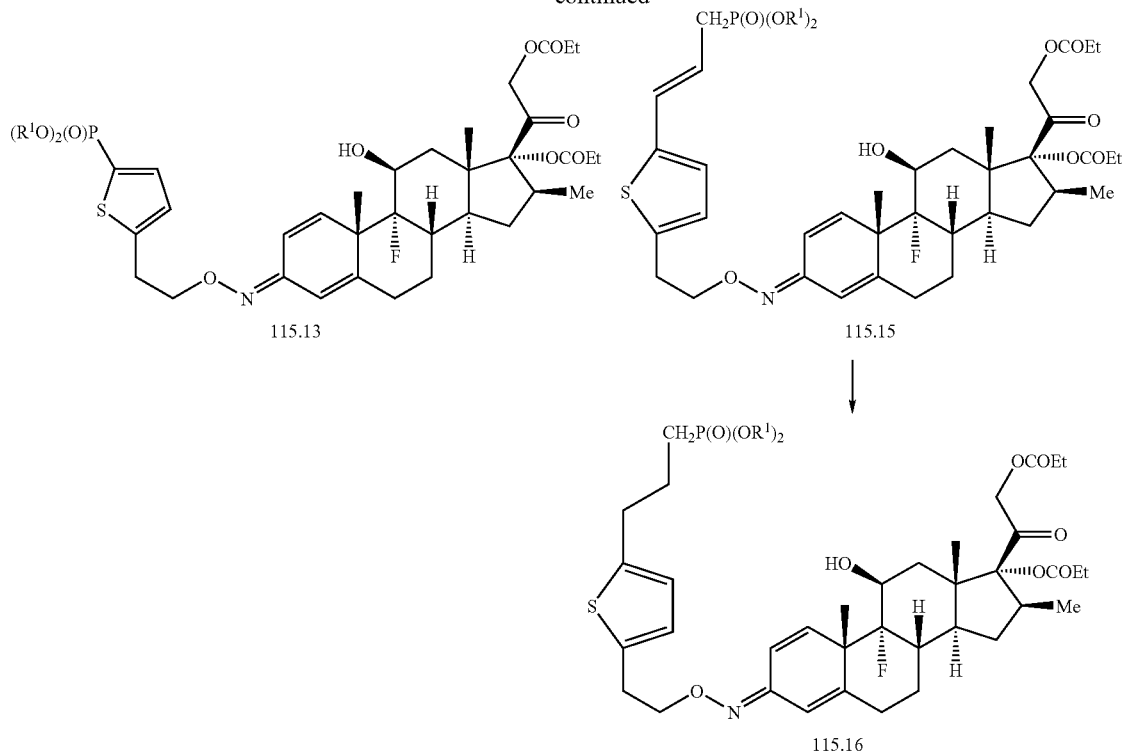

The preparation of phosphonate derivatives of diproline incorporating an iminoxy group, by means of the reaction between the substrate 114.3 and O-2-(5-bromo-2-thienyl) ethoxyhydroxylamine 115.10, prepared as described above from 2-(5-bromo-2-thienyl)ethyl bromide (J. Chem. Soc., Perkin Trans. Phys. Org. Chem., 1975, 821) is illustrated above. The resultant oxime ether is converted, by deprotection and side chain acylation, into the compound 115.11 which is then reacted, in the presence of a palladium catalyst, with a dialkyl phosphite 115.12 to afford the phosphonate 115.13. The preparation of arylphosphonates by means of a coupling reaction between aryl bromides and dialkyl phosphites is described in J. Med. Chem., 35, 1371, 1992. The reaction is performed in an inert solvent such as toluene, in the presence of a base such as triethylamine and a catalytic amount of tetrakis(triphenylphosphine)palladium(0).

Alternatively, the bromo-substituted product 115.11 is coupled, in a palladium-catalyzed Heck reaction, with a dialkyl propenyl phosphonate 115.14 (Acros) to give the unsaturated phosphonate 115.15. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 115.15 is reduced, for example by reaction with diimide, to produce the saturated analog 115.16. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane.

Using the above procedures, but employing, in place of the bromothienyl reagent 115.10, different bromo-substituted aryl or heteroaryl alkoxy hydroxylamines, and/or different dialkyl alkenyl phosphonates, the products analogous to the compounds 115.13, 115.15 and 115.16 are obtained.

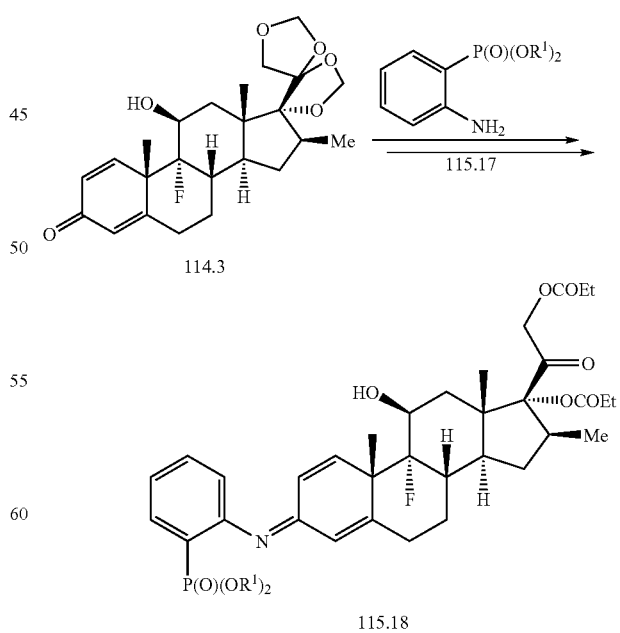

The preparation of phosphonate derivatives of diproline in which the phosphonate is attached by means of an imino group is illyustrated above. In this procedure, the substrate 114.3 is reacted with a dialkyl 2-aminophenyl phosphonate 115.17 (Aurora) to give, after deprotection and side chain acylation, the imine product 115.18. The reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions, to give the product 115.18.

Using the above procedures, but employing, in place of the 2-aminophenyl phosphonate 115.17, different amino-substituted aryl or heteroaryl phosphonates, products analogous to 115.18 are obtained.

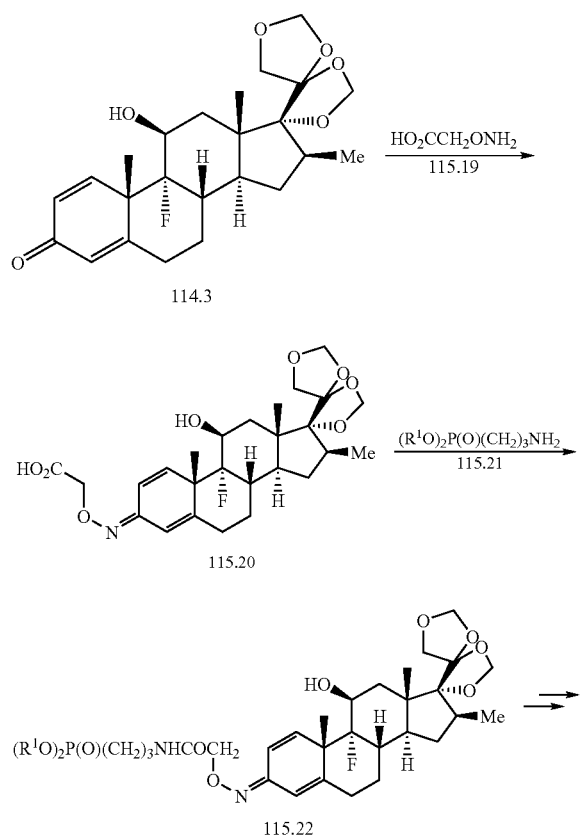

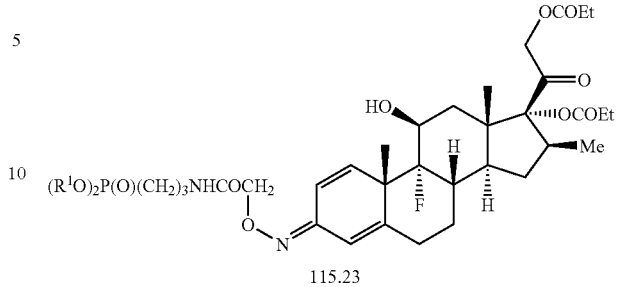

An alternative method for the preparation of phosphonate derivatives in which the phosphonate is attached by means of an oximino group is illustrated above. In this procedure, the dienone 114.3 is reacted with O-(carboxymethyl)hydroxylamine 115.19 (Interchim) to yield, after deprotection and side chain acylation, the oxime 115.19. The reaction of steroidal 1,4-dien-3-ones with hydroxylamine is described in J. Steroid Bioch., 1976, 7, 795. The reaction is performed between equimolar amounts of the reactants in a polar organic solvent such as pyridine or methanol, optionally in the presence of acetic acid or sodium acetate. The oxime 115.20 is then reacted with a dialkyl 3-hydroxyphenyl phosphonate 115.21 (Epsilon) in a Mitsonobu reaction, to yield the substituted oxime 115.22. The preparation of aromatic ethers and thioethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol and the hydroxy or mercapto component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656. The product 115.22 is then transformed, by deprotection and acylation, into the diester 115.23.

Using the above procedures, but employing, in place of the phosphonate 115.22 different dialkyl hydroxy-substituted aryl or heteroaryl phosphonates, the products analogous to 115.23 are obtained.

EXAMPLE 116

Preparation of Representative Diproline Derivatives

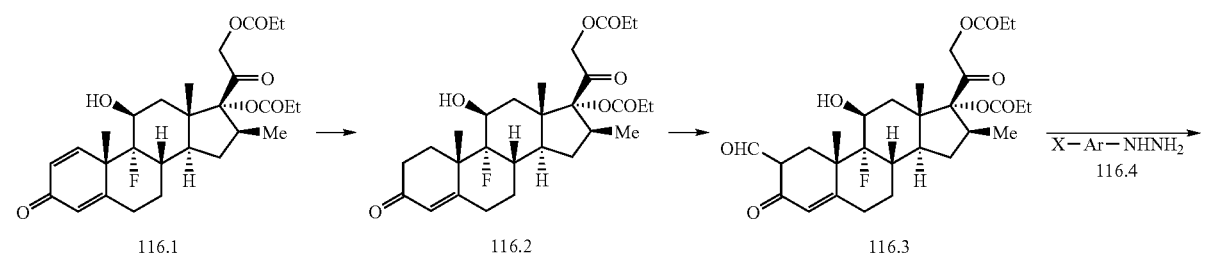

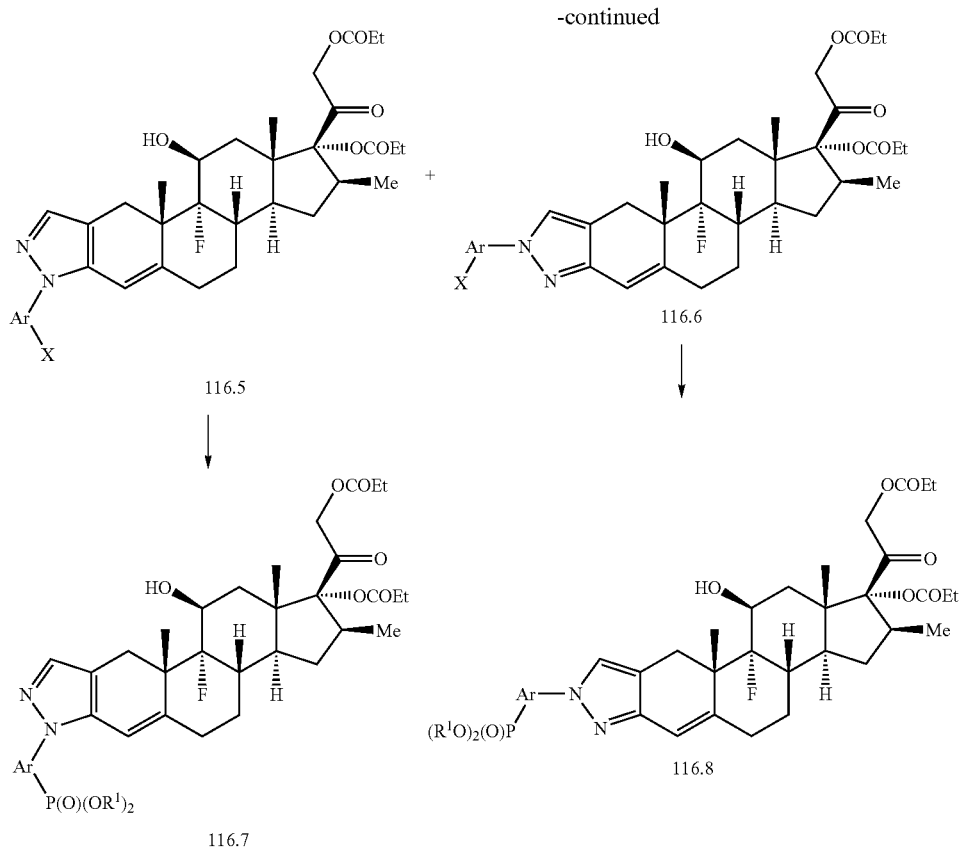

The preparation of phosphonate esters of diproline in which the phosphonate group is attached to the 1' or 2' position of the pyrazole ring, by means of an aromatic or heteroaromatic group, a heteroatom and a variable carbon chain is illustrated above. In this procedure, Diprolene 116.1 is reduced to afford the 1,2-dihydro product, 116.2. The catalytic hydrogenation reaction is effected by the use of tris(triphenylphosphine)rhodium(I) chloride, for example as described in J. Med. Chem., 2001, 44, 602. The product is then reacted with ethyl formate and a base such as sodium hydride, in an inert solvent such as toluene or dimethylformamide, as described in Australian Patent Application 275950409, to afford the 2-formyl product 116.3. Optionally, the substrate 116.1 is protected, for example as described in example 114, prior to the formylation reaction, as described in J. Am. Chem. Soc., 1964, 86, 1520. The 2-formyl product is then reacted with an aryl or heteroaryl hydrazine 116.4, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 116.5 and 116.6. The ring-forming reaction is performed between equimolar amounts of the reactants in an acidic solvent such as acetic acid, as described in J. Am. Chem. Soc., 1964, 86, 1520. The pyrazoles 116.5 and 116.6 are then transformed, respectively into the phosphonates 116.7 and 116.8.

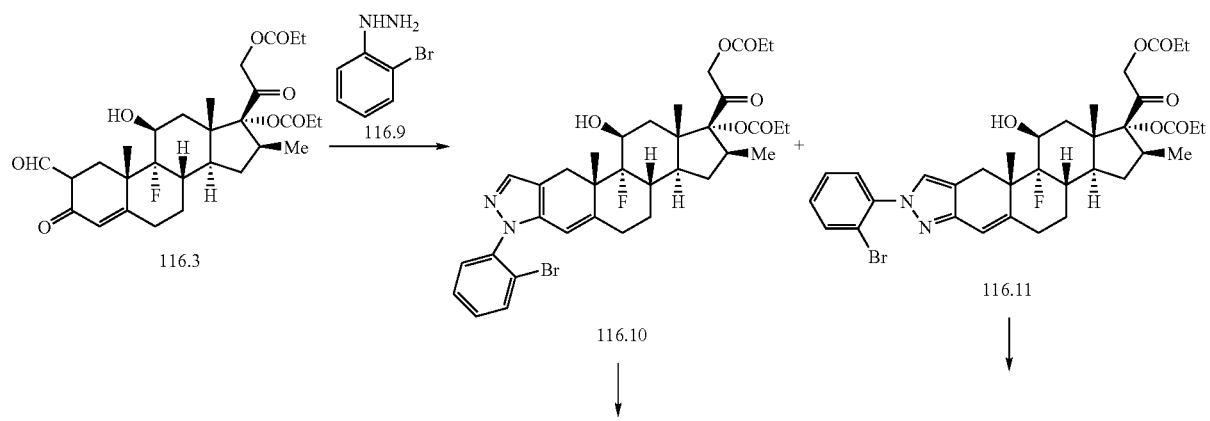

-continued

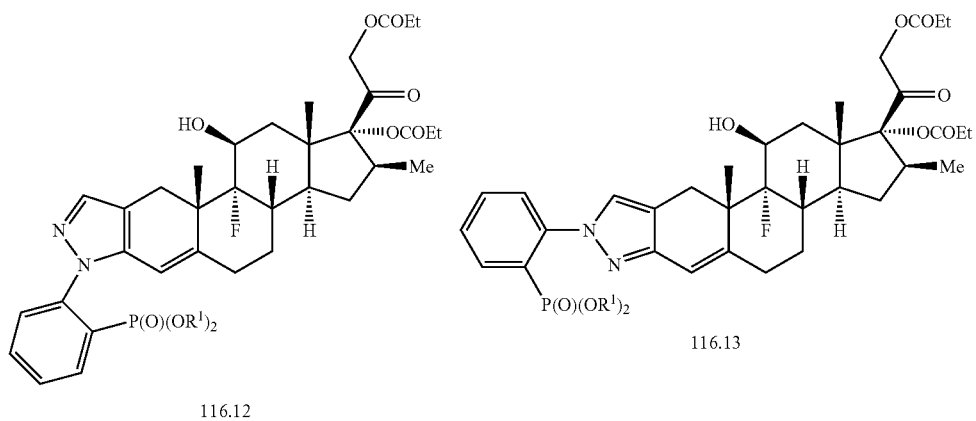

116.12

116.13

The preparation of phosphonate derivatives of diproline in which the phosphonate is attached by means of a phenyl group is illustrated above. In this sequence, the ketoaldehyde 116.3 is reacted, as described above, with 2-bromophenylhydrazine 116.9 (Fluka), to give the isomeric pyrazole products 116.10 and 16.11. The products are then reacted, as described above, with a dialkyl phosphite $HP(O)(OR^1)_2$ and a palladium catalyst, to afford respectively the phosphonates 116.12 and 116.13. Using the above procedures, but employing, in place of 2-bromophenyl hydrazine, different bromoaryl or bromoheteroaryl hydrazines 116.4, the products 116.7 and 116.8 are obtained.

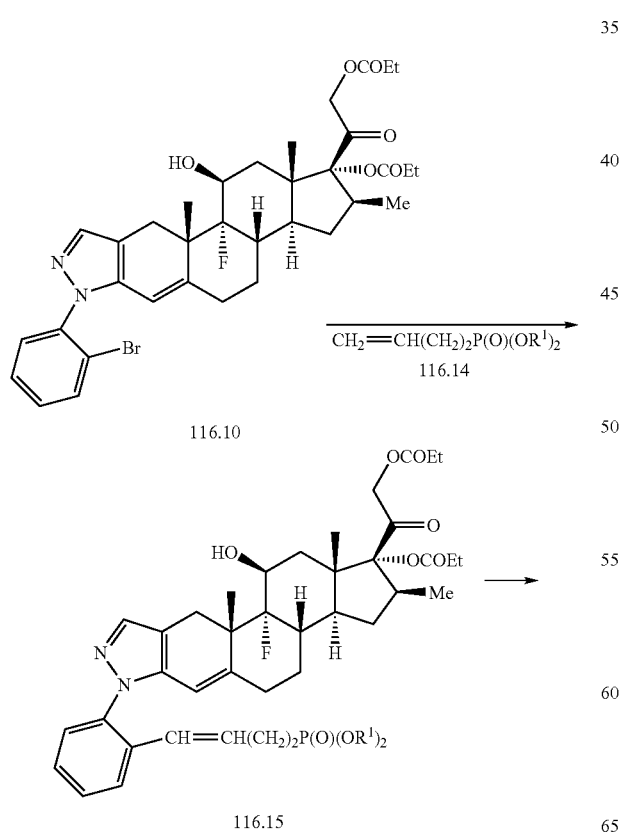

-continued

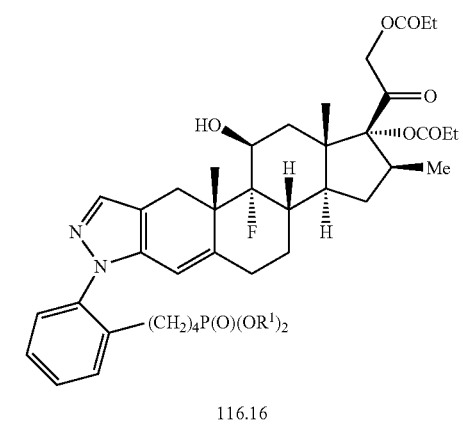

116.16

The preparation of phosphonate diproline derivatives in which the phosphonate is attached by means of an aromatic or heteroaromatic group and a saturated or unsaturated alkyl chain is illustrated above. In this procedure, the bromophenyl-substituted pyrazole 116.10 is coupled in a Heck reaction, as described above, with, for example a dialkyl butenyl phosphonate 116.14 (Org. Lett., 2001, 3, 217) to give the unsaturated phosphonate product 116.15. Optionally, the product is reduced, as described above, to give the saturated analog 116.16. Application of the above procedures to the isomeric bromophenyl pyrazole 116.11 affords the products isomeric with 116.15 and 116.16. Using the above procedures, but employing, in place of the phosphonate 116.14, different dialkyl alkenyl phosphonates, and/or different bromoaryl or heteroaryl pyrazoles 116.5 or 116.6, the products analogous to 116.15 and 116.16 are obtained.

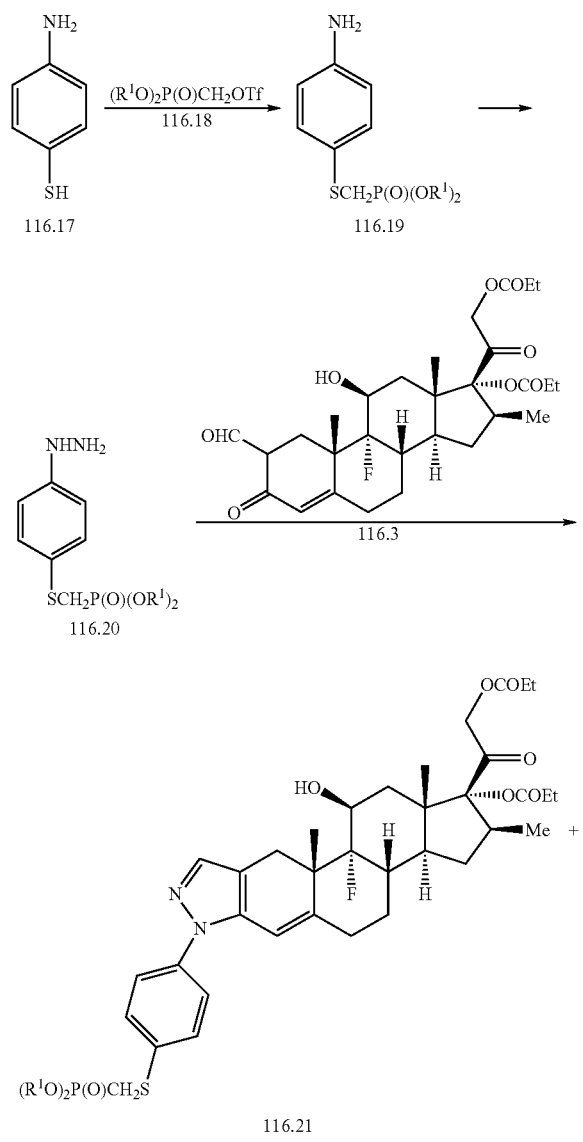

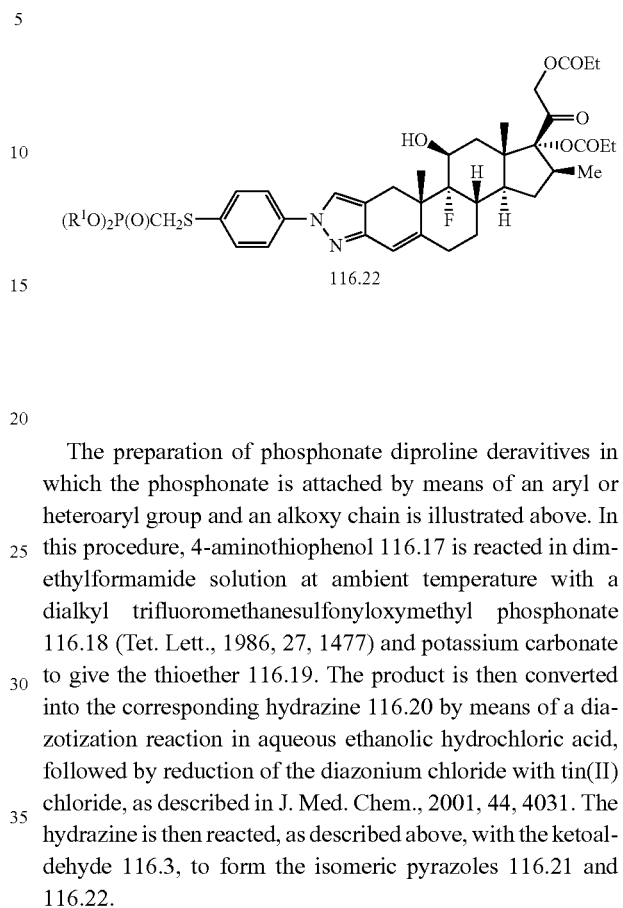

The preparation of phosphonate diproline deravitives in which the phosphonate is attached by means of an aryl or heteroaryl group and an alkoxy chain is illustrated above. In this procedure, 4-aminothiophenol 116.17 is reacted in dimethylformamide solution at ambient temperature with a dialkyl trifluoromethanesulfonyloxymethyl phosphonate 116.18 (Tet. Lett., 1986, 27, 1477) and potassium carbonate to give the thioether 116.19. The product is then converted into the corresponding hydrazine 116.20 by means of a diazotization reaction in aqueous ethanolic hydrochloric acid, followed by reduction of the diazonium chloride with tin(II) chloride, as described in J. Med. Chem., 2001, 44, 4031. The hydrazine is then reacted, as described above, with the ketoaldehyde 116.3, to form the isomeric pyrazoles 116.21 and 116.22.

Using the above procedures, but employing, in place of the triflate 116.18, different dialkylphosphono alkyl bromides or triflates, and/or different aromatic or heteroaromatic mercapto or hydroxyamines, the products analogous to 116.21 and 116.22 are obtained.

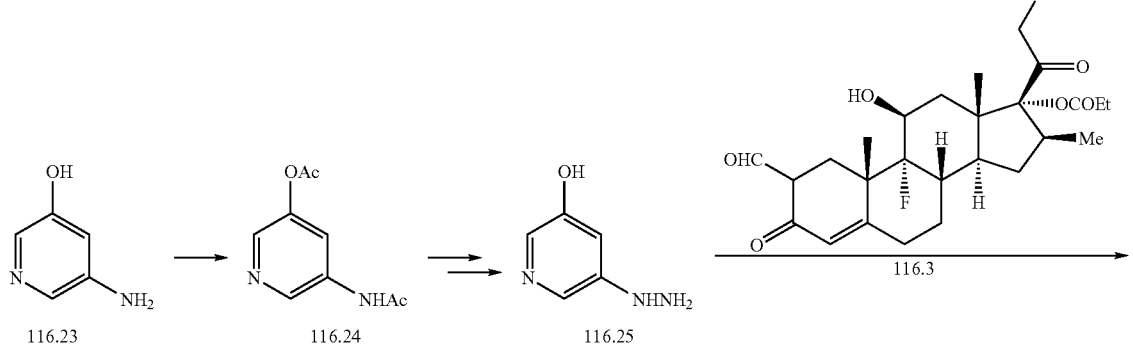

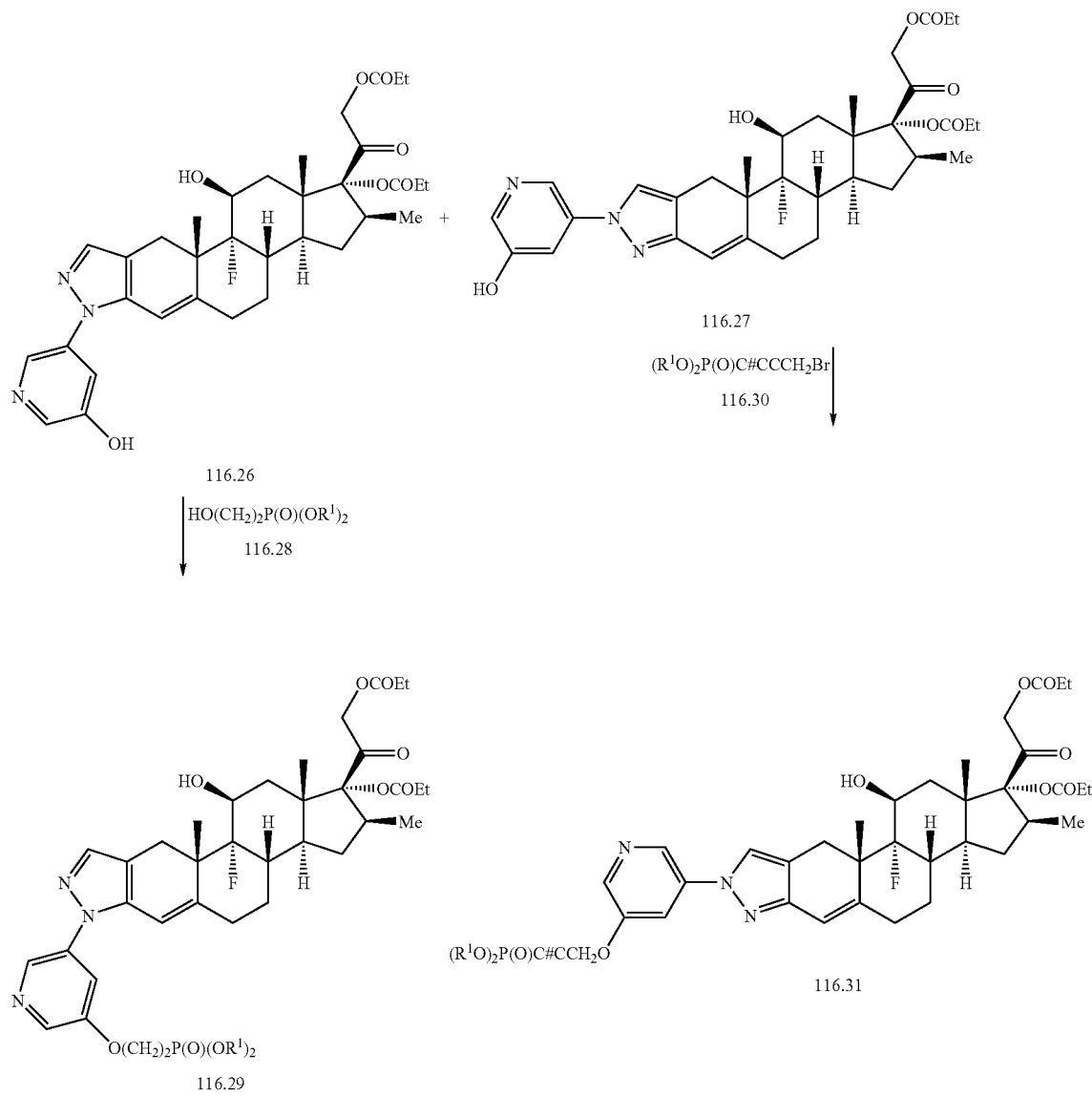

The preparation of phosphonate diprolone derivatives in which the phosphonate is attached by means of a pyridyl group a heteroatom and a variable carbon chain is illustrated above. In this procedure, 3-amino-5-hydroxypyridine is converted, by reaction with acetic anhydride, into the diacetyl analog 116.24. The product is then transformed by diazotization and reduction, as described above, into the hydrazine 116.25. The hydrazine is then reacted with the ketoaldehyde 116.3 to give the isomeric pyrazoles 116.26 and 116.27. The 2'-pyridyl product 116.26 is reacted in a Mitsonobu reaction, as described above, with a dialkyl hydroxyethyl phosphonate 116.28 (Zh. Obschei. Khim., 1973,43, 2364) to afford the ether 116.29. Application of this procedure to the isomeric phenol 116.27 affords the product isomeric to 116.29.

Alternatively, the isomeric phenol 116.27 is reacted, in dimethylformamide solution at about 800, with one molar equivalent of a dialkyl bromopropynyl phosphonate 116.30 (Bioorg. Med. Chem. Lett., 1994,4, 273) and cesium carbonate, to prepare the phosphonate 116.31. Application of this procedure to the isomeric phenol 116.26 affords the product isomeric with 116.31. Using the above procedures, but employing, in place of the carbinol 116.28 or the bromide 116.30, different thiols, alcohols or bromides, and/or different phenols 116.5 or 116.6 in which X is OH, the corresponding products analogous to 116.29 and 116.31 are obtained.

EXAMPLE 117

Preparation of Representative Diproline Derivatives

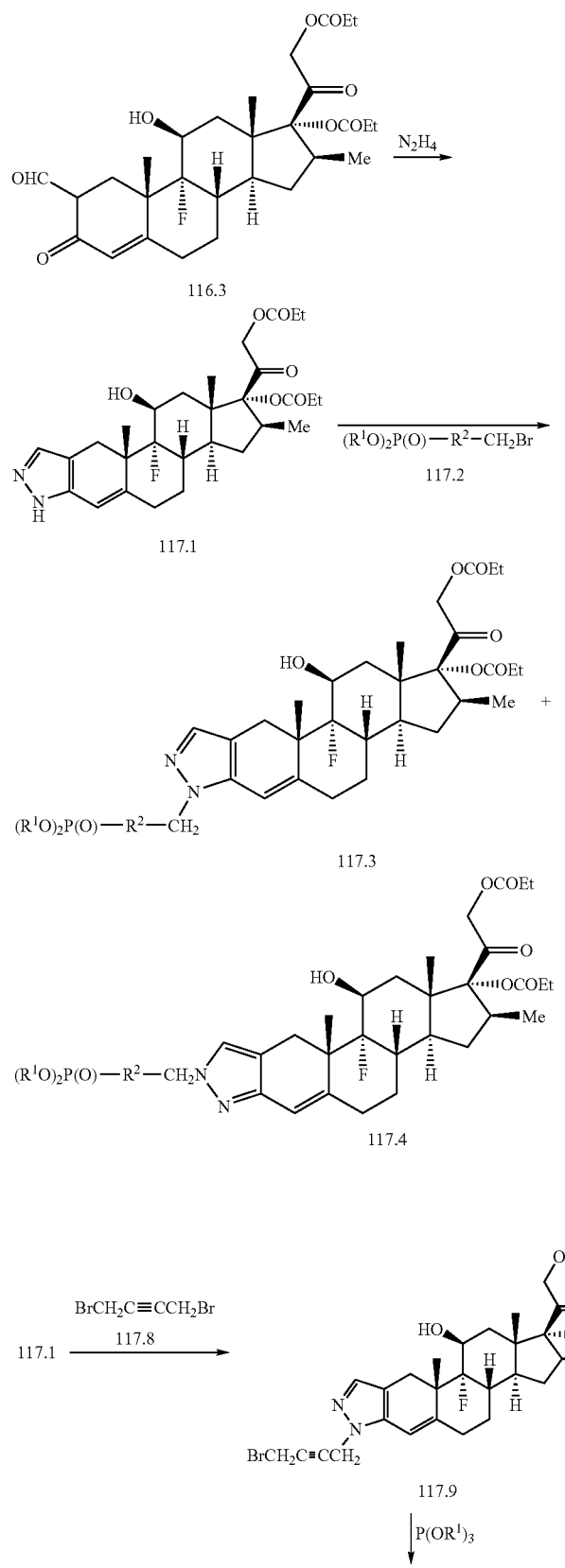

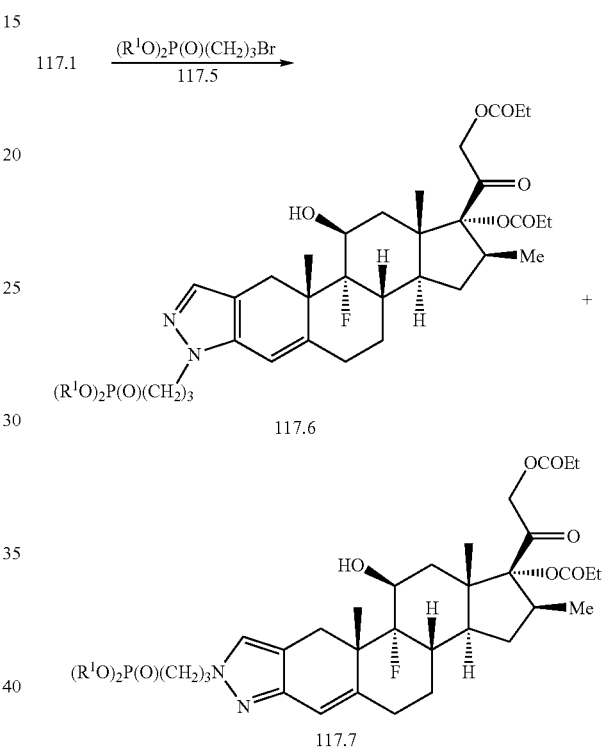

The preparation of the phosphonate diproline derivatives in which the phosphonate group is attached by means of a variable carbon linkage is illustrated above. In this procedure, the ketoaldehyde 116.3 is reacted with hydrazine, to afford the pyrazole derivative 117.1. The reaction of steroidal 2-formyl-3-ketones with hydrazine is described in J. Am. Chem. Soc, 1964, 86, 1520. The reaction is performed in acetic acid at ambient temperature. The resulting pyrazole is then reacted with a dialkyl bromomethyl phosphonate 117.2, in which $R^2$ is as defined above, to produce the isomeric 2' and 1' alkylation products 117.3 and 117.4 respectively. The alkylation of substituted pyrazoles is described, for example, in Heterocyclic Chemistry, by T. L. Gilchrist, Longman, 1992, p. 309.

Representative diproline derivatives of the invention can be prepared as illustrated above. The pyrazole 117.1 is reacted, in dimethylformamide solution at ca. 90°, with a dialkyl bromopropyl phosphonate 117.5 (Aldrich) and a base such as dimethylaminopyridine or lithium hexamethyldisilazide, to yield the isomeric alkylation products 117.6 and 117.7.

-continued

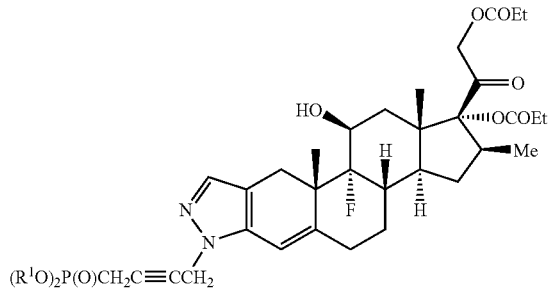

117.11

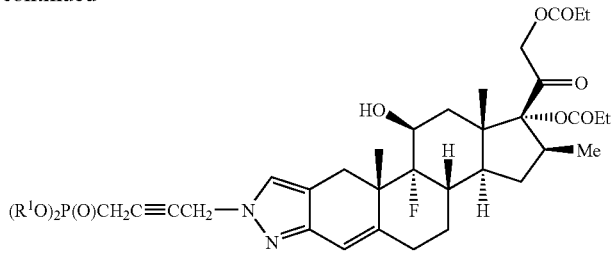

117.12

Representative diproline derivatives of the invention can be prepared as illustrated above. The pyrazole 117.1 is reacted in dimethylformamide solution at ambient temperature with one molar equivalent of 1,4-dibromobut-2-yne 117.8 (Narchem) and potassium carbonate, to afford the alkylation products 117.9 and 117.10. The products are then heated at 120° with a trialkyl phosphite in an Arbuzov reaction, to yield the phosphonates 117.11 and 117.12. The Arbuzov reaction is described in Handb. Organophosphorus Chem., 1992, 115-72. Using the above procedures, but employing, in place of the dibromide 117.8, different alkyl, alkenyl or alkynyl dibromides, the products analogous to 117.11 and 117.12 are obtained.

EXAMPLES 118-121

Aclometazone Derivatives (118-120)

The structures of Aclometasone dipropionate (J. Med. Chem., 1980, 23, 430; U.S. Pat. No. 4,124,707) and representative phosphonate esters of the invention are shown below, in which the substituent $R^1$ is H, alkyl, alkenyl, aryl or aralkyl. These compounds incorporate a phosphonate moiety $(R^1O)_2P(O)$ connected to the nucleus by means of a variable linking group, designated as "link" in the attached structures.

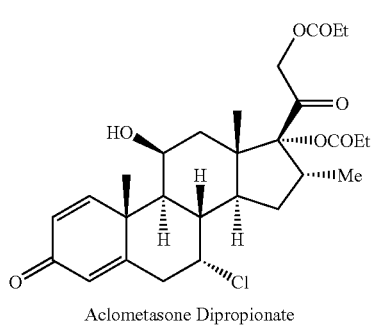

Aclometasone Dipropionate

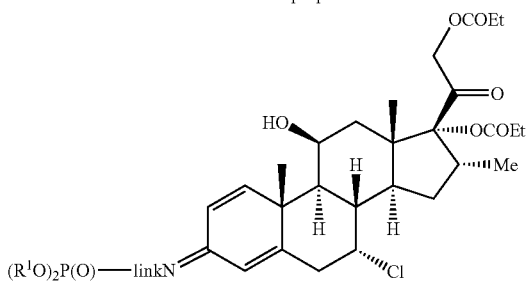

-continued

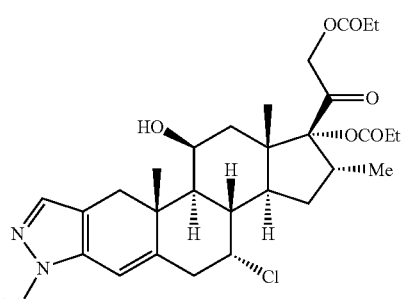

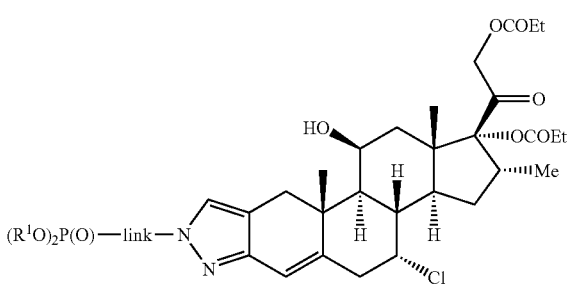

The synthesis of representative phosphonate derivatives of the invention is outlined in Examples 118-121. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 118

Preparation of Representative Aclometasone Derivatives

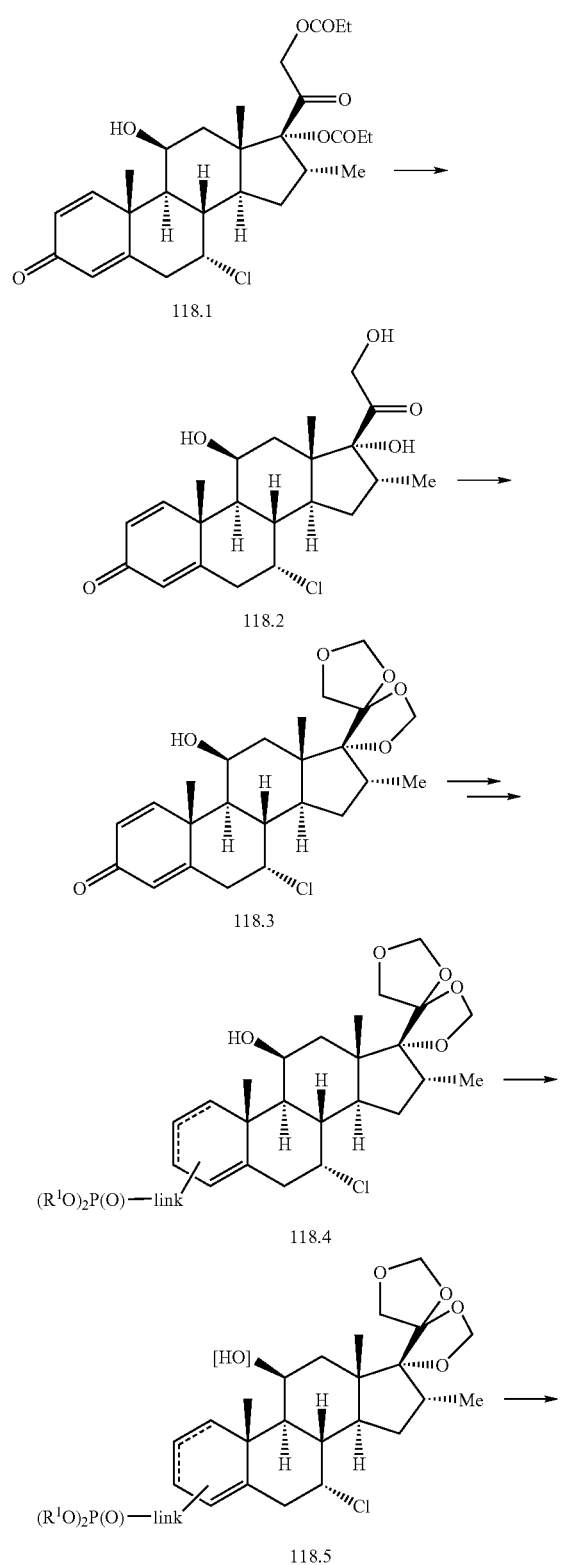

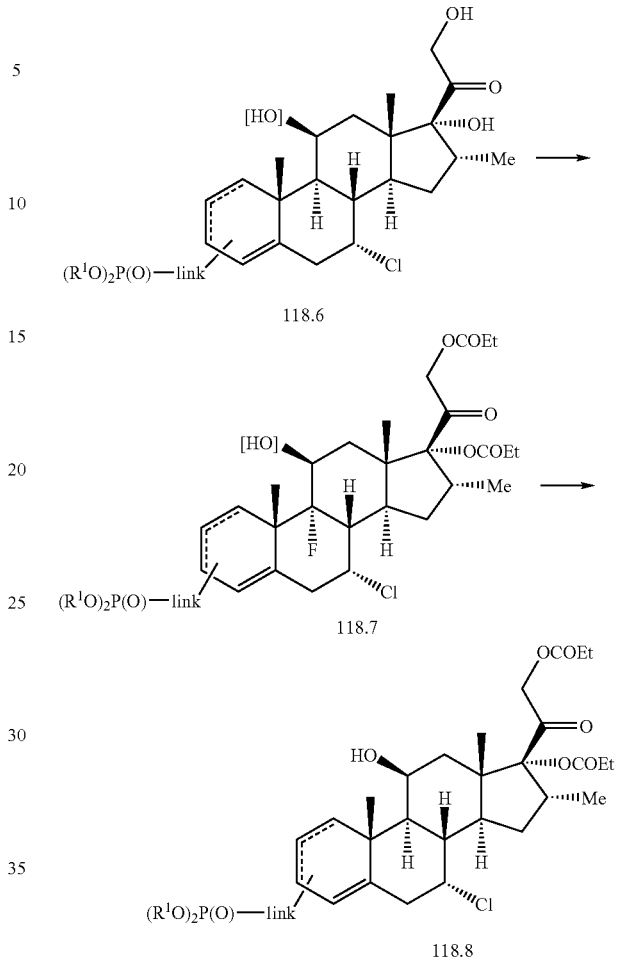

As illustrated above, a protection-deprotection sequence in which the steroid side-chain is protected as a bis-methylenedioxy (BMD) moiety. In this sequence, the propionate esters are hydrolyzed, for example by reaction with two molar equivalents of lithium hydroxide in aqueous dimethoxyethane solution at ambient temperature, to give the diol 118.2. The product is then reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 118.3. The phosphonate moiety is then introduced, using the procedures described below, to produce the phosphonate ester 118.4. Prior to hydrolysis of the BMD protecting group, the 11-hydroxyl group is protected. The protecting group is selected so that it is stable to the conditions required for removal of the BMD group, and so that it is removable without affecting the subsequently introduced 17,21-diester moiety. For example, the 11-hydroxyl group is protected by conversion to the 4-azidobutyrate ester, by reaction with 4-azidobutyryl chloride in pyridine. The 11-azidobutyrate group is then removed from the diester 118.7 by reaction with triphenylphosphine, as described in Bull. Soc. Chem. Jpn., 59, 1296, 1986. Alternatively, the 1-hydroxyl group is protected by conversion to the 2-(trimethylsilyl)ethyl carbonate, by reaction with 2-(trimethylsilyl)ethyl carbonyl chloride and pyridine. The 2-(trimethylsilyl) carbonate is removed from the diester 118.7 by reaction with tetrabutylammonium fluoride in tetrahydrofuran at ambient temperature, as described in Tet. Lett., 22, 969, 1981.

Alternatively, the 11-hydroxyl group is protected by conversion to the trichloroacetyl ester, by reaction with trichloroacetyl chloride in dimethylformamide-pyridine. The trichloroacetyl ester is removed by reaction with ethanolic ammonia at ambient temperature, as described in Coll. Czech. Chem. Commun., 27, 2567, 1962.

The BMD moiety in the protected product 118.5 is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the diol 118.6; the latter compound is then acylated, for example by reaction with propionic acid and dicyclohexyl carbodiimide in dimethylformamide at ambient temperature, or by reaction with propionyl chloride and triethylamine in dichloromethane, to produce the dipropionate 118.7. Deprotection of the 11-hydroxyl group, as described above, then affords the diester 118.8.

Alternatively, the 20-ketone group is protected as the diethylamine adduct by reaction with titanium tetrakis(diethylamide), as described in Protective Groups in Organic Synthesis, by T. W. Greene and P. G. M Wuts, Wiley, Second Edition 1990, p. 219.

EXAMPLE 119

Preparation of Representative Aclometasone Derivatives

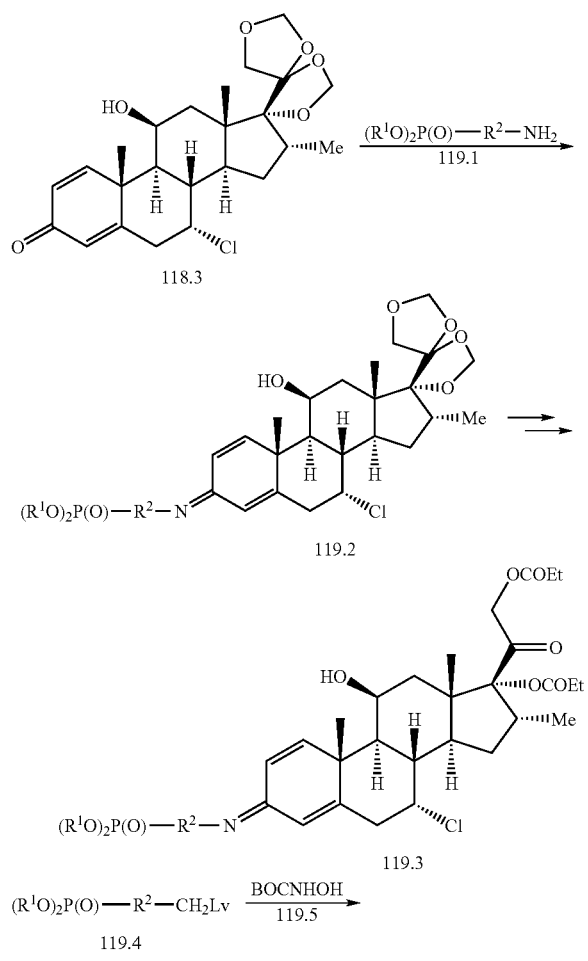

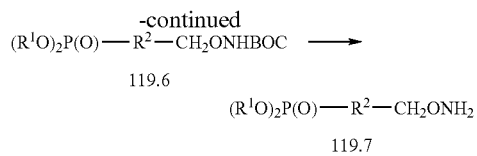

The preparation of phosphonate derivatives of Aclometasone in which the phosphonate is attached by means of an imino or iminoxy group and a variable carbon chain is illustrated above. In this procedure, the BMD-protected derivative 118.3 is reacted with an amine or hydroxylamine 119.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, to afford the imine or iminoxy product 119.2. The reaction is conducted between equimolar amounts of the reactants in an aprotic solvent such as pyridine or xylene, or in an alcoholic solvent such as ethanol, optionally in the presence of an acid catalyst to give the imine or oxime. The preparation of oximes of steroidal 3-ketones is described in Anal. Bioch., 1978, 86, 133. and in J. Mass. Spectrom., 1995, 30, 497. The BMD-protected side-chain compound 119.2 is then converted, as described in Example 118 into the diester 119.3.

The preparation of hydroxylamine ethers incorporating a phosphonate group is also illustrated above. In this procedure, a phosphonate 119.4, in which Lv is a leaving group such as bromo or trifluoromethylsulfonyloxy, is reacted with BOC-hydroxylamine 119.5 (Aldrich) to produce the ether 119.6. The reaction is conducted between equimolar amounts of the reactants in a polar solvent such as dimethylformamide or tetrahydrofuran, in the presence of a base such as potassium hydroxide or dimethylaminopyridine, to give the product 119.6. Deprotection, for example by treatment with trifluoroacetic acid, then gives the hydroxylamine ether 119.7.

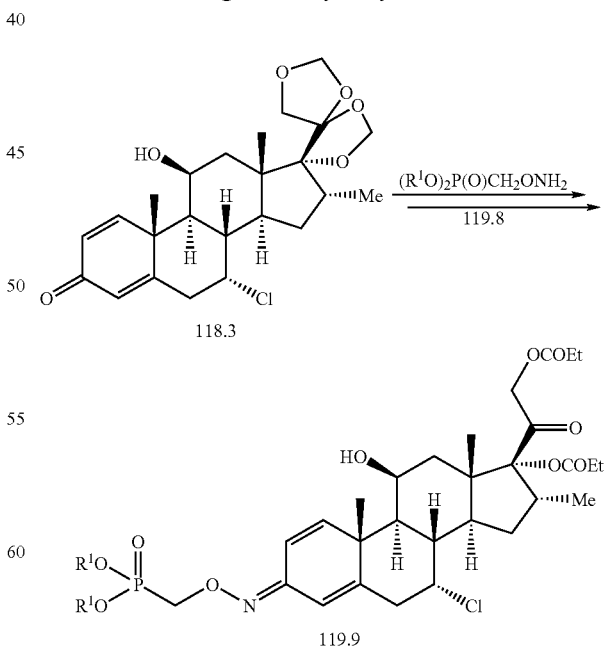

The preparation of phosphonate aclometasone derivatives in which the phosphonate is attached by means of an iminoxy group is shown above. In this procedure, the substrate 118.3 is reacted with a dialkyl phosphonomethyl hydroxylamine 119.8, prepared as described above from a dialkyl trifluoromethylsulfonyloxymethyl phosphonate (Tet. Lett., 1986, 27, 1477) and BOC-hydroxylamine, to afford, after deprotection and side chain acylation, the oxime ether 119.9. The oxime forming reaction is performed at ambient temperature in pyridine solution between equimolar amounts of the reactants. Using the above procedures, but employing, in place of the oxime ether 119.8, different oxime ethers 119.7, the corresponding products 119.3 are obtained.

tion between aryl bromides and dialkyl phosphites is described in J. Med. Chem., 35, 1371, 1992. The reaction is performed in an inert solvent such as toluene, in the presence of a base such as triethylamine and a catalytic amount of tetrakis(triphenylphosphine)palladium(0).

Alternatively, the bromo-substituted product 119.11 is coupled, in a palladium-catalyzed Heck reaction, with a dialkyl vinyl phosphonate 119.14 (Aldrich) to give the unsaturated phosphonate 119.15. The coupling of aryl halides with olefins by means of the Heck reaction is described, for example, in Advanced Organic Chemistry, by F. A. Carey and

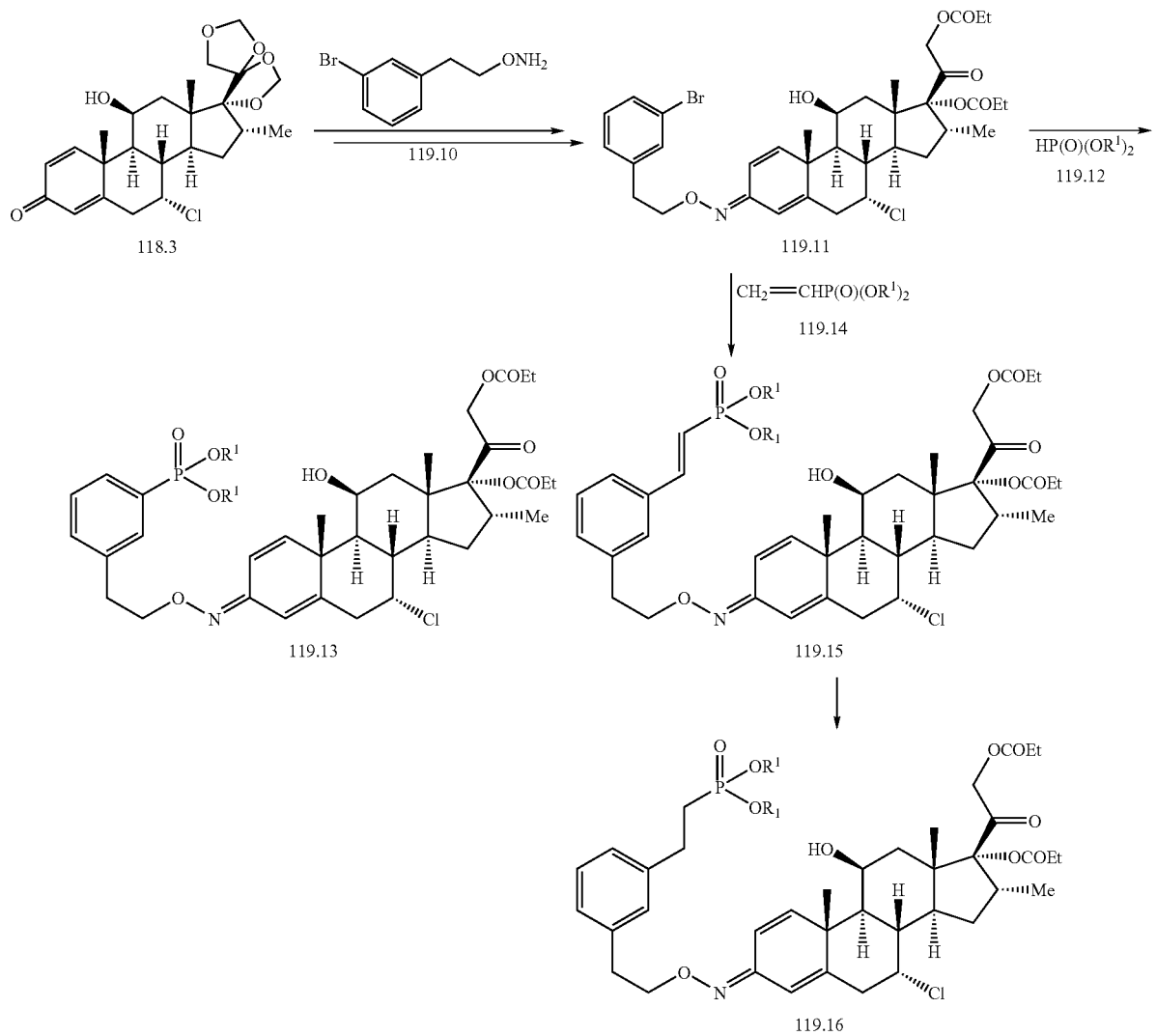

The preparation of phosphonate aclometasone derivatives incorporating an iminoxy group, by means of the reaction between the substrate 118.3 and O-2-(3-bromophenyl) ethoxyhydroxylamine 119.10, prepared as described above from 2-(3-bromophenyl)ethyl bromide is illustrated above. The resultant oxime ether is converted, by deprotection and side chain acylation, into the compound 119.11 which is then reacted, in the presence of a palladium catalyst, with a dialkyl phosphite 119.12 to afford the phosphonate 119.13. The preparation of arylphosphonates by means of a coupling reaction between aryl bromides and dialkyl phosphites is described in J. Med. Chem., 35, 1371, 1992.

R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or a palladium(II) catalyst such as palladium(II) acetate, and optionally in the presence of a base such as triethylamine or potassium carbonate. Optionally, the styrenoid double bond present in the product 119.15 is reduced, for example by reaction with diimide, to produce the saturated analog 119.16. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane.

Using the above procedures, but employing, in place of the bromophenyl reagent 119.10, different bromo-substituted aryl or heteroaryl alkoxy hydroxylamines, and/or different dialkyl alkenyl phosphonates, the products analogous to the compounds 119.13, 119.15 and 119.16 are obtained.

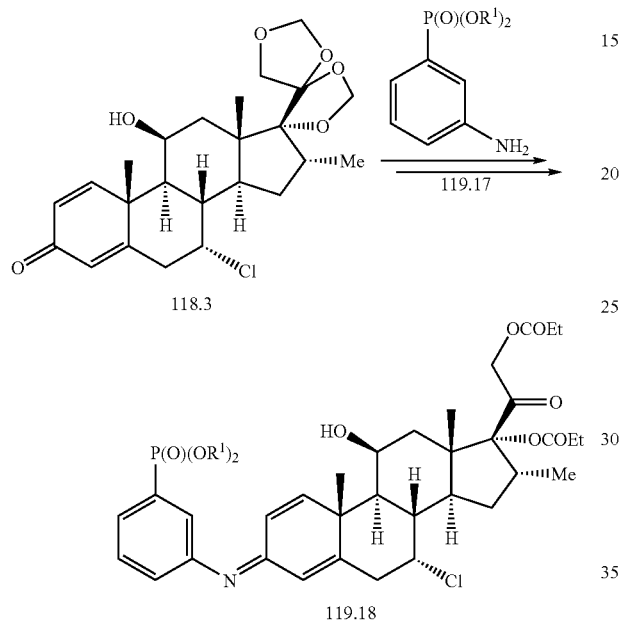

The preparation of phosphonate aclometasone derivatives in which the phosphonate is attached by means of an imino group is illustrated above. In this procedure, the substrate 118.3 is reacted with a dialkyl 3-aminophenyl phosphonate 119.17 (J. Med. Chem., 1984, 27, 654) to give, after deprotection and side chain acylation, the imine product 119.18. The reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions, to give the product 119.18. Using the above procedures, but employing, in place of the 3-aminophenyl phosphonate 119.17, different amino-substituted aryl or heteroaryl phosphonates, products analogous to 119.18 are obtained.

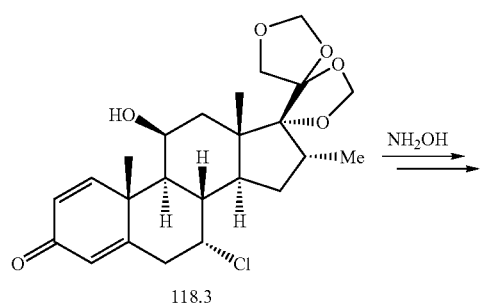

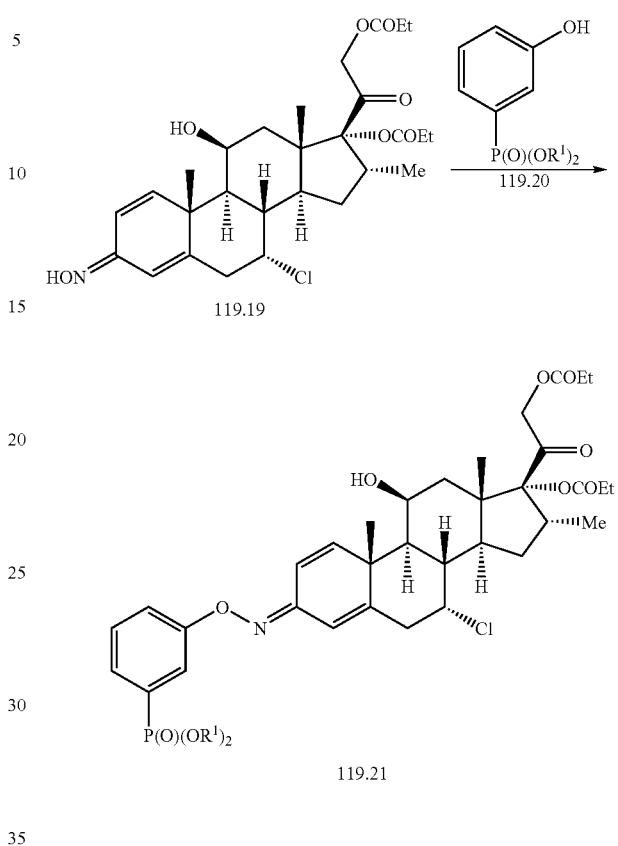

An alternative method for the preparation of phosphonate aclometasone derivatives in which the phosphonate is attached by means of an oximino group is illustrated above. In this procedure, the dienone 118.3 is reacted with hydroxylamine to yield, after deprotection and side chain acylation, the oxime 119.19. The reaction of steroidal 1,4-dien-3-ones with hydroxylamine is described in J. Steroid Bioch., 1976, 7, 795; the reaction is performed between equimolar amounts of the reactants in a polar organic solvent such as pyridine or methanol, optionally in the presence of acetic acid or sodium acetate. The oxime is then reacted with a dialkyl 3-hydroxyphenyl phosphonate 119.20 (Epsilon) in a Mitsonobu reaction, to yield the substituted oxime 119.21. The preparation of aromatic ethers and thioethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol and the hydroxy or mercapto component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656.

Using the above procedures, but employing, in place of the phosphonate 119.20, different dialkyl hydroxy-substituted aryl or heteroaryl phosphonates, the products analogous to 119.21 are obtained.

EXAMPLE 120

Preparation of Representative Aclometasone Derivatives

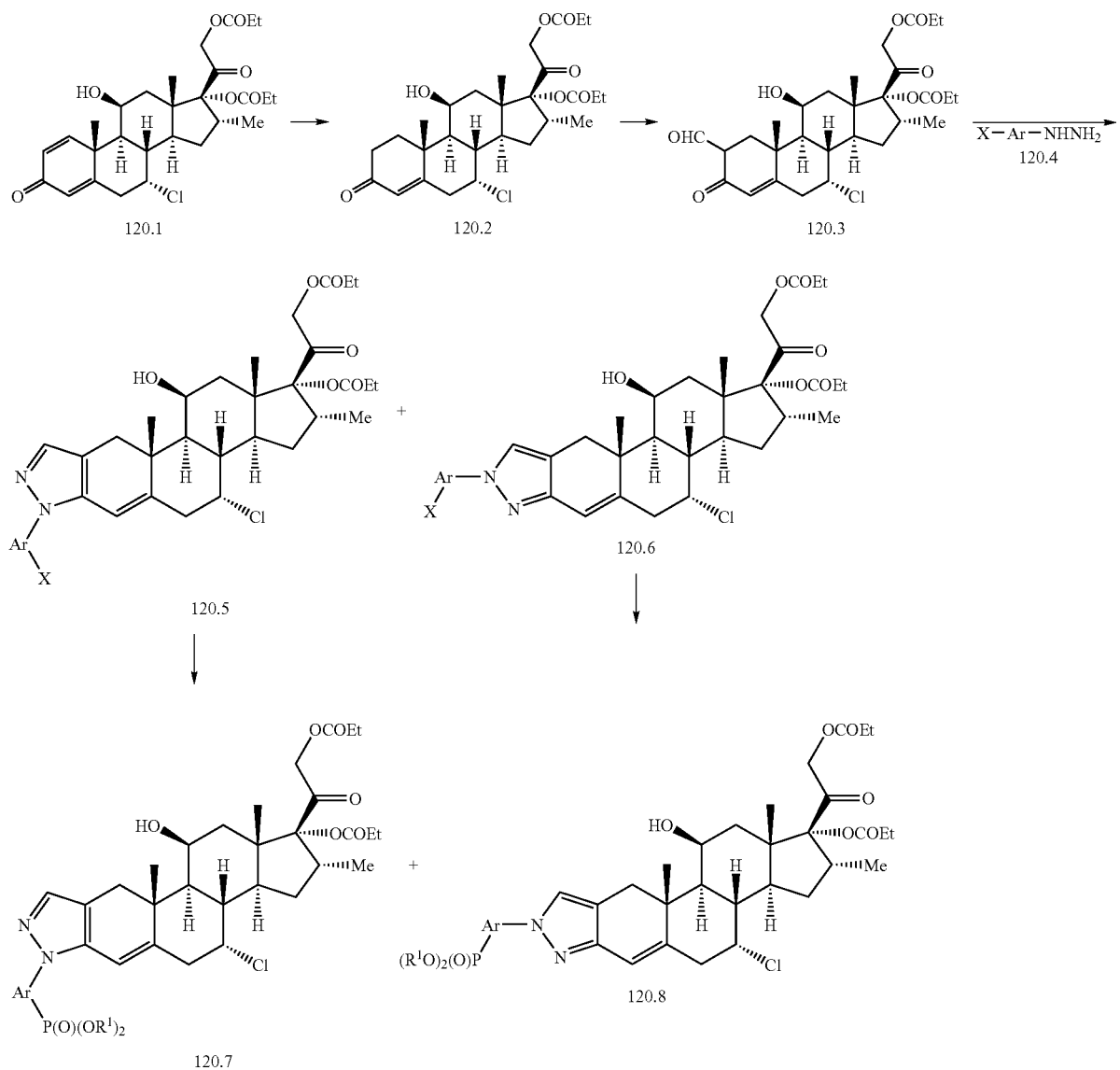

The preparation of the phosphonate aclometasone derivatives in which the phosphonate group is attached to the 1' or 2' position of the pyrazole ring, by means of an aromatic or heteroaromatic group, a heteroatom and a variable carbon chain is illustrated above. In this procedure, Aclometasone dipropionate 120.1 is reduced to afford the 1,2-dihydro product, 120.2. The catalytic hydrogenation reaction is effected by the use of tris(triphenylphosphine)rhodium (I) chloride, for example as described in J. Med. Chem., 2001, 44, 602. The product is then reacted with ethyl formate and a base such as sodium hydride, in an inert solvent such as toluene or dimethylformamide, as described in Australian Patent Application 275950409, to afford the 2-formyl product 120.3. Optionally, the substrate 120.1 is protected prior to the formylation reaction, as described in J. Am. Chem. Soc., 1964, 86, 1520. The 2-formyl product is then reacted with an aryl or heteroaryl hydrazine 120.4, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1-aryl pyrazoles 120.5 and 120.6. The ring-forming reaction is performed between equimolar amounts of the reactants in an acidic solvent such as acetic acid, as described in J. Am. Chem. Soc., 1964, 86, 1520. The pyrazoles 120.5 and 120.6 are then transformed, respectively, into the phosphonates 120.7 and 120.8.

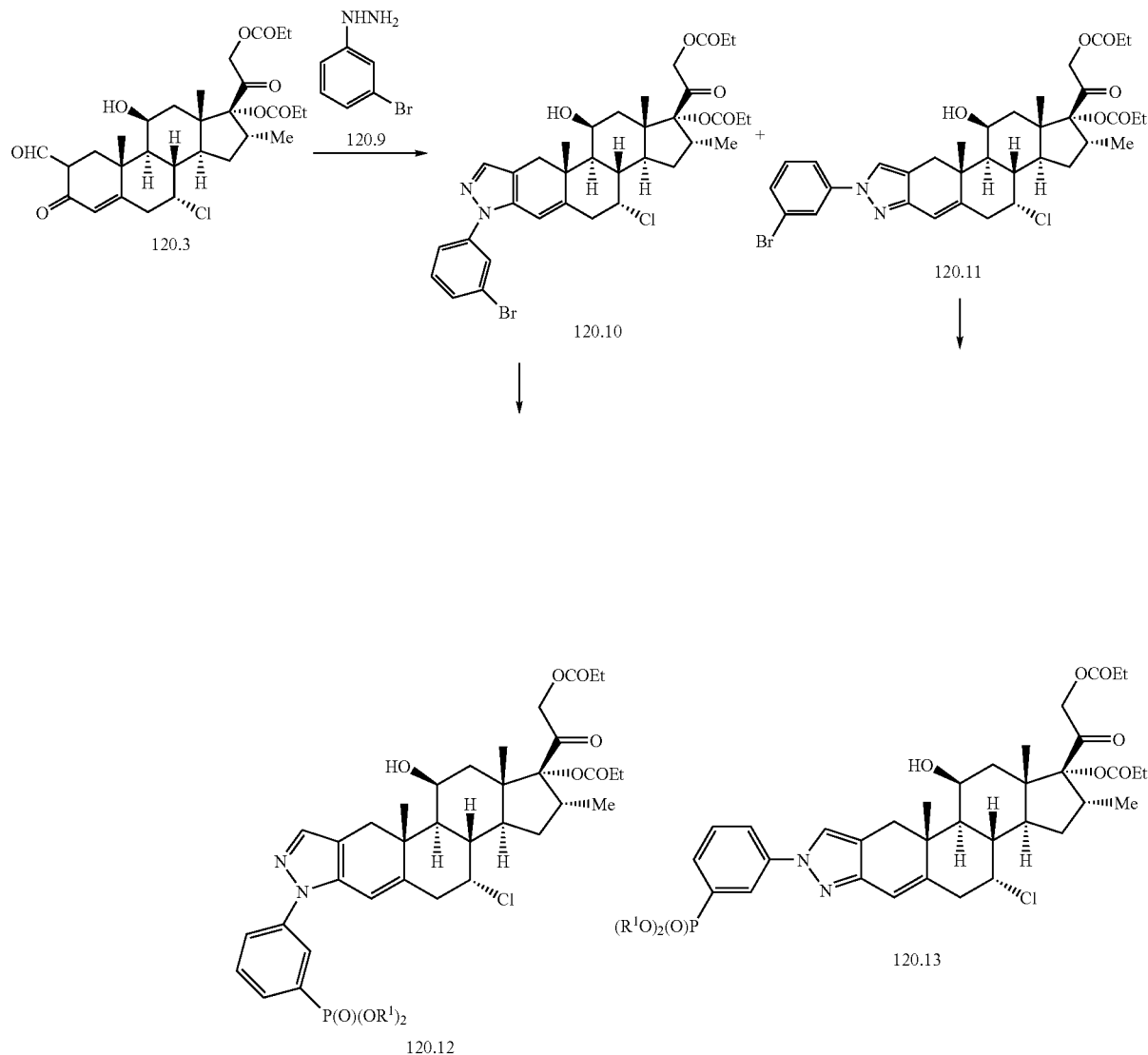

The preparation of phosphonate aclometasone derivatives in which the phosphonate is attached by means of a phenyl group is illustrated above. In this sequence, the ketoaldehyde 120.3 is reacted, as described above, with 3-bromophenylhydrazine 120.9 (Fluka), to give the isomeric pyrazole products 120.10 and 120.11. The products are then reacted, as described above, with a dialkyl phosphite $HP(O)(OR^1)_2$ and a palladium catalyst, to afford respectively the phosphonates 120.12 and 120.13.

Using the above procedures, but employing, in place of 3-bromophenyl hydrazine, different bromoaryl or bromoheteroaryl hydrazines 12.4, the corresponding products 120.7 and 120.8 are obtained.

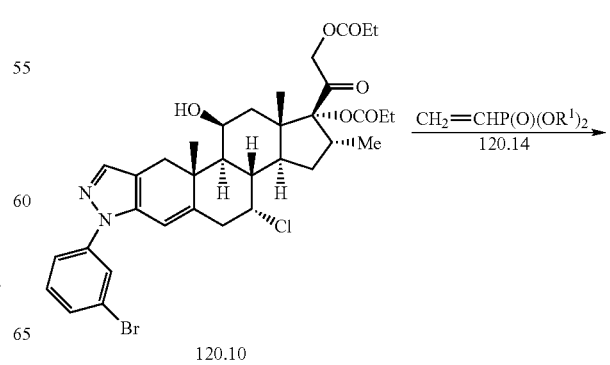

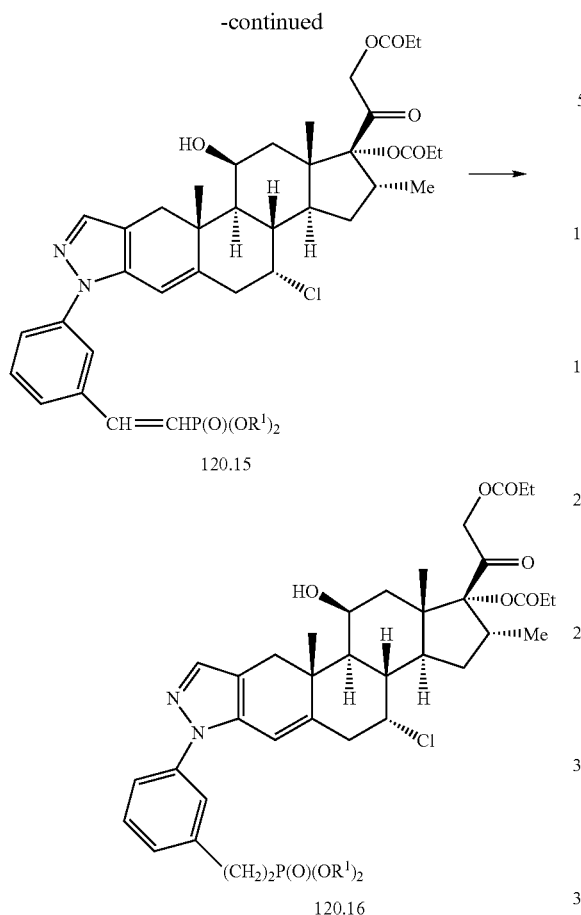

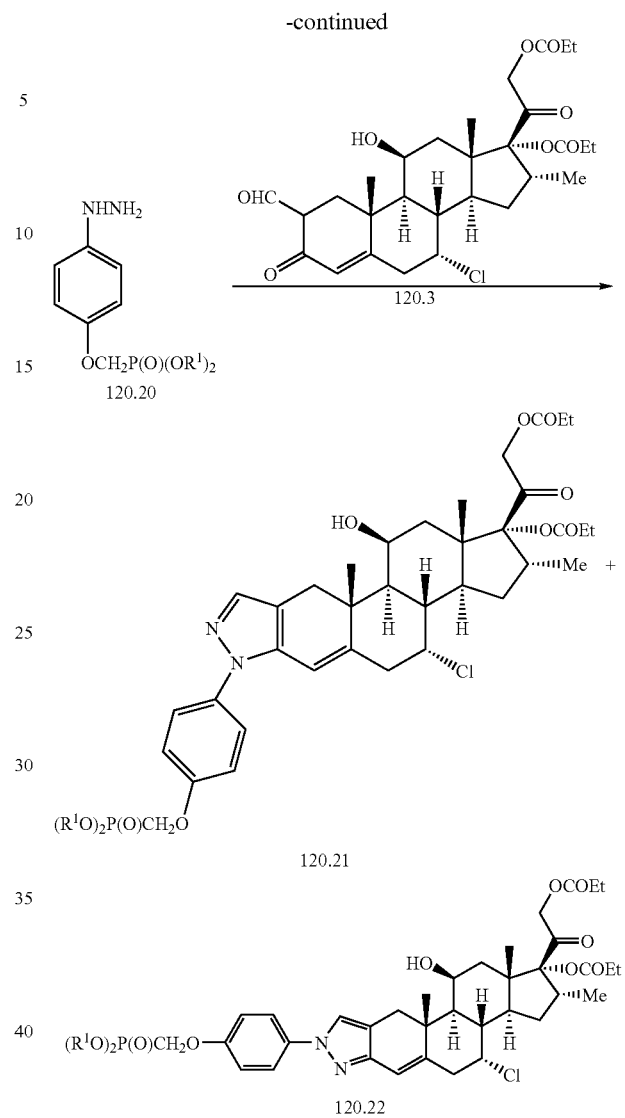

The preparation of phosphonate aclometasone derivatives in which the phosphonate is attached by means of an aromatic or heteroaromatic group and a saturated or unsaturated alkyl chain is illustrated above. In this procedure, the bromophenyl-substituted pyrazole 120.10 is coupled in a Heck reaction, as described above, with, for example a dialkyl vinyl phosphonate 120.14 (Aldrich) to give the unsaturated phosphonate product 120.15. Optionally, the product is reduced, as described above, to give the saturated analog 120.16. Application of the above procedures to the isomeric bromophenyl pyrazole 120.11 affords the products isomeric with 120.15 and 120.16.

Using the above procedures, but employing, in place of the phosphonate 120.14, different dialkyl alkenyl phosphonates, and/or different bromoaryl or heteroaryl pyrazoles 120.5 or 120.6 (X=Br) the products analogous to 120.15 and 120.16 are obtained.

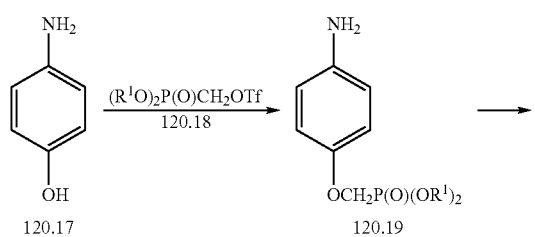

The preparation of phosphonate aclometasone derivatives in which the phosphonate is attached by means of an aryl or heteroaryl group and an alkoxy chain is illustrated above. In this procedure, 4-aminophenol 120.17 is reacted in dimethylformamide solution at ambient temperature with a dialkyl trifluoromethanesulfonyloxymethyl phosphonate 120.18 (Tet. Lett., 1986, 27, 1477) and potassium carbonate to give the ether 120.19. The product is then converted into the corresponding hydrazine 120.20 by means of a diazotization reaction in aqueous ethanolic hydrochloric acid, followed by reduction of the diazonium chloride with tin(II) chloride, as described in J. Med. Chem., 2001, 44, 4031. The hydrazine is then reacted, as described above, with the ketoaldehyde 120.3, to form the isomeric pyrazoles 120.21 and 120.22.

Using the above procedures, but employing, in place of the triflate 120.18, different dialkylphosphono alkyl bromides or triflates, and/or different aromatic or heteroaromatic hydroxyamines, the products analogous to 120.21 and 120.22 are obtained.

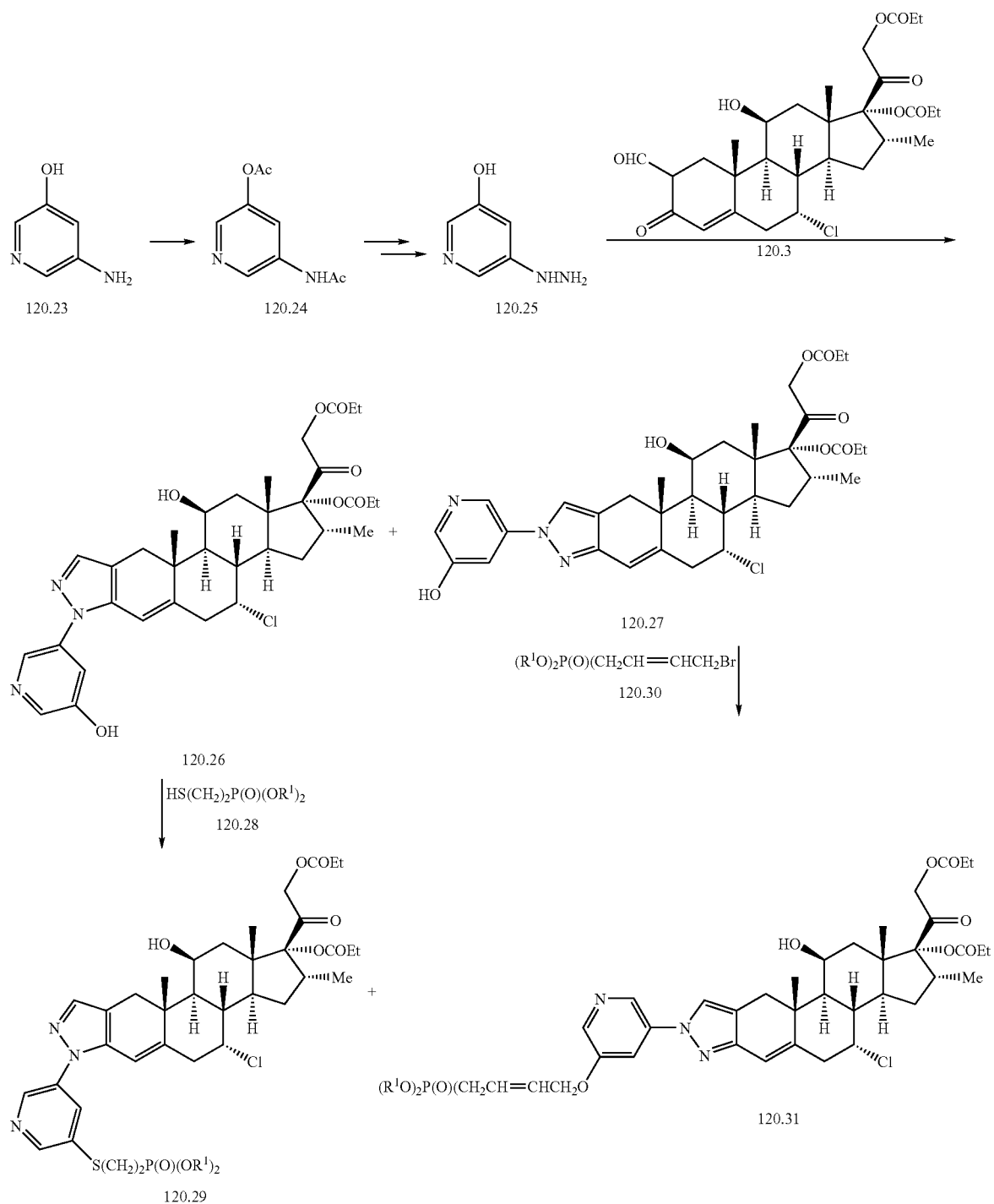

The preparation of phosphonate aclometasone derivatives in which the phosphonate is attached by means of a pyridyl group a heteroatom and a variable carbon chain is illustrated above. In this procedure, 3-amino-5-hydroxypyridine is converted, by reaction with acetic anhydride, into the diacetyl analog 120.24. The product is then transformed by diazotization and reduction, as described above, into the hydrazine 120.25. The hydrazine is then reacted with the ketoaldehyde 120.3 to give the isomeric pyrazoles 120.26 and 120.27. The 2'-pyridyl product 120.26 is reacted in a Mitsonobu reaction, as described above, with a dialkyl mercaptoethyl phosphonate 120.28 (Zh. Obschei. Khim., 1973, 43, 2364) to afford the thioether 120.29. Application of this procedure to the isomeric phenol 120.27 affords the product isomeric to 120.29.

Alternatively, the isomeric phenol 120.27 is reacted, in dimethylformamide solution at ca. 800, with one molar equivalent of a dialkyl bromobutenyl phosphonate 120.30 (J.

Med. Chem., 1992, 35, 1371) and cesium carbonate, to prepare the phosphonate 120.31. Application of this procedure to the isomeric phenol 120.26 affords the product isomeric with 120.31.

Using the above procedures, but employing, in place of the thiol 120.28 or the bromide 120.30, different thiols, alcohols or bromides, and/or different phenols 120.5 or 120.6 in which X is OH, the corresponding products analogous to 120.29 and 120.31 are obtained.

EXAMPLE 121

Preparation of Representative Aclometasone Derivatives

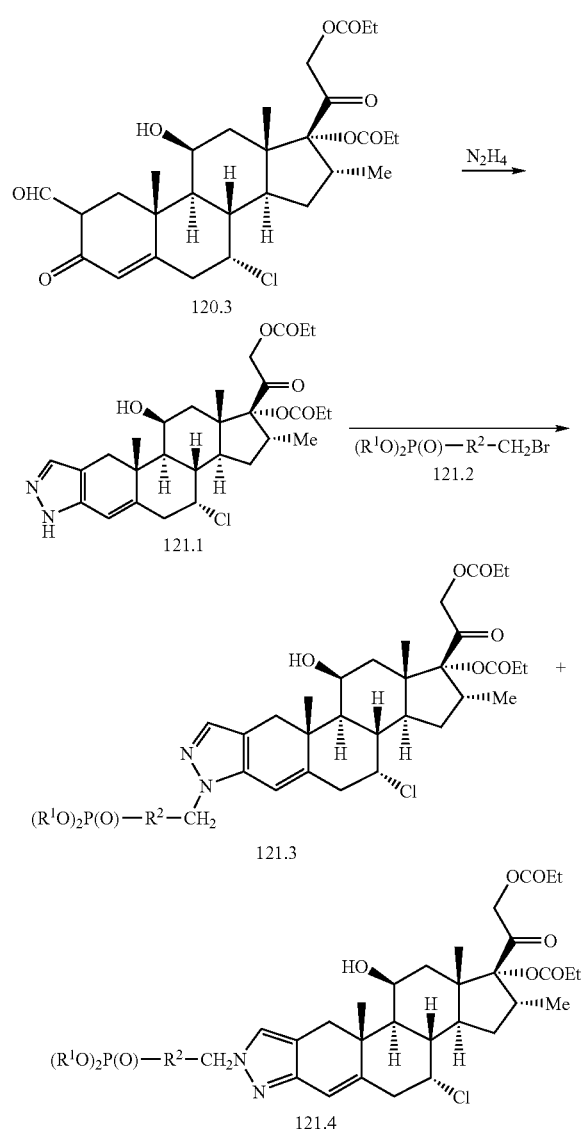

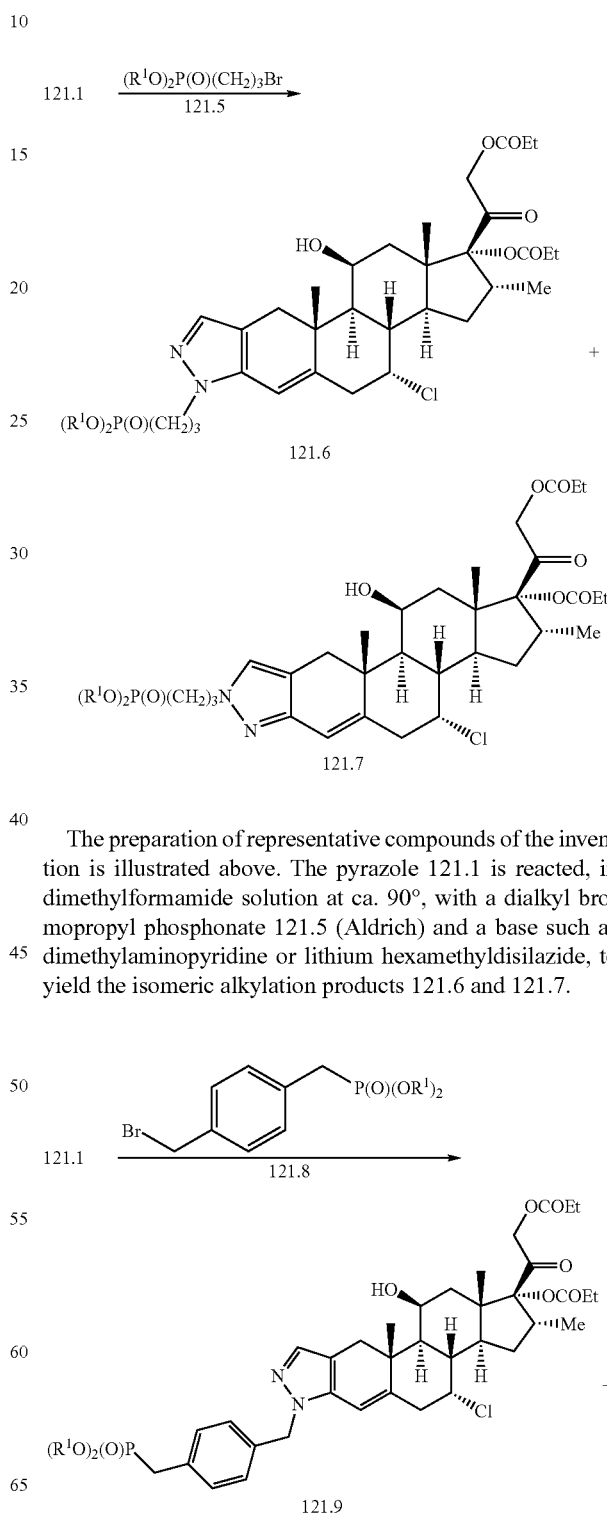

The preparation of representative compounds of the invention in which the phosphonate group is attached by means of a variable carbon linkage is illustrated above. In this procedure, the ketoaldehyde 120.3 is reacted with hydrazine, to afford the pyrazole derivative 121.1. The reaction of steroidal 2-formyl-3-ketones with hydrazine is described in J. Am. Chem. Soc, 1964, 86, 1520. The reaction is performed in acetic acid at ambient temperature. The resulting pyrazole is then reacted with a dialkyl bromomethyl phosphonate 121.2, in which $R^2$ is as defined above, to produce the isomeric 2' and 1' alkylation products 121.3 and 121.4 respectively. The alkylation of substituted pyrazoles is described, for example, in Heterocyclic Chemistry, by T. L. Gilchrist, Longman, 1992, p. 309.

The preparation of representative compounds of the invention is illustrated above. The pyrazole 121.1 is reacted, in dimethylformamide solution at ca. 90°, with a dialkyl bromopropyl phosphonate 121.5 (Aldrich) and a base such as dimethylaminopyridine or lithium hexamethyldisilazide, to yield the isomeric alkylation products 121.6 and 121.7.

-continued

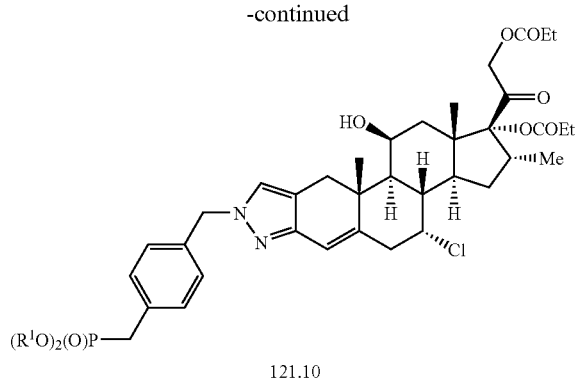

121.10

The preparation of representative compounds of the invention is illustrated above. The pyrazole 121.1 is reacted, as described above, with a dialkyl 4-bromomethyl benzyl phosphonate 121.8 (Tet. 1998, 54, 9341) to give the products 121.9 and 121.10.

EXAMPLES 122-125

Hydrocortisone Derivatives

The structures of hydrocortisone and representative phosphonate esters of the invention are shown below, in which the substituent $R^1$ is H, alkyl, alkenyl, aryl or aralkyl. These compounds incorporate a phosphonate moiety $(R^1O)_2P(O)$ connected to the nucleus by means of a variable linking group, designated as "link" in the attached structures.

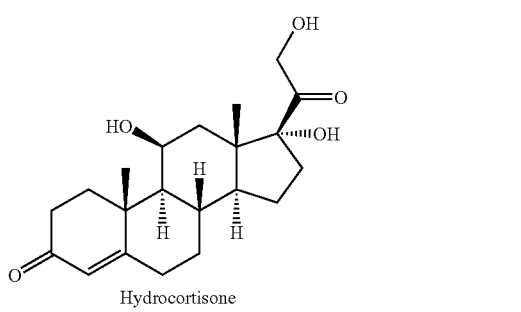

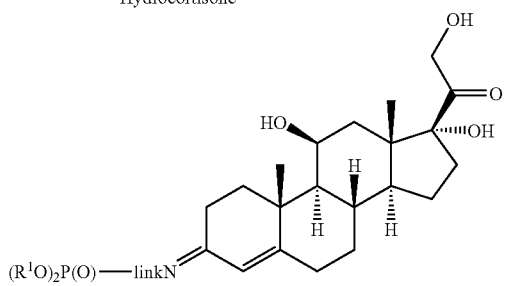

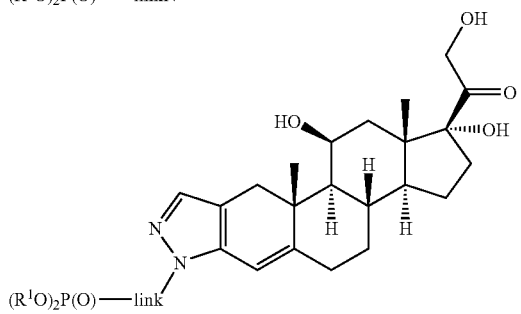

-continued

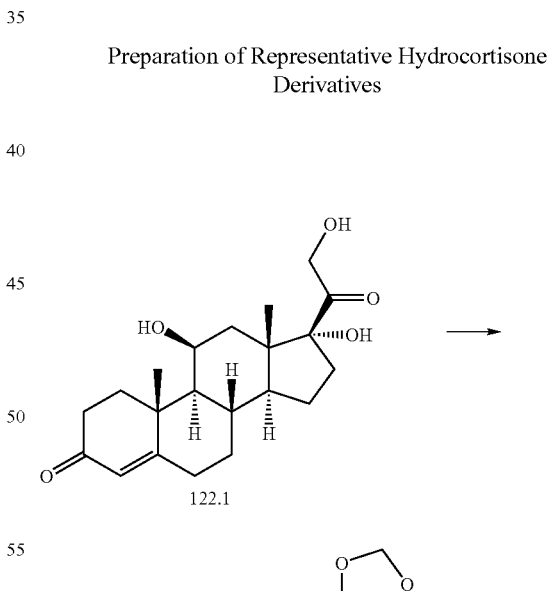

The synthesis of representative phosphonate derivatives of hydrocortisone is outlined in Examples 122-125. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 122

Preparation of Representative Hydrocortisone Derivatives

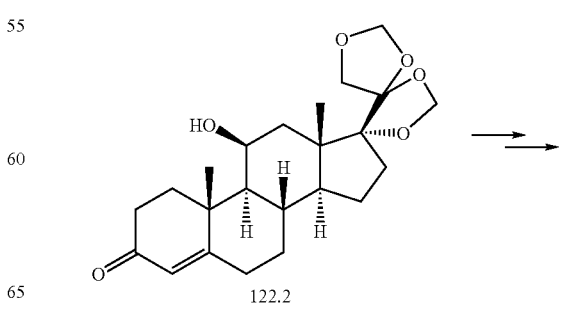

-continued

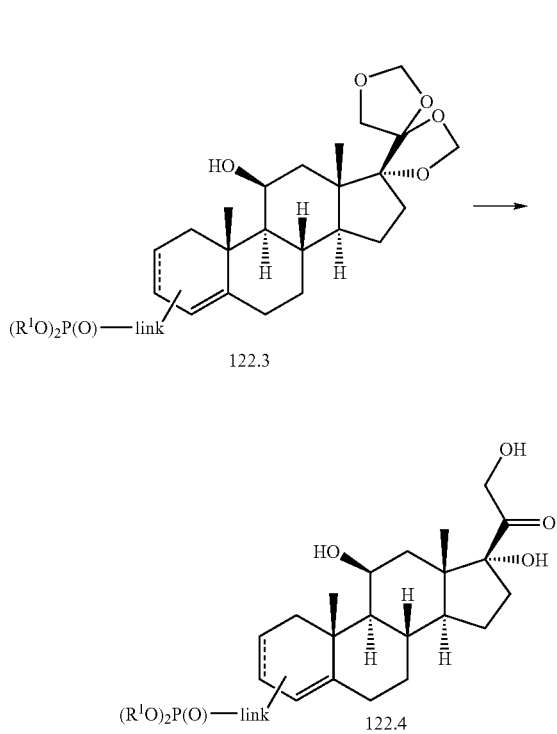

As illustrated above, the steroid side-chain is protected as a bis-methylenedioxy (BMD) moiety. In this sequence, hydrocortisone 122.1 is reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 122.2. The phosphonate moiety is then introduced, using the procedures described below, to produce the phosphonate ester 122.3. The BMD moiety is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the triol 122.4

EXAMPLE 123

Preparation of Representative Hydrocortisone Derivatives

The preparation of hydrocortisone phosphonate derivatives in which the phosphonate is attached by means of an imino or iminoxy group and a variable carbon chain is illustrated above. In this procedure, the BMD-protected derivative 122.2 is reacted with an amine or hydroxylamine 123.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime 123.2. The preparation of oximes of steroidal 3-ketones is described in Anal. Bioch., 1978, 86, 133. and in J. Mass. Spectrom., 1995, 30, 497. In cases in which X is not dialkylphosphono, the substituent X is converted, using the methods described below; into a phosphonate-containing substituent; the BMD-protected side-chain is then removed to afford the triol 123.3.

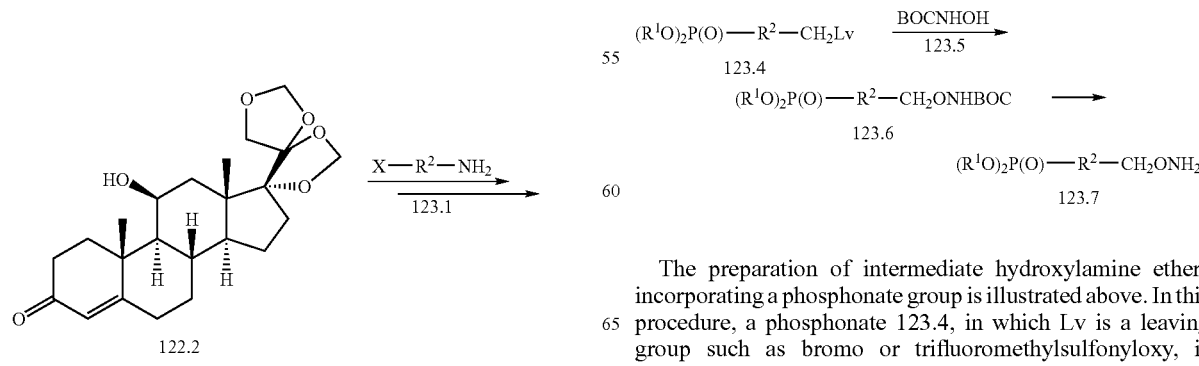

The preparation of intermediate hydroxylamine ethers incorporating a phosphonate group is illustrated above. In this procedure, a phosphonate 123.4, in which Lv is a leaving group such as bromo or trifluoromethylsulfonyloxy, is reacted with BOC-hydroxylamine 123.5 (Aldrich) to produce the ether 123.6. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 123.7.

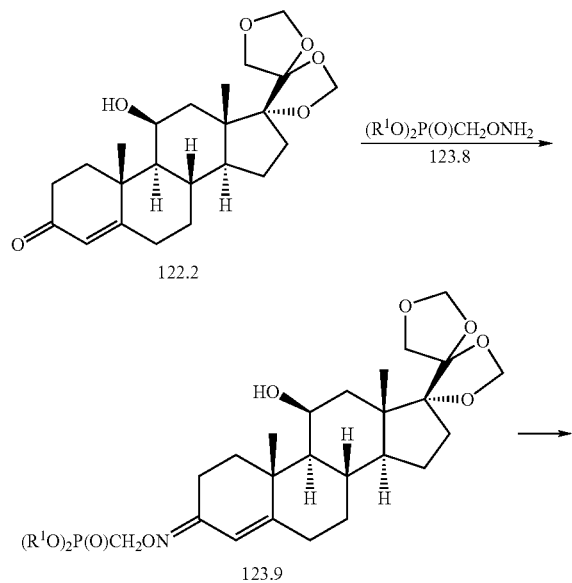

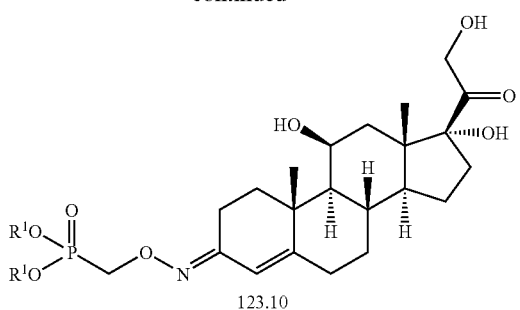

The preparation of hydrocortisone phosphonate derivatives in which the phosphonate is attached by means of an iminoxy group is illustrated above. In this procedure, the substrate 122.2 is reacted with a dialkyl phosphonomethyl hydroxylamine 123.8, prepared as described above from a dialkyl trifluoromethylsulfonyloxymethyl phosphonate (Tet. Lett., 1986, 27, 1477) and BOC-hydroxylamine, to afford the oxime 123.9 which is deprotected to afford the triol 123.10. The oxime forming reaction is typically performed at ambient temperature in ethanol-acetic acid solution between equimolar amounts of the reactants. Using the above procedures, but employing, in place of the hydroxylamine ether 123.8, different oxime ethers 123.7, the corresponding products 123.3 are obtained.

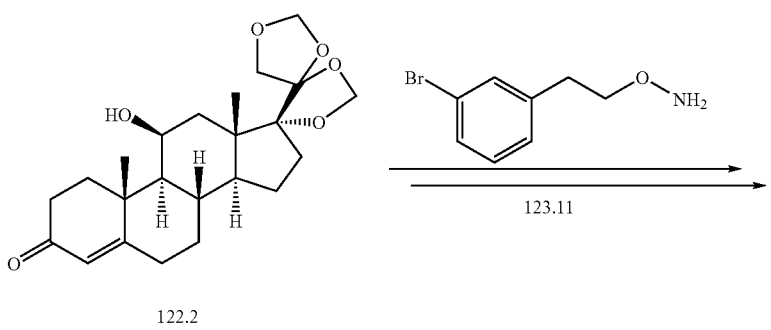

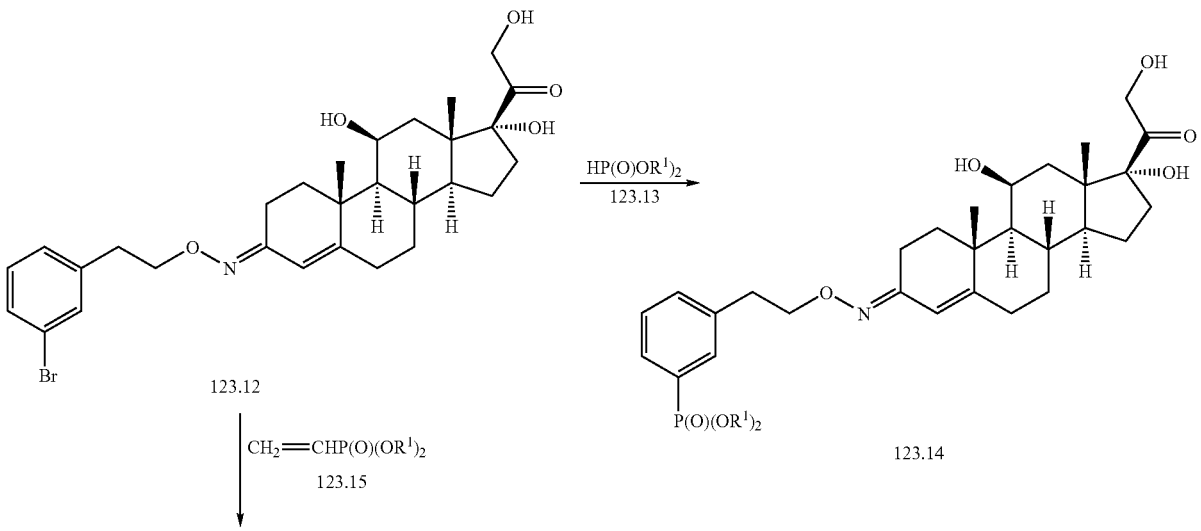

-continued

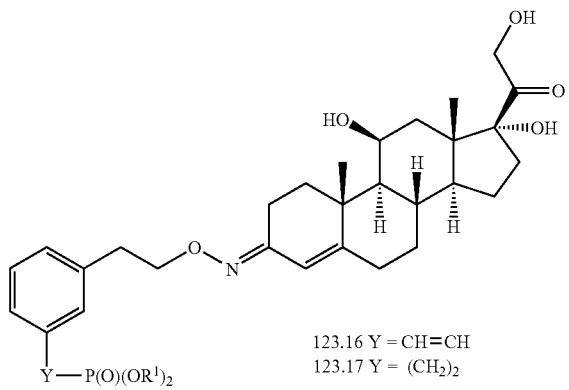

123.16 Y = CH=CH
123.17 Y = (CH₂)₂

The preparation of hydrocortisone phosphonate derivatives in which the phosphonate group is attached by means of a phenyl ethoxy group is illustrated above. In this procedure, the enone 122.2 is reacted, as described above, with O-(3-bromophenyl)ethyl hydroxylamine 123.11, prepared as described above from 2-(3-bromophenyl)ethyl bromide (French Patent FR 1481052), to give, after deprotection of the side-chain, the oxime 123.12. The product is then reacted, in the presence of a palladium catalyst, with a dialkyl phosphite 123.13 to afford the phosphonate 123.14. The preparation of arylphosphonates by means of a coupling reaction between aryl bromides and dialkyl phosphites is described in J. Med. Chem., 35, 1371, 1992. The reaction is performed in an inert solvent such as toluene, in the presence of a base such as triethylamine and a catalytic amount of tetrakis(triphenylphosphine)palladium(0).

Alternatively, the bromo compound 123.12 is coupled with a dialkyl vinylphosphonate 123.15 (Aldrich) to afford the phosphonate 123.16. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 123.16 is reduced, for example by reaction with diimide, to produce the saturated analog 123.17. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane.

Using the above procedures, but employing, in place of the bromophenyl ethoxy reagent 123.11, different bromo-substituted aryl or heteroaryl alkoxy hydroxylamines, and/or different dialkyl alkenyl phosphonates, the products analogous to the compounds 123.14, 123.16 and 123.17 are obtained.

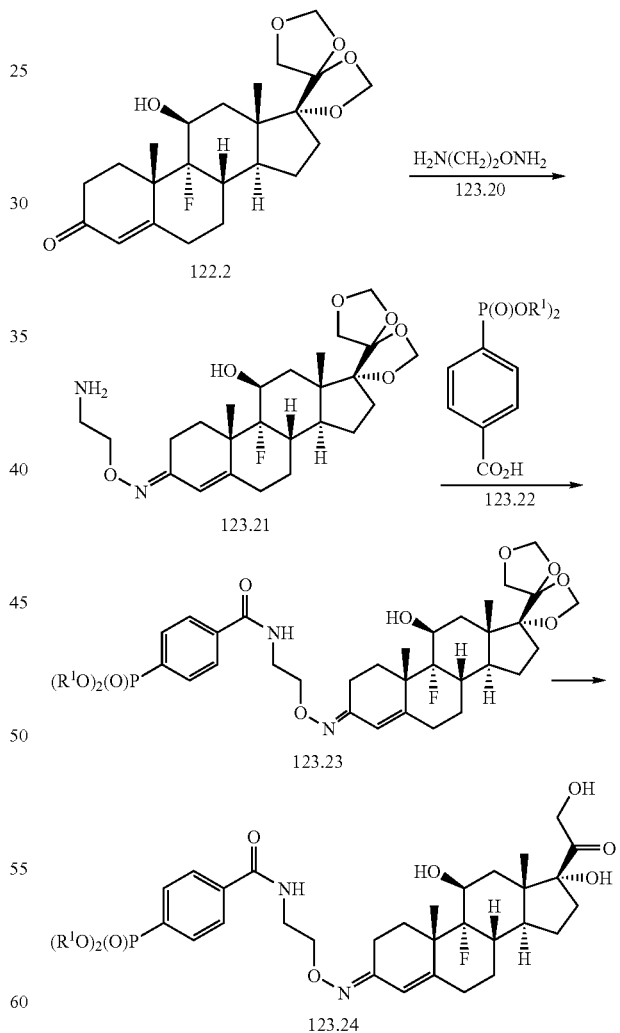

The preparation of hydrocortisone phosphonate derivatives in which the phosphonate is attached by means of an oximino group and an amide linkage is illustrated above. In this procedure, the enone 122.2 is reacted with O-(2-aminoethyl)hydroxylamine 123.20 (Pol. J. Chem., 1981, 55, 1163)

to yield the oxime 123.21. The reaction of steroidal 1,4-dien-3-ones with substituted hydroxylamines is described in J. Steroid Bioch., 1976, 7, 795. The reaction is performed between equimolar amounts of the reactants in a polar organic solvent such as pyridine or methanol, optionally in the presence of acetic acid or sodium acetate. The oxime is then coupled with a dialkyl 4-carboxyphenyl phosphonate 123.22 (Epsilon), to yield the amide oxime 123.23. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid is first converted into an activated derivative such as the acid chloride, anhydride, mixed anhydride, imidazolide and the like, and then reacted with the amine, in the presence of an organic base such as, for example, pyridine, to afford the amide. The conversion of a carboxylic acid into the corresponding acid chloride is effected by treatment of the carboxylic acid with a reagent such as, for example, thionyl chloride or oxalyl chloride in an inert organic solvent such as dichloromethane, optionally in the presence of a catalytic amount of dimethylformamide. The amide product 123.23 is then converted into the triol 123.24. Using the above procedures, but employing, in place of the hydroxylamine 123.20, different amino-substituted hydroxylamines, and/or different carboxy-substituted phosphonates, the products analogous to 123.24 are obtained.

EXAMPLE 124

Preparation of Representative Hydrocortisone Derivatives

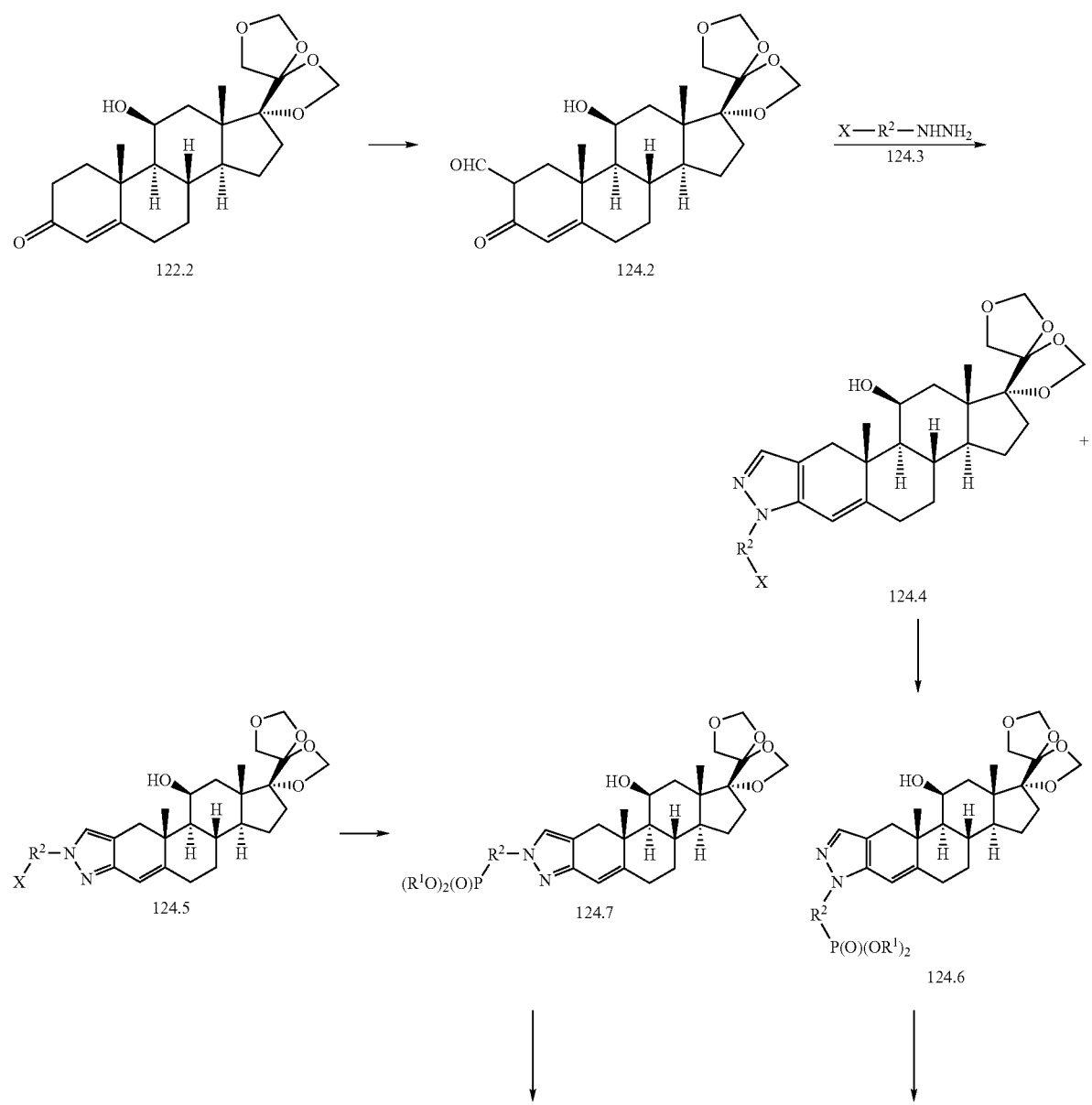

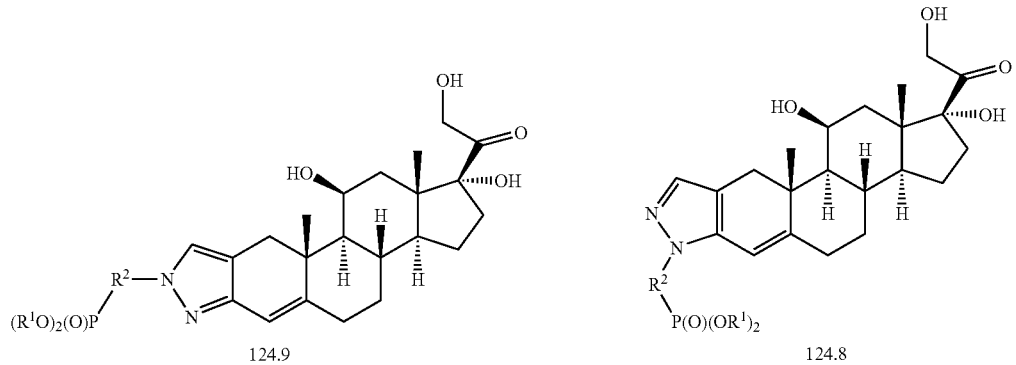

124.9            124.8

The preparation of hydrocortisone phosphonate derivatives in which the phosphonate group is attached to the 1' or 2' position of the pyrazole ring, by means of a variable carbon chain is illustrated above. In this procedure, the BMD-protected enone 124.1 is reacted with ethyl formate and a base such as sodium hydride, in an inert solvent such as toluene or dimethylformamide, as described in *J. Am. Chem. Soc.,* 1964, 86, 1520, to afford the 2-formyl product 124.2. This compound is then reacted with an alkyl, aralkyl, aryl or heteroaryl hydrazine 124.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 124.4 and 124.5. The pyrazole-forming reaction is performed between equimolar amounts of the reactants in an acidic solvent such as acetic acid, as described in *J. Am. Chem. Soc.,* 1964, 86, 1520. The pyrazoles 124.4 and 124.5 are then transformed via the BMD-protected intermediates 124.6 and 124.7, into the phosphonates 124.8 and 124.9.

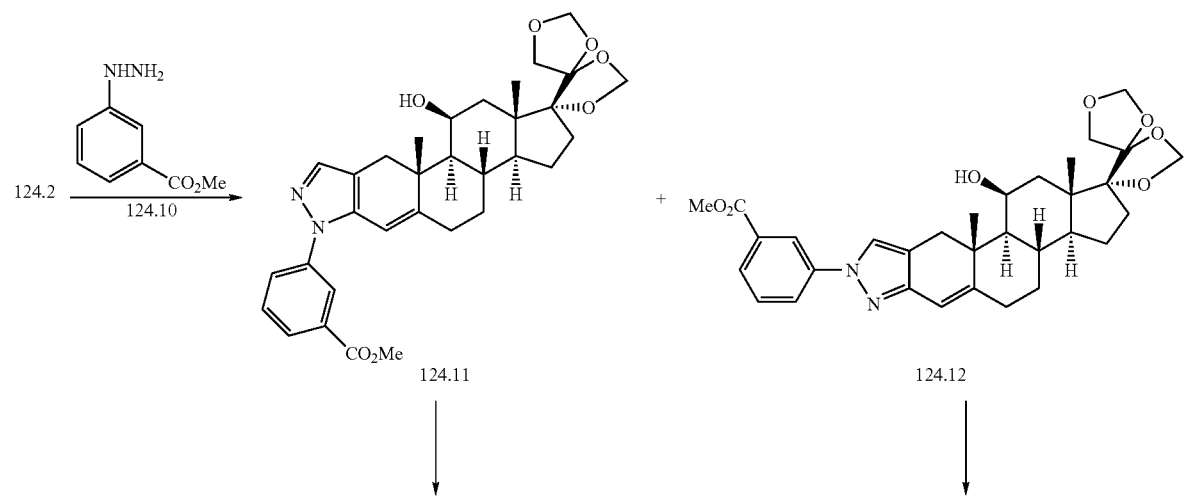

-continued
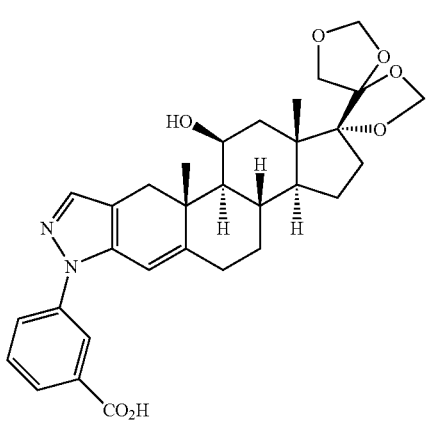
124.13
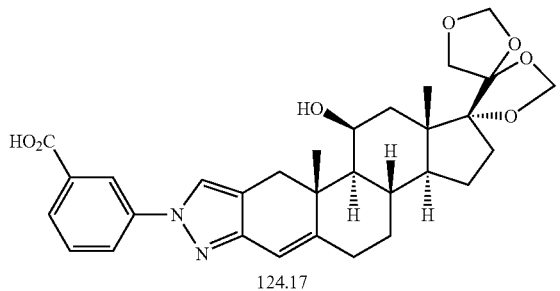
124.17
↓ HNCH₂P(O)(OR¹)₂
124.14
P(O)(OR¹)₂
NH₂
124.18
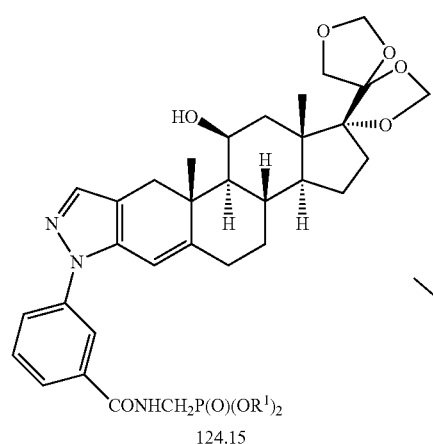
124.15
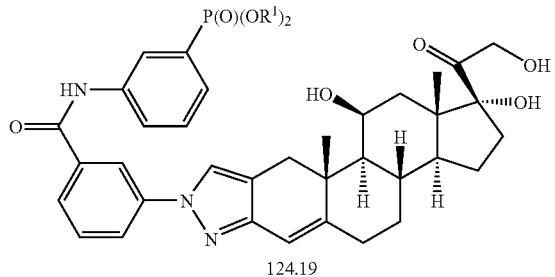
124.19
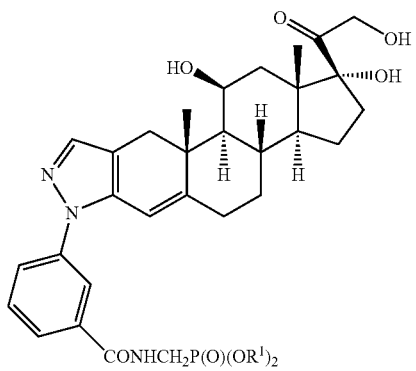
124.16

The preparation of hydrocortisone phosphonate derivatives in which the phosphonate moiety is attached by means of a phenyl ring and an amide linkage is illustrated above. In this procedure, the ketoaldehyde 124.2 is reacted, as described above, with 3-carbomethoxyphenylhydrazine 124.10 (Apin) to give the pyrazoles 124.11 and 124.12. The 2'-substituted isomer 124.11 is then reacted with one molar equivalent of lithium hydroxide in aqueous dimethoxyethane, to produce the carboxylic acid 124.13. The acid is then coupled, as described above, with a dialkyl aminomethyl phosphonate 124.14 (Interchim) to give the amide 124.15; deprotection then affords the triol 124.16.

Alternatively, the 1-substituted pyrazole 124.12 is hydrolyzed, as described above, to the carboxylic acid 124.17. The product is then coupled with a dialkyl 3-aminophenyl phosphonate 124.18 (J. Med. Chem., 1984, 27, 654) to yield after deprotection the triol amide 124.19. Using the above procedures, but employing, in place of the carbomethoxyphenyl hydrazine 124.20, different carbomethoxy-substituted aralkyl, aryl or heteroaryl alkoxy hydrazines, and/or different dialkyl amino-substituted phosphonates, the products analogous to the compounds 124.16 and 124.19 are obtained.

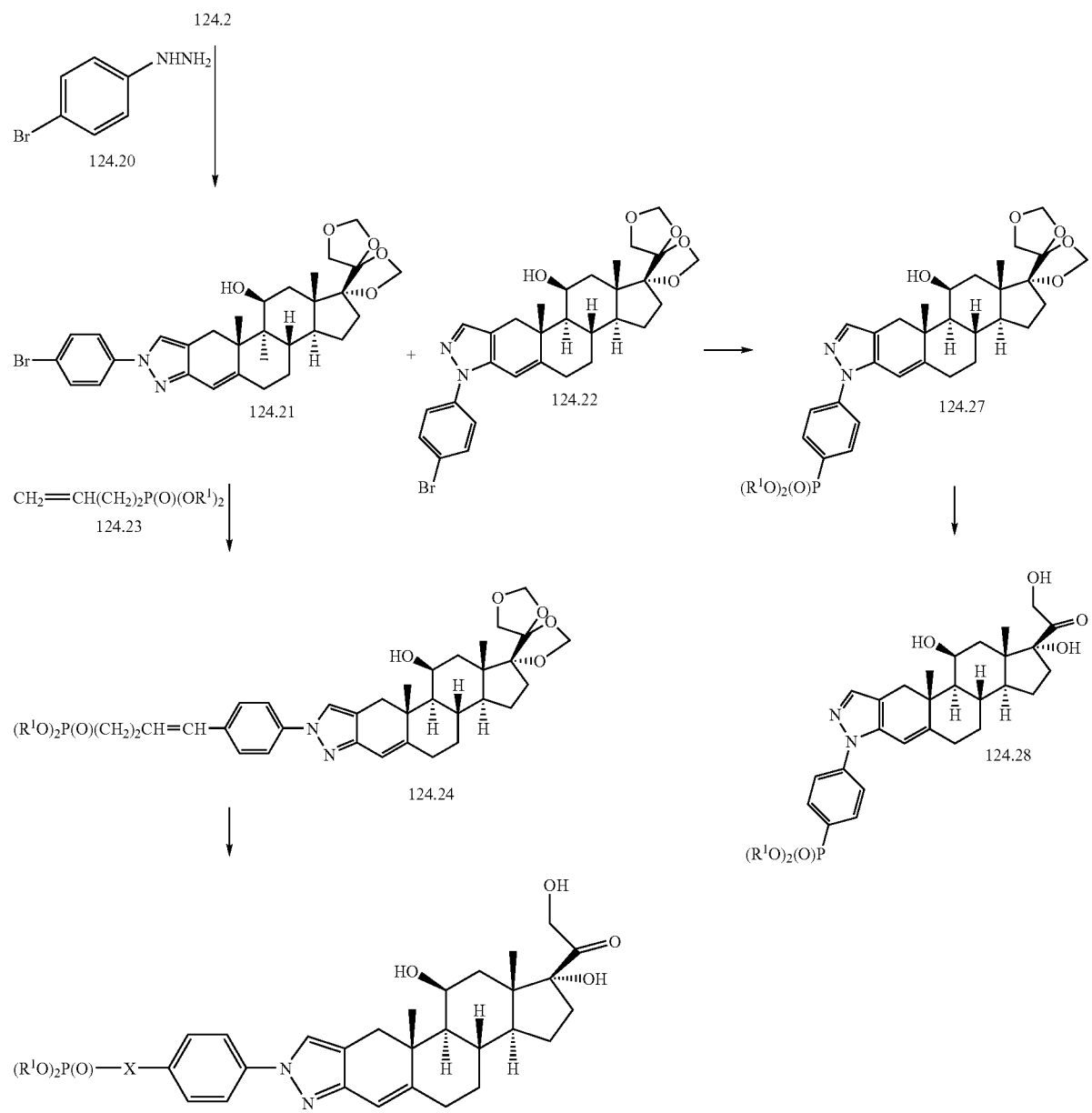

The preparation of hydrocortisone phosphonate derivatives in which the phosphonate group is attached by means of a phenyl group or a phenyl group and a saturated or unsaturated carbon chain is illustrated above. In this procedure, the ketoaldehyde 124.2 is reacted, as described above, with 4-bromophenyl hydrazine 124.20 (*J. Organomet. Chem.*, 1999, 62, 581) to produce the pyrazoles 124.21 and 124.22. The 1'-substituted isomer 124.21 is coupled, as described above, in the presence of a palladium catalyst, with a dialkyl butenyl phosphonate 124.23 (*Org. Lett.*, 2001, 3, 217) to give the phosphonate 124.24. The product is then deprotected to afford the triol 124.25. Optionally, the styrenoid double bond present in the product 124.25 is reduced, as described above, to produce the saturated analog 124.26.

Alternatively, the 2'-substituted pyrazole 124.22 is coupled, in the presence of a palladium catalyst, with a dialkyl phosphite to prepare the phosphonate 124.27 which is deprotected to give the triol 124.28. The preparation of arylphosphonates by means of a coupling reaction between aryl bromides and dialkyl phosphites is described in *J. Med. Chem.*, 35, 1371, 1992. This reaction is performed in an inert solvent such as toluene, in the presence of a base such as triethylamine and tetrakis(triphenylphosphine)-palladium(0). Using the above procedures, but employing, in place of the bromophenyl hydrazine 124.20, different bromo-substituted aralkyl, aryl or heteroaryl alkoxy hydrazines, and/or different dialkyl alkenyl phosphonates, the products analogous to the compounds 124.25, 124.26 and 124.28 are obtained.

EXAMPLE 125

Preparation of Representative Hydrocortisone Derivatives

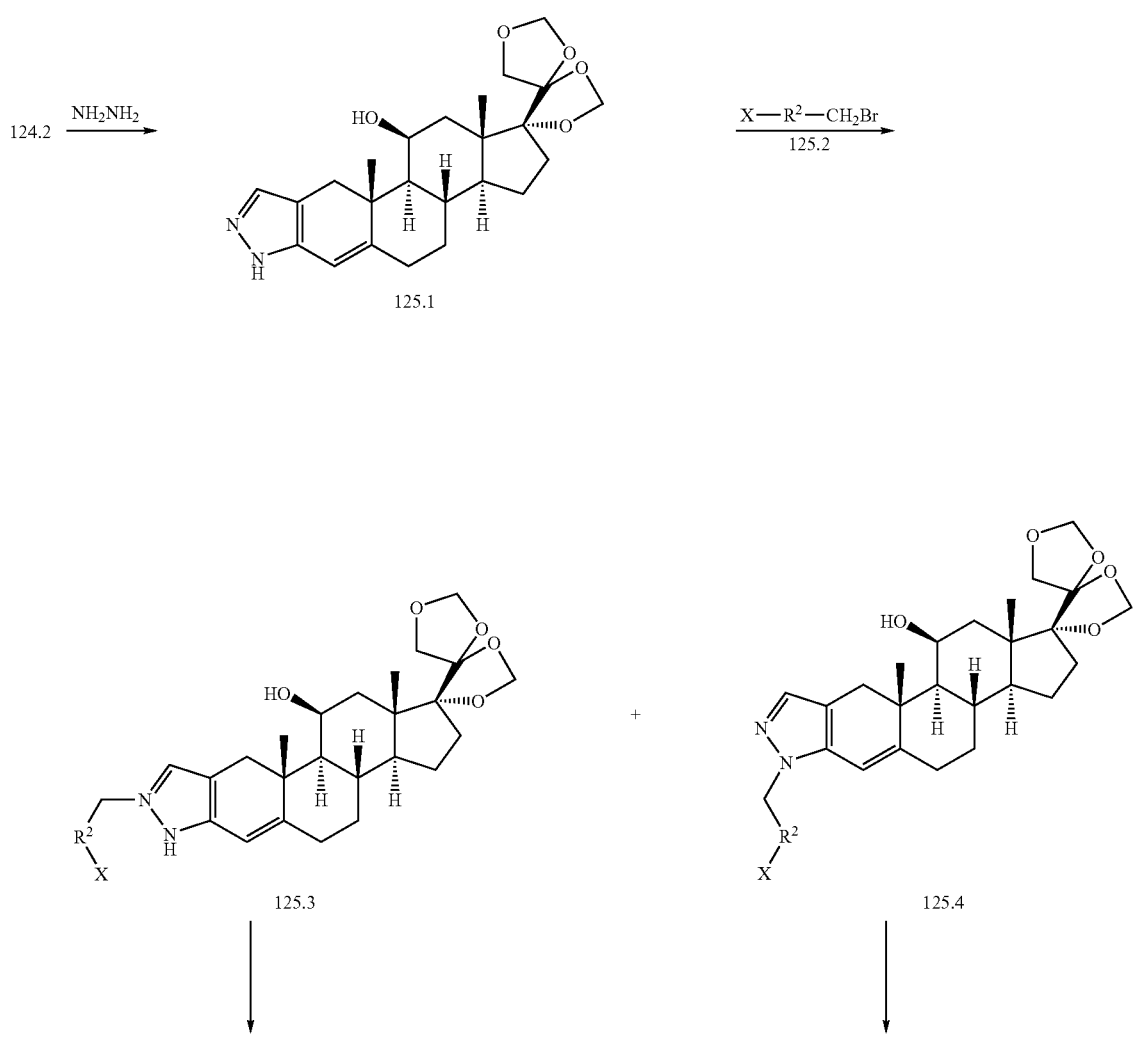

-continued

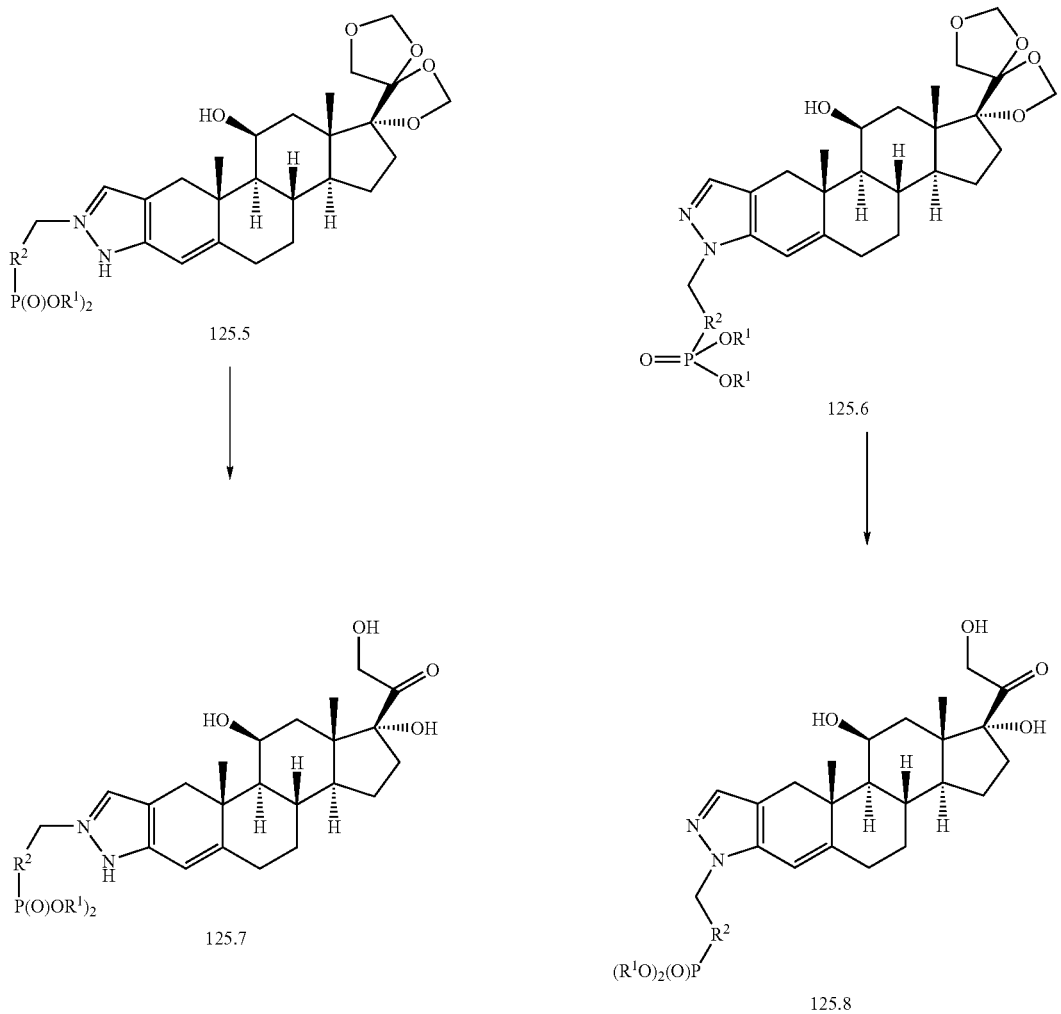

The preparation of hydrocortisone phosphonate derivatives in which the phosphonate group is attached by means of a variable carbon linkage is illustrated above. In this procedure, the ketoaldehyde 124.2 is reacted with hydrazine, to afford the pyrazole derivative 125.1. The reaction of steroidal 2-formyl-3-ketones with hydrazine is described in J. Am. Chem. Soc, 1964, 86, 1520. The reaction is performed in ethanol at reflux temperature. The pyrazole product is then reacted with a bromomethyl compound 125.2, in which $R^2$ and X are as defined above, to yield the alkylation products 125.3 and 125.4. The alkylation of substituted pyrazoles is described, for example, in Heterocyclic Chemistry, by T. L. Gilchrist, Longman, 1992, p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The products 125.3 and 125.4 are, except in cases where X is dialkylphosphono, converted into the phosphonates 125.5 and 125.6, using the procedures described herein, and deprotection then affords the triols 125.7 and 125.8.

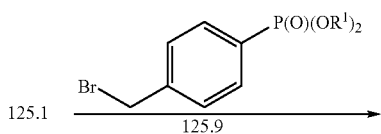

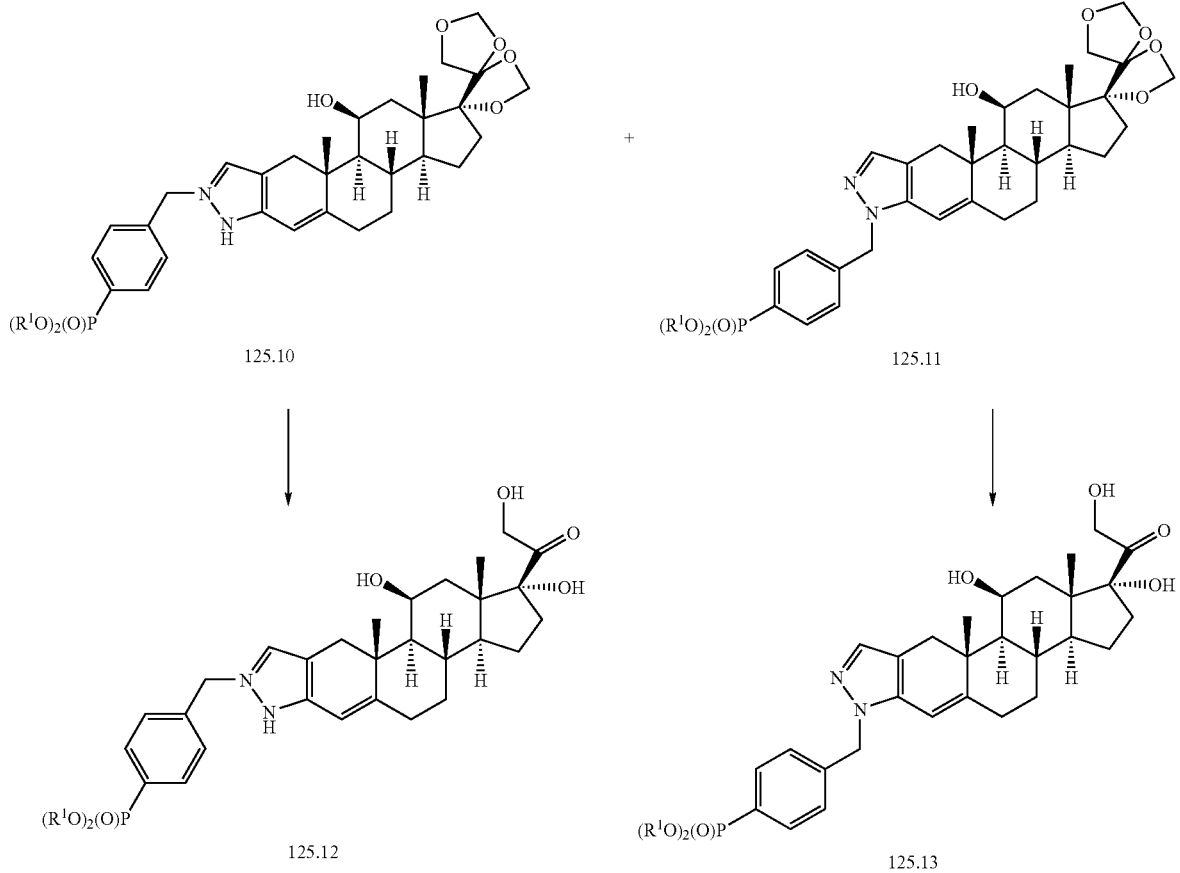
Representative hydrocortisone derivatives can be prepared as illustrated above. The pyrazole 125.1 is reacted, as described above, with one molar equivalent of a dialkyl 4-(bromomethyl)phenyl phosphonate 125.9 (WO 2003042150) to give the alkylated pyrazoles 125.10 and 125.11. Deprotection then yields the triols 125.12 and 125.13.
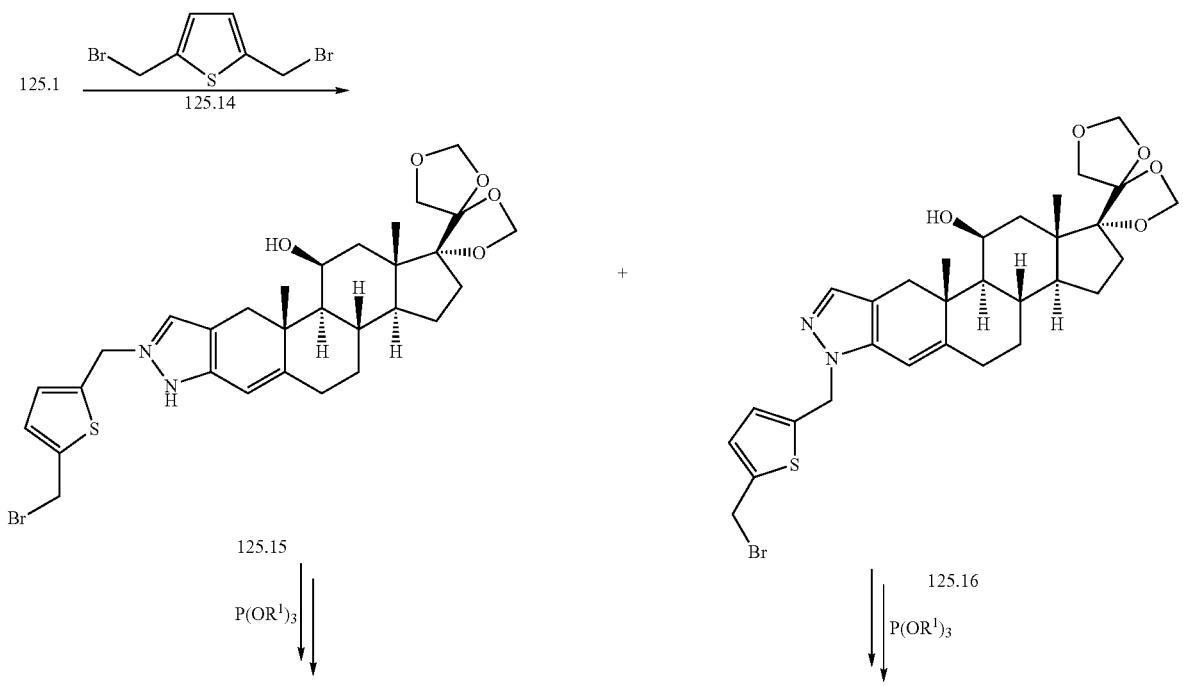

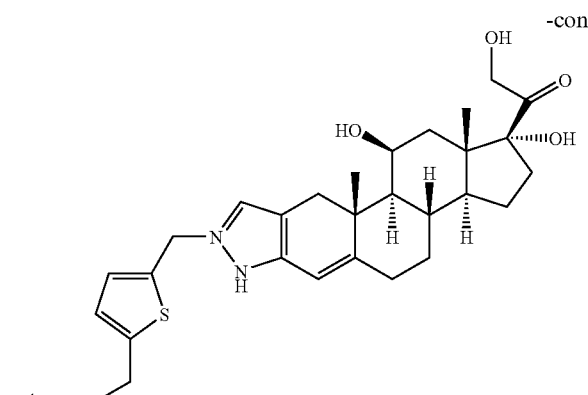

125.17

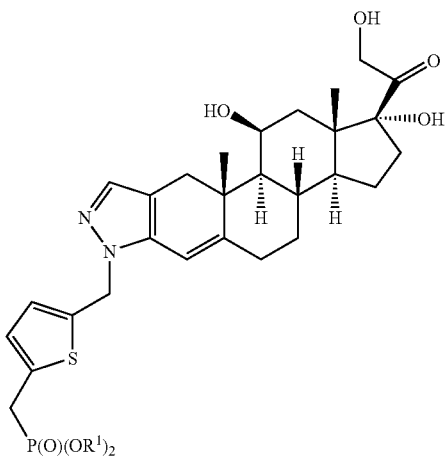

125.18

Representative hydrocortisone derivatives can be prepared as illusrated above. The pyrazole 125.1 is reacted, as described above, with 2,5-bis(bromomethyl)thiophene 125.14 (Tet. 1999, 55, 4709) to give the pyrazoles 125.15 and 125.16. The products are subjected to an Arbuzov reaction, in which the bromomethyl substituent is converted into the dialkyl phosphonomethyl substituent, by reaction with a trialkyl phosphite at 120°, to prepare, after deprotection of the side chain, the phosphonates 125.17 and 125.18. The Arbuzov reaction is described in *Handb. Organophosphorus Chem.*, 1992, 115-72. In the procedure, the substrate is heated at from 60° to about 160° with a five to fifty-fold molar excess of the trialkyl phosphite.

Using the above procedures, but employing, in place of the dibromide 125.14, different dibromides, the products analogous to 125.17 and 125.18 are obtained.

EXAMPLES 126-129

Dexamethasone Derivatives (124-126)

The structures of dexamethasone and representative phosphonate esters of the invention are shown below, in which the substituent $R^1$ is H, alkyl, alkenyl, aryl or aralkyl. These compounds incorporate a phosphonate moiety $(R^1O)_2P(O)$ connected to the nucleus by means of a variable linking group, designated as "link" in the attached structures.

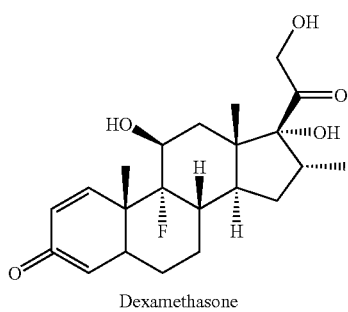

Dexamethasone

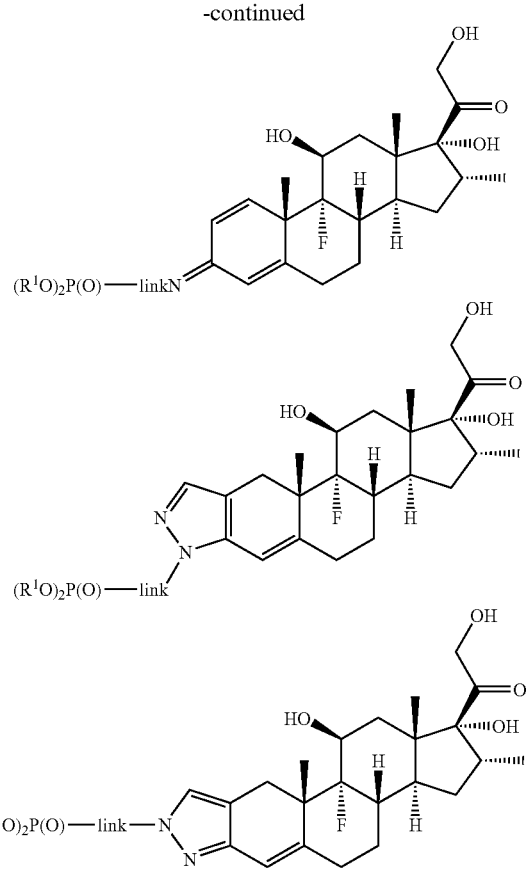

The synthesis of representative phosphonate derivatives of hydrocortisone is outlined in Examples 126-129. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 126

Preparation of Representative Dexamethasone Derivatives

The steroid side-chain is protected as a bis-methylenedioxy (BMD) moiety. In this sequence, Dexamethasone 126.1 is reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 126.2. The phosphonate moiety is then introduced, using the procedures described below, to produce the phosphonate ester 126.3. The BMD moiety is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the triol 126.4

EXAMPLE 127

Preparation of Representative Dexamethasone Derivatives

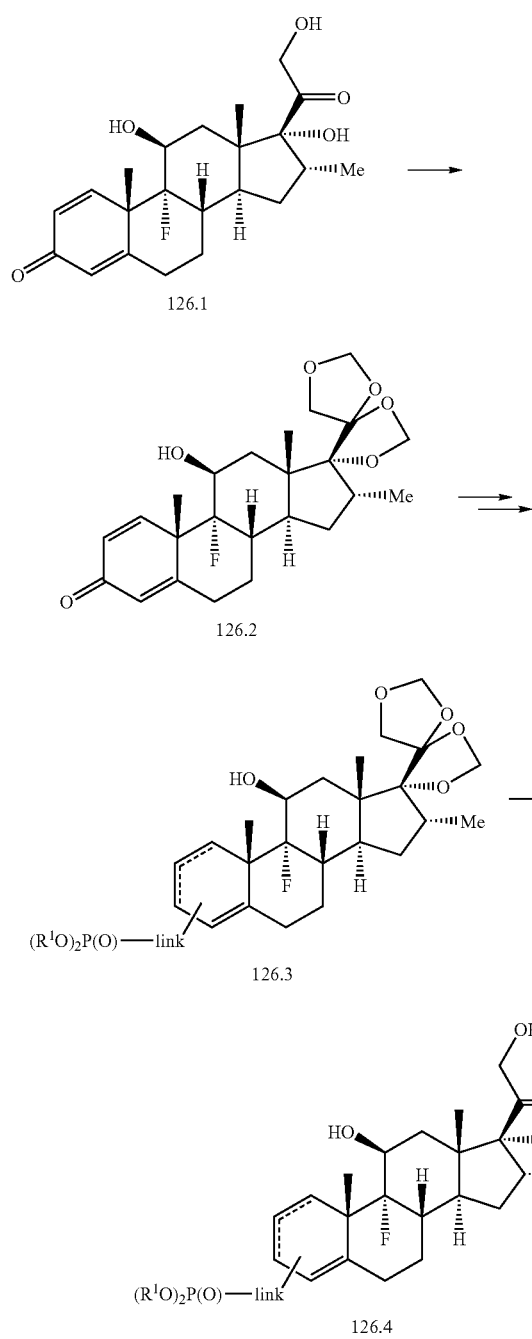

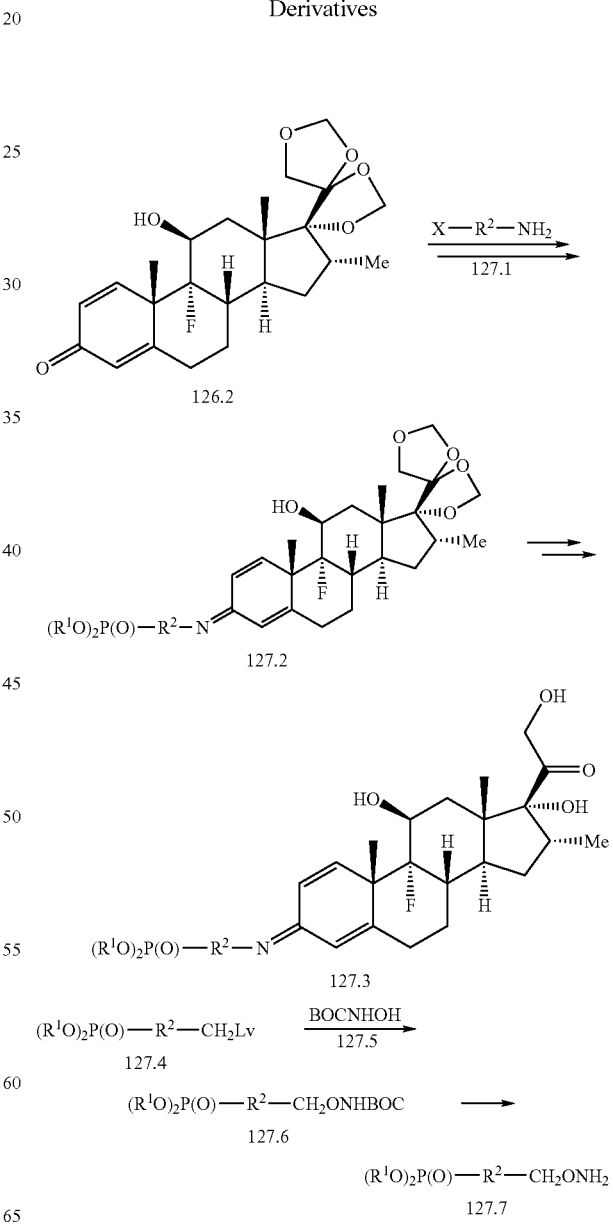

The preparation of dexamethasone phosphonates in which the phosphonate is attached by means of an imino or iminoxy group and a variable carbon chain is illustrated above. In this procedure, the BMD-protected derivative 126.2 is reacted with an amine or hydroxylamine 127.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in Anal. Bioch., 1978, 86, 133. and in J. Mass. Spectrom., 1995, 30, 497. The BMD-protected side-chain compound 127.2 is then converted into the triol 127.3.

The preparation of hydroxylamine ethers incorporating a phosphonate group is also illustrated above. In this procedure, a phosphonate 127.4, in which Lv is a leaving group such as bromo or trifluoromethylsulfonyloxy, is reacted with BOC-hydroxylamine 127.5 (Aldrich) to produce the ether 127.6. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 127.7.

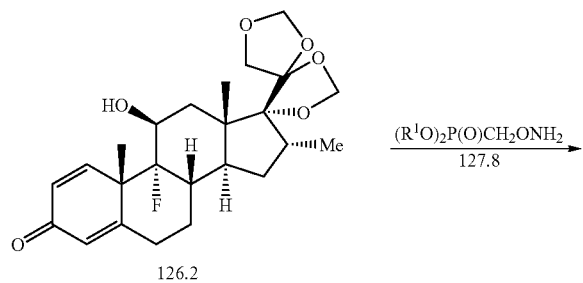

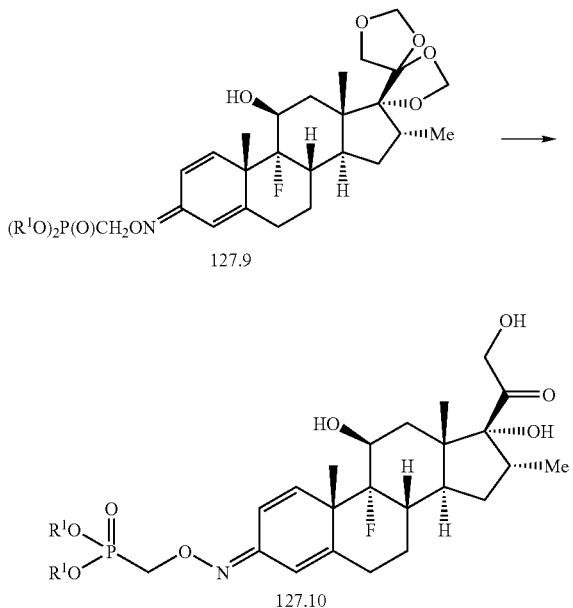

The preparation of dexamethasone phosphonates in which the phosphonate is attached by means of an iminoxy group is illustrated above. In this procedure, the substrate 126.2 is reacted with a dialkyl phosphonomethyl hydroxylamine 127.8, prepared as described above from a dialkyl trifluoromethylsulfonyloxymethyl phosphonate (*Tet. Lett.*, 1986, 27, 1477) and BOC-hydroxylamine, to afford the oxime 127.9 which is deprotected to afford the triol 127.10. The oxime forming reaction is performed at ambient temperature in ethanol-acetic acid solution between equimolar amounts of the reactants. Using the above procedures, but employing, in place of the hydroxylamine ether 127.8, different oxime ethers 127.1, the corresponding products 127.3 are obtained.

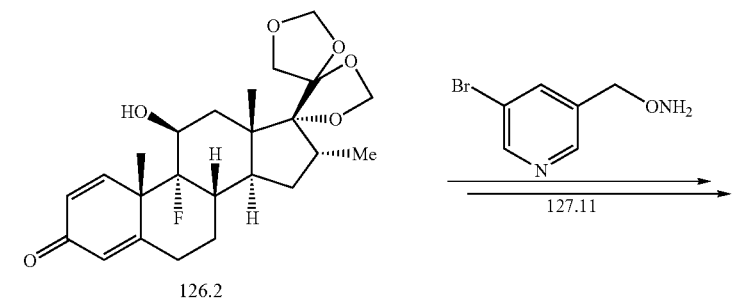

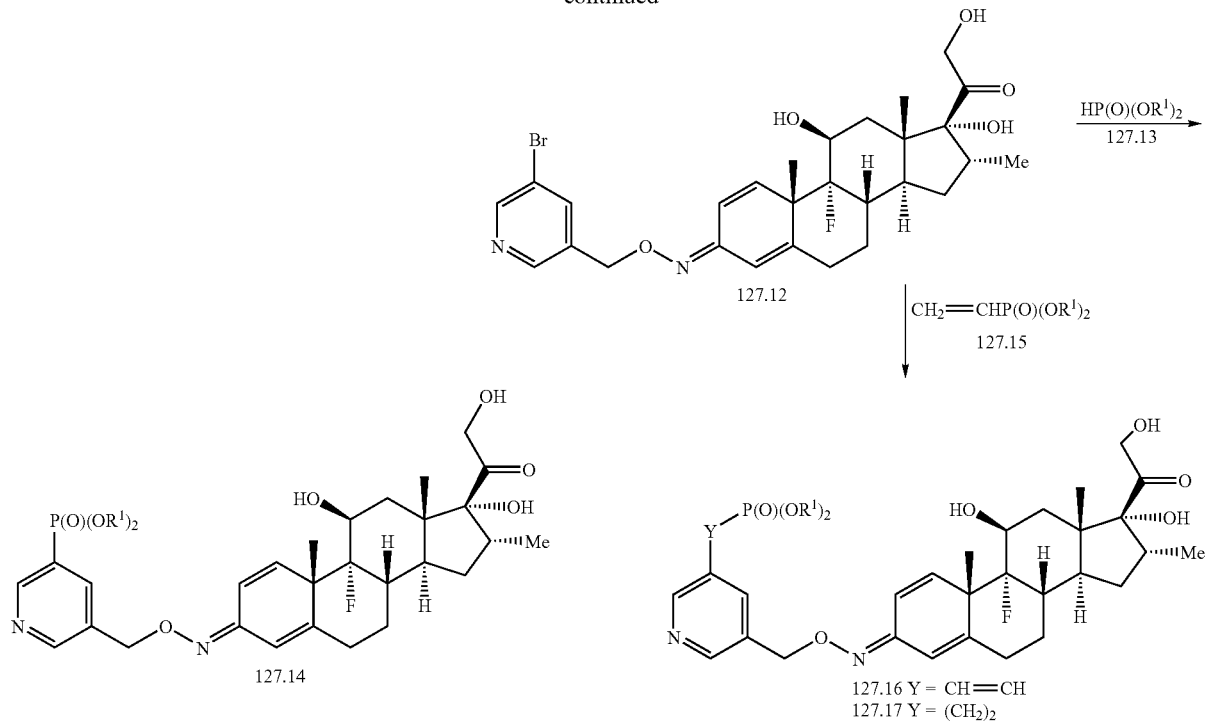

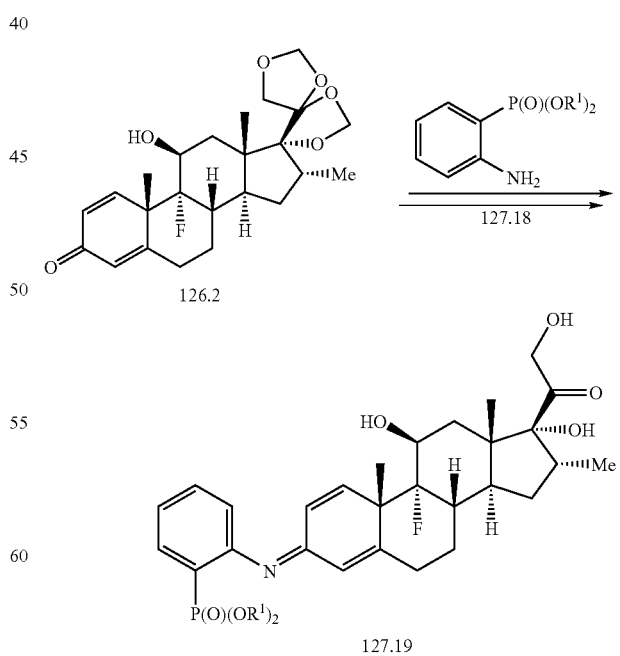

The preparation of dexamethasone compounds in which the phosphonate group is attached by means of a pyridyl methoxy group is illustrated above. In this procedure, the dienone 126.2 is reacted, as described above, with O-(3-bromo-5-pyridylmethyl)hydroxylamine 127.11, prepared as described above from 3-bromo-5-bromomethylpyridine (WO 9528400), to give, after deprotection of the side-chain, the oxime 127.12. The product is then reacted, in the presence of a palladium catalyst, with a dialkyl phosphite 127.13 to afford the phosphonate 127.14. The preparation of arylphosphonates by means of a coupling reaction between aryl bromides and dialkyl phosphites is described in J. Med. Chem., 35, 1371, 1992. The reaction is performed in an inert solvent such as toluene, in the presence of a base such as triethylamine and a catalytic amount of tetrakis(triphenylphosphine)palladium(0).

Alternatively, the bromo compound 127.12 is coupled with a dialkyl vinylphosphonate 127.15 (Aldrich) to afford the phosphonate 127.16. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 127.16 is reduced, for example by reaction with diimide, to produce the saturated analog 127.17. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane.

Using the above procedures, but employing, in place of the bromopyridyloxy reagent 127.11, different bromo-substituted aryl or heteroaryl alkoxy hydroxylamines, and/or different dialkyl alkenyl phosphonates, the products analogous to the compounds 127.14, 127.16 and 127.17 are obtained.

The preparation of dexamethasone phosphonates in which the phosphonate is attached by means of an imino group is illustrated above. In this procedure, the substrate 126.2 is reacted with a dialkyl 2-aminophenyl phosphonate 127.18, (*Syn.*, 1999, 1368) to give, after deprotection, the imine product 127.19. The reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions. Using the above procedures, but employing, in place of the 2-aminophenyl phosphonate 127.18 different amino-substituted aryl or heteroaryl phosphonates, products analogous to 127.19 are obtained.

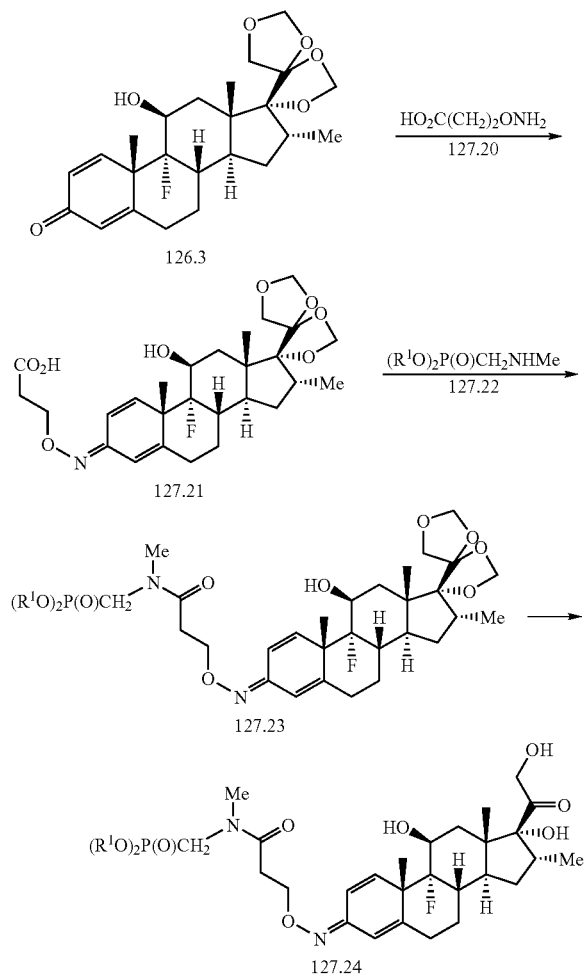

The preparation of dexamethasone phosphonates in which the phosphonate is attached by means of an oximino group and an amide linkage is illustrated above. In this procedure, the dienone 126.2 is reacted with O-(2-carboxyethyl)hydroxylamine 127.20 (*J. Med. Chem.*, 1990, 33, 1423) to yield the oxime 127.21. The reaction of steroidal 1,4-dien-3-ones with substituted hydroxylamines is described in *J. Steroid Bioch.*, 1976, 7, 795; the reaction is performed between equimolar amounts of the reactants in a polar organic solvent such as pyridine or methanol, optionally in the presence of acetic acid or sodium acetate. The oxime is then reacted with a dialkyl aminomethyl phosphonate 127.22 (AsInEx), to yield the amide oxime 127.23. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid is first converted into an activated derivative such as the acid chloride, anhydride, mixed anhydride, imidazolide and the like, and then reacted with the amine, in the presence of an organic base such as, for example, pyridine, to afford the amide. The conversion of a carboxylic acid into the corresponding acid chloride is effected by treatment of the carboxylic acid with a reagent such as, for example, thionyl chloride or oxalyl chloride in an inert organic solvent such as dichloromethane, optionally in the presence of a catalytic amount of dimethylformamide. The amide product 127.23 is then converted into the triol 127.24.

Using the above procedures, but employing, in place of the hydroxylamine 127.22, different carboxy-substituted hydroxylamines, and/or different amino-substituted phosphonates, the products analogous to 127.24 are obtained.

EXAMPLE 128

Preparation of Representative Dexamethasone Derivatives

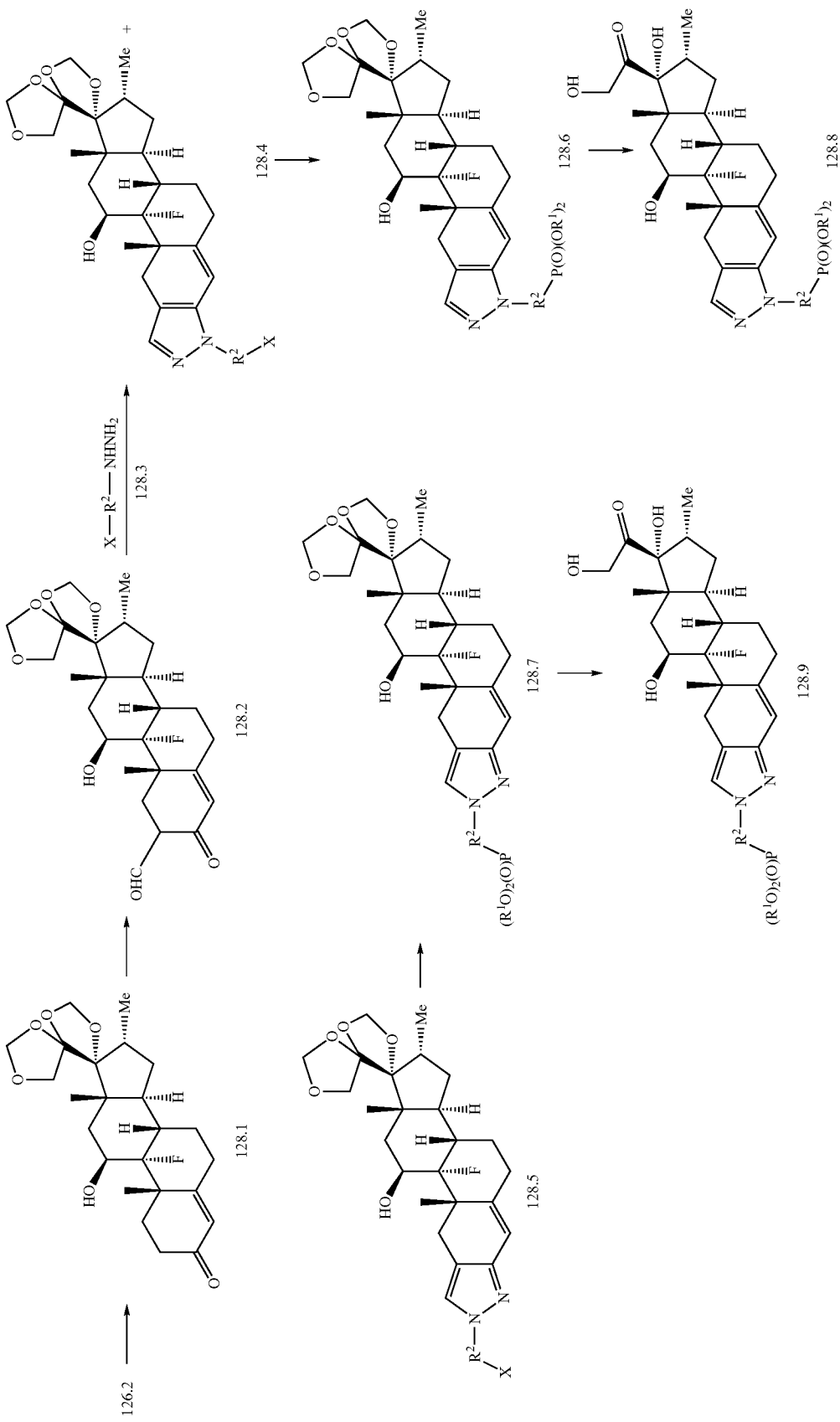

The preparation of the dexamethasone phosphonate esters in which the phosphonate group is attached to the 1' or 2' position of the pyrazole ring, by means of an aromatic or heteroaromatic group, a heteroatom and a variable carbon chain is illustrated above. In this procedure, the BMD-protected dienone 126.2 is reduced to afford the 1,2-dihydro product 128.1. The catalytic hydrogenation reaction is effected by the use of tris(triphenylphosphine)rhodium (I) chloride, for example as described in J. Med. Chem., 2001, 44, 602. The product is then reacted with ethyl formate and a base such as sodium hydride, in an inert solvent such as toluene or dimethylformamide, as described in J. Am. Chem. Soc., 1964, 86, 1520, to afford the 2-formyl product 128.2. This compound is then reacted with an alkyl, aralkyl, aryl or heteroaryl hydrazine 128.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1-aryl pyrazoles 128.4 and 128.5. The pyrazole-forming reaction is performed between equimolar amounts of the reactants in an acidic solvent such as acetic acid, as described in J. Am. Chem. Soc., 1964, 86, 1520. The pyrazoles 128.4 and 128.5 are then transformed via the BMD-protected intermediates 128.6 and 128.7, into the phosphonates 128.8 and 128.9.

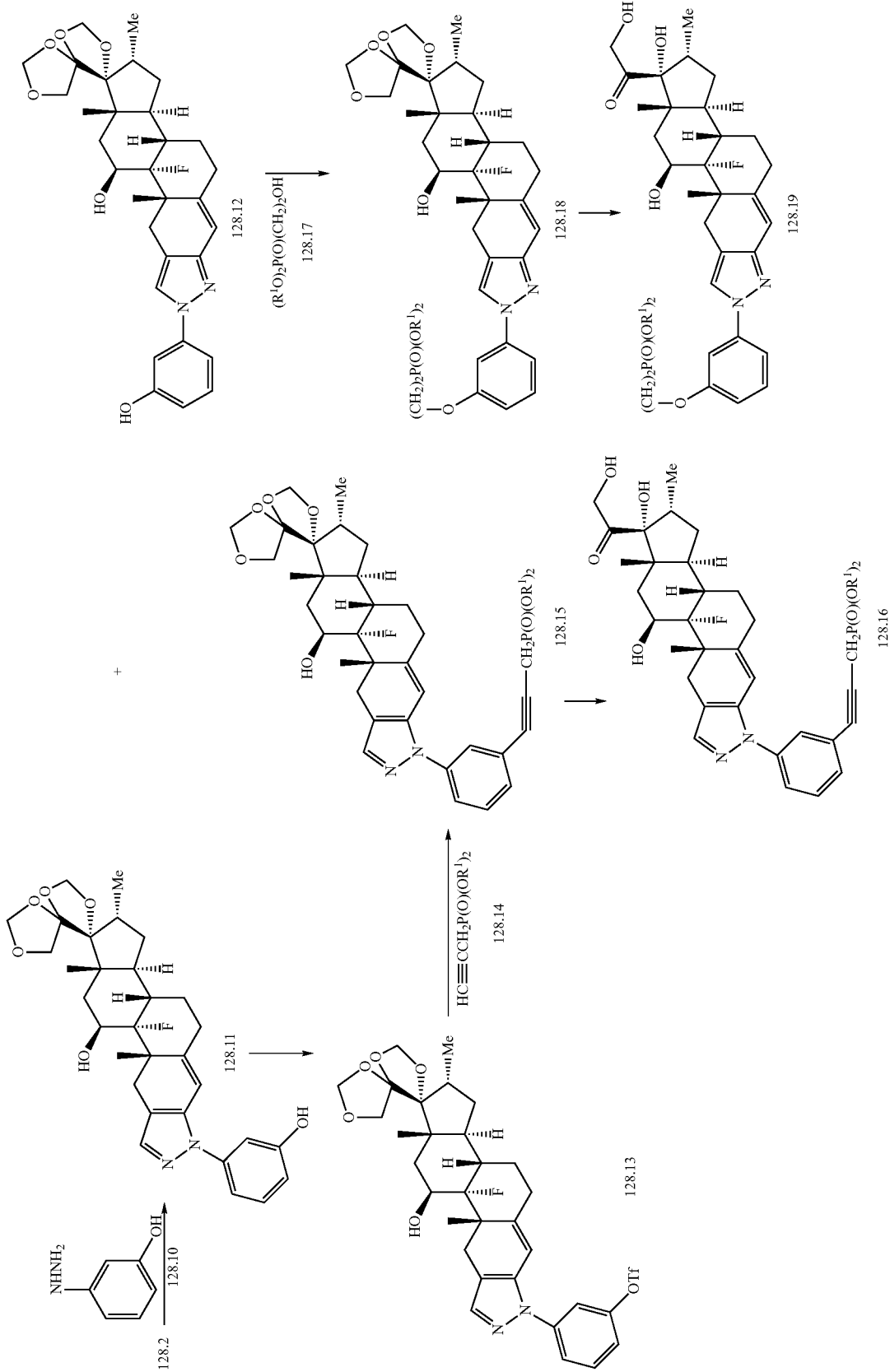

The preparation of dexamethasone phosphonates in which the phosphonate is attached by means of a phenyl ring and an alkoxy or an acetylenic linkage is illustrated above. In this procedure, the ketoaldehyde 128.2 is reacted with 3-hydroxyphenyl-hydrazine 128.10 (Japanese patent JP 03011081) to give the pyrazoles 128.11 and 128.12. The 2'-substituted isomer 128.11 is then reacted in dichloromethane solution at ambient temperature with one molar equivalent of trifluoromethylsulfonyl chloride and dimethylaminopyridine, to yield the triflate 128.13. The product is then reacted in toluene solution with a dialkyl propynyl phosphonate 128.14 (*Syn* 1999, 2027), triethylamine and a catalytic amount of tetrakis (triphenylphosphine)palladium(0), to give the acetylenic product 128.15. The palladium-catalyzed coupling reaction of aryl triflates with terminal acetylenes is described in WO 0230930. The BMD protecting group is then removed to yield the triol 128.16.

Alternatively, the 1'-substituted pyrazole 128.12 is reacted, in a Mitsonobu reaction, with a dialkyl 2-hydroxyethyl phosphonate 128.17 (Epsilon) to afford the ether 128.18. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol and the alcohol component are reacted together in an aprotic solvent such as, for example, tetrahydrofuran, in the presence of a dialkyl azodicarboxylate and a triarylphosphine, to afford the ether or thioether products. The procedure is also described in *Org. React.,* 1992, 42, 335-656. The product 128.18 is then deprotected to give the triol 128.19. Using the above procedures, but employing different acetylenic or hydroxyl-substituted phosphonates, the products analogous to 128.16 and 128.19 are obtained. The functionalization procedures are interchangeable between the pyrazole substrates 128.11 and 128.12.

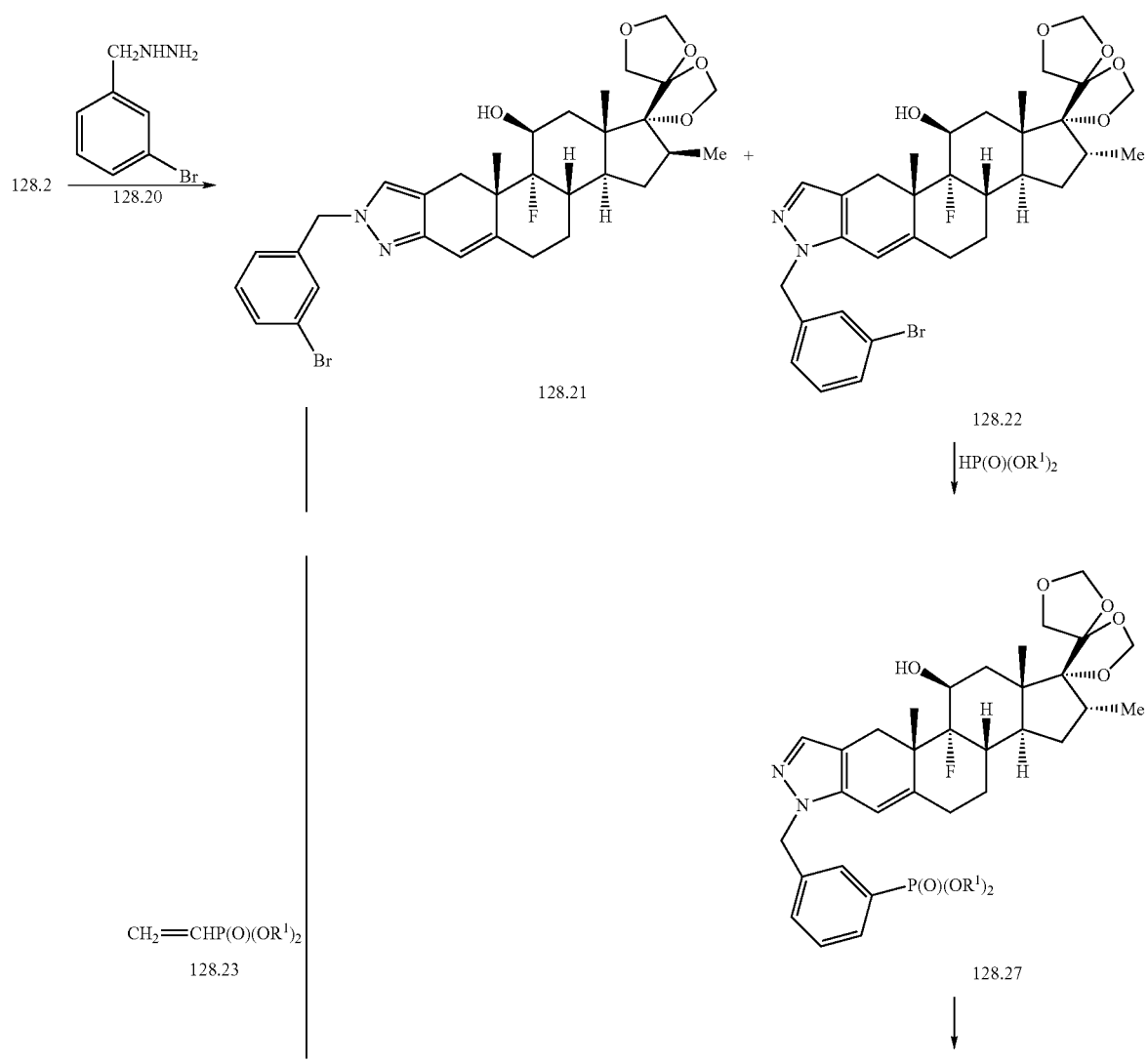

-continued

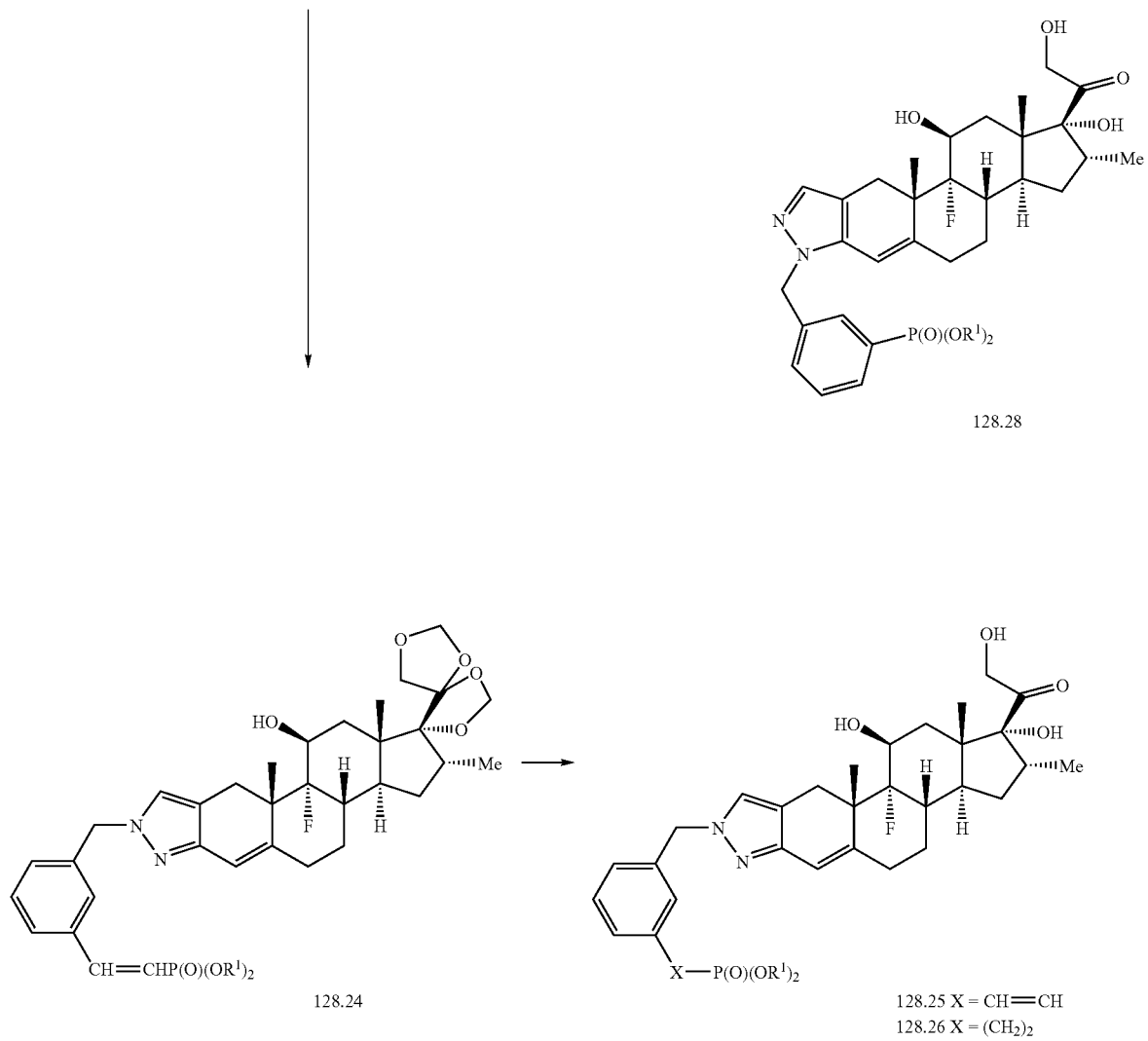

128.28

128.24

128.25 X = CH═CH
128.26 X = (CH₂)₂

The preparation of dexamethasone phosphonates in which the phosphonate group is attached by means of a benzyl group or a benzyl group and a saturated or unsaturated carbon chain is illustrated above. In this procedure, the ketoaldehyde 128.2 is reacted, as described above, with 3-bromobenzyl hydrazine 128.20 (U.S. Pat. No. 4,370,339) to produce the pyrazoles 128.21 and 128.22. The 1'-substituted isomer 128.21 is coupled, in the presence of a palladium catalyst, with a dialkyl vinylphosphonate 128.23 (Aldrich) to give the phosphonate 128.24. The product is then deprotected to afford the triol 128.25. Optionally, the styrenoid double bond present in the product 128.25 is reduced, as described above, to produce the saturated analog 128.26.

Alternatively, the 2'-substituted pyrazole 128.22 is coupled, in the presence of a palladium catalyst, with a dialkyl phosphite to prepare the phosphonate 128.27 which is deprotected to give the triol 128.28. The preparation of arylphosphonates by means of a coupling reaction between aryl bromides and dialkyl phosphites is described in J. Med. Chem., 35, 1371, 1992. This reaction is performed in an inert solvent such as toluene, in the presence of a base such as triethylamine and tetrakis(triphenylphosphine)-palladium(0).

Using the above procedures, but employing, in place of the bromobenzyl reagent 128.20, different bromo-substituted aralkyl, aryl or heteroaryl alkoxy hydrazines, and/or different dialkyl alkenyl phosphonates, the products analogous to the compounds 128.25, 128.26 and 128.28 are obtained.

EXAMPLE 129
Preparation of Representative Dexamethasone Derivatives
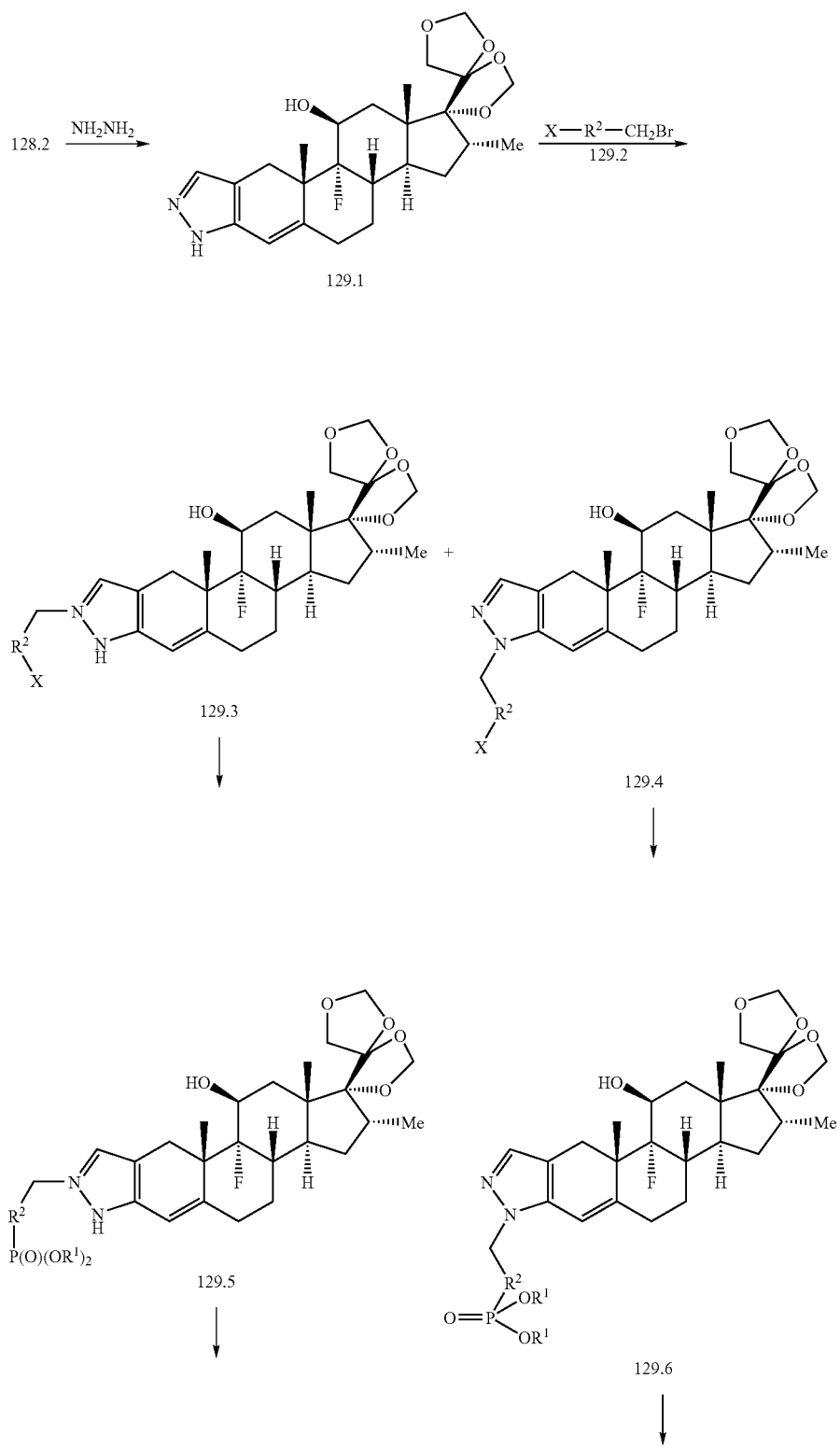

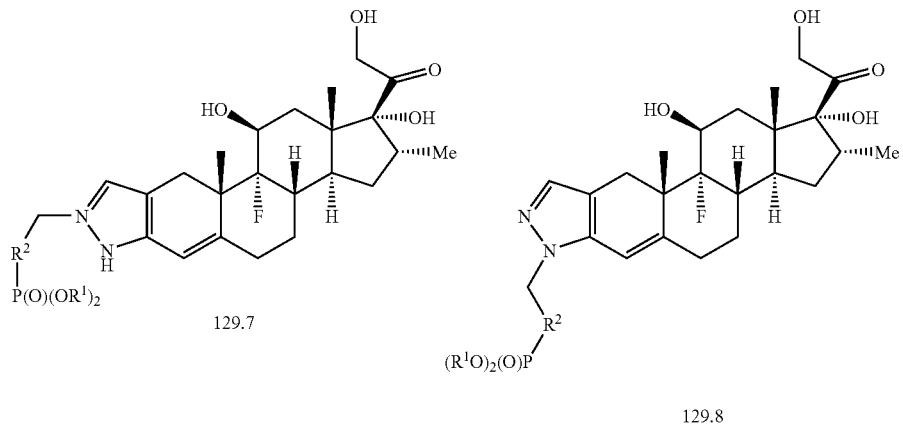

The preparation of dexamethasone phosphonate esters in which the phosphonate group is attached by means of a variable carbon linkage is illustrated above. In this procedure, the ketoaldehyde 128.2 is reacted with hydrazine, to afford the pyrazole derivative 129.1. The reaction of steroidal 2-formyl-3-ketones with hydrazine is described in *J. Am. Chem. Soc,* 1964, 86, 1520. The reaction is performed in acetic acid at ambient temperature. The pyrazole product is then reacted with a bromomethyl compound 129.2, in which $R^2$ and X are as defined above, to yield the alkylation products 129.3 and 129.4. The alkylation of substituted pyrazoles is described, for example, in Heterocyclic Chemistry, by T. L. Gilchrist, Longman, 1992, p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The products 129.3 and 129.4 are, except in cases where X is dialkylphosphono, converted into the phosphonates 129.5 and 129.6, using the procedures described herein, and deprotection then affords the triols 129.7 and 129.8.

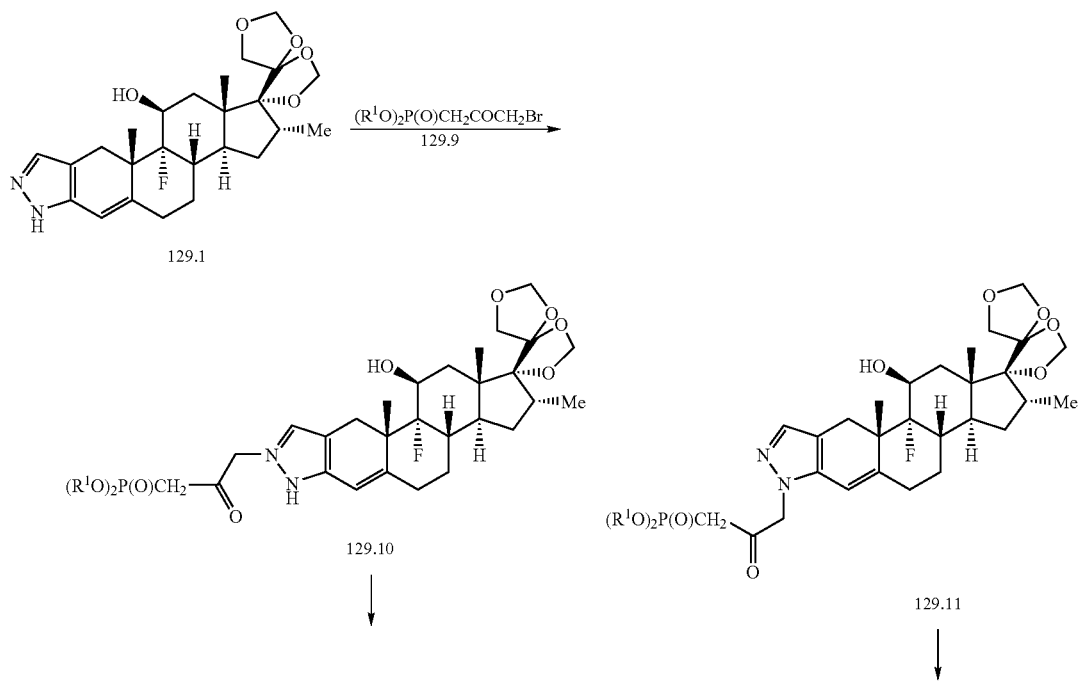

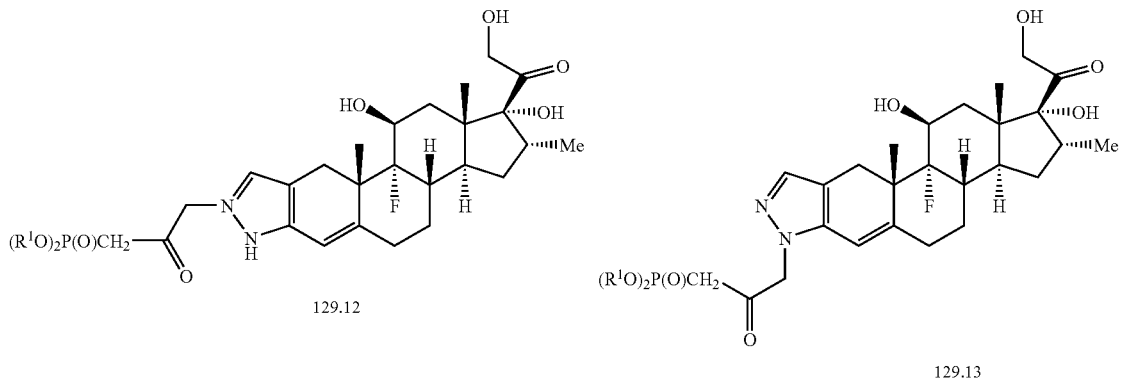
The preparation of representative compounds of the invention is illustrated above. The pyrazole 129.1 is reacted, as described above, with one molar equivalent of a dialkyl bromoacetonyl phosphonate 129.9 (*Tet.,* 1978, 34, 649) to give the alkylated pyrazoles 129.10 and 129.11. Deprotection then yields the triols 129.12 and 129.13.
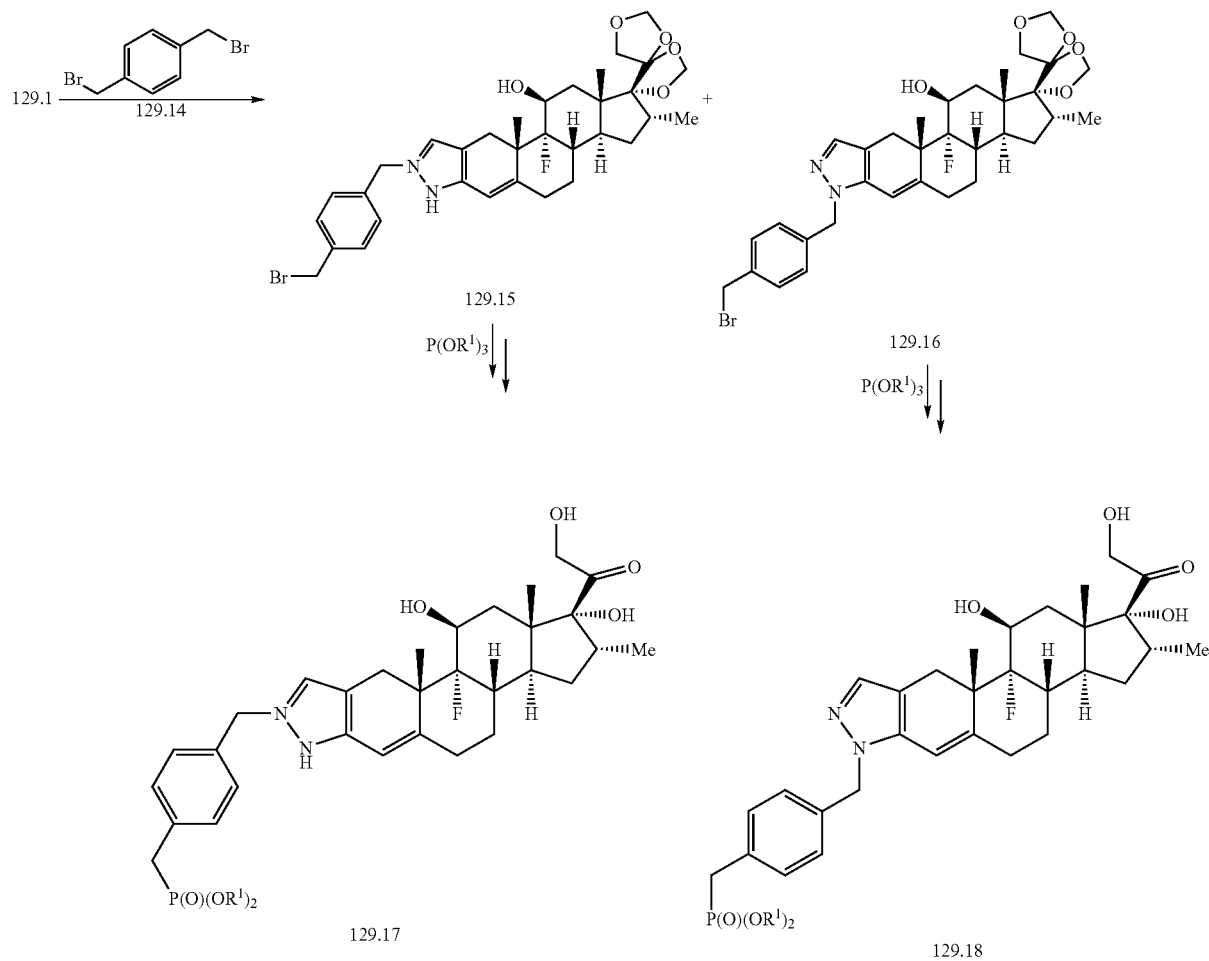

The preparation of representative compounds of the invention is illustrated above. The pyrazole 129.1 is reacted, as described above, with 1,4-bis(bromomethyl)benzene 129.14 to give the pyrazoles 129.15 and 129.16. The products are subjected to an Arbuzov reaction, in which the bromomethyl substituent is converted into the dialkyl phosphonomethyl substituent, by reaction with a trialkyl phosphite at 120°, to prepare, after deprotection of the side chain, the phosphonates 129.17 and 129.18. The Arbuzov reaction is described in Handb. Organophosphorus Chem., 1992, 115-72. In the procedure, the substrate is heated at from 60° to about 160° with a five to fifty-fold molar excess of the trialkyl phosphite. Using the above procedures, but employing, in place of the dibromide 129.14, different dibromides, the products analogous to 129.17 and 129.18 are obtained.

EXAMPLES 130-133

Beclomethasone Derivatives

The structures of Beclomethasone (British Patent GB 912378) and Vanceril (U.S. Pat. No. 4,024,131) and representative phosphonate esters of the invention are shown below, in which the substituent $R^1$ is H, alkyl, alkenyl, aryl or aralkyl. These compounds incorporate a phosphonate moiety $(R^1O)_2P(O)$ connected to the nucleus by means of a variable linking group, designated as "link" in the attached structures.

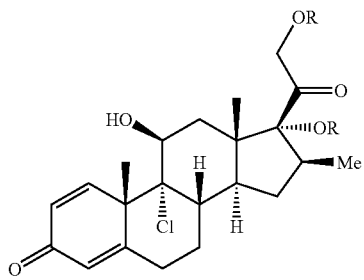

R = H: Beclometasone
R = COEt: Vanceril

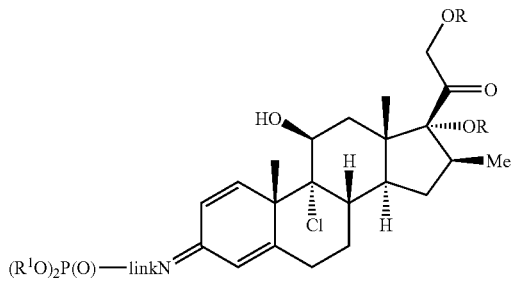

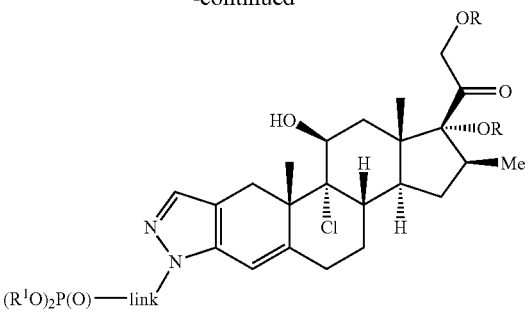

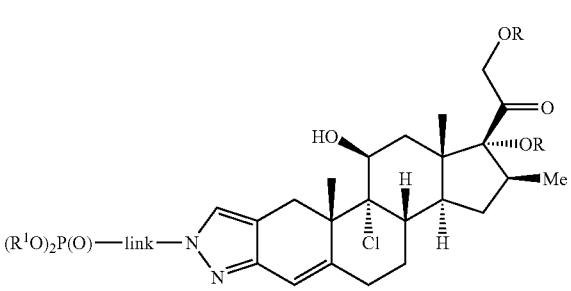

The synthesis of representative phosphonate derivatives of beclomethasone is outlined in Examples 130-133. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 130

Preparation of Representative Beclomethasone Derivatives

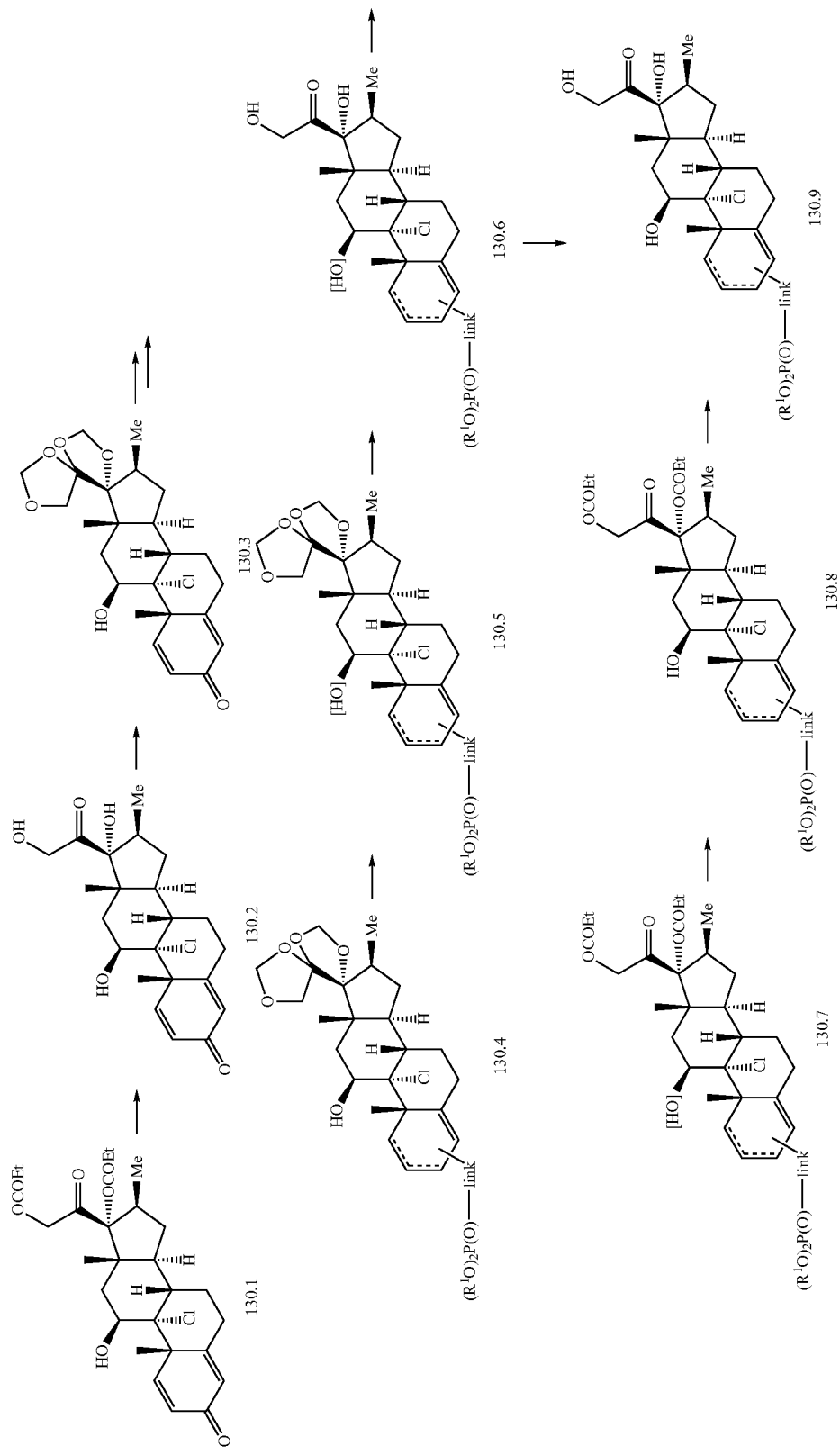

Ther preparation of representative beclomethasone derivatives of the invention is illustrated above. The propionate esters are hydrolyzed, for example by reaction with two molar equivalents of lithium hydroxide in aqueous dimethoxyethane solution at ambient temperature, to give the triol 130.2. The product is then reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 130.3. The phosphonate moiety is then introduced, using the procedures described below, to produce the phosphonate ester 130.4. Prior to hydrolysis of the BMD protecting group, the 11-hydroxyl group is protected. The protecting group is selected so that it is stable to the conditions required for removal of the BMD group, and so that it is removable without affecting the subsequently introduced 17, 21-diester moiety. For example, the 11-hydroxyl group is protected by conversion to the 4-azidobutyrate ester, by reaction with 4-azidobutyryl chloride in pyridine. The 11-azidobutyrate group is then removed from the diester 130.7 by reaction with triphenylphosphine, as described in Bull. Soc. Chem. Jpn., 59, 1296, 1986. Alternatively, the 11-hydroxyl group is protected by conversion to the 2-(trimethylsilyl)ethyl carbonate, by reaction with 2-(trimethylsilyl)ethyl carbonyl chloride and pyridine. The 2-(trimethylsilyl) carbonate is removed from the diester 130.7 by reaction with tetrabutylammonium fluoride in tetrahydrofuran at ambient temperature, as described in Tet. Lett., 22, 969, 1981.

Alternatively, the 11-hydroxyl group is protected by conversion to the trichloroacetyl ester, by reaction with trichloroacetyl chloride in dimethylformamide-pyridine. The trichloroacetyl ester is removed by reaction with ethanolic ammonia at ambient temperature, as described in Coll. Czech. Chem. Commun., 27, 2567, 1962.

The BMD moiety in the protected product 130.5 is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the triol 130.6. The latter compound is then acylated, for example by reaction with propionic acid and dicyclohexyl carbodiimide in dimethylformamide at ambient temperature, or by reaction with propionyl chloride and triethylamine in dichloromethane, to produce the dipropionate 130.7. Deprotection of the 11-hydroxyl group, as described above, then affords the diester 130.8. The protected 17,21-diol 130.8 is deprotected, as described above, to afford the 11,17,21 trihydroxy compound 130.9.

Alternatively, the 20-ketone group is protected as the diethylamine adduct by reaction with titanium tetrakis(diethylamide), as described in Protective Groups in Organic Synthesis, by T. W. Greene and P. G. M Wuts, Wiley, Second Edition 1990, p. 219.

EXAMPLE 131

Preparation of Representative Beclomethasone Derivatives

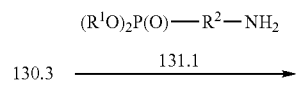

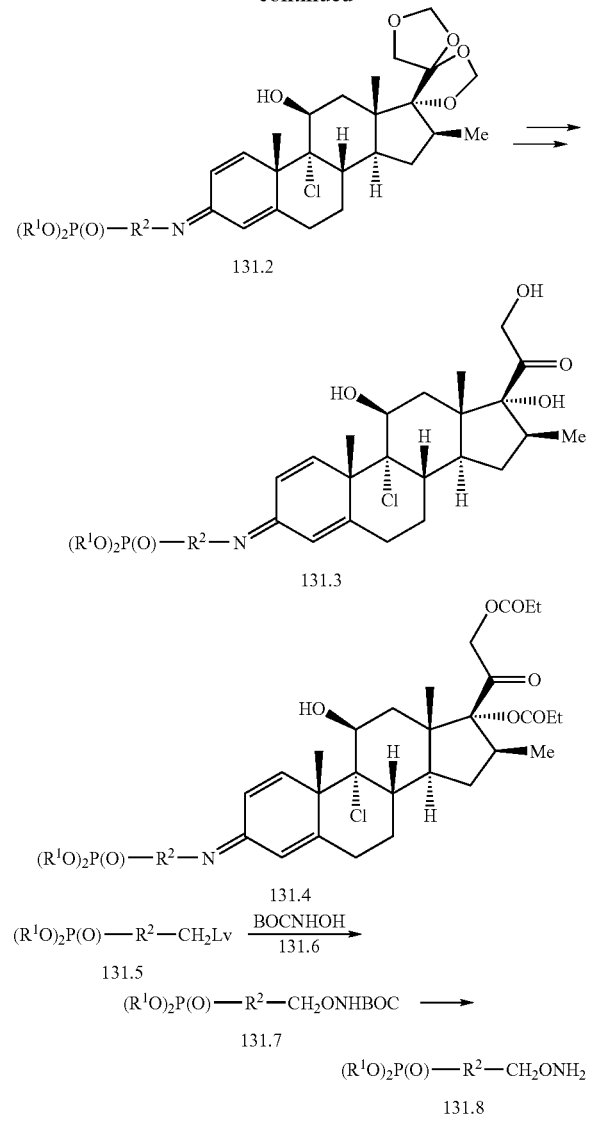

The preparation of phosphonates in which the phosphonate is attached by means of an imino or iminoxy group and a variable carbon chain is illustrated above. In this procedure, the BMD-protected derivative 130.3 is reacted with an amine or hydroxylamine 131.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, to afford the imine or iminoxy product 131.2. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in *Anal. Bioch.,* 1978, 86, 133. and in *J. Mass. Spectrom.,* 1995, 30, 497. The BMD-protected side-chain compound 131.2 is then converted into the diester 131.4 and the triol 131.3.

The preparation of hydroxylamine ethers incorporating a phosphonate group is illustrated above. In this procedure, a phosphonate 131.5, in which Lv is a leaving group such as bromo or trifluoromethylsulfonyloxy, is reacted with BOC-hydroxylamine 131.6 (Aldrich) to produce the ether 131.7. The reaction is conducted between equimolar amounts of the reactants in a polar solvent such as dimethylformamide or tetrahydrofuran, in the presence of a base such as potassium hydroxide or dimethylaminopyridine, to give the product 131.7. Deprotection, for example by treatment with trifluoroacetic acid, then gives the hydroxylamine ether 131.8.

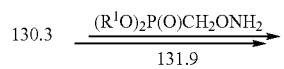

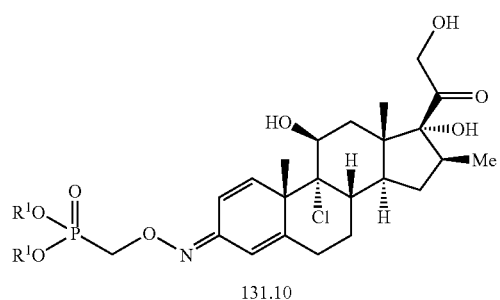

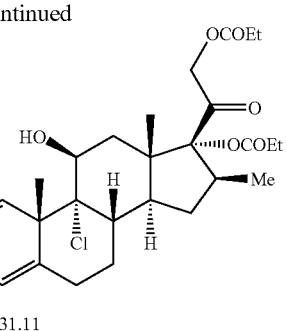

The preparation of phosphonates in which the phosphonate is attached by means of an iminoxy group is illustrated above. In this procedure, the substrate 130.3 is reacted with a dialkyl phosphonomethyl hydroxylamine 131.9, prepared as described above from a dialkyl trifluoromethylsulfonyloxymethyl phosphonate (Tet. Lett., 1986, 27, 1477) and BOC-hydroxylamine, to afford, after protection-deprotection and side chain acylation, the oxime ethers 131.10 and 131.11. The oxime forming reaction is performed at ambient temperature in pyridine solution between equimolar amounts of the reactants.

Using the above procedures, but employing, in place of the oxime ether 131.9, different oxime ethers 131.8, the corresponding products 131.3 and 131.4 are obtained.

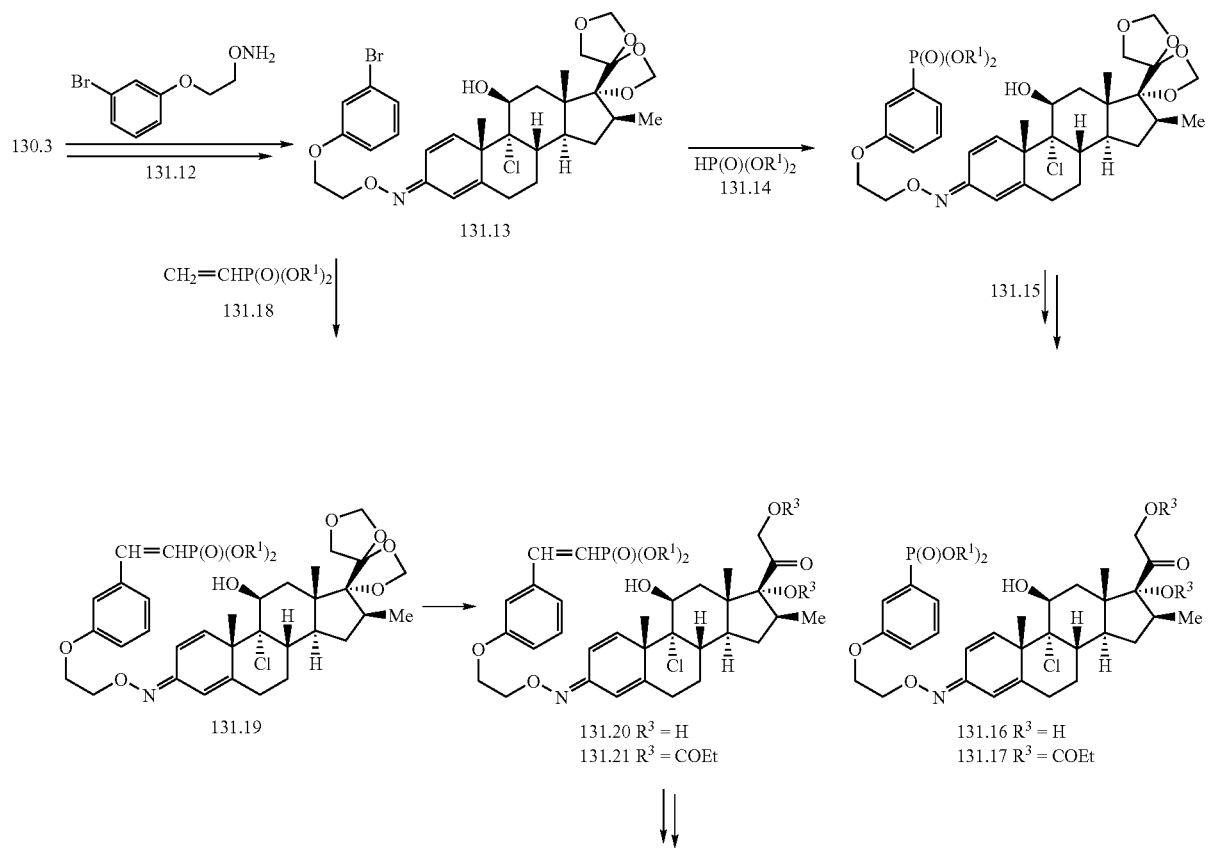

-continued

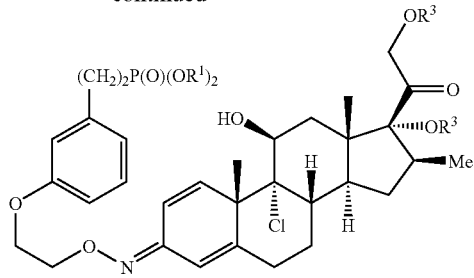

131.22 R³ = H
131.23 R³ = COEt

The preparation of phosphonates incorporating an iminoxy group, by means of the reaction between the substrate 130.3 and O-2-(3-bromophenoxy)ethoxyhydroxylamine 131.12, prepared as described above from 2-(3-bromophenoxy)ethyl bromide (French patent FR 1481052). The resultant oxime ether 131.13 is then reacted, in the presence of a palladium catalyst, with a dialkyl phosphite 131.14 to afford the phosphonate 131.15. The preparation of arylphosphonates by means of a coupling reaction between aryl bromides and dialkyl phosphites is described in J. Med. Chem., 35, 1371, 1992. The reaction is performed in an inert solvent such as toluene, in the presence of a base such as triethylamine and a catalytic amount of tetrakis(triphenylphosphine)-palladium (0). The BMD-protected product 131.15 is then converted into the triol 131.16 and the dipropionate 131.17.

Alternatively, the bromo-substituted product 131.13 is coupled, in a palladium-catalyzed Heck reaction, with a dialkyl vinyl phosphonate 131.18 (Aldrich) to give the unsaturated phosphonate 131.19. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)-palladium(0) or a palladium(II) catalyst such as palladium(II) acetate, and optionally in the presence of a base such as triethylamine or potassium carbonate. The product 131.19 is then converted into the triol 131.20 and the dipropionate 131.21.

Optionally, the styrenoid double bond present in the products 131.20 and 131.21 is reduced, for example by reaction with diimide, to produce the saturated analogs 131.22 and 131.23. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane.

Using the above procedures, but employing, in place of the bromophenoxy reagent 131.12, different bromo-substituted aryl or heteroaryl alkoxy hydroxylamines, and/or different dialkyl alkenyl phosphonates, the products analogous to the compounds 131.16, 131.17, 131.20, 131.21, 131.22 and 131.23 are obtained.

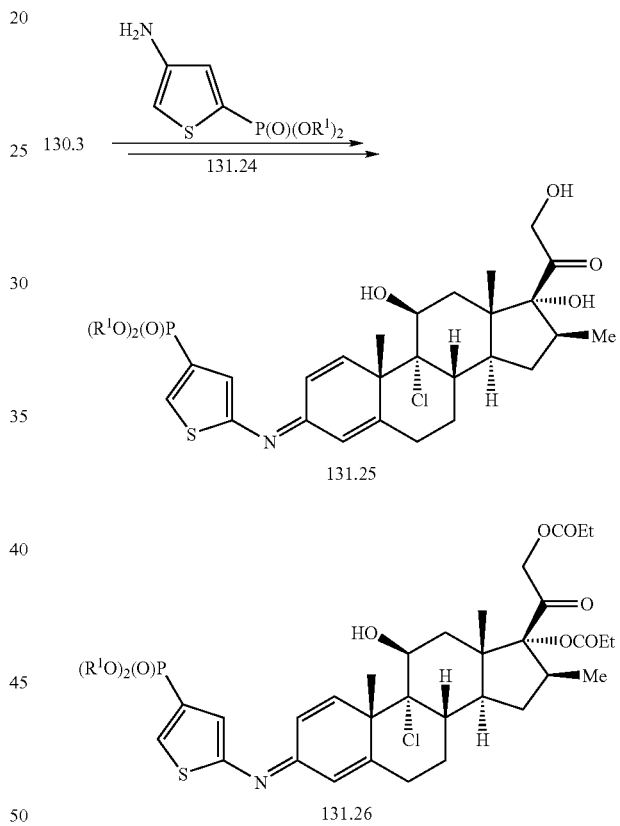

The preparation of phosphonates in which the phosphonate is attached by means of an imino group is illustrated above. In this procedure, the substrate 130.3 is reacted with a dialkyl 4-amino-2-thienyl phosphonate 131.14, prepared by the palladium-catalyzed coupling reaction between a dialkyl phosphite and 2-bromo-4-aminothiophene (Tet., 1987, 43, 3295) to give, after deprotection and side chain acylation, the imine products 131.25 and 131.26. The reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions, to give the products 131.25 and 131.26.

Using the above procedures, but employing, in place of the 3-aminothienyl phosphonate 131.24 different amino-substi-

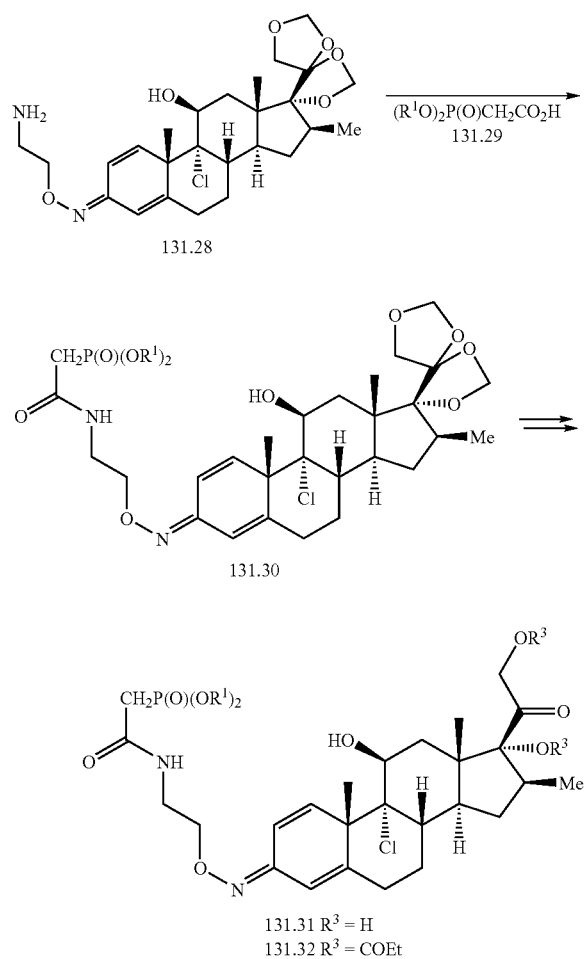

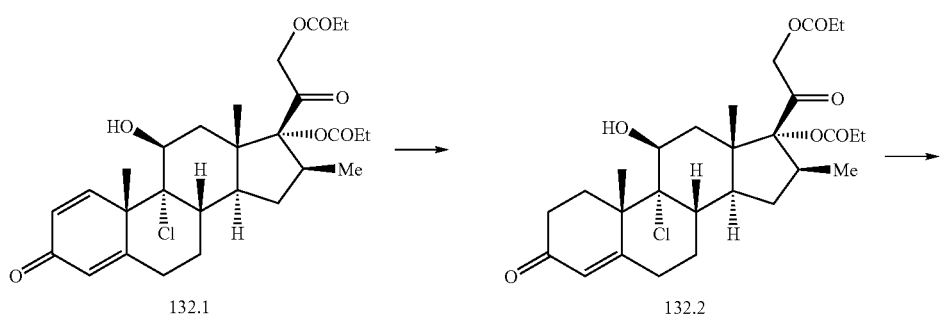

The preparation of phosphonates in which the phosphonate is attached by means of an oximino group and an amide linkage is illustrated above. In this procedure, the dienone 130.3 is reacted with O-(2-aminoethyl)hydroxylamine 131.27 (Bioorganicheskaya Khim., 1986, 12, 1662) to yield the oxime 131.28. The reaction of steroidal 1,4-dien-3-ones with hydroxylamines is described in J. Steroid Bioch., 1976, 7, 795; the reaction is performed between equimolar amounts of the reactants in a polar organic solvent such as pyridine or methanol, optionally in the presence of acetic acid or sodium acetate. The oxime is then reacted with a dialkyl phosphonoacetic acid 131.29 (Aldrich), to yield the amide oxime 131.30. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide.

The amide product 131.30 is then converted into the triol 131.31 and the dipropionate 131.32. Using the above procedures, but employing, in place of the hydroxylamine 131.27, different amino-substituted hydroxylamines, and/or different carboxy-substituted phosphonates, the products analogous to 131.31 and 131.32 are obtained.

EXAMPLE 132

Preparation of Representative Beclomethasone Derivatives

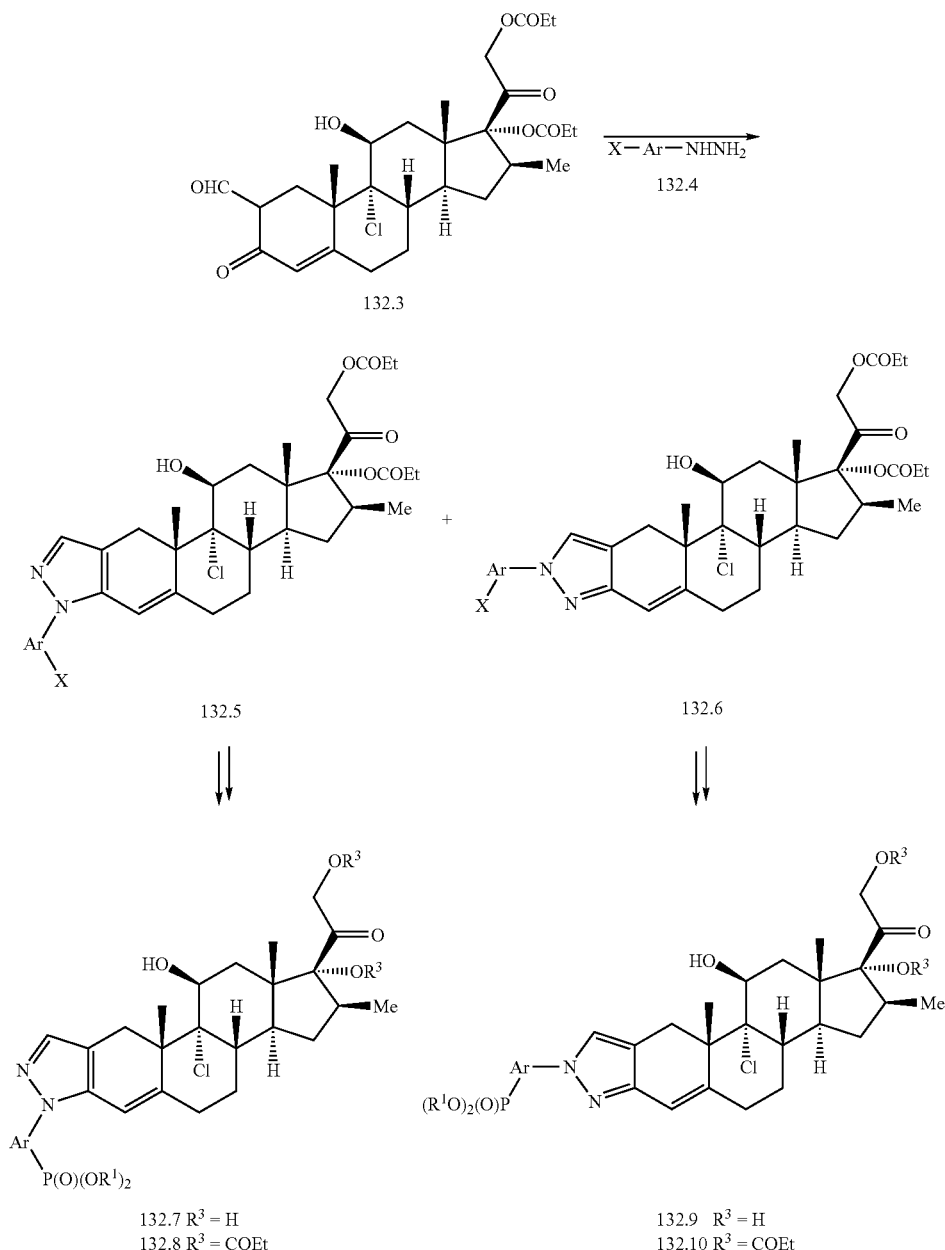

The preparation of the phosphonate esters in which the phosphonate group is attached to the 1' or 2' position of the pyrazole ring, by means of an aromatic or heteroaromatic group, a heteroatom and a variable carbon chain is illustrated above. In this procedure, Vanceril 132.1 is reduced to afford the 1,2-dihydro product, 132.2. The catalytic hydrogenation reaction is effected by the use of tris(triphenylphosphine) rhodium(I) chloride, for example as described in *J. Med. Chem.*, 2001, 44, 602. The product is then reacted with ethyl formate and a base such as sodium hydride, in an inert solvent such as toluene or dimethylformamide, as described in Australian Patent Application 275950409, to afford the 2-formyl product 132.3. Optionally, the substrate 132.1 is protected, for example as described above, prior to the reduction and formylation reactions, as described in *J. Am. Chem. Soc.*, 1964, 86, 1520. The 2-formyl product is then reacted with an aryl or heteroaryl hydrazine 132.4, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1-aryl pyrazoles 132.5 and 132.6. The pyrazole-forming reaction is performed between equimolar amounts of the reactants in an acidic solvent such as acetic acid, as described in *J. Am. Chem. Soc.*, 1964, 86, 1520. The pyrazoles 132.5 and 132.6 are then transformed, respectively, into the phosphonates 132.7, 132.8, 132.9 and 132.10.

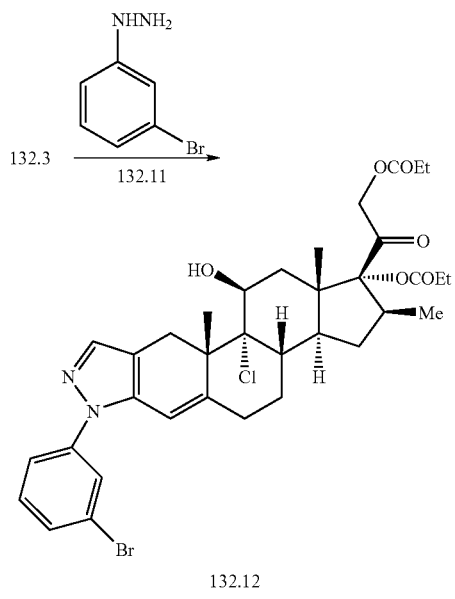

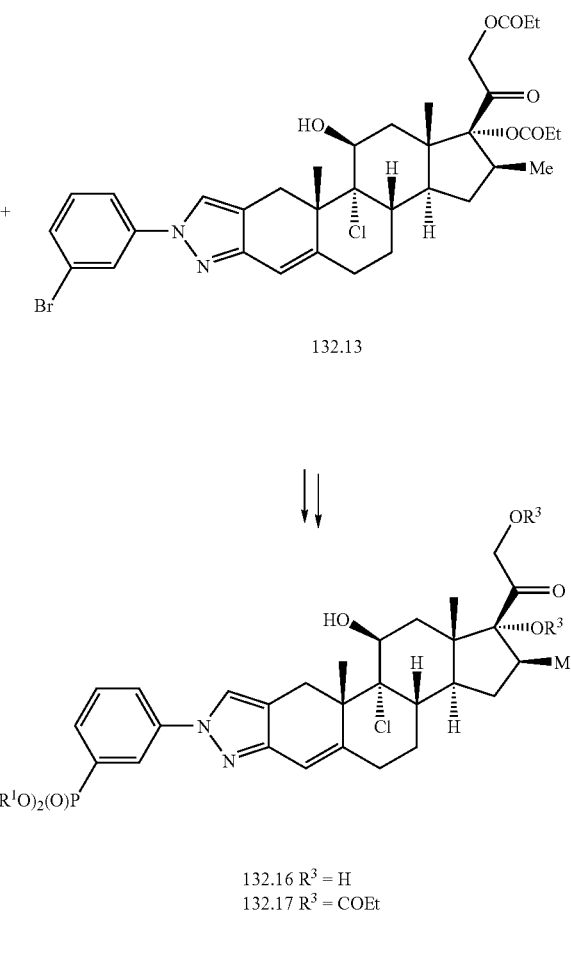

The preparation of phosphonates in which the phosphonate is attached by means of a phenyl group is illustrated above. In this sequence, the ketoaldehyde 132.3 is reacted, as described above, with 3-bromophenylhydrazine 132.11 (Fluka), to give the isomeric pyrazole products 132.12 and 132.13. The products are then reacted, as described above, with a dialkyl phosphite $HP(O)(OR^1)_2$ and a palladium catalyst, to afford respectively the phosphonates 132.15 and 132.17. Basic hydrolysis, as described above, then yields the triols 132.14 and 132.16.

Using the above procedures, but employing, in place of 3-bromophenyl hydrazine, different bromoaryl or bromoheteroaryl hydrazines 132.4, the products analogous to 132.7, 132.8, 132.9 and 132.10 are obtained.

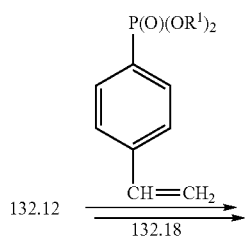

-continued

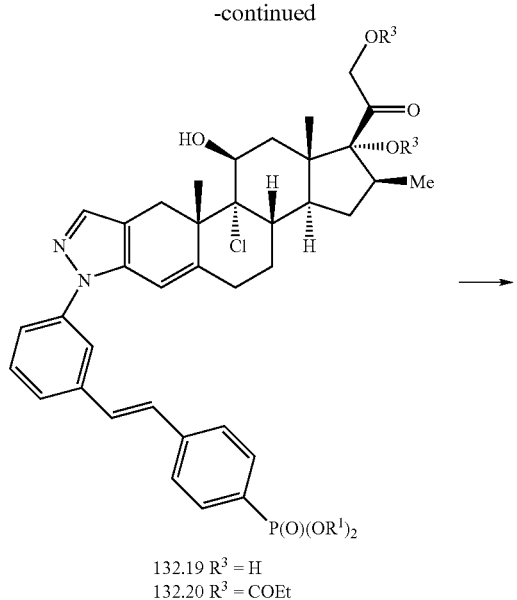

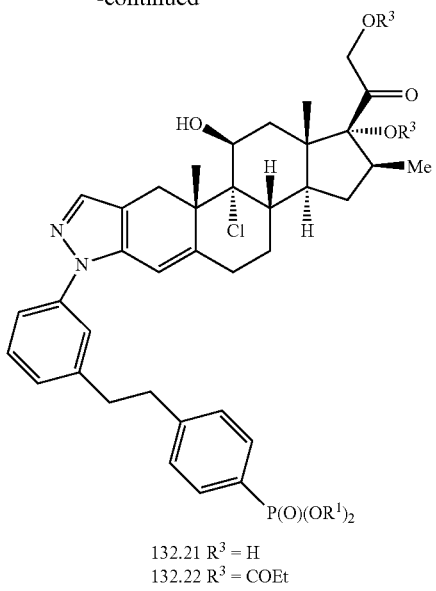

132.21 R³ = H
132.22 R³ = COEt

The preparation of phosphonates in which the phosphonate is attached by means of an aromatic or heteroaromatic group and a saturated or unsaturated alkyl chain is illustrated above. In this procedure, the bromophenyl-substituted pyrazole 132.12 is coupled in a Heck reaction, as described above, with a dialkyl 4-vinylphenyl phosphonate 132.18 (*Macromolecules,* 1998, 31, 2918) to give the unsaturated phosphonate product 132.20. Basic hydrolysis then gives the triol 132.19. Optionally, the products are reduced, as described above, to give the saturated analogs 132.21 and 132.22. Application of the above procedures to the isomeric bromophenyl pyrazole 132.13 affords the products isomeric with 132.19, 132.20, 132.21 and 132.22. Using the above procedures, but employing, in place of the phosphonate 132.18, different dialkyl alkenyl phosphonates, and/or different bromoaryl or heteroaryl pyrazoles 132.5 or 132.6 (X=Br) the products analogous to 132.19, 132.20, 132.21 and 132.22 are obtained.

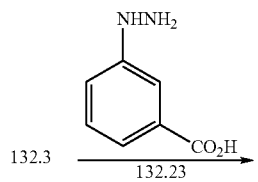

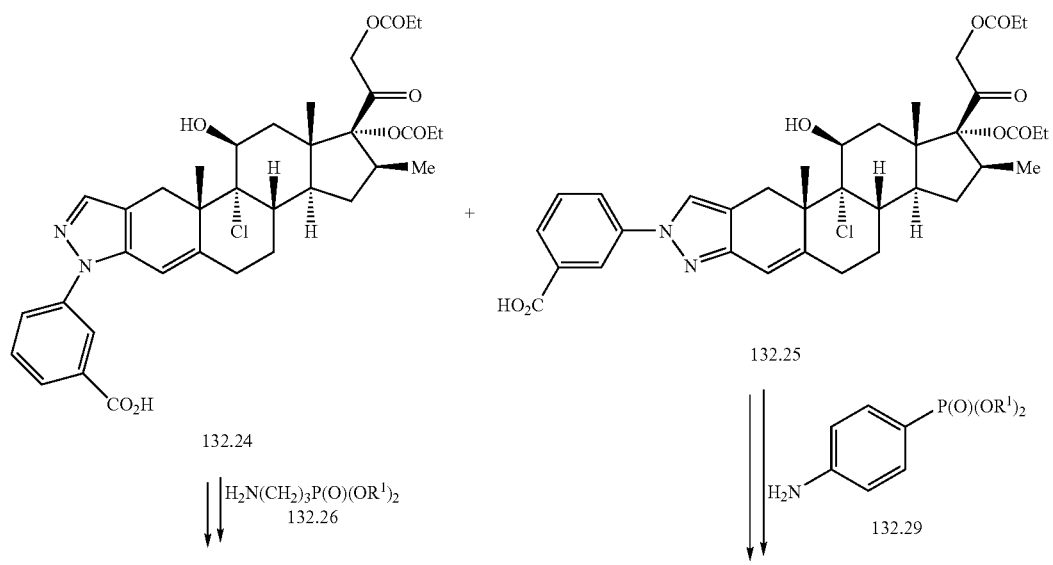

-continued

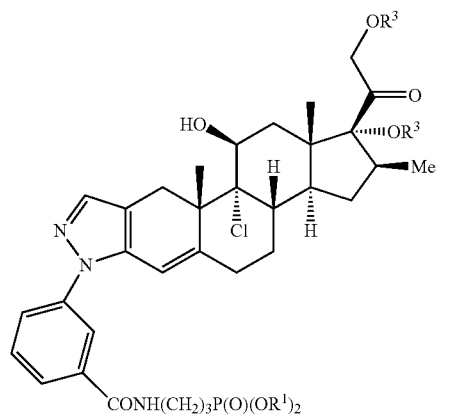

132.27 R³ = H
132.28 R³ = COEt

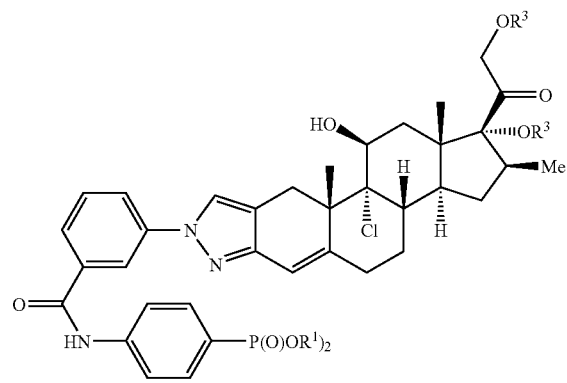

132.30 R³ = H
132.31 R³ = COEt

The preparation of phosphonates in which the phosphonate is attached by means of an aryl or heteroaryl group and an amide linkage. In this procedure, 3-carboxyphenylhydrazine 132.23 (Apin) is reacted in dimethylformamide solution at ambient temperature with the ketoaldehyde 132.3, to form the isomeric pyrazoles 132.24 and 132.25. The product 132.24 is then coupled, as described above, with a dialkyl 3-aminopropyl phosphonate 132.26 (Synthelec) to give the amide 132.27. Basic hydrolysis then produces the triol 132.27. Alternatively, the carboxylic acid 132.25 is reacted with a dialkyl 4-aminophenyl phosphonate 132.29 (Epsilon) to prepare the triol 132.30 and the diester 132.31. Using the above procedures, but employing, in place of the carboxy-substituted hydrazine 132.23, different carboxy-substituted aryl or heteroaryl hydrazines, the products analogous to 132.27, 132.28, 132.30 and 132.31 are obtained.

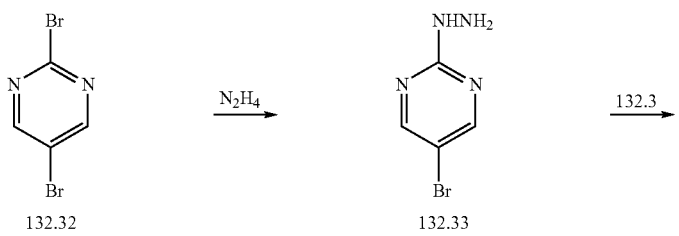

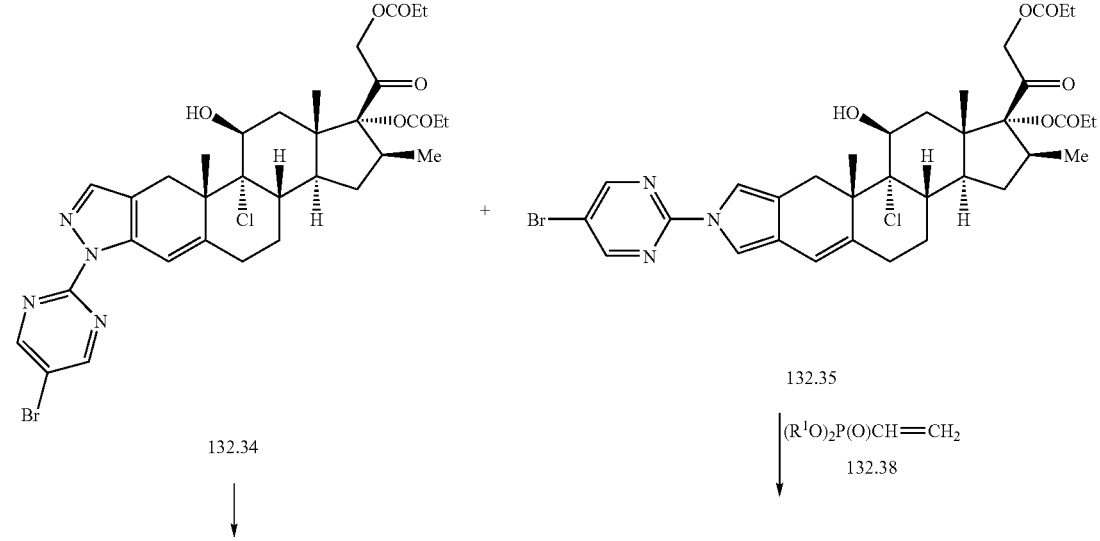

-continued

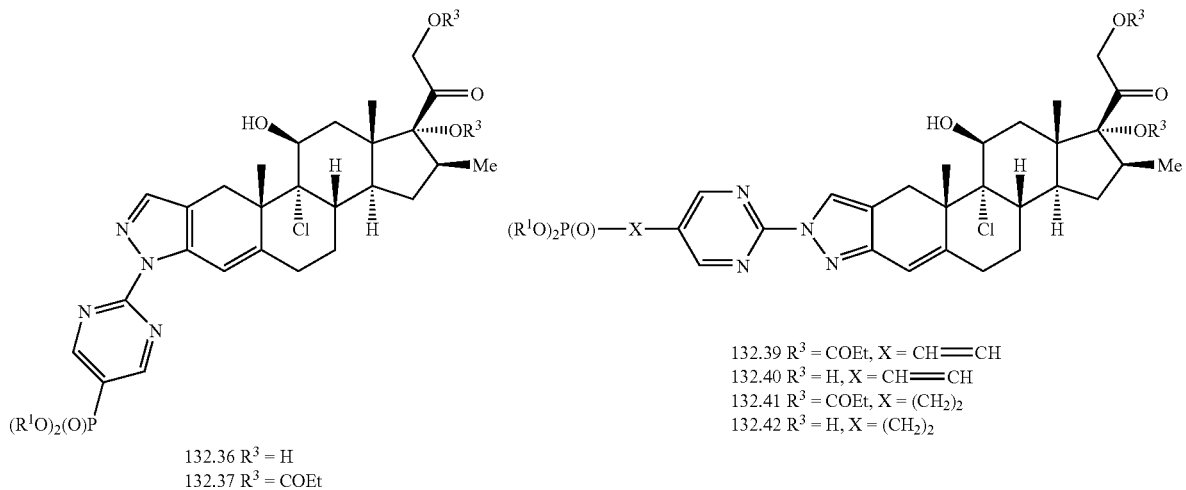

The preparation of phosphonates in which the phosphonate is attached by means of a pyrimidinyl group, either directly or with a saturated or unsaturated carbon chain is illustrated above. In this procedure, 2,5-dibromopyrimidine 132.32 (*Chem. Lett.*, 1992, 583) is reacted with hydrazine to afford 5-bromo-2-pyrimidinyl hydrazine 132.33. The preparation of pyrimidinyl hydrazines by the reaction of 2-halopyrimidines with hydrazine is described in *J. Med. Chem.*, 2002, 45, 5397. The product is then reacted with the ketoaldehyde 132.3 to yield the isomeric pyrazoles 132.34 and 132.35. The compound 132.34 is coupled, as described above, with a dialkyl phosphite to afford the phosphonate 132.37; basic hydrolysis then gives the triol 132.36.

Alternatively, the isomeric pyrazole 132.35 is coupled, as described above, with a dialkyl vinyl phosphonate 132.38 to prepare the phosphonate 132.39. Basic hydrolysis then produces the triol 132.40, and reduction of the double bond, as described above, yields the diester 132.41 and the triol 132.42.

Using the above procedures, but employing, in place of the pyrimidinyl hydrazine 132.33, different bromo-substituted aryl or heteroaryl hydrazines, and/or different alkenyl phosphonates, the products analogous to 132.36, 132.37, 132.39, 132.40, 132.41 and 132.42 are obtained.

EXAMPLE 133

Preparation of Representative Beclomethasone Derivatives

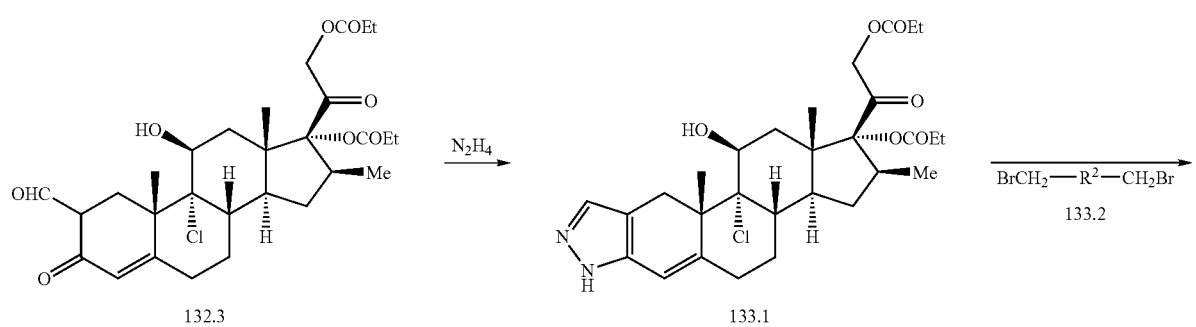

-continued

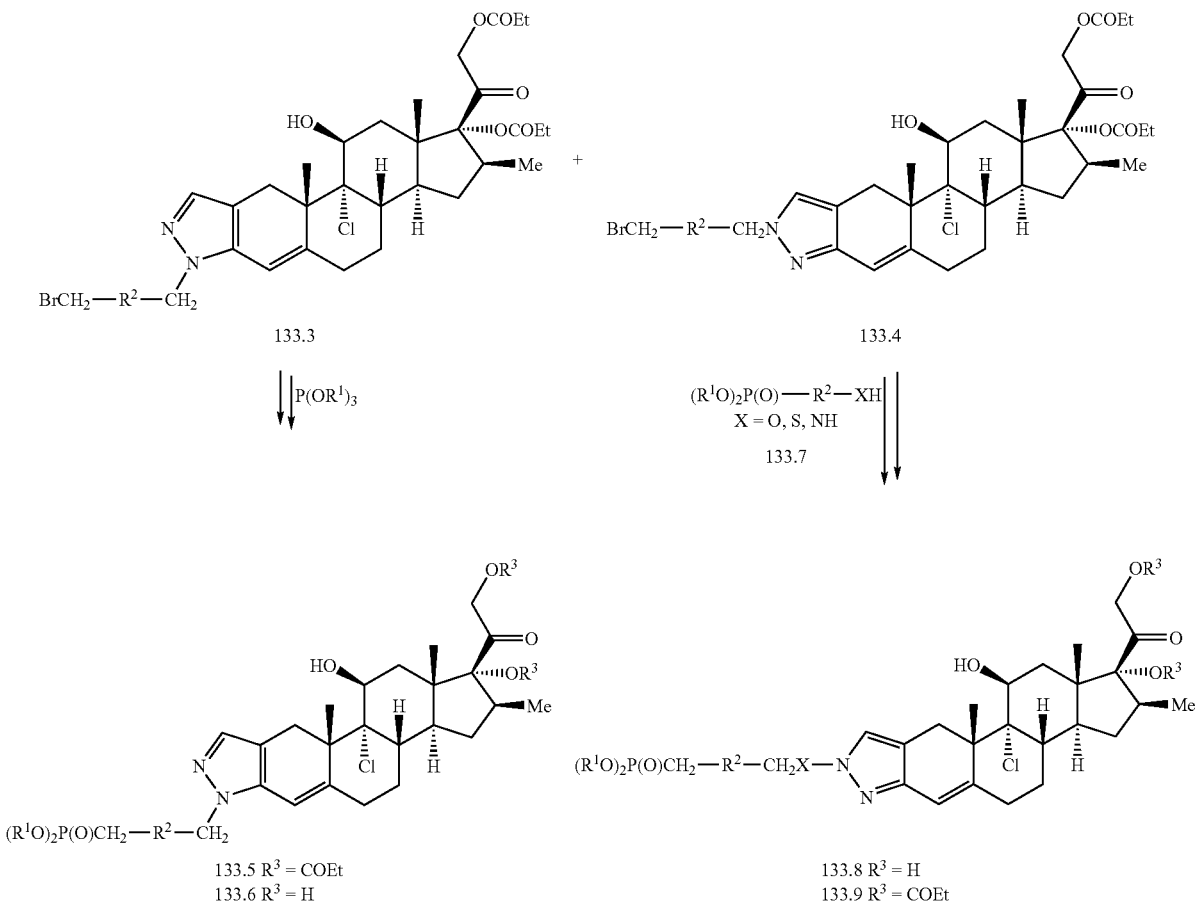

The preparation of the phosphonate esters in which the phosphonate group is attached by means of a variable carbon linkage is illustrated above. In this procedure, the ketoaldehyde 132.3 is reacted with hydrazine, to afford the pyrazole derivative 133.1. The reaction of steroidal 2-formyl-3-ketones with hydrazine is described in J. Am. Chem. Soc, 1964, 86, 1520. The reaction is performed in acetic acid at ambient temperature. The resulting pyrazole is then reacted with a bis(bromomethyl) reagent 133.2, in which $R^2$ is as defined above, to produce the isomeric 2' and 1' alkylation products 133.3 and 133.4 respectively. The alkylation of substituted pyrazoles is described, for example, in Heterocyclic Chemistry, by T. L. Gilchrist, Longman, 1992, p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The isomer 133.3 is reacted, in an Arbuzov reaction, with a trialkyl phosphite to yield the phosphonate 133.5: basic hydrolysis then gives the triol 133.6. The preparation of phosphonates by means of the reaction between an alkyl halide and a trialkyl phosphite is described in Handb. Organophosphorus Chem., 1992, 115-72. The substrate and an excess of the phosphite are heated at ca. 120° to effect the conversion. Application of the above procedure to the isomeric 1'-substituted pyrazole yields the corresponding isomeric products.

Alternatively, the bromomethyl-substituted pyrazole 133.4 is reacted with a dialkyl hydroxy, mercapto or amino-substituted phosphonate 133.7 to afford the ether, thioether or amine products 133.8 and 133.9. The displacement reaction is performed in a polar solvent such as dimethylformamide or acetonitrile, at from ambient temperature to about 70°, in the presence of an inorganic base such as potassium carbonate, or an organic base such as dimethylaminopyridine. Application of the above procedure to the isomeric 2'-substituted pyrazole yields the corresponding isomeric products.

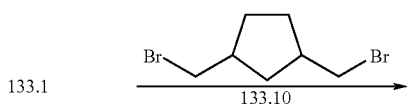

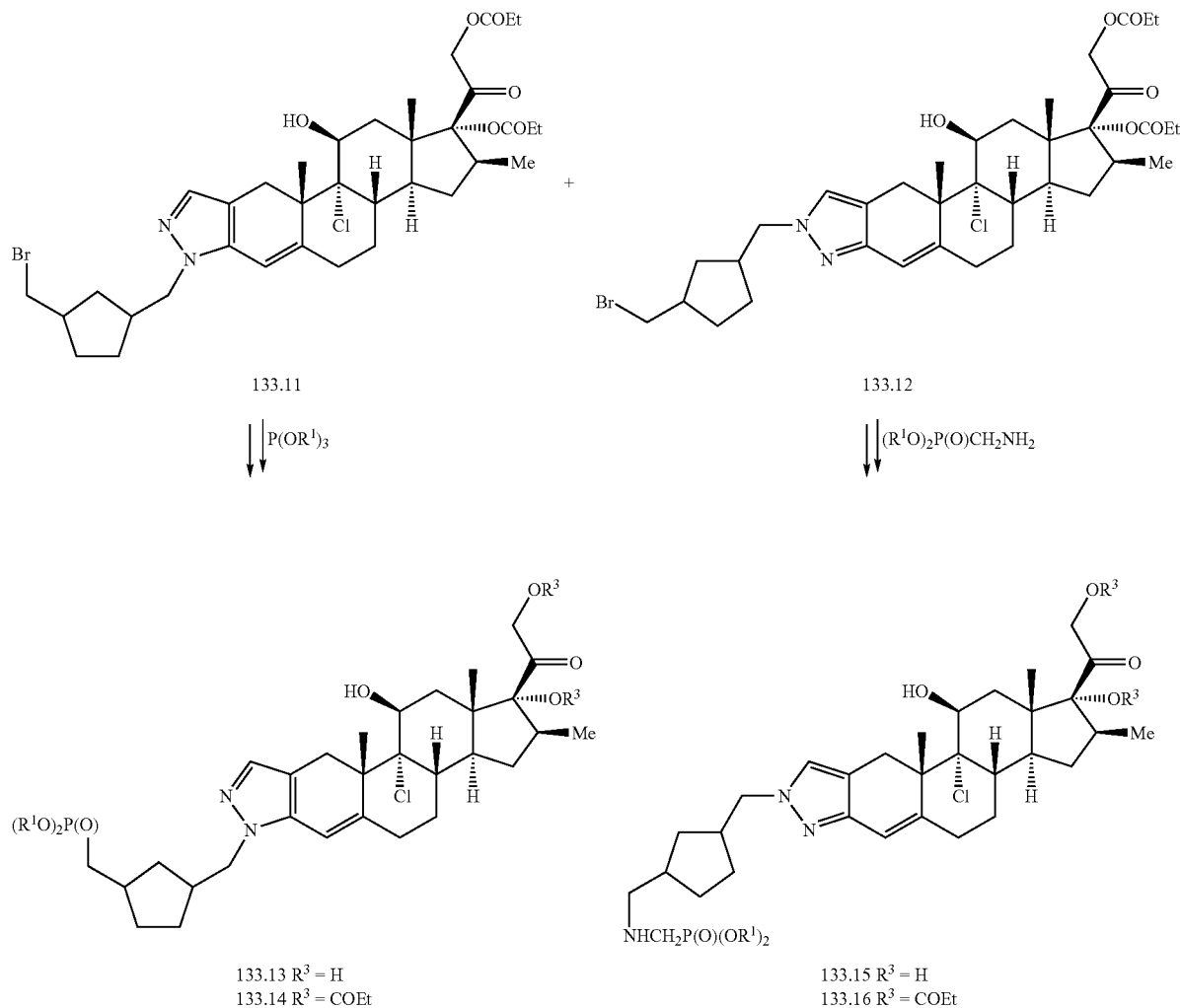

133.11

133.12

Representative compounds of the invention can be prepared is illustrated above. The pyrazole 133.1 is reacted, in dimethylformamide solution at ca. 90°, with a dialkyl 1,3-bis(bromomethyl)Cyclopentane 133.10 (*Bull. Soc. Chim. FR.*, 1975, 1295) and dimethylaminopyridine, to yield the isomeric alkylation products 133.11 and 133.12. The 2'-substituted compound 133.11 is then reacted with ten molar equivalents of a trialkyl phosphite at 100°, to yield the phosphonate 133.14. Basic hydrolysis produces the triol 133.13.

Alternatively, the 1-substituted isomer 133.12 is reacted at 70° in dimethylformamide solution with one molar equivalent of a dialkyl aminomethyl phosphonate 133.15 (Interchim) and potassium carbonate, to prepare the amine phosphonate 133.17; basic hydrolysis affords the triol 133.16. Application of the procedures to the isomeric bromomethyl compound 133.11 affords the corresponding isomeric products.

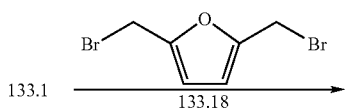

-continued

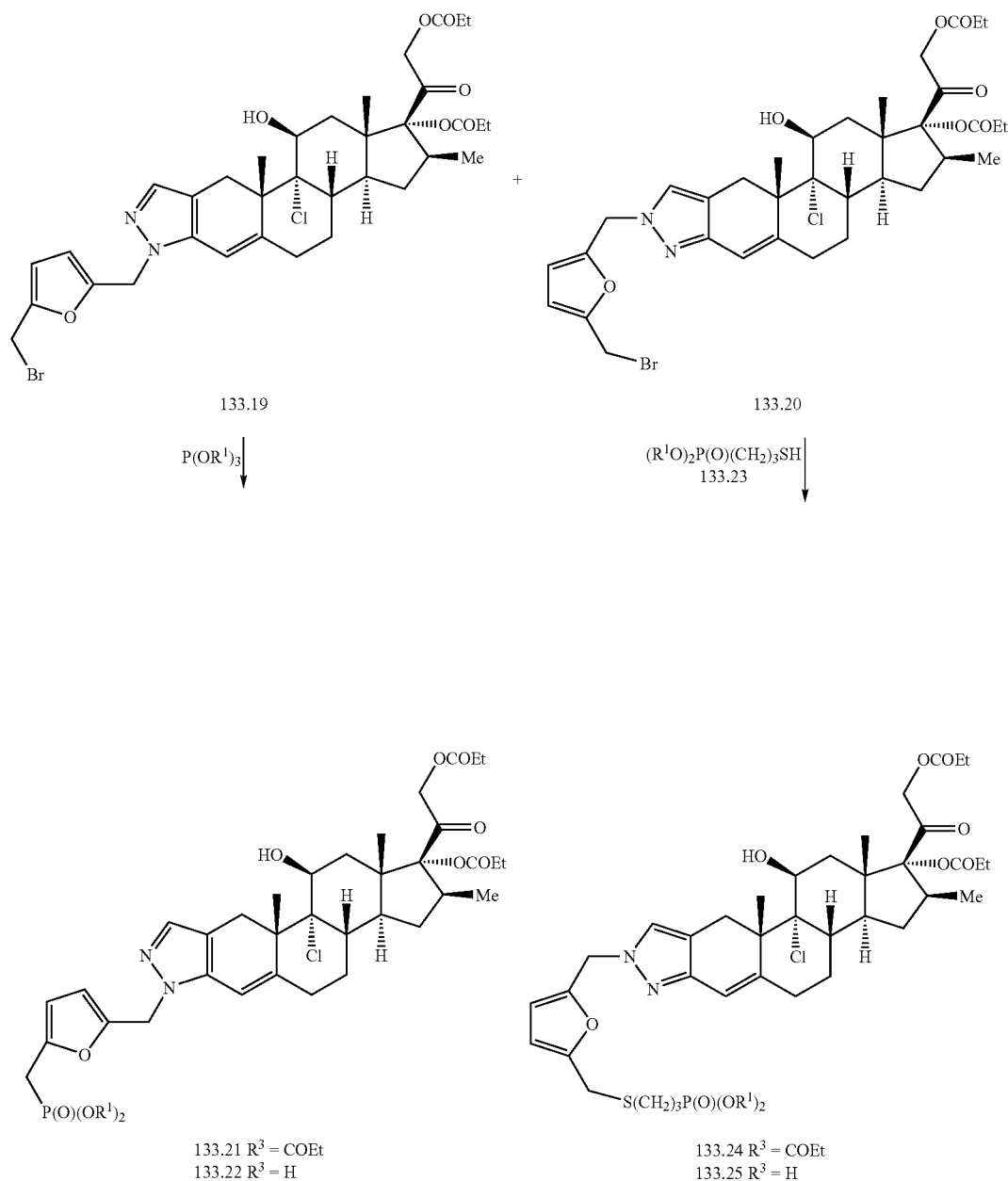

133.19

P(OR¹)₃ ↓

133.20

(R¹O)₂P(O)(CH₂)₃SH
133.23 ↓

133.21 R³ = COEt
133.22 R³ = H 133.24 R³ = COEt
133.25 R³ = H

Representative compounds of the invention can be prepared is illustrated above. The pyrazole 133.1 is reacted, as described above, with 2,5-bis(bromomethyl)furan 133.18 (Tet., 1999, 55, 4709) to give the substituted pyrazoles 133.19 and 133.20. The 2'-substituted compound 133.19 is then reacted, as described above, with a trialkyl phosphite to produce the diester phosphonate 133.21 and the triol 133.22.

Alternatively, the 1' isomer 133.20 is reacted, as described above, with a dialkyl 3-mercaptopropyl phosphonate 133.23 (WO 2000077101) to give the diester 133.24 and the triol 133.25.

Using the above procedure, but employing, in place of the mercaptoethyl phosphonate 133.23, different hydroxy, mercapto or amino-substituted phosphonates, the corresponding ether, thioether or amino products are obtained.

EXAMPLE 134

Preparation of Representative Compounds of Formulae 133-138

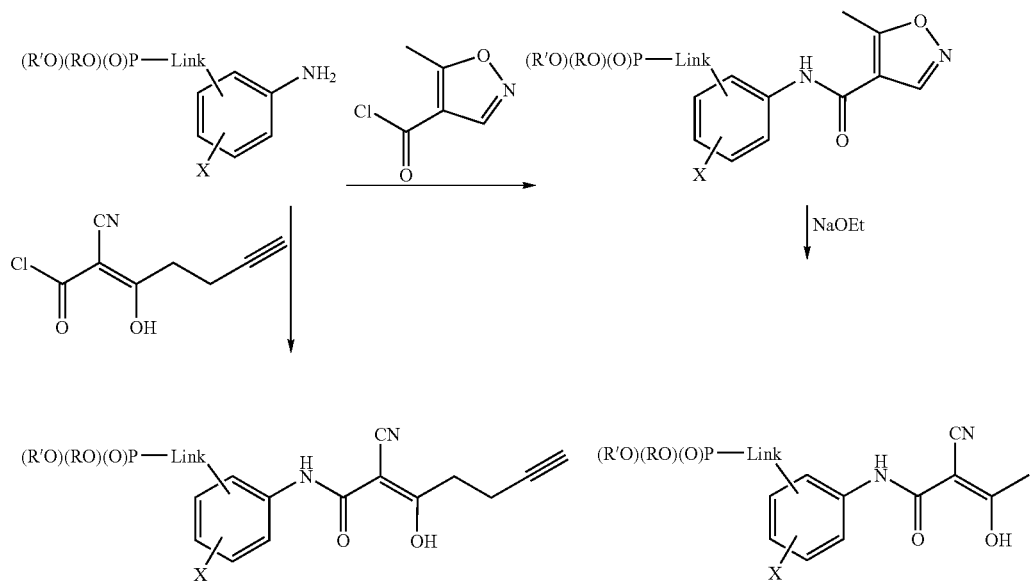

Representative compounds of Formulae 133-138 can be prepared as illustrated above. Synthetic methodology towards compounds such as these is described by Westwood et al, *J. Med. Chem.,* 1996, 39, 4608-4621.

The preparation of an intermediate aniline useful in the above general procedures is illustrated below.

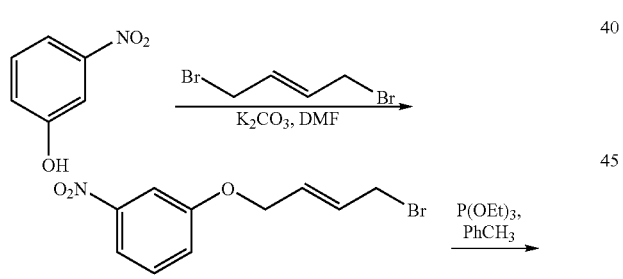

-continued

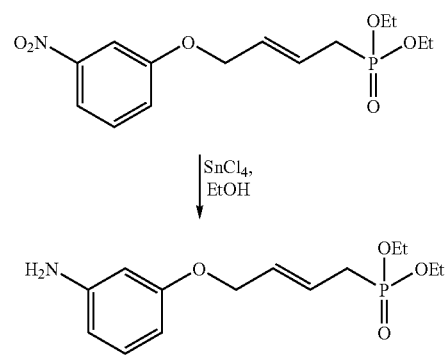

The preparation of an intermediate alkyne that can also be used in the above general procedures is illustrated below.

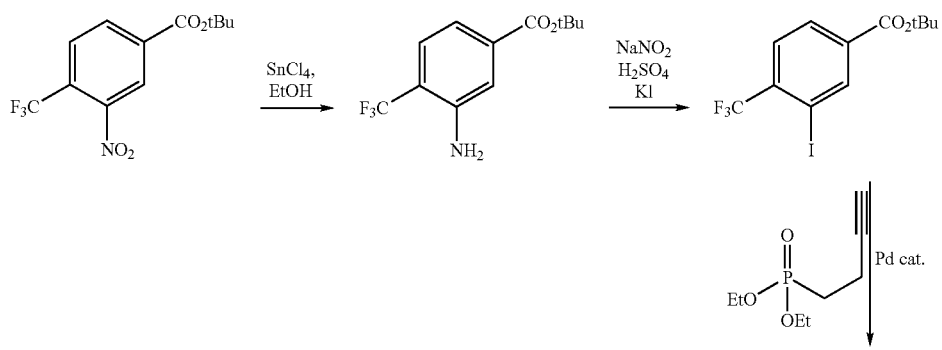

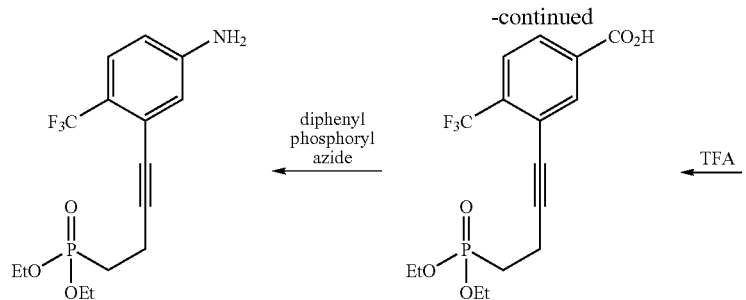

EXAMPLES 135-138

Methylprednisolone Suleptanate Derivatives

The structures of Methylprednisolone suleptanate (WO 8900558) and representative phosphonate esters of the invention are shown below, in which the substituent $R^1$ is H, alkyl, alkenyl, aryl or aralkyl. These compounds incorporate a phosphonate moiety $(R^1O)_2P(O)$ connected to the nucleus by means of a variable linking group, designated as "link" in the attached structures.

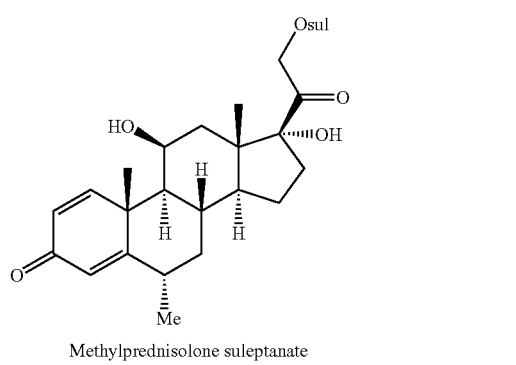

Methylprednisolone suleptanate

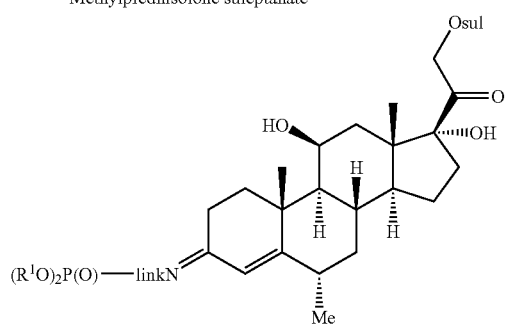

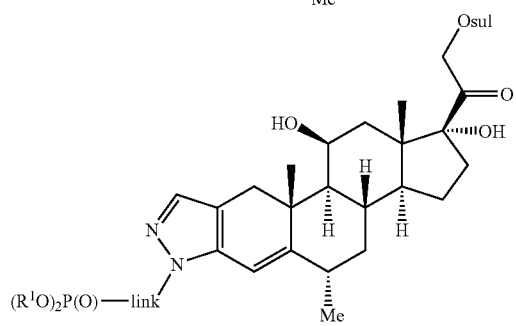

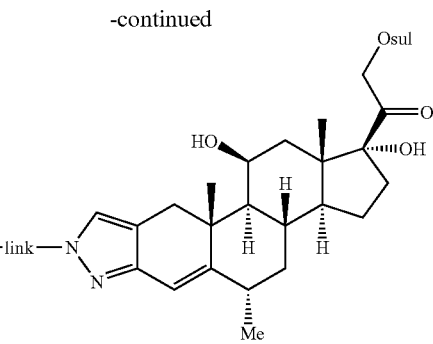

sul = $CO(CH_2)_6CONMe(CH_2)_2SO_3H$

The synthesis of representative phosphonate derivatives of methylprednisolone suleptanate is outlined in Examples 135-138. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 135

Preparation of Representative Methylprednisolone Suleptanate Derivatives

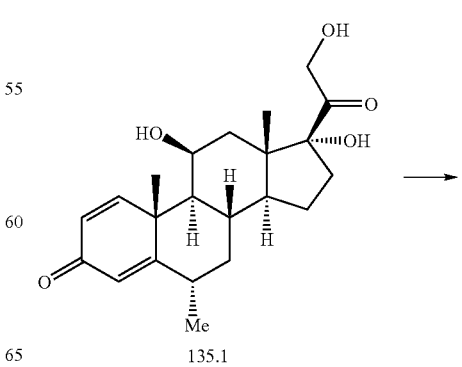

135.1

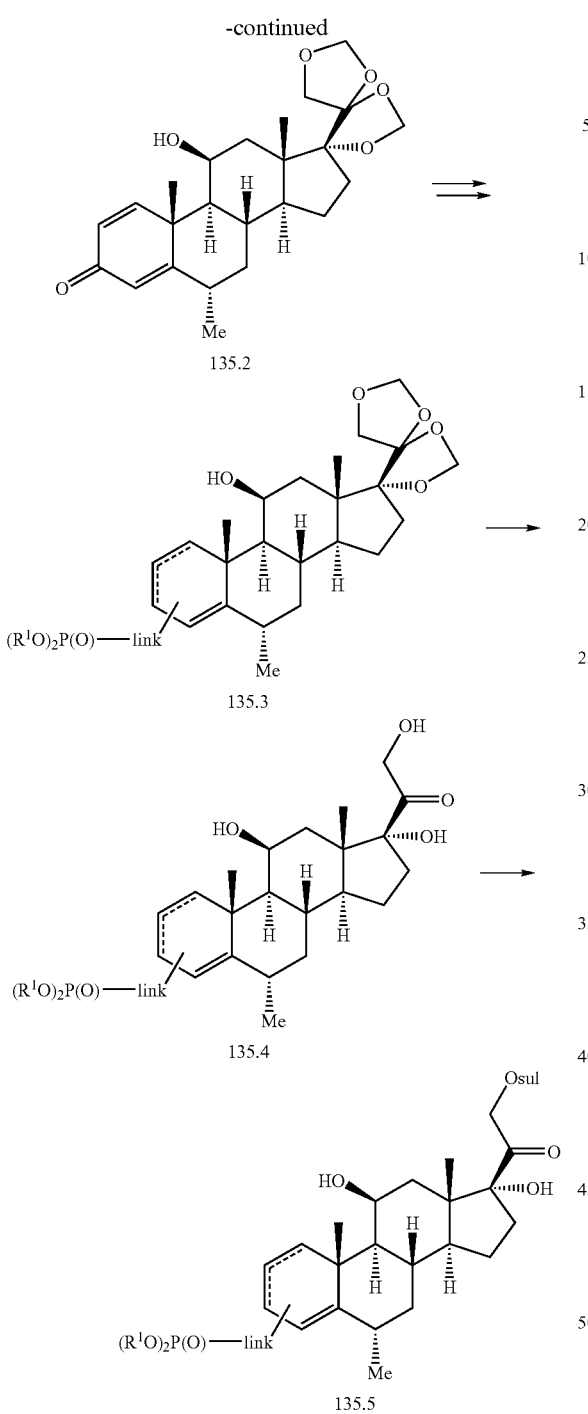

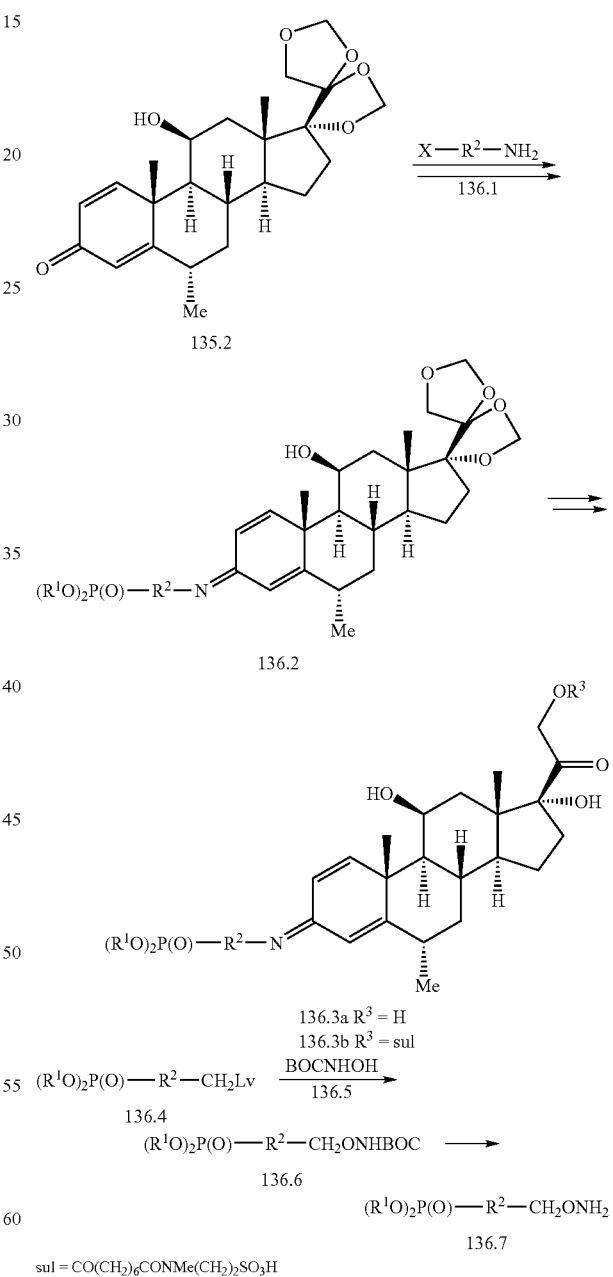

1990, p. 223, to afford the triol 135.4. The triol is then converted into the 21-suleptanate ester as described in WO 8900558. In this procedure, a mixed anhydride prepared by reacting suleptanic acid with pivaloyl chloride, in the presence of a base such as triethylamine, is reacted with the 21-hydroxy steroid 135.4 to prepare the 21-suleptanate ester 135.5.

EXAMPLE 136

Preparation of Representative Methylprednisolone Suleptanate Derivatives

Representative compounds of the invention can be prepared as illusrrated above. The steroid side-chain is protected as a bis-methylenedioxy (BMD) moiety. In this sequence, methylprednisolone 135.1 is reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 135.2. The phosphonate moiety is then introduced, using the procedures described below, to produce the phosphonate ester 135.3. The BMD moiety is then hydrolyzed, for example by treatment with 50% aqueous acetic acid, as described in Protective Groups in Organic Synthesis, by T. W. Greene and P. G. M. Wuts, Wiley, Second Edition The preparation of phosphonates in which the phosphonate is attached by means of an imino or iminoxy group and a variable carbon chain is illusrrated above. In this procedure, the BMD-protected derivative 135.2 is reacted with an amine or hydroxylamine 136.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in *Anal. Bioch.*, 1978, 86, 133. and in *J. Mass. Spectrom.*, 1995, 30, 497. The BMD-protected side-chain compound 136.2 is then converted into the triol 136.3a, and then to the suleptanate 136.3b.

The preparation of hydroxylamine ethers incorporating a phosphonate group is also illustrated above. In this procedure, a phosphonate 136.4, in which Lv is a leaving group such as bromo or trifluoromethylsulfonyloxy, is reacted with BOC-hydroxylamine 136.5 (Aldrich) to produce the ether 136.6. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 136.7.

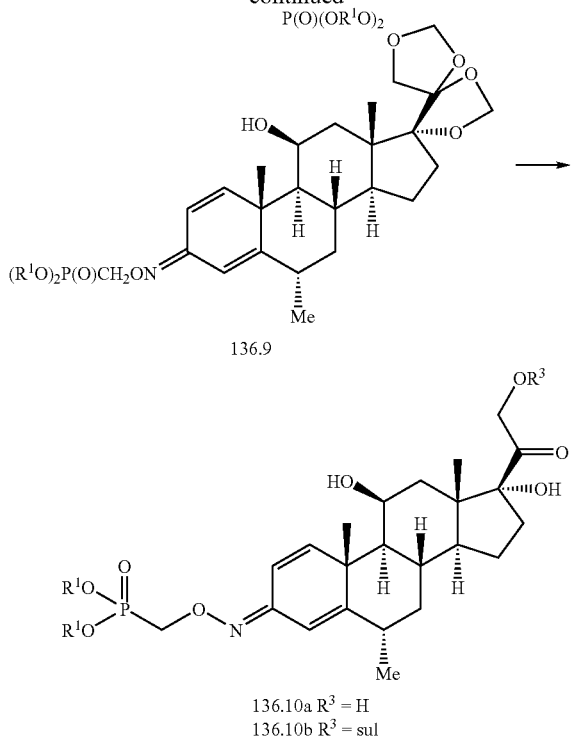

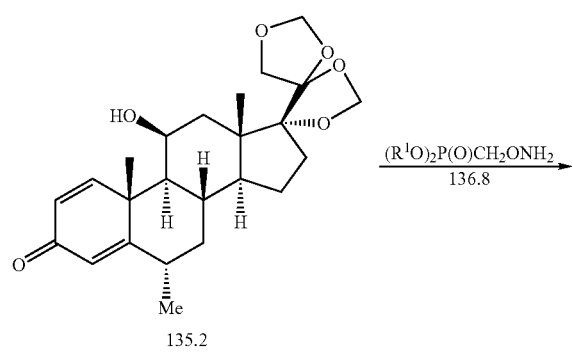

The preparation of phosphonates in which the phosphonate is attached by means of an iminoxy group is illusrrated above. In this procedure, the substrate 135.2 is reacted with a dialkyl phosphonomethyl hydroxylamine 136.8, prepared as described above from a dialkyl trifluoromethylsulfonyloxymethyl phosphonate (*Tet. Lett.*, 1986, 27, 1477) and BOC-hydroxylamine, to afford the oxime 136.9 which is deprotected to afford the triol 136.10a from which the suleptanate ester 136.10b is prepared. The oxime forming reaction is performed at ambient temperature in ethanol-acetic acid solution between equimolar amounts of the reactants.

Using the above procedures, but employing, in place of the hydroxylamine ether 136.8, different oxime ethers 136.1, the corresponding products 136.3b are obtained.

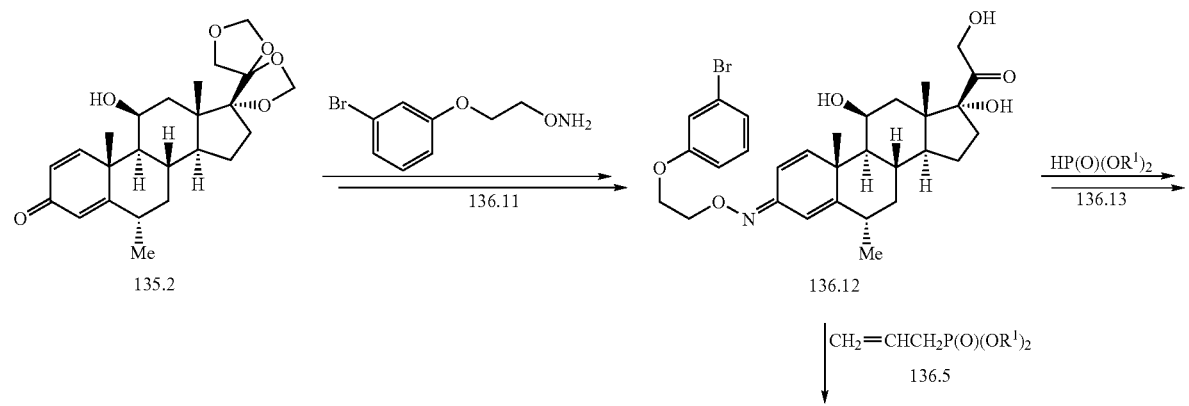

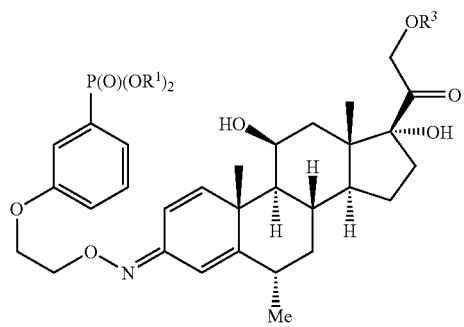

136.14a: R³ = H
136.14b: R³ = sul

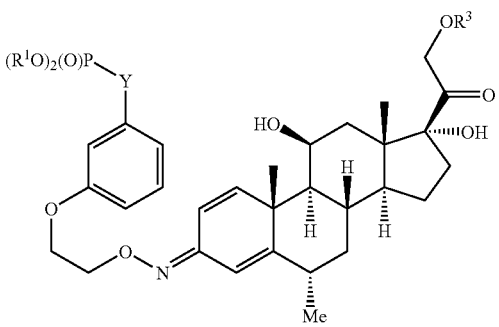

136.16a Y = CH=CHCH₂, R³ = H
136.16b Y = CH=CHCH₂, R³ = sul
136.17a Y = (CH₂)₃, R³ = H
136.17b Y = (CH₂)₃, R³ = sul The preparation of compounds in which the phosphonate group is attached by means of a phenoxyethoxy oxime group is illusrrated above. In this procedure, the dienone 135.2 is reacted, as described above, with O-(3-bromophenoxyethyl) hydroxylamine 136.11, prepared as described above from 3-bromophenoxyethyl bromide (FR 1481052) and BOC-protected hydroxylamine, to give, after deprotection of the sidechain, the oxime 136.12. The product is then reacted, in the presence of a palladium catalyst, with a dialkyl phosphite 136.13 to afford the phosphonate 136.14a. The preparation of arylphosphonates by means of a coupling reaction between aryl bromides and dialkyl phosphites is described in *J. Med. Chem.*, 35, 1371, 1992. The reaction is performed in an inert solvent such as toluene, in the presence of a base such as triethylamine and a catalytic amount of tetrakis(triphenylphosphine)palladium(0). The 21-hydroxy group is then converted into the 21-suleptanate product 136.14b.

Alternatively, the bromo compound 136.12 is coupled with a dialkyl propenylphosphonate 136.15 (Aldrich) to afford the phosphonate 136.16a. The coupling of aryl halides with olefins by means of the Heck reaction is described, for example, in Advanced Organic Chemistry, by F. A. Carey and R. J. Sundberg, Plenum, 2001, p. 503ff and in *Acc. Chem. Res.*, 12, 146, 1979. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 136.16a is reduced, for example by reaction with diimide, to produce the saturated analog 136.17a. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane. The products 136.16a and 136.17a are then converted into the suleptanate esters 136.16b and 136.17b.

Using the above procedures, but employing, in place of the bromophenoxyethoxy reagent 136.11, different bromo-substituted aryl or heteroaryl alkoxy hydroxylamines, and/or different dialkyl alkenyl phosphonates, the products analogous to the compounds 136.14b, 136.16b and 136.17b are obtained.

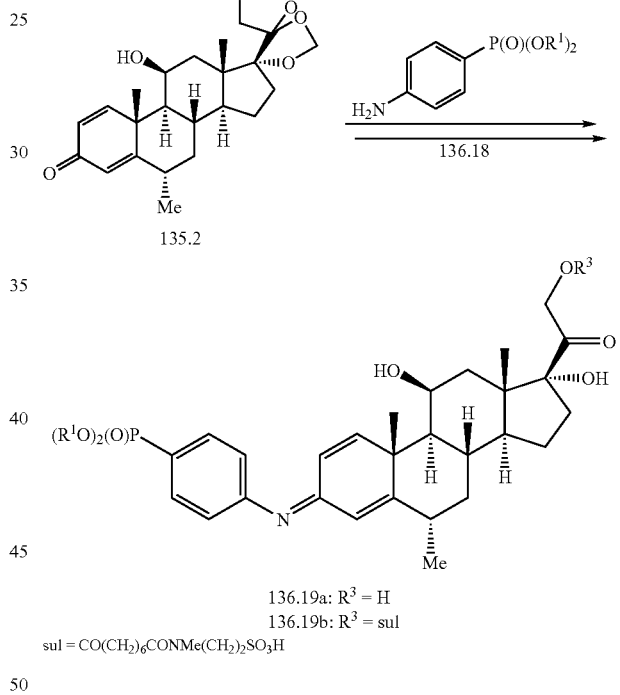

136.19a: R³ = H
136.19b: R³ = sul
sul = CO(CH₂)₆CONMe(CH₂)₂SO₃H

The preparation of phosphonates in which the phosphonate is attached by means of an imino group is illustrated above. In this procedure, the substrate 135.2 is reacted with a dialkyl 4-aminophenyl phosphonate 136.18, (Epsilon) to give, after deprotection, the imine product 136.19a. The reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions. The product is then converted into the suleptanate ester 136.19b.

Using the above procedures, but employing, in place of the 4-aminophenyl phosphonate 136.18 different amino-substituted aryl or heteroaryl phosphonates, products analogous to 136.19b are obtained.

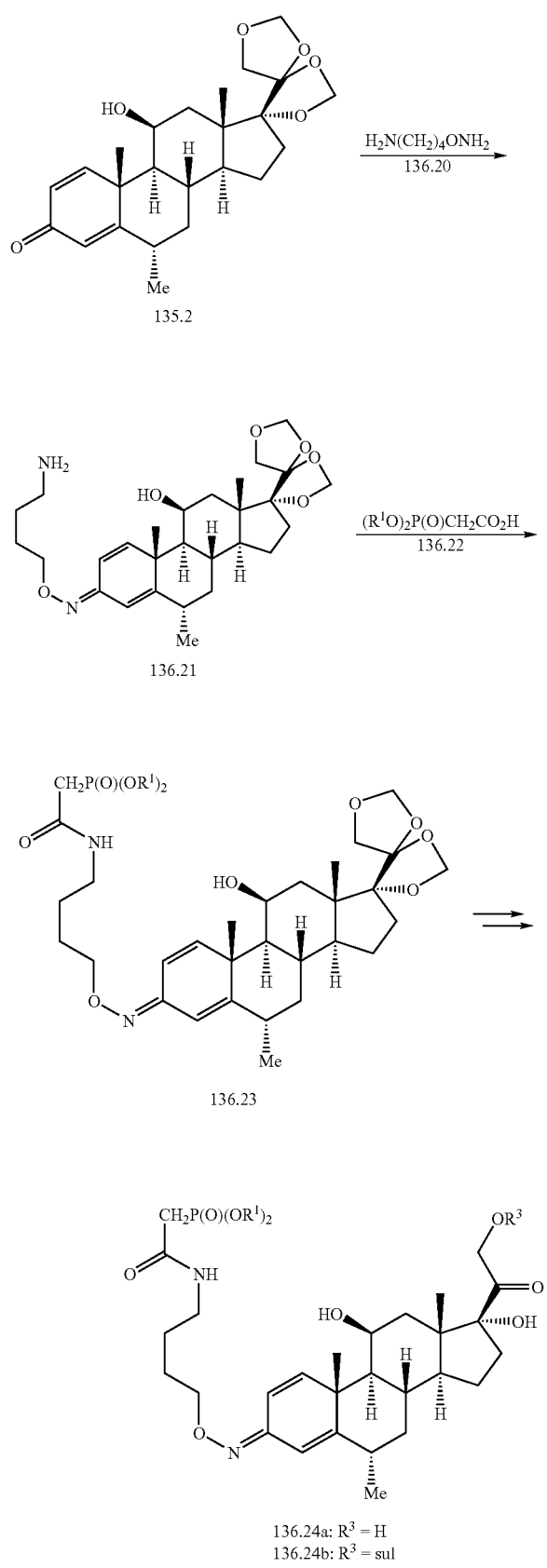

136.24a: R³ = H
136.24b: R³ = sul

The preparation of phosphonates in which the phosphonate is attached by means of an oximino group and an amide linkage is illusrrated above. In this procedure, the dienone 135.2 is reacted with O-(4-aminobutyl)hydroxylamine 136.20 (Pol. J. Chem., 1981, 55, 1163) to yield the oxime 136.21. The reaction of steroidal 1,4-dien-3-ones with substituted hydroxylamines is described in J. Steroid Bioch., 1976, 7, 795; the reaction is performed between equimolar amounts of the reactants in a polar organic solvent such as pyridine or methanol, optionally in the presence of acetic acid or sodium acetate. The oxime is then coupled with a dialkyl phosphonoacetic acid 136.22 (Aldrich), to yield the amide oxime 136.23. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid is first converted into an activated derivative such as the acid chloride, anhydride, mixed anhydride, imidazolide and the like, and then reacted with the amine, in the presence of an organic base such as, for example, pyridine, to afford the amide. The conversion of a carboxylic acid into the corresponding acid chloride is effected by treatment of the carboxylic acid with a reagent such as, for example, thionyl chloride or oxalyl chloride in an inert organic solvent such as dichloromethane, optionally in the presence of a catalytic amount of dimethylformamide. The amide product 136.23 is then converted into the suleptanate 136.24b.

Using the above procedures, but employing, in place of the hydroxylamine 136.22, different amino-substituted hydroxylamines, and/or different carboxy-substituted phosphonates, the products analogous to 136.24b are obtained.

EXAMPLE 137

Preparation of Representative Methylprednisolone Suleptanate Derivatives

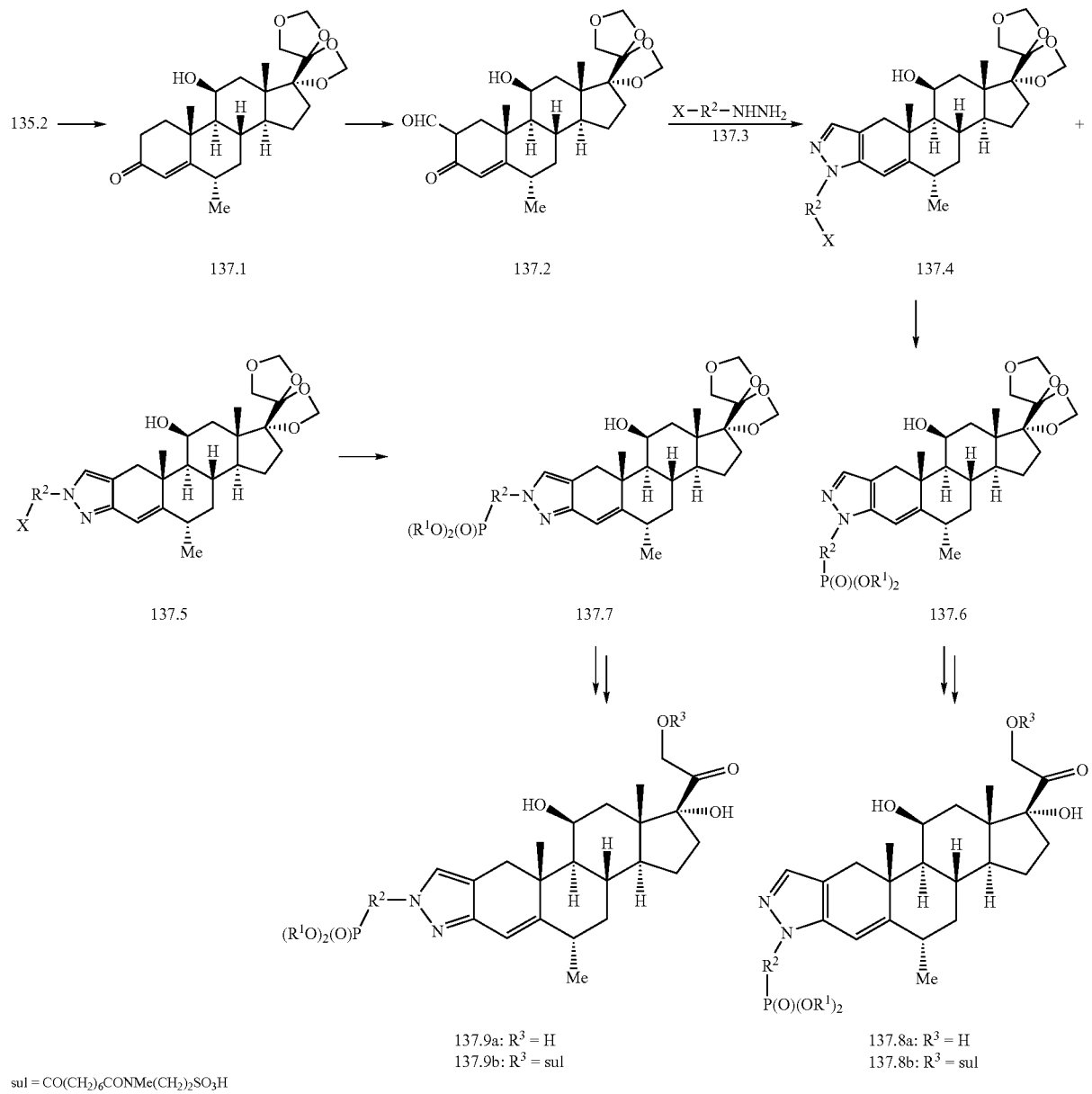

sul = CO(CH$_2$)$_6$CONMe(CH$_2$)$_2$SO$_3$H

The preparation of the phosphonate esters in which the phosphonate group is attached to the 1' or 2' position of the pyrazole ring, by means of an aromatic or heteroaromatic group, a heteroatom and a variable carbon chain is illusrrated above. In this procedure, the BMD-protected dienone 135.2 is reduced to afford the 1,2-dihydro product 137.1. The catalytic hydrogenation reaction is effected by the use of tris(triphenylphosphine)rhodium(I) chloride, for example as described in J. Med. Chem., 2001, 44, 602. The product is then reacted with ethyl formate and a base such as sodium hydride, in an inert solvent such as toluene or dimethylformamide, as described in J. Am. Chem. Soc., 1964, 86, 1520, to afford the 2-formyl product 137.2. This compound is then reacted with an alkyl, aralkyl, aryl or heteroaryl hydrazine 137.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 137.4 and 137.5. The pyrazole-forming reaction is performed between equimolar amounts of the reactants in an acidic solvent such as acetic acid, as described in J. Am. Chem. Soc., 1964, 86, 1520. The pyrazoles 137.4 and 137.5 are then transformed via the BMD-protected intermediates 137.6 and 137.7, into the phosphonate suleptanates 137.8b and 137.9b.

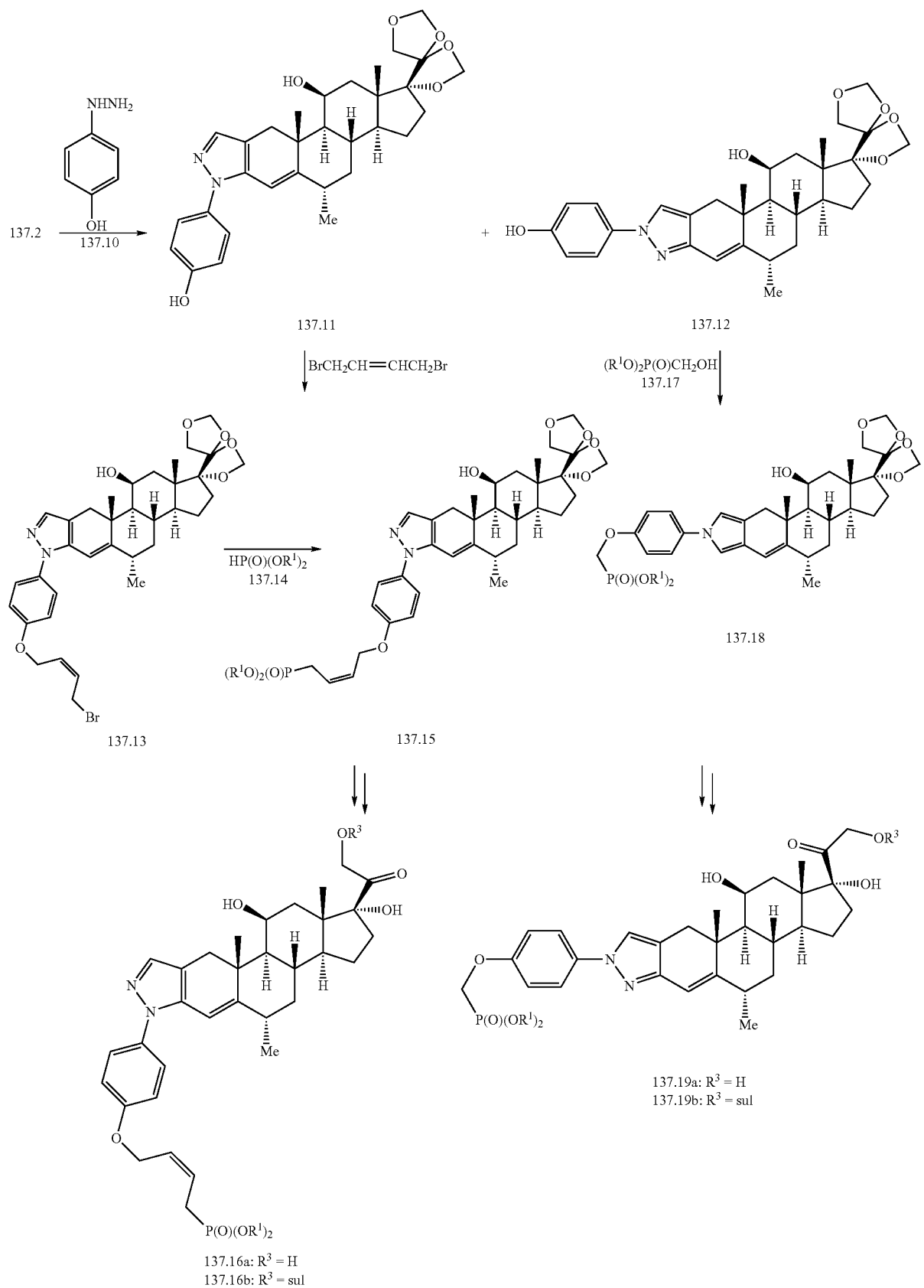

The preparation of phosphonates in which the phosphonate is attached by means of a phenyl ring and an alkoxy or an alkenyl linkage is illusrrated above. In this procedure, the ketoaldehyde 137.2 is reacted, as described above, with 4-hydroxyphenylhydrazine 137.10 (Epsilon) to give the pyrazoles 137.11 and 137.12. The 2'-substituted isomer 137.11 is then reacted in dimethylformamide solution at ambient temperature with one molar equivalent of 1,4-dibromobut-2-ene and dimethylaminopyridine, to yield the bromoether 137.13. The product is then reacted at 120° in an Arbuzov reaction with a trialkyl phosphite 137.14 to give the phosphonate product 137.15. The Arbuzov reaction, in which an alkyl bromide is transformed into the corresponding phosphonate, by heating at from 60° to about 150° with a trialkyl phosphite, is described in Handb. Organophosphorus Chem., 1992, 115-72. The BMD protecting group is then removed and the product is acylated to yield the suleptanate ester triol 137.16b.

Alternatively, the 1'-substituted pyrazole 137.12 is reacted, in a Mitsonobu reaction, with a dialkyl 2-hydroxymethyl phosphonate 137.17 (Aldrich) to afford the ether 137.18. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol and the alcohol or thiol component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656. The product 137.18 is then deprotected to give the triol 137.19a, and the latter compound is acylated to afford the suleptanate 137.19b.

Using the above procedures, but employing different dibromides or hydroxyl-substituted phosphonates, the products analogous to 137.16b and 137.19b are obtained. The functionalization procedures are interchangeable between the pyrazole substrates 137.11 and 137.12.

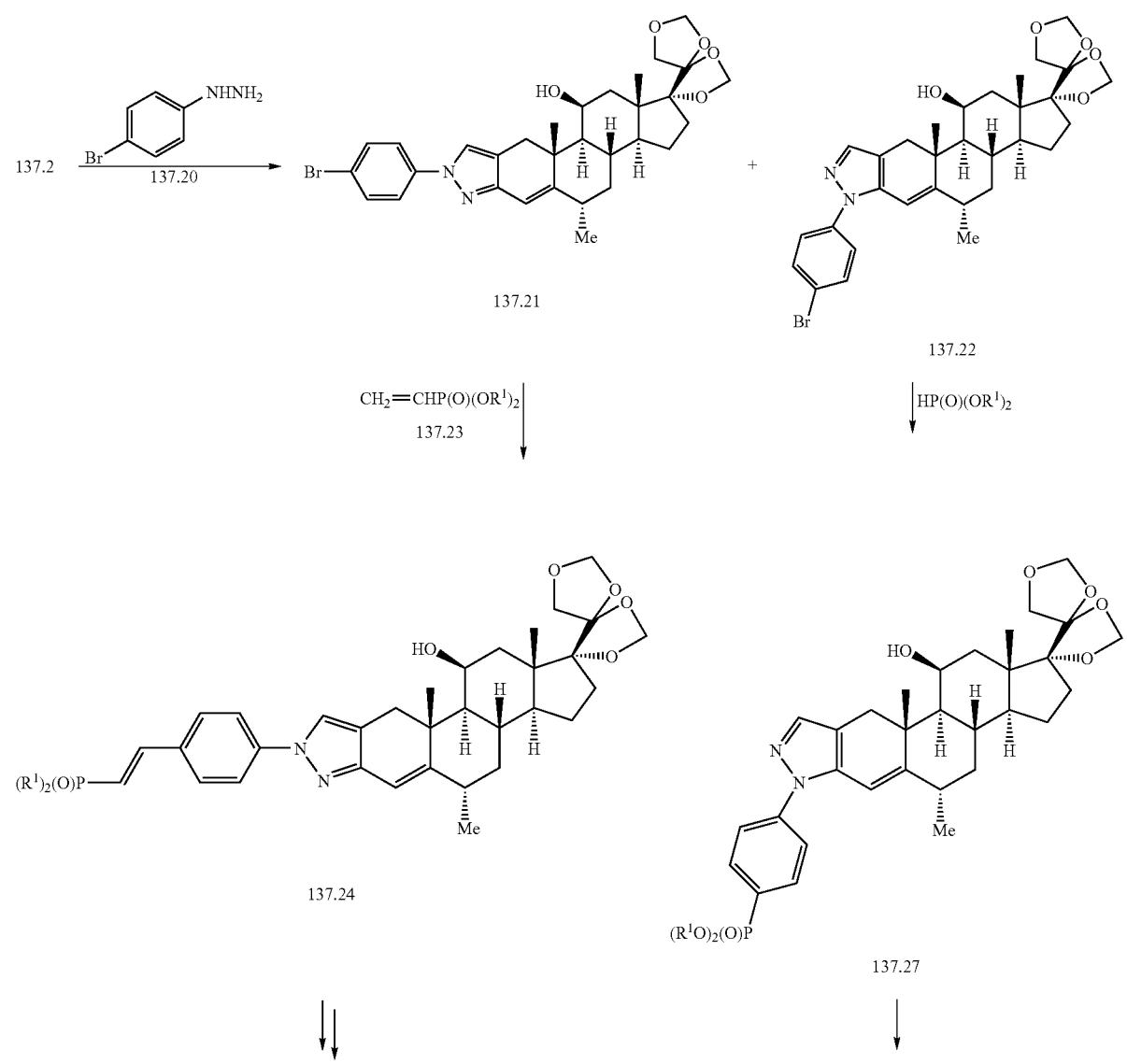

-continued

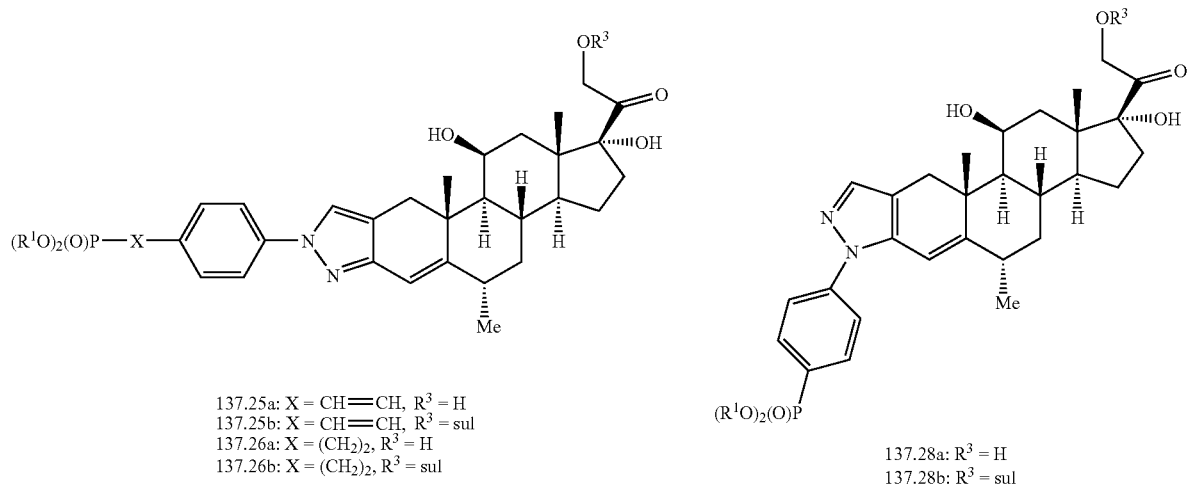

137.25a: X = CH=CH, R³ = H
137.25b: X = CH=CH, R³ = sul
137.26a: X = (CH₂)₂, R³ = H
137.26b: X = (CH₂)₂, R³ = sul 137.28a: R³ = H
137.28b: R³ = sul sul = CO(CH₂)₆CONMe(CH₂)₂SO₃H The preparation of the phosphonates in which the phosphonate group is attached by means of a phenyl ring or a phenyl ring and a saturated or unsaturated carbon chain is illustrated above. In this procedure, the ketoaldehyde 137.2 is reacted, as described above, with 4-bromophenyl hydrazine 137.20 (*J. Organomet. Chem.*, 1999, 62, 581) to produce the pyrazoles 137.21 and 137.22. The 1'-substituted isomer 137.21 is coupled, in the presence of a palladium catalyst, with a dialkyl vinylphosphonate 137.23 (Aldrich) to give the phosphonate 137.24. The product is then deprotected to afford the triol 137.25a which is converted into the suleptanate 137.25b. Optionally, the styrenoid double bond present in the product 137.25b is reduced, as described above, to produce the saturated analog 137.26b.

Alternatively, the 2'-substituted pyrazole 137.22 is coupled, in the presence of a palladium catalyst, with a dialkyl phosphite to prepare the phosphonate 137.27 which is deprotected, and the product is acylated to give the suleptanate ester 137.28b. The preparation of arylphosphonates by means of a coupling reaction between aryl bromides and dialkyl phosphites is described in *J. Med. Chem.*, 35, 1371, 1992. This reaction is performed in an inert solvent such as toluene, in the presence of a base such as triethylamine and tetrakis(triphenylphosphine)palladium(0).

Using the above procedures, but employing, in place of the bromophenyl hydrazine 137.20, different bromo-substituted aralkyl, aryl or heteroaryl alkoxy hydrazines, and/or different dialkyl alkenyl phosphonates, the products analogous to the compounds 137.25b, 137.26b and 137.28b are obtained.

EXAMPLE 138

Preparation of Representative Methylprednisolone Suleptanate Derivatives

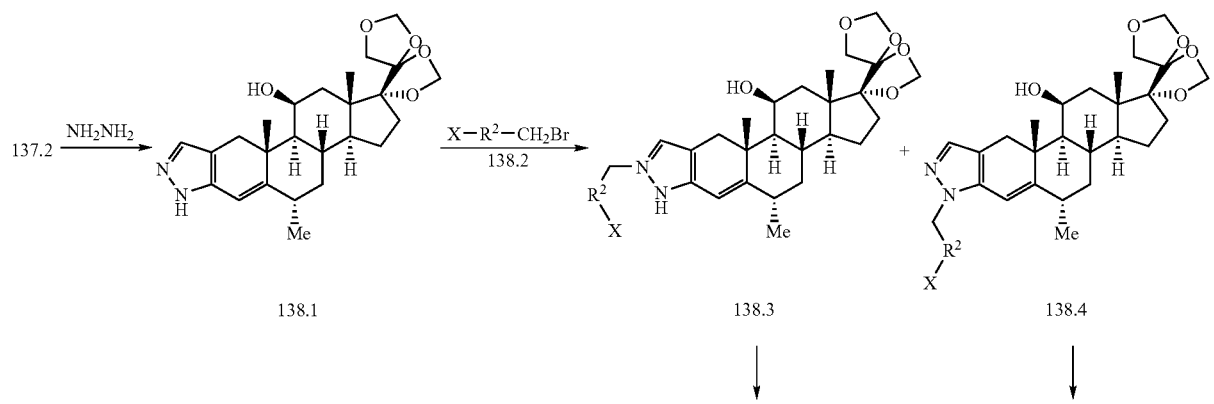

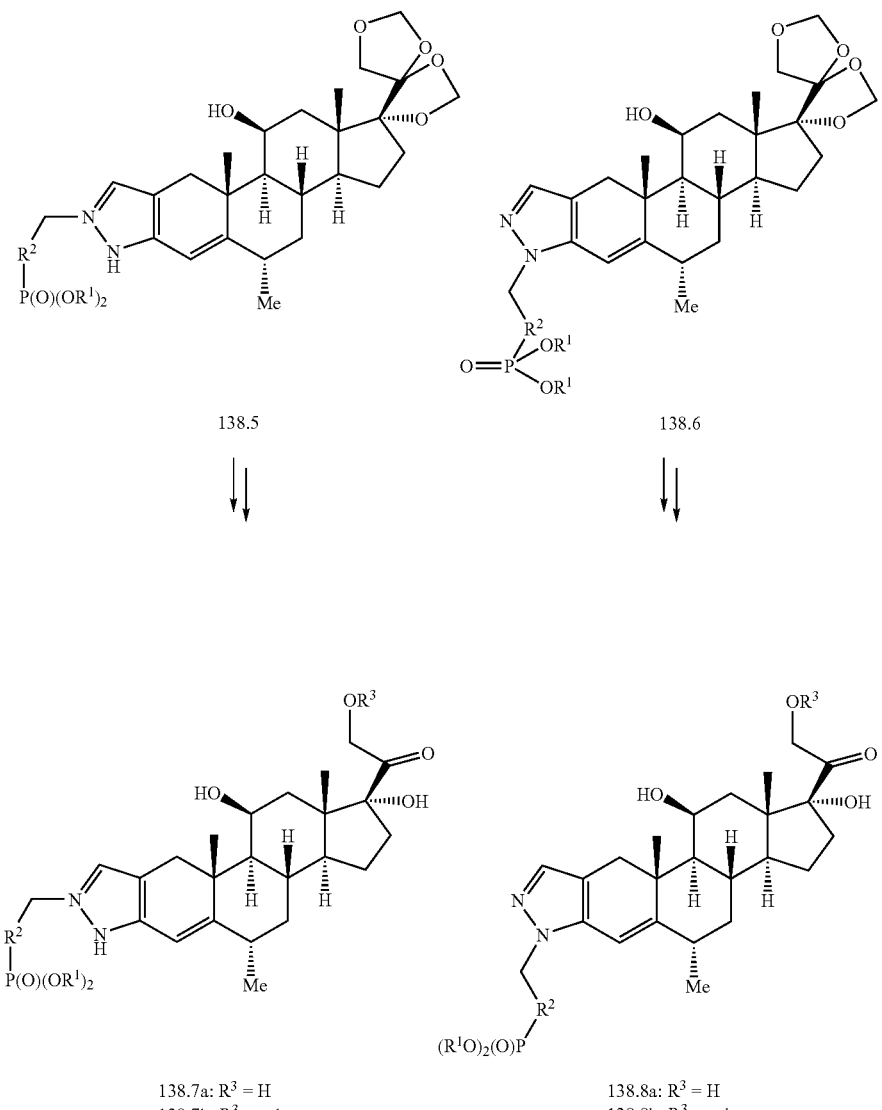

138.7a: R³ = H
138.7b: R³ = sul 138.8a: R³ = H
138.8b: R³ = sul sul = CO(CH₂)₆CONMe(CH₂)₂SO₃H The preparation of the phosphonate esters in which the phosphonate group is attached by means of a variable carbon linkage is illustrated above. In this procedure, the ketoaldehyde 137.2 is reacted with hydrazine, to afford the pyrazole derivative 138.1. The reaction of steroidal 2-formyl-3-ketones with hydrazine is described in *J. Am. Chem. Soc*, 1964, 86, 1520. The reaction is performed in acetic acid at ambient temperature. The pyrazole product is then reacted with a bromomethyl compound 138.2, in which $R^2$ and X are as defined above, to yield the alkylation products 138.3 and 138.4. The alkylation of substituted pyrazoles is described, for example, in Heterocyclic Chemistry, by T. L. Gilchrist, Longman, 1992, p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The products 138.3 and 138.4 are, except in cases where X is dialkylphosphono, converted into the phosphonates 138.5 and 138.6, using the procedures described herein, and deprotection/acylation then affords the suleptanate esters 138.7b and 138.8b.

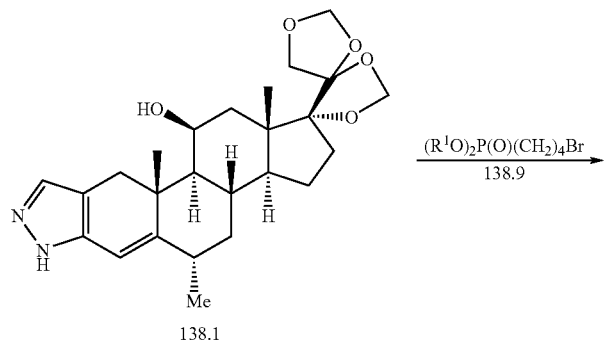
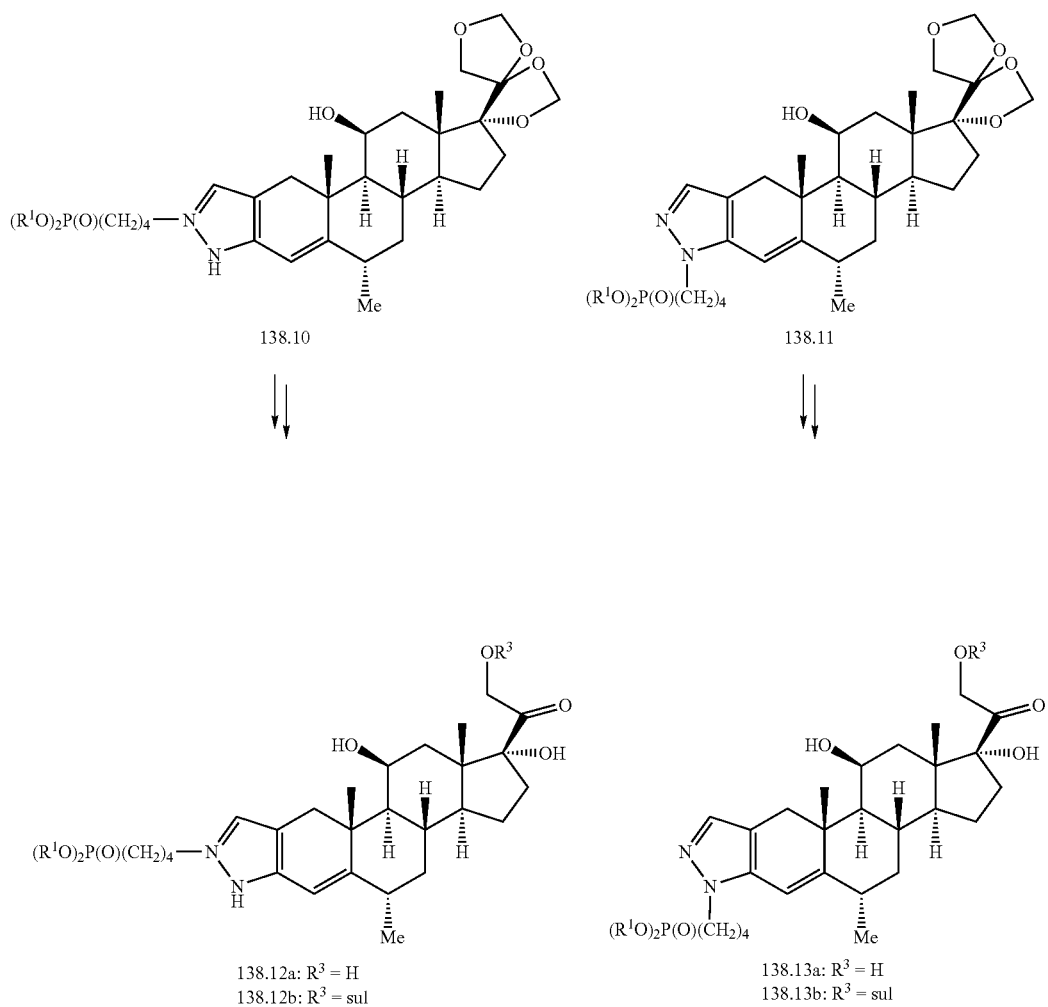
sul = CO(CH$_2$)$_6$CONMe(CH$_2$)$_2$SO$_3$H

Representative compounds of the invention can be prepared as illustrated above. The pyrazole 138.1 is reacted in tetrahydrofuran solution, as described above, with one molar equivalent of a dialkyl bromobutyl phosphonate 138.9 (*Synthesis*, 1994, 9, 909) and lithium hexamethyldisilazide to give the alkylated pyrazoles 138.10 and 138.11. Deprotection/acylation then yields the suleptanates 138.12b and 138.13b.

Representative compounds of the invention can be prepared as illustrated above. The pyrazole 138.1 is reacted in tetrahydrofuran solution, as described above, with 1,2-bis(bromomethyl)Cyclopropane 138.14 (*Tet.*, 1997, 53, 10459) to give the pyrazoles 138.15 and 138.16. The products are subjected to an Arbuzov reaction, in which the bromomethyl substituent is converted into the dialkyl phosphonomethyl

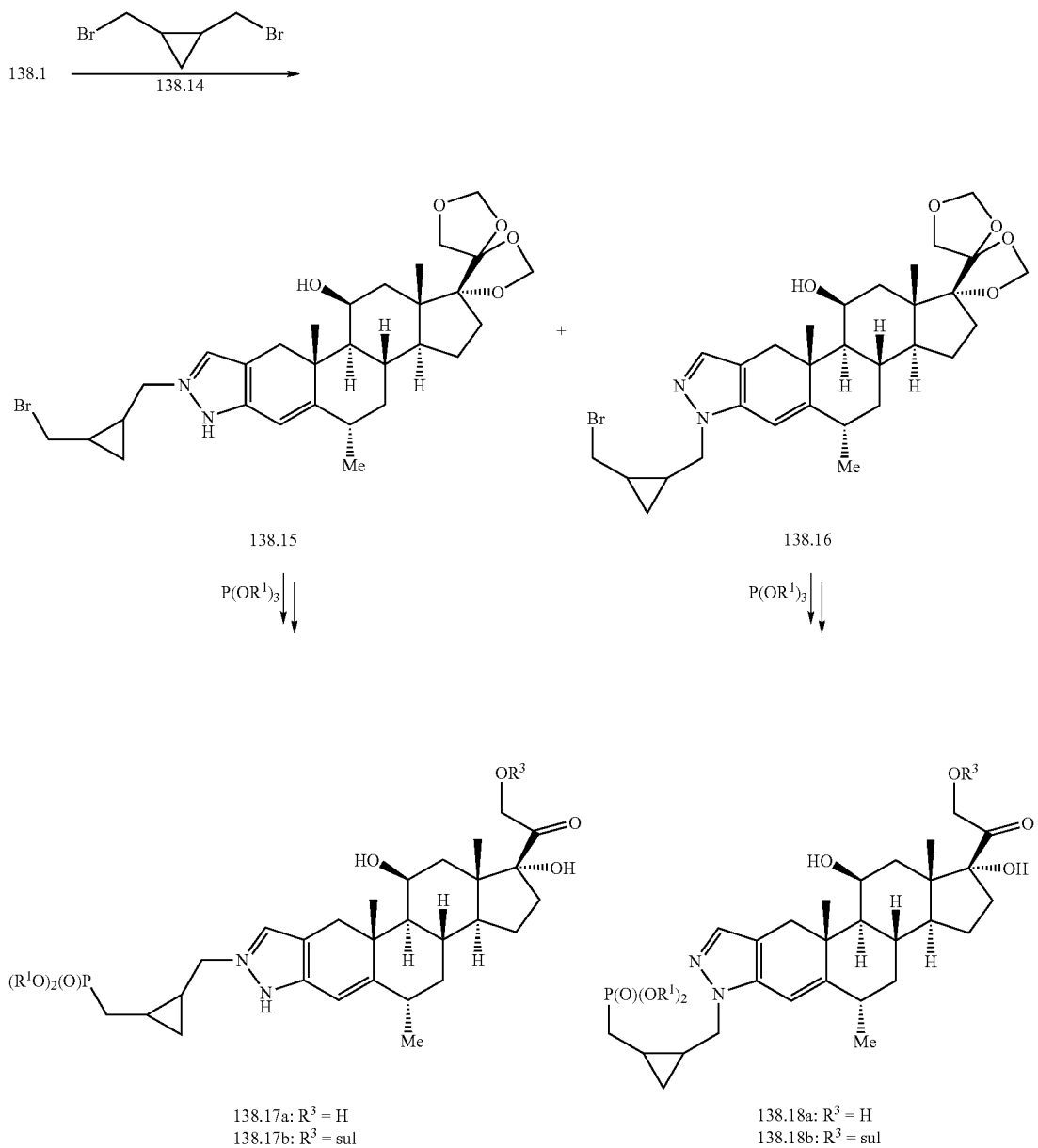

substituent, by reaction with a trialkyl phosphite at 120°, to prepare, after deprotection of the side chain and acylation, the suleptanate phosphonates 138.17b and 138.18b. The Arbuzov reaction is described in Handb. Organophosphorus Chem., 1992, 115-72. In the procedure, the substrate is heated at from 60° to about 160° with a five to fifty-fold molar excess of the trialkyl phosphite.

Using the above procedures, but employing, in place of the dibromide 138.14, different dibromides, the products analogous to 138.17b and 138.18b are obtained.

EXAMPLES 139-142

Prednisone Derivatives

The structures of prednisone (U.S. Pat. No. 2,897,464) and representative phosphonate esters of the invention are shown below, in which the substituent $R^1$ is H, alkyl, alkenyl, aryl or aralkyl. These compounds incorporate a phosphonate moiety $(R^1O)_2P(O)$ connected to the nucleus by means of a variable linking group, designated as "link" in the attached structures.

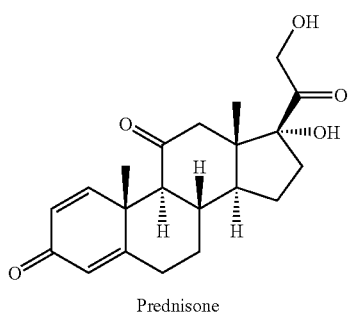
Prednisone

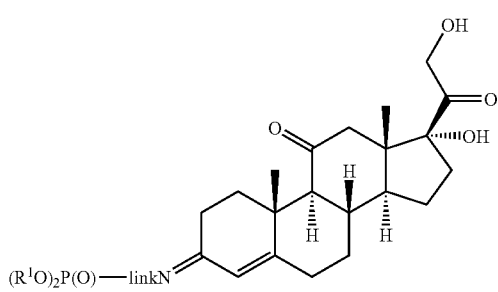

-continued

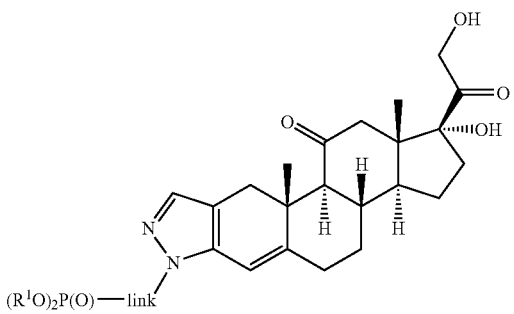

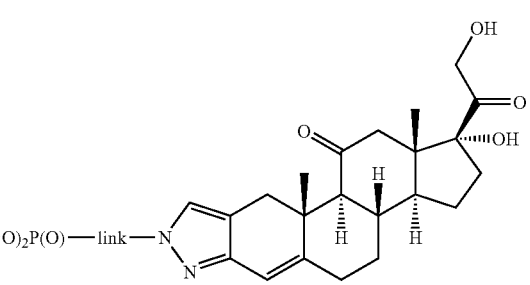

The synthesis of representative phosphonate derivatives of prednisone is outlined in Examples 139-142. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 139

Preparation of Representative Prednisone Derivatives

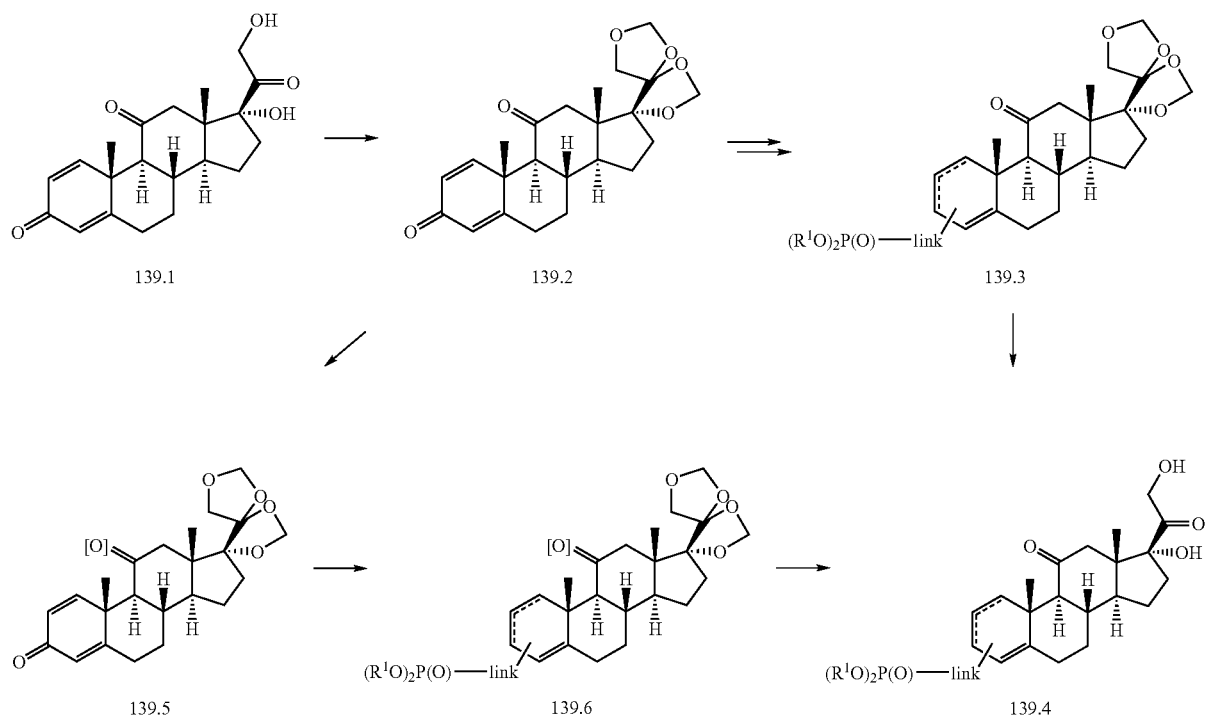

Representative compounds of the invention can be prepared as illustrated above. The steroid side-chain is protected as a bis-methylenedioxy (BMD) moiety. In this sequence, prednisone is reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 139.2. The phosphonate moiety is then introduced, using the procedures described below, to produce the phosphonate ester 139.3. The BMD moiety is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the triol 139.4. Optionally, depending on the nature of the reactions to be employed, the 11-ketone group in the BMD compound 139.2 is protected before introduction of the phosphonate group. The ketone is protected, for example, as the cyclic ethylene ketal, by reaction in toluene solution at reflux temperature with ethylene glycol and an acid catalyst, as described in J. Am. Chem. Soc., 77, 1904, 1955. Deprotection is effected by reaction with pyridinium tosylate in aqueous acetone, as described in J. Chem. Soc., Chem. Comm., 1351, 1987.

Alternatively, the 11-ketone is protected by conversion to the N,N-dimethylhydrazone. The dimethyl hydrazone is prepared by the reaction of the ketone 139.2 with N,N-dimethylhydrazine in ethanol-acetic acid, as described in *Org. Syn.*, 50, 102, 1970. The group is removed by treatment with sodium acetate and acetic acid in aqueous tetrahydrofuran, as described in *J. Am. Chem. Soc.,* 101, 5841, 1979.

Alternatively, the 11-ketone is protected as the diethylamine adduct. In this procedure, the substrate 139.2 is reacted with titanium tetrakis(diethylamide), as described in *J. Chem. Soc., Chem. Comm.,* 406, 1983, to afford the adduct. The ketone is deprotected by reaction with water in an aqueous organic solvent.

The 11-protected BMD compound 139.5 is then converted, using the procedures described below, into the phosphonate 139.6. Deprotection then yields the 11-keto diol 139.4.

EXAMPLE 140

Preparation of Representative Prednisone Derivatives

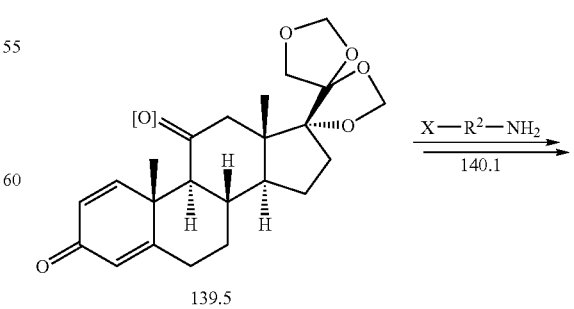

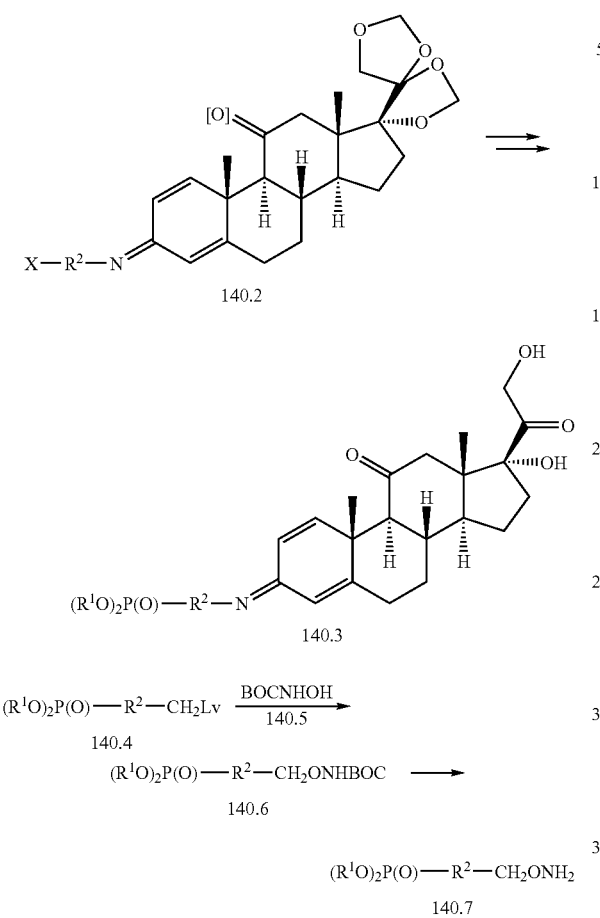

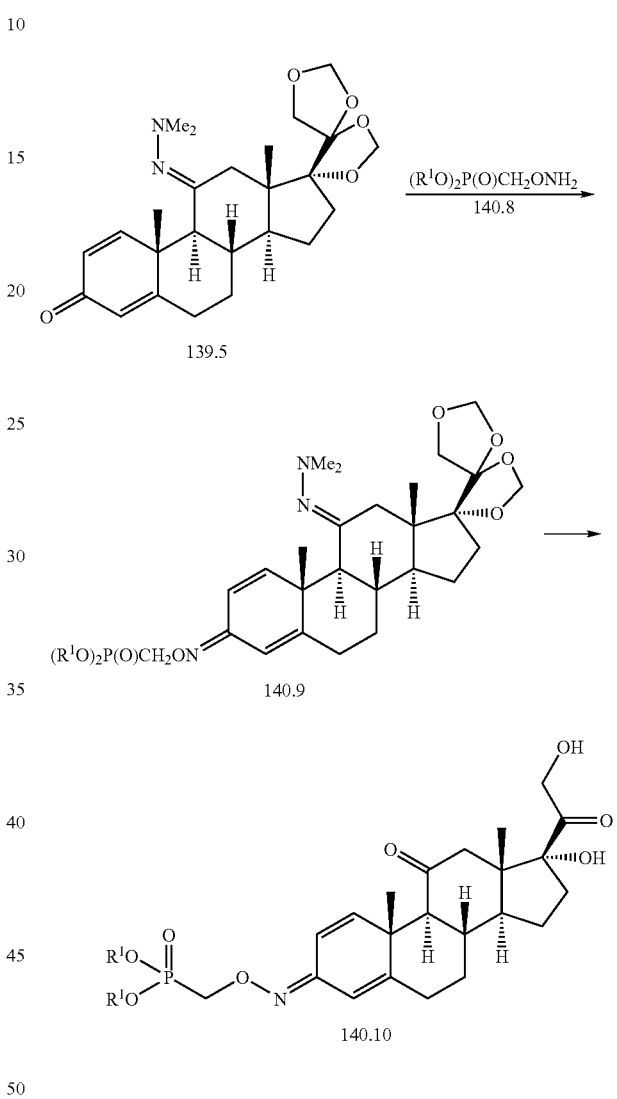

hydroxylamine 140.5 (Aldrich) to produce the ether 140.6. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 140.7.

The preparation of phosphonates in which the phosphonate is attached by means of an imino or iminoxy group and a variable carbon chain is illustrated above. In this procedure, the doubly-protected derivative 139.5 is reacted with an amine or hydroxylamine 140.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in *Anal. Bioch.*, 1978, 86, 133. and in *J. Mass. Spectrom.*, 1995, 30, 497. The protecting groups are then removed to afford the ketodiol 140.3.

The preparation of hydroxylamine ethers incorporating a phosphonate group is also illustrated above. In this procedure, a phosphonate 140.4, in which Lv is a leaving group such as bromo or trifluoromethylsulfonyloxy, is reacted with BOC- The preparation of phosphonates in which the phosphonate is attached by means of an iminoxy group is illustrated above. In this procedure, the substrate 139.5, in which the 11-ketone is protected as the dimethyl hydrazone, is reacted with a dialkyl phosphonomethyl hydroxylamine 140.8, prepared as described above from a dialkyl trifluoromethylsulfonyloxymethyl phosphonate (*Tet. Lett.*, 1986, 27, 1477) and BOC-hydroxylamine, to afford the oxime 140.9 which is deprotected by reaction with 50% aqueous acetic acid, to afford the diol 140.10. The oxime forming reaction is performed at ambient temperature in ethanol-acetic acid solution between equimolar amounts of the reactants.

Using the above procedures, but employing, in place of the hydroxylamine ether 140.8, different oxime ethers 140.1, the corresponding products 140.3 are obtained.

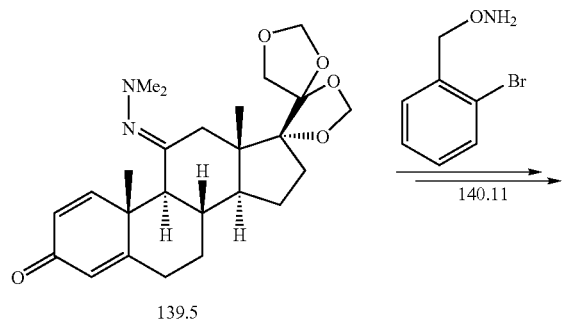

139.5

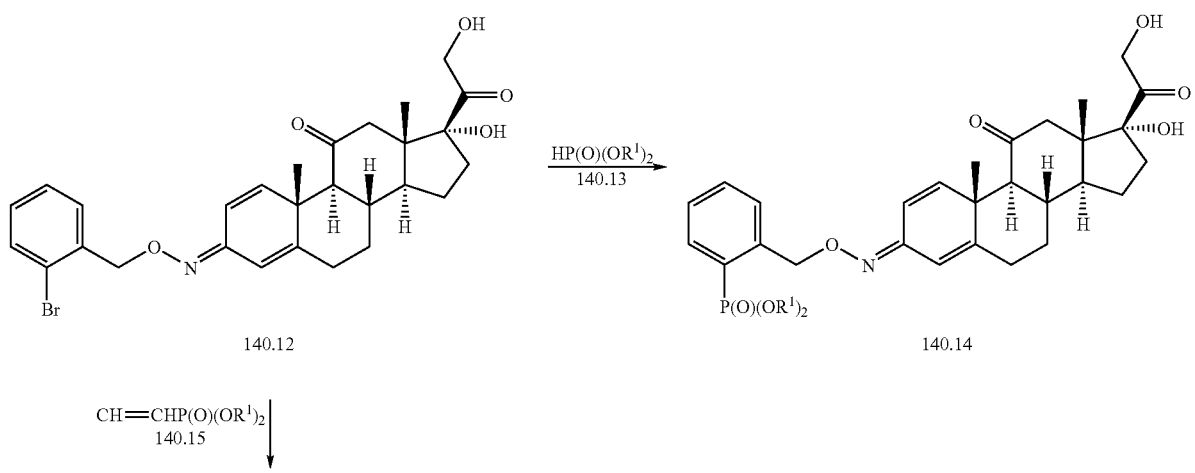

140.12        140.14

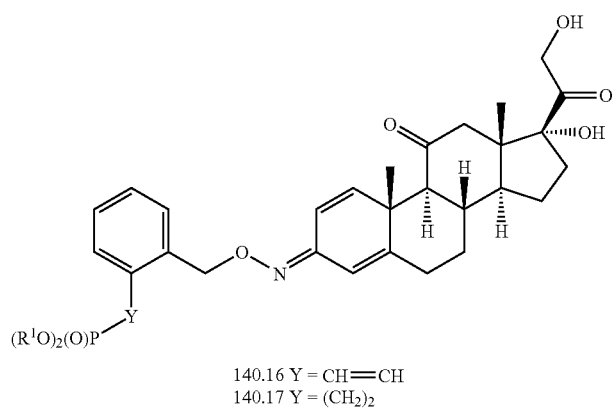

140.16 Y = CH=CH
140.17 Y = (CH₂)₂

The preparation of compounds in which the phosphonate group is attached by means of a benzyloxime group is illustrated above. In this procedure, the dienone 139.5 is reacted, as described above, with O-(2-bromobenzyl)hydroxylamine 140.11, prepared as described above from 2-bromobenzyl bromide, to give, after deprotection, the oxime 140.12. The product is then reacted, in the presence of a palladium catalyst, with a dialkyl phosphite 140.13 to afford the phosphonate 140.14. The preparation of arylphosphonates by means of a coupling reaction between aryl bromides and dialkyl phosphites is described in *J. Med. Chem.*, 35, 1371, 1992. The reaction is performed in an inert solvent such as toluene, in the presence of a base such as triethylamine and a catalytic amount of tetrakis(triphenylphosphine)palladium(0).

Alternatively, the bromo compound 140.12 is coupled with a dialkyl vinylphosphonate 140.15 (Aldrich) to afford the phosphonate 140.16. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 140.16 is reduced, for example by reaction with diimide, to produce the saturated analog 140.17. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane.

Using the above procedures, but employing, in place of the benzyloxy reagent 140.11, different bromo-substituted aryl or heteroaryl alkoxy hydroxylamines, and/or different dialkyl alkenyl phosphonates, the products analogous to the compounds 140.14, 140.16 and 140.17 are obtained.

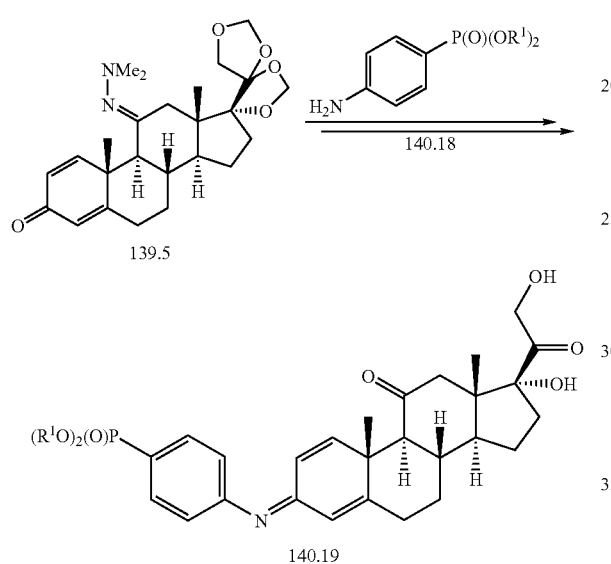

The preparation of phosphonates in which the phosphonate is attached by means of an imino group is illustrated above. In this procedure, the substrate 139.5 is reacted with a dialkyl 4-aminophenyl phosphonate 140.18, (Epsilon) to give, after deprotection, the imine product 140.19. The reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions.

Using the above procedures, but employing, in place of the 4-aminophenyl phosphonate 140.18 different amino-substituted aryl or heteroaryl phosphonates, products analogous to 140.19 are obtained.

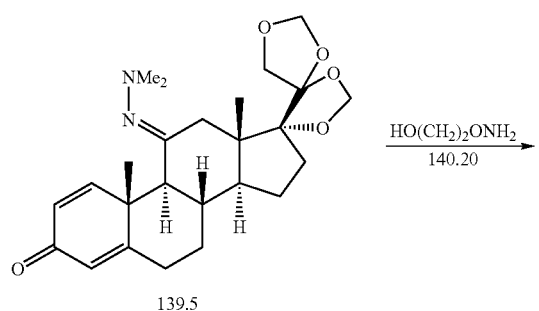

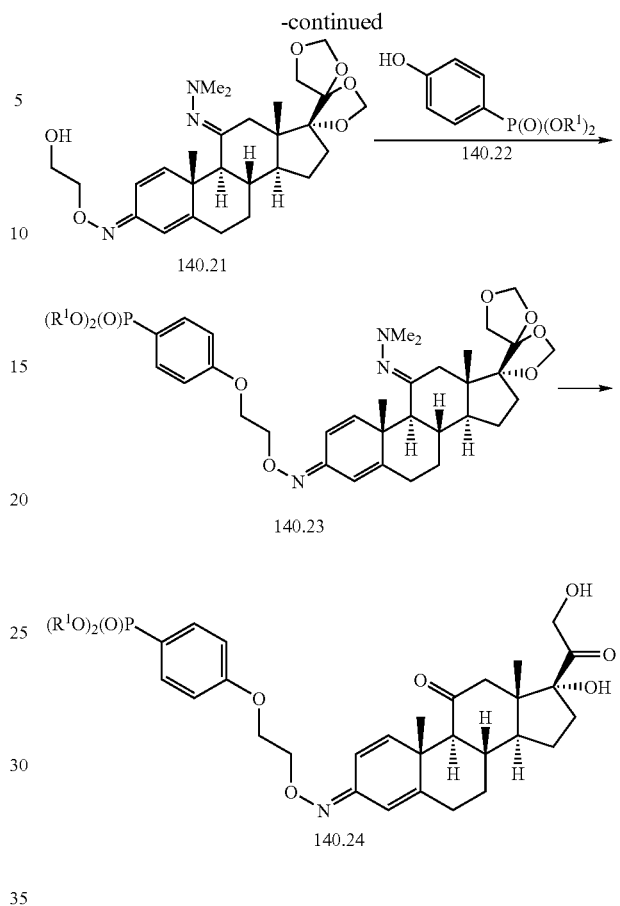

The preparation of phosphonates in which the phosphonate is attached by means of an oximino group and an ether linkage is illustrated above. In this procedure, the dienone 139.5 is reacted with O-(2-hydroxyyethyl)hydroxylamine 140.20 (*J. Chem. Soc., Chem. Comm.*, 1986, 903) to yield the oxime 140.21. The reaction of steroidal 1,4-dien-3-ones with substituted hydroxylamines is described in *J Steroid Bioch.*, 1976, 7, 795; the reaction is performed between equimolar amounts of the reactants in a polar organic solvent such as pyridine or methanol, optionally in the presence of acetic acid or sodium acetate. The oxime is then reacted in a Mitsonobu reaction with a dialkyl 4-hydroxyphenyl phosphonate 140.22 (Epsilon), to yield the ether oxime 140.23. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in *Org. React.*, 1992, 42, 335. The phenol and the alcohol or thiol component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656. The ether product 140.23 is then converted into the ketodiol 140.24.

Using the above procedures, but employing, in place of the hydroxylamine 140.20, different hydroxy-substituted hydroxylamines, and/or different hydroxy-substituted aryl phosphonates, the products analogous to 140.24 are obtained.

EXAMPLE 141

Preparation of Representative Prednisone Derivatives

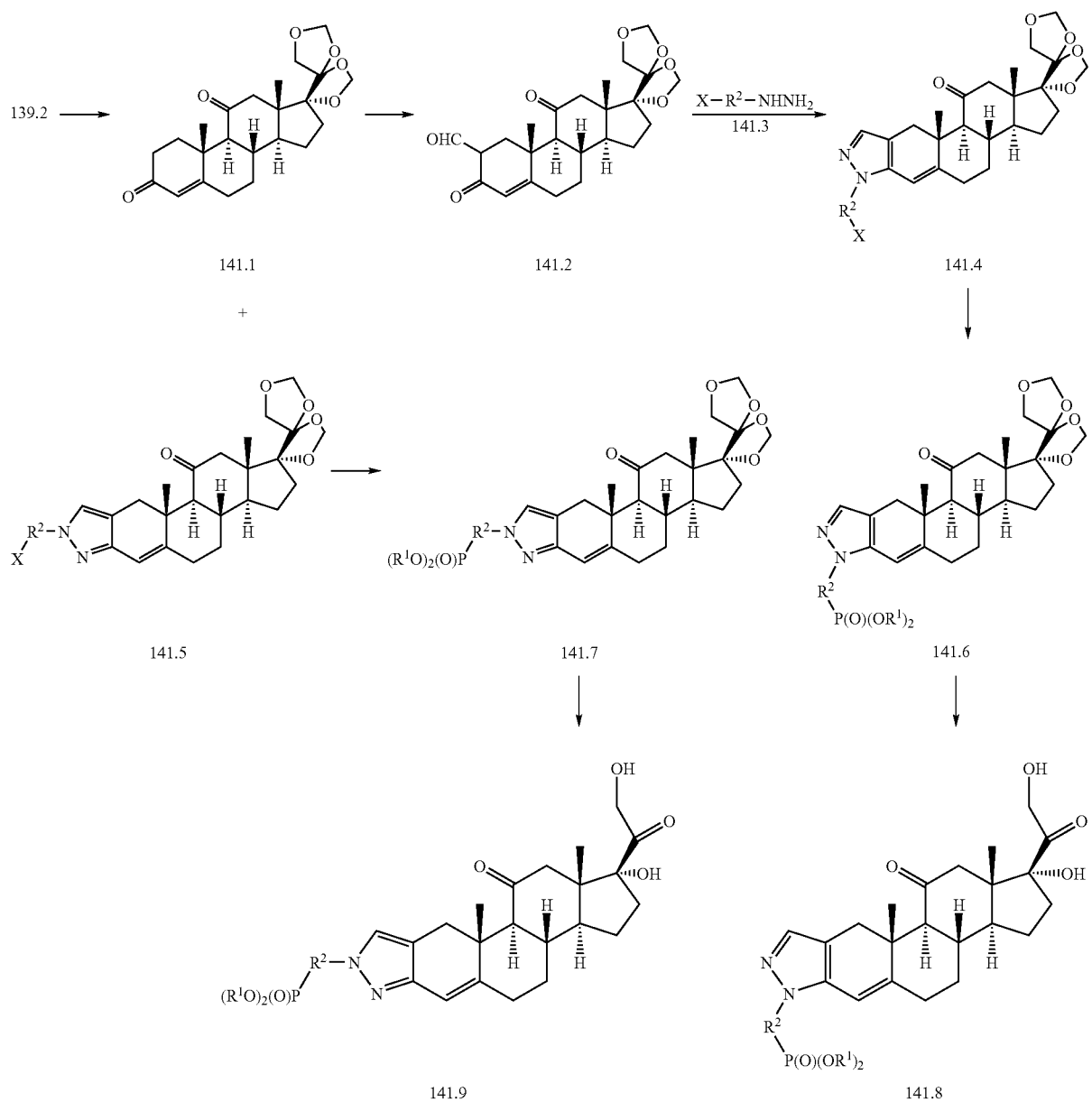

The preparation of the phosphonate esters in which the phosphonate group is attached to the 1' or 2' position of the pyrazole ring, by means of an aromatic or heteroaromatic group, a heteroatom and a variable carbon chain is illustrated above. In this procedure, the BMD-protected dienone 139.2 is reduced to afford the 1,2-dihydro product 141.1. The catalytic hydrogenation reaction is effected by the use of tris(triphenylphosphine)rhodium(I) chloride, for example as described in *J. Med. Chem.*, 2001, 44, 602. The product is then reacted with ethyl formate and a base such as sodium hydride, in an inert solvent such as toluene or dimethylformamide, as described in *J. Am. Chem. Soc.*, 1964, 86, 1520, to afford the 2-formyl product 141.2. This compound is then reacted with an alkyl, aralkyl, aryl or heteroaryl hydrazine 141.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 141.4 and 141.5. The pyrazole-forming reaction is performed between equimolar amounts of the reactants in an acidic solvent such as acetic acid, as described in *J. Am. Chem. Soc.*, 1964, 86, 1520. The pyrazoles 141.4 and 141.5 are then transformed via the BMD-protected intermediates 141.6 and 141.7, into the phosphonates 141.8 and 141.9.

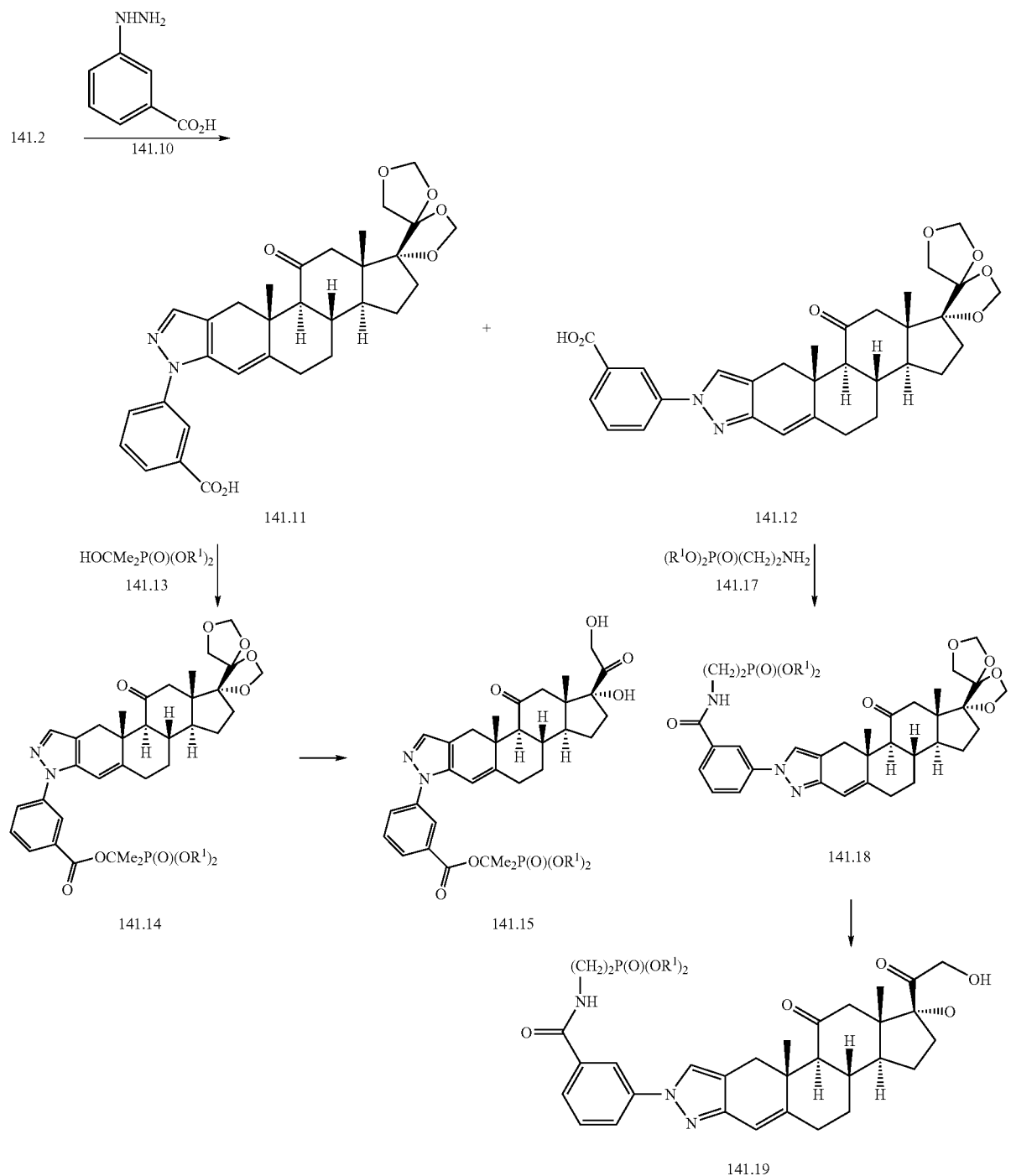

The preparation of phosphonates in which the phosphonate is attached by means of a phenyl ring and an ester or an amide linkage is illustrated above. In this procedure, the ketoaldehyde 141.2 is reacted, as described above, with 3-carboxyphenylhydrazine 141.10 (Apin) to give the pyrazoles 141.11 and 141.12. The 2'-substituted isomer 141.11 is then reacted in dichloromethane solution at ambient temperature with one molar equivalent of a dialkyl 2-hydroxy-2-methylpropyl phosphonate 141.13 (FR 2462440) and dicyclohexylcarbodiimide, to yield the ester 141.14. The protecting groups are then removed to yield the diol 141.15.

Alternatively, the 1'-substituted pyrazole 141.12 is coupled with a dialkyl 2-aminoethyl phosphonate 141.17 (Aurora) to afford the amide 141.18. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide. The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide. The product 141.18 is then deprotected to give the diol 141.19.

Using the above procedures, but employing different amino or hydroxyl-substituted phosphonates, and/or different carboxy-substituted hydrazines, the products analogous to 141.15 and 141.19 are obtained. The functionalization procedures are typically interchangeable between the pyrazole substrates 141.11 and 141.12.

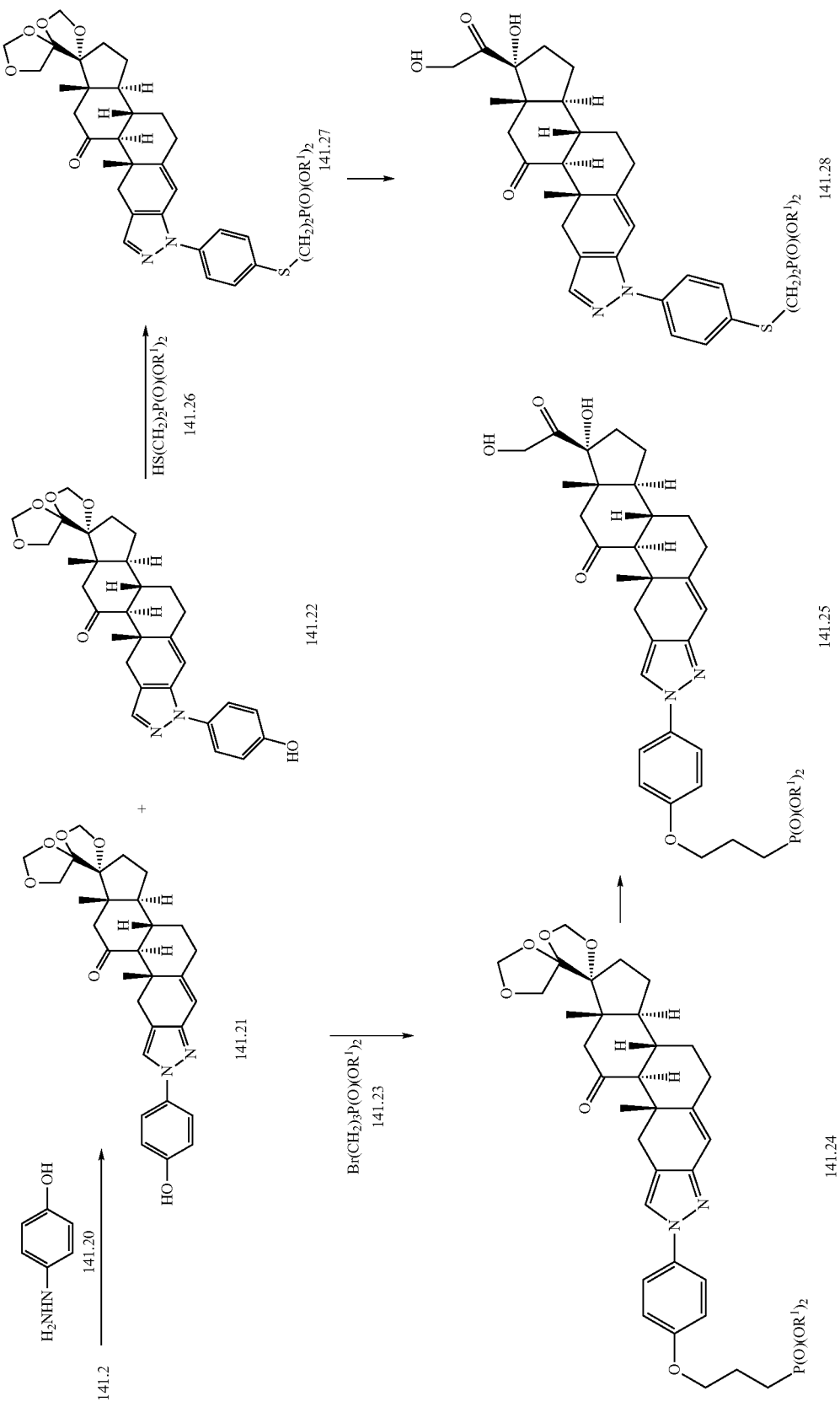

The preparation of the phosphonates in which the phosphonate group is attached by means of a phenyl group and an alkoxy or alkylthio carbon chain is illustrated above. In this procedure, the ketoaldehyde 141.2 is reacted, as described above, with 4-hydroxyphenyl hydrazine 141.20 (EP 437105) to produce the pyrazoles 141.21 and 141.22. The 1'-substituted isomer 141.21 is reacted, in dimethylformamide solution at 70°, with a dialkyl bromopropyl phosphonate 141.23 (J. Amer. Chem. Soc., 2000, 122, 1554) and potassium carbonate, to give the phosphonate 141.24. The product is then deprotected to afford the diol 141.25.

Alternatively, the 2'-substituted pyrazole 141.22 is reacted in a Mitsonobu reaction, as described above, with a dialkyl mercaptoethyl phosphonate 141.26 (Zh. Obschei. Khim., 1973, 43, 2364) to prepare the thioether phosphonate 141.27 which is deprotected to give the diol 141.28.

Using the above procedures, but employing, in place of the hydroxyphenyl reagent 141.20, different hydroxy-substituted aralkyl, aryl or heteroaryl alkoxy hydrazines, and/or different dialkyl bromo or mercapto-substituted phosphonates, the products analogous to the compounds 141.25 and 141.28 are obtained.

EXAMPLE 142

Preparation of Representative Prednisone Derivatives

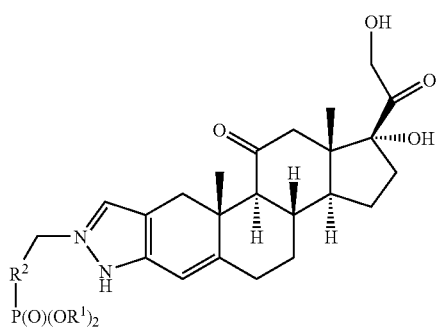

142.7

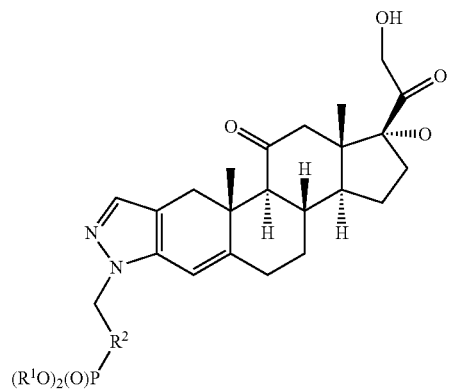

142.8

The preparation of the phosphonate esters in which the phosphonate group is attached by means of a variable carbon linkage is illustrated above. In this procedure, the ketoaldehyde 141.2 is reacted with hydrazine to afford the pyrazole derivative 142.1. The reaction of steroidal 2-formyl-3-ketones with hydrazine is described in J. Am. Chem. Soc, 1964, 86, 1520. The reaction is performed in acetic acid at ambient temperature. The pyrazole product is then reacted with a bromomethyl compound 142.2, in which $R^2$ and X are as defined above, to yield the alkylation products 142.3 and 142.4. The alkylation of substituted pyrazoles is described, for example, in Heterocyclic Chemistry, by T. L. Gilchrist, Longman, 1992, p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The products 142.3 and 142.4 are, except in cases where X is dialkylphosphono, converted into the phosphonates 142.5 and 142.6, using the procedures described herein, and deprotection then affords the diols 142.7 and 142.8.

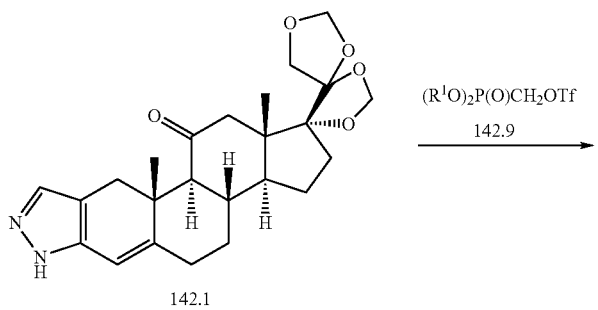

142.1

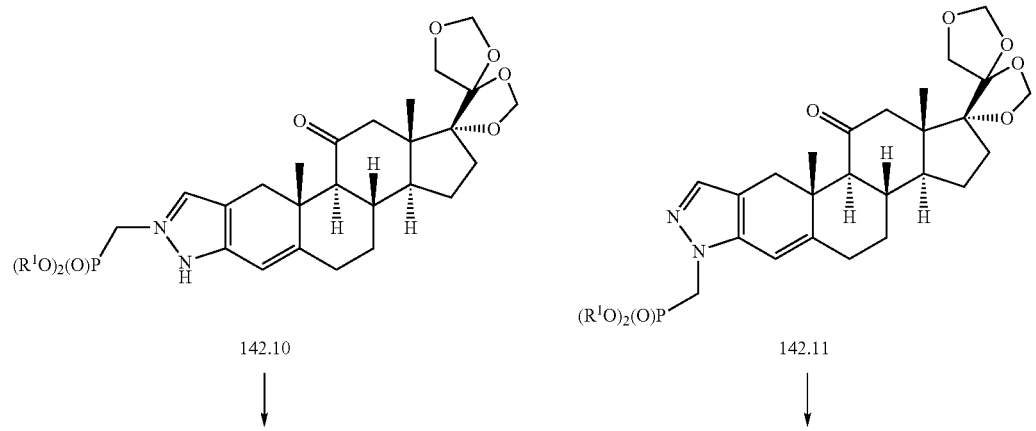

142.10           142.11

-continued
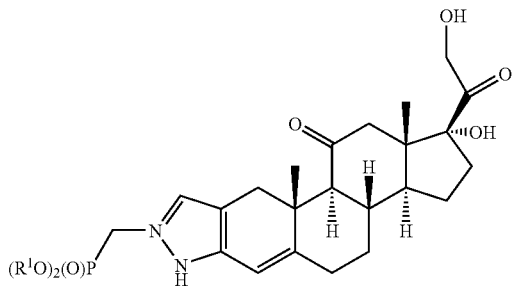
142.12
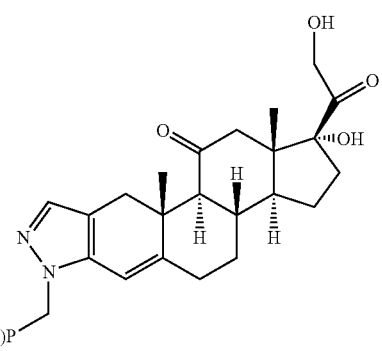
142.13
Representative compounds of the invention can be prepared as illustrated above. The pyrazole 142.1 is reacted with one molar equivalent of a dialkyl trifluoromethanesulfonyloxy phosphonate 142.9 to give the alkylated pyrazoles 142.10 and 142.11. Deprotection then yields the diols 142.12 and 142.13.
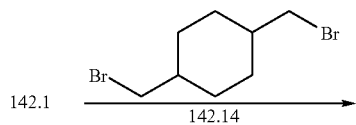
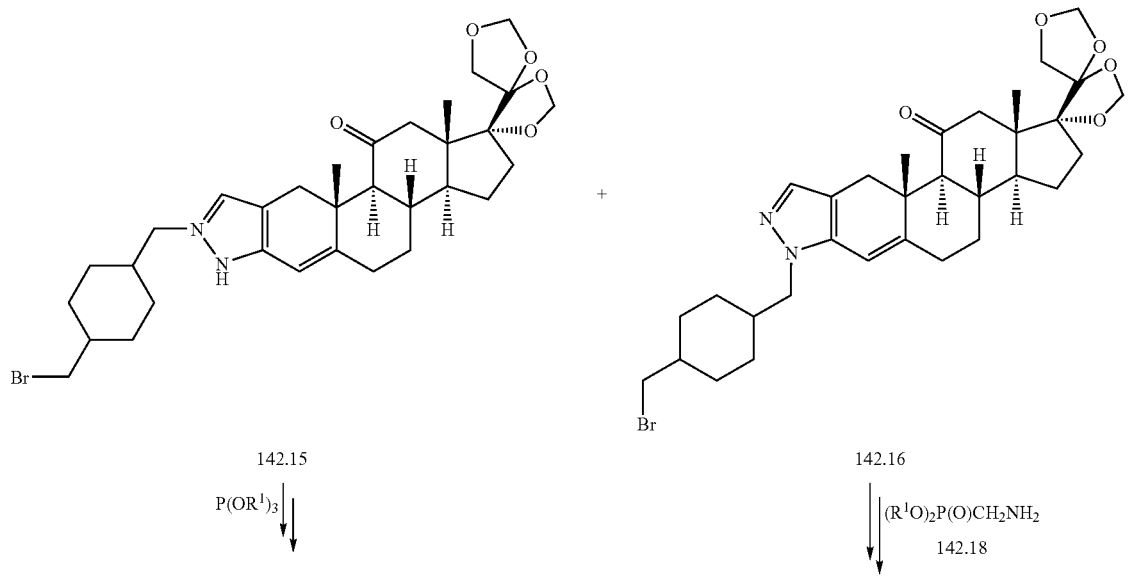

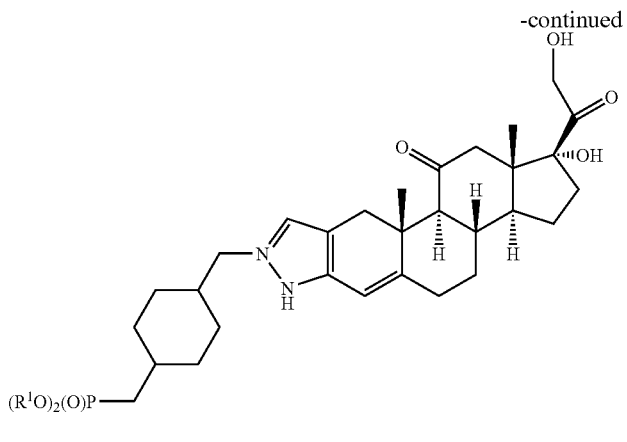

142.17

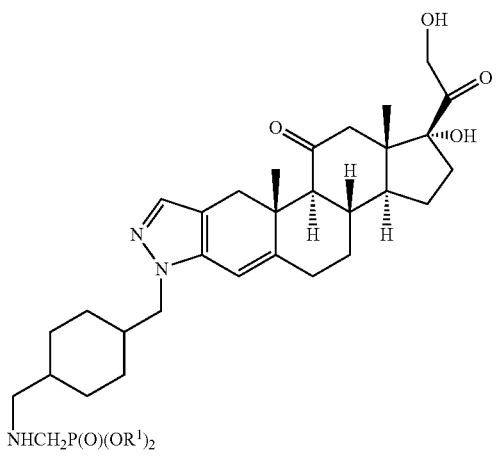

142.19

Representative compounds of the invention can be prepared as illustrated above. The pyrazole 142.1 is reacted, as described above, with 1,4-bis(bromomethyl)Cyclohexane 142.14 (Salor) to give the pyrazoles 142.15 and 142.16. The product 142.15 is subjected to an Arbuzov reaction, in which the bromomethyl substituent is converted into the dialkyl phosphonomethyl substituent, by reaction with a trialkyl phosphite at 120°, to prepare, after deprotection of the side chain, the phosphonate 142.17. The pyrazole 142.16 is reacted in dimethylformamide at 70' with potassium carbonate and a dialkyl aminomethyl phosphonate 142.18 (Interchim) to give after deprotection the amino phosphonate 142.19.

Using the above procedures, but employing, in place of the dibromide 142.14, different dibromides, and/or different amino-substituted phosphonates, the products analogous to 142.17 and 142.19 are obtained.

EXAMPLES 143-146

Clobetasol Derivatives

The structures of clobetasol (U.S. Pat. No. 3,721,687) and representative phosphonate esters of the invention are shown below, in which the substituent $R^1$ is H, alkyl, alkenyl, aryl or aralkyl. These compounds incorporate a phosphonate moiety $(R^1O)_2P(O)$ connected to the nucleus by means of a variable linking group, designated as "link" in the attached structures.

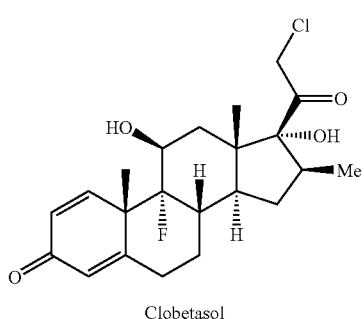

Clobetasol

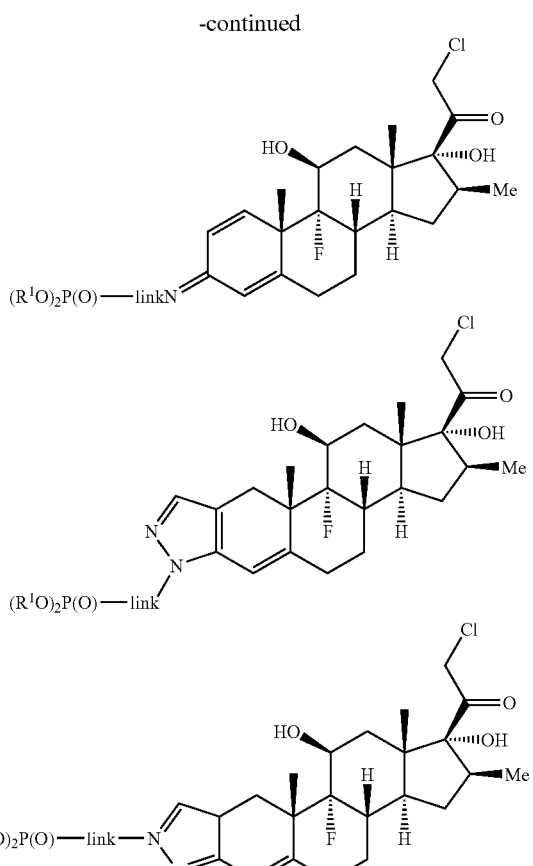

The synthesis of representative phosphonate derivatives of clobetasol is outlined in Examples 143-146. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 143

Preparation of Representative Clobetasol Derivatives

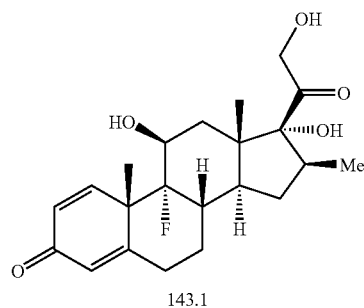
143.1

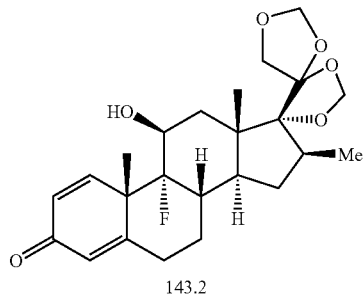
143.2

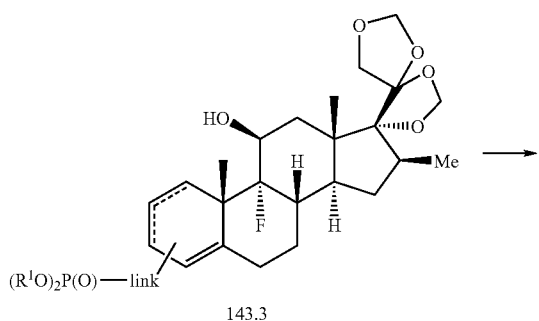
143.3

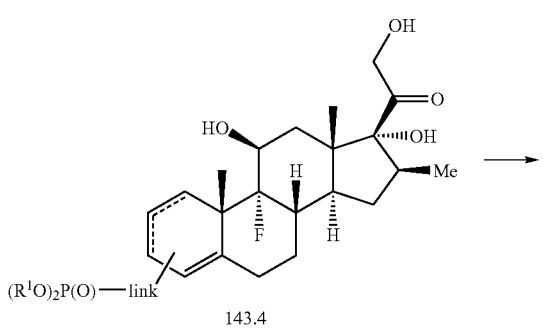
143.4

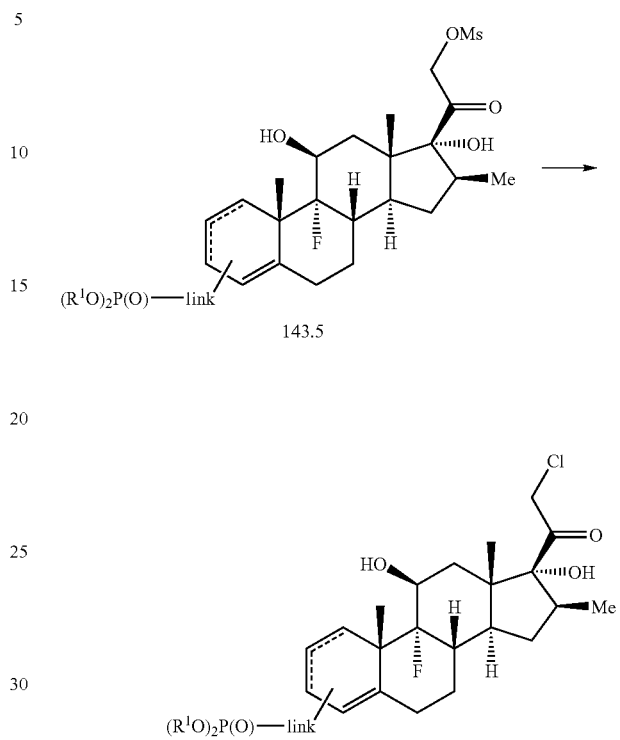

The preparation of representative compounds of the invention is illustrated above. The steroid side-chain is protected as a bis-methylenedioxy (BMD) moiety. In this sequence, 9α-fluoro-16β-methyl-11β,17α,21-trihydroxypregn-1,4-dien-3,21-dione 143.1 (U.S. Pat. No. 3,721,687) is reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 143.2. The phosphonate moiety is then introduced, using the procedures described below, to produce the phosphonate ester 143.3. The BMD moiety is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the triol 143.4. The 21-hydroxy group is then converted into the 21-chloro group as described in U.S. Pat. No. 3,721,687, Chimia, 1992, 46, 338, or J. Med. Chem., 1987, 30, 1581. In this procedure, the 21-hydroxy substrate is reacted at about 0° with one molar equivalent of methanesulfonyl chloride in a basic solvent such as pyridine, to afford the 21-mesylate 143.5. The product is then reacted, in dimethylformamide solution at about 70°, with ca. five molar equivalents of lithium chloride, to yield the 21-chloro product 143.6.

EXAMPLE 144

Preparation of Representative Clobetasol Derivatives

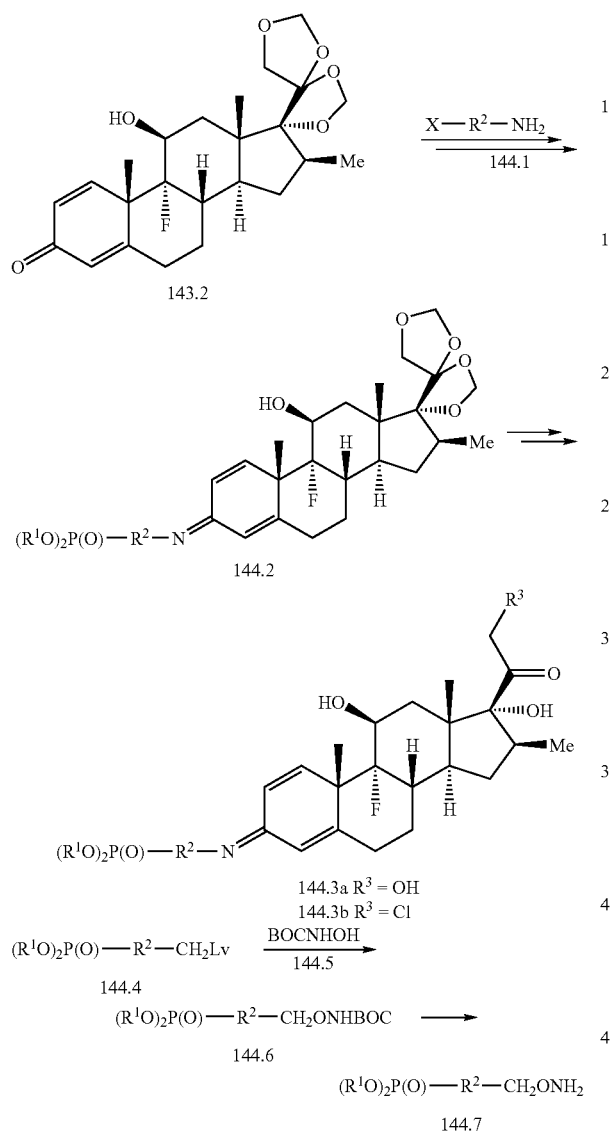

The preparation of phosphonates in which the phosphonate is attached by means of an imino or iminoxy group and a variable carbon chain is illustrated above. In this procedure, the BMD-protected derivative 143.2 is reacted with an amine or hydroxylamine 144.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime.

The preparation of oximes of steroidal 3-ketones is described in Anal. Bioch., 1978, 86, 133. and in J. Mass. Spectrom., 1995, 30, 497. The BMD-protected side-chain compound 144.2 is then converted into the triol 144.3a, and then to the 21-chloro product 144.3b.

The preparation of hydroxylamine ethers incorporating a phosphonate group is also illustrated above. In this procedure, a phosphonate 144.4, in which Lv is a leaving group such as bromo or trifluoromethylsulfonyloxy, is reacted with BOC-hydroxylamine 144.5 (Aldrich) to produce the ether 144.6. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 144.7.

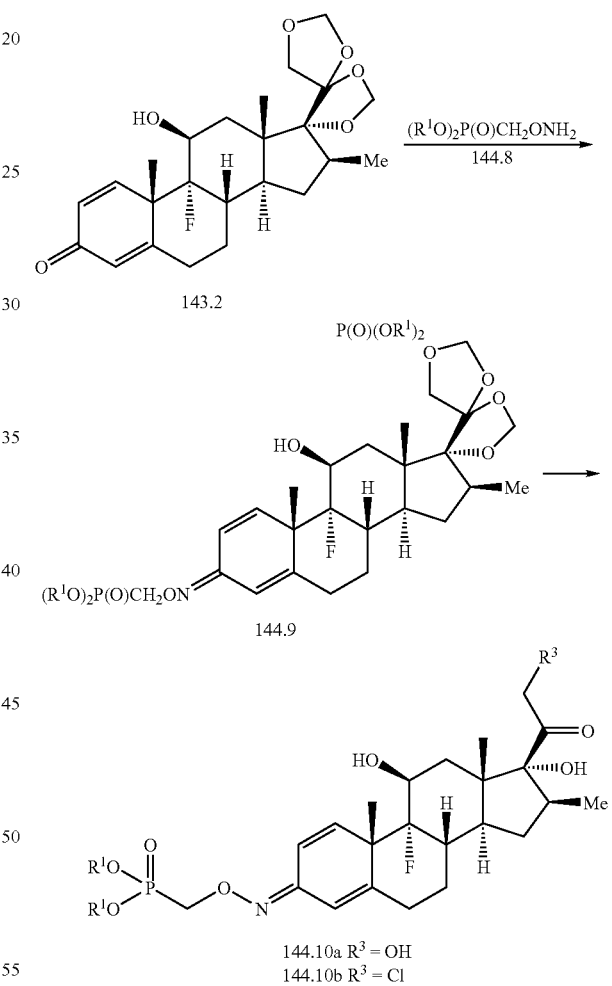

The preparation of phosphonates in which the phosphonate is attached by means of an iminoxy group is illustrated above. In this procedure, the substrate 143.2 is reacted with a dialkyl phosphonomethyl hydroxylamine 144.8, prepared as described above from a dialkyl trifluoromethylsulfonyloxymethyl phosphonate (Tet. Lett., 1986, 27, 1477) and BOC-hydroxylamine, to afford the oxime 144.9. Deprotection then affords the triol 144.10a from which the 21-chloro compound 144.10b is prepared. The oxime forming reaction is performed at ambient temperature in ethanol-acetic acid solution between equimolar amounts of the reactants. Using the above procedures, but employing, in place of the hydroxylamine ether 144.8, different oxime ethers 144.1, the corresponding products 144.3b are obtained.

nate 144.14a. The preparation of arylphosphonates by means of a coupling reaction between aryl bromides and dialkyl phosphites is described in *J. Med. Chem.*, 35, 1371, 1992. The reaction is performed in an inert solvent such as toluene, in the

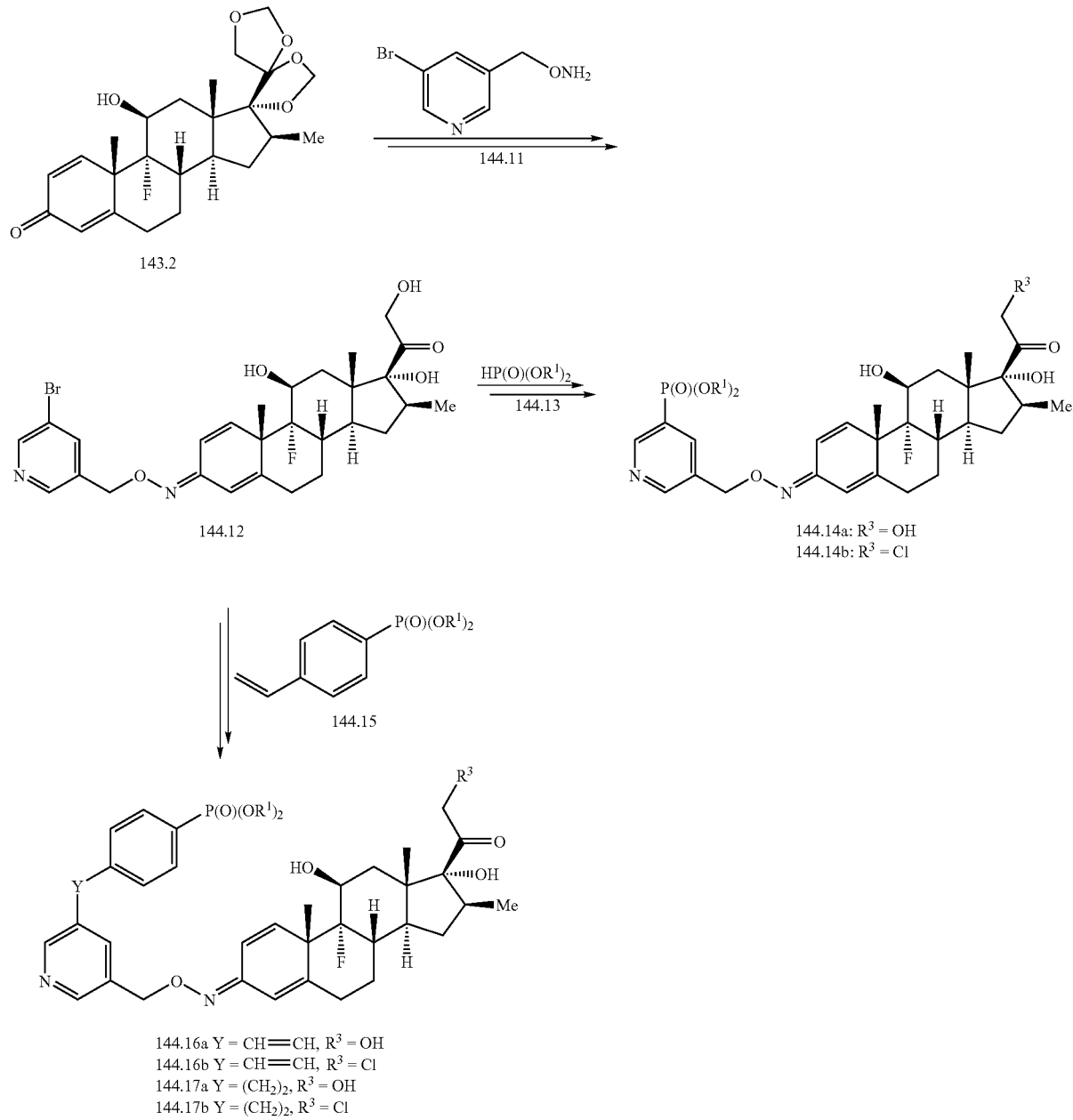

The preparation of compounds in which the phosphonate group is attached by means of a 3-pyridylmethoxy oxime group is illustrated above. In this procedure, the dienone 143.2 is reacted, as described above, with O-(5-bromo-3-pyridylmethoxy)hydroxylamine 144.11, prepared as described above from 5-bromo-3-bromomethylpyridine (WO 9528400) and BOC-protected hydroxylamine, to give, after deprotection of the side-chain, the oxime 144.12. The product is then reacted, in the presence of a palladium catalyst, with a dialkyl phosphite 144.13 to afford the phosphopresence of a base such as triethylamine and a catalytic amount of tetrakis(triphenylphosphine)-palladium(0). The 21-hydroxy group is then converted into the 21-chloro derivative 144.14b.

Alternatively, the bromo compound 144.12 is coupled with a dialkyl 4-vinylphenyl phosphonate 144.15 (Macromolecules, 1998, 31, 2918) to afford the phosphonate 144.16a. The coupling of aryl halides with olefins by means of the Heck reaction is described, for example, in Advanced Organic Chemistry, by F. A. Carey and R. J. Sundberg, Plenum, 2001, p. 503ff and in Acc. Chem. Res., 12, 146, 1979. The aryl bromide and the olefin are coupled in a polar solvent such as dimethylformamide or dioxan, in the presence of a palladium(0) catalyst such as tetrakis(triphenylphosphine) palladium(0) or palladium(II) catalyst such as palladium(II) acetate, and optionally in the presence of a base such as triethylamine or potassium carbonate. Optionally, the styrenoid double bond present in the product 144.16a is reduced, for example by reaction with diimide, to produce the saturated analog 144.17a. The reduction of olefinic bonds is described in Comprehensive Organic Transformations, by R. C. Larock, VCH, 1989, p. 6ff. The transformation is effected by means of catalytic hydrogenation, for example using a palladium on carbon catalyst and hydrogen or a hydrogen donor, or by the use of diimide or diborane. The products 144.16a and 144.17a are then converted into the 21-chloro analogs 144.16b and 144.17b.

Using the above procedures, but employing, in place of the bromopyridylmethoxy reagent 144.11, different bromo-substituted aryl or heteroaryl alkoxy hydroxylamines, and/or different dialkyl alkenyl phosphonates, the products analogous to the compounds 144.14b, 144.16b and 144.17b are obtained.

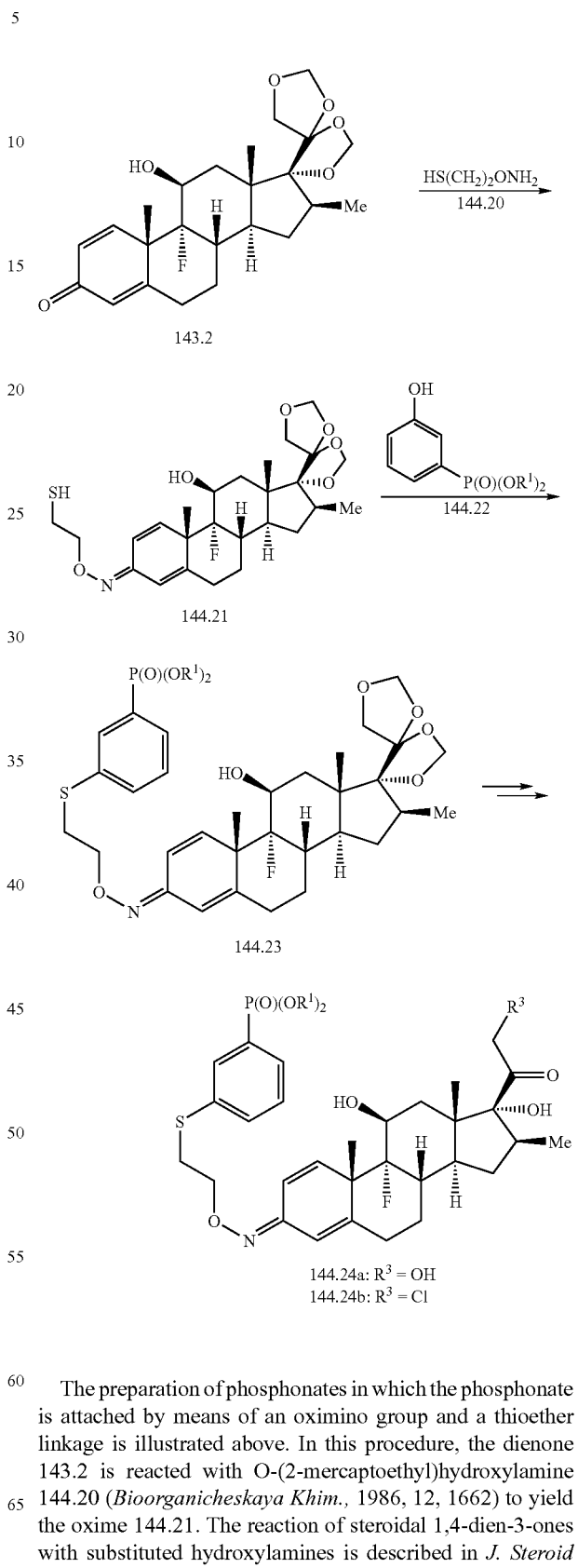

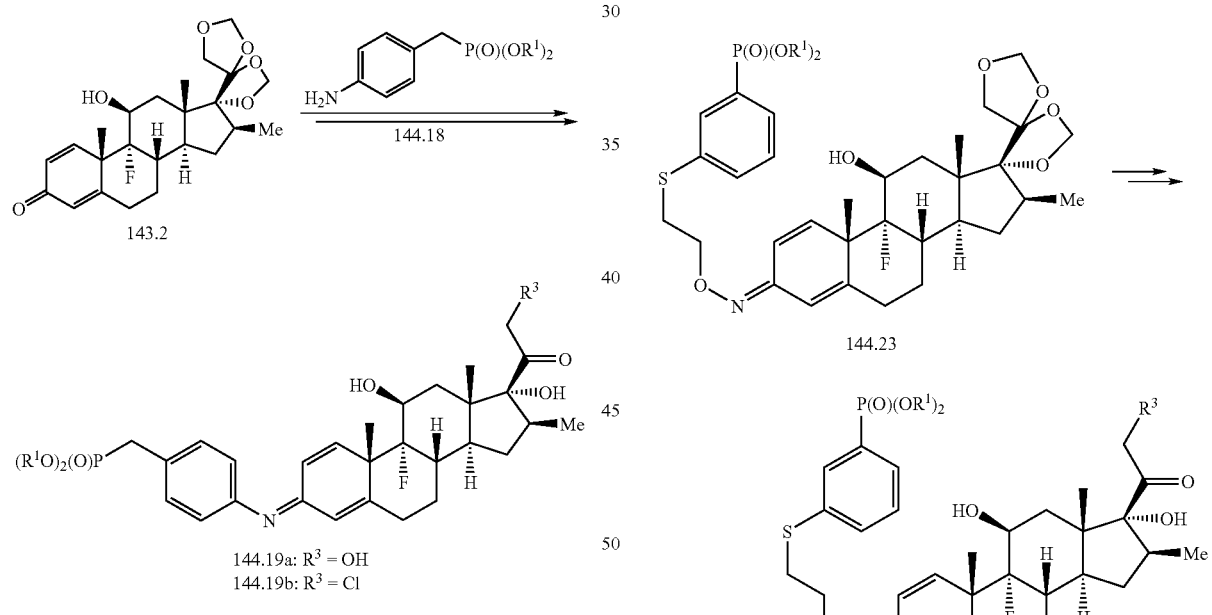

The preparation of phosphonates in which the phosphonate is attached by means of an imino group is illustrated above. In this procedure, the substrate 143.2 is reacted with a dialkyl 4-aminobenzyl phosphonate 144.18, (Fluka) to give, after deprotection, the imine product 144.19a. The reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions. The product is then converted into the 21-chloro compound 144.19b. Using the above procedures, but employing, in place of the 4-aminobenzyl phosphonate 144.18 different amino-substituted aryl or heteroaryl phosphonates, products analogous to 144.19b are obtained.

The preparation of phosphonates in which the phosphonate is attached by means of an oximino group and a thioether linkage is illustrated above. In this procedure, the dienone 143.2 is reacted with O-(2-mercaptoethyl)hydroxylamine 144.20 (Bioorganicheskaya Khim., 1986, 12, 1662) to yield the oxime 144.21. The reaction of steroidal 1,4-dien-3-ones with substituted hydroxylamines is described in J. Steroid Bioch., 1976, 7, 795; the reaction is performed between equimolar amounts of the reactants in a polar organic solvent such as pyridine or methanol, optionally in the presence of acetic acid or sodium acetate. The product is then coupled, in a Mitsonobu reaction, with a dialkyl 3-hydroxyphenyl phosphonate 144.22 (Aurora), to yield the thioether oxime 144.23. The preparation of aromatic ethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol and the alcohol or thiol component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656. The thioether product 144.23 is then converted into the 21-chloro product 144.24b.

Using the above procedures, but employing, in place of the hydroxylamine 144.22, different hydroxy or mercapto-substituted hydroxylamines, and/or different hydroxyaryl-substituted phosphonates, the products analogous to 144.24b are obtained.

EXAMPLE 145

Preparation of Representative Clobetasol Derivatives

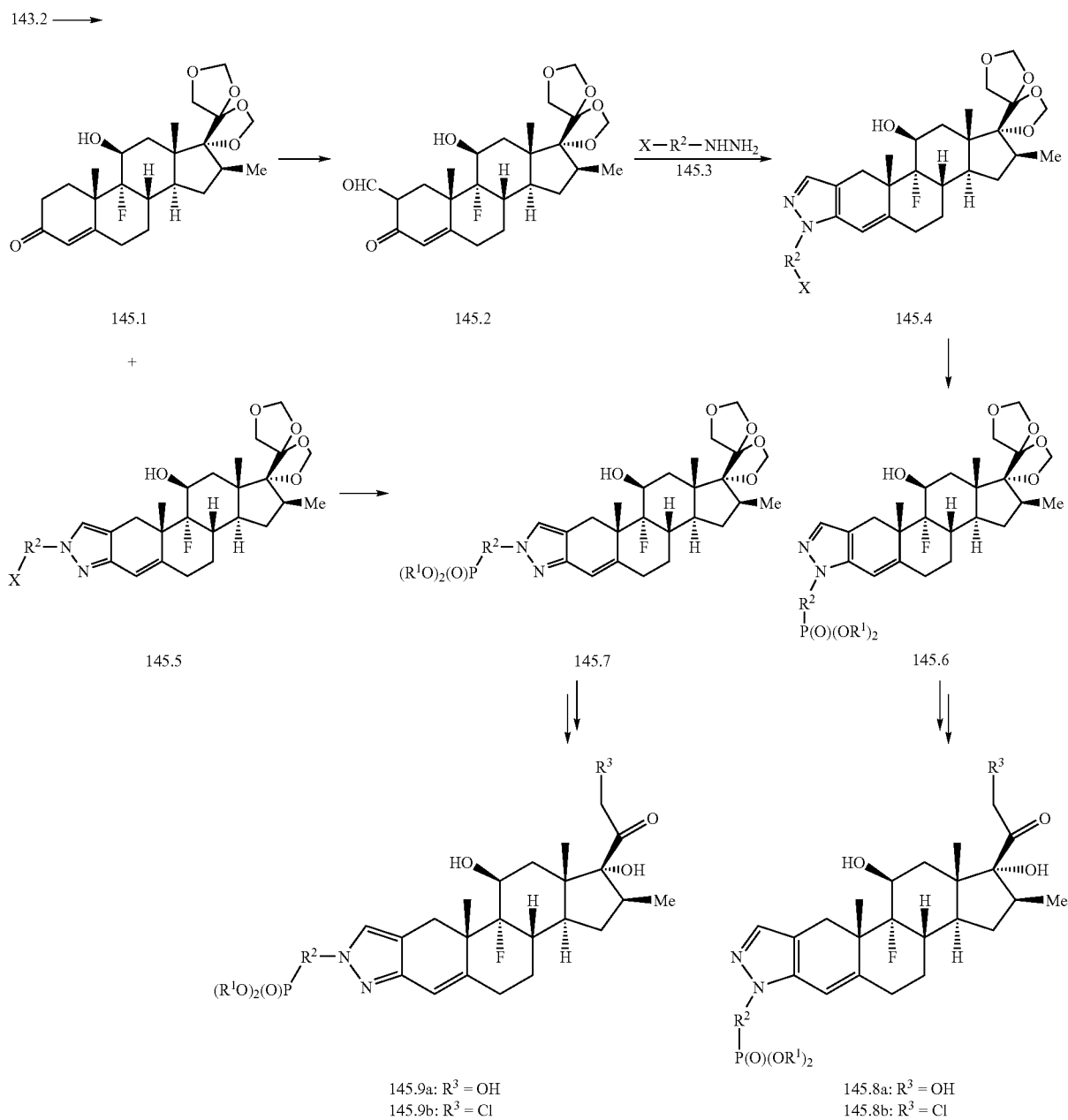

The preparation of the phosphonate esters in which the phosphonate group is attached to the 1' or 2' position of the pyrazole ring, by means of an aromatic or heteroaromatic group, a heteroatom and a variable carbon chain is illustrated above. In this procedure, the BMD-protected dienone 143.2 is reduced to afford the 1,2-dihydro product 145.1. The catalytic hydrogenation reaction is effected by the use of tris(triphenylphosphine)rhodium(I) chloride, for example as described in *J. Med. Chem.*, 2001, 44, 602. The product is then reacted with ethyl formate and a base such as sodium hydride, in an inert solvent such as toluene or dimethylformamide, as described in *J. Am. Chem. Soc.*, 1964, 86, 1520, to afford the 2-formyl product 145.2. This compound is then reacted with an alkyl, aralkyl, aryl or heteroaryl hydrazine 145.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 145.4 and 145.5. The pyrazole-forming reaction is performed between equimolar amounts of the reactants in an acidic solvent such as acetic acid, as described in *J. Am. Chem. Soc.*, 1964, 86, 1520. The pyrazoles 145.4 and 145.5 are then transformed, via the BMD-protected intermediates 145.6 and 145.7, into the 21-chloro phosphonates 145.8b and 145.9b.

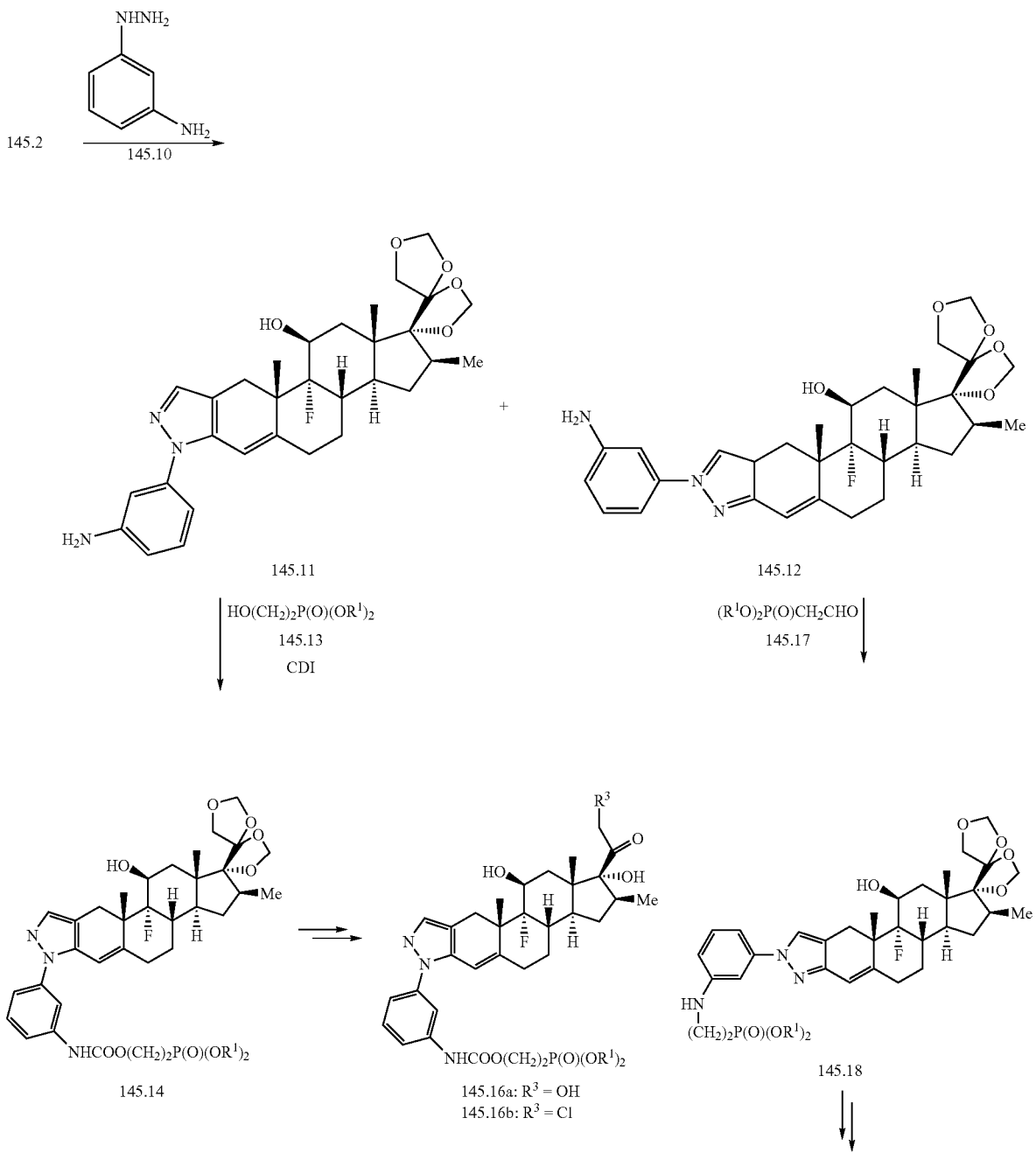

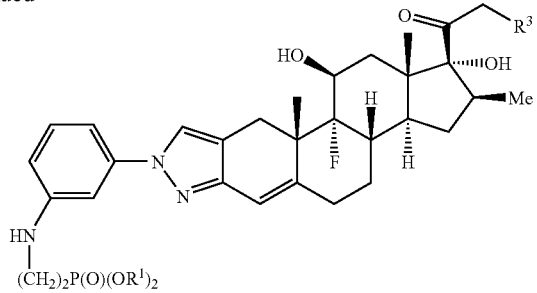

145.19a: R³ = OH
145.19b: R³ = Cl

The preparation of phosphonates in which the phosphonate is attached by means of a carbamate or an amino linkage is illustrated above. In this procedure, the ketoaldehyde 145.2 is reacted, as described above, with 3-aminophenyl-hydrazine 145.10 (EP 437105) to give the pyrazoles 145.11 and 145.12. The 2'-substituted isomer 145.11 is then reacted in dimethylformamide solution at ambient temperature with one molar equivalent of a dialkyl 2-hydroxyethyl phosphonate 145.13 (Epsilon) and carbonyl diimidazole, to yield the carbamate 145.14. The preparation of carbamates is described in Comprehensive Organic Functional Group Transformations, A. R. Katritzky, ed., Pergamon, 1995, Vol. 6, p 416ff, and in Organic Functional Group Preparations, by S. R. Sandler and W. Karo, Academic Press, 1986, p. 260ff. In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and the like, to afford the corresponding activated acylamine. The latter compound is then reacted with an alcohol to yield the carbamate. The BMD protecting group is then removed and the product is converted into the 21-chloro product 145.16b.

Alternatively, the 1'-substituted pyrazole 145.12 is reacted, in a reductive amination reaction, with a dialkyl formylmethyl phosphonate 145.17 (*Zh. Obschei. Khim.*, 1987, 57, 2793) and sodium triacetoxyborohydride, to afford the amine 145.18. The preparation of amines by means of reductive amination procedures is described, for example, in Comprehensive Organic Transformations, by R. C. Larock, VCH, p 421, and in Advanced Organic Chemistry, Part B, by F. A. Carey and R. J. Sundberg, Plenum, 2001, p 269. In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in *J. Org. Chem.*, 55, 2552, 1990. The product 145.18 is then deprotected to give the triol 145.19a, and the latter compound is transformed into the 21-chloro analog 145.19b.

Using the above procedures, but employing different formyl or hydroxyl-substituted phosphonates, and/or different amino-substituted hydrazines, the products analogous to 145.16b and 145.19b are obtained. The functionalization procedures are typically interchangeable between the pyrazole substrates 145.11 and 145.12.

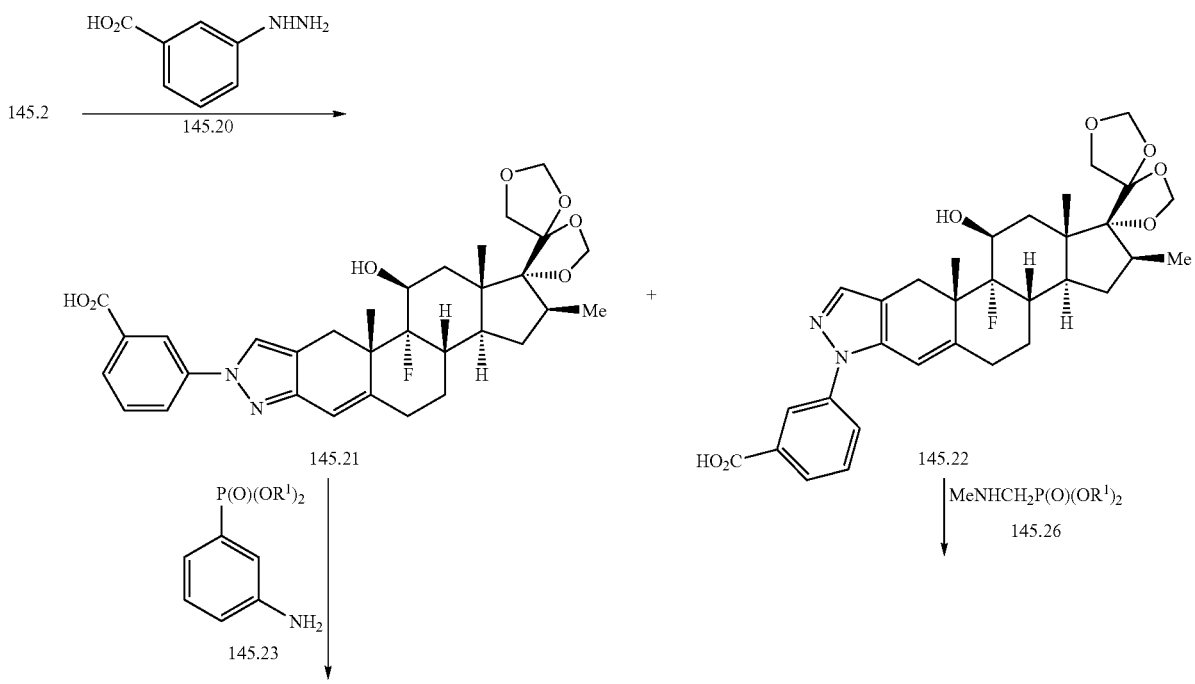

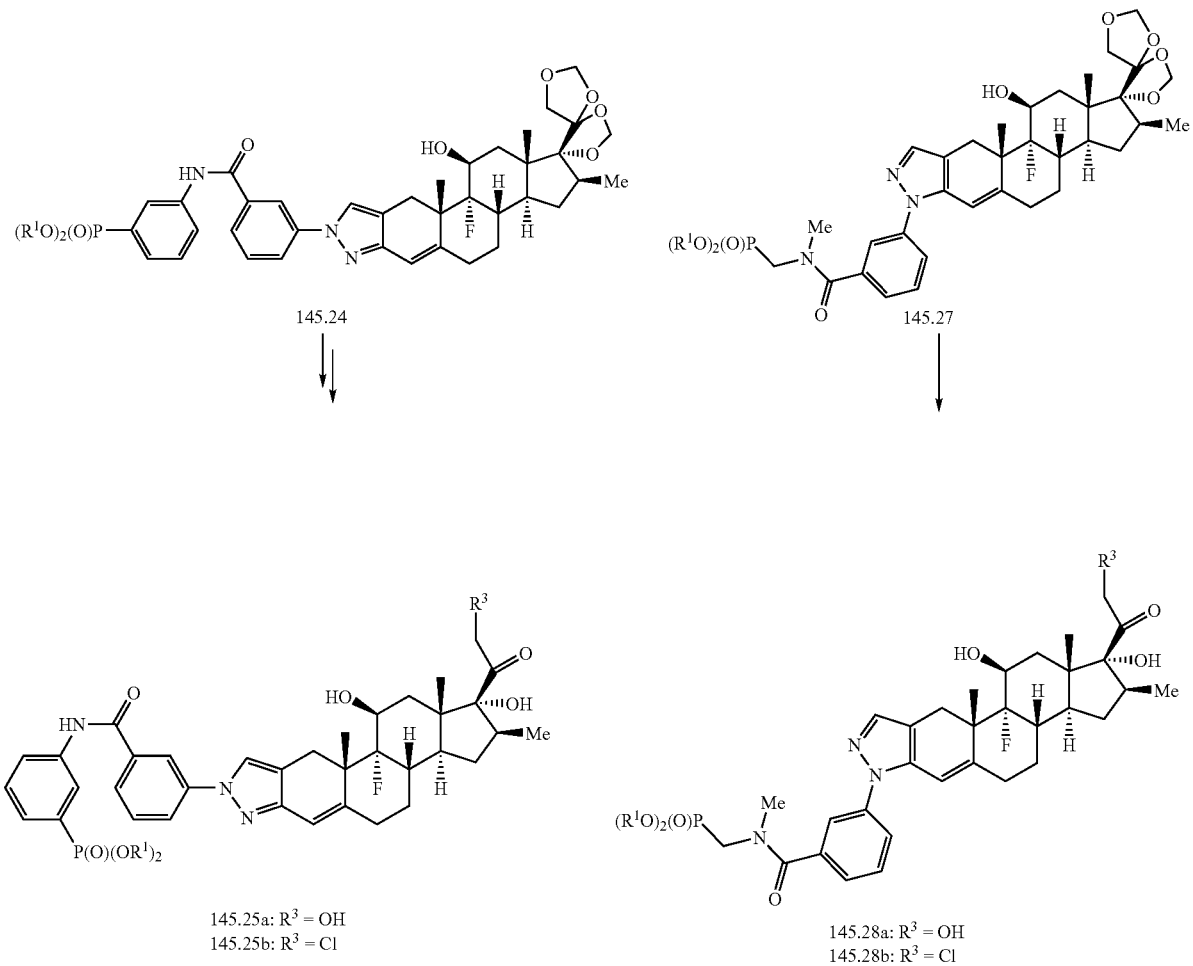

145.25a: R³ = OH
145.25b: R³ = Cl 145.28a: R³ = OH
145.28b: R³ = Cl

The preparation of the phosphonates in which the phosphonate group is attached by means of a phenyl ring and an amide linkage is illustrated above. In this procedure, the ketoaldehyde 145.2 is reacted, as described above, with 3-carboxyphenyl hydrazine 145.20 (Apin) to produce the pyrazoles 145.21 and 145.22. The 1'-substituted isomer 145.21 is coupled, in the presence of dicyclohexylcarbodiimide, with a dialkyl 3-aminophenyl phosphonate 145.23 (Aurora) to give the amide 145.24. The preparation of amides from carboxylic acids and derivatives is described, for example, in Organic Functional Group Preparations, by S. R. Sandler and W. Karo, Academic Press, 1968, p. 274, and Comprehensive Organic Transformations, by R. C. Larock, VCH, 1989, p. 972ff. The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide. The product is then deprotected to afford the triol 145.25a which is converted into the 21-chloro compound 145.25b.

Alternatively, the 2'-substituted pyrazole 145.22 is coupled, as described above, with a dialkyl methylaminomethyl phosphonate 145.26 (AsInEx) to prepare the amide phosphonate 145.27 which is deprotected, and the product is converted into the 21-chloro analog 145.28b.

Using the above procedures, but employing, in place of the carboxyphenyl hydrazine 145.20, different carboxy-substituted aralkyl, aryl or heteroaryl alkoxy hydrazines, and/or different dialkyl amino-substituted phosphonates, the products analogous to the compounds 145.25b and 145.28b are obtained.

EXAMPLE 146
Preparation of Representative Clobetasol Derivatives
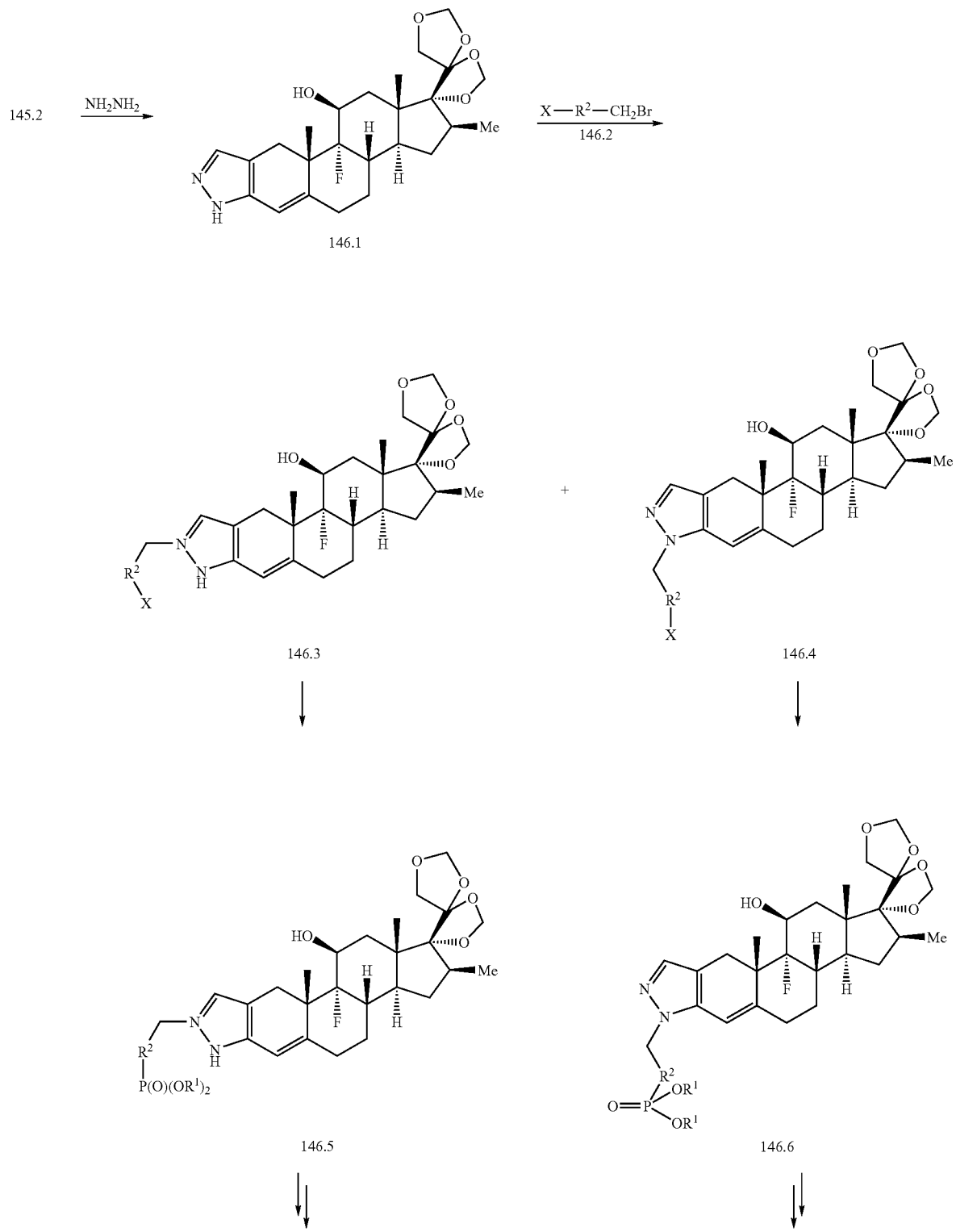

-continued

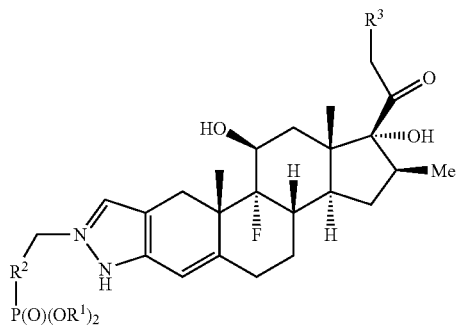

146.7a: R³ = OH
146.7b: R³ = Cl

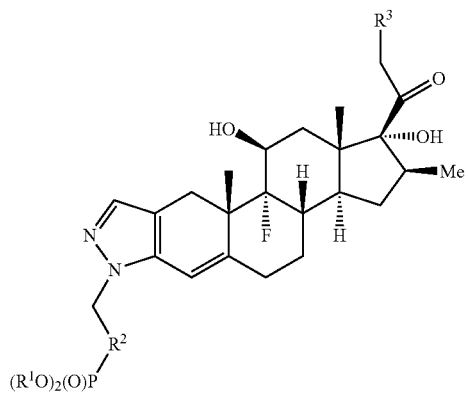

146.8a: R³ = OH
146.8b: R³ = Cl

The preparation of the phosphonate esters in which the phosphonate group is attached by means of a variable carbon linkage is illustrated above. In this procedure, the ketoaldehyde 145.2 is reacted with hydrazine, to afford the pyrazole derivative 146.1. The reaction of steroidal 2-formyl-3-ketones with hydrazine is described in *J. Am. Chem. Soc*, 1964, 86, 1520. The reaction is performed in acetic acid at ambient temperature. The pyrazole product is then reacted with a bromomethyl compound 146.2, in which R² and X are as defined above, to yield the alkylation products 146.3 and 146.4. The alkylation of substituted pyrazoles is described, for example, in Heterocyclic Chemistry, by T. L. Gilchrist, Longman, 1992, p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The products 146.3 and 146.4 are, except in cases where X is dialkylphosphono, converted into the phosphonates 146.5 and 146.6, using the procedures described herein, and deprotection/acylation then affords the 21-chloro compounds 146.7b and 146.8b.

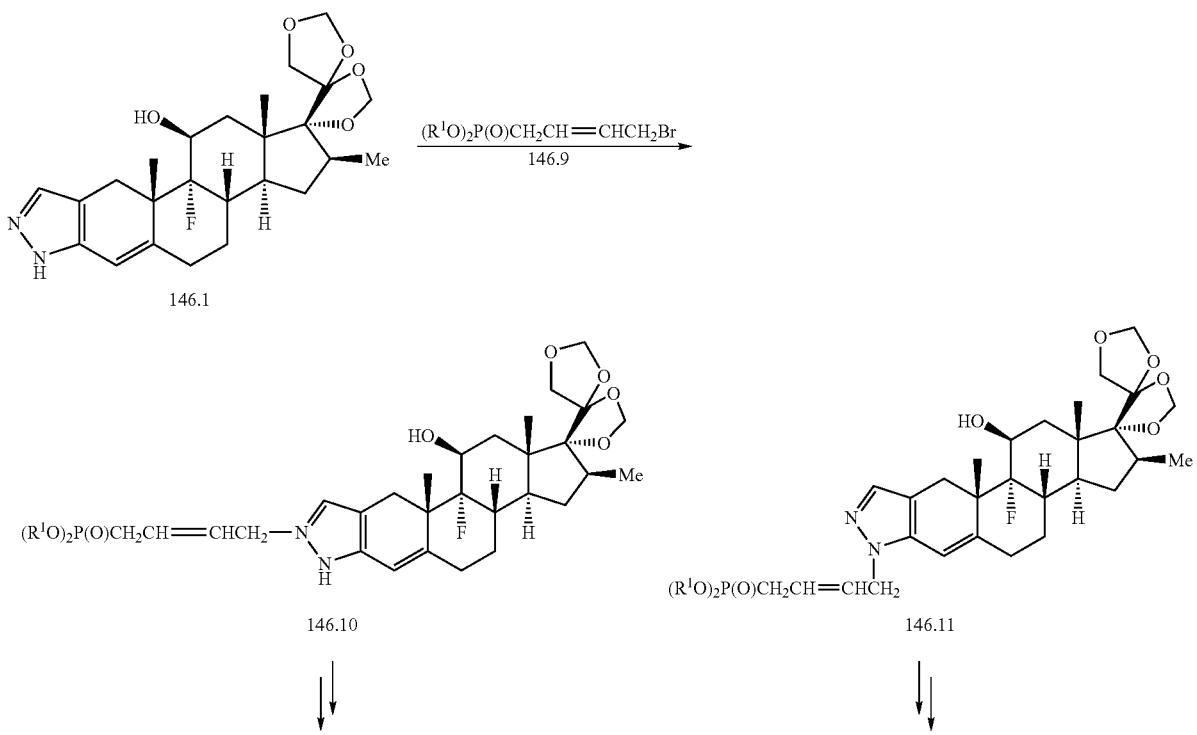

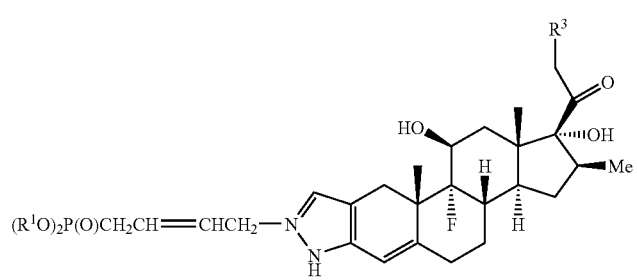

146.12a: $R^3$ = OH
146.12b: $R^3$ = Cl

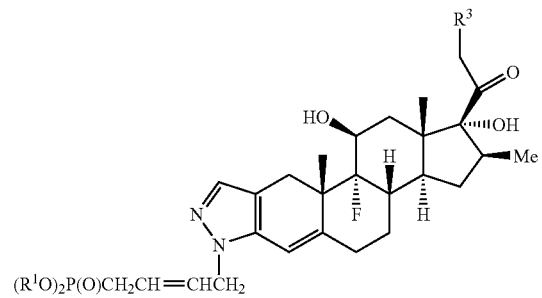

146.13a: $R^3$ = OH
146.13b: $R^3$ = Cl

The preparation of representative compounds of the invention is illustrated above. The pyrazole 146.1 is reacted in tetrahydrofuran solution, as described above, with one molar equivalent of a dialkyl bromobutenyl phosphonate 146.9 (*J. Med. Chem.*, 1992, 35, 1371) and lithium hexamethyldisilazide to give the alkylated pyrazoles 146.10 and 146.11. Deprotection/chlorination then yields the 21-chloro products 146.12b and 146.13b.

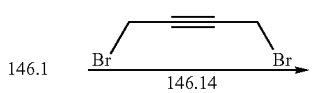

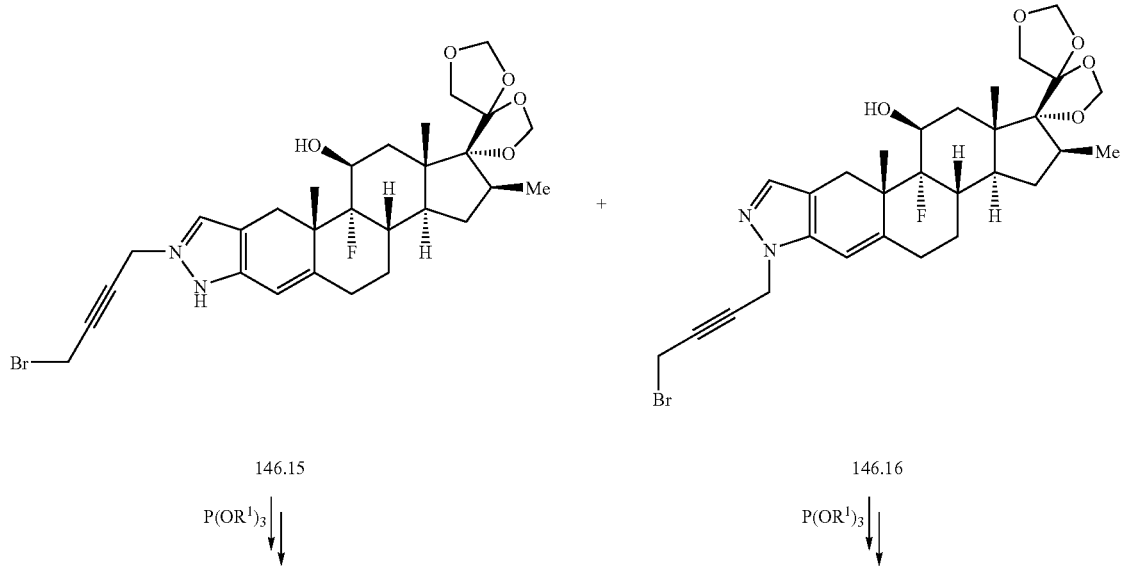

146.15           146.16

P(OR¹)₃ ↓           P(OR¹)₃ ↓

-continued

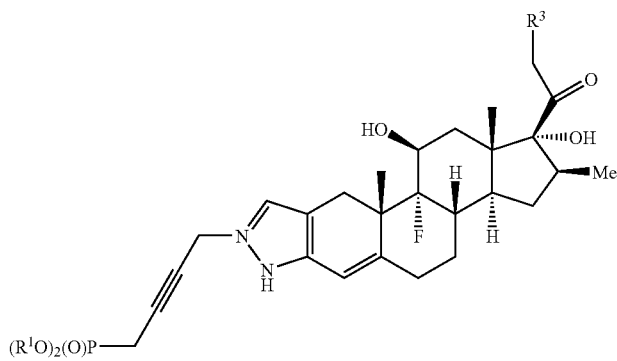

146.17a: R³ = OH
146.17b: R³ = Cl

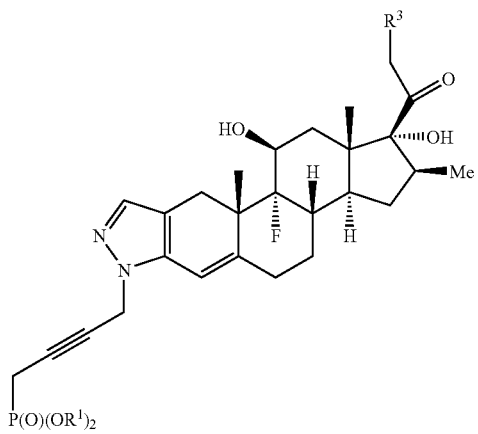

146.18a: R³ = OH
146.18b: R³ = Cl

The preparation of representative compounds of the invention is illustrated above. The pyrazole 146.1 is reacted in tetrahydrofuran solution, as described above, with 1,4-dibromobut-2-yne 146.14 (Aldrich) to give the pyrazoles 146.15 and 146.16. The products are subjected to an Arbuzov reaction, in which the bromomethyl substituent is converted into the dialkyl phosphonomethyl substituent, by reaction with a trialkyl phosphite at 1200, to prepare, after deprotection of the side chain and chlorination, the 21-chloro phosphonates 146.17b and 146.18b. The Arbuzov reaction is described in Handb. Organophosphorus Chem., 1992, 115-72. In the procedure, the substrate is heated at from 60° to about 160° with a five to fifty-fold molar excess of the trialkyl phosphite. Using the above procedures, but employing, in place of the dibromide 146.14, different dibromides, the products analogous to 146.17b and 146.18b are obtained.

EXAMPLE 147

Preparation of Representative Compounds of Formulae 148 and 149

Representative compounds of the invention can be prepared as generally described by Westwood et al, *J. Med. Chem.*, 1996, 39, 4608-4621, and according to the following general route.

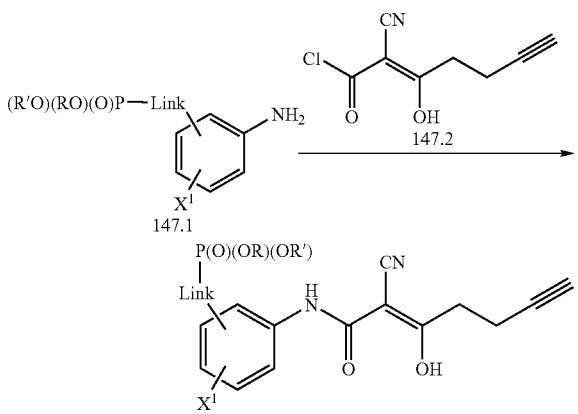

Coupling of a suitable aniline 147.1 wherein $X^1$ is hydrogen, halo, trifluoromethyl, ($C_1$-$C_3$)alkyl, cyano, or ($C_1$-$C_3$) alkoxy, with acid chloride 147.2 provides a representative compound of Formula 148 or 149.

EXAMPLE 148

Synthesis of Representative Compounds of Formulae 150-153

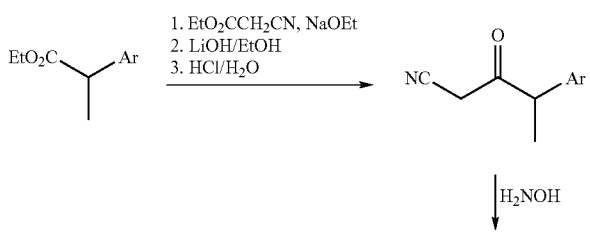

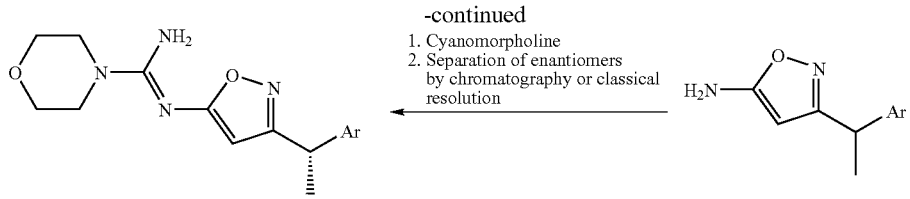

Compounds of the invention can be prepared as generally illustrated above. A β-ketonitrile is generated from a phenylacetic acid by condensation with a malononitrile ester under Claisen conditions. Reaction with hydroxylamine provides the 5-amino-1,2-oxazole which, upon condensation with cyanomorpholine provides a SMP-114 analog of the invention.

The prepration of suitable carboxylic acid intermediates that can be incorporated into the above synthetic scheme is detailed below.

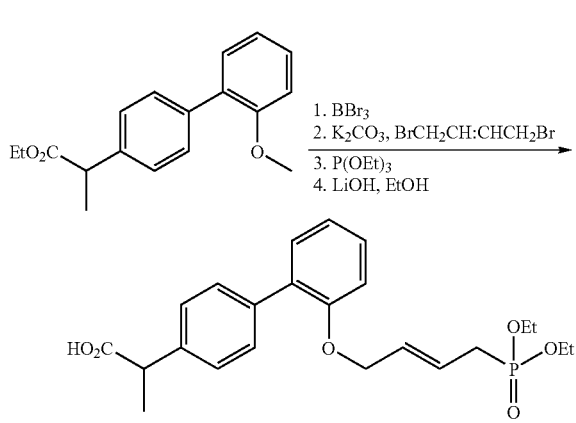

The anisole derivative is demethylated by treatment with a Lewis acid such as boron tribromide. The resulting phenol is alkylated with E-1,4-dibromobutene and the resulting monobromide is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. Saponification of the carboxylate ester gives the phenylacetic acid ready for incorporation into the synthesis of SMP-114 analogs.

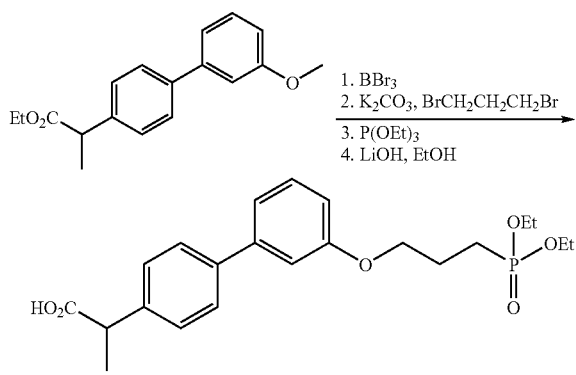

Using a procedure silimar to that described above, except replacing E-1,4-dibromobutene with 1,3-dibromopropane, a suitable intermediate can be prepared.

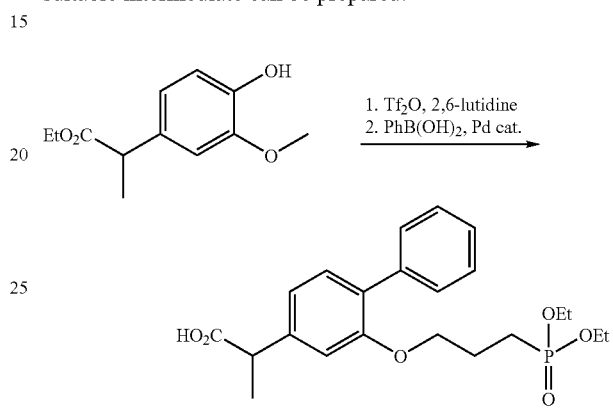

The free phenol in ethyl homovanillate is converted to the aryl triflate, and the biphenyl motif is generated by Suzuki coupling with phenylboronic acid (see *Chem. Rev.*, 1995, 95, 2457). The remaining steps are analogous to those described immediately above.

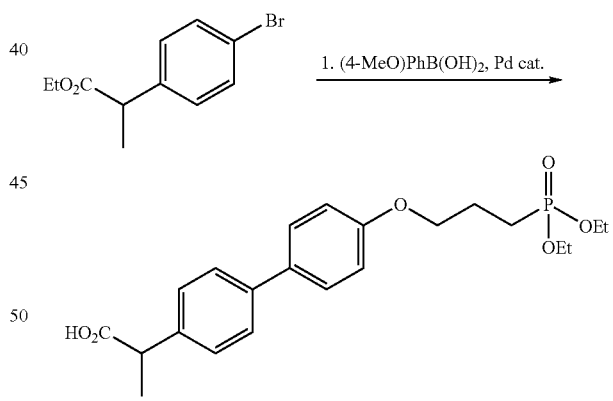

Ethyl 4-bromophenylacetate is coupled with 4-methoxyphenylboronic acid using the Suzuki method. The remaining steps are analogous to those described above.

EXAMPLE 149

Synthesis of Representative Compounds of Formulae 154-155

Compounds of the invention can be prepared as generally described by Westwood et al, *J. Med. Chem.*, 1996, 39, 4608-4621, according to the general route outline below.

Representative compounds of the invention can generally be prepared as illustrated above.

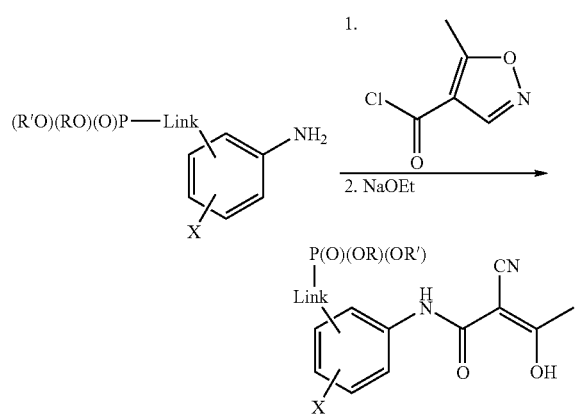

Coupling of a suitable aniline wherein X is hydrogen, halo, trifluoromethyl, cyano, or methyl with acid chloride followed by treatment with sodium ethoxide provides a representative compounds of Formulae 154 and 155.

EXAMPLE 150

Synthesis of Representative Compounds of Formulae 156

Certain specific salicylic acid analogs of the invention can be prepared as illustrated above. Salicylic acid is converted to its acid chloride by treatment with oxalyl chloride in dimethylformamide. The acid chloride is then coupled with 2-aminoethylphosphonic acid diethyl ester in the presence of a base such as triethylamine in a solvent such as dichloromethane to generate the desired amide product.

2-Aminophenol is acylated with an activated diethylphosphonoacetic acid to provide the desired amide linker compound, according to a procedure such as those reported in *J. Med. Chem.*, 1982, 25, 960-964 and *J. Med. Chem.*, 1984, 27, 600-604. The activated diethylphosphonoacetic acid is obtained by treatment in a solvent such as dimethylformamide with a coupling reagent such as diethyl cyanophosphonate and a base such as diisopropylethylamine at room temperature.

2-Bromoaniline is coupled with pent-4-ynyl-phosphonic acid diethyl ester (generated from 5-chloro-1-pentyne and triethylphosphite in a solvent such as toluene, or other Arbuzov reaction conditions: see Engel, R., Synthesis of carbon-phosphorus bonds, CRC press, 1988) under conditions such as those pioneered by Sonagashira (Sonogashira, K.; Tohda, Y.; Hagihara, N. *Tetrahedron Lett.*, 1975, 4467) to afford the desired salicylic acid analog containing a phosphonate.

EXAMPLE 151

Synthesis of Representative Compounds of Formulae 157

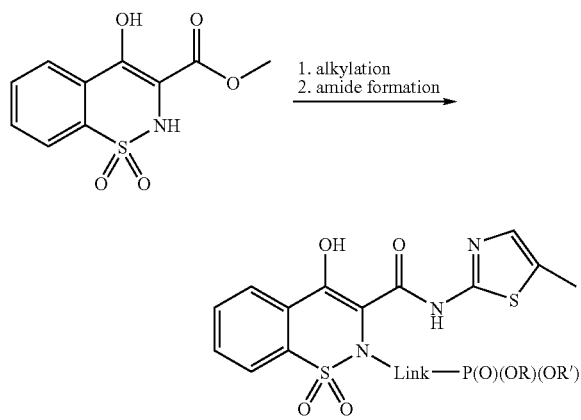

Compounds of the invention can generally be prepared as illustrated above. For example, a specific compound of the invention can be prepared as follows.

EXAMPLE 152

Synthesis of Representative Compounds of Formulae 158

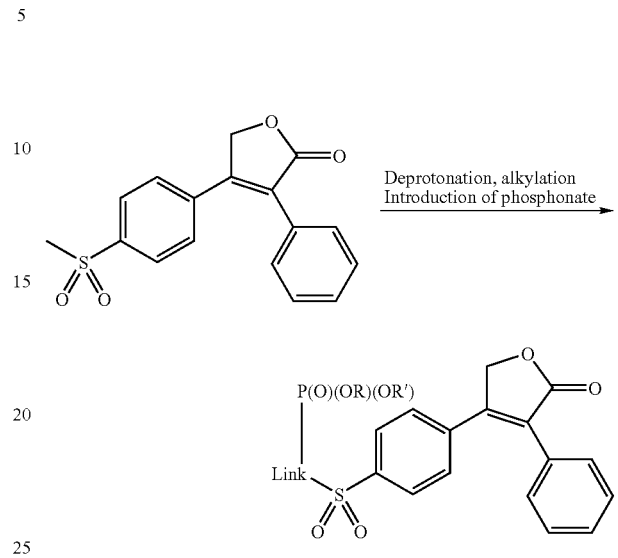

Compounds of the invention can generally be prepared as illustrated above. For example, a specific compound of the invention can be prepared as follows.

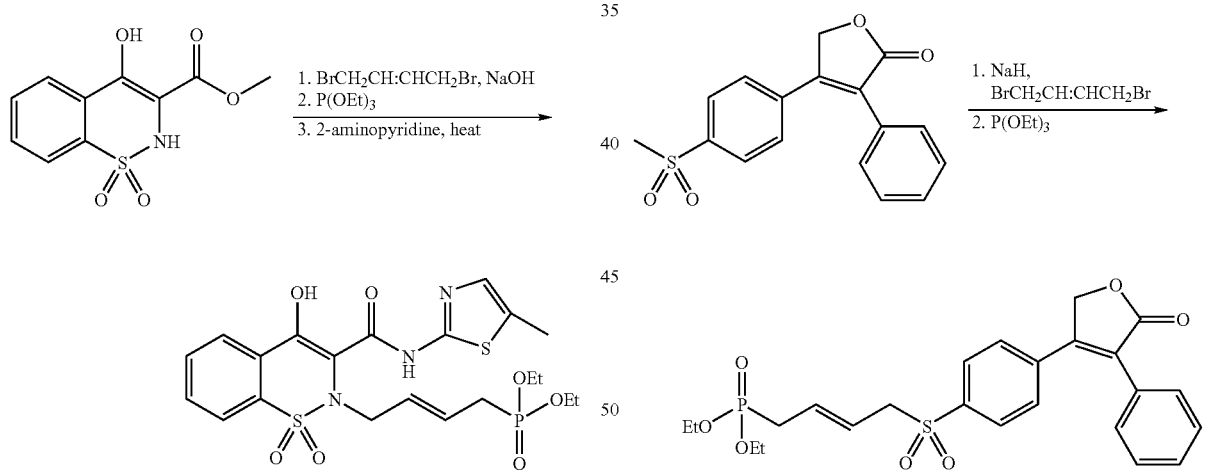

The methyl ester shown is treated in a solvent such as ethanol with excess E-1,4-dibromobutene in the presence of a base such as sodium hydroxide, as described in *J. Med. Chem.*, 1997, 40, 980. The monobromide so formed is then heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. Finally, heating with 2-aminothiazole in solvents such as xylenes, as described in *J. Med. Chem.*, 1997, 40, 980, gives the desired meloxicam analogue.

Rofecoxib is treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the mono-alkylated product is isolated by chromatography. The bromide so formed is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid.

EXAMPLE 153

Synthesis of Representative Compounds of Formulae 159

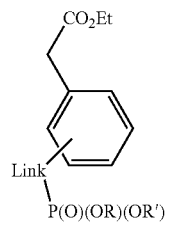

As in Ind. J. Chem., Sect B, 1990, 10, 954

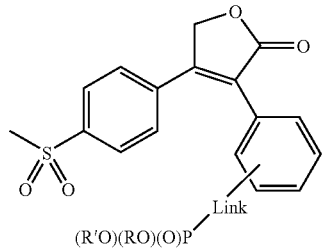

Compounds of the invention can generally be prepared as illustrated above (see also, *Ind. J. Chem., Sect B,* 1990, 10, 954.) A specific intermediate useful in the above process can be prepared as follows.

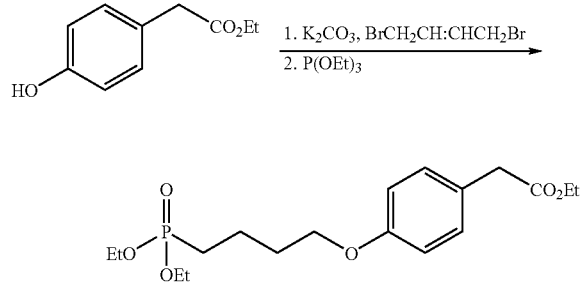

Ethyl 4-hydroxyphenylacetate is treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the monoalkylated product is isolated by chromatography. The bromide so formed is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid.

EXAMPLE 154

Synthesis of Representative Compounds of Formulae 160

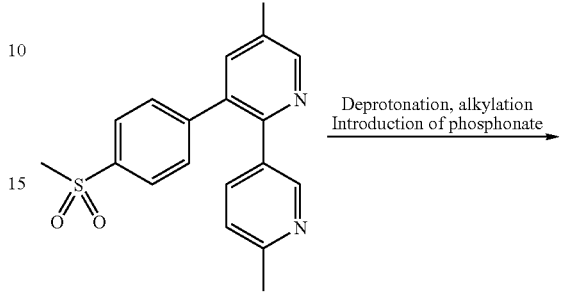

Deprotonation, alkylation
Introduction of phosphonate

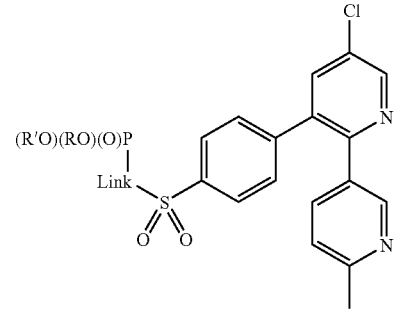

Compounds of the invention can generally be prepared as illustrated above. For example, a specific compound of the invention can be prepared as follows.

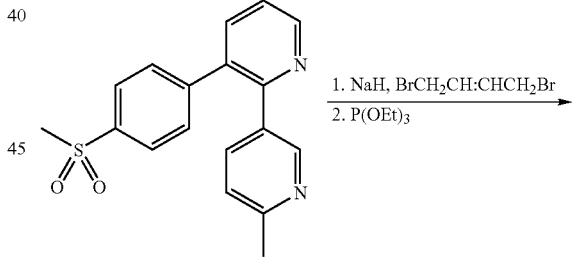

1. NaH, BrCH$_2$CH:CHCH$_2$Br
2. P(OEt)$_3$

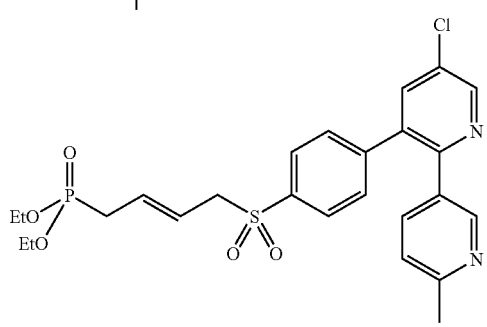

Etoricoxib is treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the mono-alkylated product is isolated by chromatography. The bromide so formed is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid.

EXAMPLE 155

Synthesis of Representative Compounds of Formulae 161

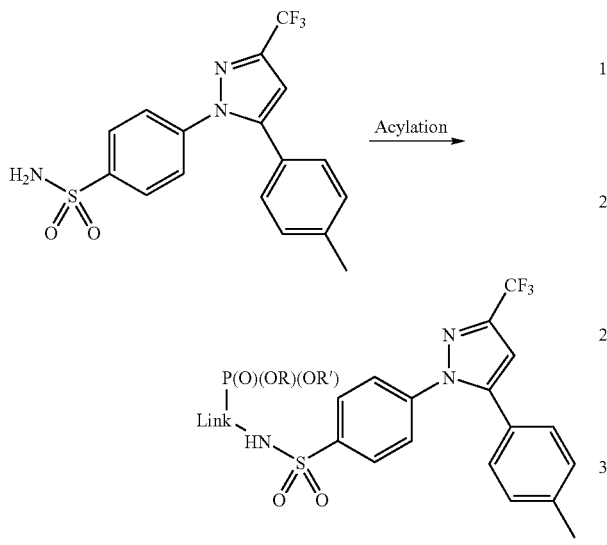

Compounds of the invention can generally be prepared as illustrated above. Acylation is achieved by reaction of the sulfonamide with an activated diethylphosphonoacetic acid to provide the desired compound, according to a procedure such as those reported in *J. Med. Chem.*, 1982, 25, 960 and *J. Med. Chem.*, 1984, 27, 600. The activated diethylphosphonoacetic acid can be obtained by treatment in a solvent such as dimethylformamide with a coupling reagent such as diethyl cyanophosphonate and a base such as diisopropylethylamine at room temperature. For example, a specific compound of the invention can be prepared as follows.

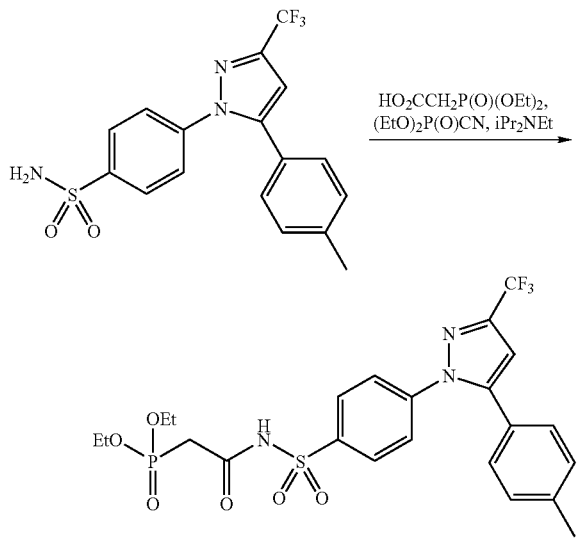

Acylation is achieved by reaction of the sulfonamide with an activated diethylphosphonoacetic acid to provide the desired compound, according to a procedure such as those reported in *J. Med. Chem.*, 1982, 25, 960 and *J. Med. Chem.*, 1984, 27, 600. The activated diethylphosphonoacetic acid can be obtained by treatment in a solvent such as dimethylformamide with a coupling reagent such as diethyl cyanophosphonate and a base such as diisopropylethylamine at room temperature.

EXAMPLE 156

Synthesis of Representative Compounds of Formulae 162

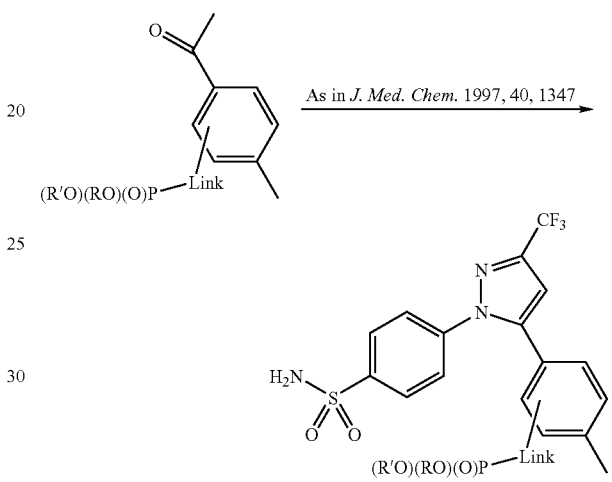

Compounds of the invention can generally be prepared as illustrated above. The synthesis of celecoxib analogs from a number of acetophenones is described in detail in *J. Med. Chem.*, 1997, 40, 1347. The synthesis of a suitable phosphonate-containing acetophenone is illustrated below.

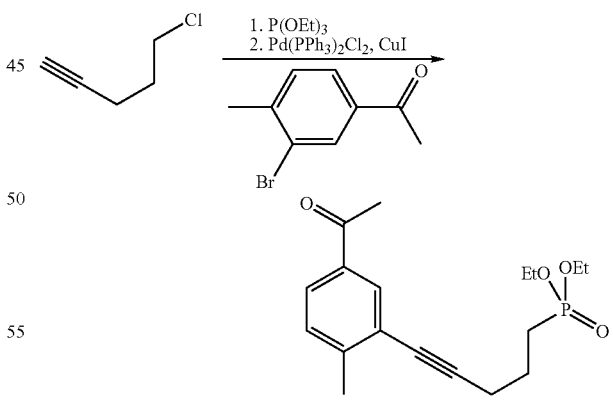

5-Chloro-1-pentyne is treated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid. This acetylene is coupled with 3'-bromo-4-methylacetophenone under conditions such as those pioneered by Sonagashira (Sonogashira, K.; Tohda, Y.; Hagihara, N. *Tetrahedron Lett.*, 1975, 4467).

EXAMPLE 157

Synthesis of Representative Compounds of Formulae 163

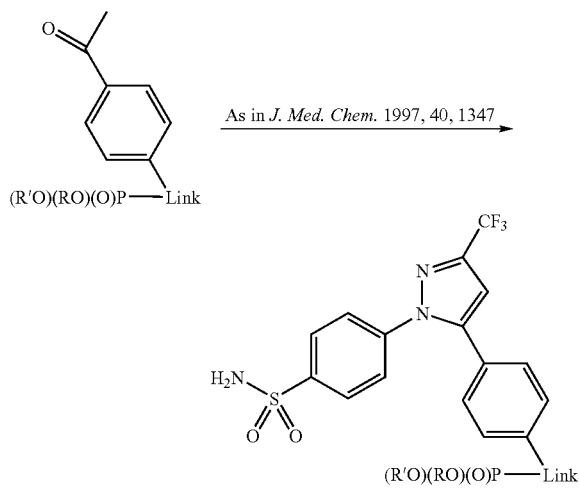

Compounds of the invention can generally be prepared as illustrated above. The synthesis of celecoxib analogs from a number of acetophenones is described in detail in *J. Med. Chem.*, 1997, 40, 1347. The synthesis of a suitable acetophenone linked at the 4' position to a phosphonate moiety is illustrated below.

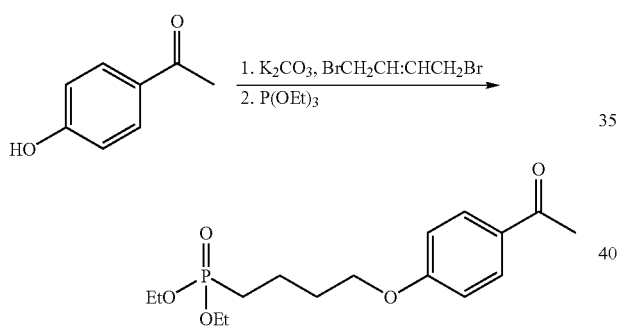

4'-Hydroxyacetophenone is treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the monoalkylated product is isolated by chromatography. The bromide so formed is heated with triethylphosphite in a solvent such as toluene (or other Arbuzov reaction conditions: see Engel, R., Synthesis of carbon-phosphorus bonds, CRC press, 1988) to generate the diethyl ester of the desired phosphonic acid.

EXAMPLES 158-161

Preparation of Halobetasol Derivatives

The synthesis of representative phosphonate derivatives of halobetasol is outlined in Examples 158-161. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 158

Preparation of Representative Halobetasol Derivatives

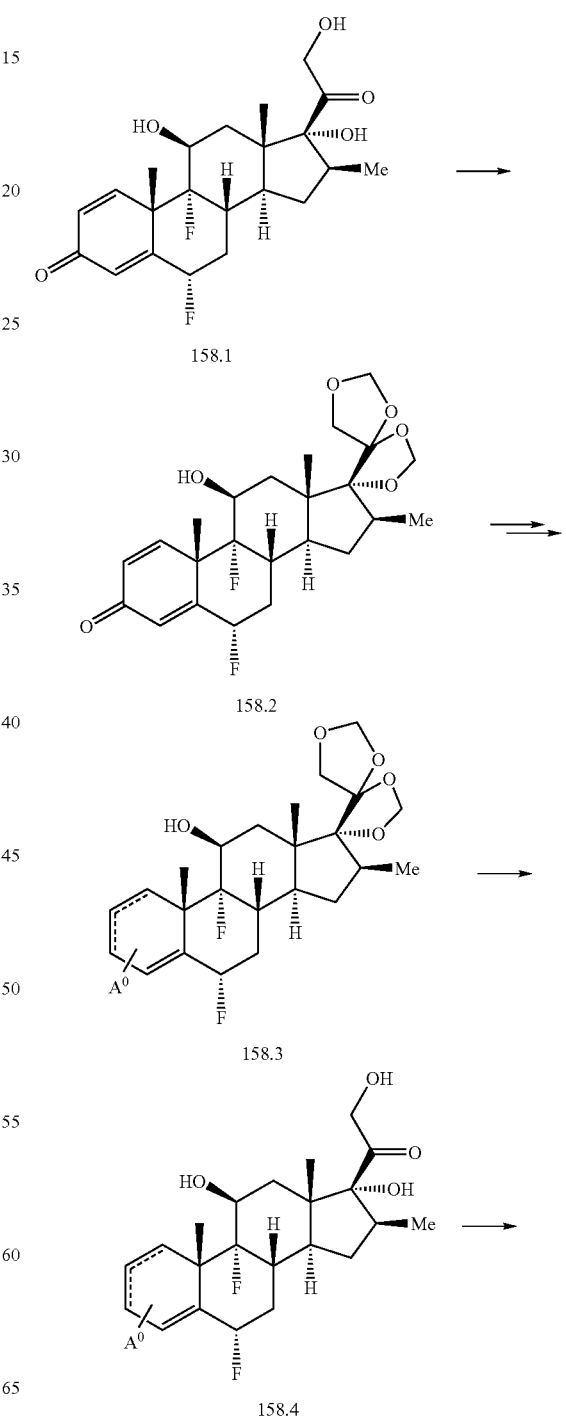

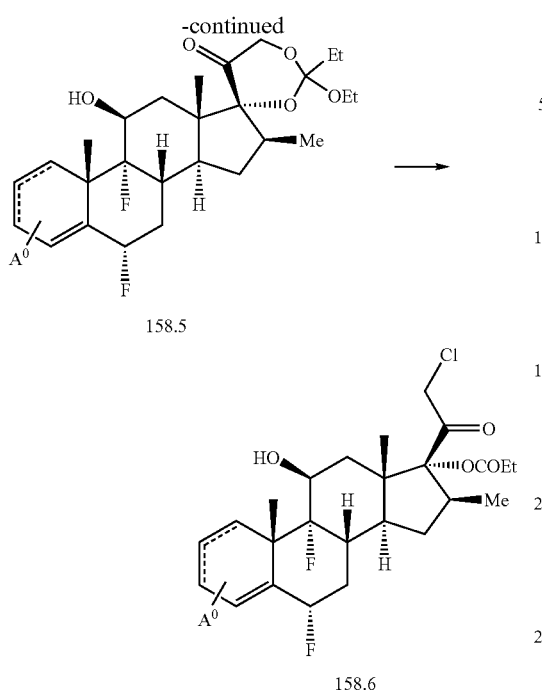

158.5

158.6

The preparation of representative compounds of the invention is illustrated above. The steroid side-chain is protected as a bis-methylenedioxy (BMD) moiety. In this sequence, 6α,9α-difluoro-16β-methyl-11β,17α,21-trihydroxypregn-1,4-dien-3,21-dione 158.1 (U.S. Pat. No. 4,619,921) is reacted with paraformaldehyde and an acid catalyst such as hydrochloric acid, as described in Protective Groups in Organic Synthesis, by T. W. Greene and P. G. M. Wuts, Wiley, Second Edition 1990, p. 223, to yield the BMD derivative 158.2. The phosphonate moiety is then introduced, using the procedures described below, to produce the phosphonate ester 158.3. The BMD moiety is then hydrolyzed, for example by treatment with 50% aqueous acetic acid, as described in Protective Groups in Organic Synthesis, by T. W. Greene and P. G. M. Wuts, Wiley, Second Edition 1990, p. 223, to afford the triol 158.4. The latter compound is then converted into the 17,21-cyclic orthoester 158.5 using the procedure described in *Chem. Pharm. Bull.*, 1986, 34, 1613. The substrate is reacted in dimethylformamide at 70° C. with two molar equivalents of triethyl orthopropionate and a catalytic amount of p-toluenesulfonic acid. The product is then reacted with an excess of trimethylsilyl chloride in dimethylformamide at ambient temperature to produce the 21-chloro 17-propionate product 158.6.

Alternatively, the substrate 158.4 is converted into the product 158.6 by means of the method described in *J. Med. Chem.*, (1987), 30: 1581. In this procedure, the 21-hydroxy group is activated by conversion to the 21-mesylate, by reaction with mesyl chloride in pyridine; the mesylate group is then displaced to yield the 21-chloro intermediate, by reaction with lithium chloride in dimethylformamide, and the 17-hydroxyl group is esterified to give the 21-chloro-17-propionate derivative 158.6. The selective acylation of the 17α hydroxyl group in the presence of an 11β hydroxyl group is described in *J. Med. Chem.*, (1987), 30: 1581.

EXAMPLE 159

Preparation of Representative Halobetasol Derivatives

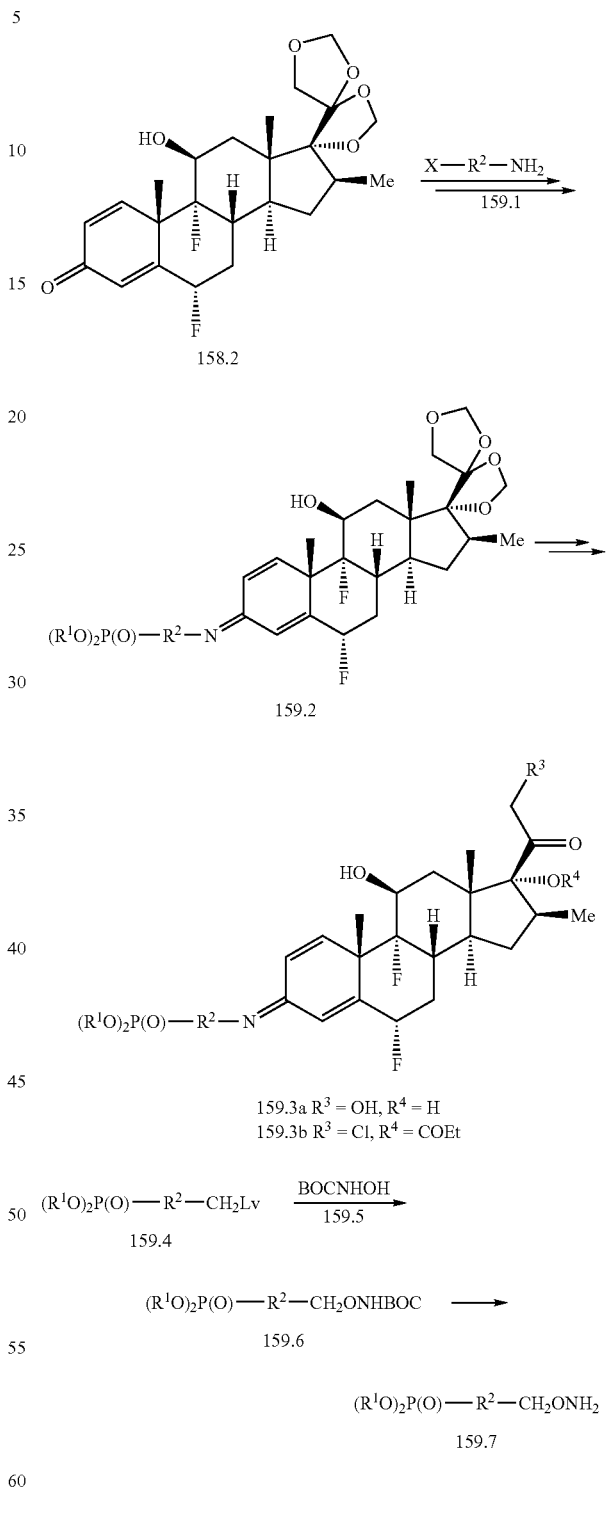

The preparation of phosphonates in which the phosphonate is attached by means of an imino or iminoxy group and a variable carbon chain is illustrated above. In this procedure, the BMD-protected derivative 158.2 is reacted with an amine or hydroxylamine 159.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in *Anal. Bioch.*, (1978), 86, 133. and in *J. Mass. Spectrom.*, (1995), 30, 497. The BMD-protectedside-chain compound 159.2 is then converted into the triol 159.3a, and then to the 21-chloro 17 propionate product 159.3b.

The preparation of hydroxylamine ethers incorporating a phosphonate group is also illustrated above. In this procedure, a phosphonate 159.4, in which Lv is a leaving group such as bromo or trifluoromethylsulfonyloxy, is reacted with BOC-hydroxylamine 159.5 (Aldrich) to produce the ether 159.6. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 159.7.

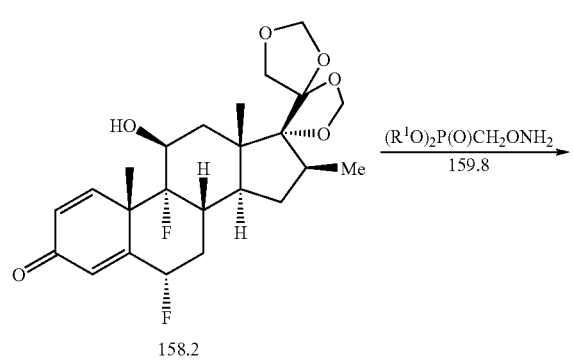

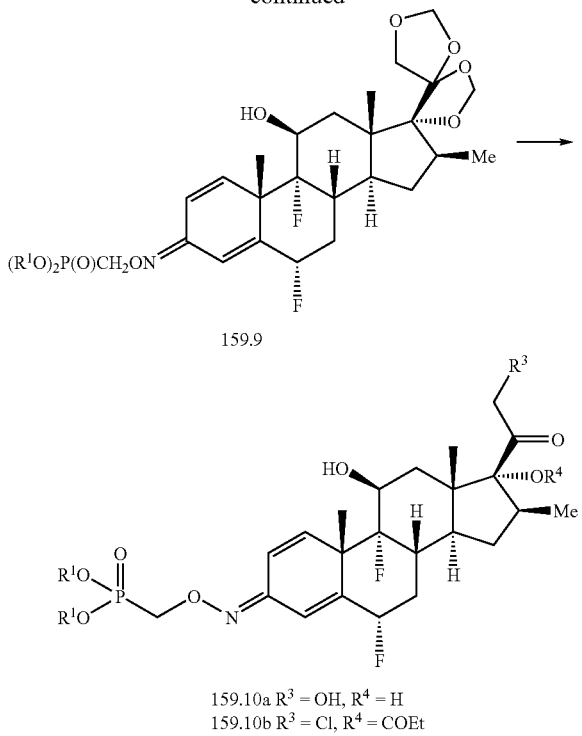

The preparation of phosphonates in which the phosphonate is attached by means of an iminoxy group is illustrated above. In this procedure, the substrate 158.2 is reacted with a dialkyl phosphonomethyl hydroxylamine 159.8, prepared as described above from a dialkyl trifluoromethylsulfonyloxymethyl phosphonate (*Tet. Lett.* 27:1477 (1986)) and BOC-hydroxylamine, to afford the oxime 159.9. Deprotection then affords the triol 159.10a from which the 21-chloro 17-propionate compound 159.10b is prepared. The oxime forming reaction is performed at ambient temperature in ethanol-acetic acid solution between equimolar amounts of the reactants.

Using the above procedures, but employing, in place of the hydroxylamine ether 159.8, different oxime ethers 159.1, the corresponding products 159.3b are obtained.

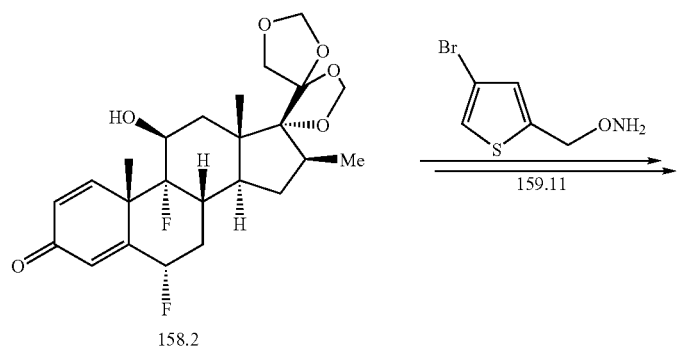

-continued

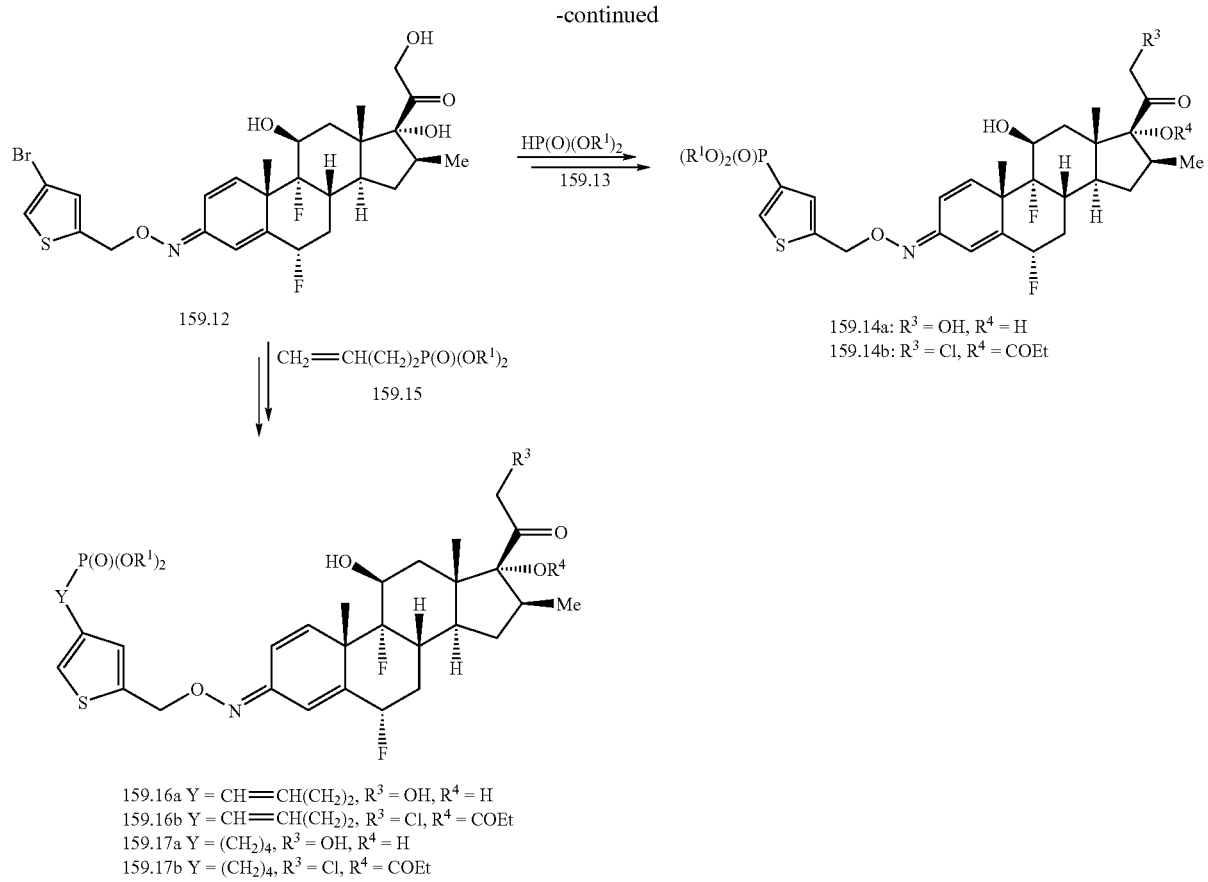

159.12

159.14a: R³ = OH, R⁴ = H
159.14b: R³ = Cl, R⁴ = COEt 159.16a Y = CH═CH(CH₂)₂, R³ = OH, R⁴ = H
159.16b Y = CH═CH(CH₂)₂, R³ = Cl, R⁴ = COEt
159.17a Y = (CH₂)₄, R³ = OH, R⁴ = H
159.17b Y = (CH₂)₄, R³ = Cl, R⁴ = COEt

The preparation of compounds in which the phosphonate group is attached by means of a thienylmethoxy oxime group is illustrated above. In this procedure, the dienone 158.2 is reacted, as described above, with O-(4-bromo-2-thienylmethoxy)hydroxylamine 159.11, prepared as described above from 4-bromo-2-bromomethylthiophene (WO 9420456) and BOC-protected hydroxylamine, to give, after deprotection of the side-chain, the oxime 159.12. The product is then reacted, in the presence of a palladium catalyst, with a dialkyl phosphite 159.13 to afford the phosphonate 159.14a. The preparation of arylphosphonates by means of a coupling reaction between aryl bromides and dialkyl phosphites is described in J. Med. Chem. 35:1371 (1992). The reaction is performed in an inert solvent such as toluene, in the presence of a base such as triethylamine and a catalytic amount of tetrakis(triphenylphosphine)-palladium(0). The 21-hydroxy compound 159.14a is then converted into the 21-chloro 17-propionate derivative 159.14b.

Alternatively, the bromo compound 159.12 is coupled with a dialkyl butenyl phosphonate 159.15 (Org. Lett. 3:217 (2001)) to afford the phosphonate 159.16a. The coupling of aryl halides with olefins by means of the Heck reaction is described, for example, in F. A. Carey and R. J. Sundberg, Advanced Organic Chemistry 503ff (Plenum, 2001) and in Acc. Chem. Res. 12:146 (1979). The aryl bromide and the olefin are coupled in a polar solvent such as dimethylformamide or dioxan, in the presence of a palladium(0) catalyst such as tetrakis(triphenyl-phosphine)palladium(0) or palladium(II) catalyst such as palladium(II) acetate, and optionally in the presence of a base such as triethylamine or potassium carbonate. Optionally, the double bond present in the product 159.16a is reduced, for example by reaction with diimide, to produce the saturated analog 159.17a. The reduction of olefinic bonds is described in R. C. Larock, Comprehensive Organic Transformations 6ff (VCH 1989). The transformation is effected by means of catalytic hydrogenation, for example using a palladium on carbon catalyst and hydrogen or a hydrogen donor, or by the use of diimide or diborane. The products 159.16a and 159.17a are then converted into the 21-chloro 17-propionate analogs 159.16b and 159.17b.

Using the above procedures, but employing, in place of the bromothienylmethoxy reagent 159.11, different bromo-substituted aryl or heteroaryl alkoxy hydroxylamines, and/or different dialkyl alkenyl phosphonates, the products analogous to the compounds 159.14b, 159.16b and 159.17b are obtained.

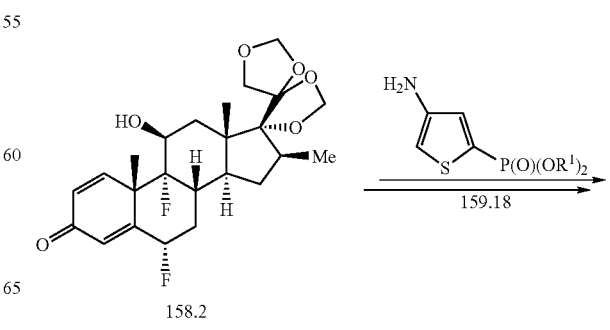

158.2

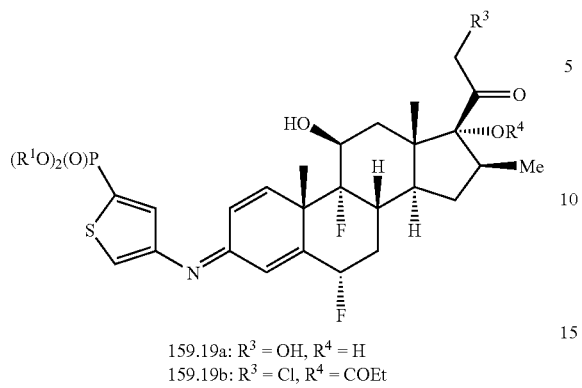

159.19a: R³ = OH, R⁴ = H
159.19b: R³ = Cl, R⁴ = COEt

The preparation of representative phosphonates of the invention is illustrated above. In this procedure, the substrate 158.2 is reacted with a dialkyl 4-amino-2-thienyl phosphonate 159.18, prepared by the palladium-catalyzed coupling, as described above, between 4-amino-2-bromothiophene (*Tet.* 43:3295 (1987)) and a dialkyl phosphite, to give, after deprotection, the imine product 159.19a. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions. The product is then converted into the 21-chloro 17-propionate compound 159.19b.

Using the above procedures, but employing, in place of the 4-aminothienyl phosphonate 159.18 different amino-substituted aryl or heteroaryl phosphonates, products analogous to 159.19b are obtained.

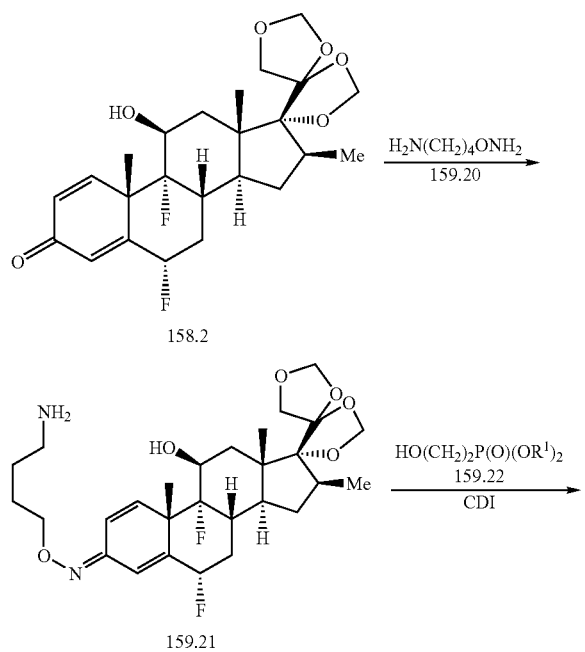

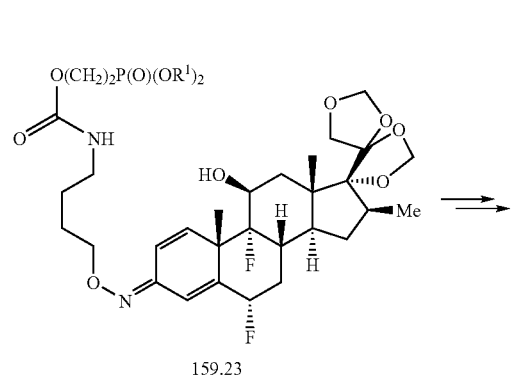

159.23

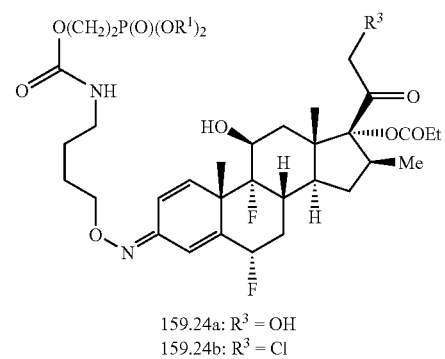

159.24a: R³ = OH
159.24b: R³ = Cl

The preparation of phosphonates in which the phosphonate is attached by means of an oximino group and an amide linkage is illustrated above. In this procedure, the dienone 158.2 is reacted with O-(4-aminobutyl)hydroxylamine 159.20 (*Pol. J. Chem.* 55:1163 (1981)) to yield the oxime 159.21. The reaction of steroidal 1,4-dien-3-ones with substituted hydroxylamines is described in *J. Steroid Bioch.* 7:795 (1976); the reaction is performed between equimolar amounts of the reactants in a polar organic solvent such as pyridine or methanol, optionally in the presence of acetic acid or sodium acetate. The product is then coupled with a dialkyl 2-hydroxyethyl phosphonate 159.22 (Epsilon) and carbonyl diimidazole, to yield the carbamate oxime 159.23. The preparation of carbamates is described in A. R. Katritzky, Comprehensive Organic Functional Group Transformations, 6:416ff (Pergamon, 1995), and in S. R. Sandler and W. Karo, Organic Functional Group Preparations, 260ff (Academic Press, 1986). In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and the like, to afford the corresponding activated acylamine. The latter compound is then reacted with an alcohol to yield the carbamate. The carbamate product 159.23 is then converted into the 21-chloro 17-propionate product 159.24b.

Using the above procedures, but employing, in place of the hydroxylamine 159.22, different amino-substituted hydroxylamines, and/or different hydroxy-substituted phosphonates, the products analogous to 159.24b are obtained.

EXAMPLE 160

Preparation of Representative Halobetasol Derivatives

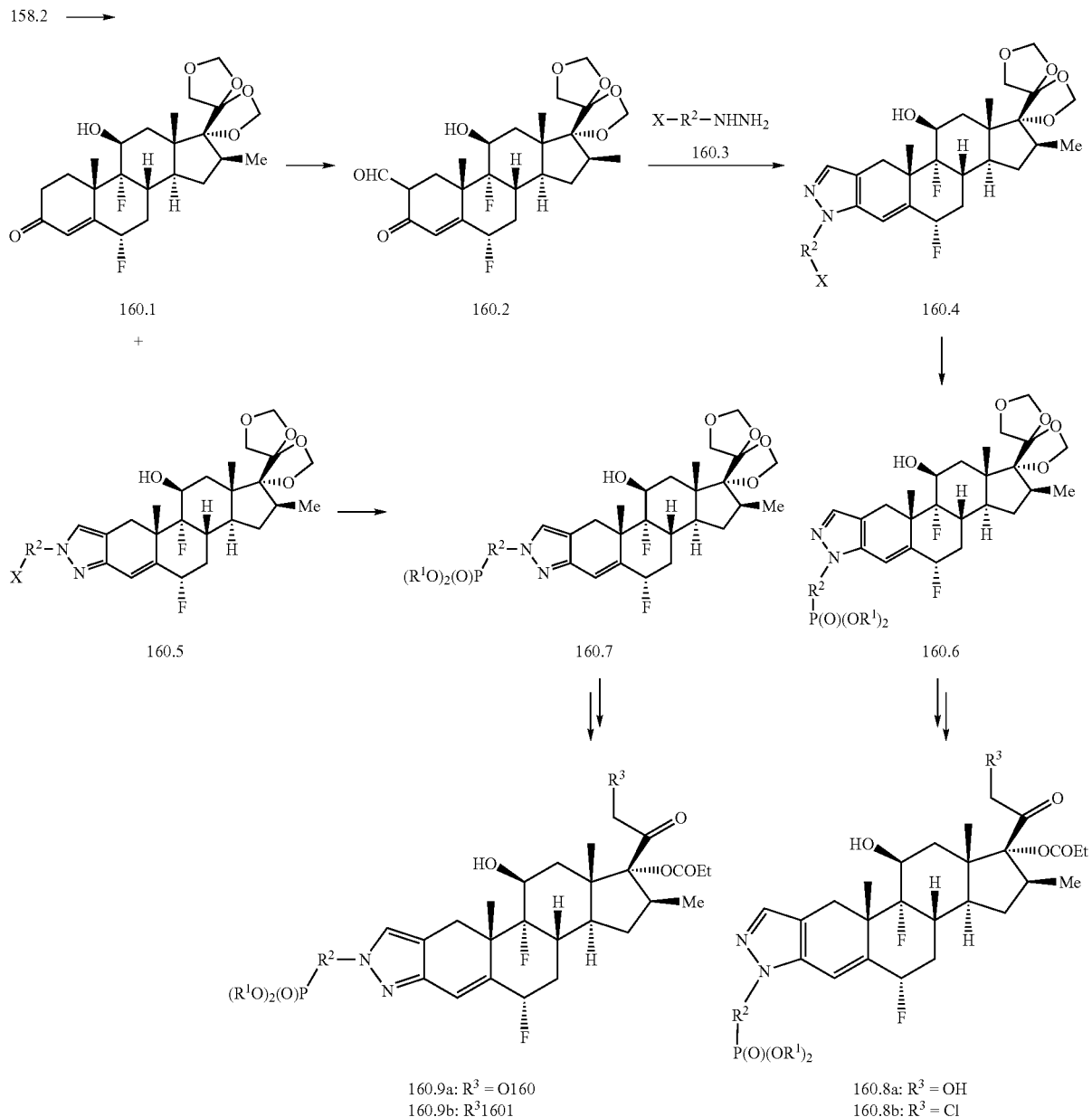

The preparation of the phosphonate esters in which the phosphonate group is attached to the 1' or 2' position of the pyrazole ring, by means of an aromatic or heteroaromatic group, a heteroatom and/or a variable carbon chain is illustrated above. In this procedure, the BMD-protected dienone 158.2 is reduced to afford the 1,2-dihydro product 160.1. The catalytic hydrogenation reaction is effected by the use of tris(triphenylphosphine)rhodium(I) chloride, for example as described in *J. Med. Chem.* 44:602 (2001). The product is then reacted with ethyl formate and a base such as sodium hydride, in an inert solvent such as toluene or dimethylformamide, as described in *J. Am. Chem. Soc.* 86:1520 (1964), to afford the 2-formyl product 160.2. This compound is then reacted with an alkyl, aralkyl, aryl or heteroaryl hydrazine 160.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 160.4 and 160.5. The pyrazole-forming reaction is performed between equimolar amounts of the reactants in an acidic solvent such as acetic acid, as described in *J. Am. Chem. Soc.* 86:1520 (1964). The pyrazoles 160.4 and 160.5 are then transformed via the BMD-protected intermediates 160.6 and 160.7, into the 21-chloro 17-propionate phosphonates 160.8b and 160.9b.

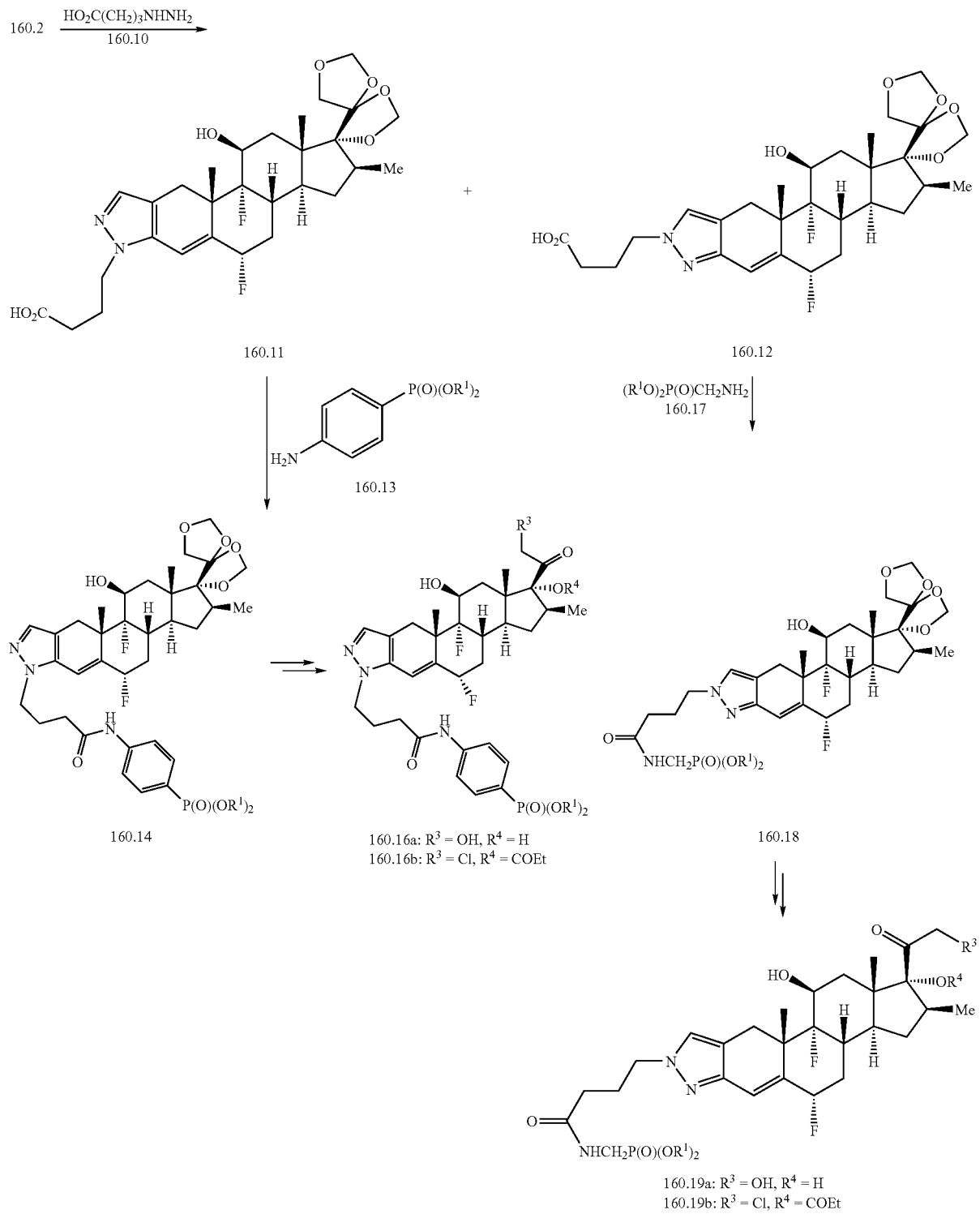

The preparation of phosphonates in which the phosphonate is attached by means of an amide linkage is illustrated above. In this procedure, the ketoaldehyde 160.2 is reacted, as described above, with 3-carboxypropyl hydrazine 160.10 (*Ind. J. Exp. Biol.* 32:218 (1994)) to give the pyrazoles 160.11 and 160.12. The 2'-substituted isomer 160.11 is then reacted in dimethylformamide solution at ambient temperature with one molar equivalent of a dialkyl 4-aminophenyl phosphonate 160.13 (Epsilon) and dicyclohexyl carbodiimide, to yield the amide 160.14. The preparation of amides from carboxylic acids and derivatives is described, for example, in S. R. Sandler and W. Karo, Organic Functional Group Preparations, 274 (Academic Press, 1968), and R. C. Larock, Comprehensive Organic Transformations, 972ff (VCH, 1989). The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide.

The BMD protecting group is then removed and the product is converted into the 21-chloro 17-propionate product 160.16b.

Alternatively, the 1'-substituted pyrazole 160.12 is coupled, as described above, with a dialkyl aminomethyl phosphonate 160.17 (Interchim), to afford the amide 160.18. The product 160.18 is then deprotected to give the triol 160.19a, and the latter compound is transformed into the 21-chloro 17-propionate 160.19b.

Using the above procedures, but employing different amino-substituted phosphonates, and/or different carboxy-substituted hydrazines, the products analogous to 160.16b and 160.19b are obtained. The functionalization procedures are interchangeable between the pyrazole substrates 160.11 and 160.12.

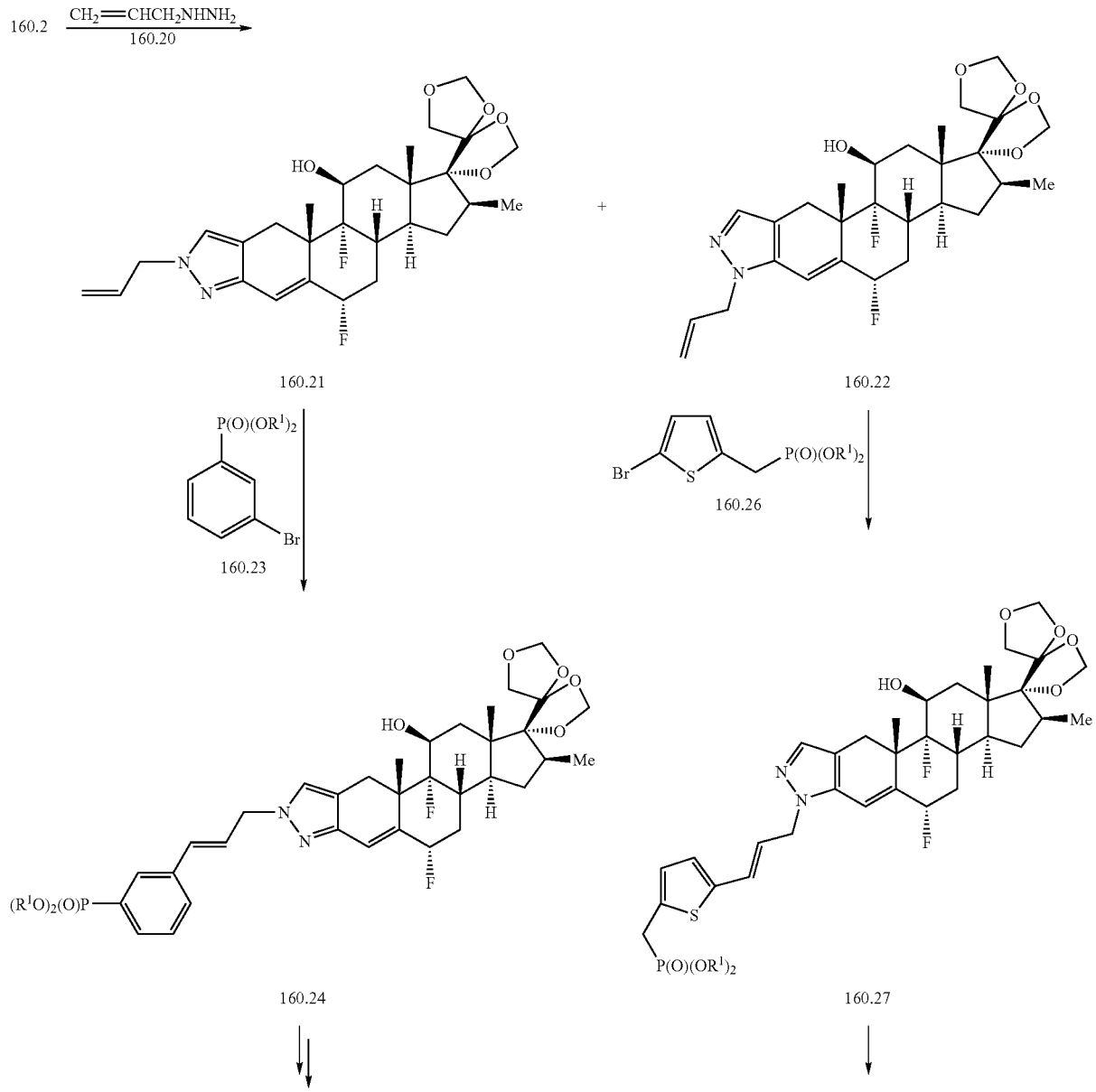

-continued

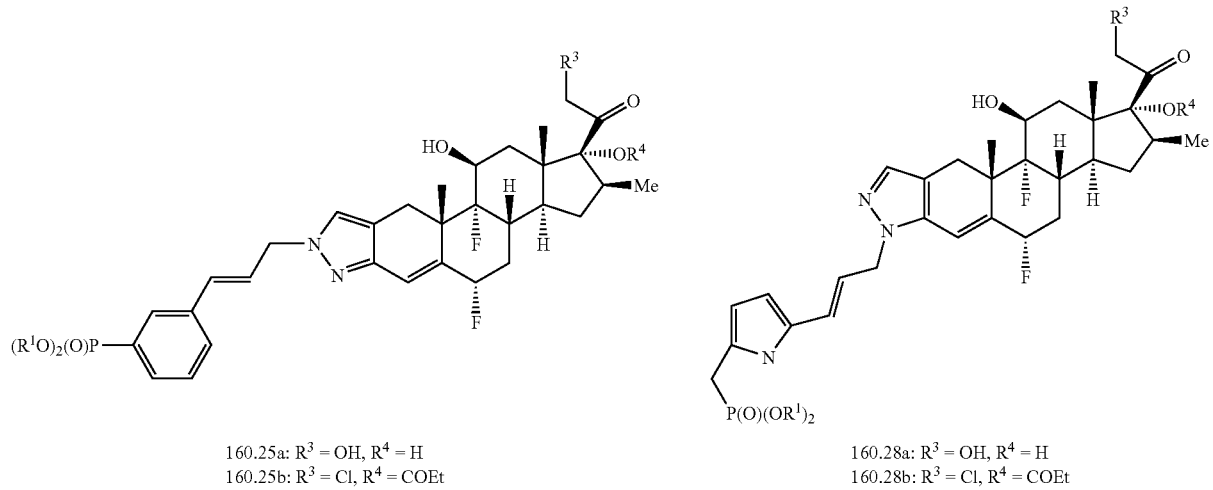

160.25a: R³ = OH, R⁴ = H
160.25b: R³ = Cl, R⁴ = COEt 160.28a: R³ = OH, R⁴ = H
160.28b: R³ = Cl, R⁴ = COEt

The preparation of the phosphonates in which the phosphonate group is attached by means of an aryl ring and a propenyl linkage is illustrated above. In this procedure, the ketoaldehyde 160.2 is reacted, as described above, with allyl hydrazine 160.20 (*Zh. Org. Khim.*, 3:983 (1967)) to produce the pyrazoles 160.21 and 160.22. The 1'-substituted isomer 160.21 is coupled with a dialkyl 3-bromophenyl phosphonate 160.23 (Epsilon) to give the phosphonate 160.24. The product is then deprotected to afford the triol 160.25a which is converted into the 21-chloro 17-propionate compound 160.25b.

Alternatively, the 2'-substituted pyrazole 160.22 is coupled, as described above, with a dialkyl 5-bromo-2-thienyl phosphonate 160.26 (*Syn.*, 455 (2003)) to prepare the phosphonate 160.27 which is deprotected, and the product is converted into the 21-chloro 17-propionate analog 160.28b.

Using the above procedures, but employing, in place of the propenyl hydrazine 160.20, different alkenyl hydrazines, and/or different dialkyl bromo-substituted phosphonates, the products analogous to the compounds 160.25b and 160.28b are obtained.

EXAMPLE 161

Preparation of Representative Halobetasol Derivatives

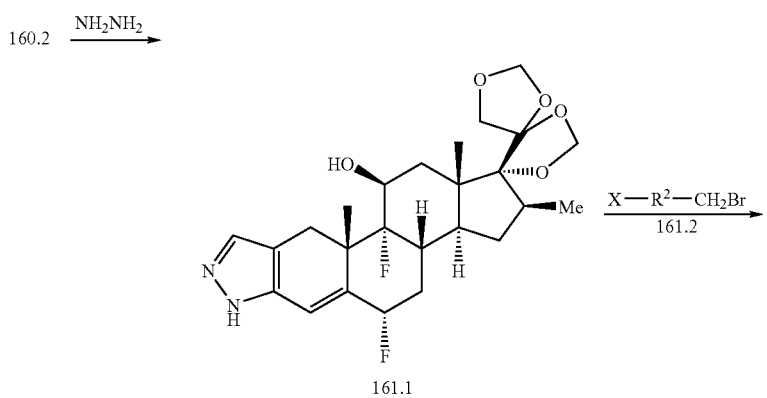

-continued

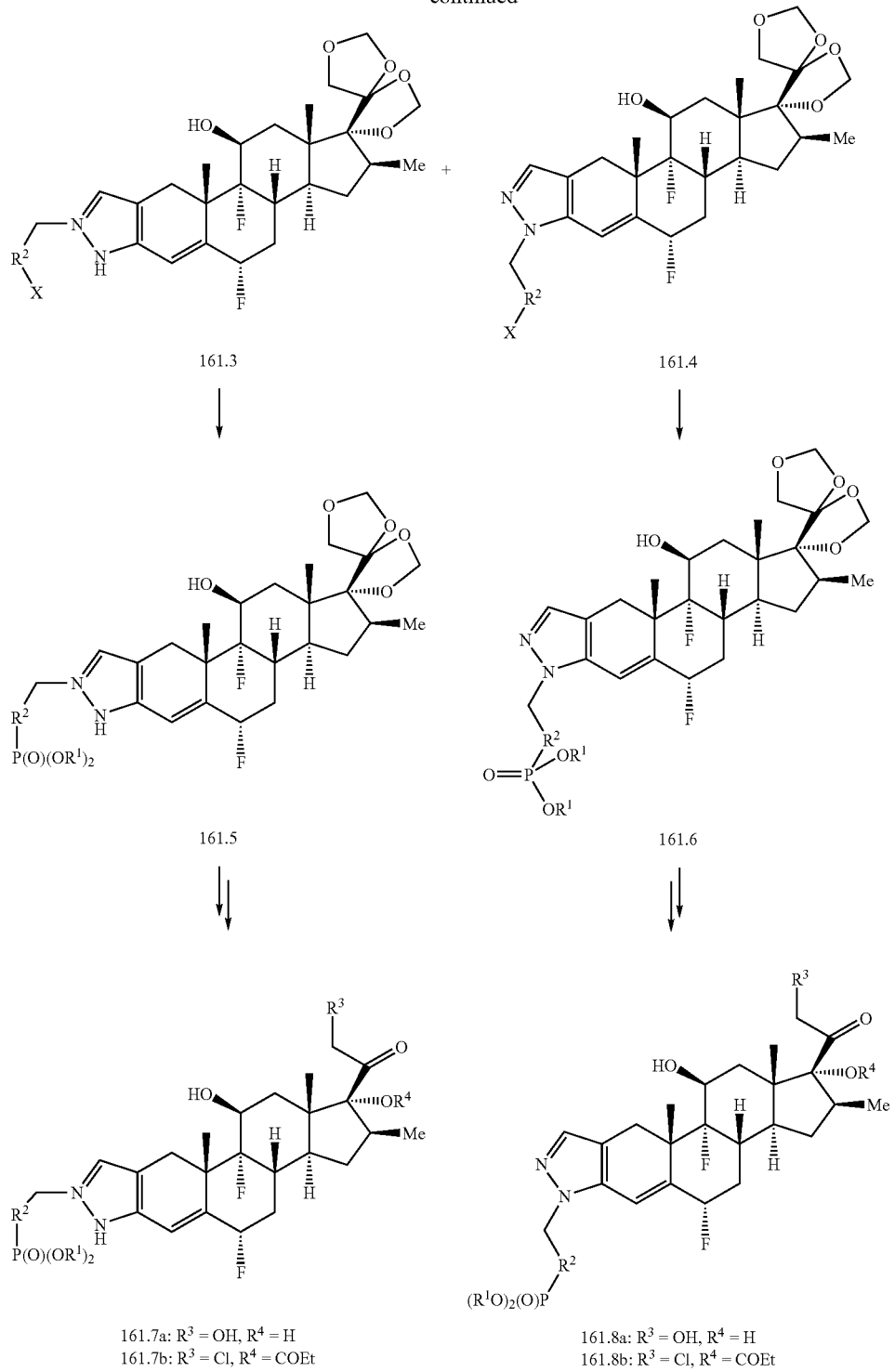

161.7a: R³ = OH, R⁴ = H
161.7b: R³ = Cl, R⁴ = COEt 161.8a: R³ = OH, R⁴ = H
161.8b: R³ = Cl, R⁴ = COEt

The preparation of the phosphonate esters in which the phosphonate group is attached by means of a variable carbon linkage is illustrated above. In this procedure, the ketoaldehyde 160.2 is reacted with hydrazine, to afford the pyrazole derivative 161.1. The reaction of steroidal 2-formyl-3-ketones with hydrazine is described in *J. Am. Chem. Soc,* 86:1520 (1964). The reaction is performed in acetic acid at ambient temperature. The pyrazole product is then reacted with a bromomethyl compound 161.2, in which $R^2$ and X are as defined above, to yield the alkylation products 161.3 and 161.4. The alkylation of substituted pyrazoles is described, for example, in T. L. Gilchrist, Heterocyclic Chemistry, 309 (Longman, 1992). The reaction is performed between equimolar amounts of the substrates in a polar solvent such as dimethylformamide or tetrahydrofuran, in the presence of a base such as dimethylaminopyridine, lithium hexamethyldisilazide and the like. The products 161.3 and 161.4 are, except in cases where X is dialkylphosphono, converted into the phosphonates 161.5 and 161.6, using the procedures described herein, and deprotection/chlorination/acylation then affords the 21-chloro 17-propionate compounds 161.7b and 161.8b.

Representative compounds of the invention can be prepared as illustrated above. The pyrazole 161.1 is reacted with 2-bromobenzyl bromide 161.9 to give the pyrazoles 161.10 and 161.11. The products are then coupled, as described above, with a dialkyl phosphite, to afford after side-chain deprotection and modification, as described above, the 21-chloro 17 propionates 161.12b and 161.13b.

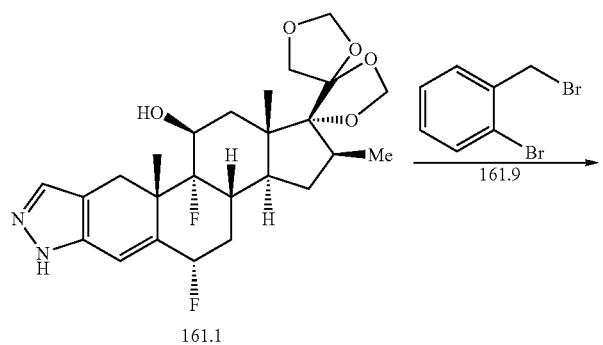

161.1

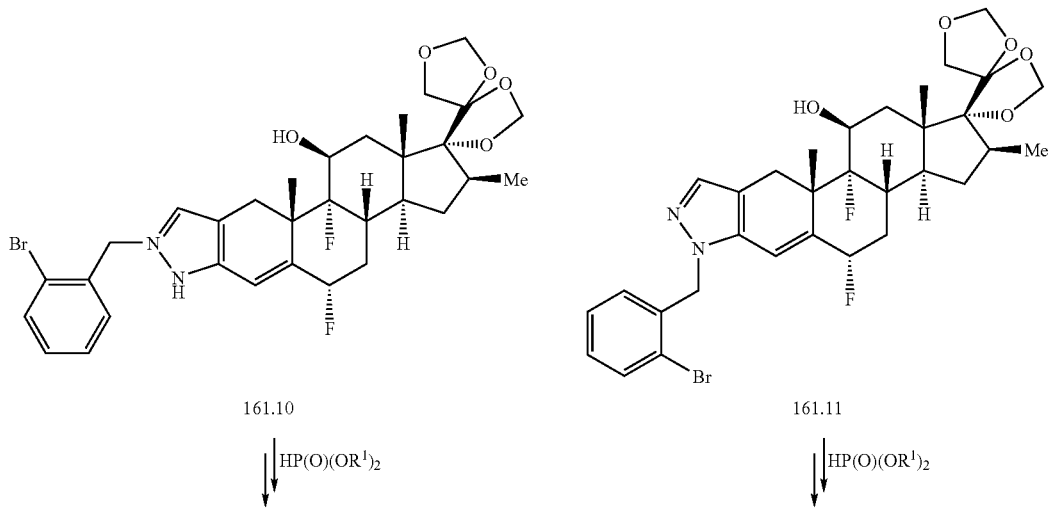

161.10

161.11

HP(O)(OR¹)₂

HP(O)(OR¹)₂

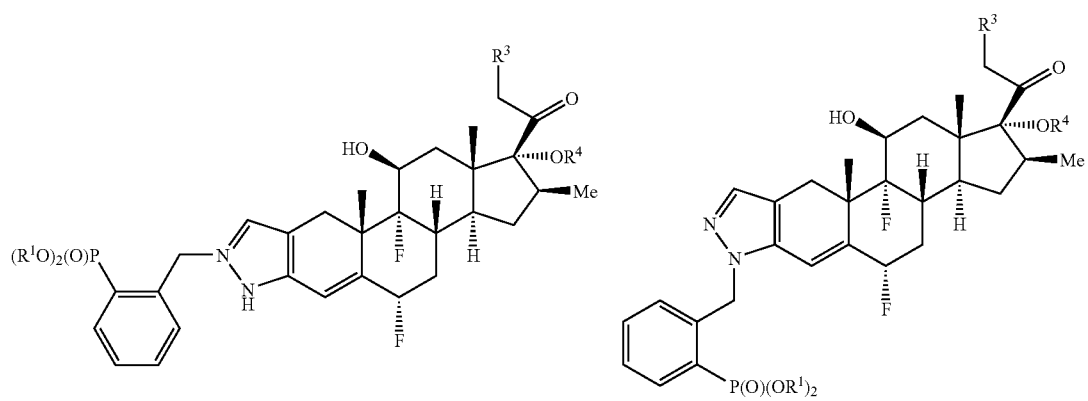

161.12a: R³ = OH, R⁴ = H
161.12b: R³ = Cl, R⁴ = COEt 161.13a: R³ = OH, R⁴ = H
161.13b: R³ = Cl, R⁴ = COEt

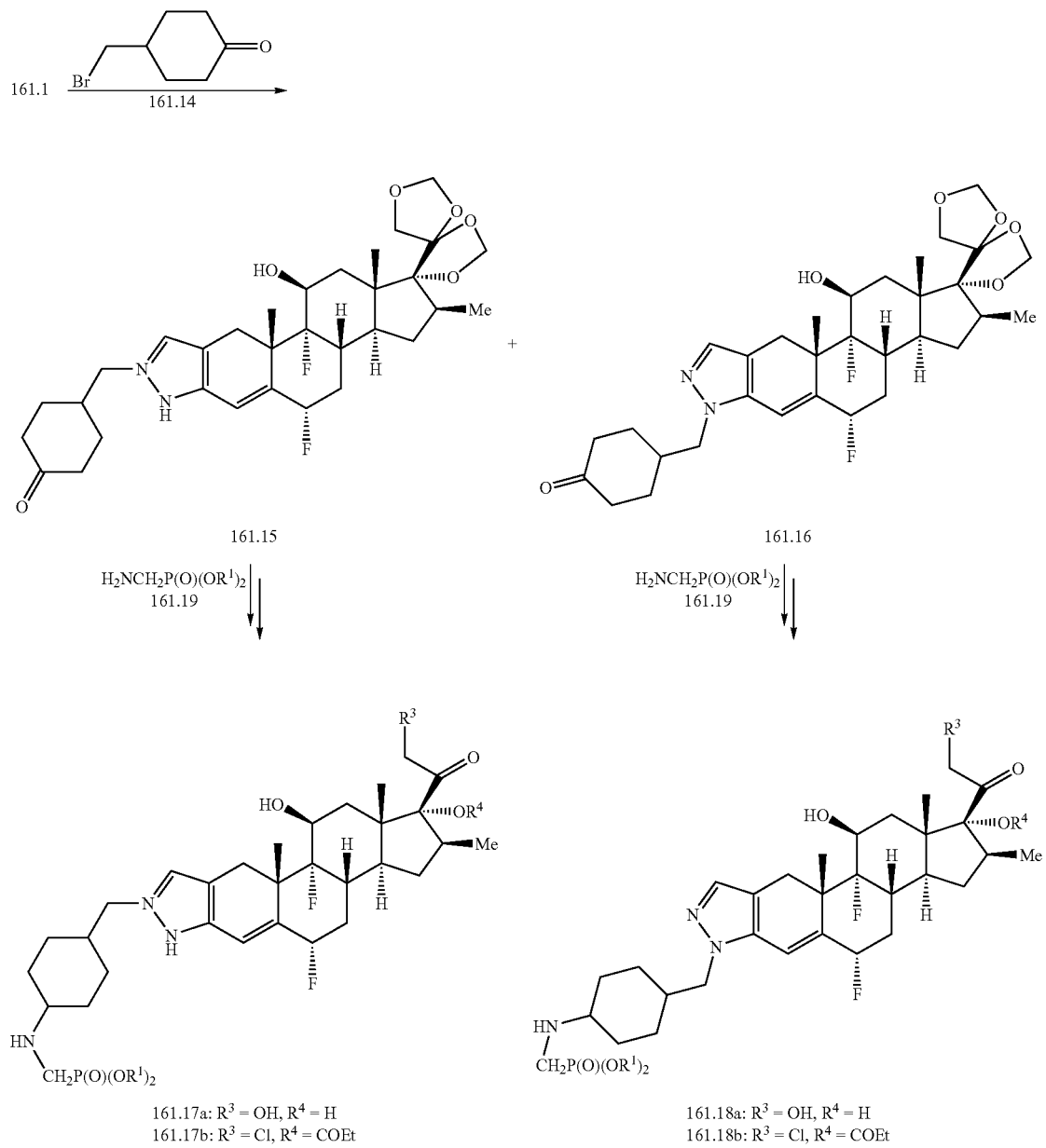

Representative compounds of the invention can be prepared as illustrated above. The pyrazole 161.1 is reacted in tetrahydrofuran solution, as described above, with 4-bromomethyl cyclohexanone 161.14 (WO 9737959) to give the alkylation products 161.15 and 161.16. The 1'-substituted isomer 161.15 is then reacted, in a reductive amination reaction, with a dialkyl aminomethyl phosphonate (Interchim) and sodium cyanoborohydride, to yield, after deprotection and side-chain modification, the 21-chloro 17-propionate 161.17b.

The preparation of amines by means of reductive amination procedures is described, for example, in R. C. Larock, Comprehensive Organic Transformations, 421 (VCH, 1989), and in F. A. Carey and R. J. Sundberg, Advanced Organic Chemistry, Part B, 269 (Plenum, 2001). In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in *J. Org. Chem.*, 55:2552 (1990).

The 2'-substituted pyrazole 161.16 is subjected to the same series of reaction to give the amine phosphonate 161.18b.

Using the above procedures, but employing different bromomethyl-substituted aldehydes or ketones, and/or different amino-substituted phosphonates, the products analogous to 161.17b and 161.18b are obtained.

EXAMPLE 162

Synthesis of Representative Compounds of Formulae 164

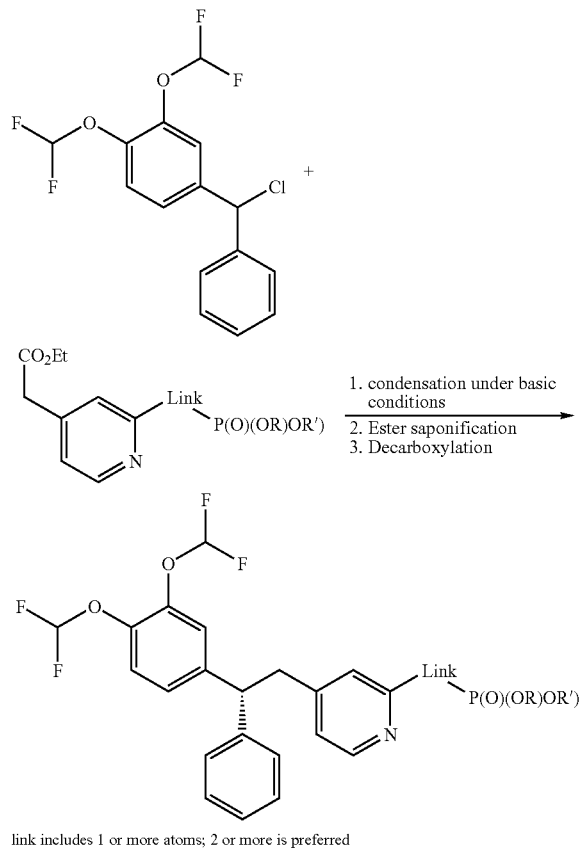

link includes 1 or more atoms; 2 or more is preferred

Compounds of the invention can generally be prepared as illustrated above. The chloride is made from (3,4-bis-difluoromethoxy-phenyl)-phenyl-methanone (cf U.S. Pat. No. 5,622,977) by reduction with sodium borohydride in ethanol and treatment of the resulting alcohol with triphenylphosphine, carbon tetrachloride and diisopropyl azodicarboxylate in a solvent such as tetrahydrofuran. The condensation is achieved by treatment of the two reagents with sodium ethoxide in ethanol. The ethyl ester in the product is saponified by treatment with lithium hydroxide in ethanol, and the resulting acid is decarboxylated by heating under acidic conditions. The two enantiomers of the product may be separated by chromatography.

For example, a specific pyridine reagent can be prepared as follows.

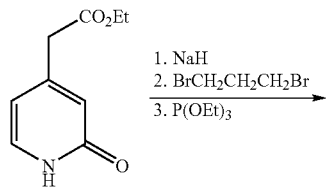

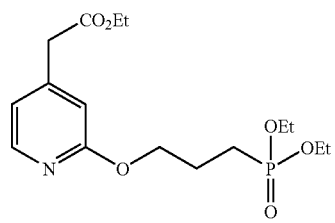

(2-Oxo-1,2-dihydro-pyridin-4-yl)-acetic acid ethyl ester is treated with a base such as sodium hydride in a solvent such as tetrahydrofuran. After bubbling ceases, an excess of 1,3-dibromopropane is added. After quenching the reaction with aqueous ammonium chloride and extracting the product with an organic solvent such as ethyl acetate, the mono-bromide is isolated by chromatography. The bromide is then heated with triethylphosphite in a solvent such as toluene to generate the diethyl ester of the desired phosphonic acid.

EXAMPLES 163-166

Ciclesonide Derivatives

The synthesis of representative phosphonate derivatives of ciclesonide is outlined in Examples 166-169. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 163

Preparation of Representative Ciclesonide Derivatives

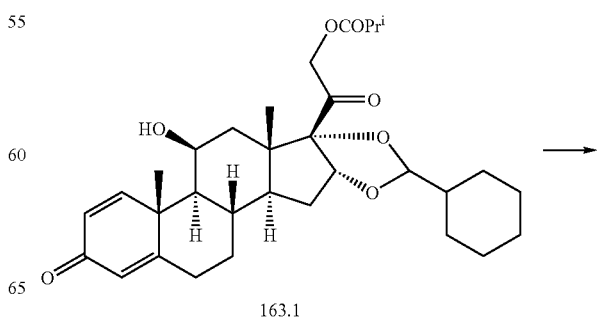

163.1

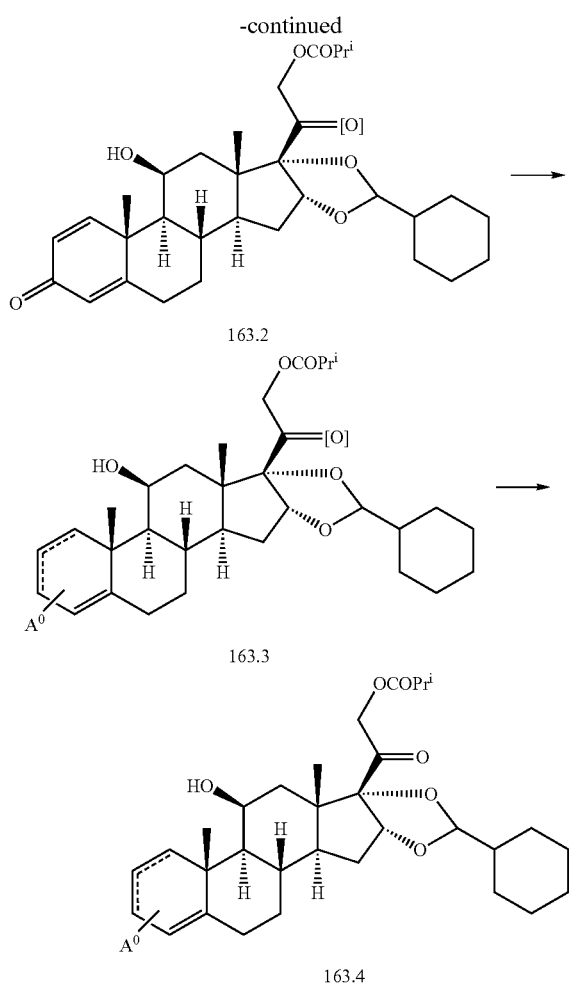

163.2

163.3

163.4

EXAMPLE 164

Preparation of Representative Ciclesonide Derivatives

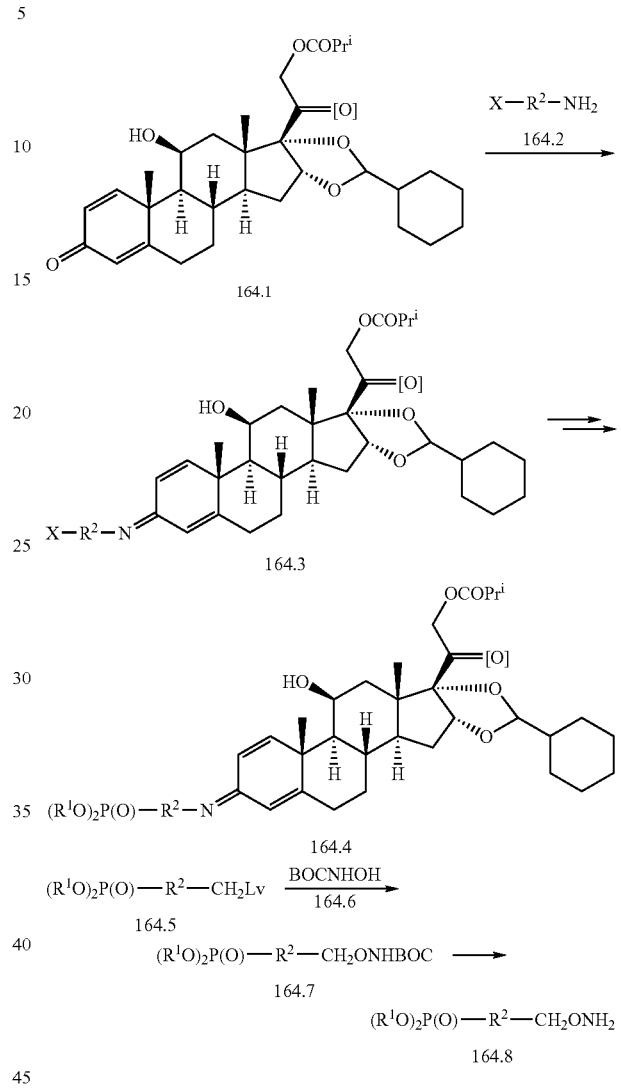

164.1

164.3

164.4

$(R^1O)_2P(O)-R^2-CH_2Lv \xrightarrow[164.6]{BOCNHOH}$ 164.5

$(R^1O)_2P(O)-R^2-CH_2ONHBOC \longrightarrow$ 164.7

$(R^1O)_2P(O)-R^2-CH_2ONH_2$ 164.8

Representative compounds of the invention can be pepared as follows. Ciclesonide 163.1 (U.S. Pat. No. 5,482,934) is protected to afford the derivative 163.2. The ketone is protected, for example, by conversion to the cyclic ethylene ketal, by reaction in toluene solution at reflux temperature with ethylene glycol and an acid catalyst, as described in *J. Am. Chem. Soc.*, 77:1904 (1955). Deprotection is effected by reaction with pyridinium tosylate in aqueous acetone, as described in *J. Chem. Soc. Chem. Comm.* 1351 (1987).

Alternatively, the 20-ketone is protected by conversion to the N,N-dimethylhydrazone. The dimethyl hydrazone is prepared by the reaction of the ketone 163.1 with N,N-dimethylhydrazine in ethanol-acetic acid, as described in *Org. Syn.* 50:102 (1970). The group is removed by treatment with sodium acetate and acetic acid in aqueous tetrahydrofuran, as described in *J. Am. Chem. Soc.* 101:5841 (1979).

Alternatively, the 20-ketone is protected as the diethylamine adduct. In this procedure, the substrate 163.1 is reacted with titanium tetrakis(diethylamide), as described in *J. Chem. Soc. Chem. Comm.* 406 (1983), to afford the adduct. The ketone is deprotected by reaction with water in an aqueous organic solvent.

The protected compound 163.2 is then converted into the phosphonate-containing analog 163.3, using the procedures described below, and the protecting group is then removed, as described above, to give the phosphonate 163.4.

The preparation of phosphonates in which the phosphonate is attached by means of an imino or iminoxy group and a variable carbon chain is illustrated above. In this procedure, the protected derivative 164;1 is reacted with an amine or hydroxylamine 164.2, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime 164.3. The preparation of oximes of steroidal 3-ketones is described in *Anal. Bioch.* 86:133 (1978) and in *J. Mass. Spectrom.* 30:497 (1995). The protecting group is then removed to afford the 20-keto phosphonate product 164.4.

The preparation of hydroxylamine ethers incorporating a phosphonate group is also illustrated above. In this procedure, a phosphonate 164.5, in which Lv is a leaving group such as bromo or trifluoromethylsulfonyloxy, is reacted with BOC-hydroxylamine 164.6 (Aldrich) to produce the ether 164.7. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 164.8. The above procedure is also employed for the preparation of substituted hydroxylamines which are precursors to phosphonates.

In this procedure, the substrate 164.1, in which the 20-ketone is protected as the dimethyl hydrazone derivative, is reacted with a dialkyl phosphonomethyl hydroxylamine 164.8, prepared as described above from a dialkyl trifluoromethylsulfonyloxymethyl phosphonate (*Tetrahedron Lett.* 27:1477 (1986)) and BOC-hydroxylamine, to afford the oxime 164.10. Deprotection affords the 20-keto phosphonate 164.11. The oxime forming reaction is performed at ambient temperature in ethanol-acetic acid solution between equimolar amounts of the reactants.

Using the above procedures, but employing, in place of the hydroxylamine ether 164.8, different oxime ethers 164.2, the corresponding products 164.4 are obtained.

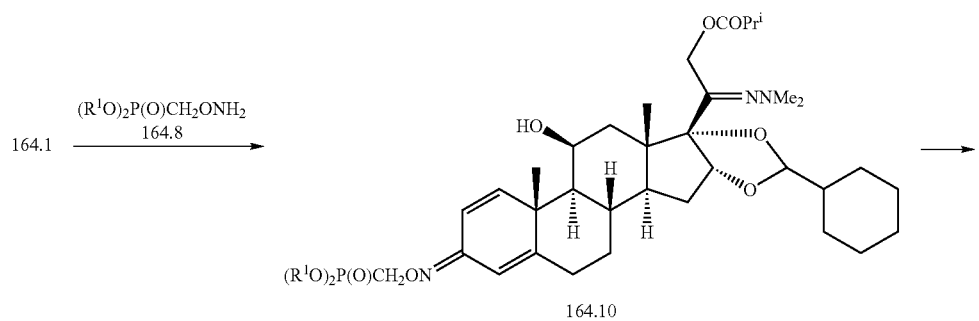

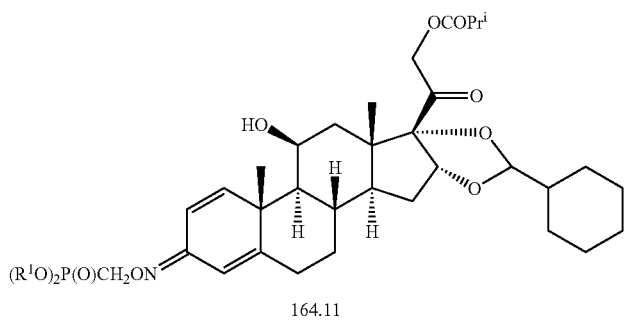

The preparation of phosphonates in which the phosphonate is attached by means of an iminoxy group is illustrated above.

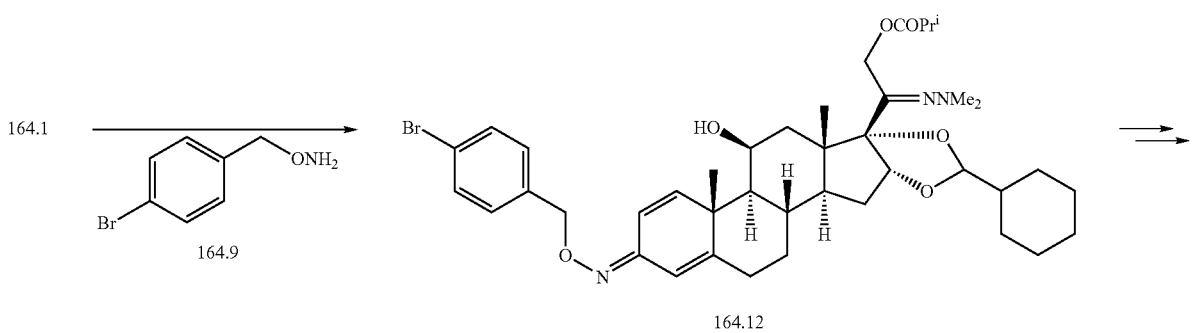

-continued

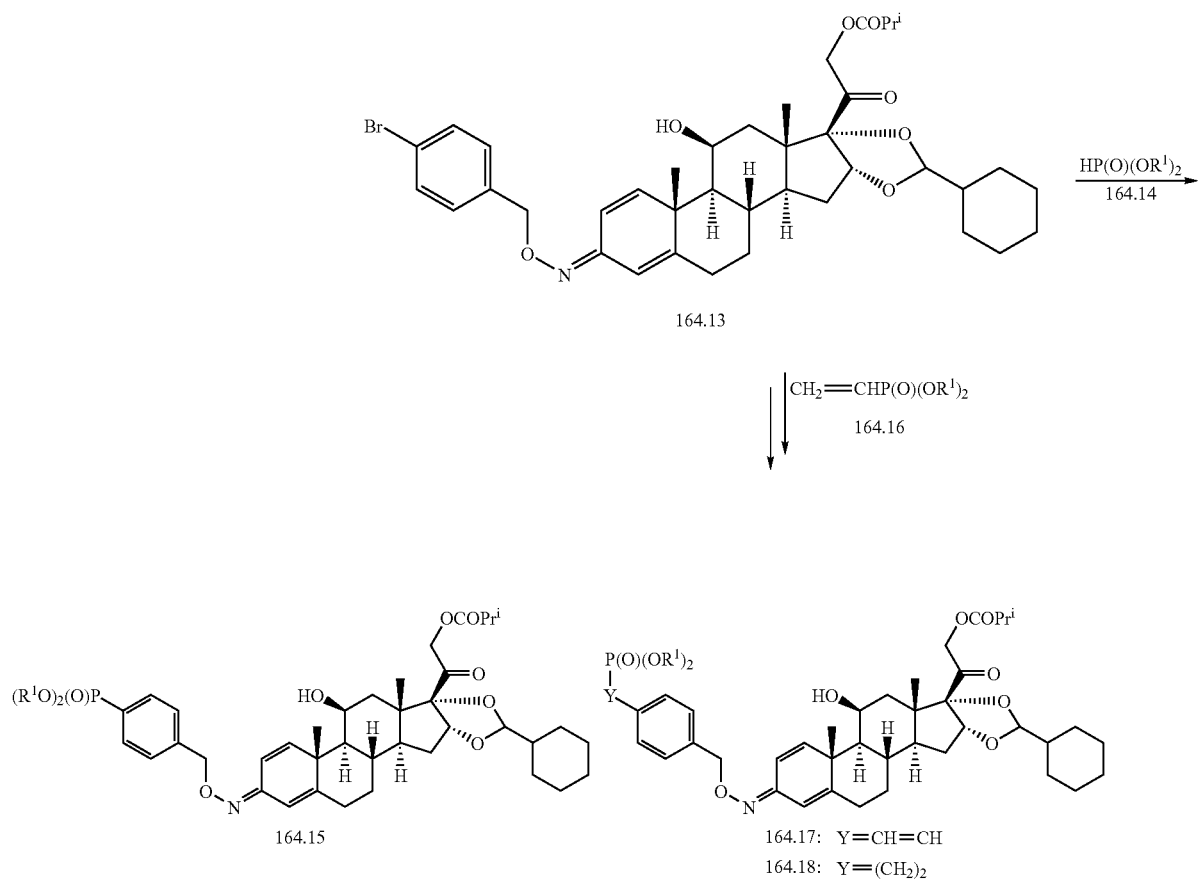

The preparation of compounds in which the phosphonate group is attached by means of a benzyloxy oxime group is illustrated above. In this procedure, the dienone 164.1, in which the 20-ketone is protected as the dimethyl hydrazone, is reacted, as described above, with O-(4-bromobenzyloxy) hydroxylamine 164.9, prepared as described above from 4-bromobenzyl bromide and BOC-protected hydroxylamine 164.6, to give the oxime 164.12. The protecting group is then removed to yield the 20-keto product 164.13. The latter product is then reacted, in the presence of a palladium catalyst, with a dialkyl phosphite 164.14 to afford the phosphonate 164.15. The preparation of arylphosphonates by means of a coupling reaction between aryl bromides and dialkyl phosphites is described in *J. Med. Chem.* 35:1371 (1992). The reaction is performed at ca. 100° C. in an inert solvent such as toluene, in the presence of a base such as triethylamine and a catalytic amount of tetrakis(triphenylphosphine)palladium (0).

Alternatively, the bromo compound 164.13 is coupled with a dialkyl vinyl phosphonate 164.16 (Aldrich) to afford the phosphonate 164.17. The coupling of aryl halides with olefins by means of the Heck reaction is described, for example, in F. A. Carey and R. J. Sundberg, *Advanced Organic Chemistry* 503ff (Plenum, 2001) and in *Acc. Chem. Res.* 12:146 (1979). The aryl bromide and the olefin are coupled in a polar solvent such as dimethylformamide or dioxan, in the presence of a palladium(0) catalyst such as tetrakis(triphenyl-phosphine) palladium(0) or palladium(II) catalyst such as palladium(II) acetate, and optionally in the presence of a base such as triethylamine or potassium carbonate. Optionally, the styrenoid double bond present in the product 164.17 is reduced, for example by reaction with diimide, to produce the saturated analog 164.18. The reduction of olefinic bonds is described in R. C. Larock, *Comprehensive Organic Transformations* 6ff (VCH 1989). The transformation is effected by means of catalytic hydrogenation, for example using a palladium on carbon catalyst and hydrogen or a hydrogen donor, or by the use of diimide or diborane.

Using the above procedures, but employing, in place of the bromobenzyloxy reagent 164.9, different bromo-substituted aryl or heteroaryl alkoxy hydroxylamines, and/or different dialkyl alkenyl phosphonates, products analogous to the compounds 164.15, 164.17 and 164.18 are obtained.

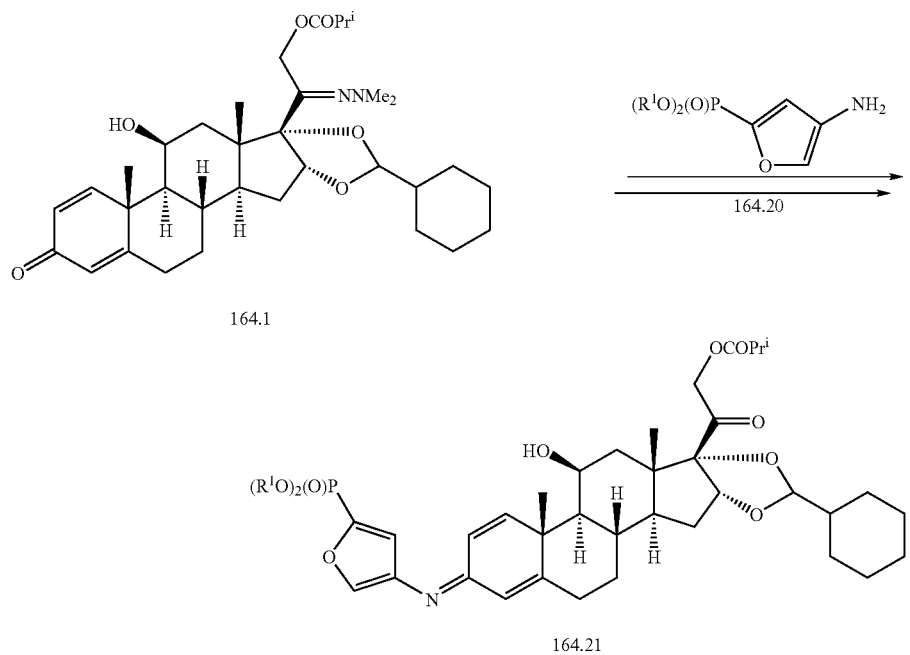

164.1

164.21

The preparation of phosphonates in which the phosphonate is attached by means of a 3-furylimino group is illustrated above. In this procedure, the substrate 164.1, in which the 20-ketone is protected as the dimethylhydrazone, is reacted with a dialkyl 4-amino-2-furyl phosphonate 164.20, prepared by the palladium catalyzed coupling reaction, as described above, between 4-amino-2-bromofuran (*Tetrahedron Lett.* 43:3295 (1987)) and a dialkyl phosphite, to give, after deprotection, the imine product 164.21. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions.

Using the above procedures, but employing, in place of the 4-amino-2-furyl phosphonate 164.20 different amino-substituted aryl or heteroaryl phosphonates, products analogous to 164.21 are obtained.

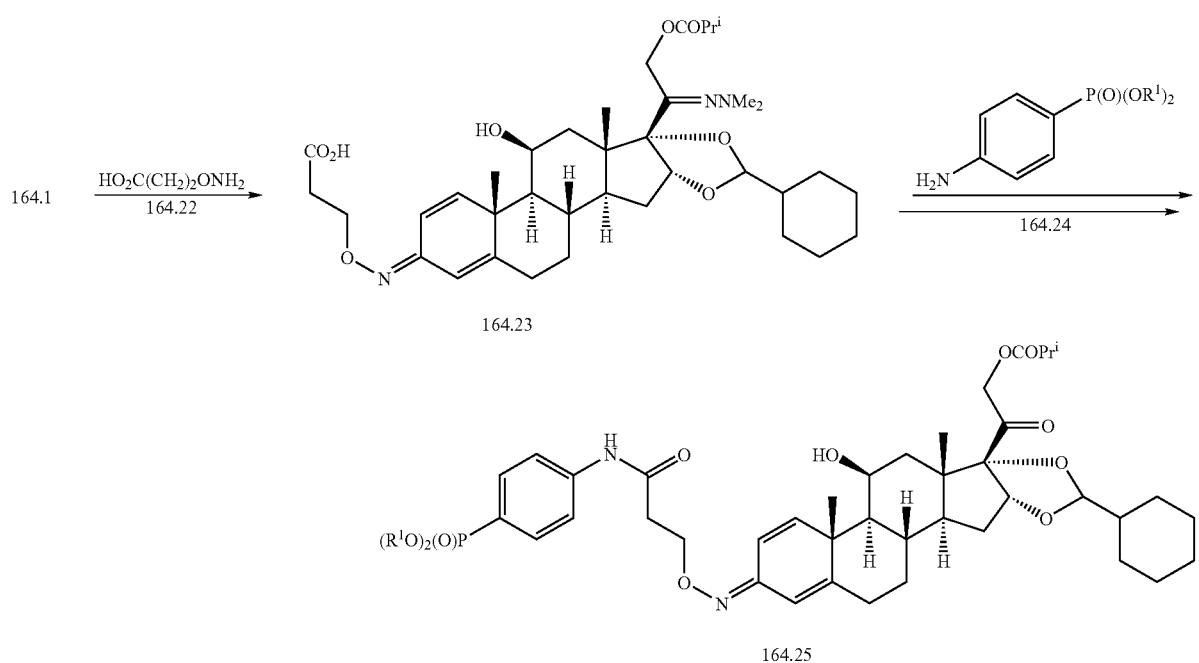

The preparation of phosphonates in which the phosphonate is attached by means of an oximino group and an amide linkage is illustrated above. In this procedure, the dienone 164.1, in which the 20-ketone is protected as the dimethylhydrazone, is reacted with O-(2-carboxyethyl)hydroxylamine 164.22 (*J. Med. Chem.* 33:1423 (1990)) to yield the oxime 164.23. The reaction of steroidal 1,4-dien-3-ones with substituted hydroxylamines is described in *J. Steroid Bioch.* 7:795 (1976); the reaction is performed between equimolar amounts of the reactants in a polar organic solvent such as pyridine or methanol, optionally in the presence of acetic acid or sodium acetate. The product 164.23 is then coupled with a dialkyl 4-aminophenyl phosphonate 164.24 (Epsilon) and dicyclohexylcarbodiimide, to yield, after deprotection the amide oxime 164.25. The preparation of amides from carboxylic acids and derivatives is described, for example, in S. R. Sandler and W. Karo, Organic Functional Group Preparations 274 (Academic Press, 1968) and R. C. Larock, *Comprehensive Organic Transformations* 972ff (VCH, 1989). The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide.

Using the above procedures, but employing, in place of the carboxy-substituted hydroxylamine 164.22, different carboxy-substituted hydroxylamines, and/or different amino-substituted phosphonates, products analogous to 164.25 are obtained.

EXAMPLE 165

Preparation of Representative Ciclesonide Derivatives

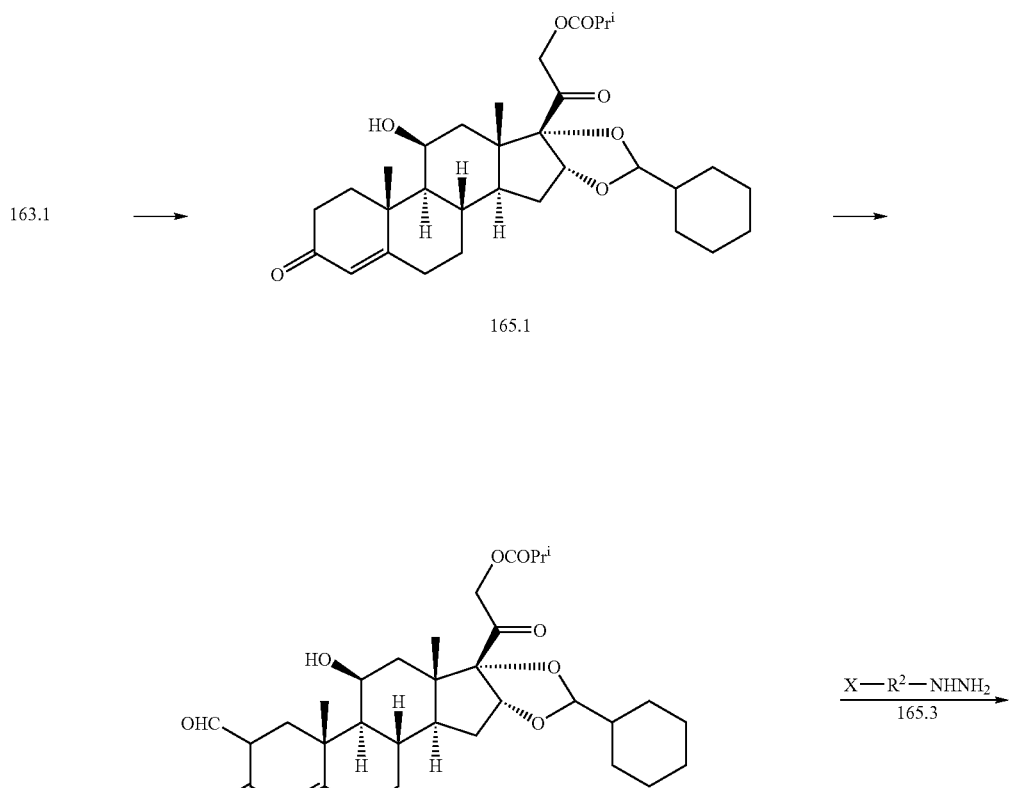

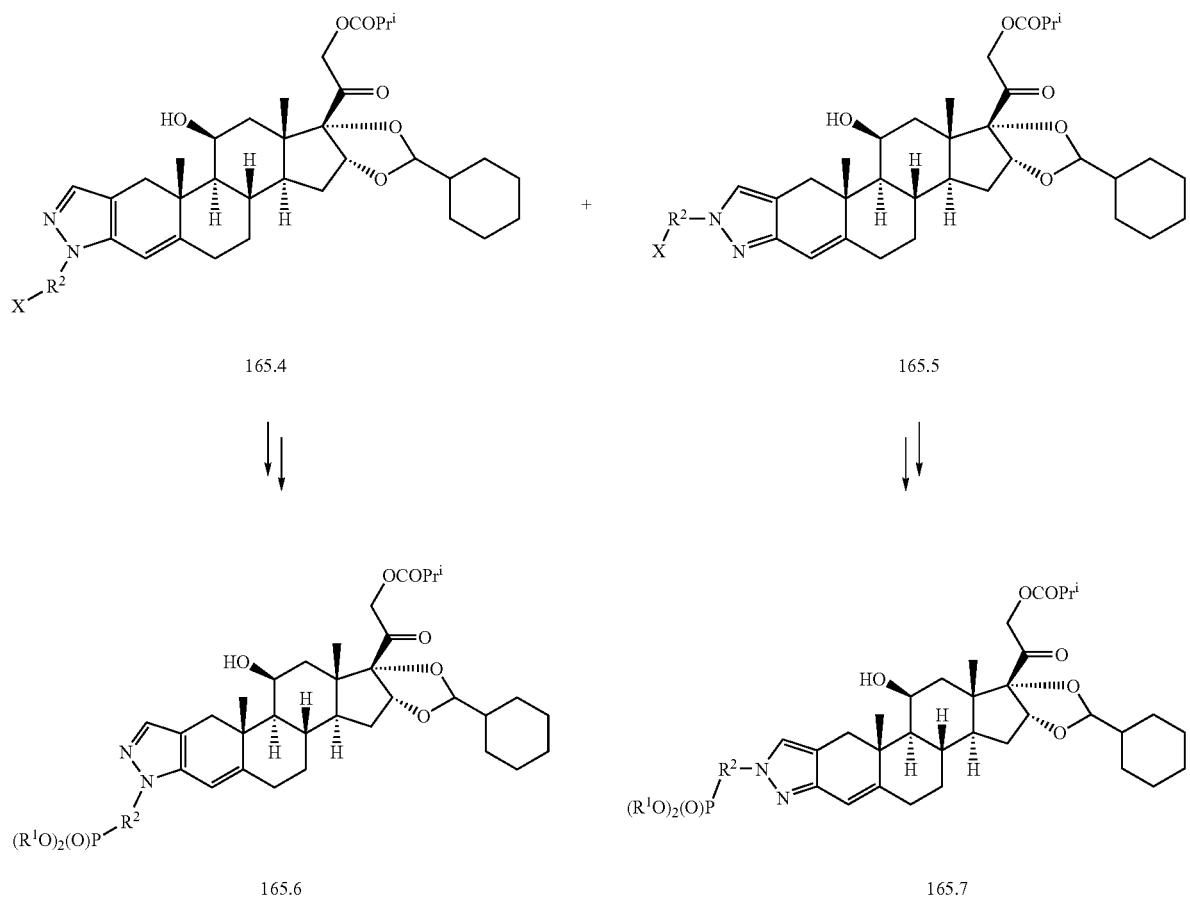

165.4        165.5

165.6        165.7

The preparation of the phosphonate esters in which the phosphonate group is attached to the 1' or 2' position of the pyrazole ring, by means of an aromatic or heteroaromatic group, a heteroatom and/or a variable carbon chain is illustrated above. In this procedure, the dienone 163.1 is reduced to afford the 1,2-dihydro product 165.1. The catalytic hydrogenation reaction is effected by the use of tris(triphenylphosphine)rhodium(I) chloride, for example as described in *J. Med. Chem.* 44:602 (2001). The product is then reacted with ethyl formate and a base such as sodium hydride, in an inert solvent such as toluene or dimethylformamide, as described in *J. Am. Chem. Soc.* 86:1520 (1964), to afford the 2-formyl product 165.2. This compound is then reacted with an alkyl, aralkyl, aryl or heteroaryl hydrazine 165.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 165.4 and 165.5. The pyrazole-forming reaction is performed between equimolar amounts of the reactants in an acidic solvent such as acetic acid, as described in *J. Am. Chem. Soc.* 86:1520 (1964). The pyrazoles 165.4 and 165.5 are then transformed into the phosphonates 165.6 and 165.7.

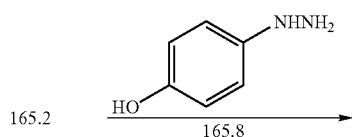

165.2        165.8

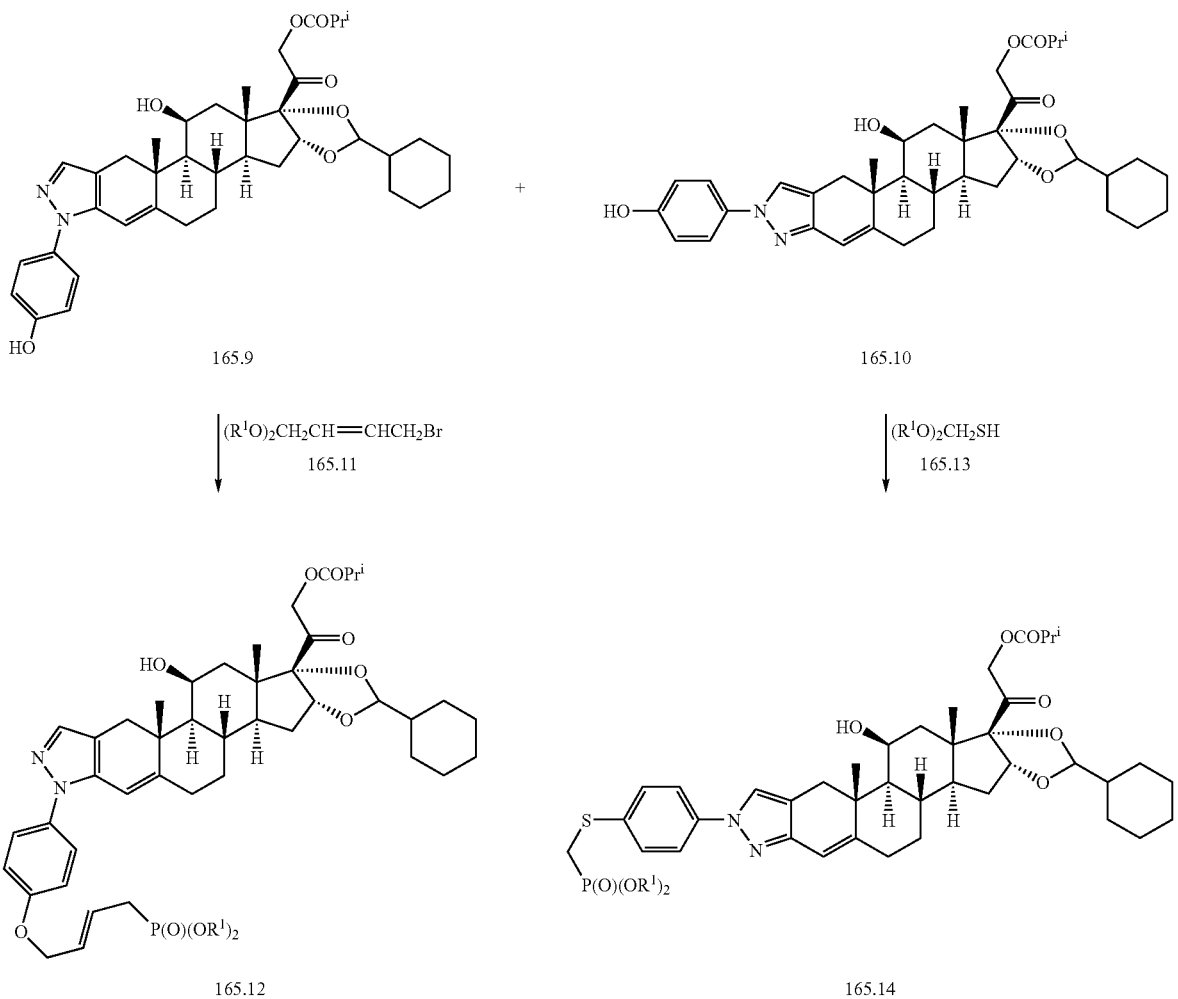

The preparation of phosphonates in which the phosphonate is attached by means of an alkoxy or alkylthio linkage is illustrated above. In this procedure, the ketoaldehyde 165.2 is reacted, as described above, with 4-hydroxyphenyl hydrazine 165.8 (EP 437105) to give the pyrazoles 165.9 and 165.10. The 2'-substituted isomer 165.9 is then reacted in dimethylformamide solution at ca. 70° C. with a dialkyl bromobutenyl phosphonate 165.11 (J. Med. Chem. 35:1371 (1992)) and potassium carbonate, to yield the ether phosphonate 165.12.

The isomeric pyrazole 165.10 is reacted, in a Mitsonobu reaction, with a dialkyl mercaptomethyl phosphonate 165.13 (J. Med. Chem. 26:1688 (1985)) to yield the thioether phosphonate 165.14. The preparation of aromatic ethers and thioethers by means of the Mitsonobu reaction is described, for example, in R. C. Larock, *Comprehensive Organic Transformations* 448 (VCH, 1989), in F. A. Carey and R. J. Sundberg, *Advanced Organic Chemistry, Part B* 153-4 (Plenum, 2001), and in *Org. React.* 42:335 (1992). The phenol and the alcohol or thiol component are reacted together in an aprotic solvent such as, for example, tetrahydrofuran, in the presence of a dialkyl azodicarboxylate and a triarylphosphine, to afford the ether or thioether products. The procedure is also described in *Org. React.* 42:335-656 (1992).

Using the above procedures, but employing different hydroxy-substituted hydrazines, and/or different bromo- or mercapto-substituted phosphonates, products analogous to 165.12 and 165.14 are obtained.

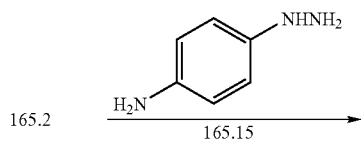

-continued

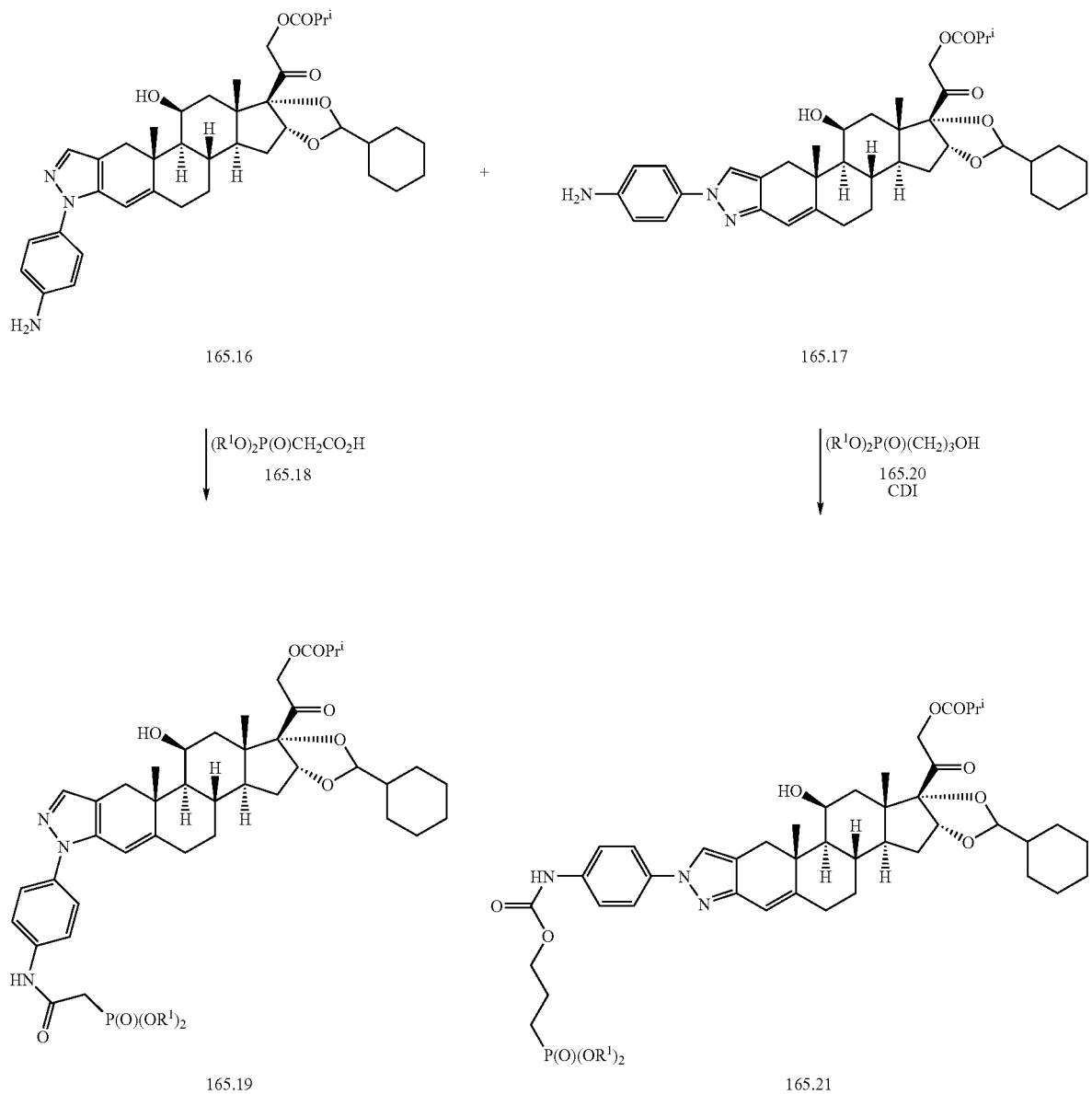

The preparation of the phosphonates in which the phosphonate group is attached by means of a phenyl group and an amide or carbamate linkage is illustrated above. In this procedure, the ketoaldehyde 165.2 is reacted, as described above, with 4-aminophenyl hydrazine 165.15 (Epsilon) to produce the pyrazoles 165.16 and 165.17. The 2'-substituted isomer 165.16 is coupled, as described above, with a dialkyl phosphonoacetic acid 165.18 (Aldrich) and dicyclohexyl carbodiimide, to give the amide phosphonate 165.19.

Alternatively, the 1'-substituted pyrazole 165.17 is reacted with a dialkyl 3-hydroxypropyl phosphonate 165.20 (*Zh. Obschei. Khim.* 43:2364 (1973)), and carbonyl diimidazole to prepare the carbamate phosphonate 165.21. The preparation of carbamates is described in *Comprehensive Organic Functional Group Transformations* Vol. 6 416ff (A. R. Katritzky, ed., Pergamon, 1995) and in S. R. Sandler and W. Karo, *Organic Functional Group Preparations* 260ff (Academic Press, 1986). In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and the like, to afford the corresponding activated acylamine. The latter compound is then reacted with an alcohol to yield the carbamate.

Using the above procedures, but employing, in place of the 4-aminophenyl hydrazine 165.15, different amino-substituted hydrazines, and/or different dialkyl carboxy or hydroxy-substituted phosphonates, products analogous to the compounds 165.19 and 165.21 are obtained.

EXAMPLE 166
Preparation of Representative Ciclesonide Derivatives
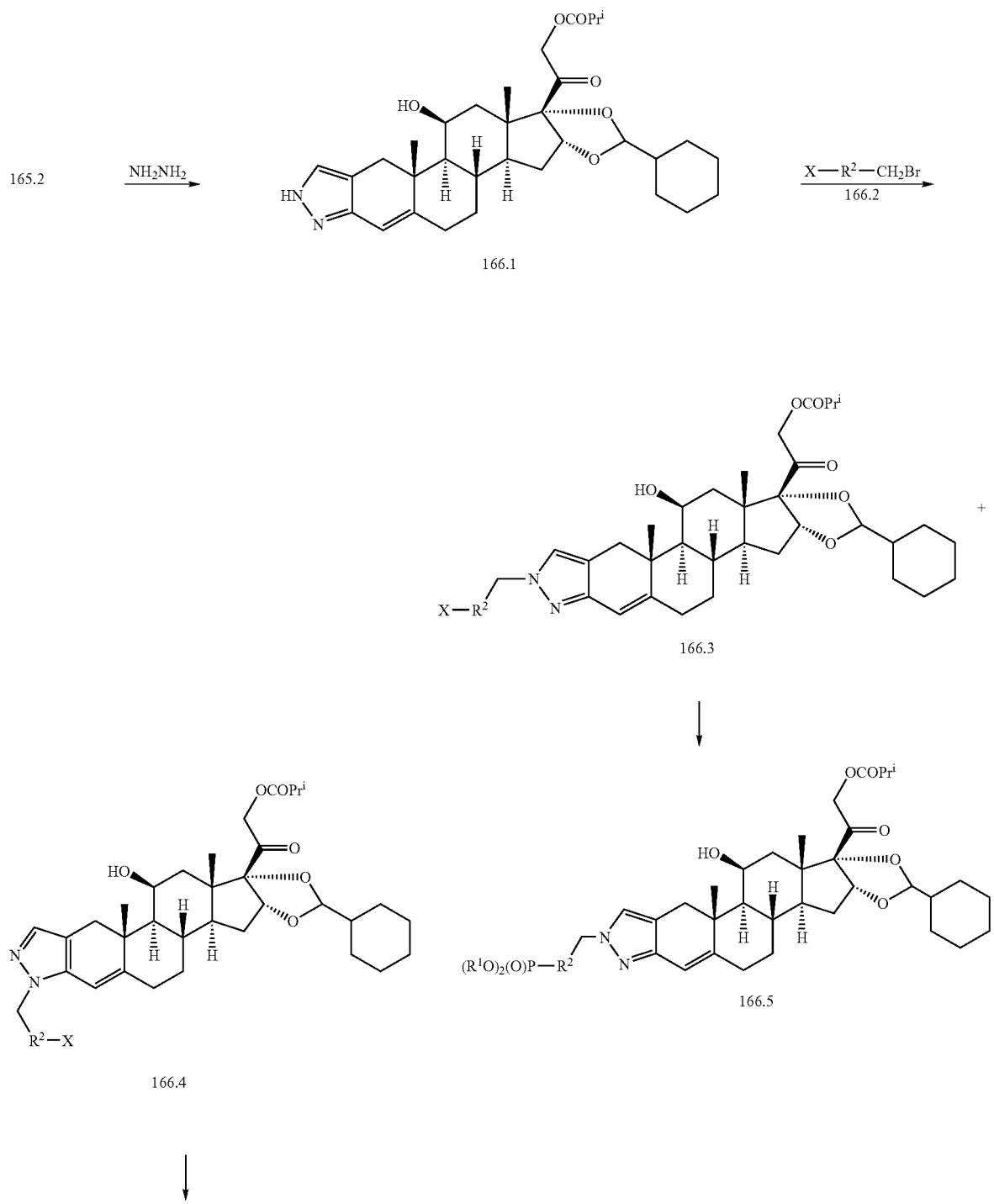

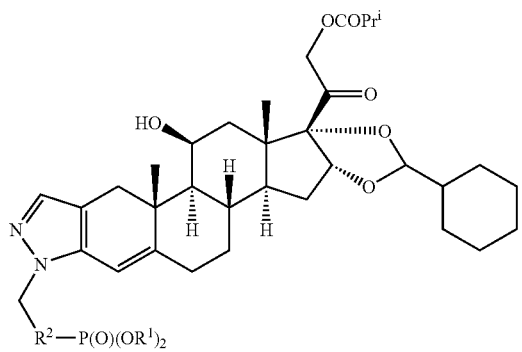

166.6

The preparation of the phosphonate esters in which the phosphonate group is attached by means of a variable carbon linkage is illustrated above. In this procedure, the ketoaldehyde 165.2 is reacted with hydrazine, to afford the pyrazole derivative 166.1. The reaction of steroidal 2-formyl-3-ketones with hydrazine is described in *J. Am. Chem. Soc.* 86:1520 (1964). The reaction is performed in acetic acid at ambient temperature. The pyrazole product is then reacted with a bromomethyl compound 166.2, in which $R^2$ and X are as defined above, or a reactive bromoheteroaromatic reagent, to yield the alkylation products 166.3 and 166.4. The alkylation of substituted pyrazoles is described, for example, in T. L. Gilchrist, *Heterocyclic Chemistry* 309 (Longman, 1992). The reaction is performed between equimolar amounts of the substrates in a polar solvent such as dimethylformamide or tetrahydrofuran, in the presence of a base such as dimethylaminopyridine, lithium hexamethyldisilazide and the like. The products 166.3 and 166.4 are, except in cases where X is dialkylphosphono, converted into the phosphonates 166.5 and 166.6, using the procedures described herein.

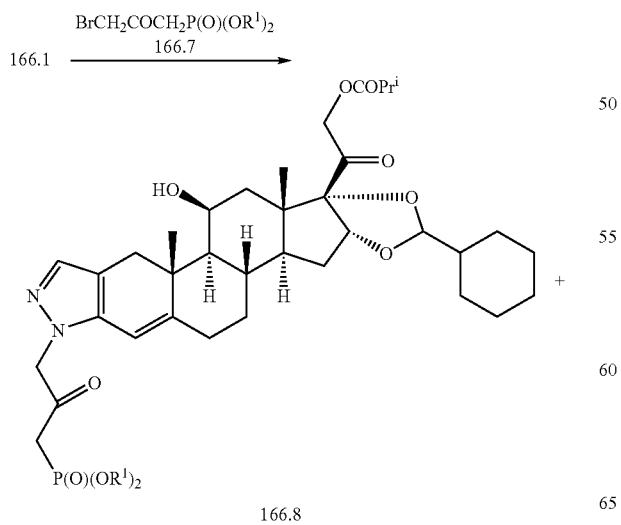

166.8

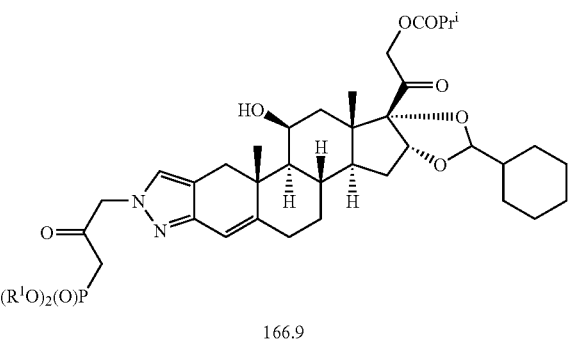

166.9

Representative compounds of the invention can be prepared as illustrated above. The pyrazole 166.1 is reacted, as described above, with a dialkyl acetonyl phosphonate 166.7 (*Tetrehedron Lett.* 34:649 (1978)) to give the pyrazoles 166.8 and 166.9.

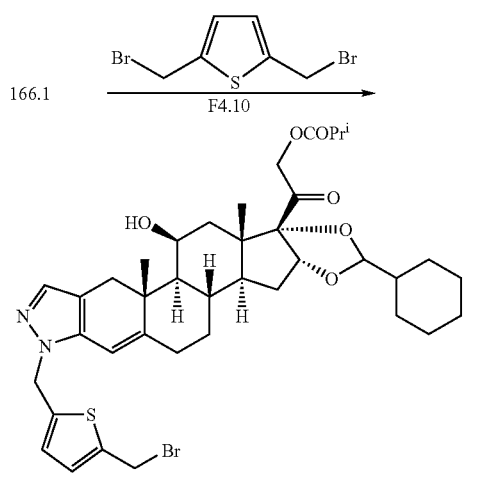

166.1

166.11

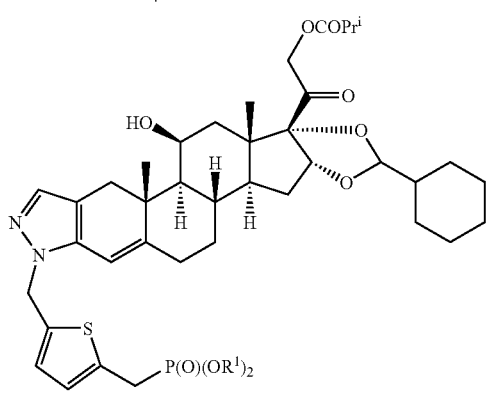

166.13

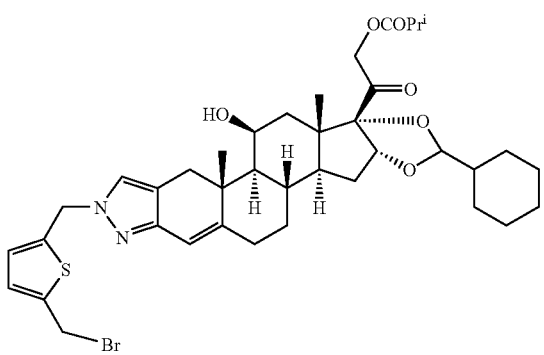

166.12

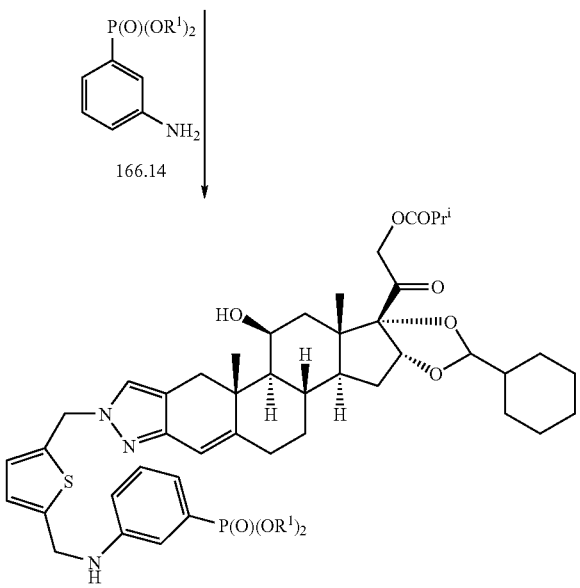

166.15

Representative compounds of the invention can be prepared as illustrated above. The pyrazole 166.1 is reacted in tetrahydrofuran solution, with 2,5-bis(bromomethyl) thiophene 166.10 (*Tetrahedron Lett.* 55:4709 (1999)) and potassium hexamethyl disilazide, to give the alkylation products 166.11 and 166.12. The 2'-substituted isomer 166.11 is then reacted, in a Arbuzov reaction, with a trialkyl phosphite to yield the phosphonate 166.13. The Arbuzov reaction is described in *Handb. Organophosphorus Chem.* 115 (1992). In this procedure, in which a bromo substituent is converted into the corresponding phosphonate, the substrate is heated at from about 60° C. to about 160° C. with a five to fifty-fold molar excess of a trialkyl phosphite, to effect the transformation.

The 2'-substituted pyrazole 166.14 is reacted at 70° C. in dimethylformamide solution with one molar equivalent of a dialkyl 3-aminophenyl phosphonate 166.14 and cesium carbonate, to give the amine phosphonate 166.15.

Using the above procedures, but employing different dibromides, and/or different amino-substituted phosphonates, products analogous to 166.13 and 166.15 are obtained.

EXAMPLES 167-170

Deflazacort Derivatives

The synthesis of representative phosphonate derivatives of deflazacort is outlined in Examples 167-170. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 167

Preparation of Representative Deflazacort Derivatives

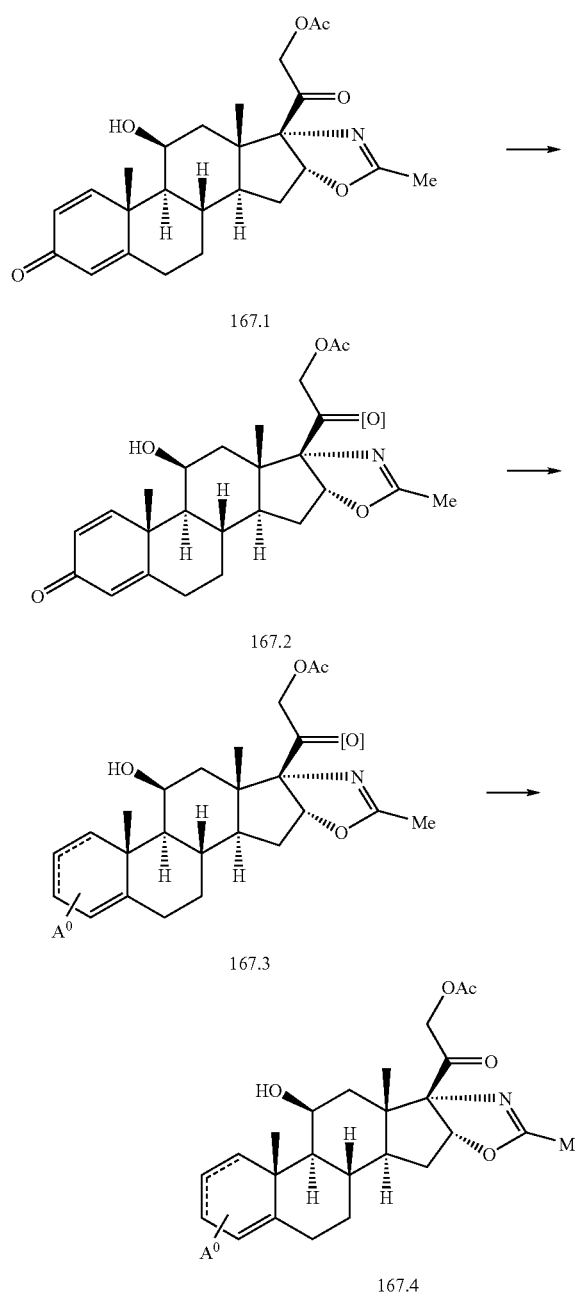

perature with ethylene glycol and an acid catalyst, as described in *J. Am. Chem. Soc.*, 77:1904 (1955). Deprotection is effected by reaction with pyridinium tosylate in aqueous acetone, as described in *J. Chem. Soc. Chem. Comm.* 1351 (1987).

Alternatively, the 20-ketone is protected by conversion to the N,N-dimethylhydrazone. The dimethyl hydrazone is prepared by the reaction of the ketone 167.1 with N,N-dimethylhydrazine in ethanol-acetic acid, as described in *Org. Syn.* 50:102 (1970). The group is removed by treatment with sodium acetate and acetic acid in aqueous tetrahydrofuran, as described in *J. Am. Chem. Soc.* 101:5841 (1979).

Alternatively, the 20-ketone is protected as the diethylamine adduct. In this procedure, the substrate 167.1 is reacted with titanium tetrakis-(diethylamide), as described in *J. Chem. Soc. Chem. Comm.* 406 (1983), to afford the adduct. The ketone is deprotected by reaction with water in an aqueous organic solvent.

The protected compound 167.2 is then converted into the phosphonate-containing analog 167.3, using the procedures described below, and the protecting group is then removed, as described above, to give the phosphonate 167.4.

EXAMPLE 168

Preparation of Representative Deflazacort Derivatives

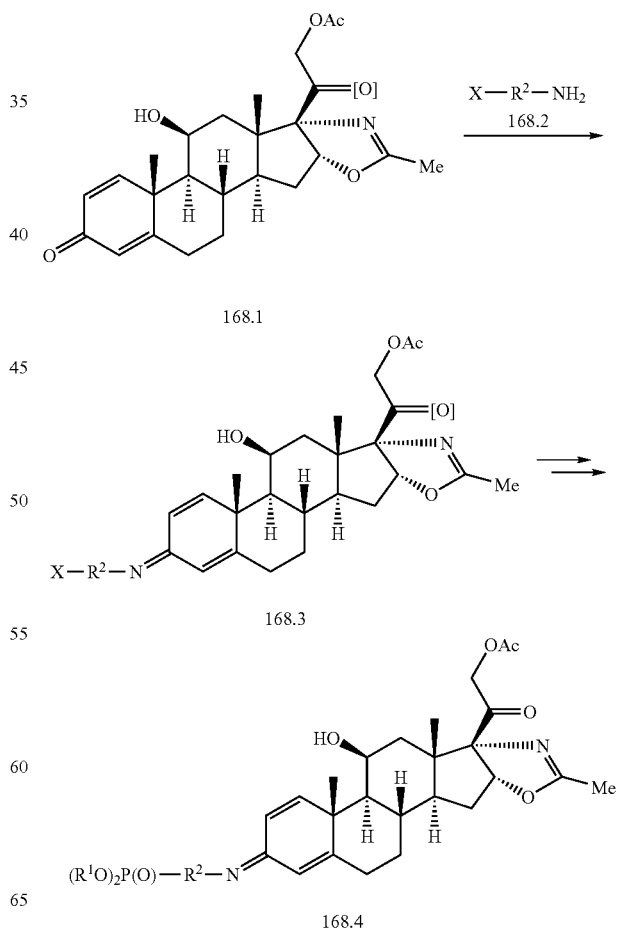

Representative compounds of the invention can be prepared as illustrated above. Deflazacort 167.1 (U.S. Pat. No. 3,436,389) is protected to afford the derivative 167.2. The ketone is protected, for example, by conversion to the cyclic ethylene ketal, by reaction in toluene solution at reflux tem- -continued

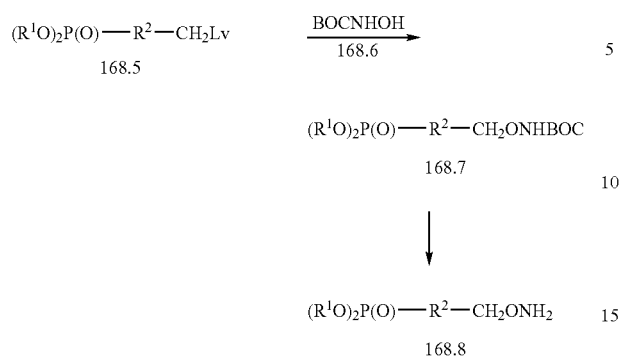

The preparation of phosphonates in which the phosphonate is attached by means of an imino or iminoxy group and a variable carbon chain as illustrated above. In this procedure, the protected derivative 168.1 is reacted with an amine or hydroxylamine 168.2, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime 168.3. The preparation of oximes of steroidal 3-ketones is described in *Anal. Bioch.* 86:133 (1978) and in *J. Mass. Spectrom.* 30:497 (1995). The protecting group is then removed to afford the 20-keto phosphonate product 168.4.

The preparation of hydroxylamine ethers incorporating a phosphonate group is also illustrated. In this procedure, a phosphonate 168.5, in which Lv is a leaving group such as bromo or trifluoromethylsulfonyloxy, is reacted with BOC-hydroxylamine 168.6 (Aldrich) to produce the ether 168.7. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 168.8. The above procedure is also employed for the preparation of substituted hydroxylamines which are precursors to phosphonates.

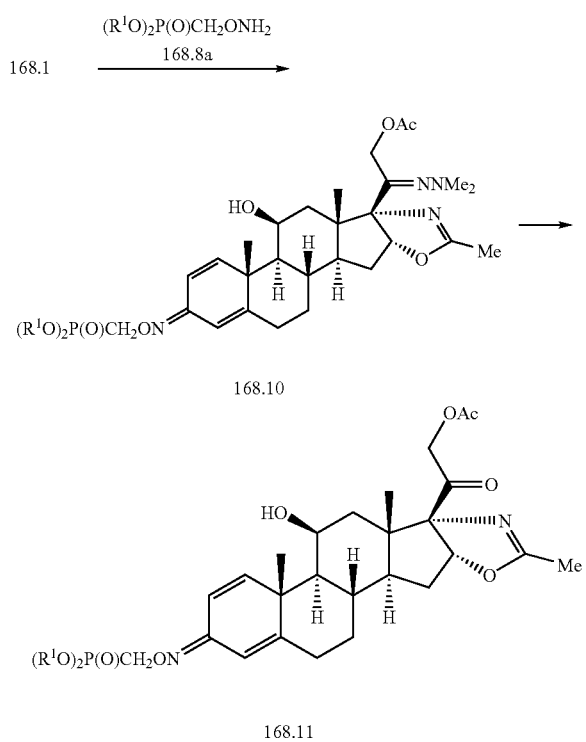

The preparation of phosphonates in which the phosphonate is attached by means of an iminoxy group as illustrated above. In this procedure, the substrate 168.1, in which the 20-ketone is protected as the dimethyl hydrazone derivative, is reacted with a dialkyl phosphonomethyl hydroxylamine 168.8a, prepared as described above from a dialkyl trifluoromethylsulfonyloxymethyl phosphonate (*Tetrahedron Lett.* 27:1477 (1986)) and BOC-hydroxylamine, to afford the oxime 168.10. Deprotection then affords the 20-keto phosphonate 168.11. The oxime forming reaction is performed at ambient temperature in ethanol-acetic acid solution between equimolar amounts of the reactants.

Using the above procedures, but employing, in place of the hydroxylamine ether 168.8a, different oxime ethers 168.2, the corresponding products 168.4 are obtained.

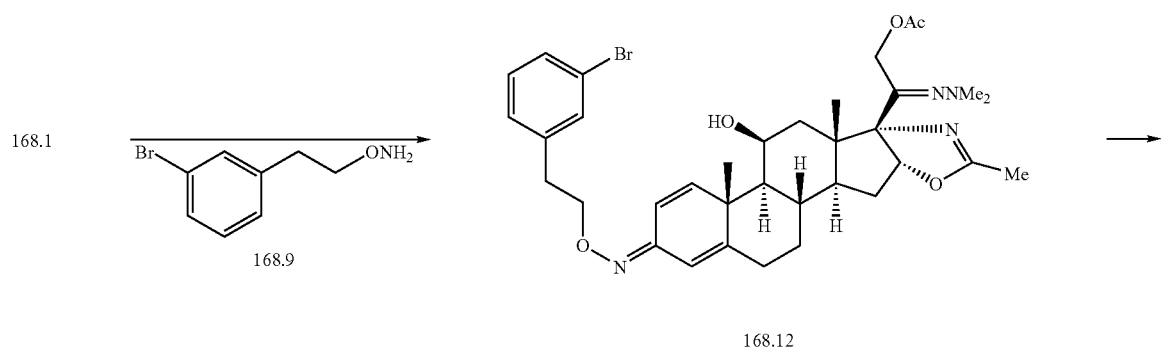

-continued

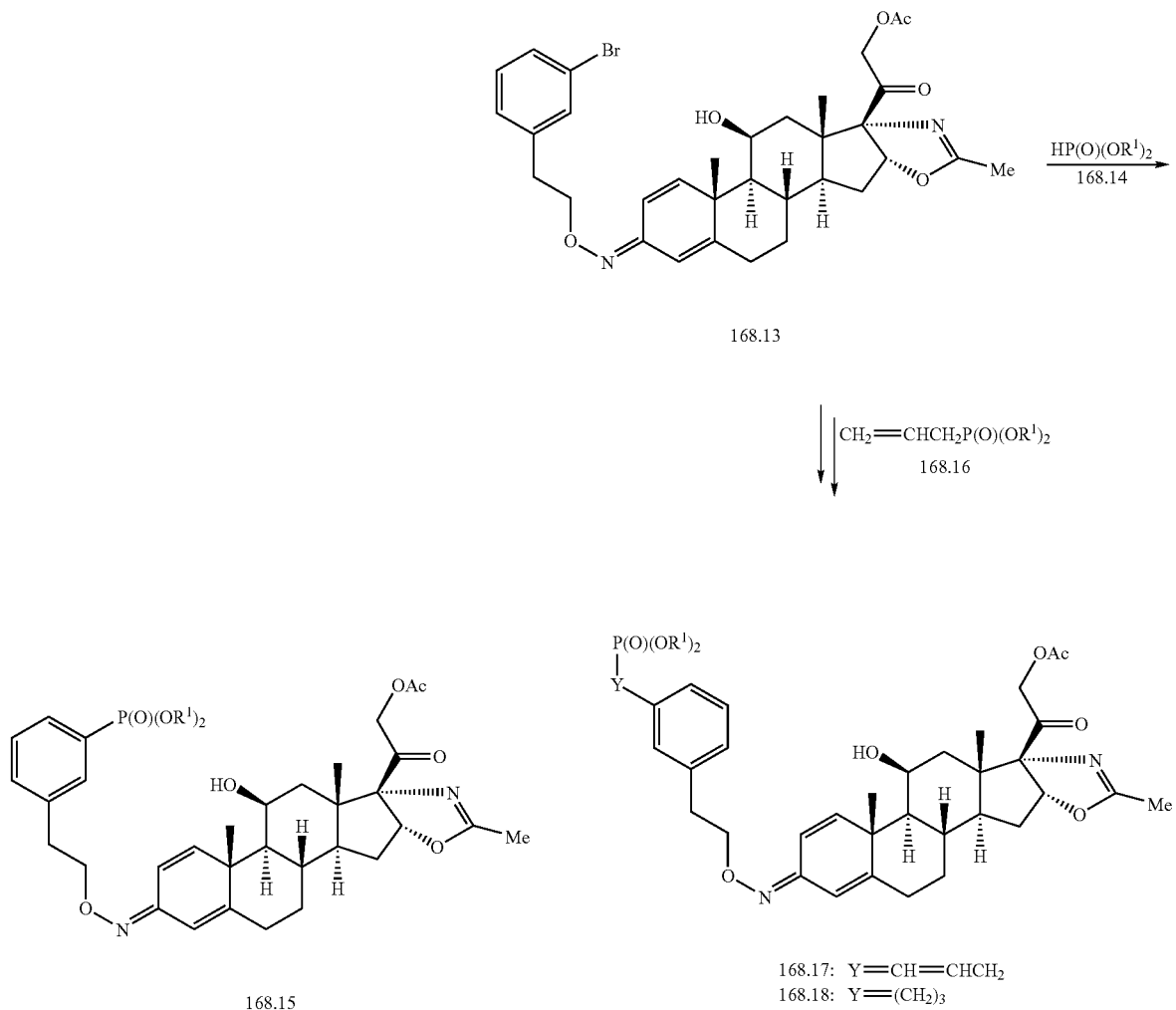

The preparation of compounds in which the phosphonate group is attached by means of a phenylethoxy oxime group as illustrated above. In this procedure, the dienone 168.1, in which the 20-ketone is protected as the dimethyl hydrazone, is reacted, as described above, with O-(3-bromo-phenylethoxy)hydroxylamine 168.9, prepared as described above from 3-bromophenylethyl bromide (French Patent FR 1481052), and BOC-protected hydroxylamine 168.6, to give the oxime 168.12. The protecting group is then removed to yield the 20-keto product 168.13. The latter product is then reacted, in the presence of a palladium catalyst, with a dialkyl phosphite 168.14 to afford the phosphonate 168.15. The preparation of arylphosphonates by means of a coupling reaction between aryl bromides and dialkyl phosphites is described in *J. Med. Chem.* 35:1371 (1992). The reaction is performed at ca. 100° C. in an inert solvent such as toluene, in the presence of a base such as triethylamine and a catalytic amount of tetrakis(triphenylphosphine)palladium(0).

Alternatively, the bromo compound 168.13 is coupled with a dialkyl propenyl phosphonate 168.16 (Aldrich) to afford the phosphonate 168.17. The coupling of aryl halides with olefins by means of the Heck reaction is described, for example, in F.

A. Carey and R. J. Sundberg, *Advanced Organic Chemistry* 503ff (Plenum, 2001) and in *Acc. Chem. Res.* 12:146 (1979). The aryl bromide and the olefin are coupled in a polar solvent such as dimethylformamide or dioxan, in the presence of a palladium(0) catalyst such as tetrakis(triphenyl-phosphine)palladium(0) or palladium(II) catalyst such as palladium(II) acetate, and optionally in the presence of a base such as triethylamine or potassium carbonate. Optionally, the styrenoid double bond present in the product 168.17 is reduced, for example by reaction with diimide, to produce the saturated analog 168.18. The reduction of olefinic bonds is described in R. C. Larock, *Comprehensive Organic Transformations* 6ff (VCH 1989). The transformation is effected by means of catalytic hydrogenation, for example using a palladium on carbon catalyst and hydrogen or a hydrogen donor, or by the use of diimide or diborane.

Using the above procedures, but employing, in place of the bromophenylethyl reagent 168.9, different bromo-substituted aryl or heteroaryl alkoxy hydroxylamines, and/or different dialkyl alkenyl phosphonates, products analogous to the compounds 168.15, 168.17 and 168.18 are obtained.

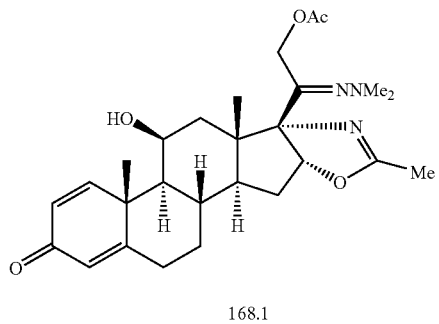
168.1

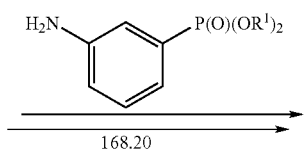
168.20

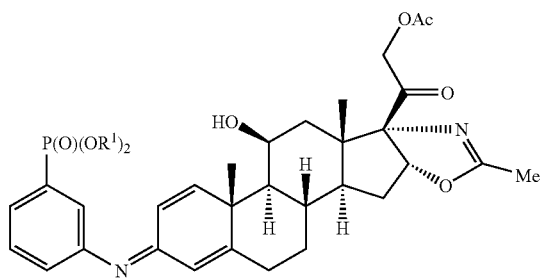
168.21

The preparation of phosphonates in which the phosphonate is attached by means of a 3-phenylimino group as illustrated above. In this procedure, the substrate 168.1, in which the 20-ketone is protected as the dimethylhydrazone, is reacted with a dialkyl 3-aminophenyl phosphonate 168.20 (*J. Med. Chem.* 27:654 (1984)), to give, after deprotection, the imine product 168.21. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions.

Using the above procedures, but employing, in place of the 3-aminophenyl phosphonate 168.20 different amino-substituted aryl or heteroaryl phosphonates, products analogous to 168.21 are obtained.

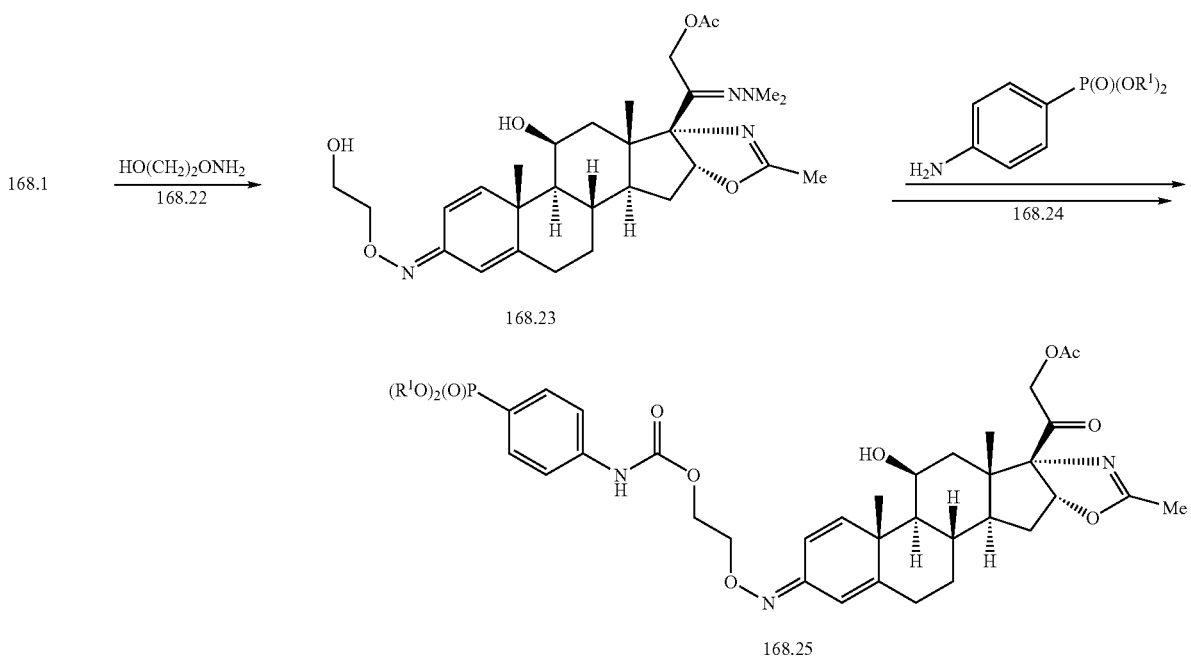

The preparation of phosphonates in which the phosphonate is attached by means of an oximino group and a carbamate linkage as illustrated above. In this procedure, the dienone 168.1, in which the 20-ketone is protected as the dimethylhydrazone, is reacted with O-(2-hydroxyethyl)hydroxylamine 168.22 (*J. Chem. Soc. Chem. Comm.* 903 (1986)) to yield the oxime 168.23. The reaction of steroidal 1,4-dien-3-ones with substituted hydroxylamines is described in *J. Steroid Bioch.* 7:795 (1976); the reaction is performed between equimolar amounts of the reactants in a polar organic solvent such as pyridine or methanol, optionally in the presence of acetic acid or sodium acetate. The product 168.23 is then coupled with a dialkyl 4-aminophenyl phosphonate 168.24 (Epsilon) and carbonyl diimidazole, to yield, after deprotection, the carbamate oxime 168.25. The preparation of carbamates is described in *Comprehensive Organic Functional Group Transformations Vol.* 6 416ff (A. R. Katritzky, ed., Pergamon, 1995) and in S. R. Sandler and W. Karo, *Organic Functional Group Preparations* 260ff (Academic Press, 1986). In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and the like, to afford the corresponding activated acylamine. The latter compound is then reacted with an alcohol to yield the carbamate.

Using the above procedures, but employing, in place of the hydroxy-substituted hydroxylamine 168.22, different hydroxy-substituted hydroxylamines, and/or different amino-substituted phosphonates, the products analogous to 168.25 are obtained.

EXAMPLE 169

Preparation of Representative Deflazacort Derivatives

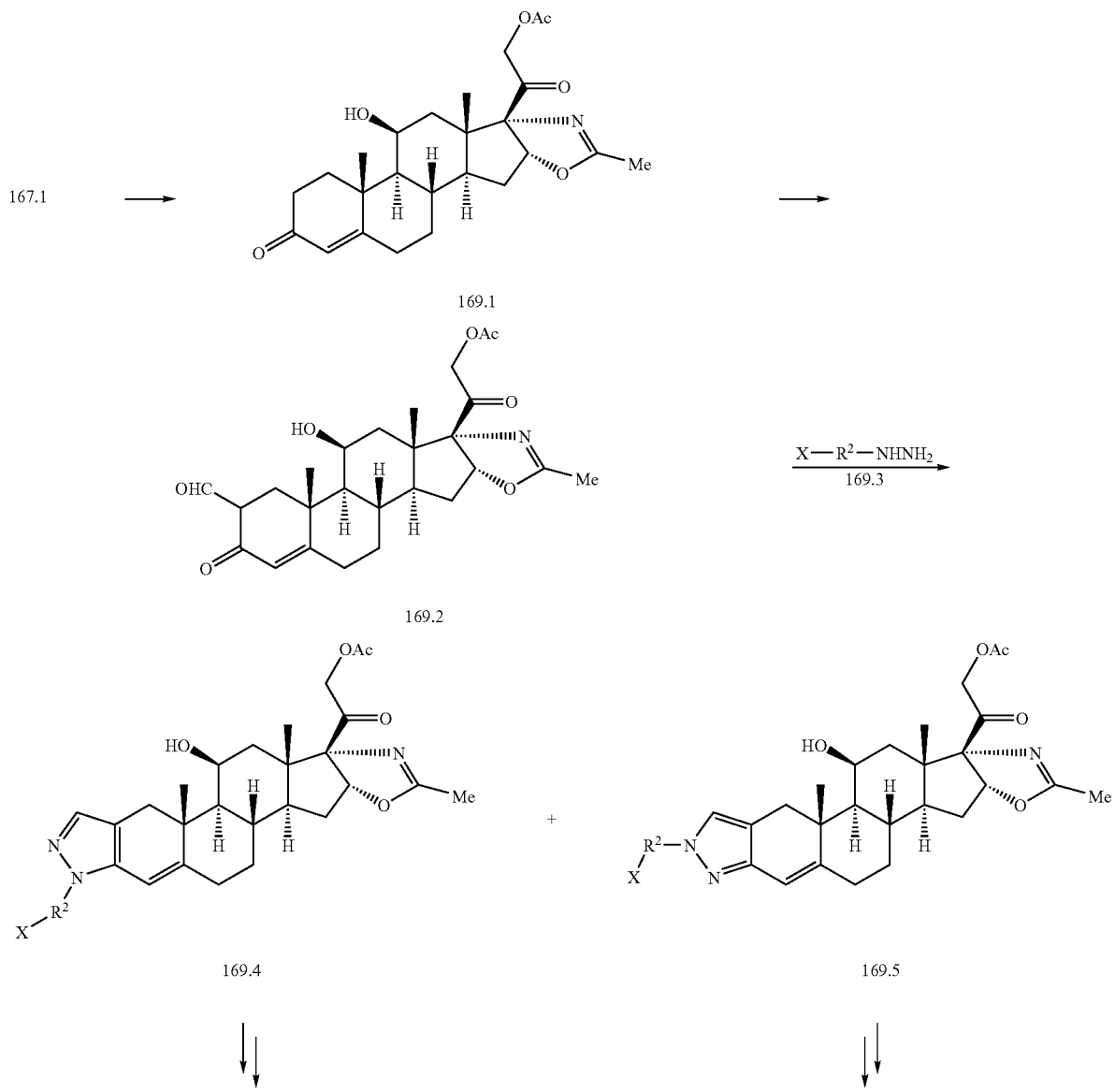

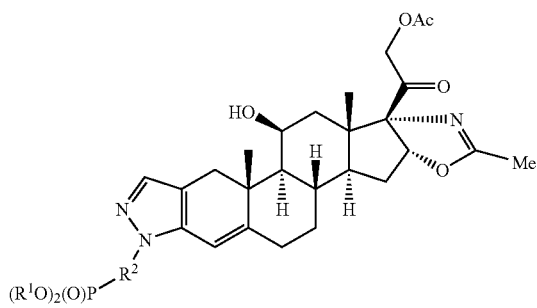

169.6

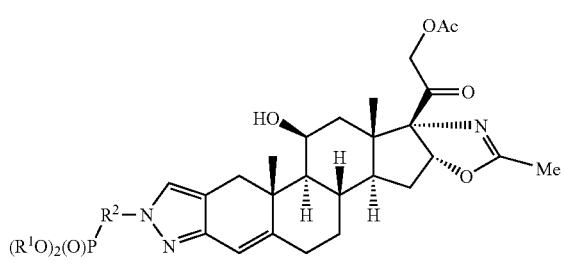

169.7

The preparation of the phosphonate esters in which the phosphonate group is attached to the 1' or 2' position of the pyrazole ring, by means of an aromatic or heteroaromatic group, a heteroatom and/or a variable carbon chain as illustrated above. In this procedure, the dienone 167.1 is reduced to afford the 1,2-dihydro product 169.1. The catalytic hydrogenation reaction is effected by the use of tris(triphenylphosphine)rhodium(I) chloride, for example, as described in *J. Med. Chem.* 44:602 (2001). The product is then reacted with ethyl formate and a base such as sodium hydride, in an inert solvent such as toluene or dimethylformamide, as described in *J. Am. Chem. Soc.* 86:1520 (1964), to afford the 2-formyl product 169.2. This compound is then reacted with an alkyl, aralkyl, aryl or heteroaryl hydrazine 169.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 169.4 and 169.5. The pyrazole-forming reaction is performed between equimolar amounts of the reactants in an acidic solvent such as acetic acid, as described in *J. Am. Chem. Soc.* 86:1520 (1964). The pyrazoles 169.4 and 169.5 are then transformed into the phosphonates 169.6 and 169.7.

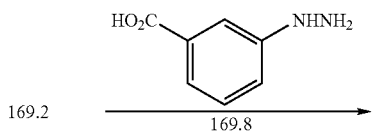

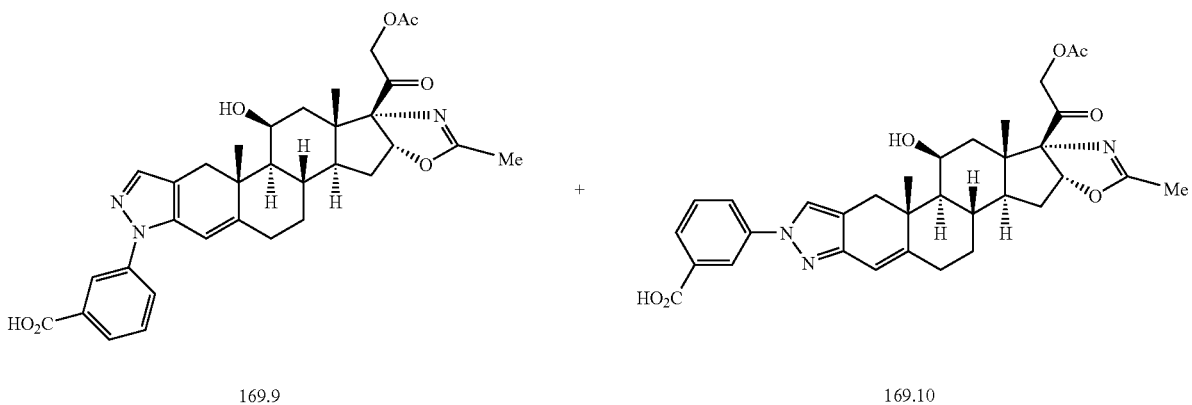

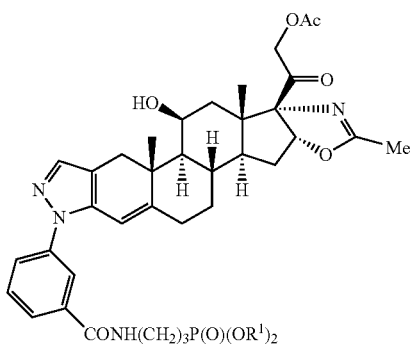

169.12

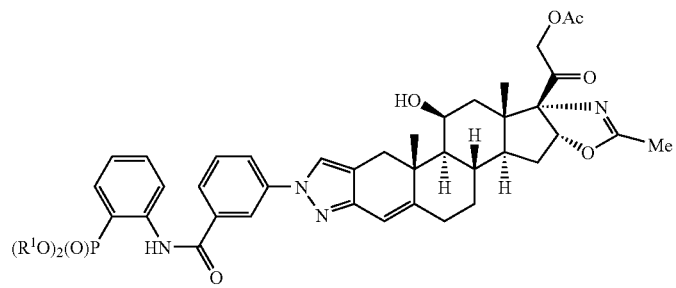

169.14

The preparation of phosphonates in which the phosphonate is attached by means of an amide linkage is illustrated above. In this procedure, the ketoaldehyde 169.2 is reacted, as described above, with 3-carboxyphenyl hydrazine 169.8 (Apin) to give the pyrazoles 169.9 and 169.10. The 2'-substituted isomer 169.9 is then coupled in dimethylformamide solution at ambient temperature with a dialkyl 3-aminopropyl phosphonate 169.11 (Acros) and dicyclohexyl carbodiimide, to yield the amide phosphonate 169.12. The preparation of amides from carboxylic acids and derivatives is described, for example, in S. R. Sandler and W. Karo, *Organic Functional Group Preparations* 274 (Academic Press, 1986), and R. C. Larock, *Comprehensive Organic Transformations* 972ff (VCH, 1989). The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide.

The isomeric pyrazole 169.10 is reacted, as described above, with a dialkyl 2-aminophenyl phosphonate 169.13 (Acros) to yield the amide phosphonate 169.14.

Using the above procedures, but employing different carboxy-substituted hydrazines, and/or different amino-substituted phosphonates, the products analogous to 169.12 and 169.14 are obtained.

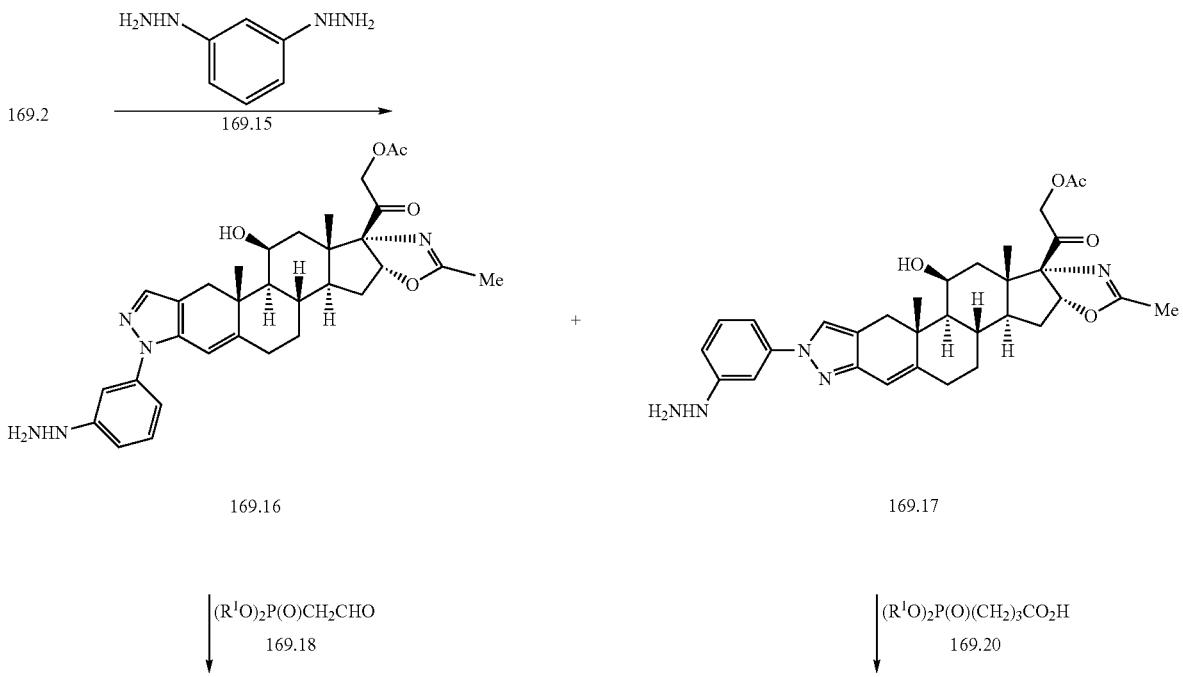

-continued

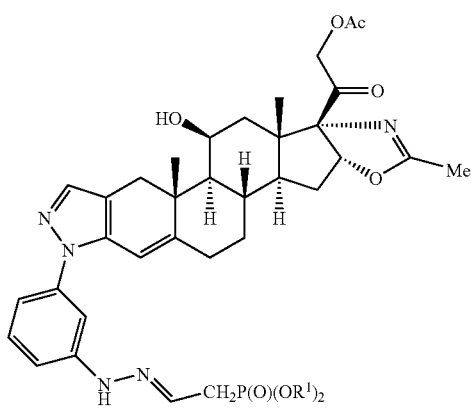

169.19

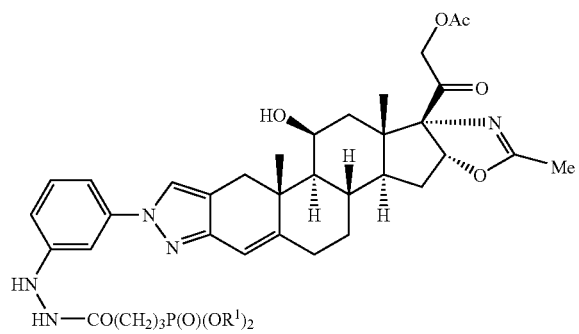

169.21

The preparation of the phosphonates in which the phosphonate group is attached by means of a phenyl group and a hydrazone or acyl hydrazine linkage is illustrated above. In this procedure, the ketoaldehyde 169.2 is reacted, as described above, with 1,3-bis(hydrazino)benzene 169.15 (*Bull. Soc. Chim. Fr.* 1371 (1975)) to produce the pyrazoles 169.16 and 169.17. The 2'-substituted isomer 169.16 is reacted in tetrahydrofuran solution at ambient temperature with one molar equivalent of a dialkylphosphono acetaldehyde (Aurora), to give the hydrazone phosphonate 169.19.

Alternatively, the 1'-substituted pyrazole 169.17 is coupled, as described above, with a dialkylphosphono butyric acid 169.20 (Epsilon) and dicyclohexyl carbodiimide to prepare the phosphonate 169.21.

Using the above procedures, but employing, in place of the 1,3-bis(hydrazino)phenyl hydrazine 169.15, different bis hydrazines, and/or different dialkyl formyl or carboxy-substituted phosphonates, the products analogous to the compounds 169.19 and 169.21 are obtained.

EXAMPLE 170

Preparation of Representative Deflazacort Derivatives

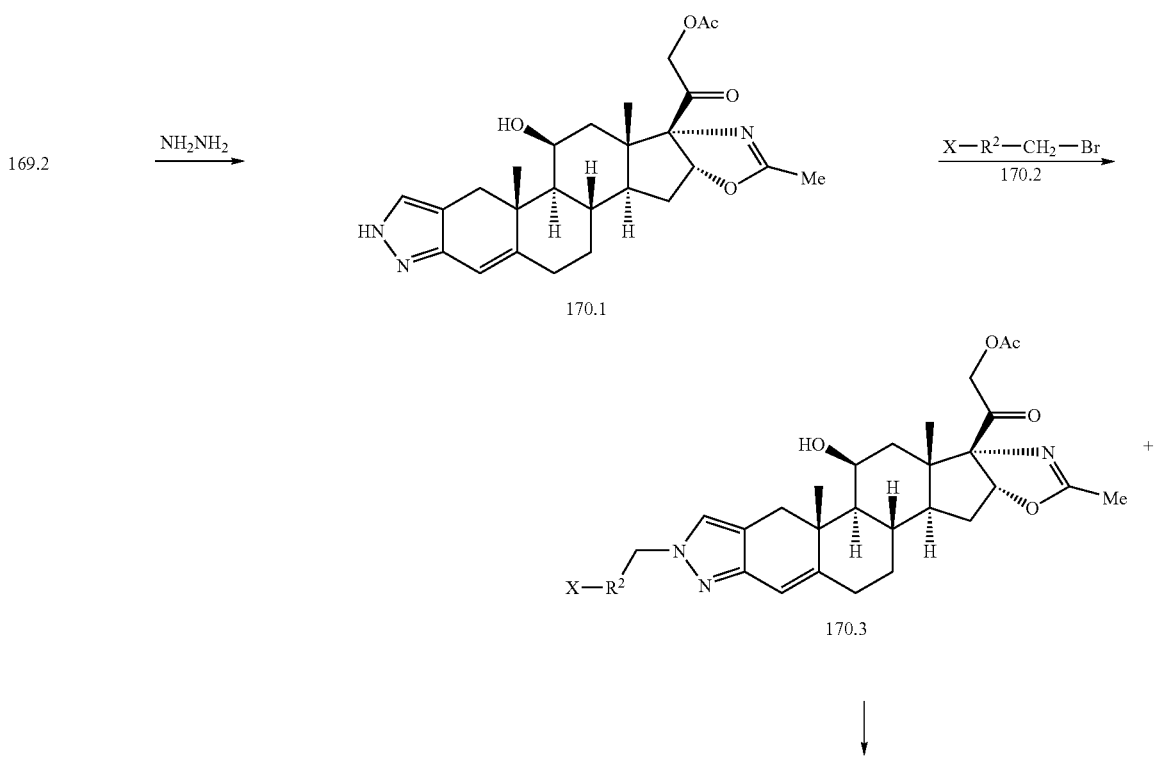

-continued

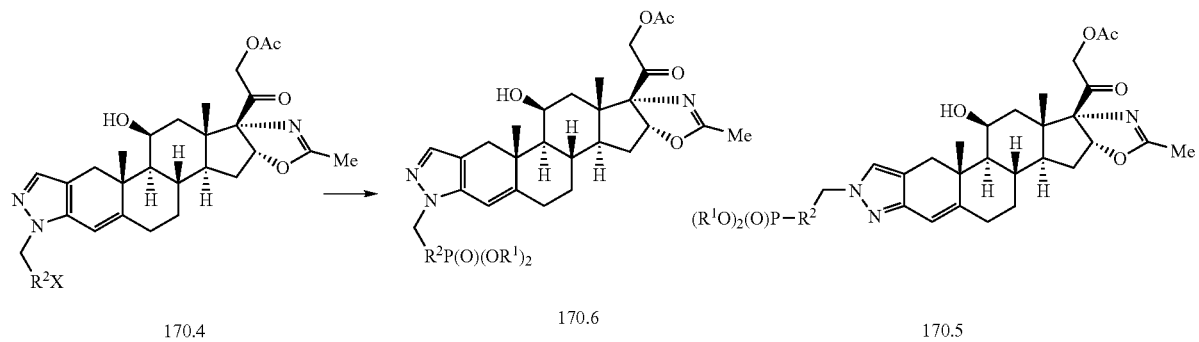

170.4    170.6    170.5

The preparation of the phosphonate esters in which the phosphonate group is attached by means of a variable carbon linkage as illustrated above. In this procedure, the ketoaldehyde 169.2 is reacted with hydrazine to afford the pyrazole derivative 170.1. The reaction of steroidal 2-formyl-3-ketones with hydrazine is described in *J. Am. Chem. Soc.* 86:1520 (1964). The reaction is performed in acetic acid at ambient temperature. The pyrazole product is then reacted with a bromomethyl compound 170.2, in which $R^2$ and X are as defined above, or a reactive bromoheteroaromatic reagent, to yield the alkylation products 170.3 and 170.4. The alkylation of substituted pyrazoles is described, for example, in T. L. Gilchrist, *Heterocyclic Chemistry* 309 (Longman, 1992). The reaction is performed between equimolar amounts of the substrates in a polar solvent such as dimethylformamide or tetrahydrofuran, in the presence of a base such as dimethylaminopyridine, lithium hexamethyldisilazide and the like. The products 170.3 and 170.4 are, except in cases where X is dialkylphosphono, converted into the phosphonates 170.5 and 170.6, using the procedures described herein.

-continued

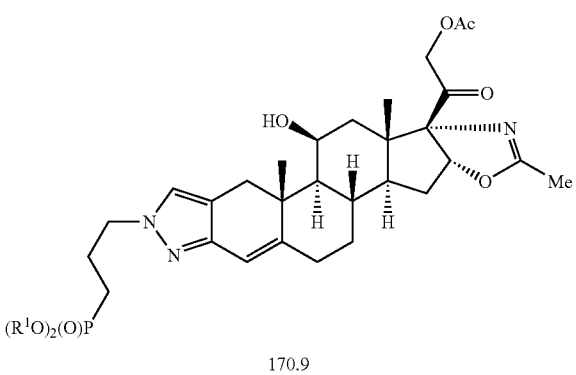

170.9

Representative compounds of the invention can be prepared as illustrated above. The pyrazole 170.1 is reacted in dimethylformamide solution at 70° C. with one molar equivalent of a dialkyl bromopropyl phosphonate 170.7 (Synthelec) and cesium carbonate, to give the pyrazoles 170.8 and 170.9.

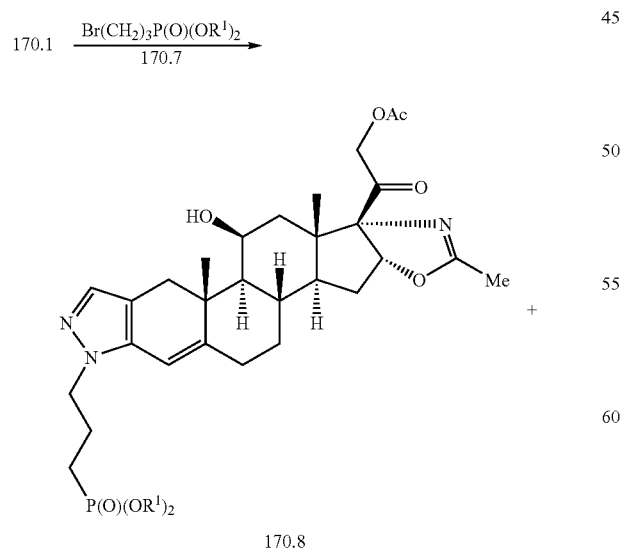

170.8

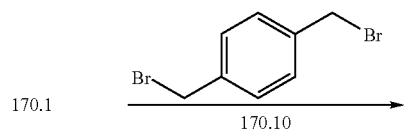

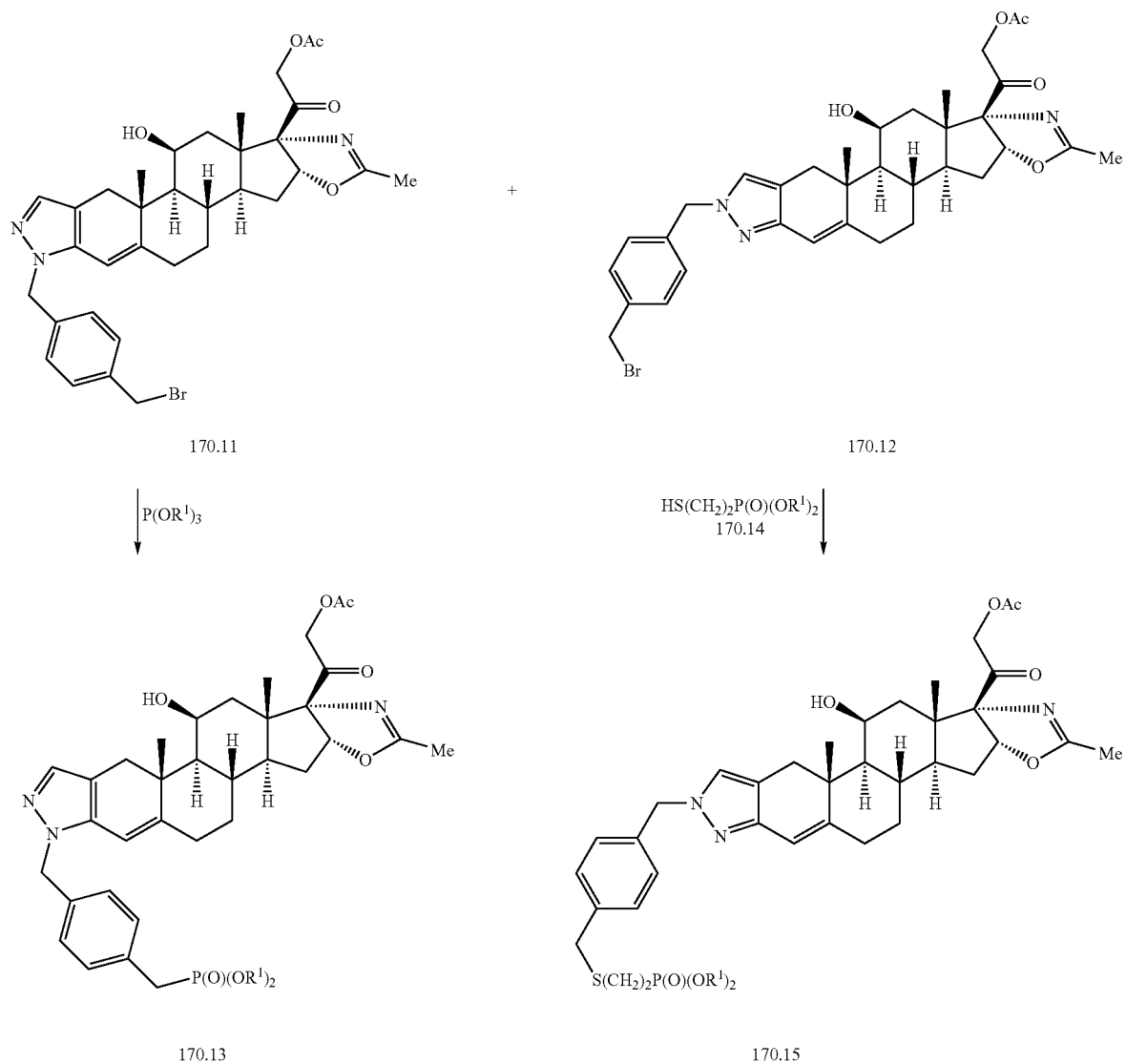

Representative compounds of the invention can be prepared as illustrated above. The pyrazole 170.1 is reacted in tetrahydrofuran solution with 1,4-bis(bromomethyl)benzene 170.10 and potassium hexamethyl disilazide, to give the alkylation products 170.11 and 170.12. The 2'-substituted isomer 170.11 is then reacted, in an Arbuzov reaction, with a trialkyl phosphite to yield the phosphonate 170.13. The Arbuzov reaction is described in *Handb. Organophosphorus Chem.* 115 (1992). In this procedure, in which a bromo substituent is converted into the corresponding phosphonate, the substrate is heated at from about 60° C. to about 160° C. with a five to fifty-fold molar excess of a trialkyl phosphite, to effect the transformation.

The 2'-substituted pyrazole 170.14 is reacted at 70° C. in dimethylformamide solution with one molar equivalent of a dialkyl mercaptoethyl phosphonate 170.14 (*Zh. Obschei. Khim.* 43:2364 (1973)) and cesium carbonate, to give the thioether phosphonate 170.15.

Using the above procedures, but employing different dibromides, and/or different mercapto-substituted phosphonates, products analogous to 170.13 and 170.15 are obtained.

EXAMPLES 171-174

Flunisolide Derivatives

The synthesis of representative phosphonate derivatives of Flunisolide is outlined in Examples 171-174. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 171

Preparation of Representative Flunisolide Derivatives

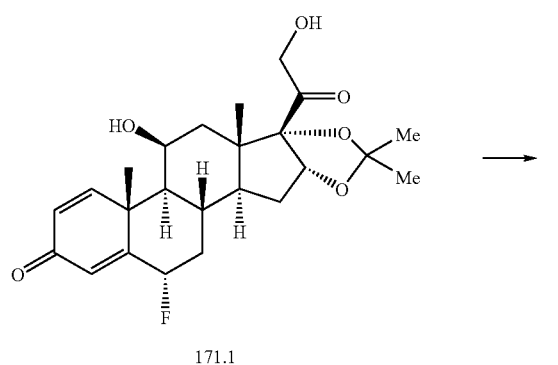
171.1

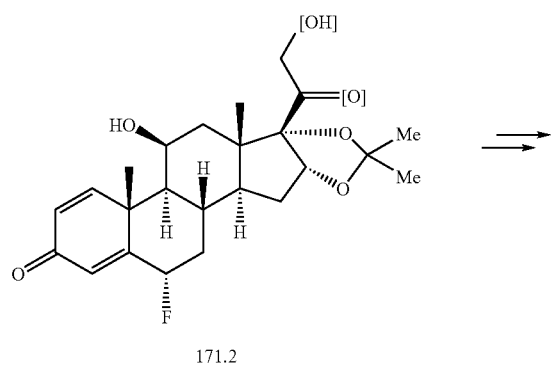
171.2

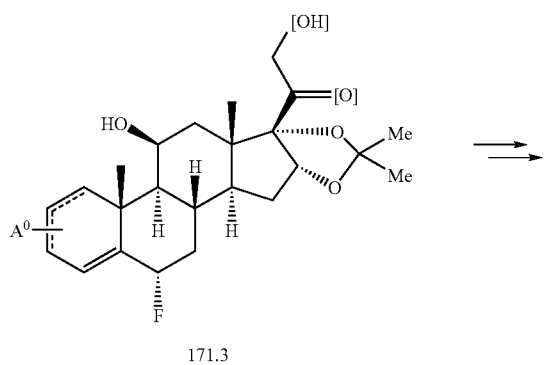
171.3

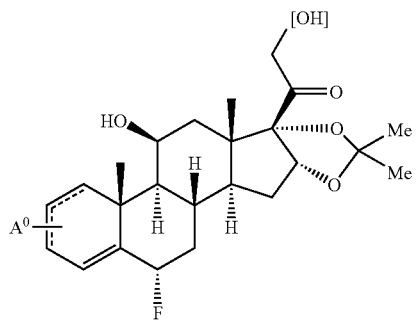
171.4

Representative compounds of the invention can be prepared as illustrated above. The 20-ketone group and/or the 21-hydroxyl group of Flunisolide 171.1 (U.S. Pat. No. 3,124,571) are protected to afford the derivative 171.2. The ketone is protected, for example, by conversion to the cyclic ethylene ketal, by reaction in toluene solution at reflux temperature with ethylene glycol and an acid catalyst, as described in *J. Am. Chem. Soc.,* 77:1904 (1955). Deprotection is effected by reaction with pyridinium tosylate in aqueous acetone, as described in *J. Chem. Soc. Chem. Comm.* 1351 (1987).

Alternatively, the 20-ketone is protected by conversion to the N,N-dimethylhydrazone. The dimethyl hydrazone is prepared by the reaction of the ketone 171.1 with N,N-dimethylhydrazine in ethanol-acetic acid, as described in *Org. Syn.* 50:102 (1970). The group is removed by treatment with sodium acetate and acetic acid in aqueous tetrahydrofuran, as described in *J. Am. Chem. Soc.* 101:5841 (1979).

Alternatively, the 20-ketone is protected as the diethylamine adduct. In this procedure, the substrate 171.1 is reacted with titanium tetrakis(diethylamide), as described in *J. Chem. Soc. Chem. Comm.* 406 (1983), to afford the adduct. The ketone is deprotected by reaction with water in an aqueous organic solvent.

The 21-hydroxyl group is protected, for example, by conversion to the acetate ester, by reaction with one molar equivalent of acetyl chloride in dichloromethane/pyridine. The 21-acetoxy group is removed by reaction with one molar equivalent of lithium hydroxide in aqueous dimethoxyethane.

Alternatively, the 21-hydroxyl group is protected by conversion to the tert.butyl dimethylsilyl ether, by reaction in dimethylformamide solution with one molar equivalent of tert.butylchlorodimethylsilane and imidazole, as described in *J. Am. Chem. Soc.* 94:6190 (1972). The silyl ether is removed by reaction with tetrabutylammonium fluoride in tetrahydrofuran solution, as described in *J. Am. Chem. Soc.* 94:6190 (1972).

The protected compound 171.2 is then converted into the phosphonate-containing analog 171.3 and the protecting group or groups are then removed, as described above, to give the phosphonate 171.4.

EXAMPLE 172

Preparation of Representative Flunisolide Derivatives

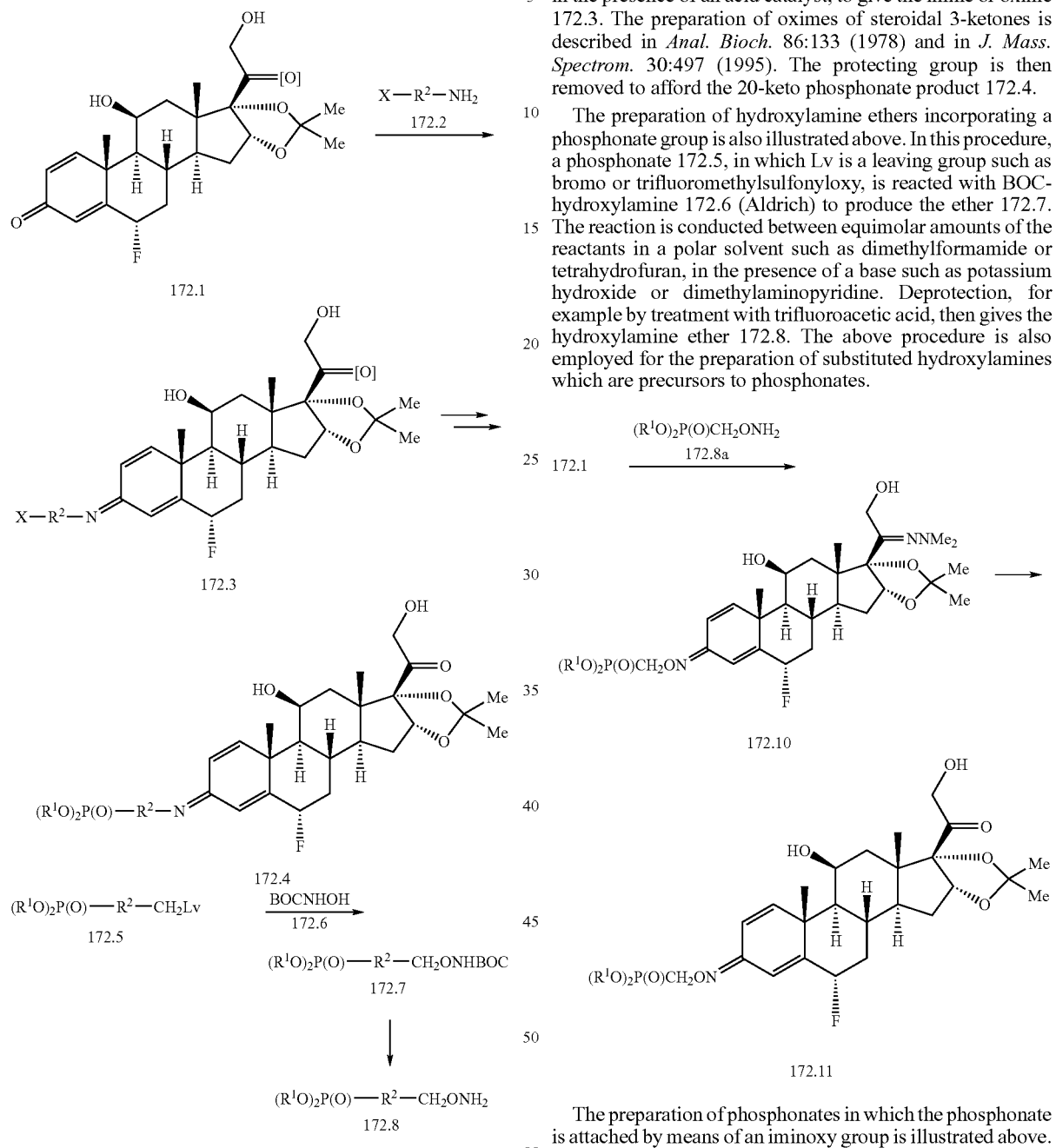

The preparation of phosphonates in which the phosphonate is attached by means of an imino or iminoxy group and a variable carbon chain is illustrated above. In this procedure, the ketone-protected derivative 172.1 is reacted with an amine or hydroxylamine 172.2, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime 172.3. The preparation of oximes of steroidal 3-ketones is described in *Anal. Bioch.* 86:133 (1978) and in *J. Mass. Spectrom.* 30:497 (1995). The protecting group is then removed to afford the 20-keto phosphonate product 172.4.

The preparation of hydroxylamine ethers incorporating a phosphonate group is also illustrated above. In this procedure, a phosphonate 172.5, in which Lv is a leaving group such as bromo or trifluoromethylsulfonyloxy, is reacted with BOC-hydroxylamine 172.6 (Aldrich) to produce the ether 172.7. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 172.8. The above procedure is also employed for the preparation of substituted hydroxylamines which are precursors to phosphonates.

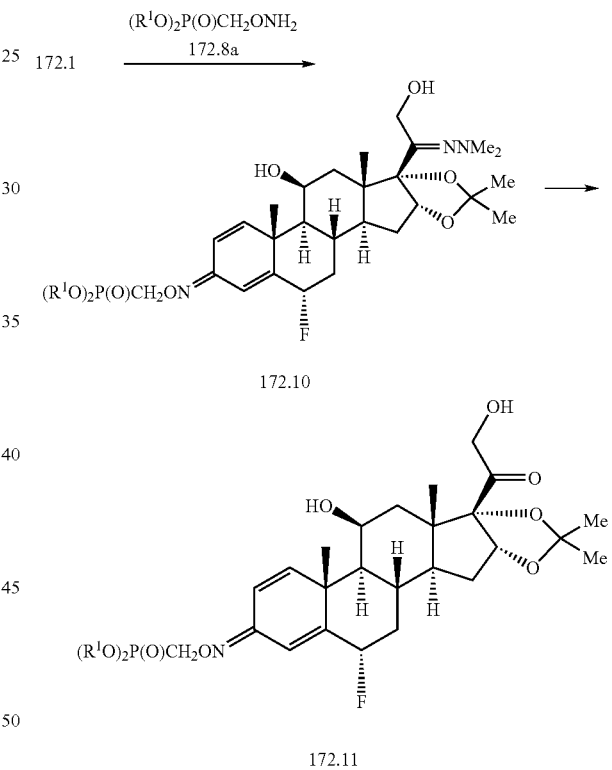

The preparation of phosphonates in which the phosphonate is attached by means of an iminoxy group is illustrated above. In this procedure, the substrate 172.1, in which the 20-ketone is protected as the dimethyl hydrazone derivative, is reacted with a dialkyl phosphonomethyl hydroxylamine 172.8a, prepared as described above from a dialkyl trifluoromethylsulfonyloxymethyl phosphonate (*Tetrahedron Lett.* 27:1477 (1986)) and BOC-hydroxylamine, to afford the oxime 172.10. Deprotection affords the 20-keto phosphonate 172.11. The oxime forming reaction is performed at ambient temperature in ethanol-acetic acid solution between equimolar amounts of the reactants.

Using the above procedures, but employing, in place of the hydroxylamine ether 172.8a, different oxime ethers 172.2, the corresponding products 172.4 are obtained.

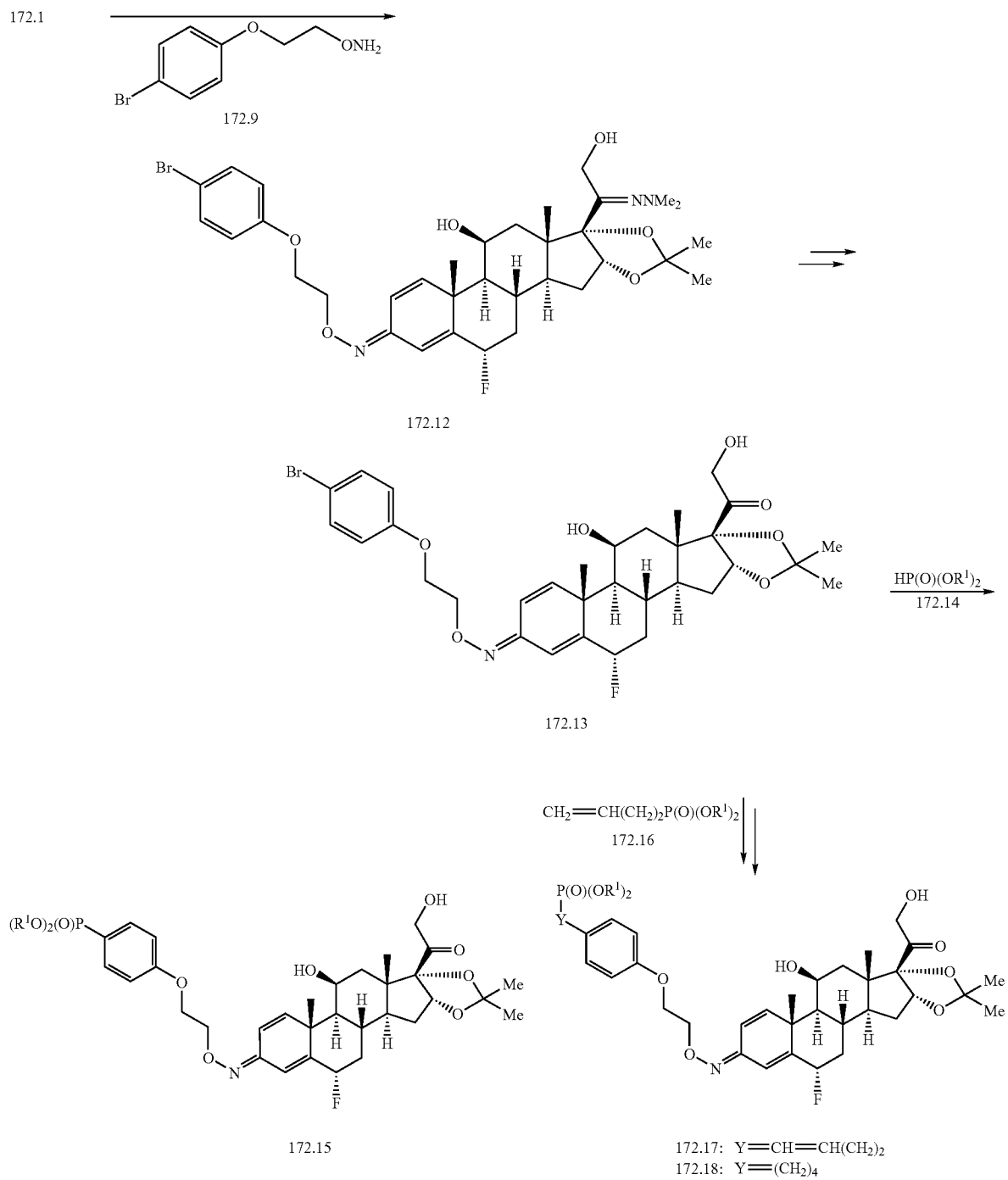

The preparation of compounds in which the phosphonate group is attached by means of a phenoxyethoxy oxime group is illustrated above. In this procedure, the dienone 172.1, in which the 20-ketone is protected as the dimethyl hydrazone, is reacted, as described above, with O-(4-bromophenoxyethoxy)hydroxylamine 172.9, prepared as described above from 4-bromophenoxyethyl bromide (FR 1481052), and BOC-protected hydroxylamine 172.6, to give the oxime 172.12. The protecting group is then removed to yield the 20-keto product 172.13. The latter product is then reacted, in the presence of a palladium catalyst, with a dialkyl phosphite 172.14 to afford the phosphonate 172.15. The preparation of arylphosphonates by means of a coupling reaction between aryl bromides and dialkyl phosphites is described in *J. Med. Chem.* 35:1371 (1992). The reaction is performed at ca. 100° C. in an inert solvent such as toluene, in the presence of a base such as triethylamine and a catalytic amount of tetrakis(triphenylphosphine)palladium(0).

Alternatively, the bromo compound 172.13 is coupled with a dialkyl butenyl phosphonate 172.16 (*Org. Lett.* 3:217 (2001)) to afford the phosphonate 172.17. The coupling of aryl halides with olefins by means of the Heck reaction is described, for example, in F. A. Carey and R. J. Sundberg, *Advanced Organic Chemistry* 503ff (Plenum, 2001) and in

*Acc. Chem. Res.* 12:146 (1979). The aryl bromide and the olefin are coupled in a polar solvent such as dimethylformamide or dioxane, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 172.17 is reduced, for example by reaction with diimide, to produce the saturated analog 172.18. The reduction of olefinic bonds is described in R. C. Larock, *Comprehensive Organic Transformations* 6ff (VCH 1989). The transformation is effected by means of catalytic hydrogenation, for example using a palladium on carbon catalyst and hydrogen or a hydrogen donor, or by the use of diimide or diborane.

Using the above procedures, but employing, in place of the bromophenoxyethyl reagent 172.9, different bromo-substituted aryl or heteroaryl alkoxy hydroxylamines, and/or different dialkyl alkenyl phosphonates, products analogous to the compounds 172.15, 172.17 and 172.18 are obtained.

The preparation of phosphonates in which the phosphonate is attached by means of a 4-phenylimino group is illustrated above. In this procedure, the substrate 172.1, in which the 20-ketone is protected as the dimethylhydrazone, is reacted with a dialkyl 4-aminophenyl phosphonate 172.20 (Epsilon), to give, after deprotection, the imine product 172.21. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions.

Using the above procedures, but employing, in place of the 4-aminophenyl phosphonate 172.20 different amino-substituted aryl or heteroaryl phosphonates, products analogous to 172.21 are obtained.

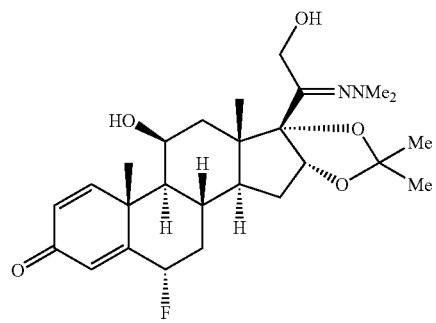

172.1

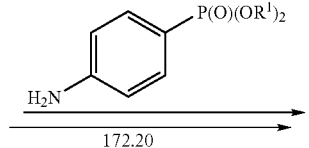

172.20

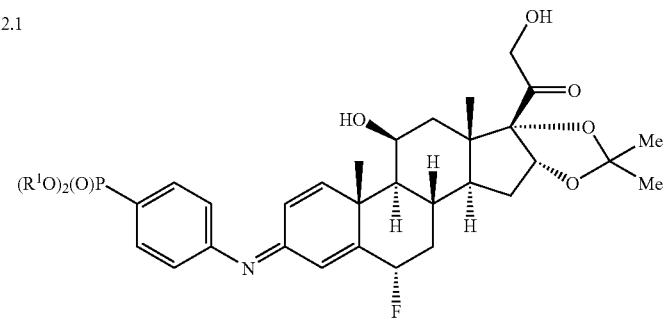

172.21

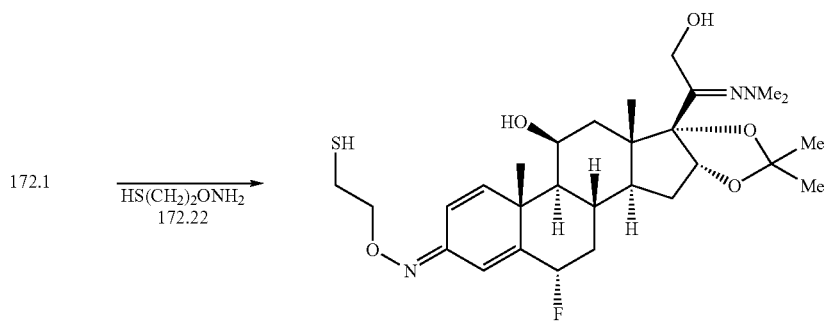

172.23

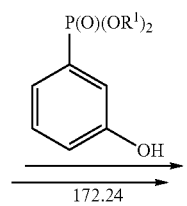

172.24

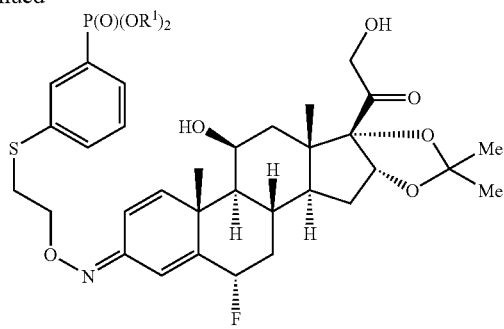

172.25

The preparation of phosphonates in which the phosphonate is attached by means of an oximino group and a thioether linkage is illustrated above. In this procedure, the dienone 172.1, in which the 20-ketone is protected as the dimethylhydrazone, is reacted with 2-mercaptoethyl hydroxylamine 172.22 (*Bioorganicheskaya Khim.* 12:1662 (1986)) to yield the oxime 172.23. The reaction of steroidal 1,4-dien-3-ones with hydroxylamines is described in *J. Steroid Bioch.* 7:795 (1976). The reaction is performed between equimolar amounts of the reactants in a polar organic solvent such as pyridine or methanol, optionally in the presence of acetic acid or sodium acetate. The product 172.23 is then coupled, in a Mitsonobu reaction, with a dialkyl 3-hydroxyphenyl phosphonate 172.24 (Aurora), to yield, after deprotection, the thioether oxime 172.25. The preparation of aromatic ethers by means of the Mitsonobu reaction is described, for example, in R. C. Larock, *Comprehensive Organic Transformations* 448 (VCH, 1989), in F. A. Carey and R. J. Sundberg, *Advanced Organic Chemistry, Part B* 153-4 (Plenum, 2001), and in *Org. React.* 42:335, (1992). The phenol and the hydroxyl or mercapto component are reacted together in an aprotic solvent such as, for example, tetrahydrofuran, in the presence of a dialkyl azodicarboxylate and a triarylphosphine, to afford the ether or thioether products. The procedure is also described in *Org. React.* 42:335-656 (1992).

Using the above procedures, but employing, in place of the mercapto-substituted hydroxylamine 172.24, different mercapto-substituted hydroxylamines, and/or different hydroxyaryl phosphonates, the products analogous to 172.25 are obtained.

EXAMPLE 173

Preparation of Representative Flunisolide Derivatives

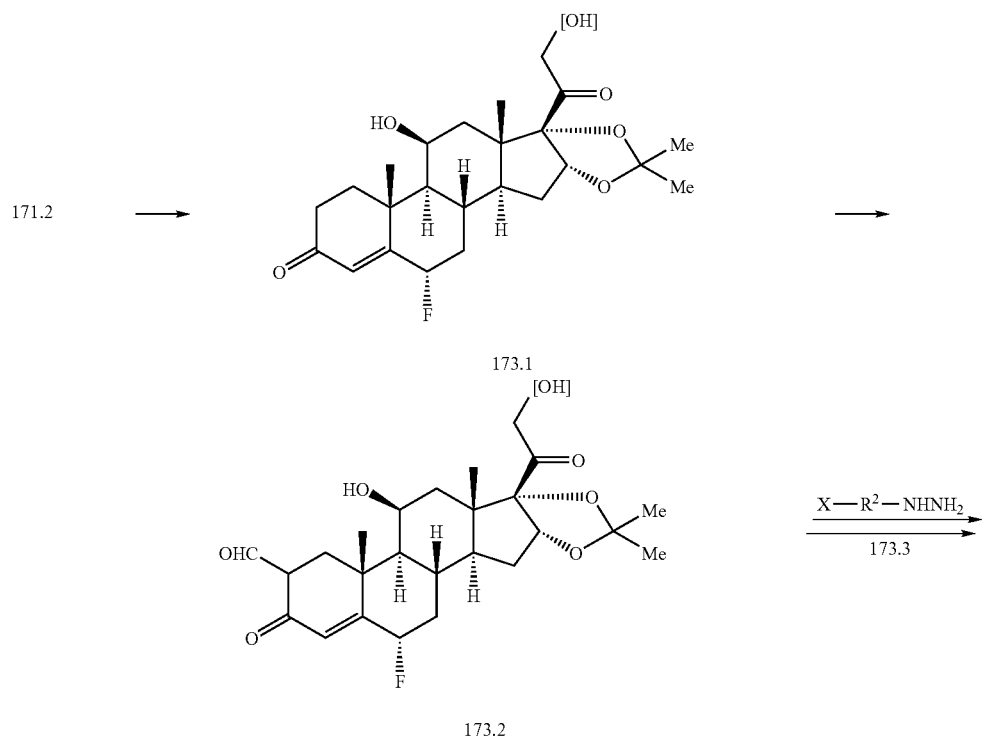

-continued

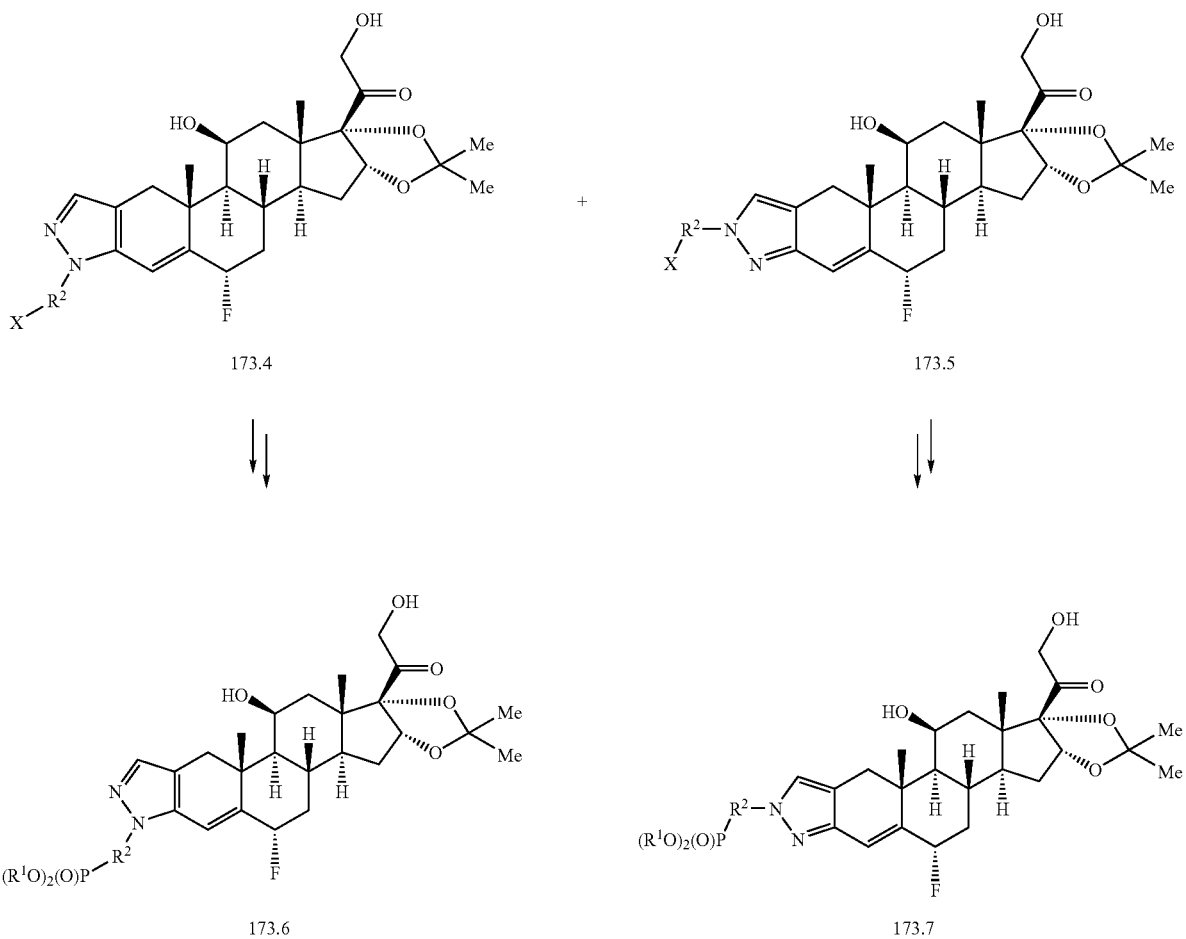

The preparation of the phosphonate esters in which the phosphonate group is attached to the 1' or 2' position of the pyrazole ring, by means of an aromatic or heteroaromatic group, a heteroatom and/or a variable carbon chain is illustrated above. In this procedure, the dienone 171.2, in which the 21-hydroxyl group is protected is reduced to afford the 1,2-dihydro product 173.1. The catalytic hydrogenation reaction is effected by the use of tris(triphenylphosphine)rhodium (I) chloride, for example as described in J. Med. Chem. 44:602 (2001). The product is then reacted with ethyl formate and a base such as sodium hydride, in an inert solvent such as toluene or dimethylformamide, as described in J. Am. Chem. Soc. 86:1520 (1964), to afford the 2-formyl product 173.2.

This compound is then reacted with an alkyl, aralkyl, aryl or heteroaryl hydrazine 173.3, in which the substituent X is either a phosphonate group or a group which is subsequently transformed into a phosphonate-containing substituent. For example, X is dialkylphosphono, bromo, hydroxy, amino, carboxyl and the like. The reaction yields, after deprotection of the 21-hydroxyl group, the isomeric 2'- and 1'-aryl pyrazoles 173.4 and 173.5. The pyrazole-forming reaction is performed between equimolar amounts of the reactants in an acidic solvent such as acetic acid, as described in J. Am. Chem. Soc. 86:1520 (1964). The pyrazoles 173.4 and 173.5 are then transformed into the phosphonates 173.6 and 173.7.

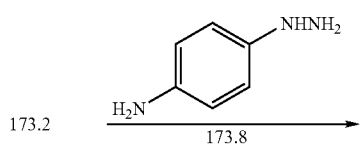

-continued

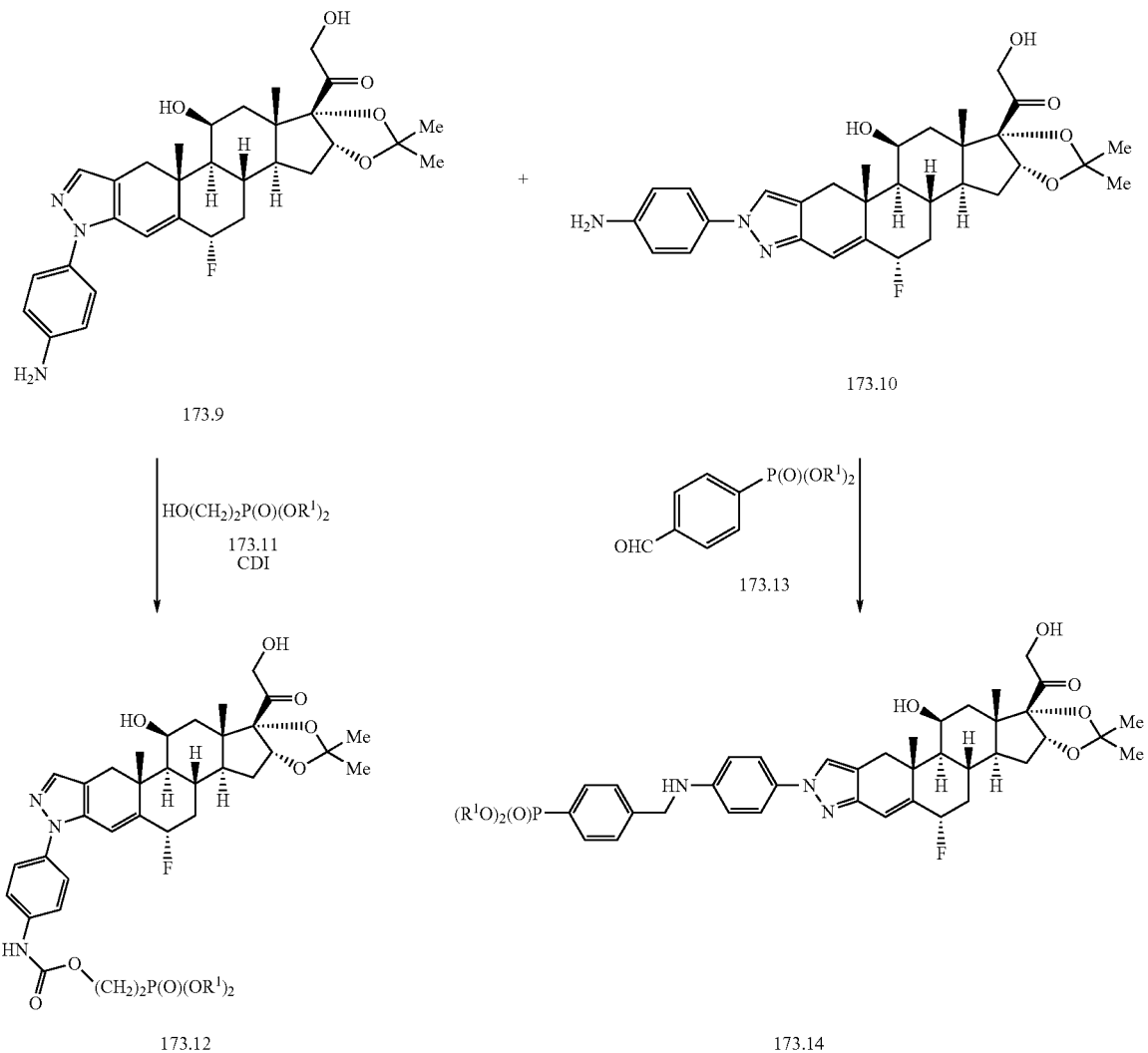

The preparation of phosphonates in which the phosphonate is attached by means of a carbamate or an amine linkage is illustrated above. In this procedure, the ketoaldehyde 173.2 is reacted, as described above, with 4-aminophenyl hydrazine 173.8 (Syn. Comm. 4:57 (1974)) to give the pyrazoles 173.9 and 173.10. The 2'-substituted isomer 173.9 is then reacted in dichloromethane solution with one molar equivalent of a dialkyl 2-hydroxyethyl phosphonate 173.11 (Aldrich) and carbonyl diimidazole (CDI) to give the carbamate 173.12. The preparation of carbamates is described in Comprehensive Organic Functional Group Transformations Vol. 6 416ff (A. R. Katritzky, ed., Pergamon, 1995) and in S. R. Sandler and W. Karo, Organic Functional Group Preparations 260ff (Academic Press, 1986). In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and the like, to afford the corresponding activated acylamine. The latter compound is then reacted with an alcohol to yield the carbamate.

The isomeric pyrazole 173.10 is reacted in a reductive amination procedure, in tetrahydrofuran solution at ambient temperature, with one molar equivalent of a dialkyl 4-formylphenyl phosphonate 173.13 (Epsilon) and sodium cyanoborohydride to yield the amine phosphonate 173.14. The preparation of amines by means of reductive amination procedures is described, for example, in R. C. Larock, Comprehensive Organic Transformations, 421 (VCH) and in F. A. Carey and R. J. Sundberg, Advanced Organic Chemistry Part B 269 (Plenum, 2001). In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in J. Org. Chem. 55:2552 (1990).

Using the above procedures, but employing different amino-substituted hydrazines, and/or different hydroxy- or formyl-substituted phosphonates, the products analogous to 173.12 and 173.14 are obtained.

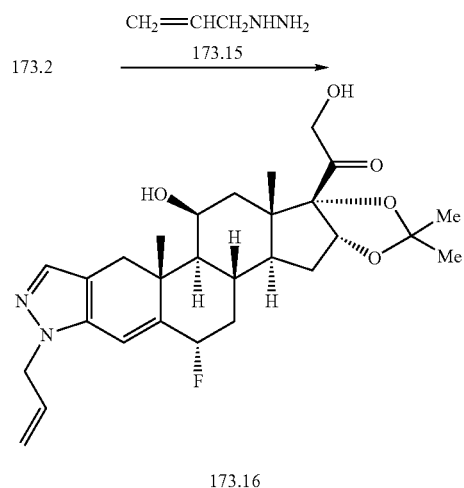

173.16

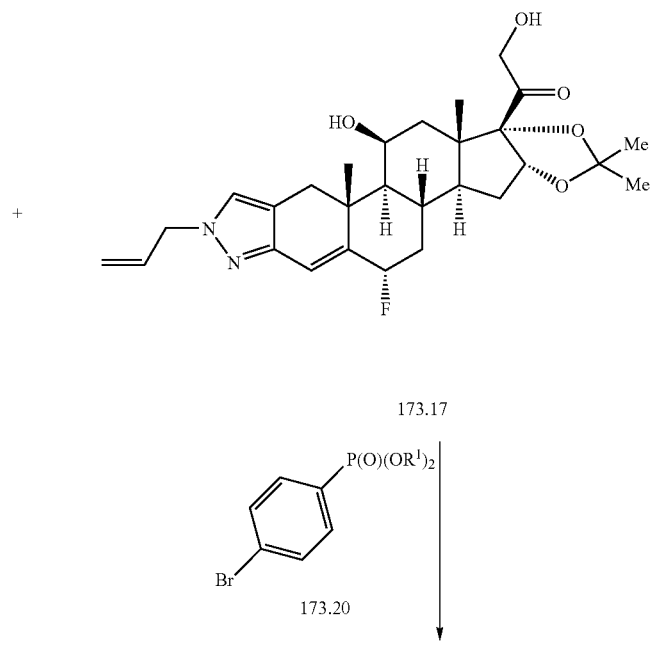

173.17

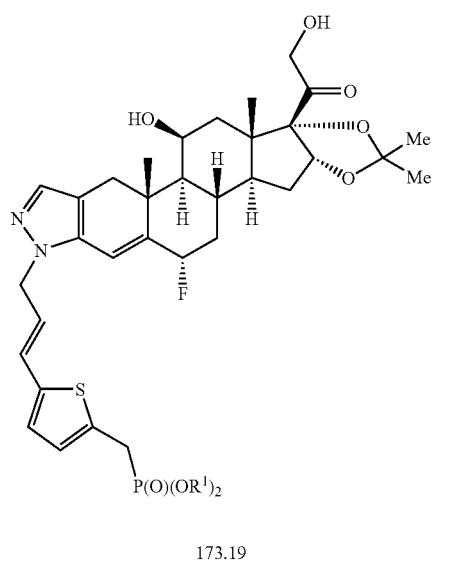

173.19

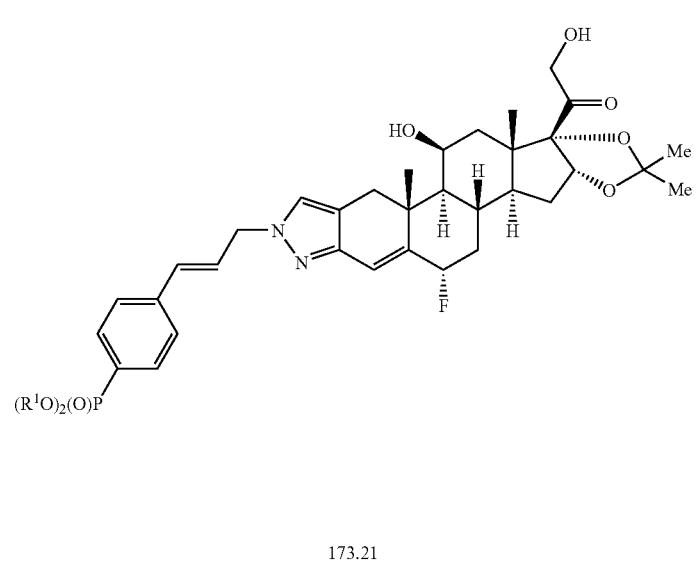

173.21

The preparation of the phosphonates in which the phosphonate group is attached by means of a propenyl group and an aromatic ring is illustrated above. In this procedure, the ketoaldehyde 173.2 is reacted, as described above, with allyl hydrazine 173.15 (*Zh. Org. Khim.* 3:983 (1967)) to produce the pyrazoles 173.16 and 173.17. The 2'-substituted isomer 173.16 is then coupled by means of a Heck reaction, as described above, with a dialkyl 5-bromo-2-thienylmethyl phosphonate 173.18 (*Syn.* 455 (2003)) to give the phosphonate 173.19.

Alternatively, the 1'-substituted pyrazole 173.22 is coupled in a Heck reaction, as described above, with a dialkyl 4-bromophenyl phosphonate 173.20 (*J. Organomet. Chem.* 581:62 (1999)) to prepare the phenylpropenyl phosphonate 173.21.

Using the above procedures, but employing, in place of the allyl hydrazine 173.15, different alkenyl hydrazines, and/or different dialkyl bromo-substituted phosphonates, the products analogous to the compounds 173.19 and 173.21 are obtained.

EXAMPLE 174

Preparation of Representative Flunisolide Derivatives

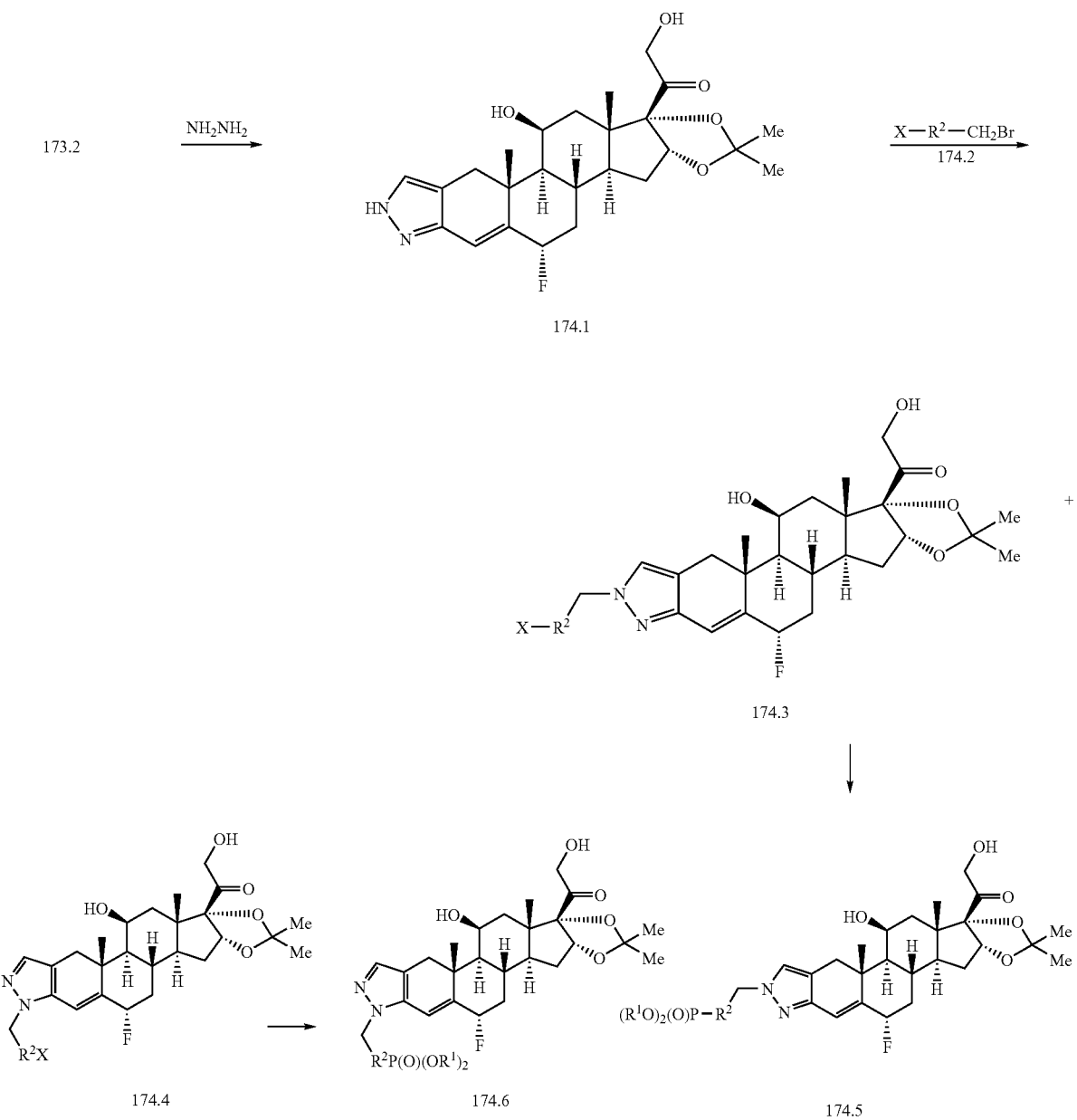

The preparation of phosphonate esters in which the phosphonate group is attached by means of a variable carbon linkage is illustrated above. In this procedure, the ketoaldehyde 173.2 is reacted with hydrazine to afford the pyrazole derivative 174.1. The reaction of steroidal 2-formyl-3-ketones with hydrazine is described in *J. Am. Chem. Soc.* 86:1520 (1964). The reaction is performed in acetic acid at ambient temperature. The pyrazole product is then reacted with a bromomethyl compound 174.2, in which $R^2$ and X are as defined above, or a reactive bromoheteroaromatic reagent, to yield the alkylation products 174.3 and 174.4. The alkylation of substituted pyrazoles is described, for example, in T. L. Gilchrist, *Heterocyclic Chemistry* 309 (Longman, 1992). The reaction is performed between equimolar amounts of the substrates in a polar solvent such as dimethylformamide or tetrahydrofuran, in the presence of a base such as dimethylaminopyridine, lithium hexamethyldisilazide and the like. The products 174.3 and 174.4 are, except in cases where X is dialkylphosphono, converted into the phosphonates 174.5 and 174.6, using the procedures described herein.

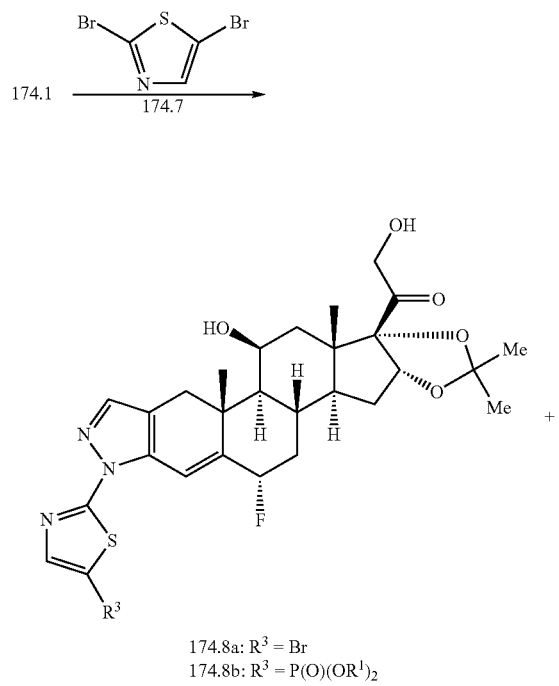

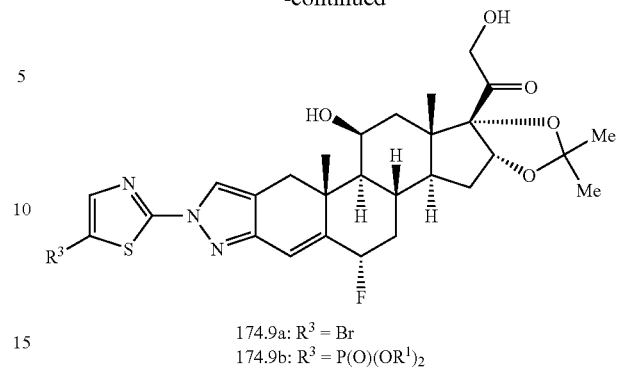

174.9a: R³ = Br
174.9b: R³ = P(O)(OR¹)₂

Representative compounds of the invention can be prepared as illustrated above. The pyrazole 174.1 is reacted in dimethylformamide solution at 70° C. with one molar equivalent of 2,5-dibromothiazole 174.7 (Aldrich) and lithium hexamethyl disilazide, to give the pyrazoles 174.8a and 174.9a. The products are then coupled, as described above, with a dialkyl phosphite to yield the phosphonates 174.8b and 174.9b.

Using the above procedures, but employing different dibromo-substituted heterocycles, the products analogous to 174.8b and 174.9b are obtained.

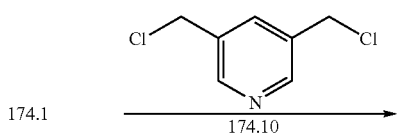

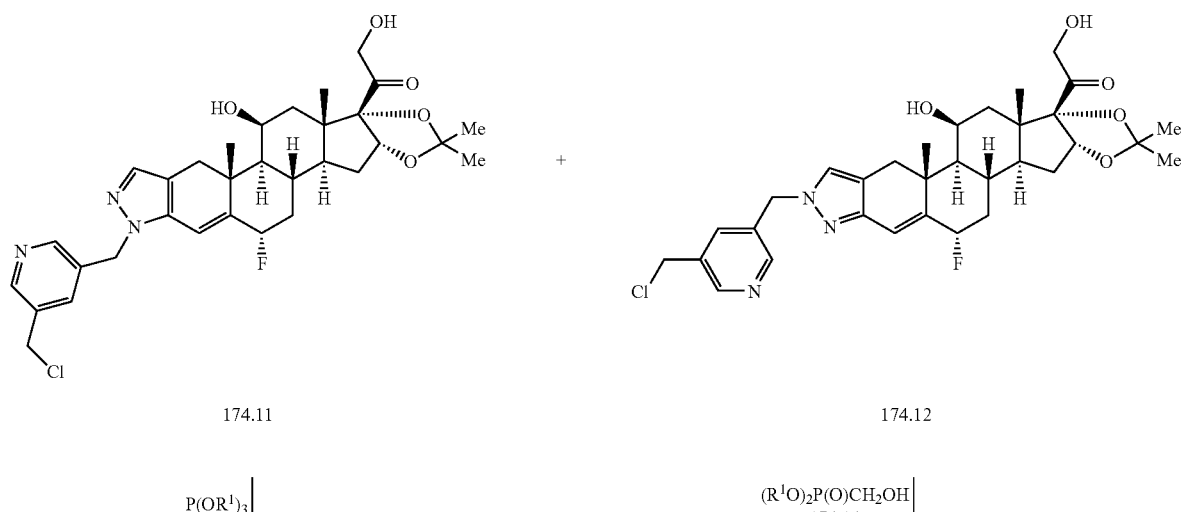

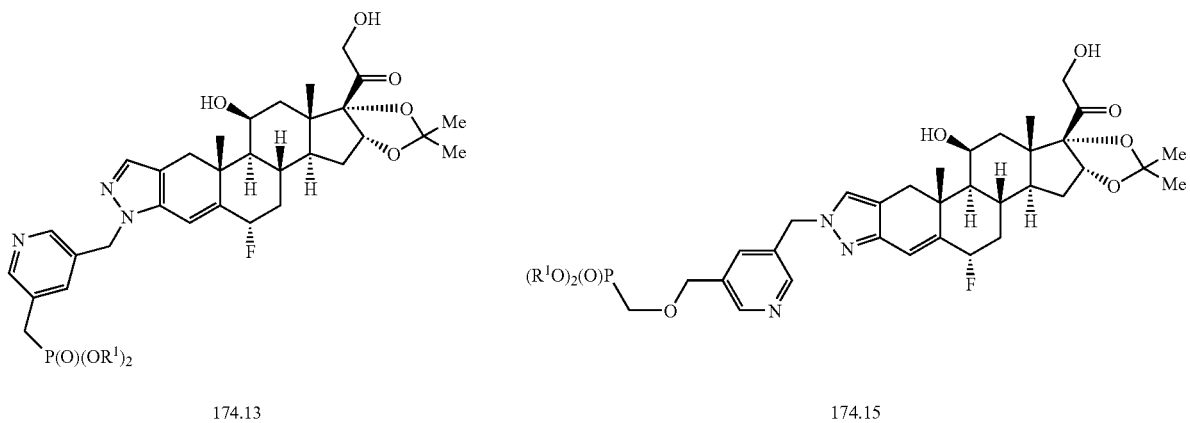

174.13

174.15

Representative compounds of the invention can be prepared as illustrated above. The pyrazole 174.1 is reacted in tetrahydrofuran solution with one molar equivalent of 3,5-bis(chloromethyl)pyridine 174.10 (*Eur. J. Inorg. Chem.* 2:163 (1998)) and potassium hexamethyl disilazide, to give the alkylation products 174.11 and 174.12. The 2'-substituted isomer 174.11 is then reacted, in an Arbuzov reaction, with a trialkyl phosphite and a catalytic amount of potassium bromide, to yield the phosphonate 174.13. The Arbuzov reaction is described in *Handb. Organophosphorus Chem.* 115 (1992). In this procedure, in which a halo substituent is converted into the corresponding phosphonate, the substrate is heated at from about 60° C. to about 160° C. with a five to fifty-fold molar excess of a trialkyl phosphite, to effect the transformation.

The 2'-substituted pyrazole 174.12 is reacted at 70° C. in dimethylformamide solution with one molar equivalent of a dialkyl hydroxymethyl phosphonate 174.14 (Aldrich) and cesium carbonate, to give the ether phosphonate 174.15.

Using the above procedures, but employing different dihalides, and/or different hydroxyl-substituted phosphonates, products analogous to 174.13 and 174.15 are obtained.

EXAMPLES 175-178

Medroxyprogesterone Derivatives

The synthesis of representative phosphonate derivatives of medroxyprogesterone is outlined in Examples 175-178. In these Examples, it may be necessary to protect certain reactive substituents from unwanted reactions by protection before the sequence described, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

EXAMPLE 175

Preparation of Representative Medroxyprogesterone

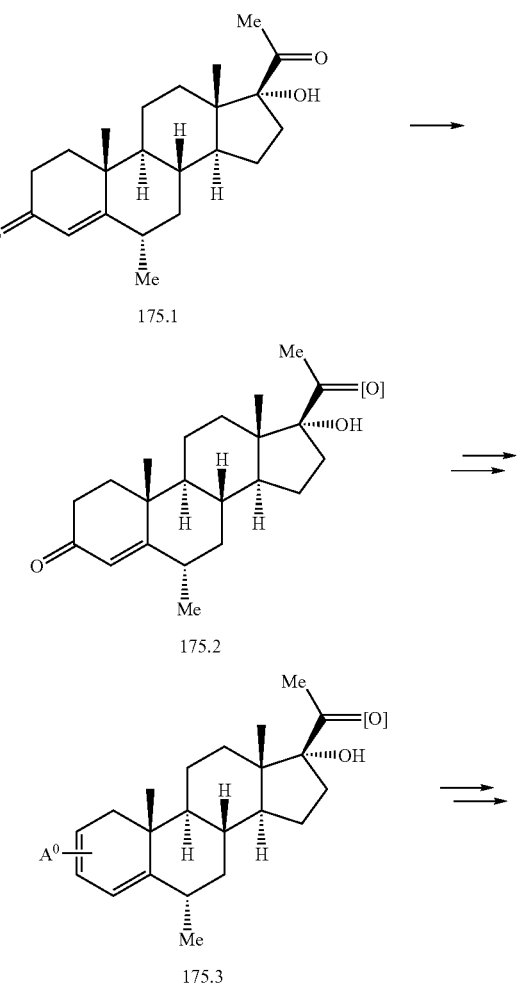

175.1

175.2

175.3

-continued

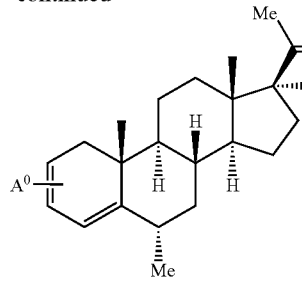
175.4

Representative compounds of the invention can be prepared as illustrated above. The 20-ketone group of medroxyprogesterone 175.1 (U.S. Pat. Nos. 3,043,832, 3,061,616, and 3,377,364) is protected to afford the derivative 175.2. The ketone is protected, for example, by conversion to the cyclic ethylene ketal, by reaction in toluene solution at reflux temperature with ethylene glycol and an acid catalyst, as described in *J. Am. Chem. Soc.*, 77:1904 (1955). Deprotection is effected by reaction with pyridinium tosylate in aqueous acetone, as described in *J. Chem. Soc. Chem. Comm.* 1351 (1987).

Alternatively, the 20-ketone is protected by conversion to the N,N-dimethylhydrazone. The dimethyl hydrazone is prepared by the reaction of the ketone 175.1 with N,N-dimethylhydrazine in ethanol-acetic acid, as described in *Org. Syn.* 50:102 (1970). The group is removed by treatment with sodium acetate and acetic acid in aqueous tetrahydrofuran, as described in *J. Am. Chem. Soc.* 101:5841 (1979).

Alternatively, the 20-ketone is protected as the diethylamine adduct. In this procedure, the substrate 175.1 is reacted with titanium tetrakis(diethylamide), as described in *J. Chem. Soc. Chem. Comm.* 406 (1983), to afford the adduct. The ketone is deprotected by reaction with water in an aqueous organic solvent.

The protected compound 175.2 is then converted into the phosphonate-containing analog 175.3, using the procedures described below, and the protecting group or groups are then removed, as described above, to give the phosphonate 175.4.

EXAMPLE 176

Preparation of Representative Medroxyprogesterone

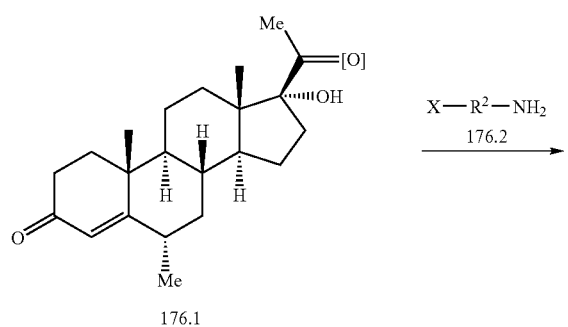

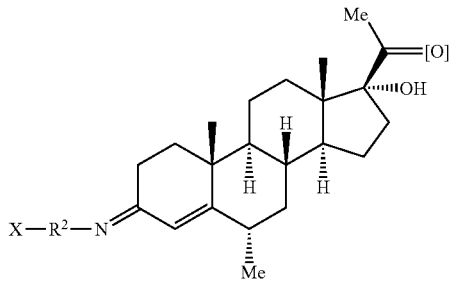
176.3

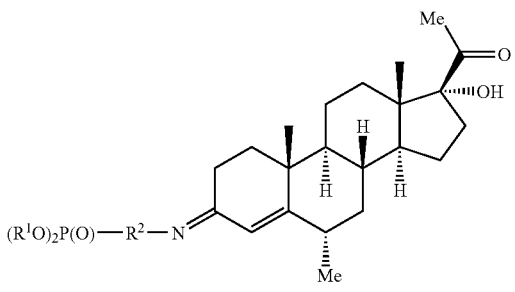
176.4

$(R^1O)_2P(O)-R^2-CH_2Lv$
176.5

$\xrightarrow{\text{BOCNHOH}}$
176.6

$(R^1O)_2P(O)-R^2-CH_2ONHBOC$
176.7

↓

$(R^1O)_2P(O)-R^2-CH_2ONH_2$
176.8

The preparation of phosphonates in which the phosphonate is attached by means of an imine or iminoxy group and a variable carbon chain is illustrated above. In this procedure, the ketone-protected derivative 176.1 is reacted with a hydroxylamine or amine 176.2, in which $R^2$ is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the oxime 176.3. The preparation of oximes of steroidal 3-ketones is described in *Anal. Bioch.* 86:133 (1978) and in *J. Mass. Spectrom.*

30:497 (1995). The protecting group is then removed to afford the 20-keto phosphonate product 176.4.

The preparation of hydroxylamine ethers incorporating a phosphonate group is also illustrated. In this procedure, a phosphonate 176.5, in which Lv is a leaving group such as bromo or trifluoromethylsulfonyloxy, is reacted with BOC-hydroxylamine 176.6 (Aldrich) to produce the ether 176.7. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 176.8. The above procedure is also employed for the preparation of substituted hydroxylamines which are precursors to phosphonates.

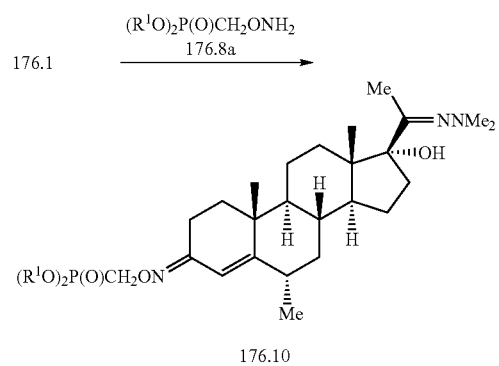

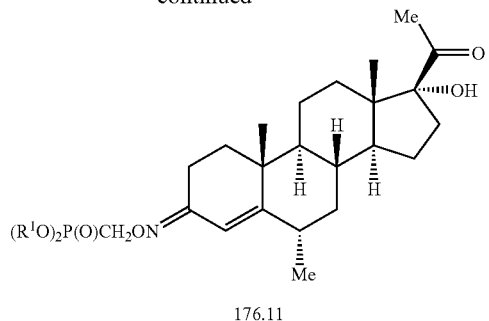

The preparation of phosphonates in which the phosphonate is attached by means of an iminoxy group is illustrated above. In this procedure, the substrate 176.1, in which the 20-ketone is protected as the dimethyl hydrazone derivative, is reacted with a dialkyl phosphonomethyl hydroxylamine 176.8a, prepared as described above from a dialkyl trifluoromethylsulfonyloxymethyl phosphonate (*Tetrahedron Lett.* 27:1477 (1986)) and BOC-hydroxylamine, to afford the oxime 176.10. Deprotection affords the 20-keto phosphonate 176.11. The oxime forming reaction is performed at ambient temperature in ethanol-acetic acid solution between equimolar amounts of the reactants.

Using the above procedures, but employing, in place of the hydroxylamine ether 176.8a, different oxime ethers 176.2, the corresponding products 176.4 are obtained.

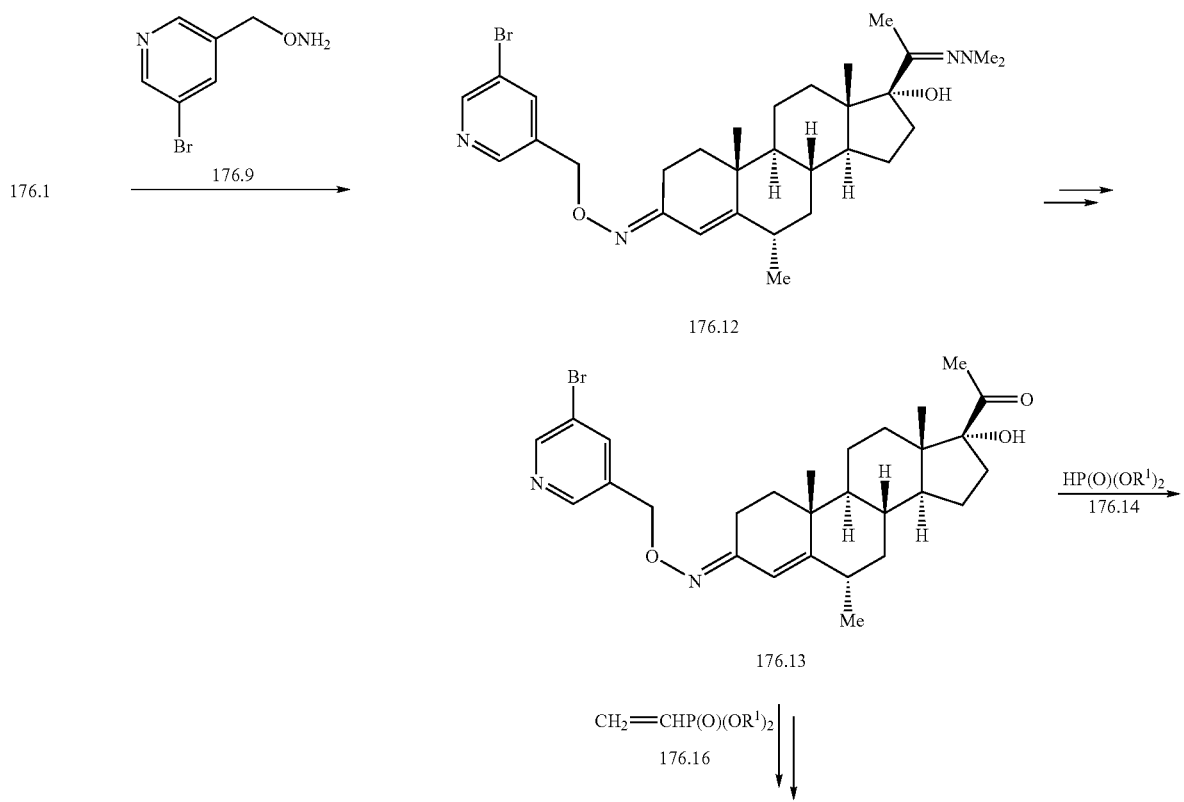

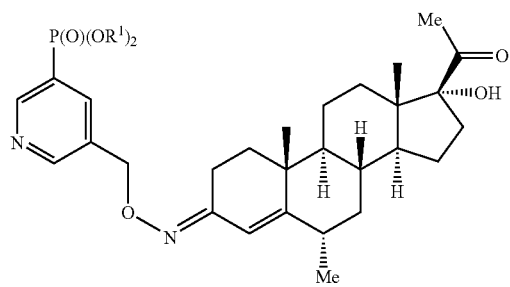

176.15

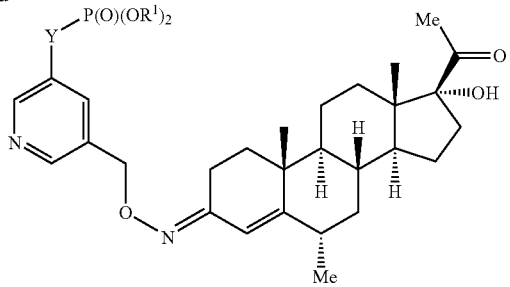

176.17: Y=CH=CH
176.18: Y=(CH$_2$)$_2$

-continued

The preparation of compounds in which the phosphonate group is attached by means of a pyridylmethoxy oxime group is illustrated above. In this procedure, the enone 176.1, in which the 20-ketone is protected as the dimethyl hydrazone, is reacted, as described above, with O-(5-bromo-3-pyridylmethoxy)hydroxylamine 176.9, prepared as described above from 5-bromo-3-bromomethylpyridine (WO 9528400) and BOC-protected hydroxylamine 176.6, to give the oxime 176.12. The protecting group is then removed to yield the 20-keto product 176.13. The latter product is then reacted, in the presence of a palladium catalyst, with a dialkyl phosphite 176.14 to afford the phosphonate 176.15. The preparation of arylphosphonates by means of a coupling reaction between aryl bromides and dialkyl phosphites is described in *J. Med. Chem.* 35:1371 (1992). The reaction is performed at ca. 100° C. in an inert solvent such as toluene, in the presence of a base such as triethylamine and a catalytic amount of tetrakis(triphenylphosphine)palladium(0).

Alternatively, the bromo compound 176.13 is coupled with a dialkyl vinylphosphonate 176.16 (Aldrich) to afford the phosphonate 176.17. The coupling of aryl halides with olefins by means of the Heck reaction is described, for example, in F. A. Carey and R. J. Sundberg, *Advanced Organic Chemistry* 503ff (Plenum, 2001) and in *Acc. Chem. Res.* 12:146 (1979). The aryl bromide and the olefin are coupled in a polar solvent such as dimethylformamide or dioxane, in the presence of a palladium(0) catalyst such as tetrakis(triphenylphosphine) palladium(0) or palladium(II) catalyst such as palladium(II) acetate, and optionally in the presence of a base such as triethylamine or potassium carbonate. Optionally, the styrenoid double bond present in the product 176.17 is reduced, for example by reaction with diimide, to produce the saturated analog 176.18. The reduction of olefinic bonds is described in R. C. Larock, *Comprehensive Organic Transformations* 6ff (VCH 1989). The transformation is effected by means of catalytic hydrogenation, for example using a palladium on carbon catalyst and hydrogen or a hydrogen donor, or by the use of diimide or diborane.

Using the above procedures, but employing, in place of the bromopyridyl reagent 176.9, different bromo-substituted aryl or heteroaryl alkoxy hydroxylamines, and/or different dialkyl alkenyl phosphonates, products analogous to the compounds 176.15, 176.17 and 176.18 are obtained.

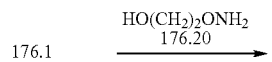

176.1 $\xrightarrow{\text{HO(CH}_2\text{)}_2\text{ONH}_2}{176.20}$

-continued

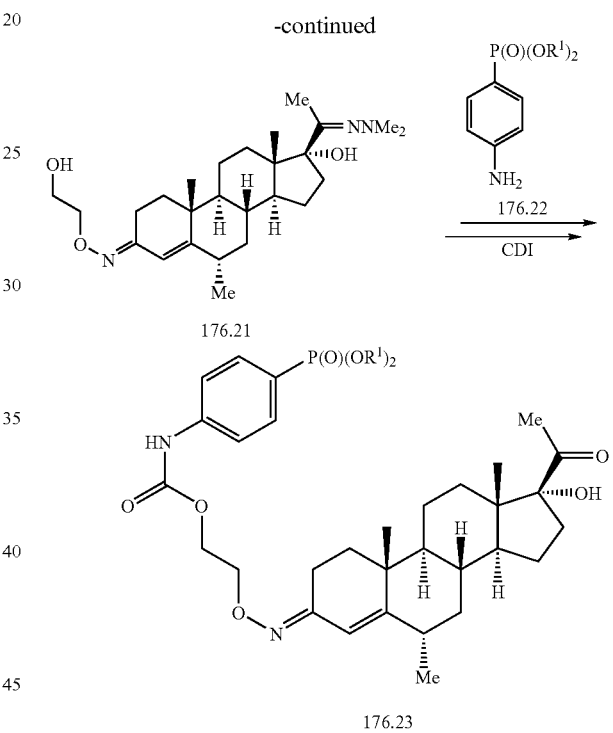

The preparation of phosphonates in which the phosphonate is attached by means of an oximino group and a carbamate linkage is illustrated above. In this procedure, the enone 176.1, in which the 20-ketone is protected as the dimethylhydrazone, is reacted with 2-hydroxyethyl hydroxylamine 176.20 (*J. Chem. Soc. Chem. Comm.* 903 (1986)) to yield the oxime 176.21. The reaction of unsaturated steroidal ketones with hydroxylamines is described in *J. Steroid Bioch.* 7:795 (1976). The reaction is performed between equimolar amounts of the reactants in a polar organic solvent such as pyridine or methanol, optionally in the presence of acetic acid or sodium acetate. The product 176.21 is then coupled with a dialkyl 4-aminophenyl phosphonate 176.22 (Epsilon) and carbonyl diimidazole, to yield, after deprotection, the carbamate oxime 176.23. The preparation of carbamates is described in *Comprehensive Organic Functional Group Transformations Vol.* 6 416ff (A. R. Katritzky, ed., Pergamon, 1995) and in S. R. Sandler and W. Karo, *Organic Functional Group Preparations* 260ff (Academic Press, 1986). In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and the like, to afford the corresponding activated acylamine. The latter compound is then reacted with an alcohol to yield the carbamate.

Using the above procedures, but employing, in place of the hydroxy-substituted hydroxylamine 176.20, different hydroxy-substituted hydroxylamines, and/or different amino-substituted phosphonates, the products analogous to 176.23 are obtained.

EXAMPLE 177

Preparation of Representative Medroxyprogesterone

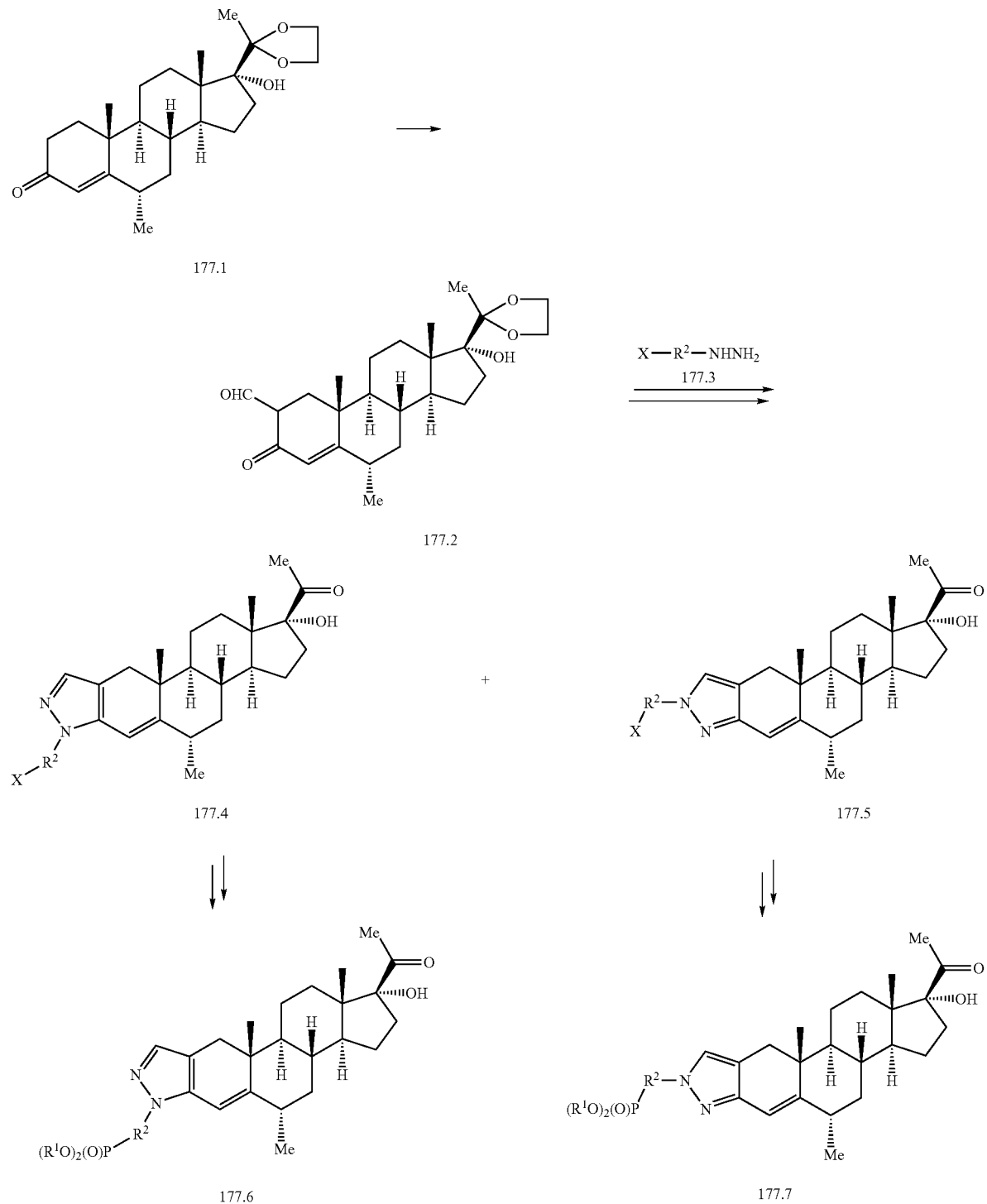

The preparation of the phosphonate esters in which the phosphonate group is attached to the 1' or 2' position of the pyrazole ring, by means of an aromatic or heteroaromatic group, a heteroatom and/or a variable carbon chain is illustrated above. In this procedure, the enone 177.1 in which the 20-ketone is protected as the cyclic ethylene ketal, is reacted with ethyl formate and a base such as sodium hydride, in an inert solvent such as toluene or dimethylformamide, as described in *J. Am. Chem. Soc.* 86:1520 (1964), to afford the 2-formyl product 177.2. This compound is then reacted with an alkyl, aralkyl, aryl or heteroaryl hydrazine 177.3, in which the substituent X is either a phosphonate group or a group which is subsequently transformed into a phosphonate-containing substituent. For example, X is dialkylphosphono, bromo, hydroxy, amino, carboxyl and the like. The reaction yields, after deprotection of the 20-ketone, the isomeric 2'- and 1'-aryl pyrazoles 177.4 and 177.5. The pyrazole-forming reaction is performed between equimolar amounts of the reactants in an acidic solvent such as acetic acid, as described in *J. Am. Chem. Soc.* 86:1520 (1964). The pyrazoles 177.4 and 177.5 are then transformed into the phosphonates 177.6 and 177.7.

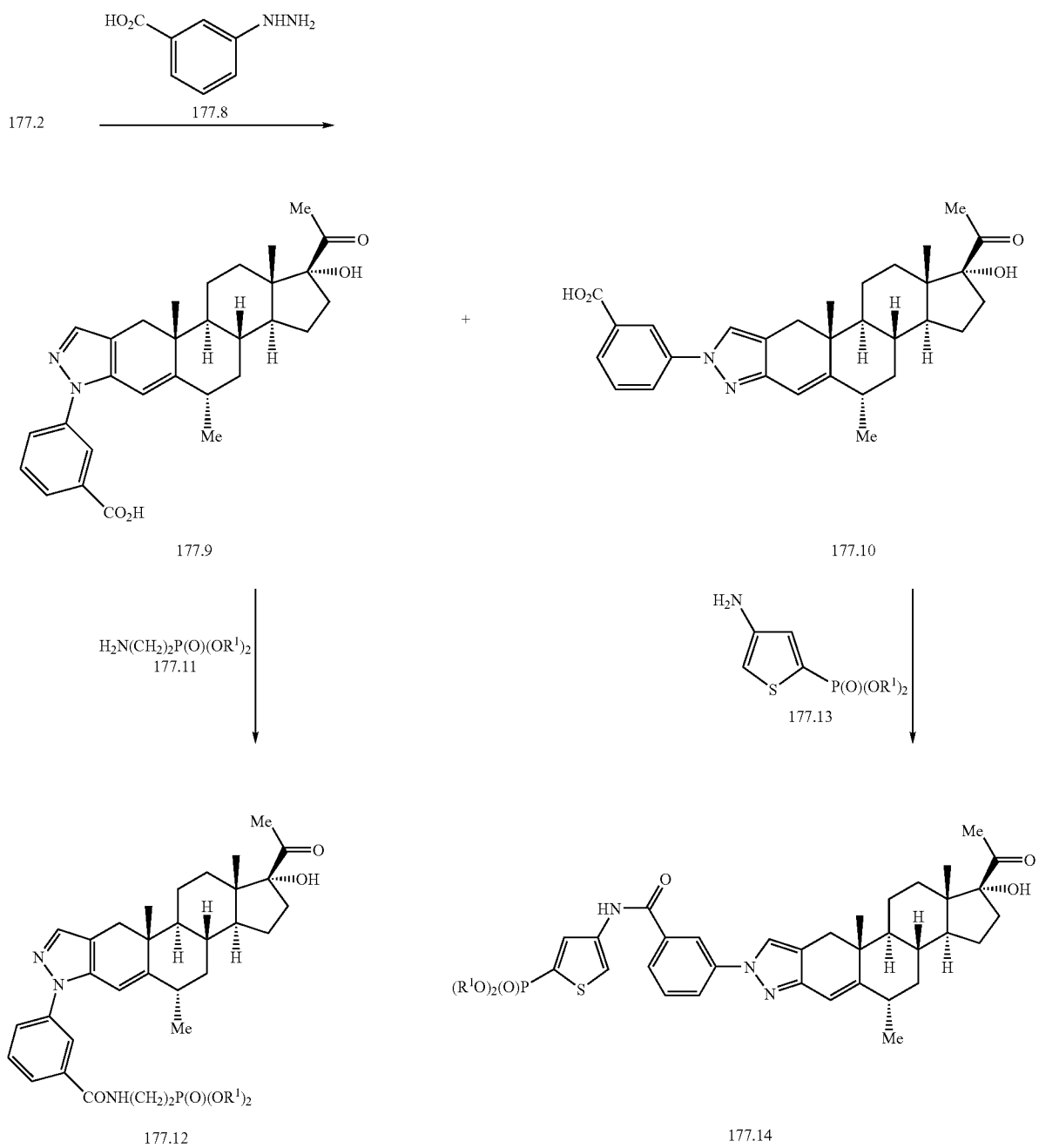

The preparation of phosphonates in which the phosphonate is attached by means of a phenyl ring and an amide linkage is illustrated above. In this procedure, the ketoaldehyde 177.2 is reacted, as described above, with 3-carboxyphenyl hydrazine 177.8 (Apin) to give the pyrazoles 177.9 and 177.10. The 2'-substituted isomer 177.9 is then reacted in dimethylformamide solution at ambient temperature with one molar equivalent of a dialkyl 2-aminoethyl phosphonate 177.11 (Aldrich) and dicyclohexyl carbodiimide, to give the amide phosphonate 177.12. The preparation of amides from carboxylic acids and derivatives is described, for example, in S. R. Sandler and W. Karo, *Organic Functional Group Preparations* 274 (Academic Press, 1968) and R. C. Larock, *Comprehensive Organic Transformations* 972ff (VCH, 1989). The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide.

The isomeric pyrazole 177.10 is reacted, as described above, with one molar equivalent of a dialkyl 4-amino-2-thienyl phosphonate R2.20, prepared by the palladium catalyzed coupling reaction, as described above, between 4-amino-2-bromothiophene (*Tetrahedron Lett.* 43:3295 (1987)) and a dialkyl phosphite, to give the amide phosphonate 177.14.

Using the above procedures, but employing different carboxy-substituted hydrazines, and/or different amino-substituted phosphonates, the products analogous to 177.12 and 177.14 are obtained.

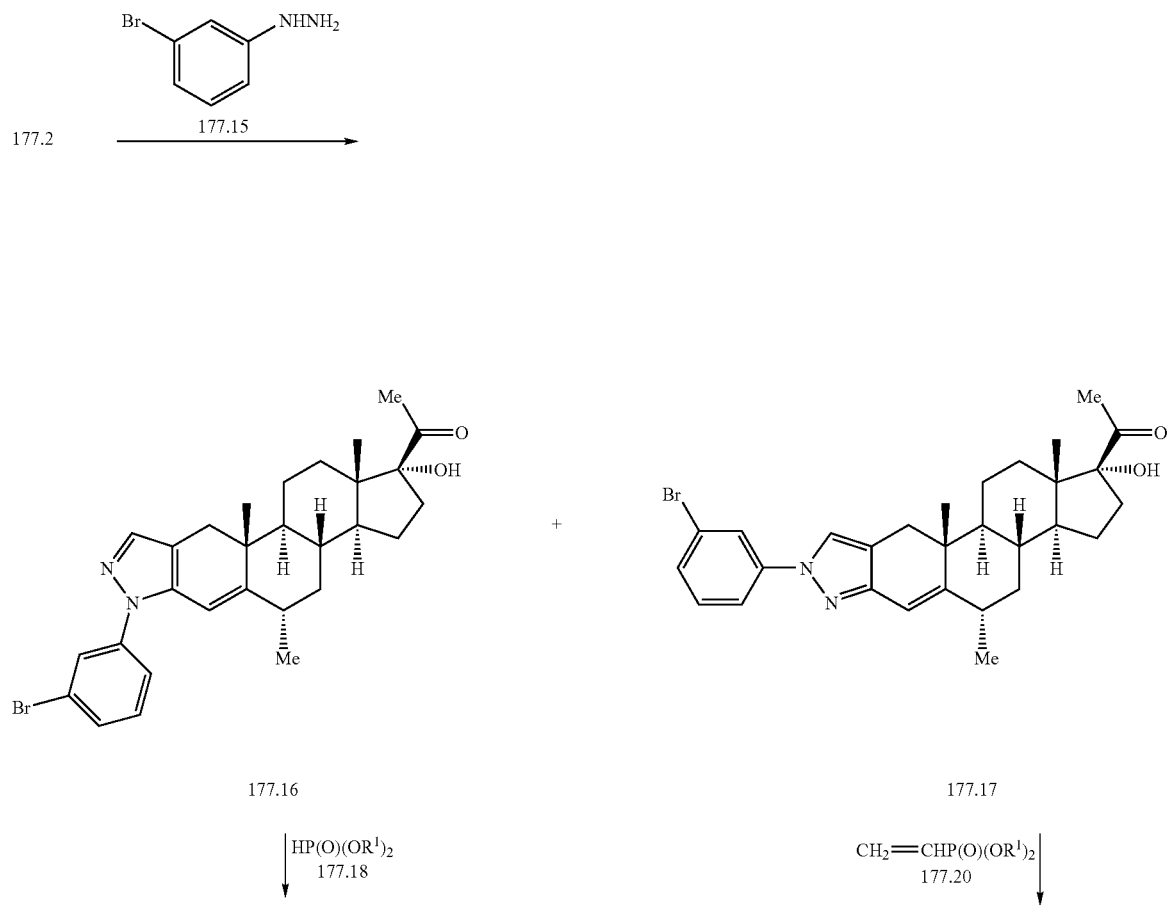

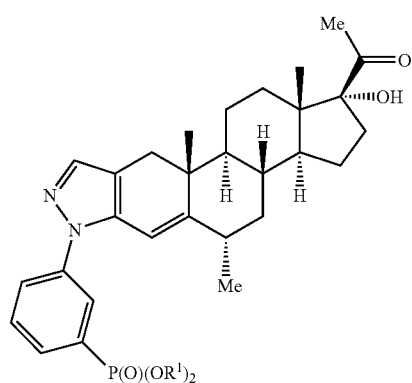

177.19

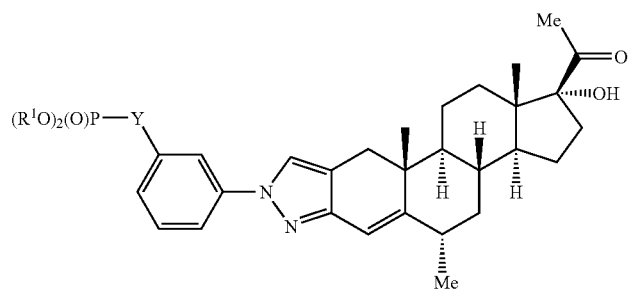

177.21a: Y=CH=CH
177.21b: Y=(CH₂)₂

The preparation of the phosphonates in which the phosphonate group is attached by means of a phenyl group or a phenyl group and a carbon chain is illustrated above. In this procedure, the ketoaldehyde 177.2 is reacted, as described above, with 3-bromophenyl hydrazine 177.15 (Fluka) to produce the pyrazoles 177.16 and 177.17. The 2'-substituted isomer 177.16 is then coupled, as described above, with a dialkyl phosphite 177.18 to afford the phosphonate 177.19.

Alternatively, the 1'-substituted pyrazole 177.17 is coupled, as described above, with a dialkyl vinylphosphonate 177.20 (Aldrich) and a palladium catalyst to prepare the vinyl phosphonate 177.21a. Optionally, the product is reduced, as described above, to give the analog 177.21b.

Using the above procedures, but employing, in place of the bromophenyl hydrazine 177.15, different bromo-substituted hydrazines, and/or different dialkyl alkenyl phosphonates, the products analogous to the compounds 177.19 and 177.21 are obtained.

EXAMPLE 178

Preparation of Representative Medroxyprogesterone

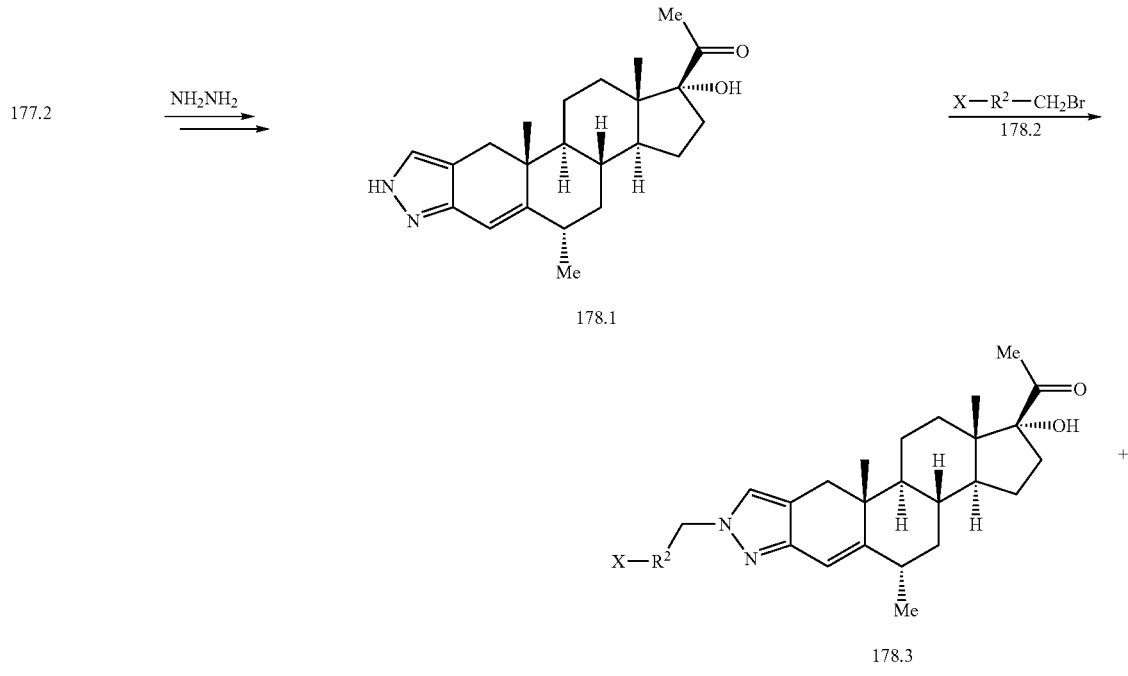

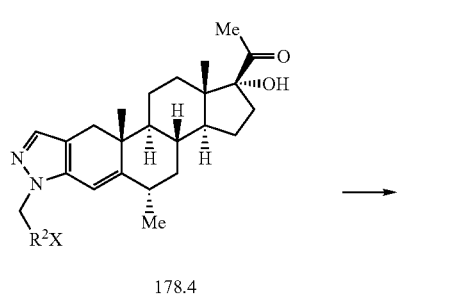

178.4

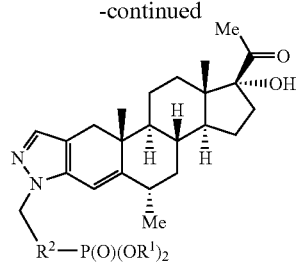

178.6

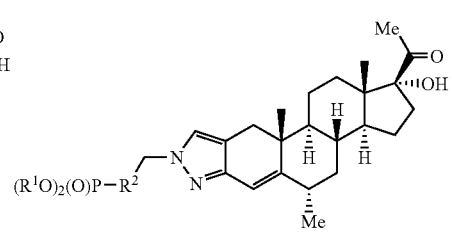

178.5

The preparation of the phosphonate esters in which the phosphonate group is attached by means of a variable carbon linkage is illustrated above. In this procedure, the ketoaldehyde 177.2 is reacted with hydrazine to afford, after deprotection of the 20-ketone, the pyrazole derivative 178.1. The reaction of steroidal 2-formyl-3-ketones with hydrazine is described in *J. Am. Chem. Soc.* 86:1520 (1964). The reaction is performed in acetic acid at ambient temperature. The pyrazole product is then reacted with a bromomethyl compound 178.2, in which $R^2$ and X are as defined above, or a reactive Tbromoheteroaromatic reagent, to yield the alkylation products 178.3 and 178.4. The alkylation of substituted pyrazoles is described, for example, in T. L. Gilchrist, *Heterocyclic Chemistry* 309 (Longman, 1992). The reaction is performed between equimolar amounts of the substrates in a polar solvent such as dimethylformamide or tetrahydrofuran, in the presence of a base such as dimethylaminopyridine, lithium hexamethyldisilazide and the like. The products 178.3 and 178.4 are, except in cases where X is dialkylphosphono, converted into the phosphonates 178.5 and 178.6, using the procedures described herein.

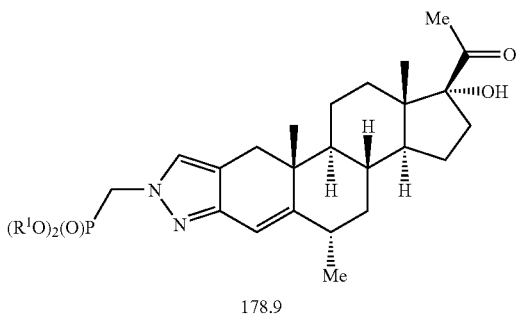

178.9

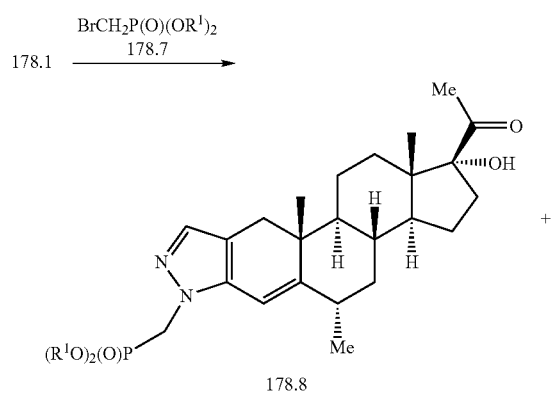

178.8

Representative compounds of the invention can be prepared as illustrated above. The pyrazole 178.1 is reacted in dimethylformamide solution at 70° C. with one molar equivalent of a dialkyl 4-bromomethyl phosphonate 178.7 (Lancaster) and lithium hexamethyl disilazide, to give the pyrazoles 178.8 and 178.9.

Using the above procedures, but employing different bromo-substituted phosphonates, the products analogous to 178.8 and 178.9 are obtained.

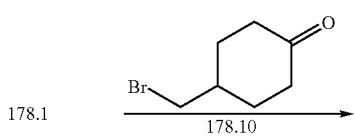

178.1    178.10

-continued

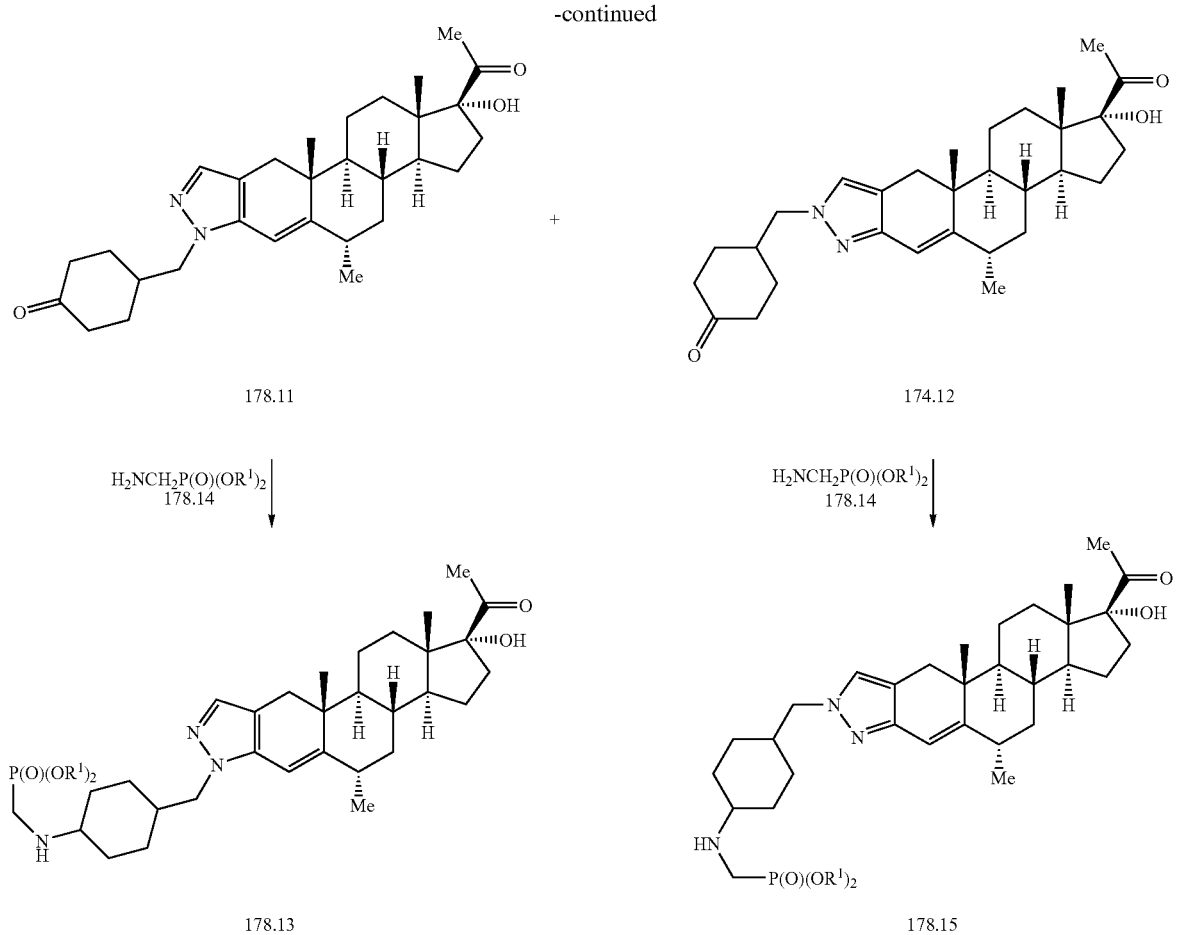

178.11

174.12

Representative compounds of the invention can be prepared as illustrated above. The pyrazole 178.1 is reacted in tetrahydrofuran solution with 4-bromomethyl cyclohexanone 178.10 (WO 9737959) and potassium hexamethyl disilazide, to give the alkylation products 178.11 and 178.12. The 2'-substituted isomer 178.11 is then reacted, in a reductive amination reaction, with a dialkyl aminomethyl phosphonate 178.14 (Interchim) and sodium triacetoxy borohydride, to yield the amine phosphonate 178.13. The preparation of amines by means of reductive amination procedures is described, for example, in R. C. Larock, *Comprehensive Organic Transformations* 421 (VCH) and in F. A. Carey and R. J. Sundberg, *Advanced Organic Chemistry, Part B* 269 (Plenum, 2001). In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in *J. Org. Chem.* 55:2552 (1990).

The 1'-substituted pyrazole 178.12 is converted by the same reaction into the isomeric amine phosphonate 178.15.

Using the above procedures, but employing different bromo-substituted aldehydes and ketones, and/or different amino-substituted phosphonates, products analogous to 178.13 and 178.15 are obtained.

EXAMPLE 179

Preparation of Representative Compounds of Formula 180

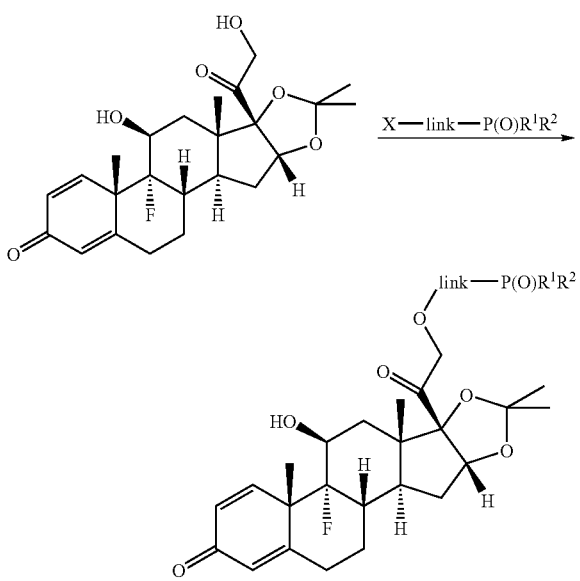

As illustrated above, derivatives of the C-21 primary hydroxy group are readily prepared by alkylating triamcinolone acetonide with the appropriate phosphonate. A specific compound of the invention can be prepared as follows.

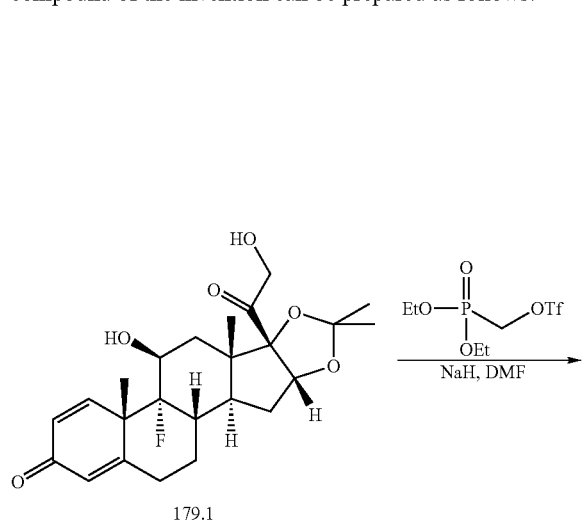

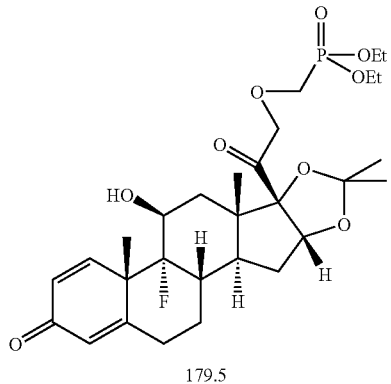

After chemoselective extraction of the primary hydroxy proton in 179.1 using one equivalent of sodium hydride, the phosphonate triflate is added to provide the ether 179.5.

EXAMPLE 180

Preparation of Representative Compounds of Formula 181

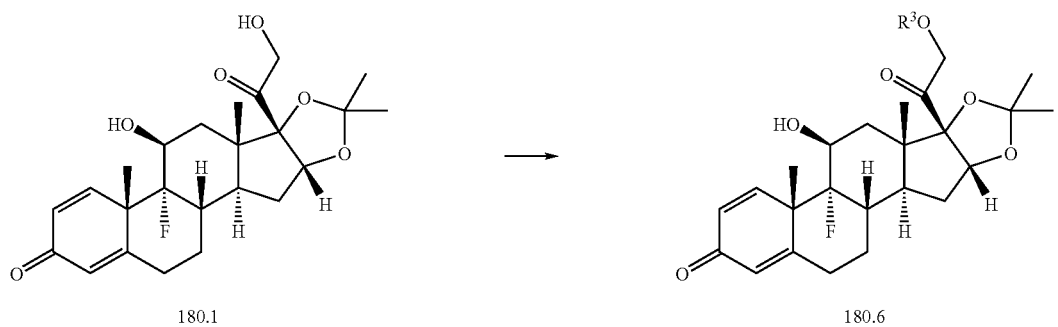

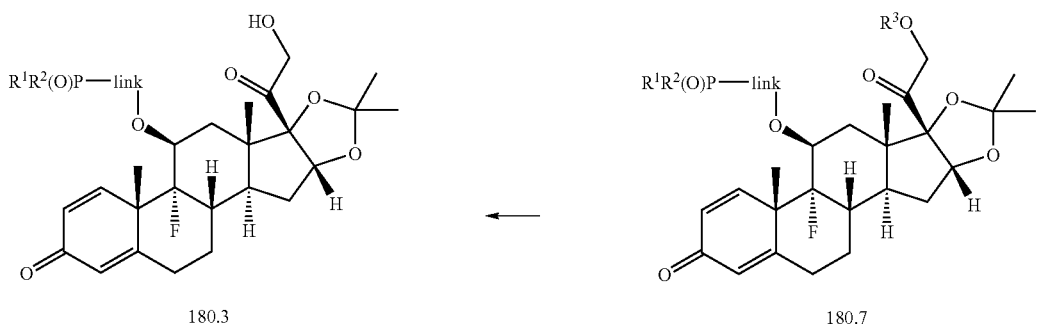

As illustrated above, by taking advantage of the reactivity difference between the primary and secondary hydroxy groups, the primary hydroxy group is masked by an appropriate protecting group. After alkylation at the secondary hydroxy moiety of 180.6 with a leaving group-attached phosphonate and subsequent deprotection, desired analog 180.3 is obtained. A specific compound of the invention can be prepared as follows.

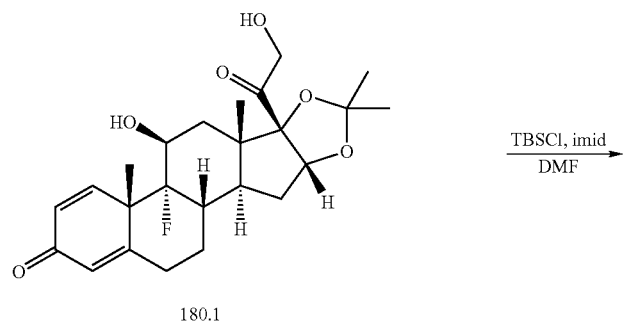

180.1

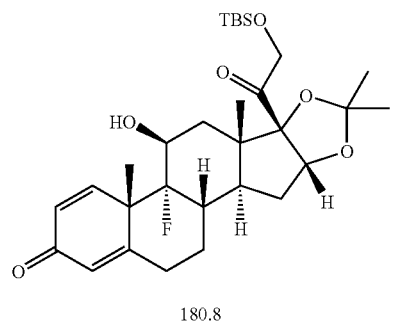

180.8

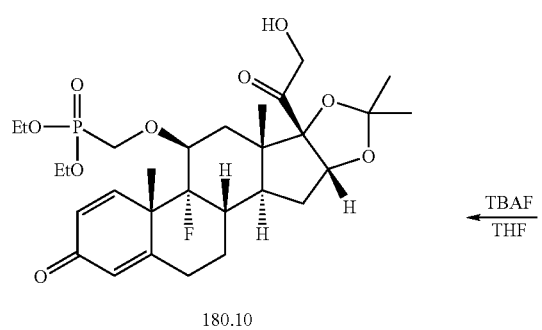

180.10

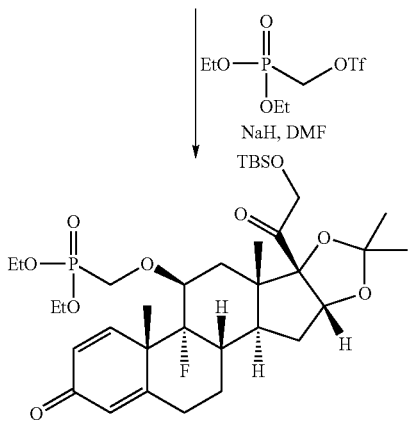

180.9

Triamcinolone acetonide 180.1 is chemoselectively protected as its silyl ether using the standard TBSCl and imidazole conditions. (*J. Am. Chem. Soc.* 1972, 94, 6190) Alkylation at the exposed secondary hydroxy group with sodium hydride and the phosphonate triflate furnishes the intermediate 180.9. Final TBAF deprotection of the silyl ether affords the desired product 180.10.

EXAMPLE 181

Preparation of Representative Compounds of Formula 182

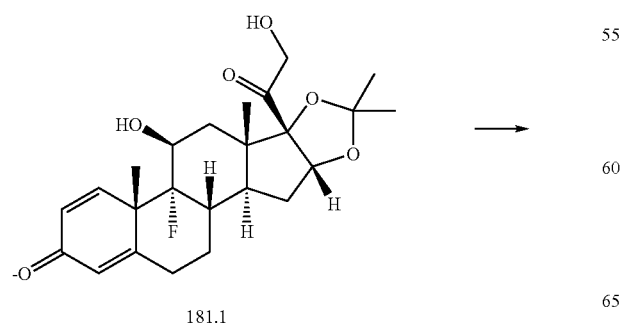

181.1

-continued

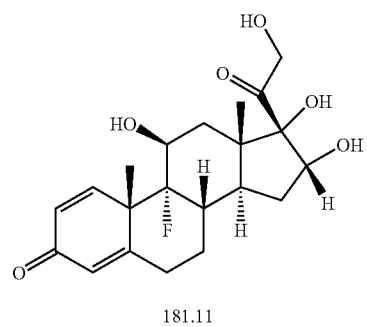

181.11

$$\downarrow OHC\text{—link—}P(O)R^1R^2$$

681

-continued

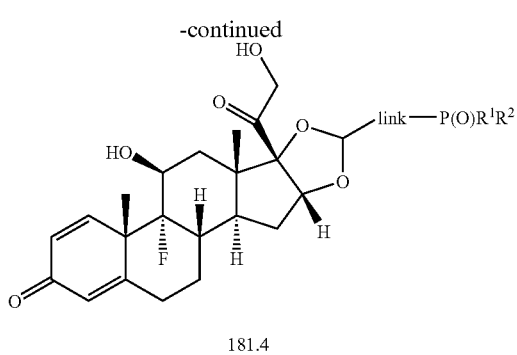

181.4

Representative compounds of the invention can be prepared as illustrated above. Phosphonate derivatives of the acetal are readily prepared from acidic hydrolysis of triamcinolone acetonide 181.1 to the diol 181.11. Acetylization of the diol with a phosphonate aldehyde furnishes the desired acetal 181.4. A specific compound of the invention can be prepared as illustrated below.

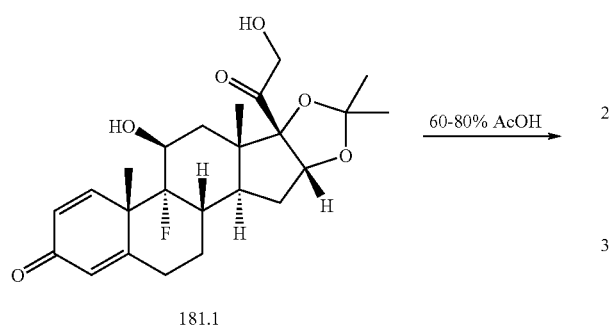

181.1

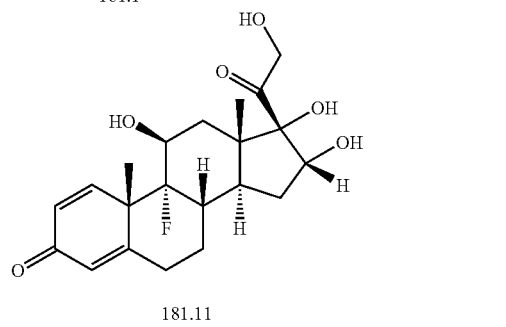

181.11

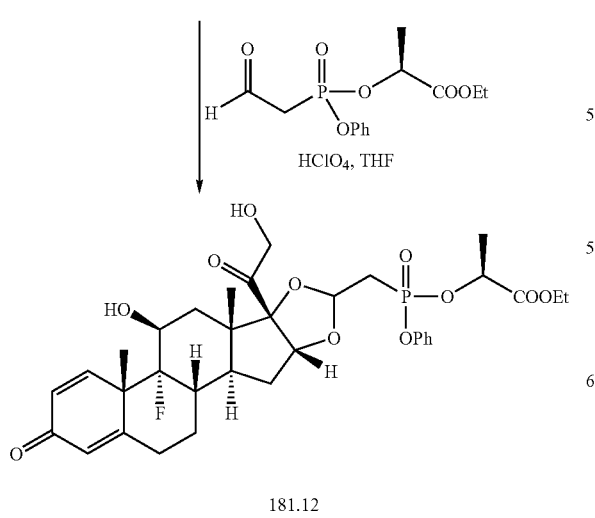

181.12

682

Triamcinolone acetonide 181.1 is first hydrolized in aqueous acetic acid. (*Can. J. Chem.* 1983, 61, 634). The resulting diol 181.11 is acetalized with the phosphonate aldehyde and perchloric acid, affording the acetal 181.12. (*J. Med. Chem.* 1996, 39, 4888-4896)

EXAMPLE 182

Preparation of Representative Compounds of Formula 183

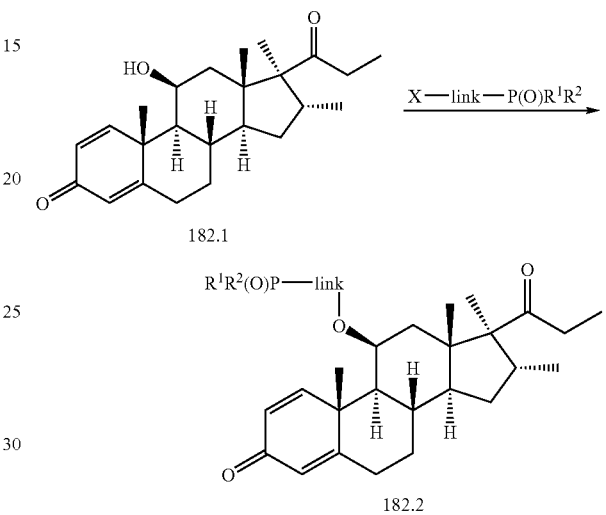

Representative compounds of the invention can be prepared as illustrated above. Derivatization at the C-11 hydroxy group is accomplished through alkylation of rimexolone 182.1 with the appropriate phosphonate, furnishing analogs of formula 182.2. A specific compound of the invention can be prepared as illustrated below.

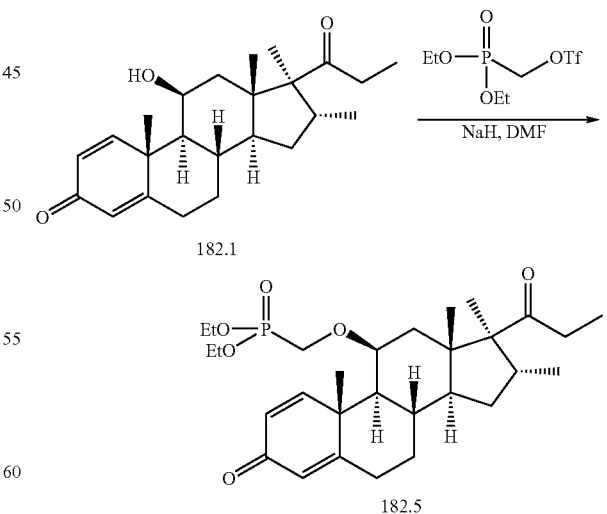

After sodium hydride extraction of the hydroxy proton in 182.1, diethyl phosphonate triflate is added to afford ether 182.5.

EXAMPLE 183

Preparation of Representative Compounds of Formula 184

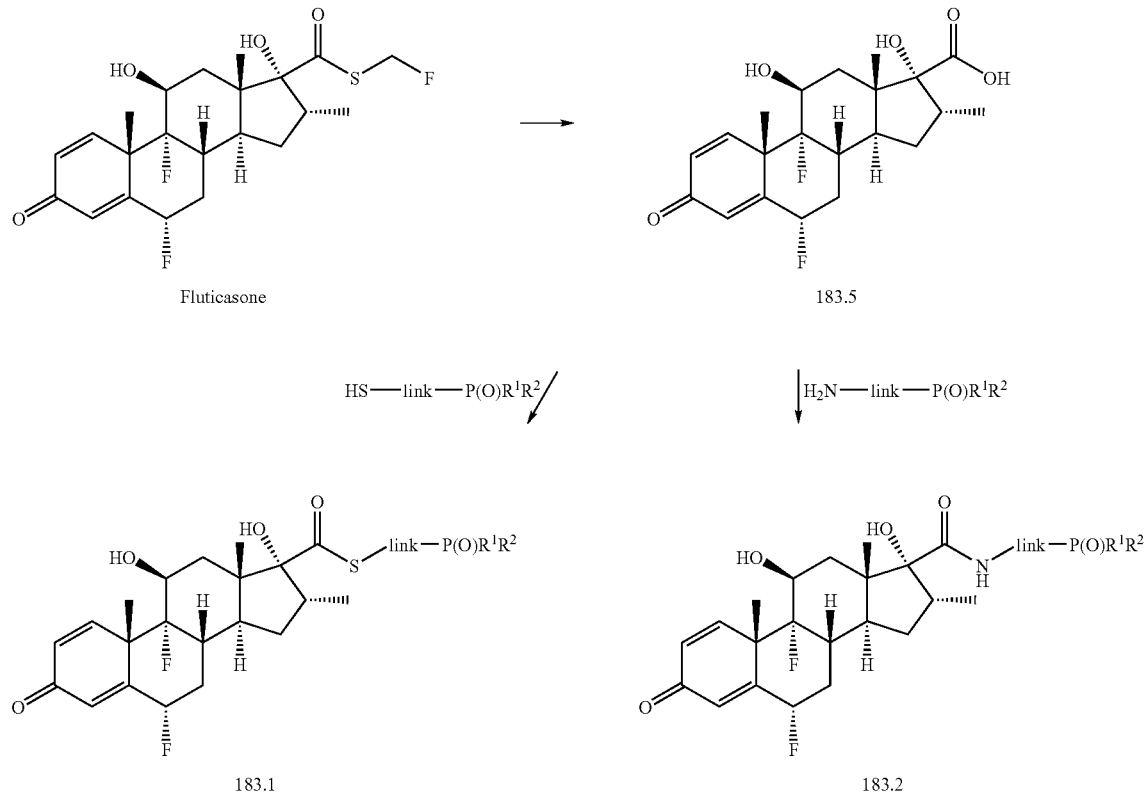

Representative compounds of the invention can be prepared as illustrated above. Derivatives of the carbonyl at C-17 are readily prepared from saponification of fluticasone to the carboxylic acid 183.5. Activation of the carboxylic acid, followed by reaction with thiophosphonate or aminophosphonate nucleophile furnishes the desired thioester 183.1 and amide 183.2, respectively. Specific compounds of the invention can be prepared as follows.

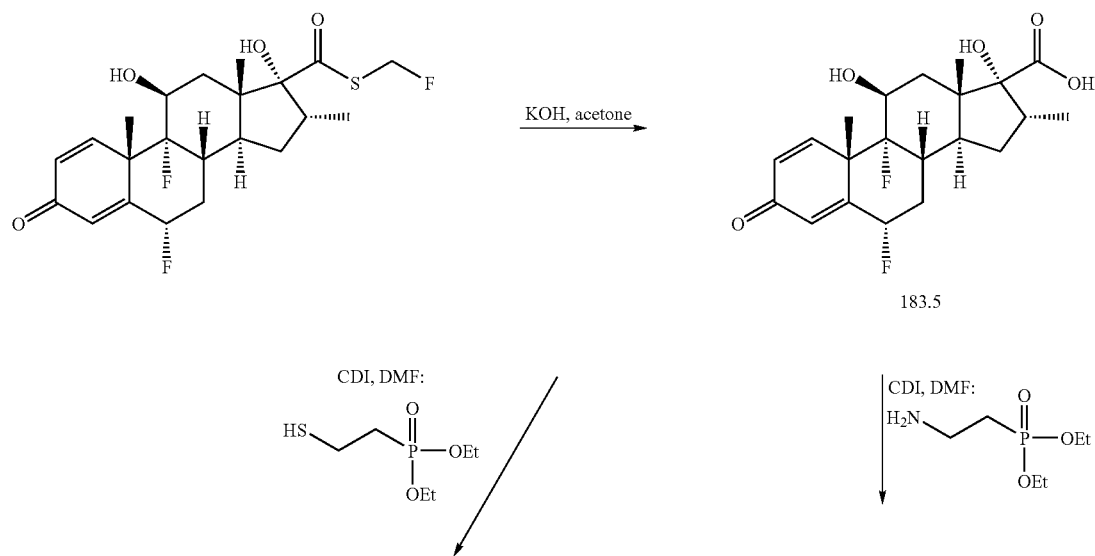

-continued

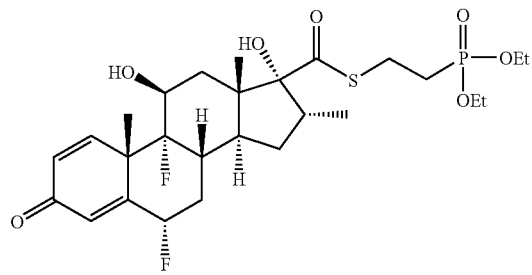

183.6

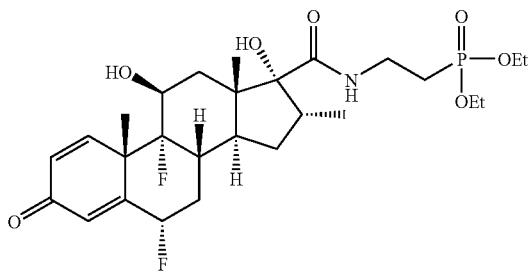

183.7

Fluticasone is first saponified with potassium hydroxide in acetone. (*Synthesis* 2002, 921-927) The resulting carboxylic acid 183.5 is activated to the carboxylic acid imidazole by the addition of 1,1'-carbonyldiimidazole (CDI). (*J. Med. Chem.* 1994, 37, 3717-3729) Treatment with the thiophosphonate affords thioester 183.6. Magnesium ethoxide may be added to help enhance the reactivity. (*Tetrahedron Lett.* 1981, 22, 3245-3246) Alternatively, the carboimidazole intermediate derived from 183.5 can be reacted with the aminophosphonate to produce amide 183.7.

EXAMPLE 184

Preparation of Representative Compounds of Formula 186

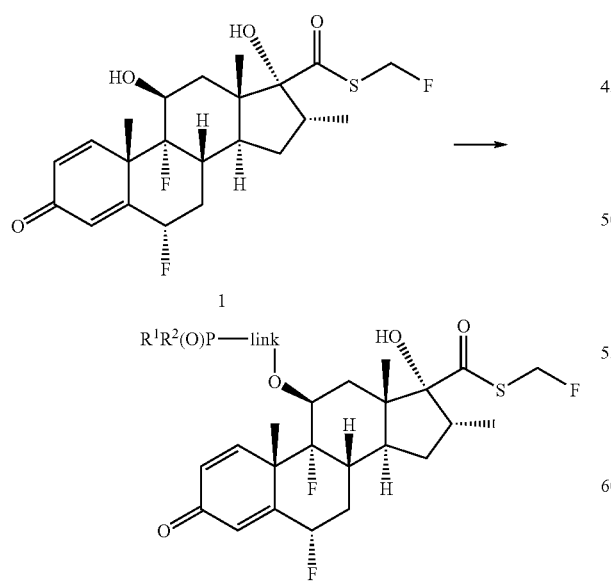

Representative compounds of the invention can be prepared as illustrated above. The less sterically hindered C-11 hydroxy group of compound 184.1 is selectively alkylated with the appropriate phosponate to give analogs of formula 184.3. A specific compound of the invention can be prepared as follows.

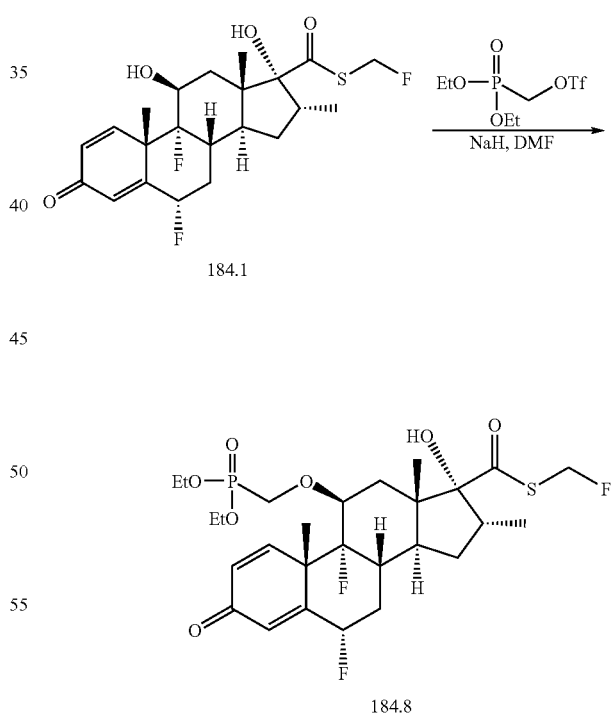

After regioselective extraction of the C-11 hydroxy proton in 184.1 using one equivalent of sodium hydride, the phosphonate triflate is added to provide the ether 184.8.

EXAMPLE 185

Preparation of Representative Compounds of Formula 187

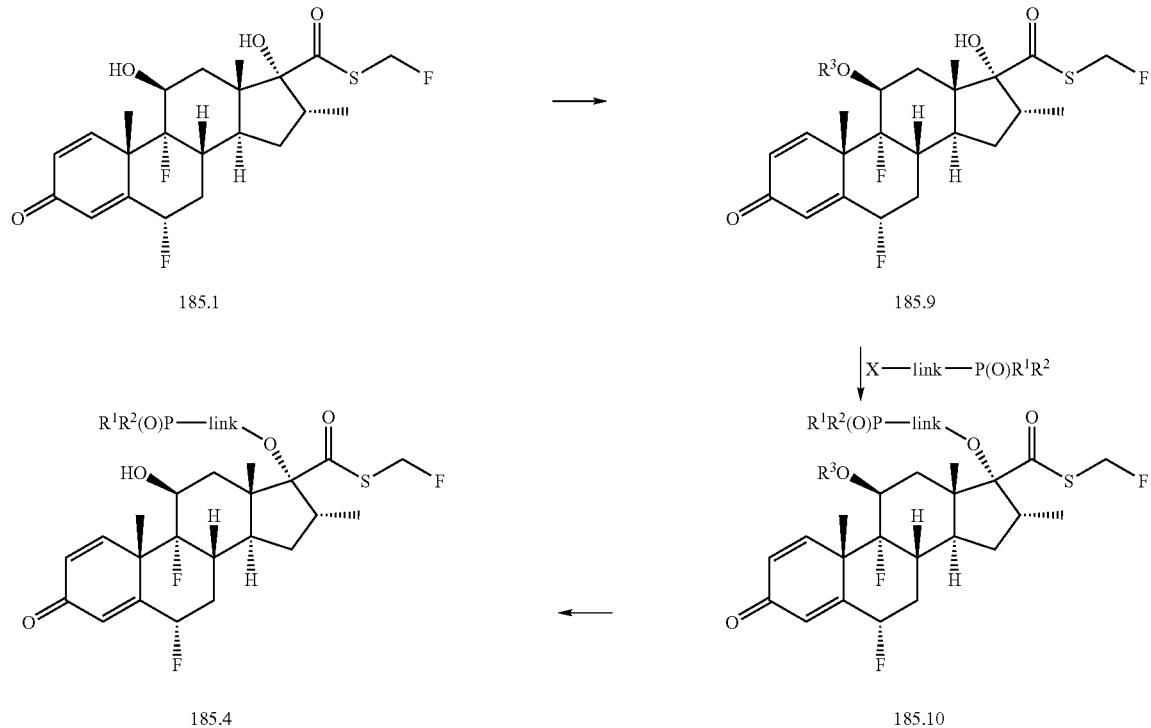

Representative compounds of the invention can be prepared as illustrated above. Again taking advantage of the reactivity difference between C-11 and C-17 hydroxy groups, the C-11 hydroxy group is masked by an appropriate protecting group. After alkylation at the C-17 hydroxy moiety of 185.9 with a leaving group-attached phosphonate and subsequent deprotection, desired analog 185.4 is obtained. A specific compound of the invention can be prepared as follows.

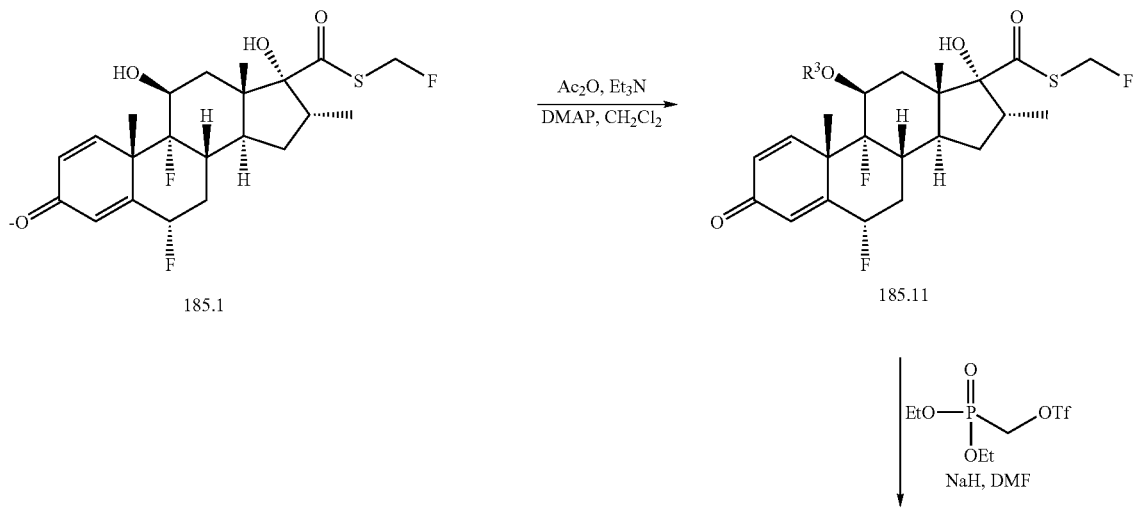

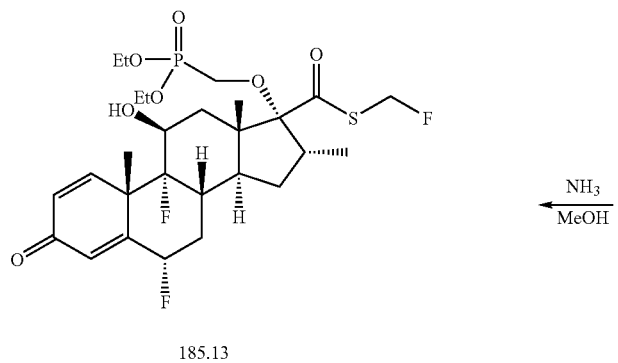

185.13

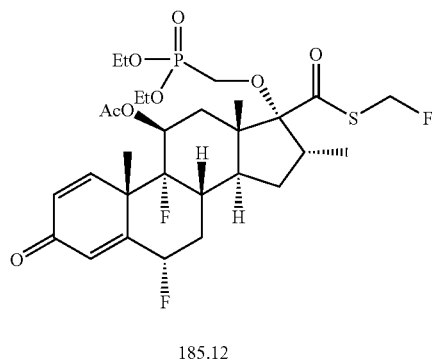

185.12

Fluticasone 185.1 is regioselectively protected as its C-11 acetate ester using the standard acetic anhydride and DMAP conditions. (*J. Org. Chem.* 1998, 63, 2342-2347) Alkcylation at the exposed C-17 hydroxy group with sodium hydride and the phosphonate triflate furnishes the intermediate 185.12. Final ammonia deprotection of the acetate affords the desired ether 185.13.

Representative compounds of the invention can be prepared as illustrated above. Derivatization at the C-11 hydroxy group is accomplished through alkylation of mometasone fuorate 186.1 with the appropriate phosphonate, furnishing analogs of formula 186.2. A specific compound of the invention can be prepared as follows.

EXAMPLE 186

Preparation of Representative Compounds of Formula 189

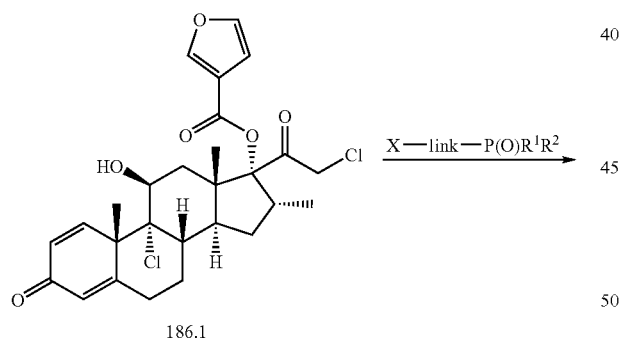

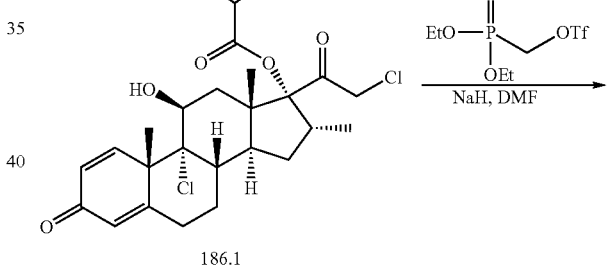

186.1

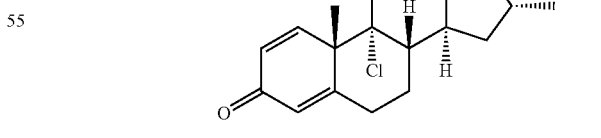

186.4

After sodium hydride extraction of the hydroxy proton in 186.1, diethyl phosphonate triflate is added to afford ether 186.4.

EXAMPLE 187

Preparation of Representative Compounds of Formula 188

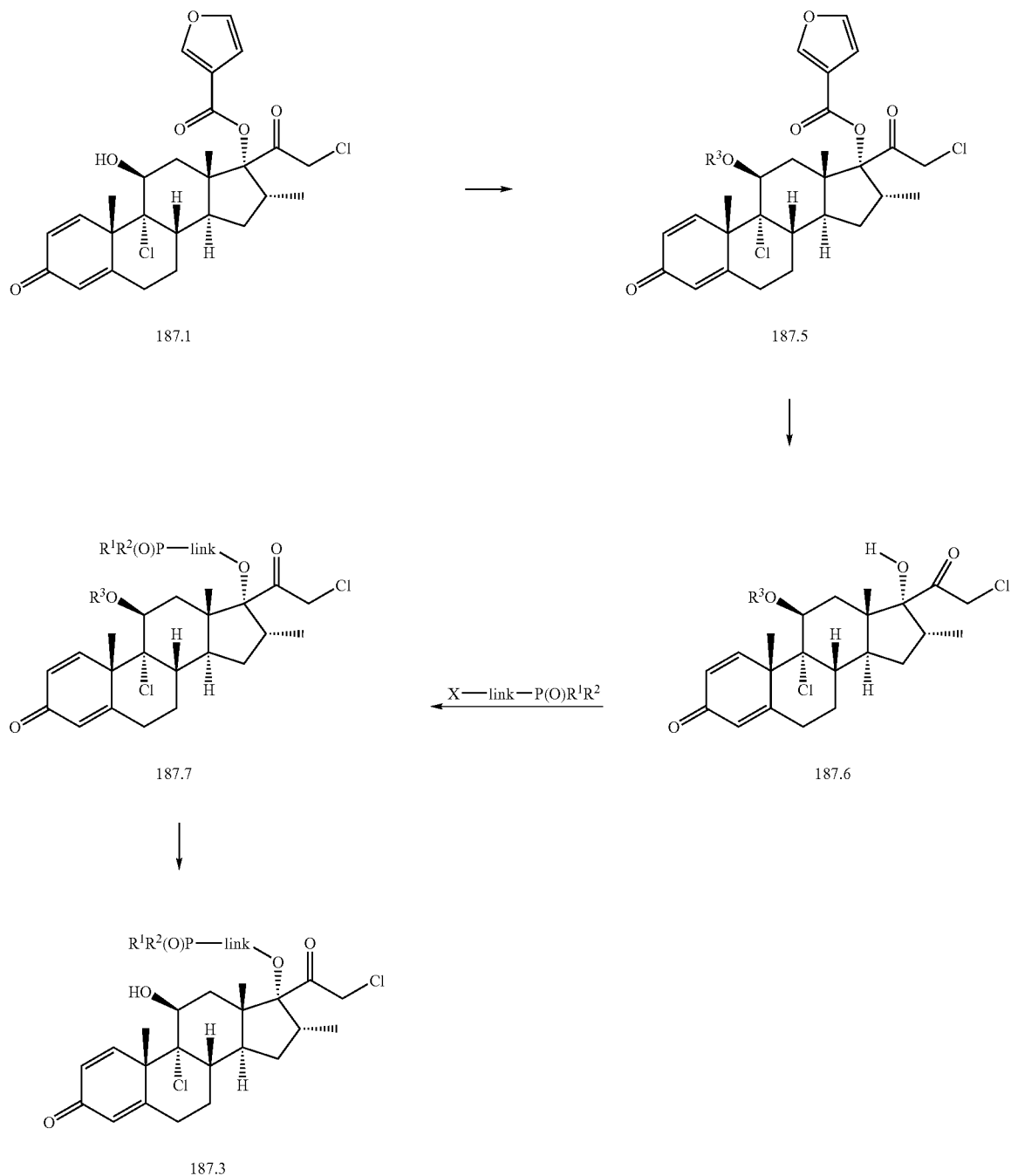

Representative compounds of the invention can be prepared as illustrated above. Following protection of the only exposed hydroxy group in mometasone fuorate 187.1, intermediate 187.5 is saponified to give alcohol 187.7. Alkylation at the C-17 hydroxy group with the appropriate phosphonate and subsequent deprotection provides the desired product 187.3. A specific compound of the invention can be prepared as follows.

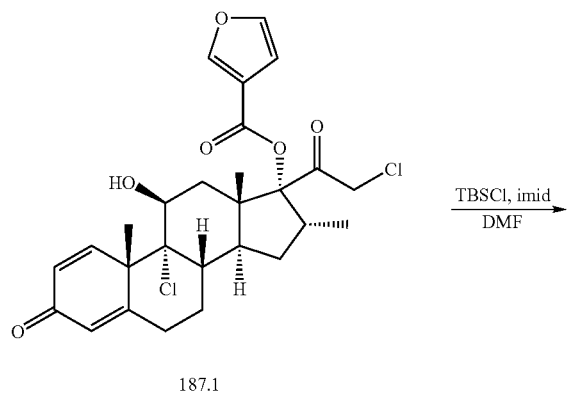

187.1

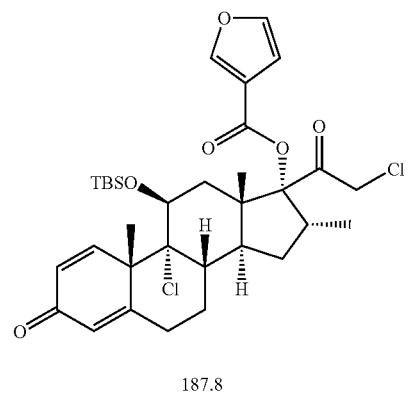

187.8

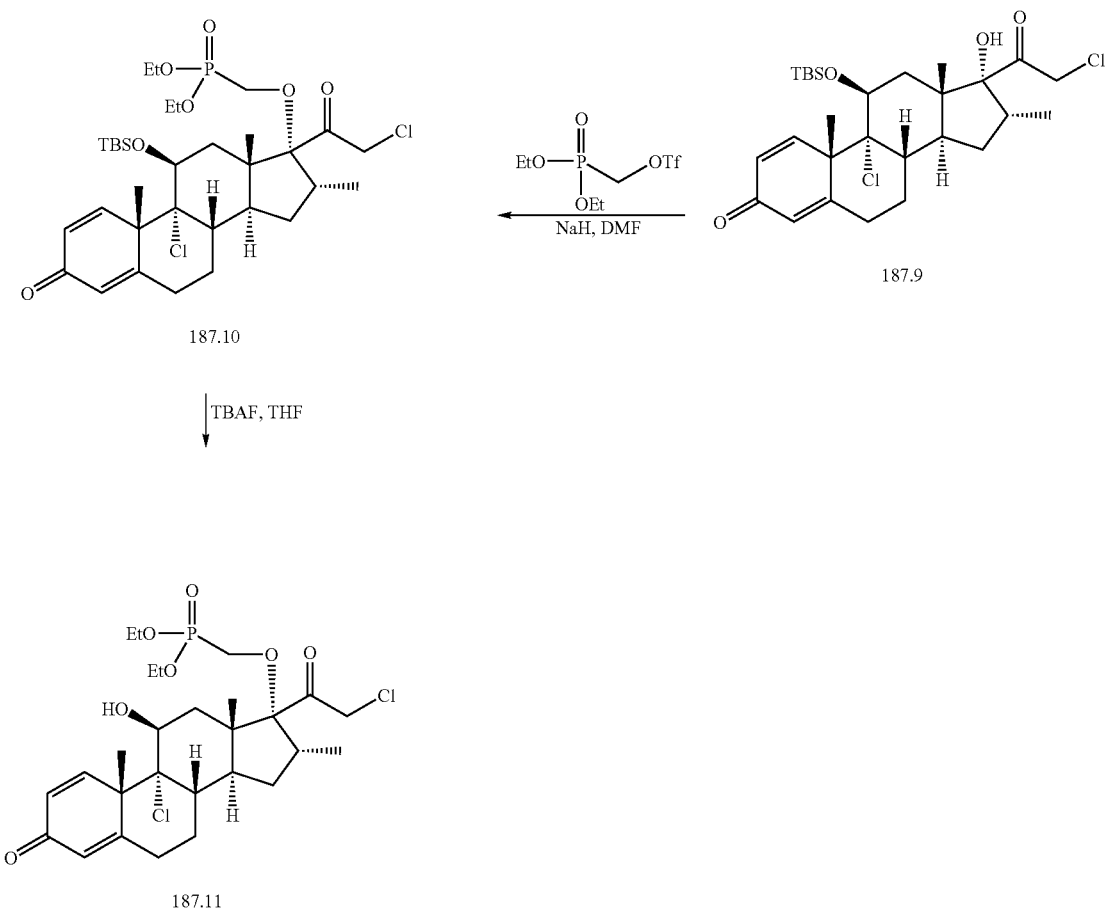

Mometasone fuorate 187.1 is protected as its silyl ether using the standard TBSCl and imidazole conditions (*J. Am. Chem. Soc.* 1972, 94, 6190). Saponification of the fuoryl ester moiety using aqueous sodium hydroxide provides the alcohol 187.9. (*J. Chem. Soc. Perkin Trans.* 1 1993, 12, 1359-1366) The tertiary hydroxy group is alkylated by the addition of sodium hydroxide and the phosphonate triflate. After deprotection of the silyl ether in intermediate 187.10 with TBAF, diethyl phosponate 187.11 results.

EXAMPLE 188

Preparation of Representative Compounds of Formula 192

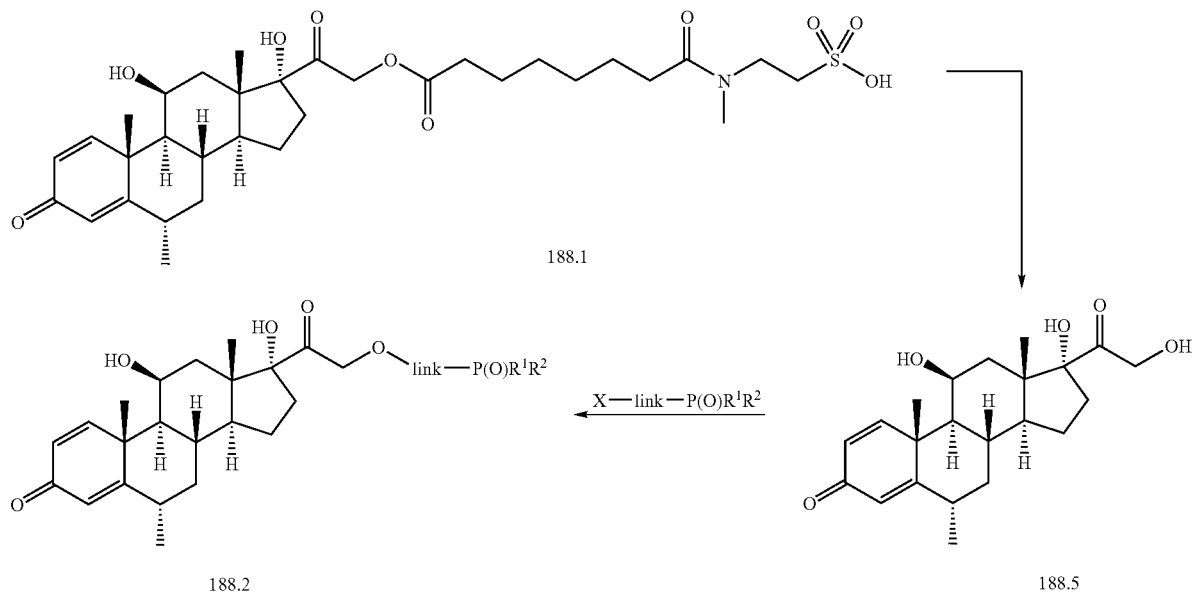

Representative compounds of the invention can be prepared as illustrated above. Since the sodium sulfonate moiety in methylprednisolone suleptanate 188.1 is the most nucleophilic site in the molecule, syntheses of analogs typically involve protection of or late stage installation of the sulfonate functional group. To employ the latter strategy, 188.1 is first saponified to furnish the triol 188.5. Alkylation at the primary hydroxy group with the appropriate phosphonate furnishes analogs of formula 188.2. A specific compound of the invention can be prepared as follows.

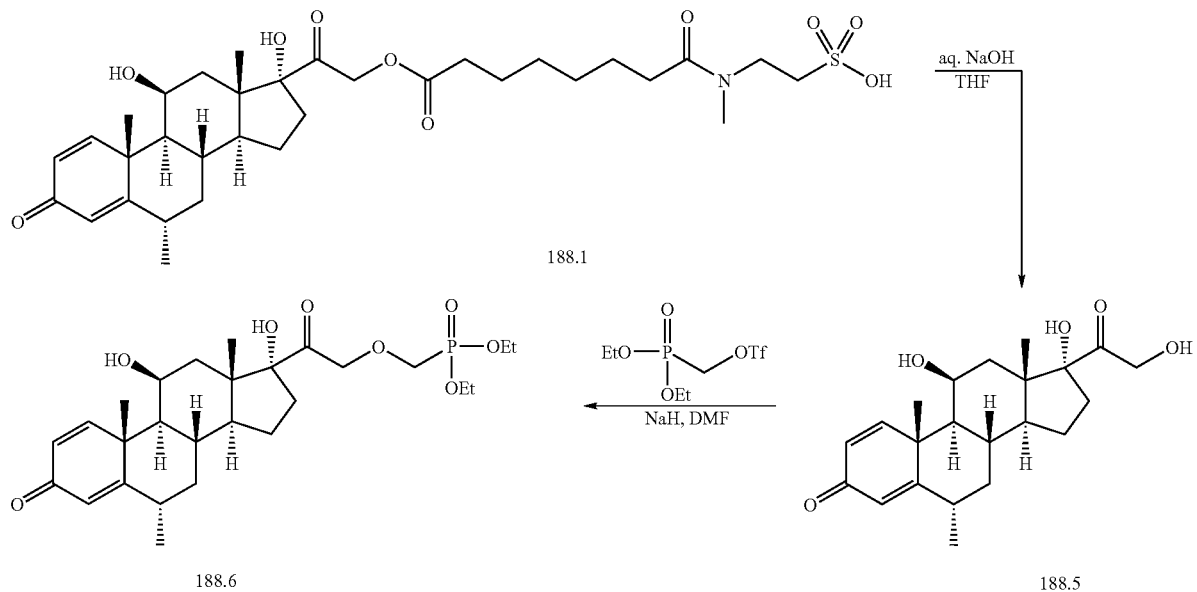

Hydrolysis of the suleptanate ester in 188.1 is accomplished by using aqueous sodium hydroxide, producing the triol 188.5. The less sterically hindered primary hydroxy group is alkylated by the addition of sodium hydroxide and the phosphonate triflate, giving diethyl phosphonate 188.6.
EXAMPLE 189
Preparation of Representative Compounds of Formula 190
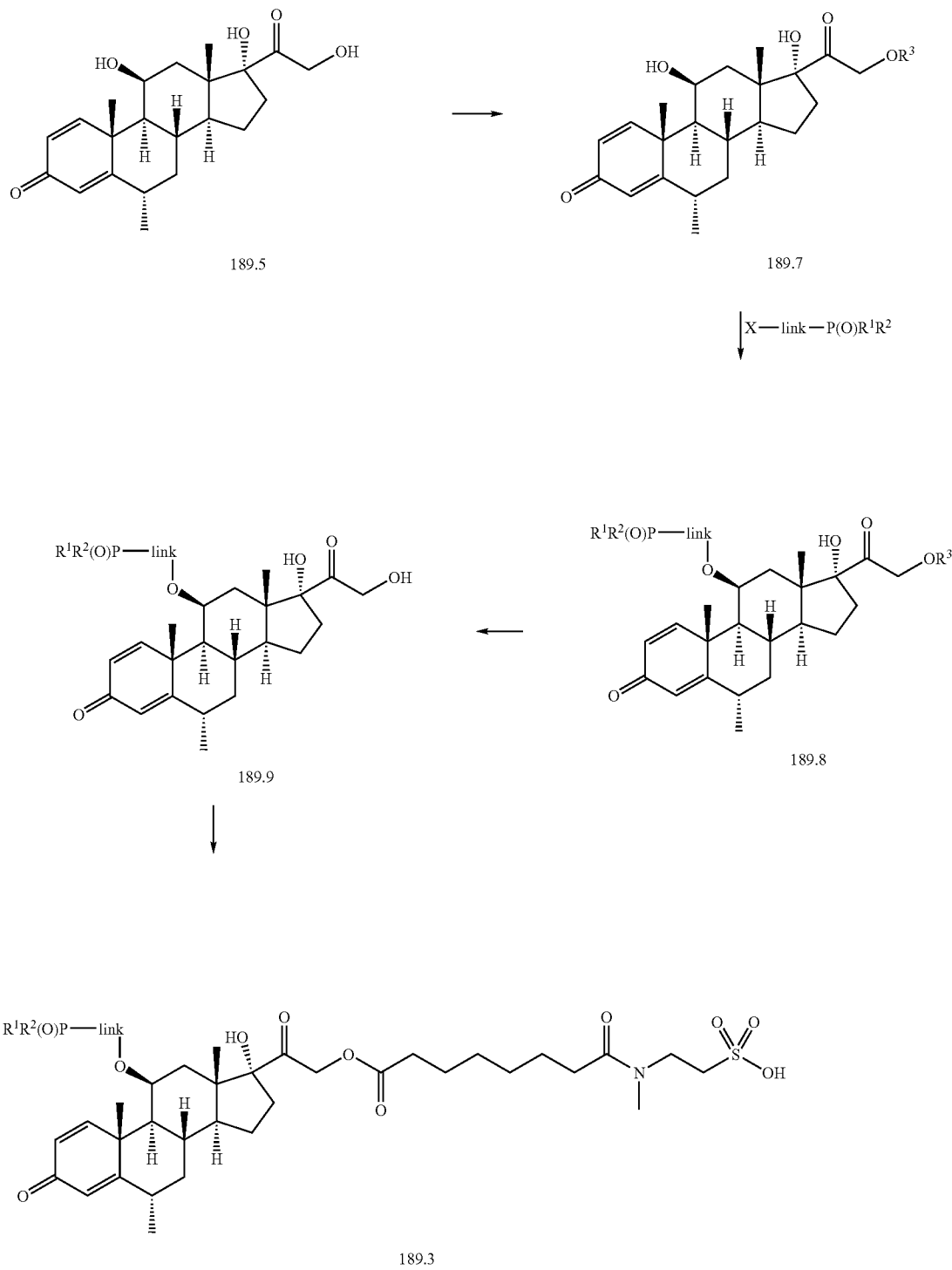

Representative compounds of the invention can be prepared as illustrated above. Following protection of the primary hydroxy group, protected intermediate 189.7 is alkylated at the more exposed C-11 hydroxy site. Deprotection and subsequent installation of the suleptanate ester provides the desired product 189.3. A specific compound of the invention can be prepared as follows.

Triol 189.5 is protected as its silyl ether using the standard TBSCl and imidazole conditions. (*J. Am. Chem. Soc.* 1972, 94, 6190) After alkylating with the diethyl phosphonate triflate, the resulting intermediate 189.11 is treated with TBAF to give the diol 189.12. Attachment of the suleptanate ester is accomplished in four steps: activation of the primary alcohol as its mesylate, Finkelstein conversion to the iodide (*Tetra-*

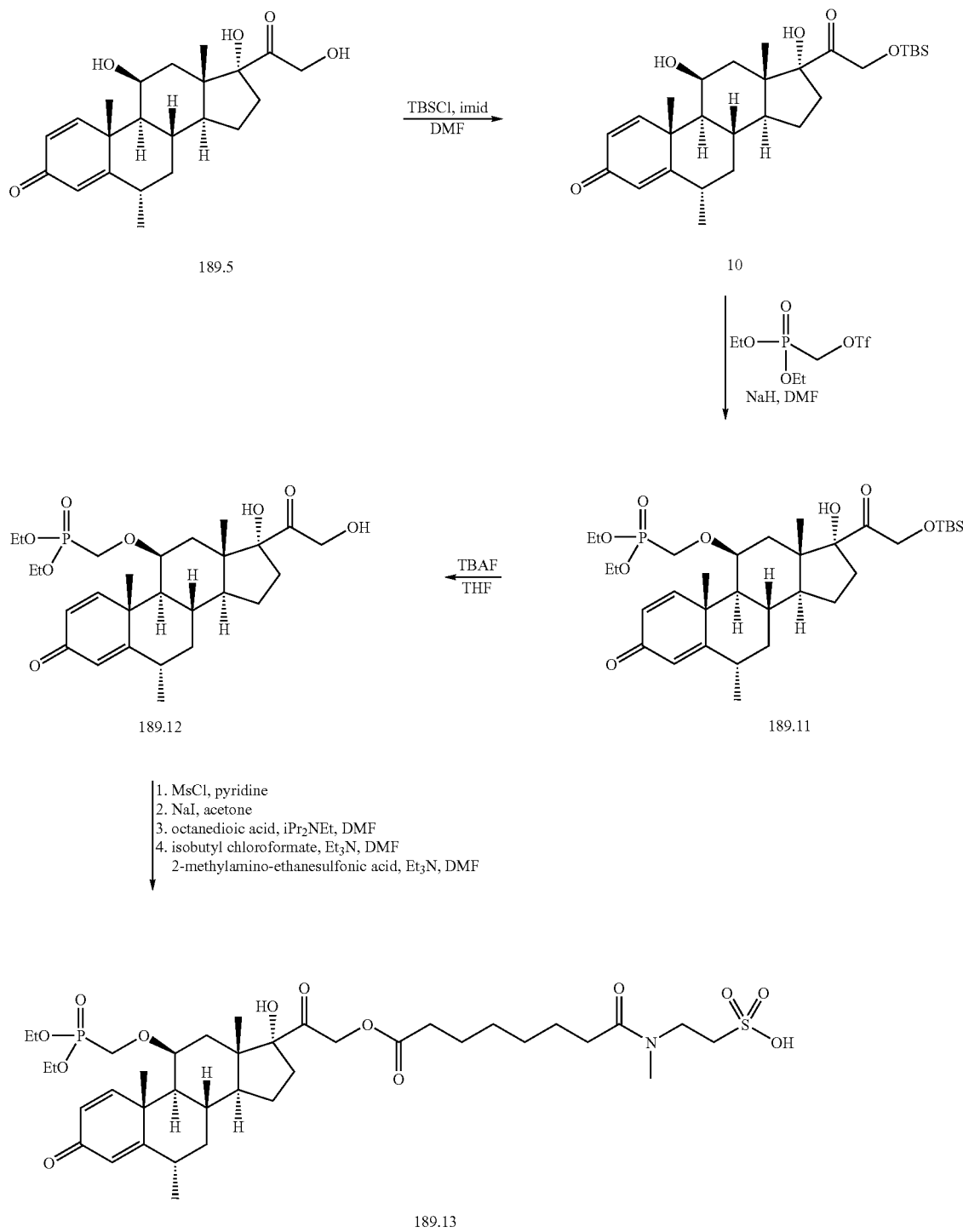

hedron Lett. 1981, 22, 2055), nucleophilic substitution with octanedioic acid, and final activation and displacement with the secondary amine provides compound 189.13. (*J. Pharm. Sci.* 1985, 74, 365-374).

EXAMPLE 190

Preparation of Representative Compounds of Formula 191

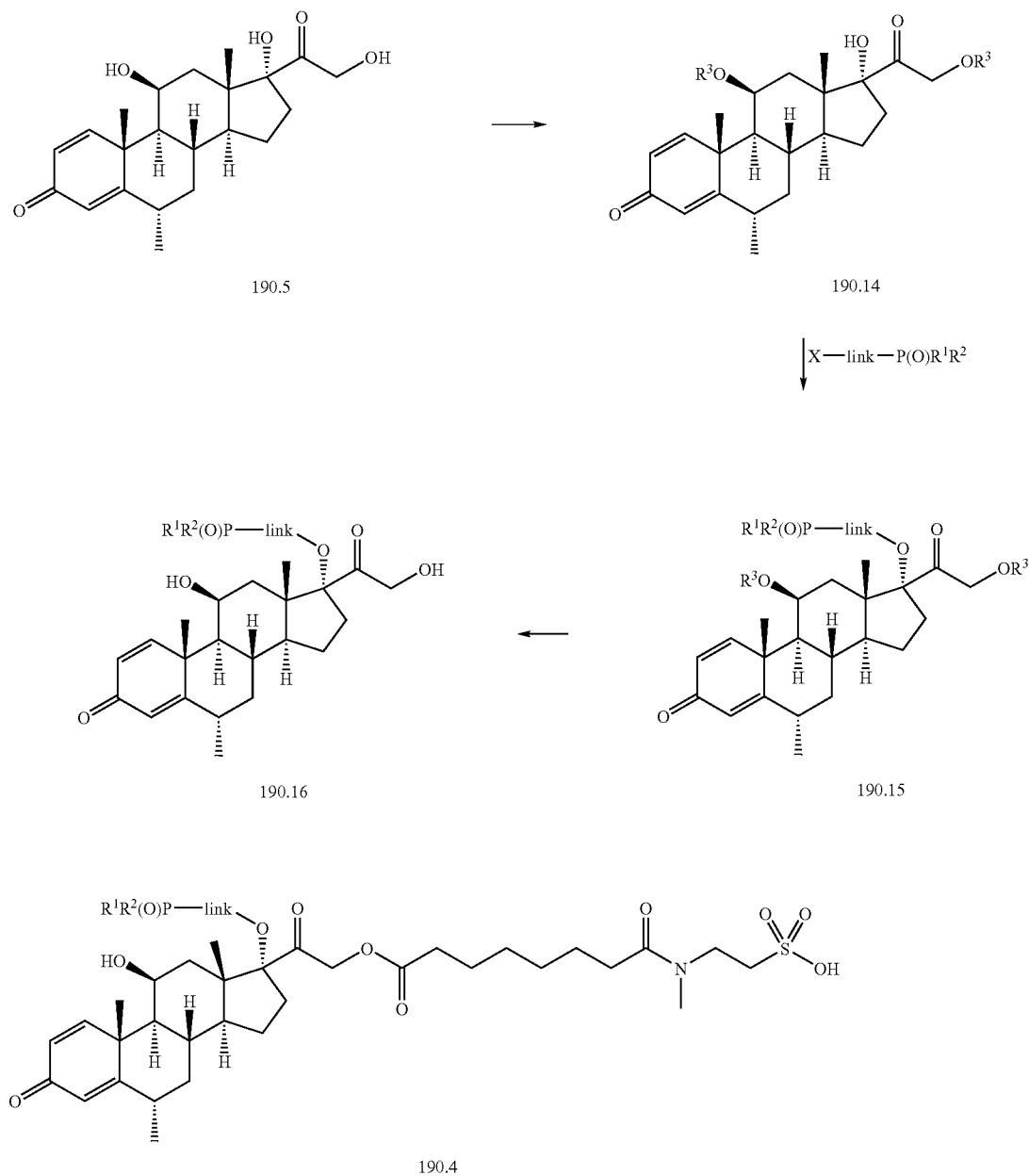

Representative compounds of the invention can be prepared as illustrated above. Protection of triol 190.5 at the two less hindered sites furnishes alcohol 190.14, which is alkylated at the only exposed hydroxy group with the appropriate phosphonate. Deprotection and formation of the suleptanate ester completes the synthesis of analog 190.4. A specific compound of the invention can be prepared as follows.

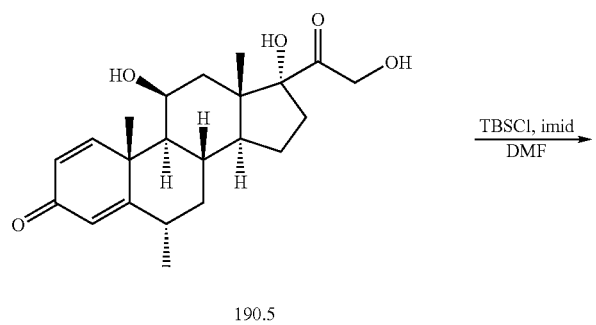

190.5

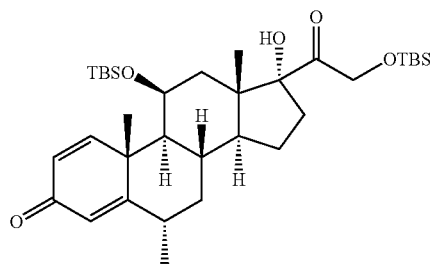

190.17

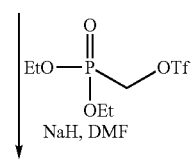

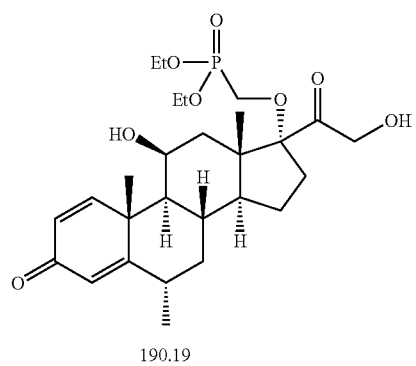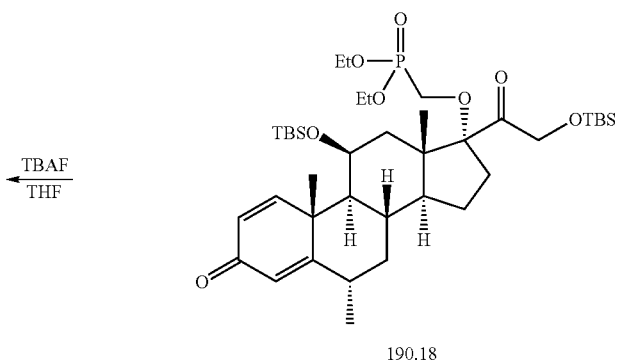

190.19          190.18

1. MsCl, pyridine
2. NaI, acetone
3. octanedioic acid, iPr$_2$NEt, DMF
4. isobutyl chloroformate, Et$_3$N, DMF
   2-methylamino-ethanesulfonic acid, Et$_3$N, DMF

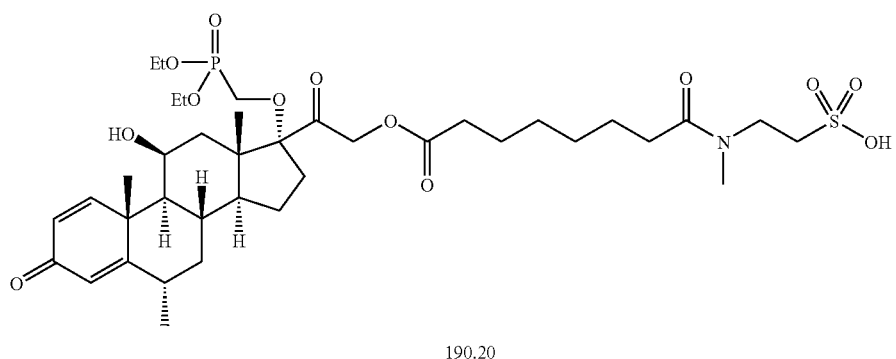

190.20

Triol 190.5 is protected as its TBS ether; however, harsher conditions should allow for bis-protection. After alkylating with the diethyl phosphonate triflate, the resulting intermediate 190.18 is treated with TBAF to give the diol 190.19. Attachment of the suleptanate ester is accomplished in four steps: activation of the primary alcohol as its mesylate, Finkelstein conversion to the iodide (*Tetrahedron Lett.* 1981, 22, 2055), nucleophilic substitution with octanedioic acid, and final activation and displacement with the secondary amine provides compound 190.20. (*J. Pharm. Sci.* 1985, 74, 365-374)

EXAMPLE 191

Preparation of Representative Compounds of Formula 193

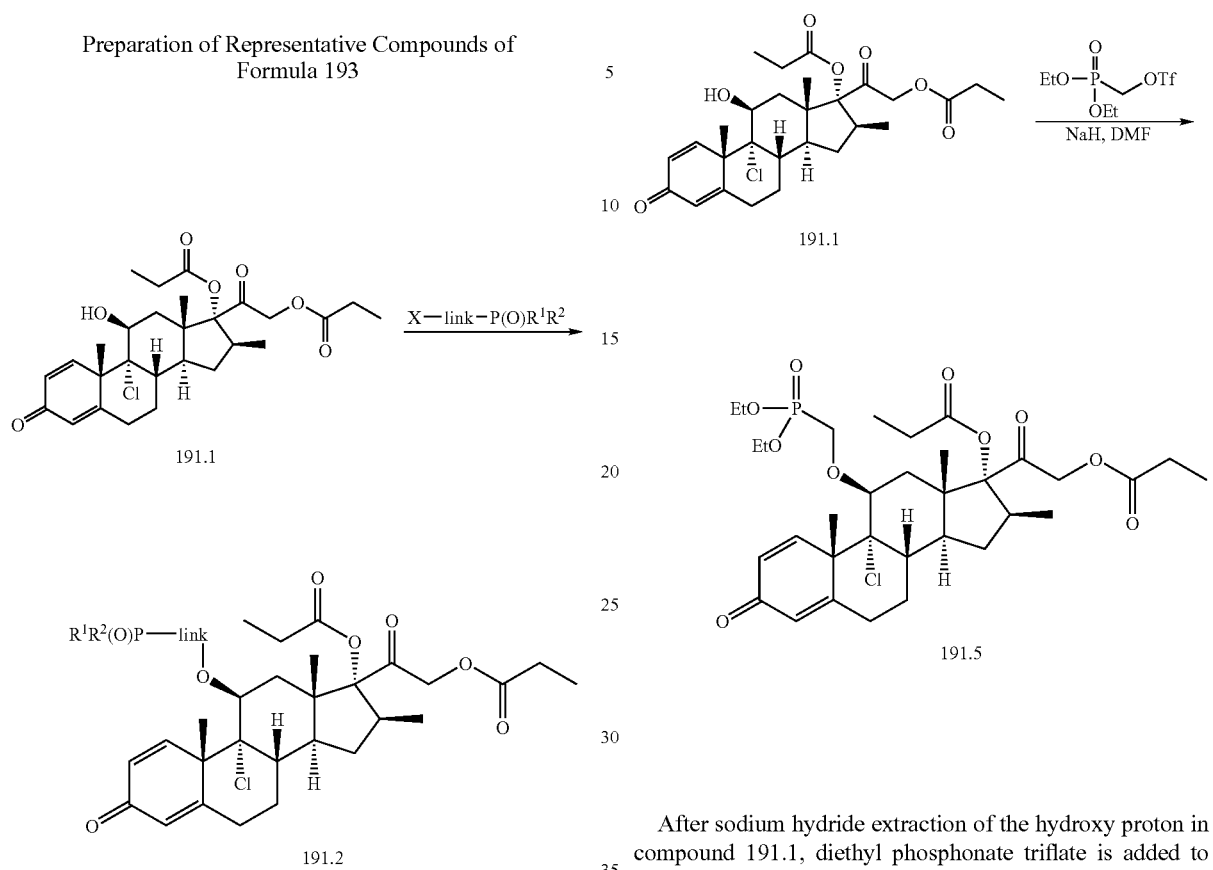

Representative compounds of the invention can be prepared as illustrated above. Derivatization at the C-11 hydroxy group is accomplished through alkylation of beclamethasone 191.1 with the appropriate phosphonate, furnishing analogs of formula 191.2. A specific compound of the invention can be prepared as follows.

After sodium hydride extraction of the hydroxy proton in compound 191.1, diethyl phosphonate triflate is added to afford ether 191.5.

EXAMPLE 192

Preparation of Representative Compounds of Formula 194

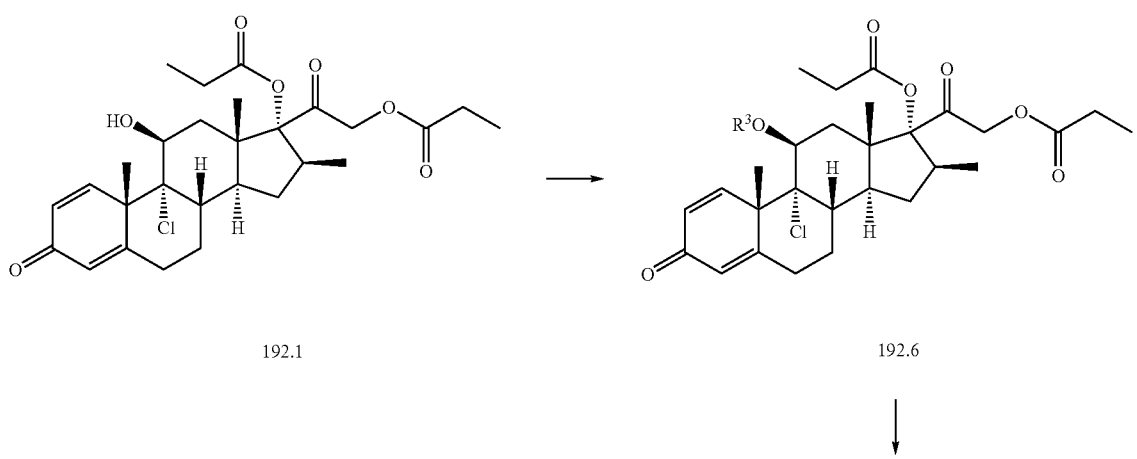

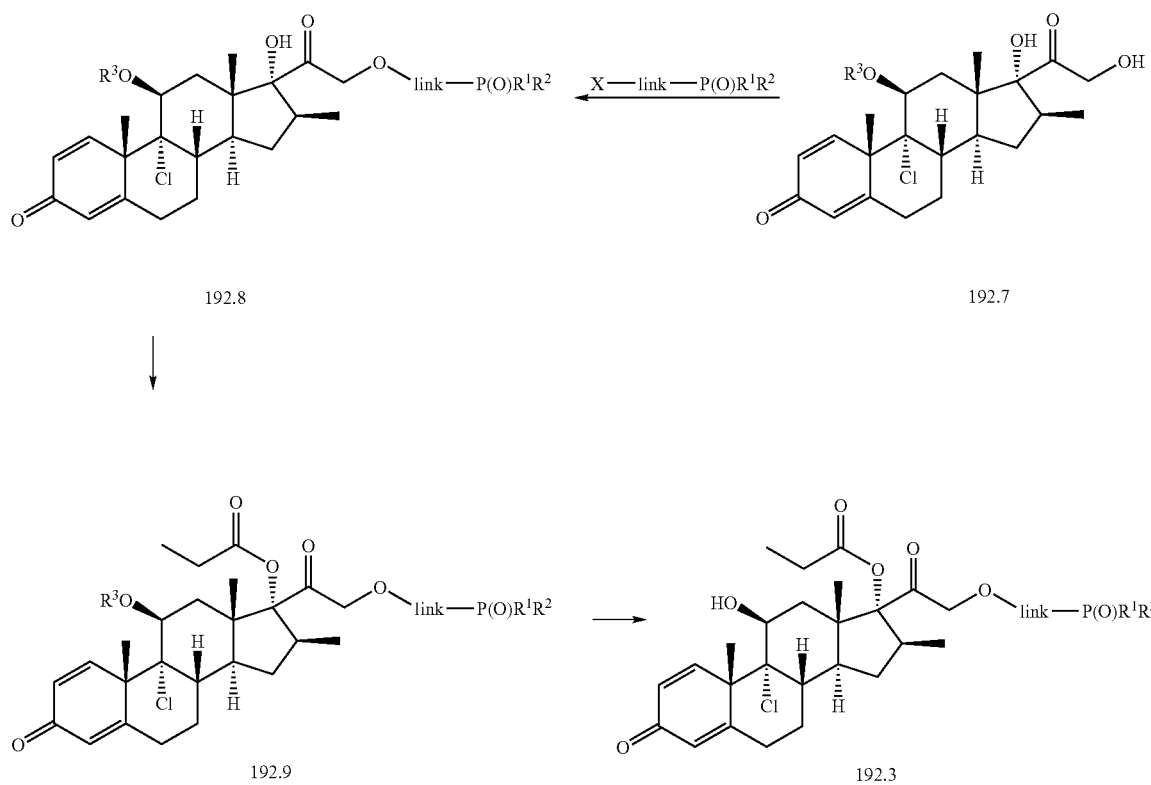

Representative compounds of the invention can be prepared as illustrated above by exploiting the reactivity differences among the three hydroxy groups available when beclamethasone 192.1 is fully hydrolized. Following protection of the only exposed hydroxy group in 192.1, intermediate 192.6 is saponified to give diol 192.7. Alkylation at the primary hydroxy group with the appropriate phosphonate and subsequent acylation provides the propionate ester 192.9. The desired product 192.3 is achieved after deprotection. A specific compound of the invention can be prepared as follows.

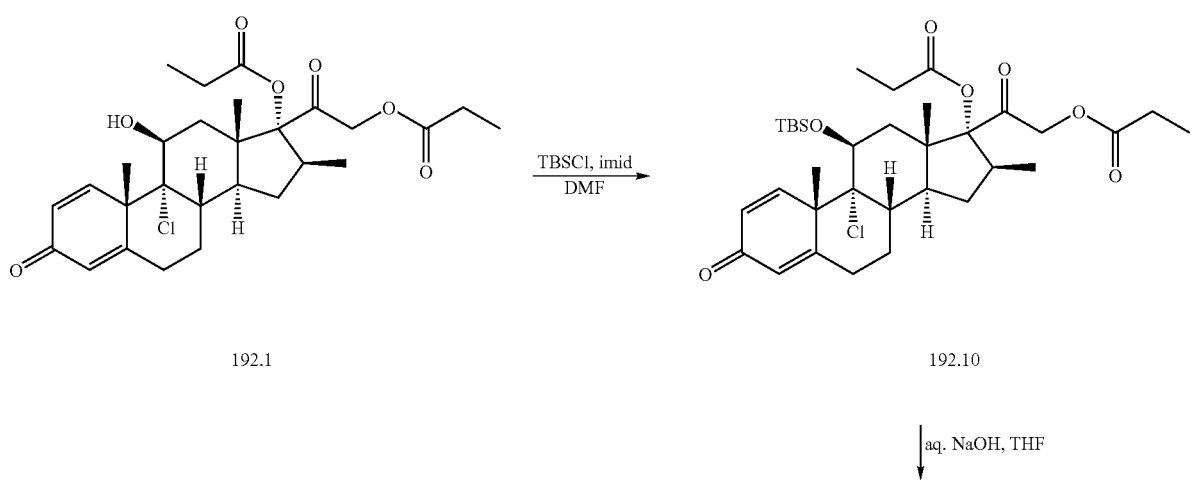

-continued

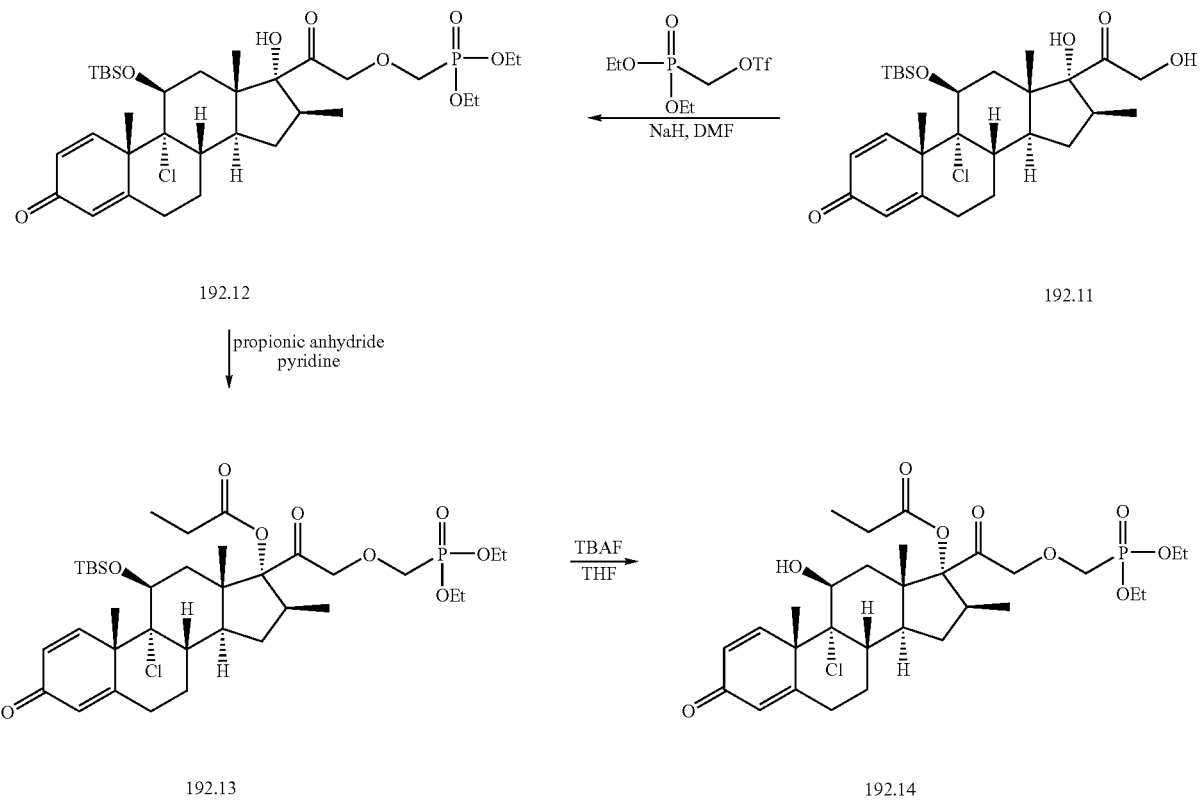

192.12 192.11

192.13 192.14

Beclamethasone 192.1 is protected as its silyl ether using the standard TBSCl and imidazole conditions (*J. Am. Chem. Soc.* 1972, 94, 6190). Saponification of both propionic ester moieties using aqueous sodium hydroxide provides the diol 192.11. The less sterically hindered primary hydroxy group is alkylated by the addition of sodium hydroxide and the phosphonate triflate. After treating intermediate 192.12 with propionic anhydride in pyridine, the previously hydrolized C-17 propionic ester is replaced. (*J. Med. Chem.* 1980, 23, 430-437) TBAF deprotection of the silyl ether furnishes diethyl phosponate 192.14.

EXAMPLE 193

Preparation of Representative Compounds of Formula 195

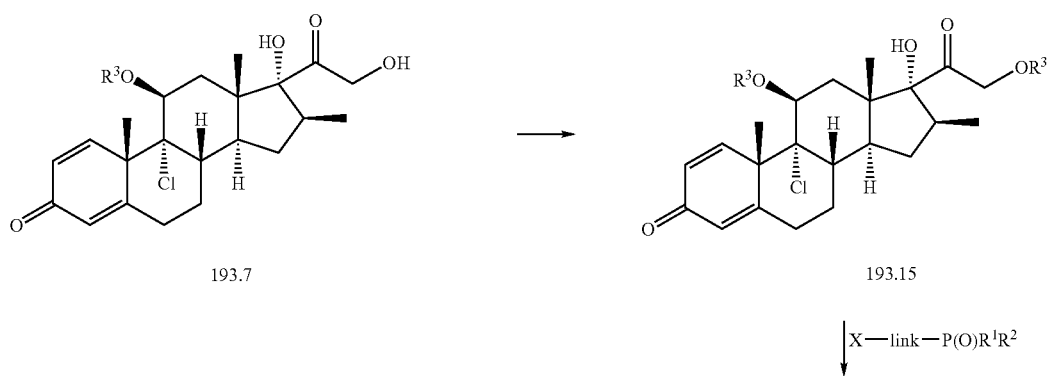

193.7 193.15

-continued

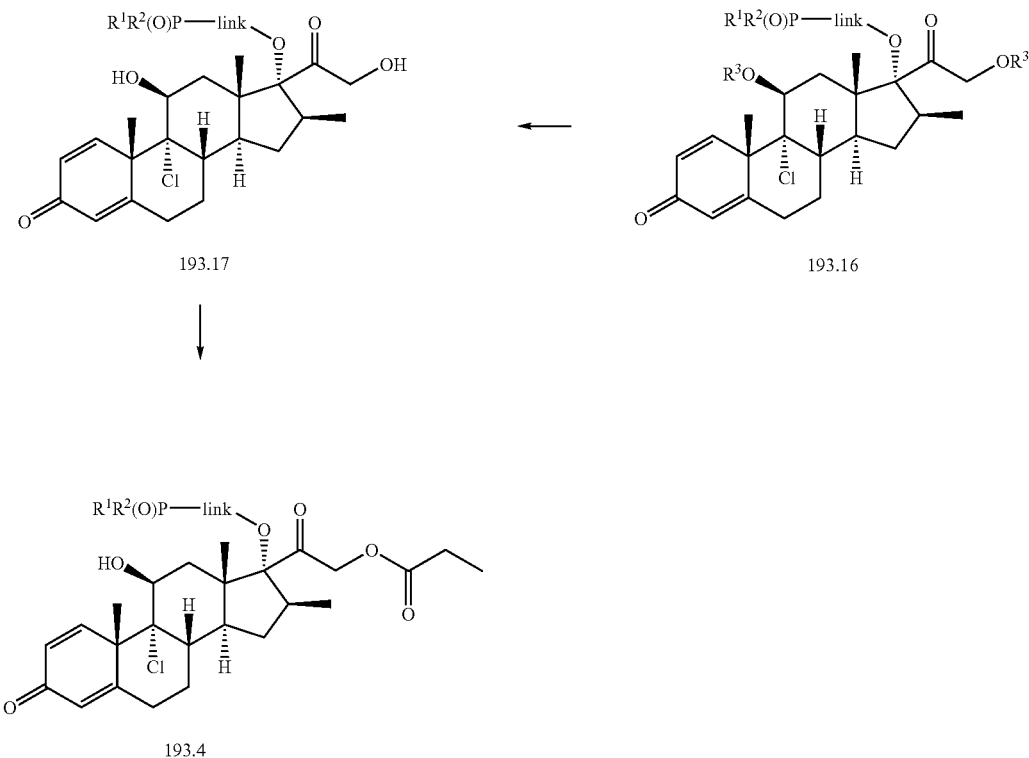

Representative compounds of the invention can be prepared as illustrated above. The two hydroxy groups of diol 193.7 are regioselectively differentiated by protection at the primary site, thus allowing alkylation at the tertiary hydroxy group. The resulting phosphonate intermediate 193.16 is then deprotected to afford the diol 193.17. The more accessible primary hydroxy group is acylated to produce the desired analog 193.4. A specific compound of the invention can be prepared as follows.

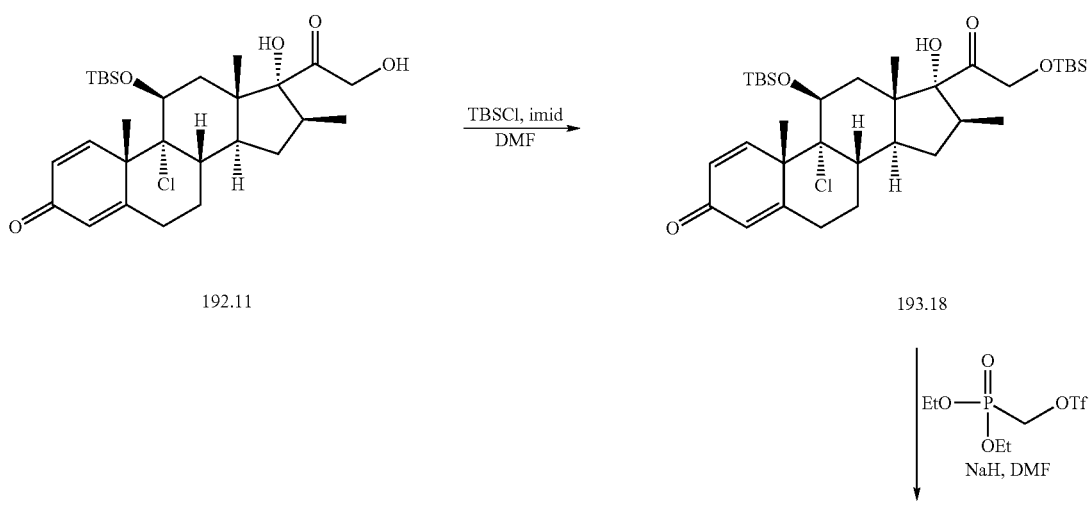

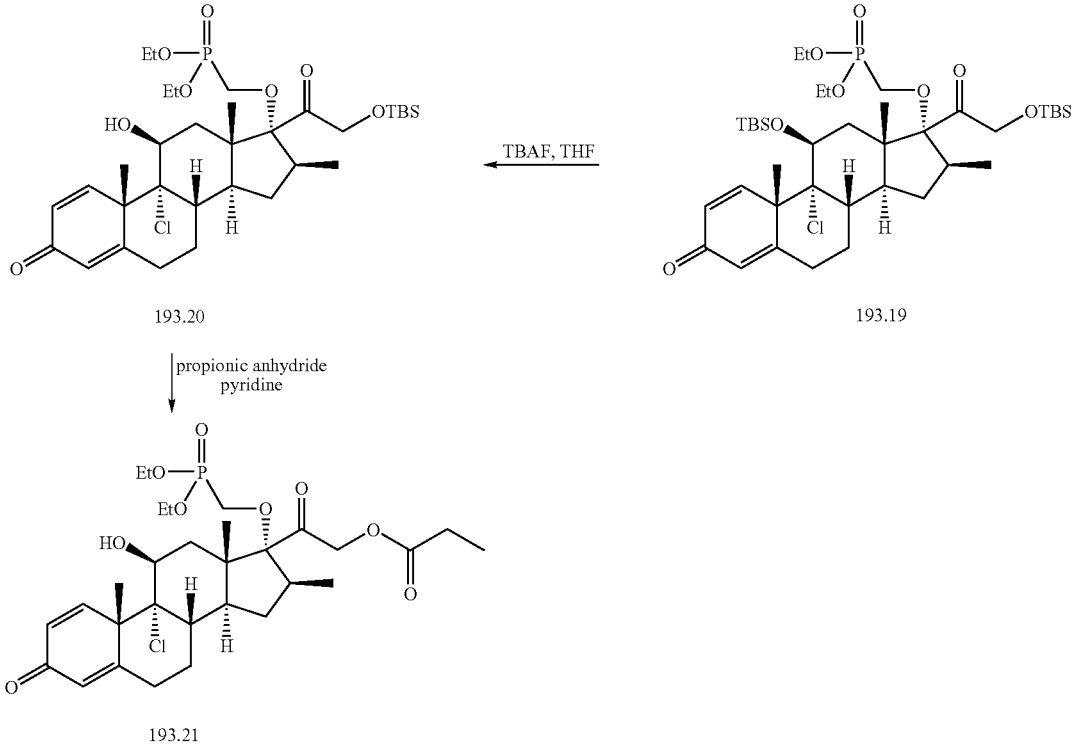

Diol 192.11 (see Example 192) is protected at the primary site as its silyl ether 193.18. Following alkylation with the diethyl phosphonate triflate, the resulting intermediate 193.19 is treated with TBAF to give diol 193.20. Propionic anhydride and pyridine are used to generate the final product 193.21. (*J. Med. Chem.* 1980, 23, 430-437)

EXAMPLE 194

Preparation of Representative Compounds of Formula 196

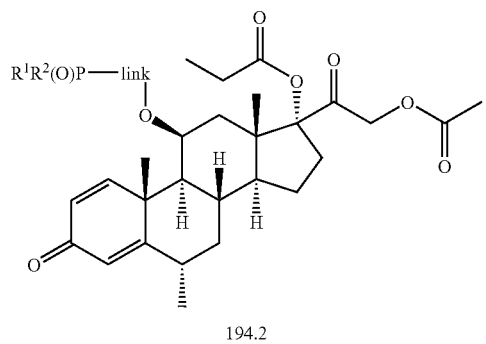

Representative compounds of the invention can be prepared as illustrated above. Derivatization at the C-11 hydroxy group is accomplished through alkylation of methylprednisolone aceponate 194.1 with the appropriate phosphonate, furnishing analogs of formula 194.2. A specific compound of the invention can be prepared as follows.

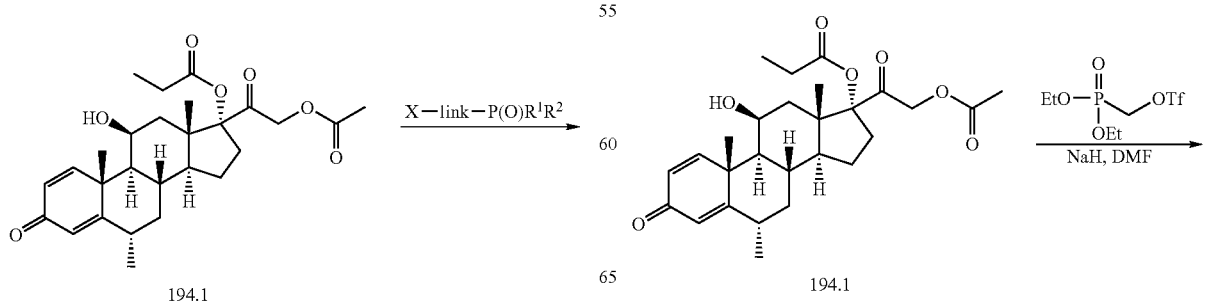

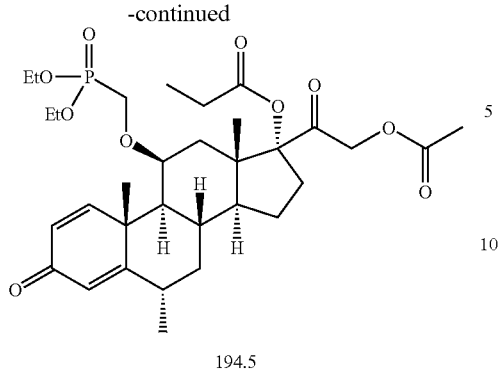
After sodium hydride extraction of the hydroxy proton in 194.1, diethyl phosphonate triflate is added to afford ether 194.5.
EXAMPLE 195
Preparation of Representative Compounds of Formula 198
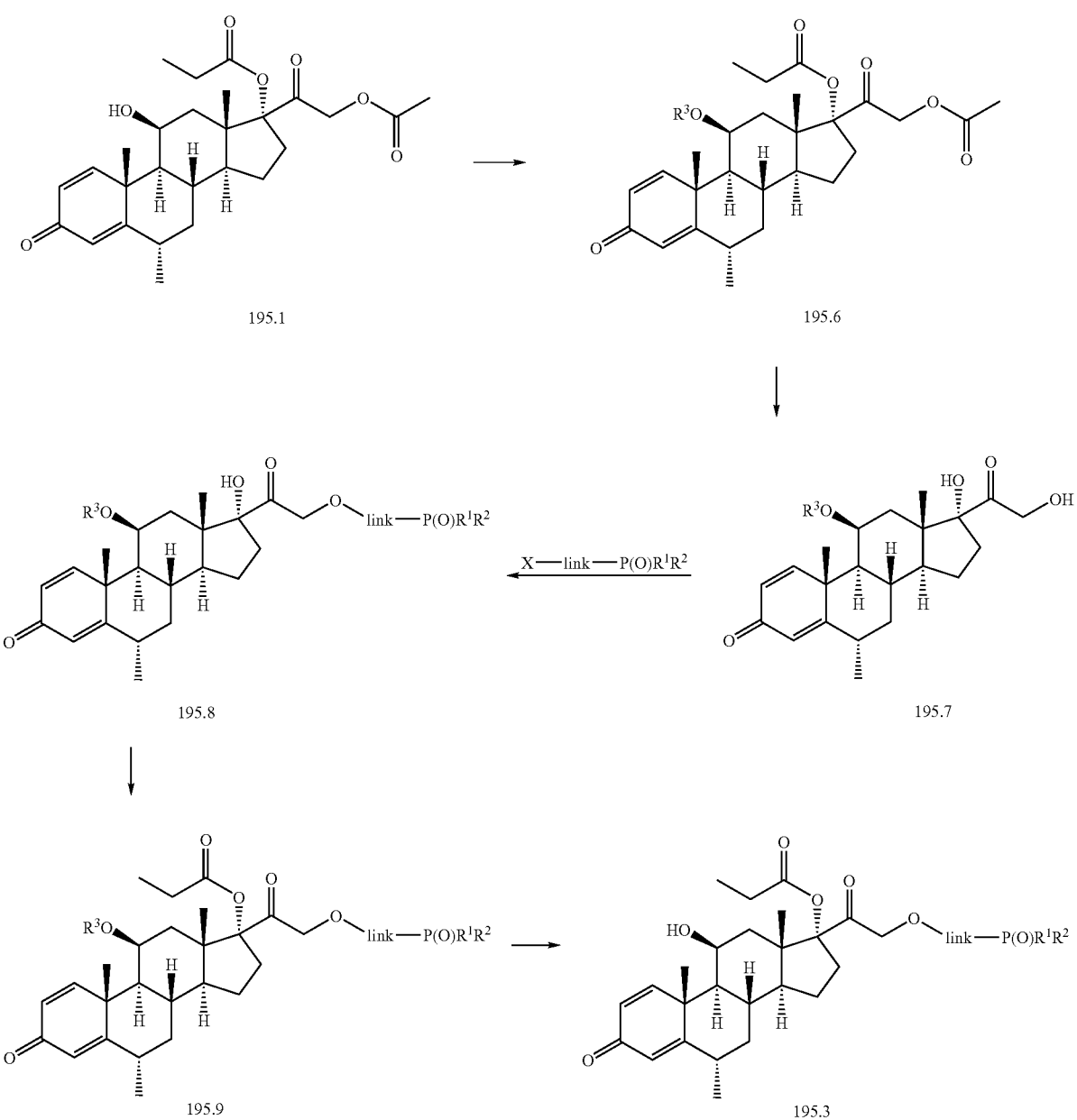

Representative compounds of the invention can be prepared as illustrated above by exploiting the reactivity differences among the three hydroxy groups available when methylprednisolone aceponate 195.1 is fully hydrolized. Following protection of the only exposed hydroxy group in 195.1, intermediate 195.6 is saponified to give diol 195.7. Alkylation at the primary hydroxy group with the appropriate phosphonate and subsequent acylation provides the propionate ester 195.9. The desired product 195.3 is achieved after deprotection. A specific compound of the invention can be prepared as follows.

Methylprednisolone aceponate 195.1 is protected as its silyl ether using the standard TBSCl and imidazole conditions. (J. Am. Chem. Soc. 1972, 94, 6190). Saponification of both ester moieties using aqueous sodium hydroxide provides the diol 195.11. The less sterically hindered primary hydroxy group is alkylated by the addition of sodium hydroxide and the phosphonate triflate. After treating intermediate 195.12 with propionic anhydride in pyridine, the previously hydrolized C-17 propionic ester is replaced. (J. Med. Chem. 1980, 23, 430-437) TBAF deprotection of the silyl ether furnishes diethyl phosponate 195.14.

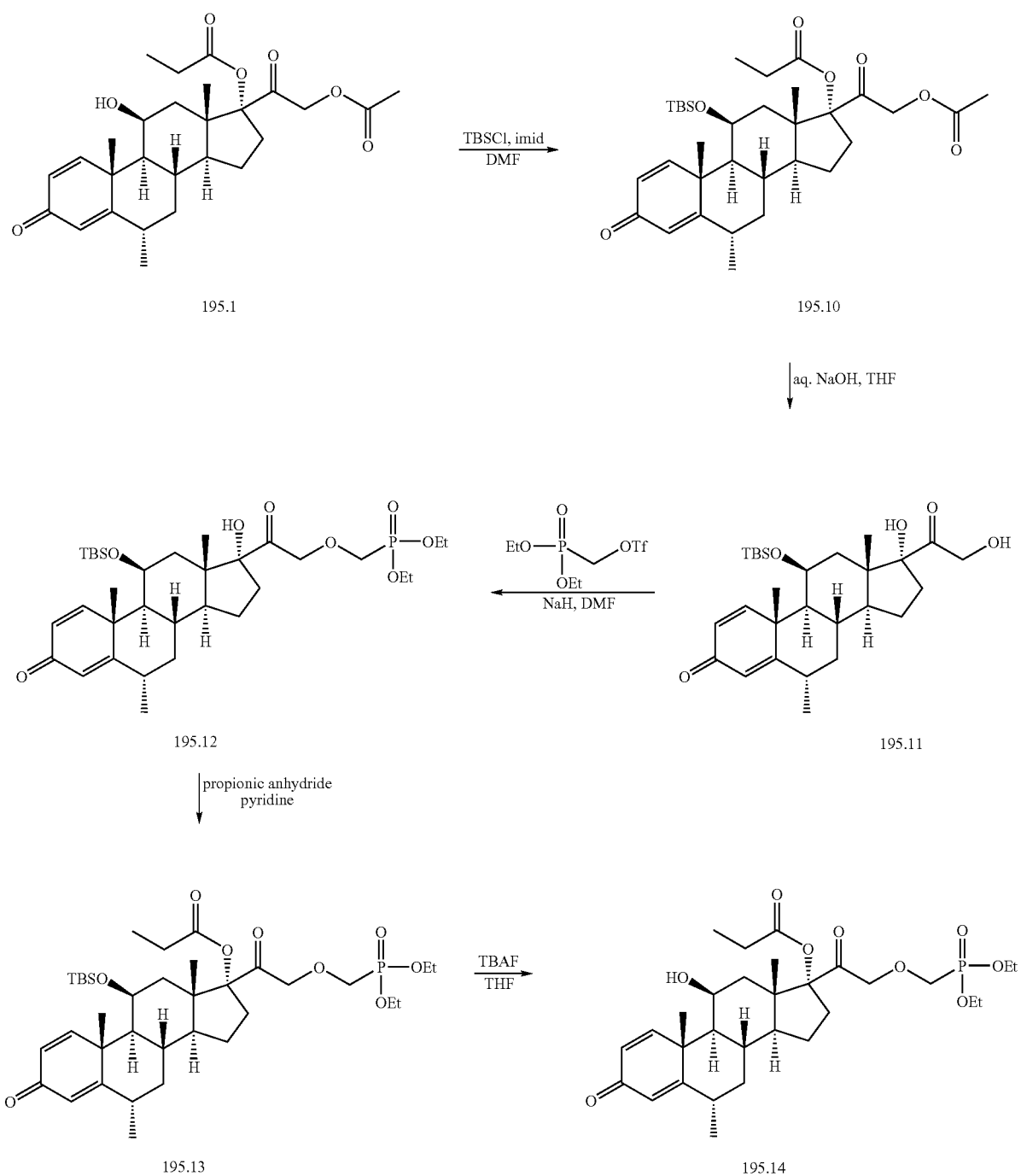

EXAMPLE 196

Preparation of Representative Compounds of Formula 197

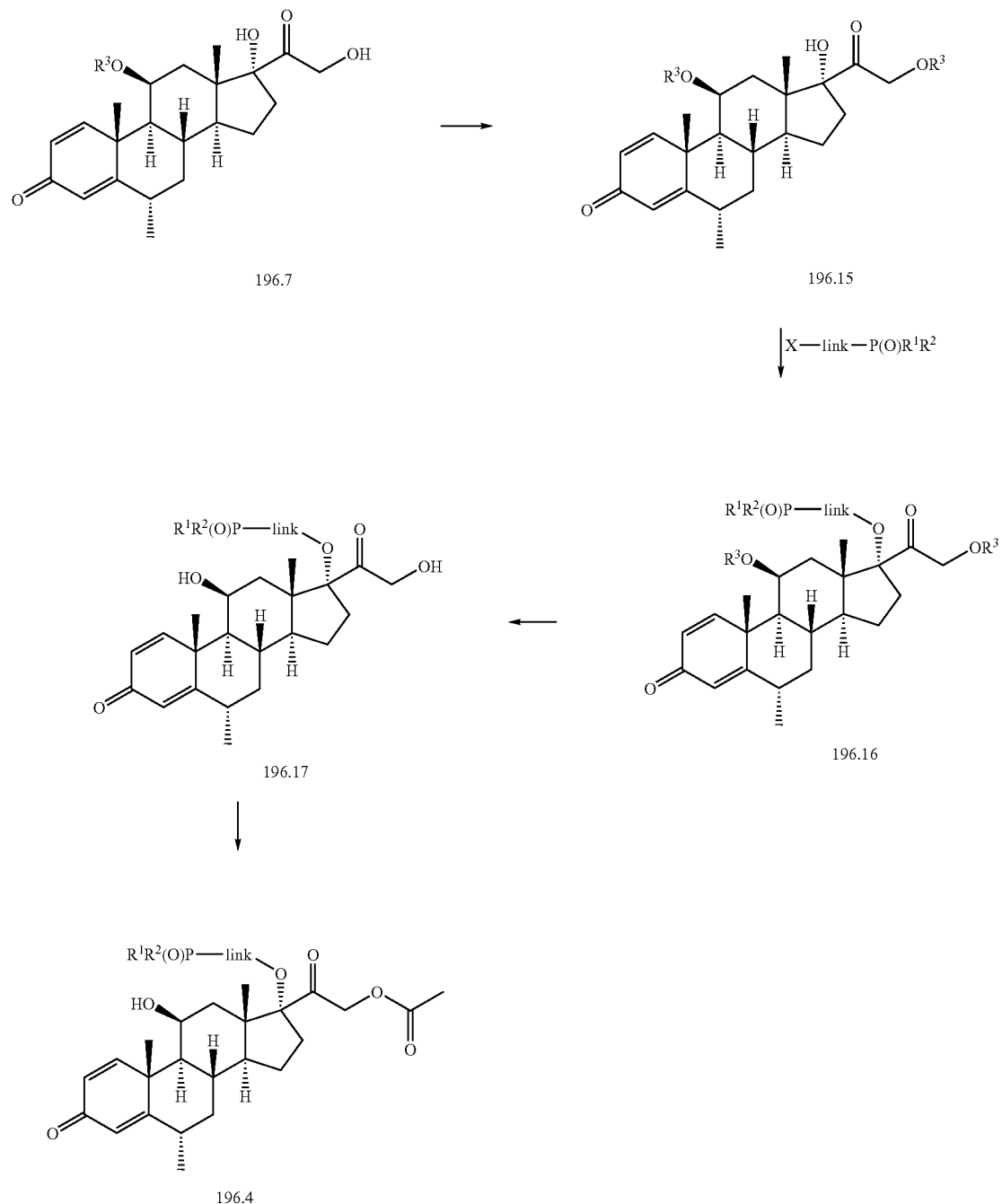

Representative compounds of the invention can be prepared as illustrated above. The two hydroxy groups of diol 196.7 are regioselectively differentiated by protection at the primary site, thus allowing alkylation at the tertiary hydroxy group. The resulting phosphonate intermediate 196.16 is then deprotected to afford the diol 196.17. Again the more accessible primary hydroxy group is acylated to produce the desired analog 196.4. A specific compound of the invention can be prepared as follows.

721
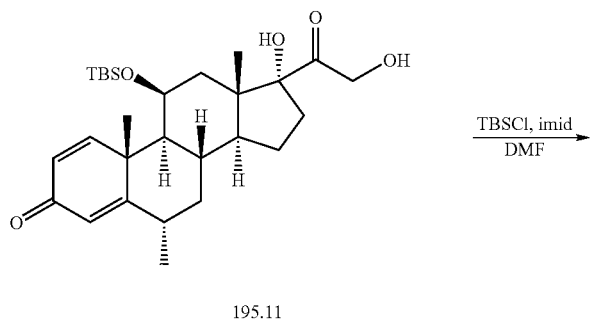
195.11
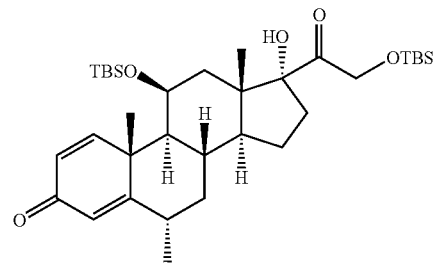
196.18
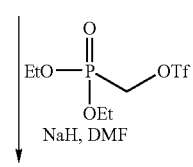
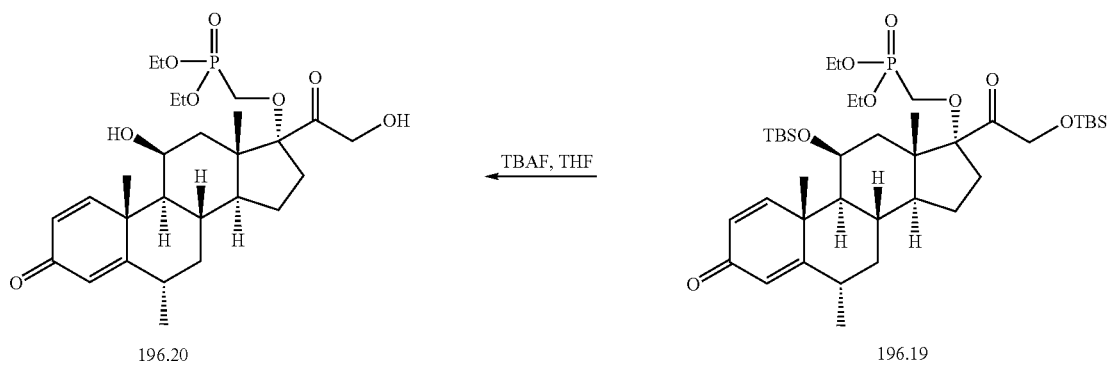
196.20                    196.19
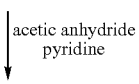
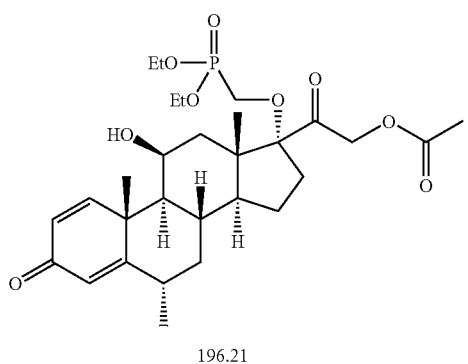
196.21
Diol 195.11 (see example 195) is protected at the primary site as its silyl ether 196.18. Following alkylation with the diethyl phosphonate triflate, the resulting intermediate 196.19 is treated with TBAF to give diol 196.20. Acetic anhydride and pyridine are used to generate the final product 196.21. (*J. Mol. Biol.* 1972, 72, 219).

EXAMPLE 197

Preparation of Representative Compounds of Formula 199

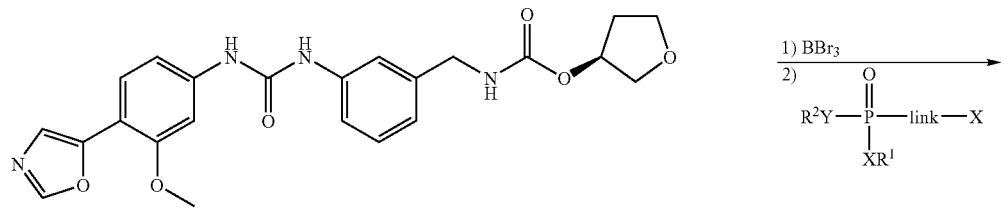

197.1

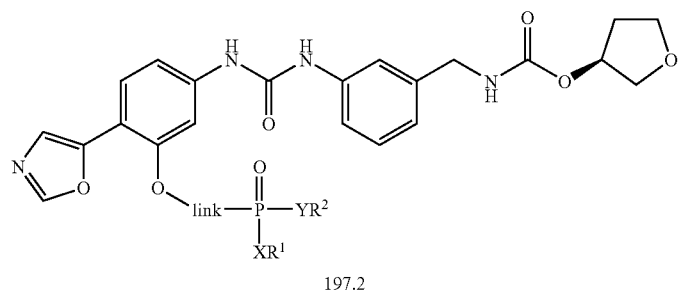

197.2

Representative compounds of the invention can be prepared as illustrated above. The phosphorus containing merimepodib analog 197.2 is synthesized from parent compounds by alkylation. Merimepodib 197.1 is obtained by the procedure as described in U.S. Pat. No. 6,054,472 and U.S. Pat. No. 6,344,465. The methoxy group of merimepodib 197.1 is demethylated to phenolic OH using a suitable reagent, such as boron tribromide. The phosphonate moiety is introduced to the phenolic OH in a suitable aprotic solvent such as, DMF and is then treated with the phosphonate reagent bearing a leaving group, for example, bromine, mesyl, tosyl, or trifluoromethanesulfonyl, in the presence of a suitable organic or inorganic base. A specific compound of the invention can be prepared as follows.

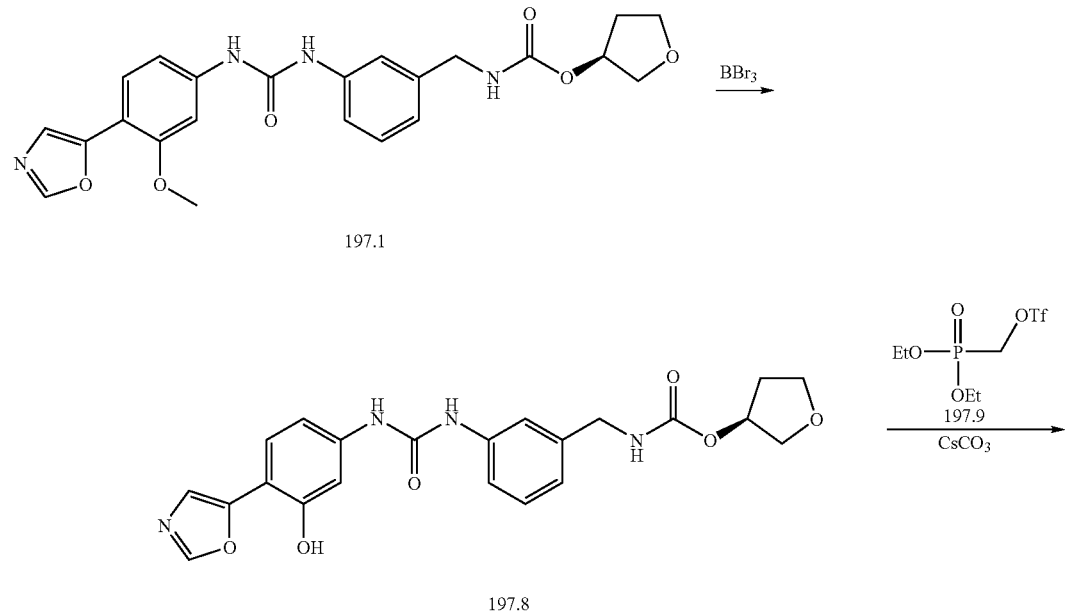

-continued

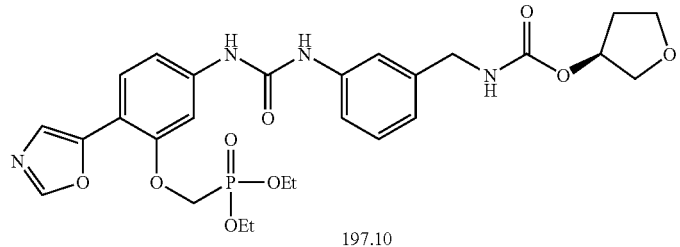
197.10

A solution of 197.1 in dichloromethane is treated with boron tribromide to obtain the demethylated compound 197.8. Compound 197.8 is then treated with cesium carbonate and one equivalent of (trifluoromethanesulfonyloxy)-methylphosphonic acid diethyl ester 197.9 to give merimepodibphosphonate 197.10. Using the above procedure but employing different phosphonate reagents, the corresponding products 197.2 bearing different linking group can be obtained.

EXAMPLE 198

Preparation of Representative Compounds of Formula 201

Representative compounds of the invention can be prepared as illustrated above. The imidazole containing intermediate 198.13 is synthesized from an aldehyde 198.12 by the procedure of Shih in *Tetrahedron Lett.* 1993, 34, 595. Compound 198.12 is prepared by a two-step procedure described in U.S. Pat. No. 5,807,876, U.S. Pat. No. 6,054,472, and U.S. Pat. No. 6,344,465. The imidazole is protected using suitable reagent, for example 2-(trimethylsilyl)ethyoxymethyl (SEM) chloride, and the compound 198.14 is converted to 198.15 by the similar procedure described for the synthesis of 197.1 in U.S. Pat. No. 6,054,472 and U.S. Pat. No. 6,344,465. After the protecting group on the imidazole of 198.15 is removed, the phosphonate containing moiety is introduced to the imidazole to provide compounds of the invention. A specific compound of the invention can be prepared as follows.

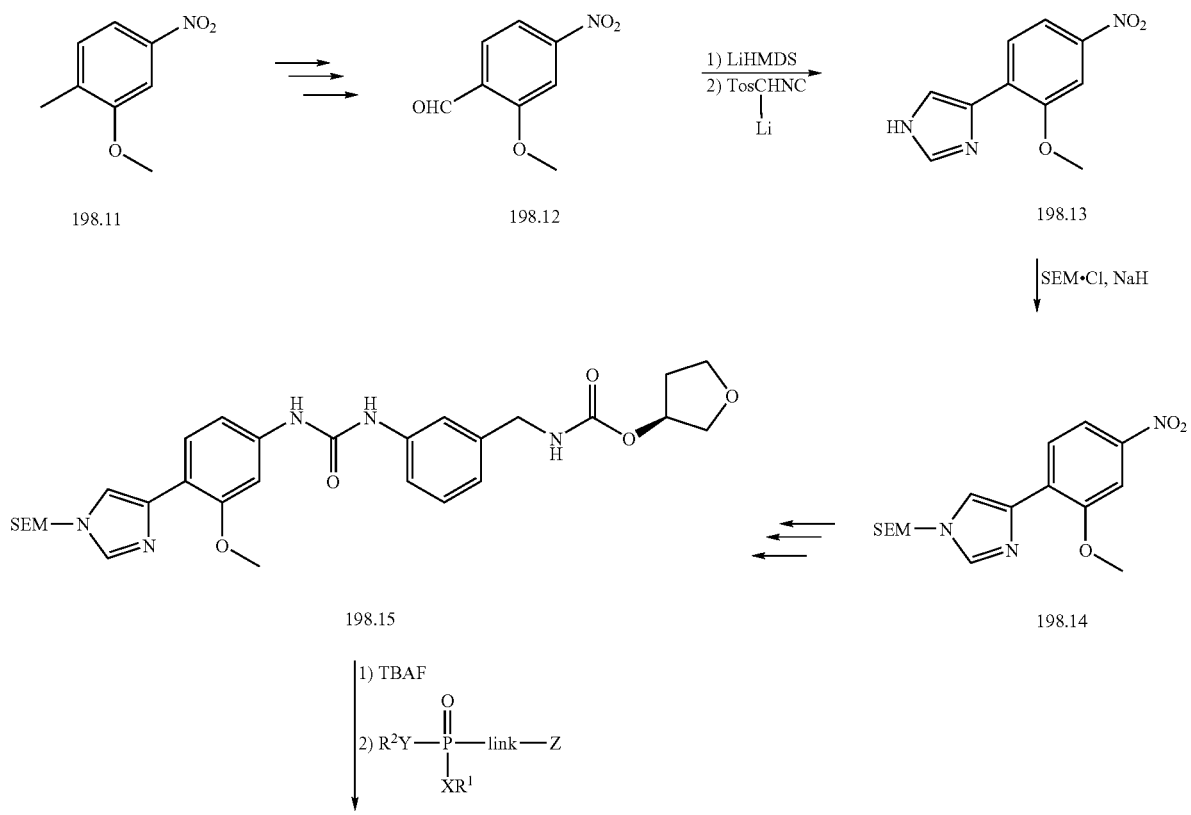

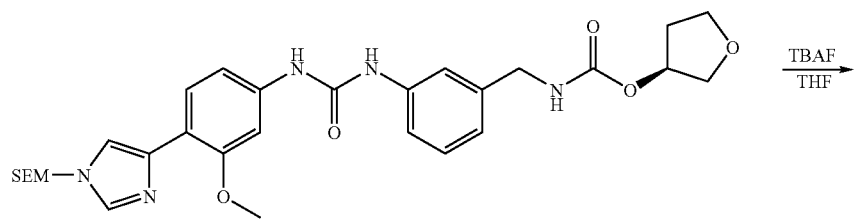
198.15
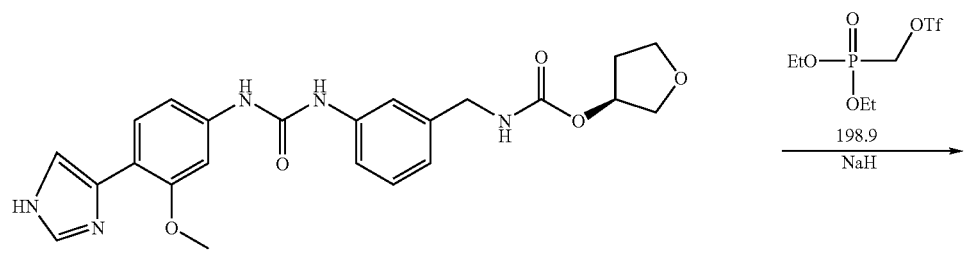
198.16
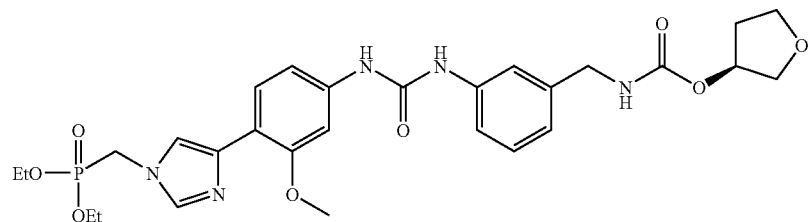
198.17
+
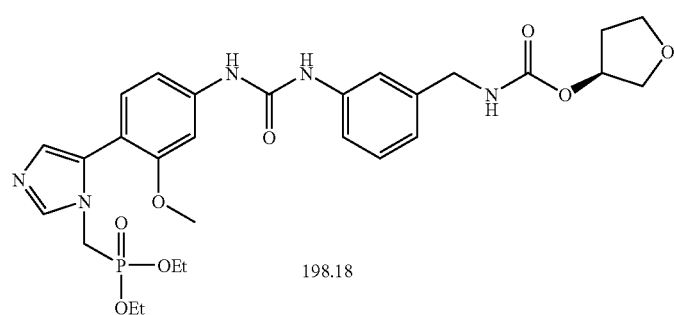
198.18
Compound 198.15 is treated with tetrabutylammonium fluoride in THF in reflux condition and the resulting 198.16 is alkylated with 198.9 using sodium hydride as a base to obtain two isomers 198.17 and 198.18, which are separated by chromatography.

EXAMPLE 199

Preparation of Representative Compounds of Formula 202

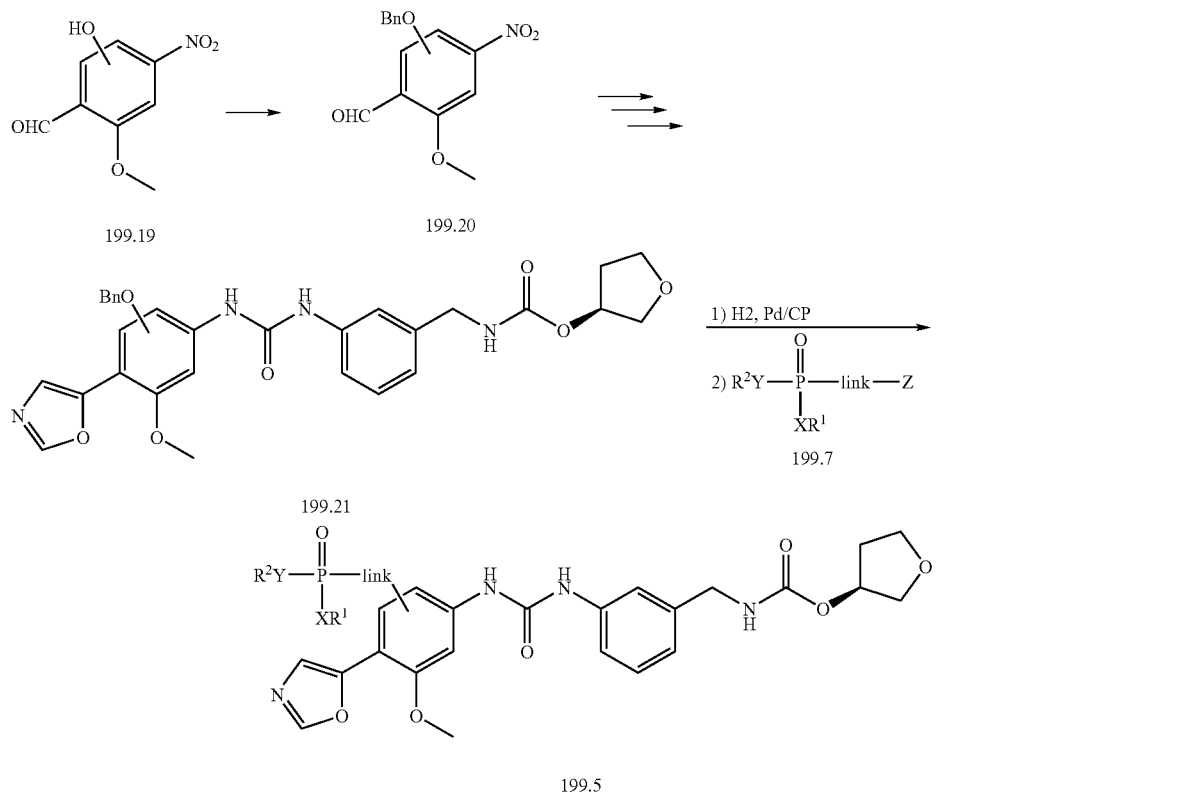

Representative compounds of the invention can be prepared as illustrated above. Tetrasubstituted benzene derivatives are obtained by literature procedures (Ichikawa and Ichibagase *Yakugaku Zasshi* 1963, 83, 103; Norio, A. et al. *Tetrahedron Lett.* 1992, 33(37), 5403). After the phenolic OH is protected with a suitable protecting group, for example benzyl group, the compound 199.21 is synthesized by the same procedure described in U.S. Pat. No. 6,054,472, and U.S. Pat. No. 6,344,465. After the protecting group is removed, the phosphonate containing moiety is introduced to the phenolic OH using the phosphonate reagent 199.7, bearing a suitable leaving group. A specific compound of the invention can be prepared as follows.

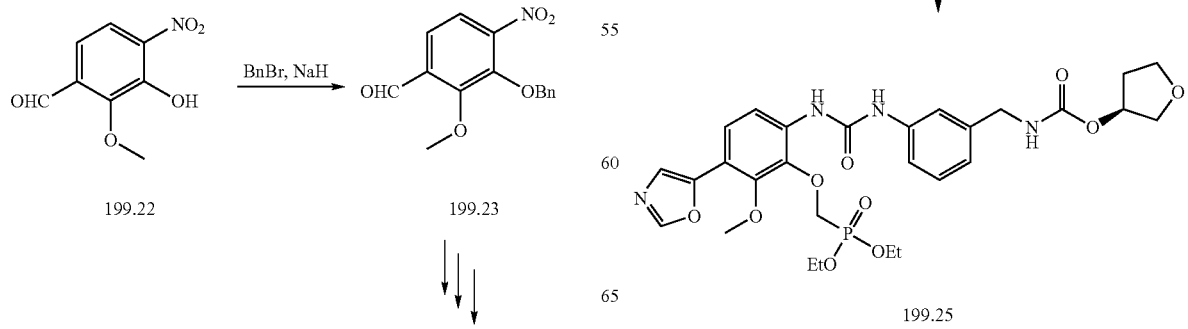

For example, a solution of 199.22, which is obtained by the procedure of Norio et al. (*Tetrahedron Lett.* 1992, 33(37), 5403), is treated with sodium hydride and one equivalent of benzyl bromide in DMF to get 199.23. Compound 199.23 is converted to 199.24 by a series of steps such as those reported in U.S. Pat. No. 6,054,472, and U.S. Pat. No. 6,344,465. After the benzyl protecting group of 199.24 is removed by catalytic hydrogenation, a phosphonate bearing moiety is attached by alkylation of the resulting phenol in DMF using sodium hydride and one equivalent of (trifluoromethanesulfonyloxy) methylphosphonic acid diethyl ester 199.9 to give 199.25.

EXAMPLE 200

Preparation of Representative Compounds of Formula 203

Representative compounds of the invention can be prepared as illustrated above. Compound 200.26 is treated with carbonyldiimidazole or triphosgene followed by the compound 200.27, which has a handle to attach phosphonate moiety. Compound 200.27 bearing an extra substituent is synthesized from the tri substituted phenol with a cyano and a nitro groups, which is either commercially available or by literature procedures (Zolfigol, M. A. et. al. *Indian J. Chem. Sect. B* 2001, 40,1191; De Jongh, R. O. et al. *Rec. Trav. Chim. Pays-Bas* 1968, 87, 1327). The resulting 200.28 is converted to 200.29 using procedures similar to those described in U.S. Pat. No. 6,054,472, and U.S. Pat. No. 6,344,465. The phosphonate moiety of 200.6 is attached after deprotection of the benzyl group of 200.29.

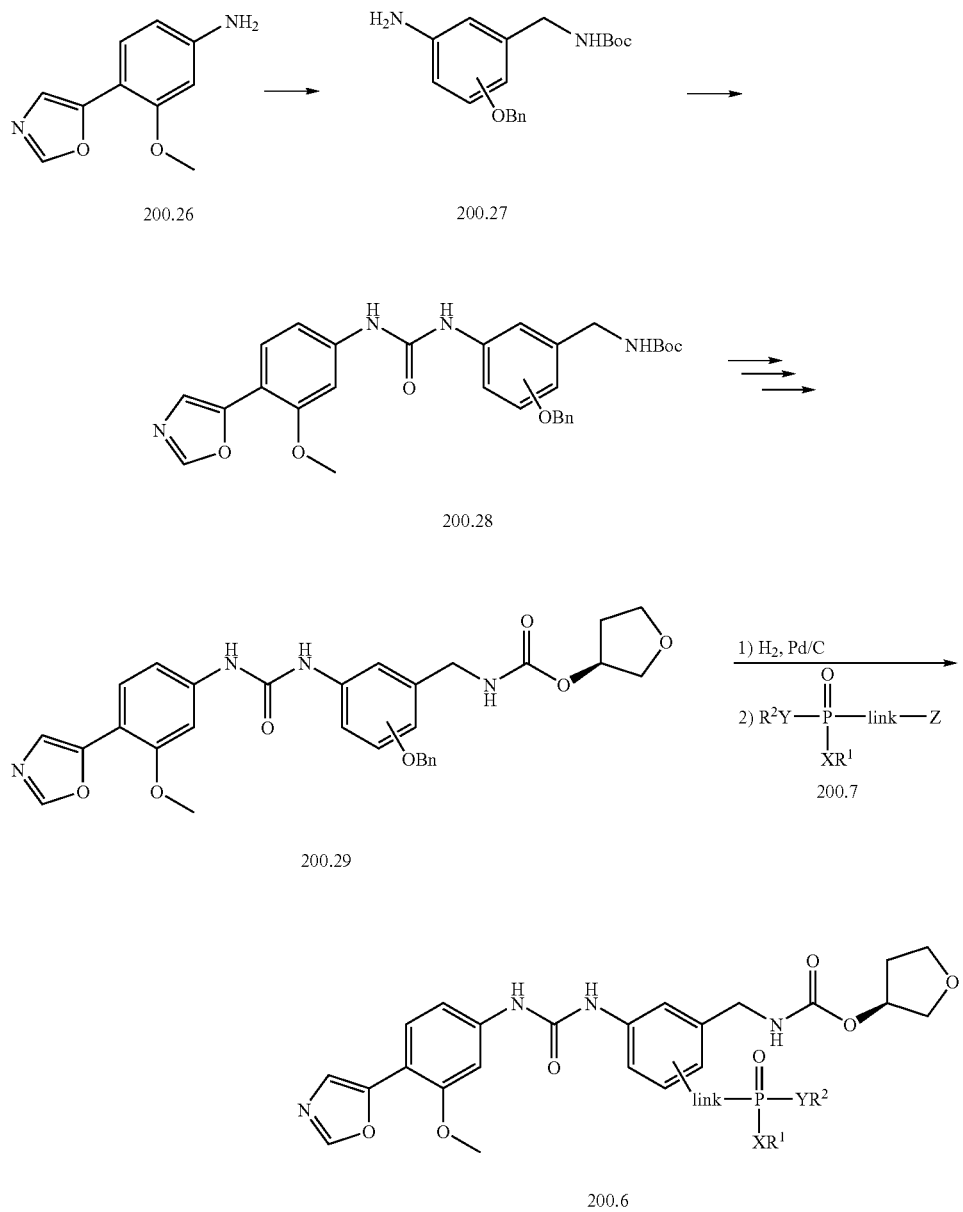

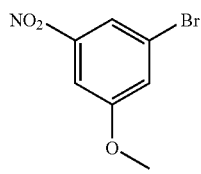
200.30
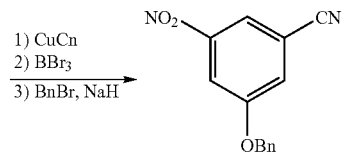
200.31
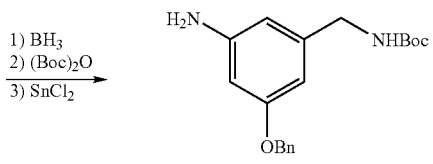
200.32
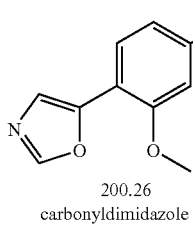
200.26
carbonyldimidazole
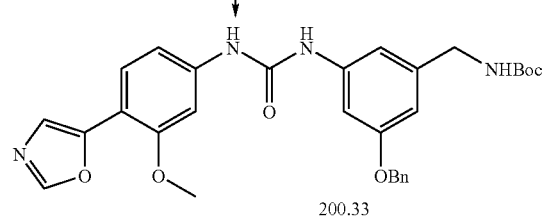
200.33
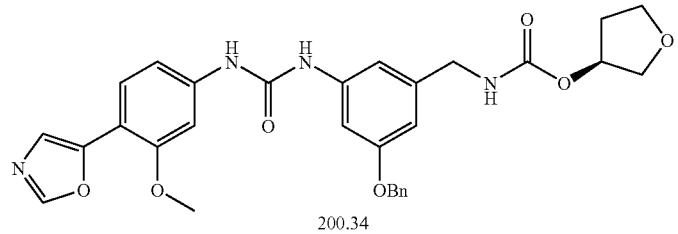
200.34
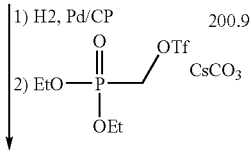
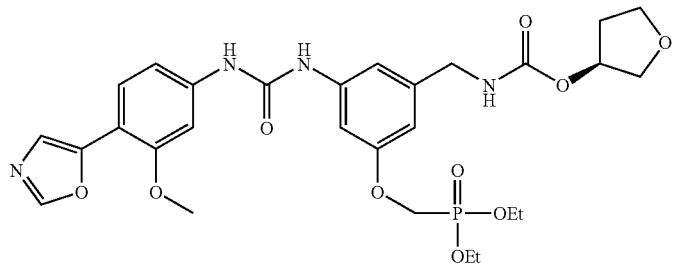
200.35
For example, the bromine substituent of compound 200.30 is substituted with cyano group by the procedure of De Jongh, R. O. et al. (*Recl. Trav. Chim. Pays-Bas* 1968, 87, 1327) and the methoxy group is converted to benzyloxy group as a protecting group, which affords compound 200.31. After selective reduction of cyano to aminomethyl group by borane, the amino group is protected with Boc group and then the reduction of the nitro group using tin(II) chloride generates compound 200.32. This substituted aniline 200.32 is then treated with a reaction mixture of the compound 200.26 and carbonyldiimidazole, as described in U.S. Pat. No. 6,054,472, and U.S. Pat. No. 6,344,465, to form the urea 200.33. Compound 200.33 is converted to 200.34. Deprotection of the benzyl group using catalytic hydrogenation followed by attachment of a phosphonate moiety using 200.9 in the presence of cesium carbonate produces compound 200.35.

EXAMPLES 201-204

Representative compounds of the invention having the following formulae can be prepared as described in Examples 201-204.

D

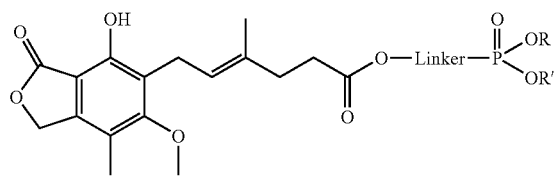

E

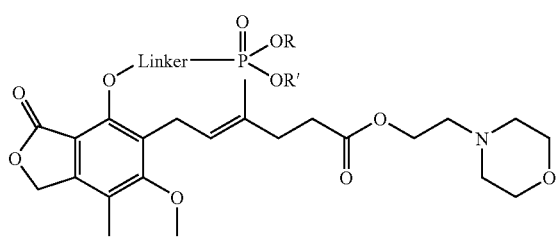

F

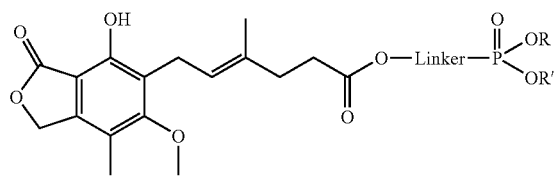

G

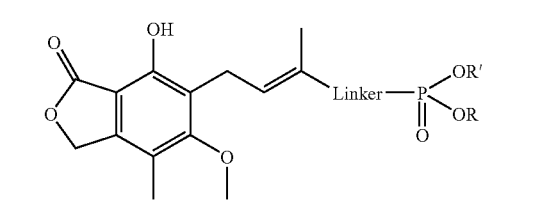

For example, three regions of mycophenolate mofetil can be utilized for the attachment of the phosphonate prodrug as demonstrated by compounds D, E, and G shown above. Also, the carboxylic acid can be replaced with a phosphonic acid as in compound F.

EXAMPLE 201

Preparation of Representative Compounds of Formula 204

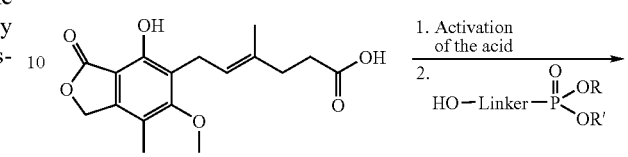

201.1

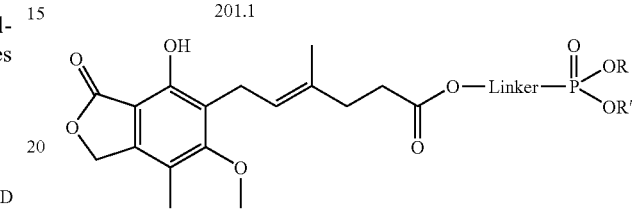

201.3

Representative compounds of the invention can be prepared as illustrated above. The morpholino ethyl moiety can serve as a prodrug functionality to improve bioavailability and can be replaced with the phosphonate prodrug handle as shown above. Mycophenolic acid is commercially available, e.g., from Sigma Chemical Company, St. Louis, Mo. Activation of the carboxylic acid 201.1 in the presence of the free phenol, followed by addition of an alcohol carrying the phosphonate group, results in the formation of the desired product 201.3 (U.S. Pat. No. 4,786,637). A specific compound of the invention can be prepared as follows.

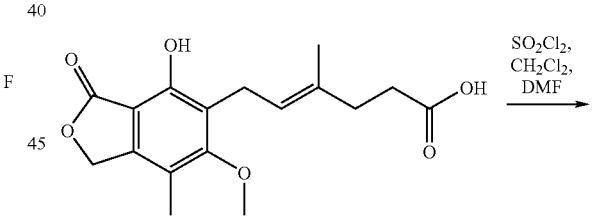

201.1

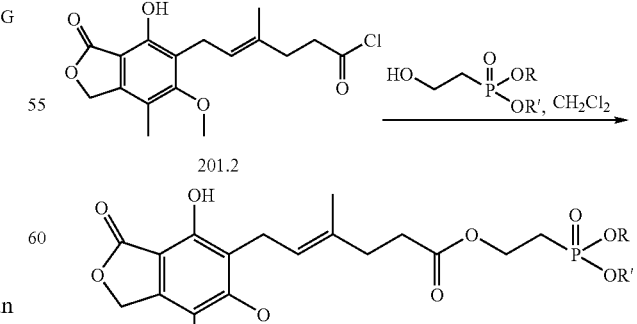

201.3

Mycophenolic acid 201.1 is dissolved in dichloromethane. Thionyl chloride is added followed by a catalytic amount of DMF. The reaction mixture is stirred at room temperature for 3 hours, after which the volatile components are removed under vacuum. The phosphonate-alcohol is dissolved in dichloromethane and chilled to about 4° C. on an ice bath. The mycophenolic acid chloride 201.2 is dissolved in dichloromethane and added to the chilled solution. After stirring for 90 minutes at about 4° C., the reaction mixture is washed with water and then with aqueous sodium bicarbonate. The organic solution is dried and evaporated to yield the phosphonate 201.3.

EXAMPLE 202

Preparation of Representative Compounds of Formula 207

Representative compounds of the invention can be prepared as illustrated above. The C-4 phenol position provides a reactive handle for further analogs as illustrated above. Once the carboxylic acid of 202.1 is blocked by morpholino ethyl, such as in compound 202.2 the phenol can be alkylated under basic conditions. Bases such as pyridine, potassium carbonate, or triethylamine are utilized. Leaving groups such as trifluoromethylsulfonate, mesylate, bromide, or iodide are attached to the phosphonate prodrug subunit and reacted, in the presence of base, with compound 202.2. Compound 202.3 can either be used directly, or in the form of a salt, compound 202.4. Among the large number of salts that can be prepared, chloride and bisulfate salts are one particular embodiment of the invention. A specific compound of the invention can be prepared as follows.

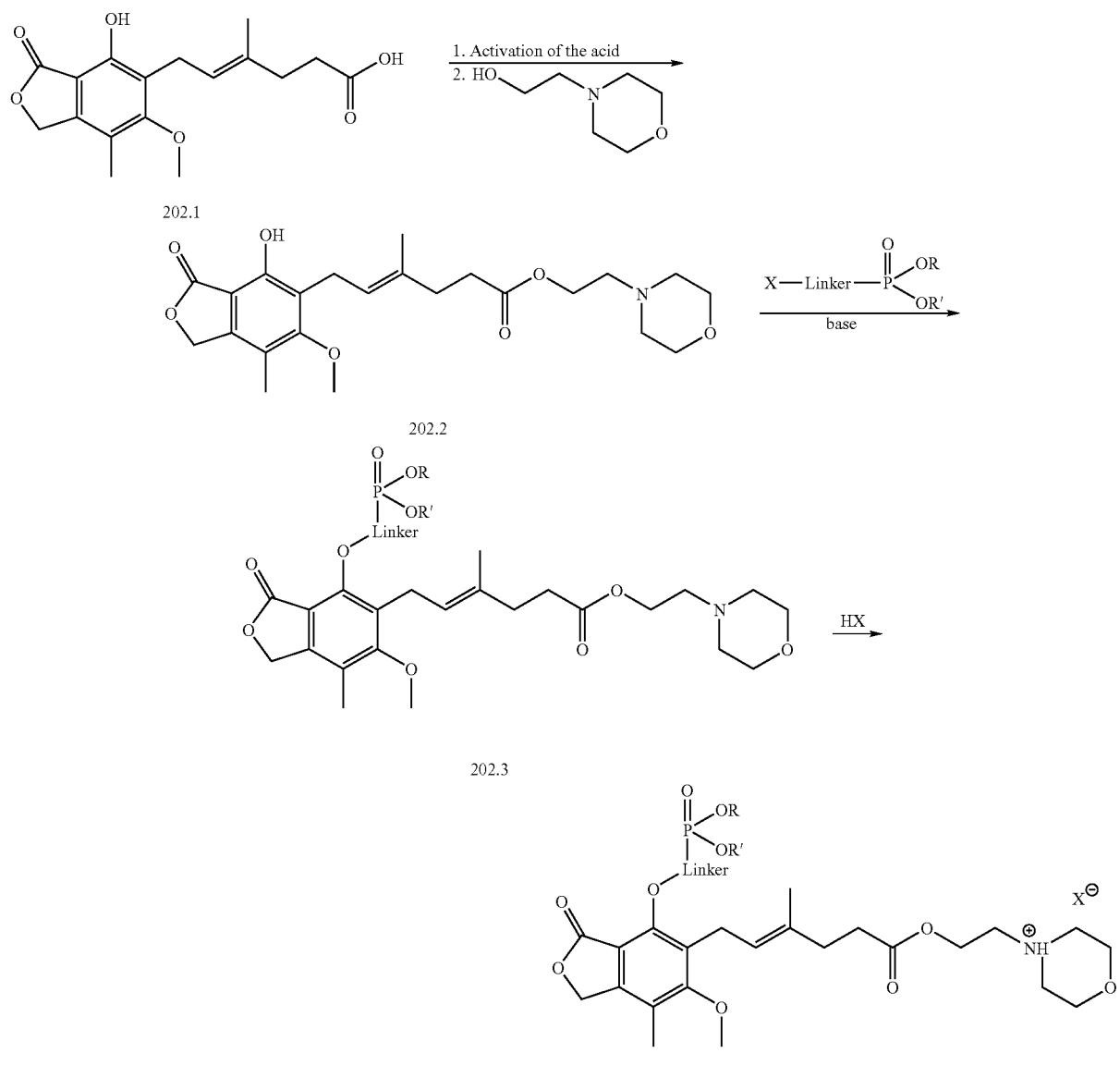

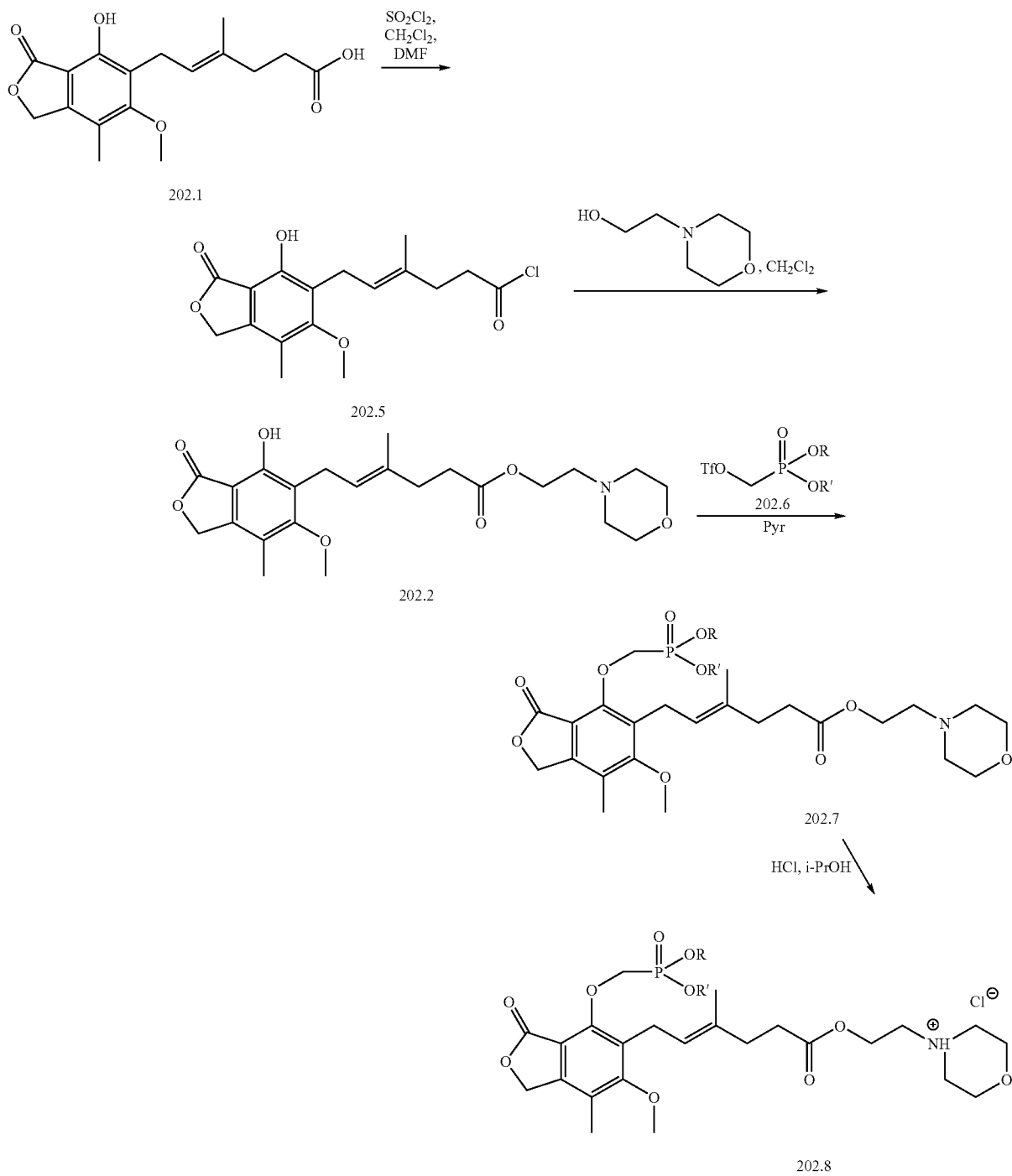

Compound 202.5 is prepared similar to compound 201.2 (described in Example 201). A solution of morpholino ethanol in dichloromethane is cooled to about 4° C. The mycophenolic acid chloride 202.5 is dissolved in dichloromethane and added to the cooled solution. Stirring this solution for about 90 minutes gives compound 202.2. The reaction mixture is washed with water and dried with sodium sulfate. Removal of the solvent provides isolated compound 202.2. Alkylation at the phenolic position of 202.2 is achieved by suspending the compound in pyridine. Triflate 202.6 is added to the solution and the mixture is stirred at room temperature for about 90 minutes. The reaction mixture is poured into water and the product is extracted with ethyl acetate. Removal of the organic layer provides compound 202.7. Hydrochloride salt of 202.7 can optionally be prepared. Compound 202.7 is dissolved in isopropanol and the solution is added to a mixture of hydrogen chloride in isopropanol. The hydrochloride salt 202.8 is collected by filtration and dried under vacuum.

EXAMPLE 203

Preparation of Representative Compounds of Formula 205

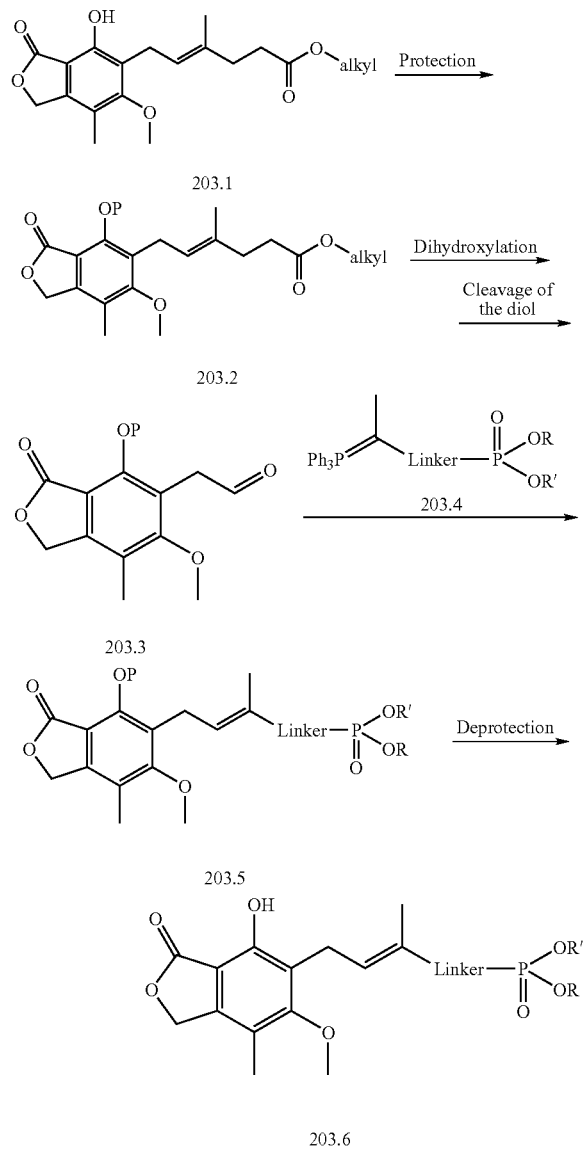

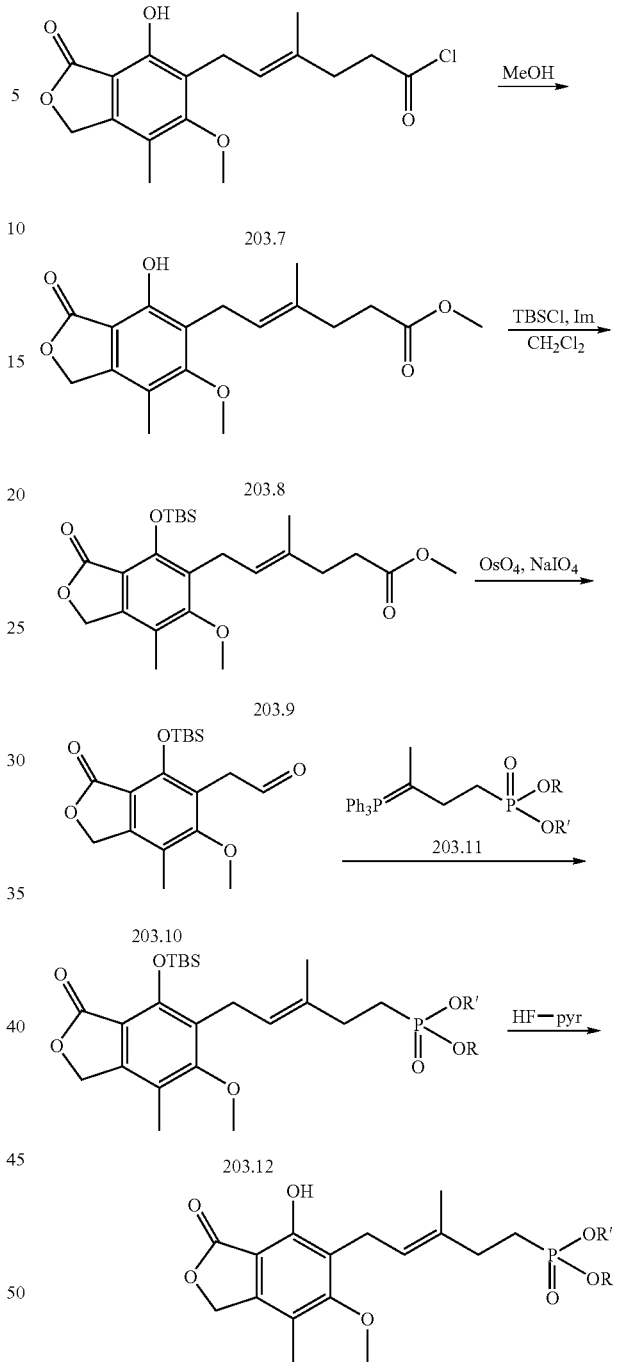

Representative compounds of the invention can be prepared as illustrated above. The carboxylic acid of mycophenolic acid can be replaced with a phosphonic acid that may also serves as a prodrug handle. In order to remove the carboxylic acid containing side chain, the acid chloride 202.5 (prepared in Example 202) is converted to ester 203.1. Protection of the phenol with a silyl group, followed by dihydroxylation and cleavage of the diol generates aldehyde 203.3 (Pankiewicz, et al., *J. Med. Chem.*, 2002, 45, 703), (Patterson et al., U.S. Pat. No. 5,444,072) (Example 20). A Wittig reaction with ylide 203.4 carrying an appropriately protected phosphonate provides the desired compound 203.5. Final deprotection yields compound 203.6. A specific compound of the invention can be prepared as follows.

Mycophenolate ester 203.8 can simply be prepared by stirring the acid chloride 203.7 with MeOH. Then, the phenol position of mycophenolate ester is protected by a silyl group such as TBS to provide compound 203.9. Once the phenol position is protected, dihydroxylation using osmium tetraoxide followed by periodinate cleavage provides aldehyde 203.10. Aldehyde 203.10 and excess of the ylide 203.11 are heated in benzene at reflux for about 24 hours. The reaction mixture is concentrated and the residue is purified by column chromatography to provide olefin 203.12 (Pankiewics et al., *J. Med. Chem.*, 2002, 45, 703). A final deprotection using HF-pyridine yields the final product 203.13.

EXAMPLE 204

Preparation of Representative Compounds of Formula 208

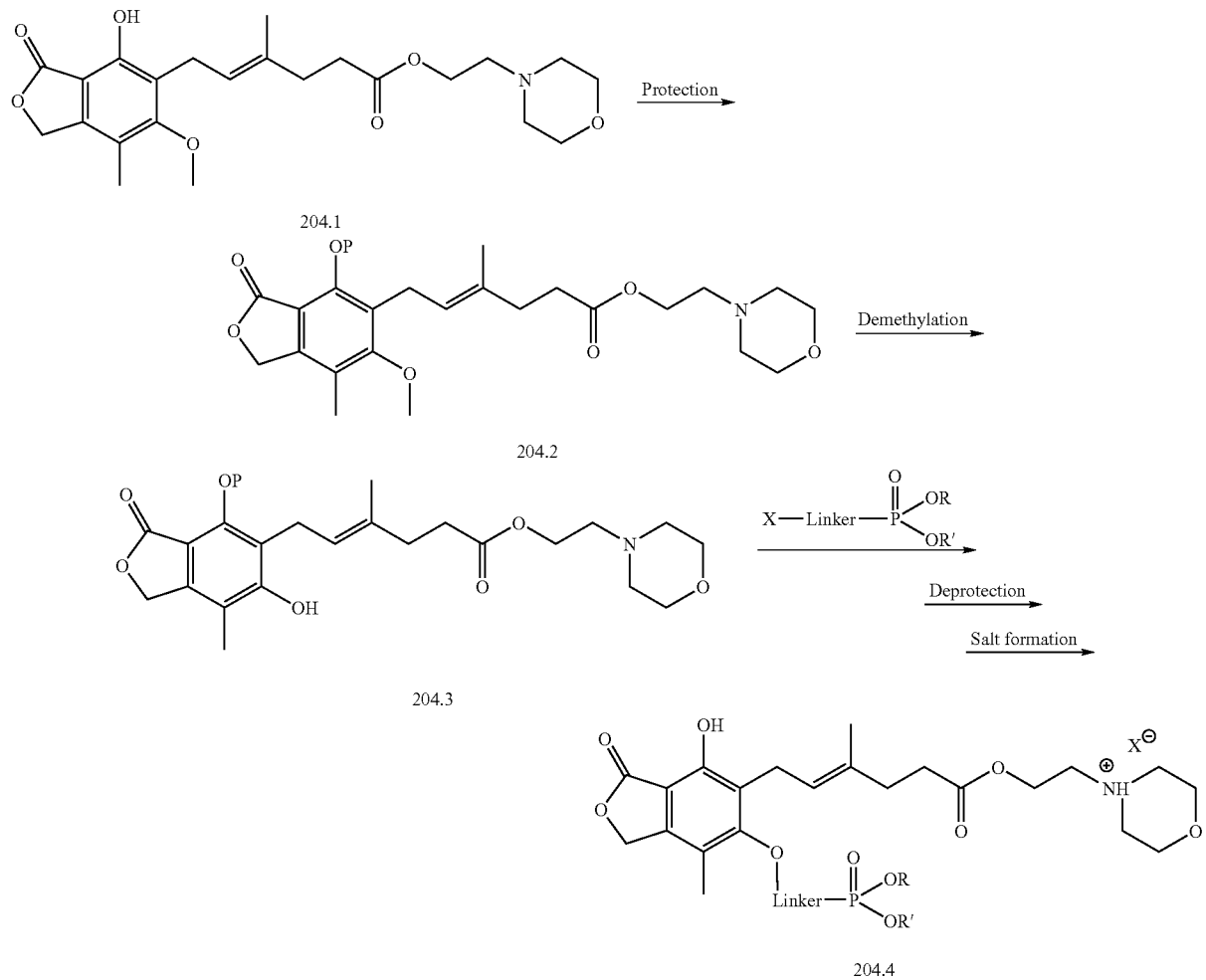

Representative compounds of the invention can be prepared as illustrated above. Another attachement point of the compound can be unmasked after demethylation of mycophenolate ester 204.2 as illustrated above. For this purpose, the 4-OH needs to be masked with a protecting group (P) such as a silyl group. Once the 6-MeO is demethylated and alkylated, the protecting group at position 4 is removed to reveal the final product 204.4. The morphonyl ethanol group is installed early and carried through the alkylation steps. A different protecting group may be installed initially and removed later. In such the latter type of synthesis, the last step is the formation of the morpholinoethyl ester prodrug. A specific compound of the invention can be prepared as described below.

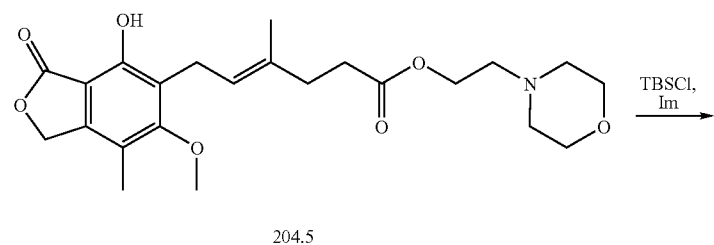

-continued
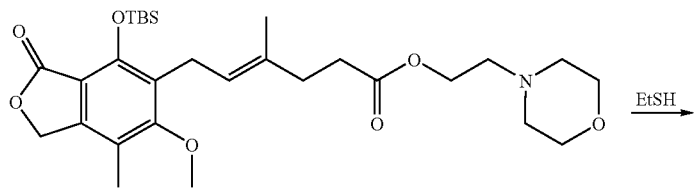
204.6
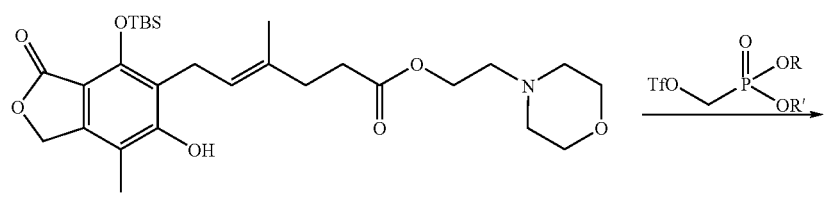
204.7
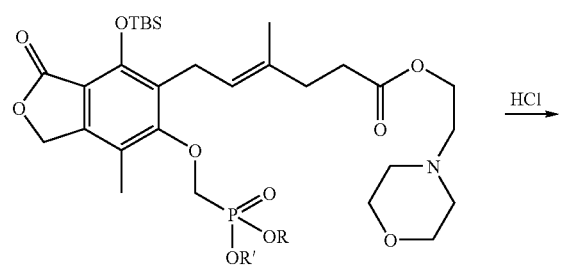
204.8
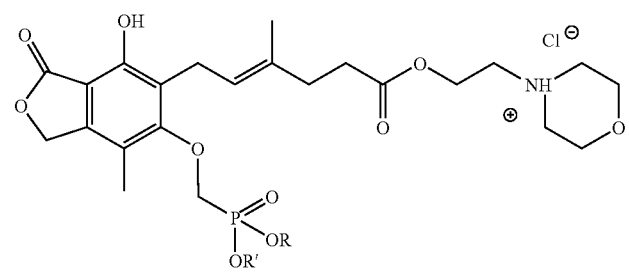
204.9
Phenol 204.5 is protected with TBS group in $CH_2Cl_2$ using imidazole as base to yield 204.6. Demethylation is performed using thiolate nucleophiles to generate compound 204.7. A variety of other methods are also available in literature as described in *Protective Groups in Organic Synthesis* by Greene and Wuts. Alklation of the 6-OH using a triflate of the phosphonate proceeds well using $K_2CO_3$ or TEA to provide 204.8. Final deprotection to remove the TBS group provides product 204.9.

EXAMPLE 205

Preparation of Representative Compounds of Formula 212

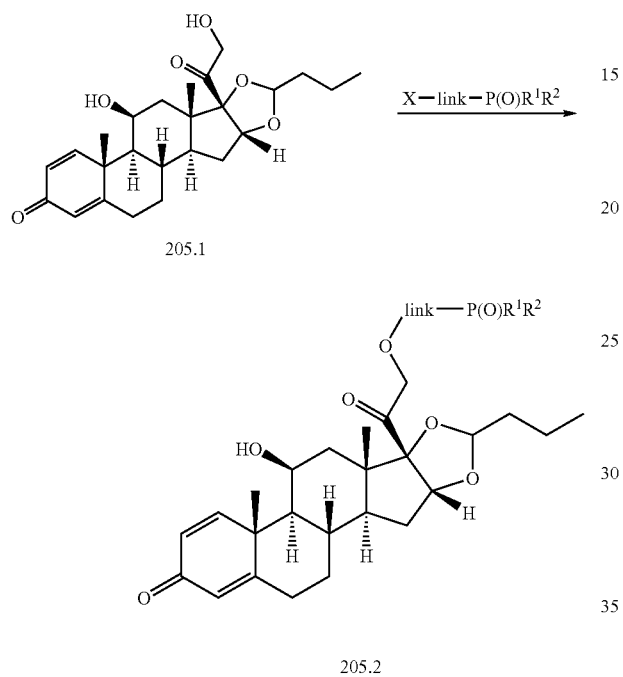

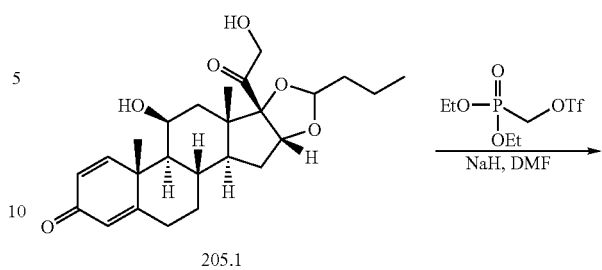

Representative compounds of the invention can be prepared as illustrated above. Derivatives of the C-21 primary hydroxy group are readily prepared by alkylating budesonide 205.1 with the appropriate phosphonate. A specific compound of the invention can be prepared as follows.

After chemoselective extraction of the primary hydroxy proton in 205.1 using one equivalent of sodium hydride, the phosphonate triflate is added to provide the ether 205.5.

EXAMPLE 206

Preparation of Representative Compounds of Formula 211

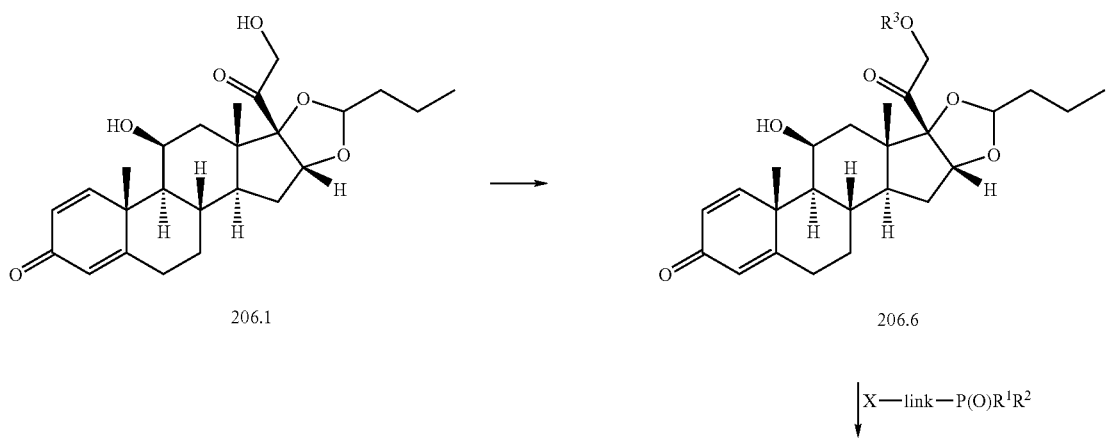

-continued

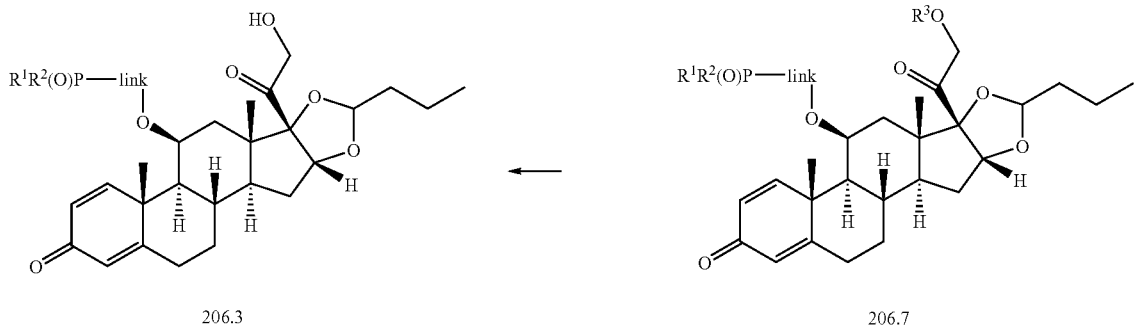

206.3    206.7

Representative compounds of the invention can be prepared as illustrated above. Again taking advantage of the reactivity difference between the primary and secondary hydroxy groups, the primary hydroxy group is masked by an appropriate protecting group. After alkylation at the secondary hydroxy moiety of 206.6 with a leaving group-attached phosphonate and subsequent deprotection, desired analog 206.3 is obtained. A specific compound of the invention can be prepared as follows.

Budesonide 206.1 is chemoselectively protected as its silyl ether using the standard TBSCl and imidazole conditions. (*J. Am. Chem. Soc.* 1972, 94, 6190) Alkylation at the exposed secondary hydroxy group with sodium hydride and the phosphonate triflate furnishes the intermediate 206.9. Final TBAF deprotection of the silyl ether affords the desired product 206.10.

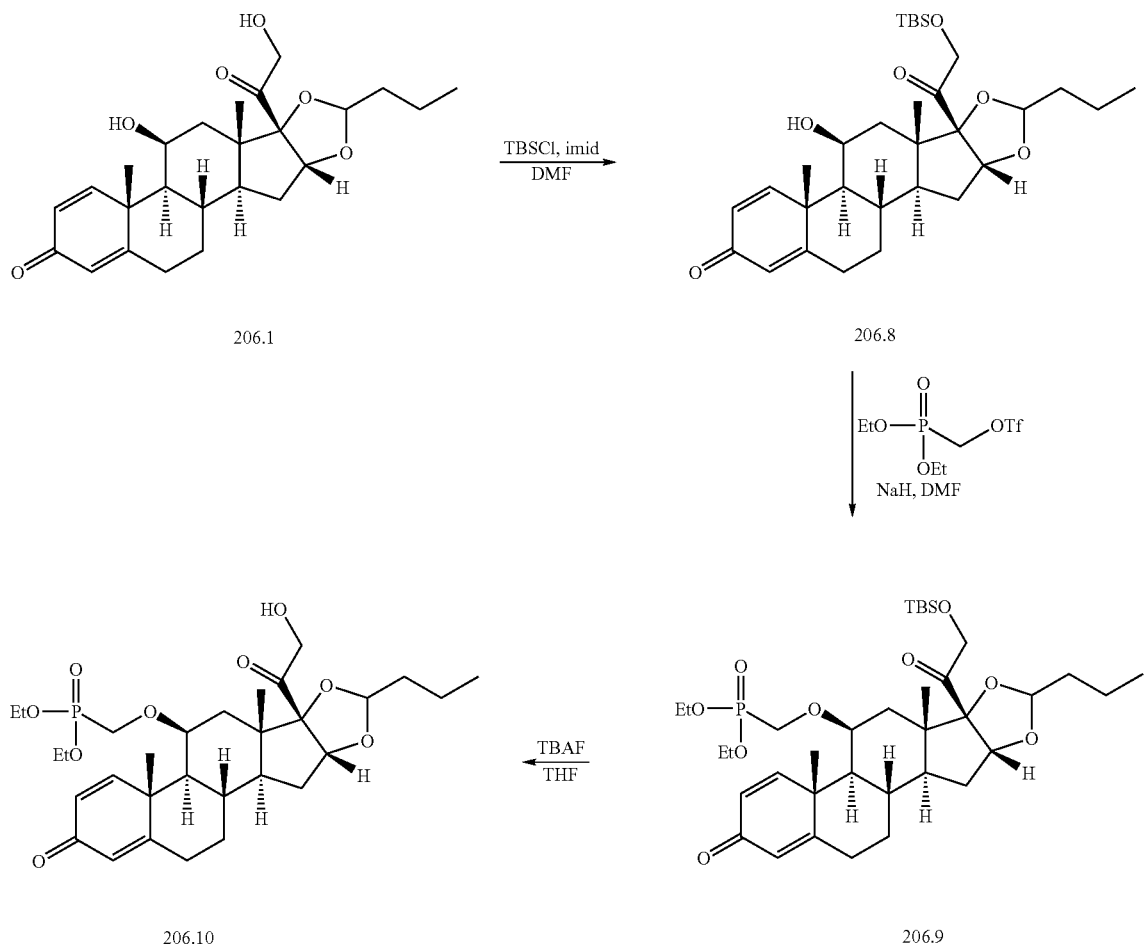

EXAMPLE 207

Preparation of Representative Compounds of Formula 213

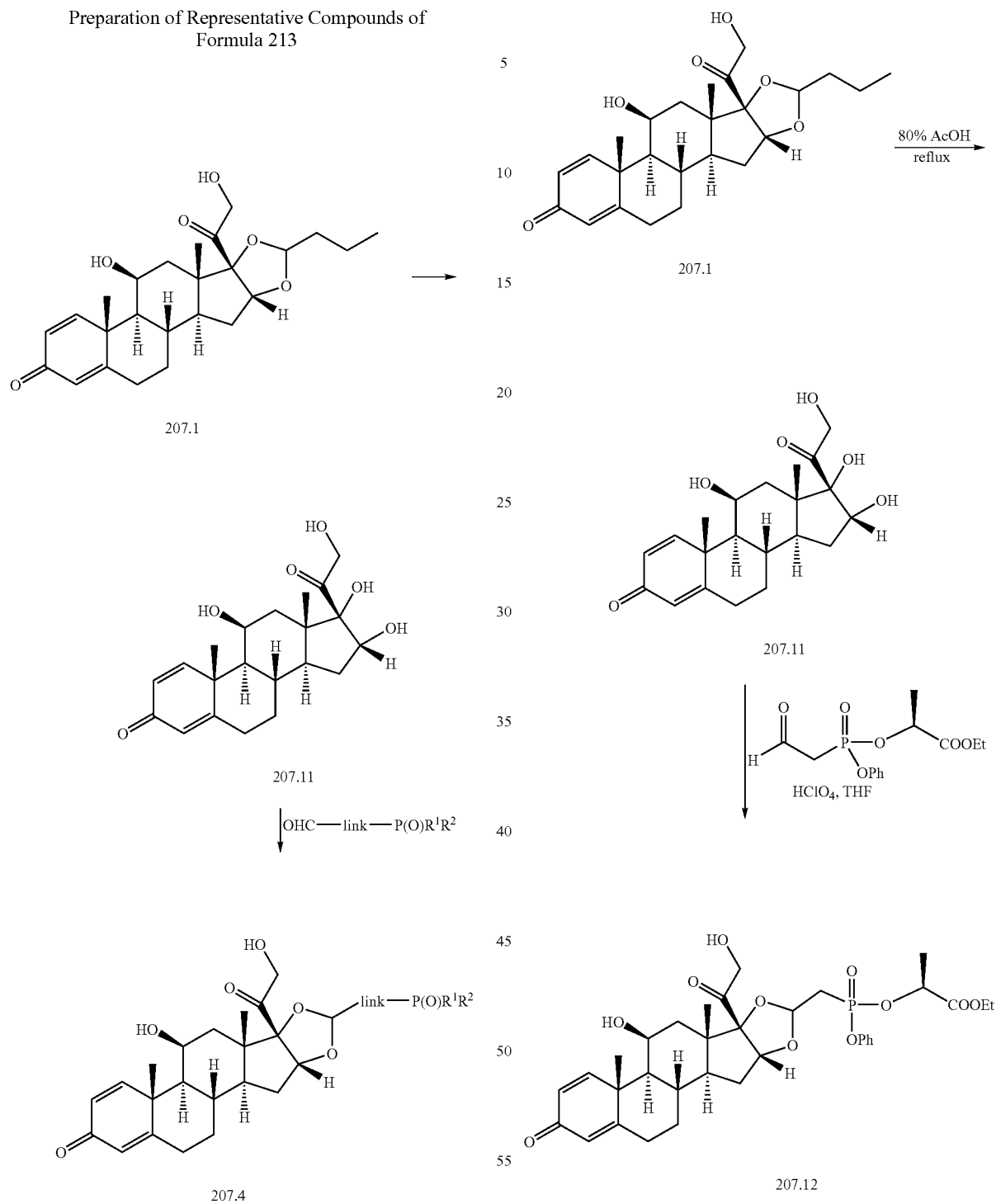

Representative compounds of the invention can be prepared as illustrated above. Phosphonate derivatives of the acetal are readily prepared from acidic hydrolysis of budesonide 207.1 to the diol 207.11. Acetylization of the diol with a phosphonate aldehyde furnishes the desired acetal 207.4. A specific compound of the invention can be prepared as follows.

Budesonide 207.1 is first hydrolized in aqueous acetic acid. (*J. Am. Chem. Soc.* 1987, 109, 1565) The resulting diol 207.11 is acetalized with the phosphonate aldehyde and perchloric acid, affording the acetal 207.12. (*J. Med. Chem.* 1996, 39, 4888-4896)

EXAMPLE 208

Preparation of Representative Compounds of Formula 220

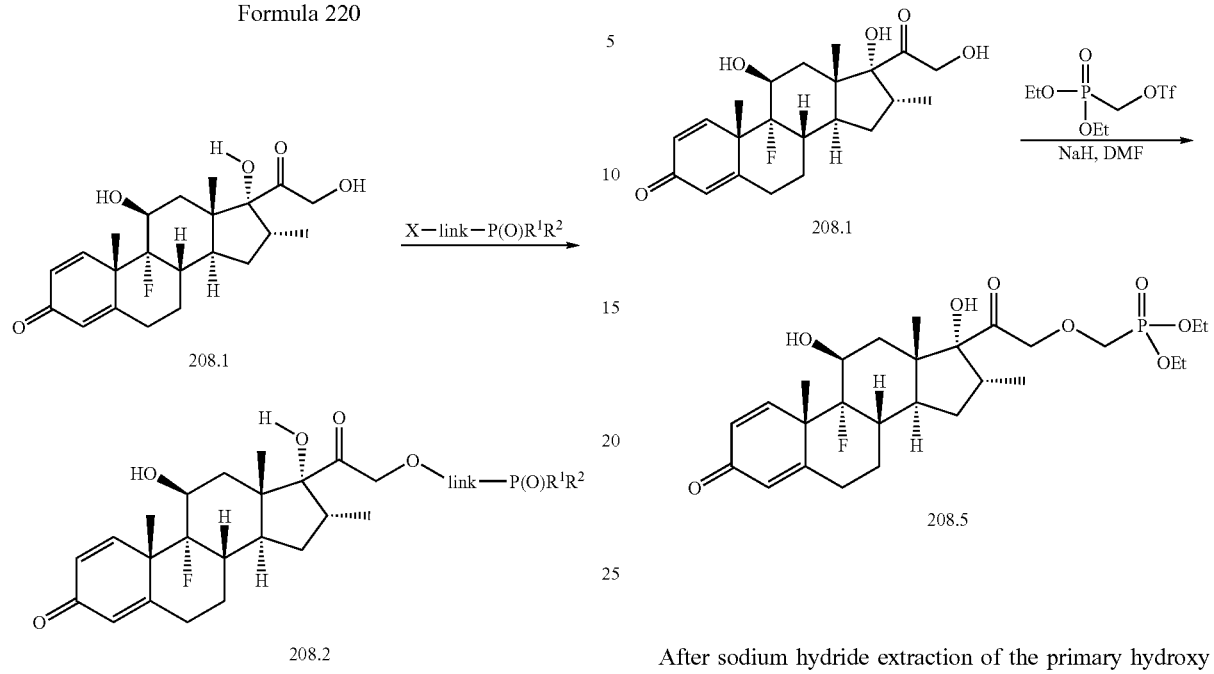

Representative compounds of the invention can be prepared as illustrated above. Derivatization at the C-21 hydroxy group is accomplished through alkylation of dexamethasone 208.1 with the appropriate phosphonate, furnishing analogs of formula 208.2. A specific compound of the invention can be prepared as follows.

After sodium hydride extraction of the primary hydroxy proton in 208.1, diethyl phosphonate triflate is added to afford ether 208.5.

EXAMPLE 209

Preparation of Representative Compounds of Formulae 215 and 218

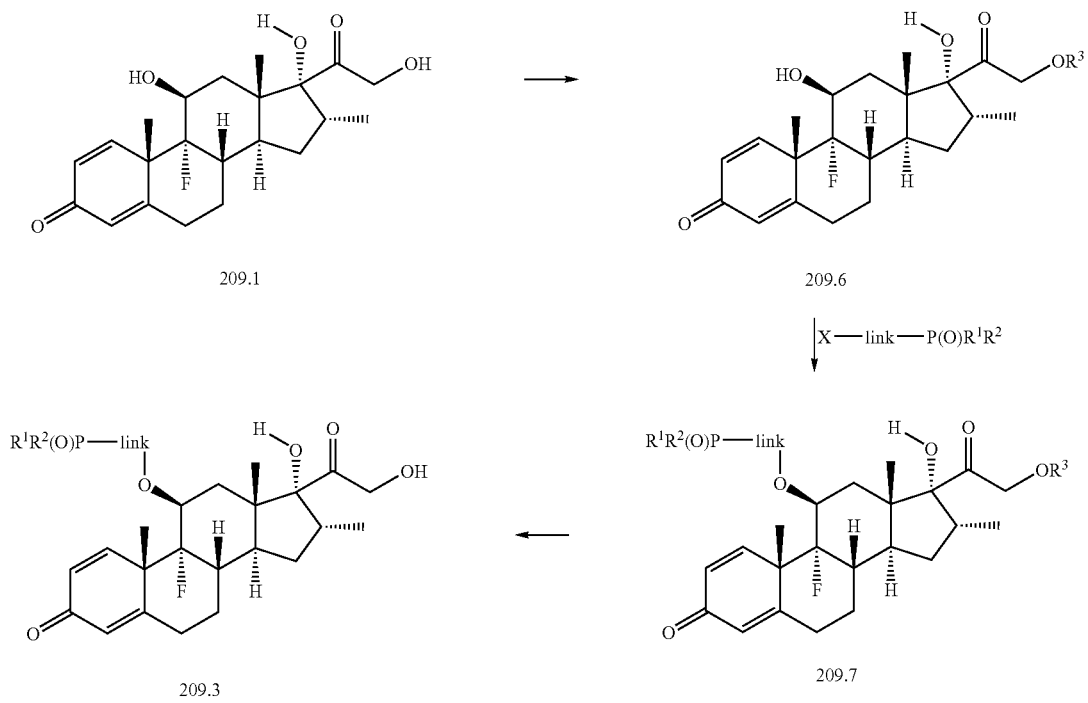

Representative compounds of the invention can be prepared as illustrated above. Phosphonate appendages linked to the C-11 hydroxy group can be attained by utilizing protecting groups on dexamethasone 209.1. Following protection of the primary hydroxy group, protected intermediate 209.6 is alkylated at the more exposed C-11 hydroxy site. Final deprotection provides the desired product 209.3. A specific compound of the invention can be prepared as follows.

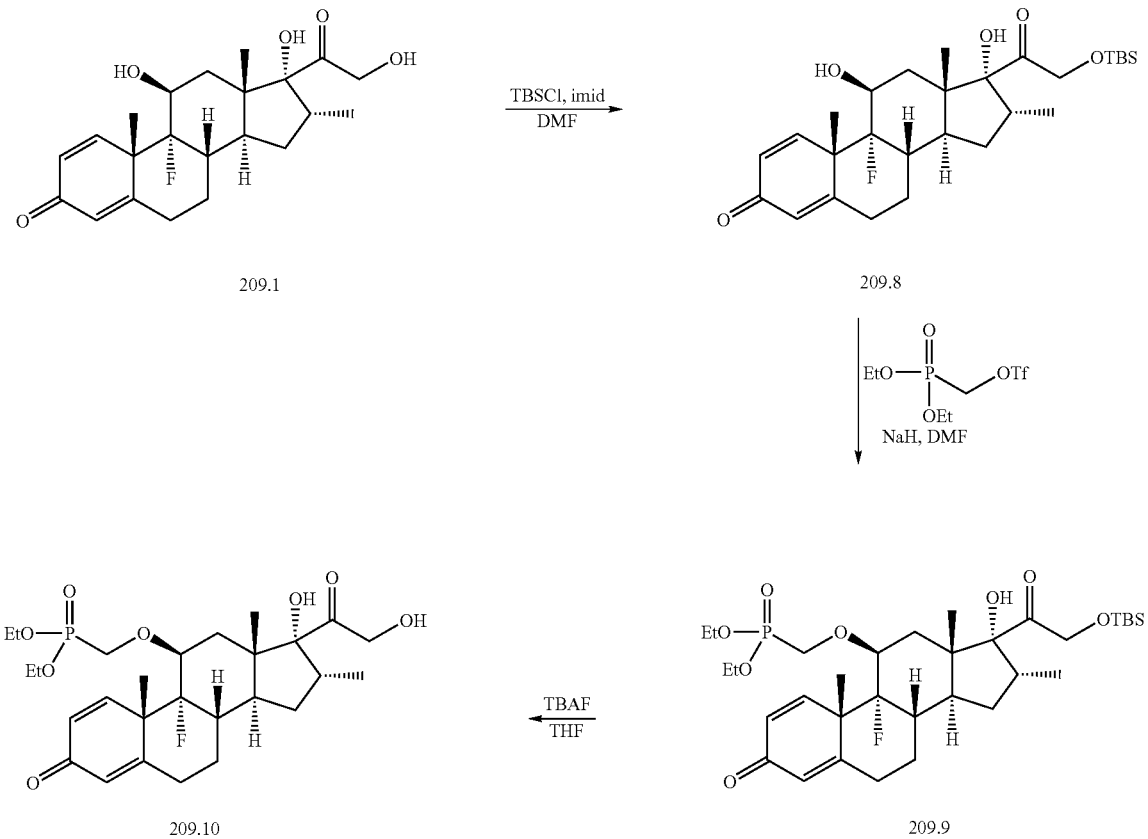

Dexamethasone 209.1 is protected as its silyl ether using the standard TBSCl and imidazole conditions (*J. Am. Chem. Soc.* 1972, 94, 6190). After alkylating with the diethyl phosphonate triflate, the resulting intermediate 209.9 is treated with TBAF to give the diol 209.10.

EXAMPLE 210

Preparation of Representative Compounds of Formulae 216 and 219

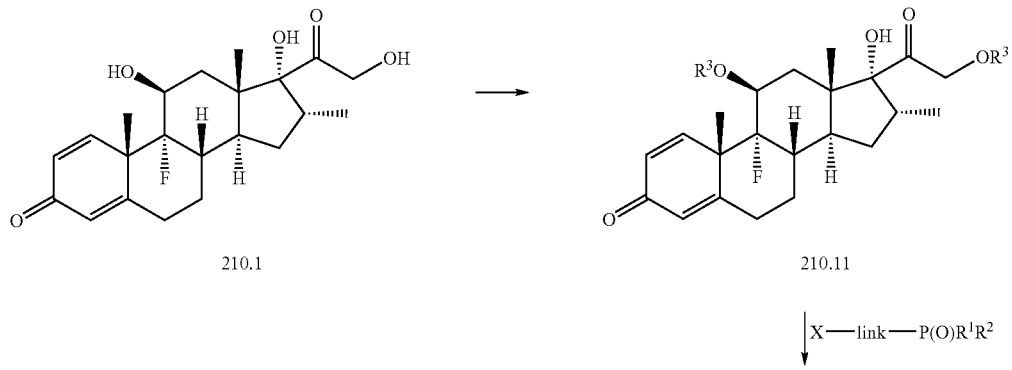

-continued

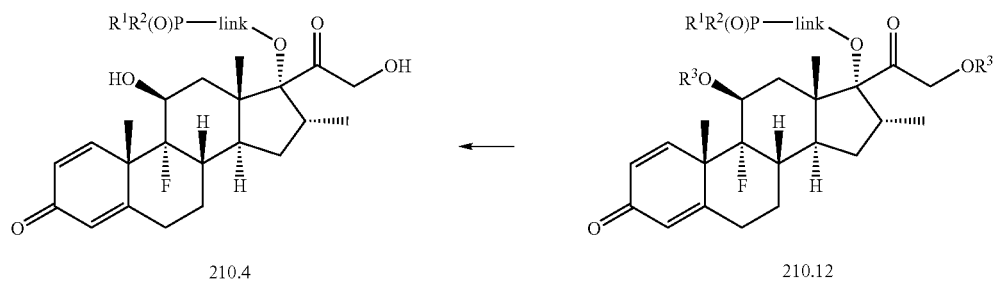

Representative compounds of the invention can be prepared as illustrated above. Protection of dexamethasone 210.1 at the two less hindered sites furnishes alcohol 210.11, which is alkylated at the only exposed hydroxy group with the appropriate phosphonate. Removal of the protecting groups completes the construction of analog 210.4. A specific compound of the invention can be prepared as follows.

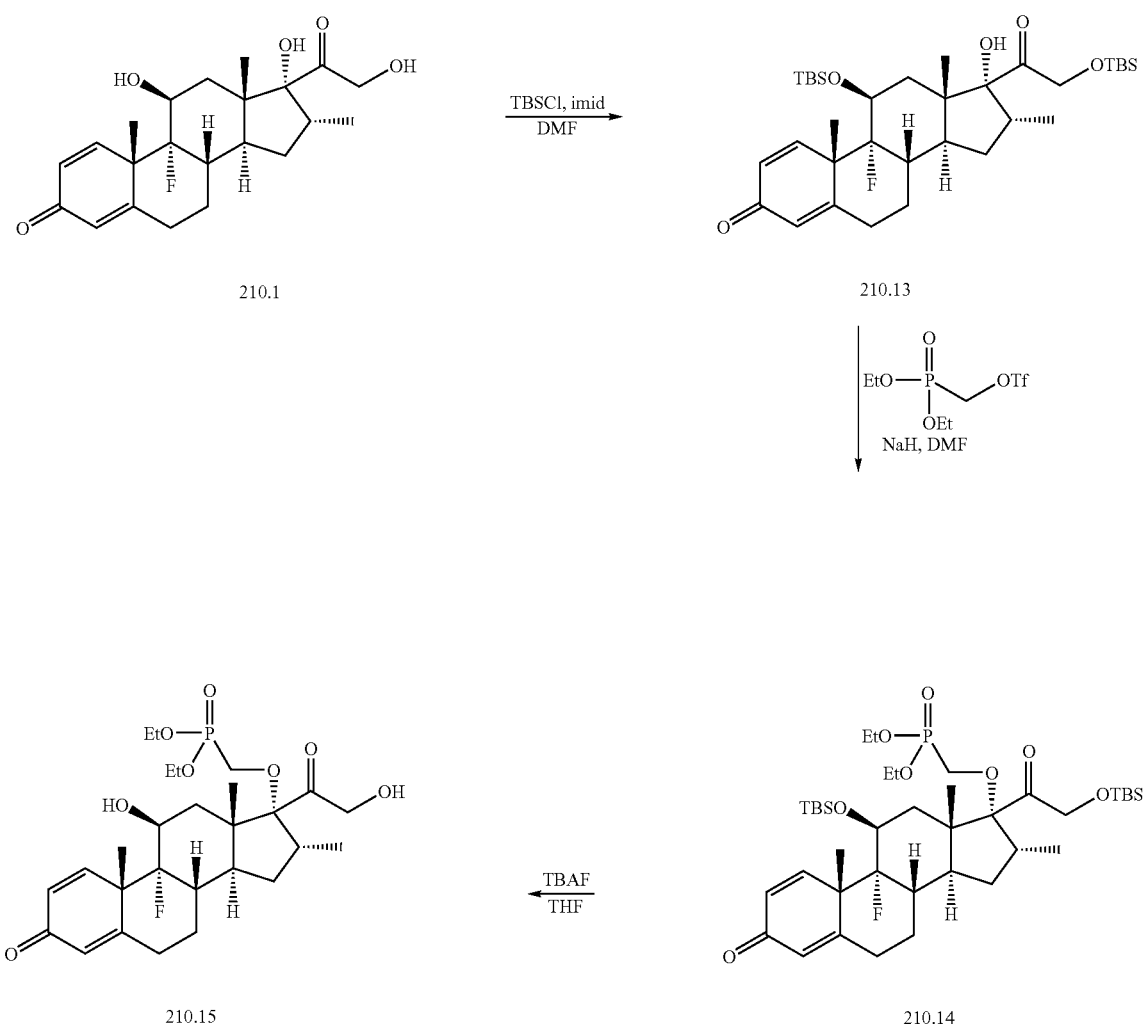

759

Again dexamethasone 210.1 is protected as its TBS ether; however, harsher conditions should allow for bis-protection. After alkylating with the diethyl phosphonate triflate, the resulting intermediate 210.14 is treated with TBAF to give the desired phosphonate 210.15.

EXAMPLE 211

Preparation of Representative Compounds of Formulae 221-224

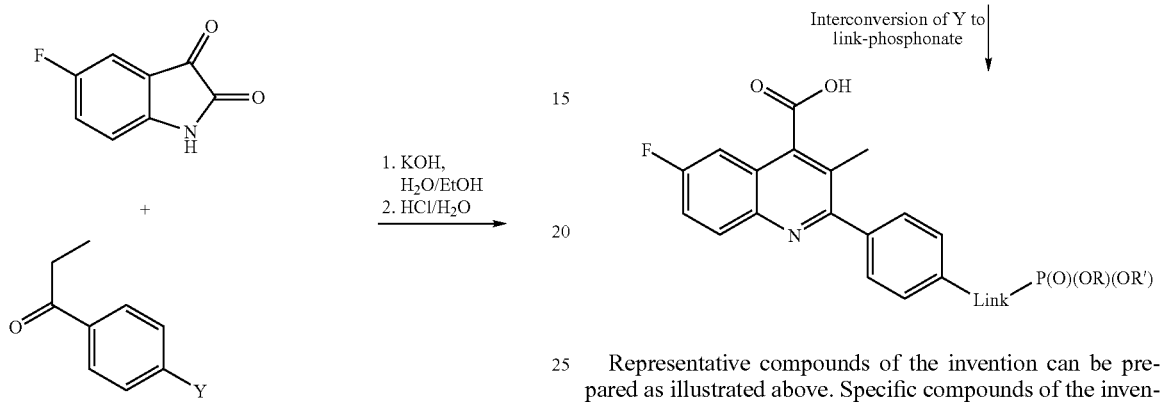

Representative compounds of the invention can be prepared as illustrated above. Specific compounds of the invention can be prepared as illustrated below.

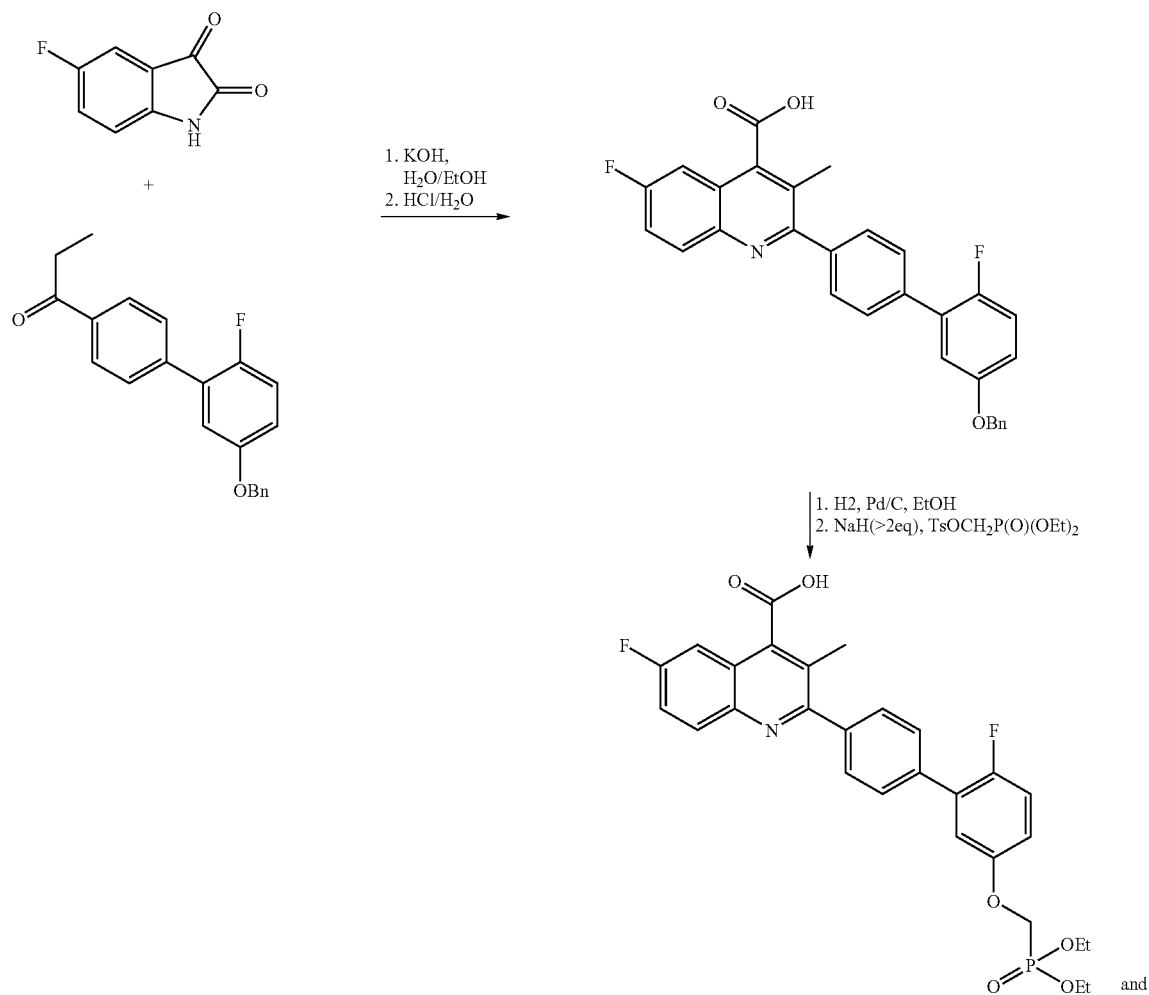

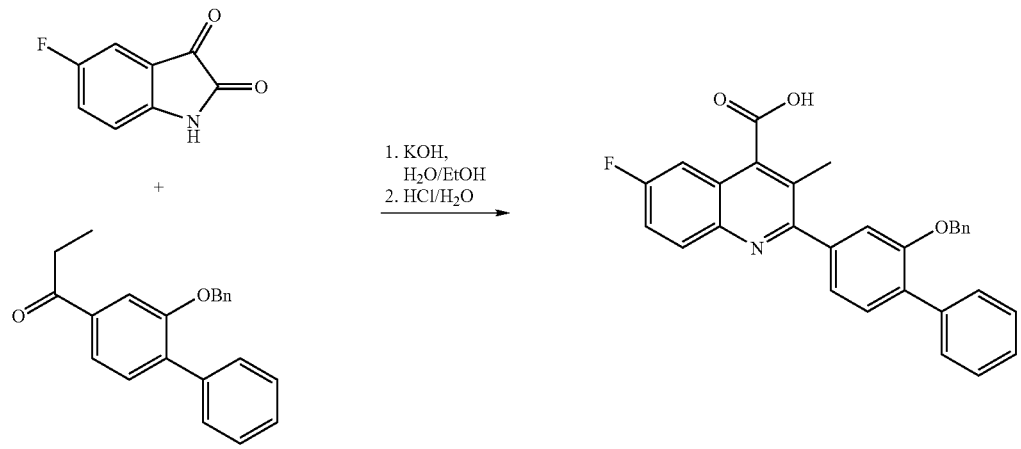

EXAMPLE 212

Preparation of Representative Compounds of Formula 225

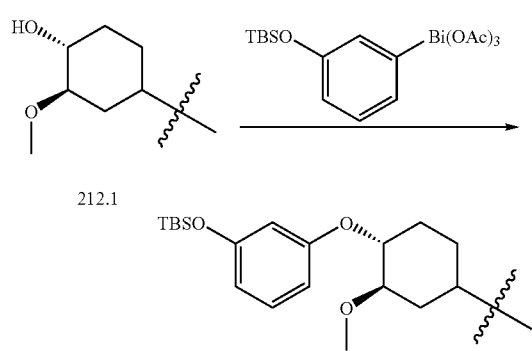

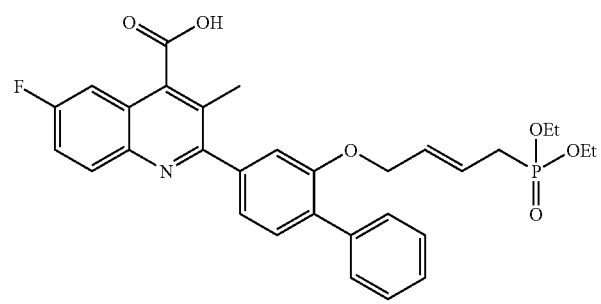

Representative macrolide compounds of the invention, wherein the structure 212.1 is understood to be the compound tacrolimus, ascomycin or sirolimus, can be prepared as illustrated above, for example, using an aryl bismuth reagent such as that shown is described in *Bioorg. Med. Chem. Lett,* 1995, 5, 1035. Additionally, silver salts have been used to mediate alkylations on immunosuppresive macrolides such as these: see *J. Med. Chem.,* 1998, 41, 1764. Specific compounds of the invention can be prepared as illustrated below.

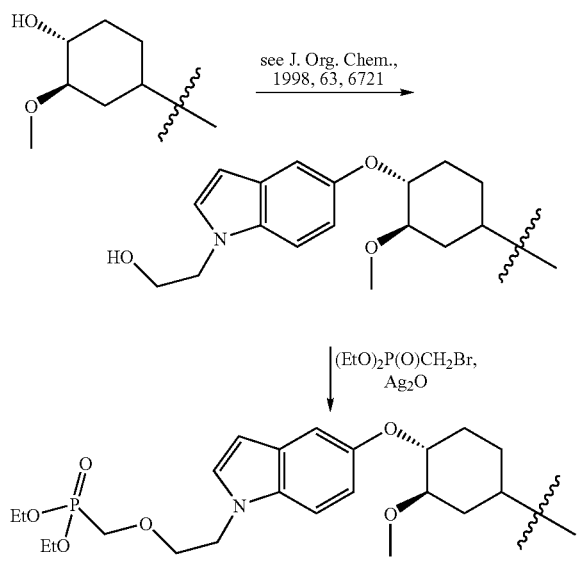

EXAMPLE 213

Preparation of a Representative Compound of Formula 231-(2-{4-[(2,4-Diamino-pteridin-6-ylmethyl)-methyl-amino]-benzoylamino}-methyl)phosphonic acid diethyl ester

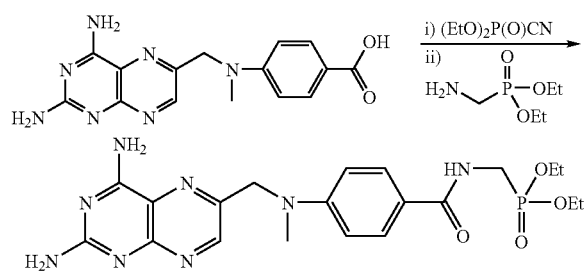

To a solution of 4-[(2,4-diamino-pteridin-6-ylmethyl)-methyl-amino]-benzoic acid hemihydrochloride dihydrate (67.0 mg, 177 μmol) in DMF (3.0 mL) was added diethyl cyanophosphonate (34.8 μL, 230 μmol) and diisopropylethylamine (Hunig's Base, DIEA, 30.4 μL, 177 μmol). The solution was stirred at ambient temperature for 4 hours when diethyl(aminomethyl)-phosphonate (45.4 mg, 177 μmol) was added. The solution was stirred for 4 additional hours, when complete consumption of the starting materials was observed. The reaction was worked up by removal of the solvent in vacuo and purifying the residue by silica gel chromatography using MeOH—CH$_2$Cl$_2$ (10-30%). The product collected from this chromatography step was sufficiently pure to be carried on to the next reaction. A small amount of the product (20 mg) was repurified by RP HPLC on C$_{18}$ column using H$_2$O/acetonitrile (2-95%) to provide 12.9 mg (76%) of the pure product. $^1$H NMR (300 MHz, DMSO-d$_6$) δ 1.19 (t, 6H, J=7.2 Hz), 3.21 (s, 3H), 3.70 (m, 2H), 4.00 (q, 4H, J=7.2 Hz), 4.81 (s, 2H), 6.81 (d, 2H, J=9 Hz), 7.71 (d, 2H, J=9 Hz), 8.40 (br s, 1H), 8.61 (s, 1H). $^{31}$P (121.4 MHz, DMSO-d$_6$) δ 23.4. MS (m/z) 475.2 [M+H]$^+$, 597.2 [M+Na]$^+$.

EXAMPLE 214

Preparation of Representative Compound of Formula 231-(2-{4-[(2,4-Diamino-pteridin-6-ylmethyl)-methyl-amino]-benzoylamino}-methyl)-phosphonic acid To a solution of crude (2-{4-[(2,4-Diamino-pteridin-6-yl-methyl)-methyl-amino]-benzoylamino}-ethyl)-phosphonic acid diethyl ester post silica column chromatography (60 mg, 126 μmol) in dry DMF (0.90 mL) was added trimethylsilyl bromide (bromotrimethylsilane, TMSBr, 130.6 μL, 1,010 μmol) at ambient temperature. The solution was then heated at 70° C. for 4.0 hours, after which the reaction mixture was allowed to cool to room temperature. The solvent volume was reduced to ~700 μL in vacuo and diluted with H$_2$O (100 μL). This solution was purified by RP HPLC on C$_{18}$ column using H$_2$O/acetonitrile (2-95%) to provide 26.8 mg (51%) of the desired compound as a yellow solid. $^1$H NMR (300 MHz, DMSO-d$_6$) δ 3.18 (s, 3H), 3.50 (m, 2H), 4.77 (s, 2H), 6.79 (d, 2H, J=9 Hz), 7.79 (d, 2H, J=9 Hz), 8.07 (br s, 1H), 8.56 (s, 1H); MS (m/z) 419.2 [M+H]$^+$.

EXAMPLE 215

Preparation of Representative Compound of Formula 231-(2-{4-[(2,4-Diamino-pteridin-6-ylmethyl)-methyl-amino]-benzoylamino}-ethyl)phosphonic acid diethyl ester

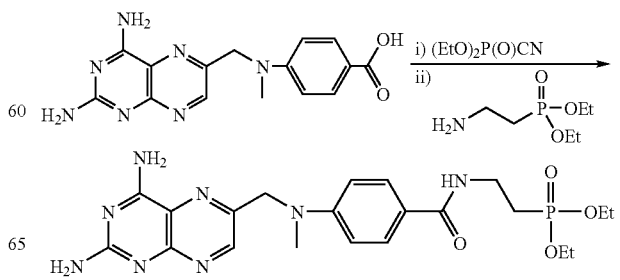

To a solution of 4-[(2,4-diamino-pteridin-6-ylmethyl)-methyl-amino]-benzoic acid hemihydrochloride dihydrate (61.2 mg, 161 μmol) in DMF (2.8 mL) were added diethyl cyanophosphonate (31.8 μL, 210 μmol) and DIEA (27.8 μL, 161 μmol). The solution was stirred at ambient temperature for 4 hours, when diethyl(aminoethyl)phosphonate (43.8 mg, 161 μmol) was added. The solution was stirred for 3 additional hours, by which time complete consumption of the starting materials was observed. The reaction was worked up by removal of the solvent in vacuo and purifying the residue by silica gel chromatography using MeOH—CH$_2$Cl$_2$ (10-30%). The product collected from this chromatography step was sufficiently pure to be carried on to the next reaction. A small amount of the product (32 mg) was re-purified by RP HPLC on C$_{18}$ column using H$_2$O/acetonitrile (2-95%) to provide 19 mg (70%) of the pure product. $^1$H NMR (300 MHz, DMSO-d$_6$) δ 1.21 (t, 6H, J=7 Hz), 1.95-2.05 (m, 2H), 3.20 (s, 3H), 3.13-3.22 (m, 2H), 3.98 (appt septet, 4H, J=7 Hz), 4.79 (s, 2H), 6.80 (d, 2H, J=9 Hz), 7.65 (d, 2H, J=9 Hz), 8.20 (br s, 1H), 8.60 (s, 1H). $^{31}$P (121.4 MHz, DMSO-d$_6$) δ 28.9. MS (m/z) 489.2 [M+H]$^+$, 511.2 [M+Na]$^+$.

EXAMPLE 216

Preparation of Representative Compound of Formula 231-(2-{4-[(2,4-Diamino-pteridin-6-ylmethyl)-methyl-amino]-benzoylamino}-ethyl)-phosphonic acid

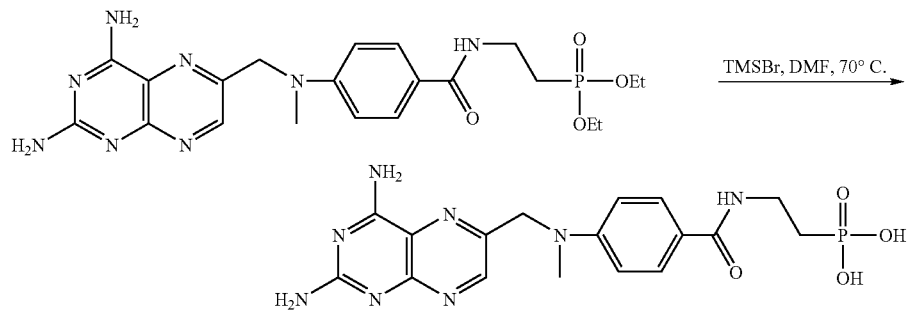

To a solution of crude (2-{4-[(2,4-diamino-pteridin-6-ylmethyl)-methyl-amino]-benzoylamino}-ethyl)-phosphonic acid diethyl ester post silica column chromatography (61 mg, 125 μmol) in dry DMF (1.00 mL) was added TMSBr (129.0 μL, 999.2 μmol) at ambient temperature. The solution was then heated at 70° C. for 5.5 hours, when LCMS analysis demonstrated the reaction to be 90% complete. The reaction mixture was allowed to cool to room temperature and stirred for an additional 12 hours. The reaction was worked up by removal of the solvent in vacuo and dissolving the residue in DMF/H$_2$O (800 μL, 1:1) and 1N aqueous NaOH (15 μL). The product was purified by RP HPLC on C$_{18}$ column using H$_2$O/acetonitrile (2-95%) to provide 29 mg (53%) of the desired compound as a yellow solid. $^1$H NMR (300 MHz, DMSO-d$_6$) δ 1.67-1.85 (m, 2H), 3.19 (s, 3H), 3.25-3.40 (m, 2H), 4.76 (s, 2H), 6.71 (br s, 2H), 5.80 (d, 2H, J=9 Hz), 7.64 (d, 2H, J=9 Hz), 7.73 (br s, 2H), 8.15 (br s, 1H), 8.56 (s, 1H). $^{31}$P (121.4 MHz, DMSO-d$_6$) δ 23.0. MS (m/z) 431.3 [M−H]$^-$.

EXAMPLE 217

Preparation of Representative Compound of Formula 231-(2-{4-[(2,4-Diamino-pteridin-6-ylmethyl)-methyl-amino]-benzoylamino}-propyl)-phosphonic acid diethyl ester

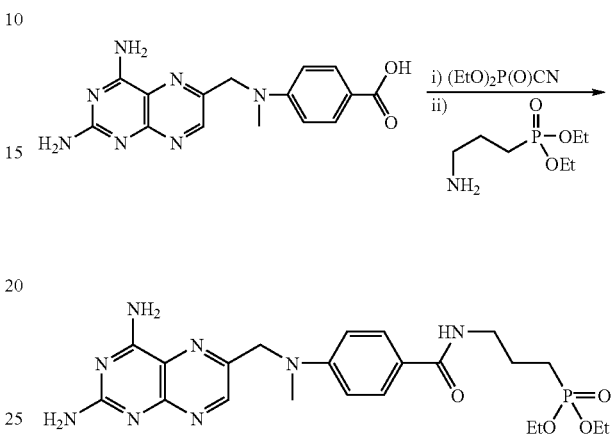

To a solution of 4-[(2,4-diamino-pteridin-6-ylmethyl)-methyl-amino]-benzoic acid hemihydrochloride dihydrate (61.2 mg, 161 μmmol) in DMF (2.8 mL) were added diethyl cyanophosphonate (31.8 μL, 210 μmol) and DIEA (27.8 μL, 161 μmol). The solution was stirred at ambient temperature for 3 hours, when diethyl(aminopropyl)phosphonate (34.9 mg, 122.6 μmol) was added. The solution was stirred for 2 additional hours, whereupon complete consumption of the starting materials was observed. The reaction was worked up by removal of the solvent in vacuo and purifying the residue by silica gel chromatography using MeOH—CH$_2$Cl$_2$ (10-30%). The product (65.5 mg) collected from this chromatography step was sufficiently pure to be carried on to the next reaction. A small amount (32.8 mg) was re-purified by RP HPLC on C$_{18}$ column using H$_2$O/acetonitrile (2-95%) to provide 23.2 mg (75%) of the pure product. $^1$H NMR (300 MHz, DMSO-d$_6$) δ 1.20 (t, 6H, J=7.2 Hz), 1.64-1.75 (m, 4H), 3.22 (s, 3H), 3.41 (m, 2H), 3.98 (appt septet, 4H, J=7.2 Hz), 4.85 (s, 2H), 6.79 (d, 2H, J=9 Hz), 7.68 (d, 2H, J=9 Hz), 8.17 (br s, 1H), 8.70 (s, 1H); $^{31}$P (121.4 MHz, DMSO-d$_6$) δ 31.9; MS (m/z) 503.2 [M+H]$^+$.

EXAMPLE 218

Preparation of Representative Compound of Formula 231-(2-{4-[(2,4-Diamino-pteridin-6-ylmethyl)-methyl-amino]-benzoylamino}-propyl)-phosphonic acid

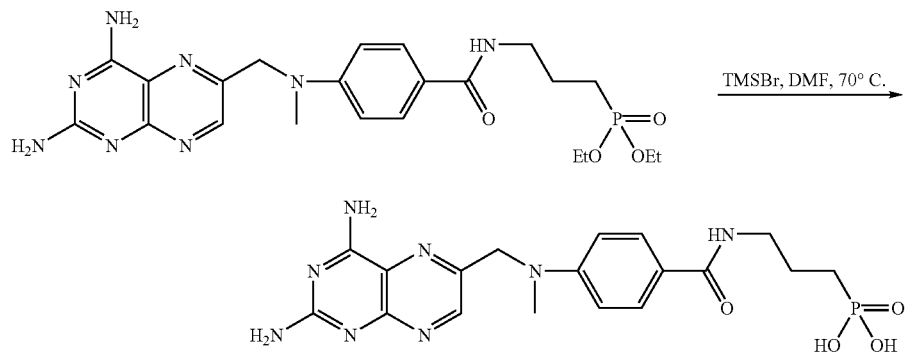

To a solution of crude (2-{4-[(2,4-diamino-pteridin-6-yl-methyl)-methyl-amino]-benzoylamino}-propyl)-phosphonic acid diethyl ester post silica column chromatography (32.2 mg, 66.2 µmol) in dry DMF (0.50 mL) was added TMSBr (68.0 µL, 529.6 µmol) at ambient temperature. The solution was then heated at 70° C. for 1.0 hour, when LCMS analysis demonstrated the reaction to be complete. The reaction mixture was allowed to cool to room temperature, and water (60 µL) and methanol (60 µL) were added. The crude reaction mixture was purified by RP HPLC on $C_{18}$ column using $H_2O$/acetonitrile (2-95%) to provide 11.2 mg (38%) of the desired compound as a yellow solid. $^1$H NMR (300 MHz, DMSO-$d_6$) δ 1.50 (m, 2H), 1.61 (m, 2H), 3.22 (s, 3H), 3.25-3.40 (m, 2H), 4.84 (s, 2H), 6.80 (d, 2H, J=9 Hz), 7.69 (d, 2H, J=9 Hz), 8.20 (br s, 1H), 8.69 (s, 1H). $^{31}$P (121.4 MHz, DMSO-$d_6$) δ 26.3. MS (m/z) 447.3 [M−H]$^-$.

EXAMPLE 219

Preparation of Representative Compound of Formula 231-2-[(2-{4-[(2,4-diaminopteridin-6-ylmethyl)methylamino]benzoylamino}-ethyl)phenoxyphosphi-noyloxy]propionic acid ethyl ester [diastereomeric mixture at phosphorus]

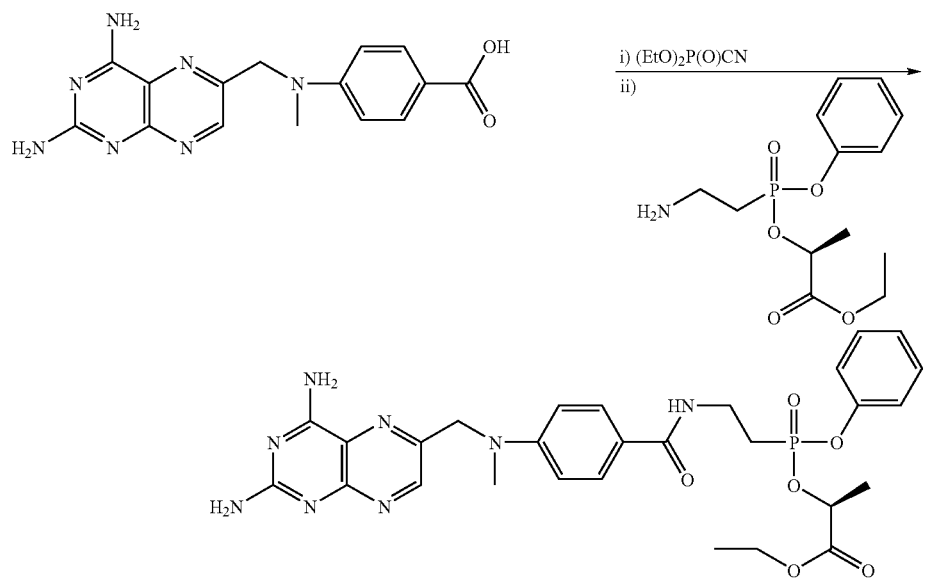

To a solution of 4-[(2,4-diamino-pteridin-6-ylmethyl)-methyl-amino]-benzoic acid hemihydrochloride dihydrate (60.0 mg, 158.3 µmol) in DMF (2.5 mL) were added diethyl cyanophosphonate (31.2 µL, 205.7 µmol) and DIEA (81.8 µL, 474.9 µmol). The solution was stirred at ambient temperature for 3.5 hours, when a solution of (S)-2-[(2-aminoethyl)phenoxyphosphinoyloxy]-propionic acid ethyl ester mono acetic acid salt (57.1 mg, 158.3 µmol; mixture of diastereomers at phosphorus) in DMF (200 µL) was added. The solution was stirred for 1.5 additional hours, whereupon complete consumption of the starting materials was observed. The solvent was removed in vacuo and the crude material was purified by silica gel chromatography using MeOH—CH$_2$Cl$_2$ (10-30%). A small amount of the product (24.8 mg) was repurified by RP HPLC on C$_{18}$ column using H$_2$O/acetonitrile (2-95%) to provide 15.8 mg (65%) of the pure product. $^1$H NMR (300 MHz, DMSO-d$_6$) δ 1.17-1.27 (m, 3H), 1.32 (d, 2H, J=7.5 Hz), 1.42 (d, 1H, J=7.5 Hz) 2.27 (m, 2H), 3.19 (s, 3H), 3.53 (m, 2H), 4.08-4.14 (m, 2H), 4.77 (s, 2H), 4.98 (m, 1H), 6.72 (br s, 1H), 6.81 (d, 2H, J=9 Hz), 7.21 (m, 3H), 7.36 (m, 2H), 7.66 (d, 2H, J=9 Hz), 8.26 (br s, 1H), 8.56 (s, 1H); $^{31}$P (121.4 MHz, DMSO-d$_6$) δ 26.6, 27.4. MS (m/z) 609.2 [M+H]$^+$.

EXAMPLE 220

Preparation of Representative Compound of Formula 231-2-[(2-{4-[(2,4-diaminopteridin-6-ylmethyl)methylamino]benzoylamino}-ethyl)phenoxyphosphinoyloxy]-propionic acid [diastereomeric mixture at phosphorus]

noyloxy]propionic acid ethyl ester (mixture of diastereomers at phosphorus; 40.0 mg, 65.7 μmol) in DMF (0.4 mL), acetonitrile (0.2 mL) and water (0.2 mL) was added aqueous sodium hydroxide (1 N, 131.4 μL). The solution was stirred at ambient temperature for 4 hours. The solvents were removed in vacuo and the crude product was purified by RP HPLC on C$_{18}$ column using H$_2$O/acetonitrile (2-95%) to provide 23.7 mg (71.3%) of the pure product. $^1$H NMR (300 MHz, DMSO-d$_6$) δ 1.30 (d, 2H, J=6.9 Hz), 1.79 (m, 2H), 3.21 (s, 3H), 3.37 (m, 2H), 4.61 (m, 1H), 4.81 (s, 2H), 6.79 (d, 2H, J=8.7 Hz), 7.64 (d, 2H, J=9.7 Hz), 8.25 (br s, 1H), 8.63 (s, 1H); $^{31}$P (121.4 MHz, DMSO-d$_6$) δ 25.1. MS (m/z) 505.2 [M+H]$^+$.

EXAMPLE 221

Preparation of Representative Compound of Formula 231-2-[(2-{4-[(2,4-diaminopteridin-6-ylmethyl)methylamino]benzoylamino}ethyl)phenoxyphosphinoyloxy]propionic acid ethyl ester [diastereomerically pure at phosphorus]

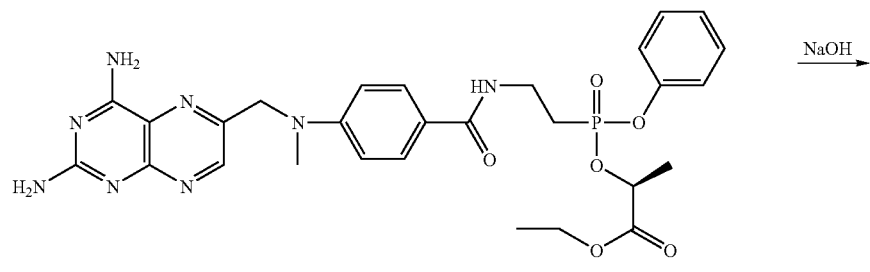

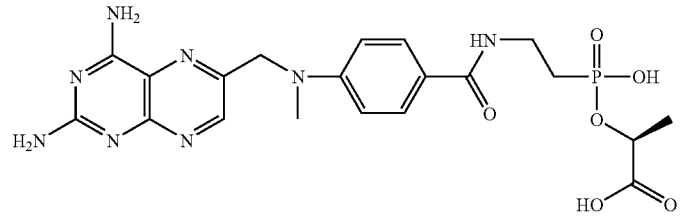

To a solution of 2-[(2-{4-[(2,4-diaminopteridin-6-ylmethyl)methyl-amino]benzoyl amino}ethyl)phenoxyphosphi-

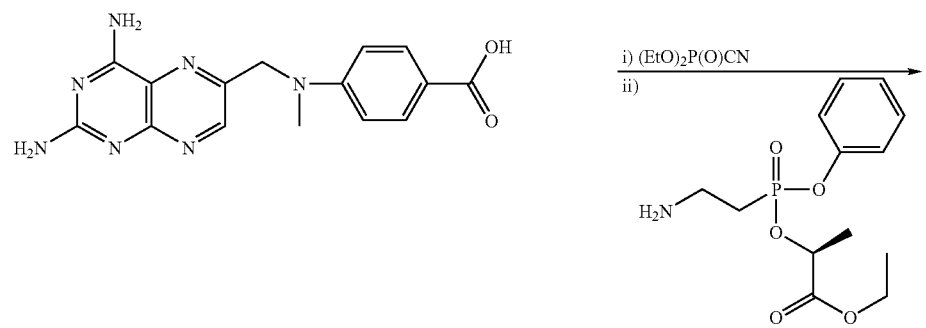

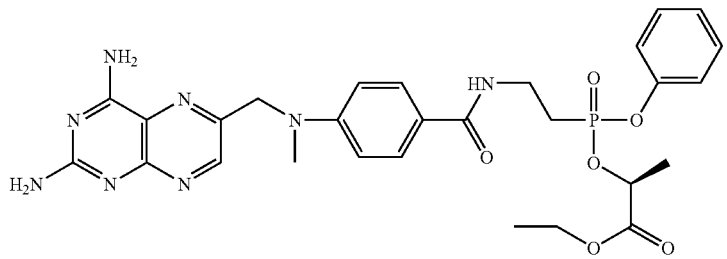

To a solution of 4-[(2,4-diaminopteridin-6-ylmethyl)-methyl-amino]benzoic acid hemihydrochloride dihydrate (101.9 mg, 268.9 μmol) in DMF (3.3 mL) were added diethyl cyanophosphonate (53.0 μL, 349.5 μmol) and DIEA (138.0 μL, 806.7 μmol). The solution was stirred at ambient temperature for 2.5 hours, whereupon (S)-2-[(2-aminoethyl)phenoxyphosphinoyloxy]-propionic acid ethyl ester mono acetic acid salt (diastereomerically pure at phosphorus; 268.9 μmol) in DMF (500 μL) was added. The solution was stirred for 30 additional minutes, whereupon complete consumption of the starting materials was observed. The solvent was removed in vacuo and the crude material was purified by silica gel chromatography using MeOH—CH$_2$Cl$_2$ (10-30%). A small amount of the product (40.0 mg) was repurified by RP HPLC on C$_{18}$ column using H$_2$O/acetonitrile (2-95%) to provide 28.7 mg (75.1%) of the pure product. $^1$H NMR (300 MHz, DMSO-d$_6$) δ 1.15 (t, 3H, J=7.2 Hz), 1.44 (d, 3H, J=6.9 Hz), 2.26 (m, 2H), 3.23 (s, 3H), 3.51 (m, 2H), 4.09 (q, 2H, J=7.2 Hz), 4.86 (s, 2H), 5.01 (m, 1H), 6.81 (d, 2H, J=9.3 Hz), 7.21 (m, 3H), 7.35 (m, 2H), 7.68 (d, 2H, J=9.3 Hz), 8.29 (br s, 1H), 8.71 (s, 1H); $^{31}$P (121.4 MHz, DMSO-d$_6$) δ 26.6. MS (m/z) 609.2 [M+H]$^+$.

EXAMPLE 222

Preparation of Representative Compound of Formula 231-2-[(2-{4-[(2,4-diaminopteridin-6-ylmethyl)methylamino]benzoylamino}-ethyl)-phenoxyphosphinoylamino]propionic acid ethyl ester (mixture of diastereomers at phosphorus)

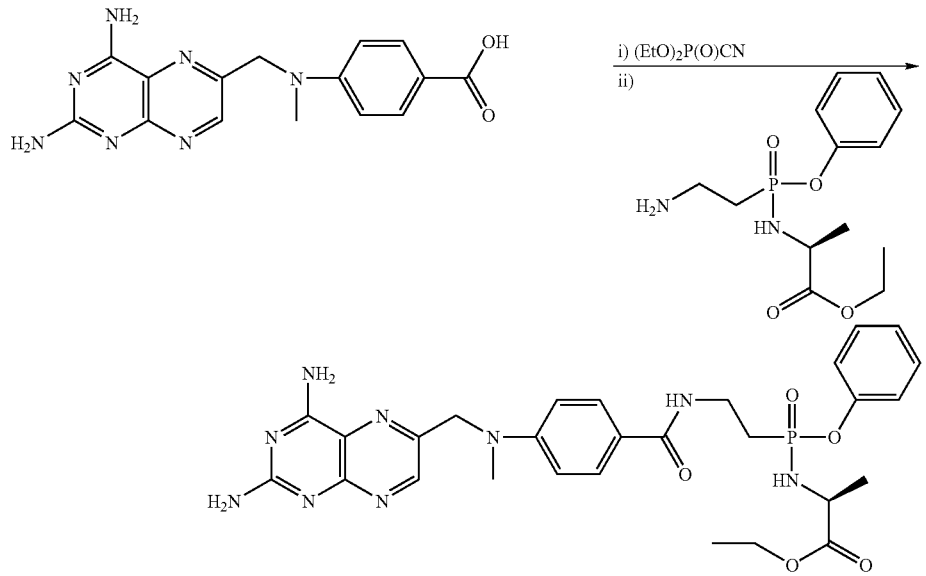

To a solution of 4-[(2,4-diamino-pteridin-6-ylmethyl)-methyl-amino]-benzoic acid hemihydrochloride dihydrate (39.6 mg, 104.0 μmol) in DMF (1.2 mL) were added diethyl cyanophosphonate (20.6 μL, 136.1 μmol) and DIEA (36.0 μL, 209.4 μmol). The solution was stirred at ambient temperature for 3 hours, when (S)-2-[(2-aminoethyl)phenoxyphosphinoylamino]propionic acid ethyl ester mono acetic acid salt (mixture of diastereomers at phosphorus; 104.0 μmol) in DMF (200 μL) was added. The solution was stirred for 30 minutes when complete consumption of the starting materials was observed. An aliquot (66%) of the reaction was purified by silica gel chromatography using MeOH—CH$_2$Cl$_2$ (10-30%), yielding 27.2 mg of crude product. A small amount of the product (10 mg) was repurified by RP HPLC on C$_{18}$ column using H$_2$O/acetonitrile (2-95%) to provide 4.2 mg (26%) of the pure product. $^1$H NMR (300 MHz, DMSO-d$_6$) δ 1.11 (t, 3H, J=6.9 Hz), 1.18 (d, 3H, J=7.2 Hz), 2.06-2.17 (m, 2H), 3.20 (s, 3H), 3.51 (m, 2H), 3.88 (m, 1H), 4.02 (m, 2H), 4.79 (s, 2H), 5.61 (m, 1H), 6.80 (d, 2H, J=9 Hz), 6.98 (br s, 1H), 7.18 (m, 3H), 7.32 (m, 2H), 7.67 (d, 2H, J=9 Hz), 8.20 (br s, 1H), 8.59 (s, 1H) $^{31}$P (121.4 MHz, DMSO-$d_6$) δ 29.5, 30.1. MS (m/z) 608.2 [M+H]$^+$.

EXAMPLE 223

Preparation of Representative Compound of Formula 231-2-{4-[(2,4-Diamino-pteridin-6-ylmethyl)-methyl-amino]-benzoylamino}-6-(diethoxy-phosphoryl)-hexanoic acid

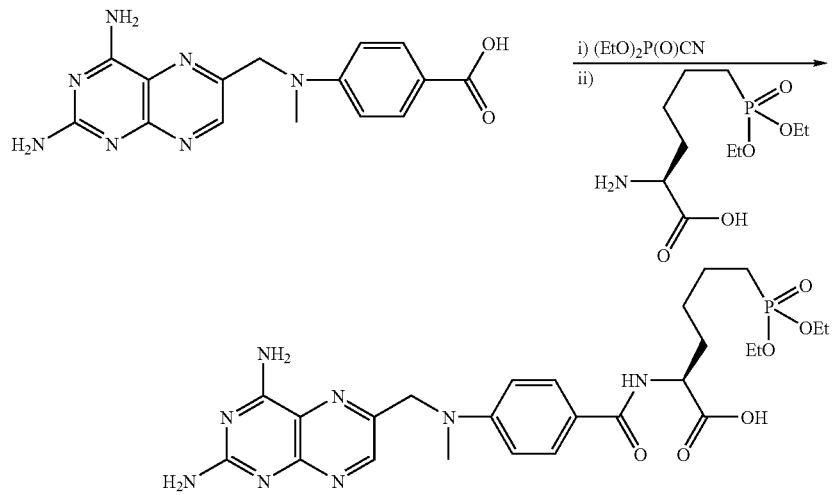

To a solution of 4-[(2,4-diamino-pteridin-6-ylmethyl)-methyl-amino]-benzoic acid hemihydrochloride dihydrate (63.0 mg, 166.2 μmol) in DMF (2.8 mL) were added diethyl cyano phosphonate (30.8 μL, 199.4 μmol) and DIEA (85.8 μL, 498.6 μmol). The solution was stirred at ambient temperature for 3.5 hours when (L)-2-amino-6-diethylphosphonatohexanoic acid (44.3 mg, 166.2 μmol) was added. The solution was stirred for 48 additional hours. The reaction was worked up by removal of the solvent in vacuo and purifying the residue by silica gel chromatography using MeOH—CH$_2$Cl$_2$ (10-30%). The product (87 mg) collected from this chromatography step was sufficiently pure to be carried on to the next reaction. An aliquot of the product (51.0 mg) was repurified by RP HPLC on C$_{18}$ column using H$_2$O/acetonitrile (2-95%) to provide 24.7 mg (44%) of the pure product. $^1$H NMR (300 MHz, DMSO-$d_6$) δ 1.18 (t, 6H, J=6.9 Hz), 1.42 (m, 4H), 1.65 (m, 4H), 3.20 (s, 3H), 3.92 (m, 4H), 4.29 (m, 1H), 4.78 (s, 2H), 6.72 (br s, 1H), 6.81 (d, 2H, J=9 Hz), 7.73 (d, 2H, J=9 Hz), 8.14 (d, 1H, J=7.8 Hz), 8.56 (s, 1H); $^{31}$P (121.4 MHz, DMSO-$d_6$) δ 31.8; MS (m/z) 574.3 [M]$^+$.

EXAMPLE 224

Preparation of Representative Compound of Formula 231-2-{4-[(2,4-Diaminopteridin-6-ylmethyl)methylamino]benzoylamino}-6-(phosphoryl)hexanoic acid

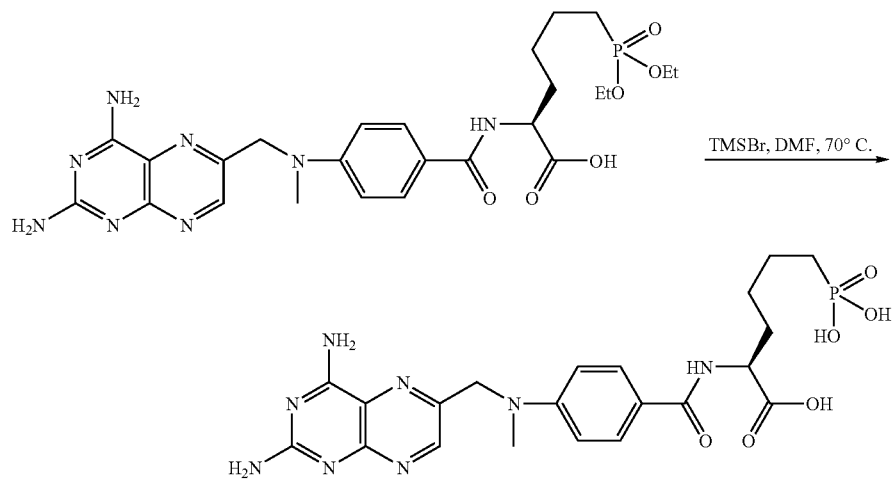

To a solution of crude (2-{4-[(2,4-diamino-pteridin-6-yl-methyl)-methylamino]-benzoylamino})-2' (L)-(6'-(phosphonic acid diethyl ester) hexanoic acid) post silica column chromatography (20 mg, 34.6 μmol) in dry DMF (0.60 mL) was added TMSBr (18.0 μL, 139.2 μmol) at ambient temperature. The solution was then heated at 70° C. for 18 hours, after which the reaction mixture was allowed to cool to room temperature. The solvent was removed in vacuo and dissolved in DMF (400 μL) and water (60 μL). This solution was purified by RP HPLC on $C_{18}$ column using $H_2O$/acetonitrile (2-95%) to provide 8.9 mg (49%) of the product as a yellow solid. $^1$H NMR (300 MHz, DMSO-$d_6$) δ 1.45 (m, 6H), 1.75 (m, 2H), 3.20 (s, 3H), 4.25 (m, 1H), 4.77 (s, 2H), 6.62 (br s, 1H), 6.80 (d, 2H, J=8.7 Hz), 7.73 (d, 2H, J=8.7 Hz), 8.14 (br s, 1H), 8.55 (s, 1H); MS (m/z) 519.2 [M+H]$^+$.

EXAMPLE 225

Preparation of Representative Compound of the Invention—2-{4-[(2,4-Diamino-pteridin-6-ylmethyl)-methyl-amino]-benzoylamino)-6'-(mono phenyl-phosphonate)hexanoic acid

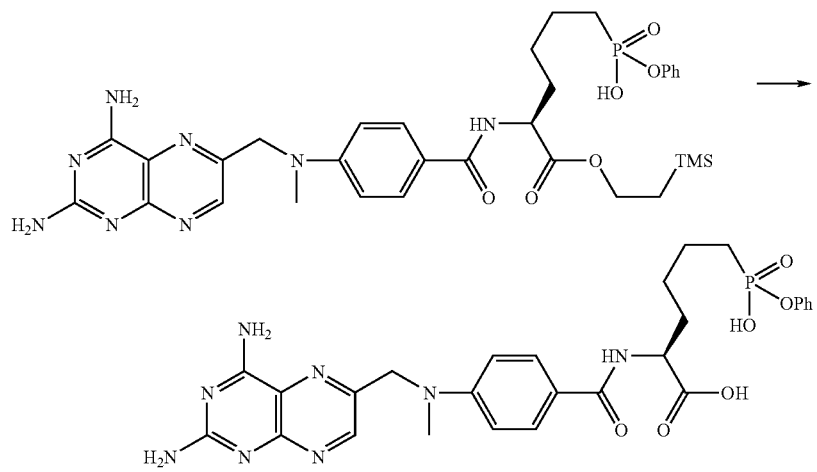

The ethyl-TMS ester is hydrolyzed under suitable conditions to provide the corresponding acid of the invention.

The intermediate 2-{4-[(2,4-Diamino-pteridin-6-ylmethyl)-methyl-amino]-benzoylamino}-6'-(mono phenyl-phosphonate)-hexanoic acid TMS ethanol ester can be prepared as follows.

a. (L)-2-Cbz-Amino-hexanoic acid-6-phosphonic acid

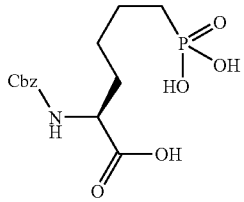

To a suspension of (L)-2-amino-6-(diethoxyphosphonyl) hexanoic acid (106 mg, 396.8 μmol) in dry DMF (2.00 mL) was added TMSBr (307.0 μL, 2,381.0 μmol) at ambient temperature. The solution was then heated at 70° C. for 2 hours, after which the reaction mixture was allowed to cool to room temperature. The solvent was removed in vacuo. The crude material was dissolved in water (0.25 mL) and NaOH (1-N, 2.50 mL). Benzyl chloroformate (79.3 μL, 555.5 μmol) was added and stirring at room temperature was continued. After 2 hours, the solution was washed with ether (2 mL) and the aqueous layer was acidified with aqueous HCl to pH 1. The aqueous layer was extracted with EtOAc (3×5 mL). The combined organic extracts were dried over sodium sulfate. Filtration and evaporation of solvents yielded a crude product, which was sufficiently pure for further transformations. $^1$H NMR (300 MHz, DMSO-$d_6$) δ 1.42-1.65 (m, 8H), 3.90 (m, 1H), 5.02 (s, 2H), 7.32 (s, 5H), 7.55 (m, 1H), 7.94 (s, 1H); $^{31}$P (121.4 MHz, DMSO-$d_6$) δ 26.5; MS (m/z) 345.6 [M+H]$^+$.

b. (L)-2—Aminohexanoic acid 2' TMS ethyl ester-6-phosphonic acid mono phenyl ester

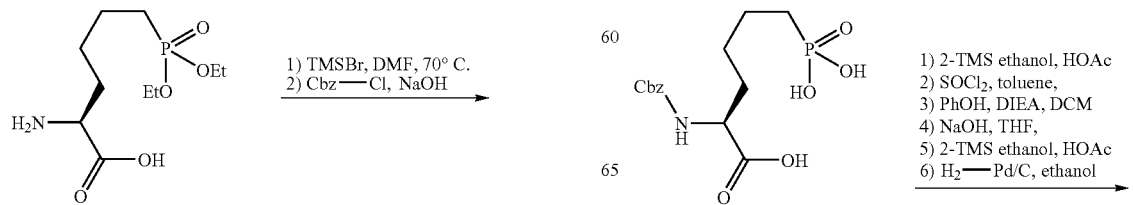

1) 2-TMS ethanol, HOAc
2) $SOCl_2$, toluene,
3) PhOH, DIEA, DCM
4) NaOH, THF,
5) 2-TMS ethanol, HOAc
6) $H_2$—Pd/C, ethanol

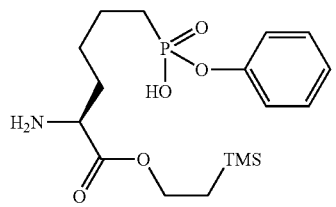

To a solution of (L)-2-Cbz-amino-hexanoic acid-6-phosphonic acid (137.3 mg, 397.9 μmol) in 2-TMS ethanol (2.5 mL) was added acetyl chloride (50 μL). Stirring at room temperature was continued. After 22 hours complete conversion was observed. The solvents were removed in vacuo. The crude material was sufficiently pure for the next step.

One half of the crude material (198.9 μmol) was dissolved in toluene (3.0 mL) at room temperature. Thionyl chloride (167.2 mg, 1,416.0 μmol) was added and the reaction mixture was heated at 70° C. (oil bath). After 4 hours, the reaction was cooled to room temperature and the solvent was removed in vacuo. The crude material was re-dissolved in methylene chloride (2.0 mL) and a solution of phenol (36.6 mg, 389.0 μmol) and DIEA (67.0 μL, 389.0 μmol) in methylene chloride (1.0 mL) was added. Stirring at room temperature was continued. After 4 hrs the solvents were removed in vacuo.

The crude material was dissolved in tetrahydrofuran (THF) (3.0 mL) and aqueous sodium hydroxide solution (1N, 0.885 mL) was added. Stirring at room temperature was continued. After 14 hours the solvent was removed in vacuo to provide the crude phosphonate mono phenyl ester (63.8 mg). This material was dissolved in 2-TMS ethanol (1.0 mL) and acetyl chloride (20 μL) was added. Stirring at room temperature was continued. After 22 hours complete conversion to the carboxylate ester was observed. The solvents were removed in vacuo. The material was sufficiently pure for the next step.

One half of the crude material (75 μmol) was dissolved in ethanol (1.5 mL). Pd/C (5%, 20 mg) was added and the reaction was placed under an atmosphere of hydrogen gas. After 1.5 hours Celite was added and the crude reaction mixture was filtered through Celite. The solvents were removed in vacuo and the crude material was used in the next step without further purification.

c. 2-{4-[(2,4-diamino-pteridin-6-ylmethyl)-methyl-amino]-benzoylamino}-6'-(mono phenyl-phosphonate)-hexanoic acid TMS ethanol ester

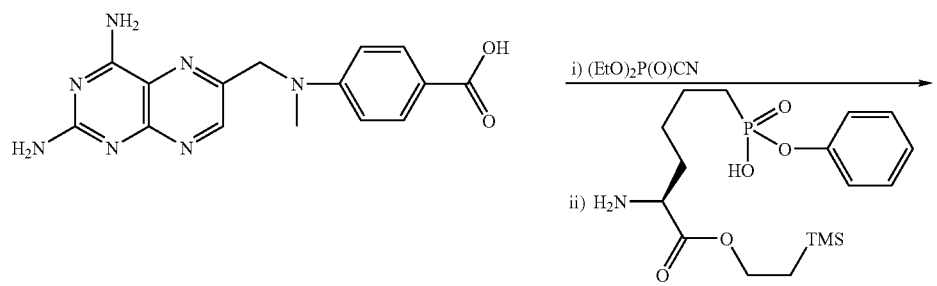

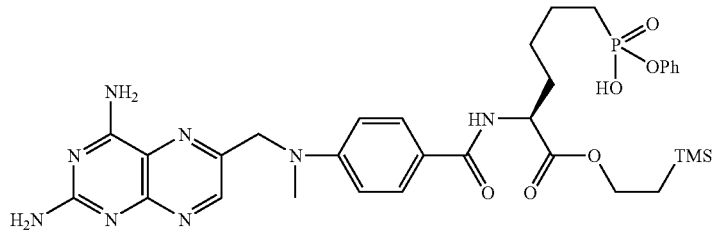

To a solution of 4-[(2,4-diamino-pteridin-6-ylmethyl)-methyl-amino]-benzoic acid hemihydrochloride dihydrate (22.7 mg, 60.0 μmol) in DMF (0.80 mL) were added diethyl cyano phosphonate (12.4 μL, 78.0 μmol) and DIEA (31.0 μL, 180.0 μmol). The solution was stirred at ambient temperature for one hour when (L)-2-amino-6-monophenoxyphosphonato-hexanoic acid 2' TMS ethyl ester (70.5 μmol), suspended in DMF (0.2 mL), was added. The solution was stirred for 3.5 additional hours. The crude reaction mixture was purified by RP HPLC on $C_{18}$ column using $H_2O$/acetonitrile (5-95%) to provide 19.4 mg (46%) of 2-{4-[(2,4-diamino-pteridin-6-yl-methyl)-methyl-amino]-benzoylamino}-6'-(mono phenyl-phosphonate)-hexanoic acid TMS ethanol ester. $^1$H NMR (300 MHz, DMSO-$d_6$) δ 0.0 (s, 9H), 0.91 (t, 2H, J=8.1 Hz), 1.42-1.53 (m, 4H), 1.67-1.76 (m, 4H), 3.24 (s, 3H), 4.10 (t, 2H, J=8.1 Hz), 4.29 (m, 1H), 4.86 (s, 2H), 6.81 (d, 2H, J=9 Hz), 7.12 (m, 3H), 7.31 (m, 2H), 7.74 (d, 2H, J=9 Hz), 8.14 (d, 1H, J=7.8 Hz), 8.71 (s, 1H); $^{31}$P (121.4 MHz, DMSO-$d_6$) δ 26.2; MS (m/z) 695.2 [M]$^+$.

EXAMPLE 226

Preparation of Representative Compound of the Invention—2-{4-[(2,4-Diamino-pteridin-6-ylmethyl) methylamino]benzoylamino}-6'-(mono phenyl mono (S) ethyl lactate-phosphonate)hexanoic acid To a solution of 2-{4-[(2,4-diamino-pteridin-6-ylmethyl)-methyl-amino]-benzoylamino}-6'-(mono phenyl-phosphonate)-hexanoic acid TMS ethanol ester (14.5 mg, 20.8 µmol, Example 225) in DMF (0.70 mL) was added PyBOP (32.4 mg, 62.4 µmol), DIEA (21.4 mg, 166.4 µmol) and (S) ethyl lactate (19.6 mg, 166.4 µmol). The reaction mixture was stirred at room temperature for one hour. The crude reaction

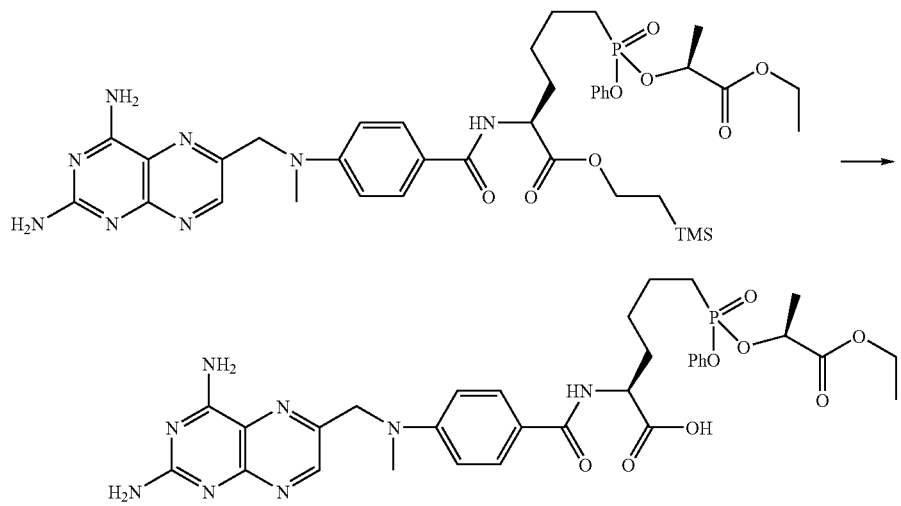

The ethyl-TMS ester is hydrolyzed under suitable conditions to provide the corresponding acid of the invention.

The intermediate 2-{4-[(2,4-diamino-pteridin-6-ylmethyl)-methyl-amino]-benzoylamino}-6'-(mono phenyl mono (S) ethyl lactate-phosphonate)-hexanoic acid TMS ethanol ester can be prepared as follows.

a. 2-{4-[(2,4-Diamino-pteridin-6-ylmethyl)-methyl-amino]-benzoylamino}-6'-(mono phenyl mono (S) ethyl lactate-phosphonate)-hexanoic acid TMS ethanol ester mixture was purified by RP HPLC on $C_{18}$ column using $H_2O$/acetonitrile (5-95%) to provide 13.5 mg (81%) of the pure product as a mixture of diastereomers at phosphorus (~4:1). $^1H$ NMR (300 MHz, CDCl$_3$) δ 0.0 (s, 9H), 1.02 (t, 2H, J=8.7 Hz), 1.23 (t, 3H, J=9.3 Hz), 1.35 (d, 2.4H, J=6.6 Hz), 1.42-1.53 (m, 4.6H), 1.67-1.86 (m, 4H), 3.14 (s, 3H), 4.03-4.27 (m, 4H), 4.71 (br s, 3H), 4.98 (m, 0.8H), 5.10 (m, 0.2H), 6.57 (d, 2H, J=7.5 Hz), 7.00 (m, 1H), 7.16 (m, 3H), 7.30 (m, 2H), 7.63 (d, 2H, J=7.5 Hz), 8.43 (s, 1H); $^{31}$P (121.4 MHz, DMSO-d$_6$) δ 30.5, 29.2; MS (m/z) 795.2 [M]$^+$.

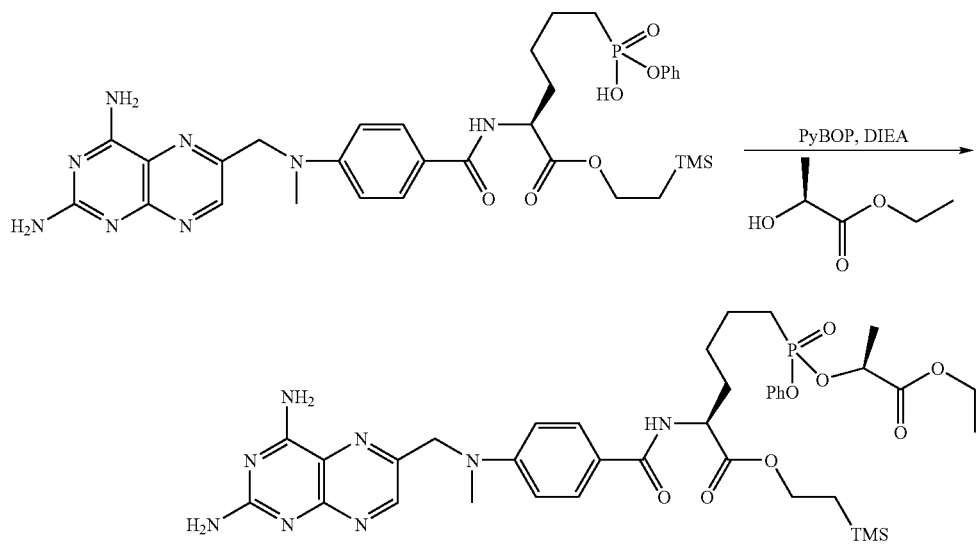

EXAMPLE 227

Preparation of Representative Compound of Formula 253

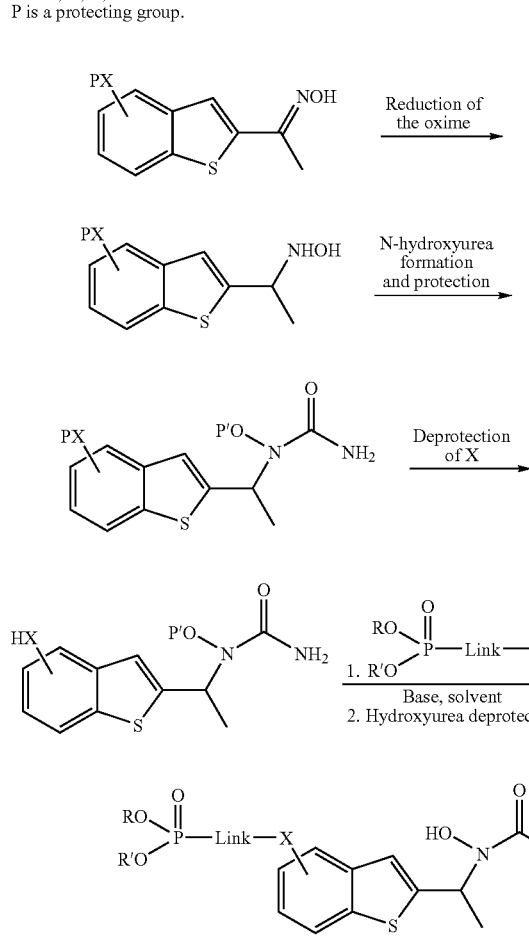

Representative compounds of the invention can be prepared as illustrated above. A specific compound of the invention can be prepared as follows.

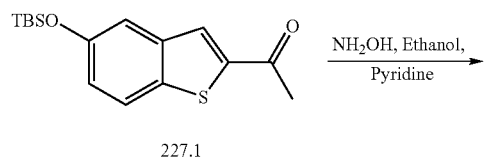

1-(5-Hydroxy-benzo[b]thiophen-2-yl)-ethanone (prepared as described in Krubsack, A. J. et al., *J. Org. Chem.*, 1975, 40, 3179) is protected using a TBS group as described in Greene, T., Protective groups in organic synthesis, Wiley-Interscience, 1999 to provide compound 227.1 (in which X=O and P=TBS). Treatment of compound 227.1 with hydroxylamine in ethanol/pyridine provides oxime 227.2. Reduction of the oxime using borane pyridine complex yields the hydroxylamine 227.3. Exposure of the hydroxylamine to gaseous HCl followed by phosgene yields a carbamoyl chloride which is transformed to the N-hydroxyurea 227.4 with aqueous ammonia (U.S. Pat. No. 4,873,259). Protection of the N-hydroxyurea may be not be necessary, but to avoid subsequent alkylation on this group, the OH is blocked with a benzyl group. Removal of the phenolic protecting group using TBAF exposes the necessary handle for placement of the pro-drug group. Treatment of the phenol with a base such as NaH or $Cs_2CO_3$ in solvents such as DMF or THF followed by addition of phosphonomethyltriflate (prepared according to *Tetrahedron Lett.*, 1986, 27, 1477) yields the desired phosphonate pro-drug. Final deblocking of the N-hydroxyurea can be achieved by hydrogenolysis conditions as described in U.S. Pat. No. 4,873,259.

EXAMPLE 228

Preparation of Representative Compound of Formula 238

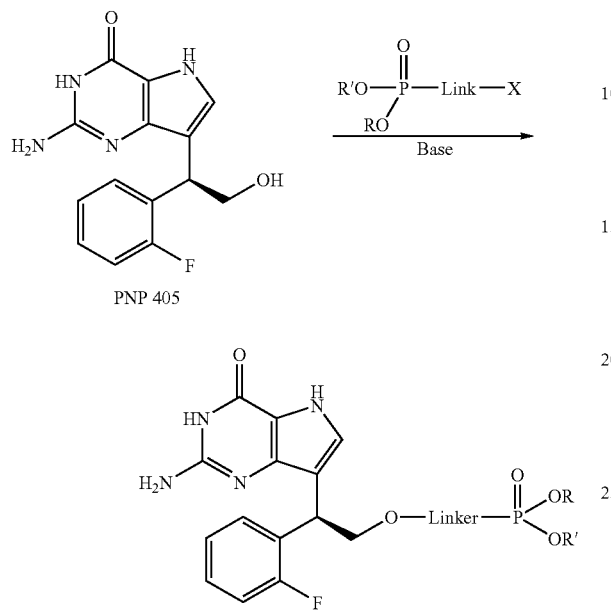

Representative compounds of the invention can be prepared as illustrated above. A specific compound of the invention can be prepared as follows.

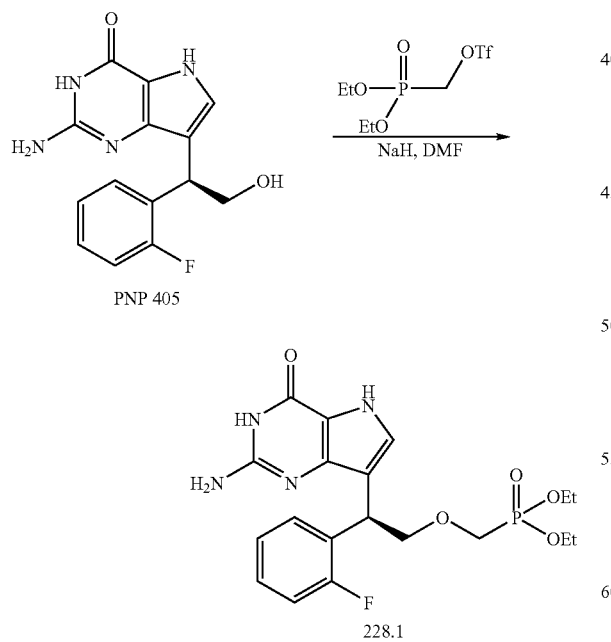

PNP-405 is prepared according to the method of Littler, B. J. et al., 7th International Conference on Organic Process Research and Development, New Orleans, La., Mar. 16-19, 2003. PNP-405 is treated in a solvent such as tetrahydrofuran or dimethylformamide with a base such as sodium hydride. When bubbling ceases; diethyl phosphonomethyltriflate (prepared according to Tetrahedron Lett., 1986, 27, 1477) is added, to provide compound 228.1 as the desired product.

EXAMPLE 229

Preparation of Representative Compound of Formula 236

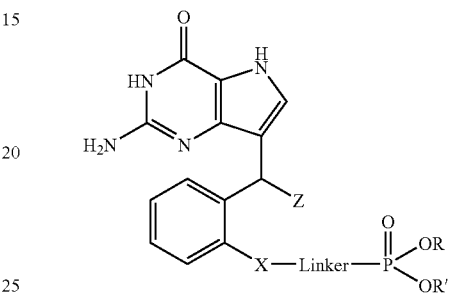

Representative compounds of the general formula above (where X=O, Z=CH$_2$OH) can be prepared using procedures similar to those described by Littler, B. J. et al., 7th International Conference on Organic Process Research and Development, New Orleans, La., Mar. 16-19, 2003. A specific compound of the invention can be prepared as follows.

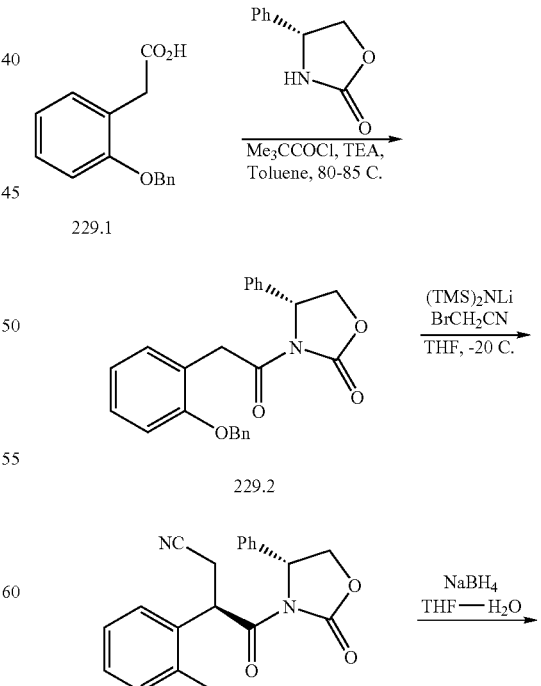

-continued

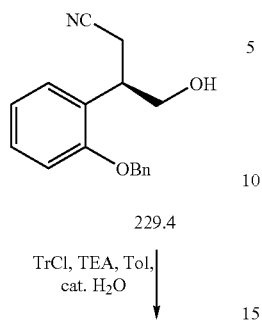
229.4

TrCl, TEA, Tol, cat. H₂O ↓

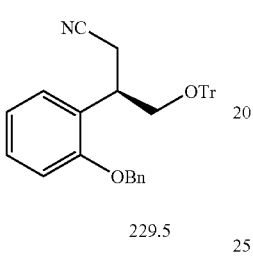
229.5

The starting material, 2-benzyloxyphenylacetic acid (provided by Avocado) can be acylated via the mixed anhydride with the oxazolidinone shown at 80-85° C., with triethylamine as base. A low-temperature alkylation with bromoacetonitrile results in the formation of compound 229.3 with good diastereomeric ratio. Removal of the chiral auxiliary under reductive conditions yields compound 229.4 without racemization. Protection of the resulting alcohol with the trityl group provides compound 229.5. Subsequent pyrrole ring construction as well as cyclo-guanidinylation reaction to prepare the six-membered 2-aminopyrimidone ring is performed as described below.

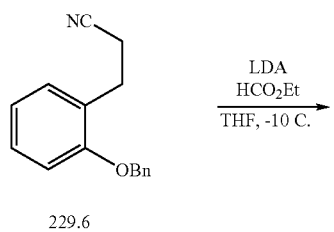
229.6

LDA
HCO₂Et
THF, -10 C.

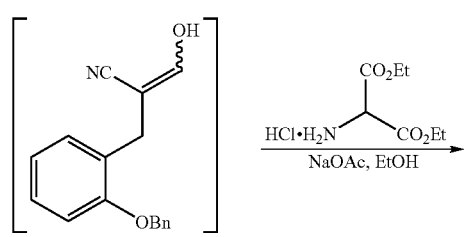
229.7

HCl·H₂N-CH(CO₂Et)(CO₂Et)
NaOAc, EtOH

-continued

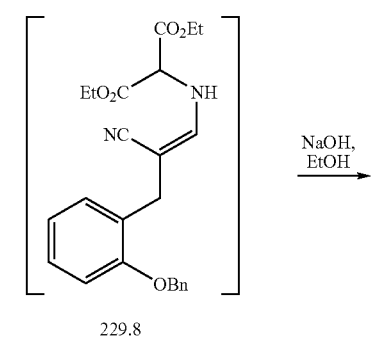
229.8

NaOH, EtOH

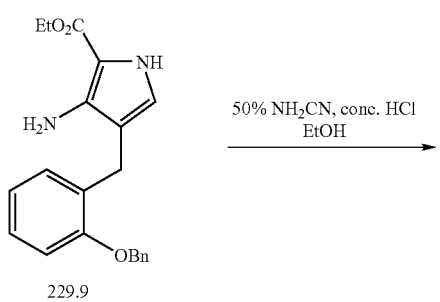
229.9

50% NH₂CN, conc. HCl
EtOH

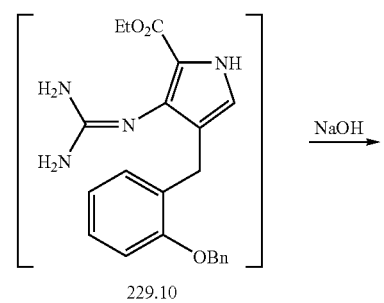
229.10

NaOH

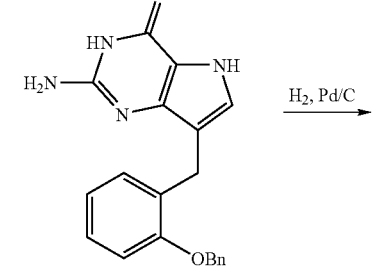
229.11

H₂, Pd/C

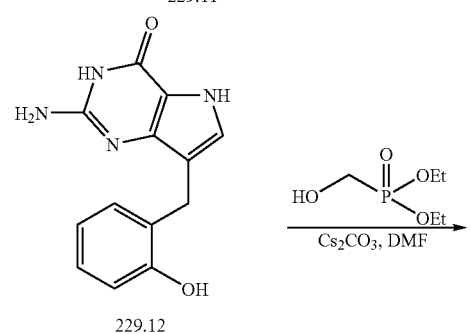
229.12

HO-CH₂-P(O)(OEt)(OEt)
Cs₂CO₃, DMF

-continued

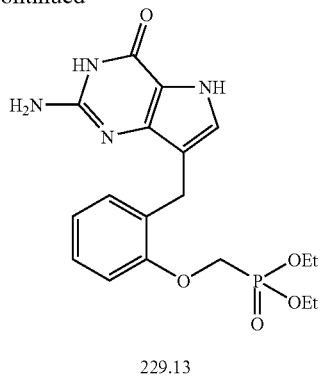

229.13

The starting material, 3-(2-Benzyloxy-phenyl)-propionitrile, is available by Lewis acid-mediated reaction of phenol with acrylonitrile according to U.S. Pat. No. 2,789,995, published in 1954. Formation of 3-hydroxy-acrylonitrile 229.7 can be achieved by exposure of 229.6 to LDA and ethyl formate. Condensation of this product with 2-amino-malonic acid diethyl ester in EtOH and sodium acetate yields compound 229.8 which undergoes a decarboxylative cyclization in the basic medium of NaOH and EtOH to provide pyrrole 229.9. The trityl protecting group on the benzylic alcohol is removed at this stage. Subsequently, guanidinylation reaction using cyanamide provides compound 229.10 which, upon treatment with sodium hydroxide, cyclizes to form the 2-aminopyrimidone ring (compound 229.11). Removal of the phenolic protecting group under hydrogenolysis conditions provides the free phenol, which is used as the attachment site for the pro-drug group. A variety of linkers may be utilized to attach the phosphonate containing moiety to the backbone molecule. A particular example in which diethyl phosphonomethyltriflate is used as the starting materials is shown. Compound 229.12 is treated in a solvent such as tetrahydrofuran or dimethylformamide with a base such as sodium hydride or cesium carbonate. When bubbling ceases, diethyl phosphonomethyltriflate (prepared according to *Tetrahedron Lett.*, 1986, 27, 1477) is added, to provide compound 229.13 as the desired product.

EXAMPLE 230

Preparation of Representative Compound of Formula 235

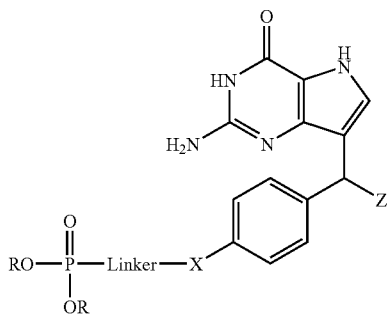

Representative compounds of the general formula above (where X=O, and Z=CH$_2$OH) can be prepared from 4-benzyloxyphenylacetic acid (available from Aldrich). The preparation of a specific compound of formula 235 is described below.

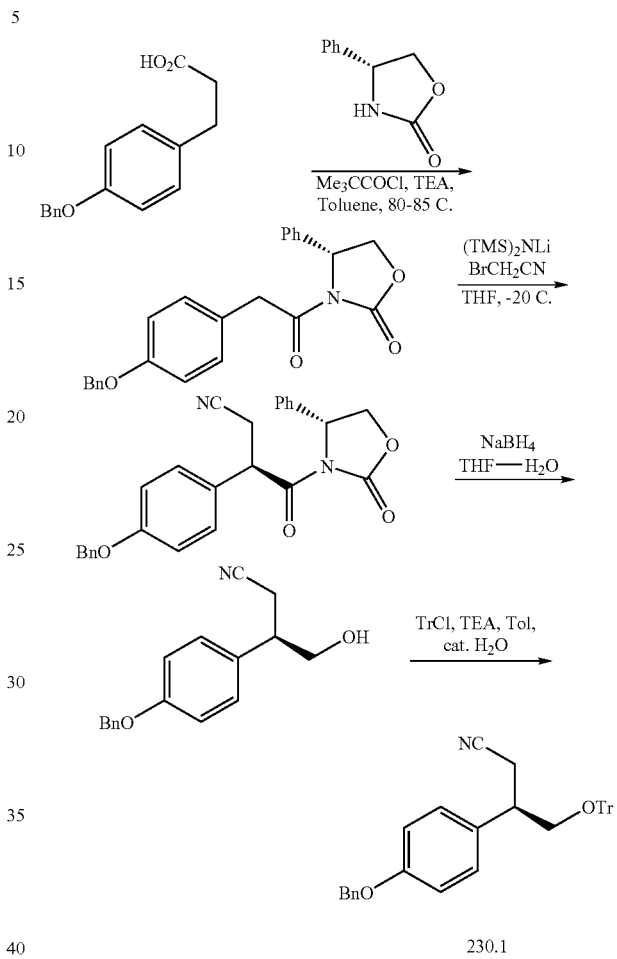

230.1

Following a similar sequence to that demonstrated in Example 229, intermediate 230.1 can be prepared. Proceeding with the sequence shown in Example 229, 230.1 can be transformed to the desired product.

EXAMPLE 231

Preparation of Representative Compound of Formula 242

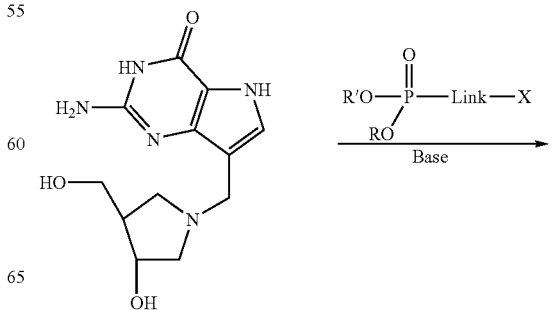

-continued

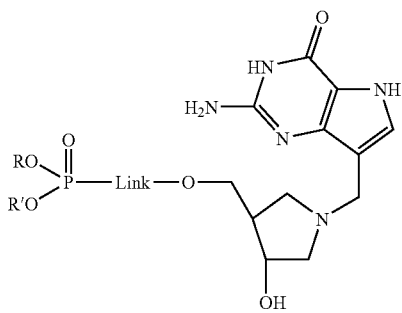

Representative compounds of the invention can be prepared as illustrated above. A specific compound of the invention can be prepared as follows.

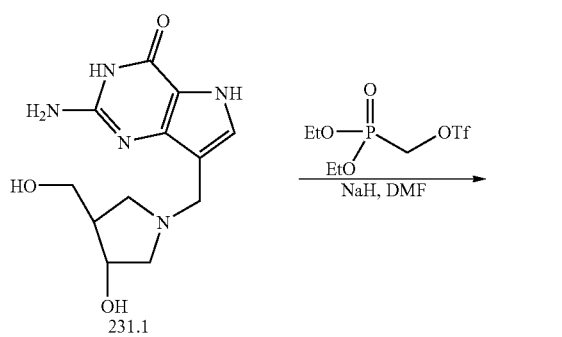

231.1

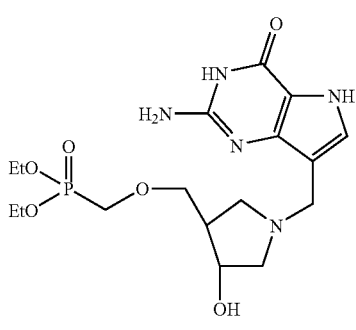

231.2

Preparation of DADMe-ImmG is reported in Lewandowics A. et al., *Biochemistry,* 2003, 42, 6057. The tertiary nitrogen of the ring may not interfere with the alkylation of the secondary alcohol and in that case does not need to be protected, although standard protection and deprotection protocols as described in Greene, T. Protective groups in organic synthesis, Wiley-Interscience, 1999 may be used if necessary. Reaction of the primary alcohol 231.1 with base followed by addition of the appropriately activated phosphonate yields the protected product. Global deprotection yields the desired phosphonate 231.2.

EXAMPLE 232

Preparation of Representative Compound of Formula 243

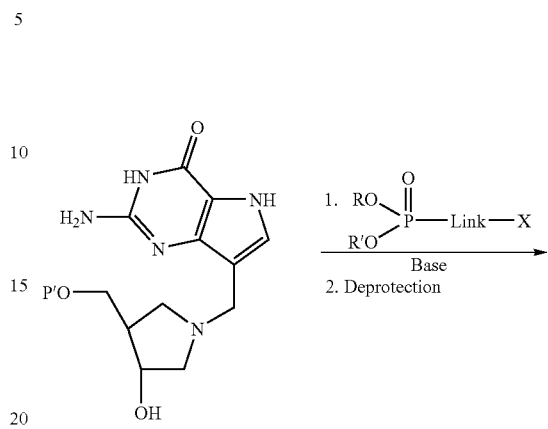

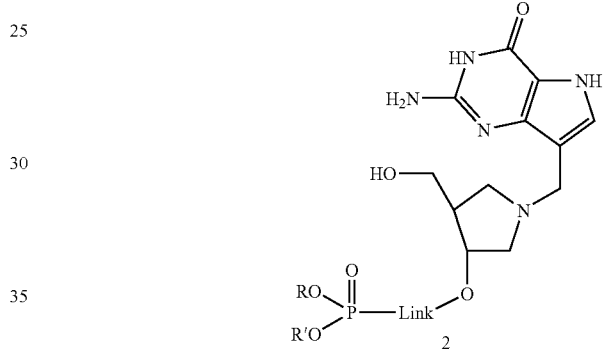

Representative compounds of the invention can be prepared as illustrated above. Preparation of DADMe-ImmG is reported in Lewandowics A. et al., *Biochemistry,* 2003, 42, 6057. Blocking of the primary alcohol can be achieved by methods described in Greene, T., Protective groups in organic synthesis, Wiley-Interscience, 1999. Reaction of the secondary alcohol in base followed by addition of the appropriately activated phosphonate yields the protected desired product. Deprotection yields the desired phosphonate. A specific compound of the invention can be prepared as follows.

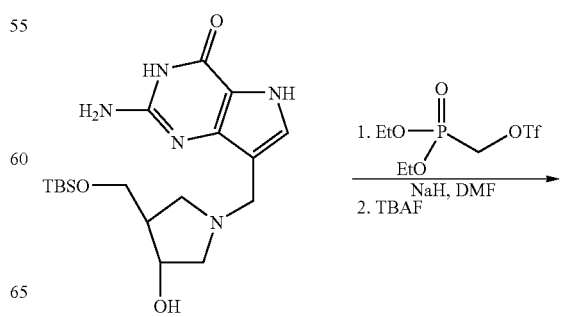

-continued

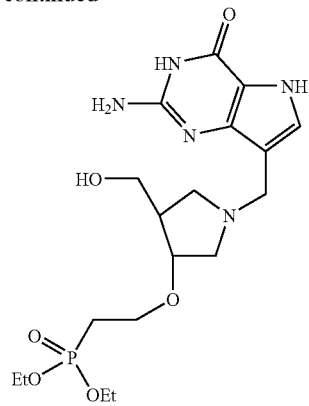

Specifically, the protected DADMe derivative can be treated with treated in a solvent such as tetrahydrofuran or dimethylformamide with a base such as sodium hydride. When bubbling ceases, diethyl phosphonoethylltriflate (prepared according to *Tetrahedron Lett.*, 1986, 27, 1477) is added, yielding the desired phosphonate ester. Removal of the protecting group can be performed as described in Greene, T., Protective groups in organic synthesis, Wiley-Interscience, 1999 to provide the desired phosphonate ester.

EXAMPLE 233

Preparation of Representative Compound of Formula 244

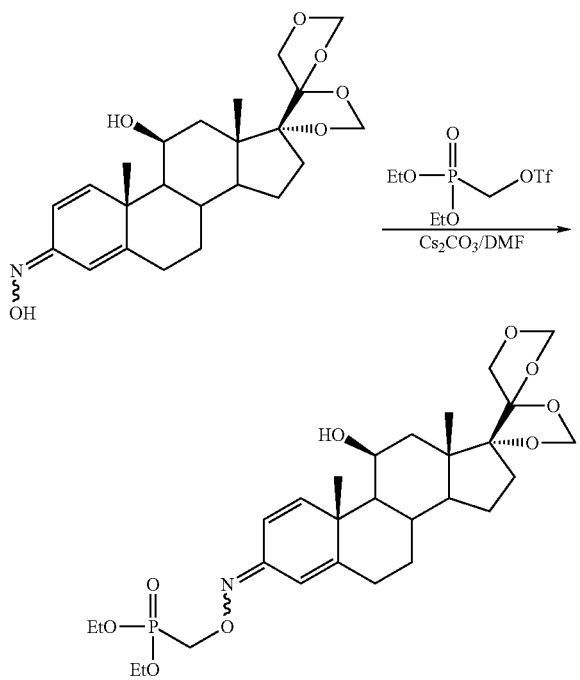

-continued

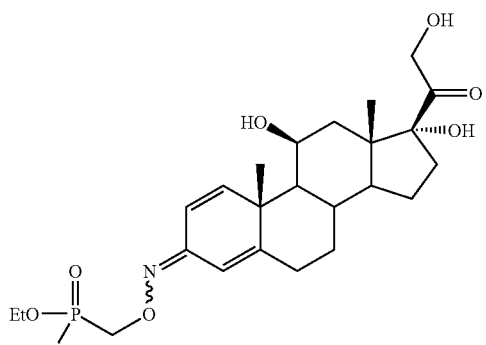

Representative compounds of the invention can be prepared as illustrated above. O-Alkylation of the oxime can be carried out by mixing the oxime and $Cs_2CO_3$ (ca. 1:1.2) in DMF at 0° C. for about 30 minutes with stirring. Addition of the triflate (1.2 eq.) followed by deprotection (*J. Med. Chem.* 2002, 45, 5397) provides the compound.

EXAMPLE 234

Preparation of Representative Compound of Formula 245

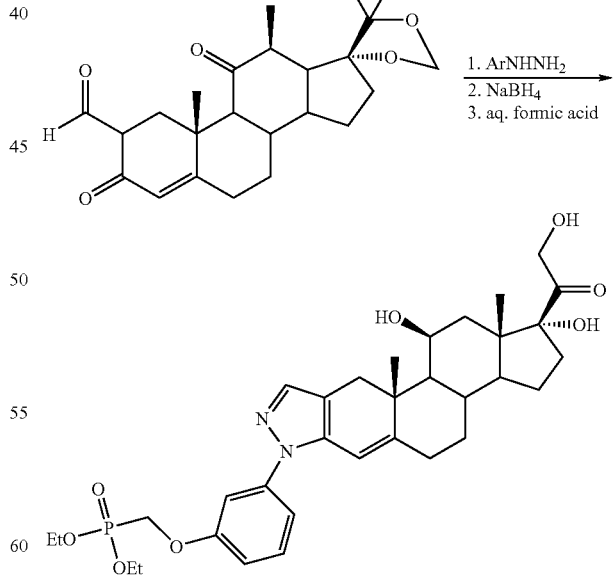

Representative compounds of the invention can be prepared as illustrated above. The pyrazole can be formed using a procedure sililar to that described in *J. Med. Chem.* 2002, 45, 5397.

EXAMPLE 235

Preparation of a Representative Compound of Formula 245

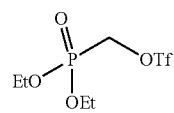
+
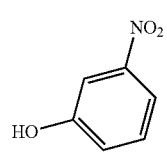
→ (Cs₂CO₃)

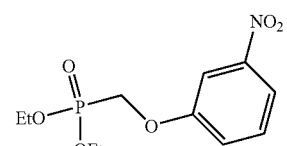
1. SnCl₂
2. NaNO₂, HCl
3. SnCl₂
→

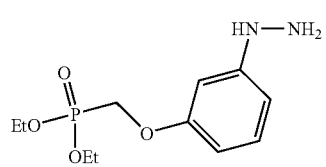
→→

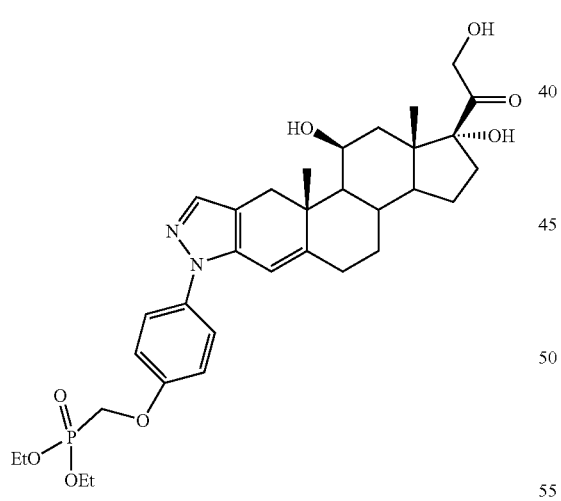

Representative compounds of the invention can be prepared as illustrated above. The hydrazine can be converted to the compound of the invention using a procedure similar to that described in Example 234.

EXAMPLES 236-240

The preparation of the following representative compounds of formulae 255-257 is illustrated in Examples 236-240.

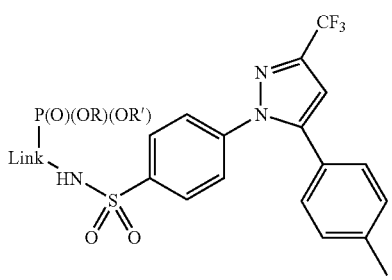

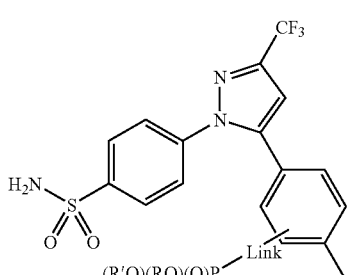

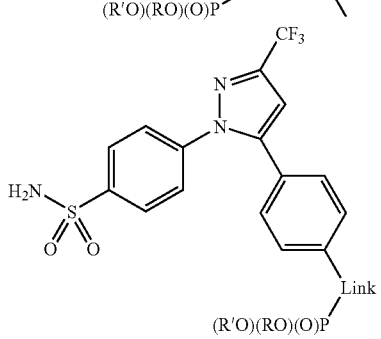

Link is 1-8, preferably 2-6 atoms

EXAMPLE 236

Preparation of Representative Compound of Formula 255

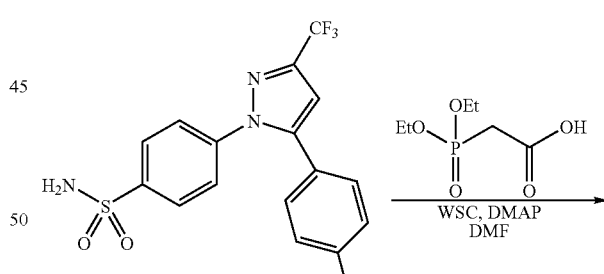
WSC, DMAP
DMF
→

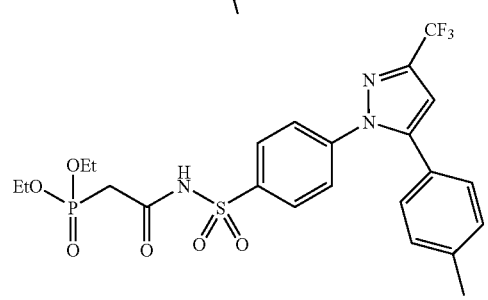

Representative compounds of the invention can be prepared as illustrated above.

EXAMPLE 237
Preparation of Representative Compound of Formula 257
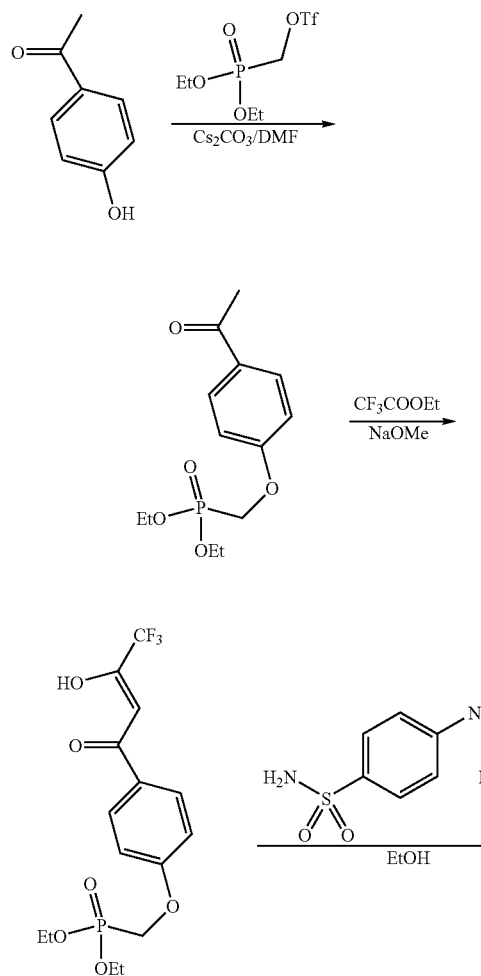
Representative compounds of the invention can be prepared as illustrated above. The pyrazole can be prepared as described in *J. Med. Chem.* 1997, 40, 1347.
EXAMPLE 238
Preparation of Representative Compound of the Invention
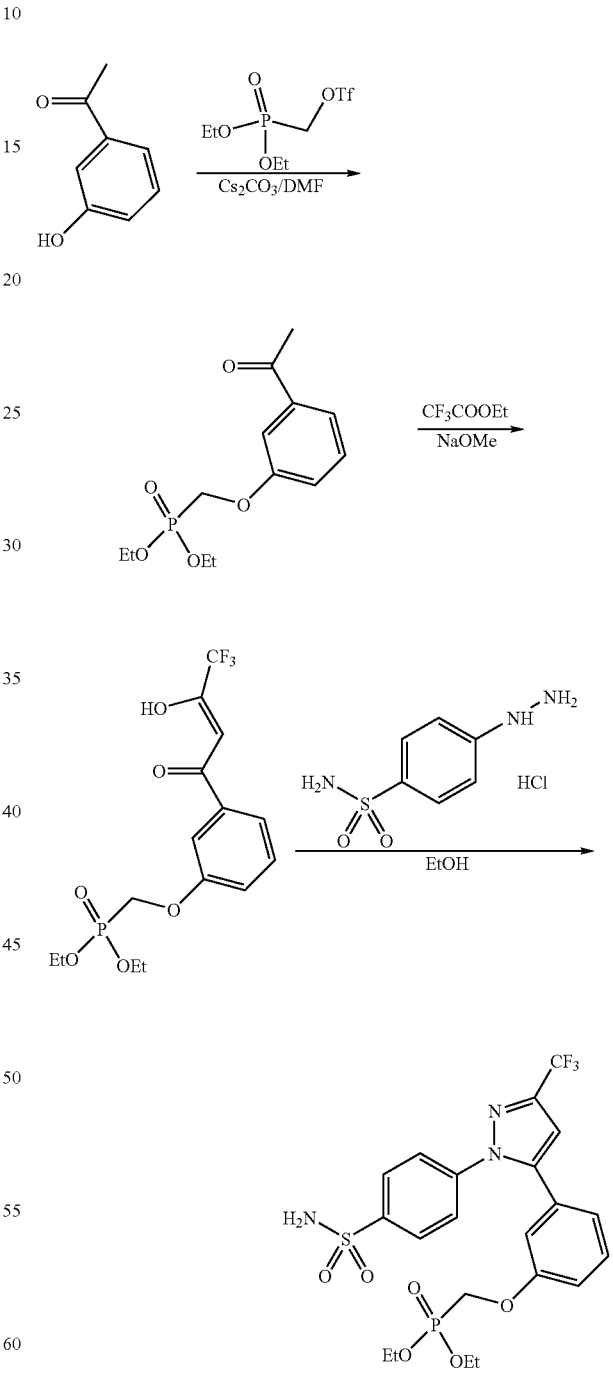
Representative compounds of the invention can be prepared as illustrated above.

EXAMPLE 239
Preparation of Representative Compound of Formula 256
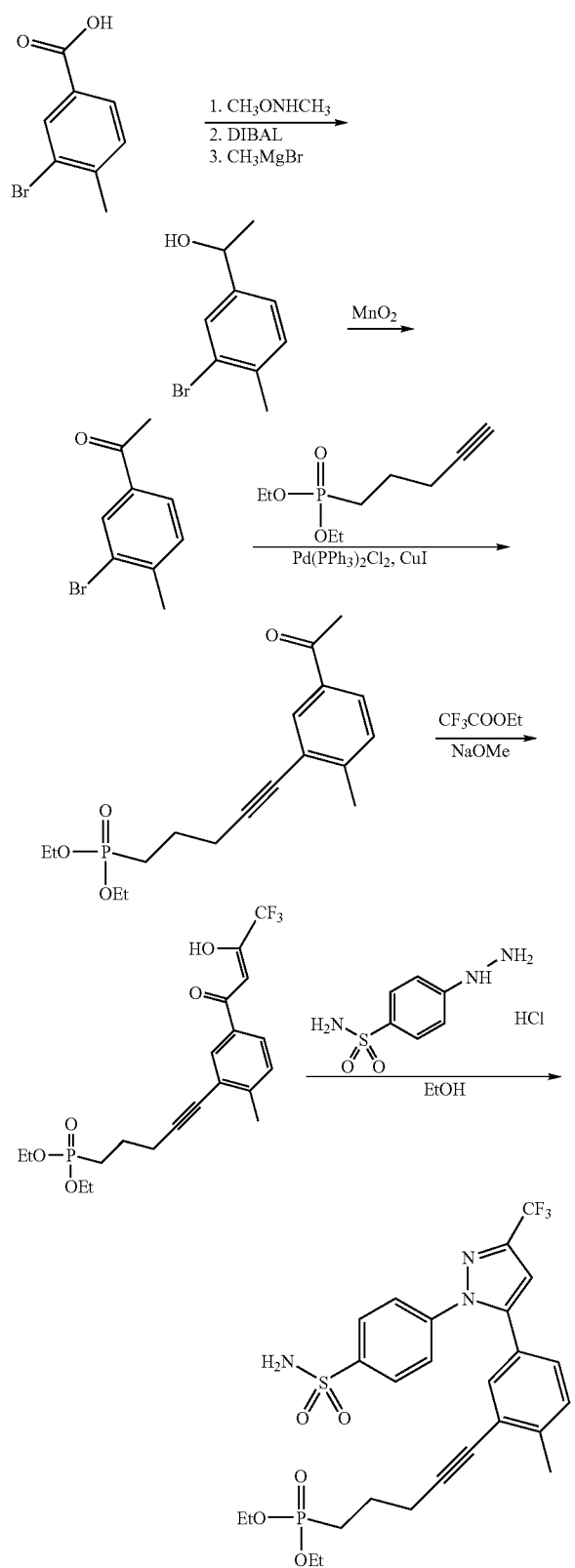
Representative compounds of the invention can be prepared as illustrated above.
The intermediate alkyne can be prepared as follows.
EXAMPLE 240
Preparation of Representative Compound of Formula 257
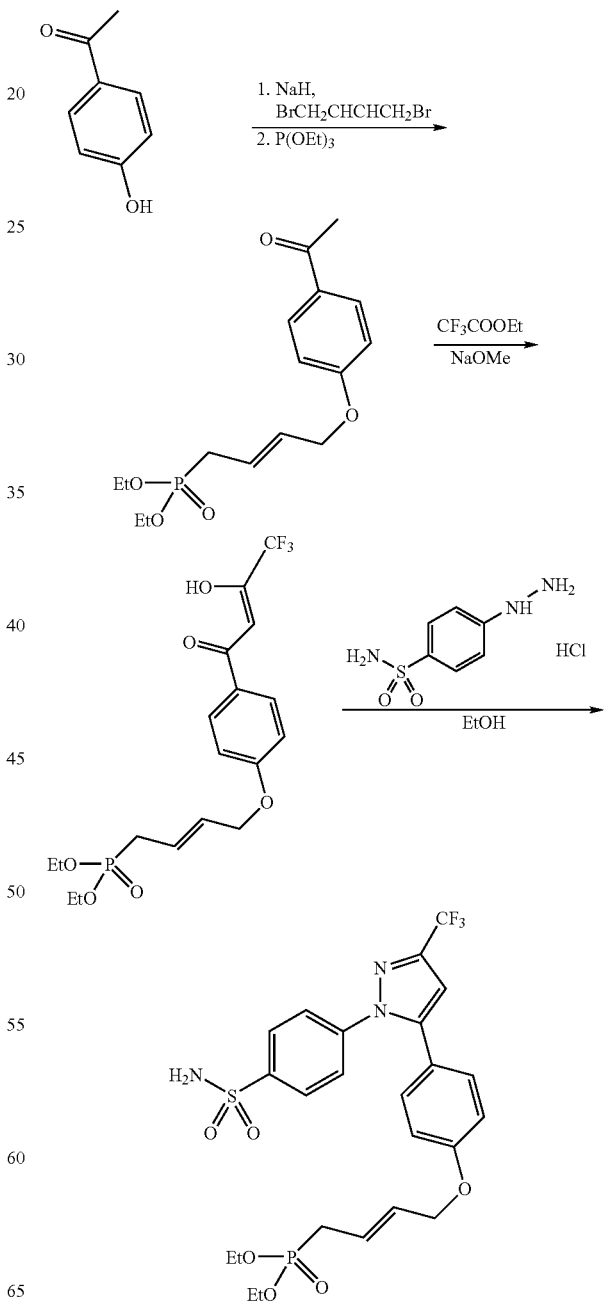

Representative compounds of the invention can be prepared as illustrated above.
EXAMPLE 241
Preparation of a Representative Compound of Formula 248
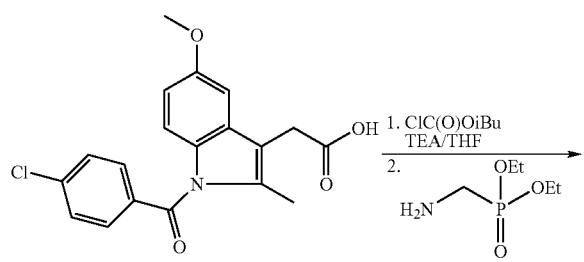
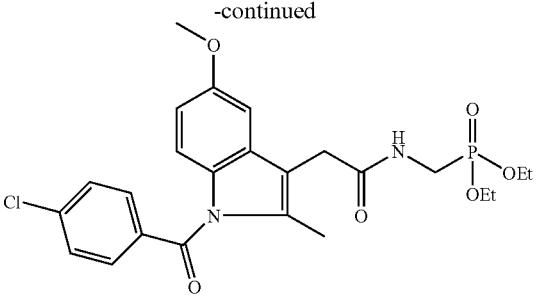
Representative compounds of the invention can be prepared as illustrated above.
EXAMPLE 242
Preparation of Representative Compounds of Formulae 248
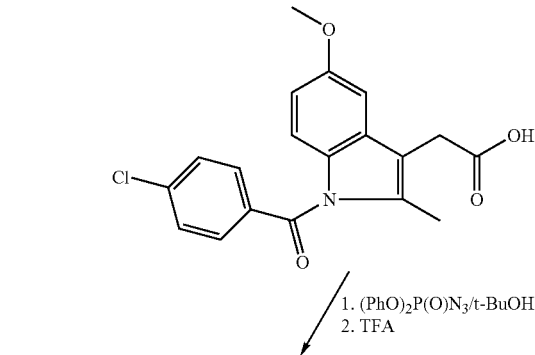
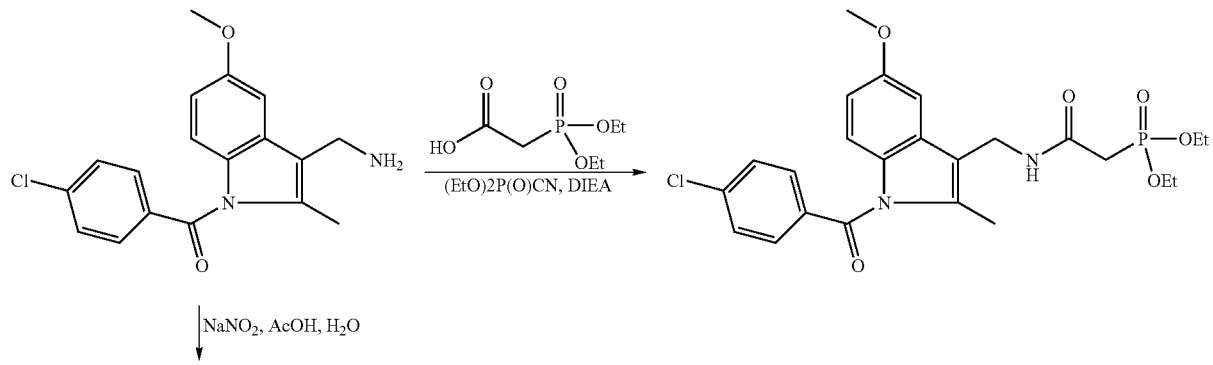
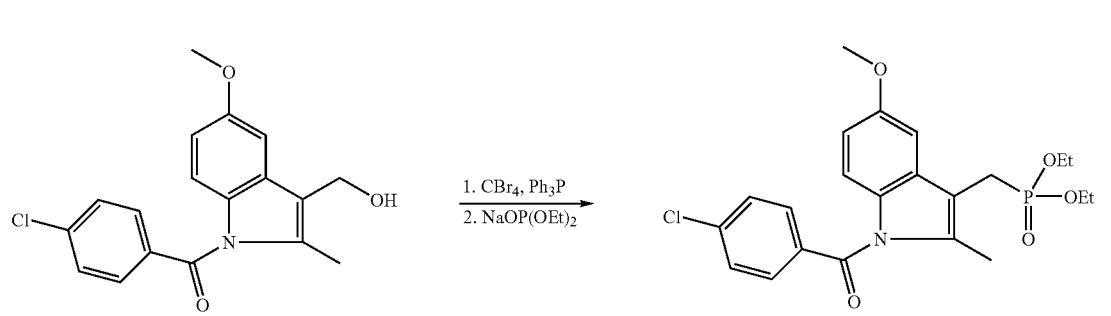

Representative compounds of the invention can be prepared as illustrated above.

EXAMPLE 243

Preparation of Representative Compounds of Formulae 250

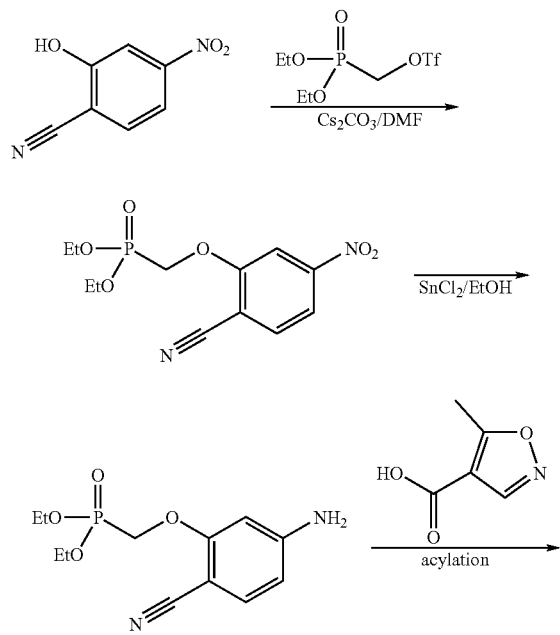

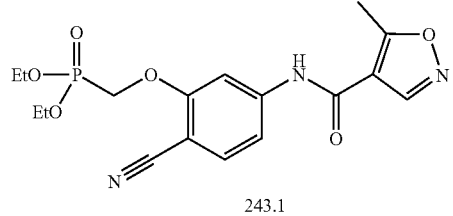

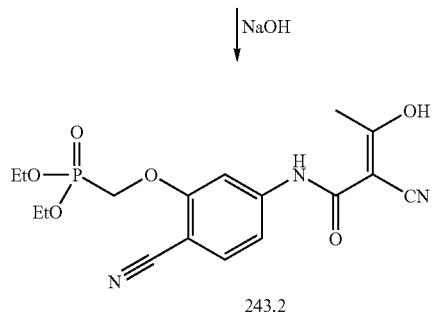

Representative compounds of the invention can be prepared as illustrated above using procedures similar to those described in *J. Med. Chem.* 1996, 39, 4608. Treatment of compound of the invention 243.1 with base provides compound 243.2 which is also a compound of the invention.

EXAMPLE 244

Preparation of Representative Compounds of Formulae 250

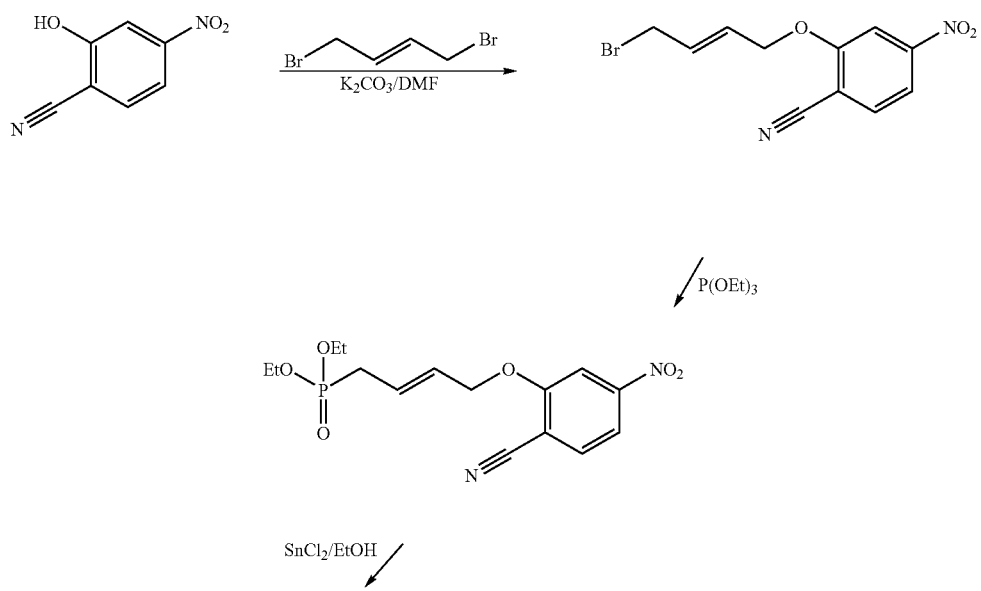

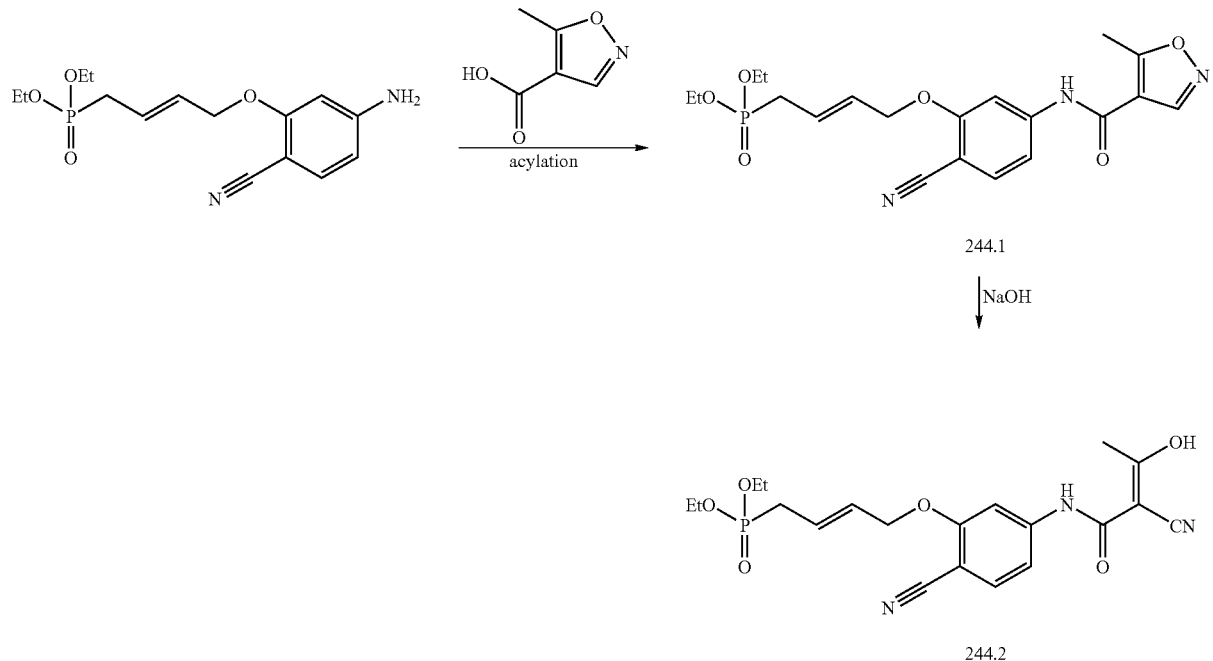

244.1

244.2

Representative compounds of the invention can be prepared as illustrated above. Treatment of compound of the invention 244.1 with base provides compound 244.2 which is also a compound of the invention.

EXAMPLE 245

Preparation of Representative Compounds of Formulae 251

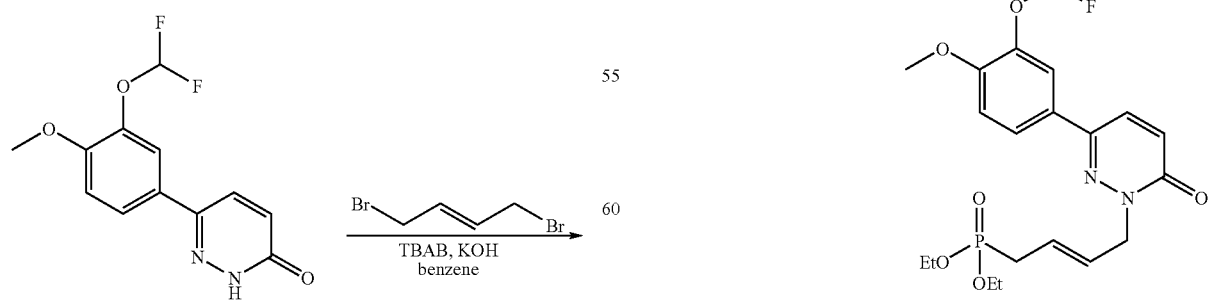

Representative compounds of the invention can be prepared as illustrated above. The N-alkylation of 6-aryl-3-pyridazinones is described in *J. Med. Chem.* 1983, 26, 373.

EXAMPLE 246
Preparation of Representative Compounds of Formulae 251
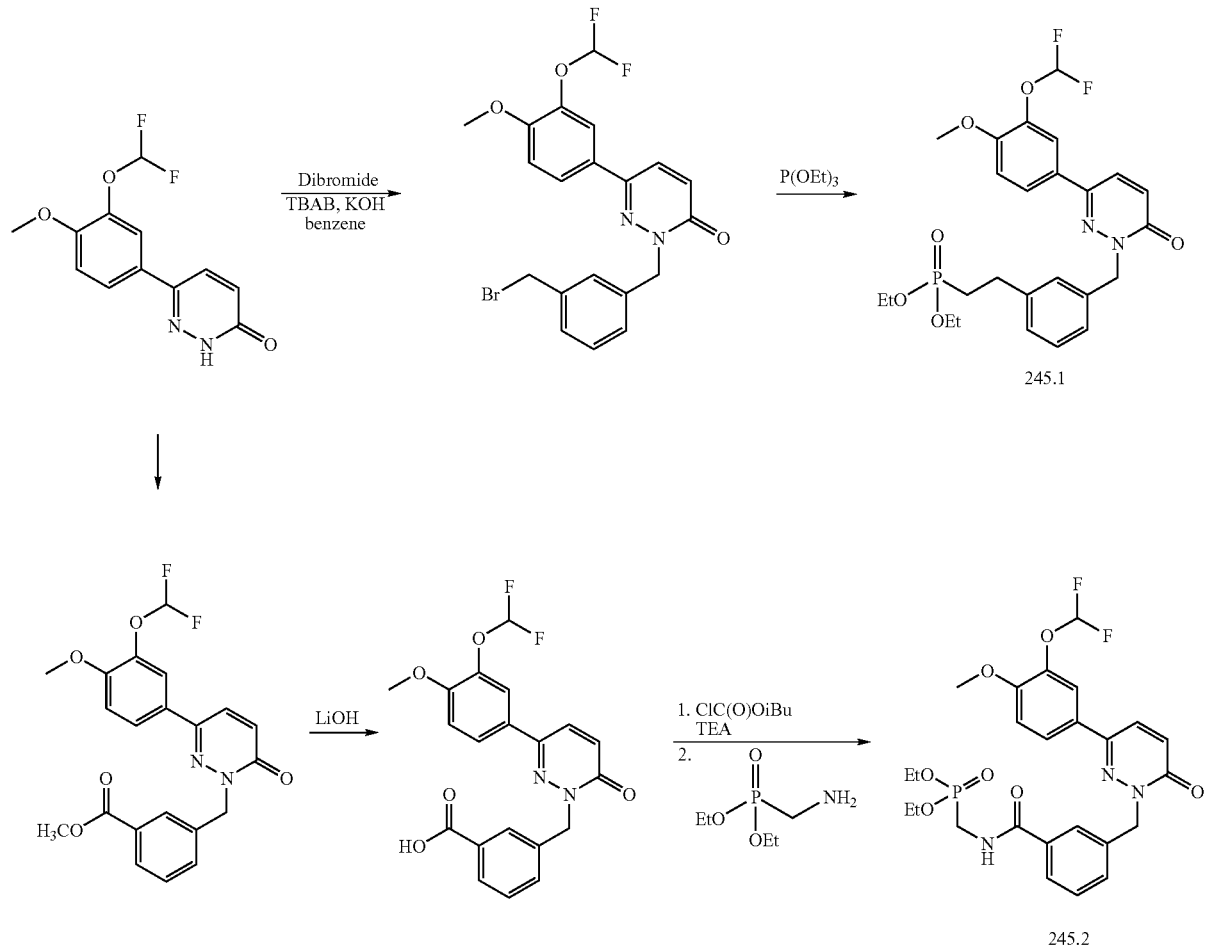
Representative compounds of the invention (245.1 and 245.2) can be prepared as illustrated above.
EXAMPLE 247
Preparation of Representative Compounds of Formulae 254
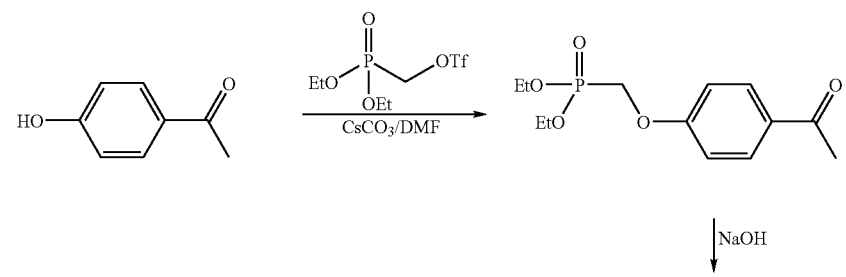

-continued
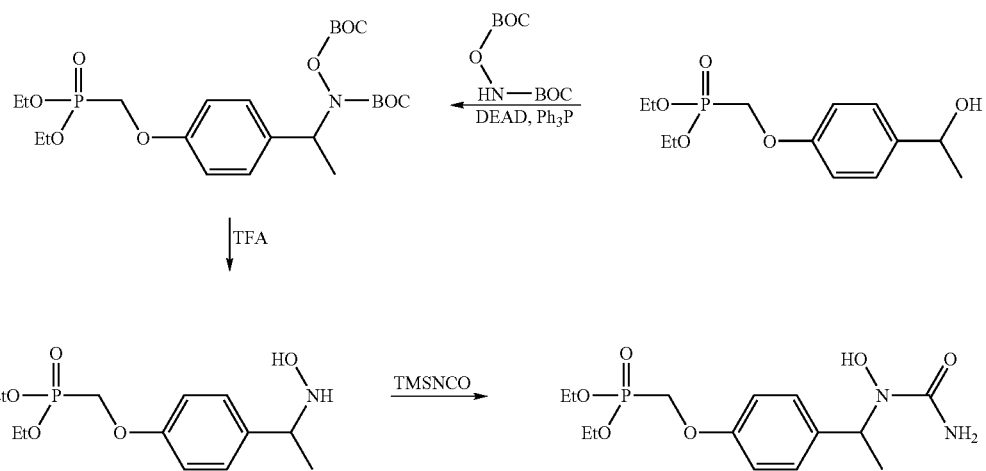
Representative compounds of the invention can be prepared as illustrated above. The synthesis of N-hydroxyureas is described in *J. Med. Chem.* 1997, 40, 1955.
EXAMPLE 248
Preparation of Representative Compounds of Formulae 254
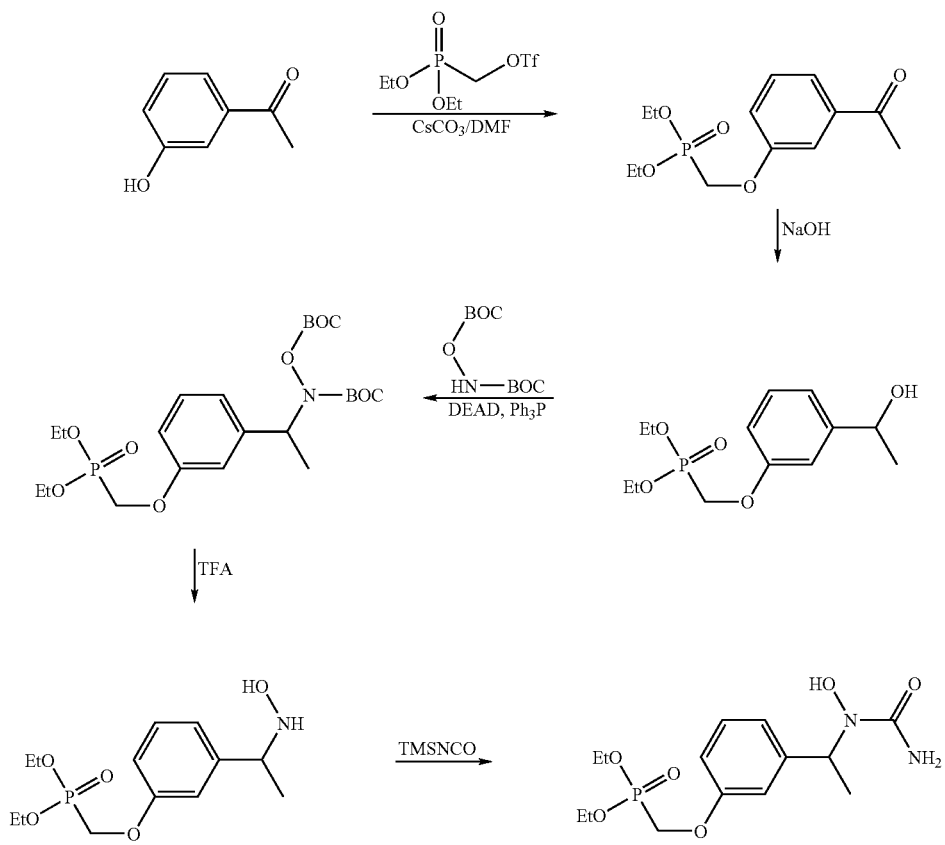

Representative compounds of the invention can be prepared as illustrated above.
EXAMPLE 249
Preparation of Representative Compounds of Formulae 253
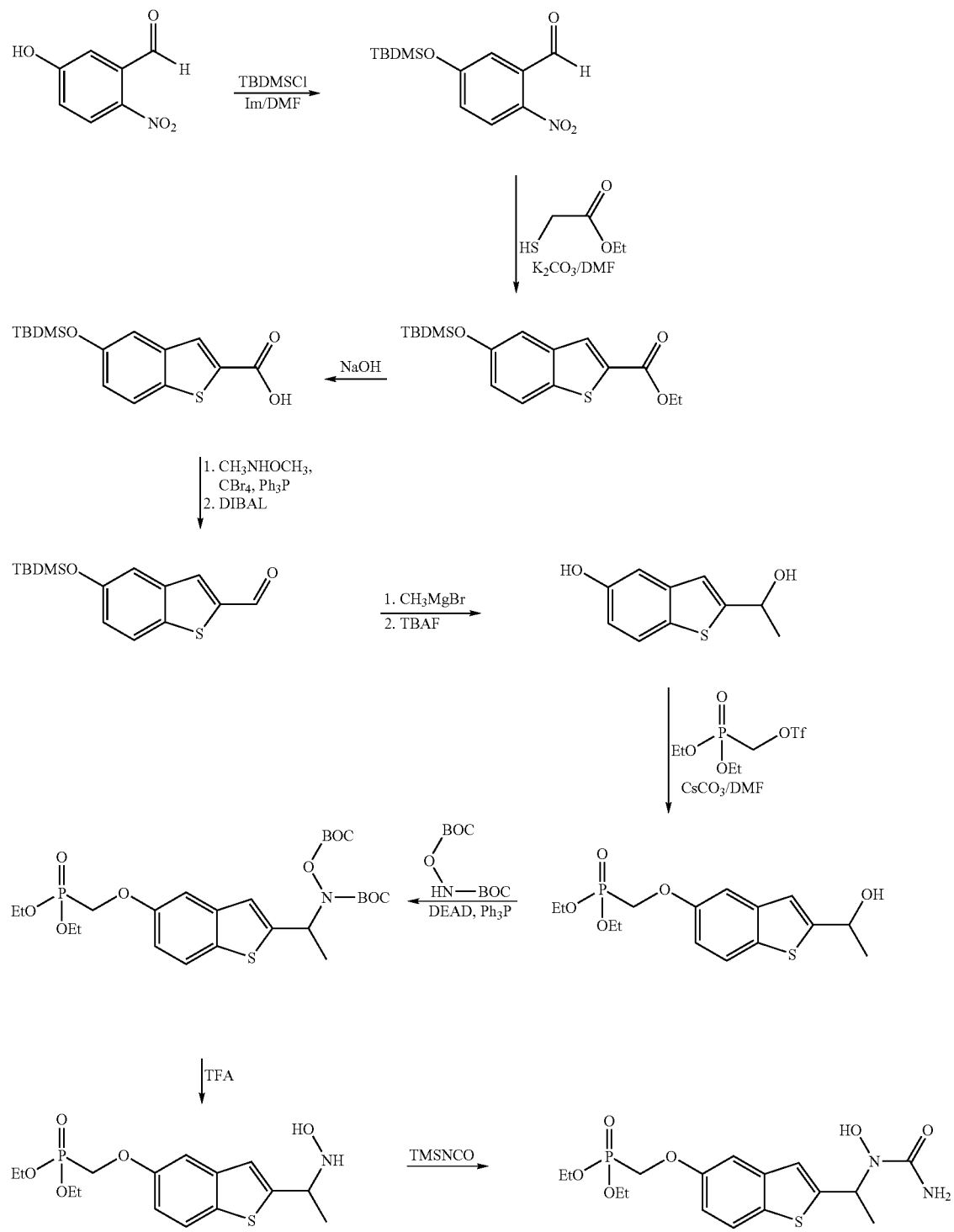

Representative compounds of the invention can be prepared as illustrated above.

EXAMPLE 250

Preparation of Representative Compounds of Formulae 253

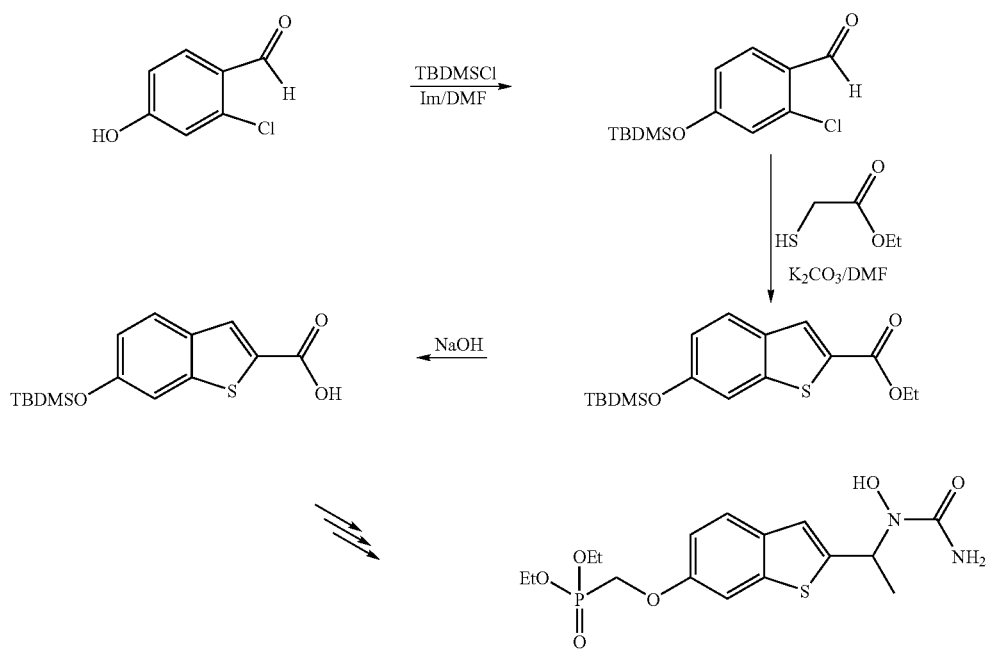

Representative compounds of the invention can be prepared as illustrated above. The synthesis of substituted benzothiophenes is described in *J. Med. Chem.* 2000, 43, 690.

EXAMPLE 251

Preparation of Representative Compounds of the Invention

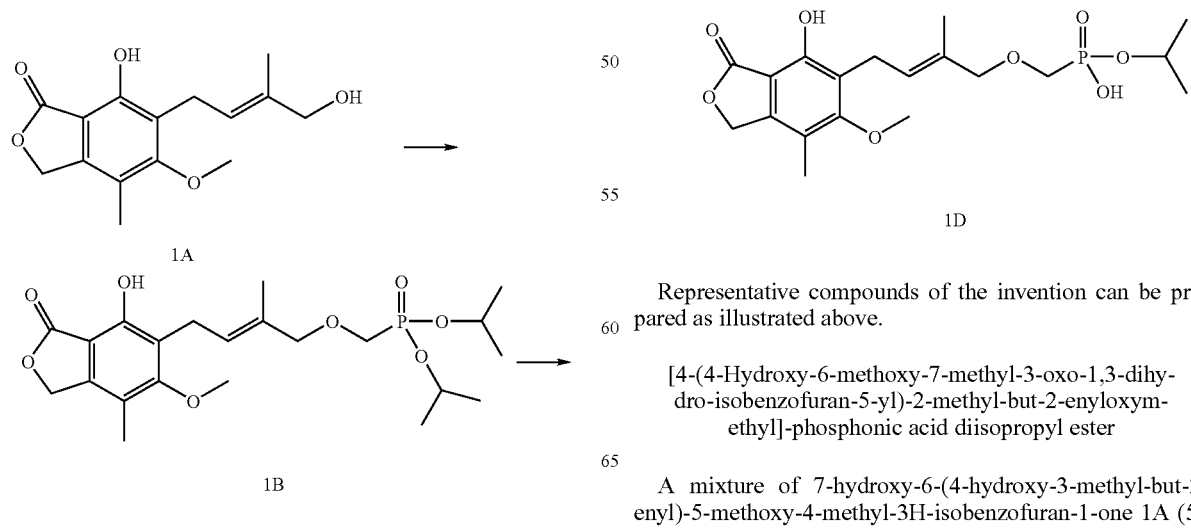

Representative compounds of the invention can be prepared as illustrated above.

[4-(4-Hydroxy-6-methoxy-7-methyl-3-oxo-1,3-dihydro-isobenzofuran-5-yl)-2-methyl-but-2-enyloxymethyl]-phosphonic acid diisopropyl ester A mixture of 7-hydroxy-6-(4-hydroxy-3-methyl-but-2-enyl)-5-methoxy-4-methyl-3H-isobenzofuran-1-one 1A (50 mg, 0.18 mmol, Pankiewicz et al., *J. Med. Chem.*, 45, 703), diisopropyl bromomethylphosphonate (93 mg, 0.36 mmol) and lithium t-butoxide (1M in THF, 0.54 mL) in DMF (3 mL) was heated at 70° C. for 5 hours. The reaction was quenched with 1N HCl. The mixture was poured into 5% aqueous lithium chloride, extracted with ethyl acetate, and concentrated. The residue was purified by chromatography on silica gel, affording [4-(4-hydroxy-6-methoxy-7-methyl-3-oxo-1,3-dihydro-isobenzofuran-5-yl)-2-methyl-but-2-enyloxymethyl]-phosphonic acid diisopropyl ester 1B (25 mg, 32%); $^1$H NMR (300 MHz, CDCl$_3$) δ1.25 (m, 12H), 1.79 (s, 3H), 2.05 (s, 3H), 3.37 (d, J=6.6 Hz, 2H), 3.58 (d, 2H), 3.77 (s, 3H), 3.97 (m, 2H), 4.68 (m, 2H), 5.19 (s, 2H), 5.45 (t, J=6.6 Hz, 1H), 7.83 (s, 1H) ppm.

[4-(4-Hydroxy-6-methoxy-7-methyl-3-oxo-1,3-dihydro-isobenzofuran-5-yl)-2-methyl-but-2-enyloxymethyl]-phosphonic acid and [4-(4-Hydroxy-6-methoxy-7-methyl-3-oxo-1,3-dihydro-isobenzofuran-5-yl)-2-methyl-but-2-enyloxymethyl]-phosphonic acid monoisopropyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid diisopropyl ester 1B (25 mg, 0.055 mmol) and 2,6-lutidine (0.18 mL, 1.65 mmol) in acetonitrile was added trimethylsilyl bromide (0.126 mL, 1.1 mmol) at 0° C. The mixture was allowed to warm to room temperature and stirred for 4 hours. The reaction was quenched with methanol at 0° C., and the resulting mixture was concentrated. The residue was purified by preparative reverse-phase HPLC to afford, after removal of the solvent, [4-(4-hydroxy-6-methoxy-7-methyl-3-oxo-1,3-dihydro-isobenzofuran-5-yl)-2-methyl-but-2-enyloxymethyl]-phosphonic acid 1C as an oil (17 mg, 83%); $^1$H NMR (300 MHz, CD$_3$OD) δ 1.81 (s, 3H), 2.06 (s, 3H), 3.40 (d, J=6.6 Hz, 2H), 3.50 (d, 2H), 3.77 (s, 3H), 3.97 (s, 2H), 5.20 (s, 2H), 5.47 (t, J=6.6 Hz, 1H) and [4-(4-hydroxy-6-methoxy-7-methyl-3-oxo-1,3-dihydro-isobenzofuran-5-yl)-2-methyl-but-2-enyloxymethyl]-phosphonic acid monoisopropyl ester 1D as an oil (2 mg, 7%); $^1$H NMR (300 MHz, CD$_3$OD) δ 1.23 (d, 6H), 1.81 (s, 3H), 2.08 (s, 3H), 3.40 (d, J=6.6 Hz, 2H), 3.50 (d, 2H), 3.77 (s, 3H), 3.90 (s, 2H), 4.50 (m, 1H), 5.20 (s, 2H), 5.47 (t, J=6.6 Hz, 1H) ppm.

EXAMPLE 252

Preparation of Representative Compounds of the Invention

Representative compounds of the invention can be prepared as illustrated below.

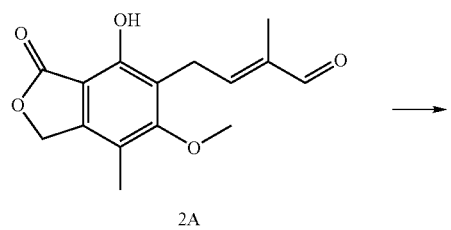

2A

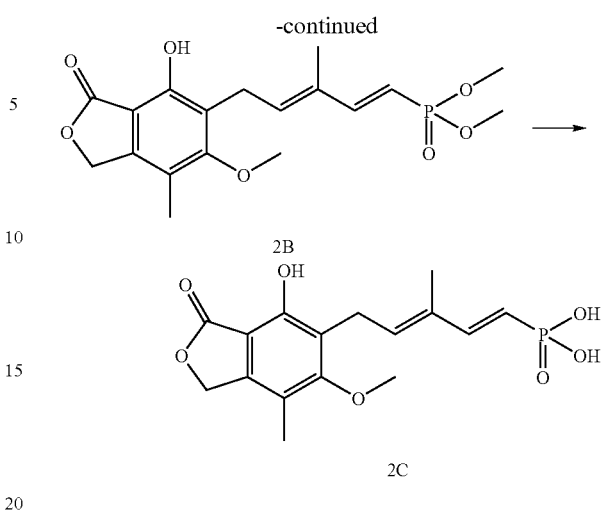

[5-(4-Hydroxy-6-methoxy-7-methyl-3-oxo-1,3-dihydro-isobenzofuran-5-yl)-3-methyl-penta-1,3-dienyl]-phosphonic acid dimethyl ester To a solution of tetramethylmethylene diphosphonate (102 mg, 0.44 mmol) in THF (2.5 mL) was added a THF solution of sodium bis(trimethysilyl)amide (1.0 M, 0.44 mL). After stirring for 30 minutes, a solution of 4-(4-hydroxy-6-methoxy-7-methyl-3-oxo-1,3-dihydro-isobenzofuran-5-yl)-2-methyl-but-2-enal 2A (30 mg, 0.11 mmol, Pankiewicz et al., *J. Med. Chem.*, 45, 703) in THF (2.5 mL) was added, and stirring was continued for an additional 15 minutes. The reaction was quenched with saturated aqueous ammonium chloride. The mixture was extracted with ethyl acetate. After evaporation of solvent, the residue was purified by chromatography on silica gel eluting with ethyl acetate (50% to 100%)/hexanes, affording [5-(4-hydroxy-6-methoxy-7-methyl-3-oxo-1,3-dihydro-isobenzofuran-5-yl)-3-methyl-penta-1,3-dienyl]-phosphonic acid dimethyl ester 2B (30 mg, 71%) as an oil; $^1$H NMR (300 MHz, CDCl$_3$) δ 1.80 (s, 3H), 2.04 (s, 3H), 3.45 (d, J=6.6 Hz, 2H), 3.76 (s, 3H), 3.88 (d, 6H), 5.20 (s, 3H), 5.55 (m, 1H), 5.95 (m, 1H), 7.05 (m, 1H), 7.65 (s, 1H) ppm.

[5-(4-Hydroxy-6-methoxy-7-methyl-3-oxo-1,3-dihydro-isobenzofuran-5-yl)-3-methyl-penta-1,3-dienyl]-phosphonic acid To a solution of [5-(4-hydroxy-6-methoxy-7-methyl-3-oxo-1,3-dihydro-isobenzofuran-5-yl)-3-methyl-penta-1,3-dienyl]-phosphonic acid dimethyl ester 2B (22 mg, 0.057 mmol) and 2,6-lutidine (0.22 mL, 1.71 mmol) in acetonitrile was added trimethylsilyl bromide (0.183 mL, 1.71 mmol) at 0° C. The mixture was allowed to warm to room temperature and stirred for 1 hour. The reaction was quenched with methanol at 0° C., and the resulting mixture was concentrated. The residue was purified by preparative reverse-phase HPLC to afford, after removal of the solvent, [5-(4-hydroxy-6-methoxy-7-methyl-3-oxo-1,3-dihydro-isobenzofuran-5-yl)-3-methyl-penta-1,3-dienyl]-phosphonic acid 2C as a solid (13 mg, 65%); $^1$H NMR (300 MHz, CD$_3$OD) δ 1.91 (s, 3H), 2.10 (s, 3H), 3.55 (d, J=6.6 Hz, 2H), 3.75 (s, 3H), 5.2 (s, 2H), 5.6-5.8 (m, 2H), 6.9 (m, 1H) ppm.

EXAMPLE 253

Preparation of Representative Compounds of the Invention

Representative compounds of the invention can be prepared as illustrated below.

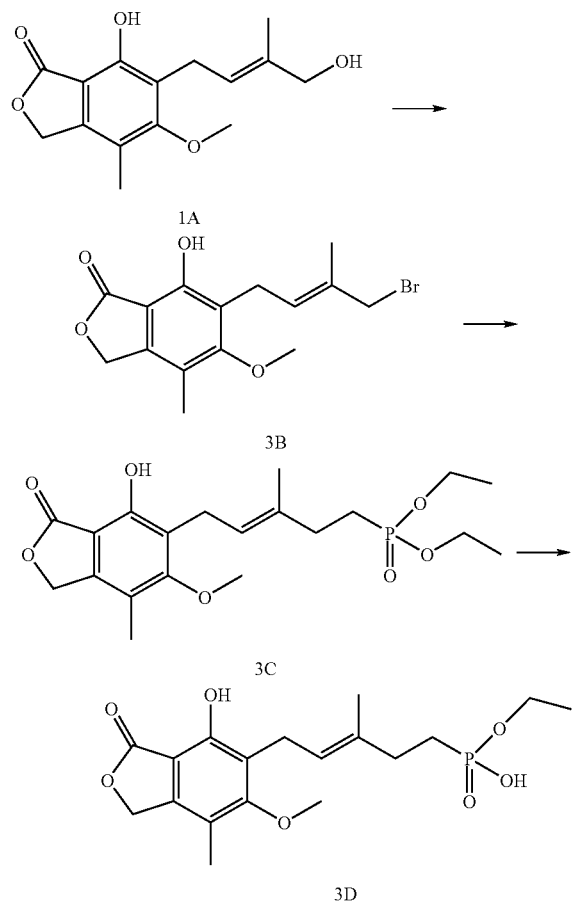

6-(4-Bromo-3-methyl-but-2-enyl)-7-hydroxy-5-methoxy-4-methyl-3H-isobenzofuran-1-one Polymer-supported triphenylphosphine (3 mmol/g, 0.5 g) was soaked in dichloromethane (10 mL) for 1 hour 7-Hydroxy-6-(4-hydroxy-3-methyl-but-2-enyl)-5-methoxy-4-methyl-3H-isobenzofuran-1-one 1A (100 mg, 0.36 mmol) and carbon tetrabromide (143 mg, 0.43 mmol) were sequentially added and the mixture was shaken for 1 hour at room temperature. More carbon tetrabromide (143 mg, 0.43 mmol) was added and the mixture was shaken further for 1 hour. The mixture was filtered and the filtrate was concentrated. The residue was chromatographed on silica gel (0% to 60% ethyl acetate/hexanes) to afford 6-(4-bromo-3-methyl-but-2-enyl)-7-hydroxy-5-methoxy-4-methyl-3H-isobenzofuran-1-one 3B as an oil (52 mg, 42%); $^1$H NMR (300 MHz, CDCl$_3$) δ 1.95 (s, 3H), 2.16 (s, 3H), 3.44 (d, J=7.2 Hz, 2H), 3.78 (s, 3H), 3.98 (s, 2H), 5.21 (s, 2H), 5.68 (t, J=7.2 Hz, 1H), 7.71 (brs, 1H) ppm.

[5-(4-Hydroxy-6-methoxy-7-methyl-3-oxo-1,3-dihydro-isobenzofuran-5-yl)-3-methyl-pent-3-enyl]-phosphonic acid diethyl ester n-Butyl lithium (1.6 M in hexanes, 1 mL) was added to an equal volume of THF at −20° C. A solution of diethyl methylphosphonate (220 mg, 1.45 mmol) in THF (1 mL) was then added dropwise and the solution was stirred for 30 minutes. After cooling at −60° C., the solution was transferred via a cannula to a vial containing copper(I) iodide (276 mg, 1.45 mmol), and the resulting mixture was stirred for 1 hour at −30° C. A solution of 6-(4-bromo-3-methyl-but-2-enyl)-7-hydroxy-5-methoxy-4-methyl-3H-isobenzofuran-1-one 3B (50 mg, 0.15 mmol) in THF (1 mL) was added and the mixture was allowed to warm to 0° C. for 2 hours before saturated aqueous ammonium chloride was added. The reaction mixture was acidified with 2 N HCl and extracted with ethyl acetate. The ethyl acetate extract was concentrated and the residue was chromatographed on silica gel (40% to 100% ethyl acetate/hexanes), affording [5-(4-hydroxy-6-methoxy-7-methyl-3-oxo-1,3-dihydro-isobenzofuran-5-yl)-3-methyl-pent-3-enyl]-phosphonic acid diethyl ester 3C as an oil (27 mg, contaminated with the starting diethyl methylphosphonate); $^1$H NMR (300 MHz, CDCl$_3$) δ 1.32 (m, 6H), 1.8-1.9 (m, 5H), 2.18 (s, 3H), 2.25 (m, 2H), 3.42 (d, J=7.2 Hz, 2H), 3.78 (s, 3H), 4.15 (m, 4H), 5.21 (s, 2H), 5.24 (t, J=7.2 Hz, 1H), 7.65 (s, 1H) ppm.

[5-(4-Hydroxy-6-methoxy-7-methyl-3-oxo-1,3-dihydro-isobenzofuran-5-yl)-3-methyl-pent-3-enyl]-phosphonic acid monoethyl ester A mixture of [5-(4-hydroxy-6-methoxy-7-methyl-3-oxo-1,3-dihydro-isobenzofuran-5-yl)-3-methyl-pent-3-enyl]-phosphonic acid diethyl ester 3C (27 mg, 0.066 mmol), LiOH (200 mg), MeOH (3 mL) and water (1 mL) was stirred at 70° C. for 4 hours. After cooling, the reaction solution was acidified with 2 N HCl, mixed with brine, and extracted with ethyl acetate/acetonitrle. The organic extract was concentrated and the residue was purified by preparative reverse-phase HPLC (acetonitrile and 0.1% aqueous CF$_3$COOH), affording [5-(4-hydroxy-6-methoxy-7-methyl-3-oxo-1,3-dihydro-isobenzofuran-5-yl)-3-methyl-pent-3-enyl]-phosphonic acid monoethyl ester 3D (7 mg, 28%); $^1$H NMR (300 MHz, CD$_3$OD) δ 1.28 (t, J=6.9 Hz, 3H), 1.7-1.9 (m, 5H), 2.20 (s, 3H), 2.2-2.3 (m, 2H), 3.41 (d, J=6.6 Hz, 2H), 3.80 (s, 3H), 4.02 (m, 2H), 5.2-5.3 (m, 3H) ppm.

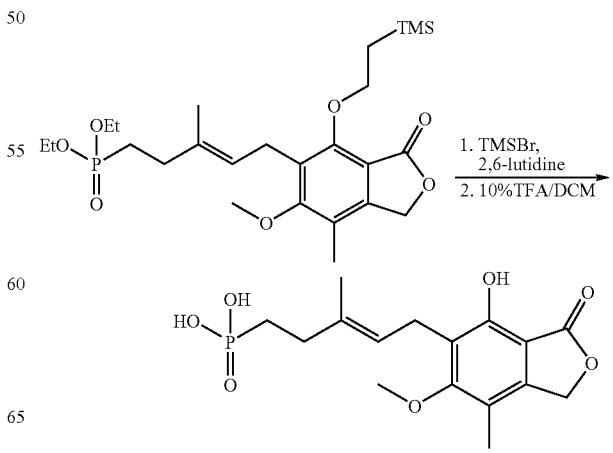

[5-(4-Hydroxy-6-methoxy-7-methyl-3-oxo-1,3-dihydro-isobenzofuran-5-yl)-3-methyl-pent-3-enyl]-phosphonic acid To a solution of {5-[6-Methoxy-7-methyl-3-oxo-4-(2-trimethylsilanyl-ethoxy)-1,3-dihydro-sobenzofuran-5-yl]-3-methyl-pent-3-enyl}-phosphonic acid diethyl ester (20 mg, 0.039 mmol) in DMF (0.5 mL) and DCM (0.5 mL) was added TMSBr (50.5 µL, 0.39 mmol) followed by 2,6-lutidine (45.3 µL, 0.39 mmol). The reaction was allowed to proceed for one hour when it was complete, as judged by LCMS. The reaction mixture was quenched with MeOH and concentrated to dryness. The residue was purified by preparative reverse-phase HPLC. The fraction containing the desired product was concentrated and treated with 10% TFA/DCM for 5 minutes. After concentration, the residue was purified by preparative reverse-phase HPLC to provide 7 mg (50%) of [5-(4-Hydroxy-6-methoxy-7-methyl-3-oxo-1,3-dihydro-isobenzofuran-5-yl)-3-methyl-pent-3-enyl]-phosphonic acid as a solid. $^1$H NMR (300 MHz, CD$_3$OD) δ 1.66-1.78 (m, 5H), 2.10 (s, 3H), 2.16-2.22 (m, 2H), 3.34 (d, J=7.2 Hz, 2H), 3.72 (s, 3H), 5.16 (s, 2H), 5.20 (t, J=7.2 Hz, 1H) ppm; $^{31}$P (121.4 MHz, CD$_3$OD) δ 31.57 ppm; MS (m/z) 355 [M−H]$^-$, 357 [M+H]$^+$.

EXAMPLE 254

Preparation of Representative Compounds of the Invention

Representative compounds of the invention can be prepared as illustrated below.

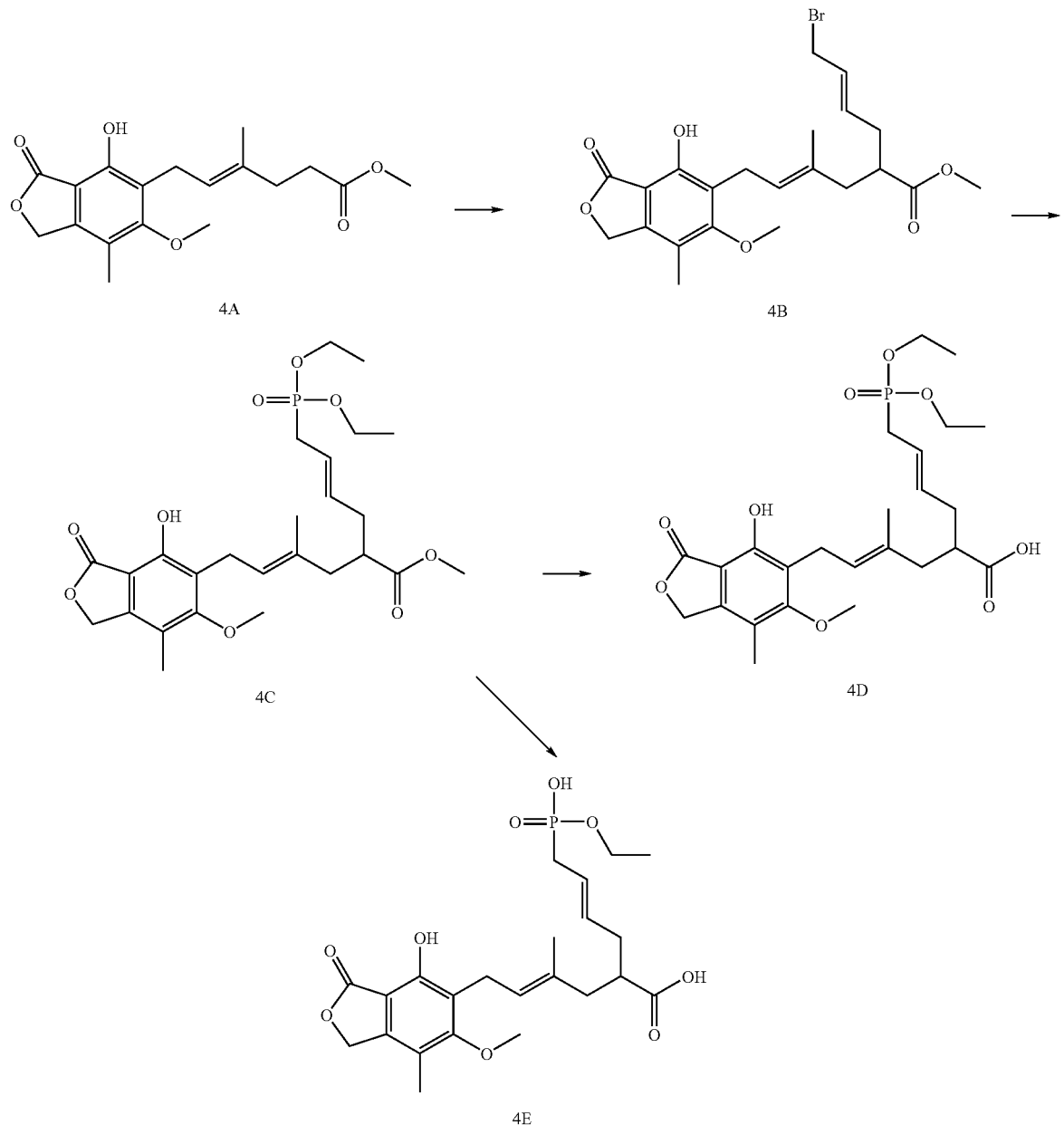

2-(4-Bromo-but-2-enyl)-6-(4-hydroxy-6-methoxy-7-methyl-3-oxo-1,3-dihydro-isobenzofuran-5-yl)4-methyl-hex-4-enoic acid methyl ester To a cooled (−78° C.) solution of mycophenolic acid methyl ester 4A (138 mg, 0.41 mmol) in THF (2.5 mL) was added a THF solution of sodium bis(trimethysilyl)amide (1.0 M, 0.98 mL). After stirring for 30 minutes, a solution of 1,4-dibromo-2-butene (950 mg, 4.1 mmol) in THF (2.5 mL) was added and stirring was continued for 10 minutes. The resulting mixture was warmed to −30° C. and stored at this temperature for 16 hours. The reaction was quenched with saturated aqueous ammonium chloride. The mixture was extracted with ethyl acetate to give, after evaporation of the solvent, a residue that was purified by chromatography on silica gel eluting with ethyl acetate (0% to 40%)/hexanes, affording 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester 4B (150 mg, 78%) as an oil; $^1$H NMR (300 MHz, CDCl$_3$) δ 1.75 (s, 3H), 2.0-2.4 (m, 8H), 2.62 (m, 1H), 3.37 (d, J=6.6 Hz, 2H), 3.58 (s, 3H), 3.76 (s, 3H), 3.88 (d, J=4.8 Hz, 2H), 5.1-5.3 (m, 3H), 5.67 (brs, 2H), 7.67 (s, 1H) ppm.

2-[4-(Diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester A solution of 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester 4B (140 mg, 0.30 mmol) and triethylphosphite (600 mg, 3.6 mmol) in toluene (30 mL) was stirred at reflux for 20 hours. The mixture was concentrated and chromatographed on silica gel eluting with ethyl acetate (60% to 100%)/hexanes, affording 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester 4C as an oil (70 mg, 43%); $^1$H NMR (300 MHz, CDCl$_3$) δ 1.27 (m, 6H), 1.79 (s, 3H), 2.0-2.7 (m, 8H), 3.37 (d, J=6.6 Hz), 3.52 (s, 3H), 3.75 (s, 3H), 4.08 (m, 4H), 5.20 m, 3H), 5.45 (m, 2H) ppm.

2-[4-(Diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid A mixture of 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester 4C (33 mg, 0.063 mmol) and lithium hydroxide (44 mg) in a mixture of THF (6 mL) and water (1 mL) was stirred at room temperature for 6 hours. The organic solvent was removed and the residue was partitioned between ethyl acetate and 5% aqueous sodium bicarbonate. The aqueous layer was acidified with 2 N HCl and extracted with ethyl acetate. The ethyl acetate extract was concentrated, affording 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 4D as an oil (30 mg, 100%); $^1$H NMR (300 MHz, CDCl$_3$) δ 1.27 (m, 6H), 1.79 (s, 3H), 2.0-2.7 (m, 8H), 3.37 (d, J=6.6 Hz), 3.75 (s, 3H), 4.08 (m, 4H), 5.19 (s, 2H), 5.25 (m, 1H), 5.44 (m, 1H), 5.55 (m, 1H), 5.45 (m, 2H) ppm.

2-[4-(Ethoxy-hydroxy-phosphoryl)-but-2-enyl]-6(4-hydroxy-6-methoxy-7-methyl-3-oxo-1,3-dihydro-isobenzofuran-5-yl)-4-methyl-hex-4-enoic acid A mixture of 2-[4-(diethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester 4C (25 mg, 0.048 mmol) and lithium hydroxide (200 mg) in a mixture of methanol (3 mL) and water (1 mL) was stirred at 70° C. for 2 hours. The organic solvent was evaporated and the residue acidified with 2N HCl and extracted with ethyl acetate/acetonitrile. The organic extract was concentrated, and the residue was purified by preparative reverse-phase HPLC (acetonitrile and 0.1% aqueous CF$_3$COOH), affording 2-[4-(ethoxy-hydroxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 4E as an oil (15 mg, 89%); $^1$H NMR (300 MHz, CD$_3$OD) δ 1.25 (t, J=6.9 Hz, 3H), 1.81 (s, 3H), 2.1-2.6 (m, 8H), 3.40 (d, J=6.6 Hz, 2H), 3.77 (s, 3H), 3.97 (m, 2H), 5.1-5.3 (m, 3H), 5.67 (brs, 2H) ppm.

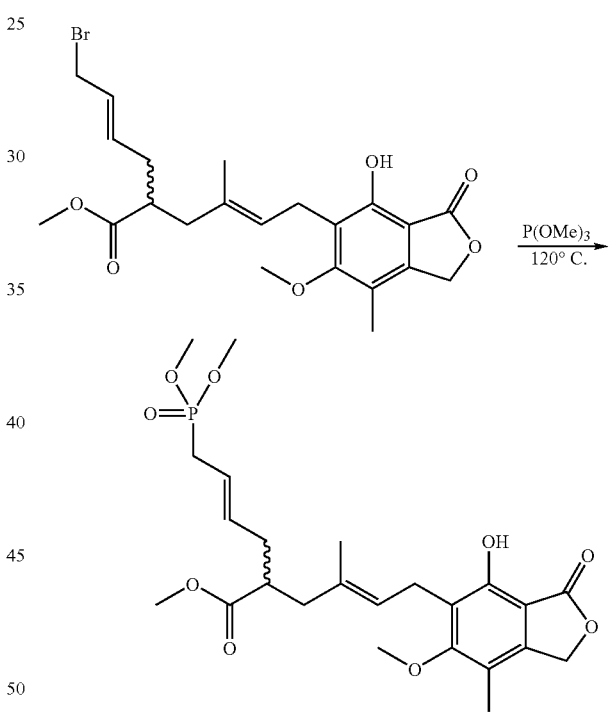

2-[4-(Dimethoxy-phosphoryl)but-2-enyl]-6-(4-hydroxy-6-methoxy-7-methyl-3-oxo-1,3-dihydro-isobenzofuran-5-yl)-4-methyl-hex-4-enoic acid methyl ester Under a N$_2$ atmosphere, a solution of 2-(4-bromo-but-2-enyl)-6-(4-hydroxy-6-methoxy-7-methyl-3-oxo-1,3-dihydro-isobenzofuran-5-yl)-4-methyl-hex-4-enoic acid methyl ester (490 mg, 1.05 mmol) in trimethylphosphite (2.5 mL, 21.1 mmol) was heated at 120° C. for 1 hour. The reaction was allowed to cool to room temperature. The reaction mixture was worked up by removal of the solvent in vacuo followed by chromatography using EtOAc-hexanes to provide 460 mg (88%) of the product as an oil. ¹H NMR (300 MHz, CDCl₃) δ 1.77 (s, 3H), 2.081-2.31 (m, 4H), 2.15 (s, 3H), 2.52 (d, 1H, J=22 Hz), 2.54 (d, 1H, J=22 Hz), 2.55-2.63 (m, 1H), 3.36 (d, 2H, J=7 Hz), 3.57 (s, 3H), 3.72 (d, 6H, J=11 Hz), 3.76 (s, 3H), 5.20 (s, 2H), 5.20-5.26 (m, 1H), 5.36-5.56 (m, 2H), 7.69 (s, 1H) ppm; ³¹P (121.4 MHz, CDCl₃) δ 30.1 ppm; MS (m/z) 497.2 [M+H]⁺, 519.2 [M+Na]⁺.

Hz), 2.57-2.64 (m, 1H), 3.38 (d, 2H, J=7 Hz), 3.72 (d, 6H, J=11 Hz) 3.76 (s, 3H), 5.20 (s, 2H), 5.27 (t, 1H, J=6 Hz), 5.36-5.63 (m, 2H) ppm; ³¹P (121.4 MHz, CDCl₃) δ 30.5 ppm; MS (m/z) 481.2 [M−H]⁻.

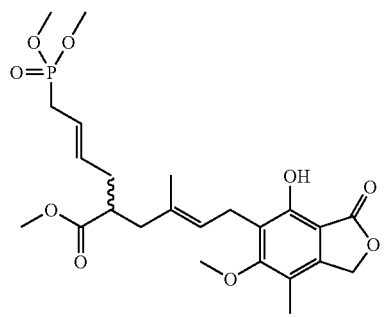

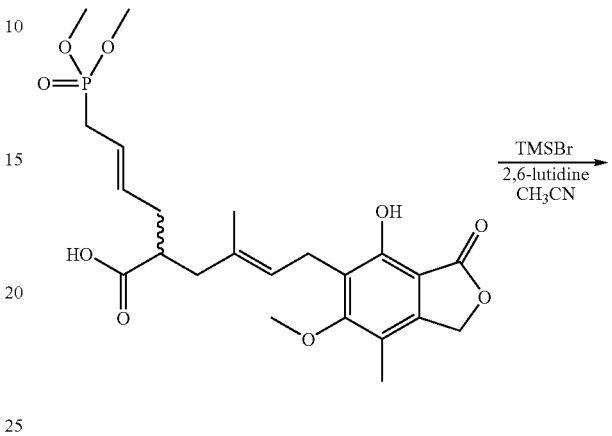

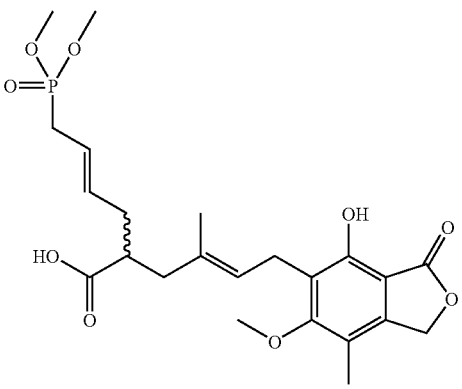

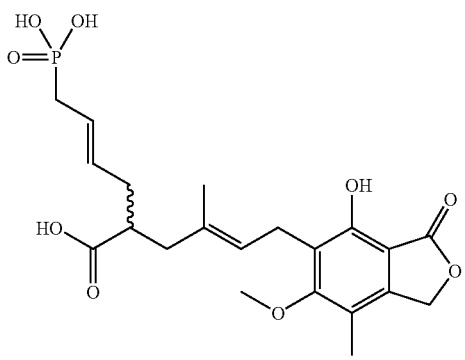

2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid 2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid methyl ester (460 mg, 0.927 mmol) in a solution of 1:1:2 of H₂O, MeOH, THF (8 mL) was stirred with LiOH·H₂O (78 mg, 1.86 mmol) at ambient temperature for 12 hours. A second batch of LiOH·H₂O (40 mg, 0.952 mmol) was added. The reaction mixture was stirred at room temperature for another 16 hours, after which no further progress was observed. The reaction was quenched by addition of a saturated aqueous solution of NH₄Cl. The organic layer was removed in vacuo and the product was extracted with EtOAc from the aqueous layer, which had been acidified by addition of 5 drops of 2 N HCl. The product was further purified by chromatography to provide the desired product. ¹H NMR (300 MHz, CDCl₃) δ 1.79 (s, 3H), 2.08-2.38 (m, 4H), 2.15 (s, 3H), 2.53 (d, 1H, J=22 Hz), 2.60 (d, 1H, J=22

2-[4-(2-[4-(Dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid To a solution of 2-[4-(dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid (25 mg, 0.052 mmol) in acetonitrile (2 mL) was added 2,6-lutidine (60 μL, 0.52 mmol) and TMSBr (67 μL, 0.52 mmol). The reaction was allowed to proceed for 45 minutes when it was completed as judged by LCMS. The reaction mixture was concentrated under reduced pressure and quenched with an aqueous NaOH solution (1 mL). The product was purified by RP HPLC (using a C18 column with a gradient of H₂O, 0.1% TFA-acetonitrile, 0.1% TFA) to provide 14.2 mg (60%) of the product as a solid. ¹H NMR (300 MHz, CD₃OD) δ 1.81 (s, 3H), 2.081-2.31 (m, 4H), 2.16 (s, 3H), 2.45 (d, 1H, J=22 Hz), 2.47 (d, 1H, J=22 Hz), 2.55-2.63 (m, 1H), 3.38 (d, 2H, J=7 Hz), 3.77 (s, 3H), 5.25 (s, 2H), 5.20-5.36 (m, 1H), 5.36-5.56 (m, 2H) ppm; ³¹P (121.4 MHz, CD₃OD) δ 25.4 ppm; MS (m/z) 453 [M−H]⁻.

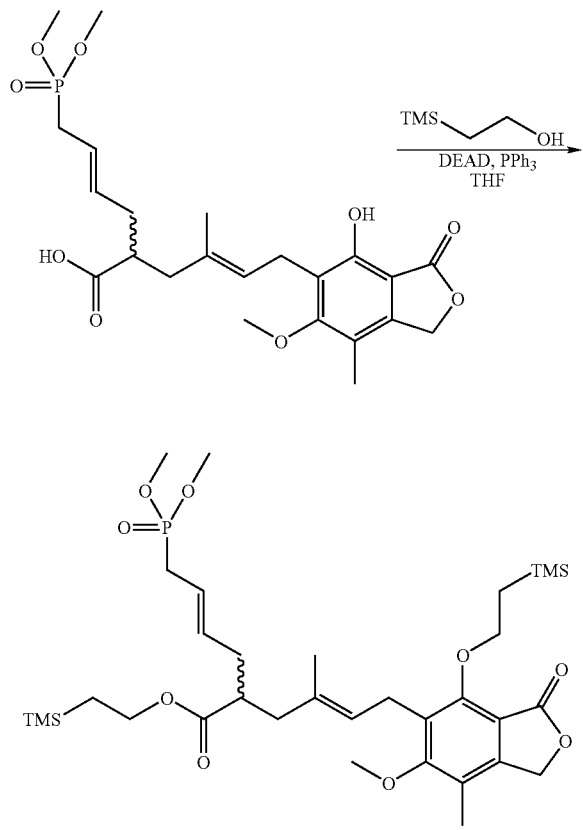

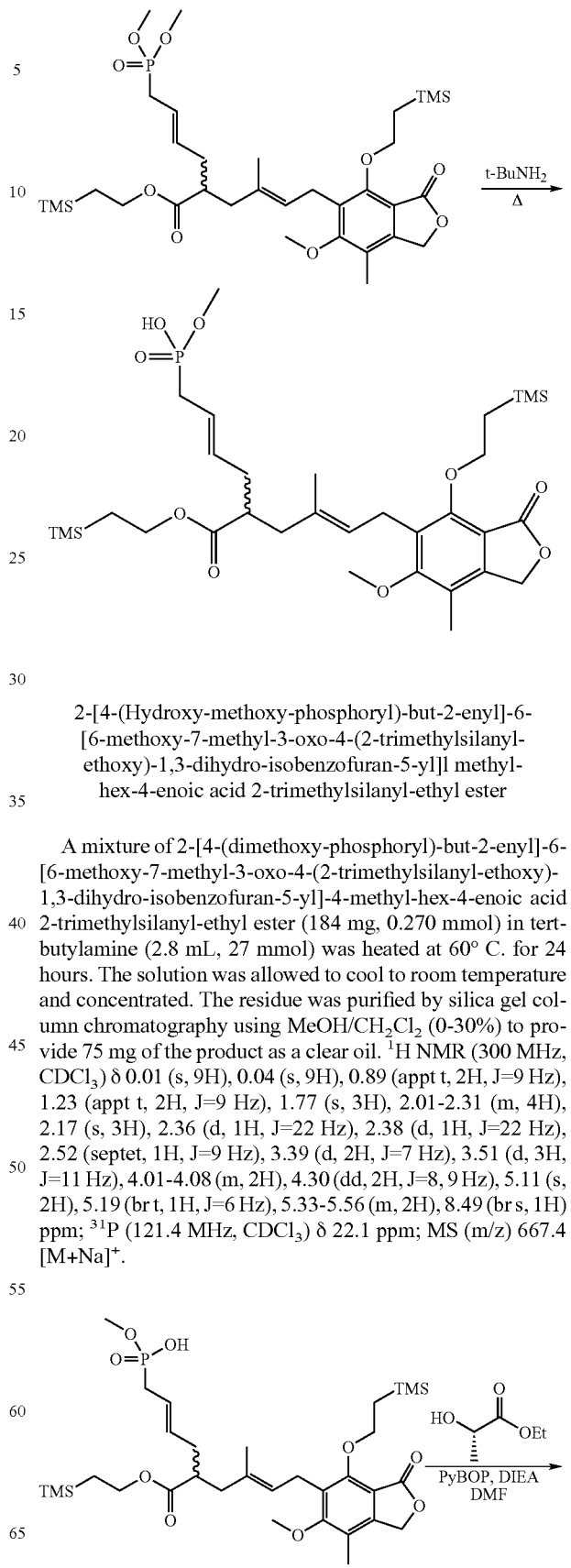

2-[4-(Dimethoxy-phosphoryl)-but-2-enyl]-66-methoxy-7-methyl-3-oxo-4-(2-trimethylsilanyl-ethoxy)-1,3-dihydro-isobenzofuran-5-yl]4-methyl-hex-4-enoic acid 2-trimethylsilanyl-ethyl ester A solution of 2-[4-(dimethoxy-phosphoryl)-but-2-enyl]-6-(4-hydroxy-6-methoxy-7-methyl-3-oxo-1,3-dihydro-isobenzofuran-5-yl)-4-methyl-hex-4-enoic acid (160 mg, 0.332 mmol) and trimethylsilylethanol (160 mg, 1.36 mmol) in THF (8.00 mL) was stirred with triphenylphosphine (345 mg, 1.33 mmol). To this solution was added diethyl azodicarboxylate (230 µL, 1.33 mmol) at 0° C. The mixture was allowed to warm to room temperature and stirred for 16 hours. Additional triphenylphosphine (180 mg, 0.692 mmol), trimethylsilylethanol (160 mg, 1.36 mmol), and diethyl azodicarboxylate (115 µL, 0.665 mmol) were added and the reaction mixture was stirred for another 1 day at room temperature. The reaction was worked up by removing the solvents in vacuo and purifying the residue by silica gel chromatography to provide 192 mg (85%) of the product as a clear oil. $^1$H NMR (300 MHz, CDCl$_3$) δ 0.03 (s, 9H), 0.05 (s, 9H), 0.93-0.96 (m, 2H), 1.20-1.29 (m, 2H), 1.78 (s, 3H), 2.01-2.32 (m, 4H), 2.17 (s, 3H), 2.51 (d, 1H, J=22 Hz), 2.58 (d, 1H, J=22 Hz), 2.50-2.60 (m, 1H), 3.37 (d, 2H, J=7 Hz), 3.72 (d, 6H, J=11 Hz), 3.76 (s, 3H), 4.08 (appt t, 2H, J=8 Hz), 4.30 (appt t, 2H, J=8 Hz), 5.12 (s, 2H), 5.15-5.25 (m, 1H), 5.36-5.63 (m, 2H) ppm; $^{31}$P (121.4 MHz, CDCl$_3$) δ 29.3 ppm; MS (m/z) 705.3 [M+Na]$^+$.

2-[4-(Hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]l methyl-hex-4-enoic acid 2-trimethylsilanyl-ethyl ester A mixture of 2-[4-(dimethoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (184 mg, 0.270 mmol) in tert-butylamine (2.8 mL, 27 mmol) was heated at 60° C. for 24 hours. The solution was allowed to cool to room temperature and concentrated. The residue was purified by silica gel column chromatography using MeOH/CH$_2$Cl$_2$ (0-30%) to provide 75 mg of the product as a clear oil. $^1$H NMR (300 MHz, CDCl$_3$) δ 0.01 (s, 9H), 0.04 (s, 9H), 0.89 (appt t, 2H, J=9 Hz), 1.23 (appt t, 2H, J=9 Hz), 1.77 (s, 3H), 2.01-2.31 (m, 4H), 2.17 (s, 3H), 2.36 (d, 1H, J=22 Hz), 2.38 (d, 1H, J=22 Hz), 2.52 (septet, 1H, J=9 Hz), 3.39 (d, 2H, J=7 Hz), 3.51 (d, 3H, J=11 Hz), 4.01-4.08 (m, 2H), 4.30 (dd, 2H, J=8, 9 Hz), 5.11 (s, 2H), 5.19 (br t, 1H, J=6 Hz), 5.33-5.56 (m, 2H), 8.49 (br s, 1H) ppm; $^{31}$P (121.4 MHz, CDCl$_3$) δ 22.1 ppm; MS (m/z) 667.4 [M+Na]$^+$.

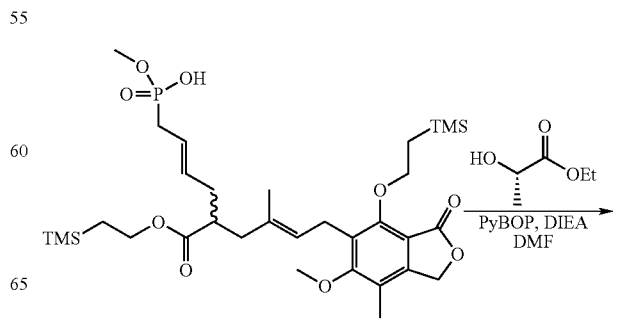

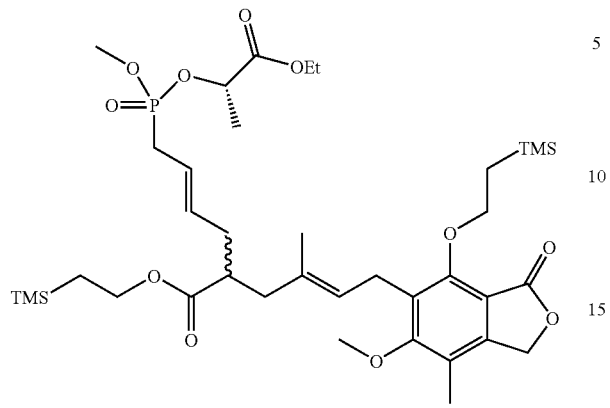

2-{4-[(1-Ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]4-methyl-hex-4-enoic acid 2-trimethylsilanyl-ethyl ester A solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (67 mg, 0.10 mmol) and PyBOP (234 mg, 0.450 mmol) in DMF (1.5 mL) was stirred with ethyl (S)-(−)-lactate (53 mg, 0.45 mmol) and DIEA (174 µL, 1.00 mmol) at ambient temperature for 1 hour, when complete consumption of the starting materials was observed. The reaction was worked up by addition of saturated aqueous sodium chloride and ethyl acetate. The organic layer was separated and washed with 5% aqueous solution of lithium chloride. The organic layer was dried in vacuo and the residue was purified by silica gel chromatography using MeOH—CH$_2$Cl$_2$ (0-20%) to provide 57 mg (74%) of the desired product as a clear oil. $^1$H NMR (300 MHz, CDCl$_3$) δ 0.02 (s, 9H), 0.05 (s, 9H), 0.88-0.94 (m, 2H), 1.20-1.30 (m, 2H), 1.29 (t, 3H, J=7 Hz), 1.45 (d, 3H, J=7 Hz), 1.78 (s, 3H), 2.01-2.31 (m, 4H), 2.17 (s, 3H), 2.50-2.58 (m, 1H), 2.65 (d, 1H, J=22 Hz), 2.67 (d, 1H, J=22 Hz), 3.39 (d, 2H, J=7 Hz), 3.69 and 3.77 (d, 3H, J=11 Hz), 3.76 (s, 3H), 4.07 (appt t, 2H, J=7 Hz), 4.20 (dq, 2H, J=3, 7 Hz), 4.29 (appt t, 2H, J=9 Hz), 4.85-4.99 (m, 1H), 5.12 (s, 2H), 5.19 (br t, 1H, J=6 Hz), 5.33-5.61 (m, 2H) ppm; $^{31}$P (121.4 MHz, CDCl$_3$) δ 28.9, 29.9 ppm; MS (m/z) 791.4 [M+Na]$^+$.

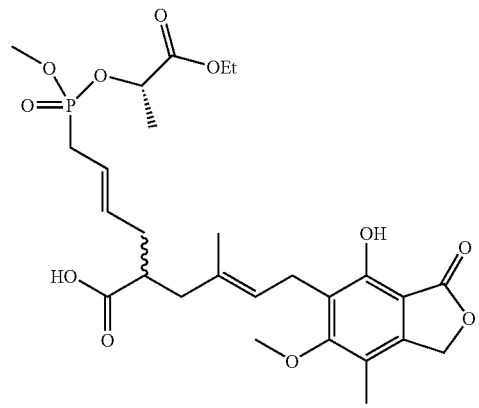

2-{4-[(1-Ethoxycarbonyl-ethoxy)-methoxy-phosphoryl]-but-2-enyl}-6-(4-hydroxy-6-methoxy-7-methyl-3-oxo-1,3-dihydro-isobenzofuran-5-yl)$_4$-methyl-hex-4-enoic acid A solution of 2-{4-[(1-ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (14 mg, 0.018 mmol) in THF (1 mL) was stirred with a 1M solution of TBAF in THF (55 µL, 0.055 mmol) for 1 hour. The reaction mixture was concentrated, acidified with 1N HCl and extracted with EtOAc. The organic layer was washed with brine and dried. The product was purified by silica gel column chromatography EtOH-EtOAc (0-10%). Further purification was performed by dissolving the product in CH$_2$Cl$_2$ and passing the compound through a 13 mm Acrodisc syringe filter with a 0.45 µm Nylon membrane to provide 8 mg (77%) of the product. $^1$H NMR (300 MHz, CDCl$_3$) δ 0.92 (t, 3H, J=7 Hz), 1.30 (d, 3H, J=8 Hz), 1.79 (s, 3H), 2.10-2.39 (m, 4H), 2.15 (s, 3H), 2.53 (d, 1H, J=8 Hz), 2.65 (d, 1H, J=22 Hz), 2.68 (d, 1H, J=22 Hz), 3.38 (d, 2H, J=7 Hz), 3.70 and 3.74 (d, 3H, J=11 Hz), 3.76 (s, 3H), 4.07 (m, 2H), 4.96 (dq, 1H, J=7 Hz), 5.20 (s, 2H), 5.27 (br t, 1H, J=7 Hz), 5.33-5.55 (m, 2H), 7.51-7.56 (m, 1H), 7.68-7.74 (m, 1H) ppm; $^{31}$P (121.4 MHz, CDCl$_3$) δ 29.0, 30.1 ppm; MS (m/z) 569.2 [M+H]$^+$, 591.3. [M+Na]$^+$.

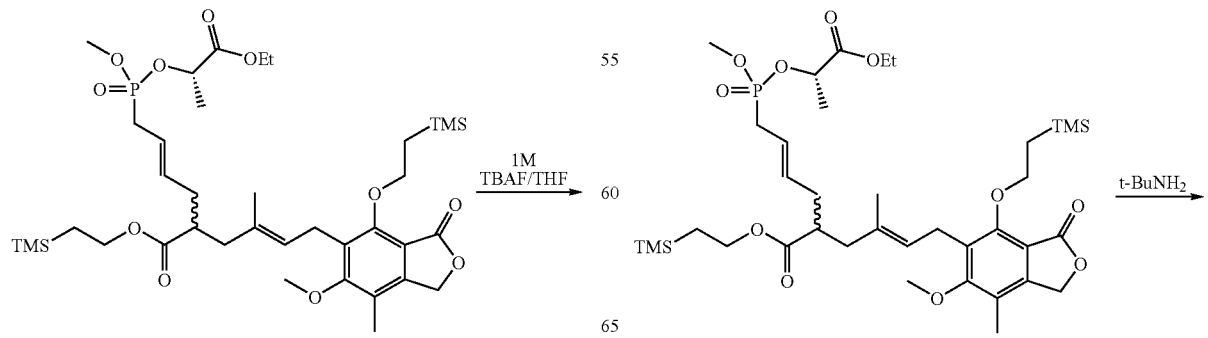

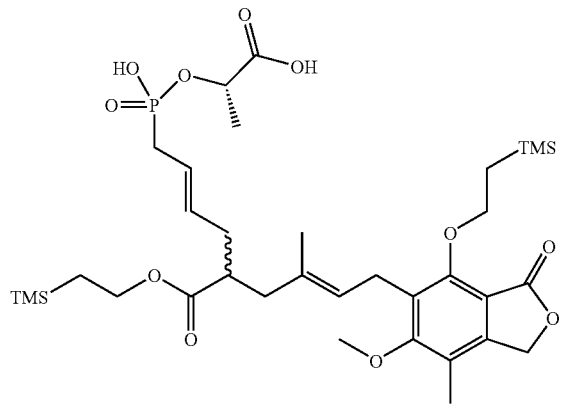

2-{4-[(1-Carboxy-ethoxy)-hydroxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-{4-[(1-ethoxycarbonyl-ethoxy)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanylethyl ester (12 mg, 0.016 mmol) in tert-butylamine (1 mL, 9.6 mmol) was heated at 65° C. for 16 hours. The solution was allowed to cool to room temperature and concentrated to provide the crude product as an oil. $^1$H NMR (300 MHz, CDCl$_3$) δ 0.03 (s, 9H), 0.04 (s, 9H), 0.86-0.98 (m, 2H), 1.22-1.33 (m, 2H), 1.50 (d, 3H, J=7 Hz), 1.78 (s, 3H), 2.05-2.30 (m, 4H), 2.10 (s, 3H), 2.48-2.63 (m, 3H), 3.40 (d, 2H, J=7 Hz), 3.76 (s, 3H), 4.08 (appt t, 2H, J=9 Hz), 4.25-4.33 (m, 2H), 4.75-4.84 (m, 1H), 5.13 (s, 2H), 5.15-5.23 (m, 1H), 5.33-5.55 (m, 2H) ppm; $^{31}$P (121.4 MHz, CDCl$_3$) δ 28.9 ppm; MS (m/z) 725.3 [M−H]$^-$.

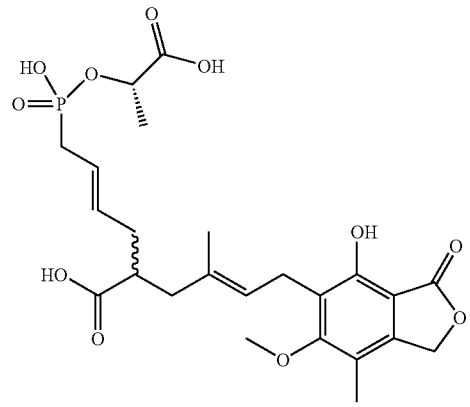

2-{4-[(1-Carboxy-ethoxy)-hydroxy-phosphoryl]-but-2-enyl}-6-(4-hydroxy-6-methoxy-7-methyl-3-oxo-1,3-dihydro-isobenzofuran-5-yl)4-methyl-hex-4-enoic acid A solution of crude 2-{4-[(1-carboxy-ethoxy)-hydroxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (AC-2101-59) and tetrabutylammonium fluoride in THF (1M, 54 μL, 0.054 mmol) was stirred with THF (1 mL) for 2 hours at ambient temperature, when more tetrabutylammonium fluoride in THF (54 μL, 0.054 mmol) was added. The reaction was stirred for an additional 16 hours, by which time the reaction was complete. The reaction mixture was concentrated in vacuo and the product was purified by RP HPLC using a Phenomenex Synergi 5μ Hydro RP 80A column (50× 21.2 mm) with eluents of H$_2$O, 0.1% TFA-CH$_3$CN, 0.1% TFA to provide the product (8.0 mg) as a clear oil. $^1$H NMR (300 MHz, CDCl$_3$) δ 1.51 (d, 3H, J=7 Hz), 1.79 (s, 3H), 2.05-2.40 (m, 4H), 2.11 (s, 3H), 2.49-2.71 (m, 3H), 3.38 (d, 2H, J=6 Hz), 3.76 (s, 3H), 4.85 (br s, 1H), 5.20 (s, 2H), 5.21-5.30 (m, 1H), 5.33-5.63 (m, 2H) ppm; $^{31}$P (121.4 MHz, CDCl$_3$) δ 27.7 ppm; MS (m/z) 525.2 [M−H]$^-$.

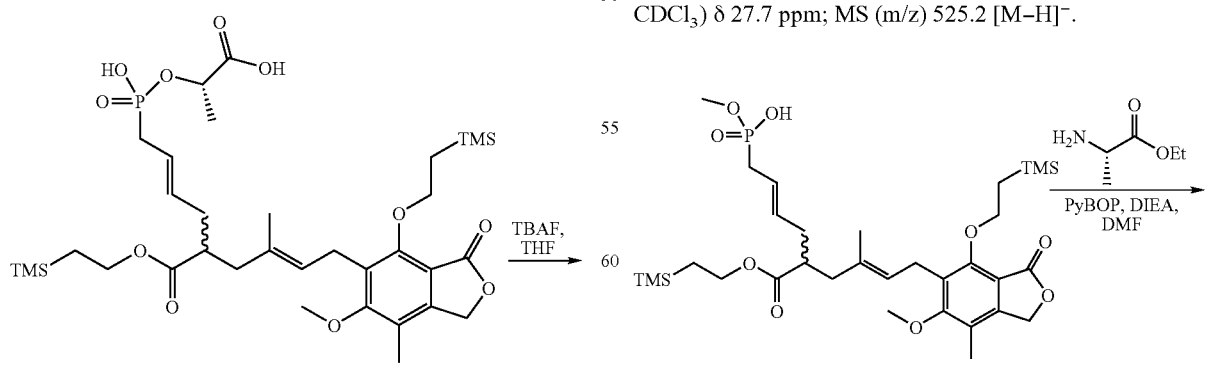

829

-continued

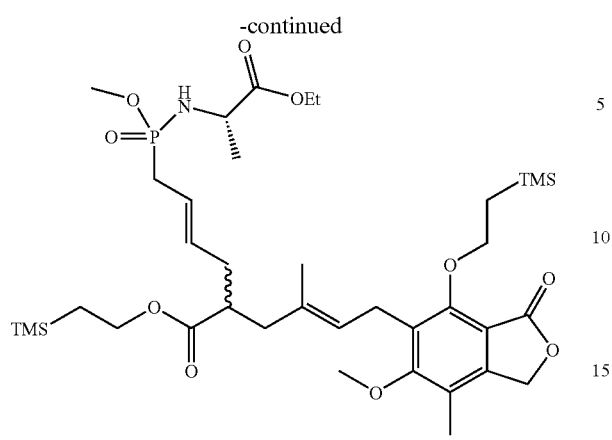

2-{4-[(1-Ethoxycarbonyl-ethylamine)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester A solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (20 mg, 0.030 mmol), PyBOP (62.4 mg, 0.120 mmol) in DMF (1.0 mL) was stirred with L-alanine ethyl ester hydrochloride (18 mg, 0.12 mmol) and DIEA (26 μL, 0.15 mmol) at ambient temperature for 1 hour, when complete consumption of the starting materials was observed. The reaction was worked up by addition of water until the reaction solution became cloudy. DMF was added dropwise until the mixture became clear again. The reaction mixture was filtered through Acrodisc (13 mm syringe filter with a 0.45 μm Nylon membrane) and purified by RP HPLC using a Phenomenex Synergi 5μ Hydro RP 80A column (50×21.2 mm), eluting with water and acetonitrile. The fractions containing the product were pooled together and concentrated in vacuo to remove the acetonitrile. The remaining solution was saturated with sodium chloride and extracted with EtOAc and acetonitrile to provide 7.2 mg of the product. $^1$H NMR (300 MHz, CDCl$_3$) δ 0.03 (s, 9H), 0.05 (s, 9H), 0.923 (appt t, 2H, J=8 Hz), 1.18-1.31 (m, 5H), 1.41 (t, 3H, J=7 Hz), 1.78 (s, 3H), 2.03-2.36 (m, 4H), 2.18 (s, 3H), 2.43-2.63 (m, 3H), 3.10-3.30 (m, 1H), 3.40 (d, 2H, J=7 Hz), 3.62 and 3.65 (d, 3H, J=11 Hz), 3.76 (s, 3H), 4.03-4.12 (m, 2H), 4.20 (dq, 2H, J=2, 7 Hz), 4.29 (appt t, 2H, J=8 Hz), 5.12 (s, 2H), 5.18-5.28 (m, 1H), 5.33-5.67 (m, 2H) ppm; $^{31}$P (121.4 MHz, CDCl$_3$) δ 30.4, 31.2 ppm; MS (m/z) 790.4 [M+Na]$^+$.

830

-continued

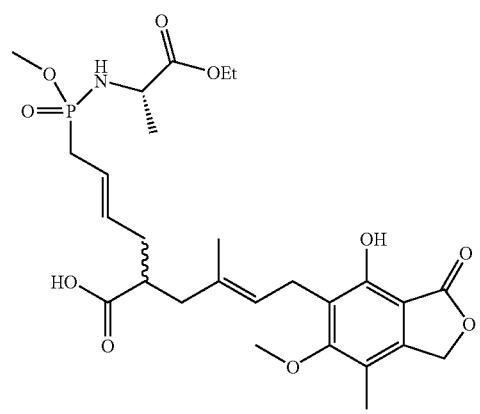

2-{4-[(1-Ethoxycarbonyl-ethylamine)-methoxy-phosphoryl]-but-2-enyl}-6 (4-hydroxy-6-methoxy-7-methyl-3-oxo-1,3-dihydro-isobenzofuran-5-yl)$_4$-methyl-hex-4-enoic acid To a solution of 2-{4-[(1-ethoxycarbonyl-ethylamine)-methoxy-phosphoryl]-but-2-enyl}-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanyl-ethyl ester (7.2 mg, 9.38 mmol) in THF (1 mL) was added TBAF (40 μL, 1M solution in THF) at room temperature. The reaction mixture was stirred for 20 minutes, when the starting material was completely converted to the desired product as judged by LCMS. The reaction mixture was dried in vacuo and re-dissolved in DMF. The product was purified by RP HPLC using a Phenomenex Synergi 5μ Hydro RP 80A column (50×21.2 mm) with eluents of H$_2$O—CH$_3$CN. The fractions containing the desired product were pooled and further purified on Dowex 50WX8-400 packed on a 4.5 cm×2 cm column to elute the sodium salt at H$_2$O-MeOH (1:1), providing 3.2 mg of the desired product. $^1$H NMR (300 MHz, CD$_3$OD) δ 1.26 (dd, 3H, J=4, 7 Hz), 1.37 (t, 3H, J=8 Hz), 1.80 (s, 3H), 2.00-2.22 (m, 4H), 2.10 (s, 3H), 2.25-2.60 (m, 3H), 3.37 (d, 2H, J=7 Hz), 3.60 and 3.65 (d, 3H, J=11 Hz), 3.74 (s, 3H), 3.83-3.96 (m, 1H), 4.18 (q, 2H, J=8 Hz), 5.15 (s, 2H), 5.25-5.42 (m, 2H), 5.55-5.69 (m, 1H) ppm; $^{31}$P (121.4 MHz, CD$_3$OD) δ 33.8, 34.2 ppm; MS (m/z) 568.2 [M+H]$^+$, 590.3 [M+Na]$^+$;

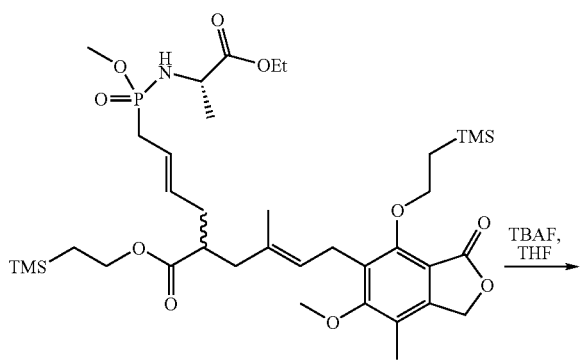

TBAF, THF →

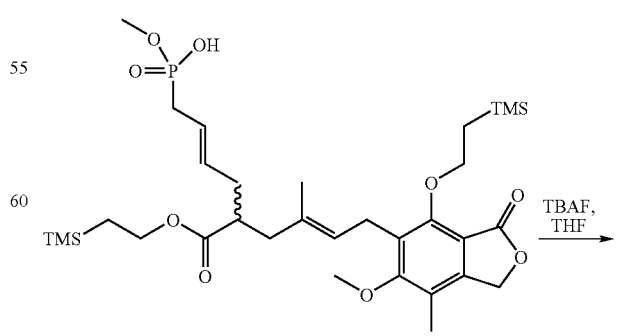

TBAF, THF →

831

-continued

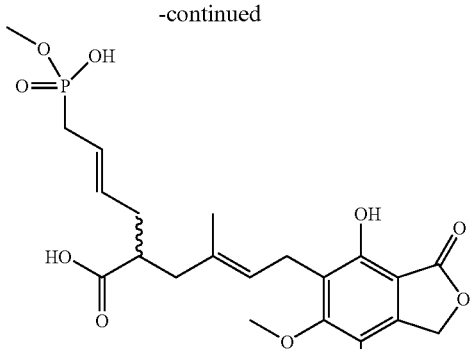

6(4-Hydroxy-6-methoxy-7-methyl-3-oxo-1,3-dihydro-isobenzofuran-5-yl)-2-[4-(hydroxy-methoxy-phosphoryl)-but-2-enyl]-4-methyl-hex-4-enoic acid To a solution of 2-[4-(hydroxy-methoxy-phosphoryl)-but-2-enyl]-6-[6-methoxy-7-methyl-3-oxo-4-(2-trimethylsilanyl-ethoxy)-1,3-dihydro-isobenzofuran-5-yl]-4-methyl-hex-4-enoic acid 2-trimethylsilanylethyl ester (11 mg, 0.016 mmol) in THF (1 mL) was added TBAF (50 µL, 1M solution in THF) at room temperature. The solution was stirred for 16 hours and concentrated. The solution was dried under reduced pressure and re-suspended in DMF (0.8 mL) and water (0.25 mL). The solution was filtered through Acrodisc (13 mm syringe filter with a 0.45 µm Nylon membrane) and purified by RP HPLC using a Phenomenex Synergi 5µ Hydro RP 80A column (50×21.2 mm) with eluents of $H_2O$, 0.1% TFA-$CH_3CN$, 0.1% TFA. The product from the column was subjected to ion exchange chromatography (Sodium salt form of Dowex 50WX8-400) using a 2×4.5 cm column eluting with $H_2O$-MeOH (1:1) to provide 7.5 mg of the desired product as an oil. $^1H$ NMR (300 MHz, $CDCl_3$) δ 1.80 (s, 3H), 2.01-2.29 (m, 5H), 2.11 (s, 3H), 2.35 (d, 2H, J=22 Hz), 3.38 (d, 2H, J=7 Hz), 3.53 (d, 3H, J=11 Hz), 3.75 (s, 3H), 5.19 (s, 2H), 5.26 (t, 1H, J=6 Hz), 5.43-5.54 (m, 2H) ppm; $^{31}P$ (121.4 MHz, $CDCl_3$) δ 23.5 ppm; MS (m/z) 469.2 $[M+H]^+$, 491.3 $[M+Na]^+$.

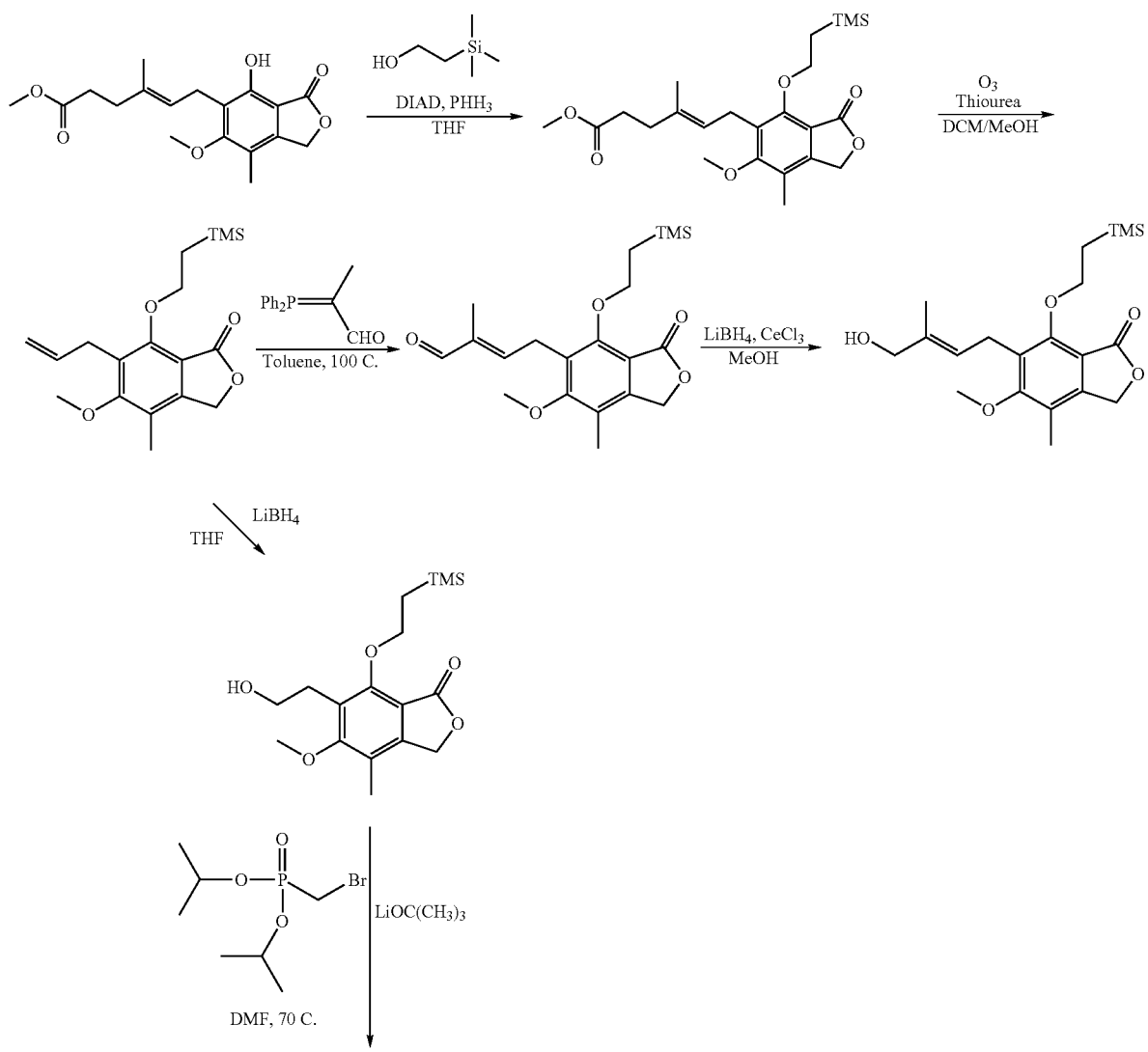

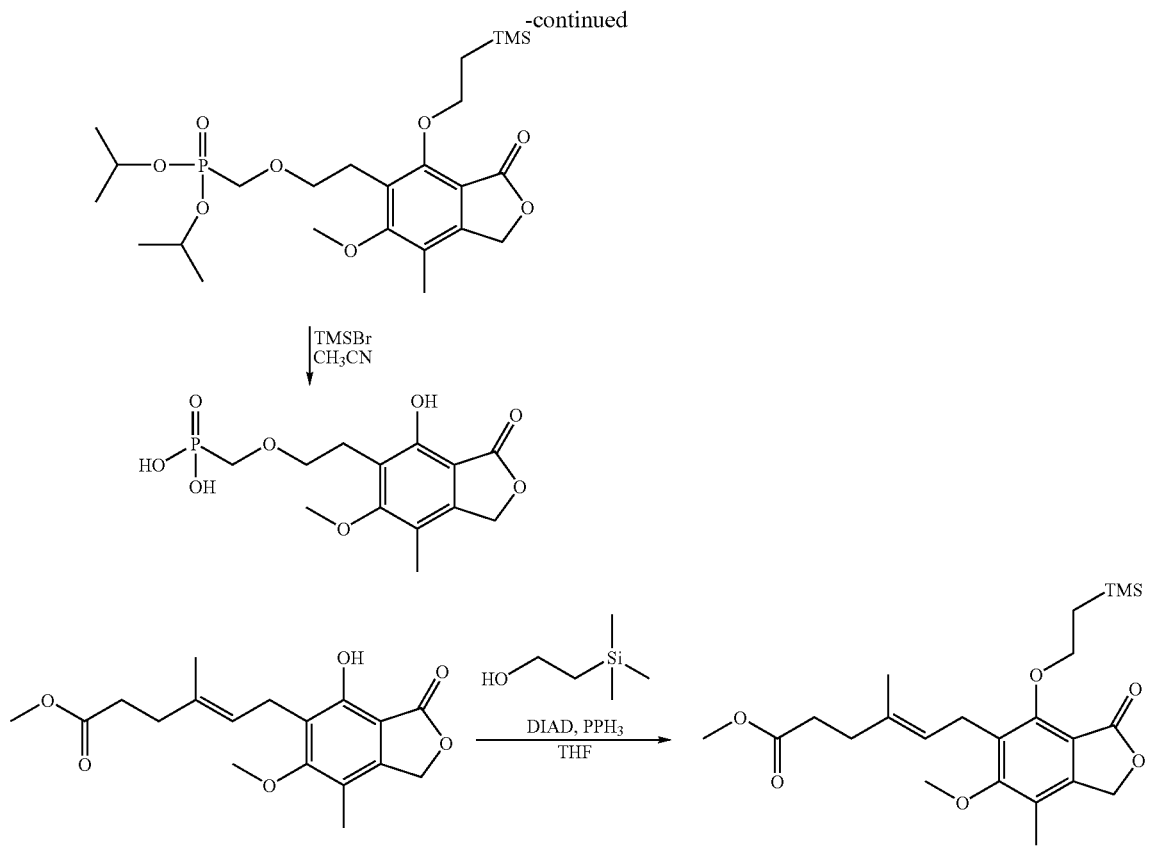

6-[6-Methoxy-7-methyl-3-oxo-4-(2-trimethylsilanyl-ethoxy)-1,3-dihydro-isobenzofuran-5-yl]4-methyl-hex-4-enoic acid methyl ester To a solution of 6-(4-hydroxy-6-methoxy-7-methyl-3-oxo-1,3-dihydro-isobenzofuran-5-yl)-4-methyl-hex-4-enoic acid methyl ester (222 mg, 0.66 mmol), triphenylphosphine (260 mg, 0.996 mmol), and diethyl azodicarboxylate (173 mg, 0.996 mmol) in THF (3 mL) at 0° C. was added a solution of 2-trimethylsilylethanol (142 µL, 0.996 mmol) in THF (3 mL). The resulting yellow solution was allowed to warm to room temperature and stirred overnight. The reaction was concentrated to dryness and ether and hexanes were added. Triphenylphosphine oxide was removed by filtration and the filtrate was concentrated and purified by silica gel chromatography to provide 248 mg of the desired product as a colorless oil. $^1$H NMR (300 MHz, CDCl$_3$) δ 0.03 (s, 9H), 1.18-1.30 (m, 2H), 1.81 (s, 3H), 2.18 (s, 3H), 2.25-2.33 (m, 2H), 2.37-2.45 (m, 2H), 3.42 (d, 2H, J=7 Hz), 3.62 (s, 3H), 3.77 (s, 3H), 4.25-4.35 (m, 2H), 5.13 (s, 2H), 5.12-5.22 (m, 1H) ppm.

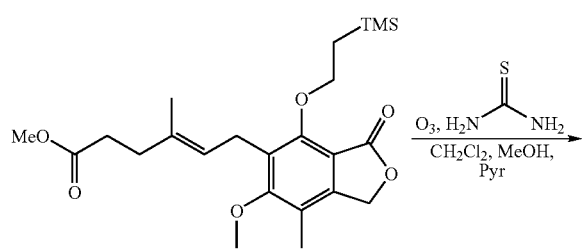

[6-Methoxy-7-methyl-3-oxo-4-(2-trimethylsilanyl-ethoxy)-1,3-dihydro-isobenzofuran-5-yl]-acetaldehyde A solution of 6-[6-methoxy-7-methyl-3-oxo-4-(2-trimethylsilanyl-ethoxy)-1,3-dihydro-isobenzofuran-5-yl]-4-methyl-hex-4-enoic acid methyl ester (618 mg, 1.42 mmol) in MeOH (10 mL), CH$_2$Cl$_2$ (10 mL) and pyridine (50 µL, 0.618 mmol) was cooled to −70° C. using a dry ice/acetone bath according to the procedure of Smith, D. B. et al., *J. Org. Chem.*, 1996, 61, 6, 2236. A stream of ozone was bubbled through the reaction via a gas dispersion tube until the reaction became blue in color (15 minutes). The ozone line was replaced with a stream of nitrogen and bubbling continued for another 15 minutes, by which time the blue color had disappeared. To this solution, thiourea (75.7 mg, 0.994 mmol) was added in one portion at −70° C., and the cooling bath was removed. The reaction was allowed to warm to room temperature and stirred for 15 hours. The reaction was worked up by filtration to remove solid thiourea S-dioxide, and then partitioned between CH$_2$Cl$_2$ and water. The organic layer was removed. The aqueous layer was washed with CH$_2$Cl$_2$ one more time, and the organic extracts were combined. The organic layer was washed with aqueous 1N HCl, saturated NaHCO$_3$ and brine. The organic extracts were dried in vacuo and the residue was purified to by silica gel chromatography to afford 357 mg (75%) of the product as a white solid. $^1$H NMR (300 MHz, CDCl$_3$) δ −0.01 (s, 9H), 1.05-1.15 (m, 2H), 2.15 (s, 3H), 3.69 (s, 3H), 3.78 (d, 2H, J=1 Hz), 4.27-4.39 (m, 2H), 5.11 (s, 2H), 9.72 (d, 1H, J=1 Hz) ppm.

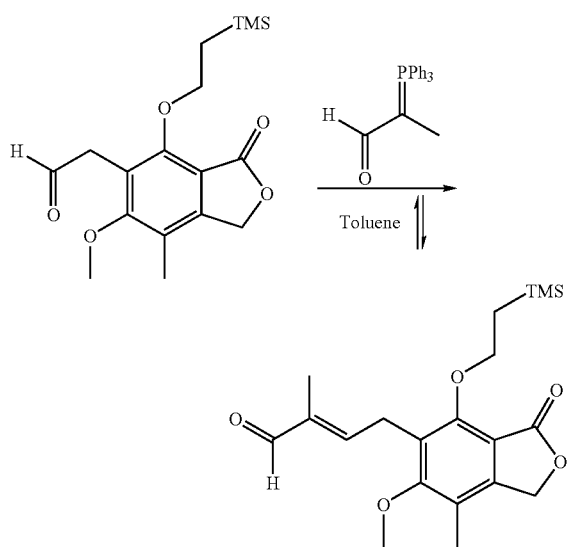

4-[6-Methoxy-7-methyl-3-oxo-4-(2-trimethylsilanyl-ethoxy)-1,3-dihydro-isobenzofuran-5-yl]-2-methyl-but-2-enal

[6-Methoxy-7-methyl-3-oxo-4-(2-trimethylsilanyl-ethoxy)-1,3-dihydro-isobenzofuran-5-yl]-acetaldehyde (70 mg, 0.21 mmol) in toluene (2 mL) was heated at 100° C. with 2-(triphenyl-phosphanylidene)-propionaldehyde (72.9 mg, 0.23 mmol) overnight. A second portion of 2-(triphenyl-phosphanylidene)-propionaldehyde (33 mg, 0.11 mmol) was added and the reaction mixture was heated for an additional day. After concentration, the residue was purified by silica gel chromatography to provide 54 mg (83%) of the desired product as a pale yellow oil. $^1$H NMR (300 MHz, CDCl$_3$) δ 0.00 (S, 9H), 1.10-1.21 (m, 2H), 1.87 (s, 3H), 2.16 (s, 3H), 3.67-3.76 (m, 2H), 3.74 (s, 3H), 4.27-4.39 (m, 2H), 5.11 (s, 2H), 6.40-6.48 (m, 1H), 9.2 (s, 1H) ppm.

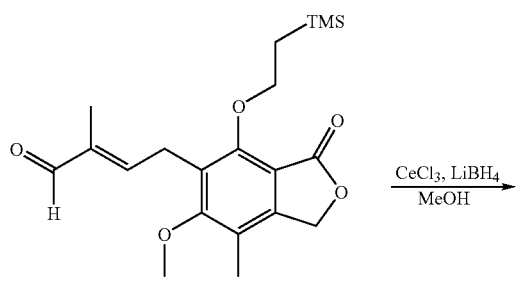

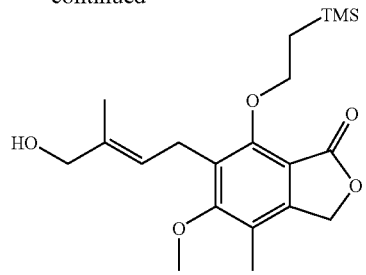

6-(4-Hydroxy-3-methyl-but-2-enyl)-5-methoxy-4-methyl-7-(2-trimethylsilanyl-ethoxy)3H-isobenzofuran-1-one A solution of 4-[6-methoxy-7-methyl-3-oxo-4-(2-trimethylsilanyl-ethoxy)-1,3-dihydro-isobenzofuran-5-yl]-2-methyl-but-2-enal (103 mg, 0.27 mmol) in methanol (5 mL) was cooled to 0° C. A solution of CeCl$_3$ (0.68 mL, MeOH:H$_2$O, 9:1) was added, followed by LiBH$_4$ (0.14 mL, 0.28 mmol of a 2M solution in THF). The ice bath was removed and the reaction mixture was allowed to warm to room temperature. The reaction mixture was stirred for an additional 40 minutes whereupon TLC indicated complete consumption of starting aldehyde. The reaction was worked up by addition of aqueous 1N HCl (0.5 mL) and the product was extracted with CH$_2$Cl$_2$. The organic layer was washed with saturated aqueous sodium bicarbonate solution and brine. The organic layer was concentrated under reduced pressure and the residue was purified by silica gel chromatography to provide 100 mg (97%) of the product as a clear liquid. $^1$H NMR (300 MHz, CDCl$_3$) δ 0.00 (s, 9H), 1.20 (dd, 2H, J=7, 8 Hz), 1.81 (s, 3H), 2.13 (s, 3H), 3.38-3.50 (m, 2H), 3.74 (s, 3H), 3.95 (s, 2H), 4.27 (dd, 2H, J=7, 8 Hz), 5.08 (s, 2H), 5.17-5.44 (m, 1H) ppm.

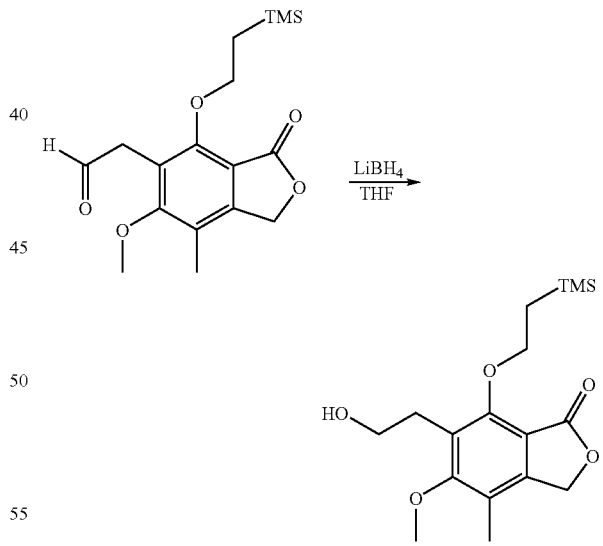

6-(2-Hydroxy-ethyl)-5-methoxy-4-methyl-7-(2-trimethylsilanyl-ethoxy)-3H-isobenzofuran-1-one To a solution of [6-methoxy-7-methyl-3-oxo-4-(2-trimethylsilanyl-ethoxy)-1,3-dihydro-isobenzofuran-5-yl]-acetaldehyde (97 mg, 0.29 mmol) in THF (5 mL) was added an aliquot of a 2 M LiBH$_4$ in THF (150 μL, 0.300 mmol). The reaction mixture was stirred at room temperature for 1 hour when complete consumption of the starting materials was observed by TLC. The reaction mixture was worked up by addition of an aqueous 1N HCl solution and extraction with EtOAc. The organic layer was dried in vacuo and the residue was purified by silica gel chromatography to provide the product. $^1$H NMR (300 MHz, CDCl$_3$) δ 0.00 (s, 9H), 1.20 (dd, 2H, J=7, 9 Hz), 2.07 (br s, 1H), 2.14 (s, 3H), 2.97 (t, 2H, J=6 Hz), 3.76 (t, 2H, J=6 Hz), 3.77 (s, 3H), 4.32 (dd, 2H, J=7, 8 Hz), 5.08 (s, 2H) ppm.

EXAMPLE 255

Preparation of Representative Compounds of the Invention

Representative compounds of the invention can be prepared as illustrated below.

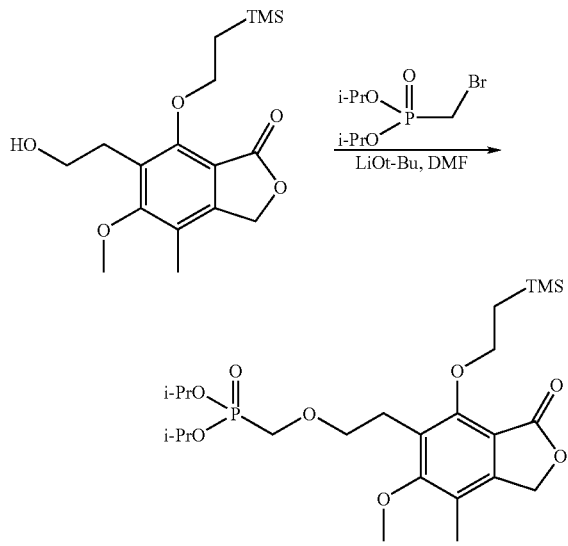

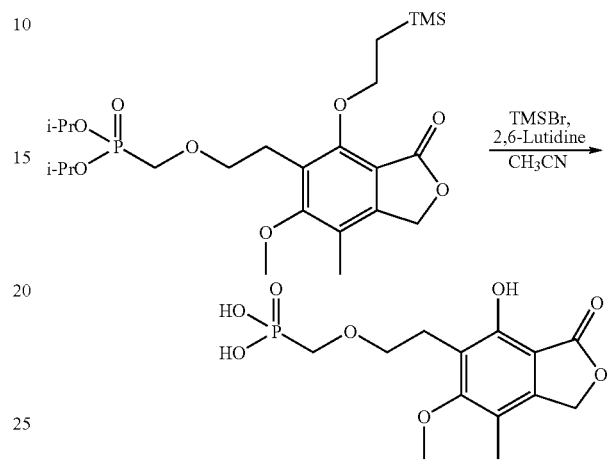

{2-[6-Methoxy-7-methyl-3-oxo-4-(2-trimethylsilanyl-ethoxy)-1,3-dihydro-isobenzofuran-5-yl]-ethoxymethyl}-phosphonic acid diisopropyl ester A mixture of 6-(2-hydroxy-ethyl)-5-methoxy-4-methyl-7-(2-trimethylsilanyl-ethoxy)-3H-isobenzofuran-1-one (79 mg, 0.23 mmol) was heated with bromomethylphosphonic acid diisopropyl ester (120 mg, 0.46 mmol) in the presence of lithium t-butoxide (22 mg, 0.27 mmol) in DMF (2 mL) at 70° C. overnight. The reaction mixture was purified by RP HPLC (acetonitrile and 0.1% aqueous CF$_3$COOH) to provide the desired product. $^1$H NMR (300 MHz, CDCl$_3$) δ 0.00 (s, 9H), 1.13-1.25 (m, 2H), 1.26 (t, 12H, J=6 Hz), 2.12 (s, 3H), 2.98 (t, 2H, J=7 Hz), 3.60-3.73 (m, 4H), 3.77 (s, 3H), 4.05-4.16 (m, 2H), 4.62-4.74 (m, 2H), 5.07 (s, 2H) ppm; MS (m/z) 539 [M+Na]$^+$.

[2-(4-Hydroxy-6-methoxy-7-methyl-3-oxo-1,3-dihydro-isobenzofuran-5-yl)-ethoxymethyl]-phosphonic acid To a solution of {2-[6-methoxy-7-methyl-3-oxo-4-(2-trimethylsilanyl-ethoxy)-1,3-dihydro-isobenzofuran-5-yl]-ethoxymethyl}-phosphonic acid diisopropyl ester (7.5 mg, 0.014 mmol) in acetonitrile (2 mL) and 2,6-lutidine (25 μL, 0.21 mmol) was added trimethylsilyl bromide (27 μL, 0.21 mmol) at room temperature. The reaction was allowed to proceed for 18 hours when completion of the reaction was indicated by LCMS. The reaction was quenched by addition of MeOH and concentration. The residue was purified by RP-HPLC using a C18 column. The collected product was dissolved in a solution of 10% TFA/CH$_2$Cl$_2$ to assure complete deprotection. The reaction mixture was lyophilized to provide the desired product. $^1$H NMR (300 MHz, CD$_3$OD) δ 2.12 (s, 3H), 2.98 (t, 2H, J=7 Hz), 3.66-3.76 (m, 4H), 3.78 (s, 3H), 5.21 (s, 2H) ppm; MS (m/z) 331 [M−H]$^-$.

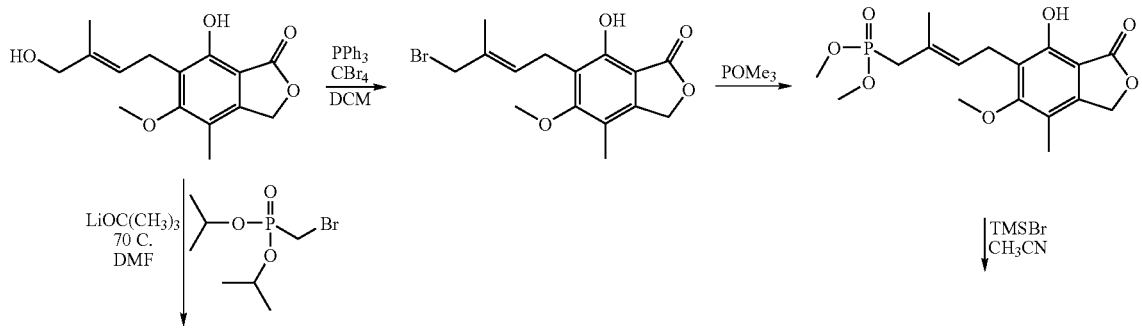

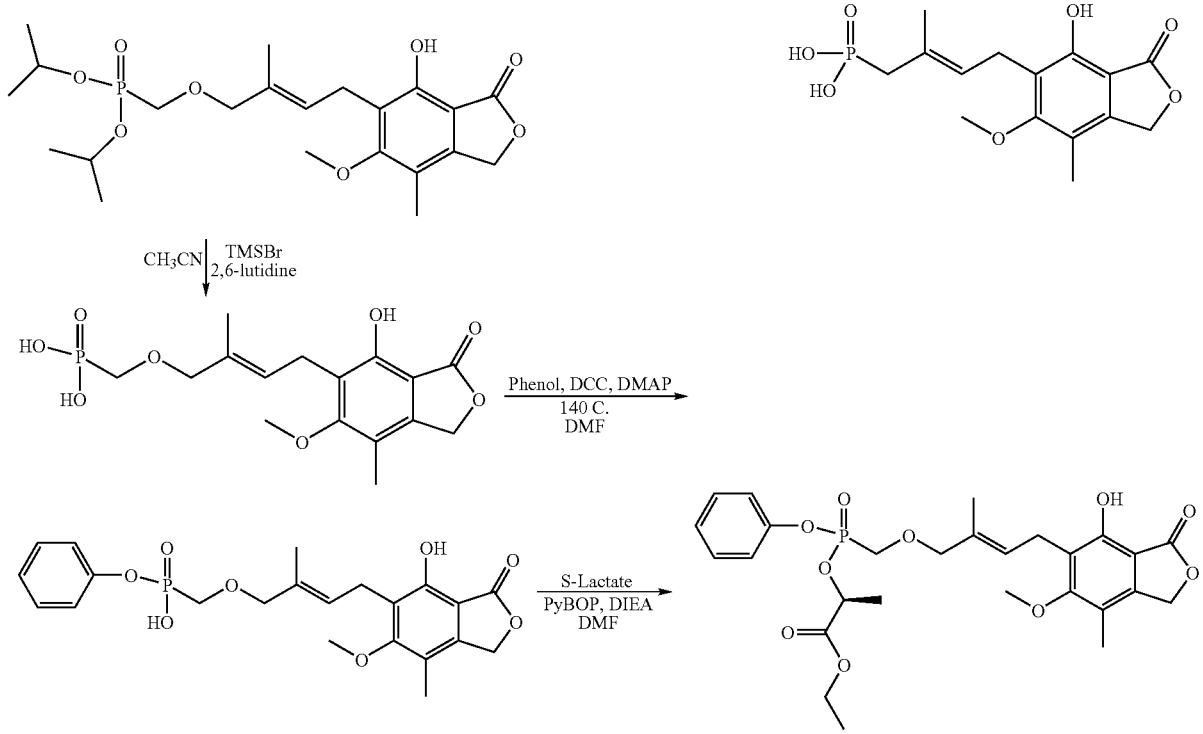

EXAMPLE 256

Preparation of Representative Compounds of the Invention

Representative compounds of the invention can be prepared as illustrated below.

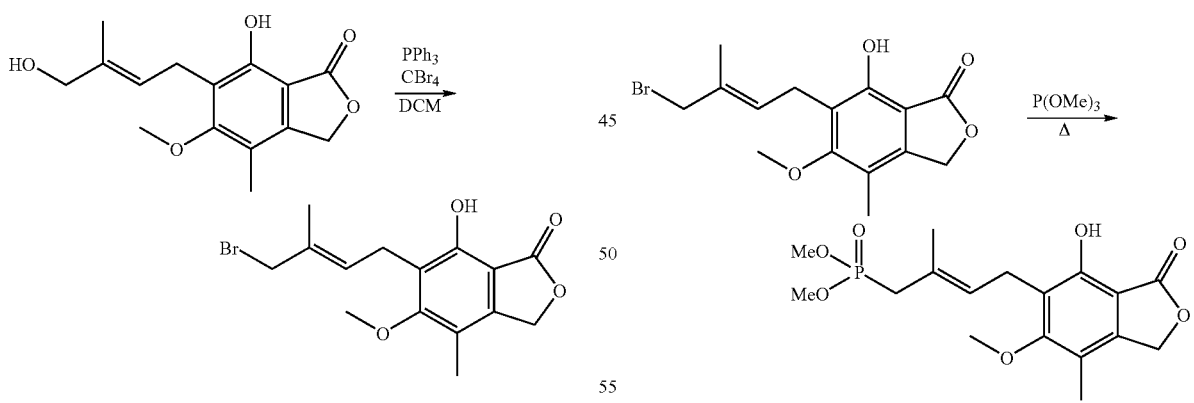

6-(4-Bromo-3-methyl-but-2-enyl)-7-hydroxy-5-methoxy-4-methyl-3H-isobenzofuran-1-one Polymer-supported triphenylphosphine (3 mmol/g, 0.5 g) was soaked in dichloromethane (10 mL) for 1 hour 7-Hydroxy-6-(4-hydroxy-3-methyl-but-2-enyl)-5-methoxy-4-methyl-3H-isobenzofuran-1-one (100 mg, 0.36 mmol) and carbon tetrabromide (143 mg, 0.43 mmol) were added sequentially and the mixture was shaken for 1 hour at room temperature. More carbon tetrabromide (143 mg, 0.43 mmol) was added and the mixture was shaken further for 1 hour The mixture was filtered and the filtrate was concentrated. The residue was chromatographed on silica gel (0% to 60% ethyl acetate/hexanes) to afford 6-(4-bromo-3-methyl-but-2-enyl)-7-hydroxy-5-methoxy-4-methyl-3H-isobenzofuran-1-one as an oil (52 mg, 42%); $^1$H NMR (300 MHz, CDCl$_3$) δ 1.95 (s, 3H), 2.16 (s, 3H), 3.44 (d, J=7.2, 2H), 3.78 (s, 3H), 3.98 (s, 2H), 5.21 (s, 2H), 5.68 (t, J=7.2 Hz, 1H), 7.71 (brs, 1H) ppm.

[4-(4-Hydroxy-6-methoxy-7-methyl-3-oxo-1,3-dihydro-isobenzofuran-5-yl)-2-methyl-but-2-enyl]-phosphonic acid dimethyl ester A solution of 6-(4-bromo-3-methyl-but-2-enyl)-7-hydroxy-5-methoxy-4-methyl-3H-isobenzofuran-1-one (33 mg, 0.097 mmol) in trimethylphosphite (1.0 mL, 8.5 mmol) was heated to 100° C. for 1 hour, whereupon complete reaction was indicated by LCMS. The reaction was worked up by removal of the excess reagent under reduced pressure and the residue was purified by silica gel chromatography using EtOAc-hexanes (20-100%) to provide 20 mg (60%) of the desired product. $^1$H NMR (300 MHz, CDCl$_3$) δ 1.90 (s, 3H), 2.09 (s, 3H), 2.48 (d, 2H, J=22 Hz), 3.38 (t, 2H, J=6 Hz), 3.64 (d, 6H, J=11 Hz), 3.72 (s, 3H), 5.14 (s, 2H), 5.33 (q, 1H, J=6 Hz), 7.65 (br s, 1H) ppm; MS (m/z) 371 [M+H]$^+$.

EXAMPLE 257

Preparation of Representative Compounds of the Invention

Representative compounds of the invention can be prepared as illustrated below.

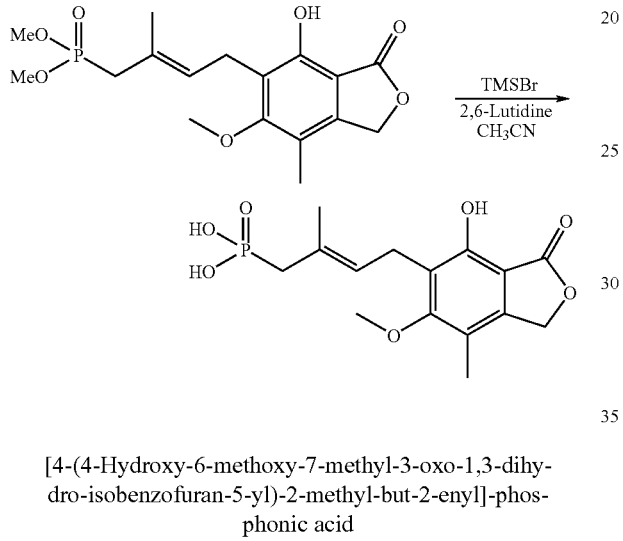

[4-(4-Hydroxy-6-methoxy-7-methyl-3-oxo-1,3-dihydro-isobenzofuran-5-yl)-2-methyl-but-2-enyl]-phosphonic acid To a solution of [4-(4-hydroxy-6-methoxy-7-methyl-3-oxo-1,3-dihydro-isobenzofuran-5-yl)-2-methyl-but-2-enyl]-phosphonic acid dimethyl ester (18 mg, 0.049 mmol) in acetonitrile (2 mL) was added TMSBr (63 µL, 0.49 mmol) and 2,6-lutidine (85 µL, 0.73 mmol) at 0° C. The reaction solution was allowed to warm to room temperature and stirred for 2 hours when completion of the reaction was observed by LCMS. The reaction was cooled to 0° C. and quenched by the addition of MeOH. The reaction mixture was concentrated under reduced pressure and the residue was purified by RP HPLC using a C18 column with a gradient of H$_2$O-acetonitrile (5-0%) over 20 minutes to provide 12.2 mg (73%) of the product. $^1$H NMR (300 MHz, CD$_3$OD) δ 1.95 (s, 3H), 2.15 (s, 3H), 2.48 (d, 2H, J=22 Hz), 3.44 (t, 2H, J=6 Hz), 3.79 (s, 3H), 5.24 (s, 2H), 5.38 (q, 1H, J=7 Hz), 6.87 (br s, 1H) ppm; MS (m/z) 341 [M–H]$^-$.

EXAMPLE 258

Preparation of Representative Compounds of the Invention

Representative compounds of the invention can be prepared as illustrated below.

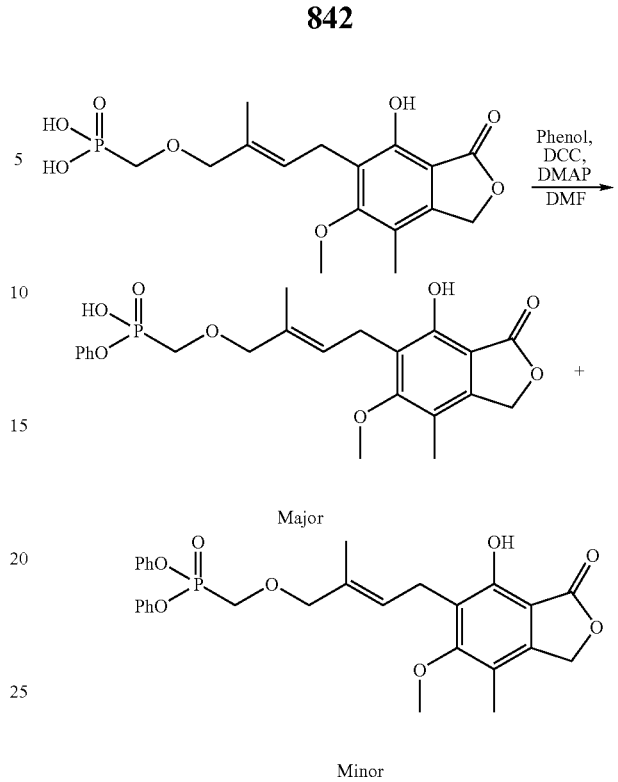

[4-(4-Hydroxy-6-methoxy-7-methyl-3-oxo-1,3-dihydro-isobenzofuran-5-yl)-2-methyl-but-2-enyloxymethyl]-phosphonic acid monophenyl ester and [4-(4-Hydroxy-6-methoxy-7-methyl-3-oxo-1,3-dihydro-isobenzofuran-5-yl)-2-methyl-but-2-enyloxymethyl]-phosphonic acid diphenyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid (49 mg, 0.13 mmol) in DMF (0.4 mL) and phenol (62 mg, 0.65 mmol) was added dicyclohexyl carbodiimide (107 mg, 0.52 mmol) and DMAP (8 mg, 0.065 mmol) in DMF (0.6 mL), slowly at 0° C. The reaction was allowed to warm to room temperature and heated to 140° C. for 10 hours. After cooling to room temperature the mixture was filtered and extracted with aqueous 1N NaOH solution. The aqueous layer was acidified with aqueous 1N HCl and extracted with EtOAc. The organic layer was dried over Na$_2$SO$_4$ and concentrated to dryness. The residue was purified by RP HPLC to provide 18.5 mg of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (major product, Example 8) as a pale yellow solid and 4.1 mg of [4-(4-hydroxy-6-methoxy-7-methyl-3-oxo-1,3-dihydro-isobenzofuran-5-yl)-2-methyl-but-2-enyloxymethyl]-phosphonic acid diphenyl ester (minor product) also as a pale yellow solid. Major product: $^1$H NMR (300 MHz, CD$_3$OD) δ 1.82 (s, 3H), 2.16 (s, 3H), 3.46 (d, 2H, J=7 Hz), 3.70 (d, 2H, J=8 Hz), 3.77 (s, 3H), 3.96 (s, 2H), 5.25 (s, 2H), 5.52 (t, 1H, J=8 Hz), 7.10-7.21 (m, 3H), 7.30 (t, 2H, J=8 Hz) ppm; $^{31}$P (121.4 MHz, CD$_3$OD) δ 17.3 ppm; MS (m/z) 449.0 [M+H]$^+$, 471.2 [M+Na]$^+$. Minor product: $^1$H NMR (300 MHz, CD$_3$OD) δ 1.82 (s, 3H), 2.15 (s, 3H), 3.47 (d, 2H, J=7 Hz), 3.77 (s, 3H), 3.98-4.06 (m, 4H), 5.25 (s, 2H), 5.50-5.61 (m, 1H), 7.10-7.25 (m, 6H), 7.30-7.41 (m, 4H) ppm; $^{31}$P (121.4 MHz, CD$_3$OD) δ 16.3 ppm; MS (m/z) 525.2 [M+H]$^+$, 547.2 [M+Na]$^+$.

EXAMPLE 259

Preparation of Representative Compounds of the Invention

Representative compounds of the invention can be prepared as illustrated below.

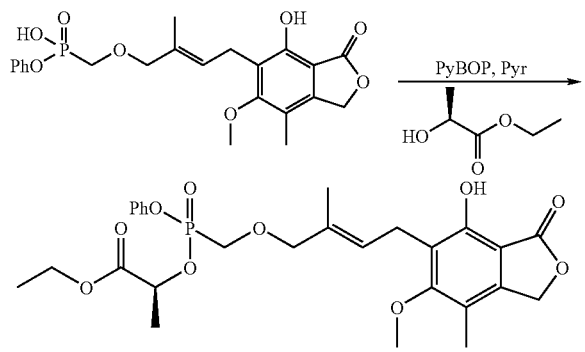

2-{[4-(4-Hydroxy-6-methoxy-7-methyl-3-oxo-1,3-dihydro-isobenzofuran-5-yl)-2-methyl-but-2-enyloxymethyl]-phenoxy-phosphinoyloxy}-propionic acid ethyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (18.5 mg, 0.040 mmol) and ethyl (S)-(−)-lactate (47 μL, 0.400 mmol) in pyridine (0.5 mL) was added PyBOP (32 mg, 0.060 mmol). The solution was stirred at room temperature for 1 hour, when an additional portion of PyBOP (21 mg, 0.040 mmol) was added. The solution was stirred for another hour and concentrated. The residue was purified by HPLC to provide 7.5 mg of the desired product as a clear oil. $^1$H NMR (300 MHz, CD$_3$OD) δ 1.22 and 1.25 (t, 3H, J=7 Hz), 1.42 and 1.50 (d, 3H, J=7 Hz), 1.82 and 1.83 (s, 3H), 2.16 (s, 3H), 3.47 (d, 2H, J=7 Hz), 3.78 (s, 3H), 3.89 (d, 1H, J=8 Hz), 3.93-4.02 (m, 3H), 4.10-4.22 (m, 2H), 4.94-5.08 (m, 1H), 5.25 (s, 2H), 5.50-5.60 (m, 1H), 7.15-7.27 (m, 3H), 7.33-7.41 (m, 2H) ppm; $^{31}$P (121.4 MHz, CD$_3$OD) δ 18.9, 20.3 ppm (diastereomers at phosphorus); MS (m/z) 549.2 [M+H]$^+$, 571.3 [M+Na]$^+$.

EXAMPLE 260

Preparation of Representative Compounds of the Invention

Representative compounds of the invention can be prepared as illustrated below.

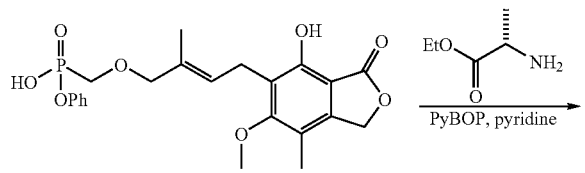

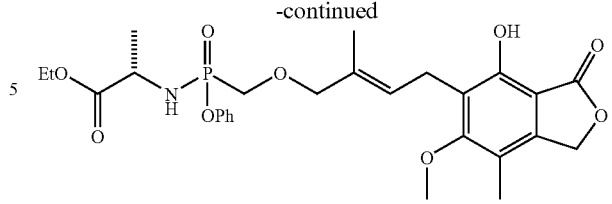

2-{[4-(4-Hydroxy-6-methoxy-7-methyl-3-oxo-1,3-dihydro-isobenzofuran-5-yl)-2-methyl-but-2-enyloxymethyl]-phenoxy-phosphinoylamino}-propionic acid ethyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid monophenyl ester (20 mg, 0.045 mmol) and L-alanine ethyl ester hydrochloride (68.5 mg, 0.45 mmol) in pyridine (1.0 mL) was added PyBOP (70 mg, 0.114 mmol). After stirring overnight, the mixture was concentrated and the residue purified by RP HPLC using a C18 column with a gradient of H$_2$O, 0.1% TFA-acetonitrile, 0.1% TFA to provide 3.6 mg of the product as a colorless gel. $^1$H NMR (300 MHz, CD$_3$OD) δ 1.17-1.3 (m, 6H), 1.8-1.9 (m, 3H), 2.16 (s, 3H), 3.17 (m, 1H), 3.47 (d, 2H), 3.72-3.8 (m, 5H), 3.92-4.2 (m, 4H), 5.25 (s, 2H), 5.54 (m, 1H), 7.18 (m, 3H), 7.33 (m, 2H) ppm; $^{31}$P (121.4 MHz, CD$_3$OD) δ 24.1, 25.0 ppm (diastereomers at phosphorus); MS (m/z) 546.2 [M−H]$^+$.

EXAMPLE 261

Preparation of Representative Compounds of the Invention

Representative compounds of the invention can be prepared as illustrated below.

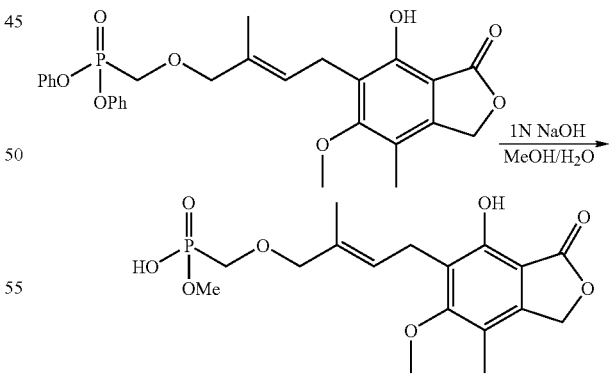

[4-(4-Hydroxy-6-methoxy-7-methyl-3-oxo-1,3-dihydro-isobenzofuran-5-yl)-2-methyl-but-2-enyloxymethyl]-phosphonic acid monomethyl ester To a solution of [4-(4-hydroxy-6-methoxy-7-methyl-3-oxo-1,3-dihydro-isobenzofuran-5-yl)-2-methyl-but-2-enyloxymethyl]-phosphonic acid diphenyl ester (53 mg, 0.1 mmol) in methanol (0.5 mL) was added an aqueous solution of 1N NaOH (300 µL). After stirring overnight, the mixture was concentrated and the residue purified by RP HPLC using a C18 column with a gradient of H$_2$O, 0.1% TFA-acetonitrile, 0.1% TFA to provide 5 mg of the product as a colorless gel, together with the phosphonic acid monophenyl ester (7 mg) and the phosphonic acid dimethyl ester (14.5 mg). $^1$H NMR (300 MHz, CD$_3$OD) δ 1.84 (s, 3H), 2.16 (s, 3H), 3.47 (d, 2H, J=7 Hz), 3.6 (d, 2H, J=12 Hz), 3.75 (d, 3H, J=11 Hz), 3.79 (s, 3H), 3.94 (s, 2H), 5.26 (s, 2H), 5.53 (t, 1H, J=7 Hz) ppm; $^{31}$P (121.4 MHz, CD$_3$OD) δ 21.5 ppm; MS (m/z) 385.2 [M−H]$^+$, 387.1 [M+H]$^+$.

room temperature. The solution was stirred for 2 days when it was quenched by addition of saturated aqueous sodium bicarbonate solution and EtOAc. The organic layer was separated and concentrated under reduced pressure. The residue was purified by RP HPLC using a C18 column with a gradient of H$_2$O, 0.1% TFA-acetonitrile, 0.1% TFA to provide 115 mg (96%) of the product as an oil. $^1$H NMR (300 MHz, CDCl$_3$) δ 0.04 (s, 9H), 1.16-1.27 (m, 2H), 1.34 (t, 6H, J=7 Hz), 1.94 (s, 3H), 2.18 (s, 3H), 2.20-2.31 (m, 2H), 3.13-3.31 (m, 2H), 3.48 (d, 2H, J=7 Hz), 3.54 (s, 2H), 3.78 (s, 3H), 4.14 (pent, 4H, J=7 Hz), 4.30-4.37 (m, 2H), 5.13 (s, 2H), 5.65 (t, 1H, J=7 Hz), 6.23 (br s, 2H) ppm; $^{31}$P (121.4 MHz, CDCl$_3$) δ 27.8 ppm; MS (m/z) 542.3 [M+H]$^+$, 564.2 [M+Na]$^+$.

EXAMPLE 262

Preparation of Representative Compounds of the Invention

Representative compounds of the invention can be prepared as illustrated below.

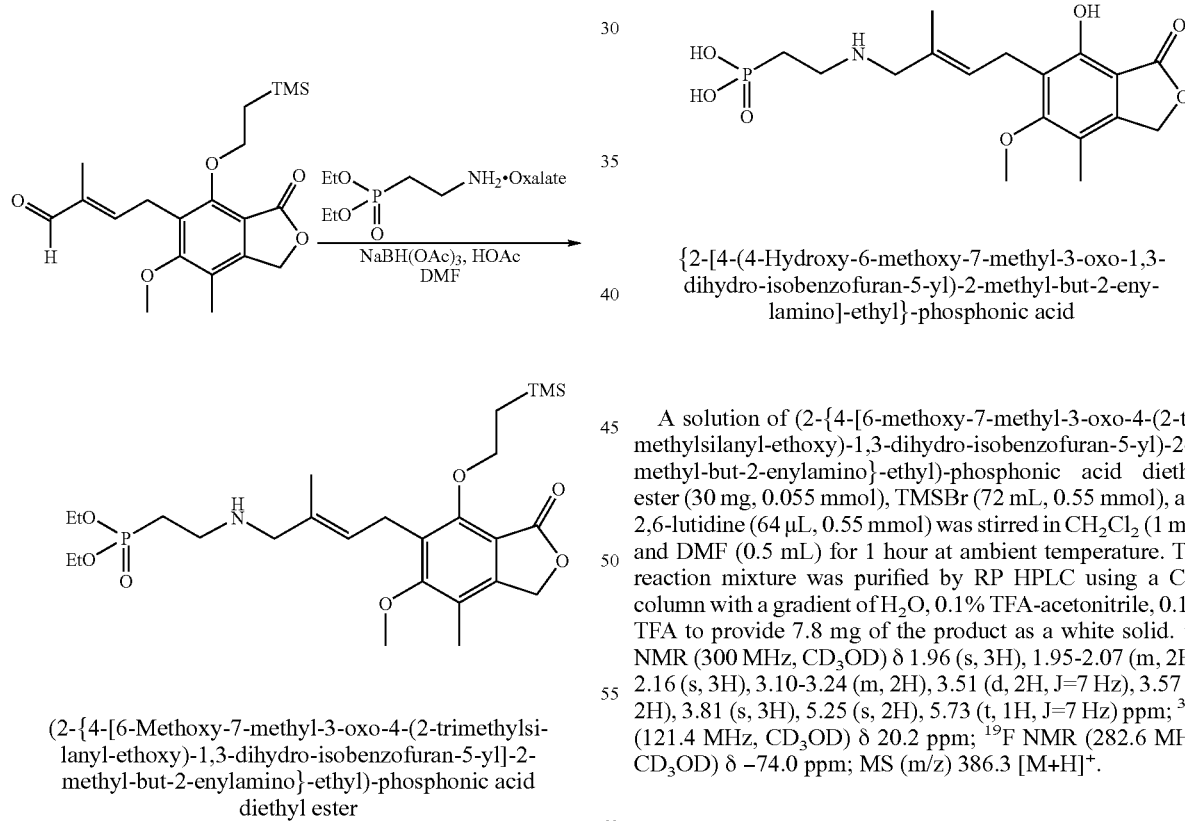

(2-{4-[6-Methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester To a solution of 4-[6-methoxy-7-methyl-3-oxo-4-(2-trimethylsilanyl-ethoxy)-1,3-dihydro-isobenzofuran-5-yl]-2-methyl-but-2-enal (84 mg, 0.22 mmol), (2-amino-ethyl)-phosphonic acid diethyl ester oxalate (91 mg, 0.33 mmol), and sodium triacetoxyborohydride (93 mg, 0.44 mmol) in DMF (1.5 mL) was added acetic acid (60 µL, 1.0 mmol) at {2-[4-(4-Hydroxy-6-methoxy-7-methyl-3-oxo-1,3-dihydro-isobenzofuran-5-yl)-2-methyl-but-2-enylamino]-ethyl}-phosphonic acid A solution of (2-{4-[6-methoxy-7-methyl-3-oxo-4-(2-trimethylsilanyl-ethoxy)-1,3-dihydro-isobenzofuran-5-yl)-2-methyl-but-2-enylamino}-ethyl)-phosphonic acid diethyl ester (30 mg, 0.055 mmol), TMSBr (72 mL, 0.55 mmol), and 2,6-lutidine (64 µL, 0.55 mmol) was stirred in CH$_2$Cl$_2$ (1 mL) and DMF (0.5 mL) for 1 hour at ambient temperature. The reaction mixture was purified by RP HPLC using a C18 column with a gradient of H$_2$O, 0.1% TFA-acetonitrile, 0.1% TFA to provide 7.8 mg of the product as a white solid. $^1$H NMR (300 MHz, CD$_3$OD) δ 1.96 (s, 3H), 1.95-2.07 (m, 2H), 2.16 (s, 3H), 3.10-3.24 (m, 2H), 3.51 (d, 2H, J=7 Hz), 3.57 (s, 2H), 3.81 (s, 3H), 5.25 (s, 2H), 5.73 (t, 1H, J=7 Hz) ppm; $^{31}$P (121.4 MHz, CD$_3$OD) δ 20.2 ppm; $^{19}$F NMR (282.6 MHz, CD$_3$OD) δ −74.0 ppm; MS (m/z) 386.3 [M+H]$^+$.

EXAMPLE 263

Preparation of Representative Compounds of the Invention

Representative compounds of the invention can be prepared as illustrated below.

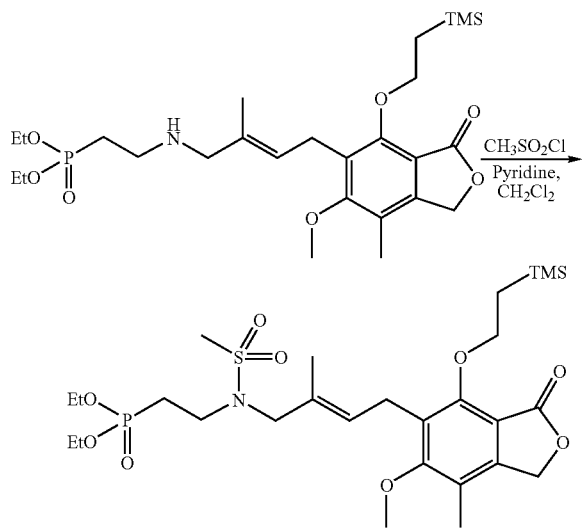

[2-(Methanesulfonyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (45 mg, 0.092 mmol) in CH$_2$Cl$_2$ (0.5 mL) was stirred with methanesulfonyl chloride (21 µL, 0.28 mmol) and pyridine (45 µL, 0.55 mmol) at ambient temperature overnight. The reaction was quenched by addition of 2 drops of water. The reaction mixture was concentrated and purified by RP HPLC using a C18 column with a gradient of H$_2$O, 0.1% TFA-acetonitrile, 0.1% TFA to provide 36 mg of the product (63%) as a clear gel. $^1$H NMR (300 MHz, CDCl$_3$) δ 0.05 (s, 9H), 1.18-1.29 (m, 2H), 1.29 (t, 6H, J=7 Hz), 1.85 (s, 3H), 2.00-2.13 (m, 2H), 2.19 (s, 3H), 2.85 (s, 3H), 3.32-3.43 (m, 2H), 3.47 (d, 2H, J=7 Hz), 3.69 (s, 2H), 3.79 (s, 3H), 4.05 (pent, 4H, J=7 Hz), 4.30-4.37 (m, 2H), 5.13 (s, 2H), 5.45 (t, 1H, J=7 Hz) ppm; $^{31}$P (121.4 MHz, CD$_3$Cl) δ 27.5 ppm; MS (m/z) 642.2 [M+Na]$^+$.

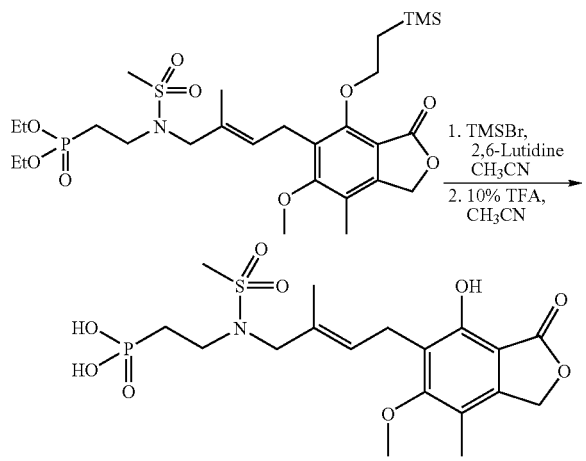

(2-{[4-(4-Hydroxy-6-methoxy-7-methyl-3-oxo-1,3-dihydro-isobenzofuran-5-yl)-2-methyl-but-2-enyl]-methanesulfonyl-amino}-ethyl)-phosphonic acid A solution of [2-(methanesulfonyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (18 mg, 0.029 mmol) in acetonitrile (0.5 mL) was stirred with TMSBr (38 µL, 0.29 mmol) and 2,6-lutidine (34 µL, 0.29 mmol) for 2 hours at room temperature. The reaction was worked up by addition of EtOAc and aqueous 1N HCl. The organic layer was washed with brine and the solvent was removed in vacuo. The residue was suspended in a solution of 10% TFA-CH$_2$Cl$_2$ for 10 minutes before it was dried to provide 9.9 mg of the desired product (73%) as a white solid. $^1$H NMR (300 MHz, DMSO-d6) δ 1.76 (s, 3H), 1.76-1.88 (m, 2H), 2.10 (s, 3H), 2.87 (s, 3H), 3.24-3.35 (m, 2H), 3.39 (d, 2H, J=7 Hz), 3.65 (s, 2H), 3.75 (s, 3H), 5.22 (s, 2H), 5.41-5.48 (m, 1H) ppm; $^{31}$P (121.4 MHz, DMSO-d$_6$) δ 21.4 ppm; MS (m/z) 464.1 [M+H]$^+$.

EXAMPLE 264

Preparation of Representative Compounds of the Invention

Representative compounds of the invention can be prepared as illustrated below.

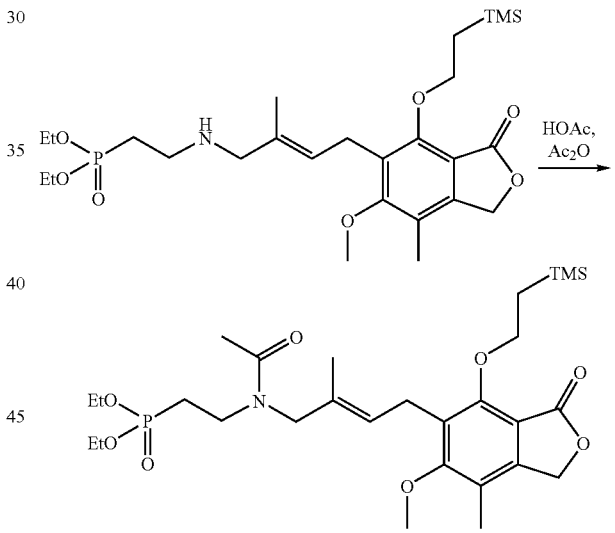

[2-(Acetyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester To a solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (32 mg, 0.059 mmol) in acetic acid (0.5 mL) was added acetic anhydride (0.5 mL). The solution was stirred at room temperature for 90 minutes when it was quenched by addition of 2 drops of water. The solution was dried in vacuo and the residue was purified by RP HPLC using a C18 column with a gradient of H$_2$O, 0.1% TFA-acetonitrile, 0.1% TFA to provide 28 mg of the product (81%) as a clear gel. The NMR data of this compound shows two rotamers in a ratio of 70:30. $^1$H NMR (300 MHz, CDCl$_3$) δ 0.05 (s, 9H), 1.17-1.27 (m, 2H), 1.30 and 1.31 (t, 6H, J=7 Hz), 1.70-1.79 (m, 2H), 1.76 (s, 3H), 2.00 (s, 3H), 2.18 (s, 3H), 3.40-3.52 (m, 2H), 3.46 (d, 2H, J=7 Hz), 3.77 (s, 3H), 3.79 and 3.93 (s, 3H), 4.07 (pent, 4H, J=7 Hz), 4.27-4.35 (m, 2H), 5.13 (s, 2H), 5.22-5.30 (m, 1H) ppm; $^{31}$P (121.4 MHz, CDCl$_3$) δ 27.5 and 28.9 ppm; MS (m/z) 584.1 [M+H]$^+$, 606.2 [M+Na]$^+$.

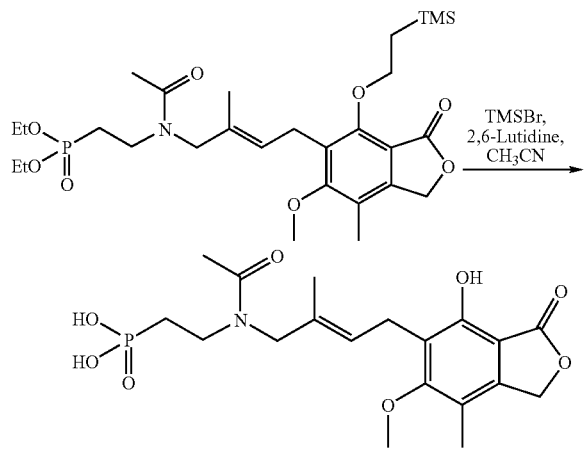

(2-{Acetyl-[4-(4-hydroxy-6-methoxy-7-methyl-3-oxo-1,3-dihydro-isobenzofuran-5-yl)-2-methyl-but-2-enyl]-amino}-ethyl)-phosphonic acid To a solution of [2-(acetyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (14 mg, 0.024 mmol) in acetonitrile (0.5 mL) was added TMSBr (31 μL, 0.24 mmol) and 2,6-lutidine (28 μL, 0.24 mmol). The solution was stirred at room temperature for 1 hour. The reaction was quenched by addition of methanol and aqueous 1N HCl. The product was extracted with EtOAc. The combined organic extracts were dried over Na$_2$SO$_4$ and concentrated in vacuo. The product was purified by RP HPLC using a C18 column with a gradient of H$_2$O, 0.1% TFA-acetonitrile, 0.1% TFA to provide 5.4 mg of the product (53%) as a white solid. The NMR data of this compound shows two rotamers. $^1$H NMR (300 MHz, CDCl$_3$) δ 1.67 and 1.73 (s, 3H), 1.85-2.12 (m, 5H), 2.13 (s, 3H), 3.30-3.61 (m, 4H), 3.75 (s, 3H), 3.76 (br s, 2H), 5.17 (s, 2H), 5.31 (br s, 1H) ppm; $^{31}$P (121.4 MHz, CDCl$_3$) δ 27.5 and 28.8 ppm; MS (m/z) 428.2 [M+H]$^+$, 450.2 [M+Na]$^+$.

EXAMPLE 265

Preparation of Representative Compounds of the Invention

Representative compounds of the invention can be prepared as illustrated below.

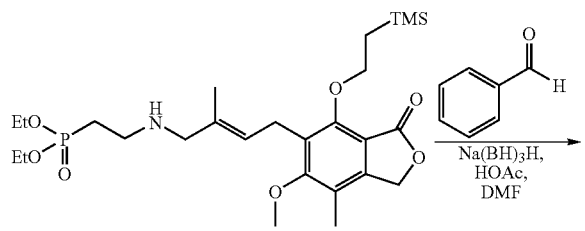

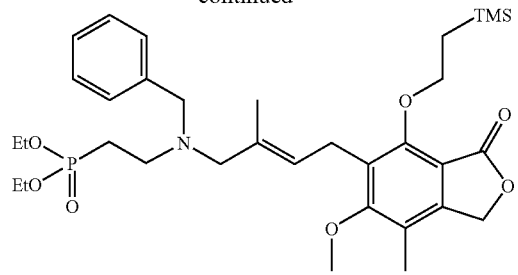

[2-(Benzyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester A solution of (2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (30 mg, 0.055 mmol), benzaldehyde (5.6 μL, 0.055 mmol), and sodium triacetoxyborohydride (23 mg, 0.11 mmol) was stirred with acetic acid (15.7 μL, 0.28 mmol) in DMF (0.5 mL) at room temperature over night. The reaction was quenched with a 10% aqueous Na$_2$CO$_3$ solution and the product was extracted with EtOAc. The organic layer was dried and concentrated under reduced pressure. The product was purified purified by RP HPLC using a C18 column with a gradient of H$_2$O, 0.1% TFA-acetonitrile, 0.1% TFA to provide 15 mg of the product (43%) as a clear gel. $^1$H NMR (300 MHz, CDCl$_3$) δ 0.02 (s, 9H), 1.18-1.25 (m, 2H), 1.24 (t, 6H, J=7 Hz), 1.86 (s, 3H), 1.88-2.02 (m, 2H), 2.16 (s, 3H), 2.65-2.74 (m, 2H), 3.93 (s, 2H), 3.46 (br d, 4H, J=7 Hz), 3.76 (s, 3H), 4.00 (pent, 4H, J=7 Hz), 4.25-4.34 (m, 2H), 5.11 (s, 2H), 5.34-5.43 (m, 1H), 7.18-7.33 (m, 5H) ppm; $^{31}$P (121.4 MHz, CDCl$_3$) δ 30.9 ppm; MS (m/z) 632.4 [M+H]$^+$, 654.3 [M+Na]$^+$.

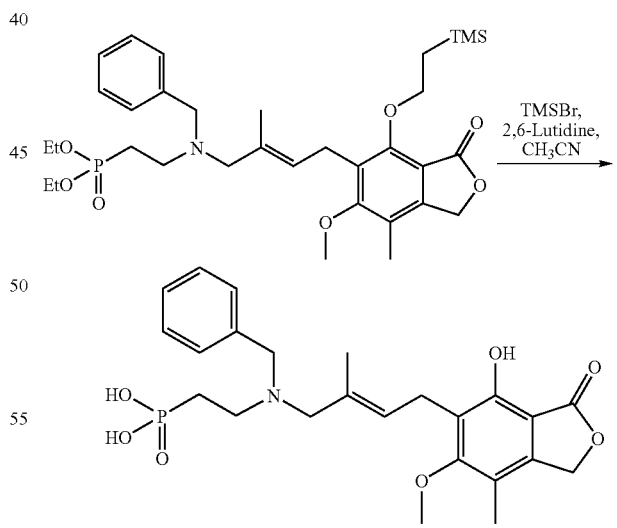

(2-{Benzyl-[4-(4-hydroxy-6-methoxy-7-methyl-3-oxo-1,3-dihydro-isobenzofuran-5-yl)-2-methyl-but-2-enyl]-amino}-ethyl)-phosphonic acid A solution of (2-{4-[6-methoxy-7-methyl-3-oxo-4-(2-trimethylsilanyl-ethoxy)-1,3-dihydro-isobenzofuran-5-yl]-2- methyl-but-2-enylamino}-ethyl)-phosphonic acid diethyl ester (15 mg, 0.024 mmol) in acetonitrile (0.5 mL) was treated with TMSBr (31 μL, 0.24 mmol) and 2,6-lutidine (28 μL, 0.24 mmol). The solution was stirred at ambient temperature for 1 hour, when it was quenched with methanol. The solvent was removed under reduced pressure and the residue was purified by RP HPLC using a C18 column with a gradient of H$_2$O, 0.1% TFA-acetonitrile, 0.1% TFA to provide 11 mg of the product (93%) as a white solid. $^1$H NMR (300 MHz, CD$_3$OD) δ 1.89 (s, 3H), 2.03-2.15 (m, 2H), 2.14 (s, 3H), 3.30-3.47 (m, 2H), 3.50 (br s, 2H), 3.62 (br s, 2H), 3.79 (s, 3H), 4.28 (s, 2H), 5.23 (s, 2H), 5.76 (br s, 1H), 7.46 (br s, 5H) ppm; $^{31}$P (121.4 MHz, CDCl$_3$) δ 20.1 ppm; MS (m/z) 476.3 [M+H]$^+$, 498.3 [M+Na]$^+$.

EXAMPLE 266

Preparation of Representative Compounds of the Invention

Representative compounds of the invention can be prepared as illustrated below.

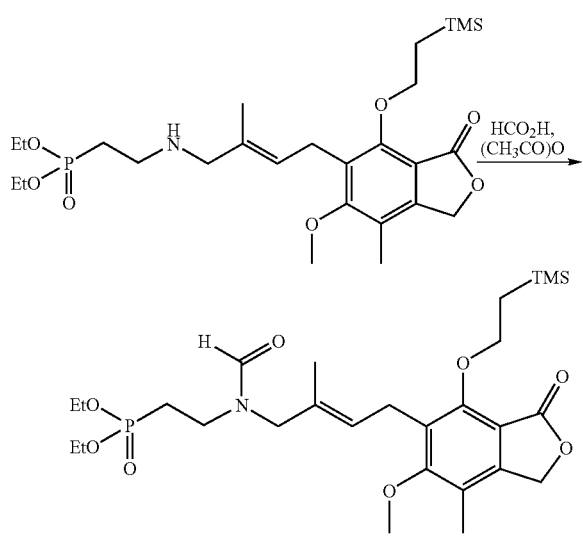

[2-(Formyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester To a solution of (2-{4-[6-Methoxy-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (74 mg, 0.14 mmol) in formic acid (1 mL) was added formic anhydride (1 mL) and the solution was stirred at room temperature for 1 hour. The reaction mixture was concentrated and the crude product carried onto the next step. The NMR data of this compound shows two rotamers with the ratio of 70:30. $^1$H NMR (300 MHz, CDCl$_3$) δ 0.05 (s, 9H), 1.18-1.28 (m, 2H), 1.28 and 1.30 (t, 6H, J=7 Hz), 1.74 (s, 3H), 1.84-2.08 (m, 2H), 2.19 (s, 3H), 3.34-3.45 (m, 2H), 3.47 (d, 2H, J=7 Hz), 3.72 and 3.87 (s, 2H), 3.78 and 3.79 (s, 3H), 4.06 and 4.07 (pent, 4H, J=7 Hz), 4.26-4.37 (m, 2H), 5.13 (s, 2H), 5.30-5.46 (m, 1H), 8.03 and 8.19 (s, 1H) ppm; $^{31}$P (121.4 MHz, CDCl$_3$) δ 27.5 and 28.1 ppm; MS (m/z) 570.1 [M+H]$^+$, 592.2 [M+Na]$^+$.

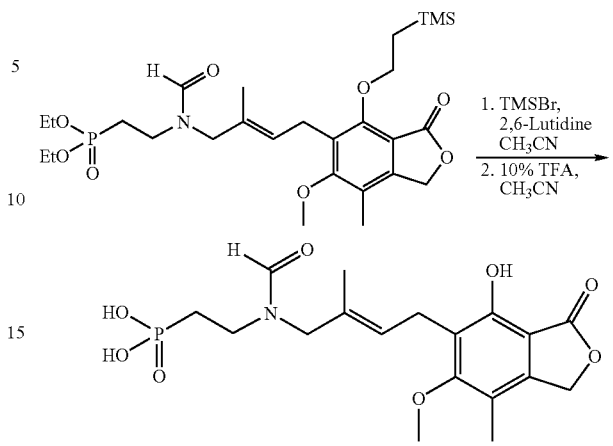

(2-{Formyl-[4-(4-hydroxy-6-methoxy-7-methyl-3-oxo-1,3-dihydro-isobenzofuran-5-yl)-2-methyl-but-2-enyl]-amino}-ethyl)-phosphonic acid To a solution of crude [2-(formyl-{4-[6-methoxy-7-methyl-3-oxo-4-(2-trimethylsilanyl-ethoxy)-1,3-dihydro-isobenzofuran-5-yl]-2-methyl-but-2-enyl}-amino)-ethyl]-phosphonic acid diethyl ester (78 mg, 0.14 mmol) in acetonitrile (1 mL) was added TMSBr (177 μl, 1.4 mmol) and 2,6-lutidine (163 μL, 1.4 mmol). The solution was stirred at room temperature for 1 hour when it was quenched by addition of methanol and 1N aqueous HCl. The product was extracted with EtOAc and purified by RP HPLC using a C18 column with a gradient of H$_2$O, 0.1% TFA-acetonitrile, 0.1% TFA to provide 29 mg of the product as a white solid. The NMR data of this compound shows two rotamers with the ratio of approximately 70:30. $^1$H NMR (300 MHz, CD$_3$OD) δ 1.62 and 1.64 (s, 3H), 1.83-1.98 (m, 2H), 2.16 (s, 3H), 3.38-3.55 (m, 4H), 3.78 (s, 3H), 3.80 and 3.91 (s, 2H), 5.22 (s, 2H), 5.39-5.52 (m, 1H), 8.03 and 8.18 (s, 1H) ppm; MS (m/z) 414.2 [M+H]$^+$, 436.2 [M+Na]$^+$.

EXAMPLE 267

Preparation of Representative Compounds of the Invention

Representative compounds of the invention can be prepared as illustrated below.

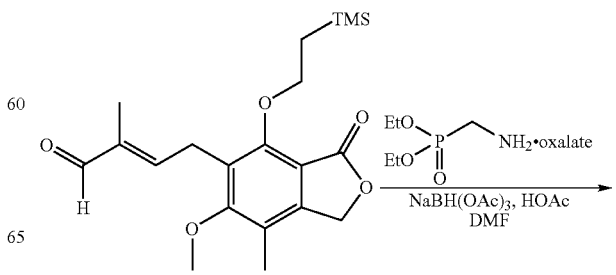

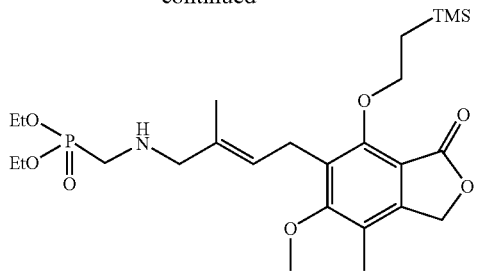

({4-[6-Methoxy-7-methyl-3-oxo-4-(2-trimethylsila-nyl-ethoxy)-1,3-dihydro-isobenzofuran-5-yl]-2-methyl-but-2-enylamino}-methyl)-phosphonic acid diethyl ester To a solution of 4-[6-methoxy-7-methyl-3-oxo-4-(2-trimethylsilanyl-ethoxy)-1,3-dihydro-isobenzofuran-5-yl]-2-methyl-but-2-enal (500 mg, 1.33 mmol), (2-aminomethyl) phosphonic acid diethyl ester oxalate (376 mg, 1.46 mmol), sodium triacetoxyborohydride (563 mg, 2.66 mmol) in DMF (10 mL) was added acetic acid (380 µL, 6.65 mmol) at room temperature. The solution was stirred overnight when it was quenched by addition of saturated aqueous sodium bicarbonate solution and EtOAc. The organic layer was separated and concentrated under reduced pressure. The residue was purified by silica gel chromatography to provide 500 mg (71%) of the product as an oil. $^1$H NMR (300 MHz, CDCl$_3$) δ 0.00 (s, 9H), 1.13-1.23 (m, 2H), 1.25 and 1.27 (t, 6H, J=7 Hz), 1.65-1.75 (m, 2H), 1.77 (s, 3H), 2.13 (s, 3H), 2.80 (s, 1H), 3.14 (s, 2H), 3.41 (d, 2H, J=7 Hz), 3.73 (s, 3H), 4.08 and 4.09 (pent, 4H, J=7 Hz), 4.20-4.30 (m, 2H), 5.08 (s, 2H), 5.30 (t, 1H, J=7 Hz) ppm; $^{31}$P (121.4 MHz, CDCl$_3$) δ 26.5 ppm; MS (m/z) 528.1 [M+H]$^+$, 550.2 [M+Na]$^+$.

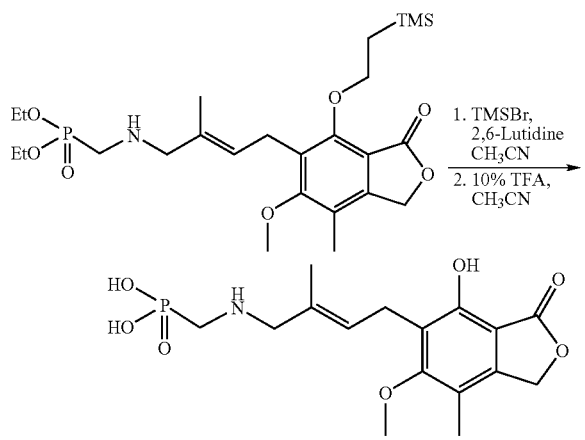

{[4-(4-Hydroxy-6-methoxy-7-methyl-3-oxo-1,3-dihydro-isobenzofuran-5-yl)-2-methyl-but-2-enylamino]-methyl}-phosphonic acid To a solution of ({4-[6-methoxy-7-methyl-3-oxo-4-(2-trimethylsilanyl-ethoxy)-1,3-dihydro-isobenzofuran-5-yl]-2-methyl-but-2-enylamino}-methyl)-phosphonic acid diethyl ester (20 mg, 0.038 mmol) in DMF (0.5 mL) was added TMSBr (49 µL, 0.38 mmol) and 2,6-lutidine (44 µL, 0.38 mmol). The solution was stirred at room temperature for 1 hour when it was quenched by addition of methanol. The product was purified by RP HPLC using a C18 column with a gradient of H$_2$O, 0.1% TFA-acetonitrile, 0.1% TFA to provide 5.6 mg of the product as a white solid. $^1$H NMR (300 MHz, CD$_3$OD and CDCl$_3$) δ 1.93 (s, 3H), 2.13 (s, 3H), 2.94 (br d, 2H, J=11 Hz), 3.42-3.53 (m, 2H), 3.60 (s, 2H), 3.78 (s, 3H), 5.22 (s, 2H), 5.71 (br s, 1H) ppm; $^{31}$P (121.4 MHz, CDCl$_3$) δ 8.5 ppm; MS (m/z) 372.2 [M+H]$^+$, 743.2 [2M+H]$^+$.

EXAMPLE 268

Preparation of Representative Compounds of the Invention

Representative compounds of the invention can be prepared as illustrated below.

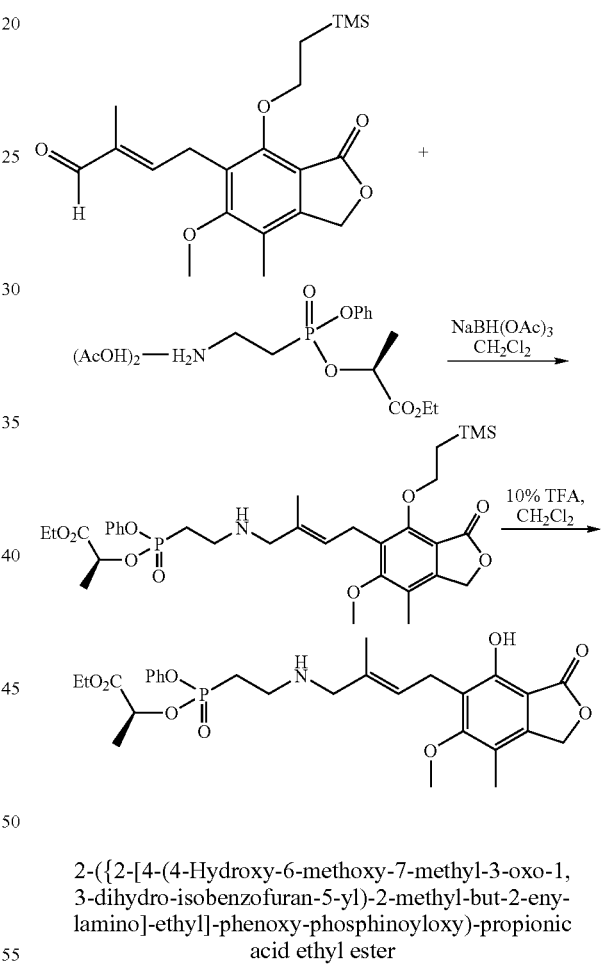

2-({2-[4-(4-Hydroxy-6-methoxy-7-methyl-3-oxo-1,3-dihydro-isobenzofuran-5-yl)-2-methyl-but-2-enylamino]-ethyl}-phenoxy-phosphinoyloxy)-propionic acid ethyl ester A solution of 4-[6-methoxy-7-methyl-3-oxo-4-(2-trimethylsilanyl-ethoxy)-1,3-dihydro-isobenzofuran-5-yl]-2-methyl-but-2-enal (188 mg, 0.5 mmol) was stirred with 2-[(2-aminoethyl)phenoxy-phosphinoyloxy]-propionic acid ethyl ester acetic acid salt (315.8 mg, 0.75 mmol) in CH$_2$Cl$_2$ (3 mL) for 2 hours at ambient temperature. Sodium triacetoxyborohydride (159 mg, 0.75 mmol) was added to the solution and the reaction was allowed to proceed for 1 hour. The reaction was quenched by addition of a saturated aqueous solution of NaHCO$_3$ and the product was extracted with EtOAc. The organic layer was removed under reduced pressure and the residue was resuspended in a 10% TFA/CH₂Cl₂ for 1 hour. The reaction mixture was concentrated and the product was purified by RP HPLC using a C18 column with a gradient of H₂O, 0.1% TFA-acetonitrile, 0.1% TFA to provide 198 mg of the product as a white solid. The NMR data of this compound shows two diastereomers at phosphorus in a ratio of approximately 45:55. ¹H NMR (300 MHz, CD₃OD) δ 1.23 and 1.24 (t, 3H, J=7 Hz), 1.38 and 1.52 (d, 3H, J=7 Hz), 1.97 and 1.98 (s, 3H), 2.14 (s, 3H), 2.44-2.66 (m, 2H), 3.31-3.48 (m, 2H), 3.51 (d, 2H, J=7 Hz), 3.66 (d, 2H, J=5 Hz), 3.80 (s, 3H), 4.10-4.27 (m, 2H), 4.90-5.10 (m, 1H), 5.20 (s, 2H), 5.73-5.82 (m, 1H), 7.15-7.27 (m, 3H), 7.35-7.45 (m, 2H) ppm; ³¹P (121.4 MHz, CD₃OD) δ 22.6, 24.3 ppm; MS (m/z) 561.9 [M+H]⁺.

EXAMPLE 269

Preparation of Representative Compounds of the Invention

Representative compounds of the invention can be prepared as illustrated below.

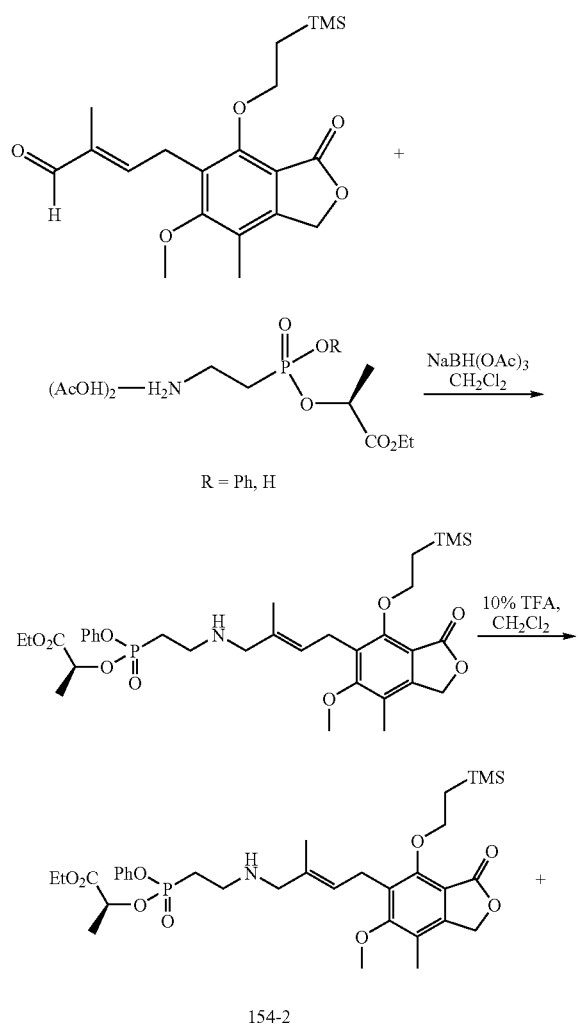

154-2

2-[Hydroxy-(2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphinoyloxy]-propionic acid ethyl ester A solution of 4-[6-methoxy-7-methyl-3-oxo-4-(2-trimethylsilanyl-ethoxy)-1,3-dihydro-isobenzofuran-5-yl]-2-methyl-but-2-enal (38 mg, 0.1 mmol) was stirred with 2-[(2-aminoethyl)-phenoxy-phosphinoyloxy]-propionic acid ethyl ester acetic acid (63 mg, 0.15 mmol) in CH₂Cl₂ (1 mL) for 2 hours at ambient temperature. Sodium triacetoxyborohydride (32 mg, 0.15 mmol) was added to the solution and the reaction was allowed to proceed for 1 hour. The reaction was quenched by addition of a saturated aqueous solution of NaHCO₃ and the product was extracted with EtOAc. The organic layer was removed under reduced pressure and the residue was resuspended in 10% TFA/CH₂Cl₂ for 1 hour. The reaction mixture was concentrated and the product was purified by RP HPLC using a C18 column with a gradient of H₂O, 0.1% TFA-acetonitrile, 0.1% TFA to provide 15 mg of the product (154-2). ¹H NMR (300 MHz, CDCl₃) δ 0.04 (s, 9H), 1.15-1.24 (m, 2H), 1.26 (t, 3H, J=7 Hz), 1.48 (d, 3H, J=7 Hz), 1.93 (s, 3H), 2.10-2.25 (m, 2H), 2.18 (s, 3H), 3.10-3.31 (m, 2H), 3.48 (d, 2H, J=7 Hz), 3.48-3.61 (m, 2H), 3.77 (s, 3H), 4.04-4.21 (m, 2H), 4.29-4.40 (m, 2H), 4.81-4.92 (m, 1H), 5.13 (s, 2H), 5.64 (t, 1H, J=7 Hz), 8.70-9.11 (m, 3H) ppm; ³¹P (121.4 MHz, CDCl₃) δ 21.9 ppm; MS (m/z) 586.3 [M+H]⁺, 1171.4 [2M+H]⁺.

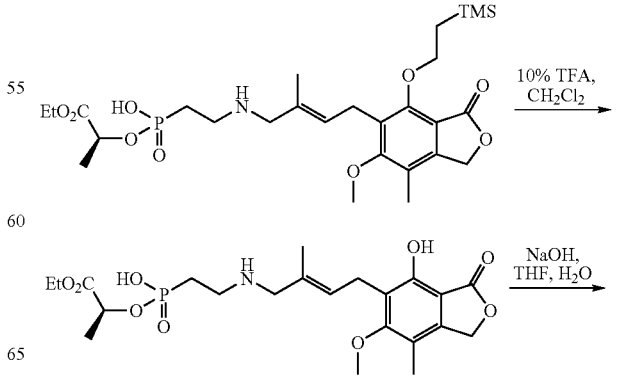

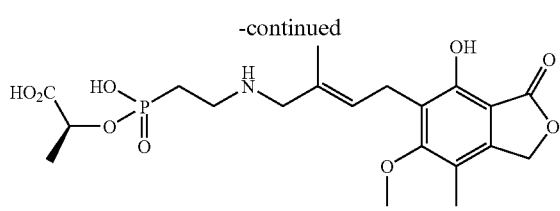

2-(Hydroxy-{2-[4-(4-hydroxy-6-methoxy-7-methyl-3-oxo-1,3-dihydro-isobenzofuran-5-yl)-2-methyl-but-2-enylamino]-ethyl}-phosphinoyloxy)-propionic acid A solution of 2-[hydroxy-(2-{4-[6-methoxy-7-methyl-3-oxo-4-(2-trimethylsilanyl-ethoxy)-1,3-dihydro-isobenzofuran-5-yl]-2-methyl-but-2-enylamino}-ethyl)-phosphinoyloxy]-propionic acid ethyl ester (15 mg, 0.026 mmol) in 10% TFA-CH$_2$Cl$_2$ (1 mL) was stirred at ambient temperature for 10 minutes. The reaction was worked up by removal of the solvent. The residue was dissolved in THF (0.5 mL) and water (0.4 mL) and 1N aqueous NaOH solution (0.1 mL) was added. The solution was stirred at room temperature for 20 minutes when it was acidified with 1N aqueous HCl solution. The resulting solution was purified by RP HPLC using a C18 column with a gradient of H$_2$O, 0.1% TFA-acetonitrile, 0.1% TFA to provide 6.8 mg of the product as a white solid. $^1$H NMR (300 MHz, CDCl$_3$) δ 1.38 (d, 3H, J=7 Hz), 1.91 (s, 3H), 2.13 (s, 3H), 2.12-2.28 (m, 2H), 3.12-3.33 (m, 2H), 3.41 (d, 2H, J=6 Hz), 3.56 (br s, 2H), 3.75 (s, 3H), 4.71-4.88 (m, 1H), 5.16 (s, 2H), 5.58-5.71 (m, 1H), 7.88 (br s, 3H), 8.60 (br s, 1H), 8.78 (br s, 1H) ppm; $^{31}$P (121.4 MHz, CDCl$_3$) δ 22.0 ppm; MS (m/z) 458.3 [M+H]$^+$, 480.3 [M+Na]$^+$.

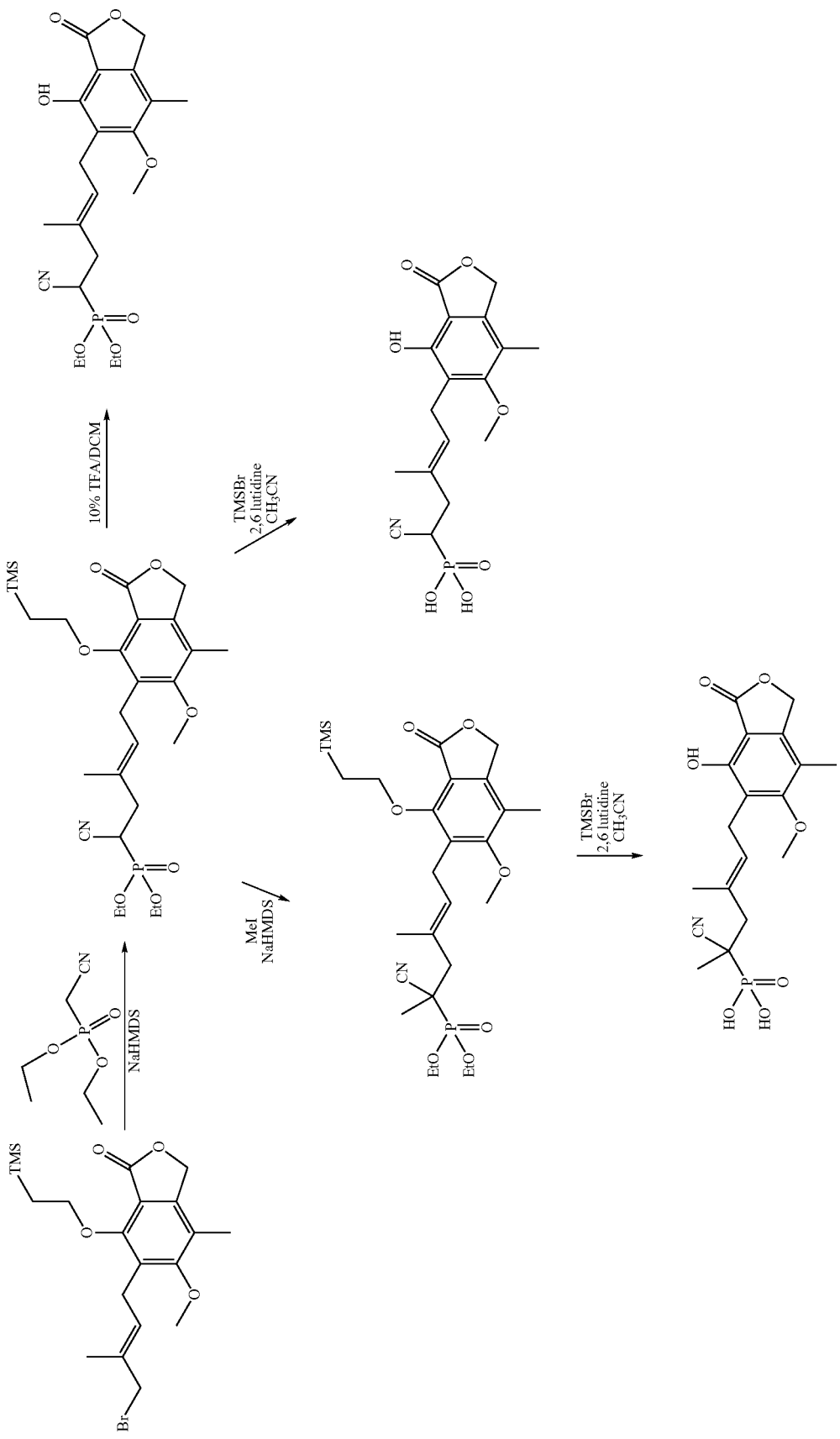

EXAMPLE 270

Preparation of Representative Compounds of the Invention

Representative compounds of the invention can be prepared as illustrated below.

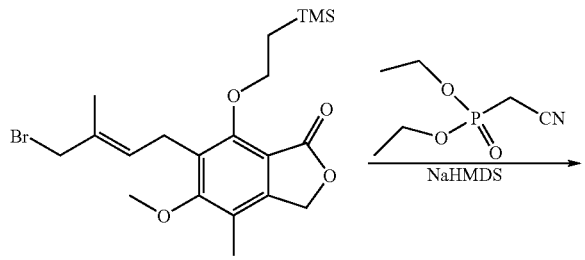

{1-Cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester To a solution of diethyl cyanomethylphosphonate (241 mg, 1.38 mmol) in THF (1 mL) was added a THF solution of sodium bis(trimethysilyl)amide (1.0 M, 1.13 mL, 1.15 mmol). After stirring for 30 minutes, the solution was added dropwise to a solution of 6-(4-bromo-3-methyl-but-2-enyl)-7-hydroxy-5-methoxy-4-methyl-3H-isobenzofuran-1-one (100 mg, 0.23 mmol) in THF (1 mL). The resulting mixture was allowed to stir at room temperature for one hour before saturated aqueous ammonium chloride was added. The reaction mixture was extracted with ethyl acetate. The organic layer was dried over sodium sulfate and concentrated to dryness. The residue was purified by silica gel column chromatography, affording 110 mg (90%) of the desired product. $^1$H NMR (300 MHz, CDCl$_3$) δ 0.04 (s, 9H), 1.24 (dd, J=7, 8 Hz, 2H), 1.36 (t, 6H), 1.86 (s, 3H), 2.17 (s, 3H), 2.43-2.57 (m, 2H), 3.04-3.17 (m, 1H), 3.47 (d, J=7.2 Hz, 2H), 3.79 (s, 3H), 4.12-4.37 (m, 6H), 5.13 (s, 2H), 5.44 (t, J=7.2 Hz, 1H) ppm; $^{31}$P (121.4 MHz, CDCl$_3$) δ 18.18 ppm; MS (m/z) 560 [M+Na]$^+$.

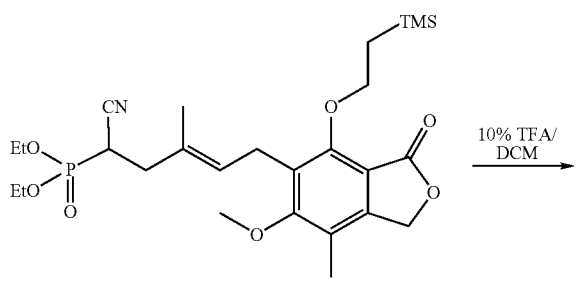

[1-Cyano-5-(4-hydroxy-6-methoxy-7-methyl-3-oxo-1,3-dihydro-isobenzofuran-5-yl)-3-methyl-pent-3-enyl]-phosphonic acid diethyl ester {1-Cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (25 mg, 0.047 mmol) was dissolved in a solution of 10% TFA/CH$_2$Cl$_2$ (5 mL) and stirred at room temperature for 2 hours. The reaction mixture was dried under reduced pressure and the product was purified by RP-HPLC to provide 16 mg (80%) of the desired product as a white solid. $^1$H NMR (300 MHz, CDCl$_3$) δ 1.38 (t, 6H), 1.86 (s, 3H), 2.15 (s, 3H), 2.40-2.58 (m, 2H), 3.01-3.14 (m, 1H), 3.45 (d, J=7.2 Hz, 2H), 3.79 (s, 3H), 4.18-4.30 (m, 4H), 5.21 (s, 2H), 5.48 (t, J=7.2 Hz, 1H) ppm; $^{31}$P (121.4 MHz, CDCl$_3$) δ 18.09 ppm; MS (m/z) 436 [M−H]$^−$, 438 [M+H]$^+$.

EXAMPLE 271

Preparation of Representative Compounds of the Invention

Representative compounds of the invention can be prepared as illustrated below.

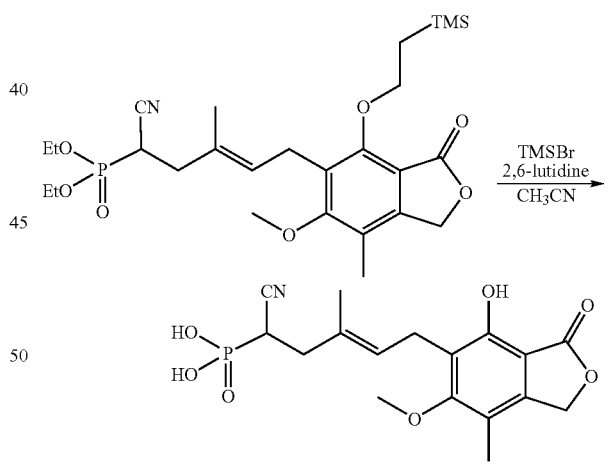

[1-Cyano-5-(4-hydroxy-6-methoxy-7-methyl-3-oxo-1,3-dihydro-isobenzofuran-5-yl)-3-methyl-pent-3-enyl]-phosphonic acid To a solution of {1-cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (35 mg, 0.065 mmol) in acetonitrile (2 mL) was added TMSBr (180 μL, 1.38 mmol) and 2,6-lutidine (160 μL, 1.38 mmol). The reaction solution was allowed stir at room temperature for one hour before quenching with MeOH. The reaction mixture was dried under reduced pressure and the residue was purified by RP HPLC using a C 18 column with a gradient of $H_2O$, 0.1% TFA-acetonitrile, 0.1% TFA to provide 15 mg (60%) of the desired product. $^1$H NMR (300 MHz, $CD_3OD$) δ 1.86 (s,3H), 2.15 (s, 3H), 2.38-2.57 (m, 2H), 3.17-3.28 (m, 1H), 3.44 (d, J=7.2 Hz, 2H), 3.80 (s, 3H), 5.25 (s, 2H), 5.47 (t, J=7.2 Hz, 1H) ppm; $^{31}$P (121.4 MHz, $CD_3OD$) δ 15.28 ppm; MS (m/z) 380 [M–H]$^-$, 382 [M+H]$^+$.

EXAMPLE 272

Preparation of Representative Compounds of the Invention

Representative compounds of the invention can be prepared as illustrated below.

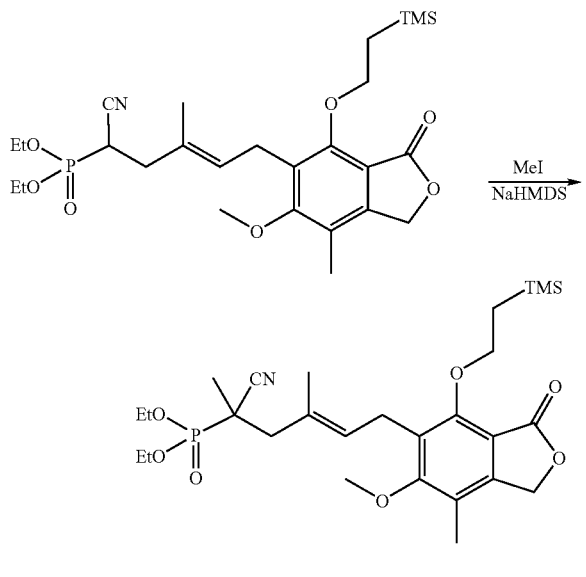

{1-Cyano-5-[6-methoxy-7-methyl-3-oxo-4-(2-trimethylsilanyl-ethoxy)-1,3-dihydro-isobenzofuran-5-yl]-1,3-dimethyl-pent-3-enyl}-phosphonic acid diethyl ester To a solution of {(1-cyano-5-[6-methoxy-7-methyl-3-oxo-4-(2-trimethylsilanyl-ethoxy)-1,3-dihydro-isobenzofuran-5-yl]-3-methyl-pent-3-enyl}-phosphonic acid diethyl ester (45 mg, 0.084 mmol) in THF (0.5 mL) was added sodium bis(trimethysilyl)amide (1.0 M, 1.13 mL, 1.15 mmol). After stirring for 20 minutes, iodomethane (52 μL, 0.84 mmol) was added dropwise and the resulting mixture was allowed to stir at room temperature for 2 hours. The reaction mixture was quenched with saturated aqueous ammonium chloride and extracted with ethyl acetate. The organic layer was dried over sodium sulfate and concentrated to dryness. The residue was purified by RP HPLC using a C18 column with a gradient of $H_2O$, 0.1% TFA-acetonitrile, 0.1% TFA to afford 6.6 mg (23%) of the desired product. $^1$H NMR (300 MHz, $CDCl_3$) δ 0.00 (s, 9H), 1.16 (dd, J=7, 8 Hz, 2H), 1.31 (t, 6H), 1.38 (d, 3H), 1.92 (s,3H), 2.17 (s, 3H), 2.23 (m, 1H), 2.65 (m, 1H), 3.30-3.42 (m, 2H), 3.73 (s, 3H), 4.14-4.27 (m, 6H), 5.08 (s, 2H), 5.28 (t, J=7.2 Hz, 1H) ppm; $^{31}$P (121.4 MHz, $CDCl_3$) δ 22.26 ppm; MS (m/z) 574 [M+Na]$^+$.

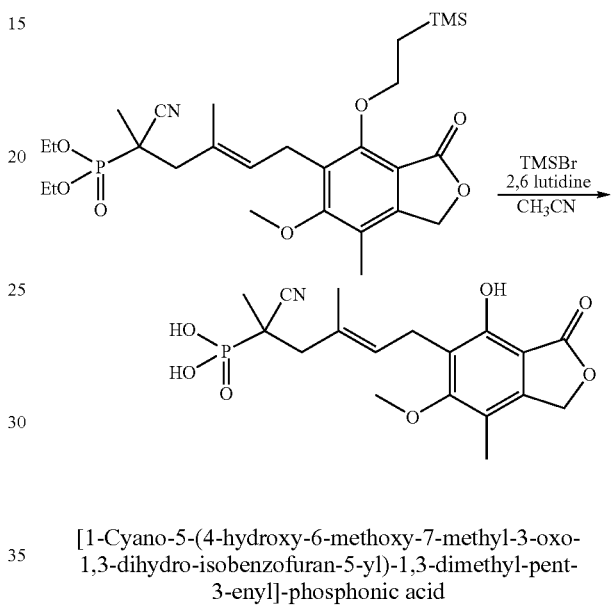

[1-Cyano-5-(4-hydroxy-6-methoxy-7-methyl-3-oxo-1,3-dihydro-isobenzofuran-5-yl)-1,3-dimethyl-pent-3-enyl]-phosphonic acid To a solution of {1-cyano-5-[6-methoxy-7-methyl-3-oxo-4-(2-trimethylsilanyl-ethoxy)-1,3-dihydro-isobenzofuran-5-yl]-1,3-dimethyl-pent-3-enyl}-phosphonic acid diethyl ester (18 mg, 0.04 mmol) in DMF (0.5 mL) and DCM (0.5 mL) was added TMSBr (51 μL, 0.4 mmol) and 2,6-lutidine (46 μL, 0.4 mmol). The reaction solution was allowed stir at room temperature overnight before quenching with MeOH. The reaction mixture was dried under reduced pressure and the residue was purified by RP HPLC using a C18 column with a gradient of $H_2O$, 0.1% TFA-acetonitrile, 0.1% TFA to provide 4.5 mg (33%) of the desired product. $^1$H NMR (300 MHz, $CD_3OD$) δ 1.37 (d, 3H), 1.87 (s, 3H), 2.13 (s, 3H), 2.26 (m, 1H), 2.64 (m, 1H), 3.39 (m, 2H), 3.75 (s, 3H), 5.18 (s, 2H), 5.34 (m, 1H) ppm; $^{31}$P (121.4 MHz, $CD_3OD$) δ 21.47 ppm; MS (m/z) 422 [M–H]$^-$, 424 [M+H]$^+$.

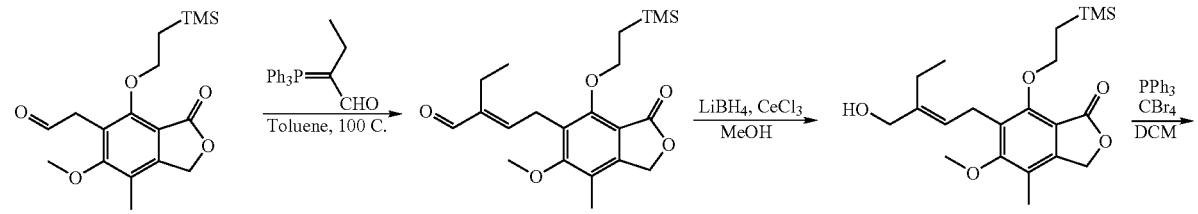

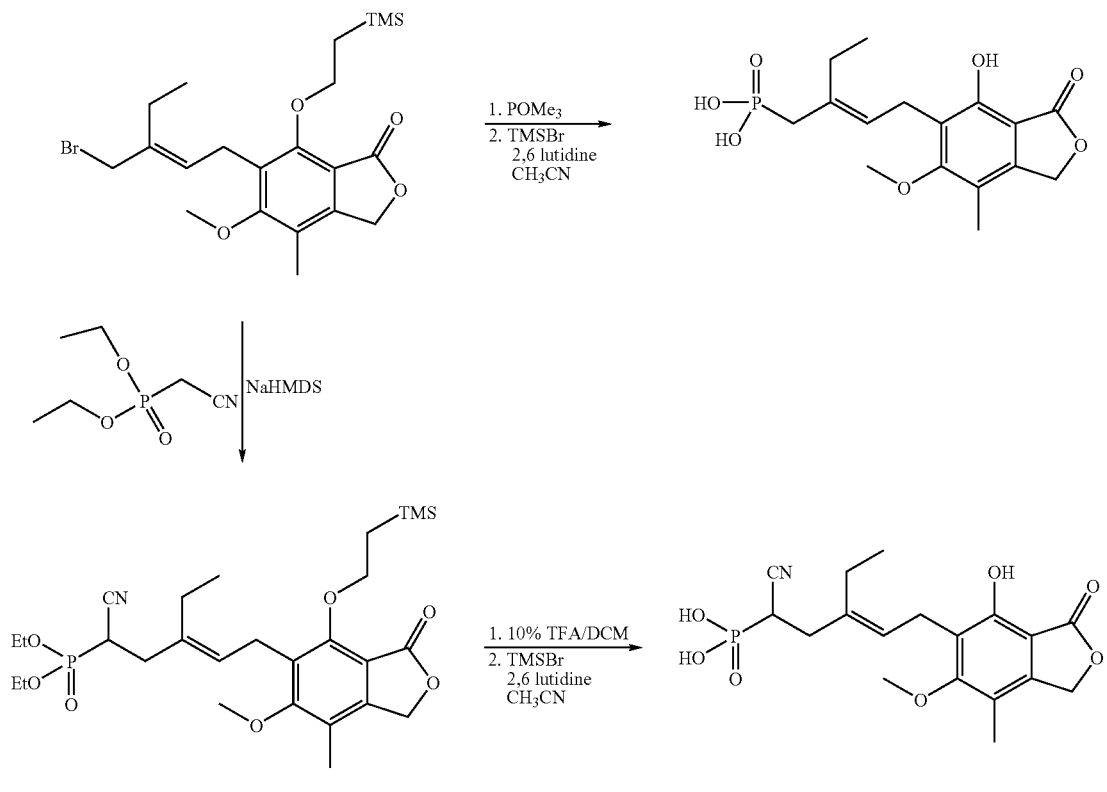

EXAMPLE 273

Preparation of Representative Compounds of the Invention

Representative compounds of the invention can be prepared as illustrated below.

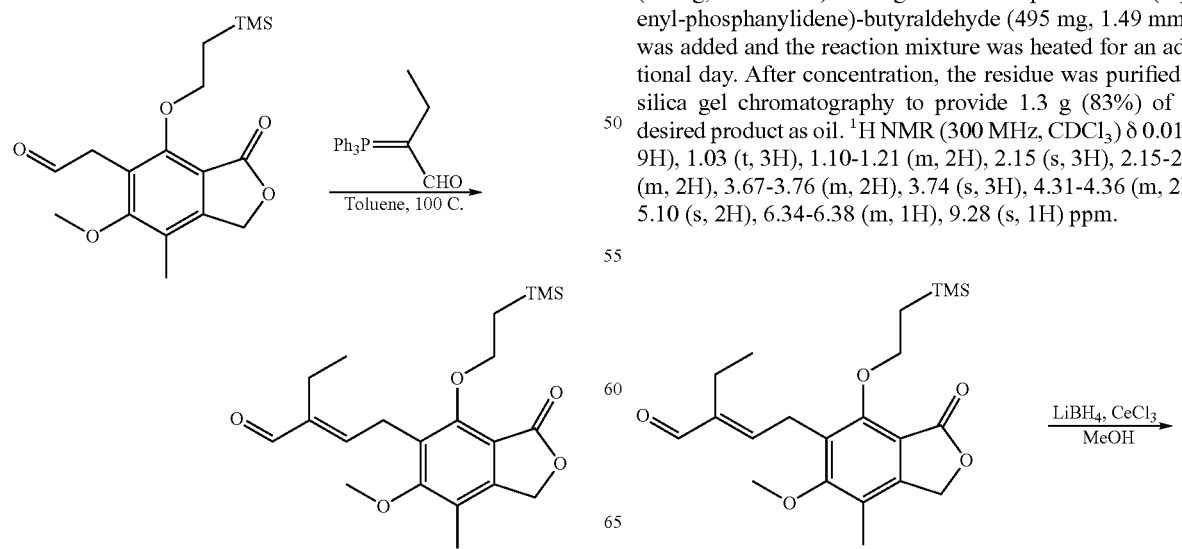

2-Ethyl-4-[6-methoxy-7-methyl-3-oxo-4-(2-trimethylsilanyl-ethoxy)-1,3-dihydro-isobenzofuran-5-yl]-but-2-enal A solution of [6-methoxy-7-methyl-3-oxo-4-(2-trimethyl-silanyl-ethoxy)-1,3-dihydro-isobenzofuran-5-yl]-acetaldehyde (1.5 g, 4.46 mmol) in toluene (14 mL) was heated at 100° C. with 2-(triphenyl-phosphanylidene)-butyraldehyde (1.68 g, 5.35 mmol) overnight. A second portion of 2-(triphenyl-phosphanylidene)-butyraldehyde (495 mg, 1.49 mmol) was added and the reaction mixture was heated for an additional day. After concentration, the residue was purified by silica gel chromatography to provide 1.3 g (83%) of the desired product as oil. $^1$H NMR (300 MHz, CDCl$_3$) δ 0.01 (s, 9H), 1.03 (t, 3H), 1.10-1.21 (m, 2H), 2.15 (s, 3H), 2.15-2.44 (m, 2H), 3.67-3.76 (m, 2H), 3.74 (s, 3H), 4.31-4.36 (m, 2H), 5.10 (s, 2H), 6.34-6.38 (m, 1H), 9.28 (s, 1H) ppm.

-continued

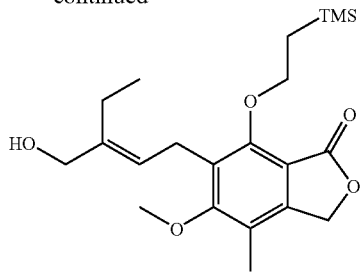

6-(3-Hydroxymethyl-pent-2-enyl)-5-methoxy-4-methyl-7-(2-trimethylsilanyl-ethoxy)-3H-isobenzofuran-1-one A solution of 2-ethyl-4-[6-methoxy-7-methyl-3-oxo-4-(2-trimethylsilanyl-ethoxy)-1,3-dihydro-isobenzofuran-5-yl]-but-2-enal (1.3 g, 3.30 mmol) in methanol (10 mL) and THF (10 mL) was cooled to 0° C. A solution of CeCl$_3$ (8.25 mL, 0.4M, MeOH:H$_2$O, 9:1) was added, followed by LiBH$_4$ (1.66 mL, 3.30 mmol of a 2M solution in THF). The ice bath was removed and the reaction mixture was allowed to warm to room temperature. The reaction mixture was stirred for an additional 40 minutes, whereupon TLC indicated complete consumption of starting aldehyde. The reaction was worked up by addition of aqueous 1N HCl and the product was extracted with EtOAc. The organic layer was washed with saturated aqueous sodium bicarbonate solution and brine. The organic layer was concentrated under reduced pressure and the residue was purified by silica gel chromatography to provide 948 mg (73%) of the product as colorless oil. $^1$H NMR (300 MHz, CDCl$_3$) δ 0.00 (s, 9H), 1.07 (t, 3H), 1.20 (dd, 2H, J=7, 8 Hz), 2.13 (s, 3H), 2.38-2.50 (m, 2H), 3.77 (s, 3H), 3.99 (s, 2H), 4.27 (dd, 2H, J=7, 8 Hz), 5.08 (s, 2H), 5.34 (t, J=7.2 Hz, 1H) ppm.

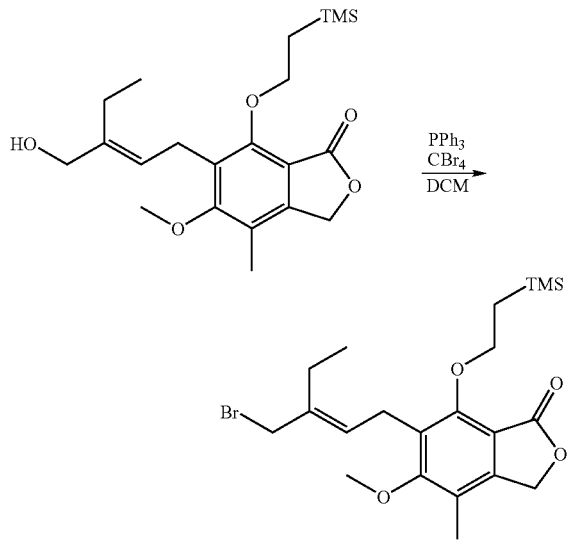

6-(3-Bromomethyl-pent-2-enyl)-5-methoxy-4-methyl-7-(2-trimethylsilanyl-ethoxy)-3H-isobenzofuran-1-one Polymer-supported triphenylphosphine (3 mmol/g, 0.66 g) was soaked in dichloromethane (6 mL) for 1 hour 6-(3-Hydroxymethyl-pent-2-enyl)-5-methoxy-4-methyl-7-(2-trimethylsilanyl-ethoxy)-3H-isobenzofuran-1-one (260 mg, 0.66 mmol) and carbon tetrabromide (657 mg, 1.98 mmol) were added sequentially and the mixture was shaken for 1 hour at room temperature. The mixture was filtered and the filtrate was concentrated. The residue was purified by silica gel chromatography to provide 233 mg (77%) of the product as a white solid. $^1$H NMR (300 MHz, CDCl$_3$) δ 0.00 (s, 9H), 1.08 (t,3H), 1.20 (dd, 2H, J=7, 8 Hz), 2.14 (s, 3H), 2.35-2.43 (m, 2H), 3.44 (d, J=7.2, 2H), 3.73 (s, 3H), 3.95 (s, 2H), 4.27 (dd, 2H, J=7, 8 Hz), 5.08 (s, 2H), 5.53 (t, J=7.2 Hz, 1H) ppm.

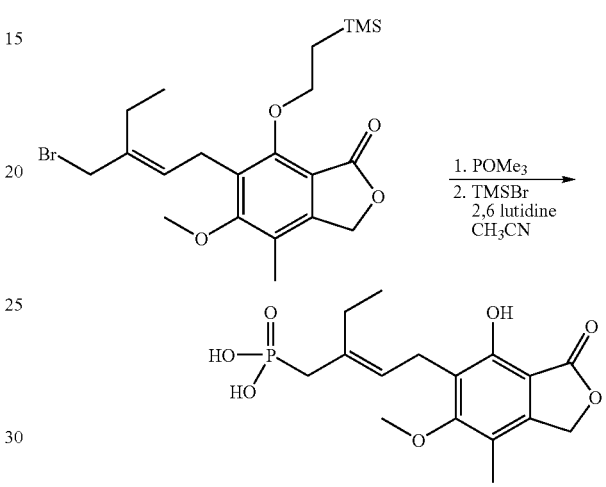

[2-Ethyl-4-(4-hydroxy-6-methoxy-7-methyl-3-oxo-1,3-dihydro-isobenzofuran-5-yl)-but-2-enyl]-phosphonic acid A solution of 6-(3-bromomethyl-pent-2-enyl)-5-methoxy-4-methyl-7-(2-trimethylsilanyl-ethoxy)-3H-isobenzofuran-1-one (230 mg, 0.5 mmol) in trimethylphosphite (1.5 mL, 12.75 mmol) was heated to 100° C. for 4 hours. The reaction was worked up by removal of excess trimethylphosphite under reduced pressure. The residue was dissolved in acetonitrile (1 mL) and TMSBr (646 µL, 5.0 mmol) and 2,6-lutidine (580 µL, 5.0 mmol) were added at 0° C. The reaction solution was allowed to warm to room temperature and stirred for 4 hours. The reaction was cooled to 0° C. and quenched with addition of MeOH. The reaction mixture was dried under reduced pressure and the residue was purified by RP HPLC using a C18 column with a gradient of H$_2$O, 0.1% TFA-acetonitrile, 0.1% TFA to provide 77 mg (58%) of the product. $^1$H NMR (300 MHz, CD$_3$OD) δ 1.08 (t, 3H), 2.16 (s, 3H), 2.43 (m, 2H), 2.48 (d, 2H, J=22 Hz), 3.46 (t, 2H, J=6 Hz), 3.79 (s, 3H), 5.25 (s, 2H), 5.38 (q, 1H, J=7 Hz) ppm.; $^{31}$P (121.4 MHz, CD$_3$OD) δ 25.65 ppm.; MS (m/z) 355 [M–H]$^-$, 357 [M+H]$^+$.

EXAMPLE 274

Preparation of Representative Compounds of the Invention

Representative compounds of the invention can be prepared as illustrated below.

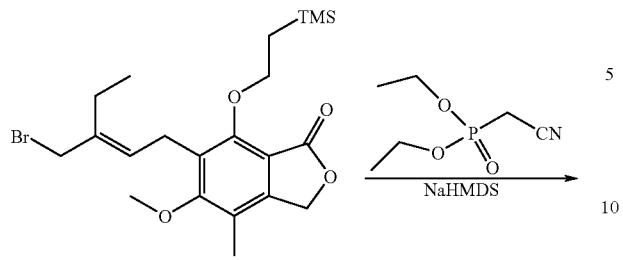
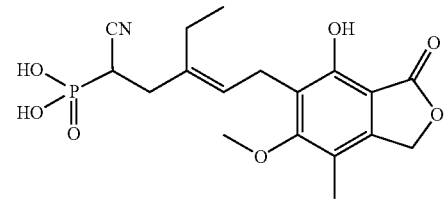

[1-Cyano-3-ethyl-5-(4-hydroxy-6-methoxy-7-methyl-3-oxo-1,3-dihydro-isobenzofuran-5-yl)-pent-3-enyl]-phosphonic acid {1-Cyano-3-ethyl-5-[6-methoxy-7-methyl-3-oxo-4-(2-trimethylsilanyl-ethoxy)-1,3-dihydro-isobenzofuran-5-yl]-pent-3-enyl}-phosphonic acid diethyl ester (19.5 mg, 0.035 mmol) was dissolved in a solution of 10% TFA/CH$_2$Cl$_2$ (2 mL) and stirred at room temperature for 10 minutes. The reaction mixture was dried under reduced pressure and purified by RP-HPLC to provide 9.5 mg (61%) of the desired product. This material was dissolved in DMF (0.5 mL) and DCM (0.5 mL) and TMSBr (27 µL, 0.2 mmol) and 2,6-lutidine (23 µL, 0.2 mmol) were added. The reaction solution was allowed stir at room temperature overnight before quenching with MeOH. The reaction mixture was dried under reduced pressure and the residue was purified by RP HPLC using a C18 column with a gradient of H$_2$O, 0.1% TFA-acetonitrile, 0.1% TFA to provide 5.1 mg (65%) of the desired product as a white solid. $^1$H NMR (300 MHz, CD$_3$OD) δ 1.10 (t,3H), 2.16 (s, 3H), 2.23-2.52 (m, 3H), 2.67 (m,1H), 3.05-3.20 (m, 1H), 3.48 (d, J=7.2, 2H), 3.81 (s, 3H), 5.26 (s, 2H), 5.43 (t, J=7.2 Hz, 1H) ppm; $^{31}$P (121.4 MHz, CD$_3$OD) δ 14.18 ppm; MS (m/z) 394 [M−H]$^−$, 396 [M+H]$^+$.

{1-Cyano-3-ethyl-5-[6-methoxy-7-methyl-3-oxo-4-(2-trimethylsilanyl-ethoxy)-1,3-dihydro-isobenzofuran-5-yl]-pent-3-enyl}-phosphonic acid diethyl ester To a solution of diethyl cyanomethylphosphonate (233 mg, 1.32 mmol) in THF (1 mL) was added a THF solution of sodium bis(trimethysilyl)amide (1.0 M, 1.21 mL, 1.21 mmol). After stirring for 30 minutes, the solution was added dropwise to a solution of 6-(3-bromomethyl-pent-2-enyl)-5-methoxy-4-methyl-7-(2-trimethylsilanyl-ethoxy)-3H-isobenzofuran-1-one (100 mg, 0.22 mmol) in THF (1 mL). The resulting mixture was allowed to stir at room temperature overnight before saturated aqueous ammonium chloride was added. The reaction mixture was extracted with ethyl acetate. The organic layer was dried over sodium sulfate and concentrated to dryness. The residue was purified by preparative reverse-phase HPLC, affording 51 mg (42%) of the desired product. $^1$H NMR (300 MHz, CDCl$_3$) δ 0.04 (s, 9H), 1.07 (t,3H), 1.24 (dd, 2H, J=7, 8 Hz), 1.36 (t, 6H), 2.12 (m, 1H), 2.18 (s, 3H), 2.35-2.47 (m, 2H), 2.67 (m,1H), 3.00-3.14 (m, 1H), 3.44 (d, J=7.2, 2H), 3.79 (s,3H), 4.12-4.37 (m, 6H), 5.13 (s, 2H), 5.38 (t, J=7.2 Hz, 1H) ppm; $^{31}$P (121.4 MHz, CDCl$_3$) δ 18.26 ppm; MS (m/z) 574 [M+Na]$^+$.

EXAMPLE 275

Preparation of Representative Compounds of the Invention

Representative compounds of the invention can be prepared as illustrated below.

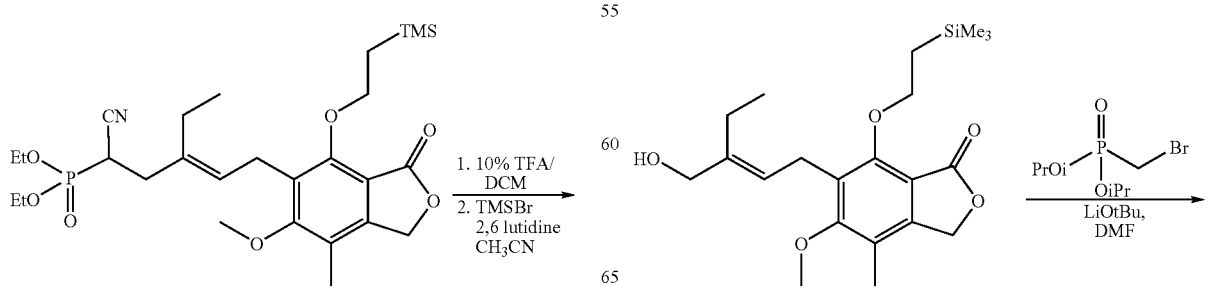

-continued

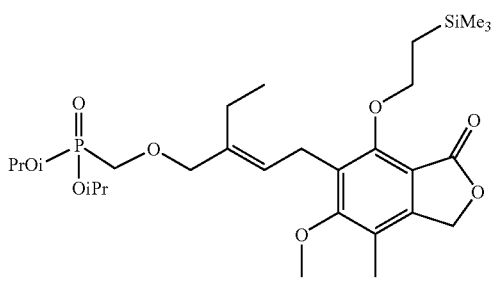

{2-Ethyl-4-[6-methoxy-7-methyl-3-oxo-4-(2-trimethylsilanyl-ethoxy)-1,3-dihydro-isobenzofuran-5-yl]-but-2-enyloxymethyl}-phosphonic acid diisopropyl ester To a solution of bromomethylphosphonate diisopropyl ester (680 mg, 2.62 mmol) and 6-(3-hydroxymethyl-pent-2-enyl)-5-methoxy-4-methyl-7-(2-trimethylsilanyl-ethoxy)-3H-isobenzofuran-1-one (688 mg, 1.75 mmol) in DMF (3 mL) was added lithium t-butoxide (1.0M in THF; 2.6 mL). The reaction was heated at 70° C. for 2 hours. After cooling to ambient temperature, more bromomethylphosphonate diisopropyl ester (680 mg, 2.62 mmol) and lithium t-butoxide (1.0M in THF; 2.6 mL) were added. The reaction mixture was heated at 70° C. for a further hour, cooled, poured into a solution of lithium chloride (5% aqueous) and extracted with ethyl acetate. The organic extract was dried and the product was purified by chromatography on silica gel, eluting with hexane-ethyl acetate to provide 347 mg (35%) of the product as a colorless oil. $^1$H NMR (300 MHz, CDCl$_3$) δ 0.04 (s, 9H), 1.09 (t, 3H, J=7.5 Hz), 1.20-1.26 (m, 2H), 1.31 (t, 12H, J=6 Hz), 2.18 (s, 3H), 2.29 (q, 2H, J=7.5 Hz), 3.5 (m, 2H), 3.59 (d, 2H, J=8.7 Hz), 3.78 (s, 3H), 3.98 (s, 2H), 4.28-4.35 (m, 2H), 4.6-4.8 (m, 2H), 5.13 (s, 2H), 5.4 (t, 1H, J=7 Hz) ppm; $^{31}$P (121.4 MHz, CDCl$_3$) δ 20.26 ppm; MS (m/z) 593.3 [M+Na]$^+$.

[2-Ethyl-4-(4-hydroxy-6-methoxy-7-methyl-3-oxo-1,3-dihydro-isobenzofuran-5-yl)-but-2-enyloxymethyl]-phosphonic acid To a solution of {2-ethyl-4-[6-methoxy-7-methyl-3-oxo-4-(2-trimethylsilanyl-ethoxy)-1,3-dihydro-isobenzofuran-5-yl]-but-2-enyloxymethyl}-phosphonic acid diisopropyl ester (347 mg, 0.61 mmol) in acetonitrile (5 mL) was added 2,6-lutidine (0.71 mL, 6.1 mmol) and bromotrimethylsilane (0.786 mL, 6.1 mmol). The mixture was stirred at room temperature for 3 hours, quenched with methanol (5 mL), concentrated, and partitioned between ethyl acetate and 1N HCl (aqueous). The organic layer was concentrated to give the free phosphonic acid as a colorless oil (205 mg, 70%). This material (20 mg) was dissolved in a solution of trifluoroacetic acid (0.3 mL) and dichloromethane (2.7 mL) and stirred for 30 minutes at ambient temperature. After concentration, the residue was purified by RP HPLC using a C18 column with a gradient of H$_2$O, 0.1% TFA-acetonitrile, 0.1% TFA to provide the product, after lyophilization, as a white solid (10 mg). $^1$H NMR (300 MHz, CDCl$_3$) δ 1.007 (t, 3H, J=7.5 Hz), 2.13 (s, 3H), 2.32 (q, 2H, J=7.5 Hz), 3.41 (d, 2H, J=6.3 Hz), 3.56 (d, 2H, J=9 Hz), 3.75 (s, 3H), 3.95 (s, 2H), 5.16 (s, 2H), 5.43 (t, 1H, J=6.3 Hz) ppm; $^{31}$P (121.4 MHz, CDCl$_3$) δ 22.8 ppm; MS (m/z) 385.2 [M−H]$^+$, 387.1 [M+H]$^+$.

EXAMPLE 276

Preparation of Representative Compounds of the Invention

Representative compounds of the invention can be prepared as illustrated below.

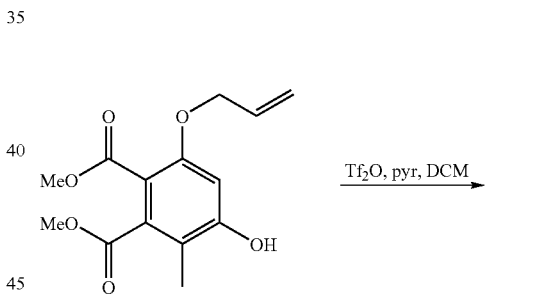

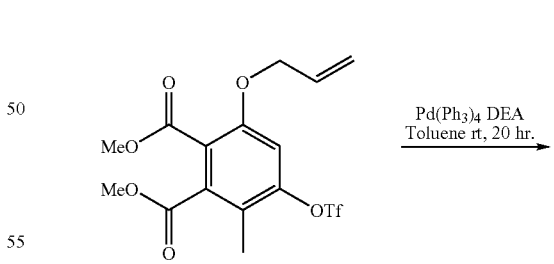

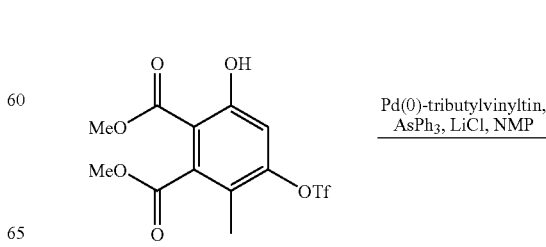

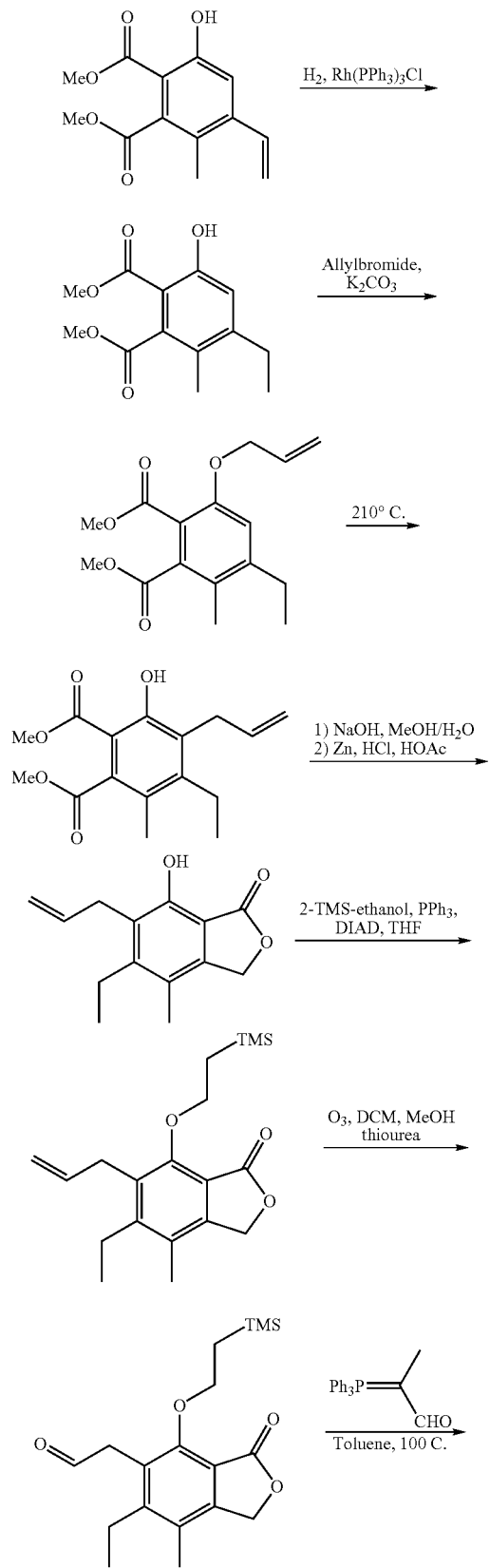
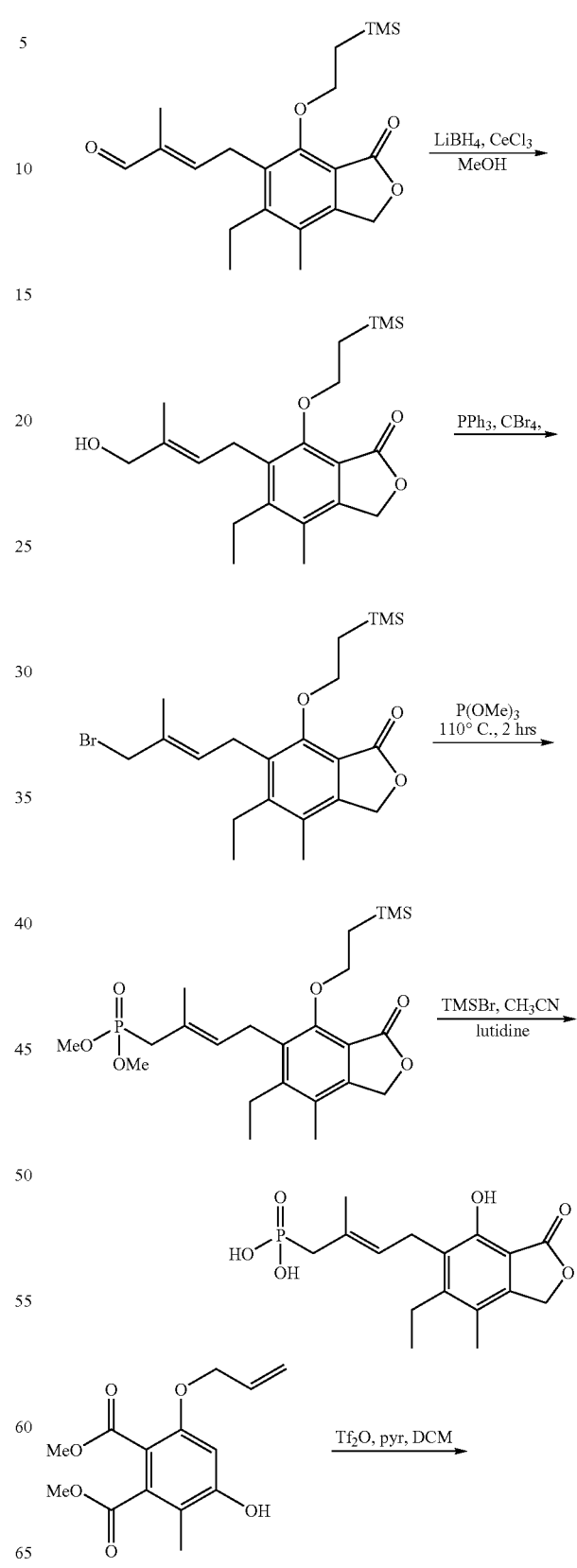

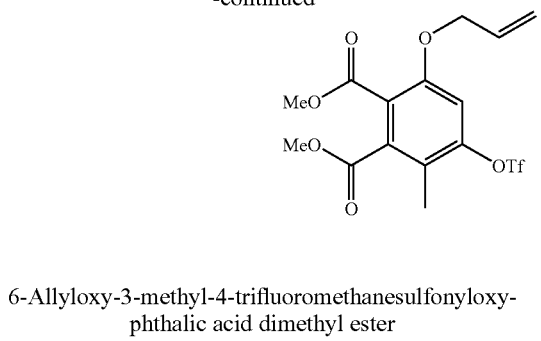

6-Allyloxy-3-methyl-4-trifluoromethanesulfonyloxy-phthalic acid dimethyl ester To a solution of 6-allyloxy-4-hydroxy-3-methyl-phthalic acid dimethyl ester (8.06 g, 28.8 mmol) [synthesized according to: J. W. Patterson, *Tetrahedron*, 1993, 49, 4789-4798] and pyridine (11.4 g, 144.0 mmol) in dichloromethane (DCM) (20 mL) at 0° C. was added triflic anhydride (12.19 g, 43.2 mmol). The reaction was stirred at 0° C. for 2 hours after which additional triflic anhydride (3 mL) was added. Stirring at 0° C. was continued for an additional hour. The reaction mixture was poured into a mixture of DCM and HCl (1N). The layers were separated and the aqueous layer was extracted with DCM. The combined organic layers were dried over sodium sulfate. Filtration and evaporation of solvents in vacuo yielded a crude product, which was purified by silica gel chromatography to provide 8.39 g of the product as an oil. $^1$H NMR (300 MHz, CDCl$_3$): δ=2.32 (s, 3H), 3.89 (s, 6H), 4.60 (m, 2H), 5.33 (d, J=9.3 Hz, 1H), 5.41 (d, J=18.6 Hz, 1H), 5.95 (m, 1H), 6.95 (s, 1H) ppm; $^{19}$F NMR (282 MHz, CDCl$_3$): δ=−74 ppm.

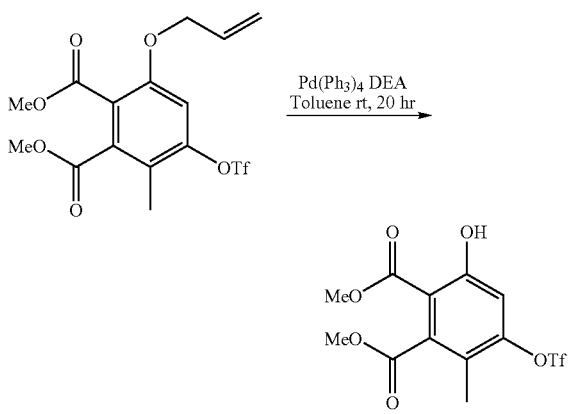

6-Hydroxy-3-methyl-4-trifluoromethanesulfonyloxy-phthalic acid dimethyl ester To a solution of 6-allyloxy-3-methyl-4-trifluoromethanesulfonyloxy-phthalic acid dimethyl ester (8.39 g, 20.3 mmol) in toluene (20 mL) was added tetrakistriphenylphosphine palladium (0.47 g, 0.40 mmol) and diethylamine (2.97 g, 40.86 mmol) at room temperature under an atmosphere of nitrogen. Stirring at room temperature was continued until all starting material was consumed. The crude reaction mixture was partitioned between diethyl ether and HCl (0.1 N). The organic layer was washed with brine and dried over sodium sulfate. Filtration and evaporation of solvents in vacuo yielded a crude material, which was purified by silica gel chromatography to provide 4.16 g (55%) of the desired product as an off-white solid. $^1$H NMR (300 MHz, CDCl$_3$): δ=2.20 (s, 3H), 3.93 (s, 3H), 3.95 (s, 3H), 7.01 (s, 1H) ppm; $^{19}$F NMR (282 MHz, CDCl$_3$): δ=−74 ppm.

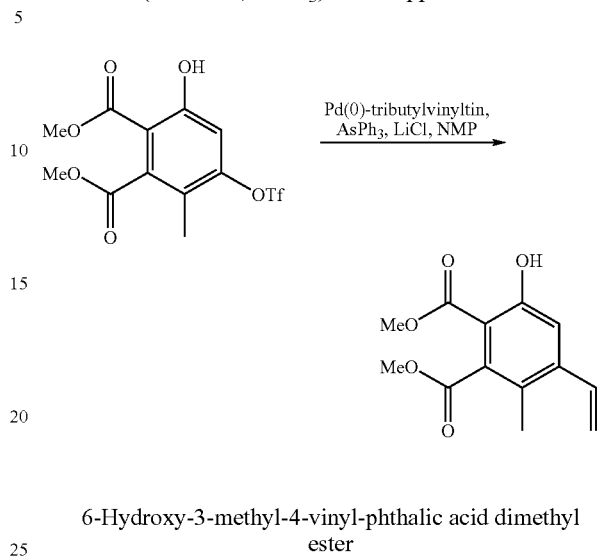

6-Hydroxy-3-methyl-4-vinyl-phthalic acid dimethyl ester

To a solution of 6-hydroxy-3-methyl-4-trifluoromethanesulfonyloxy-phthalic acid dimethyl ester (2.17 g, 5.85 mmol) in N-methylpyrolidinone (15 mL) was added lithium chloride (743 mg, 17.5 mmol) and triphenylarsine (179 mg, 0.585 mmol). Tributylvinyltin (2.04 g, 6.43 mmol) was added followed by tris(tribenzylideneacetone)dipalladium(0)-chloroform adduct (90 mg, 0.087 mmol). The reaction was placed under an atmosphere of nitrogen and heated at 60° C. for 18 hours. The reaction was cooled to room temperature and poured onto a mixture of ice (20 g), EtOAc (40 mL), and potassium fluoride (1 g). Stirring was continued for 1 hour. The aqueous layer was extracted with EtOAc and the organic extracts filtered through Celite. The combined organic layers were washed with water and dried over sodium sulfate. Filtration and evaporation of solvents in vacuo yielded a crude material, which was purified by silica gel chromatography to provide 1.27 g (87%) of the product as an off-white solid. $^1$H NMR (300 MHz, CDCl$_3$): δ=2.16 (s, 3H), 3.91 (s, 3H), 3.92 (s, 3H), 5.46 (dd, J=11.1, 1.2 Hz, 1H), 5.72 (dd, J=17.1, 0.9 Hz, 1H), 6.86 (dd, J=17.1, 11.1 Hz, 1H), 7.14 (s, 1H), 10.79 (s, 1H) ppm.

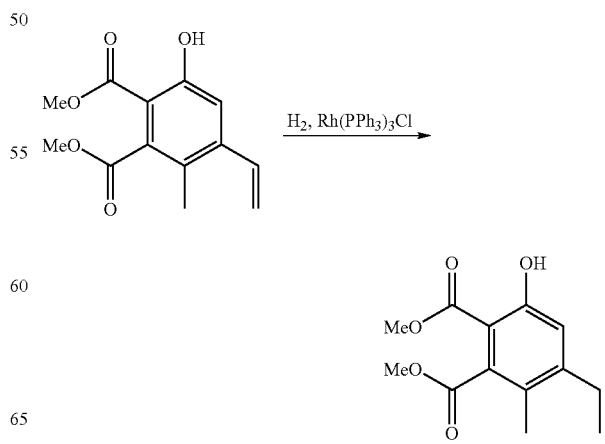

4-Ethyl-6-hydroxy-3-methyl-phthalic acid dimethyl ester

6-Hydroxy-3-methyl-4-vinyl-phthalic acid dimethyl ester (1.27 g, 5.11 mmol) was dissolved in benzene (10 mL) and EtOAc (10 mL). Tristriphenylphosphine rhodium chloride (150 mg) was added and the reaction was placed under an atmosphere of hydrogen. Stirring at room temperature was continued. After 14 hours, the solvents were removed in vacuo and the crude material was purified by silica gel chromatography to provide 1.14 g (88%) of the desired product as an off-white solid. $^1$H NMR (300 MHz, CDCl$_3$): δ=1.19 (t, J=7.8 Hz, 3H), 2.10 (s, 3H), 2.60 (q, J=7.8 Hz, 2H), 3.89 (s, 6H), 6.87 (s, 1H), 10.79 (s, 1H) ppm.

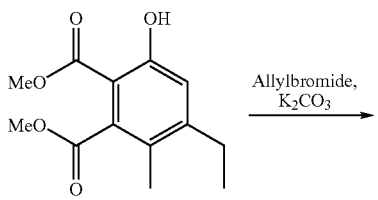

4-Ethyl-6-hydroxy-3-methyl-phthalic acid dimethyl ester (1.01 g, 4.02 mmol) was dissolved in DMF (5 mL). Potassium carbonate (3.33 g, 24.14 mmol) was added, followed by allylbromide (2.92 g, 24.14 mmol). The suspension was heated at 60° C. After 14 hours, the reaction was cooled to room temperature and filtered. The solvents were removed in vacuo and the crude material was purified by silica gel chromatography to provide 0.976 g (83%) of the desired product as a colorless oil. $^1$H NMR (300 MHz, CDCl$_3$): δ=1.16 (t, J=7.2 Hz, 3H), 2.20 (s, 3H), 2.62 (q, J=7.2 Hz, 2H), 3.83 (s, 3H), 3.84 (s, 3H), 4.57 (m, 2H), 5.26 (dd, J=9.3, 1.5 Hz, 1H), 5.41 (dd, J=13.5, 1.5 Hz, 1H), 5.98 (m, 1H), 6.82 (s, 1H) ppm.

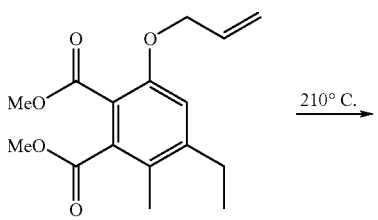

1 6-Allyloxy-4-ethyl-3-methyl-phthalic acid dimethyl ester

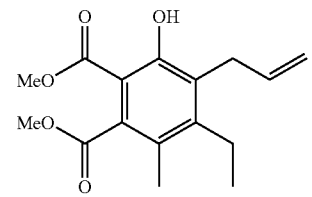

4-Allyl-5-ethyl-3-hydroxy-6-methyl-phthalic acid dimethyl ester

6-Allyloxy-4-ethyl-3-methyl-phthalic acid dimethyl ester (1.25 g, 4.28 mmol) was heated at 210° C. under an atmosphere of nitrogen. After 14 hours, the reaction was cooled to room temperature. The crude material was purified by silica gel chromatography to provide 0.971 g (77%) of the desired product as a colorless oil. $^1$H NMR (300 MHz, CDCl$_3$): δ=1.14 (t, J=7.8 Hz, 3H), 2.17 (s, 3H), 2.68 (q, J=7.8 Hz, 2H), 3.49 (m, 2H), 3.86 (s, 3H), 3.89 (s, 3H), 4.89-5.01 (m, 2H), 5.93 (m, 1H), 11.22 (s, 1H) ppm.

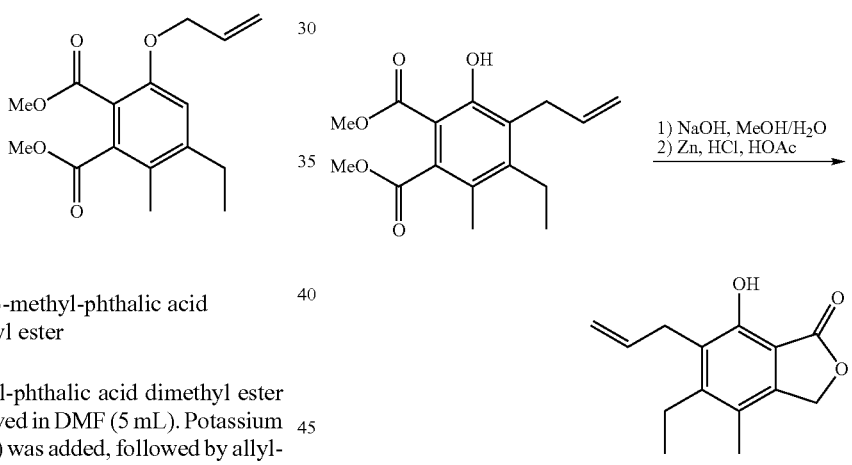

5 6-Allyl-5-ethyl-7-hydroxy-4-methyl-3H-isobenzofuran-1-one

4-Allyl-5-ethyl-3-hydroxy-6-methyl-phthalic acid dimethyl ester (0.971 g, 3.32 mmol) was dissolved in MeOH (8 mL) at room temperature. A solution of sodium hydroxide (0.798 g, 19.95 mmol) in water (10 mL) was added and the suspension was heated at 55° C. After 16 hours, the reaction was cooled to room temperature and washed with diethyl ether. The aqueous layer was acidified (1N HCl) and the suspension was extracted with EtOAc. The combined organic layers were dried over sodium sulfate. Filtration and evaporation of solvents in vacuo yielded the desired bis acid as a white solid (0.846 g, 98%, M$^+$=263). The bis acid was dissolved in acetic acid (6 mL) and HCl (conc., 1.5 mL). The reaction was heated at 80° C. Zn dust (0.635 g, 9.72 mmol, each) was added in portions every hour for 7 hours. Stirring at 80° C. was continued for additional 10 hours. The reaction was cooled to room temperature, and water was added. The resultant suspension was extracted with EtOAc. The combined organic extracts were washed with sodium bicarbonate solution and dried over sodium sulfate. Filtration and evaporation of solvents in vacuo yielded the crude product, which was purified by silica gel chromatography to provide 0.375 g (50%) of the product as a white solid. $^1$H NMR (300 MHz, CDCl$_3$): δ=1.14 (t, J=7.5 Hz, 3H), 2.18 (s, 3H), 2.71 (q, J=7.5 Hz, 2H), 3.49 (m, 2H), 4.95 (d, J=17.1 Hz, 1H), 5.02 (d, J=10.2 Hz, 1H), 5.23 (s, 2H), 5.98 (m, 1H), 7.66 (s, 1H) ppm.

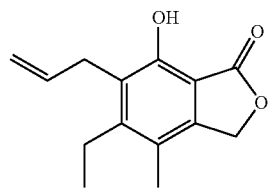 2-TMS-ethanol, PPh$_3$, DIAD, THF

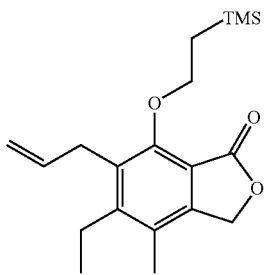

5 6-Allyl-5-ethyl-4-methyl-7-(2-trimethylsilanyl-ethoxy)$_3$H-isobenzofuran-1-one To a solution of 6-allyl-5-ethyl-7-hydroxy-4-methyl-3H-isobenzofuran-1-one (199 mg, 0.857 mmol), PPh$_3$ (337 mg, 1.286 mmol), and 2-trimethylsilylethanol in THF (3 mL) at 0° C. was added diisopropyl azodicarboxylate (259 mg, 1.286 mmol). The resulting yellow solution was allowed to warm to room temperature and stirred for one hour. The solvent was removed in vacuo and the crude material was dissolved in diethyl ether (3 mL). Hexanes (1.5 mL) were added. Triphenylphosphine oxide was removed by filtration and the filtrate was concentrated and purified by silica gel chromatography to provide the desired product (261 mg, 92%) as a clear oil. $^1$H NMR (300 MHz, CDCl$_3$): δ=0.04 (s, 9H), 1.15 (t, J=7.8 Hz, 3H), 1.25 (m, 2H), 2.20 (s, 3H), 2.73 (q, J=7.8 Hz, 2H), 3.54 (m, 2H), 4.28 (m, 2H), 4.95 (d, J=17.1 Hz, 1H), 5.02 (d, J=10.2 Hz, 1H), 5.15 (s, 2H), 5.95 (m, 1H) ppm.

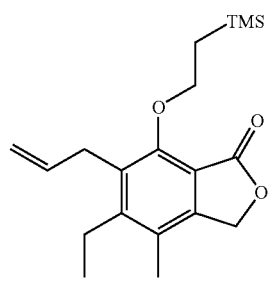 O$_3$, DCM, MeOH thiourea

-continued

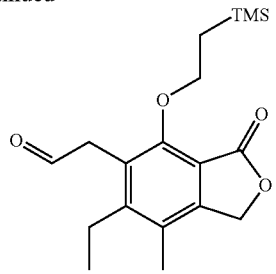

[6-Ethyl-7-methyl-3-oxo-4-(2-trimethylsilanyl-ethoxy)-1,3-dihydro-isobenzofuran-5-yl]-acetaldehyde A solution of 6-allyl-5-ethyl-4-methyl-7-(2-trimethylsilanyl-ethoxy)-3H-isobenzofuran-1-one (261 mg, 0.788 mmol) in MeOH (5 mL), CH$_2$Cl$_2$ (5 mL) and pyridine (50 μL) was cooled to −78° C. using a dry ice/acetone bath according to the procedure of Smith, D. B. et al., *J. Org. Chem.*, 1996, 61, 6, 2236. A stream of ozone was bubbled through the reaction via a gas dispersion tube until the reaction became blue in color (15 minutes). The ozone line was replaced with a stream of nitrogen and bubbling continued for another 15 minutes, by which time the blue color had disappeared. To this solution, at −78° C., was added thiourea (59.9 mg, 0.788 mmol) in one portion, and the cooling bath was removed. The reaction was allowed to warm to room temperature and stirred for 15 hours. The reaction mixture was filtered and then partitioned between CH$_2$Cl$_2$ and water. The aqueous layer was extracted with CH$_2$Cl$_2$ one more time and the organic extracts were combined, washed with aqueous 1N HCl, saturated NaHCO$_3$ and brine and dried over sodium sulfate. Filtration and evaporation of solvents in vacuo yielded the crude product, which was purified by silica gel chromatography to afford 181 mg (69%) of the product as a white solid. $^1$H NMR (300 MHz, CDCl$_3$): δ=0.04 (s, 9H), 1.11 (t, J=7.5 Hz, 3H), 1.19 (m, 2H), 2.21 (s, 3H), 2.66 (q, J=7.5 Hz, 2H), 3.90 (s, 2H), 4.36 (m, 2H), 5.18 (s, 2H), 9.71 (s, 1H) ppm.

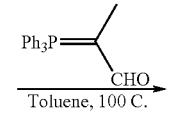 Ph$_3$P=<br/>Toluene, 100 C.

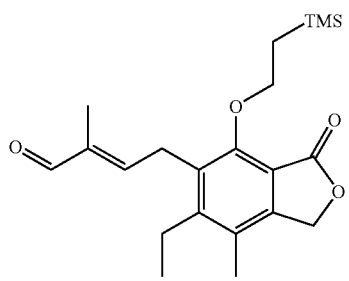

4-[6-Ethyl-7-methyl-3-oxo-4-(2-trimethylsilanyl-ethoxy)-1,3-dihydro-isobenzofuran-5-yl]-2-methyl-but-2-enal

[6-Ethyl-7-methyl-3-oxo-4-(2-trimethylsilanyl-ethoxy)-1,3-dihydro-isobenzofuran-5-yl]-acetaldehyde (90 mg, 0.269 mmol) and 2-(triphenyl-phosphorylidene)-propionaldehyde (72.9 mg, 0.23 mmol) in toluene (3 mL) were heated at 100° C. After 15 hours, a second portion of 2-(triphenyl-phosphanylidene)-propionaldehyde (33 mg, 0.111 mmol) was added and the reaction mixture was heated for additional 9 hours. The toluene was removed in vacuo, and the residue was purified by silica gel chromatography to provide 77.6 mg (77%) of the desired product as a pale yellow oil. $^1$H NMR (300 MHz, CDCl$_3$): δ=0.03 (s, 9H), 1.15 (t, J=7.5 Hz, 3H), 1.21 (m, 2H), 1.93 (s, 3H), 2.21 (s, 3H), 2.71 (q, J=7.5 Hz, 2H), 3.82 (d, J=6.9 Hz, 2H), 4.34 (m, 2H), 5.18 (s, 2H), 6.38 (m, 1H), 9.35 (s, 1H) ppm.

5-Ethyl-6-(4-hydroxy-3-methyl-but-2-enyl)$_4$-methyl-7-(2-trimethylsilanyl-ethoxy)-3H-isobenzofuran-1-one 4-[6-Ethyl-7-methyl-3-oxo-4-(2-trimethylsilanyl-ethoxy)-1,3-dihydro-isobenzofuran-5-yl]-2-methyl-but-2-enal (77.6 mg, 0.207 mmol) was dissolved in MeOH (4 mL). A solution of CeCl$_3$ (51.1 mg, 0.207 mmol) in MeOH/water (9/1, 0.66 mL) was added and the solution was cooled to 0° C. A solution of lithium borohydride in THF (2M, 0.105 mL) was added dropwise. After 15 minutes, the reaction was quenched with 1N HCl (0.5 mL). The MeOH was removed in vacuo and the crude material was partitioned between DCM and water. The aqueous layer was extracted with DCM and the combined organic layers were washed with sodium bicarbonate solution and dried over sodium sulfate. Filtration and evaporation of solvents yielded a crude oil, which was purified by silica gel chromatography to provide 57.2 mg (73%) of the desired product. $^1$H NMR (300 MHz, CDCl$_3$): δ=0.04 (s, 9H), 1.15 (t, J=7.8 Hz, 3H), 1.26 (m, 2H), 1.86 (s, 3H), 2.19 (s, 3H), 2.72 (q, J=7.8 Hz, 2H), 3.52 (d, J=6.3 Hz, 2H), 3.99 (s, 2H), 4.34 (m, 2H), 5.14 (s, 2H), 5.32 (m, 1H) ppm.

6-(4-Bromo-3-methyl-but-2-enyl)-5-ethyl-4-methyl-7-(2-trimethylsilanyl-ethoxy)-3H-isobenzofuran-1-one 5-Ethyl-6-(4-hydroxy-3-methyl-but-2-enyl)-4-methyl-7-(2-trimethylsilanyl-ethoxy)-3H-isobenzofuran-1-one (57.2 mg, 0.152 mmol) was dissolved in DCM (3.5 mL). Polymer-bound triphenylphosphine (3 mmol/g, 152.1 mg) was added and the mixture was mechanically stirred at room temperature. Carbon tetrabromide (151.3 mg, 0.456 mmol) was added and the solution was stirred at room temperature. After 2 hours, the reaction was filtered and the solvent was removed in vacuo. The crude material was purified by silica gel chromatography to provide 58.0 mg (87%) of the desired product. $^1$H NMR (300 MHz, CDCl$_3$): δ=0.04 (s, 9H), 1.15 (t, J=7.8 Hz, 3H), 1.25 (m, 2H), 1.95 (s, 3H), 2.20 (s, 3H), 2.70 (q, J=7.8 Hz, 2H), 3.52 (d, J=6.3 Hz, 2H), 3.94 (s, 2H), 4.28 (m, 2H), 5.14 (s, 2H), 5.50 (m, 1H) ppm.

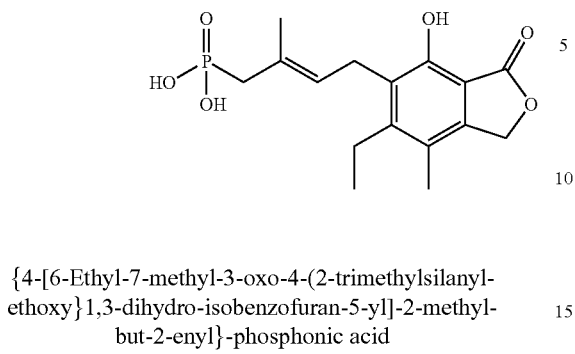

{4-[6-Ethyl-7-methyl-3-oxo-4-(2-trimethylsilanyl-ethoxy}1,3-dihydro-isobenzofuran-5-yl]-2-methyl-but-2-enyl}-phosphonic acid A solution of 4-[6'-ethyl-7'-methyl-3'-oxo-4'-(2"-trimethylsilanyl-ethoxy)-1',3'-dihydro-isobenzofuran-5'-yl]-2-methyl-but-2-enyl bromide (58 mg, 0.132. mmol) in trimethylphosphite (0.8 mL) was heated at 110° C. After 2 hours the reaction was complete. The reaction was cooled to room temperature and the excess trimethylphosphite was removed in vacuo. The crude material was used in the next step without further purification.

The crude product of the Arbuzov reaction was dissolved in MeCN (0.8 mL). Trimethylsilyl bromide (202.2 mg, 1.321 mmol) was added and the reaction was stirred at room temperature. After 15 minutes, lutidine (155.7 mg, 1.453 mmol) was added and stirring at room temperature was continued. After 2 hours, additional trimethylsilyl bromide (202.2 mg, 1.321 mmol) was added and stirring at room temperature was continued. After 4 hours, the reaction was quenched with MeOH (2 mL). The solvents were evaporated in vacuo, and the crude material was purified by RP-HPLC (eluent: water/MeCN). The product-containing fractions were combined and lyophilized to yield 2.3 mg (5.1%) of the free phosphonic acid. $^1$H NMR (300 MHz, DMSO-$d_6$): δ=1.07 (t, J=7.5 Hz, 3H), 1.84 (s, 3H), 2.14 (s, 3H), 2.64 (q, J=7.5 Hz, 2H), 3.34 (m, 4H), 5.06 (m, 1H), 5.25 (s, 2H) ppm; $^{31}$P NMR (121 MHz, DMSO-$d_6$): δ=22.19 ppm; MS=341 [M$^+$+1].

EXAMPLE 277

Preparation of Representative Compounds of the Invention

Representative compounds of the invention can be prepared as illustrated below.

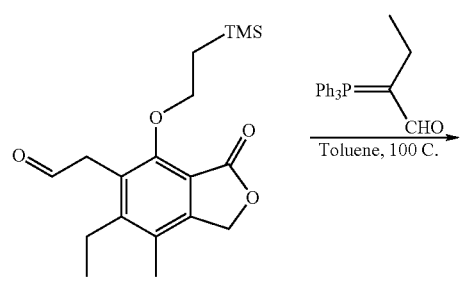

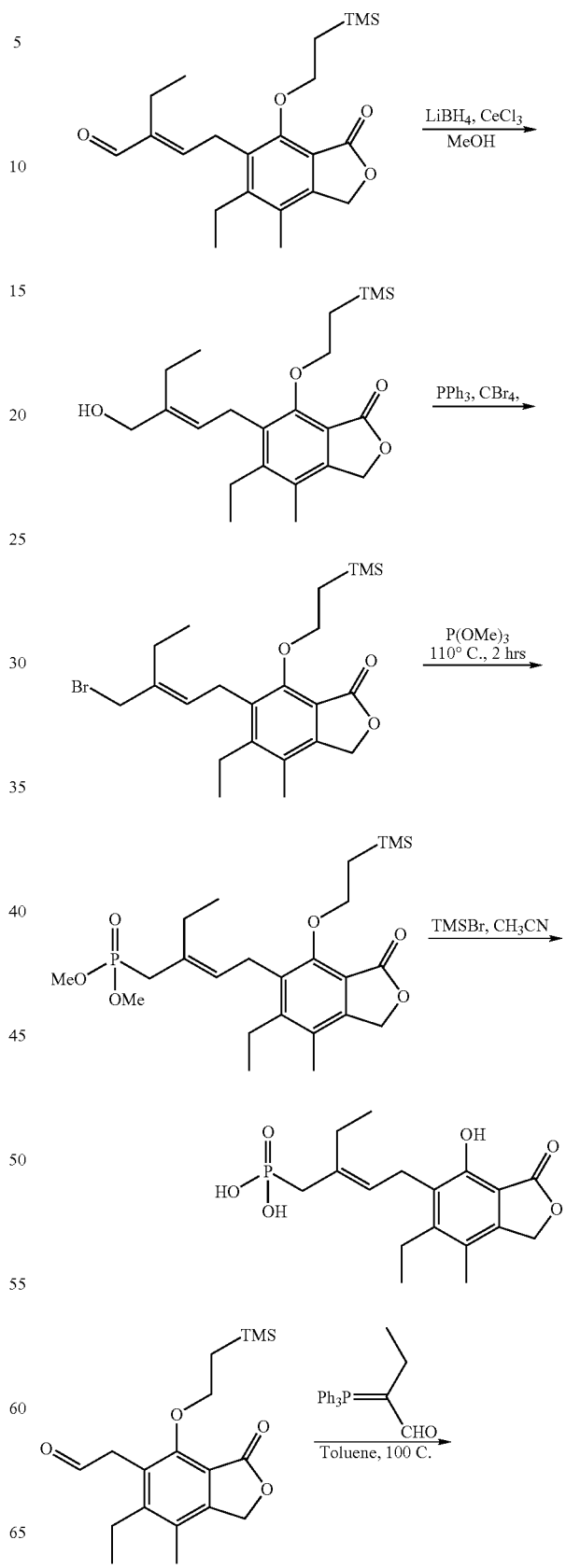

-continued

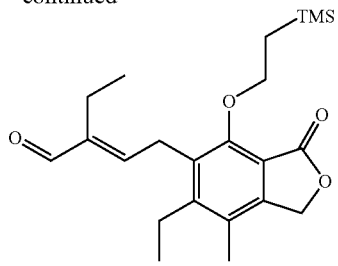

2-Ethyl-4-[6-ethyl-7-methyl-3-oxo-4-(2-trimethylsilanyl-ethoxy)-1,3-dihydro-isobenzofuran-5-yl]-but-2-enal

[6-Ethyl-7-methyl-3-oxo-4-(2-trimethylsilanyl-ethoxy)-1,3-dihydro-isobenzofuran-5-yl]-acetaldehyde (90 mg, 0.269 mmol) and 2-(triphenyl-phosphorylidene)-butyraldehyde (98.4 mg, 0.296 mmol) in toluene (3 mL) were heated at 100° C. After 15 hours, a second portion of 2-(triphenyl-phosphanylidene)-butyraldehyde (98.4 mg, 0.296 mmol) was added and the reaction mixture was heated for additional 33 hours. After concentration, the residue was purified by silica gel chromatography to provide 50.3 mg (48%) of the desired product as a pale yellow oil.

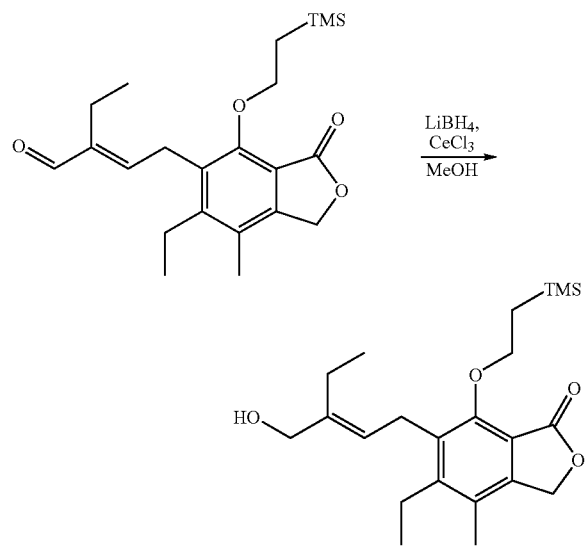

5-Ethyl-6-(3-hydroxymethyl-pent-2-enyl)$_4$-methyl-7-(2-trimethylsilanyl-ethoxy)-3H-isobenzofuran-1-one 2-Ethyl-4-[6-ethyl-7-methyl-3-oxo-4-(2-trimethylsilanyl-ethoxy)-1,3-dihydro-isobenzofuran-5-yl]-but-2-enal (50.3 mg, 0.129 mmol) was dissolved in MeOH (3 mL). A solution of CeCl$_3$ (31.9 mg, 0.129 mmol) in MeOH/water (9/1, 0.66 mL) was added and the solution was cooled to 0° C. A solution of lithium borohydride in THF (2M, 0.065 mL) was added dropwise. After 10 minutes, the reaction was quenched with 1N HCl (0.5 mL). The methanol was removed in vacuo and the crude material was partitioned between DCM and water. The aqueous layer was extracted with DCM and the combined organic layers were washed with sodium bicarbonate solution and were dried over sodium sulfate. Filtration and evaporation of solvents in vacuo yielded a crude oil, which was purified by silica gel chromatography to provide 35.4 mg (70%) of the desired product. $^1$H NMR (300 MHz, CDCl$_3$): δ=0.04 (s, 9H), 1.10-1.19 (m, 6H), 1.26 (m, 2H), 2.19 (s, 3H), 2.32 (q, J=7.5 Hz, 2H), 2.72 (q, J=7.5 Hz, 2H), 3.54 (d, J=6.6 Hz, 2H), 4.05 (s, 2H), 4.26 (m, 2H), 5.14 (s, 2H), 5.27 (m, 1H) ppm.

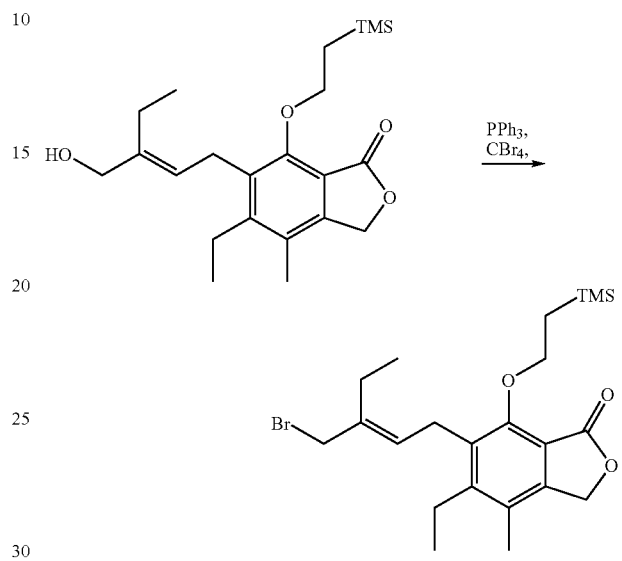

6-(3-Bromomethyl-pent-2-enyl)-5-ethyl-4-methyl-7-(2-trimethylsilanyl-ethoxy)-3H-isobenzofuran-1-one 5-Ethyl-6-(3-hydroxymethyl-pent-2-enyl)-4-methyl-7-(2-trimethylsilanyl-ethoxy)-3H-isobenzofuran-1-one (35.4 mg, 0.090 mmol) was dissolved in DCM (3.0 mL). Polymer-bound triphenylphosphine (3 mmol/g, 90.7 mg) was added, and the mixture was mechanically stirred at room temperature. Carbon tetrabromide (90.2 mg, 0.272 mmol) was added and the solution was stirred at room temperature. After 2 hours, the reaction was filtered and the solvent was removed in vacuo. The crude material was purified by silica gel chromatography to provide 32.0 mg (78%) of the desired product. The material was used in the next step without further characterization.

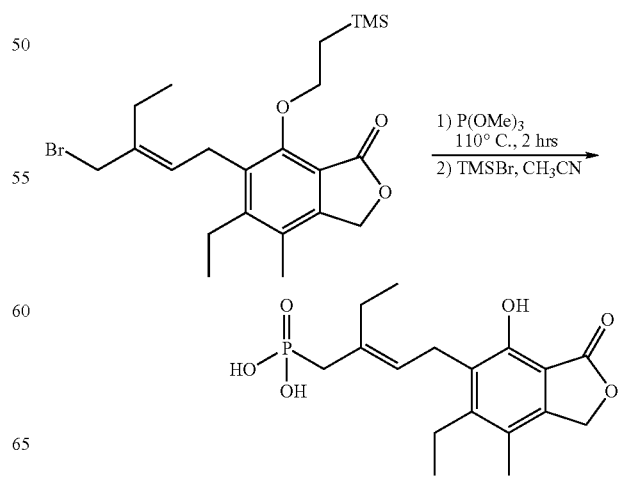

[2-Ethyl-4-(6-ethyl-4-hydroxy-7-methyl-3-oxo-1,3-dihydro-isobenzofuran-5-yl)-but-2-enyl]-phosphonic acid A solution of 6-(3-bromomethyl-pent-2-enyl)-5-ethyl-4-methyl-7-(2-trimethylsilanyl-ethoxy)-3H-isobenzofuran-1-one (32 mg, 0.070 mmol) in trimethylphosphite (0.8 mL) was heated at 110° C. After 2 hours, the reaction was complete. The reaction was cooled to room temperature and the excess trimethylphosphite was removed in vacuo. The crude material was used in the next step without further purification.

The crude product of the Arbuzov reaction was dissolved in MeCN (0.8 mL). Trimethylsilyl bromide (108.0 mg, 0.706 mmol) was added and the reaction was stirred at room temperature. After 2 hours, a second batch of trimethysilyl bromide (108.0 mg, 0.706 mmol) was added. After 3 hours, the reaction was quenched with MeOH (2 mL). The solvents were evaporated in vacuo and the crude material was purified by RP-HPLC (eluent: water/MeCN). The product-containing fractions were combined and lyophilized to yield 15.7 mg (63%) of the product. $^1$H NMR (300 MHz, DMSO-$d_6$): δ=0.98-1.09 (m, 6H), 2.10 (s, 3H), 2.30 (m, 2H), 2.64 (q, J=7.5 Hz, 2H), 3.38 (m, 4H), 5.03 (m, 1H), 5.25 (s, 2H) ppm; 31P NMR (121 MHz, DMSO-$d_6$): δ=22.26 ppm; MS=355 [M$^+$+1].

EXAMPLE 278

Preparation of Representative Compounds of the Invention

Representative compounds of the invention can be prepared as illustrated below.

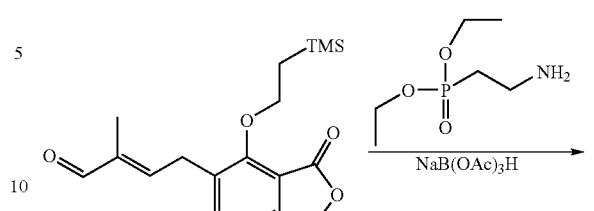

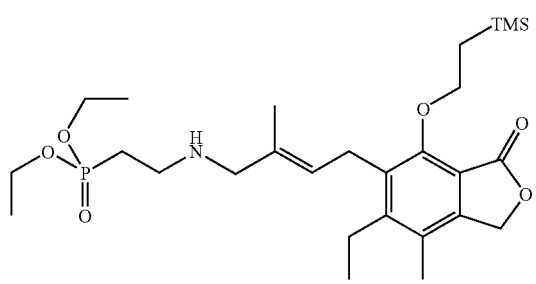

(2-{4-[6-Ethyl-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester 4-[6-Ethyl-7-methyl-3-oxo-4-(2-trimethylsilanyl-ethoxy)-1,3-dihydro-isobenzofuran-5-yl]-2-methyl-but-2-enal (19.7 mg, 0.052 mmol) and aminoethylphosphonic acid diethylester oxalate salt (15.6 mg, 0.057 mmol) were dissolved in DMF (0.5 mL). Acetic acid (15.7 mg, 0.263 mmol) was added, followed by sodium triacetoxyborohydride (22.3 mg, 0.105 mmol). After 4 hours, the crude reaction mixture was purified by RP-HPLC (eluent: water/MeCN) to provide 27.7 mg (97%) of the desired product after lyophilization. $^1$H NMR (300 MHz, CDCl$_3$): δ=0.04 (s, 9H), 1.14 (t, J=7.5 Hz, 3H), 1.26 (m, 2H), 1.30 (t, J=7.2 Hz, 6H), 1.95 (s, 3H), 2.19 (s, 3H), 2.23 (m, 2H), 2.68 (q, J=7.5 Hz, 2H), 3.18 (m, 2H), 3.53 (s, 2H), 4.13 (m, 4H), 4.28 (m, 2H), 5.15 (s, 2H), 5.51 (m, 1H) ppm; $^{31}$P NMR (121 MHz, CDCl$_3$): δ=27.39 ppm; MS=540 [M$^+$+1].

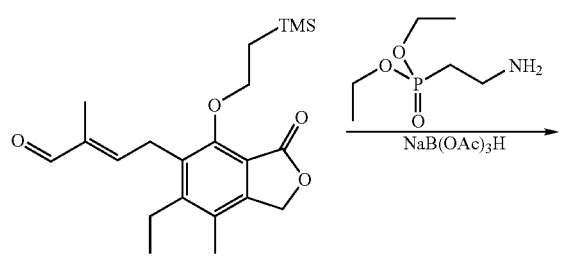

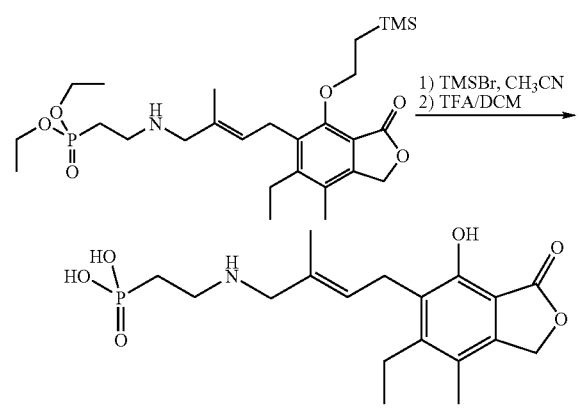

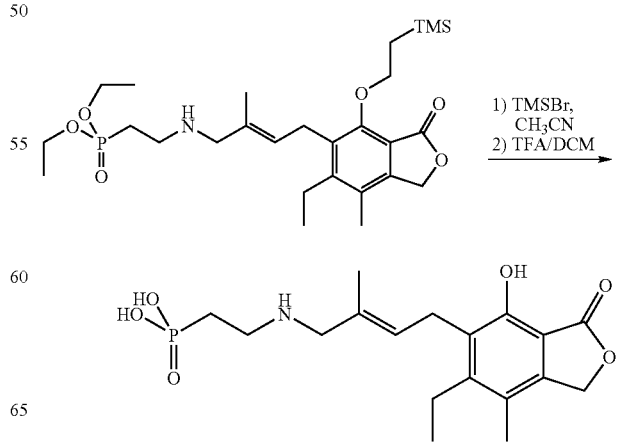

889

{2-[4-(6-Ethyl-4-hydroxy-7-methyl-3-oxo-1,3-dihydro-isobenzofuran-5-yl)-2-methyl-but-2-enylamino]-ethyl}-phosphonic acid (2-{4-[6-Ethyl-7-methyl-3-oxo-4-(2-trimethylsilanyl-ethoxy)-1,3-dihydro-isobenzofuran-5-yl]-2-methyl-but-2-enylamino}-ethyl)-phosphonic acid diethyl ester (27.7 mg, 0.051 mmol) was dissolved in DMF (0.5 mL) and DCM (0.5 mL). Trimethylsilyl bromide (78.3 mg, 0.512 mmol) was added and the reaction was stirred at room temperature. After 20 hours, the reaction was quenched with MeOH (0.3 mL). The solvents were evaporated in vacuo and the crude material was purified by RP-HPLC (eluent: water/MeCN). The product-containing fractions were combined and lyophilized to yield 14.2 mg (57%) of the free phosphonic acid [MS: 484 M$^+$+1].

The material was dissolved in DCM (0.5 mL). TFA (0.05 mL) was added and stirring at room temperature was continued. After 20 minutes, the solvents were removed in vacuo and the crude material was purified by RP-HPLC (eluent: water/MeCN*0.1% TFA). The product-containing fractions were combined and lyophilized to yield 7.6 mg (52%) of the product as the TFA salt. $^1$H NMR (300 MHz, DMSO-d$_6$): δ=1.07 (t, J=7.5 Hz, 3H), 1.84 (s, 3H), 1.90 (m, 2H), 2.11 (s, 3H), 2.63 (q, J=7.5 Hz, 2H), 2.99 (m, 2H), 3.43 (d, J=6.3 Hz, 2H), 3.51 (s, 2H), 5.26 (s, 2H), 5.45 (m, 1H) ppm; $^{31}$P NMR (121 MHz, DMSO-d$_6$): δ=20.02 ppm; MS=384 [M$^+$+1].

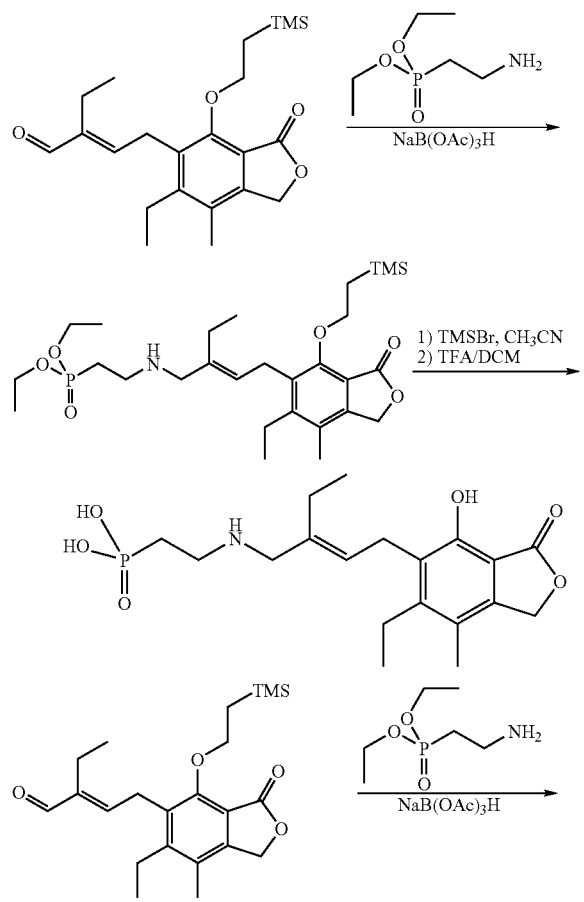

890

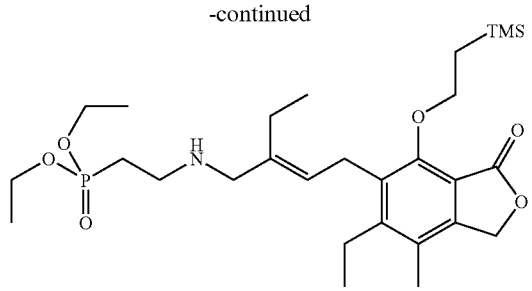

(2-{2-Ethyl-4-[6-ethyl-7-methyl-3-oxo-4-(2-trimethylsilanyl-ethoxy)-1,3-dihydro-isobenzofuran-5-yl]-but-2-enylamino}-ethyl)-phosphonic acid diethyl ester 2-Ethyl-4-[6-ethyl-7-methyl-3-oxo-4-(2-trimethylsilanyl-ethoxy)-1,3-dihydro-isobenzofuran-5-yl]-but-2-enal (26.6 mg, 0.068 mmol) and aminoethylphosphonic acid diethyl-ester oxalate salt (20.4 mg, 0.075 mmol) were dissolved in DMF (0.8 mL). Acetic acid (20.5 mg, 0.342 mmol) was added, followed by sodium triacetoxyborohydride (27.6 mg, 0.137 mmol). After 8 hours, the crude reaction mixture was purified by RP-HPLC (eluent: water/MeCN) to provide 24.9 mg (65%) of the desired product after lyophilization. $^1$H NMR (300 MHz, CDCl$_3$): δ=0.05 (s, 9H), 1.10-1.24 (m, 8H), 1.35 (t, J=7.5 Hz, 6H), 2.19 (s, 3H), 2.23 (m, 2H), 2.35 (q, J=7.8 Hz, 2H), 2.70 (q, J=7.2 Hz, 2H), 3.25 (m, 2H), 3.56 (m, 4H), 4.15 (m, 4H), 4.29 (m, 2H), 5.15 (s, 2H), 5.47 (m, 1H) ppm; $^{31}$P NMR (121 MHz, CDCl$_3$): δ=27.71 ppm; MS=554 [M$^+$+1].

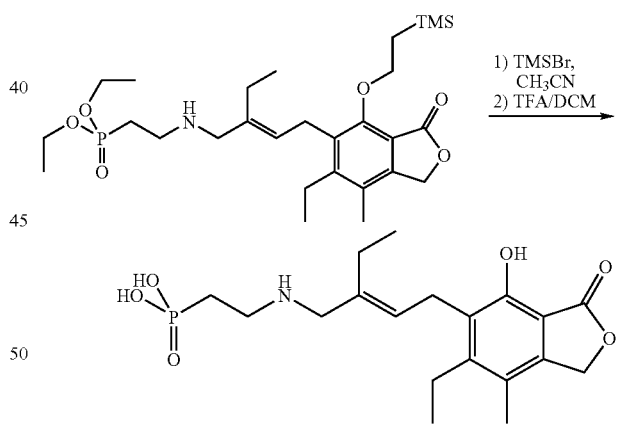

{2-[2-Ethyl-4-(6-ethyl-4-hydroxy-7-methyl-3-oxo-1,3-dihydro-isobenzofuran-5-yl)-but-2-enylamino]-ethyl}-phosphonic acid (2-{2-Ethyl-4-[6-ethyl-7-methyl-3-oxo-4-(2-trimethylsilanyl-ethoxy)-1,3-dihydro-isobenzofuran-5-yl]-but-2-enylamino}-ethyl)-phosphonic acid diethyl ester (24.9 mg, 0.045 mmol) was dissolved in DMF (0.5 mL) and DCM (0.5 mL). Trimethylsilyl bromide (68.7 mg, 0.449 mmol) was added and the reaction was stirred at room temperature. After 20 hours, the reaction was quenched with MeOH (0.15 mL). The solvents were evaporated in vacuo and the crude material was

891 purified by RP-HPLC (eluent: water/MeCN). The product-containing fractions were combined and lyophilized to yield 8.0 mg of the free phosphonic acid [MS: 498 M$^+$+1].

This material was dissolved in DCM (0.5 mL). TFA (0.05 mL) was added, and stirring at room temperature was continued. After 20 minutes, the solvents were removed in vacuo and the crude material was purified by RP-HPLC (eluent: water/MeCN*0.1% TFA). The product-containing fractions were combined and lyophilized to yield 4.4 mg (54%) of the product as the TFA salt. $^1$H NMR (300 MHz, DMSO-d$_6$): δ=1.05 (m, 6H), 1.60 (m, 2H), 2.10 (s, 3H), 2.67 (q, J=7.5 Hz, 2H), 2.63 (q, J=6.9 Hz, 2H), 2.93 (m, 2H), 3.45 (m, 4H), 5.24 (s, 2H), 5.36 (m, 1H) ppm.; $^{31}$P NMR (121 MHz, DMSO-d$_6$): δ=16.93 ppm; MS=398 [M$^+$+1].

EXAMPLE 279

Preparation of Representative Compounds of the Invention

Representative compounds of the invention can be prepared as illustrated below.

892

2-({4-[6-Ethyl-7-methyl-3-oxo-4-(2-trimethylsilanyl-ethoxy)-1,3-dihydro isobenzofuran-5-yl]-2-methyl-but-2-enyl}-phenoxy-phosphinoylamino)-propionic acid ethyl ester 4-[6'-ethyl-7'-methyl-3'-oxo-4'-(2"-trimethylsilanyl-ethoxy)-1',3'-dihydro-isobenzofuran-5'-yl]-2-methyl-but-2-en-phosphonic acid (44.8 mg, 0.101 mmol), dicyclohexylcarbodiimide (52.6 mg, 0.254 mmol), and phenol (95.8 mg, 1.018 mmol) were dissolved in pyridine (0.3 mL) and heated at 70° C. for 4 hours. The reaction mixture was cooled to room temperature and the pyridine was removed in vacuo. The crude material was partitioned between DCM and HCl (0.1N). The aqueous layer was extracted with DCM and the combined organic layers were dried over sodium sulfate. Filtration and evaporation of solvents in vacuo yielded a crude material, which was used in the next step without further purification.

The crude material was dissolved in MeCN (0.8 mL) and water (0.3 mL). Aqueous sodium hydroxide solution (2N, 0.8 mL) was added in portions (0.2 mL). After all starting material was consumed, the organic solvent was removed in vacuo and the crude material was partitioned between chloroform

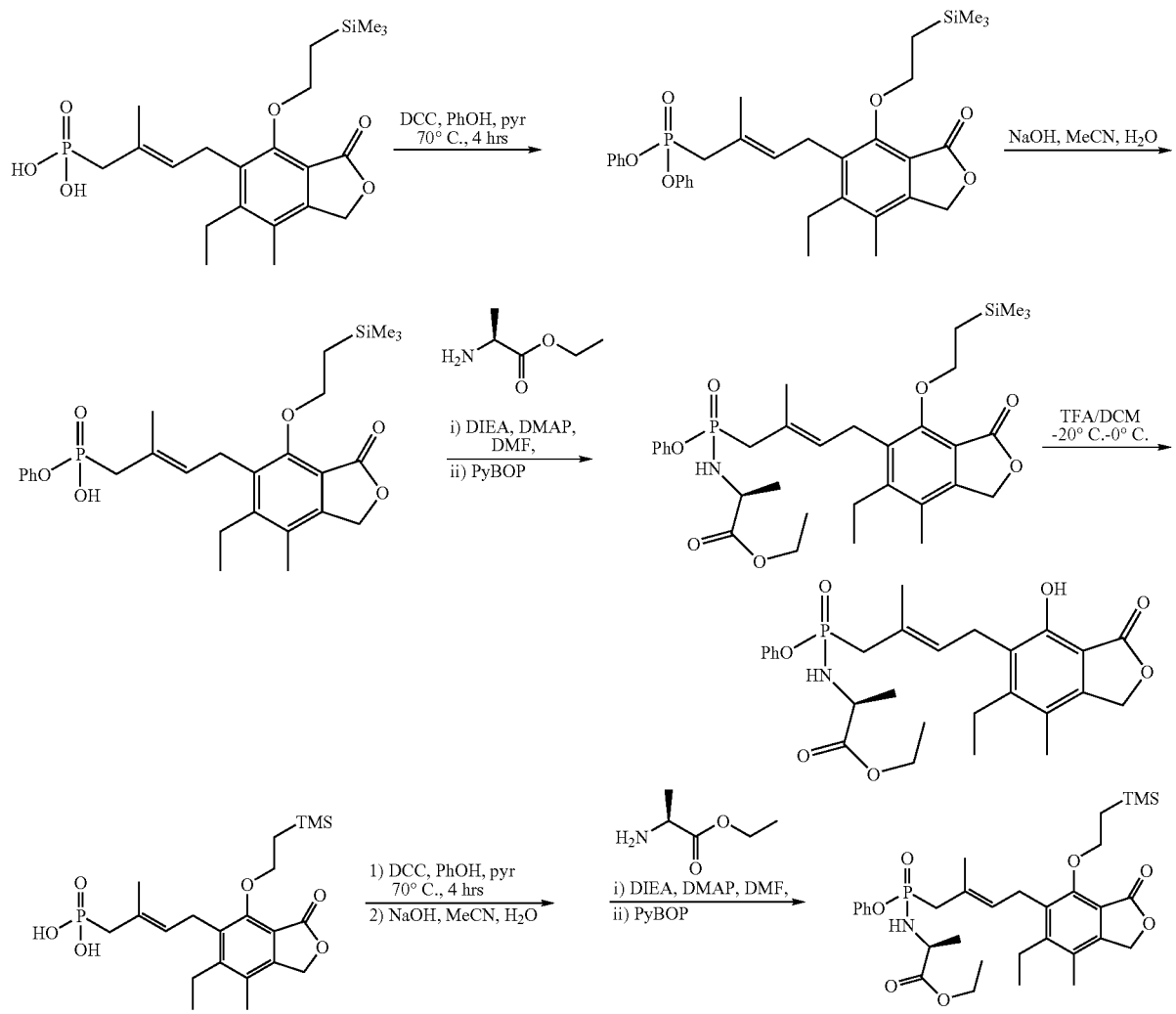

and aqueous HCl (1N). The aqueous layer was extracted with chloroform. The combined organic layers were dried over sodium sulfate. Filtration and evaporation of solvents yielded the crude product as a mixture of mono phenyl ester and the symmetrical anhydride.

The crude material of the previous step and ethyl (L)-alanine hydrochloride salt (78.1 mg, 0.509 mmol) were dissolved in DMF (0.4 mL). DMAP (1.2 mg, catalytic) was added, followed by diisopropylethylamine (131.3 mg, 1.018 mmol). Stirring at room temperature was continued. After 20 minutes, complete conversion of the anhydride was observed. After 2 hours, PyBOP (101 mg, 0.202 mmol) was added and stirring at room temperature was continued. The reaction was filtered and the crude reaction solution was purified by RP-HPLC (eluent: water/MeCN). The product-containing fractions were combined and lyophilized to yield the product (15.7 mg, 25% over three steps) as a white powder. $^1$H NMR (300 MHz, CDCl$_3$): δ=0.03 (s, 9H), 1.13-1.28 (m, 8H), 2.03 (s, 3H), 2.19 (s, 3H), 2.62-2.74 (m, 4H), 3.38 (m, 1H), 3.53 (t, J=6.3 Hz, 2H), 4.03 (m, 3H), 4.30 (m, 2H), 5.14 (s, 2H), 5.31 (m, 1H), 7.11-7.17 (m, 3H), 7.25-7.30 (m, 2H) ppm; $^{31}$P NMR (121 MHz, CDCl$_3$): δ=27.04, 27.73 ppm; MS=615 [M$^+$+1].

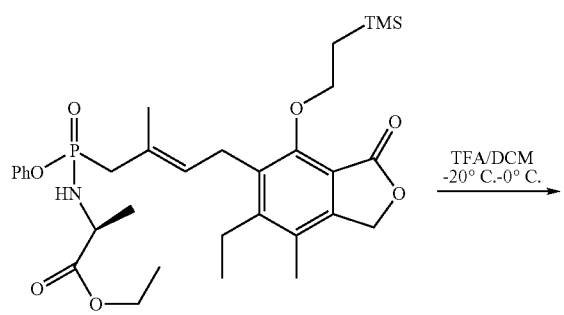

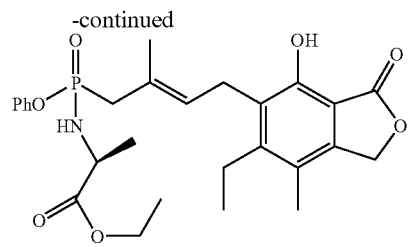

2-{[4-(6-Ethyl-4-hydroxy-7-methyl-3-oxo-1,3-dihydro-isobenzofuran-5-yl)-2-methyl-but-2-enyl]-phenoxy-phosphinoylamino}-propionic acid ethyl ester 2-({4-[6-Ethyl-7-methyl-3-oxo-4-(2-trimethylsilanyl-ethoxy)-1,3-dihydro-isobenzofuran-5-yl]-2-methyl-but-2-enyl}-phenoxy-phosphinoylamino)-propionic acid ethyl ester (7.5 mg, 0.012 mmol) was dissolved in TFA/DCM (10%, 0.3 mL) at −20° C. The reaction mixture was warmed to 0° C. and stirred at this temperature for 45 minutes. Pyridine (0.09 mL) was added the solvents were removed in vacuo. The crude material was purified by RP-HPLC (eluent: water/MeCN). The product-containing fractions were combined and lyophilized, yielding a white powder (5.5 mg, 87%). $^1$H NMR (300 MHz, CDCl$_3$): δ=1.12-1.29 (m, 6H), 2.03 (s, 3H), 2.17 (s, 3H), 2.65-2.74 (m, 4H), 3.38 (m, 1H), 3.53 (t, J=6.3 Hz, 2H), 4.03 (m, 3H), 5.22 (s, 2H), 5.36 (m, 1H), 7.11-7.16 (m, 3H), 7.24-7.30 (m, 2H), 7.72 (m, 1H) ppm; $^{31}$P NMR (121 MHz, CDCl$_3$): δ=27.11, 27.57 ppm; MS=515 [M$^+$+1].

EXAMPLE 280

Preparation of Representative Compounds of the Invention

Representative compounds of the invention can be prepared as illustrated below.

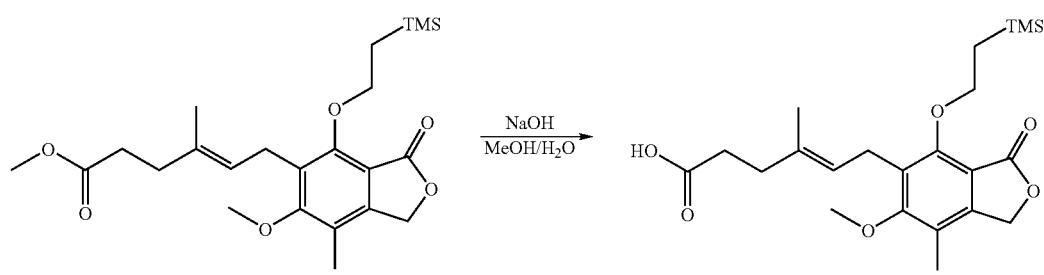

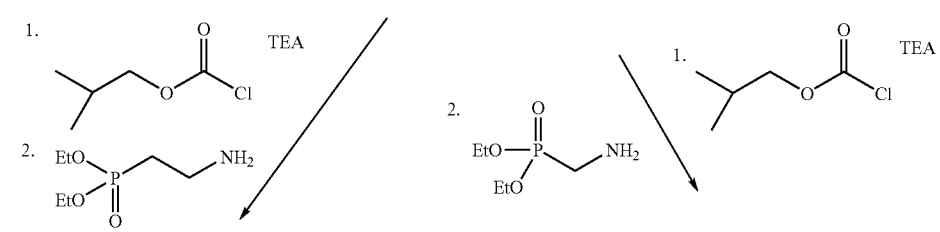

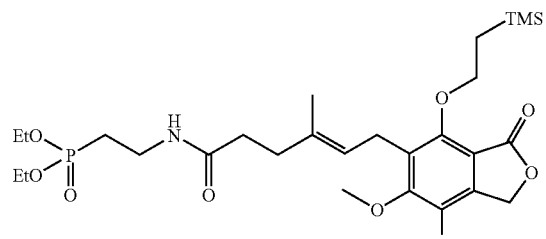

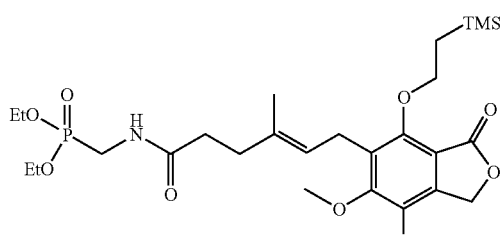

TMSBr, 2,6-lutidine ↓          TMSBr, 2,6-lutidine ↓

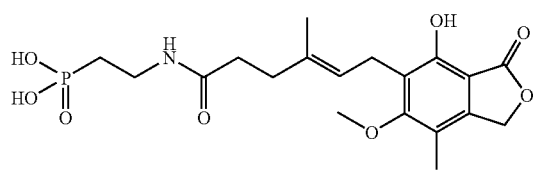

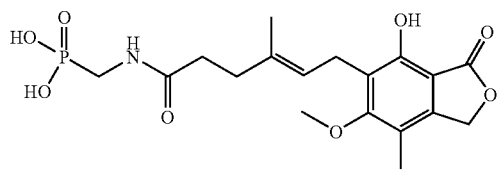

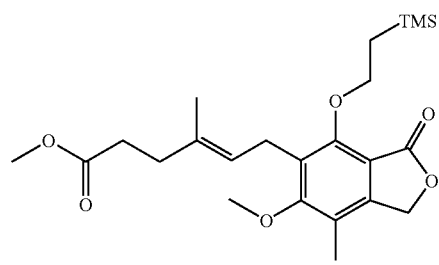

NaOH / MeOH/H₂O →

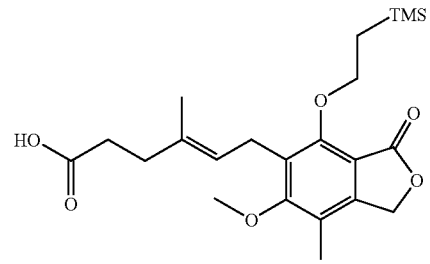

6-[6-Methoxy-7-methyl-3-oxo-4-(2-trimethylsilanyl-ethoxy)-1,3-dihydro-isobenzofuran-5-yl]4-methyl-hex-4-enoic acid A mixture of 6-[6-methoxy-7-methyl-3-oxo-4-(2-trimethylsilanyl-ethoxy)-1,3-dihydro-isobenzofuran-5-yl]-4-methyl-hex-4-enoic acid methyl ester (1.5 g, 3.45 mmol) and sodium hydroxide (552 mg) in a mixture of methanol (20 mL) and water (7 mL) was stirred at room temperature for one hour. The solution was acidified with 1N HCl. The precipitate was collected by suction filtration and washed with water to give the desired product (1.2 g, 83%). $^1$H NMR (300 MHz, CDCl$_3$) δ 0.02 (s, 9H), 1.15-1.22 (m, 2H), 1.76 (s, 3H), 2.13 (s, 3H), 2.12-2.28 (m, 2H), 2.35-2.41 (m, 2H), 3.37 (d, 2H, J=7 Hz), 3.71 (s, 3H), 4.22-4.28 (m, 2H), 5.07 (s, 2H), 5.13-5.17 (m, 1H) ppm; MS (m/z) 419.3 [M−H]$^-$, 443.2 [M+Na]$^+$.

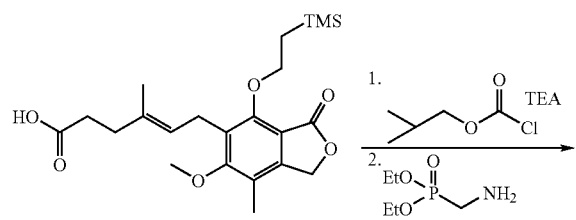

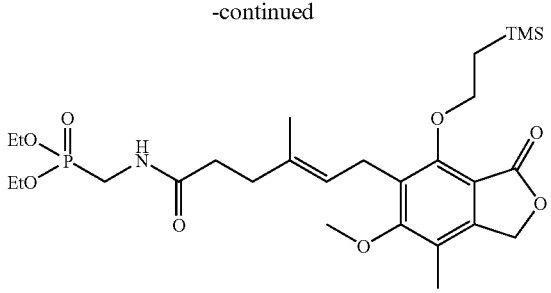

({6-[6-Methoxy-7-methyl-3-oxo-4-(2-trimethylsilanyl-ethoxy)-1,3-dihydro-isobenzofuran-5-yl]4-methyl-hex-4-enoylamino}-methyl)-phosphonic acid diethyl ester To a solution of 6-[6-methoxy-7-methyl-3-oxo-4-(2-trimethylsilanyl-ethoxy)-1,3-dihydro-isobenzofuran-5-yl]-4-methyl-hex-4-enoic acid (50 mg, 0.12 mmol) in THF (1 mL) was added isobutyl chloroformate (17 µL, 0.13 mmol) and triethylamine (50 µL, 0.36 mmol) at 0° C. After stirring at 0° C. for 2 hours, diethyl (aminomethyl) phosphonate oxalate (62 mg, 0.26 mmol) was added and stirring was continued at room temperature for 20 minutes. After removal of solvent, the residue was purified by preparative reverse-phase HPLC to afford 54.8 mg (81%) of the desired product. ¹H NMR (300 MHz, CDCl₃) δ 0.03 (s, 9H), 1.15-1.22 (m, 2H), 1.31 (t, 6H), 1.81 (s, 3H), 2.18 (s, 3H), 2.30 (m, 4H), 3.41 (d, 2H, J=7 Hz), 3.65 (dd, 2H, J=6, 12 Hz), 3.77 (s, 3H), 3.77-4.16 (m, 4H), 4.26-4.32 (m,2H), 5.12 (s, 2H), 5.17-5.19 (m, 1H), 5.86 (bs, 1H) ppm; ³¹P (121.4 MHz, CDCl₃) δ 23.01 ppm; MS (m/z) 568 [M−H]⁻, 592 [M+Na]⁺.

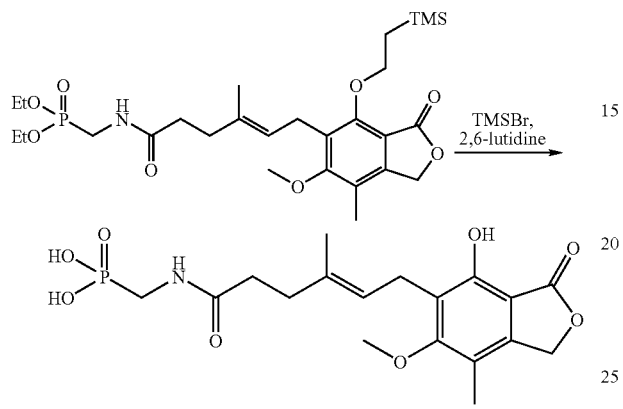

{[6-(4-Hydroxy-6-methoxy-7-methyl-3-oxo-1,3-dihydro-isobenzofuran-5-yl)-4-methyl-hex-4-enoylamino]methyl}-phosphonic acid To a solution of ({6-[6-methoxy-7-methyl-3-oxo-4-(2-trimethylsilanyl-ethoxy)-1,3-dihydro-isobenzofuran-5-yl]-4-methyl-hex-4-enoylamino}-methyl)-phosphonic acid diethyl ester (40 mg, 0.07 mmol) in acetonitrile (1 mL) was added TMSBr (91 μL, 0.7 mmol) followed by 2,6-lutidine (81.5 μL, 0.7 mmol). The reaction was allowed to proceed overnight when it was completed as judged by LCMS. The reaction mixture was quenched with MeOH and concentrated to dryness. The residue was purified by preparative reverse-phase HPLC to afford 2.6 mg (9%) of desired product as a white solid. ¹H NMR (300 MHz, CD₃OD) δ 1.67 (s, 3H), 2.17 (m, 5H), 2.30-2.46 (m, 2H), 2.80-2.86 (m, 2H), 3.55 (m, 2H), 3.82 (s, 3H), 5.26 (s, 3H) ppm; ³¹P (121.4 MHz, CD₃OD) δ 10.27 ppm; MS (m/z) 412 [M−H]⁻, 414 [M+H]⁺.

EXAMPLE 281

Preparation of Representative Compounds of the Invention

Representative compounds of the invention can be prepared as illustrated below.

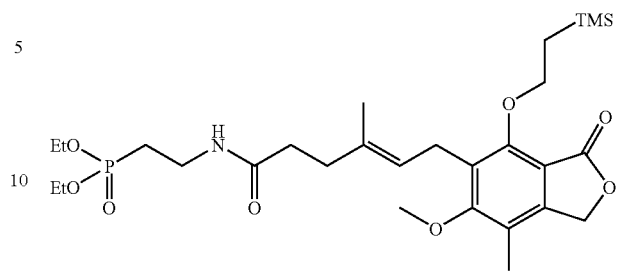

(2-{6-[6-Methoxy-7-methyl-3-oxo-4-(2-trimethylsilanyl-ethoxy)-1,3-dihydro-isobenzofuran-5-yl]4-methyl-hex-4-enoylamino}-ethyl)-phosphonic acid diethyl ester To a solution of 6-[6-methoxy-7-methyl-3-oxo-4-(2-trimethylsilanyl-ethoxy)-1,3-dihydro-isobenzofuran-5-yl]-4-methyl-hex-4-enoic acid (50 mg, 0.12 mmol) in THF (1 mL) was added isobutyl chloroformate (17 μL, 0.13 mmol) and triethylamine (50 μL, 0.36 mmol) at 0° C. After stirring at 0° C. for 2 hours, diethyl (aminoethyl) phosphonate oxalate (62 mg, 0.26 mmol) was added and stirred at room temperature was continued for one hour. After removal of solvent, the residue was purified by preparative reverse-phase HPLC to afford 37 mg (54%) of the desired product as a white solid. ¹H NMR (300 MHz, CDCl₃) δ 0.03 (s, 9H), 1.15-1.22 (m, 2H), 1.31 (t, 6H), 1.81 (s, 3H), 1.85-1.93 (m,2H), 2.18 (s, 3H), 2.30 (m, 4H), 3.41 (d, 2H, J=7 Hz), 3.48-3.54 (m, 2H), 3.77 (s, 3H), 3.77-4.16 (m, 4H), 4.26-4.32 (m,2H), 5.12 (s, 2H), 5.17-5.19 (m, 1H), 6.30 (bs, 1H) ppm; ³¹P (121.4 MHz, CDCl₃) δ 29.91 ppm; MS (m/z) 584 [M+H]⁺.

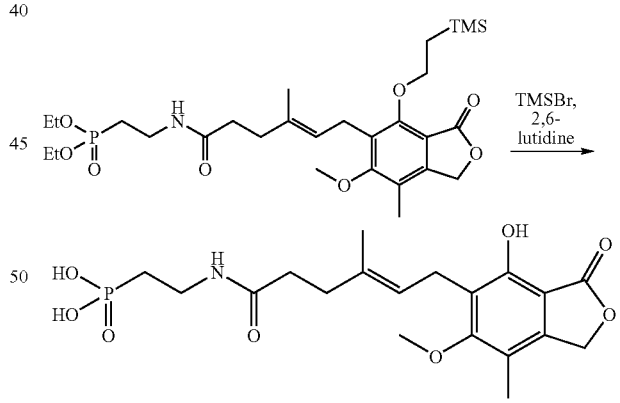

{2-[6-(4-Hydroxy-6-methoxy-7-methyl-3-oxo-1,3-dihydro-isobenzofuran-5-yl)-4-methyl-hex-4-enoylamino]-ethyl}-phosphonic acid To a solution of (2-{6-[6-methoxy-7-methyl-3-oxo-4-(2-trimethylsilanyl-ethoxy)-1,3-dihydro-isobenzofuran-5-yl]-4-methyl-hex-4-enoylamino}-ethyl)-phosphonic acid diethyl ester (36.6 mg, 0.063 mmol) in acetonitrile (1 mL) was added TMSBr (81 μL, 0.63 mmol) followed by 2,6-lutidine (73 μL, 0.63 mmol). The reaction was allowed to proceed overnight, when it was completed as judged by LCMS. The reaction mixture was quenched with MeOH and concentrated to dryness. The residue was purified by preparative reverse-phase HPLC to afford 5.8 mg (29%) of desired product as a white solid. $^1$H NMR (300 MHz, CD$_3$OD) δ 1.80 (s, 3H), 2.14 (m, 5H), 2.25 (m, 4H), 3.35 (m, 2H), 3.38-3.38 (m, 2H), 3.75 (s, 3H), 5.23 (s, 3H) ppm; $^{31}$P (121.4 MHz, CD$_3$OD) δ 26.03 ppm; MS (m/z) 426 [M−H]$^−$, 428 [M+H]$^+$.

EXAMPLE 282

Preparation of Representative Compounds of the Invention

Representative compounds of the invention can be prepared as illustrated below.

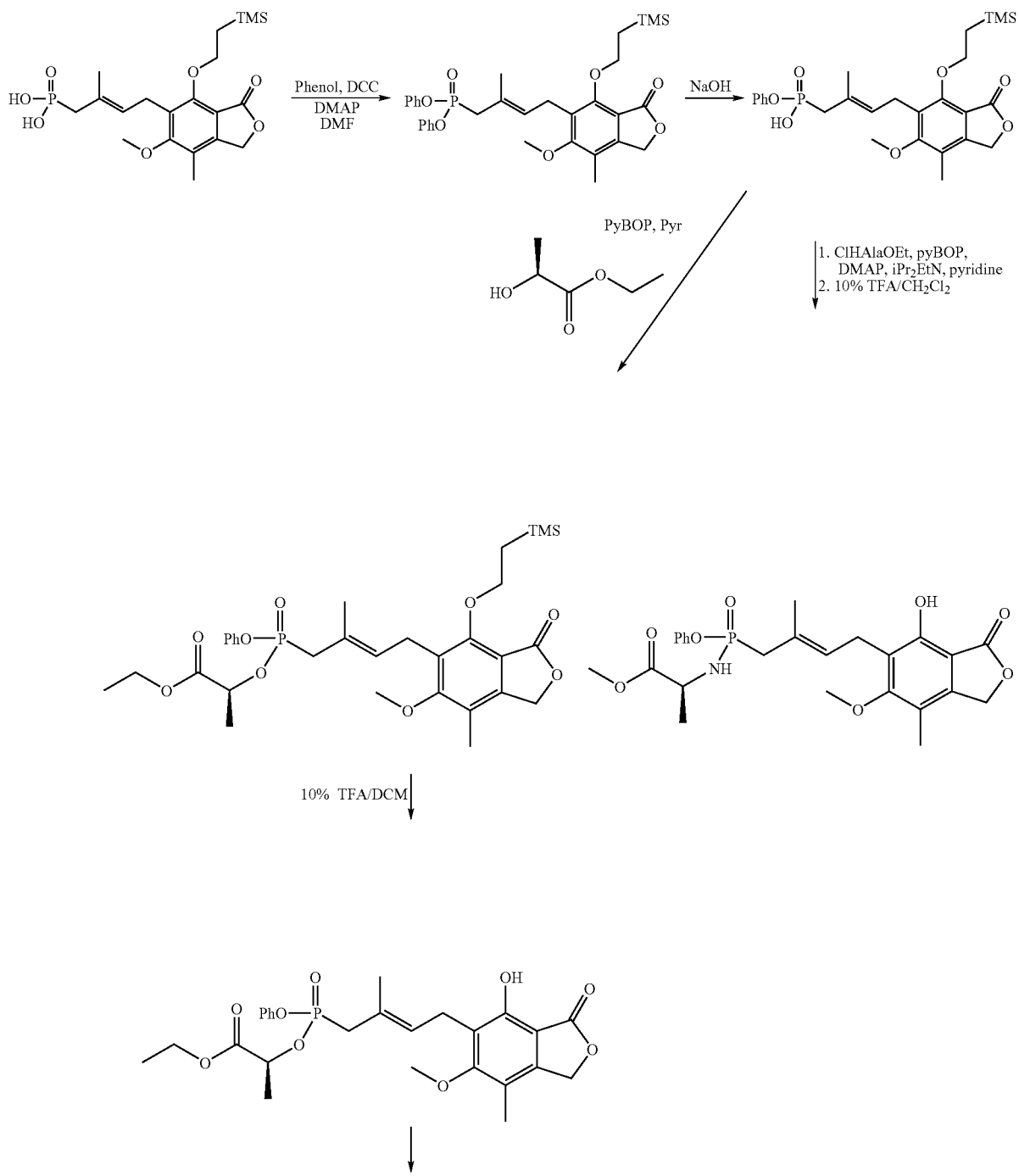

-continued

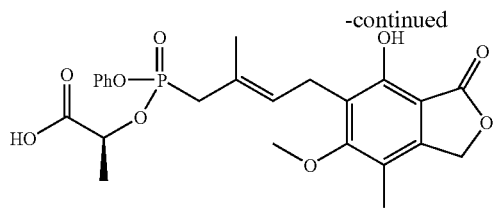

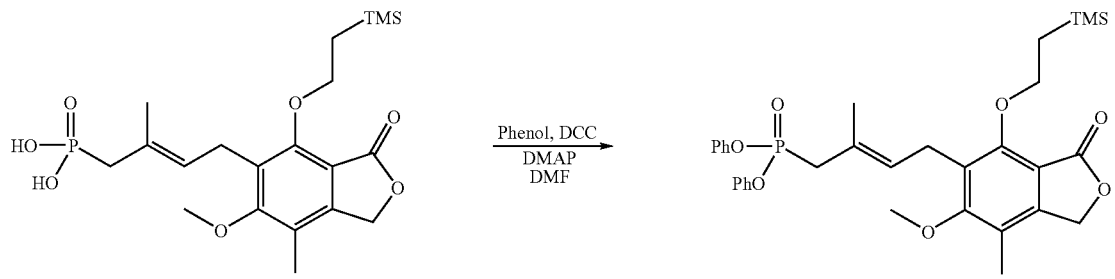

4-[6-Methoxy-7-methyl-3-oxo-4-(2-trimethylsilanyl-ethoxy)-1,3-dihydro-isobenzofuran-5-yl]-2-methyl-but-2-enyl}-phosphonic acid diphenyl ester To a solution of [{4-[6-methoxy-7-methyl-3-oxo-4-(2-tri-methylsilanyl-ethoxy)-1,3-dihydro-isobenzofuran-5-yl]-2-methyl-but-2-enyl}-phosphonic acid (260 mg, 0.59 mmol) in DMF (6 mL) and phenol (555 mg, 5.9 mmol) was added dicyclohexyl carbodiimide (1.21 g, 5.9 mmol) and DMAP (36 mg, 0.295 mmol). The reaction mixture was heated to 140° C. for 30 minutes. After cooling to room temperature, the mixture was partitioned between EtOAc/Hexane (1:1) and 5% aqueous LiCl solution. The organic layer was washed with 5% aqueous LiCl solution repeatedly, then dried over Na$_2$SO$_4$. After removal of solvent, the residue was purified by silica gel chromatography to provide 75 mg (21%) of the desired product. MS (m/z) 617 [M+Na]$^+$.

{4-[6-Methoxy-7-methyl-3-oxo-4-(2-trimethylsila-nyl-ethoxy)-1,3-dihydro-isobenzofuran-5-yl]-2-methyl-but-2-enyl}-phosphonic acid monophenyl ester To a solution of {4-[6-methoxy-7-methyl-3-oxo-4-(2-tri-methylsilanyl-ethoxy)-1,3-dihydro-isobenzofuran-5-yl]-2-methyl-but-2-enyl}-phosphonic acid diphenyl ester (75 mg, 0.126 mmol) in THF (5 mL) was added 1N NaOH (0.1 mL) solution. The mixture was allowed to stir at room temperature for 16 hours. EtOAc was added and the resulting mixture was washed with 1H HCl. The organic layer was concentrated to dryness and the residue was purified by RP HPLC using a C18 column with a gradient of H$_2$O, 0.1% TFA-acetonitrile, 0.1% TFA to provide 24.8 mg (38%) of the desired product. MS (m/z) 517 [M−H]$^-$, 541 [M+Na]$^+$.

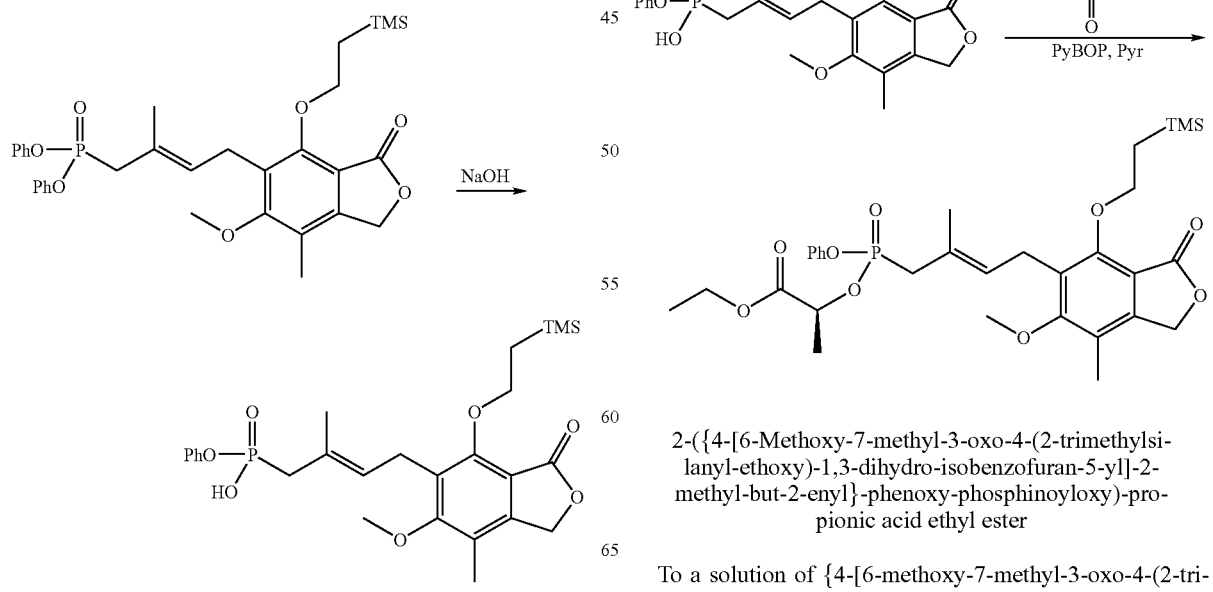

2-({4-[6-Methoxy-7-methyl-3-oxo-4-(2-trimethylsi-lanyl-ethoxy)-1,3-dihydro-isobenzofuran-5-yl]-2-methyl-but-2-enyl}-phenoxy-phosphinoyloxy)-pro-pionic acid ethyl ester To a solution of {4-[6-methoxy-7-methyl-3-oxo-4-(2-tri-methylsilanyl-ethoxy)-1,3-dihydro-isobenzofuran-5-yl]-2- methyl-but-2-enyl}-phosphonic acid monophenyl ester (25 mg, 0.048 mmol) and ethyl (S)-(−)-lactate (34 mg, 0.288 mmol) in pyridine (1 mL) was added PyBOP (125 mg, 0.24 mmol). The solution was stirred at room temperature for 16 hours and concentrated. The residue was purified by RP HPLC using a C18 column with a gradient of H$_2$O, 0.1% TFA-acetonitrile, 0.1% TFA to provide 24 mg (83%) of the desired product. MS (m/z) 641 [M+Na]$^+$.

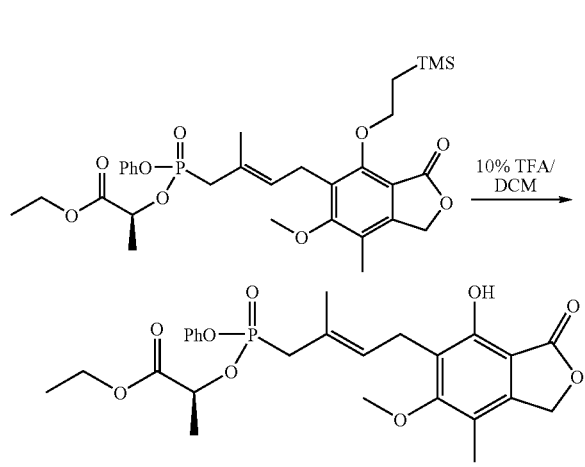

2-{[4-(4-Hydroxy-6-methoxy-7-methyl-3-oxo-1,3-dihydro-isobenzofuran-5-yl)-2-methyl-but-2-enyl]-phenoxy-phosphinoyloxy}-propionic acid ethyl ester To a solution of 2-({4-[6-methoxy-7-methyl-3-oxo-4-(2-trimethylsilanyl-ethoxy)-1,3-dihydro-isobenzofuran-5-yl]-2-methyl-but-2-enyl}-phenoxy-phosphinoyloxy)-propionic acid ethyl ester (24 mg, 0.039 mmol) in DCM (1 mL) was added TFA (0.5 mL) and the mixture was stirred at room temperature for 10 minutes. The reaction mixture was dried under reduced pressure and the residue was purified by RP-HPLC to provide 18 mg (90%) of the desired product as a clear oil. $^1$H NMR (300 MHz, CDCl$_3$) δ 1.18-1.34 (m, 3H), 1.36-1.48 (dd,3H), 2.02 (m, 3H), 2.17 (s, 3H), 2.78-2.98 (dd, 2H), 3.45 (m, 2H), 3.79 (s, 3H), 4.05-4.25 (m, 2H), 4.97 (m, 1H), 5.21 (s, 2H), 5.48 (t, J=7.2 Hz, 1H), 7.05-7.18 (m, 5H) ppm; $^{31}$P (121.4 MHz, CDCl$_3$) δ 24.59, 26.13 ppm; MS (m/z) 517 [M−H]$^−$, 519 [M+H]$^+$.

EXAMPLE 283

Preparation of Representative Compounds of the Invention

Representative compounds of the invention can be prepared as illustrated below.

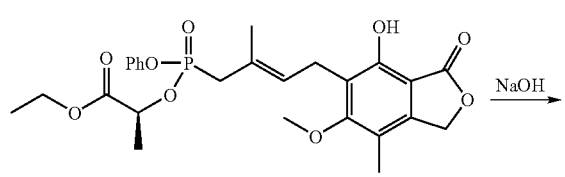

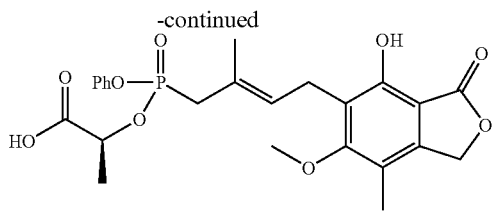

2-{[4-(4-Hydroxy-6-methoxy-7-methyl-3-oxo-1,3-dihydro-isobenzofuran-5-yl)-2-methyl-but-2-enyl]-phenoxy-phosphinoyloxy}-propionic acid To a solution of 2-{[4-(4-hydroxy-6-methoxy-7-methyl-3-oxo-1,3-dihydro-isobenzofuran-5-yl)-2-methyl-but-2-enyl]-phenoxy-phosphinoyloxy}-propionic acid ethyl ester (10 mg, 0.019 mmol) in THF (3 mL) was added 1N NaOH (232 µL), and the mixture was stirred at room temperature for 1 hour. The reaction mixture was dried under reduced pressure and the residue was purified by RP-HPLC to provide 6 mg (77%) of the desired product as a clear oil. $^1$H NMR (300 MHz, CD$_3$OD) δ 1.41 (d, J=7 Hz, 3H), 1.97 (s, 3H), 2.16 (s, 3H), 2.59 (d, J=22 Hz, 2H), 3.45 (m, 2H), 3.79 (s, 3H), 4.83 (m, 1H), 5.26 (s, 2H), 5.43 (t, J=7.2 Hz, 1H) ppm; $^{31}$P (121.4 MHz, CD$_3$OD) δ 27.02 ppm; MS (m/z) 413 [M−H]$^−$, 415 [M+H]$^+$.

EXAMPLE 284

Preparation of Representative Compounds of the Invention

Representative compounds of the invention can be prepared as illustrated below.

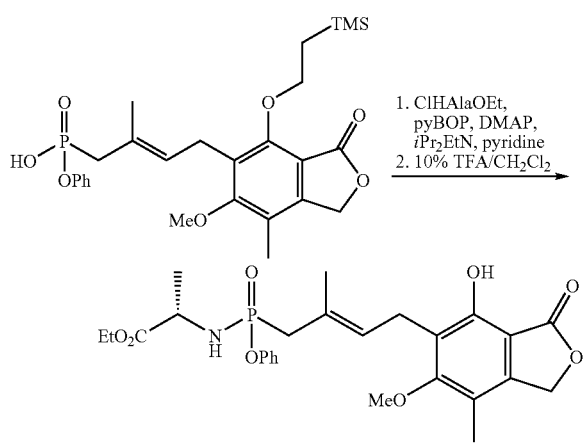

2-{[4-(4-Hydroxy-6-methoxy-7-methyl-3-oxo-1,3-dihydro-isobenzofuran-5-yl)-2-methyl-but-2-enyl]-phenoxy-phosphinoylamino}-propionic acid ethyl ester {4-[6-methoxy-7-methyl-3-oxo-4-(2-trimethylsilanyl-ethoxy)-1,3-dihydro-isobenzofuran-5-yl]-2-methyl-but-2- enyl}-phosphonic acid monophenyl ester (1 g, ~1.9 mmol) was combined with pyBOP (2 g, 4 mmol) and DMAP (120 mg, 0.96 mmol). A solution of L-alanine ethyl ester hydrochloride salt (2.9 g, 19 mmol) and diisopropylethylamine (6.7 mL, 38 mmol) in pyridine (5 mL) was added to the monoacid mixture and the reaction was stirred at room temperature for 12 hours. The reaction mixture was then concentrated and purified twice by column chromatography (1% MeOH/CH$_2$Cl$_2$ 3% MeOH/CH$_2$Cl$_2$). The resulting oil was dissolved in a vigorously-stirred solution of 10% TFA/CH$_2$Cl$_2$ (30 mL) at −40° C. The reaction was gradually warmed to 0° C. After about 3 hours, the reaction was complete. Pyridine (4.5 mL) was added, and the reaction mixture was concentrated. The product was purified by preparative TLC (5% MeOH/CH$_2$Cl$_2$) and concentrated to give 210 mg (21%) of the desired product as a light yellow oil. $^1$H NMR (300 MHz, CDCl$_3$) δ 7.83-7.70 (m, 1H), 7.30-7.20 (m, 2H), 7.18-7.03 (m, 3H), 5.60-5.35 (m, 1H), 5.21 (s, 2H), 4.17-3.95 (m, 3H), 3.79 (s, 3H), 3.60-3.40 (m, 3H), 2.80-2.60 (m, 2H), 2.17 (m, 3H), 2.01 (m, 3H), 1.30-1.10 (m, 6H) ppm; $^{31}$P NMR (121 MHz, CDCl$_3$) δ 28.0, 27.5 ppm; MS (m/z) 516 [M−H]$^-$.

EXAMPLE 285

Preparation of Representative Compounds of the Invention

Representative compounds of the invention can be prepared as illustrated below.

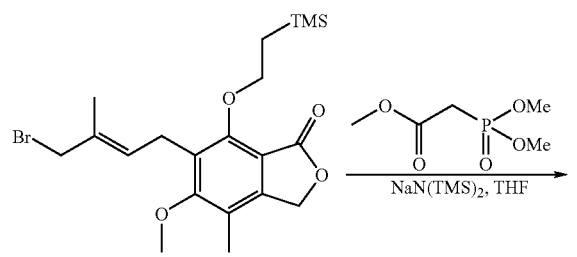

2-(Dimethoxy-phosphoryl)-6-[6-methoxy-7-methyl-3-oxo-4-(2-trimethylsilanyl-ethoxy)-1,3-dihydro-isobenzofuran-5-yl]4-methyl-hex-4-enoic acid methyl ester To a solution of trimethylphosphonoacetate (63 μL, 0.39 mmol) in THF (1 mL) was added NaN(TMS)$_2$ (0.39 mmol, 0.39 mL) at ambient temperature. After 30 minutes, a solution of 6-(4-bromo-3-methyl-but-2-enyl)-5-methoxy-4-methyl-7-(2-trimethylsilanyl-ethoxy)-3H-isobenzofuran-1-one (69 mg, 0.156 mmol) in THF (1 mL) was added. The reaction mixture was stirred for 2 hours, when a precipitate was observed. The reaction mixture was worked up by addition of a saturated aqueous solution of ammonium chloride and extraction of the product with EtOAc. The organic extract was dried and the product was purified using silica gel chromatography with 0-100% EtOAc-Hexanes to provide 40 mg of the desired product as a colorless oil. $^1$H NMR (300 MHz, CDCl$_3$) δ 0.05 (s, 9H), 1.20-1.26 (m, 2H), 1.79 (s, 3H), 2.17 (s, 3H), 2.42-2.72 (m, 2H), 3.19 (ddd, 1H, J=4, 12, 23 Hz), 3.39 (d, 2H, J=7 Hz), 3.62 (s, 3H), 3.75 (s, 3H), 3.77-3.84 (m, 6H), 4.27-4.34 (m, 2H), 5.12 (s, 2H), 5.24 (t, 1H, J=7 Hz) ppm; $^{31}$P (121.4 MHz, CDCl$_3$) δ 25.1 ppm; MS (m/z) 565.2 [M+Na]$^+$.

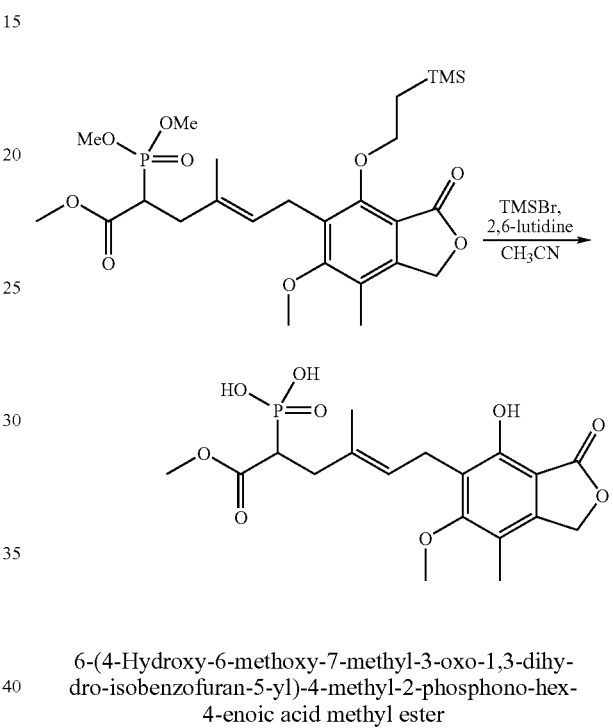

6-(4-Hydroxy-6-methoxy-7-methyl-3-oxo-1,3-dihydro-isobenzofuran-5-yl)-4-methyl-2-phosphono-hex-4-enoic acid methyl ester To a solution of 2-(dimethoxy-phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester (30 mg, 0.055 mmol) in acetonitrile (2 mL) was added trimethylsilyl bromide (0.18 mL). After 10 minutes, 2,6-lutidine (0.16 mL) was added to the reaction at ambient temperature. The reaction was allowed to proceed for 16 hours before it was concentrated to dryness. The residue was resuspended in a solution of DMF:H$_2$O (8:2, 1 mL) and purified by RP HPLC using a C18 column with a gradient of H$_2$O, 0.1% TFA-acetonitrile, 0.1% TFA to provide 18 mg of the product as a white powder. $^1$H NMR (300 MHz, CD$_3$OD) δ 1.81 (s, 3H), 2.16 (s, 3H), 2.40-2.49 (m, 1H), 2.63 (dt, 1H, J=6, 17 Hz), 3.07 (ddd, 1H, J=4,12,23 Hz), 3.38(3, 2H, J=7 Hz), 3.52 (s, 3H), 3.77 (s, 3H), 5.25 (s, 2H), 5.28 (t, 1H, J=7 Hz) ppm; $^{31}$P (121.4 MHz, CDCl$_3$) δ 19.5 ppm; MS (m/z) 415.2 [M+H]$^+$, 437.2 [M+Na]$^+$.

EXAMPLE 286

Preparation of Representative Compounds of the Invention

Representative compounds of the invention can be prepared as illustrated below.

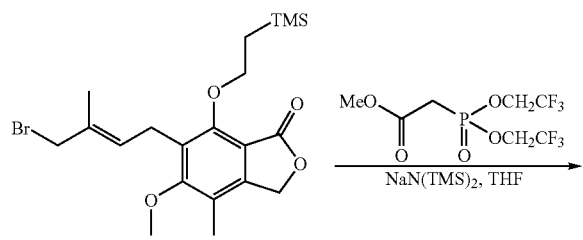

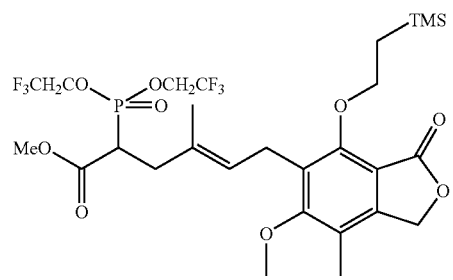

2-(Bis-(2,2,2-trifluoroethoxy)phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester To a solution of [bis-(2,2,2-trifluoro-ethoxy)-phosphoryl]-acetic acid methyl ester (186 μL, 0.88 mmol) in anhydrous THF (2 mL) was added a solution of 1N NaN(TMS)₂ in THF (0.88 mL, 0.88 mmol). The solution was stirred at room temperature for 30 minutes, whereupon a solution of 6-(4-bromo-3-methyl-but-2-enyl)-5-methoxy-4-methyl-7-(2-trimethylsilanyl-ethoxy)-3H-isobenzofuran-1-one (98 mg, 0.22 mmol) in THF (1 mL) was added. The reaction mixture was stirred overnight when a precipitate was observed. The reaction mixture was worked up by addition of a saturated aqueous solution of ammonium chloride and extraction of the product with EtOAc. The organic extract was dried and the product was purified by RP HPLC using a C18 column with a gradient of H₂O, 0.1% TFA-acetonitrile, 0.1% TFA to provide 72 mg (48%) of the product as a colorless oil. ¹H NMR (300 MHz, CDCl₃) δ 0.05 (s, 9H), 1.22 (t, 3H, J=7 Hz), 1.81 (s, 3H), 2.18 (s, 3H), 2.5-2.7 (m, 2H), 3.3 (ddd, 1H, J=4, 12,23 Hz), 3.40 (d, 2H, J=7 Hz), 3.65 (s, 3H), 3.76 (s, 3H), 4.29-5.13 (m, 6H), 5.13 (s, 2H), 5.28 (t, 1H, J=7 Hz) ppm; MS (m/z) 701.2 [M+Na]⁺.

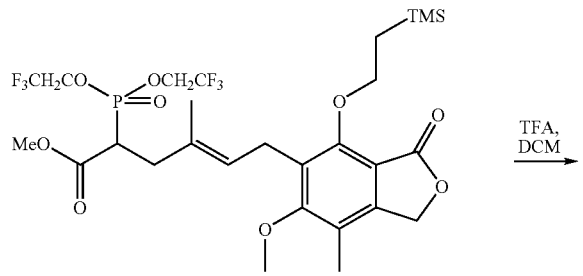

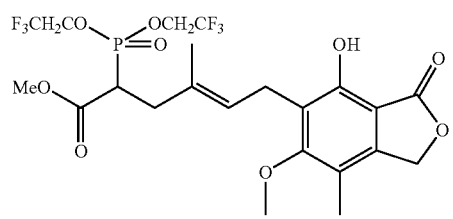

2-(Bis-(2,2,2-trifluoroethoxy)phosphoryl)-6-[6-methoxy-7-methyl-3-oxo-4-(2-hydroxyoxy)-1,3-dihydro-isobenzofuran-5-yl]4-methyl-hex-4-enoic acid methyl ester

[2-(Bis-(2,2,2-trifluoroethoxy)phosphoryl)-6-[6-methoxy-7-methyl-3-oxo-4-(2-trimethylsilanyl-ethoxy)-1,3-dihydro-isobenzofuran-5-yl]-4-methyl-hex-4-enoic acid methyl ester (70 mg) was dissolved in a solution of 10% trifluoroacetic acid in dichloromethane (5 mL). After 10 minutes, the mixture was concentrated and the product was purified by RP HPLC using a C18 column with a gradient of H₂O, 0.1% TFA-acetonitrile, 0.1% TFA to provide 45 mg (75%) of the product as a colorless oil. ¹H NMR (300 MHz, CDCl₃) δ 1.81 (s, 3H), 2.16 (s, 3H), 2.5-2.7 (m, 2H), 3.3 (ddd, 1H), 3.38 (d, 2H, J=7 Hz), 3.65 (s, 3H), 3.77 (s, 3H), 4.33-4.43 (m, 4H), 5.21 (s, 2H), 5.33 (t, 1H, J=7 Hz) ppm; ³¹P (121.4 MHz, CDCl₃) δ 25.8 ppm; MS (m/z) 601.2 [M+Na]⁺.

EXAMPLE 287

Preparation of Representative Compounds of the Invention

Representative compounds of the invention can be prepared as illustrated below.

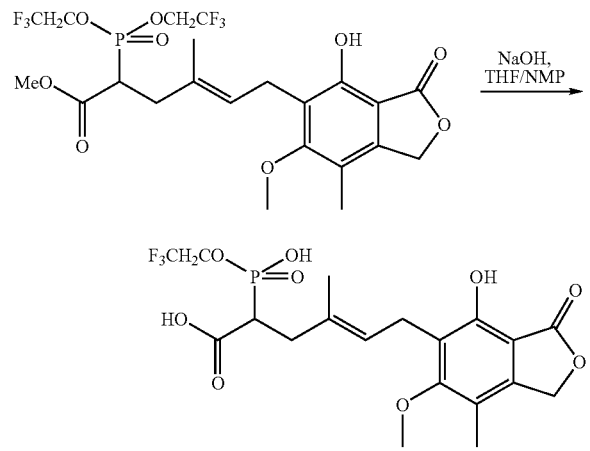

6-(4-Hydroxy-6-methoxy-7-methyl-3-oxo-1,3-dihydro-isobenzofuran-5-yl)-2-[hydroxy-(2,2,2-trifluoroethoxy)-phosphoryl]4-methyl-hex 4-enoic acid To a solution of [bis-(2,2,2-trifluoro-ethoxy)-phosphoryl]-acetic acid methyl ester (186 μL, 0.88 mmol) in anhydrous THF (0.5 mL) was added a solution of 1N NaOH (aqueous; 0.06 mL) and N-methylpyrrolidinone (0.2 mL). After 6.5 hours, another aliquot of 1N NaOH (0.06 mL) was added and the mixture was stirred overnight. After concentration, the residue was suspended in DMF (<1 mL), neutralized with a few drops of TFA and purified by RP HPLC using a C18 column with a gradient of $H_2O$, 0.1% TFA-acetonitrile, 0.1% TFA to provide 5.6 mg (72%) of the product as a white powder after lyophilization. $^1H$ NMR (300 MHz, $CD_3OD$) δ 1.83 (s, 3H), 2.16 (s, 3H), 2.43-2.51 (m, 1H), 2.59-2.70 (m, 1H), 3.13 (ddd, 1H), 3.40 (d, 2H), 3.76 (s, 3H), 4.36-4.47 (m, 2H), 5.25 (s, 2H), 5.34 (t, 1H, J=7 Hz) ppm; MS (m/z) 505.2 $[M+Na]^+$.

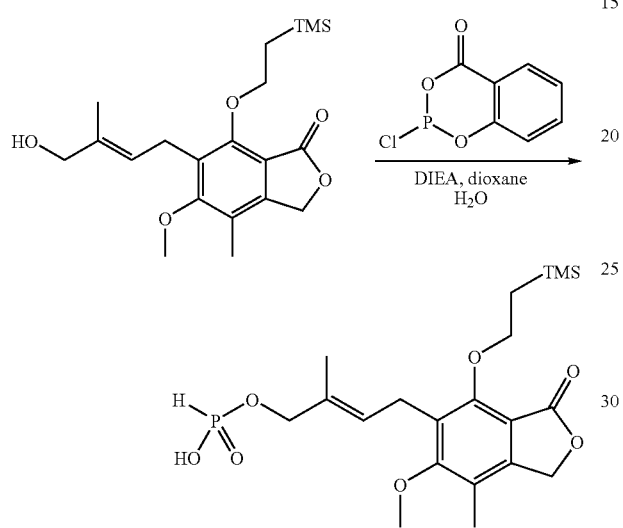

EXAMPLE 288

Preparation of Representative Compounds of the Invention

Representative compounds of the invention can be prepared as illustrated below.

Phosphorous acid mono-{4-[6-methoxy-7-methyl-3-oxo-4-(2-trimethylsilanyl-ethoxy)-1,3-dihydro-isobenzofuran-5-yl]-2-methyl-but-2-enyl}ester To a solution of 6-(4-hydroxy-3-methyl-but-2-enyl)-5-methoxy-4-methyl-7-(2-trimethylsilanyl-ethoxy)-3H-isobenzofuran-1-one (75 mg, 0.20 mmol) and DIEA (49 μL, 0.28 mmol) in dioxane (2 mL) was added 2-chloro-4H-1,3,2-benzodioxaphosphorin-4-one (56.7 mg, 0.28 mmol) according the procedure of Shadid, B. et al., *Tetrahedron*, 1989, 45, 12, 3889. After 10 minutes, another portion of 2-chloro-4H-1,3,2-benzodioxaphosphorin-4-one (40 mg, 0.20 mmol) and DIEA (35 μL, 0.20 mmol) were added. The reaction was allowed to proceed at room temperature for an additional hour, after which it was quenched by the addition of $H_2O$. The solution was stirred for another 10 minutes and concentrated in vacuo to a small volume. The product was triturated with diethyl ether and coevaporated from acetonitrile (4×10 mL) to provide the product. $^1H$ NMR (300 MHz, $CDCl_3$) δ 0.03 (s, 9H), 1.08-1.30 (m, 2H), 1.84 (br s, 3H), 2.17 (s, 3H), 3.46 (br s, 2H), 3.76 (s, 3H), 4.21-4.39 (m, 4H), 5.12 (s, 2H), 5.43-5.60 (m, 1H), 7.83 (br s, 1H); $^{31}P$ (121.4 MHz, $CDCl_3$) δ 7.22; MS (m/z) 441 $[M-H]^-$.

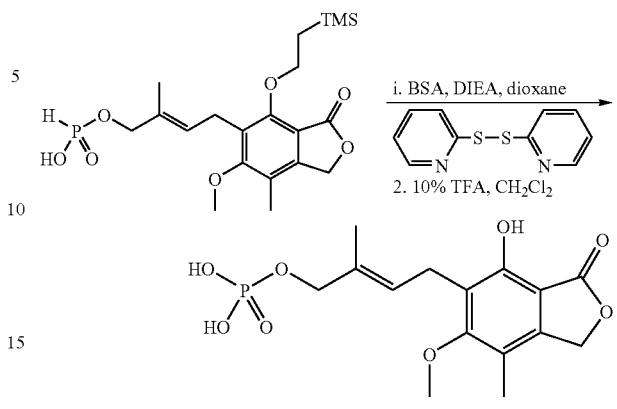

EXAMPLE 289

Preparation of Representative Compounds of the Invention

Representative compounds of the invention can be prepared as illustrated below.

Phosphoric acid mono-{4-[6-methoxy-7-methyl-3-oxo-4-(2-trimethylsilanyl-ethoxy)-1,3-dihydro-isobenzofuran-5-yl]-2-methyl-but-2-enyl}ester A solution of phosphorous acid mono-{4-[6-methoxy-7-methyl-3-oxo-4-(2-trimethylsilanyl-ethoxy)-1,3-dihydro-isobenzofuran-5-yl]-2-methyl-but-2-enyl}ester (27 mg, 0.06 mmol) in dioxane (1 mL) was stirred with DIEA (21 μL, 0.12 mmol) and N,O-bis(trimethylsilyl)acetamide (29 μL, 0.12 mmol) at room temperature for 3 hours. To the reaction solution was added 2,2'-dipyridyldisulfide (16 mg, 0.072 mmol) and the mixture was allowed to stir for an additional 2 hours at room temperature. The reaction mixture was diluted by addition of $H_2O$ and the solution was stirred for 2 more hours when it was concentrated. The residue was dissolved in a solution of 10% $TFA/CH_2Cl_2$ and stirred at room temperature for 9 hours. The reaction mixture was dried under reduced pressure and the product was purified by reverse-phase HPLC to provide the desired product as a white solid. $^1H$ NMR (300 MHz, $CD_3OD$) δ 1.87 (s, 3H), 2.16 (s, 3H), 3.47 (d, 2H, J=7 Hz), 3.79 (s, 3H), 4.28 (d, 2H, J=6 Hz), 5.26 (s, 2H), 5.50-5.61 (m, 1H); $^{31}P$ (121.4 MHz, $CD_3OD$) δ 0.50; MS (m/z) 357 $[M-H]^-$.

EXAMPLE 290

Specific Embodiments of the Invention

Several compounds of the invention are presented below.

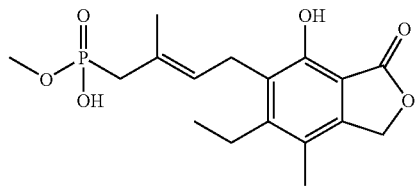

911

-continued

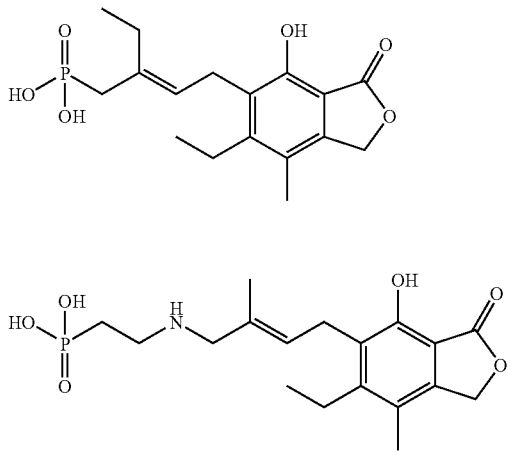

EXAMPLE 291

Preparation of Representative Compounds of the Invention

Additional representative compounds of the invention, and intermediates thereof, can be prepared according to the methods presented below.

912

Synthesis of Phenacetaldehydes with Variants at $R_1$, $R_2$

The parent compound ($R^1$=OMe; $R_2$=Me) is accessible by semi-synthesis from mycophenolic acid as follows:

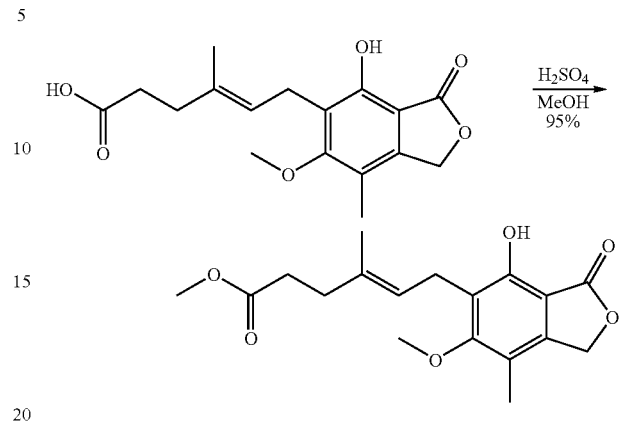

To a solution of mycophenolic acid (500 g, 1.56 mol) in MeOH (4 L) under nitrogen atmosphere was added sulfuric acid (10 mL) dropwise, and the suspension was stirred at room temperature. After 2 hours, the reaction became homogeneous, and soon thereafter a precipitate was formed. The reaction was allowed to stir at room temperature for 10 hours, at which time TLC indicated complete reaction. The reaction was cooled in an ice bath to 10° C. and then filtered using a Buchner funnel. The filter cake was washed with ice cold methanol (750 mL) followed by hexanes (750 mL) and then dried to give 497 g (95%) of the desired product as a solid: $^1$H NMR (300 MHz, CDCl$_3$) δ, 1.81 (s, 3H), 2.18 (s, 3H), 2.15 (s,

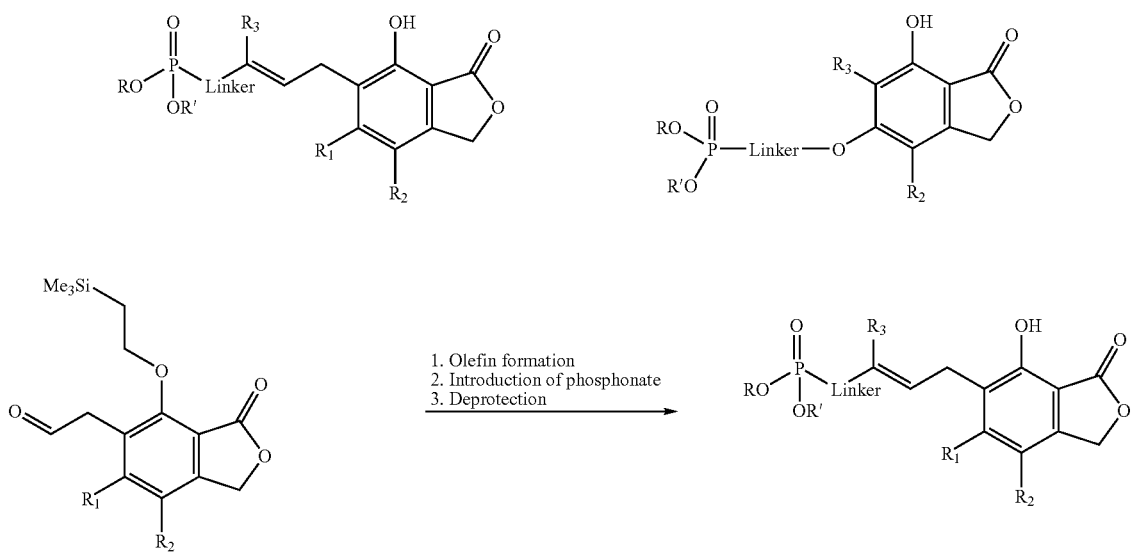

Linker = 0-8 atoms, preferably 1-6;
$R_1$ = OMe, OEt, vinyl, Et, cyclopropyl, NHMe, NHCHO
$R_2$ = Me, Cl, CF$_3$
$R_3$ = H, Me, cyclopropyl, Et, vinyl, CF$_3$
$R_4$ = H, Cl, Me, Et, cyclopropyl, vinyl, allyl, 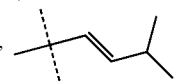

3H), 2.37-2.50 (m, 4H), 3.38 (d, 2H, J=7 Hz), 3.62 (s, 3H), 3.77 (s, 3H), 5.13 (s, 2H), 5.22 (m, 1H), 7.17 (s, 1H).

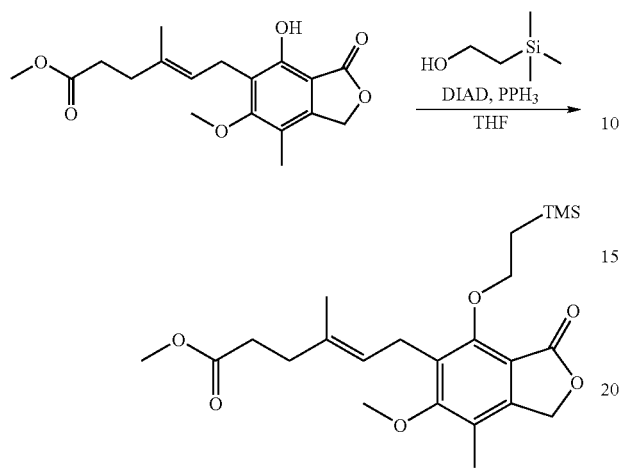

To a solution (3.99 g, 11.9 mmol), PPh₃ (4.68 g, 17.9 mmol), and diisopropyl azodicarboxylate (3.46 mL, 17.9 mmol) in THF (60 mL) at 0° C. was added a solution of 2-trimethylsilylethanol (2.05 mL, 14.3 mmol) in THF (20 mL). The resulting yellow solution was allowed to warm to room temperature and stirred for 4 hours. The reaction was worked up by concentrating the solution to dryness and addition of ether and hexanes. Triphenylphosphine oxide was removed by filtration and the filtrate was concentrated and purified by silica gel chromatography to provide 4.8 g (100%) as a clear oil: ¹H NMR (300 MHz, CDCl₃) δ 0.03 (s, 9H), 1.18-1.30 (m, 2H), 1.81 (s, 3H), 2.18 (s, 3H), 2.25-2.33 (m, 2H), 2.37-2.45 (m, 2H), 3.42 (d, 2H, J=7 Hz), 3.62 (s, 3H), 3.77 (s, 3H), 4.25-4.35 (m, 2H), 5.13 (s, 2H), 5.12-5.22 (m, 1H).

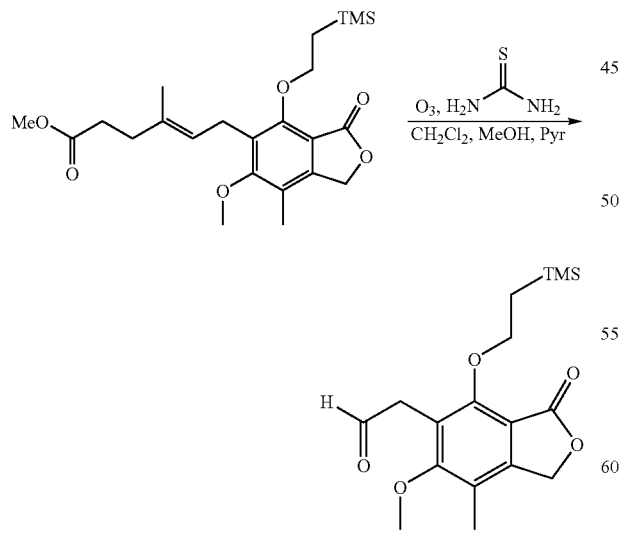

A solution (9.6 g, 22 mmol) in MeOH (90 mL), CH₂Cl₂ (90 mL) and pyridine (0.7 mL) was cooled to −70° C. using a dry ice/acetone bath. A stream of ozone was bubbled through the reaction via a gas dispersion tube until the reaction became blue in color (1.5 hours). The ozone line was replaced with a stream of nitrogen and bubbling continued for another 30 minutes, by which time the blue color had disappeared. To this solution at −70° C. was added thiourea (1.2 g, 15.4 mmol) in one portion, and the cooling bath was removed. The reaction was allowed to warm to room temperature and stirred for 15 hours. The reaction was worked up by filtration to remove solid thiourea S-dioxide, and then partitioned between CH₂Cl₂ and water. The organic layer was removed. The aqueous layer was washed with CH₂Cl₂ and the organic extracts were combined, washed with aqueous 1N HCl, saturated NaHCO₃ and brine, and dried in vacuo. The residue was purified by silica gel chromatography to afford 7.3 g (99%) as a white solid: ¹H NMR (300 MHz, CDCl₃) δ −0.01 (s, 9H), 1.05-1.15 (m, 2H), 2.15 (s, 3H), 3.69 (s, 3H), 3.78 (d, 2H, J=1 Hz), 4.27-4.39 (m, 2H), 5.11 (s, 2H), 9.72 (d, 1H, J=1 Hz).

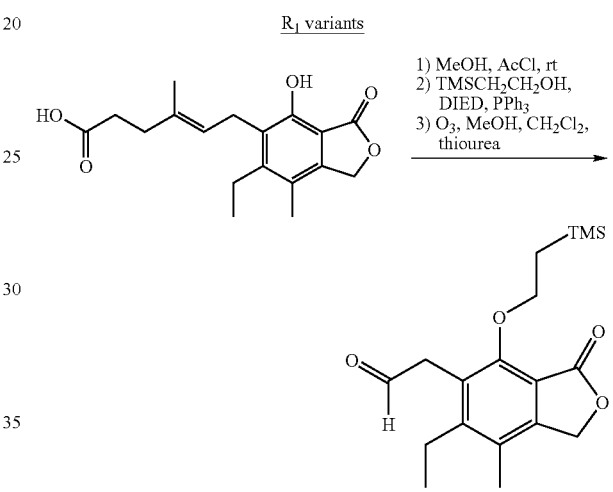

The starting material, synthesized according to *J. Med. Chem.*, 1996, 39, 4181-4196, is transformed to the desired aldehyde using methods analogous to those described above.

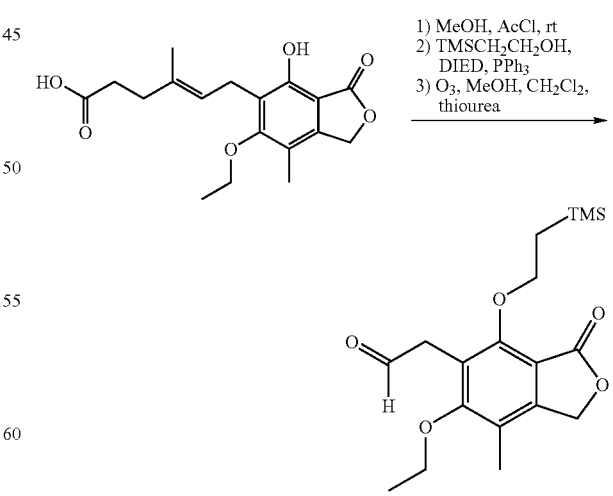

The starting material, synthesized according to *J. Med. Chem.*, 1996, 39, 4181-4196, is transformed to the desired aldehyde using methods analogous to those described above.

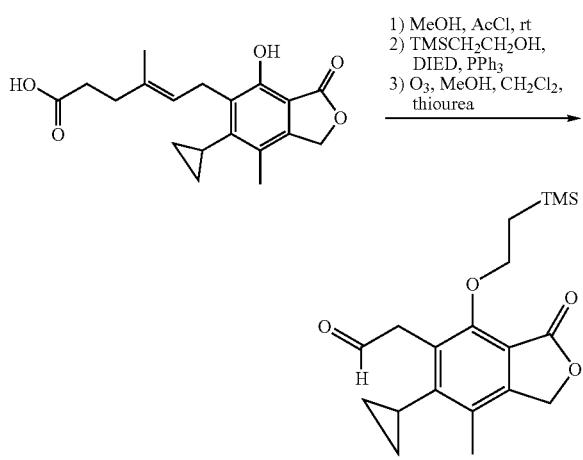

The starting material, synthesized according to *J. Med. Chem.*, 1996, 39, 4181-4196, is transformed to the desired aldehyde using methods analogous to those described above.

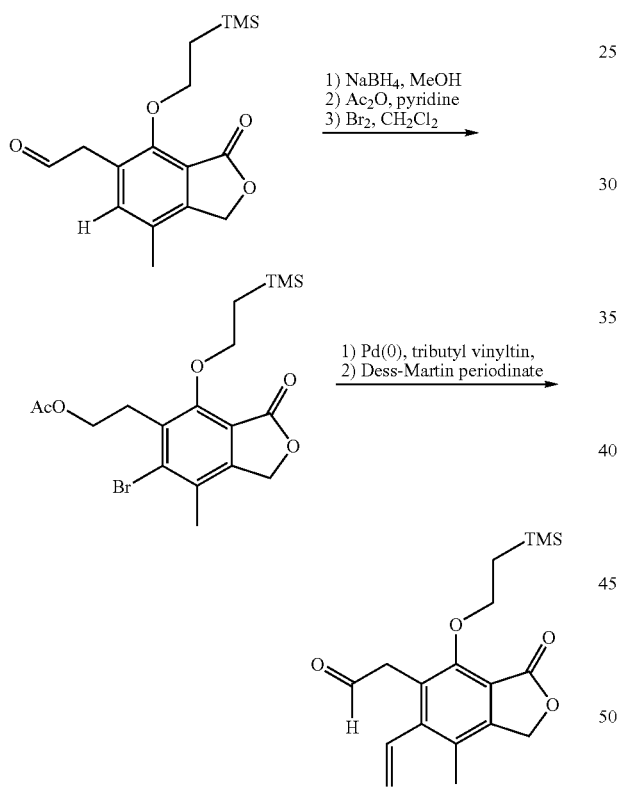

The aldehyde is dissolved in an organic solvent such as methanol and sodium borohydride is added. At the end of the reaction, aqueous HCl solution is added and the solvent is removed in vacuo. Further purification is achieved by chromatography.

The resulting alcohol is dissolved in an organic solvent such as dichloromethane (DCM). Pyridine and acetic anhydride are added and stirring at room temperature is continued. At the end of the reaction additional DCM is added and the solution is washed with aqueous HCl solution, aqueous sodium bicarbonate solution, and dried over sodium sulfate. Filtration and evaporation of the solvent in vacuo gives the crude product. Further purification is achieved by chromatography.

The acetate is dissolved in DCM and bromine is added, according to a procedure from *J. Med. Chem.*, 1996, 39, 4181-4196. At the end of the reaction, additional DCM is added and the solution is washed with aqueous sodium thiosulfate solution and brine. The organic layer is dried over sodium sulfate. Filtration and evaporation of solvents yields the crude material. Further purification is achieved by chromatography.

The product of the previous step, lithium chloride, triphenylarsine, tributylvinyltin, and tris(dibenzylideneacetone)dipalladium(0)-chloroform adduct are heated in an organic solvent such as N-methylpyrrolidinone at an elevated temperature of approximately 55° C., according to a procedure from *J. Med. Chem.*, 1996, 39, 4181-4196. At the end of the reaction, the mixture is cooled to room temperature and poured into a mixture of ice, potassium fluoride, water, and ethyl acetate. Stirring is continued for one hour. The suspension is filtered through Celite and extracted with ethyl acetate. The combined organic extracts are dried over sodium sulfate. The solvents are removed in vacuo and the crude material is further purified by chromatography.

The product of the previous step is dissolved in an organic solvent such as DCM or THF. 1,1,1-tris(acyloxy)-1,1-dihydro-1,2benziodoxol-3-(1H)-one (Dess-Martin reagent) is added and the solution is stirred at room temperature, according to a procedure from *J. Org. Chem.*, 1984, 48, 4155-4156. At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude product. Further purification is achieved by chromatography.

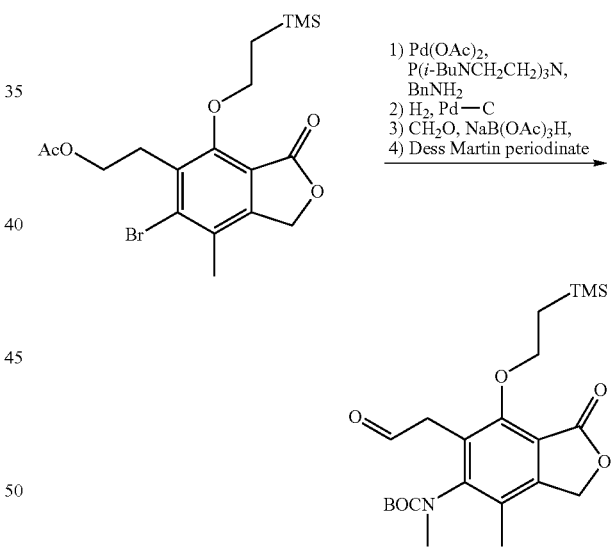

The starting material is dissolved in an organic solvent such as toluene. P(isobutylNCH$_2$CH$_2$)$_3$N, palladium(II)acetate, sodium tert.butoxide, and benzylamine are added and the mixture was heated at 80° C., according to a procedure from *J. Org. Chem.*, 2003, 68, 452-459. At the end of the reaction, the mixture is cooled to room temperature and the solvents are removed in vacuo. The crude material is purified by chromatography. Any residual acetate is removed by brief treatment with methanolic sodium methoxide.

The benzyl-protected aniline is dissolved in an organic solvent such as DMF. Palladium on carbon is added and the reaction mixture is placed under an atmosphere of hydrogen. At the end of the reaction, the mixture is filtered through Celite. The solvents are removed in vacuo. Further purification is achieved by chromatography.

The resulting primary aniline is dissolved in an organic solvent such as THF, acetonitrile, or DMF and is treated with formaldehyde and sodium triacetoxyborohydride as described in *J. Org. Chem*, 1996, 61, 3849-3862. The reaction is quenched with aqueous sodium bicarbonate and the product is extracted with an organic solvent such as ethyl acetate. The crude material is treated with di-t-butyl dicarbonate in an organic solvent such as dimethylformamide and aqueous sodium hydroxide. The resulting carbamate is purified by chromatography.

The primary alcohol product is dissolved in an organic solvent such as DCM or THF. 1,1,1-tris(acyloxy)-1,1-dihydro-1,2benziodoxol-3-(1H)-one (Dess-Martin reagent) is added and the solution is stirred at room temperature, according to a procedure from *J. Org. Chem.*, 1984, 48, 4155-4156. At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude product. Further purification is achieved by chromatography.

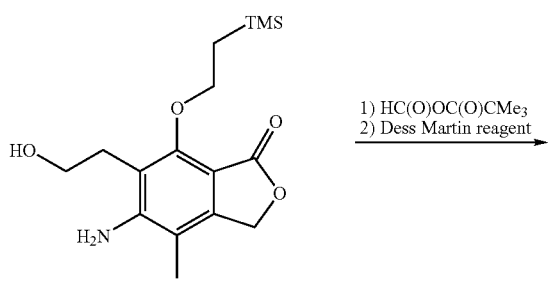

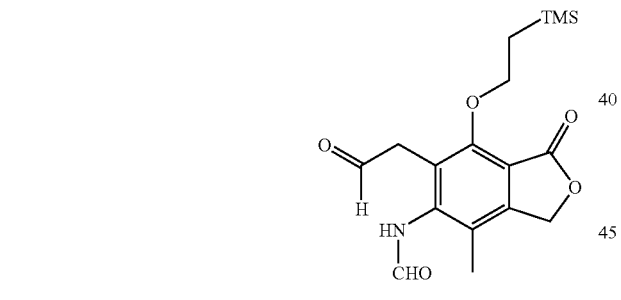

The starting material is dissolved in an organic solvent such as DCM or THF and is treated with the mixed anhydride of formic and pivalic acids, according to a procedure from *Recl. Trav. Chem. Pay-Bas*, 1982, 101, 460. At the end of the reaction, the solvent and all volatiles are removed in vacuo and the crude product is further purified by chromatography.

The product is dissolved in an organic solvent such as DCM or THF. 1,1,1-Tris(acyloxy)-1,1-dihydro-1,2-benziodoxol-3-(1H)-one (Dess-Martin reagent) is added and the solution was stirred at room temperature, according to a procedure from *J. Org. Chem.*, 1984, 48, 4155-4156. At the end of the reaction diethyl ether is added, followed by aqueous sodium hydroxide solution. The layers are separated and the organic layer is washed with aqueous sodium hydroxide solution, water, and dried over sodium sulfate. Filtration and evaporation of solvents yields the crude product. Further purification is achieved by chromatography.

$R_2$ variants

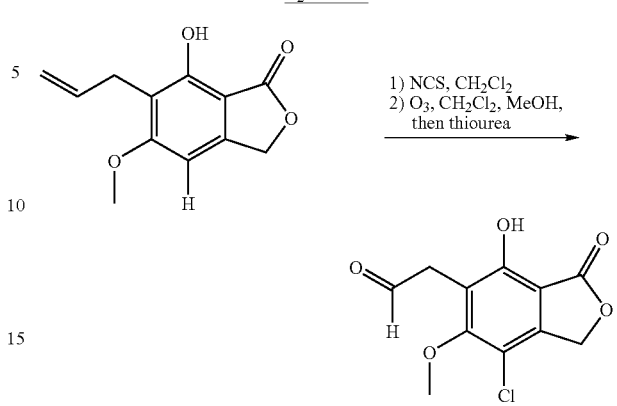

The starting material is dissolved in an organic solvent such as DMF and reacted with N-chlorosuccinimide, according to a procedure from *J. Med. Chem.*, 1996, 39, 4181-4196. After the starting material is consumed the reaction mixture is poured into water and the product is extracted with diethyl ether. The combined organic layers are dried over sodium sulfate. Filtration and evaporation of the solvent yields a crude reaction product.

The product of step one is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution and brine. The solution is dried over sodium sulfate. Filtration and evaporation of the solvents yields the crude aldehyde. Further purification is achieved by chromatography.

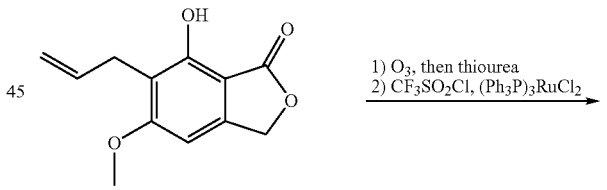

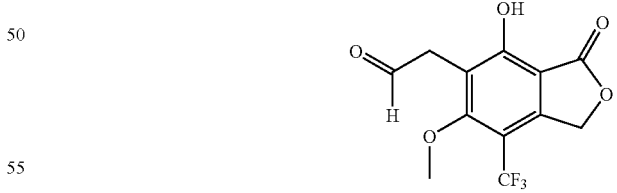

The starting material is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution, and brine. The solution is dried over sodium sulfate. Filtration and evaporation of the solvents yields the crude aldehyde. Further purification is achieved by chromatography.

The product of step one is dissolved in an organic solvent such as benzene. Trifluoromethanesulfonyl chloride and dichlorotris(triphenylphosphine)rhuthenium are added and the solution is degassed. The reaction mixture is heated at 120° C., according to a procedure from *J. Chem. Soc., Perkin* nylidene)-propionaldehyde (6.8 g, 20.5 mmol) overnight. After concentration, the residue was purified by silica gel chromatography to provide 4.24 g (72%) of the unsaturated aldehyde as a pale yellow solid. $^1$H NMR (300 MHz, CDCl$_3$) δ 0.00 (s, 9H), 1.10-1.21 (m, 2H), 1.87 (s, 3H), 2.16 (s, 3H), 3.67-3.76 (m, 2H), 3.74 (s, 3H), 4.27-4.39 (m, 2H), 5.11 (s, 2H), 6.40-6.48 (m, 1H), 9.2 (s, 1H).

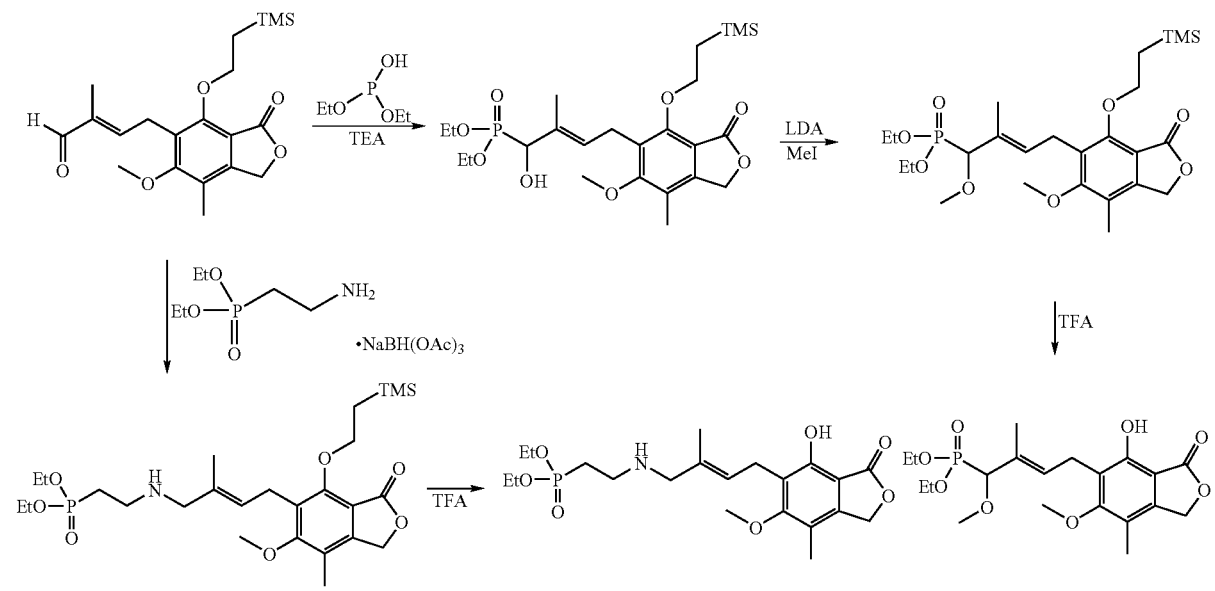

*Trans. I*, 1994, 1339-1346. At the end of the reaction the mixture is cooled to room temperature and the solvent is removed in vacuo. Further product purification is achieved by chromatography.

Synthesis of Olefins and Linkers to Phosphonates

The trimethylsilyethyl protected aldehyde is treated with diethylphosphite in a solvent such as acetonitrile in the presence of a base such as triethylamine to afford the hydroxy phosphonate, according to a procedure such as that reported in *Tetrahedron*, 1995, 51, 2099. The hydroxy phosphonate is O-akylated and then the protecting group is removed by treatment with either trifluoroacetic acid or tetrabutylammonium fluoride to generate the desired methoxy phosphonate analog.

Alternatively, the aldehyde is mixed with diethyl (2-aminoethyl)phosphonate and treated with a reducing agent such as sodium triacetoxyborohydride to generate the amino phosphonate analog.

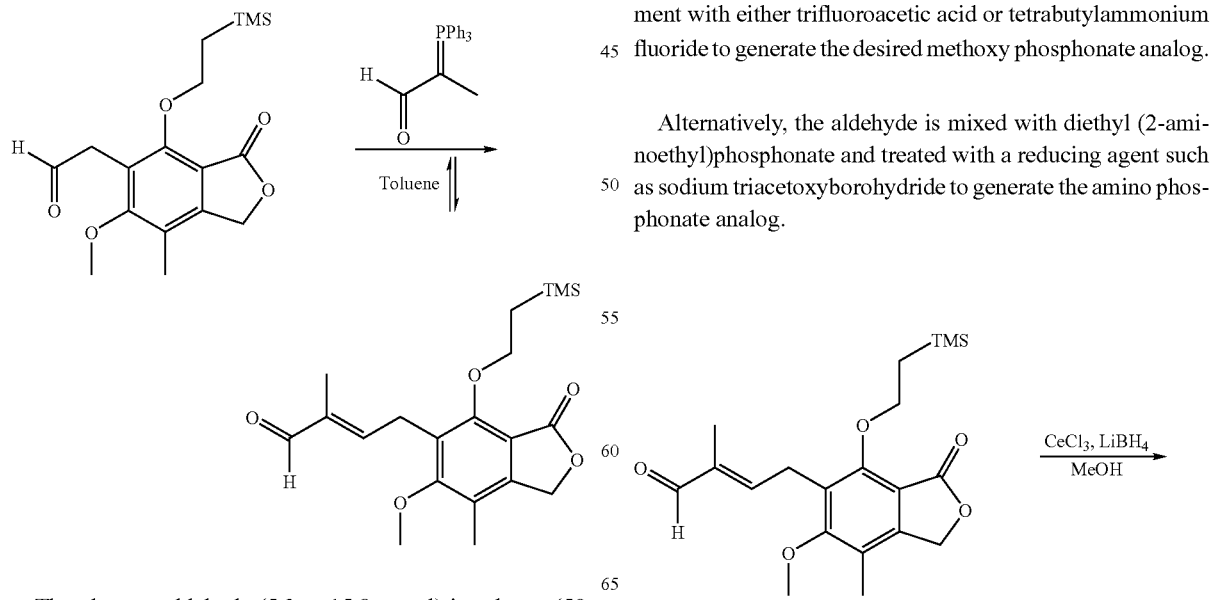

The phenacetaldehyde (5.3 g, 15.8 mmol) in toluene (50 mL) was heated at 100° C. with 2-(triphenyl-phospha- -continued

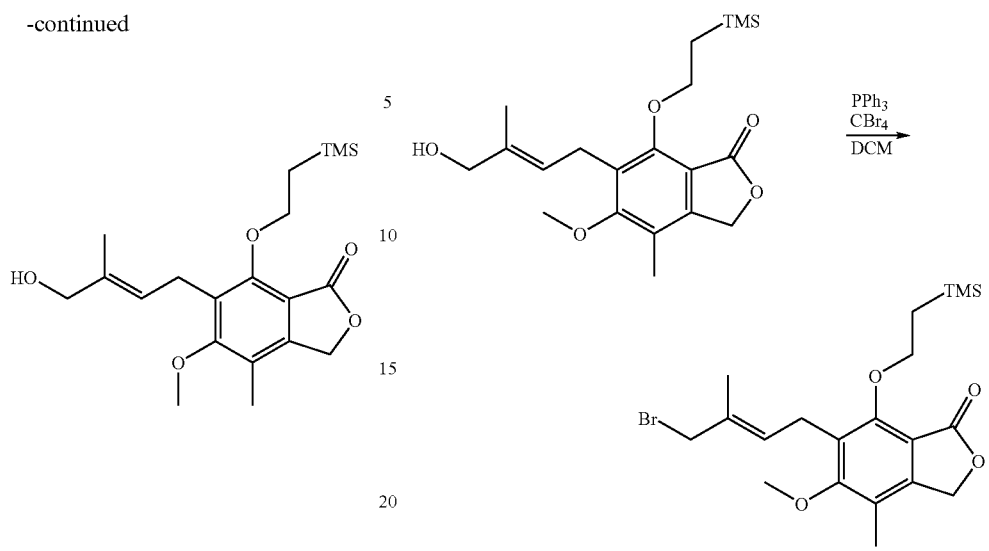

A solution of 4-[6-methoxy-7-methyl-3-oxo-4-(2-trimethylsilanyl-ethoxy)-1,3-dihydro-isobenzofuran-5-yl]-2-methyl-but-2-enal (103 mg, 0.27 mmol) in methanol (5 mL) was cooled to 0° C. A solution of CeCl₃ (0.68 mL, MeOH:H₂O, 9:1) was added, followed by LiBH₄ (0.14 mL, 0.28 mmol of Polymer-supported triphenylphosphine is soaked in DCM for 1 hour. The allylic alcohol and carbon tetrabromide are sequentially added. When the reaction is complete, the mixture is filtered and the filtrate concentrated. The bromide is purified as necessary by chromatography.

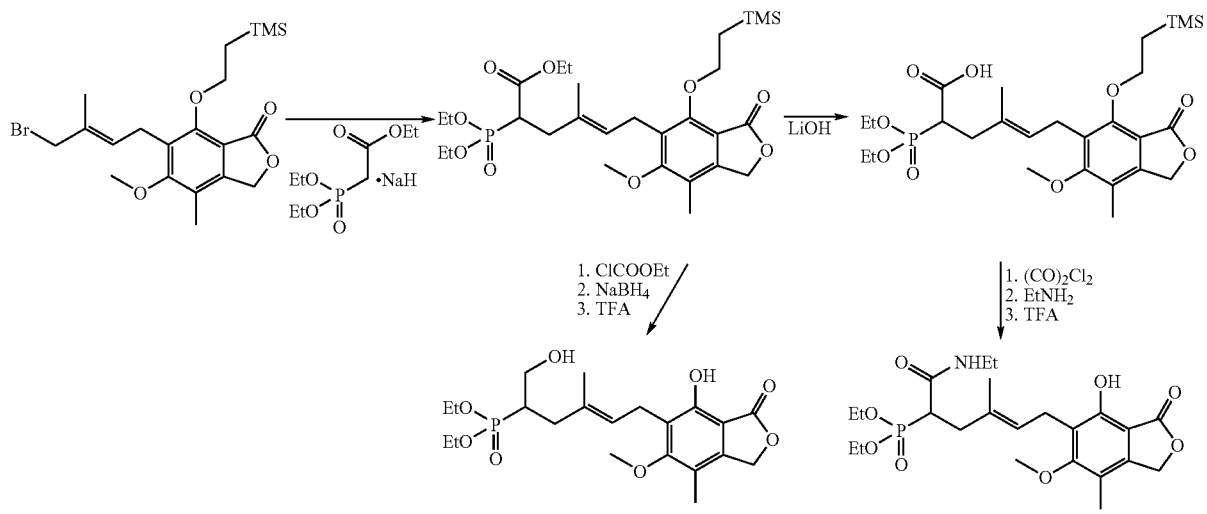

a 2M solution in THF). The ice bath was removed and the reaction mixture was allowed to warm to room temperature. The reaction mixture was stirred for an additional 40 minutes whereupon TLC indicated complete consumption of starting aldehyde. The reaction was worked up by addition of aqueous 1N HCl (0.5 mL) and the product was extracted with CH₂Cl₂. The organic layer was washed with saturated aqueous sodium bicarbonate solution and brine. The organic layer was concentrated under reduced pressure and the residue was purified by silica gel chromatography to provide 100 mg (97%) of the product as a clear liquid. ¹H NMR (300 MHz, CDCl₃) δ 0.00 (s, 9H), 1.20 (dd, 2H, J=7, 8 Hz), 1.81 (s, 3H), 2.13 (s, 3H), 3.38-3.50 (m, 2H), 3.74 (s, 3H), 3.95 (s, 2H), 4.27 (dd, 2H, J=7, 8 Hz), 5.08 (s, 2H), 5.17-5.44 (m, 1H).

The allylic bromide is treated in an inert organic solvent such as dimethylformamide with an alkali metal salt of ethyl diethoxyphosphorylacetate (prepared by reacting ethyl diethoxyphosphorylacetate with sodium hexamethyldisilazide or sodium hydride) to afford the ethoxycarbonyl phosphonate, according to a procedure such as that described in WO 9522538. The carboxylic ester group is converted to both the carboxylic amide and the hydroxymethyl groups according to the methods conventionally utilized for amide formations and ester reductions. For example, the carboxylic ester is saponified with aqueous lithium hydroxide. The acid is activated with ethyl chloroformate and reduced with sodium borohydride to generate, after removal of the protecting group, the hydroxymethyl phosphonate analog. The acid is also converted to its acyl chloride and then reacted with ethylamine to afford the amide analog.

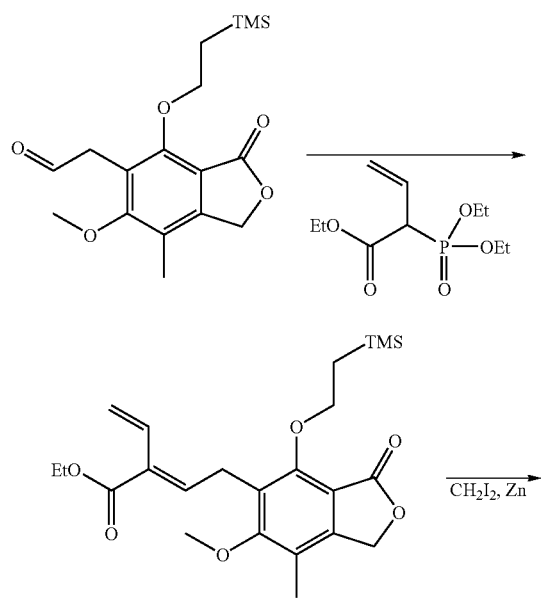

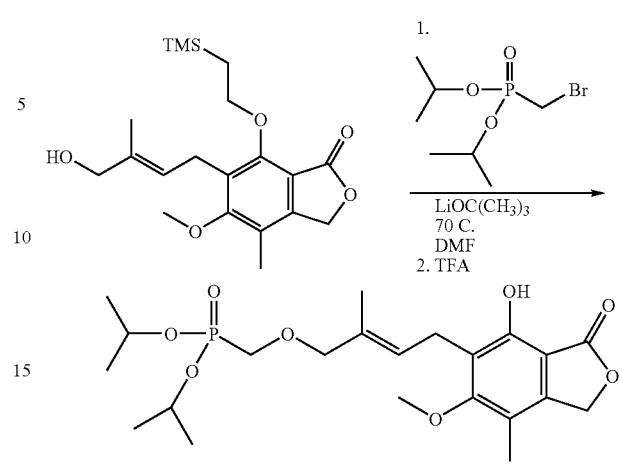

The allylic alcohol is treated with bromomethylphosphonic acid diisopropyl ester in the presence of a base such as lithium t-butoxide in a solvent such as dimethylformamide. The phenol protecting group is then removed by treatment with trifluoroacetic acid.

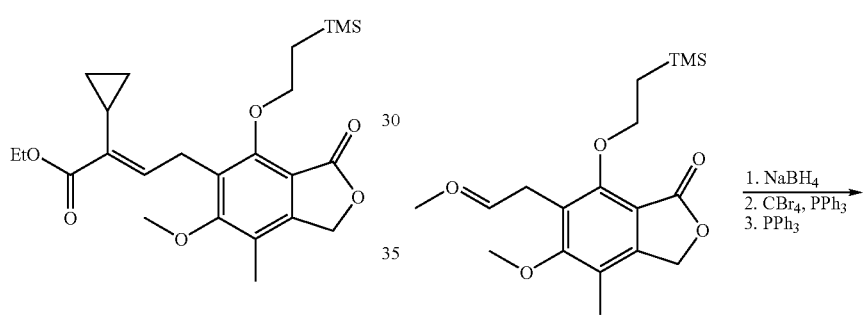

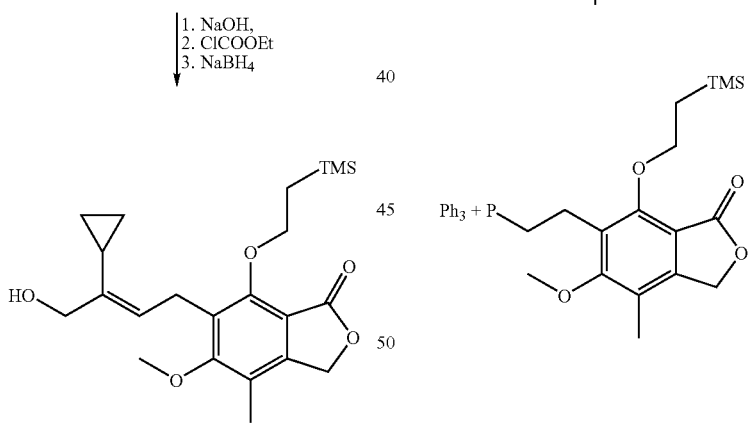

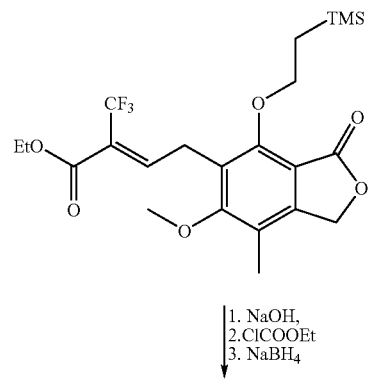

The aryl acetaldehyde is coupled with 2-(diethoxyphosphoryl)-but-3-enoic acid ethyl ester to generate the 2-vinyl substituted ester, according to a procedure such as that reported in *Synthesis*, 1999, 282. The 2-vinyl group is converted to the 2-cyclopropyl group under cyclopropanation conditions such as those described in *Tetrahedron Lett.* 1998, 39, 8621. The ester is converted to the alcohol, which, optionally, can be further subjected to reactions such as that described below to generate various phosphonate-containing mycophenolic acid analogues.

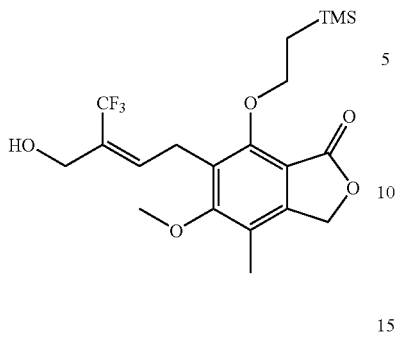

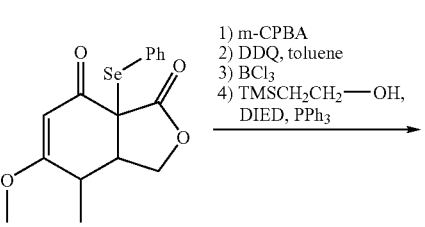

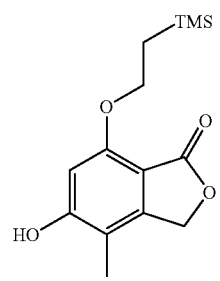

The phenacetaldehyde can alternatively be converted to the allyl phosphonium salt, according to a procedure such as that reported in *J. Org. Chem.* 1987, 52, 849. The phosphonium salt is then treated with the commercially available 3,3,3-trifluoro-2-oxo-propionic acid ethyl ester and a base such as sodium hydride to generate the 2-trifluoromethyl substituted ester. The ester is converted to the alcohol, which, optionally, can be further subjected to reactions described earlier to generate mycophenolic acid analogues with various side chains containing the phosphonate group.

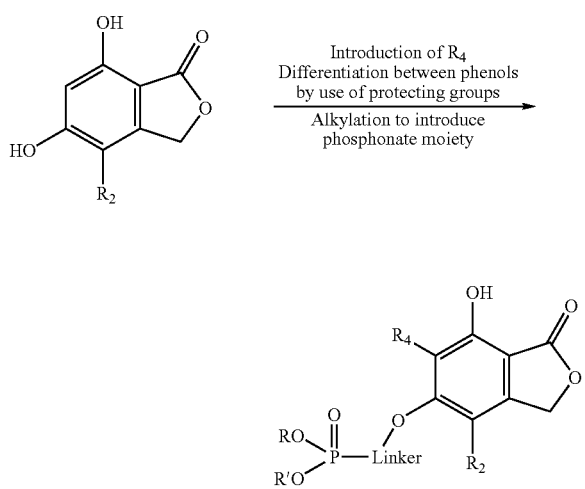

The enone (synthesis reviewed in *Tetrahedron*, 1985, 41, 4881-4889) and the diene (*Chem. Pharm. Bull.*, 1989, 37, 2948-2951) are dissolved in an organic solvent such as toluene, stirred at room temperature for 24 hours and heated to reflux for additional 5 hours, according to a procedure from *J. Med. Chem.*, 1996, 39, 4181-4196. The reaction mixture is cooled to room temperature and the solvent removed in vacuo. The crude reaction product is further purified by chromatography.

The product of step one is dissolved in an organic solvent such as DCM and m-chloroperbenzoic acid is added, according to a procedure from *J. Med. Chem.*, 1996, 39, 4181-4196. At the end of the reaction, the solution is poured into aqueous sodium hydrogen sulfite solution. The organic layer is washed with saturated aqueous sodium bicarbonate solution and is dried over sodium sulfate. Filtration and evaporation of solvents yields the crude product.

The crude product is dissolved in an organic solvent such as toluene and treated with dichlorodicyanoquinone (DDQ), according to a procedure from *J. Med. Chem.*, 1996, 39, 4181-4196. At the end of the reaction the solvent is removed in vacuo and the crude material is further purified by chromatography.

The product is dissolved in an organic solvent such as DCM and treated with boron trichloride at reflux temperature, according to a modified procedure from *J. Med. Chem.*, 1996, 39, 46-55. At the end of the reaction the solution is washed with aqueous HCl solution. The solution is dried over sodium sulfate. Removal of the solvent yields the crude reaction product. Further purification is achieved by chromatography.

The product of the previous step and triphenylphosphine are dissolved in an organic solvent such as tetrahydrofuran (THF). Diisopropylazodicarboxylate (DIAD) is added dropwise at 0° C. Stirring is continued. A solution of 2-trimethylsilyl ethanol in THF is added and stirring is continued. At the end of the reaction, the solvent is removed in vacuo. The crude reaction solid is extracted with a mixture of organic solvents such as hexanes and diethylether. The washings are combined and the solvents removed in vacuo. The desired product is further purified and separated from the undesired regioisomer by chromatography.

Introduction of $R_4$ Variants

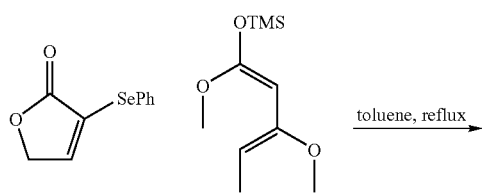

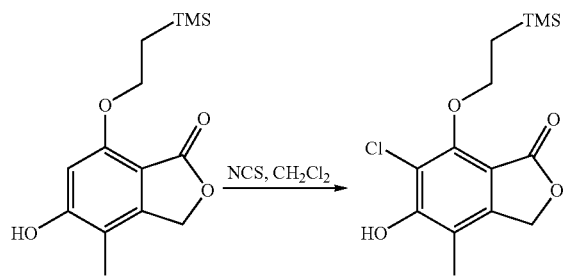

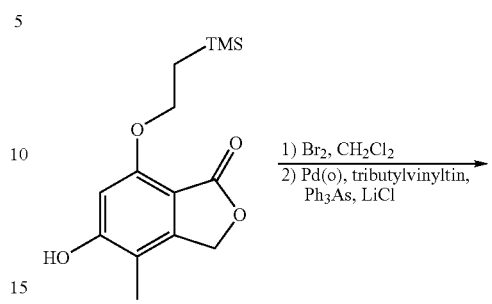

When all starting material is consumed, the reaction is filtered and the solvent removed in vacuo. Further purification is achieved by chromatography.

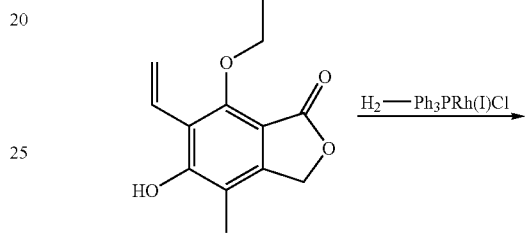

The starting material is dissolved in an organic solvent such as dimethylformamide (DMF) and reacted with N-chlorosuccinimide, according to a procedure from *J. Med. Chem.*, 1996, 39, 4181-4196. After the starting material is consumed the reaction mixture is poured into water and the product is extracted with diethyl ether. The combined organic layers are dried over sodium sulfate. Filtration and evaporation of the solvents yields the crude product. Further purification is achieved by chromatography.

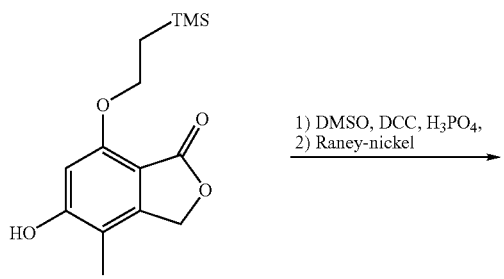

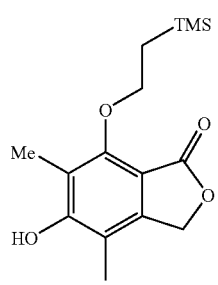

The starting material is dissolved in an organic solvent such as benzene and reacted with dimethyl sulfoxide (DMSO), dicyclohexylcarbodiimide (DCC), and orthophosphoric acid according to a procedure from *J. Am. Chem. Soc.*, 1966, 88, 5855-5866. At the end of the reaction, the suspension is filtered and the organic layer washed with aqueous sodium bicarbonate solution and dried over sodium sulfate. Filtration and evaporation of solvents yields the crude material. Further purification is achieved by chromatography.

The product of step one is dissolved in an organic solvent such as DCM or THF and treated with Raney nickel, according to procedures reviewed in *Chem. Rev.*, 1962, 62, 347-404.

The starting material is dissolved in an organic solvent such as DCM and bromine is added, according to a procedure from *J. Med. Chem.*, 1996, 39, 4181-4196. At the end of the reaction, additional DCM is added and the solution washed with aqueous sodium thiosulfate solution and brine. The organic layer is dried over sodium sulfate. Filtration and evaporation of solvents yields the crude material. Further purification is achieved by chromatography on silica gel.

The starting material, lithium chloride, triphenylarsine, tributylvinyltin, and tris(dibenzylideneacetone)dipalladium (0)-chloroform adduct are heated in an organic solvent such as N-methylpyrrolidinone at an elevated temperature of approximately 55° C., according to a procedure from *J. Med. Chem.*, 1996, 39, 4181-4196. At the end of the reaction, the mixture is cooled to room temperature and poured into a mixture of ice, potassium fluoride, water, and ethyl acetate. Stirring is continued for 1 hour. The suspension is filtered through Celite and extracted with ethyl acetate. The combined organic extracts are dried over sodium sulfate. The solvents are removed in vacuo and the crude material is further purified by chromatography.

The product of step two is dissolved in a mixture of organic solvents such as benzene and ethyl acetate. Tris(triphenylphosphine)rhodium(I) chloride is added and the reaction is placed under an atmosphere of hydrogen, according to a procedure from *J. Med. Chem.*, 1996, 39, 4181-4196. The

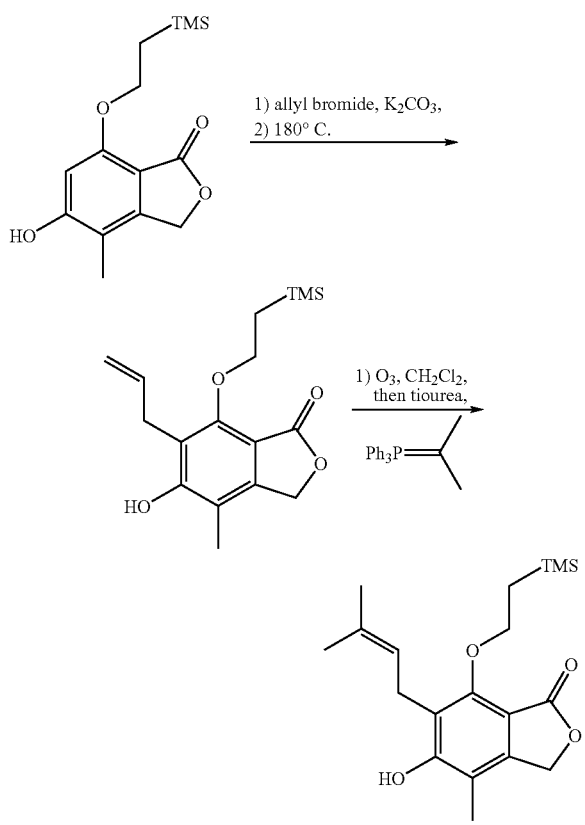

The starting material is dissolved in an organic solvent such as DMF. Potassium carbonate and allyl bromide are added and stirring at room temperature is continued, according to a procedure from *J. Med. Chem.*, 1996, 39, 4181-4196. After all the starting material is consumed, aqueous HCl solution and diethyl ether are added and the organic layer is collected and the solvent is removed in vacuo.

The crude material is dissolved in N,N diethylaniline and the reaction mixture is heated at an elevated temperature of ca. 180° C. At the end of the reaction, the mixture is cooled to room temperature and poured into a mixture of aqueous HCl (2N) and ethyl actetate. The organic layer is washed with aqueous HCl (2N) and dried over sodium sulfate. Filtration and removal of the solvents yields the crude product. Further purification is achieved by chromatography.

The product of step 2 is dissolved in a mixture of organic solvents such as methanol, DCM, and pyridine. The solution is cooled to −78° C. and ozone is bubbled into the solution until a blue color persists. The excess ozone is removed with a nitrogen stream. The reaction mixture is warmed to room temperature and thiourea is added. Stirring at room temperature is continued. The reaction mixture is filtered and partitioned between DCM and water. The aqueous layer is extracted with DCM and the combined organic layers are washed with HCl (1 N), saturated aqueous sodium bicarbonate solution and brine. The solution is dried over sodium sulfate. Filtration and evaporation of the solvents yields the crude aldehyde. Further purification is achieved by chromatography.

The aldehyde is dissolved in an organic solvent such as THF and is reacted with triphenylphosphonium sec.propyl bromide and potassium tert.butoxide, according to procedures reviewed in *Chem. Rev.*, 1989, 89, 863-927. At the end of the reaction, the solvent is removed in vacuo and the crude material purified by chromatography.

Introduction of Linkers to Phosphonates

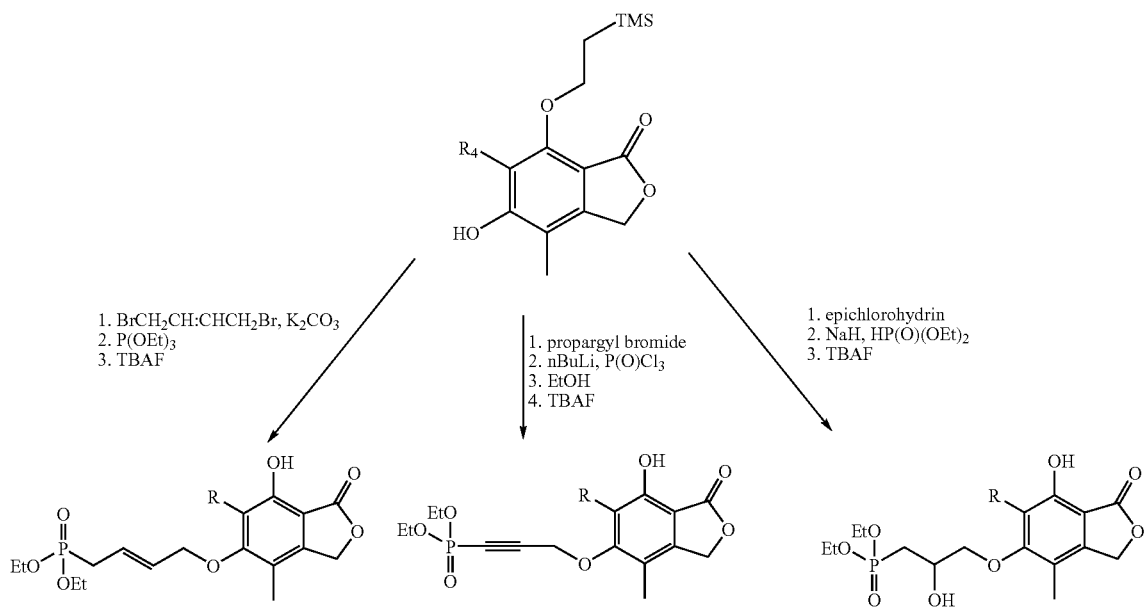

The phenols shown herein may optionally be alkylated with the reagent of choice. Optionally, the phosphonate moiety will be part of such a reagent. Alternatively, it will be introduced in a subsequent step by a variety of means, of which three are illustrated above. For example, an alkyl halide may be heated with triethylphosphite in a solvent such as toluene (or other Arbuzov reaction conditions: see Engel, R., "Synthesis of Carbon-phosphorus Bonds," CRC press, 1988). Alternatively, an epoxide may be reacted with the anion of a dialkyl phosphinate. In a further example, the phosphonate reagent may be the electrophile, e.g., an acetylide anion may be condensed with phosphorus oxychloride and the intermediate dichlorophosphonate quenched with ethanol to generate the diethyl ester of the desired phosphonic acid.

EXAMPLE 292

Preparation of Representative Celecoxib Compounds of the Invention

Specific compounds of the invention can be prepared as illustrated as follows.

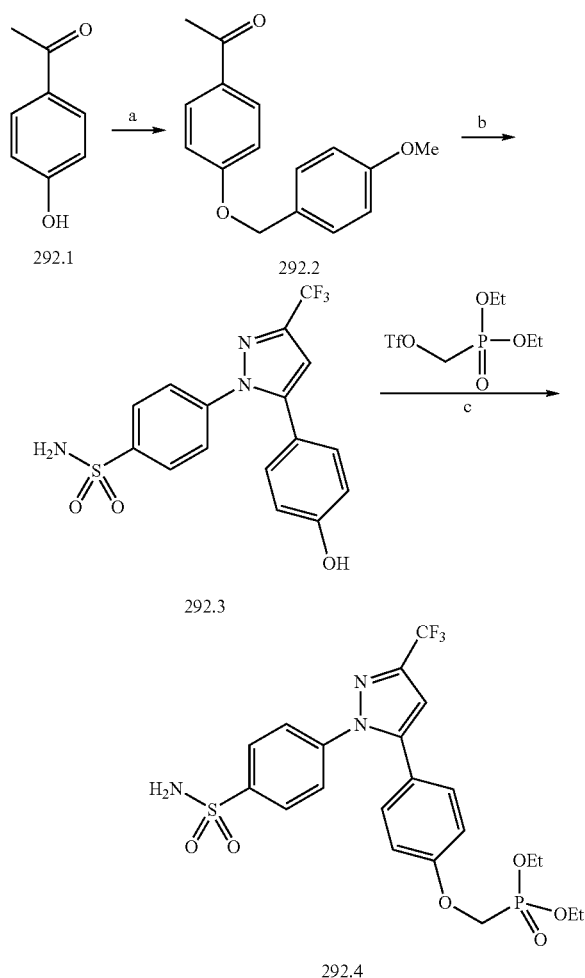

Reagents & Conditions: (a) PMBCl, $K_2CO_3$, acetone, rt; (b) (i) $CF_3COOEt$, NaH, THF, $-20°$ C.-rt; (ii) 4-sulfonamidophenylhydrazine, EtOH, reflux, overnight; (c) $Cs_2CO_3$, DMF, $0°$ C.-rt.

Synthesis of Compound 292.2.

4-Hydroxyacetophenone (1.6 g, 11.02 mmol) was dissolved in dry acetone (15 mL) under an argon atmosphere, and p-methoxybenzyl chloride (1.42 mL, 12.12 mmol) was added, followed by powdered $K_2CO_3$ (2.28 g, 16.53 mmol) at room temperature. The reaction mixture was stirred overnight and solids were filtered off. The filtrate was concentrated to a syrup, dissolved in 20 mL of $CHCl_3$ and washed with deionized water (2×5 mL). The organic layer was dried over $Na_2SO_4$, concentrated and purified by silica gel column chromatography (cyclohexane:EtOAc, 2:1) to afford pure compound 292.2 as semi-solid (600 mg, 22%). ESI-MS: m/z 257 $[M+H]^+$.

Synthesis of Compound 292.3.

Step 1. Compound 292.2 (100 mg, 0.39 mmol) was dissolved in dry THF (3 mL) and cooled to $-20°$ C. NaH (24 mg, 0.98 mmol) was added. The mixture was stirred for 5 minutes and ethyl trifluoroacetate (56 µL, 0.47 mmol) was added at $-20°$ C. The mixture was allowed to warm to room temperature with stirring for 24 hours. After cooling to $0°$ C., MeOH (2 mL) was added and the mixture was concentrated to a syrup, which was dissolved in 10 mL of $CHCl_3$ and washed with 1N HCl (5 mL) and deionized water (5 mL). The organic layer was dried over $Na_2SO_4$ and concentrated to give a light yellow semi-solid compound (130 mg) that was used without further purification.

Step 2. The crude product from Step 1 (130 mg, 0.37 mmol) was dissolved in absolute ethanol (10 mL). 4-Sulfonamidophenylhydrazine hydrochloride (105 mg, 0.56 mmol) was added, and the reaction mixture was heated at reflux overnight, after which TLC (Cyclohexane:EtOAc, 2:1) showed complete consumption of starting material. The mixture was cooled, concentrated to a syrup, dissolved in 20 mL of EtOAc, washed with deionized water (2×5 mL), dried over $Na_2SO_4$ and concentrated to give a yellow syrup. Purification by silica gel column chromatography (cyclohexane:EtOAc, 2:1) afforded the compound as light yellow solid (123 mg, 66%). HPLC: 98.6% pure (Sphereclone 5 µL, $H_2O$:MeCN, 20 min linear from 10-90% MeCN, 1.0 mL/min). ESI-MS: m/z 384 $[M+H]^+$. $^1H$ NMR (300 MHz, DMSO-$d_6$, $D_2O$ exchanged): δ 7.88-7.85 (2H, m, ArH), 7.54-7.50 (2H, m, ArH), 7.13-7.09 (3H, m, ArH), 6.79-6.75 (2H, m, ArH).

Synthesis of Compound 292.4.

Compound 292.3 (70 mg, 0.14 mmol) was dissolved in 3 mL of dry DMF under an argon atmosphere. Diethylphosphonomethyl-O-triflate (51 mg, 0.17 mmol) and $Cs_2CO_3$ (69 mg, 0.21 mmol) were added. The reaction mixture was stirred overnight at room temperature. Deionized water (10 mL) was added and the mixture was extracted with ethyl acetate (2×15 mL). The ethyl acetate layer was washed with 1N HCl (5 mL) and deionized water (10 mL) and dried over $Na_2SO_4$. Concentration gave a syrup that on purification by preparative-TLC (1 plate, 20×20 cm, 2000 microns, solvent: $CHCl_3$:MeOH, 95:5) gave a gummy yellow solid (20 mg, 27% yield). HPLC: 97.8% pure (Sphereclone 5 µL, $H_2O$:MeCN, 20 min linear from 10-90% MeCN, 1.0 mL/min). ESI-MS: m/z 534 $[M+H]^+$. $^1H$ NMR (300 MHz, $CDCl_3$): δ 7.91 (2H, d, J=8.8 Hz, ArH), 7.46 (2H, d, J=8.8 Hz, ArH), 7.16 (2H, d, J=8.9 Hz, ArH), 6.96 (2H, d, J=8.9 Hz, ArH), 6.73 (1H, s, CH), 5.07 (2H, br s, NH), 4.31-4.22 (6H, m, 3×$OCH_2$), 1.37 (6H, t, J=7.1 Hz, 2×$CH_3$). $^{31}P$ NMR ($CDCl_3$, $H_3PO_4$ as external reference): δ 19.14

EXAMPLE 293

Preparation of Representative Triamcinolone Acetonide Derivatives

The syntheses of the phosphonate compounds of this invention, and of the intermediate compounds involved in their synthesis, is described below.

Protection of Reactive Substituents.

Depending on the reaction conditions employed, it may be necessary to protect certain reactive substituents from unwanted reactions by protection before the described reaction, and to deprotect the substituents afterwards, according to the knowledge of one skilled in the art. Protection and deprotection of functional groups are described, for example, in T. W. Greene and P. G. M. Wuts, *Protective Groups in Organic Synthesis* (Second Edition, Wiley, 1991). The protection and deprotection of steroidal ketones and alcohols is described in J. Fried and J. A. Edwards, *Organic Reactions in Steroid Chemistry, Vol.* 1 375ff (van Nostrand Reinhold, 1972). Reactive substituents which may be protected are shown in the accompanying schemes as, for example, [OH], [O], etc.

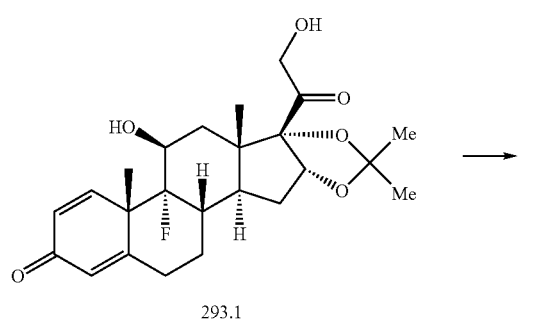

293.1

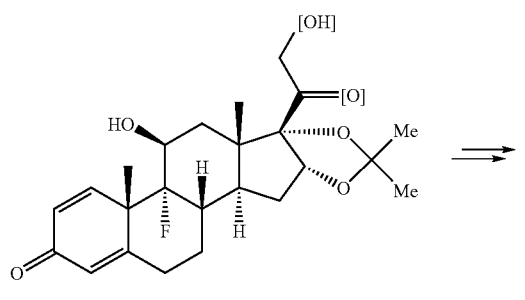

293.2

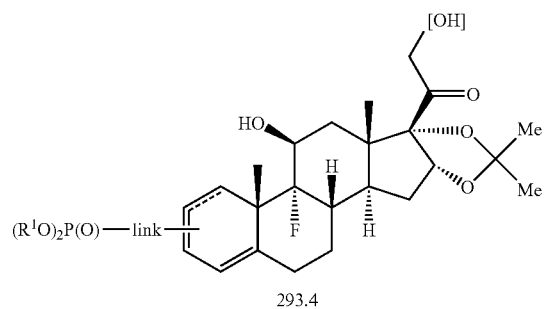

293.3

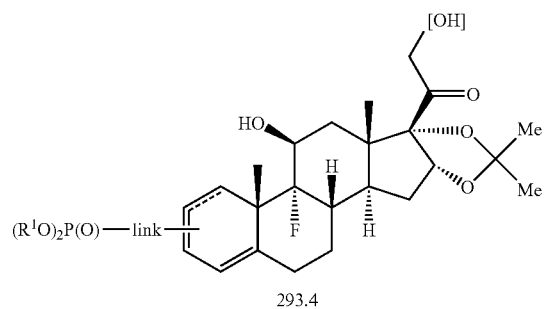

293.4

For example, a protection-deprotection sequence is depicted above in which the 20-ketone group and/or the 21-hydroxyl group of Triamcinolone acetonide 293.1 are protected to afford the derivative 293.2. The ketone is protected, for example, by conversion to the cyclic ethylene ketal, by reaction in toluene solution at reflux temperature with ethylene glycol and an acid catalyst, as described in *J. Am. Chem. Soc.*, 77:1904 (1955). Deprotection is effected by reaction with pyridinium tosylate in aqueous acetone, as described in *J. Chem. Soc. Chem. Comm.* 1351 (1987).

Alternatively, the 20-ketone is protected by conversion to the N,N-dimethylhydrazone. The dimethyl hydrazone is prepared by the reaction of the ketone 293.1 with N,N-dimethylhydrazine in ethanol-acetic acid, as described in *Org. Syn.* 50:102 (1970). The group is removed by treatment with sodium acetate and acetic acid in aqueous tetrahydrofuran, as described in *J. Am. Chem. Soc.* 101:5841 (1979).

Alternatively, the 20-ketone is protected as the diethylamine adduct. In this procedure, the substrate 293.1 is reacted with titanium tetrakis(diethylamide), as described in *J. Chem. Soc. Chem. Comm.* 406 (1983), to afford the adduct. The ketone is deprotected by reaction with water in an aqueous organic solvent.

The 21-hydroxyl group is protected, for example, by conversion to the acetate ester by reaction with one molar equivalent of acetyl chloride in dichloromethane/pyridine. The 21-acetoxy group is removed by reaction with one molar equivalent of lithium hydroxide in aqueous dimethoxyethane.

Alternatively, the 21-hydroxyl group is protected by conversion to the tert.butyl dimethylsilyl ether, by reaction in dimethylformamide solution with one molar equivalent of tert.butylchlorodimethylsilane and imidazole, as described in *J. Am. Chem. Soc.*, 94: 6190, 1972. The silyl ether is removed by reaction with tetrabutylammonium fluoride in tetrahydrofuran solution, as described in *J. Am. Chem. Soc.* 94:6190 (1972).

The protected compound 293.2 is then converted into the phosphonate-containing analog 293.3, using the procedures described below, and the protecting group or groups are then removed, as described above, to give the phosphonate 293.4.

EXAMPLE 294

Preparation of Representative Triamcinolone Acetonide Derivatives

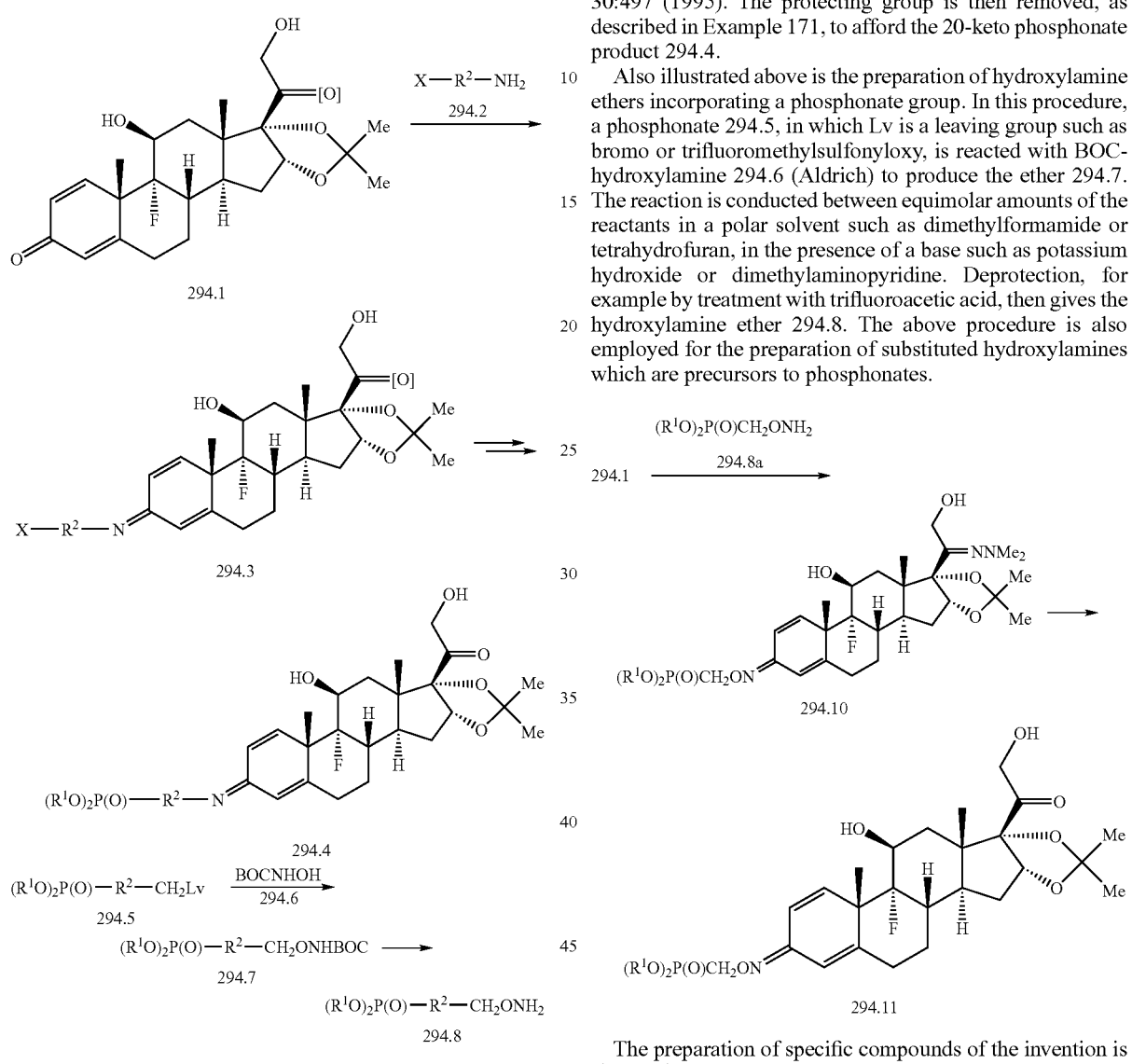

The preparation of phosphonates of compounds of the invention in which the phosphonate is attached by means of an imino or iminoxy group and a variable carbon chain is shown above.

In this procedure, the ketone-protected derivative 294.1 is reacted with an amine or hydroxylamine 294.2, in which $R^2$ is an alkyl, alkenyl, cycloalkyl or cycloalkenyl group, optionally incorporating a heteroatom O, S or N, or a functional group such as an amide, ester, oxime, sulfoxide or sulfone, etc., or an optionally substituted aryl, heteroaryl or aralkyl group, optionally incorporating a heteroatom O, S or N, and X is either a phosphonate group or a group that is subsequently converted into a phosphonate-containing substituent. For example, X may be dialkylphosphono, bromo, hydroxy, amino, carboxy and the like.

The reaction is conducted between equimolar amounts of the reactants in an aprotic solvent such as pyridine or xylene, or in an alcoholic solvent such as ethanol, optionally in the presence of an acid catalyst, to give the imine or oxime 294.3. The preparation of oximes of steroidal 3-ketones is described in *Anal. Bioch.* 86:133 (1978) and in *J. Mass. Spectrom.* 30:497 (1995). The protecting group is then removed, as described in Example 171, to afford the 20-keto phosphonate product 294.4.

Also illustrated above is the preparation of hydroxylamine ethers incorporating a phosphonate group. In this procedure, a phosphonate 294.5, in which Lv is a leaving group such as bromo or trifluoromethylsulfonyloxy, is reacted with BOC-hydroxylamine 294.6 (Aldrich) to produce the ether 294.7. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 294.8. The above procedure is also employed for the preparation of substituted hydroxylamines which are precursors to phosphonates.

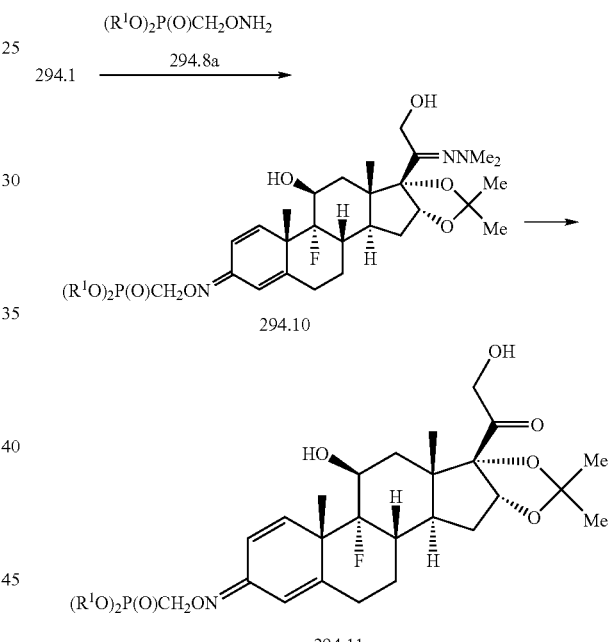

The preparation of specific compounds of the invention is shown above.

In particular, the preparation of phosphonates of the invention in which the phosphonate is attached by means of an iminoxy group is shown. In this procedure, the substrate 294.1, in which the 20-ketone is protected as the dimethyl hydrazone derivative, is reacted with a dialkyl phosphonomethyl hydroxylamine 294.8a, prepared as described above from a dialkyl trifluoromethylsulfonyloxymethyl phosphonate (*Tetrahedron Lett.* 27:1477 (1986)) and BOC-hydroxylamine, to afford the oxime 294.10. Deprotection, as described herein, e.g., in Example 171, then affords the 20-keto phosphonate 294.11. The oxime forming reaction is performed at ambient temperature in ethanol-acetic acid solution between equimolar amounts of the reactants.

Using the above procedures, but employing, in place of the hydroxylamine ether 294.8a, different oxime ethers 294.2, the corresponding products 294.4 are obtained.

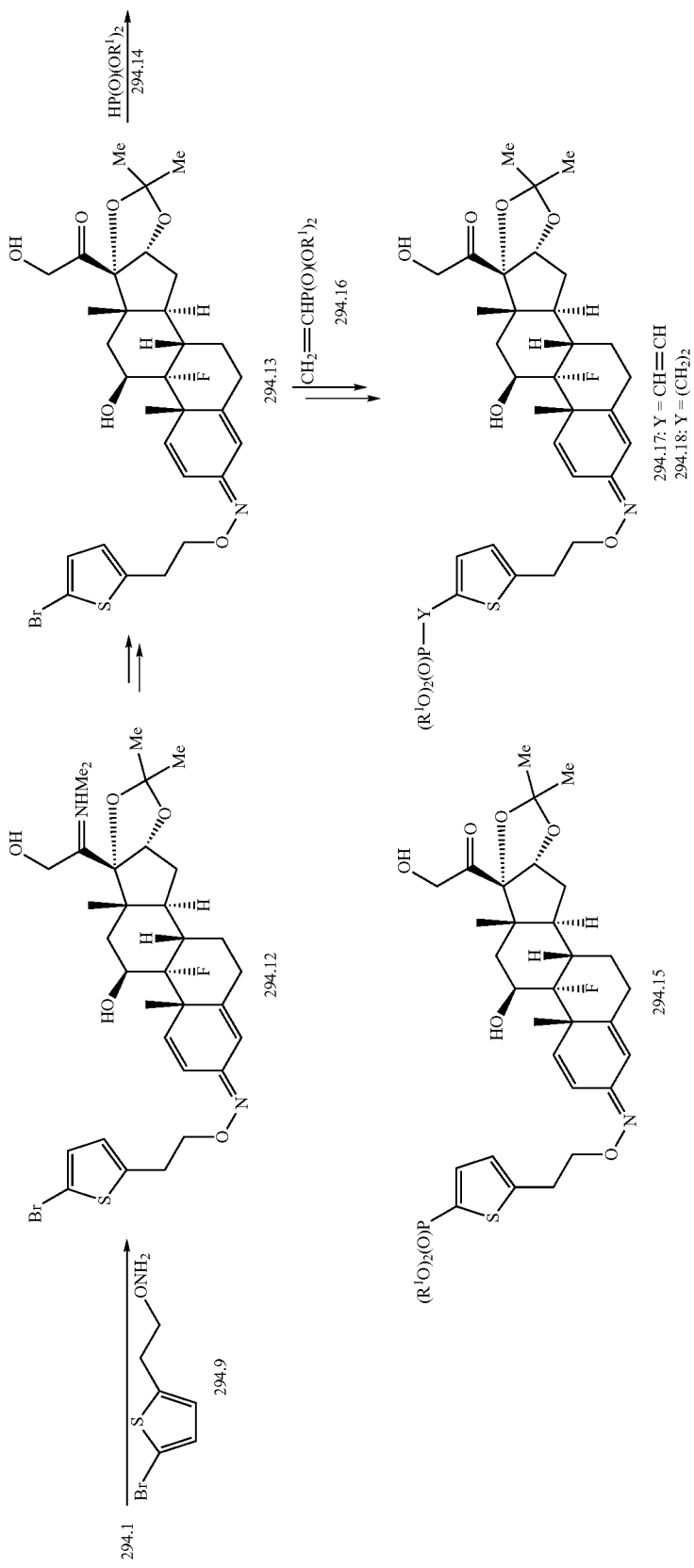

Synthesis of specific compounds of the invention is illustrated above. In particular, the preparation of compounds of the invention in which the phosphonate group is attached by means of a thienylethoxy oxime group is shown. In this procedure, the dienone 294.1, in which the 20-ketone is protected as the dimethyl hydrazone, is reacted, as described above, with O-(5-bromo-2-thienylethoxy)hydroxylamine 294.9, prepared as described above from 5-bromo-2-thienylethyl bromide (Syn., 2003, 455), and BOC-protected hydroxylamine 294.6, to give the oxime 294.12. The protecting group is then removed to yield the 20-keto product 294.13. The latter product is then reacted, in the presence of a palladium catalyst, with a dialkyl phosphite 294.14 to afford the phosphonate 294.15. The preparation of arylphosphonates by means of a coupling reaction between aryl bromides and dialkyl phosphites is described in *J. Med. Chem.* 35:1371 (1992). The reaction is performed at ca. 100° in an inert solvent such as toluene, in the presence of a base such as triethylamine and a catalytic amount of tetrakis(triphenylphosphine)palladium(0).

Alternatively, the bromo compound 294.13 is coupled with a dialkyl vinyl phosphonate 294.16 (Aldrich) to afford the phosphonate 294.17. The coupling of aryl halides with olefins by means of the Heck reaction is described, for example, in F. A. Carey and R. J. Sundberg, *Advanced Organic Chemistry* 503ff (Plenum, 2001) and in *Acc. Chem. Res.* 12:146 (1979). The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 294.17 is reduced, for example by reaction with diimide, to produce the saturated analog 294.18. The reduction of olefinic bonds is described in R. C. Larock, *Comprehensive Organic Transformations* 6ff (VCH 1989). The transformation is effected by means of catalytic hydrogenation, for example using a palladium on carbon catalyst and hydrogen or a hydrogen donor, or by the use of diimide or diborane.

Using the above procedures, but employing, in place of the bromothienylethyl reagent 294.9, different bromo-substituted aryl or heteroaryl alkoxy hydroxylamines, and/or different dialkyl alkenyl phosphonates, the products analogous to the compounds 294.15, 294.17 and 294.18 are obtained.

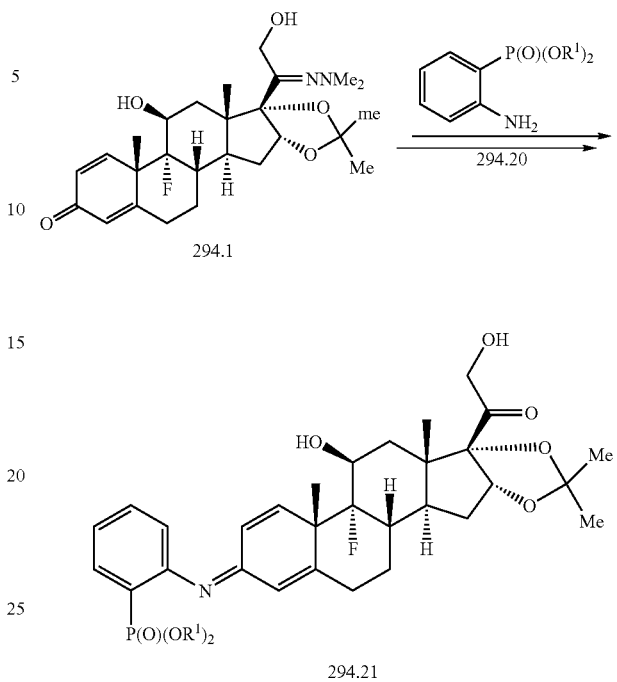

The preparation of phosphonates of the invention in which the phosphonate is attached by means of a 2-phenylimino group is illustrated above. In this procedure, the substrate 294.1, in which the 20-ketone is protected as the dimethylhydrazone, is reacted with a dialkyl 2-aminophenyl phosphonate 294.20 (Syn., 1999, 1368), to give, after deprotection, the imine product 294.21. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions.

Using the above procedures, but employing, in place of the 2-aminophenyl phosphonate 294.20 different amino-substituted aryl or heteroaryl phosphonates, products analogous to 294.21 are obtained.

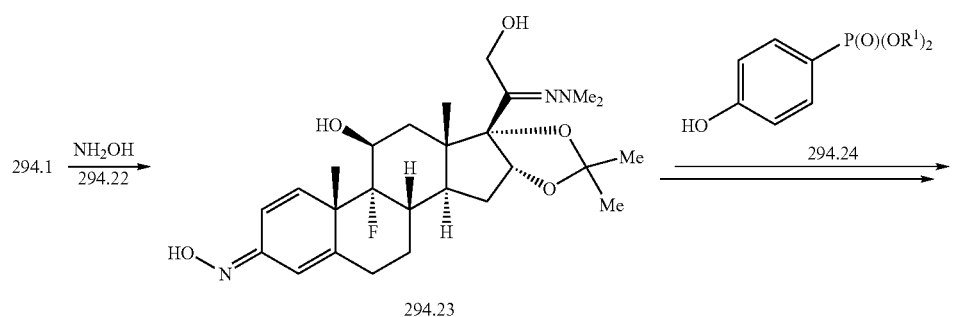

-continued

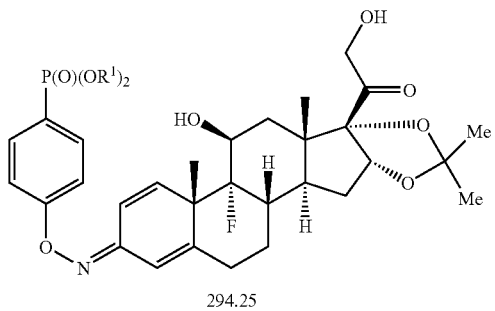

294.25

Illustrated above is the preparation of phosphonates of the invention in which the phosphonate is attached by means of an oximino group and an ether linkage. In this procedure, the dienone 294.1, in which the 20-ketone is protected as the dimethylhydrazone, is reacted with hydroxylamine 294.22 to yield the oxime 294.23. The reaction of steroidal 1,4-dien-3-ones with hydroxylamines is described in *J. Steroid Bioch.* 7:795 (1976). The reaction is performed between equimolar amounts of the reactants in a polar organic solvent such as pyridine or methanol, optionally in the presence of acetic acid or sodium acetate.

The product 294.23 is then coupled, in a Mitsonobu reaction, with a dialkyl 4-hydroxyphenyl phosphonate 294.24 (Epsilon), to yield, after deprotection, the ether oxime 294.25. The preparation of aromatic ethers by means of the Mitsonobu reaction is described, for example, in R. C. Larock, *Comprehensive Organic Transformations* 448 (VCH, 1989), in F. A. Carey and R. J. Sundberg, *Advanced Organic Chemistry, Part B* 153-4 (Plenum, 2001), and in *Org. React.* 42:335, (1992). The phenol and the hydroxyl component are reacted together in an aprotic solvent such as, for example, tetrahydrofuran, in the presence of a dialkyl azodicarboxylate and a triarylphosphine, to afford the ether or thioether products. The procedure is also described in *Org. React.* 42:335-656 (1992).

Using the above procedures, but employing, in place of the hydroxyaryl-substituted phosphonate 294.24, different hydroxyaryl-substituted phosphonates, the products analogous to 294.25 are obtained.

EXAMPLE 295

Preparation of Representative Triamcinolone Acetonide Derivatives

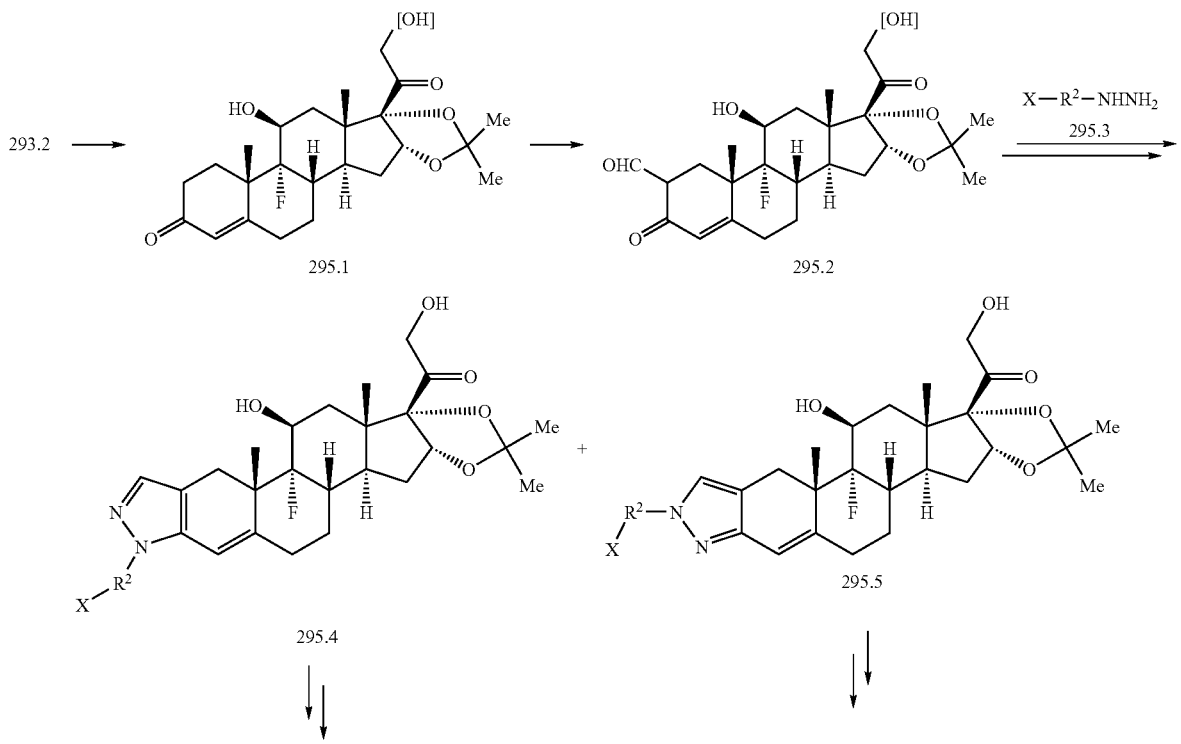

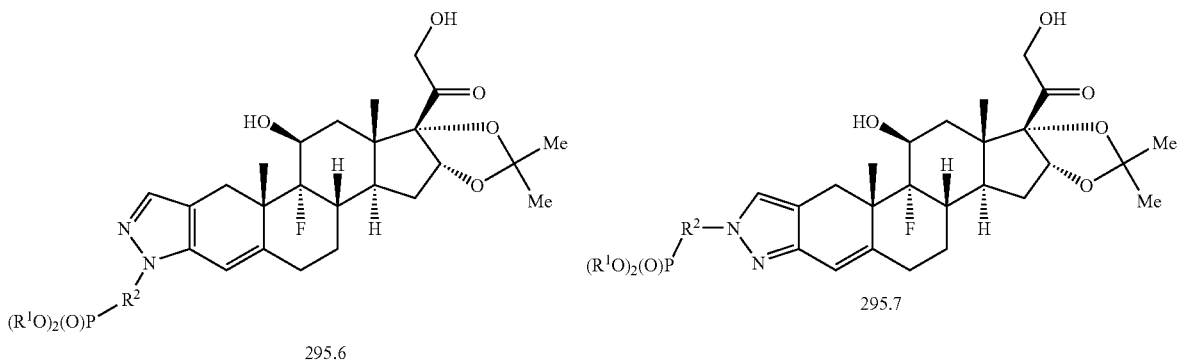

295.6

295.7

Illustrated above is the preparation of phosphonate esters of the invention in which the phosphonate group is attached to the 1' or 2' position of the pyrazole ring, by means of an aromatic or heteroaromatic group, a heteroatom and/or a variable carbon chain. In this procedure, the dienone 293.1, in which the 21-hydroxyl group is protected as described in Example 293, is reduced to afford the 1,2-dihydro product 295.1. The catalytic hydrogenation reaction is effected by the use of tris(triphenylphosphine)rhodium (I) chloride, for example as described in *J. Med. Chem.* 44:602 (2001). The product is then reacted with ethyl formate and a base such as sodium hydride, in an inert solvent such as toluene or dimethylformamide, as described in *J. Am. Chem. Soc.* 86:1520 (1964), to afford the 2-formyl product 295.2. This compound is then reacted with an alkyl, aralkyl, aryl or heteroaryl hydrazine 295.3, in which the substituent X is either a phosphonate group or a group which is subsequently transformed into a phosphonate-containing substituent. For example, X may be dialkylphosphono, bromo, hydroxy, amino, carboxyl and the like. The reaction yields, after deprotection of the 21-hydroxyl group, the isomeric 2'- and 1'-aryl pyrazoles 295.4 and 295.5. The pyrazole-forming reaction is performed between equimolar amounts of the reactants in an acidic solvent such as acetic acid, as described in *J. Am. Chem. Soc.* 86:1520 (1964). The pyrazoles 295.4 and 295.5 are then transformed, for example by the procedures described herein, into the phosphonates 295.6 and 295.7.

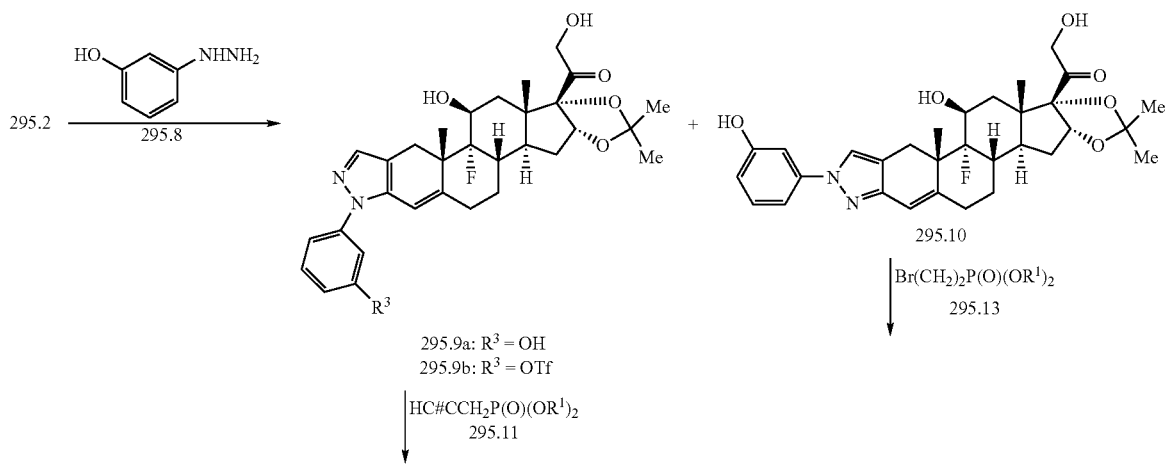

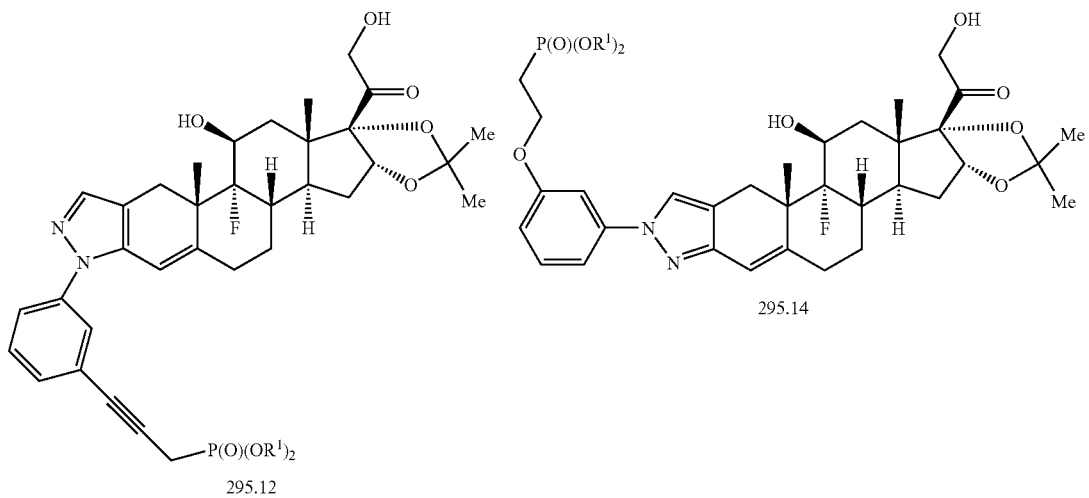

The preparation of specific compounds of the invention in which the phosphonate is attached by means of an ether or an acetylenic linkage is shown above.

In this procedure, the ketoaldehyde 295.2 is reacted, as described above, with 3-hydroxyphenyl hydrazine 295.8 (JP 03011081) to give the pyrazoles 295.9a and 295.10. The 2'-substituted isomer 295.9a is then reacted in dichloromethane solution with one molar equivalent of trifluoromethanesulfonyl chloride and pyridine, to give the triflate 295.9b. The product is then reacted in toluene solution with a dialkyl propynyl phosphonate 295.11 (Syn 1999, 2027), triethylamine and a catalytic amount of tetrakis(triphenylphosphine)palladium(0), to give the acetylenic product 295.12. The palladium-catalyzed coupling reaction of aryl triflates with terminal acetylenes is described in WO 0230930.

The isomeric pyrazole 295.10 is reacted, in dimethylformamide solution at 70°, with one molar equivalent of a dialkyl 2-bromoethyl phosphonate 295.13 (Aldrich) and potassium carbonate to yield the ether phosphonate 295.14.

Using the above procedures, but employing different hydroxy-substituted hydrazines, and/or different acetylenic or bromo-substituted phosphonates, products analogous to 295.12 and 295.14 are obtained.

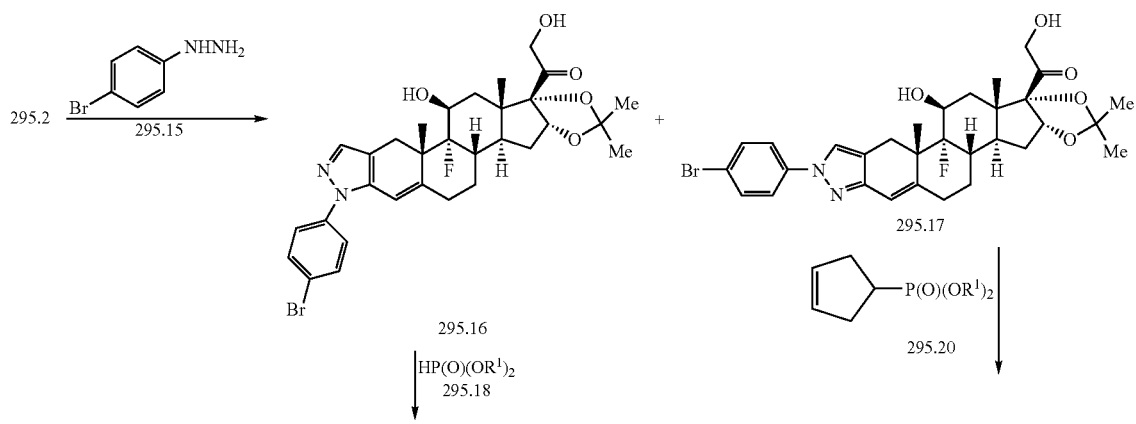

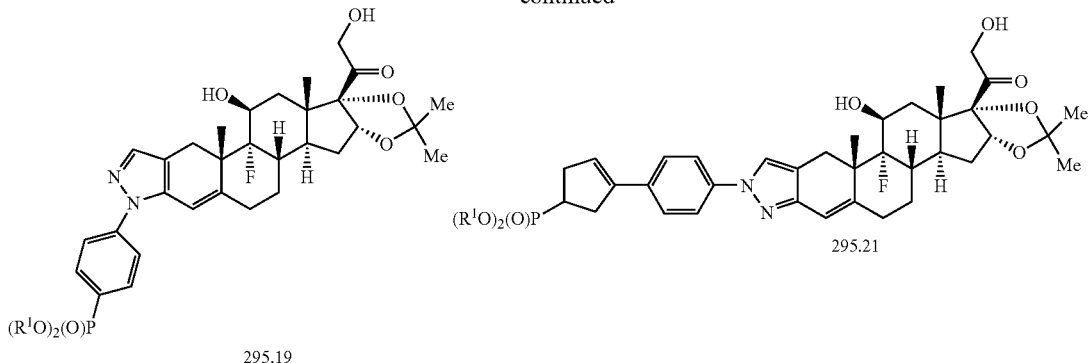

The preparation of phosphonates of the invention in which the phosphonate group is attached by means of a phenyl group or a phenylcyclopentenyl linkage is shown above. In this procedure, the ketoaldehyde 295.2 is reacted, as described above, with 4-bromophenyl hydrazine 295.15 (*J. Organomet. Chem.*, 62:581(1999)) to produce the pyrazoles 295.16 and 295.17. The 2'-substituted isomer 295.16 is then coupled, as described above, with a dialkyl phosphite 295.18 to give the phosphonate 295.19.

Alternatively, the 1-substituted pyrazole 295.22 is coupled in a Heck reaction, as described above, with a dialkyl cyclopentenyl phosphonate 295.20 (*Syn. Comm.*, 28:83(1998)) to prepare the cyclopentenyl phosphonate 295.21.

Using the above procedures, but employing, in place of the 4-bromophenyl hydrazine 295.15, different bromo-substituted hydrazines, and/or different dialkyl alkenyl-substituted phosphonates, the products analogous to the compounds 295.19 and 295.21 are obtained.

EXAMPLE 296

Preparation of Representative Triamcinolone Acetonide Derivatives

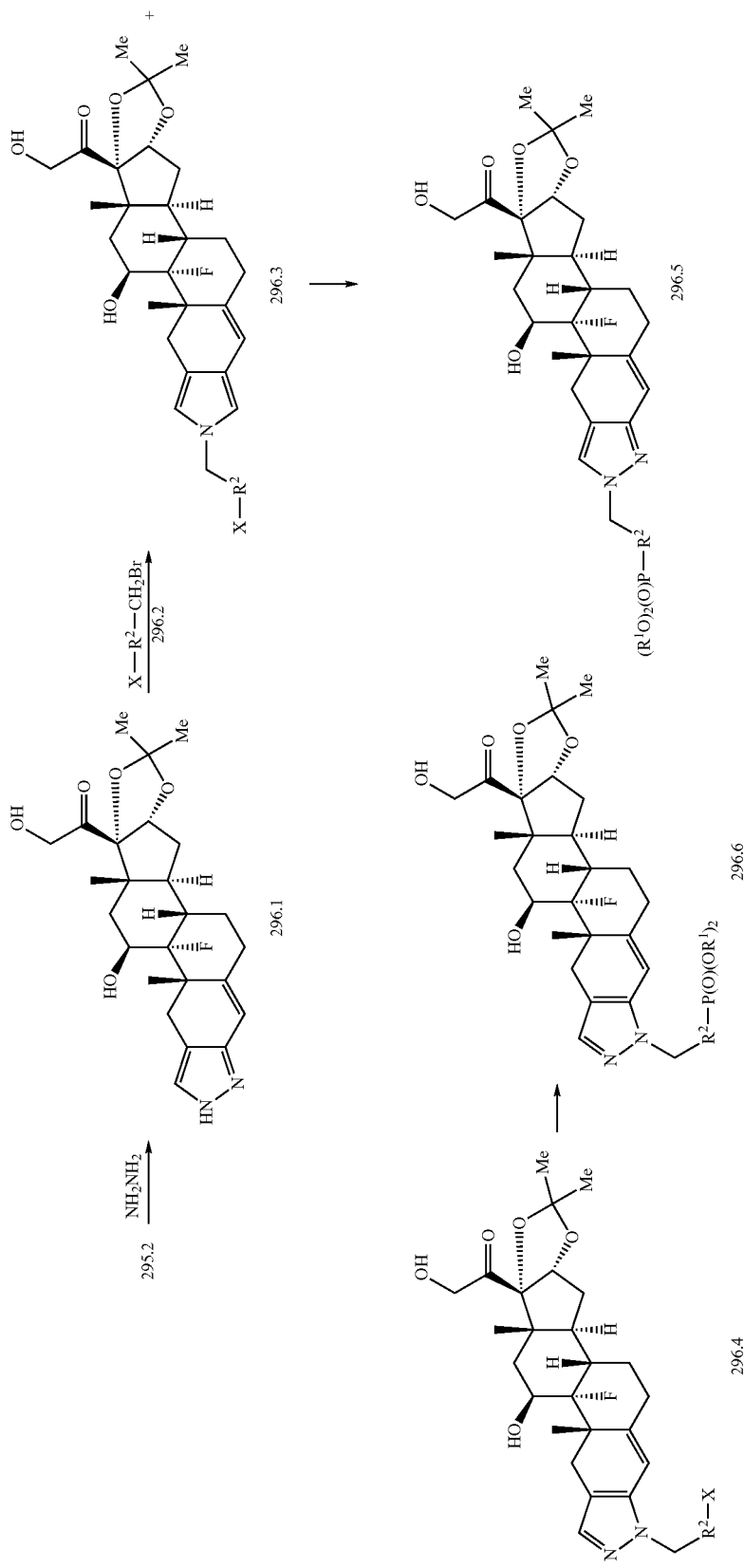

The preparation of phosphonate esters of the invention in which the phosphonate group is attached by means of a variable carbon linkage is illustrated above.

In this procedure, the ketoaldehyde 295.2 is reacted with hydrazine to afford the pyrazole derivative 296.1. The reaction of steroidal 2-formyl-3-ketones with hydrazine is described in *J. Am. Chem. Soc,* 86:1520 (1964). The reaction is performed in acetic acid at ambient temperature. The pyrazole product is then reacted with a bromomethyl compound 296.2, in which $R^2$ and X are as defined above, or a reactive bromoheteroaromatic reagent, to yield the alkylation products 296.3 and 296.4. The alkylation of substituted pyrazoles is described, for example, in T. L. Gilchrist, *Heterocyclic Chemistry* 309 (Longman, 1992). The reaction is performed between equimolar amounts of the substrates in a polar solvent such as dimethylformamide or tetrahydrofuran, in the presence of a base such as dimethylaminopyridine, lithium hexamethyldisilazide and the like. The products 296.3 and 296.4 are, except in cases where X is dialkylphosphono, converted into the phosphonates 296.5 and 296.6, using the procedures described herein.

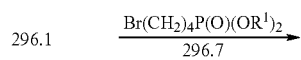

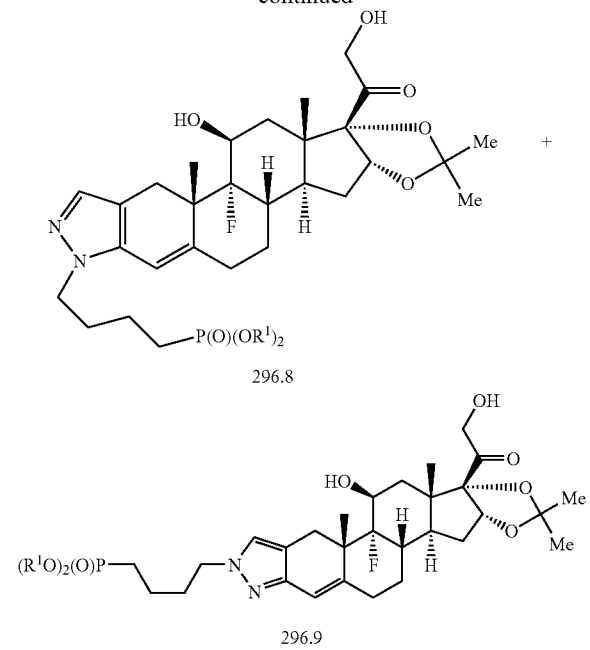

Specific compounds of the invention are shown above. The pyrazole 296.1 is reacted in dimethylformamide solution at 70° with one molar equivalent of a dialkyl 4-bromobutyl phosphonate 296.7 (Synthelec) and cesium carbonate, to give the pyrazoles 296.8 and 296.9.

Using the above procedures, but employing different bromo-substituted phosphonates, the products analogous to 296.8 and 296.9 are obtained.

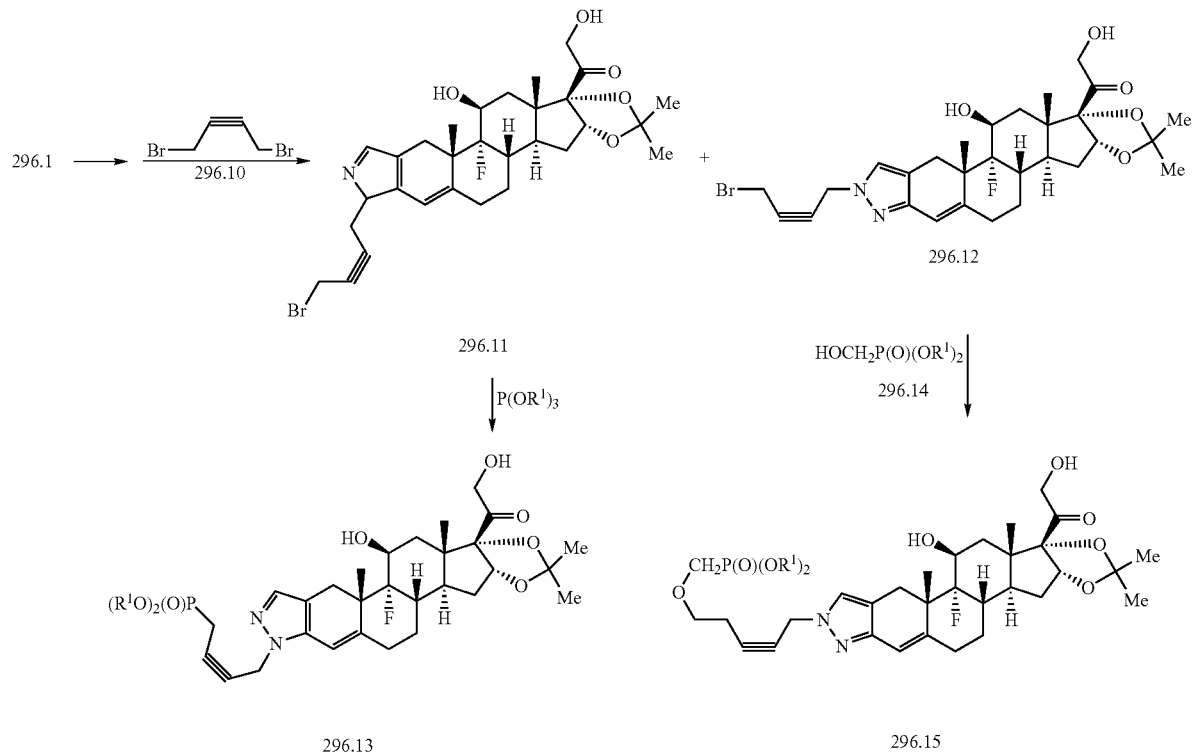

Specific compounds of the invention are shown above. The pyrazole 296.1 is reacted in tetrahydrofuran solution with 1,4-dibromobut-2-yne 296.10 and potassium hexamethyl disilazide, to give the alkylation products 296.11 and 296.12. The 2'-substituted isomer 296.11 is then reacted, in a Arbuzov reaction, with a trialkyl phosphite to yield the phosphonate 296.13. The Arbuzov reaction is described in *Handb. Organophosphorus Chem.*, 115 (1992). In this procedure, in which a bromo substituent is converted into the corresponding phosphonate, the substrate is heated at from about 60° to about 160° with a five to fifty-fold molar excess of a trialkyl phosphite, to effect the transformation.

The 2'-substituted pyrazole 296.14 is reacted at 70° in dimethylformamide solution with one molar equivalent of a dialkyl hydroxymethyl phosphonate 296.14 (Aldrich) and cesium carbonate, to give the ether phosphonate 296.15.

Using the above procedures, but employing different dibromides, and/or different hydroxyl-substituted phosphonates, the products analogous to 296.13 and 296.15 are obtained.

EXAMPLE 297

Preparation of Representative Mometasone Furoate Derivatives

Preparation of representative compounds of the invention is described hereinbelow.

Protection of Reactive Substituents

Depending on the reaction conditions employed, it may be necessary to protect certain reactive substituents from unwanted reactions by protection before the described sequence is reacted, and to deprotect the substituents afterwards, according to the knowledge of one skilled in the art. Protection and deprotection of functional groups are described, for example, in Protective Groups in Organic Synthesis, by T. W. Greene and P. G. M. Wuts, Wiley, Second Edition 1990. The protection and deprotection of steroidal ketones and alcohols is described in Organic Reactions in Steroid Chemistry, Vol. 1, J. Fried and J. A. Edwards, van Nostrand Reinhold, 1972, p. 375ff. Reactive substituents which may be protected are shown in the accompanying schemes as, for example, [OH], [O], etc.

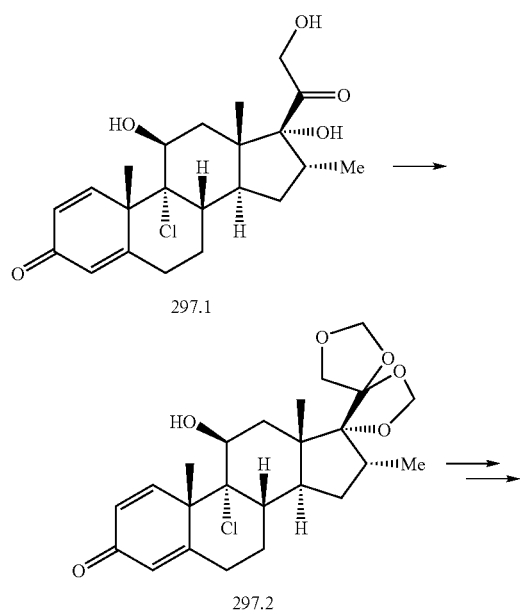

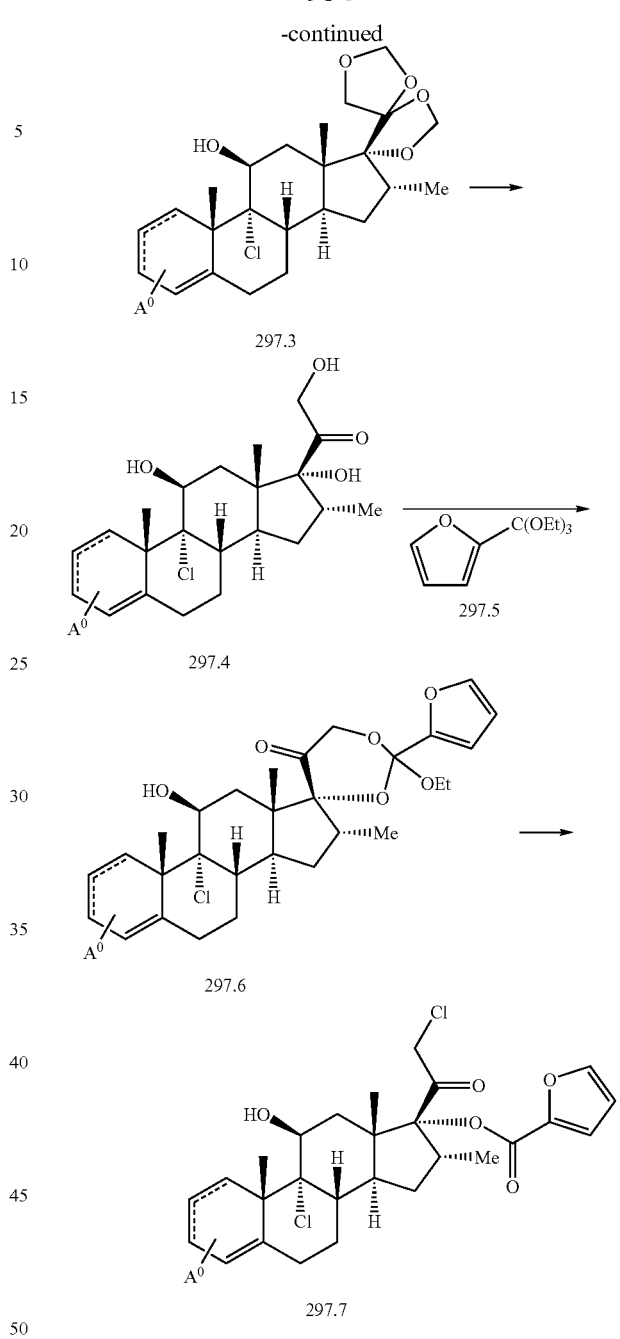

For example, depicted above is a protection-deprotection sequence in which the steroid side-chain is protected as a bis-methylenedioxy (BMD) moiety. In this sequence, 9α-chloro-16α-methyl-11β,17α,21-trihydroxypregn-1,4-dien-3,21-dione 297.1 (U.S. Pat. No. 4,472,393) is reacted with paraformaldehyde and an acid catalyst such as hydrochloric acid, as described in "Protective Groups in Organic Synthesis," by T. W. Greene and P. G. M. Wuts, Wiley, Second Edition 1990, p. 223, to yield the BMD derivative 297.2.

The phosphonate moiety is then introduced, using the procedures described below, to produce the phosphonate ester 297.3. The BMD moiety is then hydrolyzed, for example by treatment with 50% aqueous acetic acid, as described in "Protective Groups in Organic Synthesis," by T. W. Greene and P. G. M. Wuts, Wiley, Second Edition 1990, p. 223, to afford the triol 297.4. The latter compound is then converted into the 17,21-cyclic orthoester 297.6 using the procedure described in *Chem. Pharm. Bull.*, 34:1613(1986). The substrate is reacted in dimethylformamide at 70° C. with two molar equivalents of triethyl ortho-2-furoate 297.5 (*Zh. Org. Khim.*, 50:1348(1980)) and a catalytic amount of p-toluenesulfonic acid. The product is then reacted with an excess of trimethylsilyl chloride in dimethylformamide at ambient temperature to produce the 21-chloro 17-(2-furoate) product 297.7.

Alternatively, the substrate 297.4 is converted into the product 297.7 by means of the method described in *J. Med. Chem.*, 1987, 30:1581(1987). In this procedure, the 21-hydroxy group is activated by conversion to the 21-mesylate, by reaction with mesyl chloride in pyridine; the mesylate group is then displaced to yield the 21-chloro intermediate, by reaction with lithium chloride in dimethylformamide, and the 17-hydroxyl group is esterified to give the 21-chloro-17-(2-furoate) derivative 297.7. The selective acylation of the 17α-hydroxyl group in the presence of an 11β hydroxyl group is described in *J. Med. Chem.*, 30:1581(1987).

EXAMPLE 298

Preparation of Representative Mometasone Furoate Derivatives

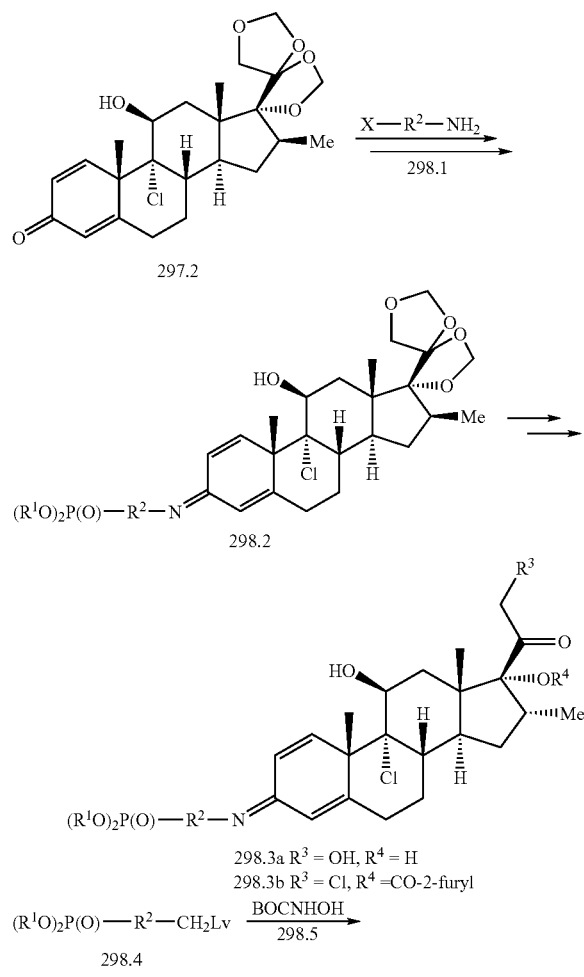

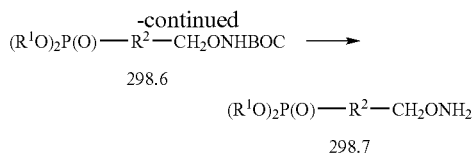

The preparation of phosphonates of the invention in which the phosphonate is attached by means of an imino or iminoxy group and a variable carbon chain is illustrated above.

In this procedure, the BMD-protected derivative 297.2 is reacted with an amine or hydroxylamine 298.1, in which $R^2$ is an alkyl, alkenyl, cycloalkyl or cycloalkenyl group, optionally incorporating a heteroatom O, S or N, or a functional group such as an amide, ester, oxime, sulfoxide or sulfone, etc., or an optionally substituted aryl, heteroaryl or aralkyl group, optionally incorporating a heteroatom O, S or N, and X is either a phosphonate group or a group that is subsequently converted into a phosphonate-containing substituent. For example, X may be dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime. The preparation of oximes of steroidal 3-ketones is described in *Anal. Bioch.*, 86:133(1978). and in *J. Mass. Spectrom.*, 30:497(1995). The BMD-protected side-chain compound 298.2 is then converted into the triol 298.3a, and then to the 21-chloro 17-(2-furoate) product 298.3b, as described herein.

Also illustrated above is the preparation of hydroxylamine ethers incorporating a phosphonate group. In this procedure, a phosphonate 298.4, in which Lv is a leaving group such as bromo or trifluoromethylsulfonyloxy, is reacted with BOC-hydroxylamine 298.5 (Aldrich) to produce the ether 298.6. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 298.7.

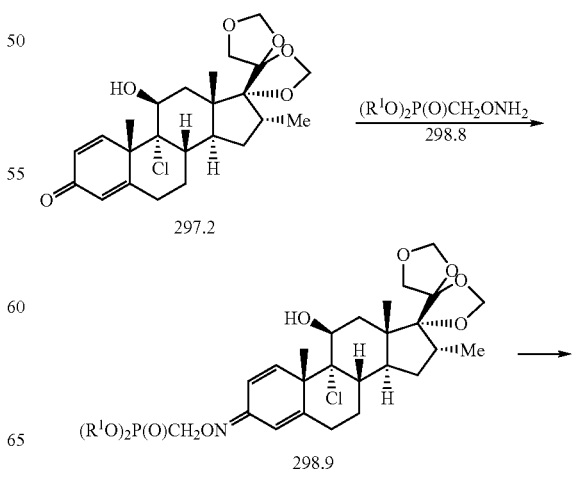

-continued

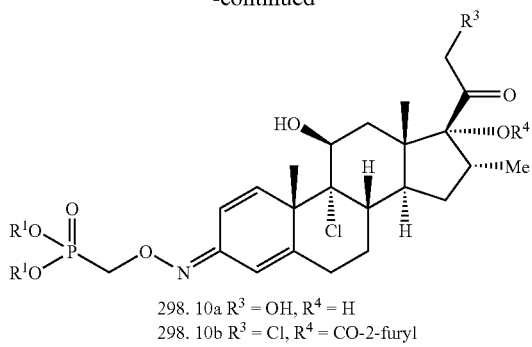

298.10a R³ = OH, R⁴ = H
298.10b R³ = Cl, R⁴ = CO-2-furyl

The synthesis of specific compounds of the invention is shown above. The preparation of phosphonates of the invention in which the phosphonate is attached by means of an iminoxy group is illustrated. In this procedure, the substrate 297.2 is reacted with a dialkyl phosphonomethyl hydroxylamine 298.8, prepared as described above from a dialkyl trifluoromethylsulfonyloxymethyl phosphonate (*Tet. Lett.*, 27:1477(1986)) and BOC-hydroxylamine, to afford the oxime 298.9. Deprotection then affords the triol 298.10a from which the 21-chloro 17-(2-furoate) compound 298.10b is prepared, using the procedures described in Example 297. The oxime forming reaction is performed at ambient temperature in ethanol-acetic acid solution between equimolar amounts of the reactants.

Using the above procedures, but employing, in place of the hydroxylamine ether 298.8, different oxime ethers 298.1, the corresponding products 298.3b are obtained.

The synthesis of specific compounds of the invention is shown above. The preparation of compounds of the invention in which the phosphonate group is attached by means of a pyridylmethoxy oxime group is illustrated above. In this procedure, the dienone 297.2 is reacted, as described above, with O-(5-bromo-3-pyridylmethoxy)hydroxylamine 298.11, prepared as described above from 5-bromo-3-bromomethylpyridine (EP 511865) and BOC-protected hydroxylamine 298.5, to give, after deprotection of the side-chain, the oxime 298.12. The product is then reacted, in the presence of a palladium catalyst, with a dialkyl phosphite 298.13 to afford the phosphonate 298.14a. The preparation of arylphosphonates by means of a coupling reaction between aryl bromides and dialkyl phosphites is described in *J. Med. Chem.*, 35: 1371(1992). The reaction is performed at ca. 100° C. in an inert solvent such as toluene, in the presence of a base such as triethylamine and a catalytic amount of tetrakis(triphenylphosphine)palladium(0). The 21-hydroxy compound 298.14a is then converted, as described in Example 297, into the 21-chloro 17-(2-furoate) derivative 298.14b.

Alternatively, the bromo compound 298.12 is coupled with a dialkyl vinyl phosphonate 298.15 (Aldrich) to afford the phosphonate 298.16a. The coupling of aryl halides with olefins by means of the Heck reaction is described, for example, in F. A. Carey and R. J. Sundberg, "Advanced Organic Chemistry," 503ff (Plenum, 2001) and in *Acc. Chem. Res.*, 12:146 (1979). The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethyl amine or potassium carbonate. Optionally, the double bond present in the product 298.16a is reduced, for

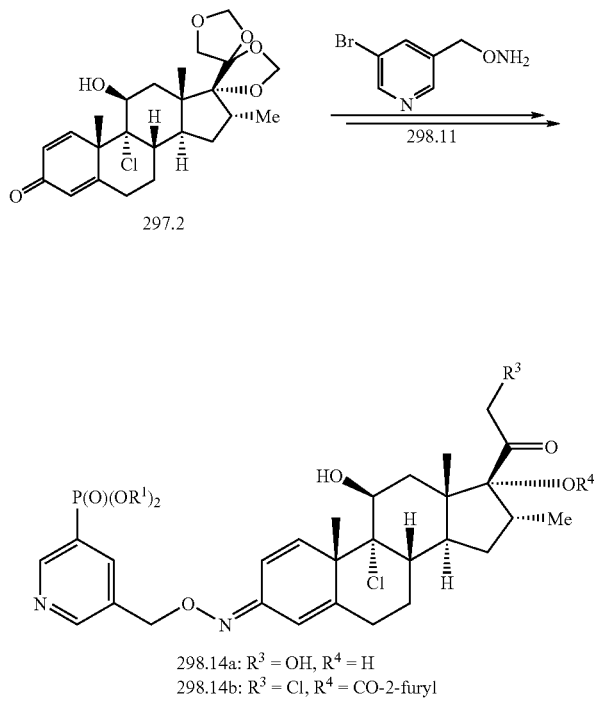

298.14a: R³ = OH, R⁴ = H
298.14b: R³ = Cl, R⁴ = CO-2-furyl

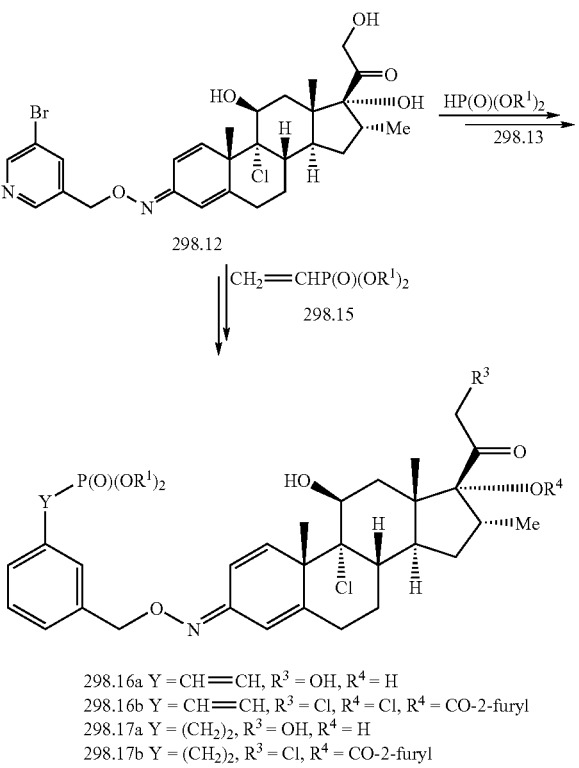

298.16a Y = CH═CH, R³ = OH, R⁴ = H
298.16b Y = CH═CH, R³ = Cl, R⁴ = Cl, R⁴ = CO-2-furyl
298.17a Y = (CH₂)₂, R³ = OH, R⁴ = H
298.17b Y = (CH₂)₂, R³ = Cl, R⁴ = CO-2-furyl example by reaction with diimide, to produce the saturated analog 298.17a. The reduction of olefinic bonds is described in R. C. Larock, "Comprehensive Organic Transformations," 6ff (VCH, 1989). The transformation is effected by means of catalytic hydrogenation, for example, using a palladium on carbon catalyst and hydrogen or a hydrogen donor, or by the use of diimide or diborane. The products 298.16a and 298.17a are then converted into the 21-chloro 17-(2-furoate) analogs 298.16b and 298.17b.

Using the above procedures, but employing, in place of the bromopyridylmethoxy reagent 298.11, different bromo-substituted aryl or heteroaryl alkoxy hydroxylamines, and/or different dialkyl alkenyl phosphonates, the products analogous to the compounds 298.14b, 298.16b and 298.17b are obtained.

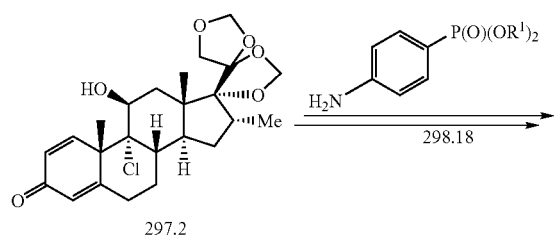

-continued

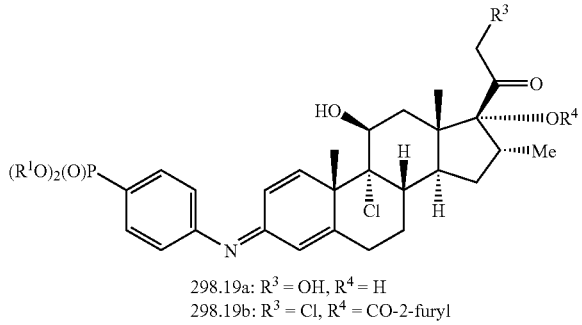

298.19a: $R^3$ = OH, $R^4$ = H
298.19b: $R^3$ = Cl, $R^4$ = CO-2-furyl

The preparation of specific compounds of the invention is depicted above. The preparation of phosphonates of the invention in which the phosphonate is attached by means of an imino group. In this procedure, the substrate 297.2 is reacted with a dialkyl 4-aminophenyl phosphonate 298.18 (Epsilon) to give, after deprotection, the imine product 298.19a. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions. The product is then converted into the 21-chloro 17-(2-furoate) compound 298.19b.

Using the above procedures, but employing, in place of the 4-aminophenyl phosphonate 298.18 different amino-substituted aryl or heteroaryl phosphonates, products analogous to 298.19b are obtained.

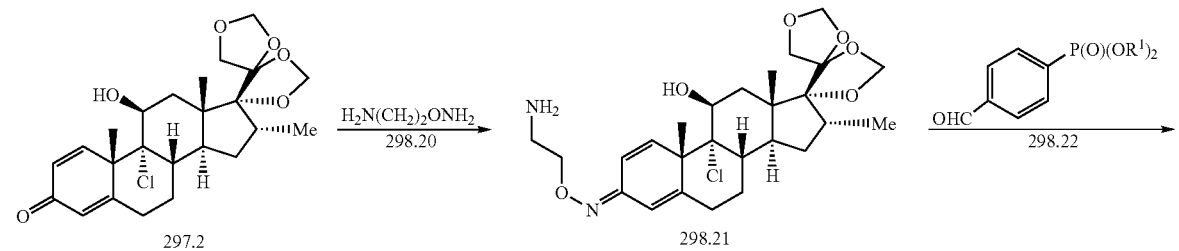

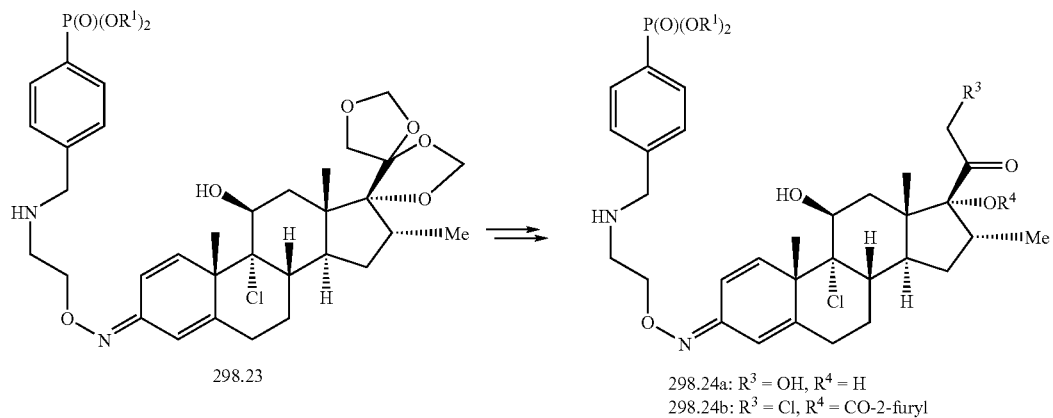

298.24a: $R^3$ = OH, $R^4$ = H
298.24b: $R^3$ = Cl, $R^4$ = CO-2-furyl

The preparation of specific compounds of the invention is shown above. Phosphonates of the invention in which the phosphonate is attached by means of an oximino group and an amine linkage are illustrated. In this procedure, the dienone 297.2 is reacted with O-(2-aminoethyl)hydroxylamine 298.20 (*Pol. J. Chem.*, 55:1163(1981)) to yield the oxime 298.21. The reaction of steroidal 1,4-dien-3-ones with substituted hydroxylamines is described in *J. Steroid Bioch.*, 7:795(1976); the reaction is performed between equimolar amounts of the reactants in a polar organic solvent such as pyridine or methanol, optionally in the presence of acetic acid or sodium acetate. The product is then reacted, in a reductive amination procedure, with a dialkyl 4-formylphenyl phosphonate 298.22 (Epsilon) and sodium triacetoxybrorhydride, to yield the amine oxime 298.23. The preparation of amines by means of reductive amination procedures is described, for example, in R. C. Larock, "Comprehensive Organic Transformations," 421 (VCH), and in F. A. Carey and R. J. Sundberg, "Advanced Organic Chemistry," Part B, 269 (Plenum, 2001). In this procedure, the amine component and the aldehyde or ketone component are reacted together in the presence of a reducing agent such as, for example, borane, sodium cyanoborohydride, sodium triacetoxyborohydride or diisobutylaluminum hydride, optionally in the presence of a Lewis acid, such as titanium tetraisopropoxide, as described in *J. Org. Chem.*, 55:2552 (1990).

The amine product 298.23 is then converted, as described in Example 297, into the 21-chloro 17-(2-furoate) product 298.24b.

Using the above procedures, but employing, in place of the hydroxylamine 298.22, different amino-substituted hydroxylamines, and/or different formyl-substituted phosphonates, the products analogous to 298.24b are obtained.

EXAMPLE 299

Preparation of Representative Mometasone Furoate Derivatives

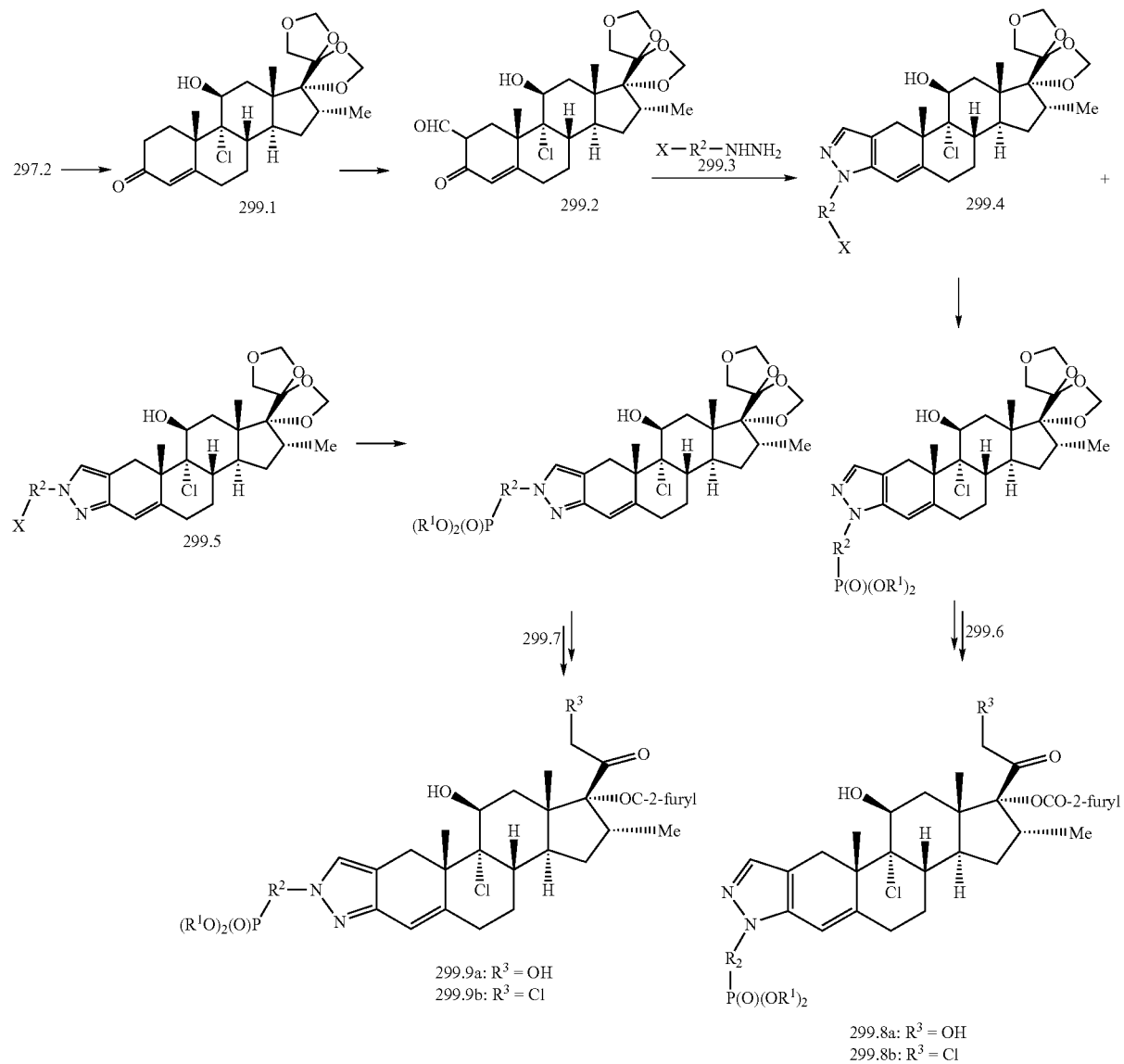

The preparation of phosphonate esters of the invention in which the phosphonate group is attached to the 1' or 2' position of the pyrazole ring, by means of an aromatic or heteroaromatic group, a heteroatom and/or a variable carbon chain is illustrated above.

In this procedure, the BMD-protected dienone 297.2 is reduced to afford the 1,2-dihydro product 299.1. The catalytic hydrogenation reaction is effected by the use of tris(triphenylphosphine)rhodium(I) chloride, for example as described in *J. Med. Chem.*, 44:602(2001). The product is then reacted with ethyl formate and a base such as sodium hydride, in an inert solvent such as toluene or dimethylformamide, as described in *J. Am. Chem. Soc.*, 86:1520(1964), to afford the 2-formyl product 299.2. This compound is then reacted with an alkyl, aralkyl, aryl or heteroaryl hydrazine 299.3, in which the substituent X is either a phosphonate group or a group that is subsequently transformed into a phosphonate-containing substituent. For example, X may be dialkylphosphono, bromo, hydroxy, amino, carboxyl and the like. The reaction yields the isomeric 2'- and 1'-aryl pyrazoles 299.4 and 299.5. The pyrazole-forming reaction is performed between equimolar amounts of the reactants in an acidic solvent such as acetic acid, as described in *J. Am. Chem. Soc.*, 86:1520(1964). The pyrazoles 299.4 and 299.5 are then transformed, for example, by the procedures described herein, via the BMD-protected intermediates 299.6 and 299.7, into the 21-chloro 17-(2-furoate) phosphonates 299.8b and 299.9b.

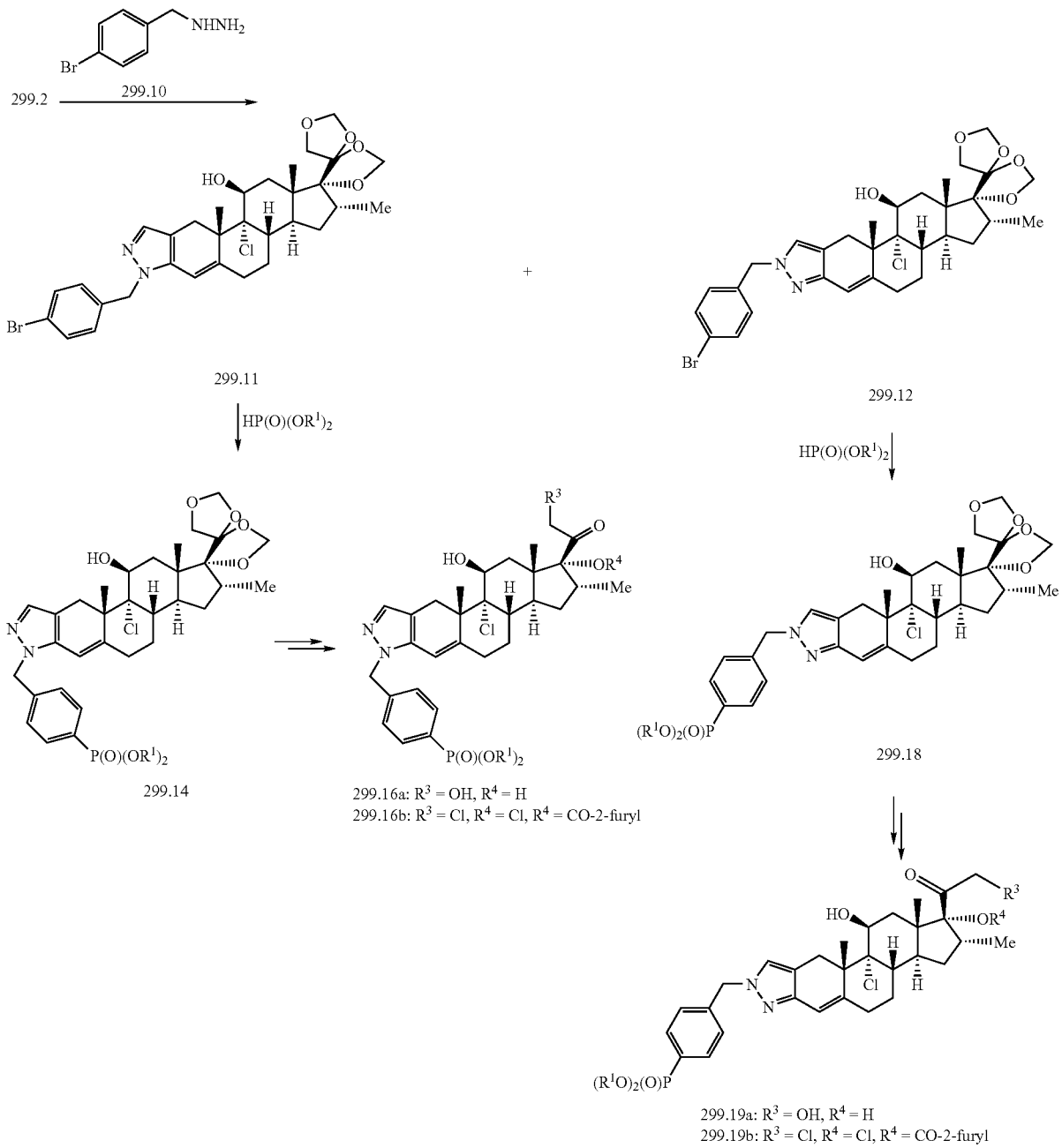

The preparation of specific compounds of the invention is depicted above. Phosphonates of the invention in which the phosphonate is attached by means of a benzyl linkage are shown above. In this procedure, the ketoaldehyde 299.2 is reacted, as described above, with 4-bromobenzyl hydrazine 299.10 (*Ann.*, 717:104(1968)) to give the pyrazoles 299.11 and 299.12. The 2'-substituted isomer 299.11 is then coupled, as described in Example 298, with a dialkyl phosphite, to yield the phosphonate 299.14. The BMD protecting group is then removed and the product is converted into the 21-chloro 17-(2-furoate) product 299.16b.

The isomeric pyrazole 299.12 is subjected to the same series of reactions to afford the isomeric product 299.19b.

Using the above procedures, but employing different bromo-substituted hydrazines, the products analogous to 299.16b and 299.19b are obtained.

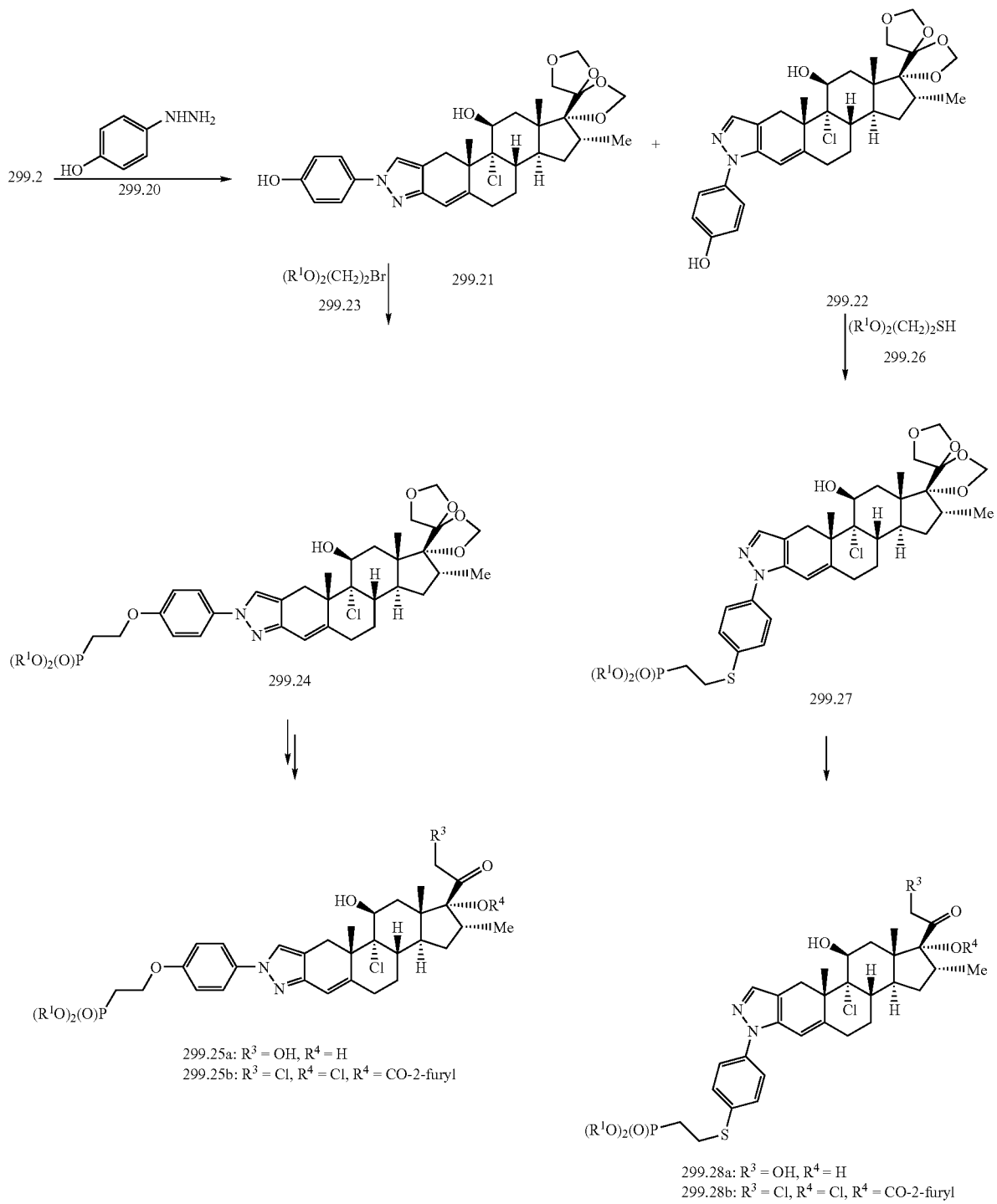

The preparation of specific compounds of the invention is shown above. Phosphonates of the invention in which the phosphonate group is attached by means of a phenyl group and an ether or thioether linkage. In this procedure, the ketoaldehyde 299.2 is reacted, as described above, with 4-hydroxyphenyl hydrazine 299.20 (EP 437105) to produce the pyrazoles 299.21 and 299.22. The 1'-substituted isomer 299.21 is reacted in dimethylformamide at 70° C., with a dialkyl 2-bromoethyl phosphonate 299.23 (Aldrich) and potassium carbonate, to give the ether phosphonate 299.24. The product is then deprotected to afford the triol 299.25a which is converted into the 21-chloro 17-(2-furoate) compound 299.25b.

Alternatively, the 2'-substituted pyrazole 299.22 is coupled, in a Mitsonobu reaction, with a dialkyl 2-mercaptoethyl phosphonate 299.26 (*Zh. Obschei. Khim.*, 43:2364(1973)) to prepare the thioether phosphonate 299.27, which is deprotected, and the product is converted into the 21-chloro 17-(2-furoate) analog 299.28b. The preparation of aromatic ethers and thioethers by means of the Mitsonobu reaction is described, for example, in R. C. Larock, "Comprehensive Organic Transformations," 448 (VCH, 1989), and in F. A. Carey and R. J. Sundberg, "Advanced Organic Chemistry," Part B, 153-4 (Plenum, 2001) and in *Org. React.*, 42:335 (1992). The phenol and the alcohol or thiol component are reacted together in an aprotic solvent such as, for example, tetrahydrofuran, in the presence of a dialkyl azodicarboxylate and a triarylphosphine, to afford the ether or thioether products. The procedure is also described in *Org. React.*, 42:335-656 (1992).

Using the above procedures, but employing, in place of the 4-hydroxyphenyl hydrazine 299.20, different hydroxy-substituted hydrazines, and/or different dialkyl bromo- or mercapto-substituted phosphonates, the products analogous to the compounds 299.25b and 299.28b are obtained.

EXAMPLE 300

Preparation of Representative Mometasone Furoate Derivatives

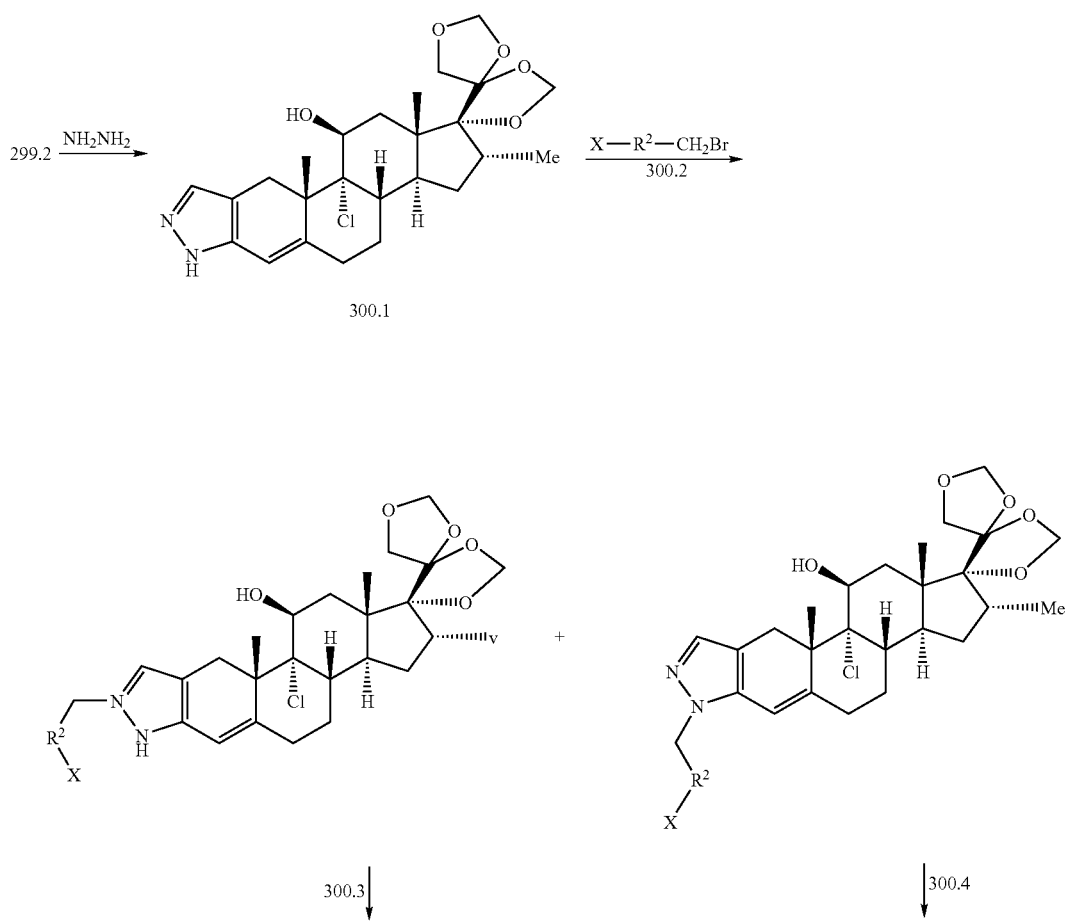

-continued

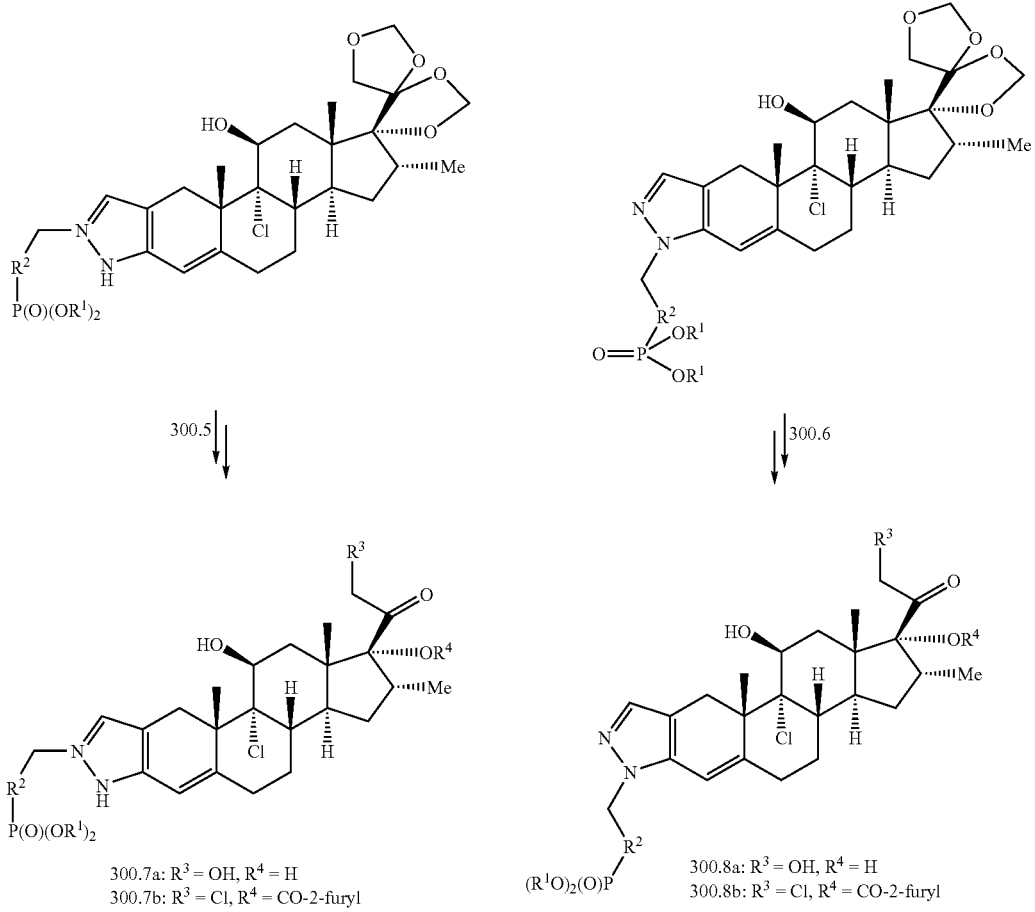

300.7a: $R^3$ = OH, $R^4$ = H
300.7b: $R^3$ = Cl, $R^4$ = CO-2-furyl 300.8a: $R^3$ = OH, $R^4$ = H
300.8b: $R^3$ = Cl, $R^4$ = CO-2-furyl The preparation of the phosphonate esters of the invention is shown above.

In this procedure, the ketoaldehyde 299.2 is reacted with hydrazine, to afford the pyrazole derivative 300.1. The reaction of steroidal 2-formyl-3-ketones with hydrazine is described in *J. Am. Chem. Soc,* 86:1520 (1964). The reaction is performed in acetic acid at ambient temperature. The pyrazole product is then reacted with a bromomethyl compound 300.2, in which $R^2$ and X are as defined above, or a reactive bromoheteroaromatic reagent, to yield the alkylation products 300.3 and 300.4. The alkylation of substituted pyrazoles is described, for example, in T. L. Gilchrist, "Heterocyclic Chemistry," 309 (Longman, 1992). The reaction is performed between equimolar amounts of the substrates in a polar solvent such as dimethylformamide or tetrahydrofuran, in the presence of a base such as dimethylaminopyridine, lithium hexamethyldisilazide and the like. The products 300.3 and 300.4, except in cases where X is dialkylphosphono, are converted into the phosphonates 300.5 and 0.6, using the procedures described herein, and deprotection/chlorination/acylation then affords the 21-chloro 17-(2-furoate) compounds 300.7b and 300.8b.

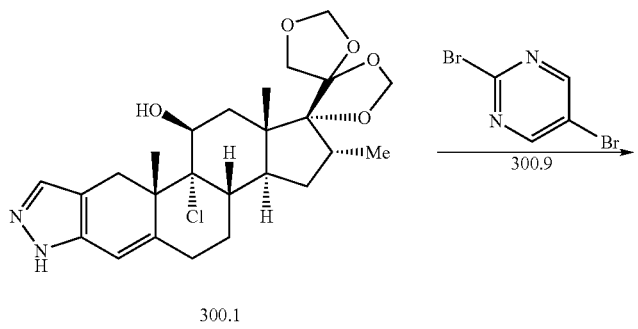

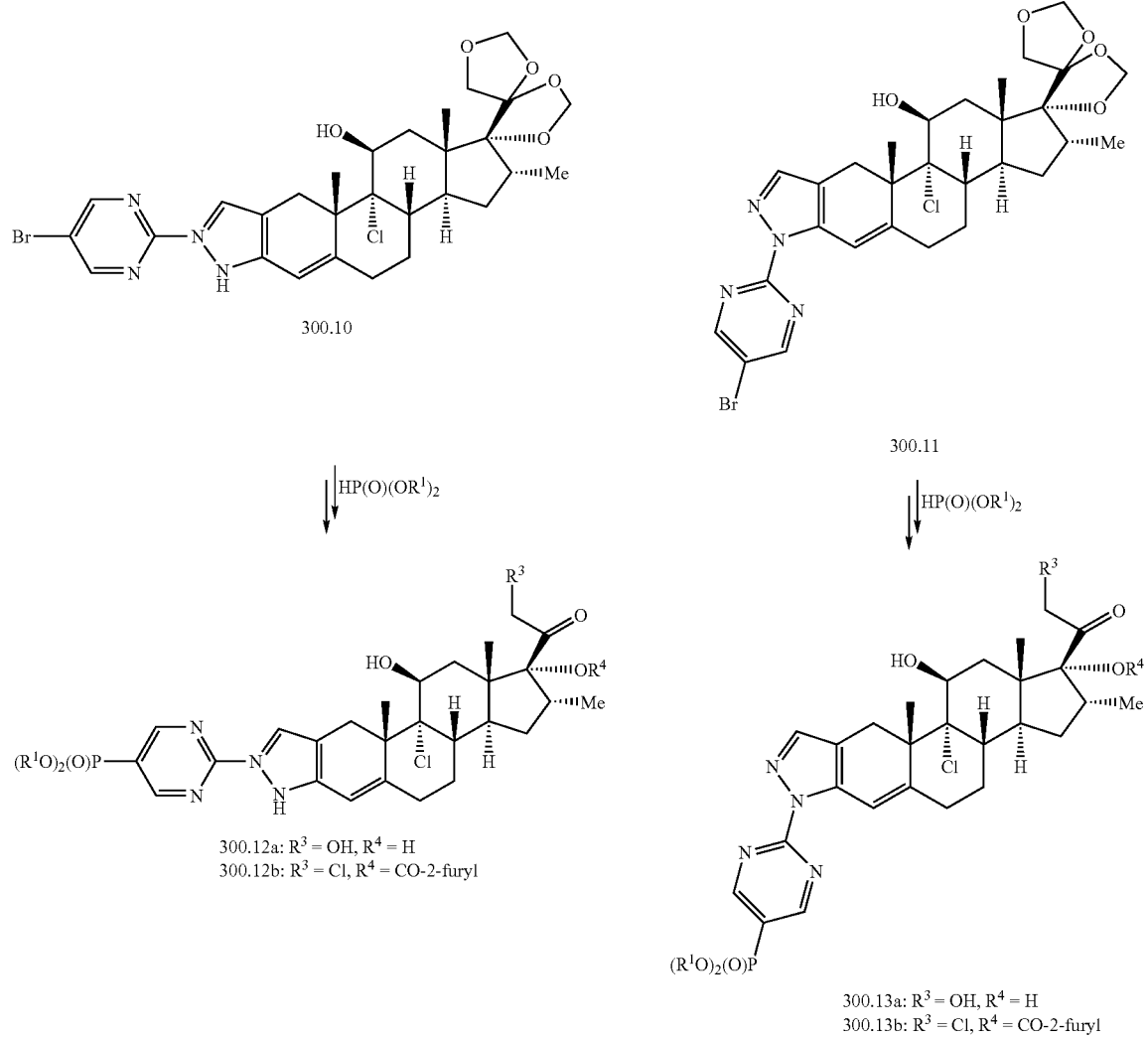
The preparation of specific compounds of the invention is shown above. The pyrazole 300.1 is reacted with 2,5-dibromopyrimidine 300.9 (*Chem. Lett.*, 583 (1992)) to give the pyrazoles 300.10 and 300.11. The products are then coupled, as described above, with a dialkyl phosphite, to afford after side-chain deprotection and modification, as described above, the 21-chloro 17-(2-furoates) 300.12b and 300.13b.
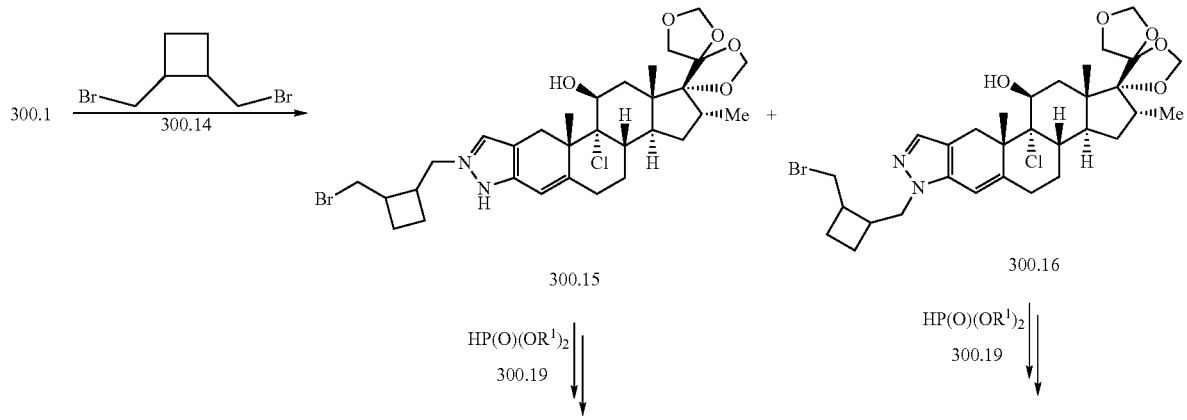

-continued

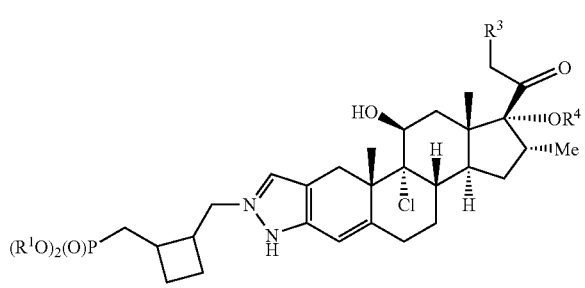

300.17a: R³ = OH, R⁴ = H
300.17b: R³ = Cl, R⁴ = CO-2-furyl

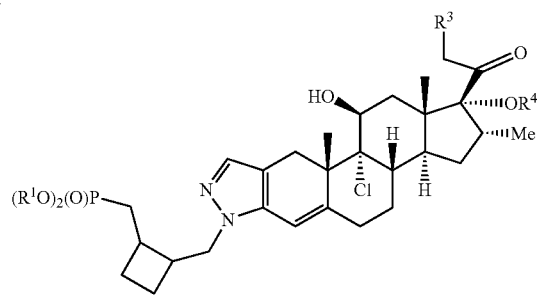

300.18a: R³ = OH, R⁴ = H
300.18b: R³ = Cl, R⁴ = CO-2-furyl

Specific compounds of the invention are prepared as shown above. The pyrazole 300.1 is reacted in tetrahydrofuran solution, with 1,2-bis(bromomethyl)Cyclobutane 300.14 (*J. Org. Chem.*, 46:3530(1981)) and potassium hexamethyl disilazide, to give the alkylation products 300.14 and 300.15. The 1'-substituted isomer 300.15 is then reacted, in an Arbuzov reaction, with a trialkyl phosphite to yield, after deprotection and side-chain modification, the 21-chloro 17-(2-furoate) 300.17b. The Arbuzov reaction is described in *Handb. Organophosphorus Chem.*, 115 (1992). In this procedure, in which a bromo substituent is converted into the corresponding phosphonate, the substrate is heated at from about 60° C. to about 160° C. with a five to fifty-fold molar excess of a trialkyl phosphite, to effect the transformation.

The 2'-substituted pyrazole 300.16 is subjected to the same series of reaction to give the amine phosphonate 300.18b.

Using the above procedures, but employing different dibromides, the products analogous to 300.17b and 300.18b are obtained.

EXAMPLE 301

Preparation of Representative Budesonide Derivatives

Representative compounds of the invention may be prepared as described herein.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in "Protective Groups in Organic Synthesis," by T. W. Greene and P. G. M. Wuts, Wiley, Second Edition 1990. The protection and deprotection of steroidal ketones and alcohols is described in "Organic Reactions in Steroid Chemistry," Vol. 1, J. Fried and J. A. Edwards, van Nostrand Reinhold, 1972, p. 375ff. Reactive substituents that may be protected are shown in the accompanying schemes as, for example, [OH], [O], etc.

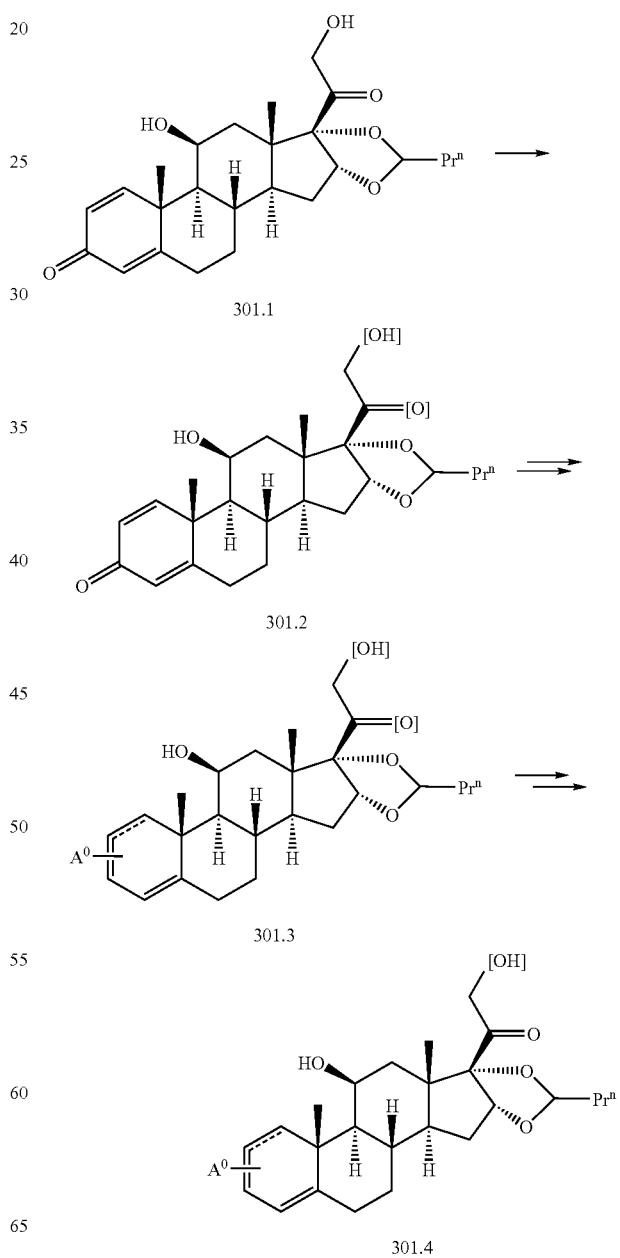

For example, depicted above is a protection-deprotection sequence in which the 20-ketone group and/or the 21-hydroxyl group of Budesonide 301.1 are protected to afford the derivative 301.2. The ketone is protected, for example, by conversion to the cyclic ethylene ketal, by reaction in toluene solution at reflux temperature with ethylene glycol and an acid catalyst, as described in *J. Am. Chem. Soc.*, 77:1904 (1955). Deprotection is effected by reaction with pyridinium tosylate in aqueous acetone, as described in *J. Chem. Soc., Chem. Comm.*, 1351 (1987).

Alternatively, the 20-ketone is protected by conversion to the N,N-dimethylhydrazone. The dimethyl hydrazone is prepared by the reaction of the ketone 301.1 with N,N-dimethylhydrazine in ethanol-acetic acid, as described in *Org. Syn.*, 50:102 (1970). The group is removed by treatment with sodium acetate and acetic acid in aqueous tetrahydrofuran, as described in *J. Am. Chem. Soc.*, 101:5841 (1979).

Alternatively, the 20-ketone is protected as the diethylamine adduct. In this procedure, the substrate 301.1 is reacted with titanium tetrakis(diethylamide), as described in *J. Chem. Soc., Chem. Comm.*, 406 (1983), to afford the adduct. The ketone is deprotected by reaction with water in an aqueous organic solvent.

The 21-hydroxyl group is protected, for example, by conversion to the acetate ester, by reaction with one molar equivalent of acetyl chloride in dichloromethane/pyridine. The 21-acetoxy group is removed by reaction with one molar equivalent of lithium hydroxide in aqueous dimethoxyethane.

Alternatively, the 21-hydroxyl group is protected by conversion to the tert.butyl dimethylsilyl ether, by reaction in dimethylformamide solution with one molar equivalent of tert.butylchlorodimethylsilane and imidazole, as described in *J. Am. Chem. Soc.*, 94:6190 (1972). The silyl ether is removed by reaction with tetrabutylammonium fluoride in tetrahydrofuran solution, as described in *J. Am. Chem. Soc.*, 94:6190 (1972).

The protected compound 301.2 is then converted into the phosphonate-containing analog 301.3, using the procedures described below, and the protecting group or groups are then removed, as described above, to give the phosphonate 301.4.

EXAMPLE 302

Preparation of Representative Budesonide Derivatives

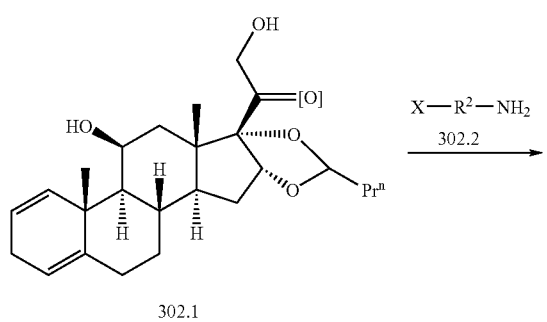

302.1

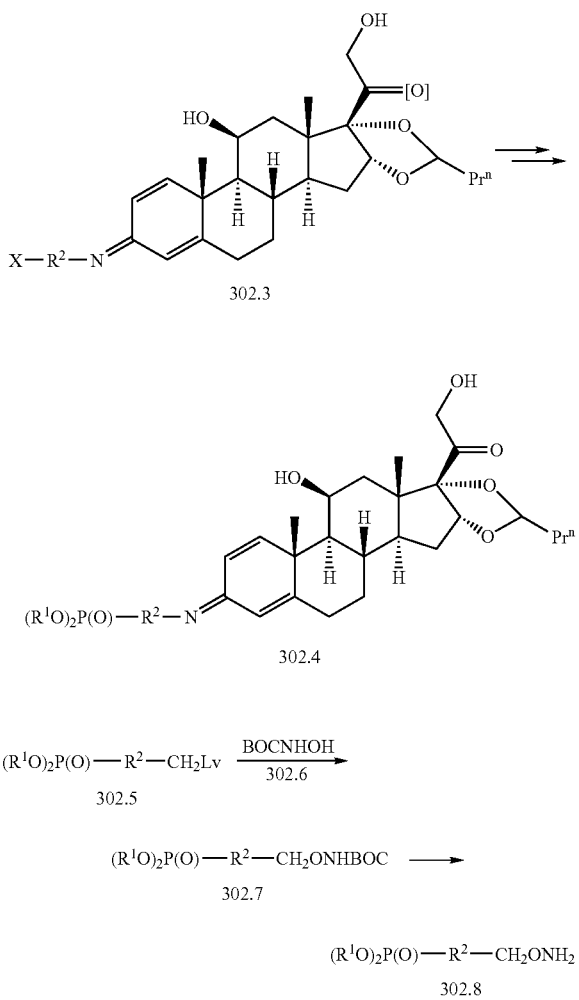

Depicted above is the preparation of compounds of the invention in which the phosphonate is attached by means of an imino or iminoxy group and a variable carbon chain. In this procedure, the ketone-protected derivative 302.1 is reacted with an amine or hydroxylamine 302.2, in which $R^2$ is an alkyl, alkenyl, cycloalkyl or cycloalkenyl group, optionally incorporating a heteroatom O, S or N, or a functional group such as an amide, ester, oxime, sulfoxide or sulfone, etc., or an optionally substituted aryl, heteroaryl or aralkyl group, optionally incorporating a heteroatom O, S or N, and X is either a phosphonate group or a group that is subsequently converted into a phosphonate-containing substituent.

For example, X may be dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime 302.3. The preparation of oximes of steroidal 3-ketones is described in *Anal. Bioch.*, 86:133 (1978) and in *J. Mass. Spectrom.*, 30: 497 (1995). The protecting group is then removed, as described in Example 301, to afford the 20-keto phosphonate product 302.4.

Also illustrated above is the preparation of hydroxylamine ethers incorporating a phosphonate group. In this procedure, a phosphonate 302.5, in which Lv is a leaving group such as bromo or trifluoromethylsulfonyloxy, is reacted with BOC-hydroxylamine 302.6 (Aldrich) to produce the ether 302.7. The reaction is conducted between equimolar amounts of the reactants in a polar solvent such as dimethylformamide or tetrahydrofuran, in the presence of a base such as potassium hydroxide or dimethylaminopyridine. Deprotection, for example, by treatment with trifluoroacetic acid, then gives the hydroxylamine ether 302.8. The above procedure is also employed for the preparation of substituted hydroxylamines which are precursors to phosphonates.

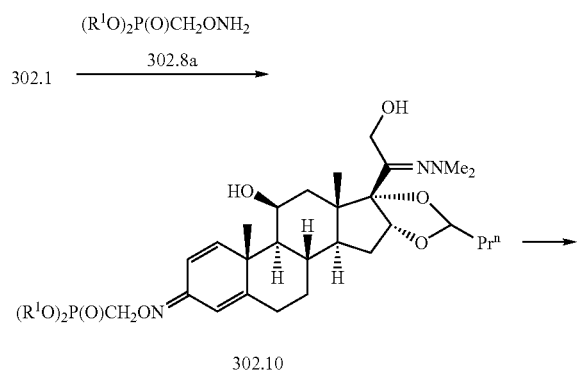

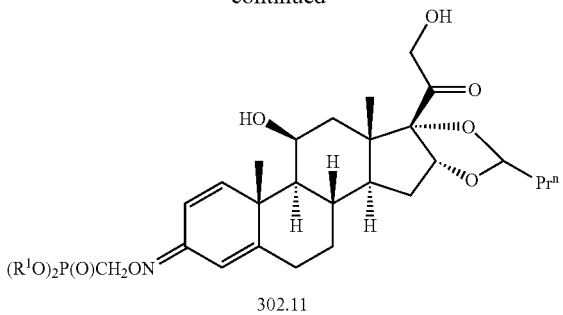

The synthesis of specific compounds of the invention is shown above. The preparation of compounds of the invention in which the phosphonate is attached by means of an iminoxy group is illustrated. In this procedure, the substrate 302.1, in which the 20-ketone is protected as the dimethyl hydrazone derivative, is reacted with a dialkyl phosphonomethyl hydroxylamine 302.8a, prepared as described above from a dialkyl trifluoromethylsulfonyloxymethyl phosphonate (*Tet. Lett.*, 27:1477 (1986) and BOC-hydroxylamine, to afford the oxime 302.10. Deprotection, as described in Example 301, then affords the 20-keto phosphonate 302.11. The oxime forming reaction is performed at ambient temperature in ethanol-acetic acid solution between equimolar amounts of the reactants.

Using the above procedures, but employing, in place of the hydroxylamine ether 302.8a, different oxime ethers 302.2, the corresponding products 302.4 are obtained.

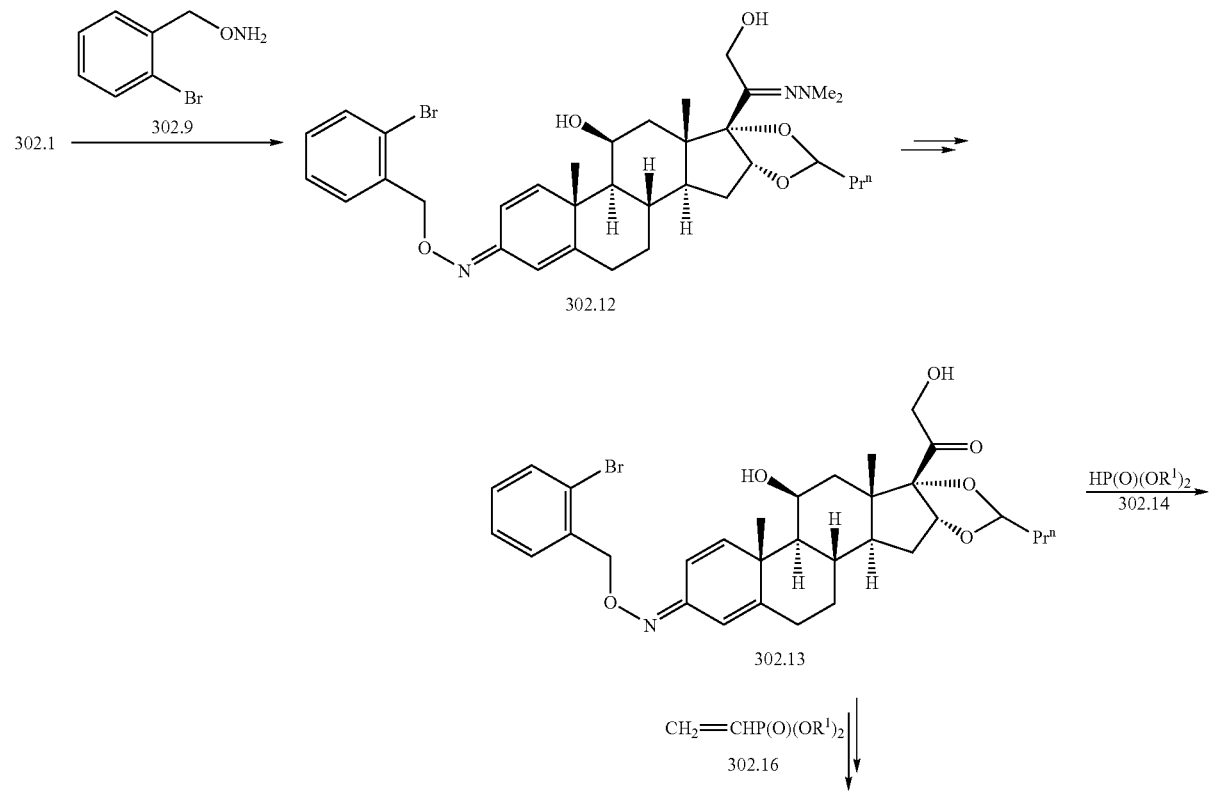

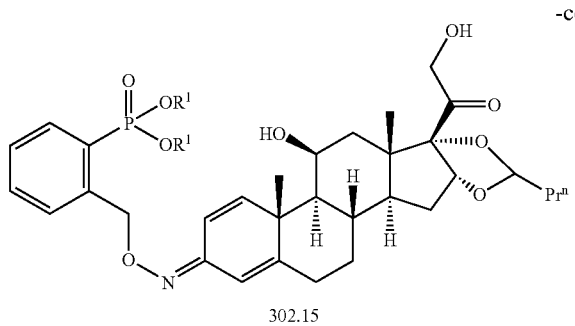

302.15

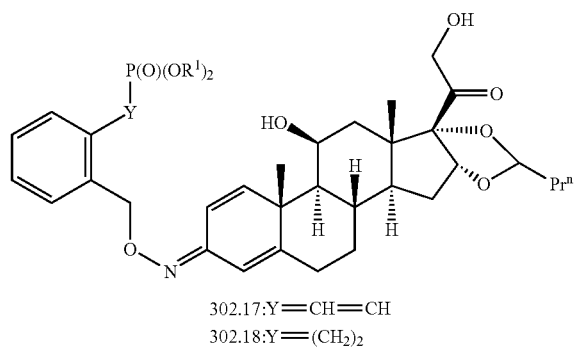

302.17: Y═CH═CH
302.18: Y═(CH₂)₂

The synthesis of specific compounds of the invention is shown above. The preparation of compounds of the invention in which the phosphonate group is attached by means of a benzyloxy oxime group is illustrated. In this procedure, the dienone 302.1, in which the 20-ketone is protected as the dimethyl hydrazone, is reacted, as described above, with O-(2-bromobenzyl)hydroxylamine 302.9, prepared as described above from 2-bromobenzyl bromide and BOC-protected hydroxylamine 302.6, to give the oxime 302.12. The protecting group is then removed to yield the 20-keto product 302.13. The latter product is then reacted, in the presence of a palladium catalyst, with a dialkyl phosphite 302.14 to afford the phosphonate 302.15. The preparation of arylphosphonates by means of a coupling reaction between aryl bromides and dialkyl phosphites is described in *J. Med. Chem.*, 35:1371 (1992). The reaction is performed at ca. 100° in an inert solvent such as toluene, in the presence of a base such as triethylamine and a catalytic amount of tetrakis(triphenylphosphine)palladium(0).

Alternatively, the bromo compound 302.13 is coupled with a dialkyl vinylphosphonate 302.16 (Aldrich) to afford the phosphonate 302.17. The coupling of aryl halides with olefins by means of the Heck reaction is described, for example, in "Advanced Organic Chemistry," by F. A. Carey and R. J. Sundberg, Plenum, 2001, p. 503ff and in *Acc. Chem. Res.*, 12:146 (1979). The aryl bromide and the olefin are coupled in a polar solvent such as dimethylformamide or dioxan, in the presence of a palladium(0) catalyst such as tetrakis(triphenylphosphine)palladium(0) or palladium(II) catalyst such as palladium(II) acetate, and optionally in the presence of a base such as triethylamine or potassium carbonate. Optionally, the styrenoid double bond present in the product 302.17 is reduced, for example, by reaction with diimide, to produce the saturated analog 302.18. The reduction of olefinic bonds is described in "Comprehensive Organic Transformations," by R. C. Larock, VCH, 1989, p. 6ff. The transformation is effected by means of catalytic hydrogenation, for example using a palladium on carbon catalyst and hydrogen or a hydrogen donor, or by the use of diimide or diborane.

Using the above procedures, but employing, in place of the bromobenzyl reagent 302.9, different bromo-substituted aryl or heteroaryl alkoxy hydroxylamines, and/or different dialkyl alkenyl phosphonates, the products analogous to the compounds 302.15, 302.17 and 302.18 are obtained.

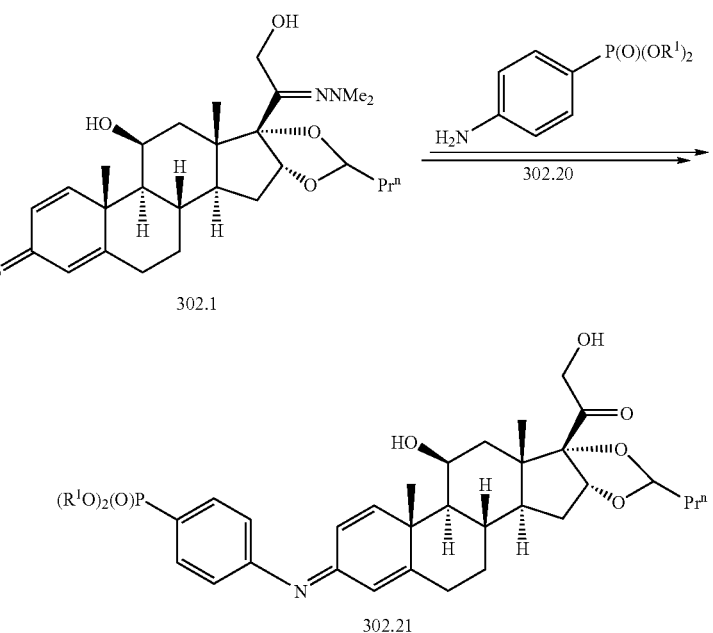

The preparation of specific compounds of the invention is shown above. The preparation of compounds of the invention in which the phosphonate is attached by means of a 4-phenylimino group is illustrated. In this procedure, the substrate 302.1, in which the 20-ketone is protected as the dimethylhydrazone, is reacted with a dialkyl 4-aminophenyl phosphonate 302.20 (Epsilon), to give, after deprotection, the imine product 302.21. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions.

Using the above procedures, but employing, in place of the 4-aminophenyl phosphonate 302.20 different amino-substituted aryl or heteroaryl phosphonates, products analogous to 302.21 are obtained.

ones with hydroxylamines is described in *J. Steroid Bioch.*, 7: 795 (1976). The reaction is performed between equimolar amounts of the reactants in a polar organic solvent such as pyridine or methanol, optionally in the presence of acetic acid or sodium acetate. The product 302.23 is then coupled with a dialkyl 2-hydroxyethyl phosphonate 302.24 (Epsilon) and carbonyl diimidazole, to yield, after deprotection, the carbamate oxime 302.25. The preparation of carbamates is described in "Comprehensive Organic Functional Group Transformations," A. R. Katritzky, ed., Pergamon, 1995, Vol. 6, p 416ff, and in "Organic Functional Group Preparations," by S. R. Sandler and W. Karo, Academic Press, 1986, p. 260ff. In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and

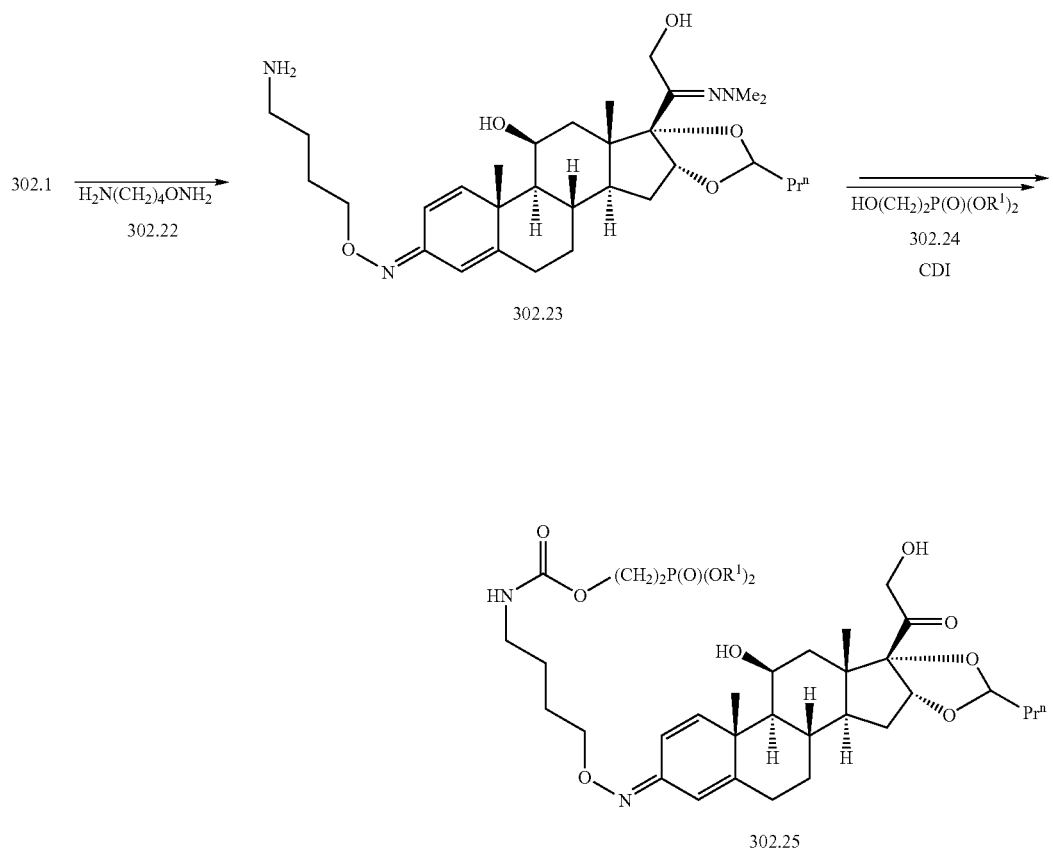

The preparation of specific compounds of the invention is shown above. The preparation of compounds of the invention in which the phosphonate is attached by means of an oximino group and a carbamate linkage is illustrated. In this procedure, the dienone 302.1, in which the 20-ketone is protected as the dimethylhydrazone, is reacted with 4-aminobutyl hydroxylamine 302.22 (*Pol. J. Chem.*, 55:1163 (1981)) to yield the oxime 302.23. The reaction of steroidal 1,4-dien-3- the like, to afford the corresponding activated acylamine. The latter compound is then reacted with an alcohol to yield the carbamate.

Using the above procedures, but employing, in place of the amino-substituted hydrazine 302.22, different amino-substituted hydrazines, and/or different hydroxy-substituted phosphonates, the products analogous to 302.25 are obtained.

EXAMPLE 303
Preparation of Representative Budesonide Derivatives
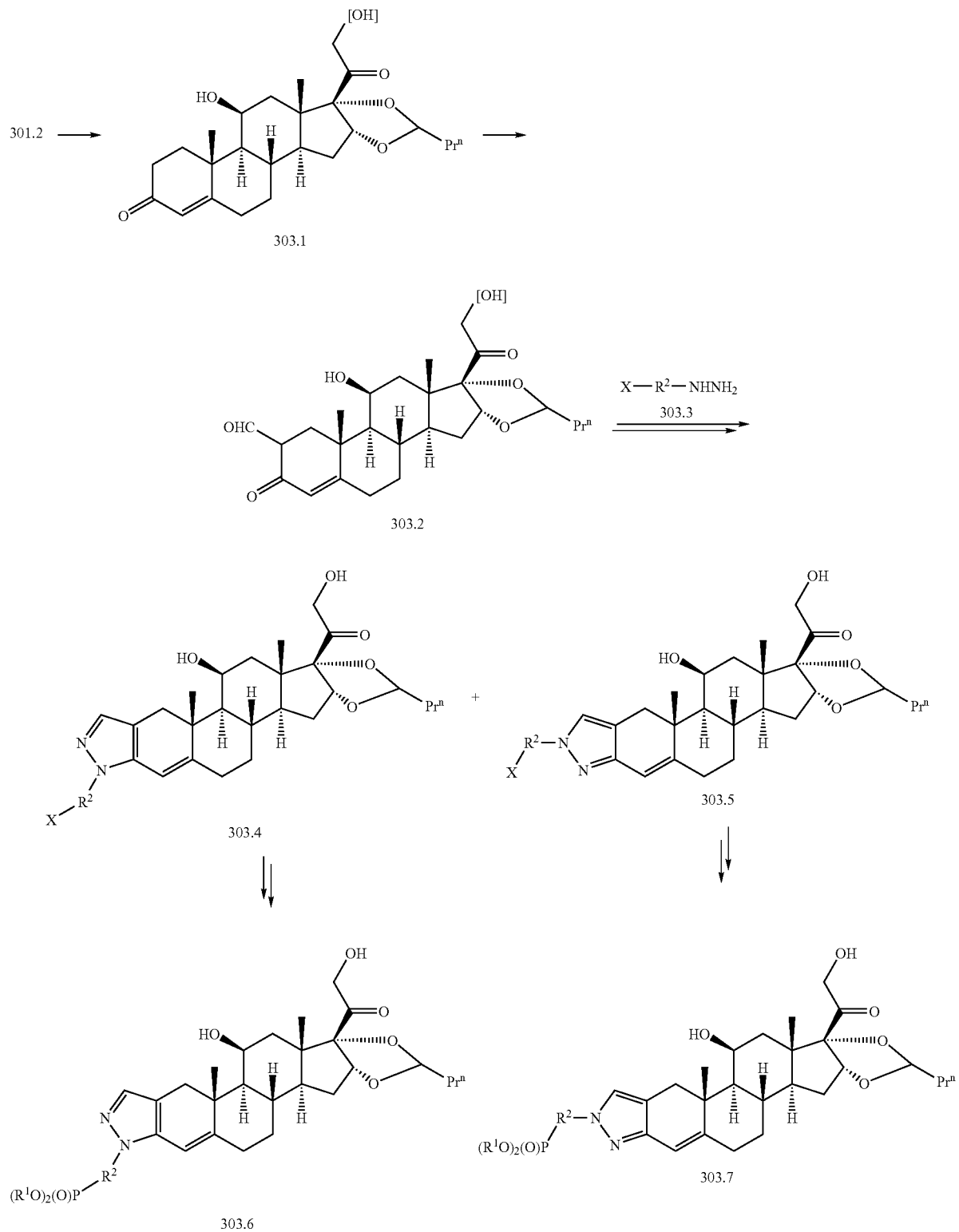

The preparation of the phosphonate esters of the invention in which the phosphonate group is attached to the 1' or 2' position of the pyrazole ring, by means of an aromatic or heteroaromatic group, a heteroatom and/or a variable carbon chain is shown above.

equimolar amounts of the reactants in an acidic solvent such as acetic acid, as described in J. Am. Chem. Soc., 1964, 86, 1520. The pyrazoles 303.4 and 303.5 are then transformed, for example by the procedures described herein, into the phosphonates 303.6 and 303.7.

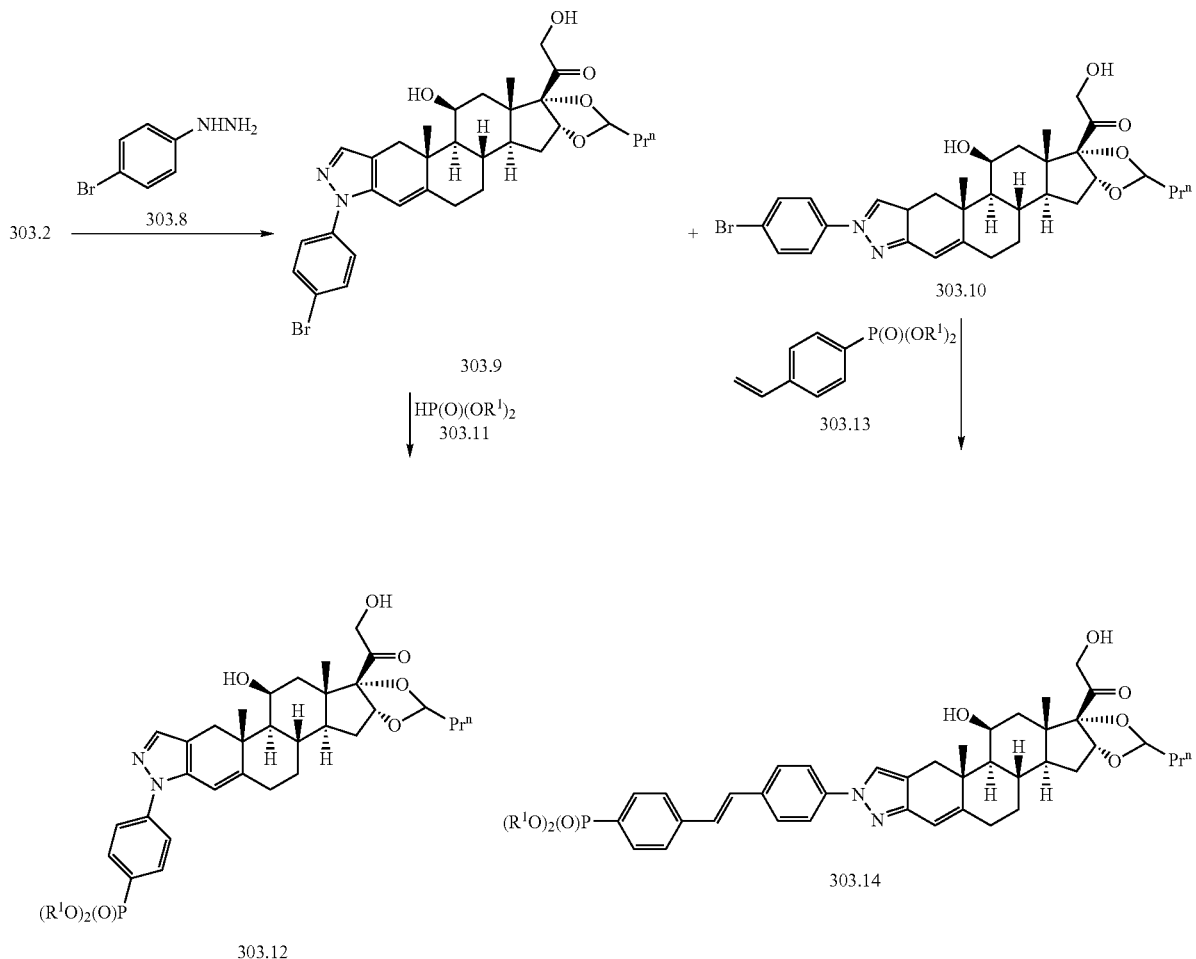

In this procedure, the dienone 301.2, in which the 21-hydroxyl group is protected as described in Example 301 is reduced to afford the 1,2-dihydro product 303.1. The catalytic hydrogenation reaction is effected by the use of tris(triphenylphosphine)rhodium(I) chloride, for example as described in J. Med. Chem., 2001, 44, 602. The product is then reacted with ethyl formate and a base such as sodium hydride, in an inert solvent such as toluene or dimethylformamide, as described in J. Am. Chem. Soc., 1964, 86, 1520, to afford the 2-formyl product 303.2. This compound is then reacted with an alkyl, aralkyl, aryl or heteroaryl hydrazine 303.3, in which the substituent X is either a phosphonate group or a group which is subsequently transformed into a phosphonate-containing substituent. For example, X may be dialkylphosphono, bromo, hydroxy, amino, carboxyl and the like. The reaction yields, after deprotection of the 21-hydroxyl group, the isomeric 2'- and 1'-aryl pyrazoles 303.4 and 303.5. The pyrazole-forming reaction is performed between The preparation of specific compounds of the invention is illustrated above. The preparation of phosphonates of the invention in which the phosphonate is attached by means of a phenyl ring or a stilbene moiety is shown. In this procedure, the ketoaldehyde 303.2 is reacted, as described above, with 4-bromophenyl hydrazine 303.8 (J. Organomet. Chem., 1999, 62, 581) to give the pyrazoles 303.9 and 303.10. The 2'-substituted isomer 303.9 is then reacted, as described above, with a dialkyl phosphite 303.11 to give the phosphonate 303.12.

The isomeric pyrazole 303.10 is reacted in a Heck reaction, as described above, with one molar equivalent of a dialkyl 4-vinylphenyl phosphonate 303.13 (Macromolecules, 1998, 31, 2918) to yield the phosphonate 303.14.

Using the above procedures, but employing different bromo-substituted hydrazines, and/or different alkenyl-substituted phosphonates, the products analogous to 303.12 and 303.14 are obtained.

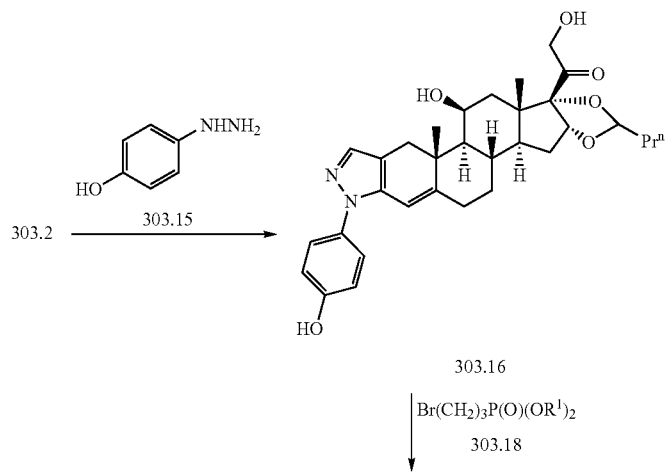

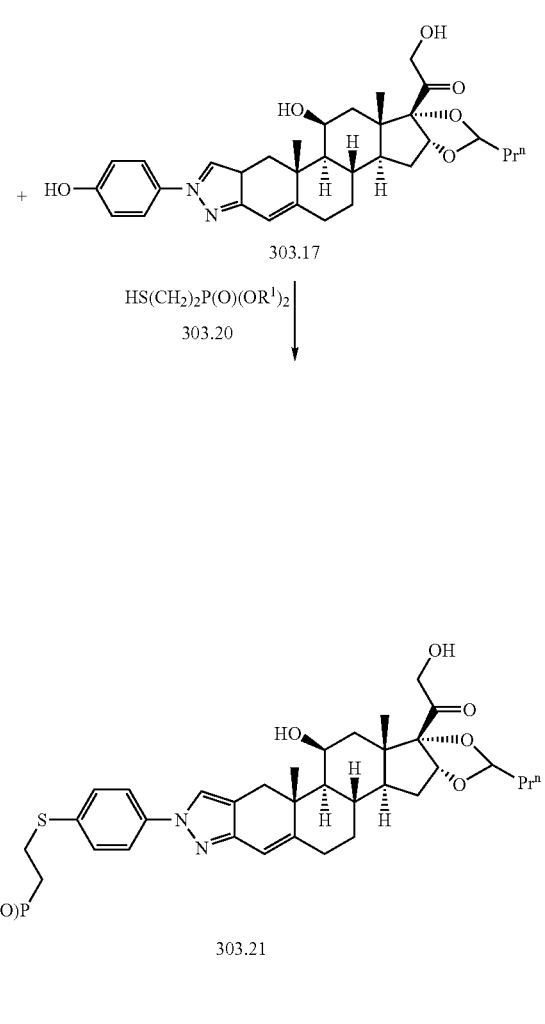

The synthesis of specific compounds of the invention is shown above. The preparation of the phosphonates of the invention in which the phosphonate group is attached by means of an alkoxy or alkylthio group and an aromatic ring is illustrated. In this procedure, the ketoaldehyde 303.2 is reacted, as described above, with 4-hydroxyphenyl hydrazine 303.15 (EP 437105) to produce the pyrazoles 303.16 and 303.17. The 2'-substituted isomer 303.16 is then reacted in dimethylformamide solution at 70° with one molar equivalent of a dialkyl bromopropyl phosphonate 303.18 (J. Amer. Chem. Soc., 2000, 122, 1554) and cesium carbonate, to give the ether phosphonate 303.19.

Alternatively, the 1'-substituted pyrazole 303.22 is coupled in a Mitsonobu reaction, with a dialkyl 2-mercaptoethyl phosphonate 303.20 (Zh. Obschei. Khim., 1973, 43, 2364) to prepare the thioether phosphonate 303.21. The preparation of aromatic ethers and thioethers by means of the Mitsonobu reaction is described, for example, in Comprehensive Organic Transformations, by R. C. Larock, VCH, 1989, p. 448, and in Advanced Organic Chemistry, Part B, by F. A. Carey and R. J. Sundberg, Plenum, 2001, p. 153-4 and in Org. React., 1992, 42, 335. The phenol and the alcohol or thiol component are reacted together in an aprotic solvent such as, for example, tetrahydrofuran, in the presence of a dialkyl azodicarboxylate and a triarylphosphine, to afford the ether or thioether products. The procedure is also described in Org. React., 1992, 42, 335-656.

Using the above procedures, but employing, in place of the hydroxyphenyl hydrazine 303.15, different hydroxyaryl hydrazines, and/or different dialkyl bromo- or mercapto-substituted phosphonates, the products analogous to the compounds 303.19 and 303.21 are obtained.

EXAMPLE 304

Preparation of Representative Budesonide Derivatives

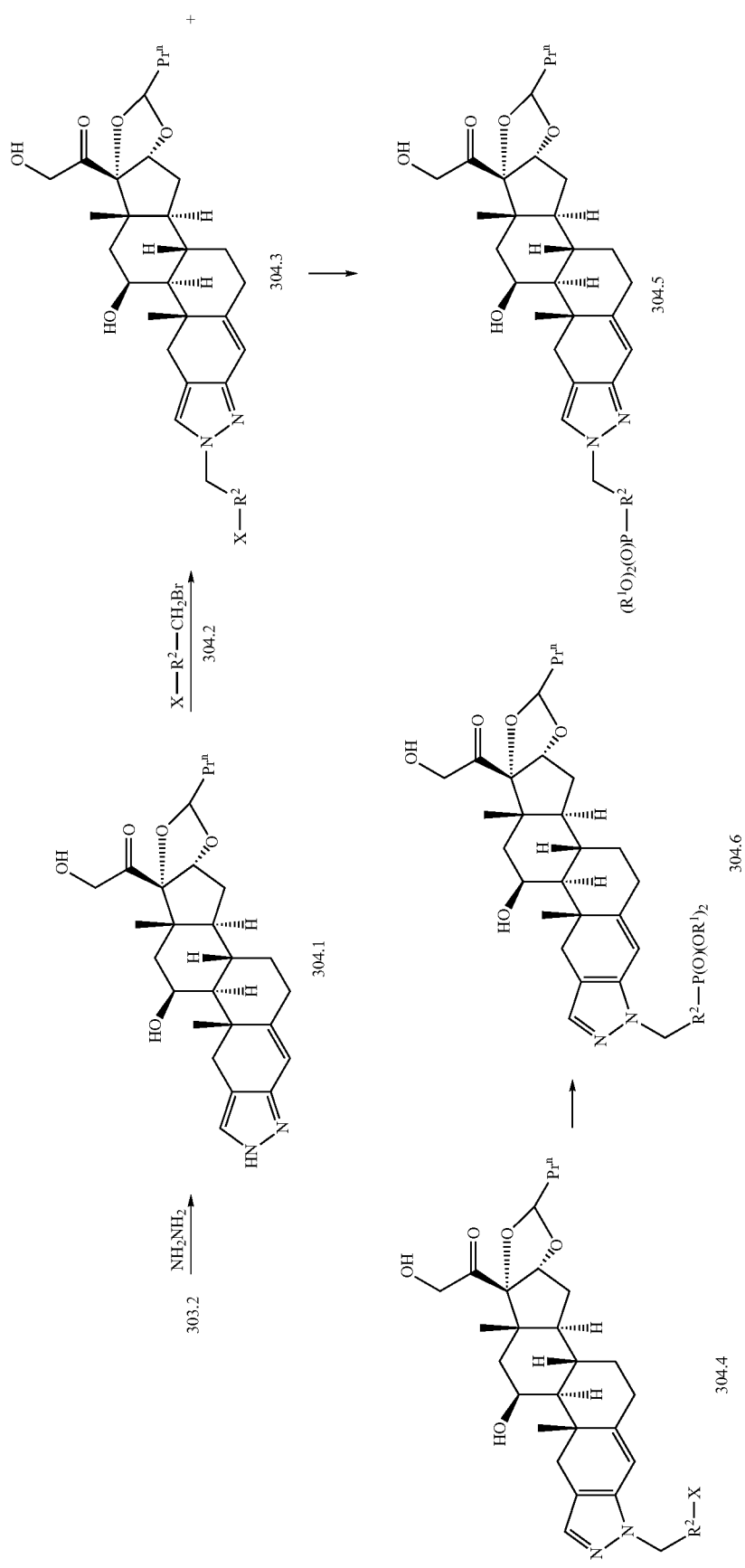

The preparation of the phosphonate esters of the invention in which the phosphonate group is attached by means of a variable carbon linkage is shown above. In this procedure, the ketoaldehyde 303.2 is reacted with hydrazine to afford the pyrazole derivative 304.1. The reaction of steroidal 2-formyl-3-ketones with hydrazine is described in J. Am. Chem. Soc, 1964, 86, 1520. The reaction is performed in acetic acid at ambient temperature. The pyrazole product is then reacted with a bromomethyl compound 304.2, in which $R^2$ and X are as defined above, or a reactive bromoheteroaromatic reagent, to yield the alkylation products 304.3 and 304.4. The alkylation of substituted pyrazoles is described, for example, in Heterocyclic Chemistry, by T. L. Gilchrist, Longman, 1992, p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The products 304.3 and 304.4 are, except in cases where X is dialkylphosphono, converted into the phosphonates 304.5 and 304.6, using the procedures described herein.

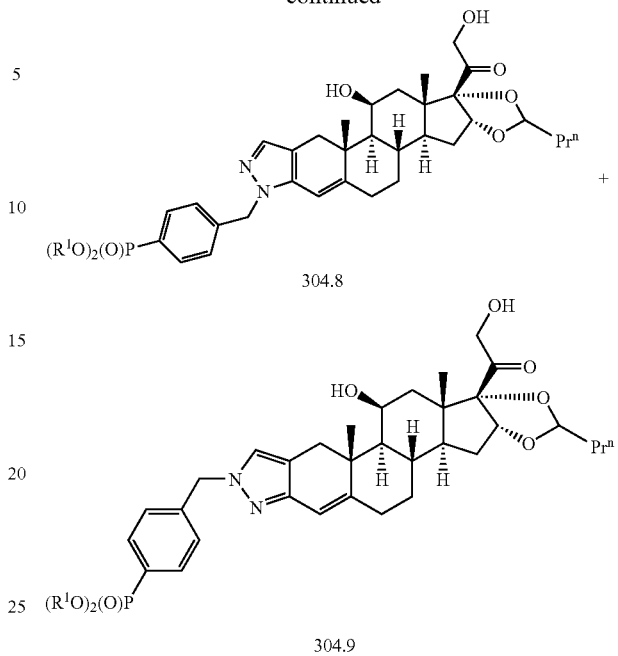

The preparation of specific compounds of the invention is shown above. The pyrazole 304.1 is reacted in dimethylformamide solution at 70° with one molar equivalent of a dialkyl 4-bromomethylphenyl phosphonate 304.7 (Tet., 1998, 54, 9341) and lithium hexamethyl disilazide, to give the pyrazoles 304.8 and 304.9. Using the above procedures, but employing different bromomethyl-substituted phosphonates, the products analogous to 304.8 and 304.9 are obtained.

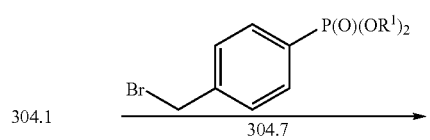

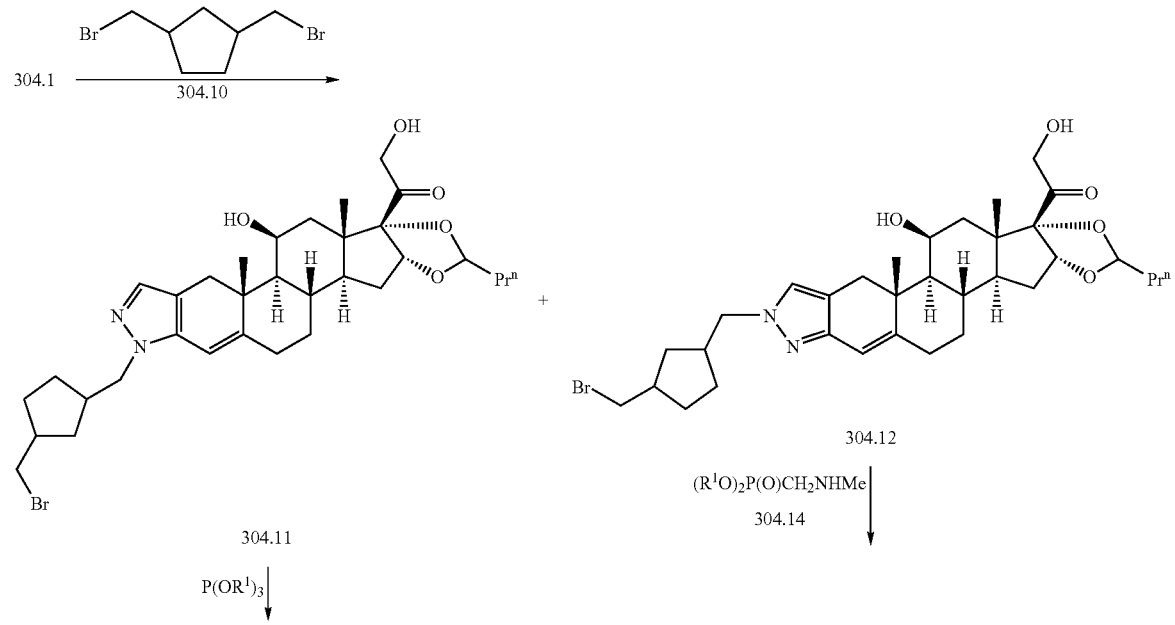

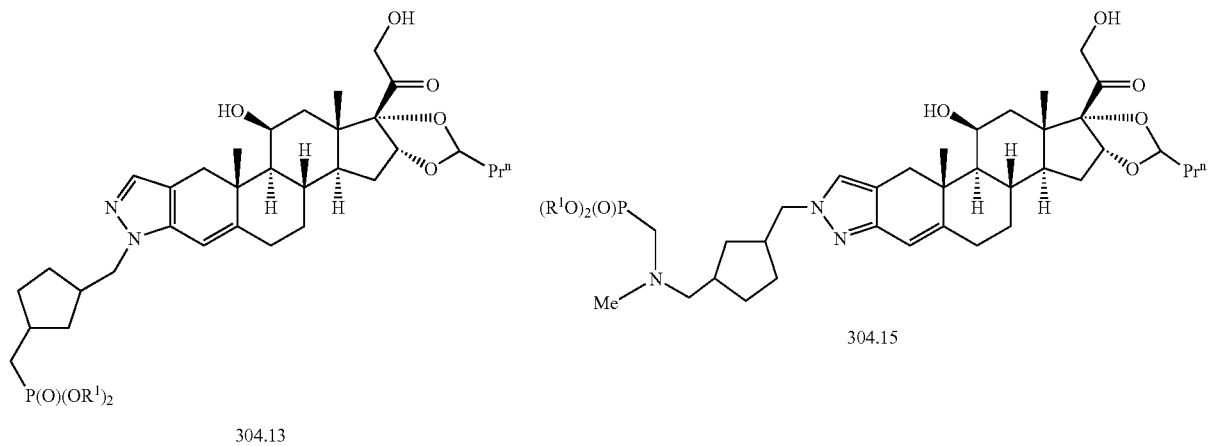

304.13

304.15

The preparation of specific compounds of the invention is shown above. The pyrazole 304.1 is reacted in tetrahydrofuran solution with 1,3-bis(bromomethyl)Cyclopentane 304.10 (Bull. Soc. Chim. FR., 1975, 1295) and sodium hydride, to give the alkylation products 304.11 and 304.12. The 2'-substituted isomer 304.11 is then reacted, in a Arbuzov reaction, with a trialkyl phosphite to yield the phosphonate 304.13. The Arbuzov reaction is described in Handb. Organophosphorus Chem., 1992, 115. In this procedure, in which a bromo substituent is converted into the corresponding phosphonate, the substrate is heated at from about 60° to about 160° with a five to fifty-fold molar excess of a trialkyl phosphite, to effect the transformation.

The 2'-substituted pyrazole 304.12 is reacted at 70° in dimethylformamide solution with one molar equivalent of a dialkyl methylaminomethyl phosphonate 304.14 (AsInEx) and cesium carbonate, to give the amine phosphonate 304.15.

Using the above procedures, but employing different dihalides, and/or different amino-substituted phosphonates, the products analogous to 304.13 and 304.15 are obtained.

EXAMPLE 305

Preparation of Representative Cyclosporin A Derivatives

In general, phosphonate interconversions of the compounds of the invention, as described in Examples 305-308, can be performed as described herein. The final compounds are synthesized according to the methods described herein. Exemplary intermediate phosphonate esters, e.g., 305.1, 305.2, 305.3 and 305.3a, are shown below and these compounds can be used to prepare final compounds, such as those illustrated below, by one skilled in the art, using known methods for synthesis of substituted phosphonates. These methods are similar to those described for the synthesis of amides. The preparation of amides from carboxylic acids and derivatives is described, for example, in "Organic Functional Group Preparations," by S. R. Sandler and W. Karo, Academic Press, 1968, p. 274. Further methods are described below for the synthesis of the phosphonate diesters and can in some cases be applied to the synthesis of phosphor-amides.

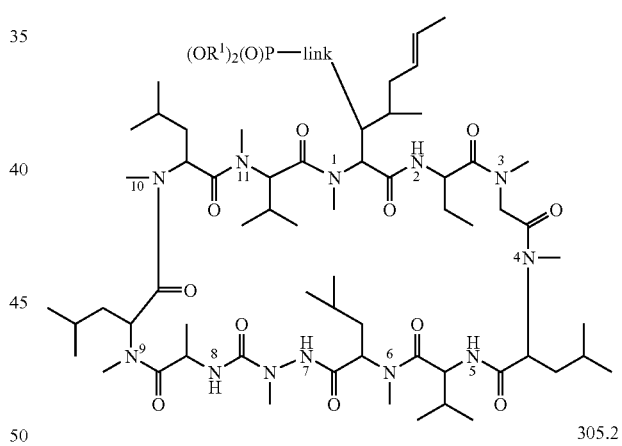

305.1

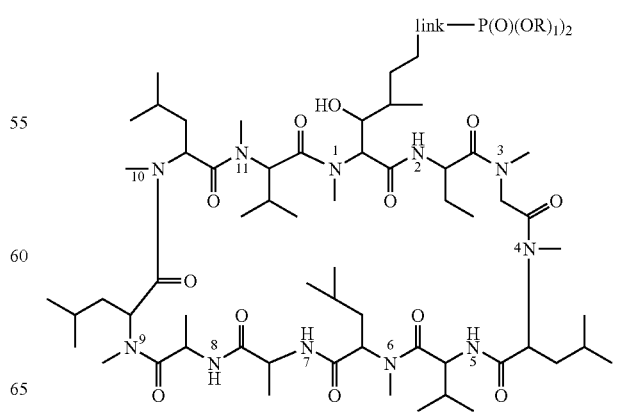

305.2

995
-continued
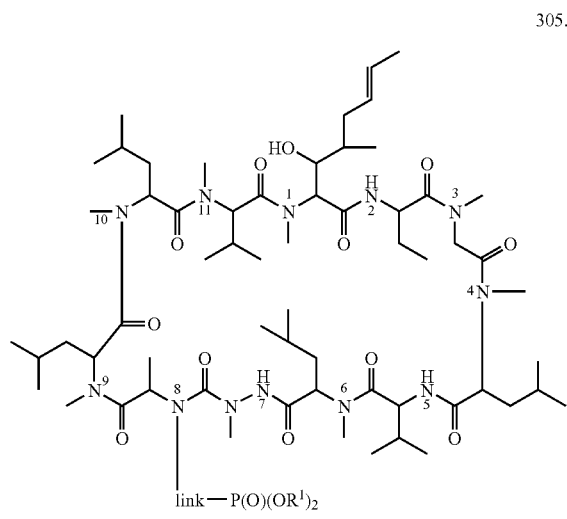
305.3
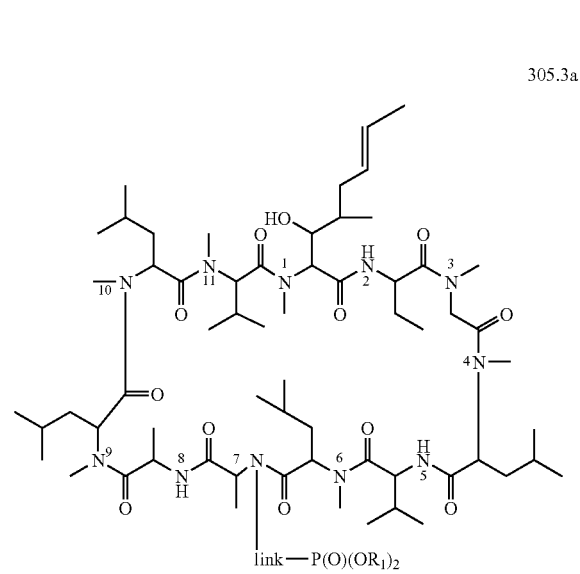
305.3a
996
-continued
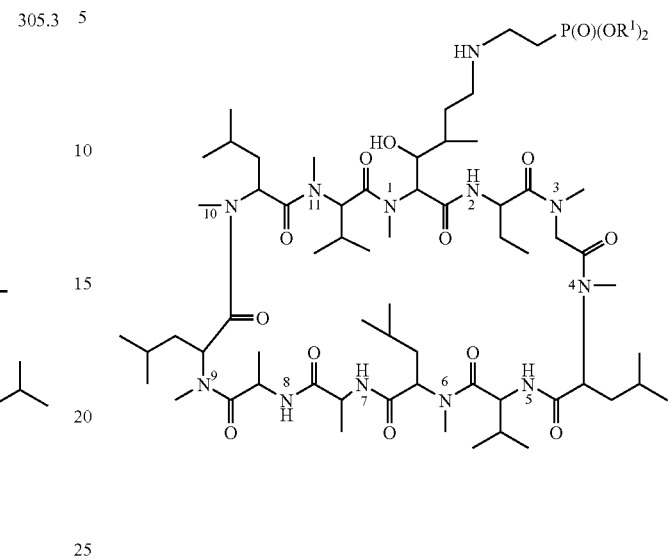
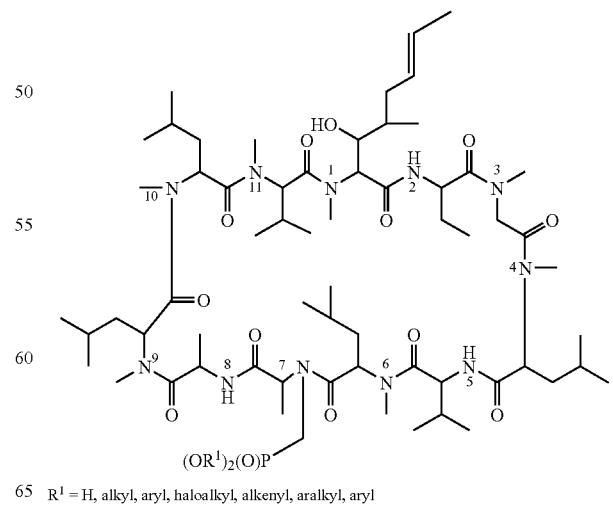
R¹ = H, alkyl, aryl, haloalkyl, alkenyl, aralkyl, aryl In the following schemes, the conversion of various substituents into the group link-P(O)($^{OR1}$)$_2$, where R$^1$ is defined as above, or indeed the final stage of P(O)RR°, as defined above, can be effected at any convenient stage of the synthetic sequence, or in the final step. The selection of an appropriate step for the introduction of the phosphonate substituent is made after consideration of the chemical procedures required, and the stability of the substrates to those procedures. It may be necessary to protect reactive groups, for example hydroxyl, amino, during the introduction of the group link-P(O)($^{OR1}$)$_2$ or P(O)RR°

In the succeeding examples, the nature of the phosphonate ester group P(O)($^{OR1}$)$_2$ can be varied, either before or after incorporation into the scaffold, by means of chemical transformations. The transformations, and the methods by which they are accomplished, are described below.

Protection of Reactive Substituents

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in "Protective Groups in Organic Synthesis," by T. W. Greene and P. G. M Wuts, Wiley, Third Edition 1999. Reactive substituents, which may be protected, are shown below as, for example, [OH], [SH], etc.

Preparation of Intermediate Phosphonates

The intermediate phosphonate esters 305.1-305.3a involved in conversion into the prodrug phosphonate moieties bearing amino acid, or lactate esters are shown above. Cyclosporin A (CsA) can be purchased from Sigma Aldrich, synthesized (see U.S. Pat. No. 4,396,542) or obtained from biological sources as described in U.S. Pat. No. 4,117,118. Other cyclosporin derivatives can be either synthetic in nature (see U.S. Pat. No. 4,396,542) or isolated by similar means to CsA (see U.S. Pat. No. 6,410,696 B1).

EXAMPLE 306

Preparation of Representative Cyclosporin A Derivatives

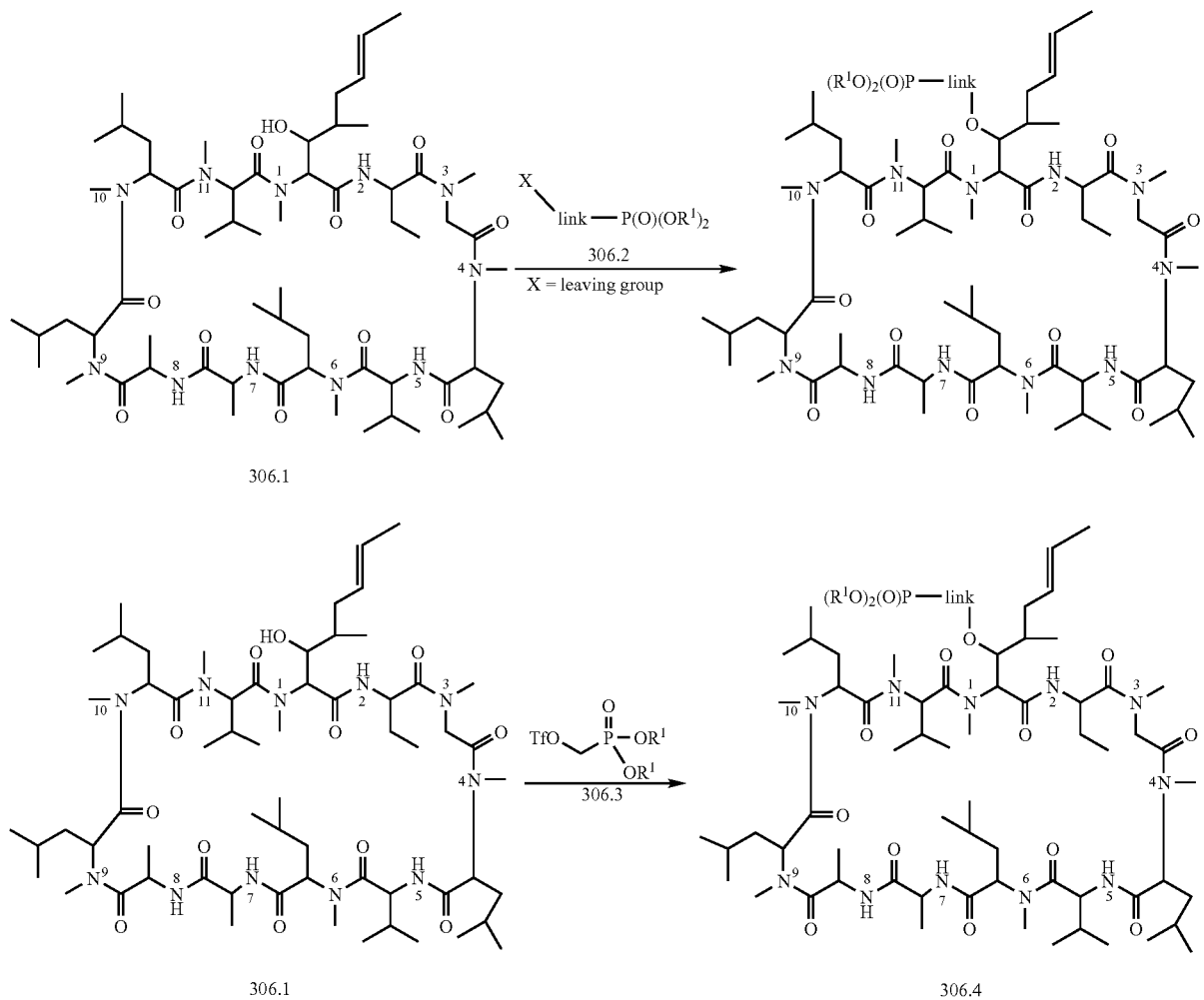

The preparation of the phosphonate linkage to CsA through the hydroxyl group of amino acid 1 to give compounds of the invention is shown above. CsA 306.1 is dissolved in a suitable solvent such as, for example, DMF or other non-protic solvent, and is then treated with the phosphonate reagent 306.2, bearing a leaving group, for example, bromine, mesyl, tosyl, or trifluoromethanesulfonyl in the presence of a suitable organic or inorganic base. For example, 306.1 dissolved in DMF, is treated with one equivalent of sodium hydride and one equivalent of (toluene-4-sulfonylmethyl)-phosphonic acid dibenzyl ester 306.3, prepared according to the procedures in JOC 1996, 61,22, p7697, to give CsA phosphonate 306.4. Using the above procedure but employing different phosphonate reagents 306.2 in place of 306.3 there are obtained the corresponding products of the invention bearing different linking groups.

EXAMPLE 307

Preparation of Representative Cyclosporin A Derivatives

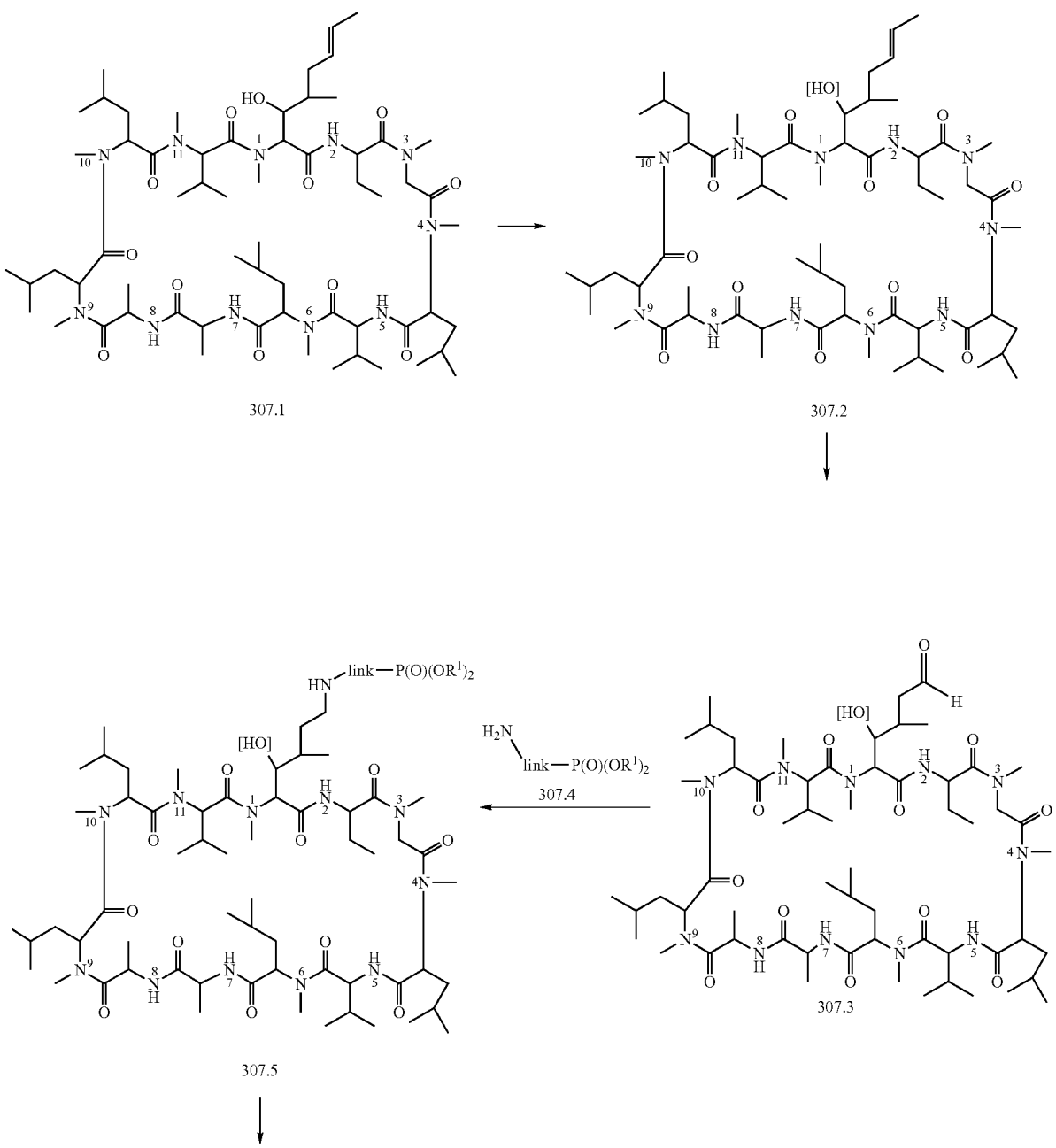

-continued

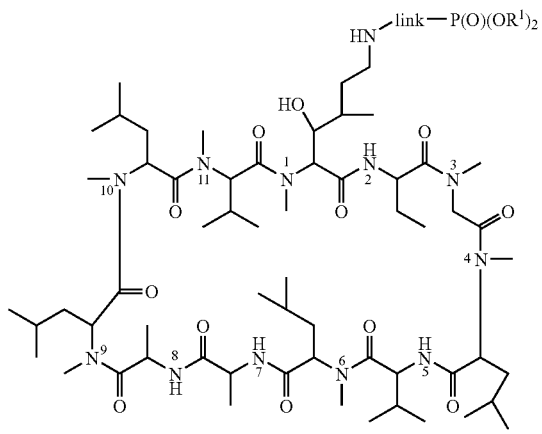
307.6

The preparation of CsA—phosphonate conjugates of the invention is illustrated above. The hydroxyl group of amino acid 1 is first protected with a suitable protecting group, for example silyl ethers, benzyl ethers, trityl ethers etc as described in Greene and Wuts, "Protecting Groups in Organic Synthesis," $3^{rd}$ Edition, John Wiley and Sons. The protected product 307.2 is then treated with an oxidizing agent, many examples of which are described in Comprehensive Organic Transformations, John Wiley & Sons, $2^{nd}$ Ed, R. C. Larock, p 1211-1215 to give the aldehyde. Aldehyde 307.3 is then treated with a amine phosphonic acid ester of the general formula 307.4 under reductive amination conditions to afford amine 307.5. The preparation of amines by means of reductive amination procedures is described, for example, in "Comprehensive Organic Transformations," by R. C. Larock, $2^{nd}$ edition, p. 835. In this procedure, the amine component and the aldehyde component are reacted together in the presence of a reducing agent such as, for example, borane, sodium cyanoborohydride or diisobutylaluminum hydride, to yield the amine product. Finally, deprotection of the hydroxyl group following procedures documented in Greene and Wuts, "Protecting Groups in Organic Synthesis," $3^{rd}$ Edition, John Wiley and Sons, p 116-121 gives the phosphonate.

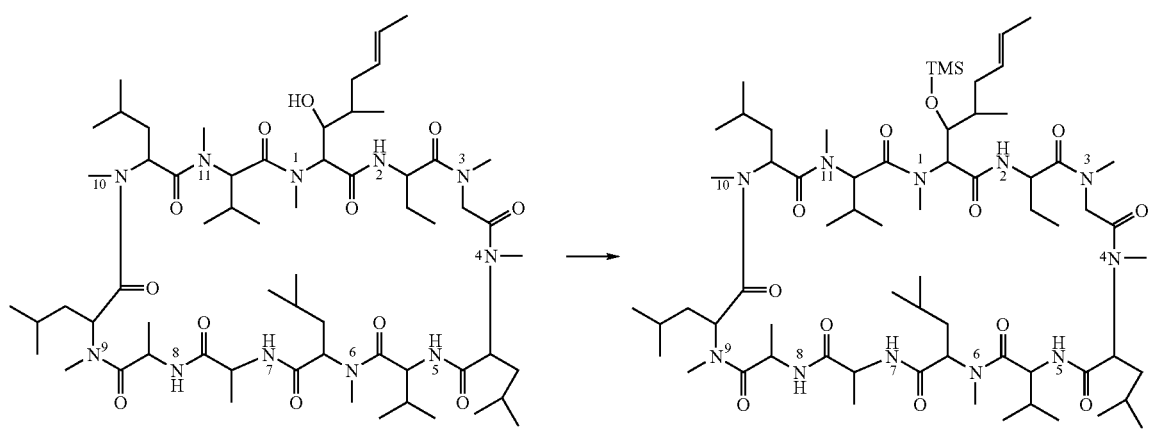
307.1 → 307.7
↓

-continued

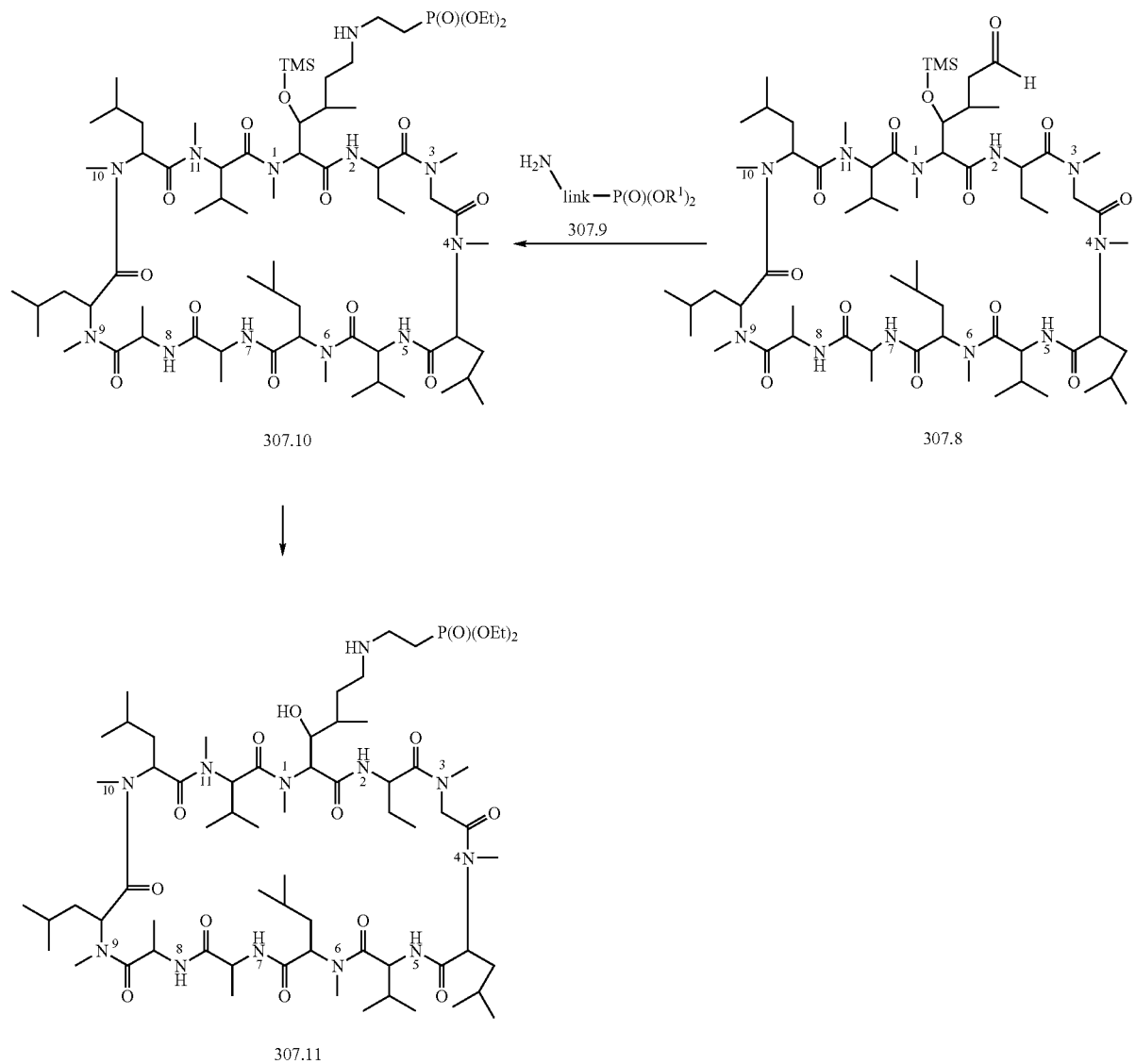

For example, 307.1 is treated in pyridine and dichloromethane with trimethylsilyl chloride, as described in U.S. Pat. No. 6,410,696 B1, to give silyl ether 307.5. Silyl ether 307.5 is then treated with ozone followed by work up with dimethyl sulfide to give aldehyde 307.8. Aldehyde 307.8 is treated with one equivalent of the hydrochloride salt of (2-amino-ethyl)-phosphonic acid ester diethyl ester 307.9, prepared according to J. Med. Chem. 1998, 41, 23, p 4439, and a suitable base, e.g., hunigs base, triethylamine, or the likes, until the imine is formed. The intermediate imine solution is then treated with sodium cyanoborohydride to give the amine 307.10. Amine 307.10 is then deprotected by treatment with TBAF in an aprotic solvent such as THF or dioxane to give phosphonate 307.11. Using the above procedure but employing different phosphonate reagents 307.4 in place of 307.9 there are obtained the corresponding products bearing different linking groups.

EXAMPLE 308

Preparation of Representative Cyclosporin A Derivatives

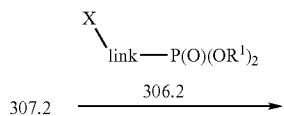

-continued

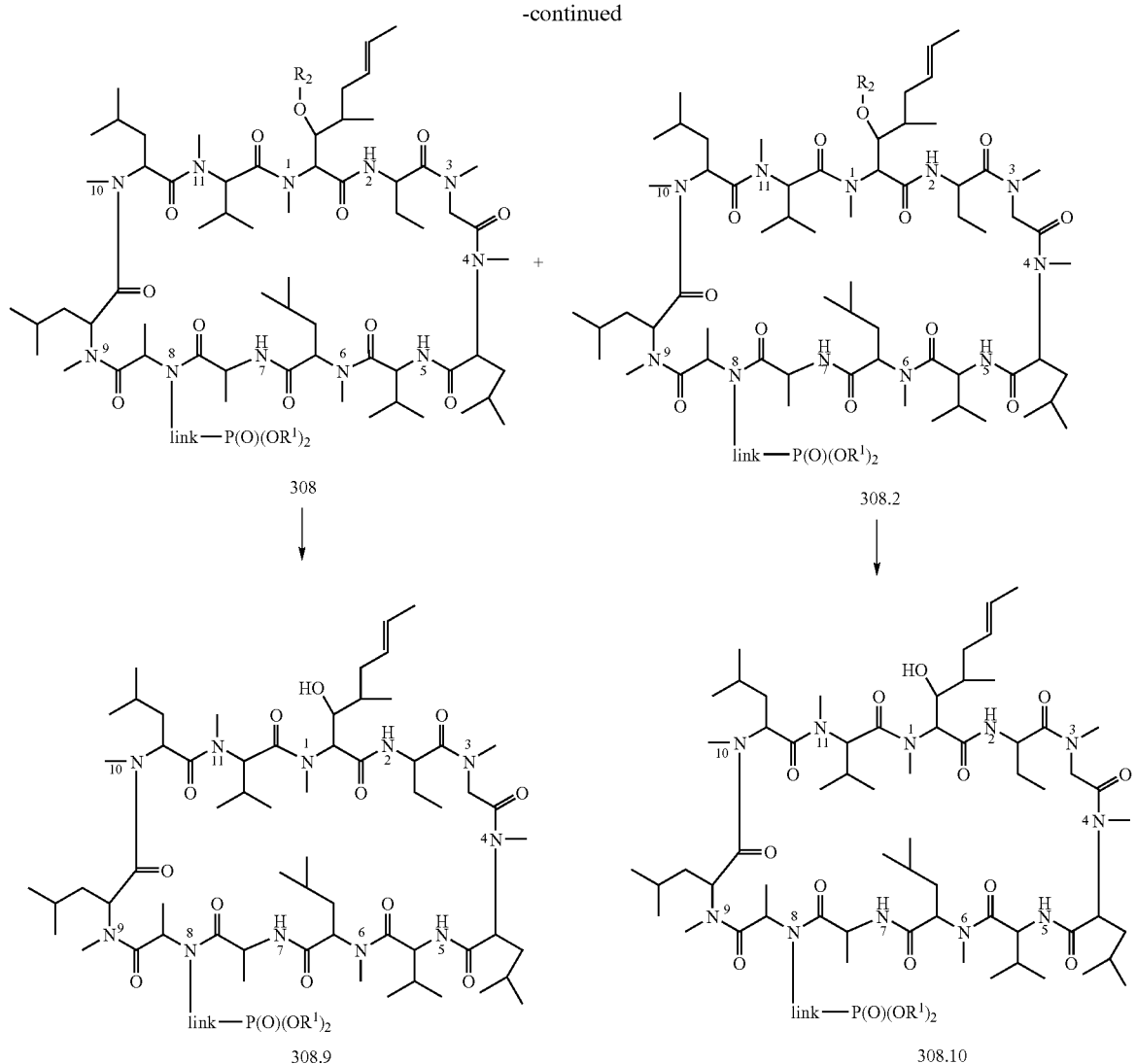

The preparation of CsA phosphonate conjugates of the invention whereby the phosphonate is linked onto the alanine nitrogen in amino acids 7 and 8 is shown above. Protected CsA 307.2 (Example 307) is first treated with a base, sufficiently basic to remove the amide proton, for example, metal hydrides, metal amides. The product is then treated with a phosphonate reagent 306.2 bearing a leaving group such as, for example, bromine, mesyl, tosyl, or trifluoromethanesulfonyl phosphonates, to give 308.1 and 308.2. The alkylated products are then separated by chromatography and independently deprotected using conventional conditions described in Greene and Wuts, Protecting groups in Organic Synthesis, $3^{rd}$ Edition, John Wiley and Sons inc. p 116-121 to give compounds of the invention. For example, silyl ether 307.5, in toluene is treated with sodium hydride and 15-crown-5-ether followed by one equivalent of bromomethyl phosphonic acid diallyl ester, 308.3 (Lancaster), to give phosphonates 308.4 and 308.5, respectively. Phosphonates 308.4 and 308.5 are then deprotected by treatment with TBAF in an aprotic solvent such as THF or dioxane to give 308.6 and 308.7, respectively, in which the linkage is a methylene group. Using the above procedure, but employing different phosphonate reagents 306.2 in place of 308.3, there are obtained the corresponding products with different linking groups.

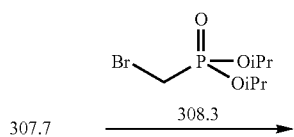

-continued

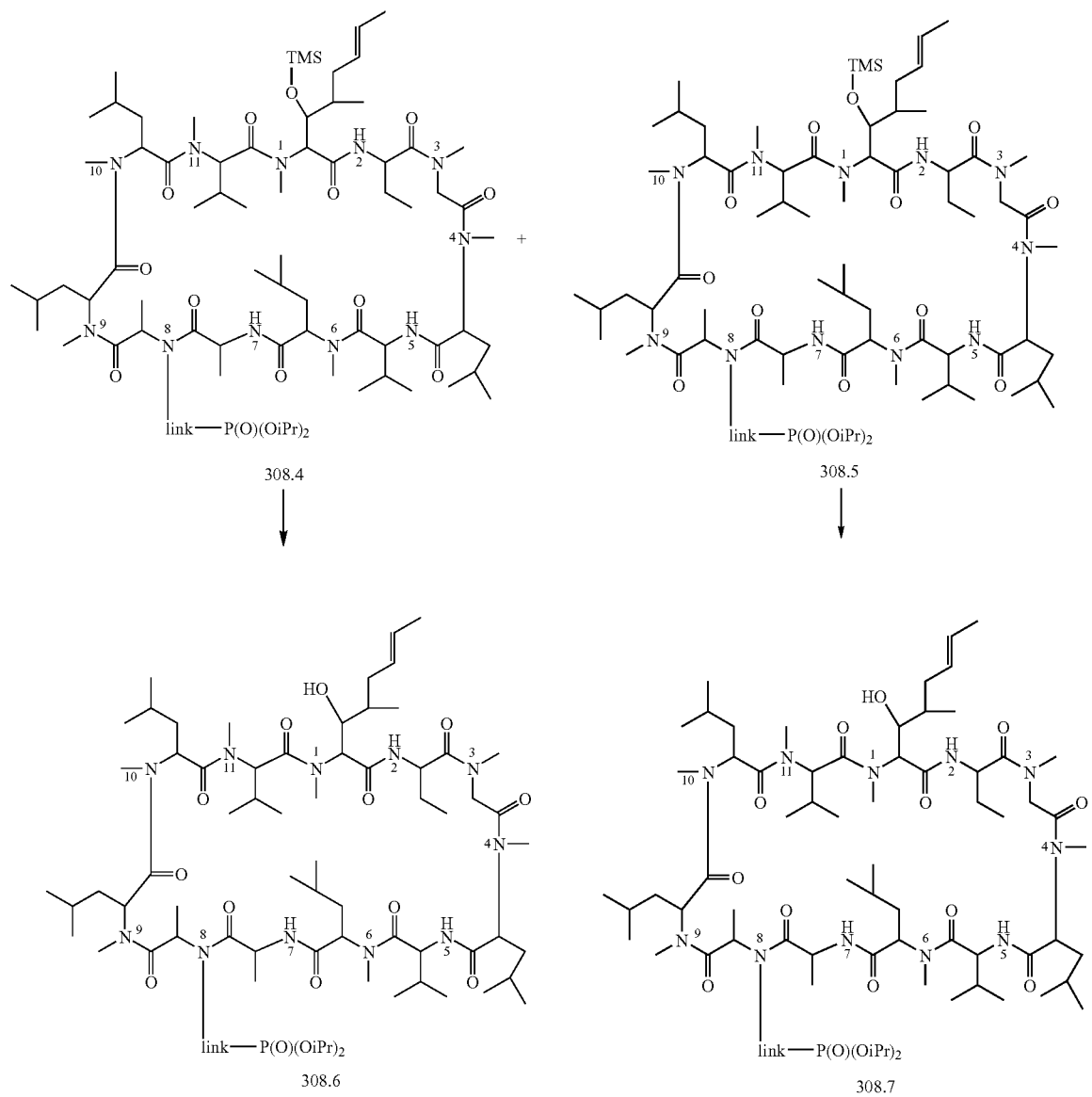

308.4

308.5

308.6

308.7

EXAMPLE 309

Preparation of Representative Mizoribine Derivatives

Representative compounds of the invention may be prepared according to the following methods.

Depending on the reaction conditions employed, it may be necessary to protect certain reactive substituents from unwanted reactions by protection before the sequence described, and to deprotect the substituents afterwards, according to the knowledge of one skilled in the art. Protection and deprotection of functional groups are described, for example, in T. W. Greene and P. G. M. Wuts, *Protective Groups in Organic Synthesis* (Second Edition, Wiley, 1991). The protection and deprotection of steroidal ketones is described in J. Fried and J. A. Edwards, *Organic Reactions in Steroid Chemistry*, Vol. 1 375ff (van Nostrand Reinhold, 1972). Reactive substituents which may be protected are shown in the accompanying schemes as, for example, [OH], [O], etc.

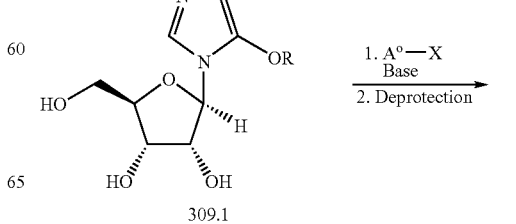

309.1

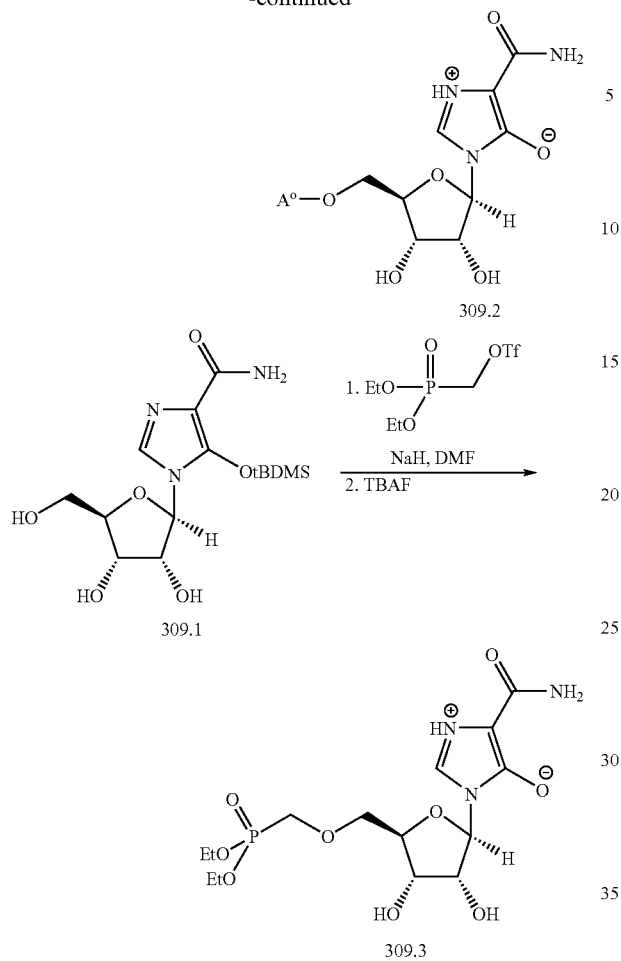

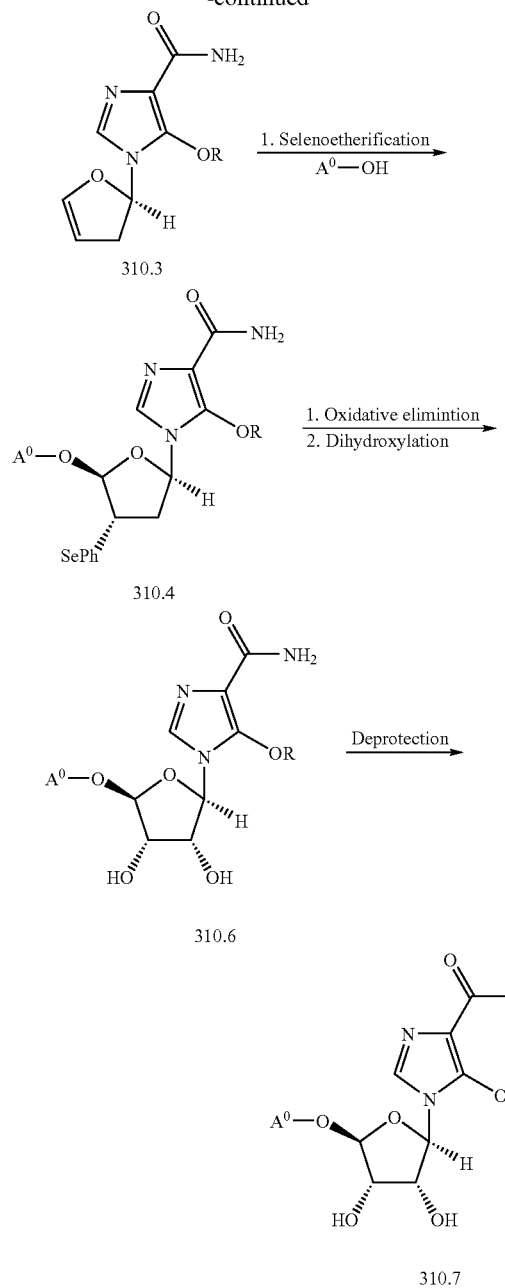

Depicted above is the preparation of phosphonates of the invention. The 5-hydroxy-1-β-D-ribofuranosyl-1H-imidazole-4-carboxamide 309.1 (prepared according to U.S. Pat. No. 3,888,843) can be treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding the desired phosphonate diester 309.2, e.g., 309.3.

EXAMPLE 310

Preparation of Representative Compounds of Mizoribine

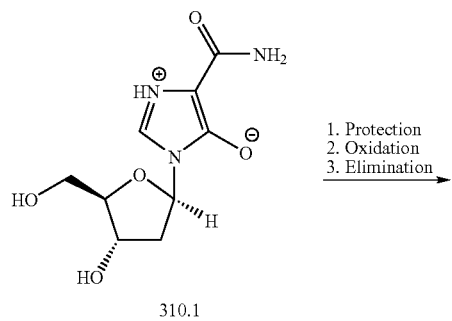

The preparation of the phosphonate esters of the invention is depicted above. Compound 310.1, 5-hydroxy-1-(4-hydroxy-5-hydroxymethyl-tetrahydro-furan-2-ylmethyl)-1H-imidazole-4-carboxylic acid amide can be prepared by addition of the imidazole base (J P Kokai 76 88965) onto the 3,5-bis-protected 2-deoxy-D-erythro-pentofuranosyl chloride (Hayashi, M. et al., *Chem. Pharm. Bull.*, 1975, 23, 1, 245; Montgomery, J. A. et al., *J. Med. Chem.*, 1969, 12, 3, 498; and Iwamoto, R. H. et al., *J. Med. Chem.*, 1963, 6, 684). Compound 310.1 is then protected on the imidazol-4-ol. Oxidation of the 5'-OH followed by elimination provides glycal 310.3 (see the procedure of Zemlicka J. et al., *J. Am. Chem. Soc.*, 1972, 94, 9, 3213). Selenoetherification provides the protected phosphonate 310.4 (Kim, C. et al., *J. Org. Chem.*, 1991, 56, 2642). Oxidative elimination of the phenylselenide (as described in Kim, C. et al., *J. Org. Chem.*, 1991, 56, 2642) followed by stereoselective dihydroxylation provides the diol 310.6. Finally, the protecting group is removed to provide 310.7.

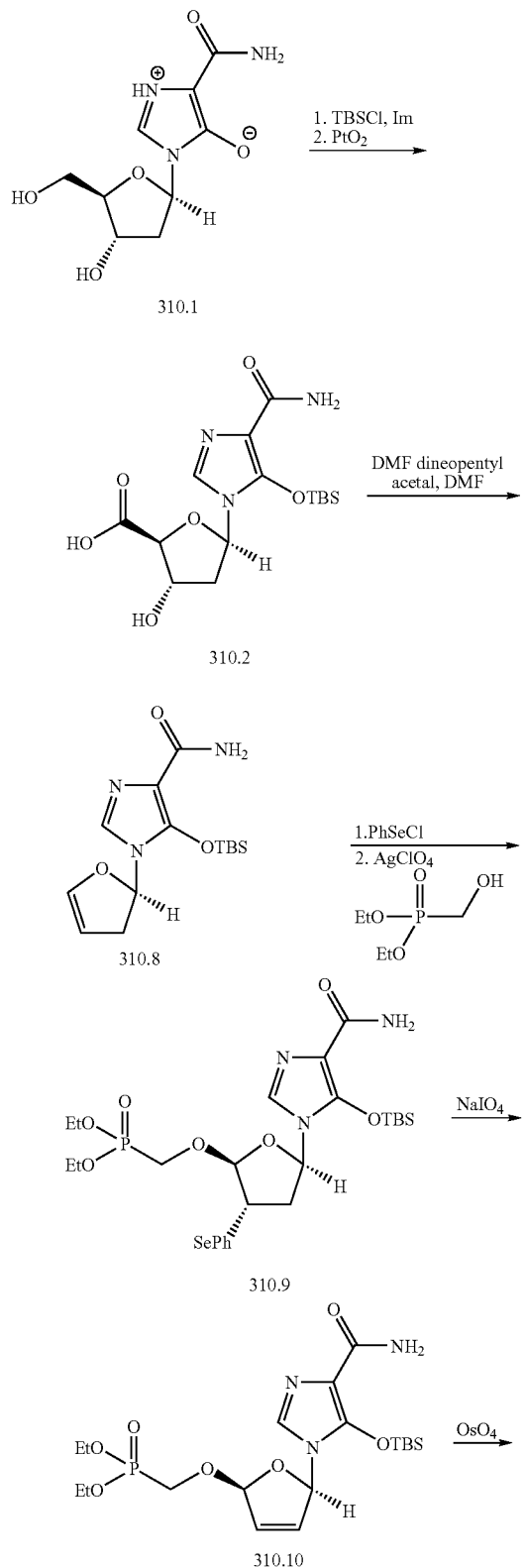

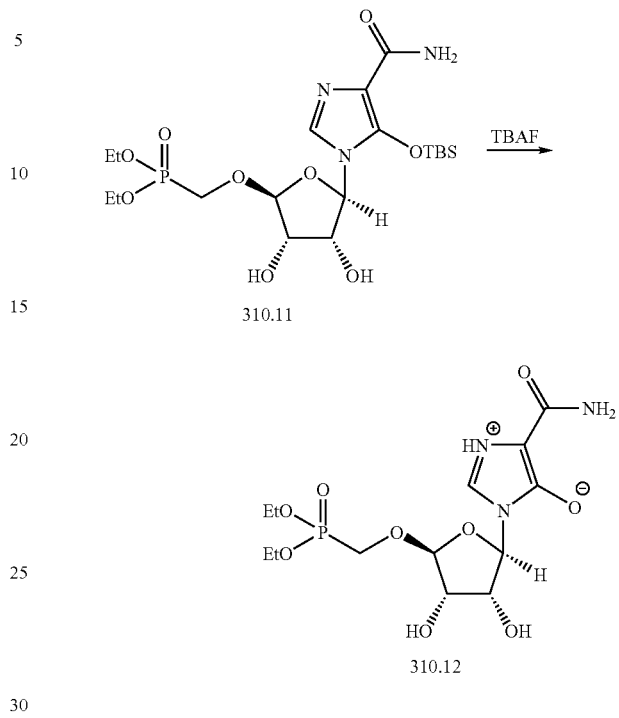

Illustrated above is the preparation of specific compounds of the invention. Specifically, compound 310.1, 5-hydroxy-1-(4-hydroxy-5-hydroxymethyl-tetrahydrofuran-2-ylmethyl)-1H-imidazole-4-carboxylic acid amide, which can be prepared by addition of the imidazole base (J P Kokai 76 88965; also Schipper, E. et al., *J. Am. Chem. Soc.*, 1952, 74, 350) onto the 3,5-bis-protected 2-deoxy-D-erythro-pentofuranosyl chloride (Hayashi, M. et al., *Chem. Pharm. Bull.*, 1975, 23, 1, 245; Montgomery, J. A. et al., *J. Med. Chem.*, 1969, 12, 3, 498; and Iwamoto, R. H. et al., *J. Med. Chem.*, 1963, 6, 684) is first protected using a TBS group. Subsequent oxidation with $PtO_2$ proceeds to provide carboxylic acid 310.2. Decarboxylative elimination is achieved using dimethylformamide dineopentyl acetal in DMF at high temperature (Zemlicka J. et al., *J. Am. Chem. Soc.*, 1972, 94, 9, 3213). Once the furanoid glycal 310.8 is in hand, it is treated with silver perchlorate in the presence of diethyl(hydroxylmethyl) phosphonate (Phillion, D. et al., Tetrahedron Lett., 1986, 27, 1477) to provide the phosphonate 310.9 (Kim, C. et al., *J. Org. Chem.*, 1991, 56, 2642). Oxidative elimination of the selenide followed by dihydroxylation using osmium tetraoxide provides a diol with the desired stereochemistry. Deprotection of the TBS group can be achieved using TBAF.

EXAMPLE 311

Preparation of Representative BCX-1777 Derivatives

In general, the preparation of the following representative compounds of the invention is illustrated below.

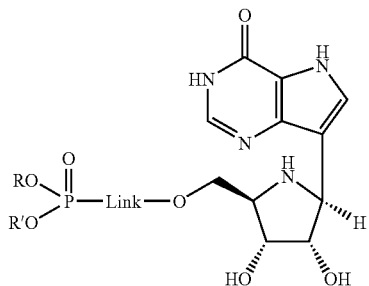

311.1

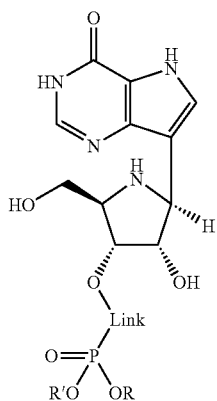

311.2

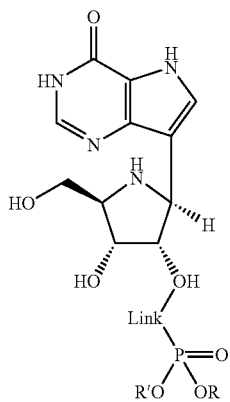

311.3

Link is 1-8 atoms in length, with 2-6 atoms preferred

Compounds of the invention such as 311.5 can be made according to the general route outlined below.

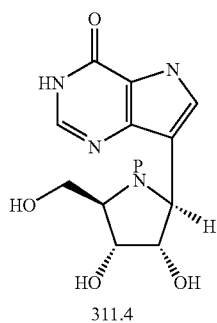

311.4

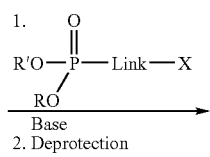

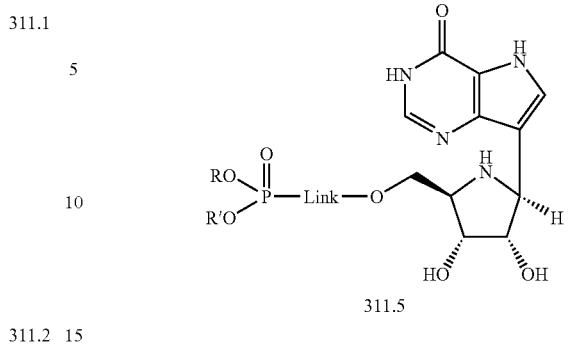

311.5

A specific compound of the invention may be prepared as follows:

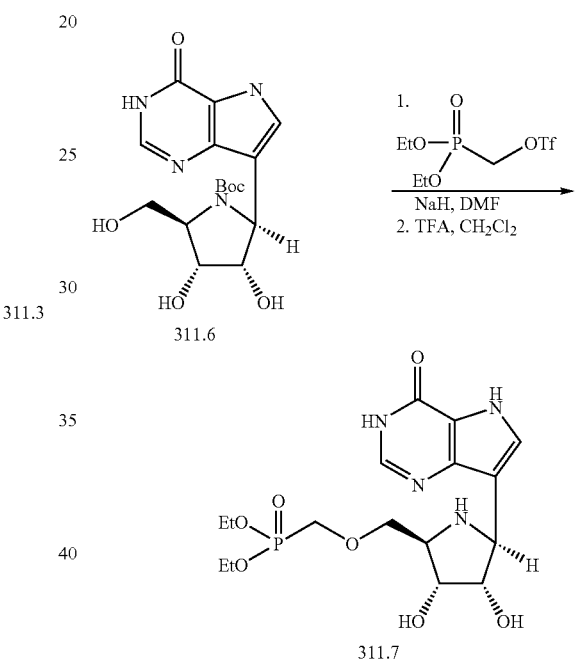

311.6

311.7

The Boc-protected (1S)-1-(9-deazaguanin-9-yl)-1,4-dideoxy-1,4-imino-D-ribitol, compound 311.6, is prepared by stirring the (1S)-1-(9-deazaguanin-9-yl)-1,4-dideoxy-1,4-imino-D-ribitol (WO 9,919,338 and Evans, G. B. et al., *Tetrahedron*, 2000, 56, 3053, also reported in Evans, G. B. et al., *J. Med. Chem.* 2003, 46, 3412) with BOC anhydride as described in Greene, T., Protective groups in organic synthesis, Wiley-Interscience, 1999. Compound 311.6 is then treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding the desired phosphonate 311.6 after deprotection of the BOC group using trifluoroacetic acid (TFA).

EXAMPLE 312

Preparation of Representative BCX-1777 Derivatives

The preparation of representative compounds of the invention are shown below. Compounds such as 312.2 and 312.3 can be made according to the general route outlined below.

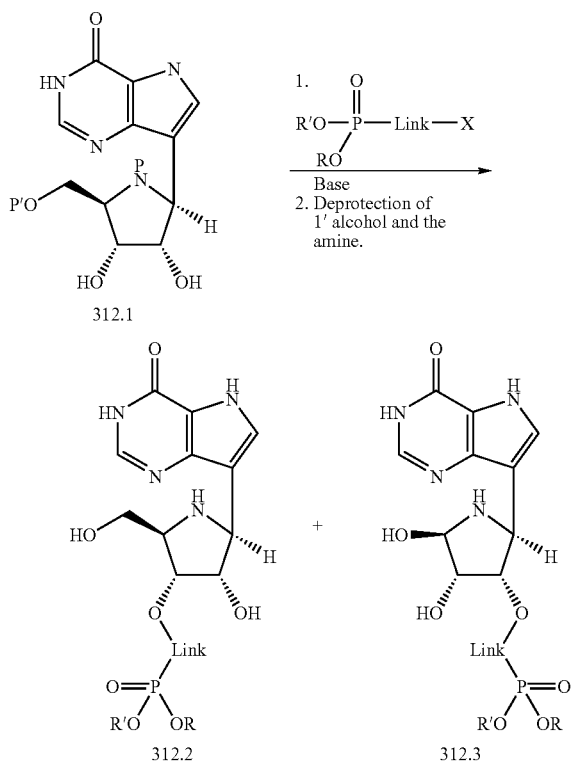

A specific compound of the invention can be prepared as follows:

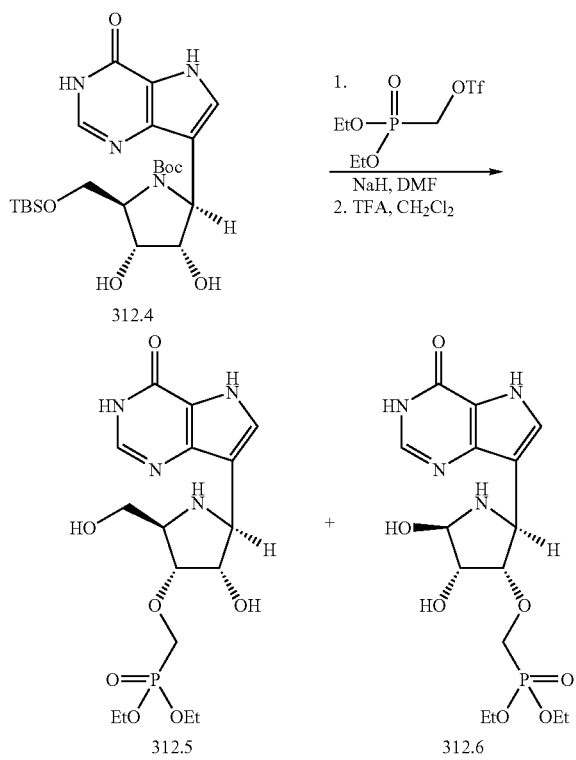

The Boc-protected (1S)-1-(9-deazaguanin-9-yl)-1,4-dideoxy-1,4-imino-D-ribitol, compound 312.4, is prepared by stirring the (1S)-1-(9-deazaguanin-9-yl)-1,4-dideoxy-1,4-imino-D-ribitol (WO 9,919,338 and Evans, G. B. et al., *Tetrahedron*, 2000, 56, 3053, also reported in Evans, G. B. et al., *J. Med. Chem.* 2003, 46, 3412) with BOC anhydride as described in Greene, T., "Protective Groups in Organic Synthesis," Wiley-Interscience, 1999. Subsequent protection of the primary alcohol using a TBS group can be achieved using TBSCl and imidazole in solvents such as $CH_2Cl_2$ as described in Greene, T. "Protective Groups in Organic Synthesis," Wiley-Interscience, 1999 to provide compound 312.1. Compound 312.1 is then treated in a solvent such as tetrahydrofuran or dimethylformamide with a base such as sodium hydride. When bubbling ceases, diethyl phosphonomethyltriflate (prepared according to *Tetrahedron Lett.*, 1986, 27, 1477) is added, yielding a mixture of the desired phosphonate diester 312.2 and 312.3 after deprotection of the BOC group using trifluoroacetic acid (TFA). Compounds 312.2 and 312.3 can be also prepared via a more complicated 2' OH protected analog of 312.1 followed by alkylation using the diethyl phosphonomethyltriflate to provide compound 312.2 exclusively. Compound 312.3 can also be prepared by installation of a different protecting group at the 3' OH position, followed by deprotection of 2' OH and alkylation with diethyl phosphonomethyltriflate at the 2' center followed by global deprotection.

EXAMPLE 313

Preparation of Representative Zileuton Compounds of the Invention

Specific compounds of the invention can be prepared as follows:

Diethyl(trifluromethanesulfonyloxy)methylphosphonate

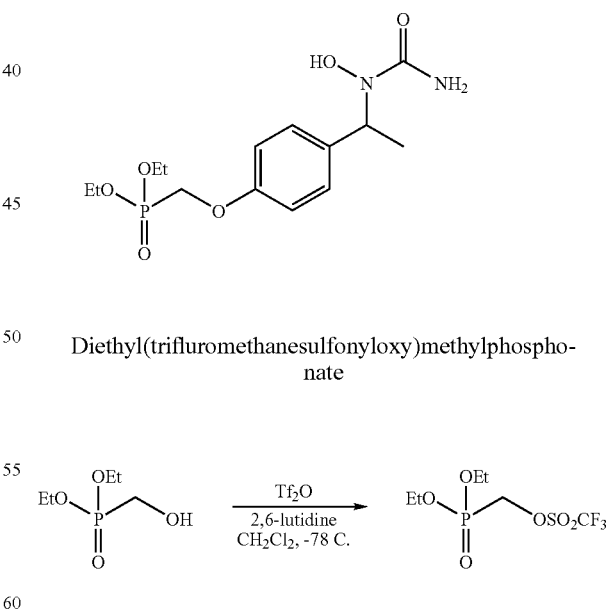

To a solution of diethyl hydroxymethylphosphonate (14.0 g, 83.27 mmol) and 2,6-lutidine (10.7 g, 99.9 mmol) in DCM (80 mL) at −78° C. was added triflic anhydride (25.83 g, 91.5 mmol), dropwise, and the solution was stirred for 15 minutes. The resulting mixture was then warmed to 0° C., stirred for 30 minutes, and diluted with ethyl acetate. The mixture was sequentially washed with 1N HCl, saturated $NaHCO_3$, and brine and then concentrated. The residue was purified by silica column chromatography (3:2 hexane/ethylacetate), affording the desired product as a clear yellowish oil. Yield (18.8 g, 75%)

MS m/z (MH)+ 301.

(4-Acetyl-phenoxymethyl)-phosphonic acid diethyl ester

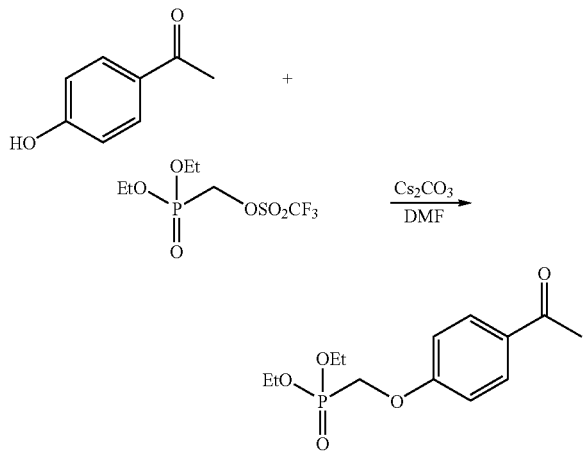

A reaction mixture of 4-hydroxyacetophenone (1.58 g, 11.10 mmol), trifluromethanesulfonic anhydride (3.66 g, 12.2 mmol) and cesium carbonate (4.34 g, 13.32 mmol) in DMF (55 mL) was stirred overnight at room temperature. The reaction mixture was diluted with water (100 mL) and the product was extracted with ethyl acetate (2×100 mL), washed with water and brine, dried over anhydrous sodium sulfate and concentrated in vacuo. The residue was purified by chromatography on silica gel, eluting with ethyl acetate/hexane (2:3), to yield the product (4.6 g, 78%).

MS m/z (MH)+ 287.

Preparation of Oxime (313.20)

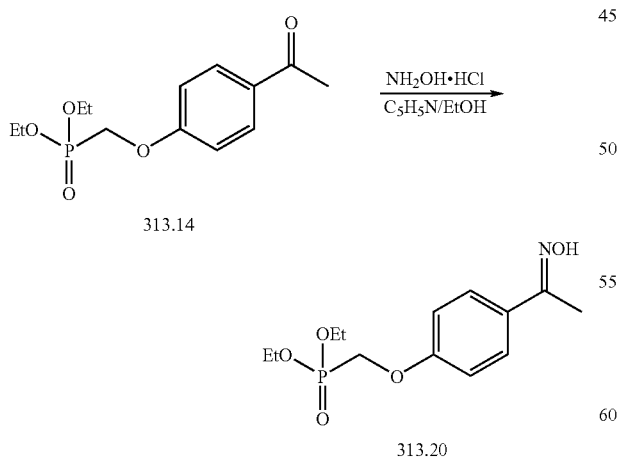

A mixture of 313.14 (1.5 g, 5.24 mmol), hydroxylamine hydrochloride (0.437 g, 6.28 mmol), pyridine (15 mL) and ethanol (15 mL) was stirred at room temperature for two days. The reaction mixture was concentrated to dryness, taken up in ether (20 mL) and washed with 3N HCl. The organic layer was dried over anhydrous sodium sulfate and concentrated in vacuo. The resulting solid was purified chromatography on silica gel, eluting with CHCl3:MeOH (98:2), to yield the desired product (1.1 g, 68%).

MS m/z (MH)+ 301.

Reduction of Oxime (313.22)

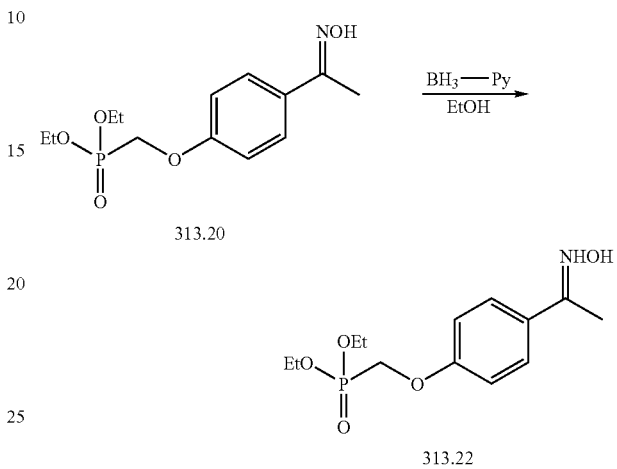

Oxime (313.20) (0.3 g, 1 mmol) was dissolved in ethanol (10 mL) and freshly-prepared BH3-Py complex (1 mL) was added. The solution was stirred for 10 minutes at room temperature, whereupon 6 N HCl (1.8 mL) was added, dropwise. Further stirring was continued for 1 hour at room temperature. The reaction mixture was then brought to pH 8-9 by addition of 2N NaOH. The product was extracted with ethyl acetate (2×50 mL), dried over anhydrous sodium sulfate and concentrated to yield a viscous liquid (0.32 g) which contained some residual pyridine but was suitable for use in the next step.

MS m/z (MH)+ 303.

Synthesis of N-hydroxy Urea (313.24)

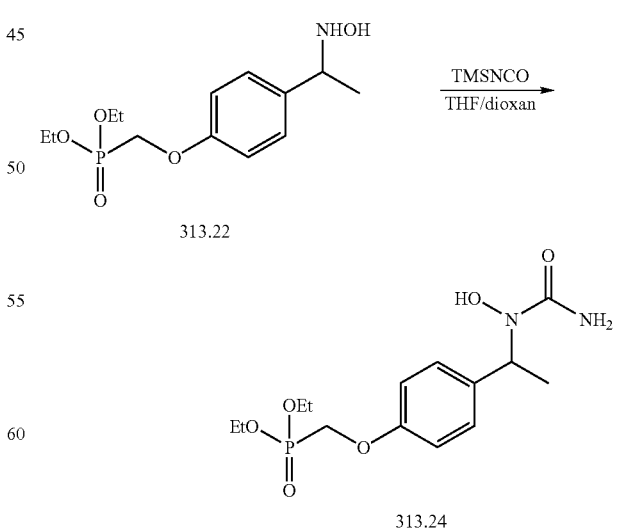

To a solution of 313.22 (0.3 g, 1 mmol) in 1,4-dioxane (5 mL) and THF (5 mL) was added trimethylsilyl isocyanate (0.16 mL, 1.2 mmol). The reaction mixture was heated at 90° C. for 1 h, cooled to room temperature and poured into a ice-cooled saturated solution of ammonium chloride. The product was extracted with ethyl acetate, washed with brine, dried over anhydrous sodium sulfate and concentrated in vacuo. The residue was purified by chromatography on silica gel, eluting with $CHCl_3$-MeOH, (96:4) to give the desired product (0.14 g, 40%). MS m/z (MH)$^+$ 347. $^1$H NMR ($CDCl_3$) δ 1.32-1.37 (m, 6H, $CH_3$) 1.48-1.51 (d, 3H, $CH_3$, 4.13-4.23 (m, 6H, —$CH_2$, —$CH_2$, $OCH_2$—P) 5.3-5.4(m,3H, —CH—, $NH_2$), 6.86-7.35 (m, 4H, $C_6H_4$), 8.29 (1H, N—OH). HPLC Purity 79% major 16% minor (sphereclone 5 μL, $H_2O$:MeCN, 20 minute linear gradient from 10-90% MeCN, 1.0 mL/min). $^{31}$P NMR ($CDCL_3$) δ 19.75-20.17, m.

Specific compounds of the invention can be prepared as follows:

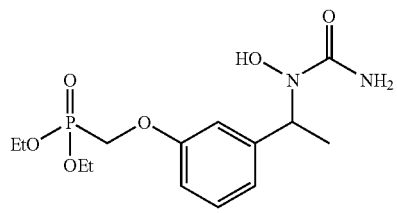

Preparation of 313.16

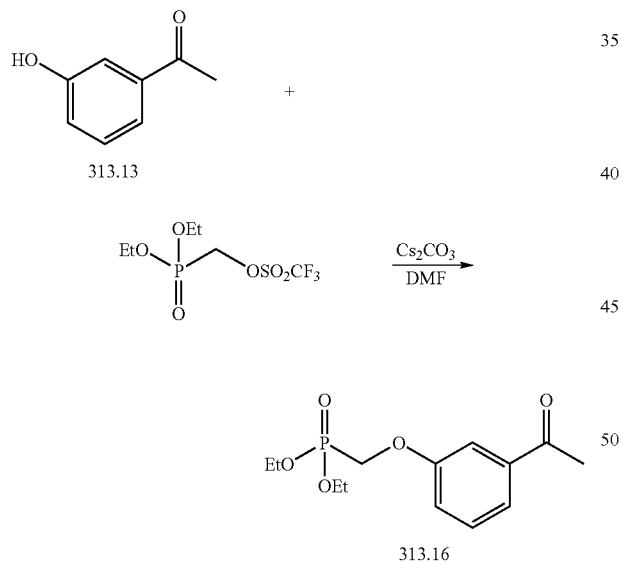

A reaction mixture of 3-hydroxyacetophenone (1.00 g, 7.32 mmol) trifluromethanesulfonic anhydride (2.46 g, 8.05 mmol) and cesium carbonate (2.86 g, 8.79 mmol) in DMF (50 mL) was stirred overnight at room temperature. The reaction mixture was diluted with water (100 mL) and the product was extracted with ethyl acetate (2×100 mL), washed with water and brine, dried over anhydrous sodium sulfate and concentrated in vacuo. The residue was purified by chromatography on silica gel, eluting with ethyl acetate/hexane (2:3), to yield the product (1.5 g, 72% yield).

MS m/z (MH)+287.

Preparation of Oxime 313.21

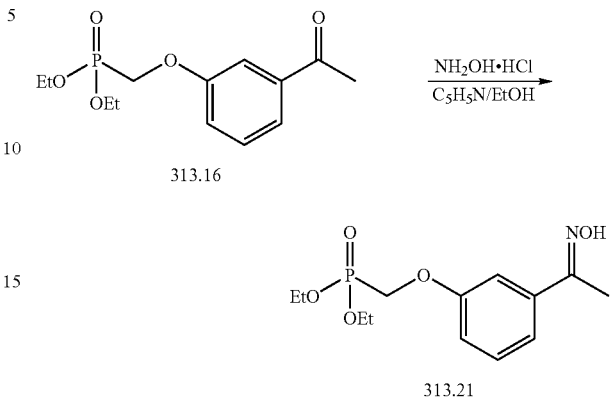

A mixture of 313.16 (0.5 g, 1.75 mmol), hydroxylamine hydrochloride (0.145 g, 2.09 mmol), pyridine (10 mL) and ethanol (10 mL) was stirred at room temperature for two days. The reaction mixture was concentrated to dryness, taken up in ether (20 mL) and washed with 3N HCl. The organic layer was dried over anhydrous sodium sulfate and concentrated in vacuo. The resulting solid was purified chromatography on silica gel, eluting with $CHCl_3$:MeOH (98:2), to yield the desired product (0.3 g, 61%).

MS m/z (MH)$^+$ 301.

Reduction of Oxime 313.25

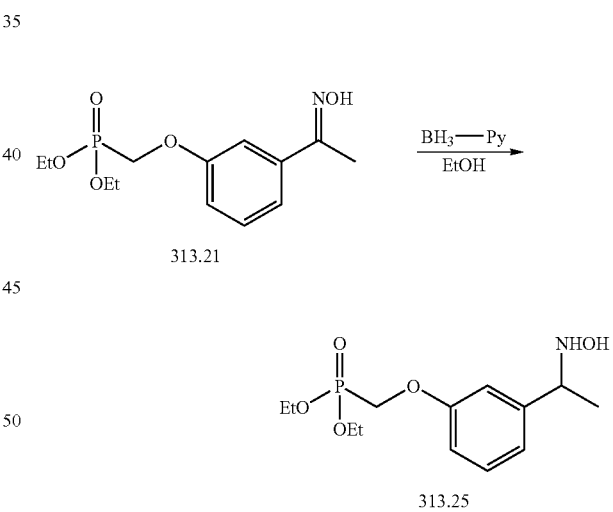

Oxime (313.21) (0.304 g, 1 mmol) was dissolved in ethanol (10 mL) and freshly-prepared $BH_3$-Py complex (1 mL) was added. The solution was stirred for 10 minutes at room temperature, whereupon 6 N HCl (1.8 mL) was added, dropwise. Further stirring was continued for 1 hour at room temperature. The reaction mixture was then brought to pH 8-9 by addition of 2N NaOH. The product was extracted with ethyl acetate (2×50 mL), dried over anhydrous sodium sulfate and concentrated to yield a viscous liquid (0.32 g) which contained some residual pyridine but was suitable for use in the next step.

MS m/z (MH)$^+$ 304.

Synthesis of N-hydroxy Urea (313.26)

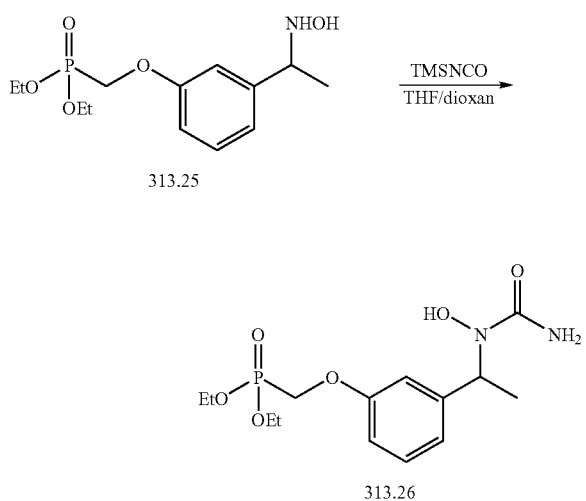

To a solution of 313.21 (0.3 g, 1 mmol) in 1,4-dioxane (5 mL) and THF (5 mL) was added trimethylsilyl isocyanate (0.16 mL, 1.2 mmol). The reaction mixture was heated at 90° C. for 1 hour, cooled to room temperature and poured into a ice-cooled saturated solution of ammonium chloride. The product was extracted with ethyl acetate, washed with brine, dried over anhydrous sodium sulfate and concentrated in vacuo. The residue was purified by chromatography on silica gel, eluting with $CHCl_3$-MeOH, (96:4) to give the desired product (0.14 g, 40%). MS m/z $(MH)^+$ 347. $^1H$ NMR $(CDCl_3)$ δ 1.30-1.38 (m, 6H, 2-$CH_3$) 1.52-1.55(d, 3H, $CH_3$, 4.1-4.37 (m, 6H, —$CH_2$, —$CH_2$, $OCH_2$—P) 5.27-5.49(m,3H, —CH—, $NH_2$) 6.81-7.27 (m, 4H, $C_6H_4$)8.13 (1H, N—OH). HPLC Purity 82% (sphereclone 5 μL $H_2O$:MeCN, 20 minute linear gradient from 10-90% MeCN, 1.0 mL/min). $^{31}P$ NMR $(CD_3OD)$ δ 21.69-22.12, m.

EXAMPLE 314

Preparation of Representative Zardaverine Compounds of the Invention

Specific compounds of the invention can be prepared as follows:

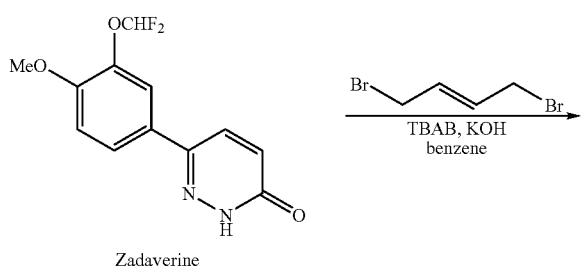

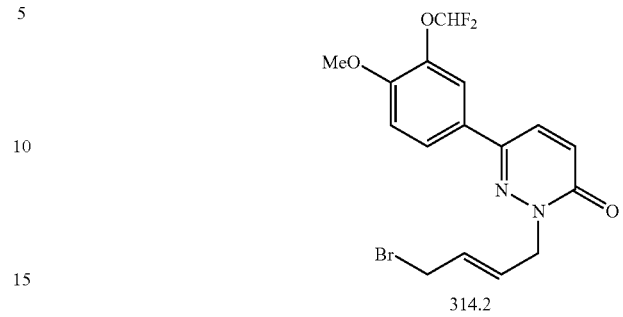

Preparation of 314.2.

A mixture of 50 mg Zardaverine (0.186 mmol), 120 mg 1,4-dibromo-2-butene (0.56 mmol), 10.5 mg (0.187 mmol) KOH and 6.5 mg (0.02 mmol) TBAB in 1 mL benzene was stirred vigorously for 6 hrs. The suspension became two phases with a clear organic upper layer. TLC indicated the total consumption of the starting material and the formation of one new compound. The mixture was mounted directly on a silica gel column (1:1 hexanes/ethyl acetate) and 65 mg of the title compound was isolated as a white solid (87% yield). ESI-MS m/z 401 $(MH)^+$. IR 1666 (C=O) $cm^{-1}$.

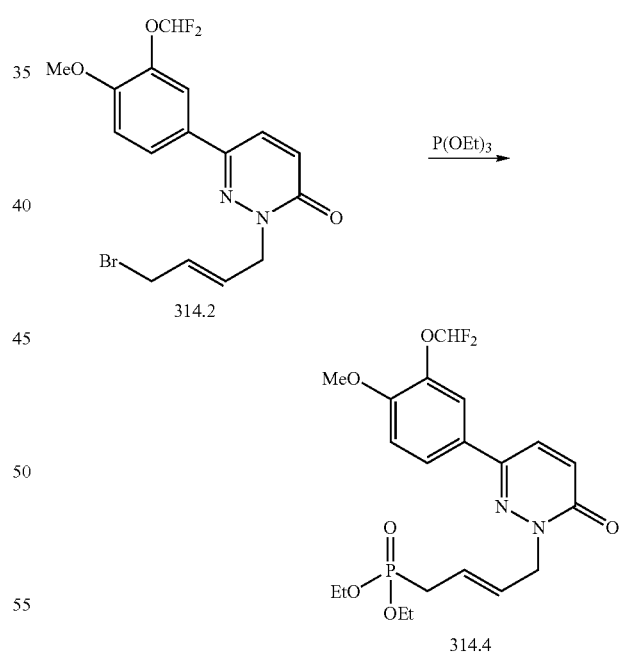

Preparation of 314.4

A solution of 65 mg 314.2 (0.125 mmol) and 0.22 mL (1.25 mmol) triethyl phosphite in 1 mL toluene was heated at reflux for 2 hrs. TLC indicated the total consumption of the starting material and the formation of one new compound. The mixture was mounted directly on a silica gel column (2% MeOH in ethyl acetate) and 65 mg of the title compound was isolated as a clear liquid (87% yield).

HPLC purity 100% (Sphereclone 5 μL, H₂O:MeCN, 20 min linear gradient from 10-90% MeCN, 1.0 mL/min). ESI-MS m/z 459 (MH)⁺. ¹H NMR (300 MHz, CDCl₃) δ 7.65 (d, J=9.6 Hz, 1 H), 7.45 (d, J=1.8 Hz, 1 H), 7.29-7.21 (m, 2 H), 7.03 (d, J=9.6 Hz, 1 H), 6.61 (t, J=74.8 Hz, 1 H), 5.98-5.72 (m, 2 H), 4.84 (t, J=5.2 Hz, 2 H), 4.07 (quintet, J=7.2 Hz, 4 H), 3.97 (s, 3 H), 2.62 (dd, J=21.4, 6.5 Hz, 2 H), 1.26 (t, J=7.0 Hz, 6 H). ³¹P NMR (120 MHz, CDCl₃) δ 27.14 (m).

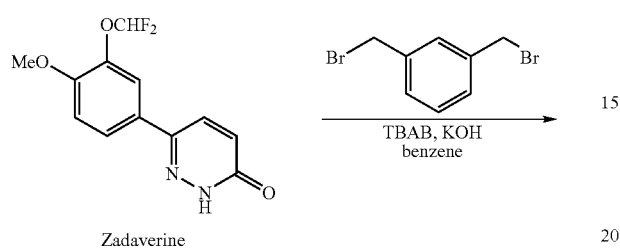

Zadaverine

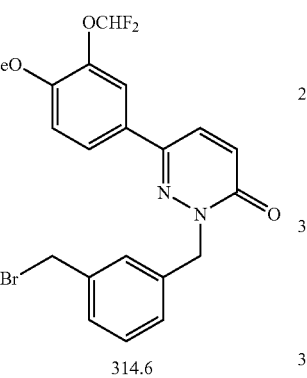

314.6

Preparation of 314.6

A mixture of 50 mg Zardaverine (0.186 mmol), 120 mg m-xylylene dibromide (0.56 mmol), 10.5 mg (0.187 mmol) KOH and 6.5 mg (0.02 mmol) TBAB in 1 mL benzene was stirred vigorously for 7.5 hrs. The suspension became two phases with a clear organic upper layer. TLC indicated the total consumption of the starting material and the formation of one new compound. The mixture was mounted directly on a silica gel column (1:1 hexanes/ethyl acetate) and 64 mg of the title compound was isolated as a white solid (77% yield). ESI-MS m/z 451 (MH)⁺.

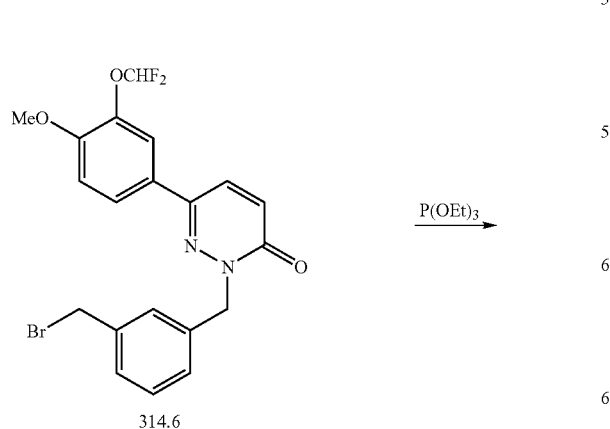

314.6

-continued

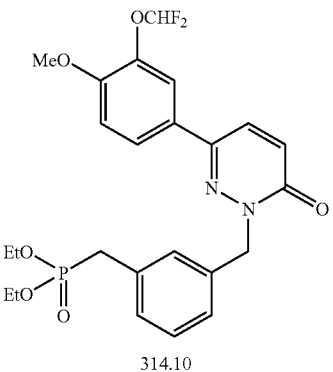

314.10

Preparation of 314.10

A solution of 64 mg 314.6 (0.142 mmol) and 0.22 mL (1.25 mmol) triethyl phosphite in 1 mL toluene was heated to reflux for 2 hrs. TLC indicated the total consumption of the starting material and the formation of one new compound. The mixture was mounted directly on a silica gel column (2% MeOH in ethyl acetate) and 70 mg of the title compound was isolated as a white solid (97% yield). HPLC purity >98% (Sphereclone 5 μL, H₂O:MeCN, 20 min linear gradient from 10-90% MeCN, 1.0 mL/min). ESI-MS m/z 509 (MH)⁺. ¹H NMR (300 MHz, CDCl₃) δ 7.64 (d, J=9.7 Hz, 1 H), 7.43 (d, J=1.8 Hz, 1 H), 7.4-7.20 (m, 6 H), 7.02 (d, J=9.7 Hz, 1 H), 6.60 (t, J=74.9 Hz, 1 H), 5.39 (s, 2 H), 4.02-3.16 (m, 4 H), 3.96 (s, 3 H), 3.13 (d, J=21.6 Hz, 2 H), 1.18 (t, J=7.1 Hz, 6 H). ³¹P NMR (120 MHz, CDCl₃) δ 26.68 (m).

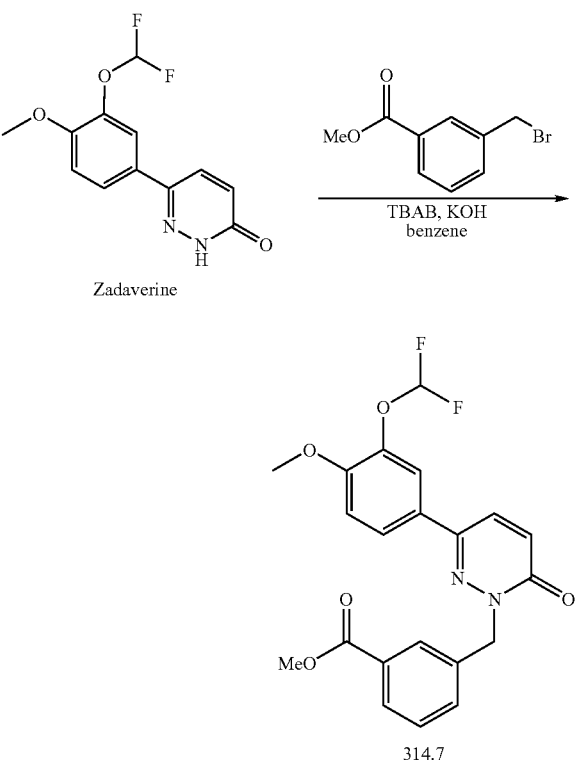

Zadaverine 314.7

Preparation of 314.7

A mixture of 38 mg Zardaverine (0.142 mmol), 128 mg methyl 3-(bromomethyl)benzoate (0.56 mmol), 10.5 mg (0.187 mmol) KOH and 6.5 mg (0.02 mmol) TBAB in 1 mL benzene was stirred vigorously for 7.5 hrs. The suspension became two phases with a clear organic upper layer. TLC indicated the total consumption of the starting material and the formation of one new compound. The mixture was mounted directly on a silica gel column (1:1 hexanes/ethyl acetate) and 55 mg of the title compound was isolated as a white solid (94% yield). ESI-MS m/z 417 (MH)$^+$.

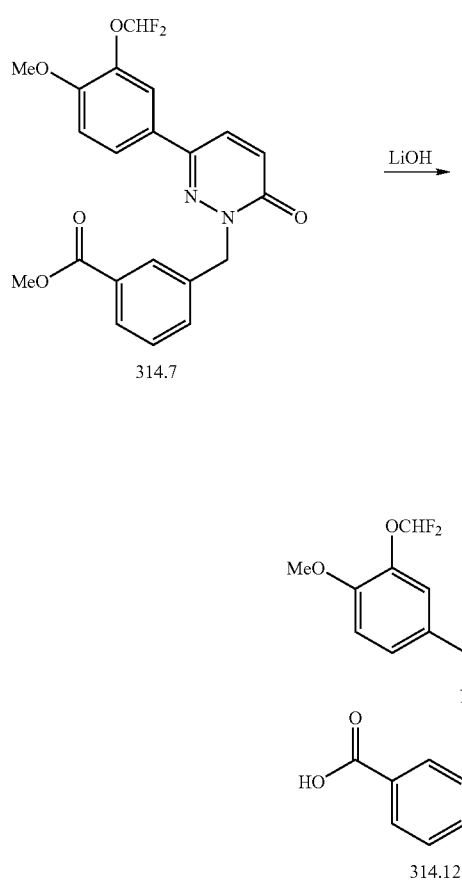

Preparation of 314.12

A mixture of 55 mg Zardaverine (0.132 mmol), 55 mg LiOH.H$_2$O (1.3 mmol), 2 mL MeOH, 1 mL THF and 0.3 mL water was stirred vigorously at room temperature overnight. TLC indicated the total consumption of the starting material and the formation of one new compound. The solvent was evaporated under reduced pressure. The residue was diluted with CH$_2$Cl$_2$, acidified with 1 N HCl, and extracted with CH$_2$Cl$_2$. The organic phase was combined, dried and concentrated to give 49 mg of white solid (92% yield), which was used without further purification. ESI-MS m/z 403 (MH)$^+$.

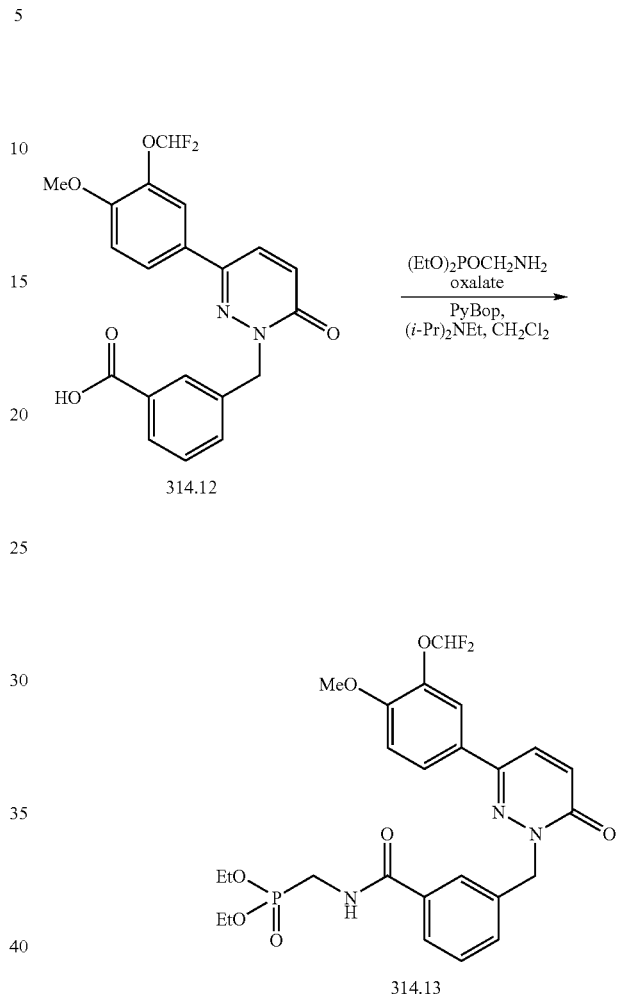

Preparation of 314.13

To a solution of 49 mg 314.12 (0.122 mmol) in 0.5 mL CH$_2$Cl$_2$ was added 76 mg PyBop (0.146 mmol) at 0° C., followed by 0.063 mL (i-Pr)$_2$NEt (0.366 mmol). The mixture was stirred at room temperature for 2 hr until TLC indicated the total consumption of the starting material. The mixture was mounted directly on a silica gel column (45:1 ethyl acetate: methanol) and 45 mg of the title compound was isolated as a yellow solid (67% yield). HPLC purity >99% (Sphereclone 5 μL, H$_2$O:MeCN, 20 min linear gradient from 10-90% MeCN, 1.0 mL/min). ESI-MS m/z 552 (MH)$^+$. $^1$H NMR (300 MHz, CDCl$_3$) δ 7.92 (s, 1 H), 7.65 (d, J=9.8 Hz, 1 H), 7.75-7.59 (m, 2 H), 7.48-7.38 (m, 2 H), 7.32-7.29 (m, 2 H), 7.03 (d, J=9.7 Hz, 1 H), 6.60 (s, br, 1 H), 6.59 (t, J=74.8 Hz, 1 H), 5.44 (s, 2 H), 4.20-4.10 (m, 4 H), 3.95 (s, 3 H), 3.89 (dd, J=12.1, 5.8 Hz, 2 H), 1.31 (t, J=7.1 Hz, 6 H). $^{31}$P NMR (120 MHz, CDCl$_3$) δ 23.21 (m).

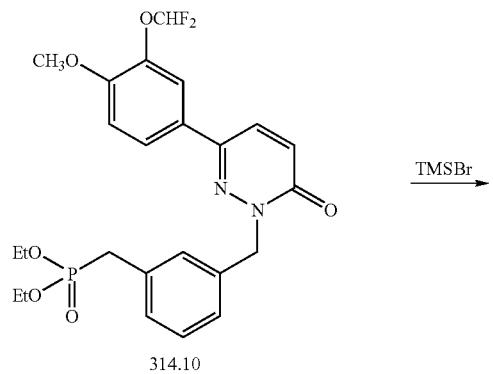

314.10

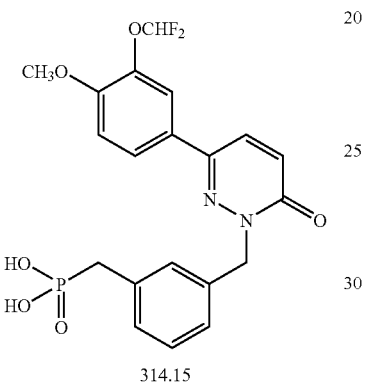

314.15

Preparation of 314.15

To 30 mg 314.10 (0.066 mmol) in 1.7 mL acetonitrile was added 0.3 mL TMSBr at 0° C., and the solution was stirred at room temperature overnight. TLC indicated the total consumption of the starting material. The mixture was cooled to 0° C. before 1 mL MeOH was added, and the mixture was stirred at room temperature for 30 min. The solvent was then removed under vacuum. A sample of 5 mg of the red residue (total 30 mg) was cooled to 0° C., 0.5 mL and 1 N NaOH was added, followed by 0.5 mL water. The mixture was stirred vigorously and then extracted with 1 mL ether 3 times. The aqueous phase was acidified to ca. pH 1 with concentrated HCl. and extracted with 2 mL portions of EtOAc 5 times. The combined EtOAc extracts were concentrated to furnish 3 mg of the title compound as a yellow solid (68% yield). HPLC purity >95% (Sphereclone 5 μL, H$_2$O:MeCN, 20 min linear gradient from 10-90% MeCN, 1.0 mL/min). ESI-MS m/z 453 (MH)$^+$. $^1$H NMR (300 MHz, DMSO-d$_6$) δ 8.09 (d, J=9.0 Hz, 1 H), 7.59-6.87 (m, 9 H), 5.31 (s, 2 H), 3.90 (s, 3 H), 2.96 (d, J=22.1 Hz, 2 H).

EXAMPLE 315

Preparation of Representative Indomethacin Compounds of the Invention.

Specific compounds of the invention can be prepared as follows.

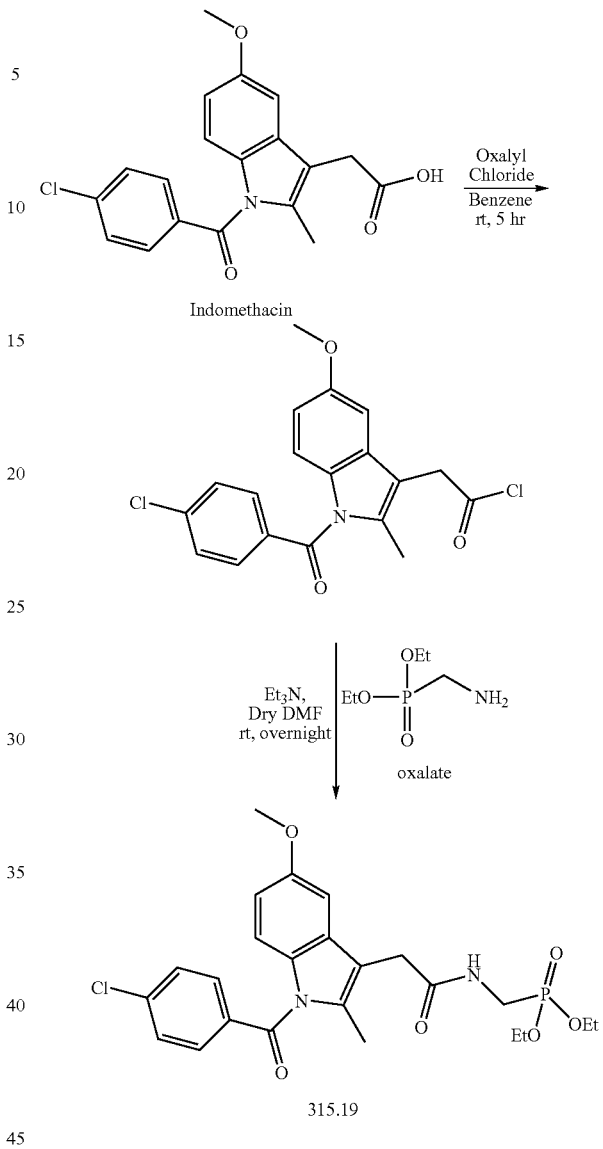

315.19

Synthesis of 315.19

Step 1: Indomethacin (500 mg, 1.40 mmol) was dissolved in dry benzene (5 mL) under an argon atmosphere, and oxalyl chloride (183 μL, 2.10 mmol) was added, followed by 1 drop of dry DMF. The reaction mixture was stirred at room temperature for 24 hrs and concentrated to dryness. The residue was co-evaporated with dry benzene (5 mL) to remove traces of oxalyl chloride. The solid obtained (556 mg) was dried under vacuum for 4 hrs at room temperature and carried over to next step without purification.

Step 2: Diethyl(aminomethyl)phosphonate oxalate (381 mg, 1.48 mmol) was dissolved in 5 mL of dry DMF under argon atmosphere. Triethylamine (413 μL, 2.96 mmol) was added, and the reaction mixture was stirred for 15 min at room temperature. The crude acid chloride (556 mg, 1.48 mmol) as a solution in 3 mL of dry DMF was added dropwise to the reaction mixture. After completion of the addition the reaction was stirred for 24 hrs at room temperature. TLC (CHCl$_3$: MeOH, 95:5) showed complete consumption of starting material. Deionized water (10 mL) was added and the mixture was extarcted with ethylacetate (2×15 mL). The ethyl acetate extracts were combined and washed with 1N HCl (5 mL) followed by deionized water (10 mL), and dried over Na$_2$SO$_4$. Concentration gave a syrup that on purification by preparative-TLC (4 plates, 20×20 cm, 2000 microns, solvent: CHCl$_3$: MeOH, 95:5) gave gummy solid. The gummy solid was crystallized from diethyl ether (3 mL) to give a solid (294 mg, 42% yield). HPLC: 99.5% pure (Sphereclone 5 μL, H$_2$O: MeCN, 20 min linear from 10-90% MeCN, 1.0 mL/min). ESI-MS m/z 507 [M+H]$^+$. $^1$H NMR (300 MHz, CDCl$_3$): δ 7.71-7.67 (2H, m, ArH), 7.51-7.48 (2H, m, ArH), 6.91-6.86 (2H, m, ArH), 6.72-6.68 (1H, dd, J=8.9 Hz, 2.3 Hz, ArH), 5.82 (1H, br s, NH), 4.08-3.99 (4H, m, OCH$_2$), 3.83 (3H, s, OCH$_3$), 3.69-3.63 (4H, m, CH$_2$), 2.39 (3H, s, CH$_3$), 1.25-1.20 (6H, t, J=7.0 Hz, CH$_3$). $^{31}$P NMR (CDCl$_3$, H$_3$PO$_4$ as external reference): δ 22.75

EXAMPLE 316

Preparation of an Additional Representative Mycophenolate Compound of the Invention A specific compound of the invention can be prepared as follows.

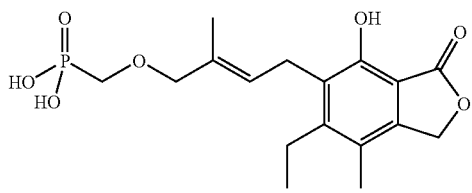

[4-(6-Ethyl-4-hydroxy-7-methyl-3-oxo-1,3-dihydro-isobenzofuran-5-yl)-2-methyl-but-2-enyloxymethyl]-phosphonic acid This product was prepared using methods similar to those described herein, e.g., in Examples 251 and 276. MS (negative mode): 369.3 [M$^+$−1].

EXAMPLE 317

Preparation of an Additional Representative Mycophenolate Compound of the Invention A specific compound of the invention can be prepared as follows.

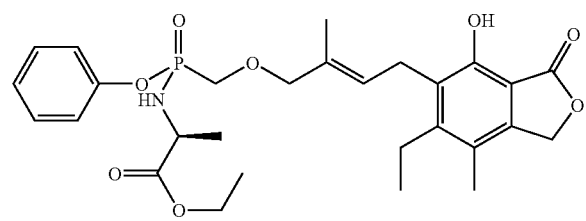

2-{[4-(6-Ethyl-4-hydroxy-7-methyl-3-oxo-1,3-dihydro-isobenzofuran-5-yl)-2-methyl-but-2-enyloxymethyl]-phenoxy-phosphinoylamino}-propionic acid ethyl ester Using methods similar to those described herein, e.g., in Example 261, the desired product was prepared, starting from Example 316. MS (positive mode): 546.3 [M$^+$+1] & 568.3 [M$^+$+Na].

EXAMPLE 318

Preparation of an Additional Representative Mycophenolate Compound of the Invention A specific compound of the invention can be prepared as follows:

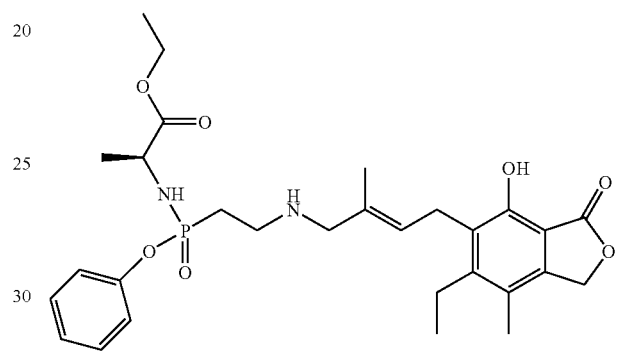

2-({2-[4-(6-Ethyl-4-hydroxy-7-methyl-3-oxo-1,3-dihydro-isobenzofuran-5-yl)-2-methyl-but-2-enylamino]-ethyl}-phenoxy-phosphinoylamino)-propionic acid ethyl ester This product was prepared using methods analogous to those described herein, e.g., in Examples 268 and 316, using 2-[(2-amino-ethyl)-phenoxy-phosphinoylamino]-propionic acid ethyl ester in the reductive amination step. MS (positive mode): 559.4 [M$^+$+1] & 581.3 [M$^+$+Na].

EXAMPLE 319

Preparation of an Additional Representative Mycophenolate Compound of the Invention A specific compound of the invention can be prepared as follows:

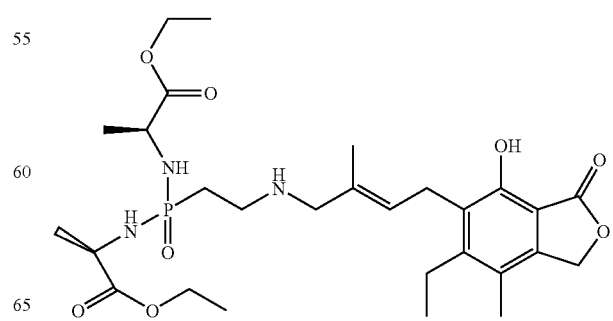

2-((1-Ethoxycarbonyl-ethylamino)-{2-[4-(6-ethyl-4-hydroxy-7-methyl-3-oxo-1,3-dihydro-isobenzofuran-5-yl)-2-methyl-but-2-enylamino]-ethyl}-phosphinoylamino)-propionic acid ethyl ester This product was prepared by methods analogous to those described herein, e.g., in Example 318, using 2-[(2-aminoethyl)-(1-ethoxycarbonyl-ethylamino)-phosphinoylamino]-propionic acid ethyl ester in the reductive amination step. MS (positive mode): 582.4 [M$^+$+1] & 604.3 [M$^+$+Na].

EXAMPLE 320

Synthesis of Representative Compounds of Formula 66

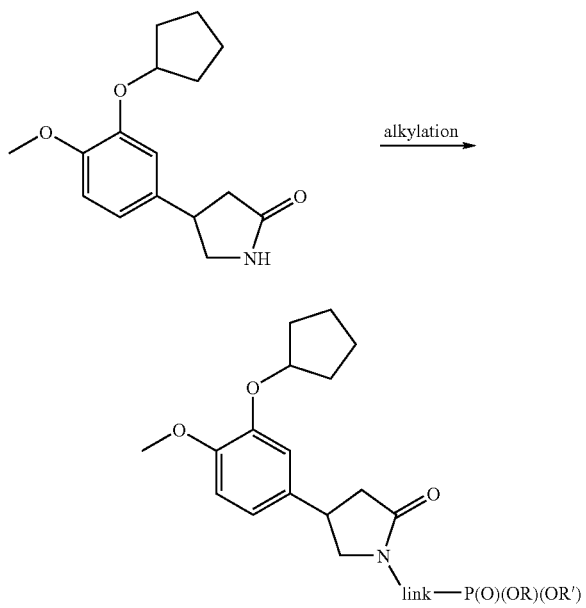

link includes 1 or more atoms;
2 or more is preferred

Representative compounds of the invention can be prepared as illustrated above. For example, a specific compound of Formula 66 can be prepared as follows.

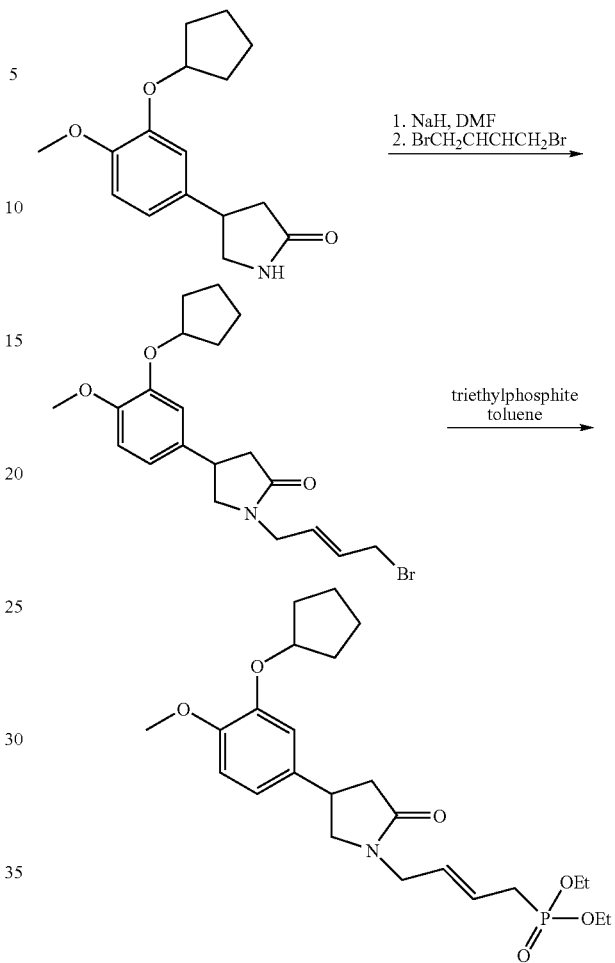

Rolipram can be treated in a solvent such as dimethylformamide or tetrahydrofuran with a base such as sodium hydride. When bubbling ceases, E-1,4-dibromobutene is added in excess. After quenching the reaction with aqueous ammonium chloride and extracting the product with an organic solvent such as ethyl acetate, the mono-alkylated product is isolated by chromatography. The allylic bromide is then heated with triethylphosphite in a solvent such as toluene to generate the diethyl ester of the desired phosphonic acid.

EXAMPLES 321-325

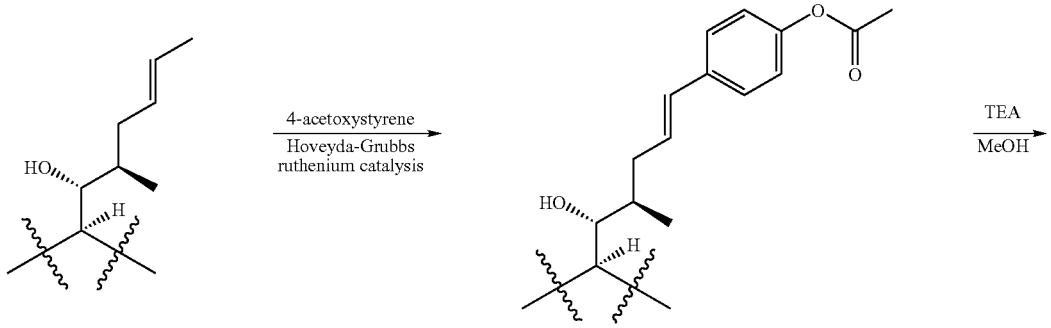

1033 1034
-continued
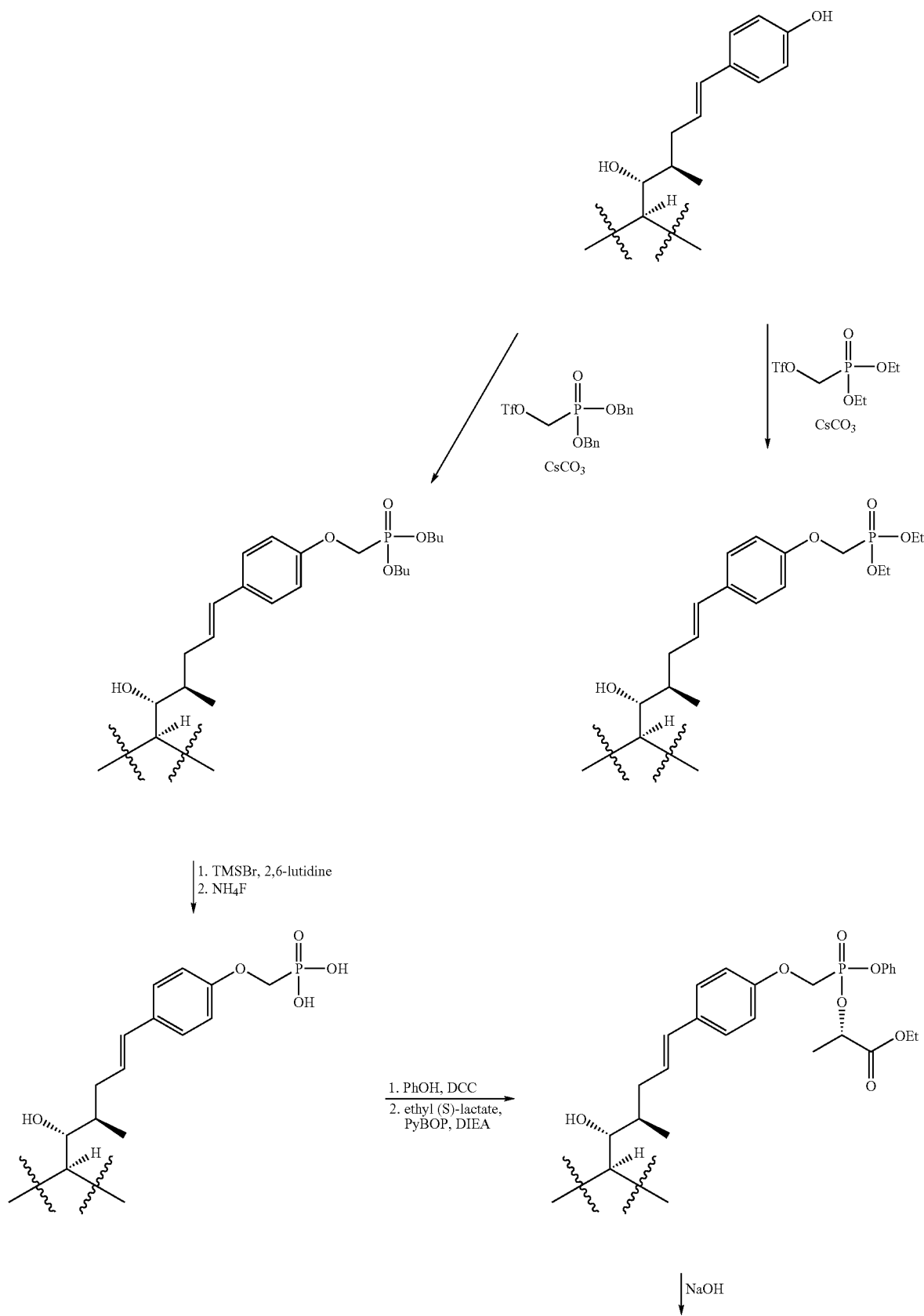

-continued
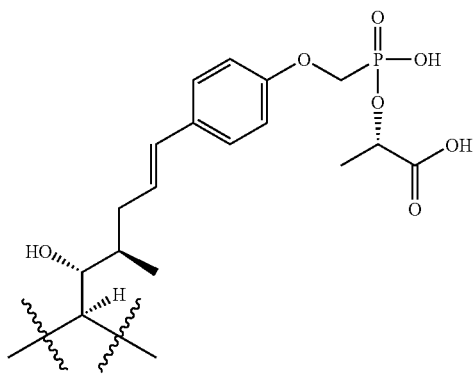
The synthetic sequence used in Examples 321-325 for preparing representative compounds of the invention is illustrated above. In the above illustration the substructure on the right below represents Cyclosporin A.
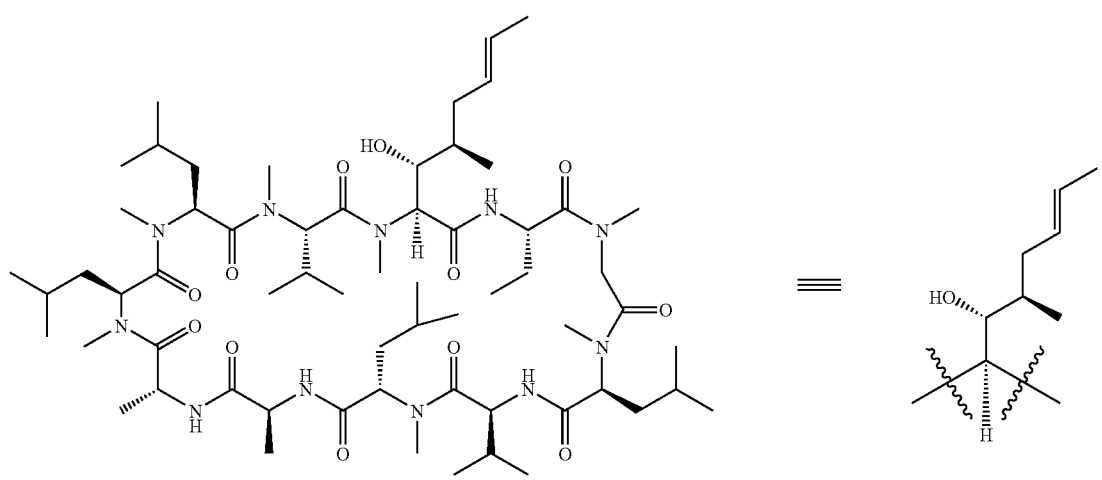
Cyclosporin A

EXAMPLE 321

Synthesis of cyclo-[[(2S, 3R, 4R, 6E)-7-(4-(diethoxyphosphoryl-methydroxy)phenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl]

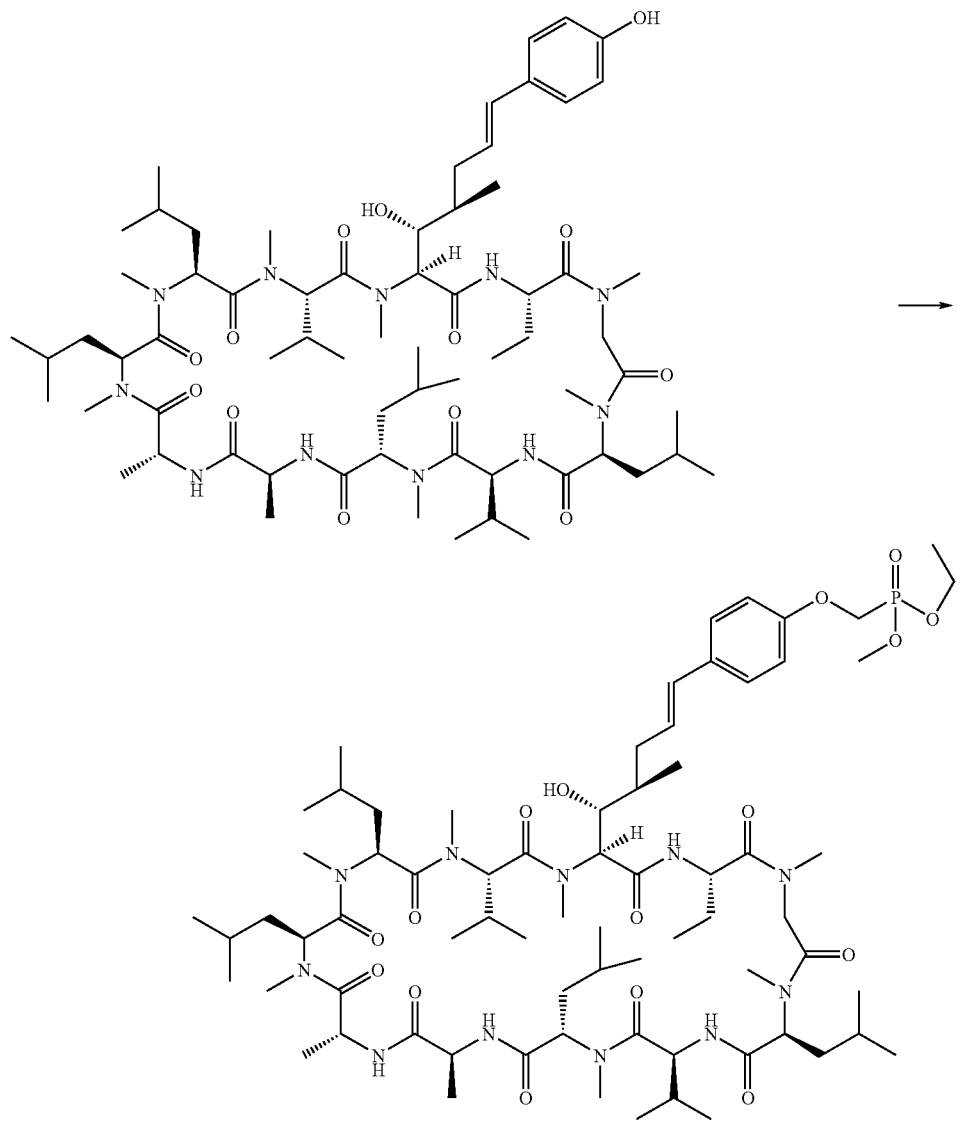

To a mixture of cyclo-[[(2S, 3R, 4R, 6E)-7-(4-hydroyphenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl] (113 mg, 0.088 mmol) and cesium carbonate (33 mg, 0.1 mmol) in DMF (1 mL) was added trifluoromethanesulfonic acid diethoxyphosphorylmethyl ester (60 mg, 0.2 mmol). The mixture was stirred at room temperature for 16 hours. The reaction was quenched with 2% aqueous lithium chloride and the mixture was extracted with ethyl acetate. The ethyl acetate extract was concentrated in vacuo. The residue was purified by silica gel column chromatography to provide the desired product (310 mg, 83%) contaminated with the unreacted starting materials, which was further purified by RP HPLC using a Phenomenex Synergi 5μ Hydro RP 80A column (50×21.2 mm) with eluents of $H_2O$—$CH_3CN$. The fractions containing the desired product were pooled and concentrated to dryness (62 mg, 49%). MS (m/z) 1431.0 [M+H]$^+$, 1428.7 [M–H]$^-$; $^{31}$P (121.4 MHz, CDCl$_3$) δ 19.5.

The intermediate compound cyclo-[[(2S, 3R, 4R, 6E)-7-(4-hydroyphenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl] was prepared as follows.

a. cyclo-[[(2S, 3R, 4R, 6E)-7-(4-Acetoxyphenyl)-4-methyl-3-hydroxy-2-(methylamino)-6-heptenoyl]-L-2-aminobutyryi-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl]

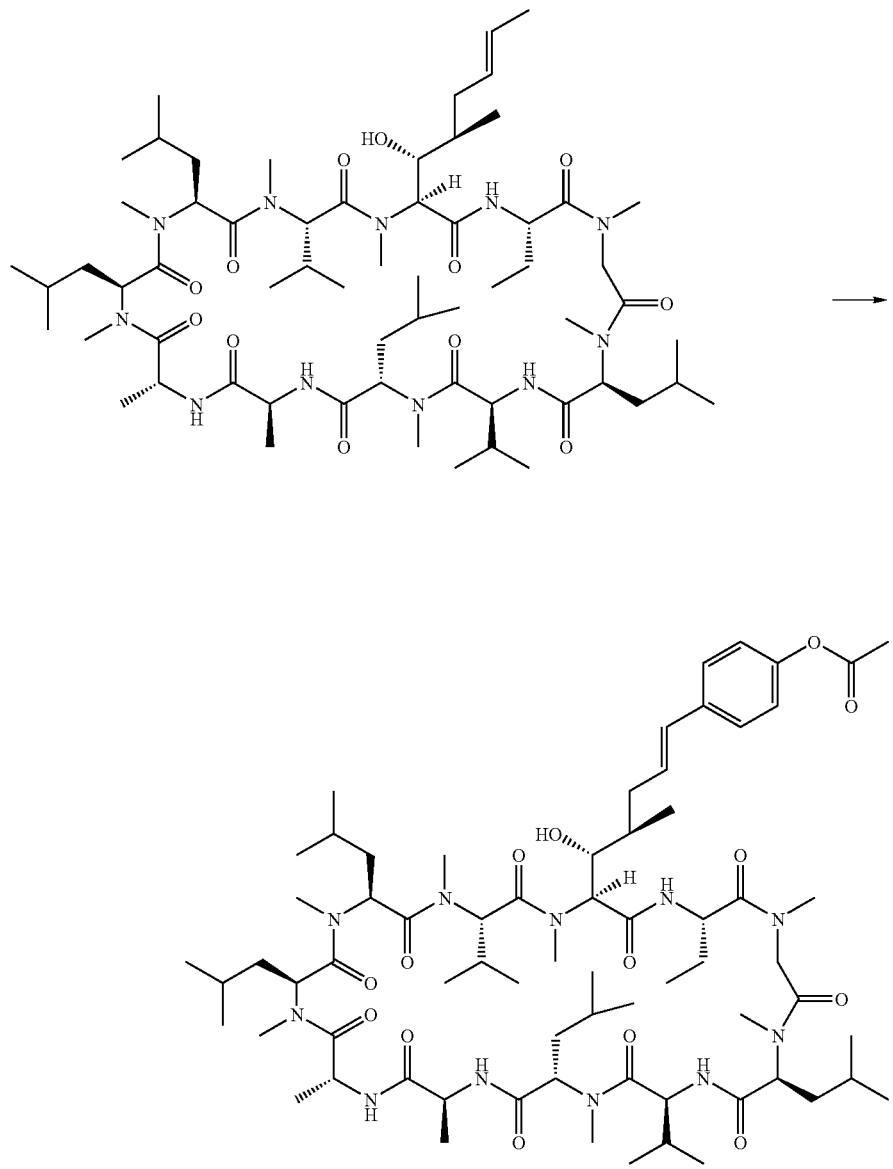

A mixture of cyclosporin A (360 mg, 0.3 mmol), 4-acetoxystyrene (730 mg, 4.5 mmol) and (1,3-bis-(2,4,6-trimethylphenyl)-2-imidazolidene)dichloro(O-isopropoxyphenylmethylene)ruthenium (Hoveyda-Grubbs catalyst, 20 mg, 0.032 mmol) in dichloromethane (1 mL) was purged with nitrogen and stirred under reflux for 16 hours. After cooling, the reaction mixture was purified by silica gel column chromatography using MeOH—$CH_2Cl_2$ to provide the product as a solid (395 mg, 99%). MS (m/z) 1322.9 [M+H]$^+$, 1344.9 [M+Na]$^+$; HPLC retention time 3.3 min. (relative to 4.1 min. of cyclosporin A; Phenominex Synergi 4 micron hydro-RP 80A 50×4.6 mm; solvents, 35% water and 65% acetonitrile; flow rate 2 mL/min.; column temperature 60° C.).

b. cyclo-[[(2S, 3R, 4R, 6E)-7-(4-Hydroxyphenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl]

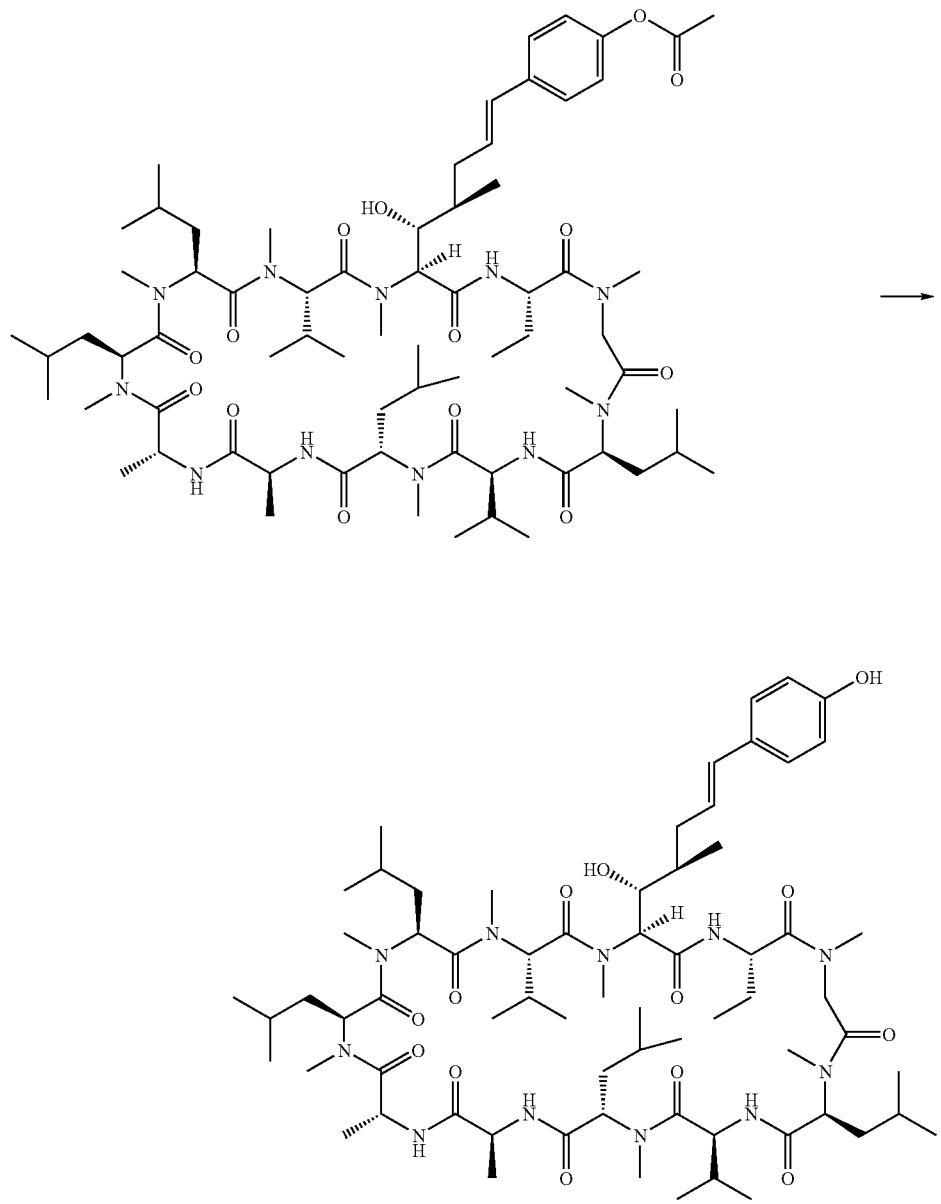

A solution of cyclo-[[(2S, 3R, 4R, 6E)-7-(4-acetoxyphenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl] (385 mg, 0.29 mmol) and triethylamine (1 mL) in MeOH (10 mL) was stirred at ambient temperature for 16 hours. The reaction mixture was concentrated in vacuo and the residue was purified by silica gel column chromatography using MeOH—CH$_2$Cl$_2$ to provide the desired product (310 mg, 83%). MS (m/z) 1280.9 [M+H]$^+$, 1278.8 [M−H]$^−$; HPLC retention time 1.6 min. (relative to 4.0 min. of cyclosporin A; Phenominex Synergi 4 micron hydro-RP 80A 50×4.6 mm; solvents, 35% water and 65% acetonitrile; flow rate 2 mL/min.; column temperature 60° C.).

EXAMPLE 322

Synthesis of cyclo-[[(2S, 3R, 4R, 6E)-7-(4-(dibenzyloxy-phosphorylmethoxy)phenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl]

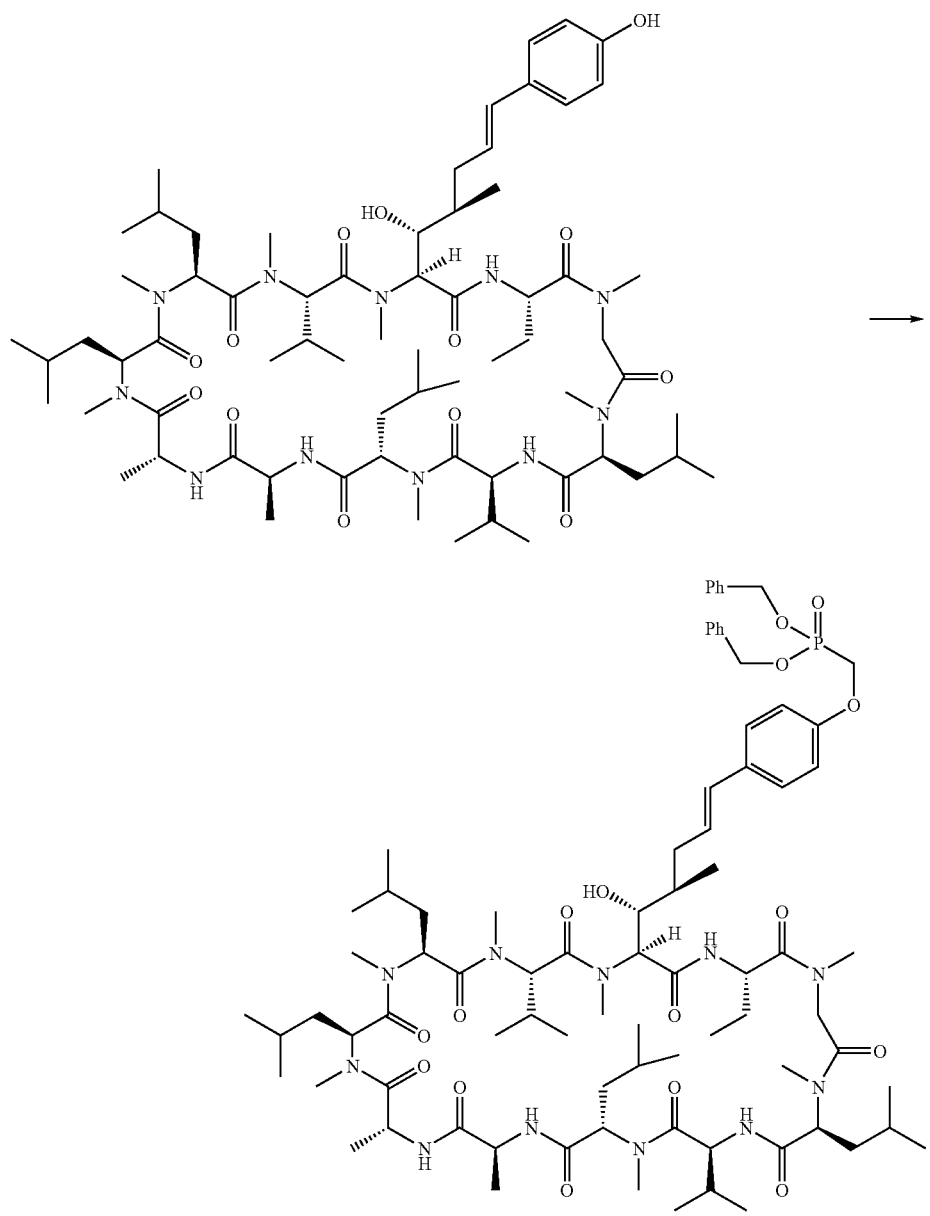

To a mixture of cyclo-[[(2S, 3R, 4R, 6E)-7-(4-hydroyphenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl] (300 mg, 0.234 mmol) and cesium carbonate (326 mg, 1 mmol) in DMF (2 mL) was added trifluoromethanesulfonic acid dibenzyloxy-phosphorylmethyl ester (60 mg, 0.2 mmol). The mixture was stirred at room temperature for 16 hours. The reaction mixture was filtered through Acrodisc (13 mm syringe filter with 0.45 micron Nylon membrane) and purified by RP HPLC using a Phenomenex Synergi 5μ Hydro RP 80A column (50×21.2 mm) with eluents of $H_2O$—$CH_3CN$. The fractions containing the desired product were pooled and concentrated to dryness, affording a white solid (115 mg, 32%). MS (m/z) 1554.9 [M+H]$^+$, 1552.7 [M−H]$^-$; $^{31}$P (121.4 MHz, CDCl$_3$) δ 20.5.

EXAMPLE 323

Synthesis of cyclo-[[(2S, 3R, 4R, 6E)-7-(4-(dihydroxy-phosphorylmethoxy)phenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl]

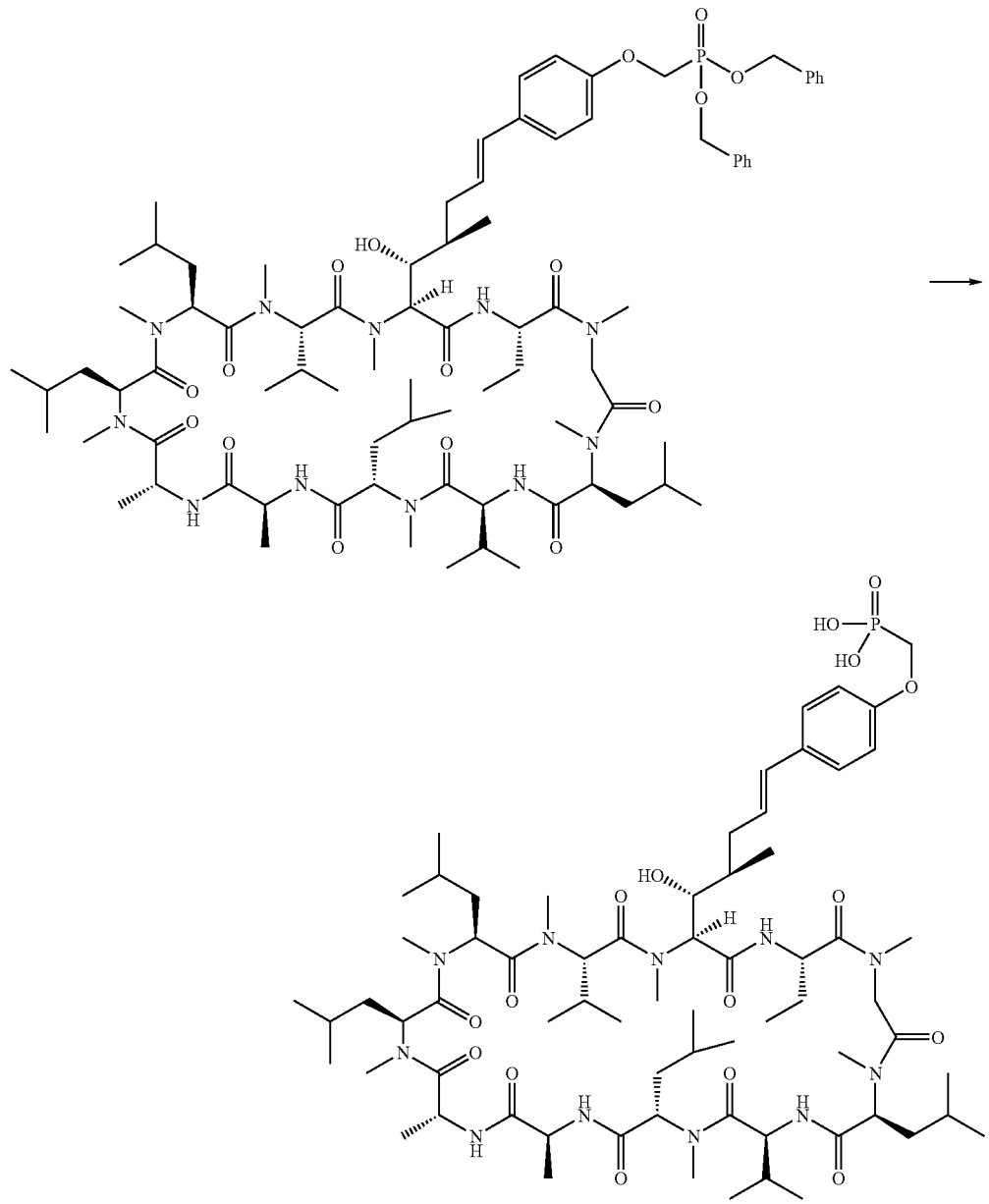

To a mixture of cyclo-[[(2S, 3R, 4R, 6E)-7-(4-(dibenzyloxyphosphoryl-methoxy)phenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl] (115 mg, 0.074 mmol) and 2,6-lutidine (40 μL, 0.35 mmol) in dichloromethane (2 mL) was added trimethylsilyl bromide (50 μL, 0.35 mmol). The mixture was stirred at room temperature for 2 hours. The reaction was quenched with methanol (1 mL) and the mixture was concentrated. The residue was treated with a solution of ammonium fluoride (0.5 M, 2 mL), stirred for 1 hour, concentrated, and partitioned between dichloromethane and 1 N HCl. The dichloromethane layer was concentrated and the crude product was purified by RP HPLC using a Phenomenex Synergi 5μ Hydro RP 80A column (50×21.2 mm) with eluents of 0.1% TFA $H_2O$-0.1% TFA $CH_3CN$. The fractions containing the desired product were pooled and concentrated to dryness, affording a hygroscopic solid (68 mg, 63%). MS (m/z) 1374.9 [M+H]$^+$, 1373.1 [M−H]$^-$; HPLC retention time 0.3 min. (relative to 4.0 min. of cyclosporin A; Phenominex Synergi 4 micron hydro-RP 80A 50×4.6 mm; solvents, 35% water and 65% acetonitrile; flow rate 2 mL/min.; column temperature 60° C.).

EXAMPLE 324

Synthesis of cyclo-[[(2S, 3R, 4R, 6E)-7-(4-(1-(S)-ethoxycarbonylethoxy)phenoxyphosphoryl-methoxy)phenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl]

A mixture of cyclo-[[(2S, 3R, 4R, 6E)-7-(4-(dihydroxy-phosphorylmethoxy)-phenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl] (34 mg, 0.023 mmol), phenol (22 mg, 0.23 mmol), dicyclohexylcarbodiimide (47 mg, 0.23 mmol) and 4-(N,N-dimethylamino)pyridine (5.6 mg, 0.046 mmol) in DMF (2 mL) was stirred at 140° C. for 20 min. After cooling, the monophenyl monophosphonic acid product was purified by RP HPLC using a Phenomenex Synergi 5μ Hydro RP 80A column (50×21.2 mm) with eluents of 0.1% TFA H$_2$O-0.1% TFA CH$_3$CN. MS (m/z) 1450.9 [M+H]$^+$, 1449.1 [M−H]$^−$; $^{31}$P (121.4 MHz, CDCl$_3$) δ 14.9. This intermediate was mixed with ethyl (S)-(−)-lactate (40 mg, 0.34 mmol), PyBOP (80 mg, 0.15 mmol), diisopropylethylamine (45 μL, 0.26 mmol) and DMF (1.7 mL). The resulting mixture was stirred at room temperature for 2 hours. After removal of insoluble impurities, the crude product was purified by RP HPLC using a Phenomenex Synergi 5μ Hydro RP 80A column (50×21.2 mm) with eluents of 0.1% TFA H$_2$O-0.1% TFA CH$_3$CN. The desired fractions were pooled and partitioned between aceto-

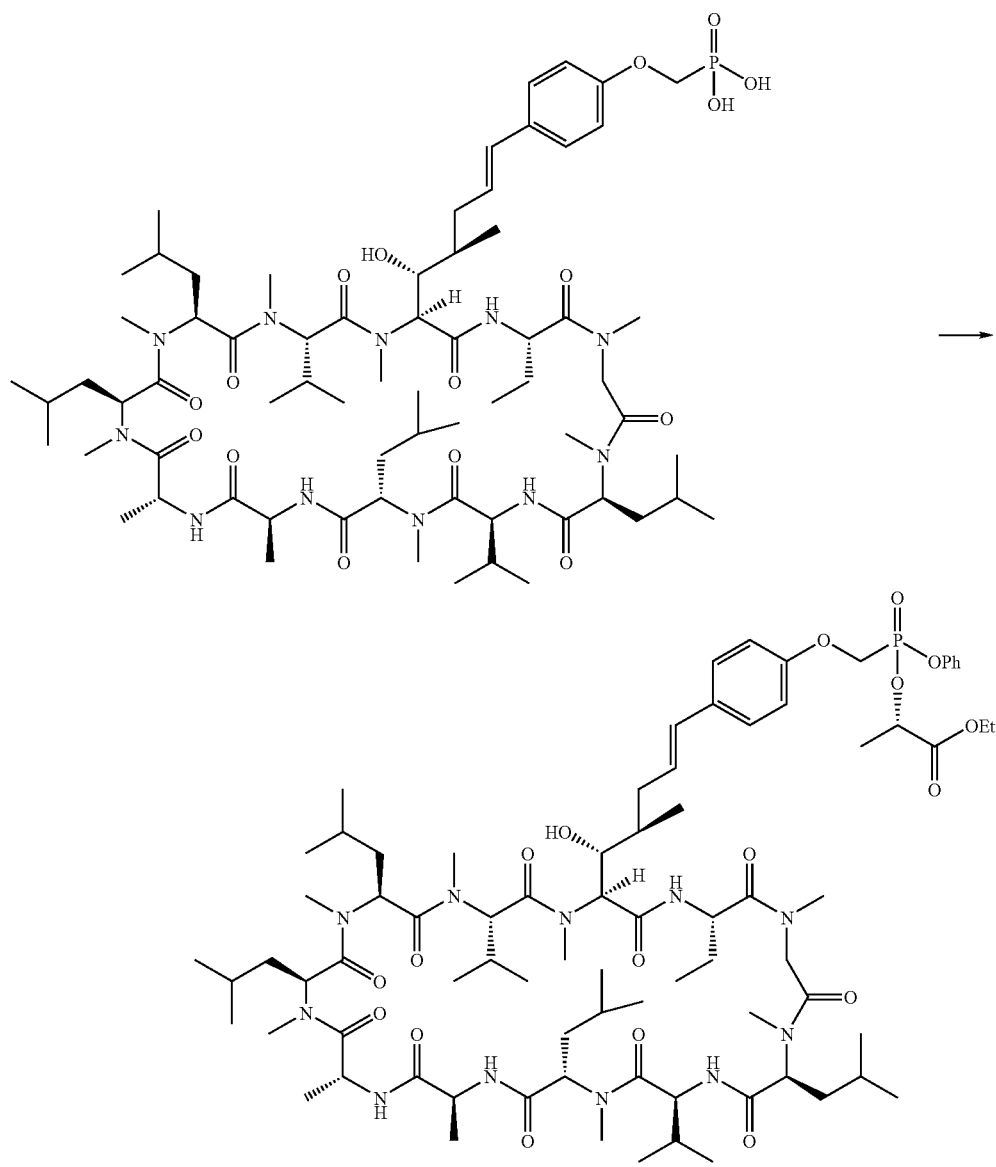

nitrile and saturated aqueous sodium bicarbonate. The organic layer was concentrated to afford the product as a solid (12 mg, 34%). MS (m/z) 1573.1 [M+Na]+, 1548.8 [M−H]−; $^{31}$P (121.4 MHz, CDCl$_3$) δ 15.3 and 17.4.

EXAMPLE 325

Synthesis of cyclo-[[(2S, 3R, 4R, 6E)-7-(4-(1-(S)-hydroxycarbonylethoxy)hydoxyphosphorylmethoxy)phenyl)-4-methyl-3-hydroxy-2-(methylamino)-6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl]

nyl)-4-methyl-3-hydroxy-2-(methylamino)-(6-heptenoyl]-L-2-aminobutyryl-sarcosyl-N-methyl-L-leucyl-L-valyl-N-methyl-L-leucyl-L-alanyl-D-alanyl-N-methyl-L-leucyl-N-methyl-L-leucyl-N-methyl-L-valyl](5 mg, 3.2 μmol) in a mixed solvent of water and acetonitrile (0.5 mL and 4.5 mL) was added 1 N NaOH (40 μL). The solutions was stirred at room temperature for 2 hours. The resulting reaction mixture was concentrated and purified by RP HPLC using a Phenomenex Synergi 5μ Hydro RP 80A column (50×21.2 mm) with eluents of 0.1% TFA R$_2$O-0.1% TFA CH$_3$CN. The desired fraction was concentrated to dryness affording the product as a solid (1.5 mg, 32%). MS (m/z) 1446.9 [M+H]+, 1444.9 [M−H]−; HPLC retention time 0.2 min. (relative to 4.0 min. of cyclosporin A; Phenominex Synergi 4 micron hydro-RP 80A

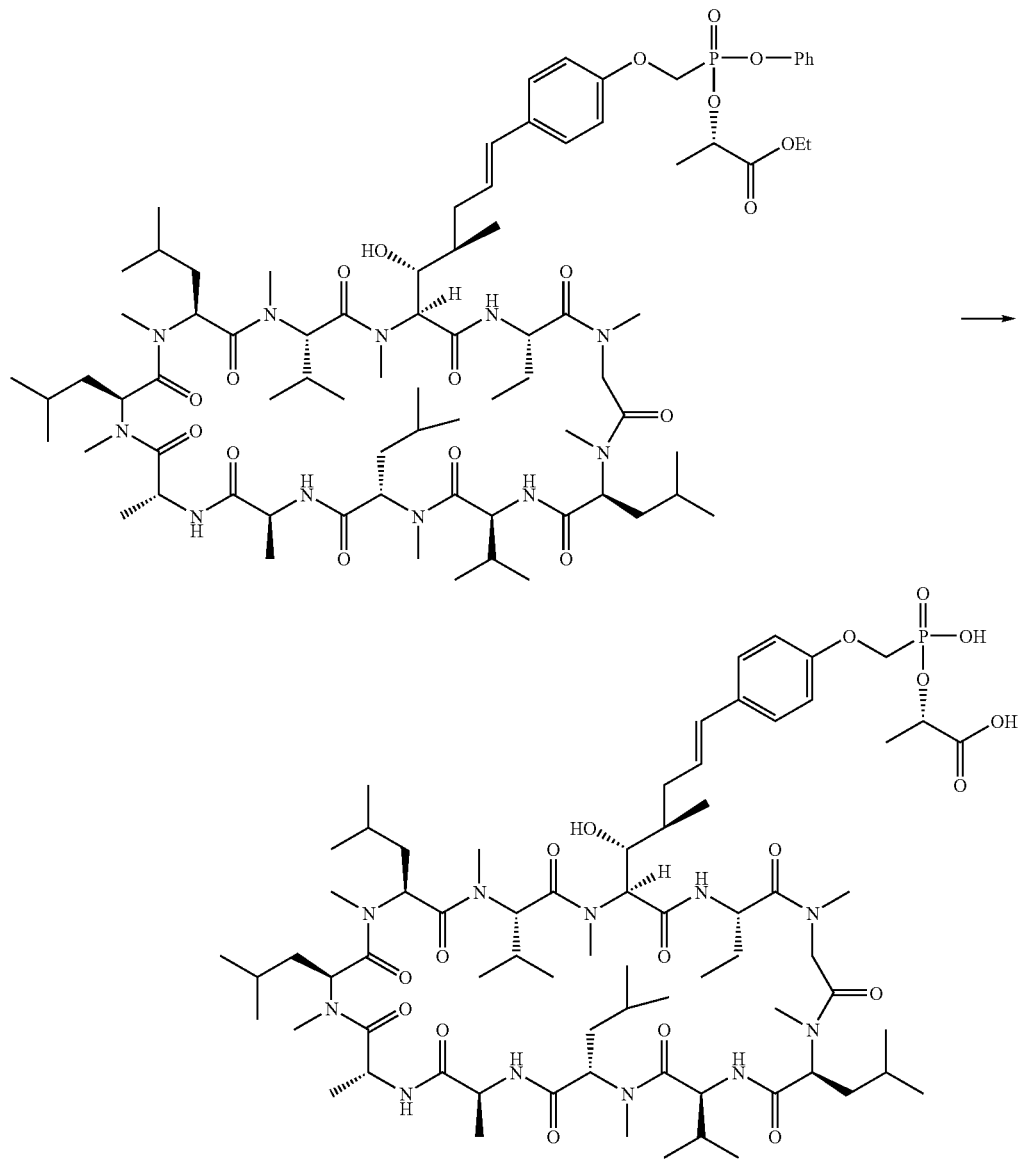

To a solution of cyclo-[[(2S, 3R, 4R, 6E)-7-(4-(1-(S)-ethoxycarbonyl-ethoxy)phenoxyphosphorylmethoxy)phe- 50×4.6 mm; solvents, 35% water and 65% acetonitrile; flow rate 2 mL/min.; column temperature 60° C.).

EXAMPLE 326

Synthesis of Representative compounds of the Invention

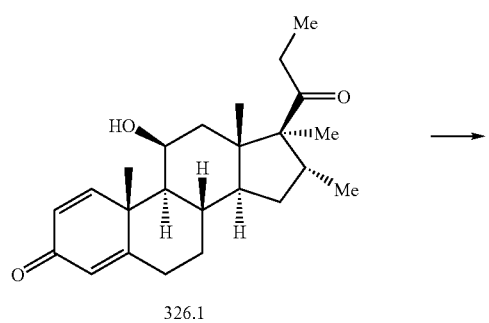

326.1

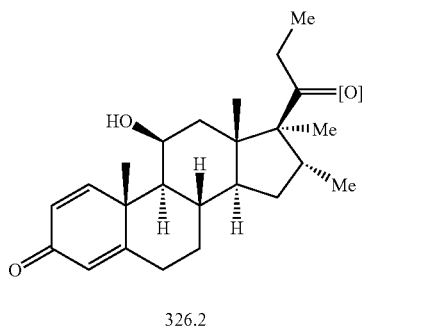

326.2

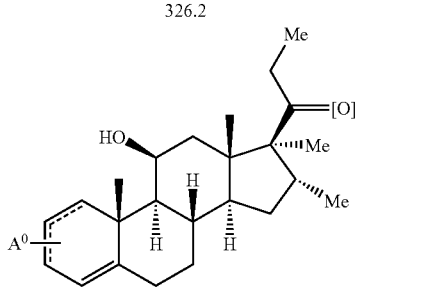

326.3

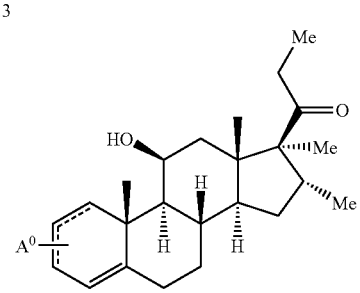

326.4

A protection-deprotection sequence in which the 20-ketone group of Rimexolone is protected to afford the derivative 326.2 is illustrated above. The ketone is protected, for example, by conversion to the cyclic ethylene ketal, by reaction in toluene solution at reflux temperature with ethylene glycol and an acid catalyst, as described in *J. Am. Chem. Soc.*, 77:1904(1955). Deprotection is effected by reaction with pyridinium tosylate in aqueous acetone, as described in *J. Chem. Soc., Chem. Comm.*, 1351 (1987).

Alternatively, the 20-ketone is protected by conversion to the N,N-dimethylhydrazone. The dimethyl hydrazone is prepared by the reaction of the ketone 326.1 with N,N-dimethylhydrazine in ethanol-acetic acid, as described in *Org. Syn.*, 50:102(1970). The group is removed by treatment with sodium acetate and acetic acid in aqueous tetrahydrofuran, as described in *J. Am. Chem. Soc.*, 101, 5841(1979).

Alternatively, the 20-ketone is protected as the diethylamine adduct. In this procedure, the substrate 326.1 is reacted with titanium tetrakis(diethylamide), as described in *J. Chem. Soc., Chem. Comm.*, 406 (1983), to afford the adduct. The ketone is deprotected by reaction with water in an aqueous organic solvent.

The protected compound 326.2 is then converted into the phosphonate-containing analog 326.3, using the procedures described below, and the protecting group or groups are then removed, as described above, to give the phosphonate 326.4.

EXAMPLE 327

Synthesis of Representative compounds of the Invention

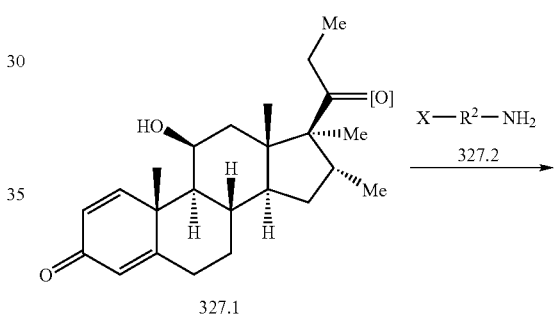

327.1

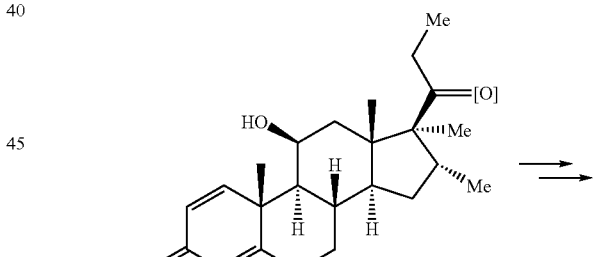

327.3

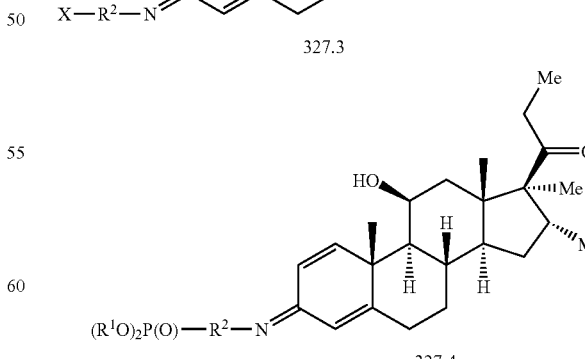

327.4

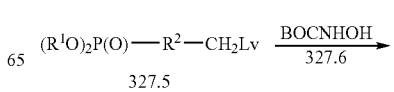

327.5

-continued (R¹O)₂P(O)—R²—CH₂ONHBOC
327.7

↓

(R¹O)₂P(O)—R²—CH₂ONH
327.8

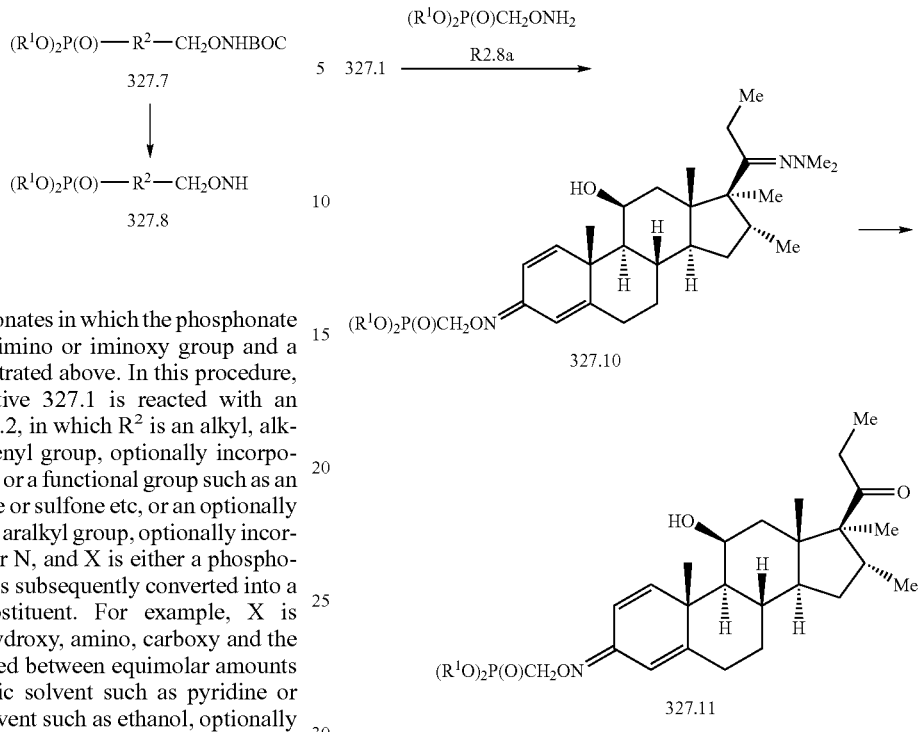

The preparation of phosphonates in which the phosphonate is attached by means of an imino or iminoxy group and a variable carbon chain is illustrated above. In this procedure, the ketone-protected derivative 327.1 is reacted with an amine or hydroxylamine 327.2, in which R² is an alkyl, alkenyl, cycloalkyl or cycloalkenyl group, optionally incorporating a heteroatom O, S or N, or a functional group such as an amide, ester, oxime, sulfoxide or sulfone etc, or an optionally substituted aryl, heteroaryl or aralkyl group, optionally incorporating a heteroatom O, S or N, and X is either a phosphonate group or a group which is subsequently converted into a phosphonate-containing substituent. For example, X is dialkylphosphono, bromo, hydroxy, amino, carboxy and the like. The reaction is conducted between equimolar amounts of the reactants in an aprotic solvent such as pyridine or xylene, or in an alcoholic solvent such as ethanol, optionally in the presence of an acid catalyst, to give the imine or oxime 327.3. The preparation of oximes of steroidal 3-ketones is described in *Anal. Bioch.*, 86:133(1978). and in *J. Mass. Spectrom.*, 30:497(1995). The protecting group is then removed to afford the 20-keto phosphonate product 327.4.

The preparation of hydroxylamine ethers incorporating a phosphonate group is also illustrated above. In this procedure, a phosphonate 327.5, in which Lv is a leaving group such as bromo or trifluoromethylsulfonyloxy, is reacted with BOC-hydroxylamine 327.6 (Aldrich) to produce the ether 327.7. The reaction is conducted between equimolar amounts of the reactants in a polar solvent such as dimethylformamide or tetrahydrofuran, in the presence of a base such as potassium hydroxide or dimethylaminopyridine. Deprotection, for example by treatment with trifluoroacetic acid, then gives the hydroxylamine ether 327.8. The above procedure is also employed for the preparation of substituted hydroxylamines which are precursors to phosphonates.

The preparation of phosphonates in which the phosphonate is attached by means of an iminoxy group is illustrated above. In this procedure, the substrate 327.1, in which the 20-ketone is protected as the dimethyl hydrazone derivative, is reacted with a dialkyl phosphonomethyl hydroxylamine 327.8a, prepared as described above from a dialkyl trifluoromethylsulfonyloxymethyl phosphonate (Tet. Lett., 1986, 27, 1477) and BOC-hydroxylamine, to afford the oxime 327.10. Deprotection affords the 20-keto phosphonate 327.11. The oxime forming reaction is typically performed at ambient temperature in ethanol-acetic acid solution between equimolar amounts of the reactants.

Using the above procedures, but employing, in place of the hydroxylamine ether 327.8a, different oxime ethers 327.2, the corresponding products 327.4 are obtained.

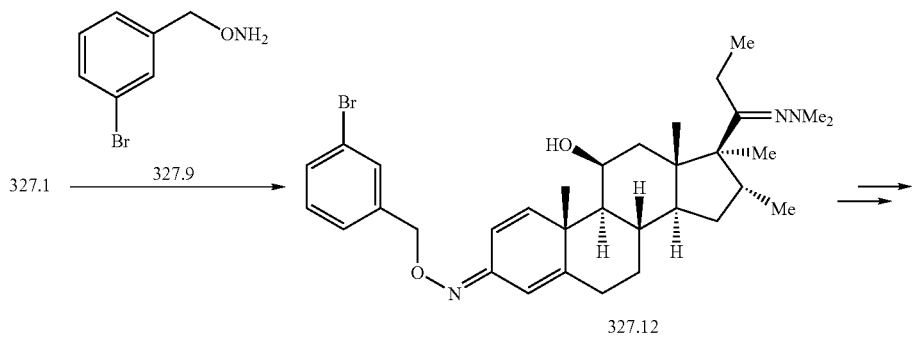

-continued

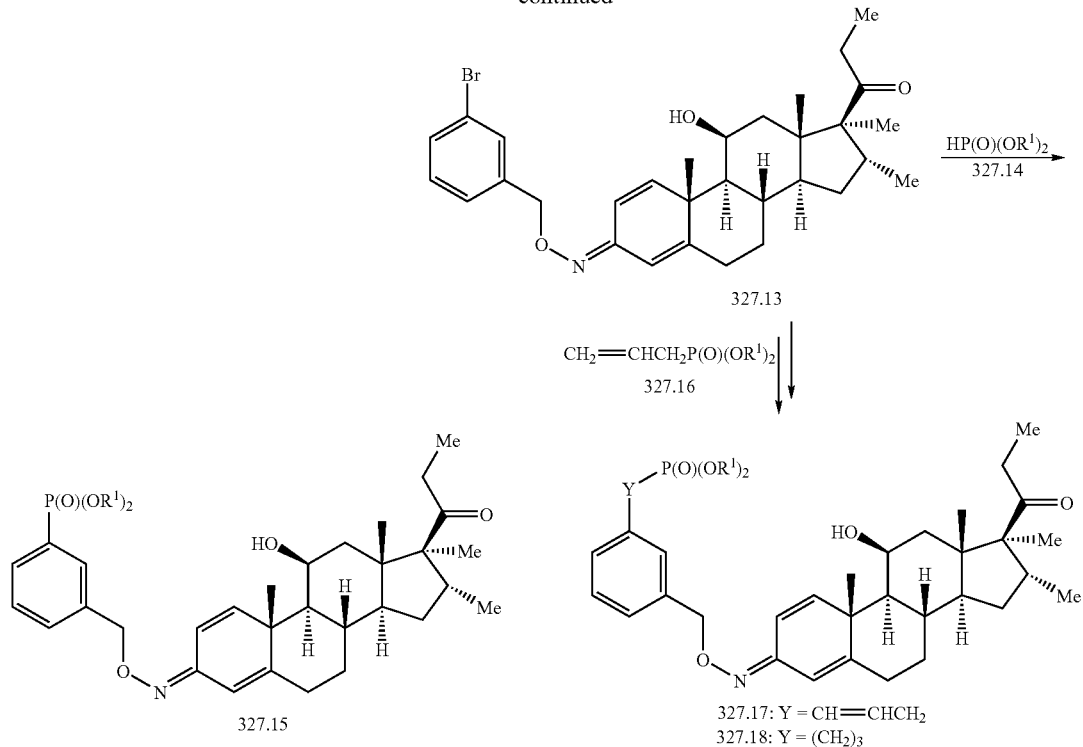

The preparation of compounds in which the phosphonate group is attached by means of a benzyloxy oxime group is illustrated above. In this procedure, the dienone 327.1, in which the 20-ketone is protected as the dimethyl hydrazone, is reacted, as described above, with O-(3-bromobenzyl)hydroxylamine 327.9, prepared as described above from 3-bromobenzyl bromide and BOC-protected hydroxylamine 327.6, to give the oxime 327.12. The protecting group is then removed to yield the 20-keto product 327.13. The latter product is then reacted, in the presence of a palladium catalyst, with a dialkyl phosphite 327.14 to afford the phosphonate 327.15. The preparation of arylphosphonates by means of a coupling reaction between aryl bromides and dialkyl phosphites is described in *J. Med. Chem.*, 35:1371(1992). The reaction is performed at ca. 100° C. in an inert solvent such as toluene, in the presence of a base such as triethylamine and a catalytic amount of tetrakis(triphenylphosphine)palladium (0).

Alternatively, the bromo compound 327.13 is coupled with a dialkyl propenylphosphonate 327.16 (Aldrich) to afford the phosphonate 327.17. The coupling of aryl halides with olefins by means of the Heck reaction is described, for example, in F. A. Carey and R. J. Sundberg, Advanced Organic Chemistry, 503ff (Plenum, 2001) and in *Acc. Chem. Res.*, 12:146(1979). The aryl bromide and the olefin are coupled in a polar solvent such as dimethylformamide or dioxan, in the presence of a palladium(0) catalyst such as tetrakis(triphenylphosphine)-palladium(0) or palladium(II) catalyst such as palladium(II) acetate, and optionally in the presence of a base such as triethylamine or potassium carbonate. Optionally, the styrenoid double bond present in the product 327.17 is reduced, for example by reaction with diimide, to produce the saturated analog 327.18. The reduction of olefinic bonds is described in R. C. Larock, Comprehensive Organic Transformations, 6ff (VCH, 1989). The transformation is effected by means of catalytic hydrogenation, for example using a palladium on carbon catalyst and hydrogen or a hydrogen donor, or by the use of diimide or diborane.

Using the above procedures, but employing, in place of the bromobenzyl reagent 327.9, different bromo-substituted aryl or heteroaryl alkoxy hydroxylamines, and/or different dialkyl alkenyl phosphonates, the products analogous to the compounds 327.15, 327.17 and 327.18 are obtained.

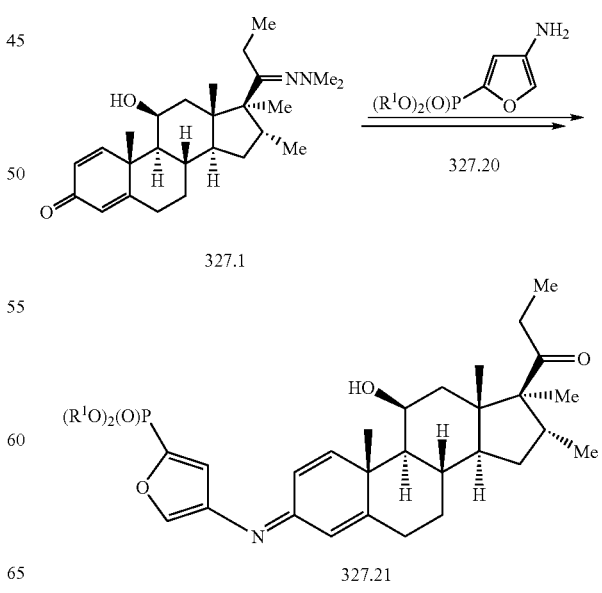

The preparation of phosphonates in which the phosphonate is attached by means of a 4-furylimino group is illustrated above. In this procedure, the substrate 327.1, in which the 20-ketone is protected as the dimethylhydrazone, is reacted with a dialkyl 4-amino-2-furyl phosphonate 327.20, prepared by the palladium catalyzed coupling reaction, as described above, between 4-amino-2-bromofuran (*Tet.*, 43:3295(1987)) and a dialkyl phosphite, to give, after deprotection, the imine product 327.21. The imine forming reaction is conducted in a hydrocarbon solvent such as toluene or xylene, at reflux temperature, in the presence of a basic catalyst such as sodium methoxide, or an acid catalyst such as p-toluenesulfonic acid, under azeotropic conditions.

Using the above procedures, but employing, in place of the 4-aminofuryl phosphonate 327.20 different amino-substituted aryl or heteroaryl phosphonates, products analogous to 327.21 are obtained.

7:795(1976); the reaction is performed between equimolar amounts of the reactants in a polar organic solvent such as pyridine or methanol, optionally in the presence of acetic acid or sodium acetate. The product 327.23 is then coupled with a dialkyl 4-aminophenyl phosphonate 327.24 (Epsilon) and dicyclohexyl carbodiimide, to yield, after deprotection, the amide oxime 327.25. The preparation of amides from carboxylic acids and derivatives is described, for example, in S. R. Sandler and W. Karo, Organic Functional Group Preparations, 274(Academic Press, 1968), and R. C. Larock, Comprehensive Organic Transformations, 972ff (VCH, 1989). The carboxylic acid is reacted with the amine in the presence of an activating agent, such as, for example, dicyclohexylcarbodiimide or diisopropylcarbodiimide, optionally in the presence of, for example, hydroxybenztriazole, N-hydroxysuccinimide or N-hydroxypyridone, in a non-protic solvent such as, for example, pyridine, DMF or dichloromethane, to afford the amide.

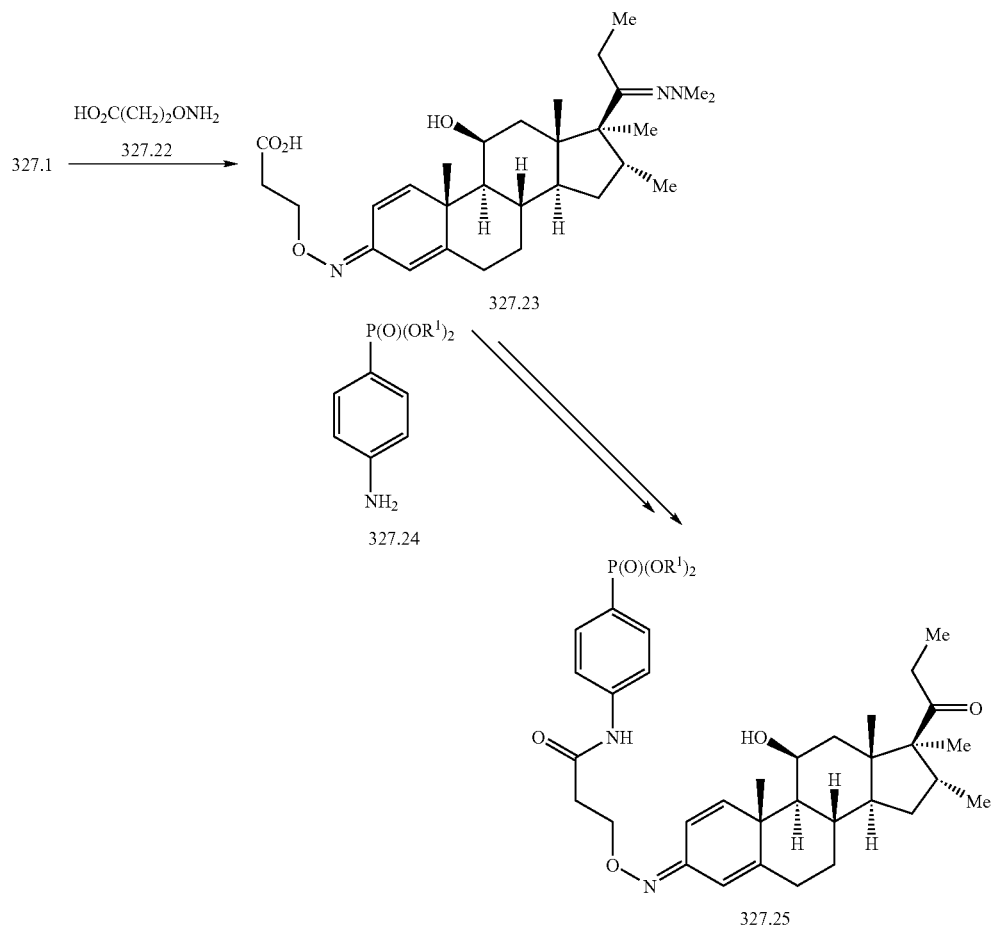

The preparation of phosphonates in which the phosphonate is attached by means of an oximino group and an amide linkage is illustrated above. In this procedure, the dienone 327.1, in which the 20-ketone is protected as the dimethylhydrazone, is reacted with 2-carboxyethyl hydroxylamine 327.22 (*J. Med. Chem.*, 33:1423(1990)) to yield the oxime 327.23. The reaction of steroidal 1,4-dien-3-ones with hydroxylamines is described in *J. Steroid Bioch.*, Alternatively, the carboxylic acid may first be converted into an activated derivative such as the acid chloride, anhydride, mixed anhydride, imidazolide and the like, and then reacted with the amine, in the presence of an organic base such as, for example, pyridine, to afford the amide.

The conversion of a carboxylic acid into the corresponding acid chloride can be effected by treatment of the carboxylic acid with a reagent such as, for example, thionyl chloride or oxalyl chloride in an inert organic solvent such as dichloromethane, optionally in the presence of a catalytic amount of dimethylformamide.

Using the above procedures, but employing, in place of the carboxy-substituted hydroxylamine 327.22, different carboxy-substituted hydroxylamines, and/or different amino-substituted phosphonates, the products analogous to 327.25 are obtained.

EXAMPLE 328

Synthesis of Representative Compounds of the Invention phine)rhodium(I) chloride, for example as described in *J. Med. Chem.*, 44:602(2001). The product is then reacted with ethyl formate and a base such as sodium hydride, in an inert solvent such as toluene or dimethylformamide, as described in *J. Am. Chem. Soc.*, 86:1520(1964), to afford the 2-formyl product 328.2. This compound is then reacted with an alkyl, aralkyl, aryl or heteroaryl hydrazine 328.3, in which the substituent X is either a phosphonate group or a group which is subsequently transformed into a phosphonate-containing substituent. For example, X is dialkylphosphono, bromo, hydroxy, amino, carboxyl and the like. The reaction yields the isomeric 2'- and 1'-aryl pyrazoles 328.4 and 328.5. The pyra-

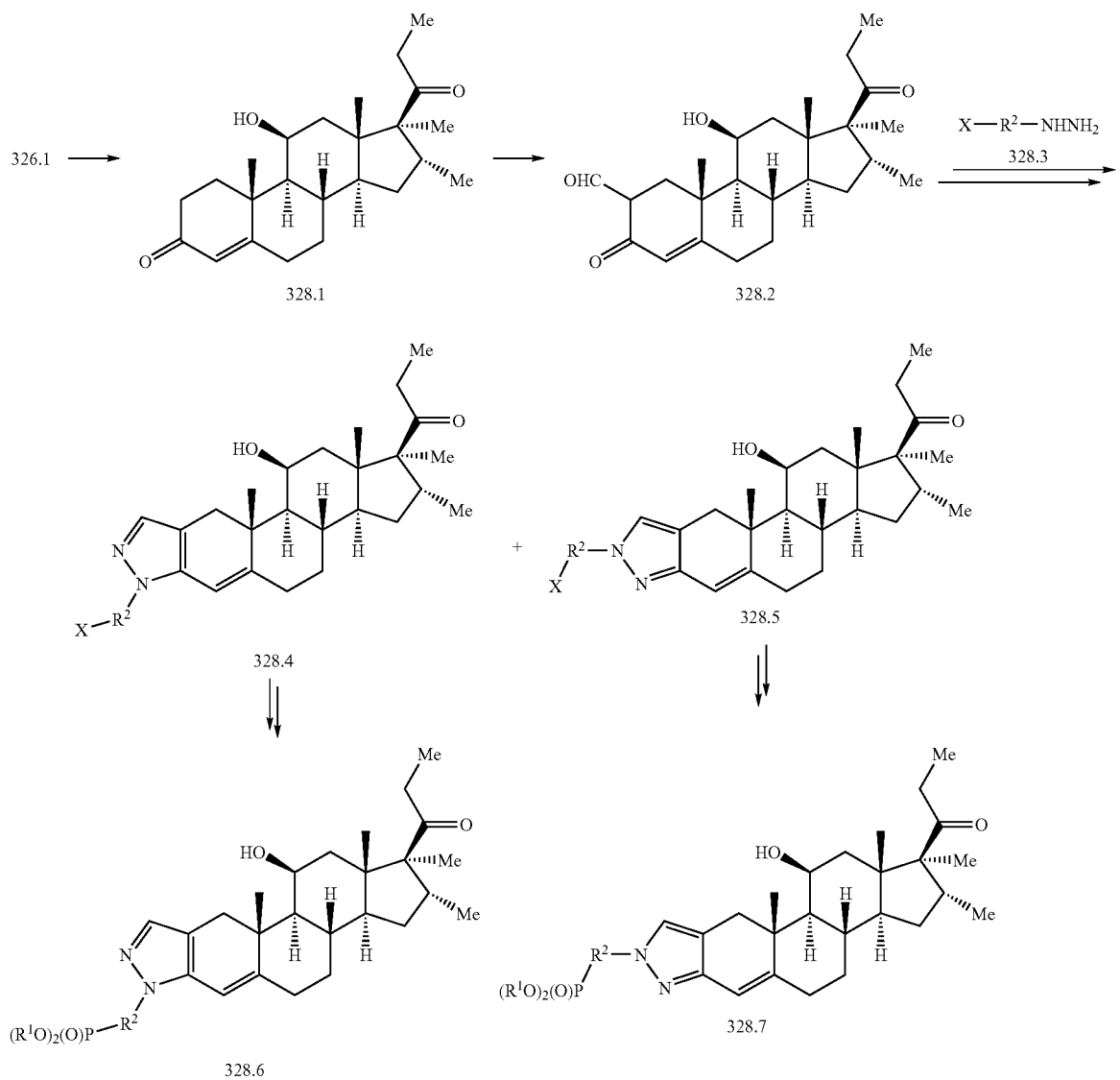

The preparation of the phosphonate esters in which the phosphonate group is attached to the 1' or 2' position of the pyrazole ring, by means of an aromatic or heteroaromatic group, a heteroatom and/or a variable carbon chain is illustrated above. In this procedure, the dienone 326.1 is reduced to afford the 1,2-dihydro product 328.1. The catalytic hydrogenation reaction is effected by the use of tris(triphenylphoszole-forming reaction is performed between equimolar amounts of the reactants in an acidic solvent such as acetic acid, as described in *J. Am. Chem. Soc.*, 86:1520(1964). The pyrazoles 328.4 and 328.5 are then transformed into the phosphonates 328.6 and 328.7. Optionally, the reduction and formylation reactions are performed on the substrate 326.2 in which the 20-ketone is protected as the cyclic ethylene ketal.

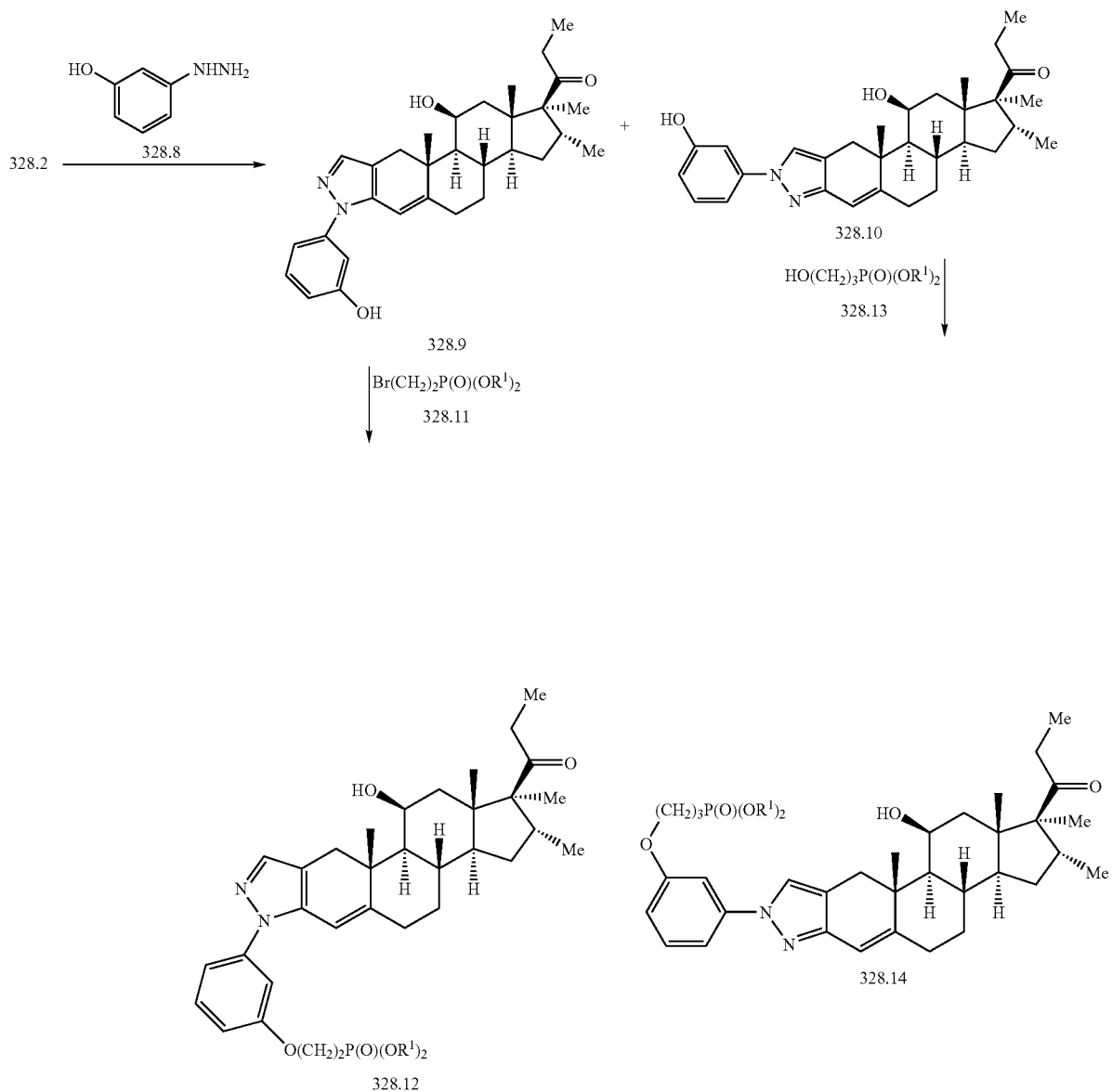

The preparation of phosphonates in which the phosphonate is attached by means of a phenyl ring and an alkoxy group is illustrated above. In this procedure, the ketoaldehyde 328.2 is reacted, as described above, with 3-hydroxyphenyl hydrazine 328.8 (JP 03011081) to give the pyrazoles 328.9 and 328.10. The 2'-substituted isomer 328.9 is then reacted in dimethylformamide solution at 70° with one molar equivalent of a dialkyl 2-bromoethyl phosphonate 328.11 (Aldrich) and potassium carbonate, to give the ethoxy phosphonate 328.12.

The isomeric pyrazole 328.10 is reacted in a Mitsonobu with one molar equivalent of a dialkyl 3-hydroxypropyl phosphonate 328.13 (*Zh. Obschei. Khim.*, 44:1834(1974)) to yield the phosphonate 328.14. The preparation of aromatic ethers by means of the Mitsonobu reaction is described, for example, in R. C. Larock, Comprehensive Organic Transformations, 448 (VCH, 1989), and in F. A. Carey and R. J. Sundberg, Advanced Organic Chemistry, Part B, 153-4(Plenum, 2001) and in *Org. React.*, 42:335(1992). The phenol and the alcohol or thiol component are reacted together in an aprotic solvent such as, for example, tetrahydrofuran, in the presence of a dialkyl azodicarboxylate and a triarylphosphine, to afford the ether or thioether products. The procedure is also described in *Org. React.*, 42:335-656(1992).

Using the above procedures, but employing different hydroxy-substituted hydrazines, and/or different bromo or hydroxy-substituted phosphonates, the products analogous to 328.12 and 328.14 are obtained.

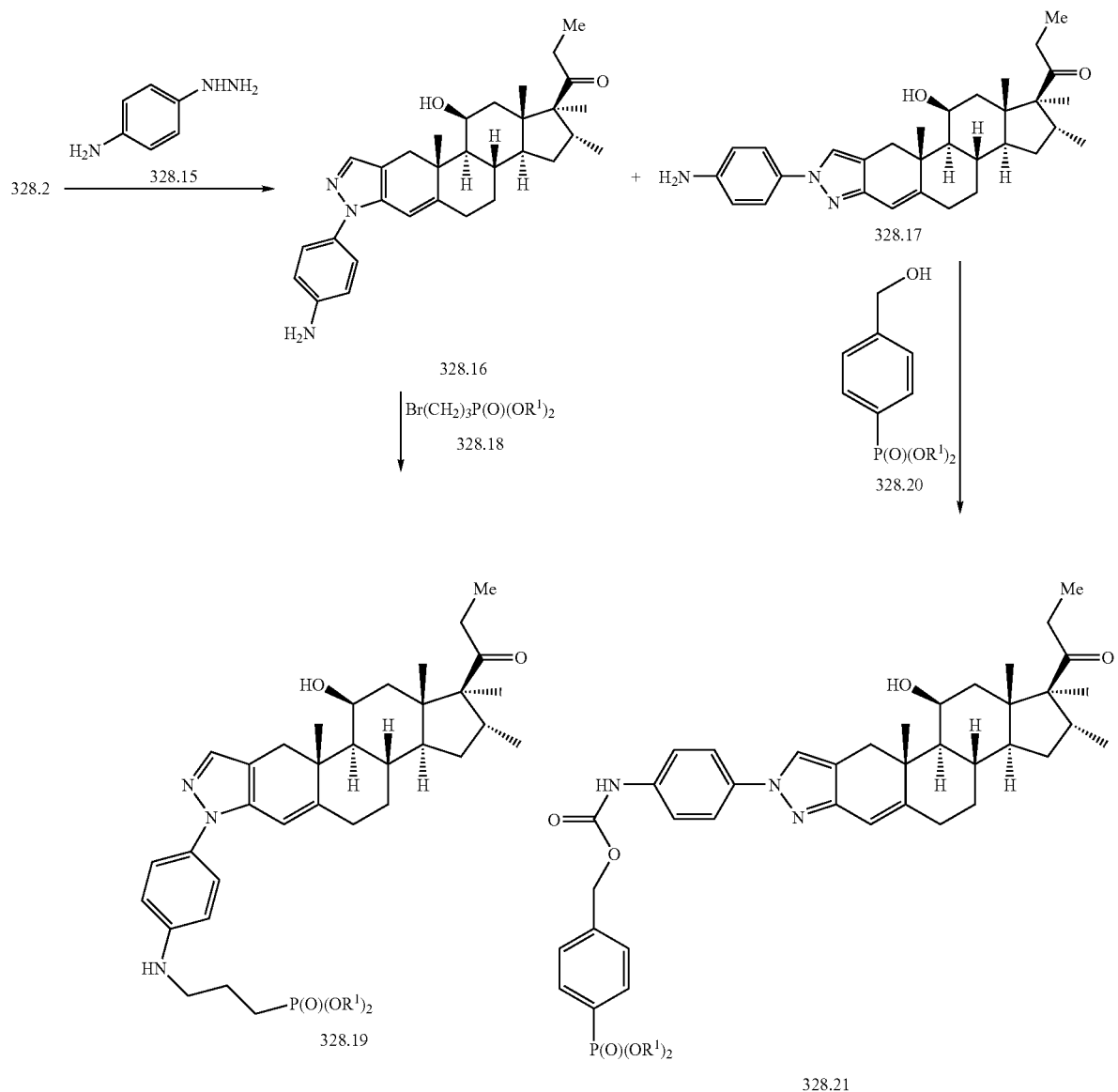

The preparation of the phosphonates in which the phosphonate group is attached by means of an amino or a carbamate group and an aromatic ring is illustrated above. In this procedure, the ketoaldehyde 328.2 is reacted, as described above, with 4-aminophenyl hydrazine 328.15 (Syn. Comm., 4:57(1974)) to produce the pyrazoles 328.16 and 328.17. The 2'-substituted isomer 328.16 is then reacted in dimethylformamide solution at 700 with one molar equivalent of a dialkyl 3-bromopropyl phosphonate 328.18 (J. Amer. Chem. Soc., 122:1554(2000)) and cesium carbonate, to give the amine phosphonate 328.19.

Alternatively, the 1'-substituted pyrazole 328.22 is coupled with a dialkyl 4-hydroxymethylphenyl phosphonate 328.20 (U.S. Pat. No. 5,569,664) and carbonyl diimidazole to prepare the carbamate phosphonate 328.21. The preparation of carbamates is described in Comprehensive Organic Functional Group Transformations, A. R. Katritzky, ed., Pergamon, 1995, Vol. 6, p 416ff, and in Organic Functional Group Preparations, by S. R. Sandler and W. Karo, Academic Press, 1986, p. 260ff. In the procedure, the amine is reacted in an inert aprotic solvent such as dichloromethane or tetrahydrofuran, with phosgene or a functional equivalent thereof, such as carbonyl diimidazole, triphosgene, pentafluorophenyl carbonate and the like, to afford the corresponding activated acylamine. The latter compound is then reacted with an alcohol to yield the carbamate. Using the above procedures, but employing, in place of the aminophenyl hydrazine 328.15, different amino-substituted hydrazines, and/or different dialkyl bromo or hydroxy-substituted phosphonates, the products analogous to the compounds 328.19 and 328.21 are obtained.

EXAMPLE 329

Synthesis of Representative compounds of the Invention

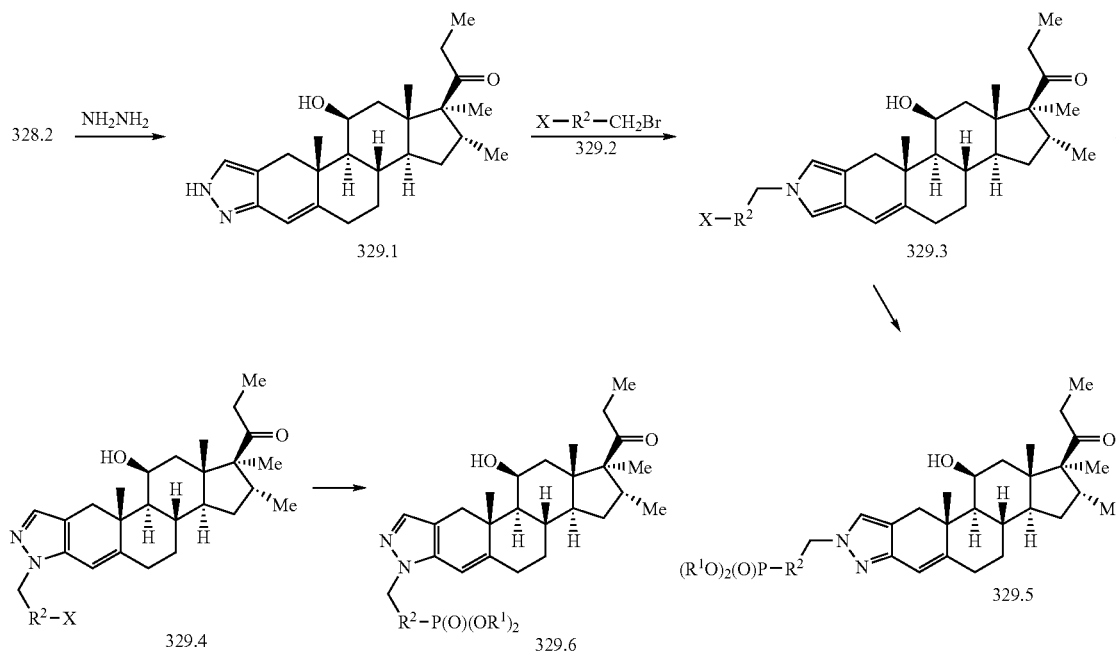

The phosphonate esters in which the phosphonate group is attached by means of a variable carbon linkage is illustrated above. In this procedure, the ketoaldehyde 328.2 is reacted with hydrazine to afford the pyrazole derivative 329.1. The reaction of steroidal 2-formyl-3-ketones with hydrazine is described in *J. Am. Chem. Soc,* 1964, 86, 1520. The reaction is performed in acetic acid at ambient temperature. The pyrazole product is then reacted with a bromomethyl compound 329.2, in which $R^2$ and X are as defined above, or a reactive bromoheteroaromatic reagent, to yield the alkylation products 329.3 and 329.4. The alkylation of substituted pyrazoles is described, for example, in Heterocyclic Chemistry, by T. L. Gilchrist, Longman, 1992, p. 309. The reaction is performed between equimolar amounts of the substrates in a polar solvent such as dimethylformamide or tetrahydrofuran, in the presence of a base such as dimethylaminopyridine, lithium hexamethyldisilazide and the like. The products 329.3 and 329.4 are, except in cases where X is dialkylphosphono, converted into the phosphonates 329.5 and 329.6, using the procedures described herein.

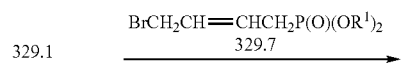

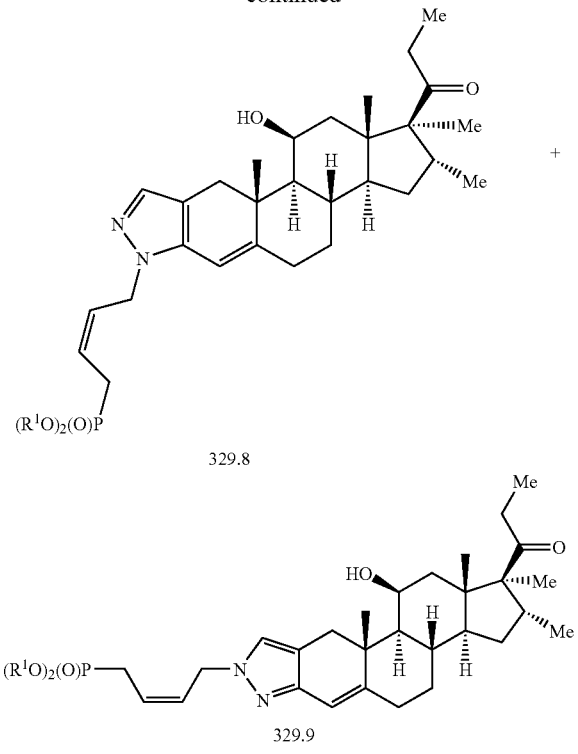

Representative compounds of the invention can be prepared as illustrated above. The pyrazole 329.1 is reacted in dimethylformamide solution at 70° C. with one molar equivalent of a dialkyl 4-bromobutenyl phosphonate 329.7 (*J. Med. Chem.*, 1992, 35, 1371) and lithium hexamethyl disilazide, to give the pyrazoles 329.8 and 329.9.

Using the above procedures, but employing different bromo-substituted phosphonates, the products analogous to 329.8 and 329.9 are obtained.

EXAMPLE 330

Synthesis of Representative compounds of the Invention

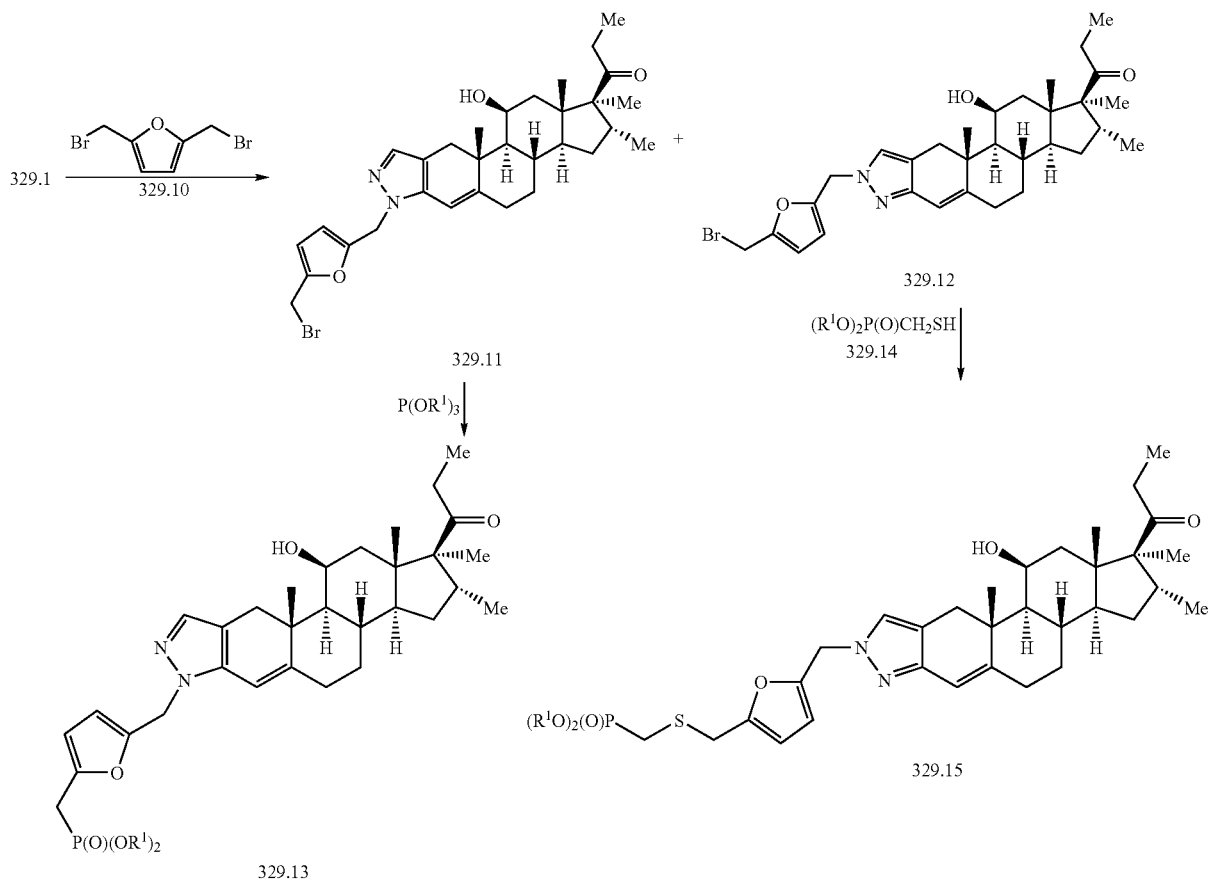

Representative compounds of the invention can be prepared as illustrated above. The pyrazole 329.1 is reacted in tetrahydrofuran solution with 2,5-bis(bromomethyl)furan 329.10 (*Tet.*, 1999, 55, 4709) and potassium hexamethyl disilazide, to give the alkylation products 329.11 and 329.12. The 2'-substituted isomer 329.11 is then reacted, in a Arbuzov reaction, with a trialkyl phosphite to yield the phosphonate 329.13. The Arbuzov reaction is described in *Handb. Organophosphorus Chem.*, 1992, 115. In this procedure, in which a bromo substituent is converted into the corresponding phosphonate, the substrate is heated at from about 60° to about 160° with a five to fifty-fold molar excess of a trialkyl phosphite, to effect the transformation.

The 1'-substituted pyrazole 329.12 is reacted at ambient temperature in dimethylformamide solution with one molar equivalent of a dialkyl mercaptomethyl phosphonate 329.14 (*J. Med. Chem.*, 1985, 26, 1688) and cesium carbonate, to give the thioether phosphonate 329.15.

Using the above procedures, but employing different dihalides, and/or different mercapto-substituted phosphonates, the products analogous to 329.13 and 329.15 are obtained.

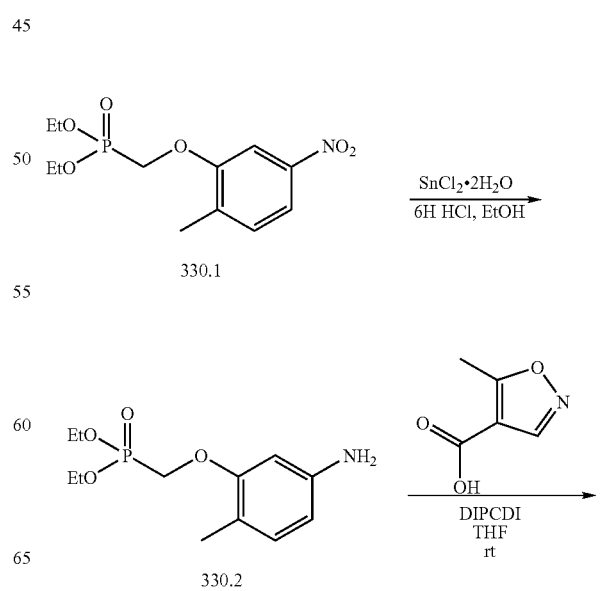

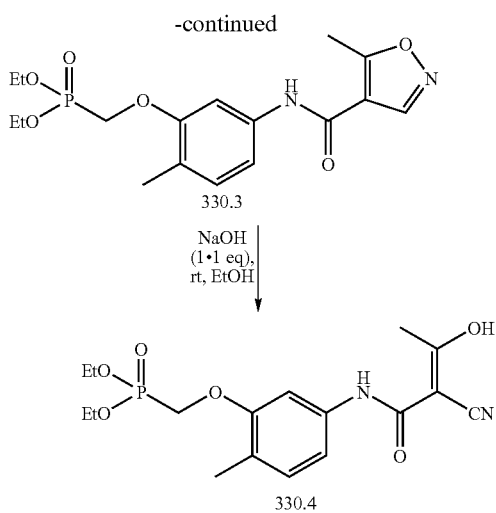

A representative compound of the invention 330.4 can be prepared as illustrated above and as described below.

Compound 303.3 (250 mg, 0.65 mmol) was dissolved in 10 mL of absolute ethanol (15 mL) under an argon atmosphere. Following the addition of NaOH (29 mg, 0.72 mmol), the reaction mixture was stirred overnight at room temperature. TLC (CHCl$_3$/MeOH, 9:1) showed completion of reaction. The reaction mixture was concentrated to a solid and dissolved in ethyl acetate (20 mL). The solution was washed with deionized water (2×10 mL) and dried over Na$_2$SO$_4$. Concentration gave a solid that was purified by silica gel column chromatography (CHCl$_3$/MeOH, 4:1), affording pure compound 330.4 as a solid (188 mg, 75%). ESI-MS m/z 383 [M+H]$^+$. $^1$H NMR (300 MHz, DMSO-d$_6$): δ 7.32 (1H, s, ArH), 6.96 (2H, s, ArH), 4.31 (2H, d, J=9.9 Hz, OCH$_2$), 4.18-4.08 (4H, m, 2×OCH$_2$), 2.08 (3H, s, CH$_3$), 2.00 (3H, s, CH$_3$), 1.26 (6H, t, J=7.0 Hz, CH$_3$). 31P NMR (121.7 MHz, DMSO-d$_6$/external H$_3$PO$_4$) β ppm 20.0-20.4 (m); HPLC: 93% pure (Sphereclone 5 μL, H$_2$O:MeCN, 20 min linear from 10-90% MeCN, 1.0 mL/min).

The intermediate compound 330.3 was prepared as follows.

a. Synthesis of Compound 330.1. 2-Methyl-5-nitrophenol (2.00 g, 13.05 mmol) was dissolved in dry DMF (10 mL) under argon atmosphere and cooled to 0° C. Diethylphosponomethyl-O-triflate (4.70 gm, 15.66 mmol) and cesium carbonate (6.38 gm, 19.58 mmol) were added sequentially. The reaction mixture was stirred at 0° C. for 4 hrs. TLC (cyclohexane/EtOAc, 1:1) showed completion of reaction. Deionized water (15 mL) was added and the mixture was extracted with EtOAC (2×50 mL). The organic layer was washed with 1N HCl (20 mL) followed by water (2×20 mL), dried over Na$_2$SO$_4$ and concentrated to a semi-solid. Purification by silica gel column chromatography (cyclohexane/EtOAc, 1:1) afforded pure compound 330.1 as an oil (3.86 g, 97%).

ESI-MS m/z 304 [M+H]$^+$.

b. Synthesis of Compound 330.2. Compound 330.1 (2.8 g, 9.24 mmol) was dissolved in 15 mL of absolute ethanol (15 mL) and 6N HCl (2 mL) under an argon atmosphere. Following the addition of SnCl$_2$.2H$_2$O (5.26 g, 27.72 mmol), the reaction mixture was stirred overnight at room temperature. TLC (CHCl$_3$/MeOH, 9:1) showed completion of reaction. The mixture was concentrated to a semi-solid and dissolved in ethyl acetate (30 mL). The ethyl acetate layer was washed with deionized water (10 mL) and satd. NaHCO$_3$ (10 mL) and dried over Na$_2$SO$_4$. Concentration gave a solid that was used without purification. ESI-MS m/z 274 [M+H]$^+$.

c. Synthesis of Compound 330.3. Crude compound K-105-48 (900 mg, 3.38 mmol) was dissolved in 15 mL of dry THF (15 mL) under an argon atmosphere. Following the addition of 5-methylisoxazole-4-carboxylic acid (381 mg, 3.00 mmol) and diisopropyl carbodiimide (511 μL, 3.30 mmol), the reaction mixture was stirred 6 h at room temperature. TLC (CHCl$_3$/MeOH, 9:1) showed completion of reaction. The reaction mixture was filtered and the filtrate concentrated to give a solid, which was dissolved in ethyl acetate (25 mL). The solution was washed with deionized water (2×10 mL) and dried over Na$_2$SO$_4$. Concentration gave a solid that was purified by silica gel column chromatography (CHCl$_3$/MeOH, 95:5) to afford pure compound 330.3 as light yellow solid (680 mg, 55%). ESI-MS m/z 383 [M+H]$^+$. $^1$H NMR (300 MHz, CDCl$_3$): δ 7.11 (1H, s, ArH), 7.06 (2H, s, ArH), 4.29-4.20 (4H, m, OCH$_2$), 4.14 (2H, d, J=10.4 Hz, OCH$_2$), 2.76 (3H, s, CH$_3$), 2.14 (3H, s, CH$_3$), 1.37 (6H, t, J=7.0 Hz, CH$_3$). $^{31}$P NMR (121.7 MHz, DMSO-d$_6$/external H$_3$PO$_4$) 5 ppm 19.7-20.0 (m); HPLC: 98% pure (Sphereclone 5/L, H$_2$O:MeCN, min linear from 10-90% MeCN, 1.0 mL/min).

EXAMPLE 331

Synthesis of Representative Prednisone Compounds of the Invention

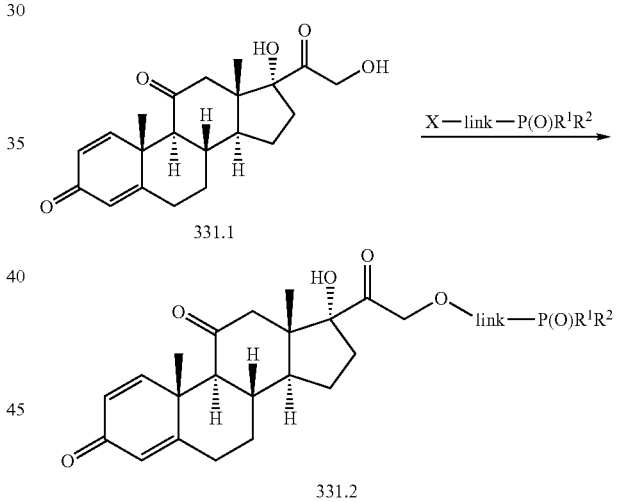

Representative compounds of the invention can be prepared as illustrated above. Derivatization at the C-21 hydroxy group is accomplished through alkylation of prednisone 331.1 with the appropriate phosphonate to provide compounds of the invention 331.2. A specific compound of the invention can be prepared as follows.

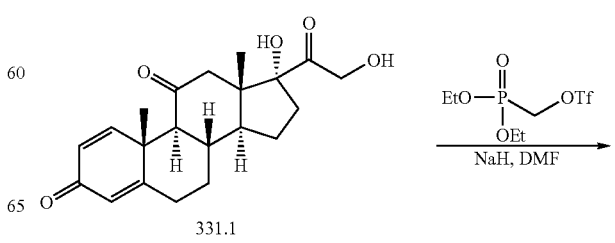

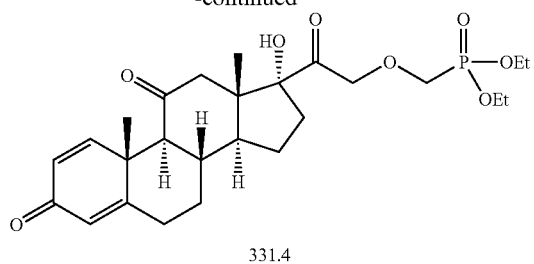

After sodium hydride extraction of the primary hydroxy proton in 331.1, diethyl phosphonate triflate is added to afford ether 331.4.

EXAMPLE 332

Synthesis of Representative Prednisone Compounds of the Invention

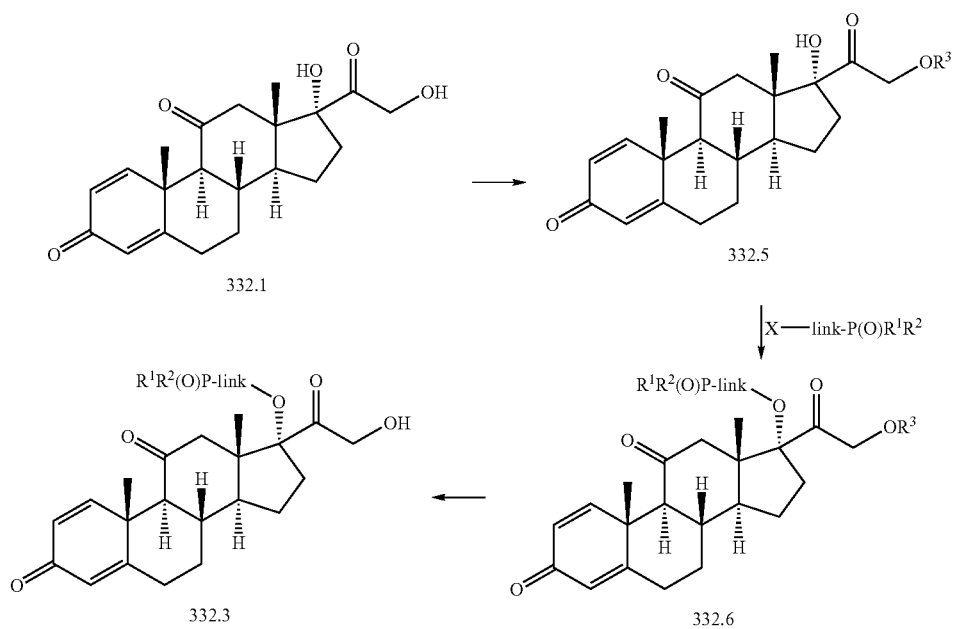

Representative compounds of the invention 332.3 can be prepared as illustrated above. Protection of prednisone 332.1 at the less hindered primary site furnishes alcohol 332.5, which is alkylated at the exposed hydroxy group with the appropriate phosphonate to provide 332.6. Removal of the protecting group completes the construction of analog 332.3. A specific compound can be prepared as follows.

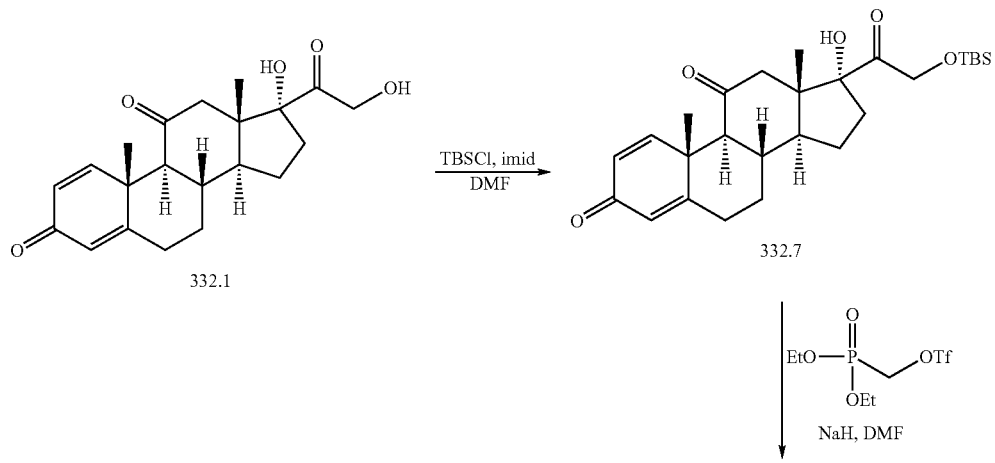

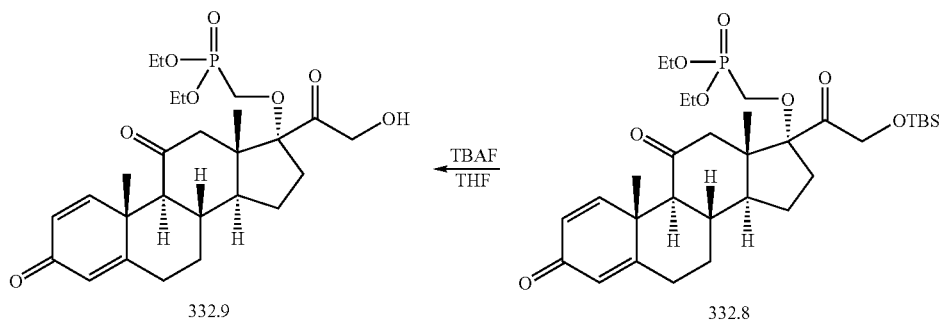

Prednisone 332.1 is mono-protected as its TBS ether 332.7. After alkylating with the diethyl phosphonate triflate, the resulting intermediate 332.8 is treated with TBAF to give the desired phosphonate 332.9.

EXAMPLE 333

By way of example and not limitation, embodiments of the invention are named below in tabular format (Table 100). These embodiments are of the general formula "MBF":

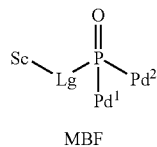

MBF

Each embodiment of MBF is depicted as a substituted nucleus (Sc). Sc is described in formula 1-296 herein, wherein $A^0$ is the point of covalent attachment of Sc to Lg, as well as in Tables 1.1 to 1.5 below. For those embodiments described in Table 100, Sc is a nucleus designated by a number and each substituent is designated in order by letter or number. Tables 1.1 to 1.5 are a schedule of nuclei used in forming the embodiments of Table 100. Each nucleus (Sc) is given a number designation from Tables 1.1 to 1.5, and this designation appears first in each embodiment name. Similarly, Tables 10.1 to 10.19 and 20.1 to 20.36 list the selected linking groups (Lg) and prodrug ($Pd^1$ and $Pd^2$) substituents, again by letter or number designation, respectively. Accordingly, a compound of the formula MBF includes compounds having Sc groups based on formula 1-296 herein as well as compounds according to Table 100 below. In all cases, compounds of the formula MBF have groups Lg, $Pd^1$ and $Pd^2$ setforth in the Tables below.

Accordingly, each named embodiment of Table 100 is depicted by a number designating the nucleus from Table 1.1-1.5, followed by a letter designating the linking group (Lg) from Table 10.1-10.19, and two numbers designating the two prodrug groups ($Pd^1$ and $Pd^2$) from Table 20.1-20.36. In graphical tabular form, each embodiment of Table 100 appears as a name having the syntax:

Sc.Lg.$Pd^1$.$Pd^2$

Each Sc group is shown having a tilda ("~"). The tilda is the point of covalent attachment of Sc to Lg. $Q^1$ and $Q^2$ of the linking groups (Lg), it should be understood, do not represent groups or atoms but are simply connectivity designations. $Q^1$ is the site of the covalent bond to the nucleus (Sc) and $Q^2$ is the site of the covalent bond to the phosphorous atom of formula MBF. Each prodrug group ($Pd^1$ and $Pd^2$) are covalently bonded to the phosphorous atom of MBF at the tilda symbol ("~") or the $A^0$ symbol. Some embodiments of Tables 10.1-10.19 and 20.1-20.36 may be designated as a combination of letters and numbers (Table 10.1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[ ]") and a covalent bond extends outside the brackets, the point of covalent attachment of Sc to Lg may be at any substitutable site on SC. Selection of the point of attachment is described herein. By way of example and not limitation, the point of attachment is selected from those depicted in the schemes and examples.

TABLE 1.1

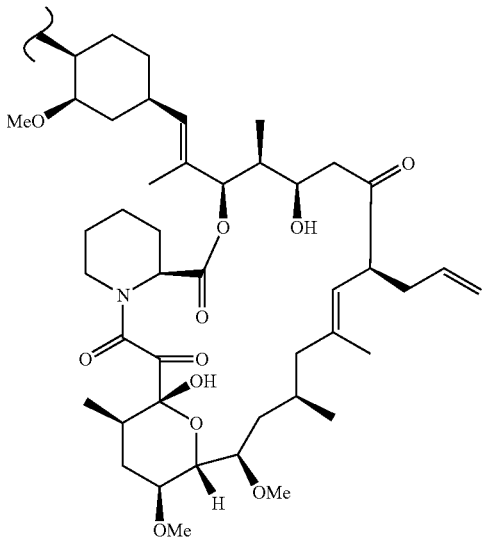

1

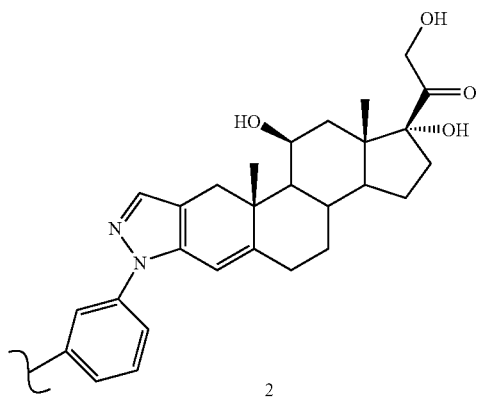

TABLE 1.4

11

12

TABLE 1.5

13

14

TABLE 10.1

| | | |
|---|---|---|
| Q¹–R⁵ᵃ–Q² | Q¹–Q² | Q¹–Y²–Q² |
| A | B | C |
| Q¹–W⁵ᵃ–Q² | Q¹–Y²–R⁵ᵃ–Q² | Q¹–R⁵ᵃ–Y²–Q² |
| D | E | F |
| Q¹–Y²–W⁵ᵃ–Q² | Q¹–W⁵ᵃ–Y²–Q² | Q¹–W⁵ᵃ–R⁵ᵃ–Q² |
| G | H | I |
| Q¹–R⁵ᵃ–W⁵ᵃ–Q² | Q¹–W⁵ᵃ–W⁵ᵃ–Q² | |
| J | K | |
| Q¹–R⁵ᵃ–W⁵ᵃ–R⁵ᵃ–Q² | Q¹–R⁵ᵃ–W⁵ᵃ–W⁵ᵃ–Q² | |
| L | M | |
| Q¹–R⁵ᵃ–W⁵ᵃ–Y²–Q² | Q¹–R⁵ᵃ–Y²–R⁵ᵃ–Q² | |
| N | O | |

TABLE 10.2

| | |
|---|---|
| Q¹–R⁵ᵃ–Y²–W⁵ᵃ–Q² | Q¹–W⁵ᵃ–R⁵ᵃ–W⁵ᵃ–Q² |
| P | Q |
| Q¹–W⁵ᵃ–R⁵ᵃ–Y²–Q² | Q¹–W⁵ᵃ–W⁵ᵃ–R⁵ᵃ–Q² |
| R | S |
| Q¹–W⁵ᵃ–W⁵ᵃ–Y²–Q² | Q¹–W⁵ᵃ–Y²–R⁵ᵃ–Q² |
| T | U |
| Q¹–W⁵ᵃ–Y²–W⁵ᵃ–Q² | Q¹–Y²–R⁵ᵃ–W⁵ᵃ–Q² |
| V | W |
| Q¹–Y²–R⁵ᵃ–Y²–Q² | Q¹–Y²–W⁵ᵃ–R⁵ᵃ–Q² |
| X | Y |
| Q¹–Y²–W⁵ᵃ–W⁵ᵃ–Q² | Q¹–Y²–W⁵ᵃ–Y²–Q² |
| Z | AA |

TABLE 10.3
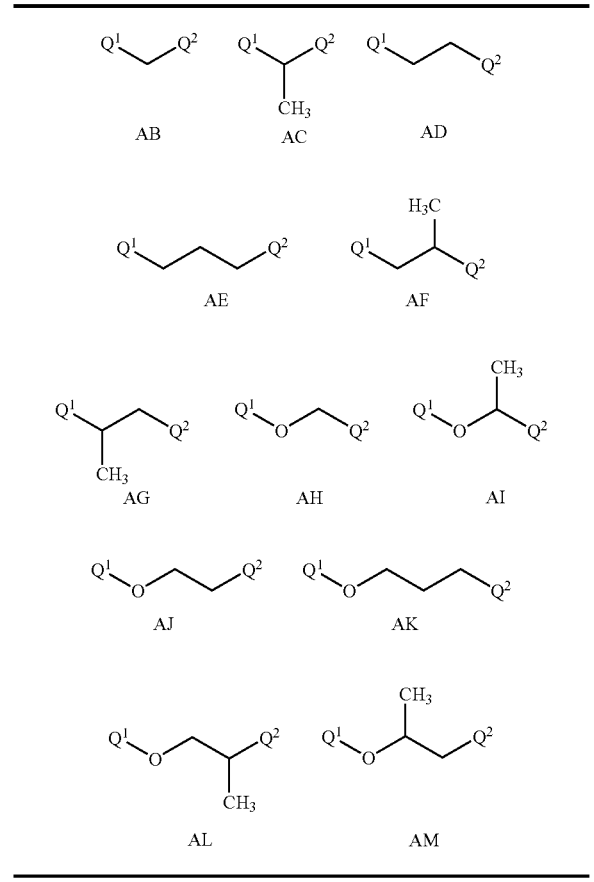
TABLE 10.4
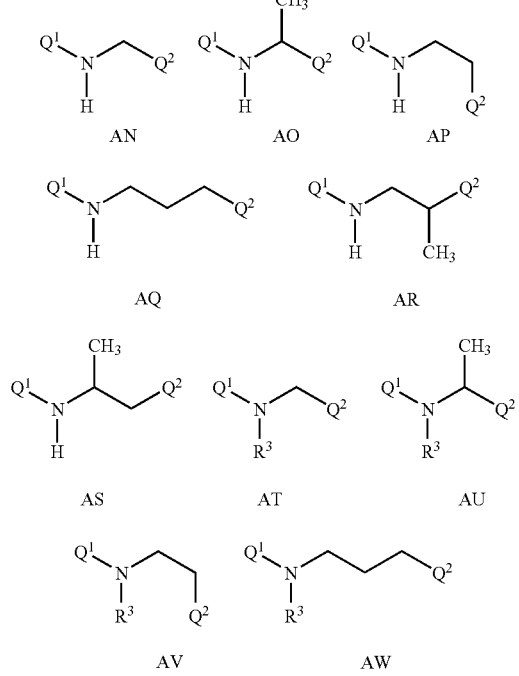
TABLE 10.4-continued
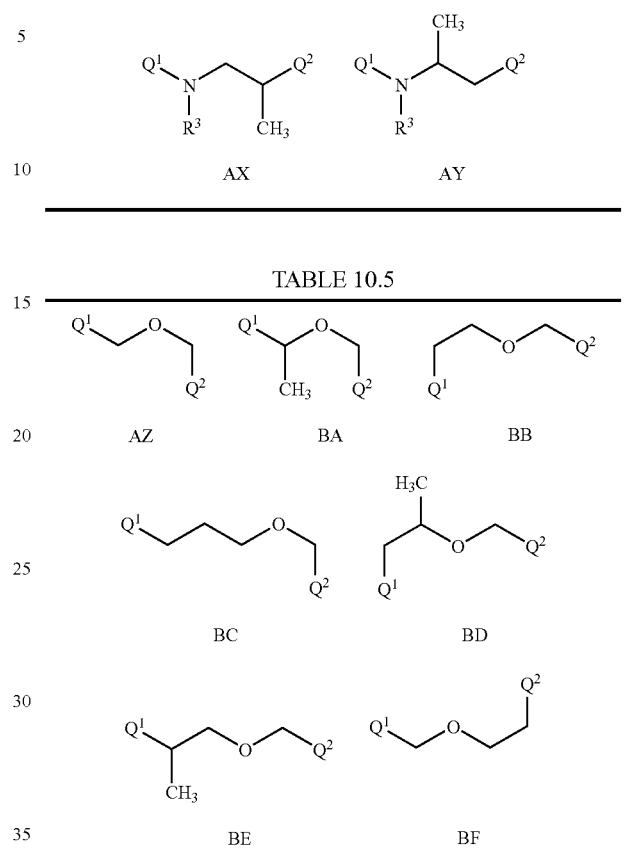
TABLE 10.5
TABLE 10.6
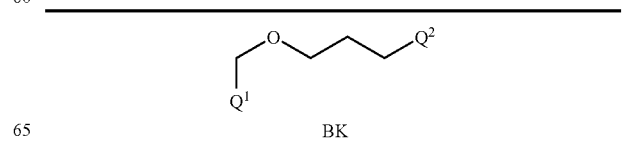

TABLE 10.6-continued
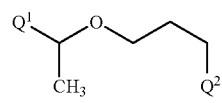
BL
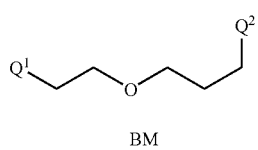
BM
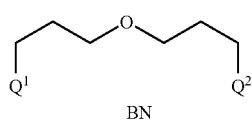
BN
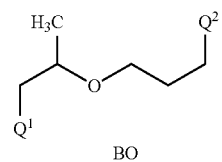
BO
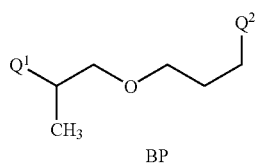
BP
TABLE 10.7
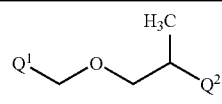
BQ
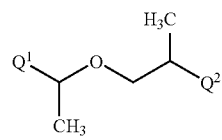
BR
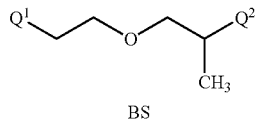
BS
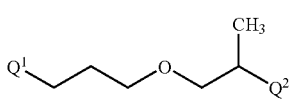
BT
TABLE 10.7-continued
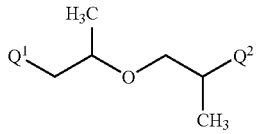
BU
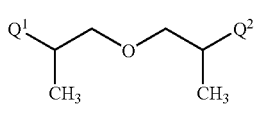
BV
TABLE 10.8
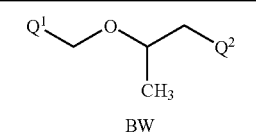
BW
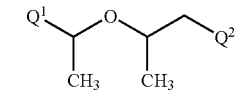
BX
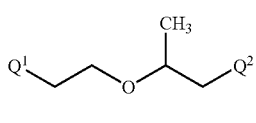
BY
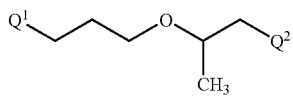
BZ
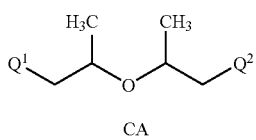
CA
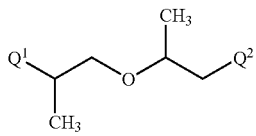
CB
TABLE 10.9
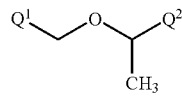
CC TABLE 10.9-continued
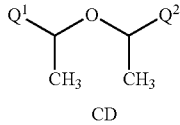
CD
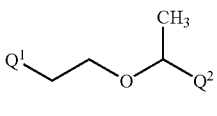
CE
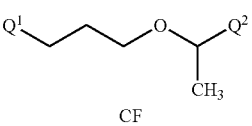
CF
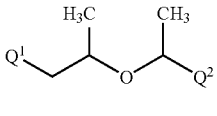
CG
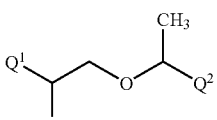
CH
TABLE 10.10
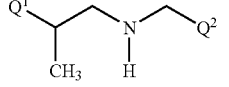
CI  CJ
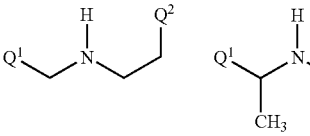
CK
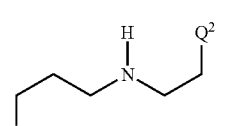
CL
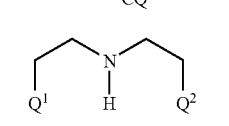
CM
TABLE 10.10-continued
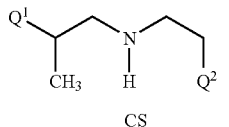
CN
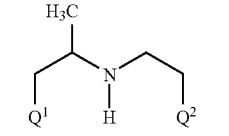
CO  CP
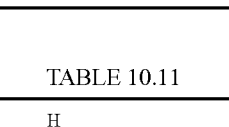
CQ
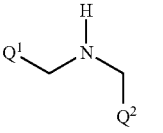
CR
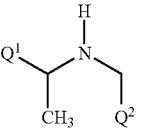
CS
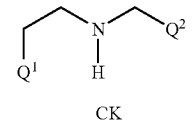
CT
TABLE 10.11
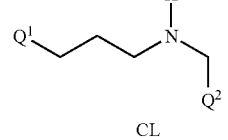
CU
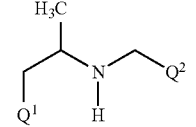
CV
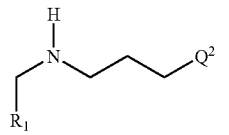
CW TABLE 10.11-continued
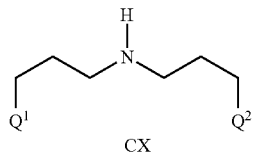
CX
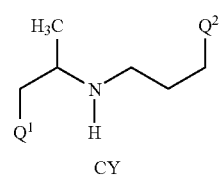
CY
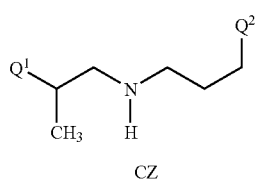
CZ
TABLE 10.12
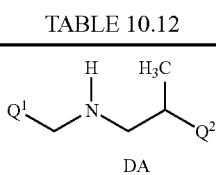
DA
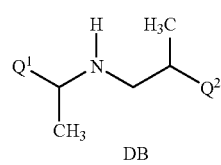
DB
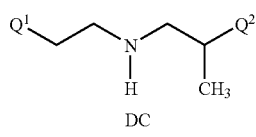
DC
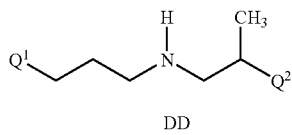
DD
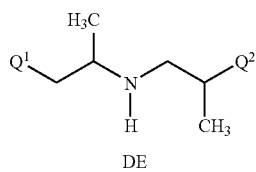
DE
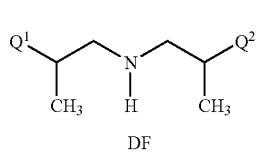
DF
TABLE 10.13
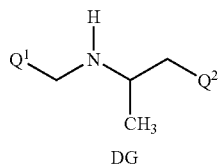
DG
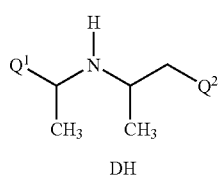
DH
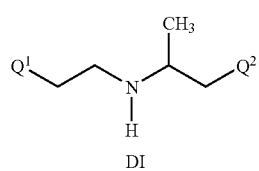
DI
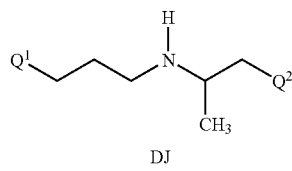
DJ
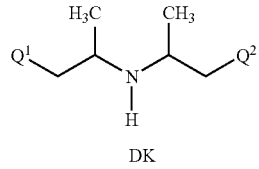
DK
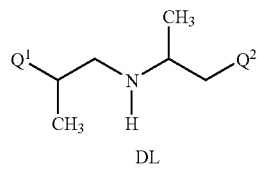
DL
TABLE 10.14
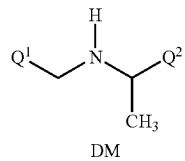
DM
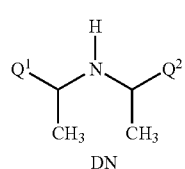
DN TABLE 10.14-continued

Q¹–CH₂CH(CH₃)–NH–Q²
DO

Q¹–(CH₂)₃–NH–CH(CH₃)–Q²
DP

Q¹–CH₂CH(CH₃)–NH–CH(CH₃)–Q²
DQ

Q¹–CH₂CH(CH₃)–CH₂–NH–CH(CH₃)–Q²
DR

TABLE 10.15

Q¹–CH₂–N(R³)–CH₂–Q²
DS

Q¹–CH(CH₃)–N(R³)–CH₂–Q²
DT

Q¹–CH₂CH₂–N(R³)–CH₂–Q²
DU

Q¹–(CH₂)₃–N(R³)–CH₂–Q²
DV

Q¹–CH₂–CH(CH₃)–N(R³)–CH₂–Q²
DW

TABLE 10.15-continued

Q¹–CH₂CH(CH₃)–N(R³)–CH₂–Q²
DX

Q¹–CH₂–N(R³)–CH₂CH₂–Q²
DY

Q¹–CH(CH₃)–N(R³)–CH₂CH₂–Q²
DZ

Q¹–(CH₂)₃–N(R³)–CH₂CH₂–Q²
EA

Q¹–CH₂CH₂–N(R³)–CH₂CH₂–Q²
EB

Q¹–CH₂CH(CH₃)–N(R³)–CH₂CH₂–Q²
EC

Q¹–CH₂–CH(CH₃)–N(R³)–CH₂CH₂–Q²
ED

TABLE 10.16

Q¹–CH₂–N(R³)–(CH₂)₃–Q²
EE

Q¹–CH(CH₃)–N(R³)–(CH₂)₃–Q²
EF

TABLE 10.16-continued
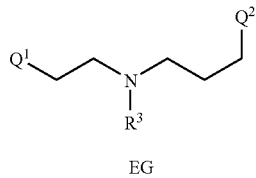
EG
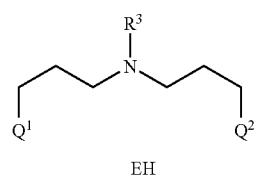
EH
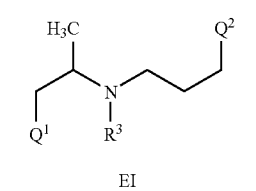
EI
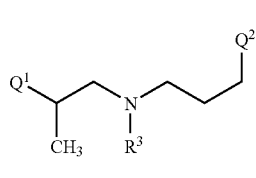
EJ
TABLE 10.17
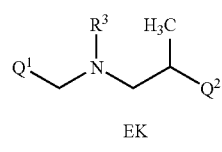
EK
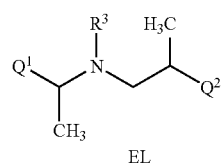
EL
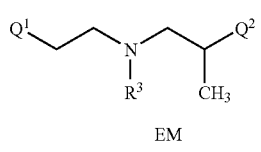
EM
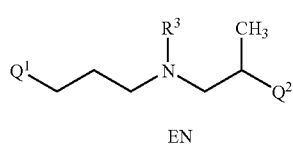
EN
TABLE 10.17-continued
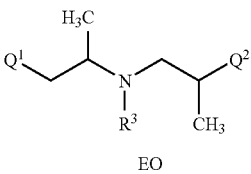
EO
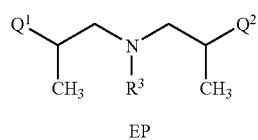
EP
TABLE 10.18
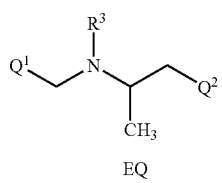
EQ
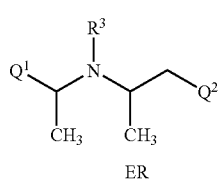
ER
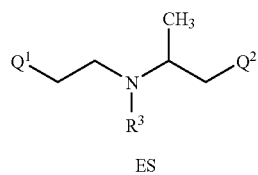
ES
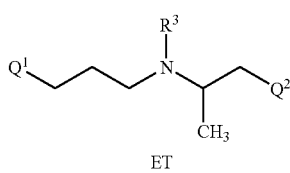
ET
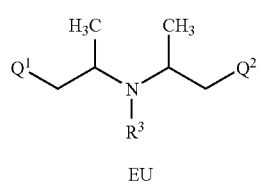
EU
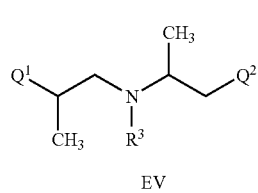
EV TABLE 10.19
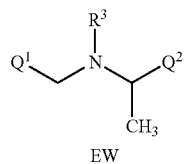
EW
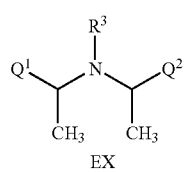
EX
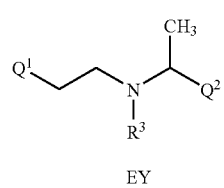
EY
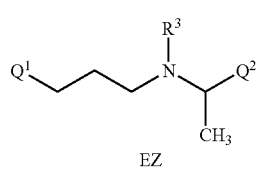
EZ
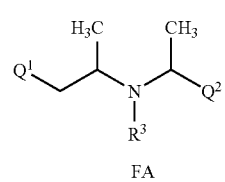
FA
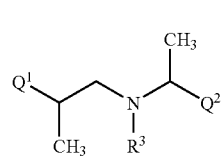
FB
TABLE 20.1
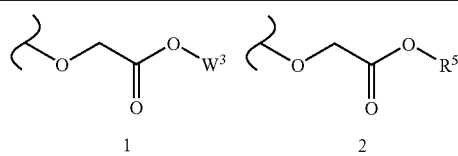
1　　　　2
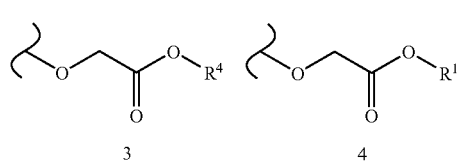
3　　　　4
TABLE 20.1-continued
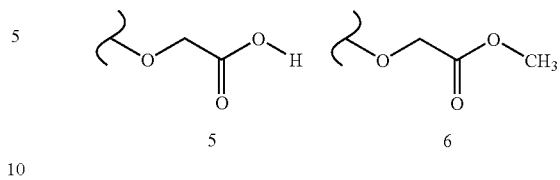
5　　　　6
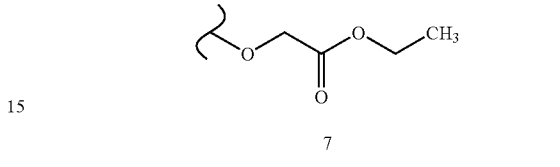
7
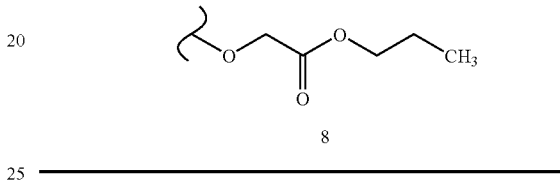
8
TABLE 20.2
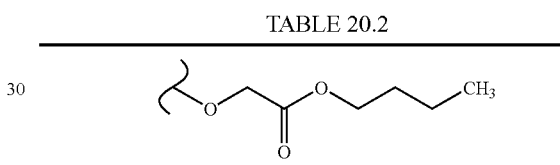
9
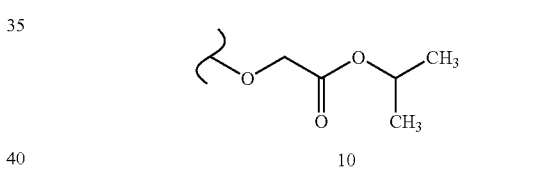
10
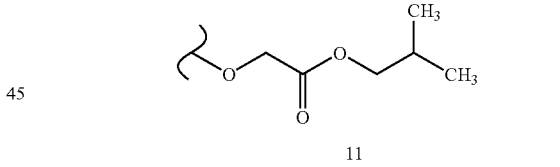
11
TABLE 20.3
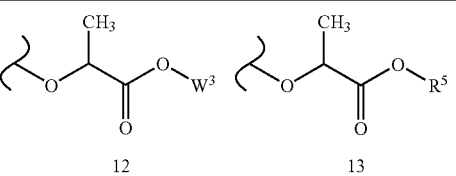
12　　　　13
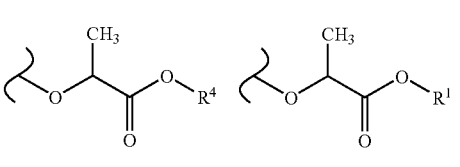
14　　　　15

TABLE 20.3-continued
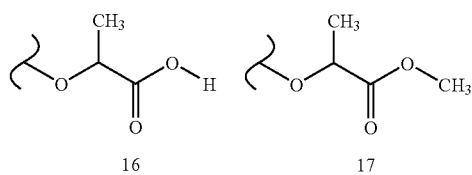
16  17
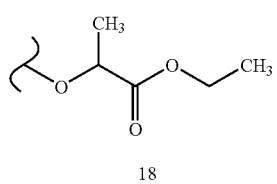
18
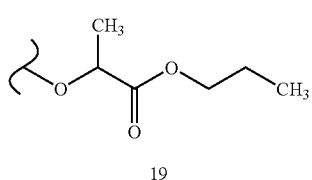
19
TABLE 20.4
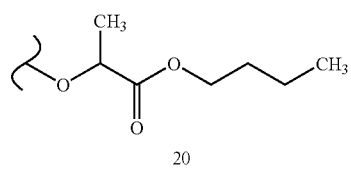
20
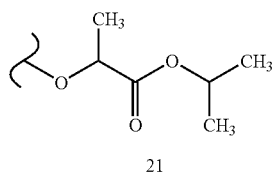
21
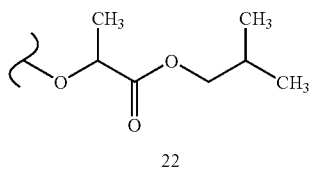
22
TABLE 20.5
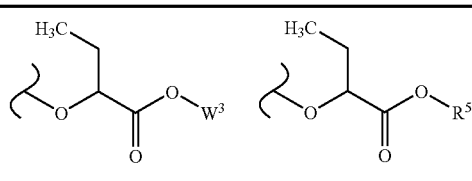
23  24
TABLE 20.5-continued
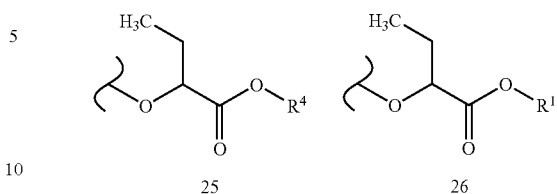
25  26
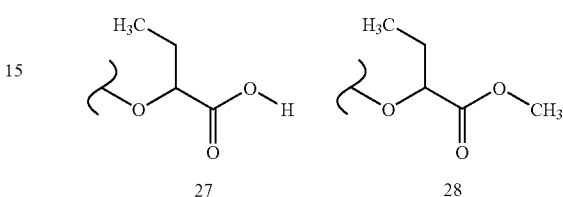
27  28
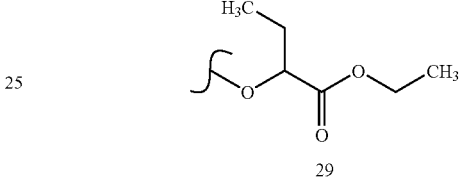
29
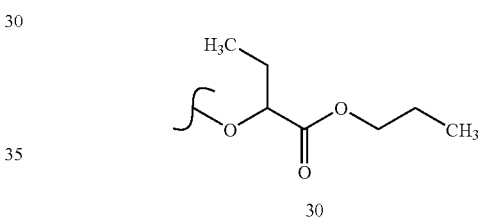
30
TABLE 20.6
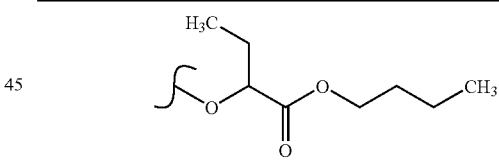
31
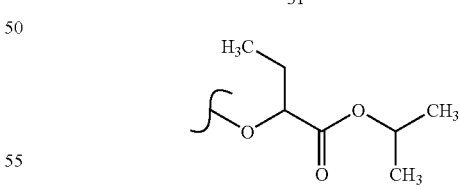
32
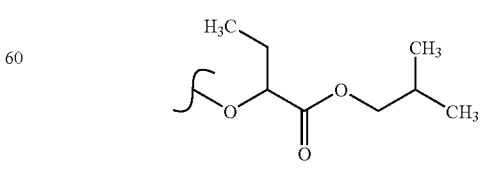
33

TABLE 20.7
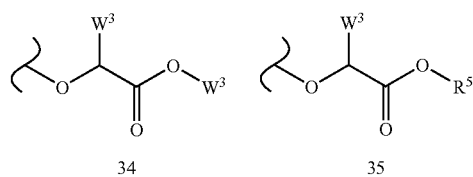
34     35
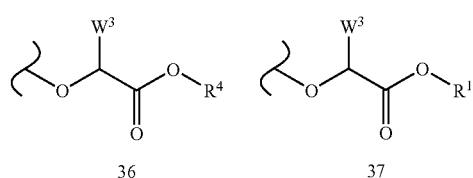
36     37
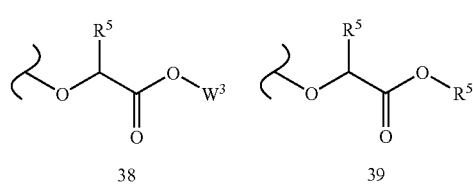
38     39
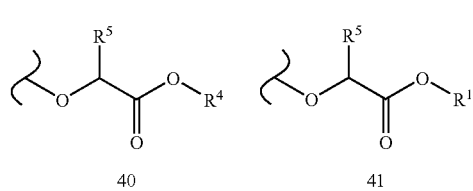
40     41
TABLE 20.8
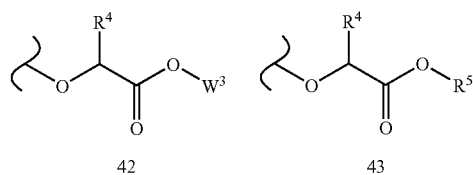
42     43
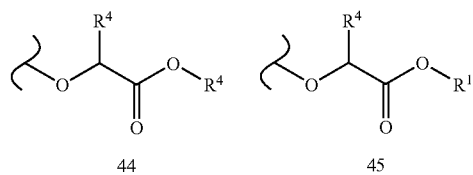
44     45
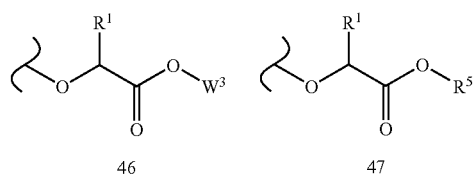
46     47
TABLE 20.8-continued
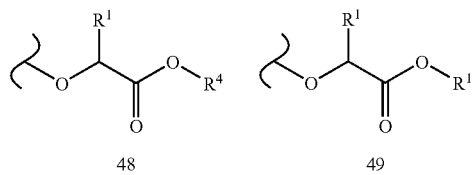
48     49
TABLE 20.9
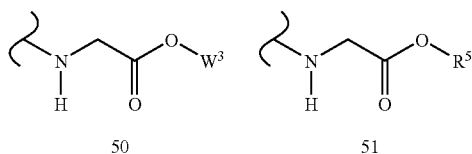
50     51
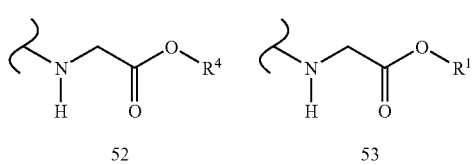
52     53
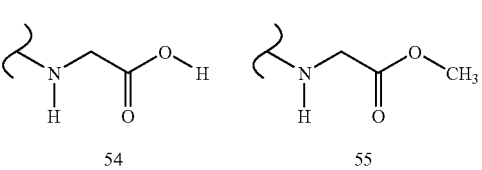
54     55
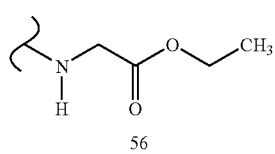
56
57
TABLE 20.10
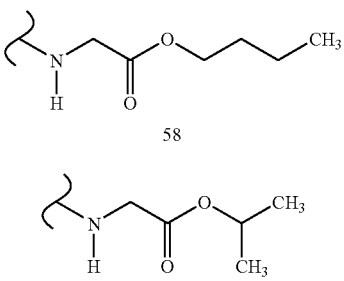
58
59

US 7,432,261 B2
1097
TABLE 20.10-continued
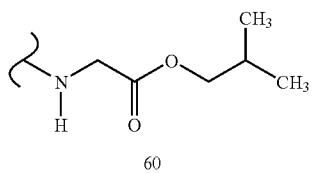
60
TABLE 20.11
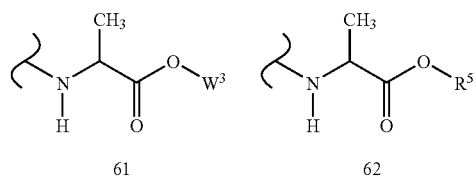
61    62
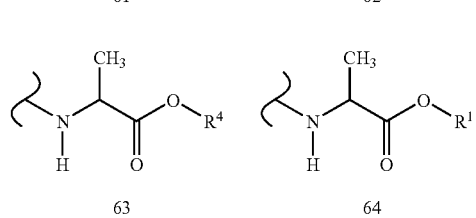
63    64
65    66
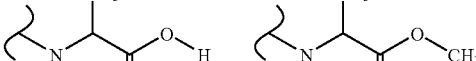
67
68
TABLE 20.12
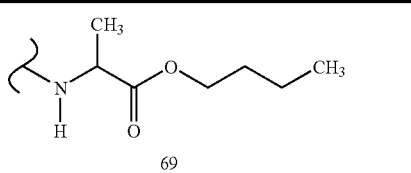
69
1098
TABLE 20.12-continued
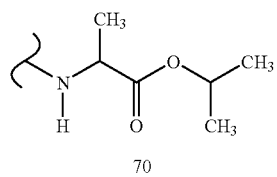
70
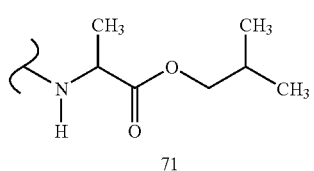
71
TABLE 20.13
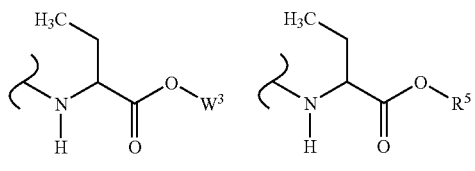
72    73
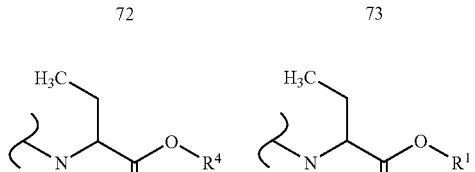
74    75
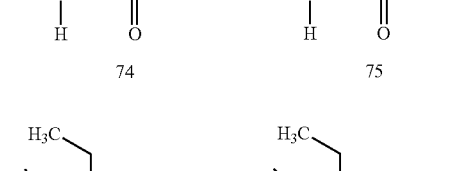
76    77
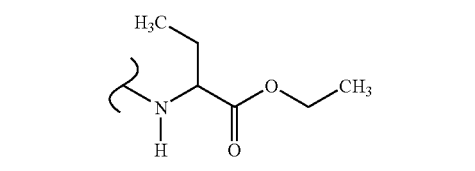
78
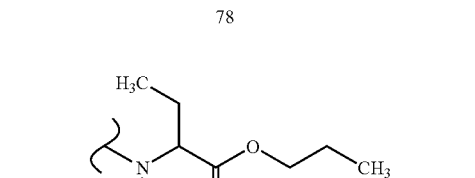
79

TABLE 20.14
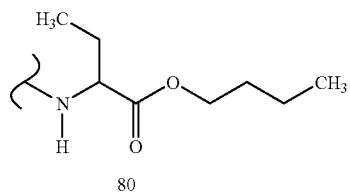
80
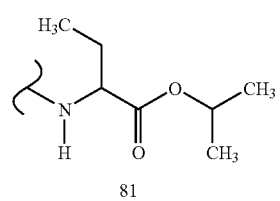
81
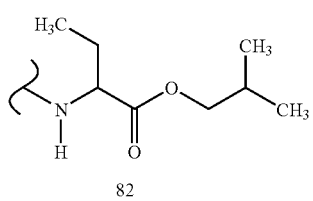
82
TABLE 20.15
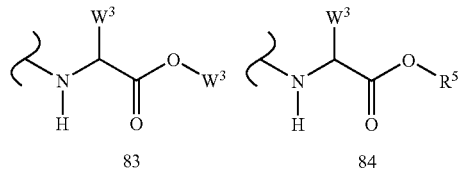
83　　　　　84
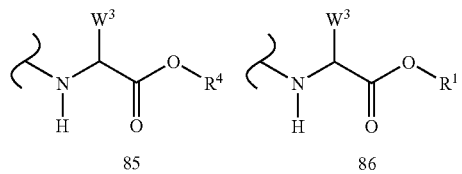
85　　　　　86
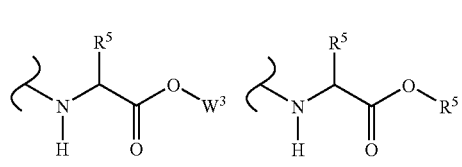
87　　　　　88
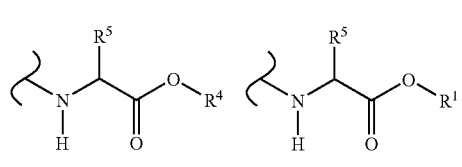
89　　　　　90
TABLE 20.16
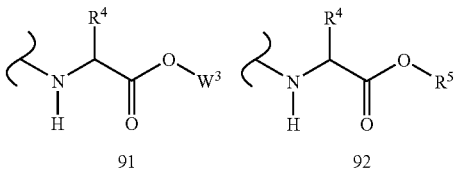
91　　　　　92
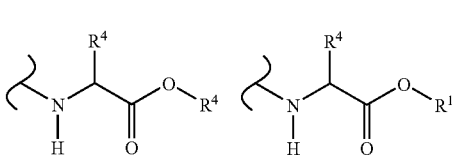
93　　　　　94
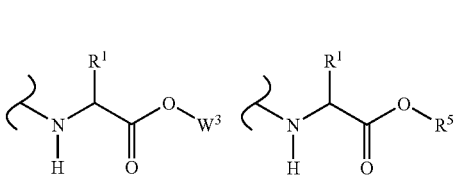
95　　　　　96
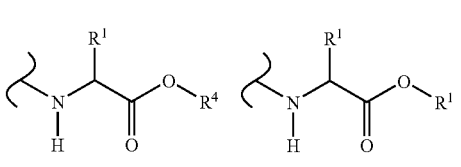
97　　　　　98
TABLE 20.17
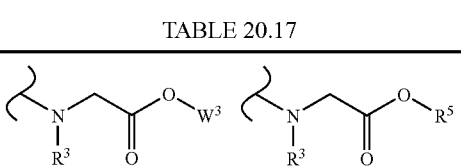
99　　　　　100
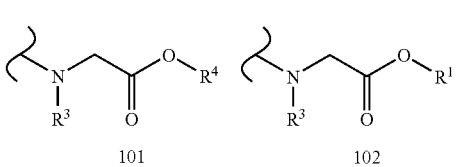
101　　　　　102
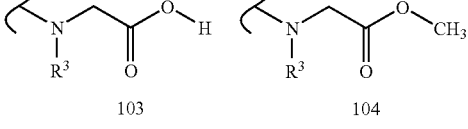
103　　　　　104
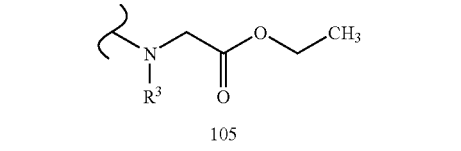
105

TABLE 20.17-continued
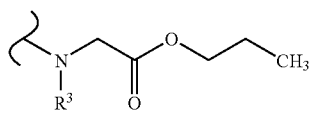
106
TABLE 20.18
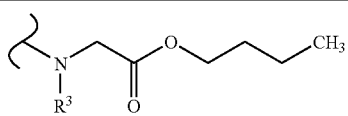
107
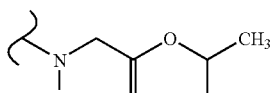
108
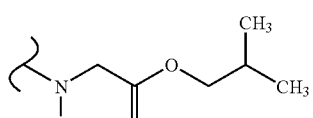
109
TABLE 20.19
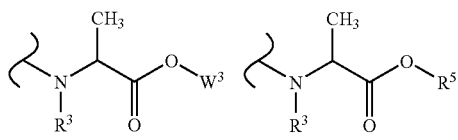
110     111
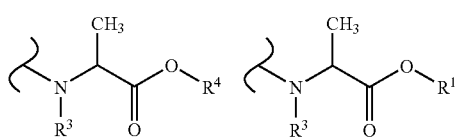
112     113
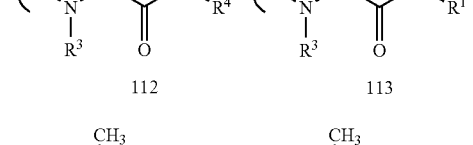
114     115
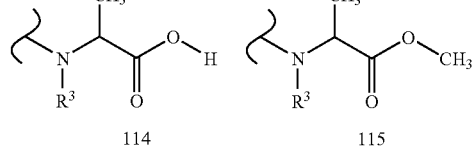
116
TABLE 20.19-continued
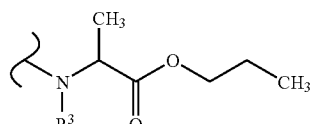
117
TABLE 20.20
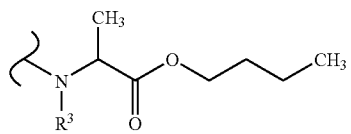
118
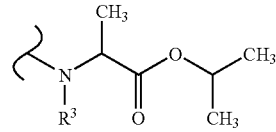
119
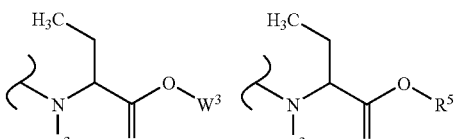
120
TABLE 20.21
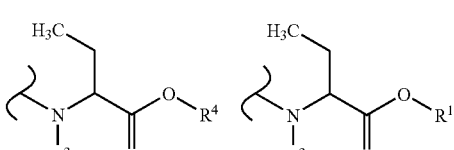
121     122
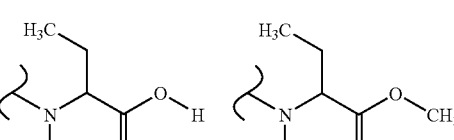
123     124
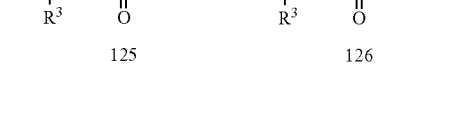
125     126

TABLE 20.21-continued
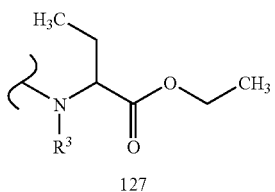
127
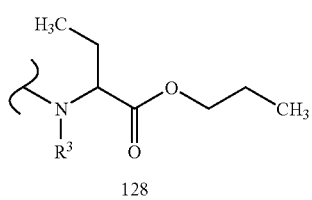
128
TABLE 20.22
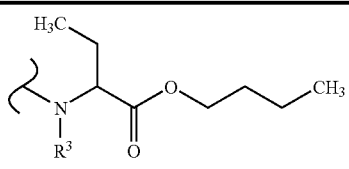
129
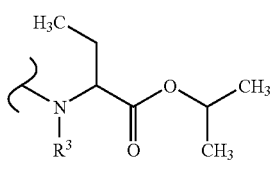
130
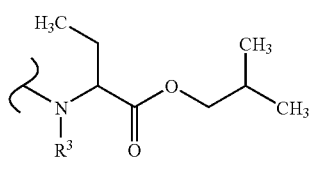
131
TABLE 20.23
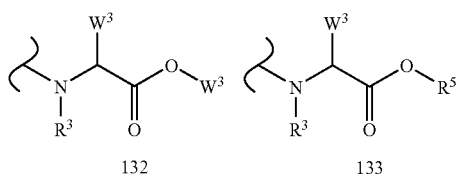
132    133
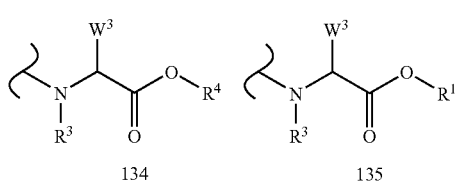
134    135
TABLE 20.23-continued
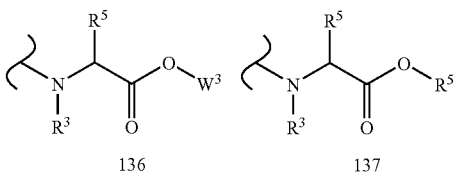
136    137
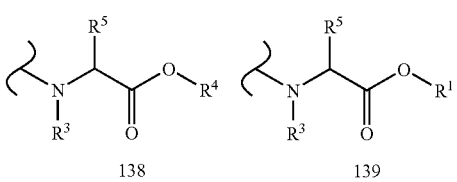
138    139
TABLE 20.24
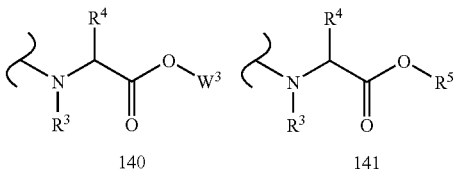
140    141
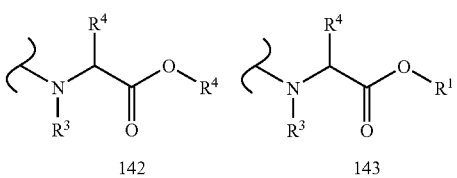
142    143
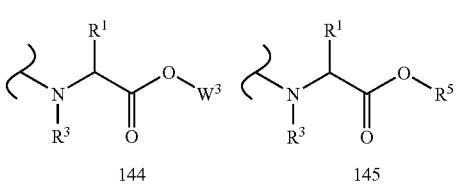
144    145
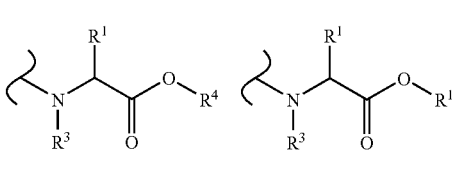
146    147
TABLE 20.25
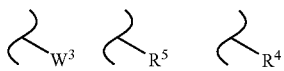 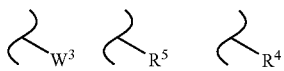 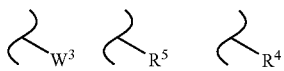
148    149    150
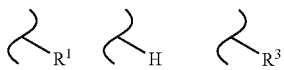 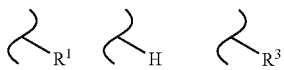 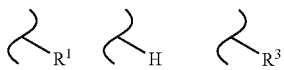
151    152    153

TABLE 20.25-continued
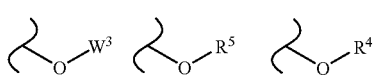
154  155  156
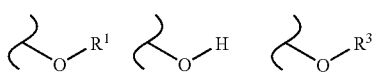
157  158  159
TABLE 20.26
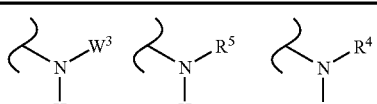
160  161  162
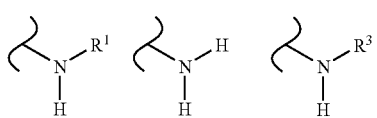
163  164  165
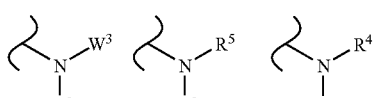
166  167  168
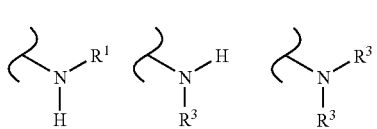
169  170  171
TABLE 20.27
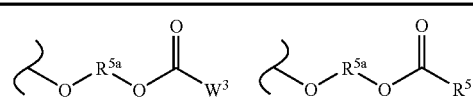
172  173
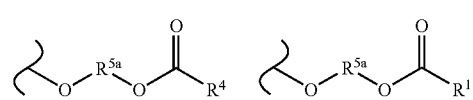
174  175
TABLE 20.27-continued
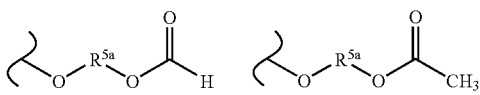
176  177
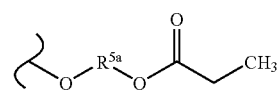
178
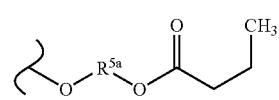
179
TABLE 20.28
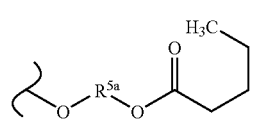
180
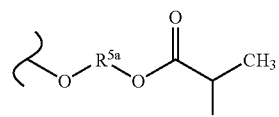
181
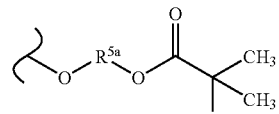
182
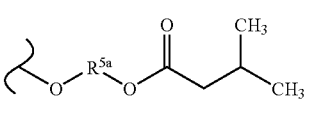
183
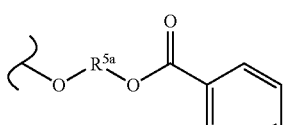
184

TABLE 20.28-continued
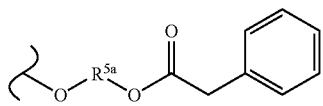
185
TABLE 20.29
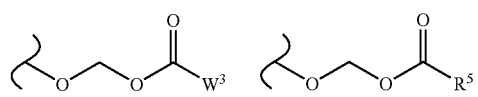
186   187
188   189
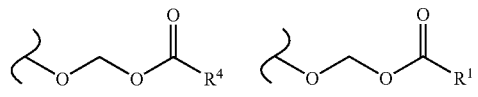
190   191
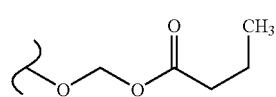
192
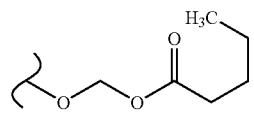
193
TABLE 20.30
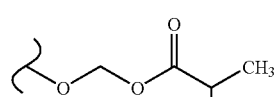
194
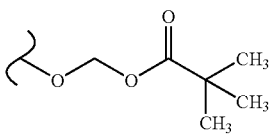
195
TABLE 20.30-continued
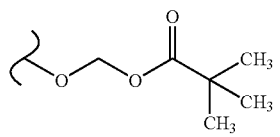
196
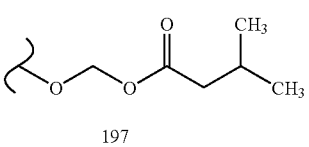
197
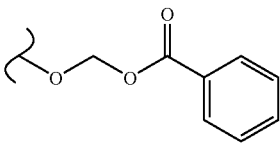
198
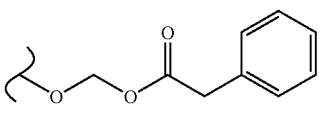
199
TABLE 20.31
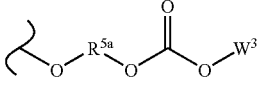
200
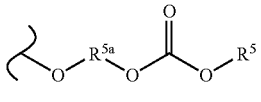
201
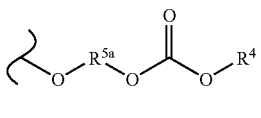
202
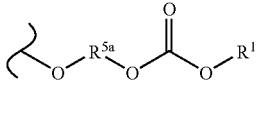
203
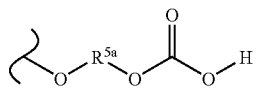
204

TABLE 20.31-continued
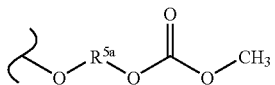
205
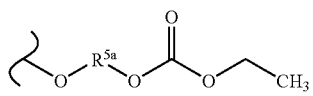
206
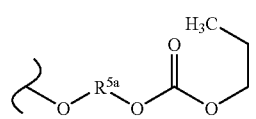
207
TABLE 20.32
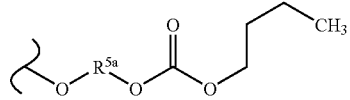
208
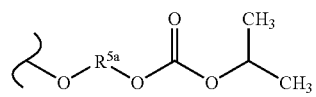
209
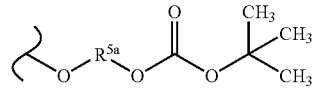
210
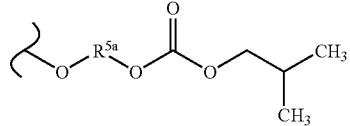
211
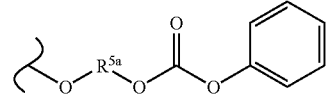
212
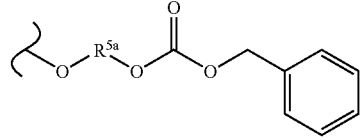
213
TABLE 20.33
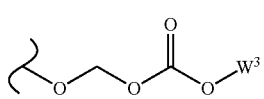
214
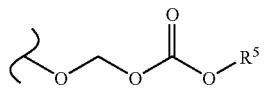
215
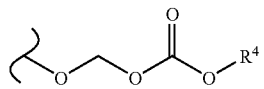
216
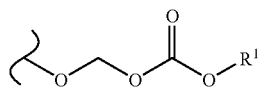
217
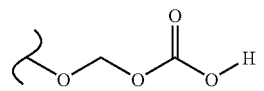
218
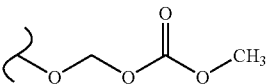
219
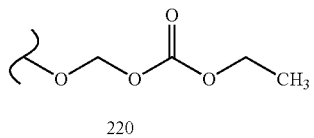
220
221
TABLE 20.34
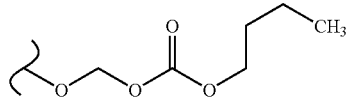
222

TABLE 20.34-continued
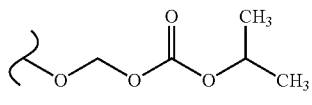
223
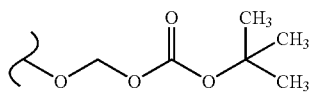
224
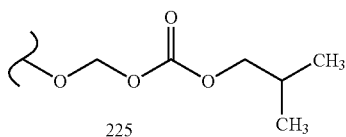
225
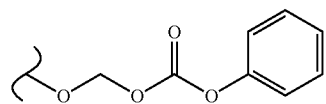
226
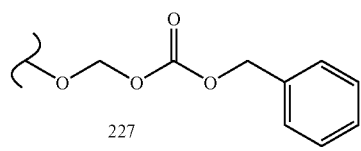
227
TABLE 20.35
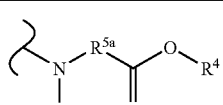
228
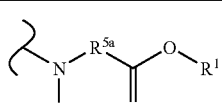
229
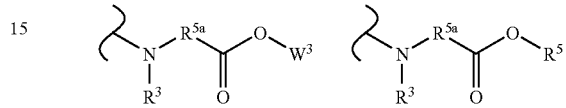
230
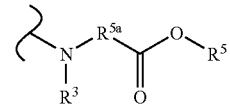
231
232
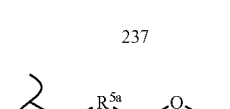
233
TABLE 20.35-continued
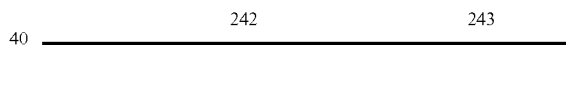
234
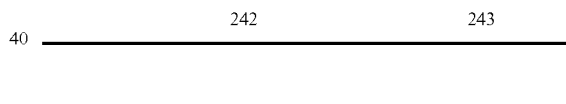
235
TABLE 20.36
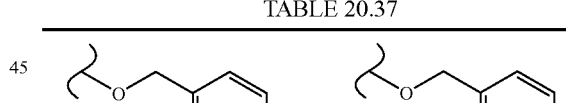
236
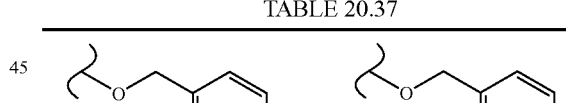
237
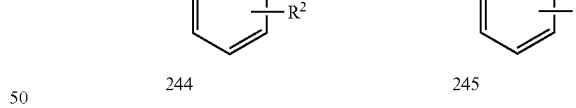
238
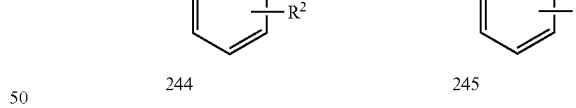
239
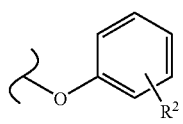
240
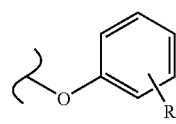
241
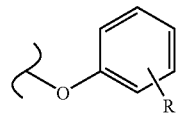
242
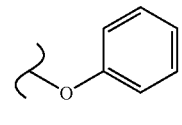
243
TABLE 20.37
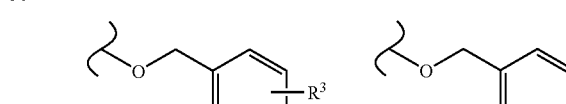
244
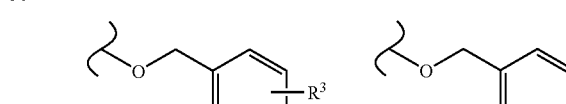
245
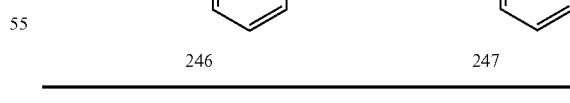
246
247
TABLE 100
Prodrugs of 1.B
1.B.228.228; 1.B.228.229; 1.B.228.230; 1.B.228.231; 1.B.228.236;
1.B.228.237; 1.B.228.238; 1.B.228.239; 1.B.228.154; 1.B.228.157; 1.B.228.166;
1.B.228.169; 1.B.228.172; 1.B.228.175; 1.B.228.240; 1.B.228.244; 1.B.229.228;

TABLE 100-continued

1.B.229.229; 1.B.229.230; 1.B.229.231; 1.B.229.236; 1.B.229.237; 1.B.229.238;
1.B.229.239; 1.B.229.154; 1.B.229.157; 1.B.229.166; 1.B.229.169; 1.B.229.172;
1.B.229.175; 1.B.229.240; 1.B.229.244; 1.B.230.228; 1.B.230.229; 1.B.230.230;
1.B.230.231; 1.B.230.236; 1.B.230.237; 1.B.230.238; 1.B.230.239; 1.B.230.154;
1.B.230.157; 1.B.230.166; 1.B.230.169; 1.B.230.172; 1.B.230.175; 1.B.230.240;
1.B.230.244; 1.B.231.228; 1.B.231.229; 1.B.231.230; 1.B.231.231; 1.B.231.236;
1.B.231.237; 1.B.231.238; 1.B.231.239; 1.B.231.154; 1.B.231.157; 1.B.231.166;
1.B.231.169; 1.B.231.172; 1.B.231.175; 1.B.231.240; 1.B.231.244; 1.B.236.228;
1.B.236.229; 1.B.236.230; 1.B.236.231; 1.B.236.236; 1.B.236.237; 1.B.236.238;
1.B.236.239; 1.B.236.154; 1.B.236.157; 1.B.236.166; 1.B.236.169; 1.B.236.172;
1.B.236.175; 1.B.236.240; 1.B.236.244; 1.B.237.228; 1.B.237.229; 1.B.237.230;
1.B.237.231; 1.B.237.236; 1.B.237.237; 1.B.237.238; 1.B.237.239; 1.B.237.154;
1.B.237.157; 1.B.237.166; 1.B.237.169; 1.B.237.172; 1.B.237.175; 1.B.237.240;
1.B.237.244; 1.B.238.228; 1.B.238.229; 1.B.238.230; 1.B.238.231; 1.B.238.236;
1.B.238.237; 1.B.238.238; 1.B.238.239; 1.B.238.154; 1.B.238.157; 1.B.238.166;
1.B.238.169; 1.B.238.172; 1.B.238.175; 1.B.238.240; 1.B.238.244; 1.B.239.228;
1.B.239.229; 1.B.239.230; 1.B.239.231; 1.B.239.236; 1.B.239.237; 1.B.239.238;
1.B.239.239; 1.B.239.154; 1.B.239.157; 1.B.239.166; 1.B.239.169; 1.B.239.172;
1.B.239.175; 1.B.239.240; 1.B.239.244; 1.B.154.228; 1.B.154.229; 1.B.154.230;
1.B.154.231; 1.B.154.236; 1.B.154.237; 1.B.154.238; 1.B.154.239; 1.B.154.154;
1.B.154.157; 1.B.154.166; 1.B.154.169; 1.B.154.172; 1.B.154.175; 1.B.154.240;
1.B.154.244; 1.B.157.228; 1.B.157.229; 1.B.157.230; 1.B.157.231; 1.B.157.236;
1.B.157.237; 1.B.157.238; 1.B.157.239; 1.B.157.154; 1.B.157.157; 1.B.157.166;
1.B.157.169; 1.B.157.172; 1.B.157.175; 1.B.157.240; 1.B.157.244; 1.B.166.228;
1.B.166.229; 1.B.166.230; 1.B.166.231; 1.B.166.236; 1.B.166.237; 1.B.166.238;
1.B.166.239; 1.B.166.154; 1.B.166.157; 1.B.166.166; 1.B.166.169; 1.B.166.172;
1.B.166.175; 1.B.166.240; 1.B.166.244; 1.B.169.228; 1.B.169.229; 1.B.169.230;
1.B.169.231; 1.B.169.236; 1.B.169.237; 1.B.169.238; 1.B.169.239; 1.B.169.154;
1.B.169.157; 1.B.169.166; 1.B.169.169; 1.B.169.172; 1.B.169.175; 1.B.169.240;
1.B.169.244; 1.B.172.228; 1.B.172.229; 1.B.172.230; 1.B.172.231; 1.B.172.236;
1.B.172.237; 1.B.172.238; 1.B.172.239; 1.B.172.154; 1.B.172.157; 1.B.172.166;
1.B.172.169; 1.B.172.172; 1.B.172.175; 1.B.172.240; 1.B.172.244; 1.B.175.228;
1.B.175.229; 1.B.175.230; 1.B.175.231; 1.B.175.236; 1.B.175.237; 1.B.175.238;
1.B.175.239; 1.B.175.154; 1.B.175.157; 1.B.175.166; 1.B.175.169; 1.B.175.172;
1.B.175.175; 1.B.175.240; 1.B.175.244; 1.B.240.228; 1.B.240.229; 1.B.240.230;
1.B.240.231; 1.B.240.236; 1.B.240.237; 1.B.240.238; 1.B.240.239; 1.B.240.154;
1.B.240.157; 1.B.240.166; 1.B.240.169; 1.B.240.172; 1.B.240.175; 1.B.240.240;
1.B.240.244; 1.B.244.228; 1.B.244.229; 1.B.244.230; 1.B.244.231; 1.B.244.236;
1.B.244.237; 1.B.244.238; 1.B.244.239; 1.B.244.154; 1.B.244.157; 1.B.244.166;
1.B.244.169; 1.B.244.172; 1.B.244.175; 1.B.244.240; 1.B.244.244;
Prodrugs of 1.D 1.D.228.228; 1.D.228.229; 1.D.228.230; 1.D.228.231; 1.D.228.236;
1.D.228.237; 1.D.228.238; 1.D.228.239; 1.D.228.154; 1.D.228.157;
1.D.228.166; 1.D.228.169; 1.D.228.172; 1.D.228.175; 1.D.228.240;
1.D.228.244; 1.D.229.228; 1.D.229.229; 1.D.229.230; 1.D.229.231;
1.D.229.236; 1.D.229.237; 1.D.229.238; 1.D.229.239; 1.D.229.154;
1.D.229.157; 1.D.229.166; 1.D.229.169; 1.D.229.172; 1.D.229.175;
1.D.229.240; 1.D.229.244; 1.D.230.228; 1.D.230.229; 1.D.230.230;
1.D.230.231; 1.D.230.236; 1.D.230.237; 1.D.230.238; 1.D.230.239;
1.D.230.154; 1.D.230.157; 1.D.230.166; 1.D.230.169; 1.D.230.172;
1.D.230.175; 1.D.230.240; 1.D.230.244; 1.D.231.228; 1.D.231.229;
1.D.231.230; 1.D.231.231; 1.D.231.236; 1.D.231.237; 1.D.231.238;
1.D.231.239; 1.D.231.154; 1.D.231.157; 1.D.231.166; 1.D.231.169;
1.D.231.172; 1.D.231.175; 1.D.231.240; 1.D.231.244; 1.D.236.228;
1.D.236.229; 1.D.236.230; 1.D.236.231; 1.D.236.236; 1.D.236.237;
1.D.236.238; 1.D.236.239; 1.D.236.154; 1.D.236.157; 1.D.236.166;
1.D.236.169; 1.D.236.172; 1.D.236.175; 1.D.236.240; 1.D.236.244;
1.D.237.228; 1.D.237.229; 1.D.237.230; 1.D.237.231; 1.D.237.236;
1.D.237.237; 1.D.237.238; 1.D.237.239; 1.D.237.154; 1.D.237.157;
1.D.237.166; 1.D.237.169; 1.D.237.172; 1.D.237.175; 1.D.237.240;
1.D.237.244; 1.D.238.228; 1.D.238.229; 1.D.238.230; 1.D.238.231;
1.D.238.236; 1.D.238.237; 1.D.238.238; 1.D.238.239; 1.D.238.154;
1.D.238.157; 1.D.238.166; 1.D.238.169; 1.D.238.172; 1.D.238.175;
1.D.238.240; 1.D.238.244; 1.D.239.228; 1.D.239.229; 1.D.239.230;
1.D.239.231; 1.D.239.236; 1.D.239.237; 1.D.239.238; 1.D.239.239;
1.D.239.154; 1.D.239.157; 1.D.239.166; 1.D.239.169; 1.D.239.172;
1.D.239.175; 1.D.239.240; 1.D.239.244; 1.D.154.228; 1.D.154.229;
1.D.154.230; 1.D.154.231; 1.D.154.236; 1.D.154.237; 1.D.154.238;
1.D.154.239; 1.D.154.154; 1.D.154.157; 1.D.154.166; 1.D.154.169;
1.D.154.172; 1.D.154.175; 1.D.154.240; 1.D.154.244; 1.D.157.228;
1.D.157.229; 1.D.157.230; 1.D.157.231; 1.D.157.236; 1.D.157.237;
1.D.157.238; 1.D.157.239; 1.D.157.154; 1.D.157.157; 1.D.157.166;
1.D.157.169; 1.D.157.172; 1.D.157.175; 1.D.157.240; 1.D.157.244;
1.D.166.228; 1.D.166.229; 1.D.166.230; 1.D.166.231; 1.D.166.236;
1.D.166.237; 1.D.166.238; 1.D.166.239; 1.D.166.154; 1.D.166.157;
1.D.166.166; 1.D.166.169; 1.D.166.172; 1.D.166.175; 1.D.166.240;
1.D.166.244; 1.D.169.228; 1.D.169.229; 1.D.169.230; 1.D.169.231;
1.D.169.236; 1.D.169.237; 1.D.169.238; 1.D.169.239; 1.D.169.154;

TABLE 100-continued

1.D.169.157; 1.D.169.166; 1.D.169.169; 1.D.169.172; 1.D.169.175;
1.D.169.240; 1.D.169.244; 1.D.172.228; 1.D.172.229; 1.D.172.230;
1.D.172.231; 1.D.172.236; 1.D.172.237; 1.D.172.238; 1.D.172.239;
1.D.172.154; 1.D.172.157; 1.D.172.166; 1.D.172.169; 1.D.172.172;
1.D.172.175; 1.D.172.240; 1.D.172.244; 1.D.175.228; 1.D.175.229;
1.D.175.230; 1.D.175.231; 1.D.175.236; 1.D.175.237; 1.D.175.238;
1.D.175.239; 1.D.175.154; 1.D.175.157; 1.D.175.166; 1.D.175.169;
1.D.175.172; 1.D.175.175; 1.D.175.240; 1.D.175.244; 1.D.240.228;
1.D.240.229; 1.D.240.230; 1.D.240.231; 1.D.240.236; 1.D.240.237;
1.D.240.238; 1.D.240.239; 1.D.240.154; 1.D.240.157; 1.D.240.166;
1.D.240.169; 1.D.240.172; 1.D.240.175; 1.D.240.240; 1.D.240.244;
1.D.244.228; 1.D.244.229; 1.D.244.230; 1.D.244.231; 1.D.244.236;
1.D.244.237; 1.D.244.238; 1.D.244.239; 1.D.244.154; 1.D.244.157;
1.D.244.166; 1.D.244.169; 1.D.244.172; 1.D.244.175; 1.D.244.240;
1.D.244.244;
Prodrugs of 1.E 1.E.228.228; 1.E.228.229; 1.E.228.230; 1.E.228.231; 1.E.228.236;
1.E.228.237; 1.E.228.238; 1.E.228.239; 1.E.228.154; 1.E.228.157; 1.E.228.166;
1.E.228.169; 1.E.228.172; 1.E.228.175; 1.E.228.240; 1.E.228.244; 1.E.229.228;
1.E.229.229; 1.E.229.230; 1.E.229.231; 1.E.229.236; 1.E.229.237; 1.E.229.238;
1.E.229.239; 1.E.229.154; 1.E.229.157; 1.E.229.166; 1.E.229.169; 1.E.229.172;
1.E.229.175; 1.E.229.240; 1.E.229.244; 1.E.230.228; 1.E.230.229; 1.E.230.230;
1.E.230.231; 1.E.230.236; 1.E.230.237; 1.E.230.238; 1.E.230.239; 1.E.230.154;
1.E.230.157; 1.E.230.166; 1.E.230.169; 1.E.230.172; 1.E.230.175; 1.E.230.240;
1.E.230.244; 1.E.231.228; 1.E.231.229; 1.E.231.230; 1.E.231.231; 1.E.231.236;
1.E.231.237; 1.E.231.238; 1.E.231.239; 1.E.231.154; 1.E.231.157; 1.E.231.166;
1.E.231.169; 1.E.231.172; 1.E.231.175; 1.E.231.240; 1.E.231.244; 1.E.236.228;
1.E.236.229; 1.E.236.230; 1.E.236.231; 1.E.236.236; 1.E.236.237; 1.E.236.238;
1.E.236.239; 1.E.236.154; 1.E.236.157; 1.E.236.166; 1.E.236.169; 1.E.236.172;
1.E.236.175; 1.E.236.240; 1.E.236.244; 1.E.237.228; 1.E.237.229; 1.E.237.230;
1.E.237.231; 1.E.237.236; 1.E.237.237; 1.E.237.238; 1.E.237.239; 1.E.237.154;
1.E.237.157; 1.E.237.166; 1.E.237.169; 1.E.237.172; 1.E.237.175; 1.E.237.240;
1.E.237.244; 1.E.238.228; 1.E.238.229; 1.E.238.230; 1.E.238.231; 1.E.238.236;
1.E.238.237; 1.E.238.238; 1.E.238.239; 1.E.238.154; 1.E.238.157; 1.E.238.166;
1.E.238.169; 1.E.238.172; 1.E.238.175; 1.E.238.240; 1.E.238.244; 1.E.239.228;
1.E.239.229; 1.E.239.230; 1.E.239.231; 1.E.239.236; 1.E.239.237; 1.E.239.238;
1.E.239.239; 1.E.239.154; 1.E.239.157; 1.E.239.166; 1.E.239.169; 1.E.239.172;
1.E.239.175; 1.E.239.240; 1.E.239.244; 1.E.154.228; 1.E.154.229; 1.E.154.230;
1.E.154.231; 1.E.154.236; 1.E.154.237; 1.E.154.238; 1.E.154.239; 1.E.154.154;
1.E.154.157; 1.E.154.166; 1.E.154.169; 1.E.154.172; 1.E.154.175; 1.E.154.240;
1.E.154.244; 1.E.157.228; 1.E.157.229; 1.E.157.230; 1.E.157.231; 1.E.157.236;
1.E.157.237; 1.E.157.238; 1.E.157.239; 1.E.157.154; 1.E.157.157; 1.E.157.166;
1.E.157.169; 1.E.157.172; 1.E.157.175; 1.E.157.240; 1.E.157.244; 1.E.166.228;
1.E.166.229; 1.E.166.230; 1.E.166.231; 1.E.166.236; 1.E.166.237; 1.E.166.238;
1.E.166.239; 1.E.166.154; 1.E.166.157; 1.E.166.166; 1.E.166.169; 1.E.166.172;
1.E.166.175; 1.E.166.240; 1.E.166.244; 1.E.169.228; 1.E.169.229; 1.E.169.230;
1.E.169.231; 1.E.169.236; 1.E.169.237; 1.E.169.238; 1.E.169.239; 1.E.169.154;
1.E.169.157; 1.E.169.166; 1.E.169.169; 1.E.169.172; 1.E.169.175; 1.E.169.240;
1.E.169.244; 1.E.172.228; 1.E.172.229; 1.E.172.230; 1.E.172.231; 1.E.172.236;
1.E.172.237; 1.E.172.238; 1.E.172.239; 1.E.172.154; 1.E.172.157; 1.E.172.166;
1.E.172.169; 1.E.172.172; 1.E.172.175; 1.E.172.240; 1.E.172.244; 1.E.175.228;
1.E.175.229; 1.E.175.230; 1.E.175.231; 1.E.175.236; 1.E.175.237; 1.E.175.238;
1.E.175.239; 1.E.175.154; 1.E.175.157; 1.E.175.166; 1.E.175.172;
1.E.175.175; 1.E.175.240; 1.E.175.244; 1.E.240.228; 1.E.240.229; 1.E.240.230;
1.E.240.231; 1.E.240.236; 1.E.240.237; 1.E.240.238; 1.E.240.239; 1.E.240.154;
1.E.240.157; 1.E.240.166; 1.E.240.169; 1.E.240.172; 1.E.240.175; 1.E.240.240;
1.E.240.244; 1.E.244.228; 1.E.244.229; 1.E.244.230; 1.E.244.231; 1.E.244.236;
1.E.244.237; 1.E.244.238; 1.E.244.239; 1.E.244.154; 1.E.244.157; 1.E.244.166;
1.E.244.169; 1.E.244.172; 1.E.244.175; 1.E.244.240; 1.E.244.244;
Prodrugs of 1.G 1.G.228.228; 1.G.228.229; 1.G.228.230; 1.G.228.231; 1.G.228.236;
1.G.228.237; 1.G.228.238; 1.G.228.239; 1.G.228.154; 1.G.228.157;
1.G.228.166; 1.G.228.169; 1.G.228.172; 1.G.228.175; 1.G.228.240;
1.G.228.244; 1.G.229.228; 1.G.229.229; 1.G.229.230; 1.G.229.231;
1.G.229.236; 1.G.229.237; 1.G.229.238; 1.G.229.239; 1.G.229.154;
1.G.229.157; 1.G.229.166; 1.G.229.169; 1.G.229.172; 1.G.229.175;
1.G.229.240; 1.G.229.244; 1.G.230.228; 1.G.230.229; 1.G.230.230;
1.G.230.231; 1.G.230.236; 1.G.230.237; 1.G.230.238; 1.G.230.239;
1.G.230.154; 1.G.230.157; 1.G.230.166; 1.G.230.169; 1.G.230.172;
1.G.230.175; 1.G.230.240; 1.G.230.244; 1.G.231.228; 1.G.231.229;
1.G.231.230; 1.G.231.231; 1.G.231.236; 1.G.231.237; 1.G.231.238;
1.G.231.239; 1.G.231.154; 1.G.231.157; 1.G.231.166; 1.G.231.169;
1.G.231.172; 1.G.231.175; 1.G.231.240; 1.G.231.244; 1.G.236.228;
1.G.236.229; 1.G.236.230; 1.G.236.231; 1.G.236.236; 1.G.236.237;
1.G.236.238; 1.G.236.239; 1.G.236.154; 1.G.236.157; 1.G.236.166;
1.G.236.169; 1.G.236.172; 1.G.236.175; 1.G.236.240; 1.G.236.244;
1.G.237.228; 1.G.237.229; 1.G.237.230; 1.G.237.231; 1.G.237.236;

TABLE 100-continued

1.G.237.237; 1.G.237.238; 1.G.237.239; 1.G.237.154; 1.G.237.157;
1.G.237.166; 1.G.237.169; 1.G.237.172; 1.G.237.175; 1.G.237.240;
1.G.237.244; 1.G.238.228; 1.G.238.229; 1.G.238.230; 1.G.238.231;
1.G.238.236; 1.G.238.237; 1.G.238.238; 1.G.238.239; 1.G.238.154;
1.G.238.157; 1.G.238.166; 1.G.238.169; 1.G.238.172; 1.G.238.175;
1.G.238.240; 1.G.238.244; 1.G.239.228; 1.G.239.229; 1.G.239.230;
1.G.239.231; 1.G.239.236; 1.G.239.237; 1.G.239.238; 1.G.239.239;
1.G.239.154; 1.G.239.157; 1.G.239.166; 1.G.239.169; 1.G.239.172;
1.G.239.175; 1.G.239.240; 1.G.239.244; 1.G.154.228; 1.G.154.229;
1.G.154.230; 1.G.154.231; 1.G.154.236; 1.G.154.237; 1.G.154.238;
1.G.154.239; 1.G.154.154; 1.G.154.157; 1.G.154.166; 1.G.154.169;
1.G.154.172; 1.G.154.175; 1.G.154.240; 1.G.154.244; 1.G.157.228;
1.G.157.229; 1.G.157.230; 1.G.157.231; 1.G.157.236; 1.G.157.237;
1.G.157.238; 1.G.157.239; 1.G.157.154; 1.G.157.157; 1.G.157.166;
1.G.157.169; 1.G.157.172; 1.G.157.175; 1.G.157.240; 1.G.157.244;
1.G.166.228; 1.G.166.229; 1.G.166.230; 1.G.166.231; 1.G.166.236;
1.G.166.237; 1.G.166.238; 1.G.166.239; 1.G.166.154; 1.G.166.157;
1.G.166.166; 1.G.166.169; 1.G.166.172; 1.G.166.175; 1.G.166.240;
1.G.166.244; 1.G.169.228; 1.G.169.229; 1.G.169.230; 1.G.169.231;
1.G.169.236; 1.G.169.237; 1.G.169.238; 1.G.169.239; 1.G.169.154;
1.G.169.157; 1.G.169.166; 1.G.169.169; 1.G.169.172; 1.G.169.175;
1.G.169.240; 1.G.169.244; 1.G.172.228; 1.G.172.229; 1.G.172.230;
1.G.172.231; 1.G.172.236; 1.G.172.237; 1.G.172.238; 1.G.172.239;
1.G.172.154; 1.G.172.157; 1.G.172.166; 1.G.172.169; 1.G.172.172;
1.G.172.175; 1.G.172.240; 1.G.172.244; 1.G.175.228; 1.G.175.229;
1.G.175.230; 1.G.175.231; 1.G.175.236; 1.G.175.237; 1.G.175.238;
1.G.175.239; 1.G.175.154; 1.G.175.157; 1.G.175.166; 1.G.175.169;
1.G.175.172; 1.G.175.175; 1.G.175.240; 1.G.175.244; 1.G.240.228;
1.G.240.229; 1.G.240.230; 1.G.240.231; 1.G.240.236; 1.G.240.237;
1.G.240.238; 1.G.240.239; 1.G.240.154; 1.G.240.157; 1.G.240.166;
1.G.240.169; 1.G.240.172; 1.G.240.175; 1.G.240.240; 1.G.240.244;
1.G.244.228; 1.G.244.229; 1.G.244.230; 1.G.244.231; 1.G.244.236;
1.G.244.237; 1.G.244.238; 1.G.244.239; 1.G.244.154; 1.G.244.157;
1.G.244.166; 1.G.244.169; 1.G.244.172; 1.G.244.175; 1.G.244.240; 1.G.244.244;
Prodrugs of 1.I 1.I.228.228; 1.I.228.229; 1.I.228.230; 1.I.228.231; 1.I.228.236; 1.I.228.237;
1.I.228.238; 1.I.228.239; 1.I.228.154; 1.I.228.157; 1.I.228.166; 1.I.228.169;
1.I.228.172; 1.I.228.175; 1.I.228.240; 1.I.228.244; 1.I.229.228; 1.I.229.229;
1.I.229.230; 1.I.229.231; 1.I.229.236; 1.I.229.237; 1.I.229.238; 1.I.229.239;
1.I.229.154; 1.I.229.157; 1.I.229.166; 1.I.229.169; 1.I.229.172; 1.I.229.175;
1.I.229.240; 1.I.229.244; 1.I.230.228; 1.I.230.229; 1.I.230.230; 1.I.230.231;
1.I.230.236; 1.I.230.237; 1.I.230.238; 1.I.230.239; 1.I.230.154; 1.I.230.157;
1.I.230.166; 1.I.230.169; 1.I.230.172; 1.I.230.175; 1.I.230.240; 1.I.230.244;
1.I.231.228; 1.I.231.229; 1.I.231.230; 1.I.231.231; 1.I.231.236; 1.I.231.237;
1.I.231.238; 1.I.231.239; 1.I.231.154; 1.I.231.157; 1.I.231.166; 1.I.231.169;
1.I.231.172; 1.I.231.175; 1.I.231.240; 1.I.231.244; 1.I.236.228; 1.I.236.229;
1.I.236.230; 1.I.236.231; 1.I.236.236; 1.I.236.237; 1.I.236.238; 1.I.236.239;
1.I.236.154; 1.I.236.157; 1.I.236.166; 1.I.236.169; 1.I.236.172; 1.I.236.175;
1.I.236.240; 1.I.236.244; 1.I.237.228; 1.I.237.229; 1.I.237.230; 1.I.237.231;
1.I.237.236; 1.I.237.237; 1.I.237.238; 1.I.237.239; 1.I.237.154; 1.I.237.157;
1.I.237.166; 1.I.237.169; 1.I.237.172; 1.I.237.175; 1.I.237.240; 1.I.237.244;
1.I.238.228; 1.I.238.229; 1.I.238.230; 1.I.238.231; 1.I.238.236; 1.I.238.237;
1.I.238.238; 1.I.238.239; 1.I.238.154; 1.I.238.157; 1.I.238.166; 1.I.238.169;
1.I.238.172; 1.I.238.175; 1.I.238.240; 1.I.238.244; 1.I.239.228; 1.I.239.229;
1.I.239.230; 1.I.239.231; 1.I.239.236; 1.I.239.237; 1.I.239.238; 1.I.239.239;
1.I.239.154; 1.I.239.157; 1.I.239.166; 1.I.239.169; 1.I.239.172; 1.I.239.175;
1.I.239.240; 1.I.239.244; 1.I.154.228; 1.I.154.229; 1.I.154.230; 1.I.154.231;
1.I.154.236; 1.I.154.237; 1.I.154.238; 1.I.154.239; 1.I.154.154; 1.I.154.157;
1.I.154.166; 1.I.154.169; 1.I.154.172; 1.I.154.175; 1.I.154.240; 1.I.154.244;
1.I.157.228; 1.I.157.229; 1.I.157.230; 1.I.157.231; 1.I.157.236; 1.I.157.237;
1.I.157.238; 1.I.157.239; 1.I.157.154; 1.I.157.157; 1.I.157.166; 1.I.157.169;
1.I.157.172; 1.I.157.175; 1.I.157.240; 1.I.157.244; 1.I.166.228; 1.I.166.229;
1.I.166.230; 1.I.166.231; 1.I.166.236; 1.I.166.237; 1.I.166.238; 1.I.166.239;
1.I.166.154; 1.I.166.157; 1.I.166.166; 1.I.166.169; 1.I.166.172; 1.I.166.175;
1.I.166.240; 1.I.166.244; 1.I.169.228; 1.I.169.229; 1.I.169.230; 1.I.169.231;
1.I.169.236; 1.I.169.237; 1.I.169.238; 1.I.169.239; 1.I.169.154; 1.I.169.157;
1.I.169.166; 1.I.169.169; 1.I.169.172; 1.I.169.175; 1.I.169.240; 1.I.169.244;
1.I.172.228; 1.I.172.229; 1.I.172.230; 1.I.172.231; 1.I.172.236; 1.I.172.237;
1.I.172.238; 1.I.172.239; 1.I.172.154; 1.I.172.157; 1.I.172.166; 1.I.172.169;
1.I.172.172; 1.I.172.175; 1.I.172.240; 1.I.172.244; 1.I.175.228; 1.I.175.229;
1.I.175.230; 1.I.175.231; 1.I.175.236; 1.I.175.237; 1.I.175.238; 1.I.175.239;
1.I.175.154; 1.I.175.157; 1.I.175.166; 1.I.175.169; 1.I.175.172; 1.I.175.175;
1.I.175.240; 1.I.175.244; 1.I.240.228; 1.I.240.229; 1.I.240.230; 1.I.240.231;
1.I.240.236; 1.I.240.237; 1.I.240.238; 1.I.240.239; 1.I.240.154; 1.I.240.157;
1.I.240.166; 1.I.240.169; 1.I.240.172; 1.I.240.175; 1.I.240.240; 1.I.240.244;
1.I.244.228; 1.I.244.229; 1.I.244.230; 1.I.244.231; 1.I.244.236; 1.I.244.237;
1.I.244.238; 1.I.244.239; 1.I.244.154; 1.I.244.157; 1.I.244.166; 1.I.244.169;
1.I.244.172; 1.I.244.175; 1.I.244.240; 1.I.244.244;

TABLE 100-continued

Prodrugs of 1.J

1.J.228.228; 1.J.228.229; 1.J.228.230; 1.J.228.231; 1.J.228.236; 1.J.228.237;
1.J.228.238; 1.J.228.239; 1.J.228.154; 1.J.228.157; 1.J.228.166; 1.J.228.169;
1.J.228.172; 1.J.228.175; 1.J.228.240; 1.J.228.244; 1.J.229.228; 1.J.229.229;
1.J.229.230; 1.J.229.231; 1.J.229.236; 1.J.229.237; 1.J.229.238; 1.J.229.239;
1.J.229.154; 1.J.229.157; 1.J.229.166; 1.J.229.169; 1.J.229.172; 1.J.229.175;
1.J.229.240; 1.J.229.244; 1.J.230.228; 1.J.230.229; 1.J.230.230; 1.J.230.231;
1.J.230.236; 1.J.230.237; 1.J.230.238; 1.J.230.239; 1.J.230.154; 1.J.230.157;
1.J.230.166; 1.J.230.169; 1.J.230.172; 1.J.230.175; 1.J.230.240; 1.J.230.244;
1.J.231.228; 1.J.231.229; 1.J.231.230; 1.J.231.231; 1.J.231.236; 1.J.231.237;
1.J.231.238; 1.J.231.239; 1.J.231.154; 1.J.231.157; 1.J.231.166; 1.J.231.169;
1.J.231.172; 1.J.231.175; 1.J.231.240; 1.J.231.244; 1.J.236.228; 1.J.236.229;
1.J.236.230; 1.J.236.231; 1.J.236.236; 1.J.236.237; 1.J.236.238; 1.J.236.239;
1.J.236.154; 1.J.236.157; 1.J.236.166; 1.J.236.169; 1.J.236.172; 1.J.236.175;
1.J.236.240; 1.J.236.244; 1.J.237.228; 1.J.237.229; 1.J.237.230; 1.J.237.231;
1.J.237.236; 1.J.237.237; 1.J.237.238; 1.J.237.239; 1.J.237.154; 1.J.237.157;
1.J.237.166; 1.J.237.169; 1.J.237.172; 1.J.237.175; 1.J.237.240; 1.J.237.244;
1.J.238.228; 1.J.238.229; 1.J.238.230; 1.J.238.231; 1.J.238.236; 1.J.238.237;
1.J.238.238; 1.J.238.239; 1.J.238.154; 1.J.238.157; 1.J.238.166; 1.J.238.169;
1.J.238.172; 1.J.238.175; 1.J.238.240; 1.J.238.244; 1.J.239.228; 1.J.239.229;
1.J.239.230; 1.J.239.231; 1.J.239.236; 1.J.239.237; 1.J.239.238; 1.J.239.239;
1.J.239.154; 1.J.239.157; 1.J.239.166; 1.J.239.169; 1.J.239.172; 1.J.239.175;
1.J.239.240; 1.J.239.244; 1.J.154.228; 1.J.154.229; 1.J.154.230; 1.J.154.231;
1.J.154.236; 1.J.154.237; 1.J.154.238; 1.J.154.239; 1.J.154.154; 1.J.154.157;
1.J.154.166; 1.J.154.169; 1.J.154.172; 1.J.154.175; 1.J.154.240; 1.J.154.244;
1.J.157.228; 1.J.157.229; 1.J.157.230; 1.J.157.231; 1.J.157.236; 1.J.157.237;
1.J.157.238; 1.J.157.239; 1.J.157.154; 1.J.157.157; 1.J.157.166; 1.J.157.169;
1.J.157.172; 1.J.157.175; 1.J.157.240; 1.J.157.244; 1.J.166.228; 1.J.166.229;
1.J.166.230; 1.J.166.231; 1.J.166.236; 1.J.166.237; 1.J.166.238; 1.J.166.239;
1.J.166.154; 1.J.166.157; 1.J.166.166; 1.J.166.169; 1.J.166.172; 1.J.166.175;
1.J.166.240; 1.J.166.244; 1.J.169.228; 1.J.169.229; 1.J.169.230; 1.J.169.231;
1.J.169.236; 1.J.169.237; 1.J.169.238; 1.J.169.239; 1.J.169.154; 1.J.169.157;
1.J.169.166; 1.J.169.169; 1.J.169.172; 1.J.169.175; 1.J.169.240; 1.J.169.244;
1.J.172.228; 1.J.172.229; 1.J.172.230; 1.J.172.231; 1.J.172.236; 1.J.172.237;
1.J.172.238; 1.J.172.239; 1.J.172.154; 1.J.172.157; 1.J.172.166; 1.J.172.169;
1.J.172.172; 1.J.172.175; 1.J.172.240; 1.J.172.244; 1.J.175.228; 1.J.175.229;
1.J.175.230; 1.J.175.231; 1.J.175.236; 1.J.175.237; 1.J.175.238; 1.J.175.239;
1.J.175.154; 1.J.175.157; 1.J.175.166; 1.J.175.169; 1.J.175.172; 1.J.175.175;
1.J.175.240; 1.J.175.244; 1.J.240.228; 1.J.240.229; 1.J.240.230; 1.J.240.231;
1.J.240.236; 1.J.240.237; 1.J.240.238; 1.J.240.239; 1.J.240.154; 1.J.240.157;
1.J.240.166; 1.J.240.169; 1.J.240.172; 1.J.240.175; 1.J.240.240; 1.J.240.244;
1.J.244.228; 1.J.244.229; 1.J.244.230; 1.J.244.231; 1.J.244.236; 1.J.244.237;
1.J.244.238; 1.J.244.239; 1.J.244.154; 1.J.244.157; 1.J.244.166; 1.J.244.169;
1.J.244.172; 1.J.244.175; 1.J.244.240; 1.J.244.244;

Prodrugs of 1.L

1.L.228.228; 1.L.228.229; 1.L.228.230; 1.L.228.231; 1.L.228.236;
1.L.228.237; 1.L.228.238; 1.L.228.239; 1.L.228.154; 1.L.228.157; 1.L.228.166;
1.L.228.169; 1.L.228.172; 1.L.228.175; 1.L.228.240; 1.L.228.244; 1.L.229.228;
1.L.229.229; 1.L.229.230; 1.L.229.231; 1.L.229.236; 1.L.229.237; 1.L.229.238;
1.L.229.239; 1.L.229.154; 1.L.229.157; 1.L.229.166; 1.L.229.169; 1.L.229.172;
1.L.229.175; 1.L.229.240; 1.L.229.244; 1.L.230.228; 1.L.230.229; 1.L.230.230;
1.L.230.231; 1.L.230.236; 1.L.230.237; 1.L.230.238; 1.L.230.239; 1.L.230.154;
1.L.230.157; 1.L.230.166; 1.L.230.169; 1.L.230.172; 1.L.230.175; 1.L.230.240;
1.L.230.244; 1.L.231.228; 1.L.231.229; 1.L.231.230; 1.L.231.231; 1.L.231.236;
1.L.231.237; 1.L.231.238; 1.L.231.239; 1.L.231.154; 1.L.231.157; 1.L.231.166;
1.L.231.169; 1.L.231.172; 1.L.231.175; 1.L.231.240; 1.L.231.244; 1.L.236.228;
1.L.236.229; 1.L.236.230; 1.L.236.231; 1.L.236.236; 1.L.236.237; 1.L.236.238;
1.L.236.239; 1.L.236.154; 1.L.236.157; 1.L.236.166; 1.L.236.169; 1.L.236.172;
1.L.236.175; 1.L.236.240; 1.L.236.244; 1.L.237.228; 1.L.237.229; 1.L.237.230;
1.L.237.231; 1.L.237.236; 1.L.237.237; 1.L.237.238; 1.L.237.239; 1.L.237.154;
1.L.237.157; 1.L.237.166; 1.L.237.169; 1.L.237.172; 1.L.237.175; 1.L.237.240;
1.L.237.244; 1.L.238.228; 1.L.238.229; 1.L.238.230; 1.L.238.231; 1.L.238.236;
1.L.238.237; 1.L.238.238; 1.L.238.239; 1.L.238.154; 1.L.238.157; 1.L.238.166;
1.L.238.169; 1.L.238.172; 1.L.238.175; 1.L.238.240; 1.L.238.244; 1.L.239.228;
1.L.239.229; 1.L.239.230; 1.L.239.231; 1.L.239.236; 1.L.239.237; 1.L.239.238;
1.L.239.239; 1.L.239.154; 1.L.239.157; 1.L.239.166; 1.L.239.169; 1.L.239.172;
1.L.239.175; 1.L.239.240; 1.L.239.244; 1.L.154.228; 1.L.154.229; 1.L.154.230;
1.L.154.231; 1.L.154.236; 1.L.154.237; 1.L.154.238; 1.L.154.239; 1.L.154.154;
1.L.154.157; 1.L.154.166; 1.L.154.169; 1.L.154.172; 1.L.154.175; 1.L.154.240;
1.L.154.244; 1.L.157.228; 1.L.157.229; 1.L.157.230; 1.L.157.231; 1.L.157.236;
1.L.157.237; 1.L.157.238; 1.L.157.239; 1.L.157.154; 1.L.157.157; 1.L.157.166;
1.L.157.169; 1.L.157.172; 1.L.157.175; 1.L.157.240; 1.L.157.244; 1.L.166.228;
1.L.166.229; 1.L.166.230; 1.L.166.231; 1.L.166.236; 1.L.166.237; 1.L.166.238;
1.L.166.239; 1.L.166.154; 1.L.166.157; 1.L.166.166; 1.L.166.169; 1.L.166.172;
1.L.166.175; 1.L.166.240; 1.L.166.244; 1.L.169.228; 1.L.169.229; 1.L.169.230;
1.L.169.231; 1.L.169.236; 1.L.169.237; 1.L.169.238; 1.L.169.239; 1.L.169.154;
1.L.169.157; 1.L.169.166; 1.L.169.169; 1.L.169.172; 1.L.169.175; 1.L.169.240;

TABLE 100-continued

1.L.169.244; 1.L.172.228; 1.L.172.229; 1.L.172.230; 1.L.172.231; 1.L.172.236; 1.L.172.237; 1.L.172.238; 1.L.172.239; 1.L.172.154; 1.L.172.157; 1.L.172.166; 1.L.172.169; 1.L.172.172; 1.L.172.175; 1.L.172.240; 1.L.172.244; 1.L.175.228; 1.L.175.229; 1.L.175.230; 1.L.175.231; 1.L.175.236; 1.L.175.237; 1.L.175.238; 1.L.175.239; 1.L.175.154; 1.L.175.157; 1.L.175.166; 1.L.175.169; 1.L.175.172; 1.L.175.175; 1.L.175.240; 1.L.175.244; 1.L.240.228; 1.L.240.229; 1.L.240.230; 1.L.240.231; 1.L.240.236; 1.L.240.237; 1.L.240.238; 1.L.240.239; 1.L.240.154; 1.L.240.157; 1.L.240.166; 1.L.240.169; 1.L.240.172; 1.L.240.175; 1.L.240.240; 1.L.240.244; 1.L.244.228; 1.L.244.229; 1.L.244.230; 1.L.244.231; 1.L.244.236; 1.L.244.237; 1.L.244.238; 1.L.244.239; 1.L.244.154; 1.L.244.157; 1.L.244.166; 1.L.244.169; 1.L.244.172; 1.L.244.175; 1.L.244.240; 1.L.244.244;

Prodrugs of 1.O

1.O.228.228; 1.O.228.229; 1.O.228.230; 1.O.228.231; 1.O.228.236; 1.O.228.237; 1.O.228.238; 1.O.228.239; 1.O.228.154; 1.O.228.157; 1.O.228.166; 1.O.228.169; 1.O.228.172; 1.O.228.175; 1.O.228.240; 1.O.228.244; 1.O.229.228; 1.O.229.229; 1.O.229.230; 1.O.229.231; 1.O.229.236; 1.O.229.237; 1.O.229.238; 1.O.229.239; 1.O.229.154; 1.O.229.157; 1.O.229.166; 1.O.229.169; 1.O.229.172; 1.O.229.175; 1.O.229.240; 1.O.229.244; 1.O.230.228; 1.O.230.229; 1.O.230.230; 1.O.230.231; 1.O.230.236; 1.O.230.237; 1.O.230.238; 1.O.230.239; 1.O.230.154; 1.O.230.157; 1.O.230.166; 1.O.230.169; 1.O.230.172; 1.O.230.175; 1.O.230.240; 1.O.230.244; 1.O.231.228; 1.O.231.229; 1.O.231.230; 1.O.231.231; 1.O.231.236; 1.O.231.237; 1.O.231.238; 1.O.231.239; 1.O.231.154; 1.O.231.157; 1.O.231.166; 1.O.231.169; 1.O.231.172; 1.O.231.175; 1.O.231.240; 1.O.231.244; 1.O.236.228; 1.O.236.229; 1.O.236.230; 1.O.236.231; 1.O.236.236; 1.O.236.237; 1.O.236.238; 1.O.236.239; 1.O.236.154; 1.O.236.157; 1.O.236.166; 1.O.236.169; 1.O.236.172; 1.O.236.175; 1.O.236.240; 1.O.236.244; 1.O.237.228; 1.O.237.229; 1.O.237.230; 1.O.237.231; 1.O.237.236; 1.O.237.237; 1.O.237.238; 1.O.237.239; 1.O.237.154; 1.O.237.157; 1.O.237.166; 1.O.237.169; 1.O.237.172; 1.O.237.175; 1.O.237.240; 1.O.237.244; 1.O.238.228; 1.O.238.229; 1.O.238.230; 1.O.238.231; 1.O.238.236; 1.O.238.237; 1.O.238.238; 1.O.238.239; 1.O.238.154; 1.O.238.157; 1.O.238.166; 1.O.238.169; 1.O.238.172; 1.O.238.175; 1.O.238.240; 1.O.238.244; 1.O.239.228; 1.O.239.229; 1.O.239.230; 1.O.239.231; 1.O.239.236; 1.O.239.237; 1.O.239.238; 1.O.239.239; 1.O.239.154; 1.O.239.157; 1.O.239.166; 1.O.239.169; 1.O.239.172; 1.O.239.175; 1.O.239.240; 1.O.239.244; 1.O.154.228; 1.O.154.229; 1.O.154.230; 1.O.154.231; 1.O.154.236; 1.O.154.237; 1.O.154.238; 1.O.154.239; 1.O.154.154; 1.O.154.157; 1.O.154.166; 1.O.154.169; 1.O.154.172; 1.O.154.175; 1.O.154.240; 1.O.154.244; 1.O.157.228; 1.O.157.229; 1.O.157.230; 1.O.157.231; 1.O.157.236; 1.O.157.237; 1.O.157.238; 1.O.157.239; 1.O.157.154; 1.O.157.157; 1.O.157.166; 1.O.157.169; 1.O.157.172; 1.O.157.175; 1.O.157.240; 1.O.157.244; 1.O.166.228; 1.O.166.229; 1.O.166.230; 1.O.166.231; 1.O.166.236; 1.O.166.237; 1.O.166.238; 1.O.166.239; 1.O.166.154; 1.O.166.157; 1.O.166.166; 1.O.166.169; 1.O.166.172; 1.O.166.175; 1.O.166.240; 1.O.166.244; 1.O.169.228; 1.O.169.229; 1.O.169.230; 1.O.169.231; 1.O.169.236; 1.O.169.237; 1.O.169.238; 1.O.169.239; 1.O.169.154; 1.O.169.157; 1.O.169.166; 1.O.169.169; 1.O.169.172; 1.O.169.175; 1.O.169.240; 1.O.169.244; 1.O.172.228; 1.O.172.229; 1.O.172.230; 1.O.172.231; 1.O.172.236; 1.O.172.237; 1.O.172.238; 1.O.172.239; 1.O.172.154; 1.O.172.157; 1.O.172.166; 1.O.172.169; 1.O.172.172; 1.O.172.175; 1.O.172.240; 1.O.172.244; 1.O.175.228; 1.O.175.229; 1.O.175.230; 1.O.175.231; 1.O.175.236; 1.O.175.237; 1.O.175.238; 1.O.175.239; 1.O.175.154; 1.O.175.157; 1.O.175.166; 1.O.175.169; 1.O.175.172; 1.O.175.175; 1.O.175.240; 1.O.175.244; 1.O.240.228; 1.O.240.229; 1.O.240.230; 1.O.240.231; 1.O.240.236; 1.O.240.237; 1.O.240.238; 1.O.240.239; 1.O.240.154; 1.O.240.157; 1.O.240.166; 1.O.240.169; 1.O.240.172; 1.O.240.175; 1.O.240.240; 1.O.240.244; 1.O.244.228; 1.O.244.229; 1.O.244.230; 1.O.244.231; 1.O.244.236; 1.O.244.237; 1.O.244.238; 1.O.244.239; 1.O.244.154; 1.O.244.157; 1.O.244.166; 1.O.244.169; 1.O.244.172; 1.O.244.175; 1.O.244.240; 1.O.244.244;

Prodrugs of 1.P

1.P.228.228; 1.P.228.229; 1.P.228.230; 1.P.228.231; 1.P.228.236; 1.P.228.237; 1.P.228.238; 1.P.228.239; 1.P.228.154; 1.P.228.157; 1.P.228.166; 1.P.228.169; 1.P.228.172; 1.P.228.175; 1.P.228.240; 1.P.228.244; 1.P.229.228; 1.P.229.229; 1.P.229.230; 1.P.229.231; 1.P.229.236; 1.P.229.237; 1.P.229.238; 1.P.229.239; 1.P.229.154; 1.P.229.157; 1.P.229.166; 1.P.229.169; 1.P.229.172; 1.P.229.175; 1.P.229.240; 1.P.229.244; 1.P.230.228; 1.P.230.229; 1.P.230.230; 1.P.230.231; 1.P.230.236; 1.P.230.237; 1.P.230.238; 1.P.230.239; 1.P.230.154; 1.P.230.157; 1.P.230.166; 1.P.230.169; 1.P.230.172; 1.P.230.175; 1.P.230.240; 1.P.230.244; 1.P.231.228; 1.P.231.229; 1.P.231.230; 1.P.231.231; 1.P.231.236; 1.P.231.237; 1.P.231.238; 1.P.231.239; 1.P.231.154; 1.P.231.157; 1.P.231.166; 1.P.231.169; 1.P.231.172; 1.P.231.175; 1.P.231.240; 1.P.231.244; 1.P.236.228; 1.P.236.229; 1.P.236.230; 1.P.236.231; 1.P.236.236; 1.P.236.237; 1.P.236.238;

TABLE 100-continued

1.P.236.239; 1.P.236.154; 1.P.236.157; 1.P.236.166; 1.P.236.169; 1.P.236.172;
1.P.236.175; 1.P.236.240; 1.P.236.244; 1.P.237.228; 1.P.237.229; 1.P.237.230;
1.P.237.231; 1.P.237.236; 1.P.237.237; 1.P.237.238; 1.P.237.239; 1.P.237.154;
1.P.237.157; 1.P.237.166; 1.P.237.169; 1.P.237.172; 1.P.237.175; 1.P.237.240;
1.P.237.244; 1.P.238.228; 1.P.238.229; 1.P.238.230; 1.P.238.231; 1.P.238.236;
1.P.238.237; 1.P.238.238; 1.P.238.239; 1.P.238.154; 1.P.238.157; 1.P.238.166;
1.P.238.169; 1.P.238.172; 1.P.238.175; 1.P.238.240; 1.P.238.244; 1.P.239.228;
1.P.239.229; 1.P.239.230; 1.P.239.231; 1.P.239.236; 1.P.239.237; 1.P.239.238;
1.P.239.239; 1.P.239.154; 1.P.239.157; 1.P.239.166; 1.P.239.169; 1.P.239.172;
1.P.239.175; 1.P.239.240; 1.P.239.244; 1.P.154.228; 1.P.154.229; 1.P.154.230;
1.P.154.231; 1.P.154.236; 1.P.154.237; 1.P.154.238; 1.P.154.239; 1.P.154.154;
1.P.154.157; 1.P.154.166; 1.P.154.169; 1.P.154.172; 1.P.154.175; 1.P.154.240;
1.P.154.244; 1.P.157.228; 1.P.157.229; 1.P.157.230; 1.P.157.231; 1.P.157.236;
1.P.157.237; 1.P.157.238; 1.P.157.239; 1.P.157.154; 1.P.157.157; 1.P.157.166;
1.P.157.169; 1.P.157.172; 1.P.157.175; 1.P.157.240; 1.P.157.244; 1.P.166.228;
1.P.166.229; 1.P.166.230; 1.P.166.231; 1.P.166.236; 1.P.166.237; 1.P.166.238;
1.P.166.239; 1.P.166.154; 1.P.166.157; 1.P.166.166; 1.P.166.169; 1.P.166.172;
1.P.166.175; 1.P.166.240; 1.P.166.244; 1.P.169.228; 1.P.169.229; 1.P.169.230;
1.P.169.231; 1.P.169.236; 1.P.169.237; 1.P.169.238; 1.P.169.239; 1.P.169.154;
1.P.169.157; 1.P.169.166; 1.P.169.169; 1.P.169.172; 1.P.169.175; 1.P.169.240;
1.P.169.244; 1.P.172.228; 1.P.172.229; 1.P.172.230; 1.P.172.231; 1.P.172.236;
1.P.172.237; 1.P.172.238; 1.P.172.239; 1.P.172.154; 1.P.172.157; 1.P.172.166;
1.P.172.169; 1.P.172.172; 1.P.172.175; 1.P.172.240; 1.P.172.244; 1.P.175.228;
1.P.175.229; 1.P.175.230; 1.P.175.231; 1.P.175.236; 1.P.175.237; 1.P.175.238;
1.P.175.239; 1.P.175.154; 1.P.175.157; 1.P.175.166; 1.P.175.169; 1.P.175.172;
1.P.175.175; 1.P.175.240; 1.P.175.244; 1.P.240.228; 1.P.240.229; 1.P.240.230;
1.P.240.231; 1.P.240.236; 1.P.240.237; 1.P.240.238; 1.P.240.239; 1.P.240.154;
1.P.240.157; 1.P.240.166; 1.P.240.169; 1.P.240.172; 1.P.240.175; 1.P.240.240;
1.P.240.244; 1.P.244.228; 1.P.244.229; 1.P.244.230; 1.P.244.231; 1.P.244.236;
1.P.244.237; 1.P.244.238; 1.P.244.239; 1.P.244.154; 1.P.244.157; 1.P.244.166;
1.P.244.169; 1.P.244.172; 1.P.244.175; 1.P.244.240; 1.P.244.244;
Prodrugs of 1.U 1.U.228.228; 1.U.228.229; 1.U.228.230; 1.U.228.231; 1.U.228.236;
1.U.228.237; 1.U.228.238; 1.U.228.239; 1.U.228.154; 1.U.228.157;
1.U.228.166; 1.U.228.169; 1.U.228.172; 1.U.228.175; 1.U.228.240;
1.U.228.244; 1.U.229.228; 1.U.229.229; 1.U.229.230; 1.U.229.231;
1.U.229.236; 1.U.229.237; 1.U.229.238; 1.U.229.239; 1.U.229.154;
1.U.229.157; 1.U.229.166; 1.U.229.169; 1.U.229.172; 1.U.229.175;
1.U.229.240; 1.U.229.244; 1.U.230.228; 1.U.230.229; 1.U.230.230;
1.U.230.231; 1.U.230.236; 1.U.230.237; 1.U.230.238; 1.U.230.239;
1.U.230.154; 1.U.230.157; 1.U.230.166; 1.U.230.169; 1.U.230.172;
1.U.230.175; 1.U.230.240; 1.U.230.244; 1.U.231.228; 1.U.231.229;
1.U.231.230; 1.U.231.231; 1.U.231.236; 1.U.231.237; 1.U.231.238;
1.U.231.239; 1.U.231.154; 1.U.231.157; 1.U.231.166; 1.U.231.169;
1.U.231.172; 1.U.231.175; 1.U.231.240; 1.U.231.244; 1.U.236.228;
1.U.236.229; 1.U.236.230; 1.U.236.231; 1.U.236.236; 1.U.236.237;
1.U.236.238; 1.U.236.239; 1.U.236.154; 1.U.236.157; 1.U.236.166;
1.U.236.169; 1.U.236.172; 1.U.236.175; 1.U.236.240; 1.U.236.244;
1.U.237.228; 1.U.237.229; 1.U.237.230; 1.U.237.231; 1.U.237.236;
1.U.237.237; 1.U.237.238; 1.U.237.239; 1.U.237.154; 1.U.237.157;
1.U.237.166; 1.U.237.169; 1.U.237.172; 1.U.237.175; 1.U.237.240;
1.U.237.244; 1.U.238.228; 1.U.238.229; 1.U.238.230; 1.U.238.231;
1.U.238.236; 1.U.238.237; 1.U.238.238; 1.U.238.239; 1.U.238.154;
1.U.238.157; 1.U.238.166; 1.U.238.169; 1.U.238.172; 1.U.238.175;
1.U.238.240; 1.U.238.244; 1.U.239.228; 1.U.239.229; 1.U.239.230;
1.U.239.231; 1.U.239.236; 1.U.239.237; 1.U.239.238; 1.U.239.239;
1.U.239.154; 1.U.239.157; 1.U.239.166; 1.U.239.169; 1.U.239.172;
1.U.239.175; 1.U.239.240; 1.U.239.244; 1.U.154.228; 1.U.154.229;
1.U.154.230; 1.U.154.231; 1.U.154.236; 1.U.154.237; 1.U.154.238;
1.U.154.239; 1.U.154.154; 1.U.154.157; 1.U.154.166; 1.U.154.169;
1.U.154.172; 1.U.154.175; 1.U.154.240; 1.U.154.244; 1.U.157.228;
1.U.157.229; 1.U.157.230; 1.U.157.231; 1.U.157.236; 1.U.157.237;
1.U.157.238; 1.U.157.239; 1.U.157.154; 1.U.157.157; 1.U.157.166;
1.U.157.169; 1.U.157.172; 1.U.157.175; 1.U.157.240; 1.U.157.244;
1.U.166.228; 1.U.166.229; 1.U.166.230; 1.U.166.231; 1.U.166.236;
1.U.166.237; 1.U.166.238; 1.U.166.239; 1.U.166.154; 1.U.166.157;
1.U.166.166; 1.U.166.169; 1.U.166.172; 1.U.166.175; 1.U.166.240;
1.U.166.244; 1.U.169.228; 1.U.169.229; 1.U.169.230; 1.U.169.231;
1.U.169.236; 1.U.169.237; 1.U.169.238; 1.U.169.239; 1.U.169.154;
1.U.169.157; 1.U.169.166; 1.U.169.169; 1.U.169.172; 1.U.169.175;
1.U.169.240; 1.U.169.244; 1.U.172.228; 1.U.172.229; 1.U.172.230;
1.U.172.231; 1.U.172.236; 1.U.172.237; 1.U.172.238; 1.U.172.239;
1.U.172.154; 1.U.172.157; 1.U.172.166; 1.U.172.169; 1.U.172.172;
1.U.172.175; 1.U.172.240; 1.U.172.244; 1.U.175.228; 1.U.175.229;
1.U.175.230; 1.U.175.231; 1.U.175.236; 1.U.175.237; 1.U.175.238;
1.U.175.239; 1.U.175.154; 1.U.175.157; 1.U.175.166; 1.U.175.169;
1.U.175.172; 1.U.175.175; 1.U.175.240; 1.U.175.244; 1.U.240.228;
1.U.240.229; 1.U.240.230; 1.U.240.231; 1.U.240.236; 1.U.240.237;

TABLE 100-continued

1.U.240.238; 1.U.240.239; 1.U.240.154; 1.U.240.157; 1.U.240.166;
1.U.240.169; 1.U.240.172; 1.U.240.175; 1.U.240.240; 1.U.240.244;
1.U.244.228; 1.U.244.229; 1.U.244.230; 1.U.244.231; 1.U.244.236;
1.U.244.237; 1.U.244.238; 1.U.244.239; 1.U.244.154; 1.U.244.157;
1.U.244.166; 1.U.244.169; 1.U.244.172; 1.U.244.175; 1.U.244.240;
1.U.244.244;
Prodrugs of 1.W 1.W.228.228; 1.W.228.229; 1.W.228.230; 1.W.228.231; 1.W.228.236;
1.W.228.237; 1.W.228.238; 1.W.228.239; 1.W.228.154; 1.W.228.157;
1.W.228.166; 1.W.228.169; 1.W.228.172; 1.W.228.175; 1.W.228.240;
1.W.228.244; 1.W.229.228; 1.W.229.229; 1.W.229.230; 1.W.229.231;
1.W.229.236; 1.W.229.237; 1.W.229.238; 1.W.229.239; 1.W.229.154;
1.W.229.157; 1.W.229.166; 1.W.229.169; 1.W.229.172; 1.W.229.175;
1.W.229.240; 1.W.229.244; 1.W.230.228; 1.W.230.229; 1.W.230.230;
1.W.230.231; 1.W.230.236; 1.W.230.237; 1.W.230.238; 1.W.230.239;
1.W.230.154; 1.W.230.157; 1.W.230.166; 1.W.230.169; 1.W.230.172;
1.W.230.175; 1.W.230.240; 1.W.230.244; 1.W.231.228; 1.W.231.229;
1.W.231.230; 1.W.231.231; 1.W.231.236; 1.W.231.237; 1.W.231.238;
1.W.231.239; 1.W.231.154; 1.W.231.157; 1.W.231.166; 1.W.231.169;
1.W.231.172; 1.W.231.175; 1.W.231.240; 1.W.231.244; 1.W.236.228;
1.W.236.229; 1.W.236.230; 1.W.236.231; 1.W.236.236; 1.W.236.237;
1.W.236.238; 1.W.236.239; 1.W.236.154; 1.W.236.157; 1.W.236.166;
1.W.236.169; 1.W.236.172; 1.W.236.175; 1.W.236.240; 1.W.236.244;
1.W.237.228; 1.W.237.229; 1.W.237.230; 1.W.237.231; 1.W.237.236;
1.W.237.237; 1.W.237.238; 1.W.237.239; 1.W.237.154; 1.W.237.157;
1.W.237.166; 1.W.237.169; 1.W.237.172; 1.W.237.175; 1.W.237.240;
1.W.237.244; 1.W.238.228; 1.W.238.229; 1.W.238.230; 1.W.238.231;
1.W.238.236; 1.W.238.237; 1.W.238.238; 1.W.238.239; 1.W.238.154;
1.W.238.157; 1.W.238.166; 1.W.238.169; 1.W.238.172; 1.W.238.175;
1.W.238.240; 1.W.238.244; 1.W.239.228; 1.W.239.229; 1.W.239.230;
1.W.239.231; 1.W.239.236; 1.W.239.237; 1.W.239.238; 1.W.239.239;
1.W.239.154; 1.W.239.157; 1.W.239.166; 1.W.239.169; 1.W.239.172;
1.W.239.175; 1.W.239.240; 1.W.239.244; 1.W.154.228; 1.W.154.229;
1.W.154.230; 1.W.154.231; 1.W.154.236; 1.W.154.237; 1.W.154.238;
1.W.154.239; 1.W.154.154; 1.W.154.157; 1.W.154.166; 1.W.154.169;
1.W.154.172; 1.W.154.175; 1.W.154.240; 1.W.154.244; 1.W.157.228;
1.W.157.229; 1.W.157.230; 1.W.157.231; 1.W.157.236; 1.W.157.237;
1.W.157.238; 1.W.157.239; 1.W.157.154; 1.W.157.157; 1.W.157.166;
1.W.157.169; 1.W.157.172; 1.W.157.175; 1.W.157.240; 1.W.157.244;
1.W.166.228; 1.W.166.229; 1.W.166.230; 1.W.166.231; 1.W.166.236;
1.W.166.237; 1.W.166.238; 1.W.166.239; 1.W.166.154; 1.W.166.157;
1.W.166.166; 1.W.166.169; 1.W.166.172; 1.W.166.175; 1.W.166.240;
1.W.166.244; 1.W.169.228; 1.W.169.229; 1.W.169.230; 1.W.169.231;
1.W.169.236; 1.W.169.237; 1.W.169.238; 1.W.169.239; 1.W.169.154;
1.W.169.157; 1.W.169.166; 1.W.169.169; 1.W.169.172; 1.W.169.175;
1.W.169.240; 1.W.169.244; 1.W.172.228; 1.W.172.229; 1.W.172.230;
1.W.172.231; 1.W.172.236; 1.W.172.237; 1.W.172.238; 1.W.172.239;
1.W.172.154; 1.W.172.157; 1.W.172.166; 1.W.172.169; 1.W.172.172;
1.W.172.175; 1.W.172.240; 1.W.172.244; 1.W.175.228; 1.W.175.229;
1.W.175.230; 1.W.175.231; 1.W.175.236; 1.W.175.237; 1.W.175.238;
1.W.175.239; 1.W.175.154; 1.W.175.157; 1.W.175.166; 1.W.175.169;
1.W.175.172; 1.W.175.175; 1.W.175.240; 1.W.175.244; 1.W.240.228;
1.W.240.229; 1.W.240.230; 1.W.240.231; 1.W.240.236; 1.W.240.237;
1.W.240.238; 1.W.240.239; 1.W.240.154; 1.W.240.157; 1.W.240.166;
1.W.240.169; 1.W.240.172; 1.W.240.175; 1.W.240.240; 1.W.240.244;
1.W.244.228; 1.W.244.229; 1.W.244.230; 1.W.244.231; 1.W.244.236;
1.W.244.237; 1.W.244.238; 1.W.244.239; 1.W.244.154; 1.W.244.157;
1.W.244.166; 1.W.244.169; 1.W.244.172; 1.W.244.175; 1.W.244.240; 1.W.244.244;
Prodrugs of 1.Y 1.Y.228.228; 1.Y.228.229; 1.Y.228.230; 1.Y.228.231; 1.Y.228.236;
1.Y.228.237; 1.Y.228.238; 1.Y.228.239; 1.Y.228.154; 1.Y.228.157; 1.Y.228.166;
1.Y.228.169; 1.Y.228.172; 1.Y.228.175; 1.Y.228.240; 1.Y.228.244; 1.Y.229.228;
1.Y.229.229; 1.Y.229.230; 1.Y.229.231; 1.Y.229.236; 1.Y.229.237; 1.Y.229.238;
1.Y.229.239; 1.Y.229.154; 1.Y.229.157; 1.Y.229.166; 1.Y.229.169; 1.Y.229.172;
1.Y.229.175; 1.Y.229.240; 1.Y.229.244; 1.Y.230.228; 1.Y.230.229; 1.Y.230.230;
1.Y.230.231; 1.Y.230.236; 1.Y.230.237; 1.Y.230.238; 1.Y.230.239; 1.Y.230.154;
1.Y.230.157; 1.Y.230.166; 1.Y.230.169; 1.Y.230.172; 1.Y.230.175; 1.Y.230.240;
1.Y.230.244; 1.Y.231.228; 1.Y.231.229; 1.Y.231.230; 1.Y.231.231; 1.Y.231.236;
1.Y.231.237; 1.Y.231.238; 1.Y.231.239; 1.Y.231.154; 1.Y.231.157; 1.Y.231.166;
1.Y.231.169; 1.Y.231.172; 1.Y.231.175; 1.Y.231.240; 1.Y.231.244; 1.Y.236.228;
1.Y.236.229; 1.Y.236.230; 1.Y.236.231; 1.Y.236.236; 1.Y.236.237; 1.Y.236.238;
1.Y.236.239; 1.Y.236.154; 1.Y.236.157; 1.Y.236.166; 1.Y.236.169; 1.Y.236.172;
1.Y.236.175; 1.Y.236.240; 1.Y.236.244; 1.Y.237.228; 1.Y.237.229; 1.Y.237.230;
1.Y.237.231; 1.Y.237.236; 1.Y.237.237; 1.Y.237.238; 1.Y.237.239; 1.Y.237.154;
1.Y.237.157; 1.Y.237.166; 1.Y.237.169; 1.Y.237.172; 1.Y.237.175; 1.Y.237.240;
1.Y.237.244; 1.Y.238.228; 1.Y.238.229; 1.Y.238.230; 1.Y.238.231; 1.Y.238.236;
1.Y.238.237; 1.Y.238.238; 1.Y.238.239; 1.Y.238.154; 1.Y.238.157; 1.Y.238.166;

TABLE 100-continued

1.Y.238.169; 1.Y.238.172; 1.Y.238.175; 1.Y.238.240; 1.Y.238.244; 1.Y.239.228;
1.Y.239.229; 1.Y.239.230; 1.Y.239.231; 1.Y.239.236; 1.Y.239.237; 1.Y.239.238;
1.Y.239.239; 1.Y.239.154; 1.Y.239.157; 1.Y.239.166; 1.Y.239.169; 1.Y.239.172;
1.Y.239.175; 1.Y.239.240; 1.Y.239.244; 1.Y.154.228; 1.Y.154.229; 1.Y.154.230;
1.Y.154.231; 1.Y.154.236; 1.Y.154.237; 1.Y.154.238; 1.Y.154.239; 1.Y.154.154;
1.Y.154.157; 1.Y.154.166; 1.Y.154.169; 1.Y.154.172; 1.Y.154.175; 1.Y.154.240;
1.Y.154.244; 1.Y.157.228; 1.Y.157.229; 1.Y.157.230; 1.Y.157.231; 1.Y.157.236;
1.Y.157.237; 1.Y.157.238; 1.Y.157.239; 1.Y.157.154; 1.Y.157.157; 1.Y.157.166;
1.Y.157.169; 1.Y.157.172; 1.Y.157.175; 1.Y.157.240; 1.Y.157.244; 1.Y.166.228;
1.Y.166.229; 1.Y.166.230; 1.Y.166.231; 1.Y.166.236; 1.Y.166.237; 1.Y.166.238;
1.Y.166.239; 1.Y.166.154; 1.Y.166.157; 1.Y.166.166; 1.Y.166.169; 1.Y.166.172;
1.Y.166.175; 1.Y.166.240; 1.Y.166.244; 1.Y.169.228; 1.Y.169.229; 1.Y.169.230;
1.Y.169.231; 1.Y.169.236; 1.Y.169.237; 1.Y.169.238; 1.Y.169.239; 1.Y.169.154;
1.Y.169.157; 1.Y.169.166; 1.Y.169.169; 1.Y.169.172; 1.Y.169.175; 1.Y.169.240;
1.Y.169.244; 1.Y.172.228; 1.Y.172.229; 1.Y.172.230; 1.Y.172.231; 1.Y.172.236;
1.Y.172.237; 1.Y.172.238; 1.Y.172.239; 1.Y.172.154; 1.Y.172.157; 1.Y.172.166;
1.Y.172.169; 1.Y.172.172; 1.Y.172.175; 1.Y.172.240; 1.Y.172.244; 1.Y.175.228;
1.Y.175.229; 1.Y.175.230; 1.Y.175.231; 1.Y.175.236; 1.Y.175.237; 1.Y.175.238;
1.Y.175.239; 1.Y.175.154; 1.Y.175.157; 1.Y.175.166; 1.Y.175.169; 1.Y.175.172;
1.Y.175.175; 1.Y.175.240; 1.Y.175.244; 1.Y.240.228; 1.Y.240.229; 1.Y.240.230;
1.Y.240.231; 1.Y.240.236; 1.Y.240.237; 1.Y.240.238; 1.Y.240.239; 1.Y.240.154;
1.Y.240.157; 1.Y.240.166; 1.Y.240.169; 1.Y.240.172; 1.Y.240.175; 1.Y.240.240;
1.Y.240.244; 1.Y.244.228; 1.Y.244.229; 1.Y.244.230; 1.Y.244.231; 1.Y.244.236;
1.Y.244.237; 1.Y.244.238; 1.Y.244.239; 1.Y.244.154; 1.Y.244.157; 1.Y.244.166;
1.Y.244.169; 1.Y.244.172; 1.Y.244.175; 1.Y.244.240; 1.Y.244.244;
Prodrugs of 2.B 2.B.228.228; 2.B.228.229; 2.B.228.230; 2.B.228.231; 2.B.228.236;
2.B.228.237; 2.B.228.238; 2.B.228.239; 2.B.228.154; 2.B.228.157; 2.B.228.166;
2.B.228.169; 2.B.228.172; 2.B.228.175; 2.B.228.240; 2.B.228.244; 2.B.229.228;
2.B.229.229; 2.B.229.230; 2.B.229.231; 2.B.229.236; 2.B.229.237; 2.B.229.238;
2.B.229.239; 2.B.229.154; 2.B.229.157; 2.B.229.166; 2.B.229.169; 2.B.229.172;
2.B.229.175; 2.B.229.240; 2.B.229.244; 2.B.230.228; 2.B.230.229; 2.B.230.230;
2.B.230.231; 2.B.230.236; 2.B.230.237; 2.B.230.238; 2.B.230.239; 2.B.230.154;
2.B.230.157; 2.B.230.166; 2.B.230.169; 2.B.230.172; 2.B.230.175; 2.B.230.240;
2.B.230.244; 2.B.231.228; 2.B.231.229; 2.B.231.230; 2.B.231.231; 2.B.231.236;
2.B.231.237; 2.B.231.238; 2.B.231.239; 2.B.231.154; 2.B.231.157; 2.B.231.166;
2.B.231.169; 2.B.231.172; 2.B.231.175; 2.B.231.240; 2.B.231.244; 2.B.236.228;
2.B.236.229; 2.B.236.230; 2.B.236.231; 2.B.236.236; 2.B.236.237; 2.B.236.238;
2.B.236.239; 2.B.236.154; 2.B.236.157; 2.B.236.166; 2.B.236.169; 2.B.236.172;
2.B.236.175; 2.B.236.240; 2.B.236.244; 2.B.237.228; 2.B.237.229; 2.B.237.230;
2.B.237.231; 2.B.237.236; 2.B.237.237; 2.B.237.238; 2.B.237.239; 2.B.237.154;
2.B.237.157; 2.B.237.166; 2.B.237.169; 2.B.237.172; 2.B.237.175; 2.B.237.240;
2.B.237.244; 2.B.238.228; 2.B.238.229; 2.B.238.230; 2.B.238.231; 2.B.238.236;
2.B.238.237; 2.B.238.238; 2.B.238.239; 2.B.238.154; 2.B.238.157; 2.B.238.166;
2.B.238.169; 2.B.238.172; 2.B.238.175; 2.B.238.240; 2.B.238.244; 2.B.239.228;
2.B.239.229; 2.B.239.230; 2.B.239.231; 2.B.239.236; 2.B.239.237; 2.B.239.238;
2.B.239.239; 2.B.239.154; 2.B.239.157; 2.B.239.166; 2.B.239.169; 2.B.239.172;
2.B.239.175; 2.B.239.240; 2.B.239.244; 2.B.154.228; 2.B.154.229; 2.B.154.230;
2.B.154.231; 2.B.154.236; 2.B.154.237; 2.B.154.238; 2.B.154.239; 2.B.154.154;
2.B.154.157; 2.B.154.166; 2.B.154.169; 2.B.154.172; 2.B.154.175; 2.B.154.240;
2.B.154.244; 2.B.157.228; 2.B.157.229; 2.B.157.230; 2.B.157.231; 2.B.157.236;
2.B.157.237; 2.B.157.238; 2.B.157.239; 2.B.157.154; 2.B.157.157; 2.B.157.166;
2.B.157.169; 2.B.157.172; 2.B.157.175; 2.B.157.240; 2.B.157.244; 2.B.166.228;
2.B.166.229; 2.B.166.230; 2.B.166.231; 2.B.166.236; 2.B.166.237; 2.B.166.238;
2.B.166.239; 2.B.166.154; 2.B.166.157; 2.B.166.166; 2.B.166.169; 2.B.166.172;
2.B.166.175; 2.B.166.240; 2.B.166.244; 2.B.169.228; 2.B.169.229; 2.B.169.230;
2.B.169.231; 2.B.169.236; 2.B.169.237; 2.B.169.238; 2.B.169.239; 2.B.169.154;
2.B.169.157; 2.B.169.166; 2.B.169.169; 2.B.169.172; 2.B.169.175; 2.B.169.240;
2.B.169.244; 2.B.172.228; 2.B.172.229; 2.B.172.230; 2.B.172.231; 2.B.172.236;
2.B.172.237; 2.B.172.238; 2.B.172.239; 2.B.172.154; 2.B.172.157; 2.B.172.166;
2.B.172.169; 2.B.172.172; 2.B.172.175; 2.B.172.240; 2.B.172.244; 2.B.175.228;
2.B.175.229; 2.B.175.230; 2.B.175.231; 2.B.175.236; 2.B.175.237; 2.B.175.238;
2.B.175.239; 2.B.175.154; 2.B.175.157; 2.B.175.166; 2.B.175.169; 2.B.175.172;
2.B.175.175; 2.B.175.240; 2.B.175.244; 2.B.240.228; 2.B.240.229; 2.B.240.230;
2.B.240.231; 2.B.240.236; 2.B.240.237; 2.B.240.238; 2.B.240.239; 2.B.240.154;
2.B.240.157; 2.B.240.166; 2.B.240.169; 2.B.240.172; 2.B.240.175; 2.B.240.240;
2.B.240.244; 2.B.244.228; 2.B.244.229; 2.B.244.230; 2.B.244.231; 2.B.244.236;
2.B.244.237; 2.B.244.238; 2.B.244.239; 2.B.244.154; 2.B.244.157; 2.B.244.166;
2.B.244.169; 2.B.244.172; 2.B.244.175; 2.B.244.240; 2.B.244.244;
Prodrugs of 2.D 2.D.228.228; 2.D.228.229; 2.D.228.230; 2.D.228.231; 2.D.228.236;
2.D.228.237; 2.D.228.238; 2.D.228.239; 2.D.228.154; 2.D.228.157;
2.D.228.166; 2.D.228.169; 2.D.228.172; 2.D.228.175; 2.D.228.240;
2.D.228.244; 2.D.229.228; 2.D.229.229; 2.D.229.230; 2.D.229.231;
2.D.229.236; 2.D.229.237; 2.D.229.238; 2.D.229.239; 2.D.229.154;
2.D.229.157; 2.D.229.166; 2.D.229.169; 2.D.229.172; 2.D.229.175;
2.D.229.240; 2.D.229.244; 2.D.230.228; 2.D.230.229; 2.D.230.230;

TABLE 100-continued

2.D.230.231; 2.D.230.236; 2.D.230.237; 2.D.230.238; 2.D.230.239;
2.D.230.154; 2.D.230.157; 2.D.230.166; 2.D.230.169; 2.D.230.172;
2.D.230.175; 2.D.230.240; 2.D.230.244; 2.D.231.228; 2.D.231.229;
2.D.231.230; 2.D.231.231; 2.D.231.236; 2.D.231.237; 2.D.231.238;
2.D.231.239; 2.D.231.154; 2.D.231.157; 2.D.231.166; 2.D.231.169;
2.D.231.172; 2.D.231.175; 2.D.231.240; 2.D.231.244; 2.D.236.228;
2.D.236.229; 2.D.236.230; 2.D.236.231; 2.D.236.236; 2.D.236.237;
2.D.236.238; 2.D.236.239; 2.D.236.154; 2.D.236.157; 2.D.236.166;
2.D.236.169; 2.D.236.172; 2.D.236.175; 2.D.236.240; 2.D.236.244;
2.D.237.228; 2.D.237.229; 2.D.237.230; 2.D.237.231; 2.D.237.236;
2.D.237.237; 2.D.237.238; 2.D.237.239; 2.D.237.154; 2.D.237.157;
2.D.237.166; 2.D.237.169; 2.D.237.172; 2.D.237.175; 2.D.237.240;
2.D.237.244; 2.D.238.228; 2.D.238.229; 2.D.238.230; 2.D.238.231;
2.D.238.236; 2.D.238.237; 2.D.238.238; 2.D.238.239; 2.D.238.154;
2.D.238.157; 2.D.238.166; 2.D.238.169; 2.D.238.172; 2.D.238.175;
2.D.238.240; 2.D.238.244; 2.D.239.228; 2.D.239.229; 2.D.239.230;
2.D.239.231; 2.D.239.236; 2.D.239.237; 2.D.239.238; 2.D.239.239;
2.D.239.154; 2.D.239.157; 2.D.239.166; 2.D.239.169; 2.D.239.172;
2.D.239.175; 2.D.239.240; 2.D.239.244; 2.D.154.228; 2.D.154.229;
2.D.154.230; 2.D.154.231; 2.D.154.236; 2.D.154.237; 2.D.154.238;
2.D.154.239; 2.D.154.154; 2.D.154.157; 2.D.154.166; 2.D.154.169;
2.D.154.172; 2.D.154.175; 2.D.154.240; 2.D.154.244; 2.D.157.228;
2.D.157.229; 2.D.157.230; 2.D.157.231; 2.D.157.236; 2.D.157.237;
2.D.157.238; 2.D.157.239; 2.D.157.154; 2.D.157.157; 2.D.157.166;
2.D.157.169; 2.D.157.172; 2.D.157.175; 2.D.157.240; 2.D.157.244;
2.D.166.228; 2.D.166.229; 2.D.166.230; 2.D.166.231; 2.D.166.236;
2.D.166.237; 2.D.166.238; 2.D.166.239; 2.D.166.154; 2.D.166.157;
2.D.166.166; 2.D.166.169; 2.D.166.172; 2.D.166.175; 2.D.166.240;
2.D.166.244; 2.D.169.228; 2.D.169.229; 2.D.169.230; 2.D.169.231;
2.D.169.236; 2.D.169.237; 2.D.169.238; 2.D.169.239; 2.D.169.154;
2.D.169.157; 2.D.169.166; 2.D.169.169; 2.D.169.172; 2.D.169.175;
2.D.169.240; 2.D.169.244; 2.D.172.228; 2.D.172.229; 2.D.172.230;
2.D.172.231; 2.D.172.236; 2.D.172.237; 2.D.172.238; 2.D.172.239;
2.D.172.154; 2.D.172.157; 2.D.172.166; 2.D.172.169; 2.D.172.172;
2.D.172.175; 2.D.172.240; 2.D.172.244; 2.D.175.228; 2.D.175.229;
2.D.175.230; 2.D.175.231; 2.D.175.236; 2.D.175.237; 2.D.175.238;
2.D.175.239; 2.D.175.154; 2.D.175.157; 2.D.175.166; 2.D.175.169;
2.D.175.172; 2.D.175.175; 2.D.175.240; 2.D.175.244; 2.D.240.228;
2.D.240.229; 2.D.240.230; 2.D.240.231; 2.D.240.236; 2.D.240.237;
2.D.240.238; 2.D.240.239; 2.D.240.154; 2.D.240.157; 2.D.240.166;
2.D.240.169; 2.D.240.172; 2.D.240.175; 2.D.240.240; 2.D.240.244;
2.D.244.228; 2.D.244.229; 2.D.244.230; 2.D.244.231; 2.D.244.236;
2.D.244.237; 2.D.244.238; 2.D.244.239; 2.D.244.154; 2.D.244.157;
2.D.244.166; 2.D.244.169; 2.D.244.172; 2.D.244.175; 2.D.244.240; 2.D.244.244;
Prodrugs of 2.E 2.E.228.228; 2.E.228.229; 2.E.228.230; 2.E.228.231; 2.E.228.236;
2.E.228.237; 2.E.228.238; 2.E.228.239; 2.E.228.154; 2.E.228.157; 2.E.228.166;
2.E.228.169; 2.E.228.172; 2.E.228.175; 2.E.228.240; 2.E.228.244; 2.E.229.228;
2.E.229.229; 2.E.229.230; 2.E.229.231; 2.E.229.236; 2.E.229.237; 2.E.229.238;
2.E.229.239; 2.E.229.154; 2.E.229.157; 2.E.229.166; 2.E.229.169; 2.E.229.172;
2.E.229.175; 2.E.229.240; 2.E.229.244; 2.E.230.228; 2.E.230.229; 2.E.230.230;
2.E.230.231; 2.E.230.236; 2.E.230.237; 2.E.230.238; 2.E.230.239; 2.E.230.154;
2.E.230.157; 2.E.230.166; 2.E.230.169; 2.E.230.172; 2.E.230.175; 2.E.230.240;
2.E.230.244; 2.E.231.228; 2.E.231.229; 2.E.231.230; 2.E.231.231; 2.E.231.236;
2.E.231.237; 2.E.231.238; 2.E.231.239; 2.E.231.154; 2.E.231.157; 2.E.231.166;
2.E.231.169; 2.E.231.172; 2.E.231.175; 2.E.231.240; 2.E.231.244; 2.E.236.228;
2.E.236.229; 2.E.236.230; 2.E.236.231; 2.E.236.236; 2.E.236.237; 2.E.236.238;
2.E.236.239; 2.E.236.154; 2.E.236.157; 2.E.236.166; 2.E.236.169; 2.E.236.172;
2.E.236.175; 2.E.236.240; 2.E.236.244; 2.E.237.228; 2.E.237.229; 2.E.237.230;
2.E.237.231; 2.E.237.236; 2.E.237.237; 2.E.237.238; 2.E.237.239; 2.E.237.154;
2.E.237.157; 2.E.237.166; 2.E.237.169; 2.E.237.172; 2.E.237.175; 2.E.237.240;
2.E.237.244; 2.E.238.228; 2.E.238.229; 2.E.238.230; 2.E.238.231; 2.E.238.236;
2.E.238.237; 2.E.238.238; 2.E.238.239; 2.E.238.154; 2.E.238.157; 2.E.238.166;
2.E.238.169; 2.E.238.172; 2.E.238.175; 2.E.238.240; 2.E.238.244; 2.E.239.228;
2.E.239.229; 2.E.239.230; 2.E.239.231; 2.E.239.236; 2.E.239.237; 2.E.239.238;
2.E.239.239; 2.E.239.154; 2.E.239.157; 2.E.239.166; 2.E.239.169; 2.E.239.172;
2.E.239.175; 2.E.239.240; 2.E.239.244; 2.E.154.228; 2.E.154.229; 2.E.154.230;
2.E.154.231; 2.E.154.236; 2.E.154.237; 2.E.154.238; 2.E.154.239; 2.E.154.154;
2.E.154.157; 2.E.154.166; 2.E.154.169; 2.E.154.172; 2.E.154.175; 2.E.154.240;
2.E.154.244; 2.E.157.228; 2.E.157.229; 2.E.157.230; 2.E.157.231; 2.E.157.236;
2.E.157.237; 2.E.157.238; 2.E.157.239; 2.E.157.154; 2.E.157.157; 2.E.157.166;
2.E.157.169; 2.E.157.172; 2.E.157.175; 2.E.157.240; 2.E.157.244; 2.E.166.228;
2.E.166.229; 2.E.166.230; 2.E.166.231; 2.E.166.236; 2.E.166.237; 2.E.166.238;
2.E.166.239; 2.E.166.154; 2.E.166.157; 2.E.166.166; 2.E.166.169; 2.E.166.172;
2.E.166.175; 2.E.166.240; 2.E.166.244; 2.E.169.228; 2.E.169.229; 2.E.169.230;
2.E.169.231; 2.E.169.236; 2.E.169.237; 2.E.169.238; 2.E.169.239; 2.E.169.154;
2.E.169.157; 2.E.169.166; 2.E.169.169; 2.E.169.172; 2.E.169.175; 2.E.169.240;
2.E.169.244; 2.E.172.228; 2.E.172.229; 2.E.172.230; 2.E.172.231; 2.E.172.236;

TABLE 100-continued

2.E.172.237; 2.E.172.238; 2.E.172.239; 2.E.172.154; 2.E.172.157; 2.E.172.166;
2.E.172.169; 2.E.172.172; 2.E.172.175; 2.E.172.240; 2.E.172.244; 2.E.175.228;
2.E.175.229; 2.E.175.230; 2.E.175.231; 2.E.175.236; 2.E.175.237; 2.E.175.238;
2.E.175.239; 2.E.175.154; 2.E.175.157; 2.E.175.166; 2.E.175.169; 2.E.175.172;
2.E.175.175; 2.E.175.240; 2.E.175.244; 2.E.240.228; 2.E.240.229; 2.E.240.230;
2.E.240.231; 2.E.240.236; 2.E.240.237; 2.E.240.238; 2.E.240.239; 2.E.240.154;
2.E.240.157; 2.E.240.166; 2.E.240.169; 2.E.240.172; 2.E.240.175; 2.E.240.240;
2.E.240.244; 2.E.244.228; 2.E.244.229; 2.E.244.230; 2.E.244.231; 2.E.244.236;
2.E.244.237; 2.E.244.238; 2.E.244.239; 2.E.244.154; 2.E.244.157; 2.E.244.166;
2.E.244.169; 2.E.244.172; 2.E.244.175; 2.E.244.240; 2.E.244.244;
Prodrugs of 2.G 2.G.228.228; 2.G.228.229; 2.G.228.230; 2.G.228.231; 2.G.228.236;
2.G.228.237; 2.G.228.238; 2.G.228.239; 2.G.228.154; 2.G.228.157;
2.G.228.166; 2.G.228.169; 2.G.228.172; 2.G.228.175; 2.G.228.240;
2.G.228.244; 2.G.229.228; 2.G.229.229; 2.G.229.230; 2.G.229.231;
2.G.229.236; 2.G.229.237; 2.G.229.238; 2.G.229.239; 2.G.229.154;
2.G.229.157; 2.G.229.166; 2.G.229.169; 2.G.229.172; 2.G.229.175;
2.G.229.240; 2.G.229.244; 2.G.230.228; 2.G.230.229; 2.G.230.230;
2.G.230.231; 2.G.230.236; 2.G.230.237; 2.G.230.238; 2.G.230.239;
2.G.230.154; 2.G.230.157; 2.G.230.166; 2.G.230.169; 2.G.230.172;
2.G.230.175; 2.G.230.240; 2.G.230.244; 2.G.231.228; 2.G.231.229;
2.G.231.230; 2.G.231.231; 2.G.231.236; 2.G.231.237; 2.G.231.238;
2.G.231.239; 2.G.231.154; 2.G.231.157; 2.G.231.166; 2.G.231.169;
2.G.231.172; 2.G.231.175; 2.G.231.240; 2.G.231.244; 2.G.236.228;
2.G.236.229; 2.G.236.230; 2.G.236.231; 2.G.236.236; 2.G.236.237;
2.G.236.238; 2.G.236.239; 2.G.236.154; 2.G.236.157; 2.G.236.166;
2.G.236.169; 2.G.236.172; 2.G.236.175; 2.G.236.240; 2.G.236.244;
2.G.237.228; 2.G.237.229; 2.G.237.230; 2.G.237.231; 2.G.237.236;
2.G.237.237; 2.G.237.238; 2.G.237.239; 2.G.237.154; 2.G.237.157;
2.G.237.166; 2.G.237.169; 2.G.237.172; 2.G.237.175; 2.G.237.240;
2.G.237.244; 2.G.238.228; 2.G.238.229; 2.G.238.230; 2.G.238.231;
2.G.238.236; 2.G.238.237; 2.G.238.238; 2.G.238.239; 2.G.238.154;
2.G.238.157; 2.G.238.166; 2.G.238.169; 2.G.238.172; 2.G.238.175;
2.G.238.240; 2.G.238.244; 2.G.239.228; 2.G.239.229; 2.G.239.230;
2.G.239.231; 2.G.239.236; 2.G.239.237; 2.G.239.238; 2.G.239.239;
2.G.239.154; 2.G.239.157; 2.G.239.166; 2.G.239.169; 2.G.239.172;
2.G.239.175; 2.G.239.240; 2.G.239.244; 2.G.154.228; 2.G.154.229;
2.G.154.230; 2.G.154.231; 2.G.154.236; 2.G.154.237; 2.G.154.238;
2.G.154.239; 2.G.154.154; 2.G.154.157; 2.G.154.166; 2.G.154.169;
2.G.154.172; 2.G.154.175; 2.G.154.240; 2.G.154.244; 2.G.157.228;
2.G.157.229; 2.G.157.230; 2.G.157.231; 2.G.157.236; 2.G.157.237;
2.G.157.238; 2.G.157.239; 2.G.157.154; 2.G.157.157; 2.G.157.166;
2.G.157.169; 2.G.157.172; 2.G.157.175; 2.G.157.240; 2.G.157.244;
2.G.166.228; 2.G.166.229; 2.G.166.230; 2.G.166.231; 2.G.166.236;
2.G.166.237; 2.G.166.238; 2.G.166.239; 2.G.166.154; 2.G.166.157;
2.G.166.166; 2.G.166.169; 2.G.166.172; 2.G.166.175; 2.G.166.240;
2.G.166.244; 2.G.169.228; 2.G.169.229; 2.G.169.230; 2.G.169.231;
2.G.169.236; 2.G.169.237; 2.G.169.238; 2.G.169.239; 2.G.169.154;
2.G.169.157; 2.G.169.166; 2.G.169.169; 2.G.169.172; 2.G.169.175;
2.G.169.240; 2.G.169.244; 2.G.172.228; 2.G.172.229; 2.G.172.230;
2.G.172.231; 2.G.172.236; 2.G.172.237; 2.G.172.238; 2.G.172.239;
2.G.172.154; 2.G.172.157; 2.G.172.166; 2.G.172.169; 2.G.172.172;
2.G.172.175; 2.G.172.240; 2.G.172.244; 2.G.175.228; 2.G.175.229;
2.G.175.230; 2.G.175.231; 2.G.175.236; 2.G.175.237; 2.G.175.238;
2.G.175.239; 2.G.175.154; 2.G.175.157; 2.G.175.166; 2.G.175.169;
2.G.175.172; 2.G.175.175; 2.G.175.240; 2.G.175.244; 2.G.240.228;
2.G.240.229; 2.G.240.230; 2.G.240.231; 2.G.240.236; 2.G.240.237;
2.G.240.238; 2.G.240.239; 2.G.240.154; 2.G.240.157; 2.G.240.166;
2.G.240.169; 2.G.240.172; 2.G.240.175; 2.G.240.240; 2.G.240.244;
2.G.244.228; 2.G.244.229; 2.G.244.230; 2.G.244.231; 2.G.244.236;
2.G.244.237; 2.G.244.238; 2.G.244.239; 2.G.244.154; 2.G.244.157;
2.G.244.166; 2.G.244.169; 2.G.244.172; 2.G.244.175; 2.G.244.240;
2.G.244.244;
Prodrugs of 2.I 2.I.228.228; 2.I.228.229; 2.I.228.230; 2.I.228.231; 2.I.228.236; 2.I.228.237;
2.I.228.238; 2.I.228.239; 2.I.228.154; 2.I.228.157; 2.I.228.166; 2.I.228.169;
2.I.228.172; 2.I.228.175; 2.I.228.240; 2.I.228.244; 2.I.229.228; 2.I.229.229;
2.I.229.230; 2.I.229.231; 2.I.229.236; 2.I.229.237; 2.I.229.238; 2.I.229.239;
2.I.229.154; 2.I.229.157; 2.I.229.166; 2.I.229.169; 2.I.229.172; 2.I.229.175;
2.I.229.240; 2.I.229.244; 2.I.230.228; 2.I.230.229; 2.I.230.230; 2.I.230.231;
2.I.230.236; 2.I.230.237; 2.I.230.238; 2.I.230.239; 2.I.230.154; 2.I.230.157;
2.I.230.166; 2.I.230.169; 2.I.230.172; 2.I.230.175; 2.I.230.240; 2.I.230.244;
2.I.231.228; 2.I.231.229; 2.I.231.230; 2.I.231.231; 2.I.231.236; 2.I.231.237;
2.I.231.238; 2.I.231.239; 2.I.231.154; 2.I.231.157; 2.I.231.166; 2.I.231.169;
2.I.231.172; 2.I.231.175; 2.I.231.240; 2.I.231.244; 2.I.236.228; 2.I.236.229;
2.I.236.230; 2.I.236.231; 2.I.236.236; 2.I.236.237; 2.I.236.238; 2.I.236.239;
2.I.236.154; 2.I.236.157; 2.I.236.166; 2.I.236.169; 2.I.236.172; 2.I.236.175;

TABLE 100-continued

2.I.236.240; 2.I.236.244; 2.I.237.228; 2.I.237.229; 2.I.237.230; 2.I.237.231;
2.I.237.236; 2.I.237.237; 2.I.237.238; 2.I.237.239; 2.I.237.154; 2.I.237.157;
2.I.237.166; 2.I.237.169; 2.I.237.172; 2.I.237.175; 2.I.237.240; 2.I.237.244;
2.I.238.228; 2.I.238.229; 2.I.238.230; 2.I.238.231; 2.I.238.236; 2.I.238.237;
2.I.238.238; 2.I.238.239; 2.I.238.154; 2.I.238.157; 2.I.238.166; 2.I.238.169;
2.I.238.172; 2.I.238.175; 2.I.238.240; 2.I.238.244; 2.I.239.228; 2.I.239.229;
2.I.239.230; 2.I.239.231; 2.I.239.236; 2.I.239.237; 2.I.239.238; 2.I.239.239;
2.I.239.154; 2.I.239.157; 2.I.239.166; 2.I.239.169; 2.I.239.172; 2.I.239.175;
2.I.239.240; 2.I.239.244; 2.I.154.228; 2.I.154.229; 2.I.154.230; 2.I.154.231;
2.I.154.236; 2.I.154.237; 2.I.154.238; 2.I.154.239; 2.I.154.154; 2.I.154.157;
2.I.154.166; 2.I.154.169; 2.I.154.172; 2.I.154.175; 2.I.154.240; 2.I.154.244;
2.I.157.228; 2.I.157.229; 2.I.157.230; 2.I.157.231; 2.I.157.236; 2.I.157.237;
2.I.157.238; 2.I.157.239; 2.I.157.154; 2.I.157.157; 2.I.157.166; 2.I.157.169;
2.I.157.172; 2.I.157.175; 2.I.157.240; 2.I.157.244; 2.I.166.228; 2.I.166.229;
2.I.166.230; 2.I.166.231; 2.I.166.236; 2.I.166.237; 2.I.166.238; 2.I.166.239;
2.I.166.154; 2.I.166.157; 2.I.166.166; 2.I.166.169; 2.I.166.172; 2.I.166.175;
2.I.166.240; 2.I.166.244; 2.I.169.228; 2.I.169.229; 2.I.169.230; 2.I.169.231;
2.I.169.236; 2.I.169.237; 2.I.169.238; 2.I.169.239; 2.I.169.154; 2.I.169.157;
2.I.169.166; 2.I.169.169; 2.I.169.172; 2.I.169.175; 2.I.169.240; 2.I.169.244;
2.I.172.228; 2.I.172.229; 2.I.172.230; 2.I.172.231; 2.I.172.236; 2.I.172.237;
2.I.172.238; 2.I.172.239; 2.I.172.154; 2.I.172.157; 2.I.172.166; 2.I.172.169;
2.I.172.172; 2.I.172.175; 2.I.172.240; 2.I.172.244; 2.I.175.228; 2.I.175.229;
2.I.175.230; 2.I.175.231; 2.I.175.236; 2.I.175.237; 2.I.175.238; 2.I.175.239;
2.I.175.154; 2.I.175.157; 2.I.175.166; 2.I.175.169; 2.I.175.172; 2.I.175.175;
2.I.175.240; 2.I.175.244; 2.I.240.228; 2.I.240.229; 2.I.240.230; 2.I.240.231;
2.I.240.236; 2.I.240.237; 2.I.240.238; 2.I.240.239; 2.I.240.154; 2.I.240.157;
2.I.240.166; 2.I.240.169; 2.I.240.172; 2.I.240.175; 2.I.240.240; 2.I.240.244;
2.I.244.228; 2.I.244.229; 2.I.244.230; 2.I.244.231; 2.I.244.236; 2.I.244.237;
2.I.244.238; 2.I.244.239; 2.I.244.154; 2.I.244.157; 2.I.244.166; 2.I.244.169;
2.I.244.172; 2.I.244.175; 2.I.244.240; 2.I.244.244;
Prodrugs of 2.J 2.J.228.228; 2.J.228.229; 2.J.228.230; 2.J.228.231; 2.J.228.236; 2.J.228.237;
2.J.228.238; 2.J.228.239; 2.J.228.154; 2.J.228.157; 2.J.228.166; 2.J.228.169;
2.J.228.172; 2.J.228.175; 2.J.228.240; 2.J.228.244; 2.J.229.228; 2.J.229.229;
2.J.229.230; 2.J.229.231; 2.J.229.236; 2.J.229.237; 2.J.229.238; 2.J.229.239;
2.J.229.154; 2.J.229.157; 2.J.229.166; 2.J.229.169; 2.J.229.172; 2.J.229.175;
2.J.229.240; 2.J.229.244; 2.J.230.228; 2.J.230.229; 2.J.230.230; 2.J.230.231;
2.J.230.236; 2.J.230.237; 2.J.230.238; 2.J.230.239; 2.J.230.154; 2.J.230.157;
2.J.230.166; 2.J.230.169; 2.J.230.172; 2.J.230.175; 2.J.230.240; 2.J.230.244;
2.J.231.228; 2.J.231.229; 2.J.231.230; 2.J.231.231; 2.J.231.236; 2.J.231.237;
2.J.231.238; 2.J.231.239; 2.J.231.154; 2.J.231.157; 2.J.231.166; 2.J.231.169;
2.J.231.172; 2.J.231.175; 2.J.231.240; 2.J.231.244; 2.J.236.228; 2.J.236.229;
2.J.236.230; 2.J.236.231; 2.J.236.236; 2.J.236.237; 2.J.236.238; 2.J.236.239;
2.J.236.154; 2.J.236.157; 2.J.236.166; 2.J.236.169; 2.J.236.172; 2.J.236.175;
2.J.236.240; 2.J.236.244; 2.J.237.228; 2.J.237.229; 2.J.237.230; 2.J.237.231;
2.J.237.236; 2.J.237.237; 2.J.237.238; 2.J.237.239; 2.J.237.154; 2.J.237.157;
2.J.237.166; 2.J.237.169; 2.J.237.172; 2.J.237.175; 2.J.237.240; 2.J.237.244;
2.J.238.228; 2.J.238.229; 2.J.238.230; 2.J.238.231; 2.J.238.236; 2.J.238.237;
2.J.238.238; 2.J.238.239; 2.J.238.154; 2.J.238.157; 2.J.238.166; 2.J.238.169;
2.J.238.172; 2.J.238.175; 2.J.238.240; 2.J.238.244; 2.J.239.228; 2.J.239.229;
2.J.239.230; 2.J.239.231; 2.J.239.236; 2.J.239.237; 2.J.239.238; 2.J.239.239;
2.J.239.154; 2.J.239.157; 2.J.239.166; 2.J.239.169; 2.J.239.172; 2.J.239.175;
2.J.239.240; 2.J.239.244; 2.J.154.228; 2.J.154.229; 2.J.154.230; 2.J.154.231;
2.J.154.236; 2.J.154.237; 2.J.154.238; 2.J.154.239; 2.J.154.154; 2.J.154.157;
2.J.154.166; 2.J.154.169; 2.J.154.172; 2.J.154.175; 2.J.154.240; 2.J.154.244;
2.J.157.228; 2.J.157.229; 2.J.157.230; 2.J.157.231; 2.J.157.236; 2.J.157.237;
2.J.157.238; 2.J.157.239; 2.J.157.154; 2.J.157.157; 2.J.157.166; 2.J.157.169;
2.J.157.172; 2.J.157.175; 2.J.157.240; 2.J.157.244; 2.J.166.228; 2.J.166.229;
2.J.166.230; 2.J.166.231; 2.J.166.236; 2.J.166.237; 2.J.166.238; 2.J.166.239;
2.J.166.154; 2.J.166.157; 2.J.166.166; 2.J.166.169; 2.J.166.172; 2.J.166.175;
2.J.166.240; 2.J.166.244; 2.J.169.228; 2.J.169.229; 2.J.169.230; 2.J.169.231;
2.J.169.236; 2.J.169.237; 2.J.169.238; 2.J.169.239; 2.J.169.154; 2.J.169.157;
2.J.169.166; 2.J.169.169; 2.J.169.172; 2.J.169.175; 2.J.169.240; 2.J.169.244;
2.J.172.228; 2.J.172.229; 2.J.172.230; 2.J.172.231; 2.J.172.236; 2.J.172.237;
2.J.172.238; 2.J.172.239; 2.J.172.154; 2.J.172.157; 2.J.172.166; 2.J.172.169;
2.J.172.172; 2.J.172.175; 2.J.172.240; 2.J.172.244; 2.J.175.228; 2.J.175.229;
2.J.175.230; 2.J.175.231; 2.J.175.236; 2.J.175.237; 2.J.175.238; 2.J.175.239;
2.J.175.154; 2.J.175.157; 2.J.175.166; 2.J.175.169; 2.J.175.172; 2.J.175.175;
2.J.175.240; 2.J.175.244; 2.J.240.228; 2.J.240.229; 2.J.240.230; 2.J.240.231;
2.J.240.236; 2.J.240.237; 2.J.240.238; 2.J.240.239; 2.J.240.154; 2.J.240.157;
2.J.240.166; 2.J.240.169; 2.J.240.172; 2.J.240.175; 2.J.240.240; 2.J.240.244;
2.J.244.228; 2.J.244.229; 2.J.244.230; 2.J.244.231; 2.J.244.236; 2.J.244.237;
2.J.244.238; 2.J.244.239; 2.J.244.154; 2.J.244.157; 2.J.244.166; 2.J.244.169;
2.J.244.172; 2.J.244.175; 2.J.244.240; 2.J.244.244;
Prodrugs of 2.L 2.L.228.228; 2.L.228.229; 2.L.228.230; 2.L.228.231; 2.L.228.236;
2.L.228.237; 2.L.228.238; 2.L.228.239; 2.L.228.154; 2.L.228.157; 2.L.228.166;

TABLE 100-continued

2.L.228.169; 2.L.228.172; 2.L.228.175; 2.L.228.240; 2.L.228.244; 2.L.229.228;
2.L.229.229; 2.L.229.230; 2.L.229.231; 2.L.229.236; 2.L.229.237; 2.L.229.238;
2.L.229.239; 2.L.229.154; 2.L.229.157; 2.L.229.166; 2.L.229.169; 2.L.229.172;
2.L.229.175; 2.L.229.240; 2.L.229.244; 2.L.230.228; 2.L.230.229; 2.L.230.230;
2.L.230.231; 2.L.230.236; 2.L.230.237; 2.L.230.238; 2.L.230.239; 2.L.230.154;
2.L.230.157; 2.L.230.166; 2.L.230.169; 2.L.230.172; 2.L.230.175; 2.L.230.240;
2.L.230.244; 2.L.231.228; 2.L.231.229; 2.L.231.230; 2.L.231.231; 2.L.231.236;
2.L.231.237; 2.L.231.238; 2.L.231.239; 2.L.231.154; 2.L.231.157; 2.L.231.166;
2.L.231.169; 2.L.231.172; 2.L.231.175; 2.L.231.240; 2.L.231.244; 2.L.236.228;
2.L.236.229; 2.L.236.230; 2.L.236.231; 2.L.236.236; 2.L.236.237; 2.L.236.238;
2.L.236.239; 2.L.236.154; 2.L.236.157; 2.L.236.166; 2.L.236.169; 2.L.236.172;
2.L.236.175; 2.L.236.240; 2.L.236.244; 2.L.237.228; 2.L.237.229; 2.L.237.230;
2.L.237.231; 2.L.237.236; 2.L.237.237; 2.L.237.238; 2.L.237.239; 2.L.237.154;
2.L.237.157; 2.L.237.166; 2.L.237.169; 2.L.237.172; 2.L.237.175; 2.L.237.240;
2.L.237.244; 2.L.238.228; 2.L.238.229; 2.L.238.230; 2.L.238.231; 2.L.238.236;
2.L.238.237; 2.L.238.238; 2.L.238.239; 2.L.238.154; 2.L.238.157; 2.L.238.166;
2.L.238.169; 2.L.238.172; 2.L.238.175; 2.L.238.240; 2.L.238.244; 2.L.239.228;
2.L.239.229; 2.L.239.230; 2.L.239.231; 2.L.239.236; 2.L.239.237; 2.L.239.238;
2.L.239.239; 2.L.239.154; 2.L.239.157; 2.L.239.166; 2.L.239.169; 2.L.239.172;
2.L.239.175; 2.L.239.240; 2.L.239.244; 2.L.154.228; 2.L.154.229; 2.L.154.230;
2.L.154.231; 2.L.154.236; 2.L.154.237; 2.L.154.238; 2.L.154.239; 2.L.154.154;
2.L.154.157; 2.L.154.166; 2.L.154.169; 2.L.154.172; 2.L.154.175; 2.L.154.240;
2.L.154.244; 2.L.157.228; 2.L.157.229; 2.L.157.230; 2.L.157.231; 2.L.157.236;
2.L.157.237; 2.L.157.238; 2.L.157.239; 2.L.157.154; 2.L.157.157; 2.L.157.166;
2.L.157.169; 2.L.157.172; 2.L.157.175; 2.L.157.240; 2.L.157.244; 2.L.166.228;
2.L.166.229; 2.L.166.230; 2.L.166.231; 2.L.166.236; 2.L.166.237; 2.L.166.238;
2.L.166.239; 2.L.166.154; 2.L.166.157; 2.L.166.166; 2.L.166.169; 2.L.166.172;
2.L.166.175; 2.L.166.240; 2.L.166.244; 2.L.169.228; 2.L.169.229; 2.L.169.230;
2.L.169.231; 2.L.169.236; 2.L.169.237; 2.L.169.238; 2.L.169.239; 2.L.169.154;
2.L.169.157; 2.L.169.166; 2.L.169.169; 2.L.169.172; 2.L.169.175; 2.L.169.240;
2.L.169.244; 2.L.172.228; 2.L.172.229; 2.L.172.230; 2.L.172.231; 2.L.172.236;
2.L.172.237; 2.L.172.238; 2.L.172.239; 2.L.172.154; 2.L.172.157; 2.L.172.166;
2.L.172.169; 2.L.172.172; 2.L.172.175; 2.L.172.240; 2.L.172.244; 2.L.175.228;
2.L.175.229; 2.L.175.230; 2.L.175.231; 2.L.175.236; 2.L.175.237; 2.L.175.238;
2.L.175.239; 2.L.175.154; 2.L.175.157; 2.L.175.166; 2.L.175.169; 2.L.175.172;
2.L.175.175; 2.L.175.240; 2.L.175.244; 2.L.240.228; 2.L.240.229; 2.L.240.230;
2.L.240.231; 2.L.240.236; 2.L.240.237; 2.L.240.238; 2.L.240.239; 2.L.240.154;
2.L.240.157; 2.L.240.166; 2.L.240.169; 2.L.240.172; 2.L.240.175; 2.L.240.240;
2.L.240.244; 2.L.244.228; 2.L.244.229; 2.L.244.230; 2.L.244.231; 2.L.244.236;
2.L.244.237; 2.L.244.238; 2.L.244.239; 2.L.244.154; 2.L.244.157; 2.L.244.166;
2.L.244.169; 2.L.244.172; 2.L.244.175; 2.L.244.240; 2.L.244.244;
Prodrugs of 2.O 2.O.228.228; 2.O.228.229; 2.O.228.230; 2.O.228.231; 2.O.228.236;
2.O.228.237; 2.O.228.238; 2.O.228.239; 2.O.228.154; 2.O.228.157;
2.O.228.166; 2.O.228.169; 2.O.228.172; 2.O.228.175; 2.O.228.240;
2.O.228.244; 2.O.229.228; 2.O.229.229; 2.O.229.230; 2.O.229.231;
2.O.229.236; 2.O.229.237; 2.O.229.238; 2.O.229.239; 2.O.229.154;
2.O.229.157; 2.O.229.166; 2.O.229.169; 2.O.229.172; 2.O.229.175;
2.O.229.240; 2.O.229.244; 2.O.230.228; 2.O.230.229; 2.O.230.230;
2.O.230.231; 2.O.230.236; 2.O.230.237; 2.O.230.238; 2.O.230.239;
2.O.230.154; 2.O.230.157; 2.O.230.166; 2.O.230.169; 2.O.230.172;
2.O.230.175; 2.O.230.240; 2.O.230.244; 2.O.231.228; 2.O.231.229;
2.O.231.230; 2.O.231.231; 2.O.231.236; 2.O.231.237; 2.O.231.238;
2.O.231.239; 2.O.231.154; 2.O.231.157; 2.O.231.166; 2.O.231.169;
2.O.231.172; 2.O.231.175; 2.O.231.240; 2.O.231.244; 2.O.236.228;
2.O.236.229; 2.O.236.230; 2.O.236.231; 2.O.236.236; 2.O.236.237;
2.O.236.238; 2.O.236.239; 2.O.236.154; 2.O.236.157; 2.O.236.166;
2.O.236.169; 2.O.236.172; 2.O.236.175; 2.O.236.240; 2.O.236.244;
2.O.237.228; 2.O.237.229; 2.O.237.230; 2.O.237.231; 2.O.237.236;
2.O.237.237; 2.O.237.238; 2.O.237.239; 2.O.237.154; 2.O.237.157;
2.O.237.166; 2.O.237.169; 2.O.237.172; 2.O.237.175; 2.O.237.240;
2.O.237.244; 2.O.238.228; 2.O.238.229; 2.O.238.230; 2.O.238.231;
2.O.238.236; 2.O.238.237; 2.O.238.238; 2.O.238.239; 2.O.238.154;
2.O.238.157; 2.O.238.166; 2.O.238.169; 2.O.238.172; 2.O.238.175;
2.O.238.240; 2.O.238.244; 2.O.239.228; 2.O.239.229; 2.O.239.230;
2.O.239.231; 2.O.239.236; 2.O.239.237; 2.O.239.238; 2.O.239.239;
2.O.239.154; 2.O.239.157; 2.O.239.166; 2.O.239.169; 2.O.239.172;
2.O.239.175; 2.O.239.240; 2.O.239.244; 2.O.154.228; 2.O.154.229;
2.O.154.230; 2.O.154.231; 2.O.154.236; 2.O.154.237; 2.O.154.238;
2.O.154.239; 2.O.154.154; 2.O.154.157; 2.O.154.166; 2.O.154.169;
2.O.154.172; 2.O.154.175; 2.O.154.240; 2.O.154.244; 2.O.157.228;
2.O.157.229; 2.O.157.230; 2.O.157.231; 2.O.157.236; 2.O.157.237;
2.O.157.238; 2.O.157.239; 2.O.157.154; 2.O.157.157; 2.O.157.166;
2.O.157.169; 2.O.157.172; 2.O.157.175; 2.O.157.240; 2.O.157.244;
2.O.166.228; 2.O.166.229; 2.O.166.230; 2.O.166.231; 2.O.166.236;
2.O.166.237; 2.O.166.238; 2.O.166.239; 2.O.166.154; 2.O.166.157;
2.O.166.166; 2.O.166.169; 2.O.166.172; 2.O.166.175; 2.O.166.240;
2.O.166.244; 2.O.169.228; 2.O.169.229; 2.O.169.230; 2.O.169.231;

TABLE 100-continued

2.O.169.236; 2.O.169.237; 2.O.169.238; 2.O.169.239; 2.O.169.154;
2.O.169.157; 2.O.169.166; 2.O.169.169; 2.O.169.172; 2.O.169.175;
2.O.169.240; 2.O.169.244; 2.O.172.228; 2.O.172.229; 2.O.172.230;
2.O.172.231; 2.O.172.236; 2.O.172.237; 2.O.172.238; 2.O.172.239;
2.O.172.154; 2.O.172.157; 2.O.172.166; 2.O.172.169; 2.O.172.172;
2.O.172.175; 2.O.172.240; 2.O.172.244; 2.O.175.228; 2.O.175.229;
2.O.175.230; 2.O.175.231; 2.O.175.236; 2.O.175.237; 2.O.175.238;
2.O.175.239; 2.O.175.154; 2.O.175.157; 2.O.175.166; 2.O.175.169;
2.O.175.172; 2.O.175.175; 2.O.175.240; 2.O.175.244; 2.O.240.228;
2.O.240.229; 2.O.240.230; 2.O.240.231; 2.O.240.236; 2.O.240.237;
2.O.240.238; 2.O.240.239; 2.O.240.154; 2.O.240.157; 2.O.240.166;
2.O.240.169; 2.O.240.172; 2.O.240.175; 2.O.240.240; 2.O.240.244;
2.O.244.228; 2.O.244.229; 2.O.244.230; 2.O.244.231; 2.O.244.236;
2.O.244.237; 2.O.244.238; 2.O.244.239; 2.O.244.154; 2.O.244.157;
2.O.244.166; 2.O.244.169; 2.O.244.172; 2.O.244.175; 2.O.244.240;
2.O.244.244;
Prodrugs of 2.P 2.P.228.228; 2.P.228.229; 2.P.228.230; 2.P.228.231; 2.P.228.236;
2.P.228.237; 2.P.228.238; 2.P.228.239; 2.P.228.154; 2.P.228.157; 2.P.228.166;
2.P.228.169; 2.P.228.172; 2.P.228.175; 2.P.228.240; 2.P.228.244; 2.P.229.228;
2.P.229.229; 2.P.229.230; 2.P.229.231; 2.P.229.236; 2.P.229.237; 2.P.229.238;
2.P.229.239; 2.P.229.154; 2.P.229.157; 2.P.229.166; 2.P.229.169; 2.P.229.172;
2.P.229.175; 2.P.229.240; 2.P.229.244; 2.P.230.228; 2.P.230.229; 2.P.230.230;
2.P.230.231; 2.P.230.236; 2.P.230.237; 2.P.230.238; 2.P.230.239; 2.P.230.154;
2.P.230.157; 2.P.230.166; 2.P.230.169; 2.P.230.172; 2.P.230.175; 2.P.230.240;
2.P.230.244; 2.P.231.228; 2.P.231.229; 2.P.231.230; 2.P.231.231; 2.P.231.236;
2.P.231.237; 2.P.231.238; 2.P.231.239; 2.P.231.154; 2.P.231.157; 2.P.231.166;
2.P.231.169; 2.P.231.172; 2.P.231.175; 2.P.231.240; 2.P.231.244; 2.P.236.228;
2.P.236.229; 2.P.236.230; 2.P.236.231; 2.P.236.236; 2.P.236.237; 2.P.236.238;
2.P.236.239; 2.P.236.154; 2.P.236.157; 2.P.236.166; 2.P.236.169; 2.P.236.172;
2.P.236.175; 2.P.236.240; 2.P.236.244; 2.P.237.228; 2.P.237.229; 2.P.237.230;
2.P.237.231; 2.P.237.236; 2.P.237.237; 2.P.237.238; 2.P.237.239; 2.P.237.154;
2.P.237.157; 2.P.237.166; 2.P.237.169; 2.P.237.172; 2.P.237.175; 2.P.237.240;
2.P.237.244; 2.P.238.228; 2.P.238.229; 2.P.238.230; 2.P.238.231; 2.P.238.236;
2.P.238.237; 2.P.238.238; 2.P.238.239; 2.P.238.154; 2.P.238.157; 2.P.238.166;
2.P.238.169; 2.P.238.172; 2.P.238.175; 2.P.238.240; 2.P.238.244; 2.P.239.228;
2.P.239.229; 2.P.239.230; 2.P.239.231; 2.P.239.236; 2.P.239.237; 2.P.239.238;
2.P.239.239; 2.P.239.154; 2.P.239.157; 2.P.239.166; 2.P.239.169; 2.P.239.172;
2.P.239.175; 2.P.239.240; 2.P.239.244; 2.P.154.228; 2.P.154.229; 2.P.154.230;
2.P.154.231; 2.P.154.236; 2.P.154.237; 2.P.154.238; 2.P.154.239; 2.P.154.154;
2.P.154.157; 2.P.154.166; 2.P.154.169; 2.P.154.172; 2.P.154.175; 2.P.154.240;
2.P.154.244; 2.P.157.228; 2.P.157.229; 2.P.157.230; 2.P.157.231; 2.P.157.236;
2.P.157.237; 2.P.157.238; 2.P.157.239; 2.P.157.154; 2.P.157.157; 2.P.157.166;
2.P.157.169; 2.P.157.172; 2.P.157.175; 2.P.157.240; 2.P.157.244; 2.P.166.228;
2.P.166.229; 2.P.166.230; 2.P.166.231; 2.P.166.236; 2.P.166.237; 2.P.166.238;
2.P.166.239; 2.P.166.154; 2.P.166.157; 2.P.166.166; 2.P.166.169; 2.P.166.172;
2.P.166.175; 2.P.166.240; 2.P.166.244; 2.P.169.228; 2.P.169.229; 2.P.169.230;
2.P.169.231; 2.P.169.236; 2.P.169.237; 2.P.169.238; 2.P.169.239; 2.P.169.154;
2.P.169.157; 2.P.169.166; 2.P.169.169; 2.P.169.172; 2.P.169.175; 2.P.169.240;
2.P.169.244; 2.P.172.228; 2.P.172.229; 2.P.172.230; 2.P.172.231; 2.P.172.236;
2.P.172.237; 2.P.172.238; 2.P.172.239; 2.P.172.154; 2.P.172.157; 2.P.172.166;
2.P.172.169; 2.P.172.172; 2.P.172.175; 2.P.172.240; 2.P.172.244; 2.P.175.228;
2.P.175.229; 2.P.175.230; 2.P.175.231; 2.P.175.236; 2.P.175.237; 2.P.175.238;
2.P.175.239; 2.P.175.154; 2.P.175.157; 2.P.175.166; 2.P.175.169; 2.P.175.172;
2.P.175.175; 2.P.175.240; 2.P.175.244; 2.P.240.228; 2.P.240.229; 2.P.240.230;
2.P.240.231; 2.P.240.236; 2.P.240.237; 2.P.240.238; 2.P.240.239; 2.P.240.154;
2.P.240.157; 2.P.240.166; 2.P.240.169; 2.P.240.172; 2.P.240.175; 2.P.240.240;
2.P.240.244; 2.P.244.228; 2.P.244.229; 2.P.244.230; 2.P.244.231; 2.P.244.236;
2.P.244.237; 2.P.244.238; 2.P.244.239; 2.P.244.154; 2.P.244.157; 2.P.244.166;
2.P.244.169; 2.P.244.172; 2.P.244.175; 2.P.244.240; 2.P.244.244;
Prodrugs of 2.U 2.U.228.228; 2.U.228.229; 2.U.228.230; 2.U.228.231; 2.U.228.236;
2.U.228.237; 2.U.228.238; 2.U.228.239; 2.U.228.154; 2.U.228.157;
2.U.228.166; 2.U.228.169; 2.U.228.172; 2.U.228.175; 2.U.228.240;
2.U.228.244; 2.U.229.228; 2.U.229.229; 2.U.229.230; 2.U.229.231;
2.U.229.236; 2.U.229.237; 2.U.229.238; 2.U.229.239; 2.U.229.154;
2.U.229.157; 2.U.229.166; 2.U.229.169; 2.U.229.172; 2.U.229.175;
2.U.229.240; 2.U.229.244; 2.U.230.228; 2.U.230.229; 2.U.230.230;
2.U.230.231; 2.U.230.236; 2.U.230.237; 2.U.230.238; 2.U.230.239;
2.U.230.154; 2.U.230.157; 2.U.230.166; 2.U.230.169; 2.U.230.172;
2.U.230.175; 2.U.230.240; 2.U.230.244; 2.U.231.228; 2.U.231.229;
2.U.231.230; 2.U.231.231; 2.U.231.236; 2.U.231.237; 2.U.231.238;
2.U.231.239; 2.U.231.154; 2.U.231.157; 2.U.231.166; 2.U.231.169;
2.U.231.172; 2.U.231.175; 2.U.231.240; 2.U.231.244; 2.U.236.228;
2.U.236.229; 2.U.236.230; 2.U.236.231; 2.U.236.236; 2.U.236.237;
2.U.236.238; 2.U.236.239; 2.U.236.154; 2.U.236.157; 2.U.236.166;
2.U.236.169; 2.U.236.172; 2.U.236.175; 2.U.236.240; 2.U.236.244;

TABLE 100-continued

2.U.237.228; 2.U.237.229; 2.U.237.230; 2.U.237.231; 2.U.237.236;
2.U.237.237; 2.U.237.238; 2.U.237.239; 2.U.237.154; 2.U.237.157;
2.U.237.166; 2.U.237.169; 2.U.237.172; 2.U.237.175; 2.U.237.240;
2.U.237.244; 2.U.238.228; 2.U.238.229; 2.U.238.230; 2.U.238.231;
2.U.238.236; 2.U.238.237; 2.U.238.238; 2.U.238.239; 2.U.238.154;
2.U.238.157; 2.U.238.166; 2.U.238.169; 2.U.238.172; 2.U.238.175;
2.U.238.240; 2.U.238.244; 2.U.239.228; 2.U.239.229; 2.U.239.230;
2.U.239.231; 2.U.239.236; 2.U.239.237; 2.U.239.238; 2.U.239.239;
2.U.239.154; 2.U.239.157; 2.U.239.166; 2.U.239.169; 2.U.239.172;
2.U.239.175; 2.U.239.240; 2.U.239.244; 2.U.154.228; 2.U.154.229;
2.U.154.230; 2.U.154.231; 2.U.154.236; 2.U.154.237; 2.U.154.238;
2.U.154.239; 2.U.154.154; 2.U.154.157; 2.U.154.166; 2.U.154.169;
2.U.154.172; 2.U.154.175; 2.U.154.240; 2.U.154.244; 2.U.157.228;
2.U.157.229; 2.U.157.230; 2.U.157.231; 2.U.157.236; 2.U.157.237;
2.U.157.238; 2.U.157.239; 2.U.157.154; 2.U.157.157; 2.U.157.166;
2.U.157.169; 2.U.157.172; 2.U.157.175; 2.U.157.240; 2.U.157.244;
2.U.166.228; 2.U.166.229; 2.U.166.230; 2.U.166.231; 2.U.166.236;
2.U.166.237; 2.U.166.238; 2.U.166.239; 2.U.166.154; 2.U.166.157;
2.U.166.166; 2.U.166.169; 2.U.166.172; 2.U.166.175; 2.U.166.240;
2.U.166.244; 2.U.169.228; 2.U.169.229; 2.U.169.230; 2.U.169.231;
2.U.169.236; 2.U.169.237; 2.U.169.238; 2.U.169.239; 2.U.169.154;
2.U.169.157; 2.U.169.166; 2.U.169.169; 2.U.169.172; 2.U.169.175;
2.U.169.240; 2.U.169.244; 2.U.172.228; 2.U.172.229; 2.U.172.230;
2.U.172.231; 2.U.172.236; 2.U.172.237; 2.U.172.238; 2.U.172.239;
2.U.172.154; 2.U.172.157; 2.U.172.166; 2.U.172.169; 2.U.172.172;
2.U.172.175; 2.U.172.240; 2.U.172.244; 2.U.175.228; 2.U.175.229;
2.U.175.230; 2.U.175.231; 2.U.175.236; 2.U.175.237; 2.U.175.238;
2.U.175.239; 2.U.175.154; 2.U.175.157; 2.U.175.166; 2.U.175.169;
2.U.175.172; 2.U.175.175; 2.U.175.240; 2.U.175.244; 2.U.240.228;
2.U.240.229; 2.U.240.230; 2.U.240.231; 2.U.240.236; 2.U.240.237;
2.U.240.238; 2.U.240.239; 2.U.240.154; 2.U.240.157; 2.U.240.166;
2.U.240.169; 2.U.240.172; 2.U.240.175; 2.U.240.240; 2.U.240.244;
2.U.244.228; 2.U.244.229; 2.U.244.230; 2.U.244.231; 2.U.244.236;
2.U.244.237; 2.U.244.238; 2.U.244.239; 2.U.244.154; 2.U.244.157;
2.U.244.166; 2.U.244.169; 2.U.244.172; 2.U.244.175; 2.U.244.240;
2.U.244.244;

Prodrugs of 2.W

2.W.228.228; 2.W.228.229; 2.W.228.230; 2.W.228.231; 2.W.228.236;
2.W.228.237; 2.W.228.238; 2.W.228.239; 2.W.228.154; 2.W.228.157;
2.W.228.166; 2.W.228.169; 2.W.228.172; 2.W.228.175; 2.W.228.240;
2.W.228.244; 2.W.229.228; 2.W.229.229; 2.W.229.230; 2.W.229.231;
2.W.229.236; 2.W.229.237; 2.W.229.238; 2.W.229.239; 2.W.229.154;
2.W.229.157; 2.W.229.166; 2.W.229.169; 2.W.229.172; 2.W.229.175;
2.W.229.240; 2.W.229.244; 2.W.230.228; 2.W.230.229; 2.W.230.230;
2.W.230.231; 2.W.230.236; 2.W.230.237; 2.W.230.238; 2.W.230.239;
2.W.230.154; 2.W.230.157; 2.W.230.166; 2.W.230.169; 2.W.230.172;
2.W.230.175; 2.W.230.240; 2.W.230.244; 2.W.231.228; 2.W.231.229;
2.W.231.230; 2.W.231.231; 2.W.231.236; 2.W.231.237; 2.W.231.238;
2.W.231.239; 2.W.231.154; 2.W.231.157; 2.W.231.166; 2.W.231.169;
2.W.231.172; 2.W.231.175; 2.W.231.240; 2.W.231.244; 2.W.236.228;
2.W.236.229; 2.W.236.230; 2.W.236.231; 2.W.236.236; 2.W.236.237;
2.W.236.238; 2.W.236.239; 2.W.236.154; 2.W.236.157; 2.W.236.166;
2.W.236.169; 2.W.236.172; 2.W.236.175; 2.W.236.240; 2.W.236.244;
2.W.237.228; 2.W.237.229; 2.W.237.230; 2.W.237.231; 2.W.237.236;
2.W.237.237; 2.W.237.238; 2.W.237.239; 2.W.237.154; 2.W.237.157;
2.W.237.166; 2.W.237.169; 2.W.237.172; 2.W.237.175; 2.W.237.240;
2.W.237.244; 2.W.238.228; 2.W.238.229; 2.W.238.230; 2.W.238.231;
2.W.238.236; 2.W.238.237; 2.W.238.238; 2.W.238.239; 2.W.238.154;
2.W.238.157; 2.W.238.166; 2.W.238.169; 2.W.238.172; 2.W.238.175;
2.W.238.240; 2.W.238.244; 2.W.239.228; 2.W.239.229; 2.W.239.230;
2.W.239.231; 2.W.239.236; 2.W.239.237; 2.W.239.238; 2.W.239.239;
2.W.239.154; 2.W.239.157; 2.W.239.166; 2.W.239.169; 2.W.239.172;
2.W.239.175; 2.W.239.240; 2.W.239.244; 2.W.154.228; 2.W.154.229;
2.W.154.230; 2.W.154.231; 2.W.154.236; 2.W.154.237; 2.W.154.238;
2.W.154.239; 2.W.154.154; 2.W.154.157; 2.W.154.166; 2.W.154.169;
2.W.154.172; 2.W.154.175; 2.W.154.240; 2.W.154.244; 2.W.157.228;
2.W.157.229; 2.W.157.230; 2.W.157.231; 2.W.157.236; 2.W.157.237;
2.W.157.238; 2.W.157.239; 2.W.157.154; 2.W.157.157; 2.W.157.166;
2.W.157.169; 2.W.157.172; 2.W.157.175; 2.W.157.240; 2.W.157.244;
2.W.166.228; 2.W.166.229; 2.W.166.230; 2.W.166.231; 2.W.166.236;
2.W.166.237; 2.W.166.238; 2.W.166.239; 2.W.166.154; 2.W.166.157;
2.W.166.166; 2.W.166.169; 2.W.166.172; 2.W.166.175; 2.W.166.240;
2.W.166.244; 2.W.169.228; 2.W.169.229; 2.W.169.230; 2.W.169.231;
2.W.169.236; 2.W.169.237; 2.W.169.238; 2.W.169.239; 2.W.169.154;
2.W.169.157; 2.W.169.166; 2.W.169.169; 2.W.169.172; 2.W.169.175;
2.W.169.240; 2.W.169.244; 2.W.172.228; 2.W.172.229; 2.W.172.230;
2.W.172.231; 2.W.172.236; 2.W.172.237; 2.W.172.238; 2.W.172.239;
2.W.172.154; 2.W.172.157; 2.W.172.166; 2.W.172.169; 2.W.172.172;

TABLE 100-continued

2.W.172.175; 2.W.172.240; 2.W.172.244; 2.W.175.228; 2.W.175.229;
2.W.175.230; 2.W.175.231; 2.W.175.236; 2.W.175.237; 2.W.175.238;
2.W.175.239; 2.W.175.154; 2.W.175.157; 2.W.175.166; 2.W.175.169;
2.W.175.172; 2.W.175.175; 2.W.175.240; 2.W.175.244; 2.W.240.228;
2.W.240.229; 2.W.240.230; 2.W.240.231; 2.W.240.236; 2.W.240.237;
2.W.240.238; 2.W.240.239; 2.W.240.154; 2.W.240.157; 2.W.240.166;
2.W.240.169; 2.W.240.172; 2.W.240.175; 2.W.240.240; 2.W.240.244;
2.W.244.228; 2.W.244.229; 2.W.244.230; 2.W.244.231; 2.W.244.236;
2.W.244.237; 2.W.244.238; 2.W.244.239; 2.W.244.154; 2.W.244.157;
2.W.244.166; 2.W.244.169; 2.W.244.172; 2.W.244.175; 2.W.244.240; 2.W.244.244;
Prodrugs of 2.Y 2.Y.228.228; 2.Y.228.229; 2.Y.228.230; 2.Y.228.231; 2.Y.228.236;
2.Y.228.237; 2.Y.228.238; 2.Y.228.239; 2.Y.228.154; 2.Y.228.157; 2.Y.228.166;
2.Y.228.169; 2.Y.228.172; 2.Y.228.175; 2.Y.228.240; 2.Y.228.244; 2.Y.229.228;
2.Y.229.229; 2.Y.229.230; 2.Y.229.231; 2.Y.229.236; 2.Y.229.237; 2.Y.229.238;
2.Y.229.239; 2.Y.229.154; 2.Y.229.157; 2.Y.229.166; 2.Y.229.169; 2.Y.229.172;
2.Y.229.175; 2.Y.229.240; 2.Y.229.244; 2.Y.230.228; 2.Y.230.229; 2.Y.230.230;
2.Y.230.231; 2.Y.230.236; 2.Y.230.237; 2.Y.230.238; 2.Y.230.239; 2.Y.230.154;
2.Y.230.157; 2.Y.230.166; 2.Y.230.169; 2.Y.230.172; 2.Y.230.175; 2.Y.230.240;
2.Y.230.244; 2.Y.231.228; 2.Y.231.229; 2.Y.231.230; 2.Y.231.231; 2.Y.231.236;
2.Y.231.237; 2.Y.231.238; 2.Y.231.239; 2.Y.231.154; 2.Y.231.157; 2.Y.231.166;
2.Y.231.169; 2.Y.231.172; 2.Y.231.175; 2.Y.231.240; 2.Y.231.244; 2.Y.236.228;
2.Y.236.229; 2.Y.236.230; 2.Y.236.231; 2.Y.236.236; 2.Y.236.237; 2.Y.236.238;
2.Y.236.239; 2.Y.236.154; 2.Y.236.157; 2.Y.236.166; 2.Y.236.169; 2.Y.236.172;
2.Y.236.175; 2.Y.236.240; 2.Y.236.244; 2.Y.237.228; 2.Y.237.229; 2.Y.237.230;
2.Y.237.231; 2.Y.237.236; 2.Y.237.237; 2.Y.237.238; 2.Y.237.239; 2.Y.237.154;
2.Y.237.157; 2.Y.237.166; 2.Y.237.169; 2.Y.237.172; 2.Y.237.175; 2.Y.237.240;
2.Y.237.244; 2.Y.238.228; 2.Y.238.229; 2.Y.238.230; 2.Y.238.231; 2.Y.238.236;
2.Y.238.237; 2.Y.238.238; 2.Y.238.239; 2.Y.238.154; 2.Y.238.157; 2.Y.238.166;
2.Y.238.169; 2.Y.238.172; 2.Y.238.175; 2.Y.238.240; 2.Y.238.244; 2.Y.239.228;
2.Y.239.229; 2.Y.239.230; 2.Y.239.231; 2.Y.239.236; 2.Y.239.237; 2.Y.239.238;
2.Y.239.239; 2.Y.239.154; 2.Y.239.157; 2.Y.239.166; 2.Y.239.169; 2.Y.239.172;
2.Y.239.175; 2.Y.239.240; 2.Y.239.244; 2.Y.154.228; 2.Y.154.229; 2.Y.154.230;
2.Y.154.231; 2.Y.154.236; 2.Y.154.237; 2.Y.154.238; 2.Y.154.239; 2.Y.154.154;
2.Y.154.157; 2.Y.154.166; 2.Y.154.169; 2.Y.154.172; 2.Y.154.175; 2.Y.154.240;
2.Y.154.244; 2.Y.157.228; 2.Y.157.229; 2.Y.157.230; 2.Y.157.231; 2.Y.157.236;
2.Y.157.237; 2.Y.157.238; 2.Y.157.239; 2.Y.157.154; 2.Y.157.157; 2.Y.157.166;
2.Y.157.169; 2.Y.157.172; 2.Y.157.175; 2.Y.157.240; 2.Y.157.244; 2.Y.166.228;
2.Y.166.229; 2.Y.166.230; 2.Y.166.231; 2.Y.166.236; 2.Y.166.237; 2.Y.166.238;
2.Y.166.239; 2.Y.166.154; 2.Y.166.157; 2.Y.166.166; 2.Y.166.169; 2.Y.166.172;
2.Y.166.175; 2.Y.166.240; 2.Y.166.244; 2.Y.169.228; 2.Y.169.229; 2.Y.169.230;
2.Y.169.231; 2.Y.169.236; 2.Y.169.237; 2.Y.169.238; 2.Y.169.239; 2.Y.169.154;
2.Y.169.157; 2.Y.169.166; 2.Y.169.169; 2.Y.169.172; 2.Y.169.175; 2.Y.169.240;
2.Y.169.244; 2.Y.172.228; 2.Y.172.229; 2.Y.172.230; 2.Y.172.231; 2.Y.172.236;
2.Y.172.237; 2.Y.172.238; 2.Y.172.239; 2.Y.172.154; 2.Y.172.157; 2.Y.172.166;
2.Y.172.169; 2.Y.172.172; 2.Y.172.175; 2.Y.172.240; 2.Y.172.244; 2.Y.175.228;
2.Y.175.229; 2.Y.175.230; 2.Y.175.231; 2.Y.175.236; 2.Y.175.237; 2.Y.175.238;
2.Y.175.239; 2.Y.175.154; 2.Y.175.157; 2.Y.175.166; 2.Y.175.169; 2.Y.175.172;
2.Y.175.175; 2.Y.175.240; 2.Y.175.244; 2.Y.240.228; 2.Y.240.229; 2.Y.240.230;
2.Y.240.231; 2.Y.240.236; 2.Y.240.237; 2.Y.240.238; 2.Y.240.239; 2.Y.240.154;
2.Y.240.157; 2.Y.240.166; 2.Y.240.169; 2.Y.240.172; 2.Y.240.175; 2.Y.240.240;
2.Y.240.244; 2.Y.244.228; 2.Y.244.229; 2.Y.244.230; 2.Y.244.231; 2.Y.244.236;
2.Y.244.237; 2.Y.244.238; 2.Y.244.239; 2.Y.244.154; 2.Y.244.157; 2.Y.244.166;
2.Y.244.169; 2.Y.244.172; 2.Y.244.175; 2.Y.244.240; 2.Y.244.244;
Prodrugs of 3.B 3.B.228.228; 3.B.228.229; 3.B.228.230; 3.B.228.231; 3.B.228.236;
3.B.228.237; 3.B.228.238; 3.B.228.239; 3.B.228.154; 3.B.228.157; 3.B.228.166;
3.B.228.169; 3.B.228.172; 3.B.228.175; 3.B.228.240; 3.B.228.244; 3.B.229.228;
3.B.229.229; 3.B.229.230; 3.B.229.231; 3.B.229.236; 3.B.229.237; 3.B.229.238;
3.B.229.239; 3.B.229.154; 3.B.229.157; 3.B.229.166; 3.B.229.169; 3.B.229.172;
3.B.229.175; 3.B.229.240; 3.B.229.244; 3.B.230.228; 3.B.230.229; 3.B.230.230;
3.B.230.231; 3.B.230.236; 3.B.230.237; 3.B.230.238; 3.B.230.239; 3.B.230.154;
3.B.230.157; 3.B.230.166; 3.B.230.169; 3.B.230.172; 3.B.230.175; 3.B.230.240;
3.B.230.244; 3.B.231.228; 3.B.231.229; 3.B.231.230; 3.B.231.231; 3.B.231.236;
3.B.231.237; 3.B.231.238; 3.B.231.239; 3.B.231.154; 3.B.231.157; 3.B.231.166;
3.B.231.169; 3.B.231.172; 3.B.231.175; 3.B.231.240; 3.B.231.244; 3.B.236.228;
3.B.236.229; 3.B.236.230; 3.B.236.231; 3.B.236.236; 3.B.236.237; 3.B.236.238;
3.B.236.239; 3.B.236.154; 3.B.236.157; 3.B.236.166; 3.B.236.169; 3.B.236.172;
3.B.236.175; 3.B.236.240; 3.B.236.244; 3.B.237.228; 3.B.237.229; 3.B.237.230;
3.B.237.231; 3.B.237.236; 3.B.237.237; 3.B.237.238; 3.B.237.239; 3.B.237.154;
3.B.237.157; 3.B.237.166; 3.B.237.169; 3.B.237.172; 3.B.237.175; 3.B.237.240;
3.B.237.244; 3.B.238.228; 3.B.238.229; 3.B.238.230; 3.B.238.231; 3.B.238.236;
3.B.238.237; 3.B.238.238; 3.B.238.239; 3.B.238.154; 3.B.238.157; 3.B.238.166;
3.B.238.169; 3.B.238.172; 3.B.238.175; 3.B.238.240; 3.B.238.244; 3.B.239.228;
3.B.239.229; 3.B.239.230; 3.B.239.231; 3.B.239.236; 3.B.239.237; 3.B.239.238;
3.B.239.239; 3.B.239.154; 3.B.239.157; 3.B.239.166; 3.B.239.169; 3.B.239.172;
3.B.239.175; 3.B.239.240; 3.B.239.244; 3.B.154.228; 3.B.154.229; 3.B.154.230;

TABLE 100-continued

3.B.154.231; 3.B.154.236; 3.B.154.237; 3.B.154.238; 3.B.154.239; 3.B.154.154;
3.B.154.157; 3.B.154.166; 3.B.154.169; 3.B.154.172; 3.B.154.175; 3.B.154.240;
3.B.154.244; 3.B.157.228; 3.B.157.229; 3.B.157.230; 3.B.157.231; 3.B.157.236;
3.B.157.237; 3.B.157.238; 3.B.157.239; 3.B.157.154; 3.B.157.157; 3.B.157.166;
3.B.157.169; 3.B.157.172; 3.B.157.175; 3.B.157.240; 3.B.157.244; 3.B.166.228;
3.B.166.229; 3.B.166.230; 3.B.166.231; 3.B.166.236; 3.B.166.237; 3.B.166.238;
3.B.166.239; 3.B.166.154; 3.B.166.157; 3.B.166.166; 3.B.166.169; 3.B.166.172;
3.B.166.175; 3.B.166.240; 3.B.166.244; 3.B.169.228; 3.B.169.229; 3.B.169.230;
3.B.169.231; 3.B.169.236; 3.B.169.237; 3.B.169.238; 3.B.169.239; 3.B.169.154;
3.B.169.157; 3.B.169.166; 3.B.169.169; 3.B.169.172; 3.B.169.175; 3.B.169.240;
3.B.169.244; 3.B.172.228; 3.B.172.229; 3.B.172.230; 3.B.172.231; 3.B.172.236;
3.B.172.237; 3.B.172.238; 3.B.172.239; 3.B.172.154; 3.B.172.157; 3.B.172.166;
3.B.172.169; 3.B.172.172; 3.B.172.175; 3.B.172.240; 3.B.172.244; 3.B.175.228;
3.B.175.229; 3.B.175.230; 3.B.175.231; 3.B.175.236; 3.B.175.237; 3.B.175.238;
3.B.175.239; 3.B.175.154; 3.B.175.157; 3.B.175.166; 3.B.175.169; 3.B.175.172;
3.B.175.175; 3.B.175.240; 3.B.175.244; 3.B.240.228; 3.B.240.229; 3.B.240.230;
3.B.240.231; 3.B.240.236; 3.B.240.237; 3.B.240.238; 3.B.240.239; 3.B.240.154;
3.B.240.157; 3.B.240.166; 3.B.240.169; 3.B.240.172; 3.B.240.175; 3.B.240.240;
3.B.240.244; 3.B.244.228; 3.B.244.229; 3.B.244.230; 3.B.244.231; 3.B.244.236;
3.B.244.237; 3.B.244.238; 3.B.244.239; 3.B.244.154; 3.B.244.157; 3.B.244.166;
3.B.244.169; 3.B.244.172; 3.B.244.175; 3.B.244.240; 3.B.244.244;
Prodrugs of 3.D 3.D.228.228; 3.D.228.229; 3.D.228.230; 3.D.228.231; 3.D.228.236;
3.D.228.237; 3.D.228.238; 3.D.228.239; 3.D.228.154; 3.D.228.157;
3.D.228.166; 3.D.228.169; 3.D.228.172; 3.D.228.175; 3.D.228.240;
3.D.228.244; 3.D.229.228; 3.D.229.229; 3.D.229.230; 3.D.229.231;
3.D.229.236; 3.D.229.237; 3.D.229.238; 3.D.229.239; 3.D.229.154;
3.D.229.157; 3.D.229.166; 3.D.229.169; 3.D.229.172; 3.D.229.175;
3.D.229.240; 3.D.229.244; 3.D.230.228; 3.D.230.229; 3.D.230.230;
3.D.230.231; 3.D.230.236; 3.D.230.237; 3.D.230.238; 3.D.230.239;
3.D.230.154; 3.D.230.157; 3.D.230.166; 3.D.230.169; 3.D.230.172;
3.D.230.175; 3.D.230.240; 3.D.230.244; 3.D.231.228; 3.D.231.229;
3.D.231.230; 3.D.231.231; 3.D.231.236; 3.D.231.237; 3.D.231.238;
3.D.231.239; 3.D.231.154; 3.D.231.157; 3.D.231.166; 3.D.231.169;
3.D.231.172; 3.D.231.175; 3.D.231.240; 3.D.231.244; 3.D.236.228;
3.D.236.229; 3.D.236.230; 3.D.236.231; 3.D.236.236; 3.D.236.237;
3.D.236.238; 3.D.236.239; 3.D.236.154; 3.D.236.157; 3.D.236.166;
3.D.236.169; 3.D.236.172; 3.D.236.175; 3.D.236.240; 3.D.236.244;
3.D.237.228; 3.D.237.229; 3.D.237.230; 3.D.237.231; 3.D.237.236;
3.D.237.237; 3.D.237.238; 3.D.237.239; 3.D.237.154; 3.D.237.157;
3.D.237.166; 3.D.237.169; 3.D.237.172; 3.D.237.175; 3.D.237.240;
3.D.237.244; 3.D.238.228; 3.D.238.229; 3.D.238.230; 3.D.238.231;
3.D.238.236; 3.D.238.237; 3.D.238.238; 3.D.238.239; 3.D.238.154;
3.D.238.157; 3.D.238.166; 3.D.238.169; 3.D.238.172; 3.D.238.175;
3.D.238.240; 3.D.238.244; 3.D.239.228; 3.D.239.229; 3.D.239.230;
3.D.239.231; 3.D.239.236; 3.D.239.237; 3.D.239.238; 3.D.239.239;
3.D.239.154; 3.D.239.157; 3.D.239.166; 3.D.239.169; 3.D.239.172;
3.D.239.175; 3.D.239.240; 3.D.239.244; 3.D.154.228; 3.D.154.229;
3.D.154.230; 3.D.154.231; 3.D.154.236; 3.D.154.237; 3.D.154.238;
3.D.154.239; 3.D.154.154; 3.D.154.157; 3.D.154.166; 3.D.154.169;
3.D.154.172; 3.D.154.175; 3.D.154.240; 3.D.154.244; 3.D.157.228;
3.D.157.229; 3.D.157.230; 3.D.157.231; 3.D.157.236; 3.D.157.237;
3.D.157.238; 3.D.157.239; 3.D.157.154; 3.D.157.157; 3.D.157.166;
3.D.157.169; 3.D.157.172; 3.D.157.175; 3.D.157.240; 3.D.157.244;
3.D.166.228; 3.D.166.229; 3.D.166.230; 3.D.166.231; 3.D.166.236;
3.D.166.237; 3.D.166.238; 3.D.166.239; 3.D.166.154; 3.D.166.157;
3.D.166.166; 3.D.166.169; 3.D.166.172; 3.D.166.175; 3.D.166.240;
3.D.166.244; 3.D.169.228; 3.D.169.229; 3.D.169.230; 3.D.169.231;
3.D.169.236; 3.D.169.237; 3.D.169.238; 3.D.169.239; 3.D.169.154;
3.D.169.157; 3.D.169.166; 3.D.169.169; 3.D.169.172; 3.D.169.175;
3.D.169.240; 3.D.169.244; 3.D.172.228; 3.D.172.229; 3.D.172.230;
3.D.172.231; 3.D.172.236; 3.D.172.237; 3.D.172.238; 3.D.172.239;
3.D.172.154; 3.D.172.157; 3.D.172.166; 3.D.172.169; 3.D.172.172;
3.D.172.175; 3.D.172.240; 3.D.172.244; 3.D.175.228; 3.D.175.229;
3.D.175.230; 3.D.175.231; 3.D.175.236; 3.D.175.237; 3.D.175.238;
3.D.175.239; 3.D.175.154; 3.D.175.157; 3.D.175.166; 3.D.175.169;
3.D.175.172; 3.D.175.175; 3.D.175.240; 3.D.175.244; 3.D.240.228;
3.D.240.229; 3.D.240.230; 3.D.240.231; 3.D.240.236; 3.D.240.237;
3.D.240.238; 3.D.240.239; 3.D.240.154; 3.D.240.157; 3.D.240.166;
3.D.240.169; 3.D.240.172; 3.D.240.175; 3.D.240.240; 3.D.240.244;
3.D.244.228; 3.D.244.229; 3.D.244.230; 3.D.244.231; 3.D.244.236;
3.D.244.237; 3.D.244.238; 3.D.244.239; 3.D.244.154; 3.D.244.157;
3.D.244.166; 3.D.244.169; 3.D.244.172; 3.D.244.175; 3.D.244.240;
3.D.244.244;
Prodrugs of 3.E 3.E.228.228; 3.E.228.229; 3.E.228.230; 3.E.228.231; 3.E.228.236;
3.E.228.237; 3.E.228.238; 3.E.228.239; 3.E.228.154; 3.E.228.157; 3.E.228.166;

TABLE 100-continued

3.E.228.169; 3.E.228.172; 3.E.228.175; 3.E.228.240; 3.E.228.244; 3.E.229.228;
3.E.229.229; 3.E.229.230; 3.E.229.231; 3.E.229.236; 3.E.229.237; 3.E.229.238;
3.E.229.239; 3.E.229.154; 3.E.229.157; 3.E.229.166; 3.E.229.169; 3.E.229.172;
3.E.229.175; 3.E.229.240; 3.E.229.244; 3.E.230.228; 3.E.230.229; 3.E.230.230;
3.E.230.231; 3.E.230.236; 3.E.230.237; 3.E.230.238; 3.E.230.239; 3.E.230.154;
3.E.230.157; 3.E.230.166; 3.E.230.169; 3.E.230.172; 3.E.230.175; 3.E.230.240;
3.E.230.244; 3.E.231.228; 3.E.231.229; 3.E.231.230; 3.E.231.231; 3.E.231.236;
3.E.231.237; 3.E.231.238; 3.E.231.239; 3.E.231.154; 3.E.231.157; 3.E.231.166;
3.E.231.169; 3.E.231.172; 3.E.231.175; 3.E.231.240; 3.E.231.244; 3.E.236.228;
3.E.236.229; 3.E.236.230; 3.E.236.231; 3.E.236.236; 3.E.236.237; 3.E.236.238;
3.E.236.239; 3.E.236.154; 3.E.236.157; 3.E.236.166; 3.E.236.169; 3.E.236.172;
3.E.236.175; 3.E.236.240; 3.E.236.244; 3.E.237.228; 3.E.237.229; 3.E.237.230;
3.E.237.231; 3.E.237.236; 3.E.237.237; 3.E.237.238; 3.E.237.239; 3.E.237.154;
3.E.237.157; 3.E.237.166; 3.E.237.169; 3.E.237.172; 3.E.237.175; 3.E.237.240;
3.E.237.244; 3.E.238.228; 3.E.238.229; 3.E.238.230; 3.E.238.231; 3.E.238.236;
3.E.238.237; 3.E.238.238; 3.E.238.239; 3.E.238.154; 3.E.238.157; 3.E.238.166;
3.E.238.169; 3.E.238.172; 3.E.238.175; 3.E.238.240; 3.E.238.244; 3.E.239.228;
3.E.239.229; 3.E.239.230; 3.E.239.231; 3.E.239.236; 3.E.239.237; 3.E.239.238;
3.E.239.239; 3.E.239.154; 3.E.239.157; 3.E.239.166; 3.E.239.169; 3.E.239.172;
3.E.239.175; 3.E.239.240; 3.E.239.244; 3.E.154.228; 3.E.154.229; 3.E.154.230;
3.E.154.231; 3.E.154.236; 3.E.154.237; 3.E.154.238; 3.E.154.239; 3.E.154.154;
3.E.154.157; 3.E.154.166; 3.E.154.169; 3.E.154.172; 3.E.154.175; 3.E.154.240;
3.E.154.244; 3.E.157.228; 3.E.157.229; 3.E.157.230; 3.E.157.231; 3.E.157.236;
3.E.157.237; 3.E.157.238; 3.E.157.239; 3.E.157.154; 3.E.157.157; 3.E.157.166;
3.E.157.169; 3.E.157.172; 3.E.157.175; 3.E.157.240; 3.E.157.244; 3.E.166.228;
3.E.166.229; 3.E.166.230; 3.E.166.231; 3.E.166.236; 3.E.166.237; 3.E.166.238;
3.E.166.239; 3.E.166.154; 3.E.166.157; 3.E.166.166; 3.E.166.169; 3.E.166.172;
3.E.166.175; 3.E.166.240; 3.E.166.244; 3.E.169.228; 3.E.169.229; 3.E.169.230;
3.E.169.231; 3.E.169.236; 3.E.169.237; 3.E.169.238; 3.E.169.239; 3.E.169.154;
3.E.169.157; 3.E.169.166; 3.E.169.169; 3.E.169.172; 3.E.169.175; 3.E.169.240;
3.E.169.244; 3.E.172.228; 3.E.172.229; 3.E.172.230; 3.E.172.231; 3.E.172.236;
3.E.172.237; 3.E.172.238; 3.E.172.239; 3.E.172.154; 3.E.172.157; 3.E.172.166;
3.E.172.169; 3.E.172.172; 3.E.172.175; 3.E.172.240; 3.E.172.244; 3.E.175.228;
3.E.175.229; 3.E.175.230; 3.E.175.231; 3.E.175.236; 3.E.175.237; 3.E.175.238;
3.E.175.239; 3.E.175.154; 3.E.175.157; 3.E.175.166; 3.E.175.169; 3.E.175.172;
3.E.175.175; 3.E.175.240; 3.E.175.244; 3.E.240.228; 3.E.240.229; 3.E.240.230;
3.E.240.231; 3.E.240.236; 3.E.240.237; 3.E.240.238; 3.E.240.239; 3.E.240.154;
3.E.240.157; 3.E.240.166; 3.E.240.169; 3.E.240.172; 3.E.240.175; 3.E.240.240;
3.E.240.244; 3.E.244.228; 3.E.244.229; 3.E.244.230; 3.E.244.231; 3.E.244.236;
3.E.244.237; 3.E.244.238; 3.E.244.239; 3.E.244.154; 3.E.244.157; 3.E.244.166;
3.E.244.169; 3.E.244.172; 3.E.244.175; 3.E.244.240; 3.E.244.244;
Prodrugs of 3.G 3.G.228.228; 3.G.228.229; 3.G.228.230; 3.G.228.231; 3.G.228.236;
3.G.228.237; 3.G.228.238; 3.G.228.239; 3.G.228.154; 3.G.228.157;
3.G.228.166; 3.G.228.169; 3.G.228.172; 3.G.228.175; 3.G.228.240;
3.G.228.244; 3.G.229.228; 3.G.229.229; 3.G.229.230; 3.G.229.231;
3.G.229.236; 3.G.229.237; 3.G.229.238; 3.G.229.239; 3.G.229.154;
3.G.229.157; 3.G.229.166; 3.G.229.169; 3.G.229.172; 3.G.229.175;
3.G.229.240; 3.G.229.244; 3.G.230.228; 3.G.230.229; 3.G.230.230;
3.G.230.231; 3.G.230.236; 3.G.230.237; 3.G.230.238; 3.G.230.239;
3.G.230.154; 3.G.230.157; 3.G.230.166; 3.G.230.169; 3.G.230.172;
3.G.230.175; 3.G.230.240; 3.G.230.244; 3.G.231.228; 3.G.231.229;
3.G.231.230; 3.G.231.231; 3.G.231.236; 3.G.231.237; 3.G.231.238;
3.G.231.239; 3.G.231.154; 3.G.231.157; 3.G.231.166; 3.G.231.169;
3.G.231.172; 3.G.231.175; 3.G.231.240; 3.G.231.244; 3.G.236.228;
3.G.236.229; 3.G.236.230; 3.G.236.231; 3.G.236.236; 3.G.236.237;
3.G.236.238; 3.G.236.239; 3.G.236.154; 3.G.236.157; 3.G.236.166;
3.G.236.169; 3.G.236.172; 3.G.236.175; 3.G.236.240; 3.G.236.244;
3.G.237.228; 3.G.237.229; 3.G.237.230; 3.G.237.231; 3.G.237.236;
3.G.237.237; 3.G.237.238; 3.G.237.239; 3.G.237.154; 3.G.237.157;
3.G.237.166; 3.G.237.169; 3.G.237.172; 3.G.237.175; 3.G.237.240;
3.G.237.244; 3.G.238.228; 3.G.238.229; 3.G.238.230; 3.G.238.231;
3.G.238.236; 3.G.238.237; 3.G.238.238; 3.G.238.239; 3.G.238.154;
3.G.238.157; 3.G.238.166; 3.G.238.169; 3.G.238.172; 3.G.238.175;
3.G.238.240; 3.G.238.244; 3.G.239.228; 3.G.239.229; 3.G.239.230;
3.G.239.231; 3.G.239.236; 3.G.239.237; 3.G.239.238; 3.G.239.239;
3.G.239.154; 3.G.239.157; 3.G.239.166; 3.G.239.169; 3.G.239.172;
3.G.239.175; 3.G.239.240; 3.G.239.244; 3.G.154.228; 3.G.154.229;
3.G.154.230; 3.G.154.231; 3.G.154.236; 3.G.154.237; 3.G.154.238;
3.G.154.239; 3.G.154.154; 3.G.154.157; 3.G.154.166; 3.G.154.169;
3.G.154.172; 3.G.154.175; 3.G.154.240; 3.G.154.244; 3.G.157.228;
3.G.157.229; 3.G.157.230; 3.G.157.231; 3.G.157.236; 3.G.157.237;
3.G.157.238; 3.G.157.239; 3.G.157.154; 3.G.157.157; 3.G.157.166;
3.G.157.169; 3.G.157.172; 3.G.157.175; 3.G.157.240; 3.G.157.244;
3.G.166.228; 3.G.166.229; 3.G.166.230; 3.G.166.231; 3.G.166.236;
3.G.166.237; 3.G.166.238; 3.G.166.239; 3.G.166.154; 3.G.166.157;
3.G.166.166; 3.G.166.169; 3.G.166.172; 3.G.166.175; 3.G.166.240;
3.G.166.244; 3.G.169.228; 3.G.169.229; 3.G.169.230; 3.G.169.231;

TABLE 100-continued

3.G.169.236; 3.G.169.237; 3.G.169.238; 3.G.169.239; 3.G.169.154;
3.G.169.157; 3.G.169.166; 3.G.169.169; 3.G.169.172; 3.G.169.175;
3.G.169.240; 3.G.169.244; 3.G.172.228; 3.G.172.229; 3.G.172.230;
3.G.172.231; 3.G.172.236; 3.G.172.237; 3.G.172.238; 3.G.172.239;
3.G.172.154; 3.G.172.157; 3.G.172.166; 3.G.172.169; 3.G.172.172;
3.G.172.175; 3.G.172.240; 3.G.172.244; 3.G.175.228; 3.G.175.229;
3.G.175.230; 3.G.175.231; 3.G.175.236; 3.G.175.237; 3.G.175.238;
3.G.175.239; 3.G.175.154; 3.G.175.157; 3.G.175.166; 3.G.175.169;
3.G.175.172; 3.G.175.175; 3.G.175.240; 3.G.175.244; 3.G.240.228;
3.G.240.229; 3.G.240.230; 3.G.240.231; 3.G.240.236; 3.G.240.237;
3.G.240.238; 3.G.240.239; 3.G.240.154; 3.G.240.157; 3.G.240.166;
3.G.240.169; 3.G.240.172; 3.G.240.175; 3.G.240.240; 3.G.240.244;
3.G.244.228; 3.G.244.229; 3.G.244.230; 3.G.244.231; 3.G.244.236;
3.G.244.237; 3.G.244.238; 3.G.244.239; 3.G.244.154; 3.G.244.157;
3.G.244.166; 3.G.244.169; 3.G.244.172; 3.G.244.175; 3.G.244.240;
3.G.244.244;

Prodrugs of 3.I

3.I.228.228; 3.I.228.229; 3.I.228.230; 3.I.228.231; 3.I.228.236; 3.I.228.237;
3.I.228.238; 3.I.228.239; 3.I.228.154; 3.I.228.157; 3.I.228.166; 3.I.228.169;
3.I.228.172; 3.I.228.175; 3.I.228.240; 3.I.228.244; 3.I.229.228; 3.I.229.229;
3.I.229.230; 3.I.229.231; 3.I.229.236; 3.I.229.237; 3.I.229.238; 3.I.229.239;
3.I.229.154; 3.I.229.157; 3.I.229.166; 3.I.229.169; 3.I.229.172; 3.I.229.175;
3.I.229.240; 3.I.229.244; 3.I.230.228; 3.I.230.229; 3.I.230.230; 3.I.230.231;
3.I.230.236; 3.I.230.237; 3.I.230.238; 3.I.230.239; 3.I.230.154; 3.I.230.157;
3.I.230.166; 3.I.230.169; 3.I.230.172; 3.I.230.175; 3.I.230.240; 3.I.230.244;
3.I.231.228; 3.I.231.229; 3.I.231.230; 3.I.231.231; 3.I.231.236; 3.I.231.237;
3.I.231.238; 3.I.231.239; 3.I.231.154; 3.I.231.157; 3.I.231.166; 3.I.231.169;
3.I.231.172; 3.I.231.175; 3.I.231.240; 3.I.231.244; 3.I.236.228; 3.I.236.229;
3.I.236.230; 3.I.236.231; 3.I.236.236; 3.I.236.237; 3.I.236.238; 3.I.236.239;
3.I.236.154; 3.I.236.157; 3.I.236.166; 3.I.236.169; 3.I.236.172; 3.I.236.175;
3.I.236.240; 3.I.236.244; 3.I.237.228; 3.I.237.229; 3.I.237.230; 3.I.237.231;
3.I.237.236; 3.I.237.237; 3.I.237.238; 3.I.237.239; 3.I.237.154; 3.I.237.157;
3.I.237.166; 3.I.237.169; 3.I.237.172; 3.I.237.175; 3.I.237.240; 3.I.237.244;
3.I.238.228; 3.I.238.229; 3.I.238.230; 3.I.238.231; 3.I.238.236; 3.I.238.237;
3.I.238.238; 3.I.238.239; 3.I.238.154; 3.I.238.157; 3.I.238.166; 3.I.238.169;
3.I.238.172; 3.I.238.175; 3.I.238.240; 3.I.238.244; 3.I.239.228; 3.I.239.229;
3.I.239.230; 3.I.239.231; 3.I.239.236; 3.I.239.237; 3.I.239.238; 3.I.239.239;
3.I.239.154; 3.I.239.157; 3.I.239.166; 3.I.239.169; 3.I.239.172; 3.I.239.175;
3.I.239.240; 3.I.239.244; 3.I.154.228; 3.I.154.229; 3.I.154.230; 3.I.154.231;
3.I.154.236; 3.I.154.237; 3.I.154.238; 3.I.154.239; 3.I.154.154; 3.I.154.157;
3.I.154.166; 3.I.154.169; 3.I.154.172; 3.I.154.175; 3.I.154.240; 3.I.154.244;
3.I.157.228; 3.I.157.229; 3.I.157.230; 3.I.157.231; 3.I.157.236; 3.I.157.237;
3.I.157.238; 3.I.157.239; 3.I.157.154; 3.I.157.157; 3.I.157.166; 3.I.157.169;
3.I.157.172; 3.I.157.175; 3.I.157.240; 3.I.157.244; 3.I.166.228; 3.I.166.229;
3.I.166.230; 3.I.166.231; 3.I.166.236; 3.I.166.237; 3.I.166.238; 3.I.166.239;
3.I.166.154; 3.I.166.157; 3.I.166.166; 3.I.166.169; 3.I.166.172; 3.I.166.175;
3.I.166.240; 3.I.166.244; 3.I.169.228; 3.I.169.229; 3.I.169.230; 3.I.169.231;
3.I.169.236; 3.I.169.237; 3.I.169.238; 3.I.169.239; 3.I.169.154; 3.I.169.157;
3.I.169.166; 3.I.169.169; 3.I.169.172; 3.I.169.175; 3.I.169.240; 3.I.169.244;
3.I.172.228; 3.I.172.229; 3.I.172.230; 3.I.172.231; 3.I.172.236; 3.I.172.237;
3.I.172.238; 3.I.172.239; 3.I.172.154; 3.I.172.157; 3.I.172.166; 3.I.172.169;
3.I.172.172; 3.I.172.175; 3.I.172.240; 3.I.172.244; 3.I.175.228; 3.I.175.229;
3.I.175.230; 3.I.175.231; 3.I.175.236; 3.I.175.237; 3.I.175.238; 3.I.175.239;
3.I.175.154; 3.I.175.157; 3.I.175.166; 3.I.175.169; 3.I.175.172; 3.I.175.175;
3.I.175.240; 3.I.175.244; 3.I.240.228; 3.I.240.229; 3.I.240.230; 3.I.240.231;
3.I.240.236; 3.I.240.237; 3.I.240.238; 3.I.240.239; 3.I.240.154; 3.I.240.157;
3.I.240.166; 3.I.240.169; 3.I.240.172; 3.I.240.175; 3.I.240.240; 3.I.240.244;
3.I.244.228; 3.I.244.229; 3.I.244.230; 3.I.244.231; 3.I.244.236; 3.I.244.237;
3.I.244.238; 3.I.244.239; 3.I.244.154; 3.I.244.157; 3.I.244.166; 3.I.244.169;
3.I.244.172; 3.I.244.175; 3.I.244.240; 3.I.244.244;

Prodrugs of 3.J

3.J.228.228; 3.J.228.229; 3.J.228.230; 3.J.228.231; 3.J.228.236; 3.J.228.237;
3.J.228.238; 3.J.228.239; 3.J.228.154; 3.J.228.157; 3.J.228.166; 3.J.228.169;
3.J.228.172; 3.J.228.175; 3.J.228.240; 3.J.228.244; 3.J.229.228; 3.J.229.229;
3.J.229.230; 3.J.229.231; 3.J.229.236; 3.J.229.237; 3.J.229.238; 3.J.229.239;
3.J.229.154; 3.J.229.157; 3.J.229.166; 3.J.229.169; 3.J.229.172; 3.J.229.175;
3.J.229.240; 3.J.229.244; 3.J.230.228; 3.J.230.229; 3.J.230.230; 3.J.230.231;
3.J.230.236; 3.J.230.237; 3.J.230.238; 3.J.230.239; 3.J.230.154; 3.J.230.157;
3.J.230.166; 3.J.230.169; 3.J.230.172; 3.J.230.175; 3.J.230.240; 3.J.230.244;
3.J.231.228; 3.J.231.229; 3.J.231.230; 3.J.231.231; 3.J.231.236; 3.J.231.237;
3.J.231.238; 3.J.231.239; 3.J.231.154; 3.J.231.157; 3.J.231.166; 3.J.231.169;
3.J.231.172; 3.J.231.175; 3.J.231.240; 3.J.231.244; 3.J.236.228; 3.J.236.229;
3.J.236.230; 3.J.236.231; 3.J.236.236; 3.J.236.237; 3.J.236.238; 3.J.236.239;
3.J.236.154; 3.J.236.157; 3.J.236.166; 3.J.236.169; 3.J.236.172; 3.J.236.175;
3.J.236.240; 3.J.236.244; 3.J.237.228; 3.J.237.229; 3.J.237.230; 3.J.237.231;
3.J.237.236; 3.J.237.237; 3.J.237.238; 3.J.237.239; 3.J.237.154; 3.J.237.157;
3.J.237.166; 3.J.237.169; 3.J.237.172; 3.J.237.175; 3.J.237.240; 3.J.237.244;

TABLE 100-continued

3.J.238.228; 3.J.238.229; 3.J.238.230; 3.J.238.231; 3.J.238.236; 3.J.238.237;
3.J.238.238; 3.J.238.239; 3.J.238.154; 3.J.238.157; 3.J.238.166; 3.J.238.169;
3.J.238.172; 3.J.238.175; 3.J.238.240; 3.J.238.244; 3.J.239.228; 3.J.239.229;
3.J.239.230; 3.J.239.231; 3.J.239.236; 3.J.239.237; 3.J.239.238; 3.J.239.239;
3.J.239.154; 3.J.239.157; 3.J.239.166; 3.J.239.169; 3.J.239.172; 3.J.239.175;
3.J.239.240; 3.J.239.244; 3.J.154.228; 3.J.154.229; 3.J.154.230; 3.J.154.231;
3.J.154.236; 3.J.154.237; 3.J.154.238; 3.J.154.239; 3.J.154.154; 3.J.154.157;
3.J.154.166; 3.J.154.169 3.J.154.172; 3.J.154.175; 3.J.154.240; 3.J.154.244;
3.J.157.228; 3.J.157.229; 3.J.157.230; 3.J.157.231; 3.J.157.236; 3.J.157.237;
3.J.157.238; 3.J.157.239; 3.J.157.154; 3.J.157.157; 3.J.157.166; 3.J.157.169;
3.J.157.172; 3.J.157.175; 3.J.157.240; 3.J.157.244; 3.J.166.228; 3.J.166.229;
3.J.166.230; 3.J.166.231; 3.J.166.236; 3.J.166.237; 3.J.166.238; 3.J.166.239;
3.J.166.154; 3.J.166.157; 3.J.166.166; 3.J.166.169; 3.J.166.172; 3.J.166.175;
3.J.166.240; 3.J.166.244; 3.J.169.228; 3.J.169.229; 3.J.169.230; 3.J.169.231;
3.J.169.236; 3.J.169.237; 3.J.169.238; 3.J.169.239; 3.J.169.154; 3.J.169.157;
3.J.169.166; 3.J.169.169; 3.J.169.172; 3.J.169.175; 3.J.169.240; 3.J.169.244;
3.J.172.228; 3.J.172.229; 3.J.172.230; 3.J.172.231; 3.J.172.236; 3.J.172.237;
3.J.172.238; 3.J.172.239; 3.J.172.154; 3.J.172.157; 3.J.172.166; 3.J.172.169;
3.J.172.172; 3.J.172.175; 3.J.172.240; 3.J.172.244; 3.J.175.228; 3.J.175.229;
3.J.175.230; 3.J.175.231; 3.J.175.236; 3.J.175.237; 3.J.175.238; 3.J.175.239;
3.J.175.154; 3.J.175.157; 3.J.175.166; 3.J.175.169; 3.J.175.172; 3.J.175.175;
3.J.175.240; 3.J.175.244; 3.J.240.228; 3.J.240.229; 3.J.240.230; 3.J.240.231;
3.J.240.236; 3.J.240.237; 3.J.240.238; 3.J.240.239; 3.J.240.154; 3.J.240.157;
3.J.240.166; 3.J.240.169; 3.J.240.172; 3.J.240.175; 3.J.240.240; 3.J.240.244;
3.J.244.228; 3.J.244.229; 3.J.244.230; 3.J.244.231; 3.J.244.236; 3.J.244.237;
3.J.244.238; 3.J.244.239; 3.J.244.154; 3.J.244.157; 3.J.244.166; 3.J.244.169;
3.J.244.172; 3.J.244.175; 3.J.244.240; 3.J.244.244;

Prodrugs of 3.L

3.L.228.228; 3.L.228.229; 3.L.228.230; 3.L.228.231; 3.L.228.236;
3.L.228.237; 3.L.228.238; 3.L.228.239; 3.L.228.154; 3.L.228.157; 3.L.228.166;
3.L.228.169; 3.L.228.172; 3.L.228.175; 3.L.228.240; 3.L.228.244; 3.L.229.228;
3.L.229.229; 3.L.229.230; 3.L.229.231; 3.L.229.236; 3.L.229.237; 3.L.229.238;
3.L.229.239; 3.L.229.154; 3.L.229.157; 3.L.229.166; 3.L.229.169; 3.L.229.172;
3.L.229.175; 3.L.229.240; 3.L.229.244; 3.L.230.228; 3.L.230.229; 3.L.230.230;
3.L.230.231; 3.L.230.236; 3.L.230.237; 3.L.230.238; 3.L.230.239; 3.L.230.154;
3.L.230.157; 3.L.230.166; 3.L.230.169; 3.L.230.172; 3.L.230.175; 3.L.230.240;
3.L.230.244; 3.L.231.228; 3.L.231.229; 3.L.231.230; 3.L.231.231; 3.L.231.236;
3.L.231.237; 3.L.231.238; 3.L.231.239; 3.L.231.154; 3.L.231.157; 3.L.231.166;
3.L.231.169; 3.L.231.172; 3.L.231.175; 3.L.231.240; 3.L.231.244; 3.L.236.228;
3.L.236.229; 3.L.236.230; 3.L.236.231; 3.L.236.236; 3.L.236.237; 3.L.236.238;
3.L.236.239; 3.L.236.154; 3.L.236.157; 3.L.236.166; 3.L.236.169; 3.L.236.172;
3.L.236.175; 3.L.236.240; 3.L.236.244; 3.L.237.228; 3.L.237.229; 3.L.237.230;
3.L.237.231; 3.L.237.236; 3.L.237.237; 3.L.237.238; 3.L.237.239; 3.L.237.154;
3.L.237.157; 3.L.237.166; 3.L.237.169; 3.L.237.172; 3.L.237.175; 3.L.237.240;
3.L.237.244; 3.L.238.228; 3.L.238.229; 3.L.238.230; 3.L.238.231; 3.L.238.236;
3.L.238.237; 3.L.238.238; 3.L.238.239; 3.L.238.154; 3.L.238.157; 3.L.238.166;
3.L.238.169; 3.L.238.172; 3.L.238.175; 3.L.238.240; 3.L.238.244; 3.L.239.228;
3.L.239.229; 3.L.239.230; 3.L.239.231; 3.L.239.236; 3.L.239.237; 3.L.239.238;
3.L.239.239; 3.L.239.154; 3.L.239.157; 3.L.239.166; 3.L.239.169; 3.L.239.172;
3.L.239.175; 3.L.239.240; 3.L.239.244; 3.L.154.228; 3.L.154.229; 3.L.154.230;
3.L.154.231; 3.L.154.236; 3.L.154.237; 3.L.154.238; 3.L.154.239; 3.L.154.154;
3.L.154.157; 3.L.154.166; 3.L.154.169; 3.L.154.172; 3.L.154.175; 3.L.154.240;
3.L.154.244; 3.L.157.228; 3.L.157.229; 3.L.157.230; 3.L.157.231; 3.L.157.236;
3.L.157.237; 3.L.157.238; 3.L.157.239; 3.L.157.154; 3.L.157.157; 3.L.157.166;
3.L.157.169; 3.L.157.172; 3.L.157.175; 3.L.157.240; 3.L.157.244; 3.L.166.228;
3.L.166.229; 3.L.166.230; 3.L.166.231; 3.L.166.236; 3.L.166.237; 3.L.166.238;
3.L.166.239; 3.L.166.154; 3.L.166.157; 3.L.166.166; 3.L.166.169; 3.L.166.172;
3.L.166.175; 3.L.166.240; 3.L.166.244; 3.L.169.228; 3.L.169.229; 3.L.169.230;
3.L.169.231; 3.L.169.236; 3.L.169.237; 3.L.169.238; 3.L.169.239; 3.L.169.154;
3.L.169.157; 3.L.169.166; 3.L.169.169; 3.L.169.172; 3.L.169.175; 3.L.169.240;
3.L.169.244; 3.L.172.228; 3.L.172.229; 3.L.172.230; 3.L.172.231; 3.L.172.236;
3.L.172.237; 3.L.172.238; 3.L.172.239; 3.L.172.154; 3.L.172.157; 3.L.172.166;
3.L.172.169; 3.L.172.172; 3.L.172.175; 3.L.172.240; 3.L.172.244; 3.L.175.228;
3.L.175.229; 3.L.175.230; 3.L.175.231; 3.L.175.236; 3.L.175.237; 3.L.175.238;
3.L.175.239; 3.L.175.154; 3.L.175.157; 3.L.175.166; 3.L.175.169; 3.L.175.172;
3.L.175.175; 3.L.175.240; 3.L.175.244; 3.L.240.228; 3.L.240.229; 3.L.240.230;
3.L.240.231; 3.L.240.236; 3.L.240.237; 3.L.240.238; 3.L.240.239; 3.L.240.154;
3.L.240.157; 3.L.240.166; 3.L.240.169; 3.L.240.172; 3.L.240.175; 3.L.240.240;
3.L.240.244; 3.L.244.228; 3.L.244.229; 3.L.244.230; 3.L.244.231; 3.L.244.236;
3.L.244.237; 3.L.244.238; 3.L.244.239; 3.L.244.154; 3.L.244.157; 3.L.244.166;
3.L.244.169; 3.L.244.172; 3.L.244.175; 3.L.244.240; 3.L.244.244;

Prodrugs of 3.O

3.O.228.228; 3.O.228.229; 3.O.228.230; 3.O.228.231; 3.O.228.236;
3.O.228.237; 3.O.228.238; 3.O.228.239; 3.O.228.154; 3.O.228.157;
3.O.228.166; 3.O.228.169; 3.O.228.172; 3.O.228.175; 3.O.228.240;
3.O.228.244; 3.O.229.228; 3.O.229.229; 3.O.229.230; 3.O.229.231;
3.O.229.236; 3.O.229.237; 3.O.229.238; 3.O.229.239; 3.O.229.154;

TABLE 100-continued

3.O.229.157; 3.O.229.166; 3.O.229.169; 3.O.229.172; 3.O.229.175;
3.O.229.240; 3.O.229.244; 3.O.230.228; 3.O.230.229; 3.O.230.230;
3.O.230.231; 3.O.230.236; 3.O.230.237; 3.O.230.238; 3.O.230.239;
3.O.230.154; 3.O.230.157; 3.O.230.166; 3.O.230.169; 3.O.230.172;
3.O.230.175; 3.O.230.240; 3.O.230.244; 3.O.231.228; 3.O.231.229;
3.O.231.230; 3.O.231.231; 3.O.231.236; 3.O.231.237; 3.O.231.238;
3.O.231.239; 3.O.231.154; 3.O.231.157; 3.O.231.166; 3.O.231.169;
3.O.231.172; 3.O.231.175; 3.O.231.240; 3.O.231.244; 3.O.236.228;
3.O.236.229; 3.O.236.230; 3.O.236.231; 3.O.236.236; 3.O.236.237;
3.O.236.238; 3.O.236.239; 3.O.236.154; 3.O.236.157; 3.O.236.166;
3.O.236.169; 3.O.236.172; 3.O.236.175; 3.O.236.240; 3.O.236.244;
3.O.237.228; 3.O.237.229; 3.O.237.230; 3.O.237.231; 3.O.237.236;
3.O.237.237; 3.O.237.238; 3.O.237.239; 3.O.237.154; 3.O.237.157;
3.O.237.166; 3.O.237.169; 3.O.237.172; 3.O.237.175; 3.O.237.240;
3.O.237.244; 3.O.238.228; 3.O.238.229; 3.O.238.230; 3.O.238.231;
3.O.238.236; 3.O.238.237; 3.O.238.238; 3.O.238.239; 3.O.238.154;
3.O.238.157; 3.O.238.166; 3.O.238.169; 3.O.238.172; 3.O.238.175;
3.O.238.240; 3.O.238.244; 3.O.239.228; 3.O.239.229; 3.O.239.230;
3.O.239.231; 3.O.239.236; 3.O.239.237; 3.O.239.238; 3.O.239.239;
3.O.239.154; 3.O.239.157; 3.O.239.166; 3.O.239.169; 3.O.239.172;
3.O.239.175; 3.O.239.240; 3.O.239.244; 3.O.154.228; 3.O.154.229;
3.O.154.230; 3.O.154.231; 3.O.154.236; 3.O.154.237; 3.O.154.238;
3.O.154.239; 3.O.154.154; 3.O.154.157; 3.O.154.166; 3.O.154.169;
3.O.154.172; 3.O.154.175; 3.O.154.240; 3.O.154.244; 3.O.157.228;
3.O.157.229; 3.O.157.230; 3.O.157.231; 3.O.157.236; 3.O.157.237;
3.O.157.238; 3.O.157.239; 3.O.157.154; 3.O.157.157; 3.O.157.166;
3.O.157.169; 3.O.157.172; 3.O.157.175; 3.O.157.240; 3.O.157.244;
3.O.166.228; 3.O.166.229; 3.O.166.230; 3.O.166.231; 3.O.166.236;
3.O.166.237; 3.O.166.238; 3.O.166.239; 3.O.166.154; 3.O.166.157;
3.O.166.166; 3.O.166.169; 3.O.166.172; 3.O.166.175; 3.O.166.240;
3.O.166.244; 3.O.169.228; 3.O.169.229; 3.O.169.230; 3.O.169.231;
3.O.169.236; 3.O.169.237; 3.O.169.238; 3.O.169.239; 3.O.169.154;
3.O.169.157; 3.O.169.166; 3.O.169.169; 3.O.169.172; 3.O.169.175;
3.O.169.240; 3.O.169.244; 3.O.172.228; 3.O.172.229; 3.O.172.230;
3.O.172.231; 3.O.172.236; 3.O.172.237; 3.O.172.238; 3.O.172.239;
3.O.172.154; 3.O.172.157; 3.O.172.166; 3.O.172.169; 3.O.172.172;
3.O.172.175; 3.O.172.240; 3.O.172.244; 3.O.175.228; 3.O.175.229;
3.O.175.230; 3.O.175.231; 3.O.175.236; 3.O.175.237; 3.O.175.238;
3.O.175.239; 3.O.175.154; 3.O.175.157; 3.O.175.166; 3.O.175.169;
3.O.175.172; 3.O.175.175; 3.O.175.240; 3.O.175.244; 3.O.240.228;
3.O.240.229; 3.O.240.230; 3.O.240.231; 3.O.240.236; 3.O.240.237;
3.O.240.238; 3.O.240.239; 3.O.240.154; 3.O.240.157; 3.O.240.166;
3.O.240.169; 3.O.240.172; 3.O.240.175; 3.O.240.240; 3.O.240.244;
3.O.244.228; 3.O.244.229; 3.O.244.230; 3.O.244.231; 3.O.244.236;
3.O.244.237; 3.O.244.238; 3.O.244.239; 3.O.244.154; 3.O.244.157;
3.O.244.166; 3.O.244.169; 3.O.244.172; 3.O.244.175; 3.O.244.240;
3.O.244.244;

Prodrugs of 3.P

3.P.228.228; 3.P.228.229; 3.P.228.230; 3.P.228.231; 3.P.228.236;
3.P.228.237; 3.P.228.238; 3.P.228.239; 3.P.228.154; 3.P.228.157; 3.P.228.166;
3.P.228.169; 3.P.228.172; 3.P.228.175; 3.P.228.240; 3.P.228.244; 3.P.229.228;
3.P.229.229; 3.P.229.230; 3.P.229.231; 3.P.229.236; 3.P.229.237; 3.P.229.238;
3.P.229.239; 3.P.229.154; 3.P.229.157; 3.P.229.166; 3.P.229.169; 3.P.229.172;
3.P.229.175; 3.P.229.240; 3.P.229.244; 3.P.230.228; 3.P.230.229; 3.P.230.230;
3.P.230.231; 3.P.230.236; 3.P.230.237; 3.P.230.238; 3.P.230.239; 3.P.230.154;
3.P.230.157; 3.P.230.166; 3.P.230.169; 3.P.230.172; 3.P.230.175; 3.P.230.240;
3.P.230.244; 3.P.231.228; 3.P.231.229; 3.P.231.230; 3.P.231.231; 3.P.231.236;
3.P.231.237; 3.P.231.238; 3.P.231.239; 3.P.231.154; 3.P.231.157; 3.P.231.166;
3.P.231.169; 3.P.231.172; 3.P.231.175; 3.P.231.240; 3.P.231.244; 3.P.236.228;
3.P.236.229; 3.P.236.230; 3.P.236.231; 3.P.236.236; 3.P.236.237; 3.P.236.238;
3.P.236.239; 3.P.236.154; 3.P.236.157; 3.P.236.166; 3.P.236.169; 3.P.236.172;
3.P.236.175; 3.P.236.240; 3.P.236.244; 3.P.237.228; 3.P.237.229; 3.P.237.230;
3.P.237.231; 3.P.237.236; 3.P.237.237; 3.P.237.238; 3.P.237.239; 3.P.237.154;
3.P.237.157; 3.P.237.166; 3.P.237.169; 3.P.237.172; 3.P.237.175; 3.P.237.240;
3.P.237.244; 3.P.238.228; 3.P.238.229; 3.P.238.230; 3.P.238.231; 3.P.238.236;
3.P.238.237; 3.P.238.238; 3.P.238.239; 3.P.238.154; 3.P.238.157; 3.P.238.166;
3.P.238.169; 3.P.238.172; 3.P.238.175; 3.P.238.240; 3.P.238.244; 3.P.239.228;
3.P.239.229; 3.P.239.230; 3.P.239.231; 3.P.239.236; 3.P.239.237; 3.P.239.238;
3.P.239.239; 3.P.239.154; 3.P.239.157; 3.P.239.166; 3.P.239.169; 3.P.239.172;
3.P.239.175; 3.P.239.240; 3.P.239.244; 3.P.154.228; 3.P.154.229; 3.P.154.230;
3.P.154.231; 3.P.154.236; 3.P.154.237; 3.P.154.238; 3.P.154.239; 3.P.154.154;
3.P.154.157; 3.P.154.166; 3.P.154.169; 3.P.154.172; 3.P.154.175; 3.P.154.240;
3.P.154.244; 3.P.157.228; 3.P.157.229; 3.P.157.230; 3.P.157.231; 3.P.157.236;
3.P.157.237; 3.P.157.238; 3.P.157.239; 3.P.157.154; 3.P.157.157; 3.P.157.166;
3.P.157.169; 3.P.157.172; 3.P.157.175; 3.P.157.240; 3.P.157.244; 3.P.166.228;
3.P.166.229; 3.P.166.230; 3.P.166.231; 3.P.166.236; 3.P.166.237; 3.P.166.238;
3.P.166.239; 3.P.166.154; 3.P.166.157; 3.P.166.166; 3.P.166.169; 3.P.166.172;
3.P.166.175; 3.P.166.240; 3.P.166.244; 3.P.169.228; 3.P.169.229; 3.P.169.230;

TABLE 100-continued

3.P.169.231; 3.P.169.236; 3.P.169.237; 3.P.169.238; 3.P.169.239; 3.P.169.154;
3.P.169.157; 3.P.169.166; 3.P.169.169; 3.P.169.172; 3.P.169.175; 3.P.169.240;
3.P.169.244; 3.P.172.228; 3.P.172.229; 3.P.172.230; 3.P.172.231; 3.P.172.236;
3.P.172.237; 3.P.172.238; 3.P.172.239; 3.P.172.154; 3.P.172.157; 3.P.172.166;
3.P.172.169; 3.P.172.172; 3.P.172.175; 3.P.172.240; 3.P.172.244; 3.P.175.228;
3.P.175.229; 3.P.175.230; 3.P.175.231; 3.P.175.236; 3.P.175.237; 3.P.175.238;
3.P.175.239; 3.P.175.154; 3.P.175.157; 3.P.175.166; 3.P.175.169; 3.P.175.172;
3.P.175.175; 3.P.175.240; 3.P.175.244; 3.P.240.228; 3.P.240.229; 3.P.240.230;
3.P.240.231; 3.P.240.236; 3.P.240.237; 3.P.240.238; 3.P.240.239; 3.P.240.154;
3.P.240.157; 3.P.240.166; 3.P.240.169; 3.P.240.172; 3.P.240.175; 3.P.240.240;
3.P.240.244; 3.P.244.228; 3.P.244.229; 3.P.244.230; 3.P.244.231; 3.P.244.236;
3.P.244.237; 3.P.244.238; 3.P.244.239; 3.P.244.154; 3.P.244.157; 3.P.244.166;
3.P.244.169; 3.P.244.172; 3.P.244.175; 3.P.244.240; 3.P.244.244;
Prodrugs of 3.U 3.U.228.228; 3.U.228.229; 3.U.228.230; 3.U.228.231; 3.U.228.236;
3.U.228.237; 3.U.228.238; 3.U.228.239; 3.U.228.154; 3.U.228.157;
3.U.228.166; 3.U.228.169; 3.U.228.172; 3.U.228.175; 3.U.228.240;
3.U.228.244; 3.U.229.228; 3.U.229.229; 3.U.229.230; 3.U.229.231;
3.U.229.236; 3.U.229.237; 3.U.229.238; 3.U.229.239; 3.U.229.154;
3.U.229.157; 3.U.229.166; 3.U.229.169; 3.U.229.172; 3.U.229.175;
3.U.229.240; 3.U.229.244; 3.U.230.228; 3.U.230.229; 3.U.230.230;
3.U.230.231; 3.U.230.236; 3.U.230.237; 3.U.230.238; 3.U.230.239;
3.U.230.154; 3.U.230.157; 3.U.230.166; 3.U.230.169; 3.U.230.172;
3.U.230.175; 3.U.230.240; 3.U.230.244; 3.U.231.228; 3.U.231.229;
3.U.231.230; 3.U.231.231; 3.U.231.236; 3.U.231.237; 3.U.231.238;
3.U.231.239; 3.U.231.154; 3.U.231.157; 3.U.231.166; 3.U.231.169;
3.U.231.172; 3.U.231.175; 3.U.231.240; 3.U.231.244; 3.U.236.228;
3.U.236.229; 3.U.236.230; 3.U.236.231; 3.U.236.236; 3.U.236.237;
3.U.236.238; 3.U.236.239; 3.U.236.154; 3.U.236.157; 3.U.236.166;
3.U.236.169; 3.U.236.172; 3.U.236.175; 3.U.236.240; 3.U.236.244;
3.U.237.228; 3.U.237.229; 3.U.237.230; 3.U.237.231; 3.U.237.236;
3.U.237.237; 3.U.237.238; 3.U.237.239; 3.U.237.154; 3.U.237.157;
3.U.237.166; 3.U.237.169; 3.U.237.172; 3.U.237.175; 3.U.237.240;
3.U.237.244; 3.U.238.228; 3.U.238.229; 3.U.238.230; 3.U.238.231;
3.U.238.236; 3.U.238.237; 3.U.238.238; 3.U.238.239; 3.U.238.154;
3.U.238.157; 3.U.238.166; 3.U.238.169; 3.U.238.172; 3.U.238.175;
3.U.238.240; 3.U.238.244; 3.U.239.228; 3.U.239.229; 3.U.239.230;
3.U.239.231; 3.U.239.236; 3.U.239.237; 3.U.239.238; 3.U.239.239;
3.U.239.154; 3.U.239.157; 3.U.239.166; 3.U.239.169; 3.U.239.172;
3.U.239.175; 3.U.239.240; 3.U.239.244; 3.U.154.228; 3.U.154.229;
3.U.154.230; 3.U.154.231; 3.U.154.236; 3.U.154.237; 3.U.154.238;
3.U.154.239; 3.U.154.154; 3.U.154.157; 3.U.154.166; 3.U.154.169;
3.U.154.172; 3.U.154.175; 3.U.154.240; 3.U.154.244; 3.U.157.228;
3.U.157.229; 3.U.157.230; 3.U.157.231; 3.U.157.236; 3.U.157.237;
3.U.157.238; 3.U.157.239; 3.U.157.154; 3.U.157.157; 3.U.157.166;
3.U.157.169; 3.U.157.172; 3.U.157.175; 3.U.157.240; 3.U.157.244;
3.U.166.228; 3.U.166.229; 3.U.166.230; 3.U.166.231; 3.U.166.236;
3.U.166.237; 3.U.166.238; 3.U.166.239; 3.U.166.154; 3.U.166.157;
3.U.166.166; 3.U.166.169; 3.U.166.172; 3.U.166.175; 3.U.166.240;
3.U.166.244; 3.U.169.228; 3.U.169.229; 3.U.169.230; 3.U.169.231;
3.U.169.236; 3.U.169.237; 3.U.169.238; 3.U.169.239; 3.U.169.154;
3.U.169.157; 3.U.169.166; 3.U.169.169; 3.U.169.172; 3.U.169.175;
3.U.169.240; 3.U.169.244; 3.U.172.228; 3.U.172.229; 3.U.172.230;
3.U.172.231; 3.U.172.236; 3.U.172.237; 3.U.172.238; 3.U.172.239;
3.U.172.154; 3.U.172.157; 3.U.172.166; 3.U.172.169; 3.U.172.172;
3.U.172.175; 3.U.172.240; 3.U.172.244; 3.U.175.228; 3.U.175.229;
3.U.175.230; 3.U.175.231; 3.U.175.236; 3.U.175.237; 3.U.175.238;
3.U.175.239; 3.U.175.154; 3.U.175.157; 3.U.175.166; 3.U.175.169;
3.U.175.172; 3.U.175.175; 3.U.175.240; 3.U.175.244; 3.U.240.228;
3.U.240.229; 3.U.240.230; 3.U.240.231; 3.U.240.236; 3.U.240.237;
3.U.240.238; 3.U.240.239; 3.U.240.154; 3.U.240.157; 3.U.240.166;
3.U.240.169; 3.U.240.172; 3.U.240.175; 3.U.240.240; 3.U.240.244;
3.U.244.228; 3.U.244.229; 3.U.244.230; 3.U.244.231; 3.U.244.236;
3.U.244.237; 3.U.244.238; 3.U.244.239; 3.U.244.154; 3.U.244.157;
3.U.244.166; 3.U.244.169; 3.U.244.172; 3.U.244.175; 3.U.244.240; 3.U.244.244;
Prodrugs of 3.W 3.W.228.228; 3.W.228.229; 3.W.228.230; 3.W.228.231; 3.W.228.236;
3.W.228.237; 3.W.228.238; 3.W.228.239; 3.W.228.154; 3.W.228.157;
3.W.228.166; 3.W.228.169; 3.W.228.172; 3.W.228.175; 3.W.228.240;
3.W.228.244; 3.W.229.228; 3.W.229.229; 3.W.229.230; 3.W.229.231;
3.W.229.236; 3.W.229.237; 3.W.229.238; 3.W.229.239; 3.W.229.154;
3.W.229.157; 3.W.229.166; 3.W.229.169; 3.W.229.172; 3.W.229.175;
3.W.229.240; 3.W.229.244; 3.W.230.228; 3.W.230.229; 3.W.230.230;
3.W.230.231; 3.W.230.236; 3.W.230.237; 3.W.230.238; 3.W.230.239;
3.W.230.154; 3.W.230.157; 3.W.230.166; 3.W.230.169; 3.W.230.172;
3.W.230.175; 3.W.230.240; 3.W.230.244; 3.W.231.228; 3.W.231.229;
3.W.231.230; 3.W.231.231; 3.W.231.236; 3.W.231.237; 3.W.231.238;

TABLE 100-continued

3.W.231.239; 3.W.231.154; 3.W.231.157; 3.W.231.166; 3.W.231.169;
3.W.231.172; 3.W.231.175; 3.W.231.240; 3.W.231.244; 3.W.236.228;
3.W.236.229; 3.W.236.230; 3.W.236.231; 3.W.236.236; 3.W.236.237;
3.W.236.238; 3.W.236.239; 3.W.236.154; 3.W.236.157; 3.W.236.166;
3.W.236.169; 3.W.236.172; 3.W.236.175; 3.W.236.240; 3.W.236.244;
3.W.237.228; 3.W.237.229; 3.W.237.230; 3.W.237.231; 3.W.237.236;
3.W.237.237; 3.W.237.238; 3.W.237.239; 3.W.237.154; 3.W.237.157;
3.W.237.166; 3.W.237.169; 3.W.237.172; 3.W.237.175; 3.W.237.240;
3.W.237.244; 3.W.238.228; 3.W.238.229; 3.W.238.230; 3.W.238.231;
3.W.238.236; 3.W.238.237; 3.W.238.238; 3.W.238.239; 3.W.238.154;
3.W.238.157; 3.W.238.166; 3.W.238.169; 3.W.238.172; 3.W.238.175;
3.W.238.240; 3.W.238.244; 3.W.239.228; 3.W.239.229; 3.W.239.230;
3.W.239.231; 3.W.239.236; 3.W.239.237; 3.W.239.238; 3.W.239.239;
3.W.239.154; 3.W.239.157; 3.W.239.166; 3.W.239.169; 3.W.239.172;
3.W.239.175; 3.W.239.240; 3.W.239.244; 3.W.154.228; 3.W.154.229;
3.W.154.230; 3.W.154.231; 3.W.154.236; 3.W.154.237; 3.W.154.238;
3.W.154.239; 3.W.154.154; 3.W.154.157; 3.W.154.166; 3.W.154.169;
3.W.154.172; 3.W.154.175; 3.W.154.240; 3.W.154.244; 3.W.157.228;
3.W.157.229; 3.W.157.230; 3.W.157.231; 3.W.157.236; 3.W.157.237;
3.W.157.238; 3.W.157.239; 3.W.157.154; 3.W.157.157; 3.W.157.166;
3.W.157.169; 3.W.157.172; 3.W.157.175; 3.W.157.240; 3.W.157.244;
3.W.166.228; 3.W.166.229; 3.W.166.230; 3.W.166.231; 3.W.166.236;
3.W.166.237; 3.W.166.238; 3.W.166.239; 3.W.166.154; 3.W.166.157;
3.W.166.166; 3.W.166.169; 3.W.166.172; 3.W.166.175; 3.W.166.240;
3.W.166.244; 3.W.169.228; 3.W.169.229; 3.W.169.230; 3.W.169.231;
3.W.169.236; 3.W.169.237; 3.W.169.238; 3.W.169.239; 3.W.169.154;
3.W.169.157; 3.W.169.166; 3.W.169.169; 3.W.169.172; 3.W.169.175;
3.W.169.240; 3.W.169.244; 3.W.172.228; 3.W.172.229; 3.W.172.230;
3.W.172.231; 3.W.172.236; 3.W.172.237; 3.W.172.238; 3.W.172.239;
3.W.172.154; 3.W.172.157; 3.W.172.166; 3.W.172.169; 3.W.172.172;
3.W.172.175; 3.W.172.240; 3.W.172.244; 3.W.175.228; 3.W.175.229;
3.W.175.230; 3.W.175.231; 3.W.175.236; 3.W.175.237; 3.W.175.238;
3.W.175.239; 3.W.175.154; 3.W.175.157; 3.W.175.166; 3.W.175.169;
3.W.175.172; 3.W.175.175; 3.W.175.240; 3.W.175.244; 3.W.240.228;
3.W.240.229; 3.W.240.230; 3.W.240.231; 3.W.240.236; 3.W.240.237;
3.W.240.238; 3.W.240.239; 3.W.240.154; 3.W.240.157; 3.W.240.166;
3.W.240.169; 3.W.240.172; 3.W.240.175; 3.W.240.240; 3.W.240.244;
3.W.244.228; 3.W.244.229; 3.W.244.230; 3.W.244.231; 3.W.244.236;
3.W.244.237; 3.W.244.238; 3.W.244.239; 3.W.244.154; 3.W.244.157;
3.W.244.166; 3.W.244.169; 3.W.244.172; 3.W.244.175; 3.W.244.240; 3.W.244.244;
Prodrugs of 3.Y 3.Y.228.228; 3.Y.228.229; 3.Y.228.230; 3.Y.228.231; 3.Y.228.236;
3.Y.228.237; 3.Y.228.238; 3.Y.228.239; 3.Y.228.154; 3.Y.228.157; 3.Y.228.166;
3.Y.228.169; 3.Y.228.172; 3.Y.228.175; 3.Y.228.240; 3.Y.228.244; 3.Y.229.228;
3.Y.229.229; 3.Y.229.230; 3.Y.229.231; 3.Y.229.236; 3.Y.229.237; 3.Y.229.238;
3.Y.229.239; 3.Y.229.154; 3.Y.229.157; 3.Y.229.166; 3.Y.229.169; 3.Y.229.172;
3.Y.229.175; 3.Y.229.240; 3.Y.229.244; 3.Y.230.228; 3.Y.230.229; 3.Y.230.230;
3.Y.230.231; 3.Y.230.236; 3.Y.230.237; 3.Y.230.238; 3.Y.230.239; 3.Y.230.154;
3.Y.230.157; 3.Y.230.166; 3.Y.230.169; 3.Y.230.172; 3.Y.230.175; 3.Y.230.240;
3.Y.230.244; 3.Y.231.228; 3.Y.231.229; 3.Y.231.230; 3.Y.231.231; 3.Y.231.236;
3.Y.231.237; 3.Y.231.238; 3.Y.231.239; 3.Y.231.154; 3.Y.231.157; 3.Y.231.166;
3.Y.231.169; 3.Y.231.172; 3.Y.231.175; 3.Y.231.240; 3.Y.231.244; 3.Y.236.228;
3.Y.236.229; 3.Y.236.230; 3.Y.236.231; 3.Y.236.236; 3.Y.236.237; 3.Y.236.238;
3.Y.236.239; 3.Y.236.154; 3.Y.236.157; 3.Y.236.166; 3.Y.236.169; 3.Y.236.172;
3.Y.236.175; 3.Y.236.240; 3.Y.236.244; 3.Y.237.228; 3.Y.237.229; 3.Y.237.230;
3.Y.237.231; 3.Y.237.236; 3.Y.237.237; 3.Y.237.238; 3.Y.237.239; 3.Y.237.154;
3.Y.237.157; 3.Y.237.166; 3.Y.237.169; 3.Y.237.172; 3.Y.237.175; 3.Y.237.240;
3.Y.237.244; 3.Y.238.228; 3.Y.238.229; 3.Y.238.230; 3.Y.238.231; 3.Y.238.236;
3.Y.238.237; 3.Y.238.238; 3.Y.238.239; 3.Y.238.154; 3.Y.238.157; 3.Y.238.166;
3.Y.238.169; 3.Y.238.172; 3.Y.238.175; 3.Y.238.240; 3.Y.238.244; 3.Y.239.228;
3.Y.239.229; 3.Y.239.230; 3.Y.239.231; 3.Y.239.236; 3.Y.239.237; 3.Y.239.238;
3.Y.239.239; 3.Y.239.154; 3.Y.239.157; 3.Y.239.166; 3.Y.239.169; 3.Y.239.172;
3.Y.239.175; 3.Y.239.240; 3.Y.239.244; 3.Y.154.228; 3.Y.154.229; 3.Y.154.230;
3.Y.154.231; 3.Y.154.236; 3.Y.154.237; 3.Y.154.238; 3.Y.154.239; 3.Y.154.154;
3.Y.154.157; 3.Y.154.166; 3.Y.154.169; 3.Y.154.172; 3.Y.154.175; 3.Y.154.240;
3.Y.154.244; 3.Y.157.228; 3.Y.157.229; 3.Y.157.230; 3.Y.157.231; 3.Y.157.236;
3.Y.157.237; 3.Y.157.238; 3.Y.157.239; 3.Y.157.154; 3.Y.157.157; 3.Y.157.166;
3.Y.157.169; 3.Y.157.172; 3.Y.157.175; 3.Y.157.240; 3.Y.157.244; 3.Y.166.228;
3.Y.166.229; 3.Y.166.230; 3.Y.166.231; 3.Y.166.236; 3.Y.166.237; 3.Y.166.238;
3.Y.166.239; 3.Y.166.154; 3.Y.166.157; 3.Y.166.166; 3.Y.166.169; 3.Y.166.172;
3.Y.166.175; 3.Y.166.240; 3.Y.166.244; 3.Y.169.228; 3.Y.169.229; 3.Y.169.230;
3.Y.169.231; 3.Y.169.236; 3.Y.169.237; 3.Y.169.238; 3.Y.169.239; 3.Y.169.154;
3.Y.169.157; 3.Y.169.166; 3.Y.169.169; 3.Y.169.172; 3.Y.169.175; 3.Y.169.240;
3.Y.169.244; 3.Y.172.228; 3.Y.172.229; 3.Y.172.230; 3.Y.172.231; 3.Y.172.236;
3.Y.172.237; 3.Y.172.238; 3.Y.172.239; 3.Y.172.154; 3.Y.172.157; 3.Y.172.166;
3.Y.172.169; 3.Y.172.172; 3.Y.172.175; 3.Y.172.240; 3.Y.172.244; 3.Y.175.228;
3.Y.175.229; 3.Y.175.230; 3.Y.175.231; 3.Y.175.236; 3.Y.175.237; 3.Y.175.238;
3.Y.175.239; 3.Y.175.154; 3.Y.175.157; 3.Y.175.166; 3.Y.175.169; 3.Y.175.172;

TABLE 100-continued

3.Y.175.175; 3.Y.175.240; 3.Y.175.244; 3.Y.240.228; 3.Y.240.229; 3.Y.240.230;
3.Y.240.231; 3.Y.240.236; 3.Y.240.237; 3.Y.240.238; 3.Y.240.239; 3.Y.240.154;
3.Y.240.157; 3.Y.240.166; 3.Y.240.169; 3.Y.240.172; 3.Y.240.175; 3.Y.240.240;
3.Y.240.244; 3.Y.244.228; 3.Y.244.229; 3.Y.244.230; 3.Y.244.231; 3.Y.244.236;
3.Y.244.237; 3.Y.244.238; 3.Y.244.239; 3.Y.244.154; 3.Y.244.157; 3.Y.244.166;
3.Y.244.169; 3.Y.244.172; 3.Y.244.175; 3.Y.244.240; 3.Y.244.244;
Prodrugs of 4.B 4.B.228.228; 4.B.228.229; 4.B.228.230; 4.B.228.231; 4.B.228.236;
4.B.228.237; 4.B.228.238; 4.B.228.239; 4.B.228.154; 4.B.228.157; 4.B.228.166;
4.B.228.169; 4.B.228.172; 4.B.228.175; 4.B.228.240; 4.B.228.244; 4.B.229.228;
4.B.229.229; 4.B.229.230; 4.B.229.231; 4.B.229.236; 4.B.229.237; 4.B.229.238;
4.B.229.239; 4.B.229.154; 4.B.229.157; 4.B.229.166; 4.B.229.169; 4.B.229.172;
4.B.229.175; 4.B.229.240; 4.B.229.244; 4.B.230.228; 4.B.230.229; 4.B.230.230;
4.B.230.231; 4.B.230.236; 4.B.230.237; 4.B.230.238; 4.B.230.239; 4.B.230.154;
4.B.230.157; 4.B.230.166; 4.B.230.169; 4.B.230.172; 4.B.230.175; 4.B.230.240;
4.B.230.244; 4.B.231.228; 4.B.231.229; 4.B.231.230; 4.B.231.231; 4.B.231.236;
4.B.231.237; 4.B.231.238; 4.B.231.239; 4.B.231.154; 4.B.231.157; 4.B.231.166;
4.B.231.169; 4.B.231.172; 4.B.231.175; 4.B.231.240; 4.B.231.244; 4.B.236.228;
4.B.236.229; 4.B.236.230; 4.B.236.231; 4.B.236.236; 4.B.236.237; 4.B.236.238;
4.B.236.239; 4.B.236.154; 4.B.236.157; 4.B.236.166; 4.B.236.169; 4.B.236.172;
4.B.236.175; 4.B.236.240; 4.B.236.244; 4.B.237.228; 4.B.237.229; 4.B.237.230;
4.B.237.231; 4.B.237.236; 4.B.237.237; 4.B.237.238; 4.B.237.239; 4.B.237.154;
4.B.237.157; 4.B.237.166; 4.B.237.169; 4.B.237.172; 4.B.237.175; 4.B.237.240;
4.B.237.244; 4.B.238.228; 4.B.238.229; 4.B.238.230; 4.B.238.231; 4.B.238.236;
4.B.238.237; 4.B.238.238; 4.B.238.239; 4.B.238.154; 4.B.238.157; 4.B.238.166;
4.B.238.169; 4.B.238.172; 4.B.238.175; 4.B.238.240; 4.B.238.244; 4.B.239.228;
4.B.239.229; 4.B.239.230; 4.B.239.231; 4.B.239.236; 4.B.239.237; 4.B.239.238;
4.B.239.239; 4.B.239.154; 4.B.239.157; 4.B.239.166; 4.B.239.169; 4.B.239.172;
4.B.239.175; 4.B.239.240; 4.B.239.244; 4.B.154.228; 4.B.154.229; 4.B.154.230;
4.B.154.231; 4.B.154.236; 4.B.154.237; 4.B.154.238; 4.B.154.239; 4.B.154.154;
4.B.154.157; 4.B.154.166; 4.B.154.169; 4.B.154.172; 4.B.154.175; 4.B.154.240;
4.B.154.244; 4.B.157.228; 4.B.157.229; 4.B.157.230; 4.B.157.231; 4.B.157.236;
4.B.157.237; 4.B.157.238; 4.B.157.239; 4.B.157.154; 4.B.157.157; 4.B.157.166;
4.B.157.169; 4.B.157.172; 4.B.157.175; 4.B.157.240; 4.B.157.244; 4.B.166.228;
4.B.166.229; 4.B.166.230; 4.B.166.231; 4.B.166.236; 4.B.166.237; 4.B.166.238;
4.B.166.239; 4.B.166.154; 4.B.166.157; 4.B.166.166; 4.B.166.169; 4.B.166.172;
4.B.166.175; 4.B.166.240; 4.B.166.244; 4.B.169.228; 4.B.169.229; 4.B.169.230;
4.B.169.231; 4.B.169.236; 4.B.169.237; 4.B.169.238; 4.B.169.239; 4.B.169.154;
4.B.169.157; 4.B.169.166; 4.B.169.169; 4.B.169.172; 4.B.169.175; 4.B.169.240;
4.B.169.244; 4.B.172.228; 4.B.172.229; 4.B.172.230; 4.B.172.231; 4.B.172.236;
4.B.172.237; 4.B.172.238; 4.B.172.239; 4.B.172.154; 4.B.172.157; 4.B.172.166;
4.B.172.169; 4.B.172.172; 4.B.172.175; 4.B.172.240; 4.B.172.244; 4.B.175.228;
4.B.175.229; 4.B.175.230; 4.B.175.231; 4.B.175.236; 4.B.175.237; 4.B.175.238;
4.B.175.239; 4.B.175.154; 4.B.175.157; 4.B.175.166; 4.B.175.169; 4.B.175.172;
4.B.175.175; 4.B.175.240; 4.B.175.244; 4.B.240.228; 4.B.240.229; 4.B.240.230;
4.B.240.231; 4.B.240.236; 4.B.240.237; 4.B.240.238; 4.B.240.239; 4.B.240.154;
4.B.240.157; 4.B.240.166; 4.B.240.169; 4.B.240.172; 4.B.240.175; 4.B.240.240;
4.B.240.244; 4.B.244.228; 4.B.244.229; 4.B.244.230; 4.B.244.231; 4.B.244.236;
4.B.244.237; 4.B.244.238; 4.B.244.239; 4.B.244.154; 4.B.244.157; 4.B.244.166;
4.B.244.169; 4.B.244.172; 4.B.244.175; 4.B.244.240; 4.B.244.244;
Prodrugs of 4.D 4.D.228.228; 4.D.228.229; 4.D.228.230; 4.D.228.231; 4.D.228.236;
4.D.228.237; 4.D.228.238; 4.D.228.239; 4.D.228.154; 4.D.228.157;
4.D.228.166; 4.D.228.169; 4.D.228.172; 4.D.228.175; 4.D.228.240;
4.D.228.244; 4.D.229.228; 4.D.229.229; 4.D.229.230; 4.D.229.231;
4.D.229.236; 4.D.229.237; 4.D.229.238; 4.D.229.239; 4.D.229.154;
4.D.229.157; 4.D.229.166; 4.D.229.169; 4.D.229.172; 4.D.229.175;
4.D.229.240; 4.D.229.244; 4.D.230.228; 4.D.230.229; 4.D.230.230;
4.D.230.231; 4.D.230.236; 4.D.230.237; 4.D.230.238; 4.D.230.239;
4.D.230.154; 4.D.230.157; 4.D.230.166; 4.D.230.169; 4.D.230.172;
4.D.230.175; 4.D.230.240; 4.D.230.244; 4.D.231.228; 4.D.231.229;
4.D.231.230; 4.D.231.231; 4.D.231.236; 4.D.231.237; 4.D.231.238;
4.D.231.239; 4.D.231.154; 4.D.231.157; 4.D.231.166; 4.D.231.169;
4.D.231.172; 4.D.231.175; 4.D.231.240; 4.D.231.244; 4.D.236.228;
4.D.236.229; 4.D.236.230; 4.D.236.231; 4.D.236.236; 4.D.236.237;
4.D.236.238; 4.D.236.239; 4.D.236.154; 4.D.236.157; 4.D.236.166;
4.D.236.169; 4.D.236.172; 4.D.236.175; 4.D.236.240; 4.D.236.244;
4.D.237.228; 4.D.237.229; 4.D.237.230; 4.D.237.231; 4.D.237.236;
4.D.237.237; 4.D.237.238; 4.D.237.239; 4.D.237.154; 4.D.237.157;
4.D.237.166; 4.D.237.169; 4.D.237.172; 4.D.237.175; 4.D.237.240;
4.D.237.244; 4.D.238.228; 4.D.238.229; 4.D.238.230; 4.D.238.231;
4.D.238.236; 4.D.238.237; 4.D.238.238; 4.D.238.239; 4.D.238.154;
4.D.238.157; 4.D.238.166; 4.D.238.169; 4.D.238.172; 4.D.238.175;
4.D.238.240; 4.D.238.244; 4.D.239.228; 4.D.239.229; 4.D.239.230;
4.D.239.231; 4.D.239.236; 4.D.239.237; 4.D.239.238; 4.D.239.239;
4.D.239.154; 4.D.239.157; 4.D.239.166; 4.D.239.169; 4.D.239.172;
4.D.239.175; 4.D.239.240; 4.D.239.244; 4.D.154.228; 4.D.154.229;

TABLE 100-continued

4.D.154.230; 4.D.154.231; 4.D.154.236; 4.D.154.237; 4.D.154.238;
4.D.154.239; 4.D.154.154; 4.D.154.157; 4.D.154.166; 4.D.154.169;
4.D.154.172; 4.D.154.175; 4.D.154.240; 4.D.154.244; 4.D.157.228;
4.D.157.229; 4.D.157.230; 4.D.157.231; 4.D.157.236; 4.D.157.237;
4.D.157.238; 4.D.157.239; 4.D.157.154; 4.D.157.157; 4.D.157.166;
4.D.157.169; 4.D.157.172; 4.D.157.175; 4.D.157.240; 4.D.157.244;
4.D.166.228; 4.D.166.229; 4.D.166.230; 4.D.166.231; 4.D.166.236;
4.D.166.237; 4.D.166.238; 4.D.166.239; 4.D.166.154; 4.D.166.157;
4.D.166.166; 4.D.166.169; 4.D.166.172; 4.D.166.175; 4.D.166.240;
4.D.166.244; 4.D.169.228; 4.D.169.229; 4.D.169.230; 4.D.169.231;
4.D.169.236; 4.D.169.237; 4.D.169.238; 4.D.169.239; 4.D.169.154;
4.D.169.157; 4.D.169.166; 4.D.169.169; 4.D.169.172; 4.D.169.175;
4.D.169.240; 4.D.169.244; 4.D.172.228; 4.D.172.229; 4.D.172.230;
4.D.172.231; 4.D.172.236; 4.D.172.237; 4.D.172.238; 4.D.172.239;
4.D.172.154; 4.D.172.157; 4.D.172.166; 4.D.172.169; 4.D.172.172;
4.D.172.175; 4.D.172.240; 4.D.172.244; 4.D.175.228; 4.D.175.229;
4.D.175.230; 4.D.175.231; 4.D.175.236; 4.D.175.237; 4.D.175.238;
4.D.175.239; 4.D.175.154; 4.D.175.157; 4.D.175.166; 4.D.175.169;
4.D.175.172; 4.D.175.175; 4.D.175.240; 4.D.175.244; 4.D.240.228;
4.D.240.229; 4.D.240.230; 4.D.240.231; 4.D.240.236; 4.D.240.237;
4.D.240.238; 4.D.240.239; 4.D.240.154; 4.D.240.157; 4.D.240.166;
4.D.240.169; 4.D.240.172; 4.D.240.175; 4.D.240.240; 4.D.240.244;
4.D.244.228; 4.D.244.229; 4.D.244.230; 4.D.244.231; 4.D.244.236;
4.D.244.237; 4.D.244.238; 4.D.244.239; 4.D.244.154; 4.D.244.157;
4.D.244.166; 4.D.244.169; 4.D.244.172; 4.D.244.175; 4.D.244.240;
4.D.244.244;
Prodrugs of 4.E 4.E.228.228; 4.E.228.229; 4.E.228.230; 4.E.228.231; 4.E.228.236;
4.E.228.237; 4.E.228.238; 4.E.228.239; 4.E.228.154; 4.E.228.157; 4.E.228.166;
4.E.228.169; 4.E.228.172; 4.E.228.175; 4.E.228.240; 4.E.228.244; 4.E.229.228;
4.E.229.229; 4.E.229.230; 4.E.229.231; 4.E.229.236; 4.E.229.237; 4.E.229.238;
4.E.229.239; 4.E.229.154; 4.E.229.157; 4.E.229.166; 4.E.229.169; 4.E.229.172;
4.E.229.175; 4.E.229.240; 4.E.229.244; 4.E.230.228; 4.E.230.229; 4.E.230.230;
4.E.230.231; 4.E.230.236; 4.E.230.237; 4.E.230.238; 4.E.230.239; 4.E.230.154;
4.E.230.157; 4.E.230.166; 4.E.230.169; 4.E.230.172; 4.E.230.175; 4.E.230.240;
4.E.230.244; 4.E.231.228; 4.E.231.229; 4.E.231.230; 4.E.231.231; 4.E.231.236;
4.E.231.237; 4.E.231.238; 4.E.231.239; 4.E.231.154; 4.E.231.157; 4.E.231.166;
4.E.231.169; 4.E.231.172; 4.E.231.175; 4.E.231.240; 4.E.231.244; 4.E.236.228;
4.E.236.229; 4.E.236.230; 4.E.236.231; 4.E.236.236; 4.E.236.237; 4.E.236.238;
4.E.236.239; 4.E.236.154; 4.E.236.157; 4.E.236.166; 4.E.236.169; 4.E.236.172;
4.E.236.175; 4.E.236.240; 4.E.236.244; 4.E.237.228; 4.E.237.229; 4.E.237.230;
4.E.237.231; 4.E.237.236; 4.E.237.237; 4.E.237.238; 4.E.237.239; 4.E.237.154;
4.E.237.157; 4.E.237.166; 4.E.237.169; 4.E.237.172; 4.E.237.175; 4.E.237.240;
4.E.237.244; 4.E.238.228; 4.E.238.229; 4.E.238.230; 4.E.238.231; 4.E.238.236;
4.E.238.237; 4.E.238.238; 4.E.238.239; 4.E.238.154; 4.E.238.157; 4.E.238.166;
4.E.238.169; 4.E.238.172; 4.E.238.175; 4.E.238.240; 4.E.238.244; 4.E.239.228;
4.E.239.229; 4.E.239.230; 4.E.239.231; 4.E.239.236; 4.E.239.237; 4.E.239.238;
4.E.239.239; 4.E.239.154; 4.E.239.157; 4.E.239.166; 4.E.239.169; 4.E.239.172;
4.E.239.175; 4.E.239.240; 4.E.239.244; 4.E.154.228; 4.E.154.229; 4.E.154.230;
4.E.154.231; 4.E.154.236; 4.E.154.237; 4.E.154.238; 4.E.154.239; 4.E.154.154;
4.E.154.157; 4.E.154.166; 4.E.154.169; 4.E.154.172; 4.E.154.175; 4.E.154.240;
4.E.154.244; 4.E.157.228; 4.E.157.229; 4.E.157.230; 4.E.157.231; 4.E.157.236;
4.E.157.237; 4.E.157.238; 4.E.157.239; 4.E.157.154; 4.E.157.157; 4.E.157.166;
4.E.157.169; 4.E.157.172; 4.E.157.175; 4.E.157.240; 4.E.157.244; 4.E.166.228;
4.E.166.229; 4.E.166.230; 4.E.166.231; 4.E.166.236; 4.E.166.237; 4.E.166.238;
4.E.166.239; 4.E.166.154; 4.E.166.157; 4.E.166.166; 4.E.166.169; 4.E.166.172;
4.E.166.175; 4.E.166.240; 4.E.166.244; 4.E.169.228; 4.E.169.229; 4.E.169.230;
4.E.169.231; 4.E.169.236; 4.E.169.237; 4.E.169.238; 4.E.169.239; 4.E.169.154;
4.E.169.157; 4.E.169.166; 4.E.169.169; 4.E.169.172; 4.E.169.175; 4.E.169.240;
4.E.169.244; 4.E.172.228; 4.E.172.229; 4.E.172.230; 4.E.172.231; 4.E.172.236;
4.E.172.237; 4.E.172.238; 4.E.172.239; 4.E.172.154; 4.E.172.157; 4.E.172.166;
4.E.172.169; 4.E.172.172; 4.E.172.175; 4.E.172.240; 4.E.172.244; 4.E.175.228;
4.E.175.229; 4.E.175.230; 4.E.175.231; 4.E.175.236; 4.E.175.237; 4.E.175.238;
4.E.175.239; 4.E.175.154; 4.E.175.157; 4.E.175.166; 4.E.175.169; 4.E.175.172;
4.E.175.175; 4.E.175.240; 4.E.175.244; 4.E.240.228; 4.E.240.229; 4.E.240.230;
4.E.240.231; 4.E.240.236; 4.E.240.237; 4.E.240.238; 4.E.240.239; 4.E.240.154;
4.E.240.157; 4.E.240.166; 4.E.240.169; 4.E.240.172; 4.E.240.175; 4.E.240.240;
4.E.240.244; 4.E.244.228; 4.E.244.229; 4.E.244.230; 4.E.244.231; 4.E.244.236;
4.E.244.237; 4.E.244.238; 4.E.244.239; 4.E.244.154; 4.E.244.157; 4.E.244.166;
4.E.244.169; 4.E.244.172; 4.E.244.175; 4.E.244.240; 4.E.244.244;
Prodrugs of 4.G 4.G.228.228; 4.G.228.229; 4.G.228.230; 4.G.228.231; 4.G.228.236;
4.G.228.237; 4.G.228.238; 4.G.228.239; 4.G.228.154; 4.G.228.157;
4.G.228.166; 4.G.228.169; 4.G.228.172; 4.G.228.175; 4.G.228.240;
4.G.228.244; 4.G.229.228; 4.G.229.229; 4.G.229.230; 4.G.229.231;
4.G.229.236; 4.G.229.237; 4.G.229.238; 4.G.229.239; 4.G.229.154;
4.G.229.157; 4.G.229.166; 4.G.229.169; 4.G.229.172; 4.G.229.175;

TABLE 100-continued

4.G.229.240; 4.G.229.244; 4.G.230.228; 4.G.230.229; 4.G.230.230;
4.G.230.231; 4.G.230.236; 4.G.230.237; 4.G.230.238; 4.G.230.239;
4.G.230.154; 4.G.230.157; 4.G.230.166; 4.G.230.169; 4.G.230.172;
4.G.230.175; 4.G.230.240; 4.G.230.244; 4.G.231.228; 4.G.231.229;
4.G.231.230; 4.G.231.231; 4.G.231.236; 4.G.231.237; 4.G.231.238;
4.G.231.239; 4.G.231.154; 4.G.231.157; 4.G.231.166; 4.G.231.169;
4.G.231.172; 4.G.231.175; 4.G.231.240; 4.G.231.244; 4.G.236.228;
4.G.236.229; 4.G.236.230; 4.G.236.231; 4.G.236.236; 4.G.236.237;
4.G.236.238; 4.G.236.239; 4.G.236.154; 4.G.236.157; 4.G.236.166;
4.G.236.169; 4.G.236.172; 4.G.236.175; 4.G.236.240; 4.G.236.244;
4.G.237.228; 4.G.237.229; 4.G.237.230; 4.G.237.231; 4.G.237.236;
4.G.237.237; 4.G.237.238; 4.G.237.239; 4.G.237.154; 4.G.237.157;
4.G.237.166; 4.G.237.169; 4.G.237.172; 4.G.237.175; 4.G.237.240;
4.G.237.244; 4.G.238.228; 4.G.238.229; 4.G.238.230; 4.G.238.231;
4.G.238.236; 4.G.238.237; 4.G.238.238; 4.G.238.239; 4.G.238.154;
4.G.238.157; 4.G.238.166; 4.G.238.169; 4.G.238.172; 4.G.238.175;
4.G.238.240; 4.G.238.244; 4.G.239.228; 4.G.239.229; 4.G.239.230;
4.G.239.231; 4.G.239.236; 4.G.239.237; 4.G.239.238; 4.G.239.239;
4.G.239.154; 4.G.239.157; 4.G.239.166; 4.G.239.169; 4.G.239.172;
4.G.239.175; 4.G.239.240; 4.G.239.244; 4.G.154.228; 4.G.154.229;
4.G.154.230; 4.G.154.231; 4.G.154.236; 4.G.154.237; 4.G.154.238;
4.G.154.239; 4.G.154.154; 4.G.154.157; 4.G.154.166; 4.G.154.169;
4.G.154.172; 4.G.154.175; 4.G.154.240; 4.G.154.244; 4.G.157.228;
4.G.157.229; 4.G.157.230; 4.G.157.231; 4.G.157.236; 4.G.157.237;
4.G.157.238; 4.G.157.239; 4.G.157.154; 4.G.157.157; 4.G.157.166;
4.G.157.169; 4.G.157.172; 4.G.157.175; 4.G.157.240; 4.G.157.244;
4.G.166.228; 4.G.166.229; 4.G.166.230; 4.G.166.231; 4.G.166.236;
4.G.166.237; 4.G.166.238; 4.G.166.239; 4.G.166.154; 4.G.166.157;
4.G.166.166; 4.G.166.169; 4.G.166.172; 4.G.166.175; 4.G.166.240;
4.G.166.244; 4.G.169.228; 4.G.169.229; 4.G.169.230; 4.G.169.231;
4.G.169.236; 4.G.169.237; 4.G.169.238; 4.G.169.239; 4.G.169.154;
4.G.169.157; 4.G.169.166; 4.G.169.169; 4.G.169.172; 4.G.169.175;
4.G.169.240; 4.G.169.244; 4.G.172.228; 4.G.172.229; 4.G.172.230;
4.G.172.231; 4.G.172.236; 4.G.172.237; 4.G.172.238; 4.G.172.239;
4.G.172.154; 4.G.172.157; 4.G.172.166; 4.G.172.169; 4.G.172.172;
4.G.172.175; 4.G.172.240; 4.G.172.244; 4.G.175.228; 4.G.175.229;
4.G.175.230; 4.G.175.231; 4.G.175.236; 4.G.175.237; 4.G.175.238;
4.G.175.239; 4.G.175.154; 4.G.175.157; 4.G.175.166; 4.G.175.169;
4.G.175.172; 4.G.175.175; 4.G.175.240; 4.G.175.244; 4.G.240.228;
4.G.240.229; 4.G.240.230; 4.G.240.231; 4.G.240.236; 4.G.240.237;
4.G.240.238; 4.G.240.239; 4.G.240.154; 4.G.240.157; 4.G.240.166;
4.G.240.169; 4.G.240.172; 4.G.240.175; 4.G.240.240; 4.G.240.244;
4.G.244.228; 4.G.244.229; 4.G.244.230; 4.G.244.231; 4.G.244.236;
4.G.244.237; 4.G.244.238; 4.G.244.239; 4.G.244.154; 4.G.244.157;
4.G.244.166; 4.G.244.169; 4.G.244.172; 4.G.244.175; 4.G.244.240;
4.G.244.244;
Prodrugs of 4.I 4.I.228.228; 4.I.228.229; 4.I.228.230; 4.I.228.231; 4.I.228.236; 4.I.228.237;
4.I.228.238; 4.I.228.239; 4.I.228.154; 4.I.228.157; 4.I.228.166; 4.I.228.169;
4.I.228.172; 4.I.228.175; 4.I.228.240; 4.I.228.244; 4.I.229.228; 4.I.229.229;
4.I.229.230; 4.I.229.231; 4.I.229.236; 4.I.229.237; 4.I.229.238; 4.I.229.239;
4.I.229.154; 4.I.229.157; 4.I.229.166; 4.I.229.169; 4.I.229.172; 4.I.229.175;
4.I.229.240; 4.I.229.244; 4.I.230.228; 4.I.230.229; 4.I.230.230; 4.I.230.231;
4.I.230.236; 4.I.230.237; 4.I.230.238; 4.I.230.239; 4.I.230.154; 4.I.230.157;
4.I.230.166; 4.I.230.169; 4.I.230.172; 4.I.230.175; 4.I.230.240; 4.I.230.244;
4.I.231.228; 4.I.231.229; 4.I.231.230; 4.I.231.231; 4.I.231.236; 4.I.231.237;
4.I.231.238; 4.I.231.239; 4.I.231.154; 4.I.231.157; 4.I.231.166; 4.I.231.169;
4.I.231.172; 4.I.231.175; 4.I.231.240; 4.I.231.244; 4.I.236.228; 4.I.236.229;
4.I.236.230; 4.I.236.231; 4.I.236.236; 4.I.236.237; 4.I.236.238; 4.I.236.239;
4.I.236.154; 4.I.236.157; 4.I.236.166; 4.I.236.169; 4.I.236.172; 4.I.236.175;
4.I.236.240; 4.I.236.244; 4.I.237.228; 4.I.237.229; 4.I.237.230; 4.I.237.231;
4.I.237.236; 4.I.237.237; 4.I.237.238; 4.I.237.239; 4.I.237.154; 4.I.237.157;
4.I.237.166; 4.I.237.169; 4.I.237.172; 4.I.237.175; 4.I.237.240; 4.I.237.244;
4.I.238.228; 4.I.238.229; 4.I.238.230; 4.I.238.231; 4.I.238.236; 4.I.238.237;
4.I.238.238; 4.I.238.239; 4.I.238.154; 4.I.238.157; 4.I.238.166; 4.I.238.169;
4.I.238.172; 4.I.238.175; 4.I.238.240; 4.I.238.244; 4.I.239.228; 4.I.239.229;
4.I.239.230; 4.I.239.231; 4.I.239.236; 4.I.239.237; 4.I.239.238; 4.I.239.239;
4.I.239.154; 4.I.239.157; 4.I.239.166; 4.I.239.169; 4.I.239.172; 4.I.239.175;
4.I.239.240; 4.I.239.244; 4.I.154.228; 4.I.154.229; 4.I.154.230; 4.I.154.231;
4.I.154.236; 4.I.154.237; 4.I.154.238; 4.I.154.239; 4.I.154.154; 4.I.154.157;
4.I.154.166; 4.I.154.169; 4.I.154.172; 4.I.154.175; 4.I.154.240; 4.I.154.244;
4.I.157.228; 4.I.157.229; 4.I.157.230; 4.I.157.231; 4.I.157.236; 4.I.157.237;
4.I.157.238; 4.I.157.239; 4.I.157.154; 4.I.157.157; 4.I.157.166; 4.I.157.169;
4.I.157.172; 4.I.157.175; 4.I.157.240; 4.I.157.244; 4.I.166.228; 4.I.166.229;
4.I.166.230; 4.I.166.231; 4.I.166.236; 4.I.166.237; 4.I.166.238; 4.I.166.239;
4.I.166.154; 4.I.166.157; 4.I.166.166; 4.I.166.169; 4.I.166.172; 4.I.166.175;
4.I.166.240; 4.I.166.244; 4.I.169.228; 4.I.169.229; 4.I.169.230; 4.I.169.231;
4.I.169.236; 4.I.169.237; 4.I.169.238; 4.I.169.239; 4.I.169.154; 4.I.169.157;

TABLE 100-continued

4.I.169.166; 4.I.169.169; 4.I.169.172; 4.I.169.175; 4.I.169.240; 4.I.169.244;
4.I.172.228; 4.I.172.229; 4.I.172.230; 4.I.172.231; 4.I.172.236; 4.I.172.237;
4.I.172.238; 4.I.172.239; 4.I.172.154; 4.I.172.157; 4.I.172.166; 4.I.172.169;
4.I.172.172; 4.I.172.175; 4.I.172.240; 4.I.172.244; 4.I.175.228; 4.I.175.229;
4.I.175.230; 4.I.175.231; 4.I.175.236; 4.I.175.237; 4.I.175.238; 4.I.175.239;
4.I.175.154; 4.I.175.157; 4.I.175.166; 4.I.175.169; 4.I.175.172; 4.I.175.175;
4.I.175.240; 4.I.175.244; 4.I.240.228; 4.I.240.229; 4.I.240.230; 4.I.240.231;
4.I.240.236; 4.I.240.237; 4.I.240.238; 4.I.240.239; 4.I.240.154; 4.I.240.157;
4.I.240.166; 4.I.240.169; 4.I.240.172; 4.I.240.175; 4.I.240.240; 4.I.240.244;
4.I.244.228; 4.I.244.229; 4.I.244.230; 4.I.244.231; 4.I.244.236; 4.I.244.237;
4.I.244.238; 4.I.244.239; 4.I.244.154; 4.I.244.157; 4.I.244.166; 4.I.244.169;
4.I.244.172; 4.I.244.175; 4.I.244.240; 4.I.244.244;

Prodrugs of 4.J

4.J.228.228; 4.J.228.229; 4.J.228.230; 4.J.228.231; 4.J.228.236; 4.J.228.237;
4.J.228.238; 4.J.228.239; 4.J.228.154; 4.J.228.157; 4.J.228.166; 4.J.228.169;
4.J.228.172; 4.J.228.175; 4.J.228.240; 4.J.228.244; 4.J.229.228; 4.J.229.229;
4.J.229.230; 4.J.229.231; 4.J.229.236; 4.J.229.237; 4.J.229.238; 4.J.229.239;
4.J.229.154; 4.J.229.157; 4.J.229.166; 4.J.229.169; 4.J.229.172; 4.J.229.175;
4.J.229.240; 4.J.229.244; 4.J.230.228; 4.J.230.229; 4.J.230.230; 4.J.230.231;
4.J.230.236; 4.J.230.237; 4.J.230.238; 4.J.230.239; 4.J.230.154; 4.J.230.157;
4.J.230.166; 4.J.230.169; 4.J.230.172; 4.J.230.175; 4.J.230.240; 4.J.230.244;
4.J.231.228; 4.J.231.229; 4.J.231.230; 4.J.231.231; 4.J.231.236; 4.J.231.237;
4.J.231.238; 4.J.231.239; 4.J.231.154; 4.J.231.157; 4.J.231.166; 4.J.231.169;
4.J.231.172; 4.J.231.175; 4.J.231.240; 4.J.231.244; 4.J.236.228; 4.J.236.229;
4.J.236.230; 4.J.236.231; 4.J.236.236; 4.J.236.237; 4.J.236.238; 4.J.236.239;
4.J.236.154; 4.J.236.157; 4.J.236.166; 4.J.236.169; 4.J.236.172; 4.J.236.175;
4.J.236.240; 4.J.236.244; 4.J.237.228; 4.J.237.229; 4.J.237.230; 4.J.237.231;
4.J.237.236; 4.J.237.237; 4.J.237.238; 4.J.237.239; 4.J.237.154; 4.J.237.157;
4.J.237.166; 4.J.237.169; 4.J.237.172; 4.J.237.175; 4.J.237.240; 4.J.237.244;
4.J.238.228; 4.J.238.229; 4.J.238.230; 4.J.238.231; 4.J.238.236; 4.J.238.237;
4.J.238.238; 4.J.238.239; 4.J.238.154; 4.J.238.157; 4.J.238.166; 4.J.238.169;
4.J.238.172; 4.J.238.175; 4.J.238.240; 4.J.238.244; 4.J.239.228; 4.J.239.229;
4.J.239.230; 4.J.239.231; 4.J.239.236; 4.J.239.237; 4.J.239.238; 4.J.239.239;
4.J.239.154; 4.J.239.157; 4.J.239.166; 4.J.239.169; 4.J.239.172; 4.J.239.175;
4.J.239.240; 4.J.239.244; 4.J.154.228; 4.J.154.229; 4.J.154.230; 4.J.154.231;
4.J.154.236; 4.J.154.237; 4.J.154.238; 4.J.154.239; 4.J.154.154; 4.J.154.157;
4.J.154.166; 4.J.154.169; 4.J.154.172; 4.J.154.175; 4.J.154.240; 4.J.154.244;
4.J.157.228; 4.J.157.229; 4.J.157.230; 4.J.157.231; 4.J.157.236; 4.J.157.237;
4.J.157.238; 4.J.157.239; 4.J.157.154; 4.J.157.157; 4.J.157.166; 4.J.157.169;
4.J.157.172; 4.J.157.175; 4.J.157.240; 4.J.157.244; 4.J.166.228; 4.J.166.229;
4.J.166.230; 4.J.166.231; 4.J.166.236; 4.J.166.237; 4.J.166.238; 4.J.166.239;
4.J.166.154; 4.J.166.157; 4.J.166.166; 4.J.166.169; 4.J.166.172; 4.J.166.175;
4.J.166.240; 4.J.166.244; 4.J.169.228; 4.J.169.229; 4.J.169.230; 4.J.169.231;
4.J.169.236; 4.J.169.237; 4.J.169.238; 4.J.169.239; 4.J.169.154; 4.J.169.157;
4.J.169.166; 4.J.169.169; 4.J.169.172; 4.J.169.175; 4.J.169.240; 4.J.169.244;
4.J.172.228; 4.J.172.229; 4.J.172.230; 4.J.172.231; 4.J.172.236; 4.J.172.237;
4.J.172.238; 4.J.172.239; 4.J.172.154; 4.J.172.157; 4.J.172.166; 4.J.172.169;
4.J.172.172; 4.J.172.175; 4.J.172.240; 4.J.172.244; 4.J.175.228; 4.J.175.229;
4.J.175.230; 4.J.175.231; 4.J.175.236; 4.J.175.237; 4.J.175.238; 4.J.175.239;
4.J.175.154; 4.J.175.157; 4.J.175.166; 4.J.175.169; 4.J.175.172; 4.J.175.175;
4.J.175.240; 4.J.175.244; 4.J.240.228; 4.J.240.229; 4.J.240.230; 4.J.240.231;
4.J.240.236; 4.J.240.237; 4.J.240.238; 4.J.240.239; 4.J.240.154; 4.J.240.157;
4.J.240.166; 4.J.240.169; 4.J.240.172; 4.J.240.175; 4.J.240.240; 4.J.240.244;
4.J.244.228; 4.J.244.229; 4.J.244.230; 4.J.244.231; 4.J.244.236; 4.J.244.237;
4.J.244.238; 4.J.244.239; 4.J.244.154; 4.J.244.157; 4.J.244.166; 4.J.244.169;
4.J.244.172; 4.J.244.175; 4.J.244.240; 4.J.244.244;

Prodrugs of 4.L

4.L.228.228; 4.L.228.229; 4.L.228.230; 4.L.228.231; 4.L.228.236;
4.L.228.237; 4.L.228.238; 4.L.228.239; 4.L.228.154; 4.L.228.157; 4.L.228.166;
4.L.228.169; 4.L.228.172; 4.L.228.175; 4.L.228.240; 4.L.228.244; 4.L.229.228;
4.L.229.229; 4.L.229.230; 4.L.229.231; 4.L.229.236; 4.L.229.237; 4.L.229.238;
4.L.229.239; 4.L.229.154; 4.L.229.157; 4.L.229.166; 4.L.229.169; 4.L.229.172;
4.L.229.175; 4.L.229.240; 4.L.229.244; 4.L.230.228; 4.L.230.229; 4.L.230.230;
4.L.230.231; 4.L.230.236; 4.L.230.237; 4.L.230.238; 4.L.230.239; 4.L.230.154;
4.L.230.157; 4.L.230.166; 4.L.230.169; 4.L.230.172; 4.L.230.175; 4.L.230.240;
4.L.230.244; 4.L.231.228; 4.L.231.229; 4.L.231.230; 4.L.231.231; 4.L.231.236;
4.L.231.237; 4.L.231.238; 4.L.231.239; 4.L.231.154; 4.L.231.157; 4.L.231.166;
4.L.231.169; 4.L.231.172; 4.L.231.175; 4.L.231.240; 4.L.231.244; 4.L.236.228;
4.L.236.229; 4.L.236.230; 4.L.236.231; 4.L.236.236; 4.L.236.237; 4.L.236.238;
4.L.236.239; 4.L.236.154; 4.L.236.157; 4.L.236.166; 4.L.236.169; 4.L.236.172;
4.L.236.175; 4.L.236.240; 4.L.236.244; 4.L.237.228; 4.L.237.229; 4.L.237.230;
4.L.237.231; 4.L.237.236; 4.L.237.237; 4.L.237.238; 4.L.237.239; 4.L.237.154;
4.L.237.157; 4.L.237.166; 4.L.237.169; 4.L.237.172; 4.L.237.175; 4.L.237.240;
4.L.237.244; 4.L.238.228; 4.L.238.229; 4.L.238.230; 4.L.238.231; 4.L.238.236;
4.L.238.237; 4.L.238.238; 4.L.238.239; 4.L.238.154; 4.L.238.157; 4.L.238.166;
4.L.238.169; 4.L.238.172; 4.L.238.175; 4.L.238.240; 4.L.238.244; 4.L.239.228;
4.L.239.229; 4.L.239.230; 4.L.239.231; 4.L.239.236; 4.L.239.237; 4.L.239.238;

TABLE 100-continued

4.L.239.239; 4.L.239.154; 4.L.239.157; 4.L.239.166; 4.L.239.169; 4.L.239.172;
4.L.239.175; 4.L.239.240; 4.L.239.244; 4.L.154.228; 4.L.154.229; 4.L.154.230;
4.L.154.231; 4.L.154.236; 4.L.154.237; 4.L.154.238; 4.L.154.239; 4.L.154.154;
4.L.154.157; 4.L.154.166; 4.L.154.169; 4.L.154.172; 4.L.154.175; 4.L.154.240;
4.L.154.244; 4.L.157.228; 4.L.157.229; 4.L.157.230; 4.L.157.231; 4.L.157.236;
4.L.157.237; 4.L.157.238; 4.L.157.239; 4.L.157.154; 4.L.157.157; 4.L.157.166;
4.L.157.169; 4.L.157.172; 4.L.157.175; 4.L.157.240; 4.L.157.244; 4.L.166.228;
4.L.166.229; 4.L.166.230; 4.L.166.231; 4.L.166.236; 4.L.166.237; 4.L.166.238;
4.L.166.239; 4.L.166.154; 4.L.166.157; 4.L.166.166; 4.L.166.169; 4.L.166.172;
4.L.166.175; 4.L.166.240; 4.L.166.244; 4.L.169.228; 4.L.169.229; 4.L.169.230;
4.L.169.231; 4.L.169.236; 4.L.169.237; 4.L.169.238; 4.L.169.239; 4.L.169.154;
4.L.169.157; 4.L.169.166; 4.L.169.169; 4.L.169.172; 4.L.169.175; 4.L.169.240;
4.L.169.244; 4.L.172.228; 4.L.172.229; 4.L.172.230; 4.L.172.231; 4.L.172.236;
4.L.172.237; 4.L.172.238; 4.L.172.239; 4.L.172.154; 4.L.172.157; 4.L.172.166;
4.L.172.169; 4.L.172.172; 4.L.172.175; 4.L.172.240; 4.L.172.244; 4.L.175.228;
4.L.175.229; 4.L.175.230; 4.L.175.231; 4.L.175.236; 4.L.175.237; 4.L.175.238;
4.L.175.239; 4.L.175.154; 4.L.175.157; 4.L.175.166; 4.L.175.169; 4.L.175.172;
4.L.175.175; 4.L.175.240; 4.L.175.244; 4.L.240.228; 4.L.240.229; 4.L.240.230;
4.L.240.231; 4.L.240.236; 4.L.240.237; 4.L.240.238; 4.L.240.239; 4.L.240.154;
4.L.240.157; 4.L.240.166; 4.L.240.169; 4.L.240.172; 4.L.240.175; 4.L.240.240;
4.L.240.244; 4.L.244.228; 4.L.244.229; 4.L.244.230; 4.L.244.231; 4.L.244.236;
4.L.244.237; 4.L.244.238; 4.L.244.239; 4.L.244.154; 4.L.244.157; 4.L.244.166;
4.L.244.169; 4.L.244.172; 4.L.244.175; 4.L.244.240; 4.L.244.244;

Prodrugs of 4.O

4.O.228.228; 4.O.228.229; 4.O.228.230; 4.O.228.231; 4.O.228.236;
4.O.228.237; 4.O.228.238; 4.O.228.239; 4.O.228.154; 4.O.228.157;
4.O.228.166; 4.O.228.169; 4.O.228.172; 4.O.228.175; 4.O.228.240;
4.O.228.244; 4.O.229.228; 4.O.229.229; 4.O.229.230; 4.O.229.231;
4.O.229.236; 4.O.229.237; 4.O.229.238; 4.O.229.239; 4.O.229.154;
4.O.229.157; 4.O.229.166; 4.O.229.169; 4.O.229.172; 4.O.229.175;
4.O.229.240; 4.O.229.244; 4.O.230.228; 4.O.230.229; 4.O.230.230;
4.O.230.231; 4.O.230.236; 4.O.230.237; 4.O.230.238; 4.O.230.239;
4.O.230.154; 4.O.230.157; 4.O.230.166; 4.O.230.169; 4.O.230.172;
4.O.230.175; 4.O.230.240; 4.O.230.244; 4.O.231.228; 4.O.231.229;
4.O.231.230; 4.O.231.231; 4.O.231.236; 4.O.231.237; 4.O.231.238;
4.O.231.239; 4.O.231.154; 4.O.231.157; 4.O.231.166; 4.O.231.169;
4.O.231.172; 4.O.231.175; 4.O.231.240; 4.O.231.244; 4.O.236.228;
4.O.236.229; 4.O.236.230; 4.O.236.231; 4.O.236.236; 4.O.236.237;
4.O.236.238; 4.O.236.239; 4.O.236.154; 4.O.236.157; 4.O.236.166;
4.O.236.169; 4.O.236.172; 4.O.236.175; 4.O.236.240; 4.O.236.244;
4.O.237.228; 4.O.237.229; 4.O.237.230; 4.O.237.231; 4.O.237.236;
4.O.237.237; 4.O.237.238; 4.O.237.239; 4.O.237.154; 4.O.237.157;
4.O.237.166; 4.O.237.169; 4.O.237.172; 4.O.237.175; 4.O.237.240;
4.O.237.244; 4.O.238.228; 4.O.238.229; 4.O.238.230; 4.O.238.231;
4.O.238.236; 4.O.238.237; 4.O.238.238; 4.O.238.239; 4.O.238.154;
4.O.238.157; 4.O.238.166; 4.O.238.169; 4.O.238.172; 4.O.238.175;
4.O.238.240; 4.O.238.244; 4.O.239.228; 4.O.239.229; 4.O.239.230;
4.O.239.231; 4.O.239.236; 4.O.239.237; 4.O.239.238; 4.O.239.239;
4.O.239.154; 4.O.239.157; 4.O.239.166; 4.O.239.169; 4.O.239.172;
4.O.239.175; 4.O.239.240; 4.O.239.244; 4.O.154.228; 4.O.154.229;
4.O.154.230; 4.O.154.231; 4.O.154.236; 4.O.154.237; 4.O.154.238;
4.O.154.239; 4.O.154.154; 4.O.154.157; 4.O.154.166; 4.O.154.169;
4.O.154.172; 4.O.154.175; 4.O.154.240; 4.O.154.244; 4.O.157.228;
4.O.157.229; 4.O.157.230; 4.O.157.231; 4.O.157.236; 4.O.157.237;
4.O.157.238; 4.O.157.239; 4.O.157.154; 4.O.157.157; 4.O.157.166;
4.O.157.169; 4.O.157.172; 4.O.157.175; 4.O.157.240; 4.O.157.244;
4.O.166.228; 4.O.166.229; 4.O.166.230; 4.O.166.231; 4.O.166.236;
4.O.166.237; 4.O.166.238; 4.O.166.239; 4.O.166.154; 4.O.166.157;
4.O.166.166; 4.O.166.169; 4.O.166.172; 4.O.166.175; 4.O.166.240;
4.O.166.244; 4.O.169.228; 4.O.169.229; 4.O.169.230; 4.O.169.231;
4.O.169.236; 4.O.169.237; 4.O.169.238; 4.O.169.239; 4.O.169.154;
4.O.169.157; 4.O.169.166; 4.O.169.169; 4.O.169.172; 4.O.169.175;
4.O.169.240; 4.O.169.244; 4.O.172.228; 4.O.172.229; 4.O.172.230;
4.O.172.231; 4.O.172.236; 4.O.172.237; 4.O.172.238; 4.O.172.239;
4.O.172.154; 4.O.172.157; 4.O.172.166; 4.O.172.169; 4.O.172.172;
4.O.172.175; 4.O.172.240; 4.O.172.244; 4.O.175.228; 4.O.175.229;
4.O.175.230; 4.O.175.231; 4.O.175.236; 4.O.175.237; 4.O.175.238;
4.O.175.239; 4.O.175.154; 4.O.175.157; 4.O.175.166; 4.O.175.169;
4.O.175.172; 4.O.175.175; 4.O.175.240; 4.O.175.244; 4.O.240.228;
4.O.240.229; 4.O.240.230; 4.O.240.231; 4.O.240.236; 4.O.240.237;
4.O.240.238; 4.O.240.239; 4.O.240.154; 4.O.240.157; 4.O.240.166;
4.O.240.169; 4.O.240.172; 4.O.240.175; 4.O.240.240; 4.O.240.244;
4.O.244.228; 4.O.244.229; 4.O.244.230; 4.O.244.231; 4.O.244.236;
4.O.244.237; 4.O.244.238; 4.O.244.239; 4.O.244.154; 4.O.244.157;
4.O.244.166; 4.O.244.169; 4.O.244.172; 4.O.244.175; 4.O.244.240;
4.O.244.244;

TABLE 100-continued

Prodrugs of 4.P

4.P.228.228; 4.P.228.229; 4.P.228.230; 4.P.228.231; 4.P.228.236;
4.P.228.237; 4.P.228.238; 4.P.228.239; 4.P.228.154; 4.P.228.157; 4.P.228.166;
4.P.228.169; 4.P.228.172; 4.P.228.175; 4.P.228.240; 4.P.228.244; 4.P.229.228;
4.P.229.229; 4.P.229.230; 4.P.229.231; 4.P.229.236; 4.P.229.237; 4.P.229.238;
4.P.229.239; 4.P.229.154; 4.P.229.157; 4.P.229.166; 4.P.229.169; 4.P.229.172;
4.P.229.175; 4.P.229.240; 4.P.229.244; 4.P.230.228; 4.P.230.229; 4.P.230.230;
4.P.230.231; 4.P.230.236; 4.P.230.237; 4.P.230.238; 4.P.230.239; 4.P.230.154;
4.P.230.157; 4.P.230.166; 4.P.230.169; 4.P.230.172; 4.P.230.175; 4.P.230.240;
4.P.230.244; 4.P.231.228; 4.P.231.229; 4.P.231.230; 4.P.231.231; 4.P.231.236;
4.P.231.237; 4.P.231.238; 4.P.231.239; 4.P.231.154; 4.P.231.157; 4.P.231.166;
4.P.231.169; 4.P.231.172; 4.P.231.175; 4.P.231.240; 4.P.231.244; 4.P.236.228;
4.P.236.229; 4.P.236.230; 4.P.236.231; 4.P.236.236; 4.P.236.237; 4.P.236.238;
4.P.236.239; 4.P.236.154; 4.P.236.157; 4.P.236.166; 4.P.236.169; 4.P.236.172;
4.P.236.175; 4.P.236.240; 4.P.236.244; 4.P.237.228; 4.P.237.229; 4.P.237.230;
4.P.237.231; 4.P.237.236; 4.P.237.237; 4.P.237.238; 4.P.237.239; 4.P.237.154;
4.P.237.157; 4.P.237.166; 4.P.237.169; 4.P.237.172; 4.P.237.175; 4.P.237.240;
4.P.237.244; 4.P.238.228; 4.P.238.229; 4.P.238.230; 4.P.238.231; 4.P.238.236;
4.P.238.237; 4.P.238.238; 4.P.238.239; 4.P.238.154; 4.P.238.157; 4.P.238.166;
4.P.238.169; 4.P.238.172; 4.P.238.175; 4.P.238.240; 4.P.238.244; 4.P.239.228;
4.P.239.229; 4.P.239.230; 4.P.239.231; 4.P.239.236; 4.P.239.237; 4.P.239.238;
4.P.239.239; 4.P.239.154; 4.P.239.157; 4.P.239.166; 4.P.239.169; 4.P.239.172;
4.P.239.175; 4.P.239.240; 4.P.239.244; 4.P.154.228; 4.P.154.229; 4.P.154.230;
4.P.154.231; 4.P.154.236; 4.P.154.237; 4.P.154.238; 4.P.154.239; 4.P.154.154;
4.P.154.157; 4.P.154.166; 4.P.154.169; 4.P.154.172; 4.P.154.175; 4.P.154.240;
4.P.154.244; 4.P.157.228; 4.P.157.229; 4.P.157.230; 4.P.157.231; 4.P.157.236;
4.P.157.237; 4.P.157.238; 4.P.157.239; 4.P.157.154; 4.P.157.157; 4.P.157.166;
4.P.157.169; 4.P.157.172; 4.P.157.175; 4.P.157.240; 4.P.157.244; 4.P.166.228;
4.P.166.229; 4.P.166.230; 4.P.166.231; 4.P.166.236; 4.P.166.237; 4.P.166.238;
4.P.166.239; 4.P.166.154; 4.P.166.157; 4.P.166.166; 4.P.166.169; 4.P.166.172;
4.P.166.175; 4.P.166.240; 4.P.166.244; 4.P.169.228; 4.P.169.229; 4.P.169.230;
4.P.169.231; 4.P.169.236; 4.P.169.237; 4.P.169.238; 4.P.169.239; 4.P.169.154;
4.P.169.157; 4.P.169.166; 4.P.169.169; 4.P.169.172; 4.P.169.175; 4.P.169.240;
4.P.169.244; 4.P.172.228; 4.P.172.229; 4.P.172.230; 4.P.172.231; 4.P.172.236;
4.P.172.237; 4.P.172.238; 4.P.172.239; 4.P.172.154; 4.P.172.157; 4.P.172.166;
4.P.172.169; 4.P.172.172; 4.P.172.175; 4.P.172.240; 4.P.172.244; 4.P.175.228;
4.P.175.229; 4.P.175.230; 4.P.175.231; 4.P.175.236; 4.P.175.237; 4.P.175.238;
4.P.175.239; 4.P.175.154; 4.P.175.157; 4.P.175.166; 4.P.175.169; 4.P.175.172;
4.P.175.175; 4.P.175.240; 4.P.175.244; 4.P.240.228; 4.P.240.229; 4.P.240.230;
4.P.240.231; 4.P.240.236; 4.P.240.237; 4.P.240.238; 4.P.240.239; 4.P.240.154;
4.P.240.157; 4.P.240.166; 4.P.240.169; 4.P.240.172; 4.P.240.175; 4.P.240.240;
4.P.240.244; 4.P.244.228; 4.P.244.229; 4.P.244.230; 4.P.244.231; 4.P.244.236;
4.P.244.237; 4.P.244.238; 4.P.244.239; 4.P.244.154; 4.P.244.157; 4.P.244.166;
4.P.244.169; 4.P.244.172; 4.P.244.175; 4.P.244.240; 4.P.244.244;

Prodrugs of 4.U

4.U.228.228; 4.U.228.229; 4.U.228.230; 4.U.228.231; 4.U.228.236;
4.U.228.237; 4.U.228.238; 4.U.228.239; 4.U.228.154; 4.U.228.157;
4.U.228.166; 4.U.228.169; 4.U.228.172; 4.U.228.175; 4.U.228.240;
4.U.228.244; 4.U.229.228; 4.U.229.229; 4.U.229.230; 4.U.229.231;
4.U.229.236; 4.U.229.237; 4.U.229.238; 4.U.229.239; 4.U.229.154;
4.U.229.157; 4.U.229.166; 4.U.229.169; 4.U.229.172; 4.U.229.175;
4.U.229.240; 4.U.229.244; 4.U.230.228; 4.U.230.229; 4.U.230.230;
4.U.230.231; 4.U.230.236; 4.U.230.237; 4.U.230.238; 4.U.230.239;
4.U.230.154; 4.U.230.157; 4.U.230.166; 4.U.230.169; 4.U.230.172;
4.U.230.175; 4.U.230.240; 4.U.230.244; 4.U.231.228; 4.U.231.229;
4.U.231.230; 4.U.231.231; 4.U.231.236; 4.U.231.237; 4.U.231.238;
4.U.231.239; 4.U.231.154; 4.U.231.157; 4.U.231.166; 4.U.231.169;
4.U.231.172; 4.U.231.175; 4.U.231.240; 4.U.231.244; 4.U.236.228;
4.U.236.229; 4.U.236.230; 4.U.236.231; 4.U.236.236; 4.U.236.237;
4.U.236.238; 4.U.236.239; 4.U.236.154; 4.U.236.157; 4.U.236.166;
4.U.236.169; 4.U.236.172; 4.U.236.175; 4.U.236.240; 4.U.236.244;
4.U.237.228; 4.U.237.229; 4.U.237.230; 4.U.237.231; 4.U.237.236;
4.U.237.237; 4.U.237.238; 4.U.237.239; 4.U.237.154; 4.U.237.157;
4.U.237.166; 4.U.237.169; 4.U.237.172; 4.U.237.175; 4.U.237.240;
4.U.237.244; 4.U.238.228; 4.U.238.229; 4.U.238.230; 4.U.238.231;
4.U.238.236; 4.U.238.237; 4.U.238.238; 4.U.238.239; 4.U.238.154;
4.U.238.157; 4.U.238.166; 4.U.238.169; 4.U.238.172; 4.U.238.175;
4.U.238.240; 4.U.238.244; 4.U.239.228; 4.U.239.229; 4.U.239.230;
4.U.239.231; 4.U.239.236; 4.U.239.237; 4.U.239.238; 4.U.239.239;
4.U.239.154; 4.U.239.157; 4.U.239.166; 4.U.239.169; 4.U.239.172;
4.U.239.175; 4.U.239.240; 4.U.239.244; 4.U.154.228; 4.U.154.229;
4.U.154.230; 4.U.154.231; 4.U.154.236; 4.U.154.237; 4.U.154.238;
4.U.154.239; 4.U.154.154; 4.U.154.157; 4.U.154.166; 4.U.154.169;
4.U.154.172; 4.U.154.175; 4.U.154.240; 4.U.154.244; 4.U.157.228;
4.U.157.229; 4.U.157.230; 4.U.157.231; 4.U.157.236; 4.U.157.237;
4.U.157.238; 4.U.157.239; 4.U.157.154; 4.U.157.157; 4.U.157.166;
4.U.157.169; 4.U.157.172; 4.U.157.175; 4.U.157.240; 4.U.157.244;

TABLE 100-continued

4.U.166.228; 4.U.166.229; 4.U.166.230; 4.U.166.231; 4.U.166.236;
4.U.166.237; 4.U.166.238; 4.U.166.239; 4.U.166.154; 4.U.166.157;
4.U.166.166; 4.U.166.169; 4.U.166.172; 4.U.166.175; 4.U.166.240;
4.U.166.244; 4.U.169.228; 4.U.169.229; 4.U.169.230; 4.U.169.231;
4.U.169.236; 4.U.169.237; 4.U.169.238; 4.U.169.239; 4.U.169.154;
4.U.169.157; 4.U.169.166; 4.U.169.169; 4.U.169.172; 4.U.169.175;
4.U.169.240; 4.U.169.244; 4.U.172.228; 4.U.172.229; 4.U.172.230;
4.U.172.231; 4.U.172.236; 4.U.172.237; 4.U.172.238; 4.U.172.239;
4.U.172.154; 4.U.172.157; 4.U.172.166; 4.U.172.169; 4.U.172.172;
4.U.172.175; 4.U.172.240; 4.U.172.244; 4.U.175.228; 4.U.175.229;
4.U.175.230; 4.U.175.231; 4.U.175.236; 4.U.175.237; 4.U.175.238;
4.U.175.239; 4.U.175.154; 4.U.175.157; 4.U.175.166; 4.U.175.169;
4.U.175.172; 4.U.175.175; 4.U.175.240; 4.U.175.244; 4.U.240.228;
4.U.240.229; 4.U.240.230; 4.U.240.231; 4.U.240.236; 4.U.240.237;
4.U.240.238; 4.U.240.239; 4.U.240.154; 4.U.240.157; 4.U.240.166;
4.U.240.169; 4.U.240.172; 4.U.240.175; 4.U.240.240; 4.U.240.244;
4.U.244.228; 4.U.244.229; 4.U.244.230; 4.U.244.231; 4.U.244.236;
4.U.244.237; 4.U.244.238; 4.U.244.239; 4.U.244.154; 4.U.244.157;
4.U.244.166; 4.U.244.169; 4.U.244.172; 4.U.244.175; 4.U.244.240;
4.U.244.244;
Prodrugs of 4.W 4.W.228.228; 4.W.228.229; 4.W.228.230; 4.W.228.231; 4.W.228.236;
4.W.228.237; 4.W.228.238; 4.W.228.239; 4.W.228.154; 4.W.228.157;
4.W.228.166; 4.W.228.169; 4.W.228.172; 4.W.228.175; 4.W.228.240;
4.W.228.244; 4.W.229.228; 4.W.229.229; 4.W.229.230; 4.W.229.231;
4.W.229.236; 4.W.229.237; 4.W.229.238; 4.W.229.239; 4.W.229.154;
4.W.229.157; 4.W.229.166; 4.W.229.169; 4.W.229.172; 4.W.229.175;
4.W.229.240; 4.W.229.244; 4.W.230.228; 4.W.230.229; 4.W.230.230;
4.W.230.231; 4.W.230.236; 4.W.230.237; 4.W.230.238; 4.W.230.239;
4.W.230.154; 4.W.230.157; 4.W.230.166; 4.W.230.169; 4.W.230.172;
4.W.230.175; 4.W.230.240; 4.W.230.244; 4.W.231.228; 4.W.231.229;
4.W.231.230; 4.W.231.231; 4.W.231.236; 4.W.231.237; 4.W.231.238;
4.W.231.239; 4.W.231.154; 4.W.231.157; 4.W.231.166; 4.W.231.169;
4.W.231.172; 4.W.231.175; 4.W.231.240; 4.W.231.244; 4.W.236.228;
4.W.236.229; 4.W.236.230; 4.W.236.231; 4.W.236.236; 4.W.236.237;
4.W.236.238; 4.W.236.239; 4.W.236.154; 4.W.236.157; 4.W.236.166;
4.W.236.169; 4.W.236.172; 4.W.236.175; 4.W.236.240; 4.W.236.244;
4.W.237.228; 4.W.237.229; 4.W.237.230; 4.W.237.231; 4.W.237.236;
4.W.237.237; 4.W.237.238; 4.W.237.239; 4.W.237.154; 4.W.237.157;
4.W.237.166; 4.W.237.169; 4.W.237.172; 4.W.237.175; 4.W.237.240;
4.W.237.244; 4.W.238.228; 4.W.238.229; 4.W.238.230; 4.W.238.231;
4.W.238.236; 4.W.238.237; 4.W.238.238; 4.W.238.239; 4.W.238.154;
4.W.238.157; 4.W.238.166; 4.W.238.169; 4.W.238.172; 4.W.238.175;
4.W.238.240; 4.W.238.244; 4.W.239.228; 4.W.239.229; 4.W.239.230;
4.W.239.231; 4.W.239.236; 4.W.239.237; 4.W.239.238; 4.W.239.239;
4.W.239.154; 4.W.239.157; 4.W.239.166; 4.W.239.169; 4.W.239.172;
4.W.239.175; 4.W.239.240; 4.W.239.244; 4.W.154.228; 4.W.154.229;
4.W.154.230; 4.W.154.231; 4.W.154.236; 4.W.154.237; 4.W.154.238;
4.W.154.239; 4.W.154.154; 4.W.154.157; 4.W.154.166; 4.W.154.169;
4.W.154.172; 4.W.154.175; 4.W.154.240; 4.W.154.244; 4.W.157.228;
4.W.157.229; 4.W.157.230; 4.W.157.231; 4.W.157.236; 4.W.157.237;
4.W.157.238; 4.W.157.239; 4.W.157.154; 4.W.157.157; 4.W.157.166;
4.W.157.169; 4.W.157.172; 4.W.157.175; 4.W.157.240; 4.W.157.244;
4.W.166.228; 4.W.166.229; 4.W.166.230; 4.W.166.231; 4.W.166.236;
4.W.166.237; 4.W.166.238; 4.W.166.239; 4.W.166.154; 4.W.166.157;
4.W.166.166; 4.W.166.169; 4.W.166.172; 4.W.166.175; 4.W.166.240;
4.W.166.244; 4.W.169.228; 4.W.169.229; 4.W.169.230; 4.W.169.231;
4.W.169.236; 4.W.169.237; 4.W.169.238; 4.W.169.239; 4.W.169.154;
4.W.169.157; 4.W.169.166; 4.W.169.169; 4.W.169.172; 4.W.169.175;
4.W.169.240; 4.W.169.244; 4.W.172.228; 4.W.172.229; 4.W.172.230;
4.W.172.231; 4.W.172.236; 4.W.172.237; 4.W.172.238; 4.W.172.239;
4.W.172.154; 4.W.172.157; 4.W.172.166; 4.W.172.169; 4.W.172.172;
4.W.172.175; 4.W.172.240; 4.W.172.244; 4.W.175.228; 4.W.175.229;
4.W.175.230; 4.W.175.231; 4.W.175.236; 4.W.175.237; 4.W.175.238;
4.W.175.239; 4.W.175.154; 4.W.175.157; 4.W.175.166; 4.W.175.169;
4.W.175.172; 4.W.175.175; 4.W.175.240; 4.W.175.244; 4.W.240.228;
4.W.240.229; 4.W.240.230; 4.W.240.231; 4.W.240.236; 4.W.240.237;
4.W.240.238; 4.W.240.239; 4.W.240.154; 4.W.240.157; 4.W.240.166;
4.W.240.169; 4.W.240.172; 4.W.240.175; 4.W.240.240; 4.W.240.244;
4.W.244.228; 4.W.244.229; 4.W.244.230; 4.W.244.231; 4.W.244.236;
4.W.244.237; 4.W.244.238; 4.W.244.239; 4.W.244.154; 4.W.244.157;
4.W.244.166; 4.W.244.169; 4.W.244.172; 4.W.244.175; 4.W.244.240; 4.W.244.244;
Prodrugs of 4.Y 4.Y.228.228; 4.Y.228.229; 4.Y.228.230; 4.Y.228.231; 4.Y.228.236;
4.Y.228.237; 4.Y.228.238; 4.Y.228.239; 4.Y.228.154; 4.Y.228.157; 4.Y.228.166;
4.Y.228.169; 4.Y.228.172; 4.Y.228.175; 4.Y.228.240; 4.Y.228.244; 4.Y.229.228;
4.Y.229.229; 4.Y.229.230; 4.Y.229.231; 4.Y.229.236; 4.Y.229.237; 4.Y.229.238;

TABLE 100-continued

4.Y.229.239; 4.Y.229.154; 4.Y.229.157; 4.Y.229.166; 4.Y.229.169; 4.Y.229.172; 4.Y.229.175; 4.Y.229.240; 4.Y.229.244; 4.Y.230.228; 4.Y.230.229; 4.Y.230.230; 4.Y.230.231; 4.Y.230.236; 4.Y.230.237; 4.Y.230.238; 4.Y.230.239; 4.Y.230.154; 4.Y.230.157; 4.Y.230.166; 4.Y.230.169; 4.Y.230.172; 4.Y.230.175; 4.Y.230.240; 4.Y.230.244; 4.Y.231.228; 4.Y.231.229; 4.Y.231.230; 4.Y.231.231; 4.Y.231.236; 4.Y.231.237; 4.Y.231.238; 4.Y.231.239; 4.Y.231.154; 4.Y.231.157; 4.Y.231.166; 4.Y.231.169; 4.Y.231.172; 4.Y.231.175; 4.Y.231.240; 4.Y.231.244; 4.Y.236.228; 4.Y.236.229; 4.Y.236.230; 4.Y.236.231; 4.Y.236.236; 4.Y.236.237; 4.Y.236.238; 4.Y.236.239; 4.Y.236.154; 4.Y.236.157; 4.Y.236.166; 4.Y.236.169; 4.Y.236.172; 4.Y.236.175; 4.Y.236.240; 4.Y.236.244; 4.Y.237.228; 4.Y.237.229; 4.Y.237.230; 4.Y.237.231; 4.Y.237.236; 4.Y.237.237; 4.Y.237.238; 4.Y.237.239; 4.Y.237.154; 4.Y.237.157; 4.Y.237.166; 4.Y.237.169; 4.Y.237.172; 4.Y.237.175; 4.Y.237.240; 4.Y.237.244; 4.Y.238.228; 4.Y.238.229; 4.Y.238.230; 4.Y.238.231; 4.Y.238.236; 4.Y.238.237; 4.Y.238.238; 4.Y.238.239; 4.Y.238.154; 4.Y.238.157; 4.Y.238.166; 4.Y.238.169; 4.Y.238.172; 4.Y.238.175; 4.Y.238.240; 4.Y.238.244; 4.Y.239.228; 4.Y.239.229; 4.Y.239.230; 4.Y.239.231; 4.Y.239.236; 4.Y.239.237; 4.Y.239.238; 4.Y.239.239; 4.Y.239.154; 4.Y.239.157; 4.Y.239.166; 4.Y.239.169; 4.Y.239.172; 4.Y.239.175; 4.Y.239.240; 4.Y.239.244; 4.Y.154.228; 4.Y.154.229; 4.Y.154.230; 4.Y.154.231; 4.Y.154.236; 4.Y.154.237; 4.Y.154.238; 4.Y.154.239; 4.Y.154.154; 4.Y.154.157; 4.Y.154.166; 4.Y.154.169; 4.Y.154.172; 4.Y.154.175; 4.Y.154.240; 4.Y.154.244; 4.Y.157.228; 4.Y.157.229; 4.Y.157.230; 4.Y.157.231; 4.Y.157.236; 4.Y.157.237; 4.Y.157.238; 4.Y.157.239; 4.Y.157.154; 4.Y.157.157; 4.Y.157.166; 4.Y.157.169; 4.Y.157.172; 4.Y.157.175; 4.Y.157.240; 4.Y.157.244; 4.Y.166.228; 4.Y.166.229; 4.Y.166.230; 4.Y.166.231; 4.Y.166.236; 4.Y.166.237; 4.Y.166.238; 4.Y.166.239; 4.Y.166.154; 4.Y.166.157; 4.Y.166.166; 4.Y.166.169; 4.Y.166.172; 4.Y.166.175; 4.Y.166.240; 4.Y.166.244; 4.Y.169.228; 4.Y.169.229; 4.Y.169.230; 4.Y.169.231; 4.Y.169.236; 4.Y.169.237; 4.Y.169.238; 4.Y.169.239; 4.Y.169.154; 4.Y.169.157; 4.Y.169.166; 4.Y.169.169; 4.Y.169.172; 4.Y.169.175; 4.Y.169.240; 4.Y.169.244; 4.Y.172.228; 4.Y.172.229; 4.Y.172.230; 4.Y.172.231; 4.Y.172.236; 4.Y.172.237; 4.Y.172.238; 4.Y.172.239; 4.Y.172.154; 4.Y.172.157; 4.Y.172.166; 4.Y.172.169; 4.Y.172.172; 4.Y.172.175; 4.Y.172.240; 4.Y.172.244; 4.Y.175.228; 4.Y.175.229; 4.Y.175.230; 4.Y.175.231; 4.Y.175.236; 4.Y.175.237; 4.Y.175.238; 4.Y.175.239; 4.Y.175.154; 4.Y.175.157; 4.Y.175.166; 4.Y.175.169; 4.Y.175.172; 4.Y.175.175; 4.Y.175.240; 4.Y.175.244; 4.Y.240.228; 4.Y.240.229; 4.Y.240.230; 4.Y.240.231; 4.Y.240.236; 4.Y.240.237; 4.Y.240.238; 4.Y.240.239; 4.Y.240.154; 4.Y.240.157; 4.Y.240.166; 4.Y.240.169; 4.Y.240.172; 4.Y.240.175; 4.Y.240.240; 4.Y.240.244; 4.Y.244.228; 4.Y.244.229; 4.Y.244.230; 4.Y.244.231; 4.Y.244.236; 4.Y.244.237; 4.Y.244.238; 4.Y.244.239; 4.Y.244.154; 4.Y.244.157; 4.Y.244.166; 4.Y.244.169; 4.Y.244.172; 4.Y.244.175; 4.Y.244.240; 4.Y.244.244;
Prodrugs of 5.B 5.B.228.228; 5.B.228.229; 5.B.228.230; 5.B.228.231; 5.B.228.236; 5.B.228.237; 5.B.228.238; 5.B.228.239; 5.B.228.154; 5.B.228.157; 5.B.228.166; 5.B.228.169; 5.B.228.172; 5.B.228.175; 5.B.228.240; 5.B.228.244; 5.B.229.228; 5.B.229.229; 5.B.229.230; 5.B.229.231; 5.B.229.236; 5.B.229.237; 5.B.229.238; 5.B.229.239; 5.B.229.154; 5.B.229.157; 5.B.229.166; 5.B.229.169; 5.B.229.172; 5.B.229.175; 5.B.229.240; 5.B.229.244; 5.B.230.228; 5.B.230.229; 5.B.230.230; 5.B.230.231; 5.B.230.236; 5.B.230.237; 5.B.230.238; 5.B.230.239; 5.B.230.154; 5.B.230.157; 5.B.230.166; 5.B.230.169; 5.B.230.172; 5.B.230.175; 5.B.230.240; 5.B.230.244; 5.B.231.228; 5.B.231.229; 5.B.231.230; 5.B.231.231; 5.B.231.236; 5.B.231.237; 5.B.231.238; 5.B.231.239; 5.B.231.154; 5.B.231.157; 5.B.231.166; 5.B.231.169; 5.B.231.172; 5.B.231.175; 5.B.231.240; 5.B.231.244; 5.B.236.228; 5.B.236.229; 5.B.236.230; 5.B.236.231; 5.B.236.236; 5.B.236.237; 5.B.236.238; 5.B.236.239; 5.B.236.154; 5.B.236.157; 5.B.236.166; 5.B.236.169; 5.B.236.172; 5.B.236.175; 5.B.236.240; 5.B.236.244; 5.B.237.228; 5.B.237.229; 5.B.237.230; 5.B.237.231; 5.B.237.236; 5.B.237.237; 5.B.237.238; 5.B.237.239; 5.B.237.154; 5.B.237.157; 5.B.237.166; 5.B.237.169; 5.B.237.172; 5.B.237.175; 5.B.237.240; 5.B.237.244; 5.B.238.228; 5.B.238.229; 5.B.238.230; 5.B.238.231; 5.B.238.236; 5.B.238.237; 5.B.238.238; 5.B.238.239; 5.B.238.154; 5.B.238.157; 5.B.238.166; 5.B.238.169; 5.B.238.172; 5.B.238.175; 5.B.238.240; 5.B.238.244; 5.B.239.228; 5.B.239.229; 5.B.239.230; 5.B.239.231; 5.B.239.236; 5.B.239.237; 5.B.239.238; 5.B.239.239; 5.B.239.154; 5.B.239.157; 5.B.239.166; 5.B.239.169; 5.B.239.172; 5.B.239.175; 5.B.239.240; 5.B.239.244; 5.B.154.228; 5.B.154.229; 5.B.154.230; 5.B.154.231; 5.B.154.236; 5.B.154.237; 5.B.154.238; 5.B.154.239; 5.B.154.154; 5.B.154.157; 5.B.154.166; 5.B.154.169; 5.B.154.172; 5.B.154.175; 5.B.154.240; 5.B.154.244; 5.B.157.228; 5.B.157.229; 5.B.157.230; 5.B.157.231; 5.B.157.236; 5.B.157.237; 5.B.157.238; 5.B.157.239; 5.B.157.154; 5.B.157.157; 5.B.157.166; 5.B.157.169; 5.B.157.172; 5.B.157.175; 5.B.157.240; 5.B.157.244; 5.B.166.228; 5.B.166.229; 5.B.166.230; 5.B.166.231; 5.B.166.236; 5.B.166.237; 5.B.166.238; 5.B.166.239; 5.B.166.154; 5.B.166.157; 5.B.166.166; 5.B.166.169; 5.B.166.172; 5.B.166.175; 5.B.166.240; 5.B.166.244; 5.B.169.228; 5.B.169.229; 5.B.169.230; 5.B.169.231; 5.B.169.236; 5.B.169.237; 5.B.169.238; 5.B.169.239; 5.B.169.154; 5.B.169.157; 5.B.169.166; 5.B.169.169; 5.B.169.172; 5.B.169.175; 5.B.169.240; 5.B.169.244; 5.B.172.228; 5.B.172.229; 5.B.172.230; 5.B.172.231; 5.B.172.236; 5.B.172.237; 5.B.172.238; 5.B.172.239; 5.B.172.154; 5.B.172.157; 5.B.172.166; 5.B.172.169; 5.B.172.172; 5.B.172.175; 5.B.172.240; 5.B.172.244; 5.B.175.228; 5.B.175.229; 5.B.175.230; 5.B.175.231; 5.B.175.236; 5.B.175.237; 5.B.175.238; 5.B.175.239; 5.B.175.154; 5.B.175.157; 5.B.175.166; 5.B.175.169; 5.B.175.172; 5.B.175.175; 5.B.175.240; 5.B.175.244; 5.B.240.228; 5.B.240.229; 5.B.240.230;

TABLE 100-continued

5.B.240.231; 5.B.240.236; 5.B.240.237; 5.B.240.238; 5.B.240.239; 5.B.240.154;
5.B.240.157; 5.B.240.166; 5.B.240.169; 5.B.240.172; 5.B.240.175; 5.B.240.240;
5.B.240.244; 5.B.244.228; 5.B.244.229; 5.B.244.230; 5.B.244.231; 5.B.244.236;
5.B.244.237; 5.B.244.238; 5.B.244.239; 5.B.244.154; 5.B.244.157; 5.B.244.166;
5.B.244.169; 5.B.244.172; 5.B.244.175; 5.B.244.240; 5.B.244.244;
Prodrugs of 5.D 5.D.228.228; 5.D.228.229; 5.D.228.230; 5.D.228.231; 5.D.228.236;
5.D.228.237; 5.D.228.238; 5.D.228.239; 5.D.228.154; 5.D.228.157;
5.D.228.166; 5.D.228.169; 5.D.228.172; 5.D.228.175; 5.D.228.240;
5.D.228.244; 5.D.229.228; 5.D.229.229; 5.D.229.230; 5.D.229.231;
5.D.229.236; 5.D.229.237; 5.D.229.238; 5.D.229.239; 5.D.229.154;
5.D.229.157; 5.D.229.166; 5.D.229.169; 5.D.229.172; 5.D.229.175;
5.D.229.240; 5.D.229.244; 5.D.230.228; 5.D.230.229; 5.D.230.230;
5.D.230.231; 5.D.230.236; 5.D.230.237; 5.D.230.238; 5.D.230.239;
5.D.230.154; 5.D.230.157; 5.D.230.166; 5.D.230.169; 5.D.230.172;
5.D.230.175; 5.D.230.240; 5.D.230.244; 5.D.231.228; 5.D.231.229;
5.D.231.230; 5.D.231.231; 5.D.231.236; 5.D.231.237; 5.D.231.238;
5.D.231.239; 5.D.231.154; 5.D.231.157; 5.D.231.166; 5.D.231.169;
5.D.231.172; 5.D.231.175; 5.D.231.240; 5.D.231.244; 5.D.236.228;
5.D.236.229; 5.D.236.230; 5.D.236.231; 5.D.236.236; 5.D.236.237;
5.D.236.238; 5.D.236.239; 5.D.236.154; 5.D.236.157; 5.D.236.166;
5.D.236.169; 5.D.236.172; 5.D.236.175; 5.D.236.240; 5.D.236.244;
5.D.237.228; 5.D.237.229; 5.D.237.230; 5.D.237.231; 5.D.237.236;
5.D.237.237; 5.D.237.238; 5.D.237.239; 5.D.237.154; 5.D.237.157;
5.D.237.166; 5.D.237.169; 5.D.237.172; 5.D.237.175; 5.D.237.240;
5.D.237.244; 5.D.238.228; 5.D.238.229; 5.D.238.230; 5.D.238.231;
5.D.238.236; 5.D.238.237; 5.D.238.238; 5.D.238.239; 5.D.238.154;
5.D.238.157; 5.D.238.166; 5.D.238.169; 5.D.238.172; 5.D.238.175;
5.D.238.240; 5.D.238.244; 5.D.239.228; 5.D.239.229; 5.D.239.230;
5.D.239.231; 5.D.239.236; 5.D.239.237; 5.D.239.238; 5.D.239.239;
5.D.239.154; 5.D.239.157; 5.D.239.166; 5.D.239.169; 5.D.239.172;
5.D.239.175; 5.D.239.240; 5.D.239.244; 5.D.154.228; 5.D.154.229;
5.D.154.230; 5.D.154.231; 5.D.154.236; 5.D.154.237; 5.D.154.238;
5.D.154.239; 5.D.154.154; 5.D.154.157; 5.D.154.166; 5.D.154.169;
5.D.154.172; 5.D.154.175; 5.D.154.240; 5.D.154.244; 5.D.157.228;
5.D.157.229; 5.D.157.230; 5.D.157.231; 5.D.157.236; 5.D.157.237;
5.D.157.238; 5.D.157.239; 5.D.157.154; 5.D.157.157; 5.D.157.166;
5.D.157.169; 5.D.157.172; 5.D.157.175; 5.D.157.240; 5.D.157.244;
5.D.166.228; 5.D.166.229; 5.D.166.230; 5.D.166.231; 5.D.166.236;
5.D.166.237; 5.D.166.238; 5.D.166.239; 5.D.166.154; 5.D.166.157;
5.D.166.166; 5.D.166.169; 5.D.166.172; 5.D.166.175; 5.D.166.240;
5.D.166.244; 5.D.169.228; 5.D.169.229; 5.D.169.230; 5.D.169.231;
5.D.169.236; 5.D.169.237; 5.D.169.238; 5.D.169.239; 5.D.169.154;
5.D.169.157; 5.D.169.166; 5.D.169.169; 5.D.169.172; 5.D.169.175;
5.D.169.240; 5.D.169.244; 5.D.172.228; 5.D.172.229; 5.D.172.230;
5.D.172.231; 5.D.172.236; 5.D.172.237; 5.D.172.238; 5.D.172.239;
5.D.172.154; 5.D.172.157; 5.D.172.166; 5.D.172.169; 5.D.172.172;
5.D.172.175; 5.D.172.240; 5.D.172.244; 5.D.175.228; 5.D.175.229;
5.D.175.230; 5.D.175.231; 5.D.175.236; 5.D.175.237; 5.D.175.238;
5.D.175.239; 5.D.175.154; 5.D.175.157; 5.D.175.166; 5.D.175.169;
5.D.175.172; 5.D.175.175; 5.D.175.240; 5.D.175.244; 5.D.240.228;
5.D.240.229; 5.D.240.230; 5.D.240.231; 5.D.240.236; 5.D.240.237;
5.D.240.238; 5.D.240.239; 5.D.240.154; 5.D.240.157; 5.D.240.166;
5.D.240.169; 5.D.240.172; 5.D.240.175; 5.D.240.240; 5.D.240.244;
5.D.244.228; 5.D.244.229; 5.D.244.230; 5.D.244.231; 5.D.244.236;
5.D.244.237; 5.D.244.238; 5.D.244.239; 5.D.244.154; 5.D.244.157;
5.D.244.166; 5.D.244.169; 5.D.244.172; 5.D.244.175; 5.D.244.240;
5.D.244.244;
Prodrugs of 5.E 5.E.228.228; 5.E.228.229; 5.E.228.230; 5.E.228.231; 5.E.228.236;
5.E.228.237; 5.E.228.238; 5.E.228.239; 5.E.228.154; 5.E.228.157; 5.E.228.166;
5.E.228.169; 5.E.228.172; 5.E.228.175; 5.E.228.240; 5.E.228.244; 5.E.229.228;
5.E.229.229; 5.E.229.230; 5.E.229.231; 5.E.229.236; 5.E.229.237; 5.E.229.238;
5.E.229.239; 5.E.229.154; 5.E.229.157; 5.E.229.166; 5.E.229.169; 5.E.229.172;
5.E.229.175; 5.E.229.240; 5.E.229.244; 5.E.230.228; 5.E.230.229; 5.E.230.230;
5.E.230.231; 5.E.230.236; 5.E.230.237; 5.E.230.238; 5.E.230.239; 5.E.230.154;
5.E.230.157; 5.E.230.166; 5.E.230.169; 5.E.230.172; 5.E.230.175; 5.E.230.240;
5.E.230.244; 5.E.231.228; 5.E.231.229; 5.E.231.230; 5.E.231.231; 5.E.231.236;
5.E.231.237; 5.E.231.238; 5.E.231.239; 5.E.231.154; 5.E.231.157; 5.E.231.166;
5.E.231.169; 5.E.231.172; 5.E.231.175; 5.E.231.240; 5.E.231.244; 5.E.236.228;
5.E.236.229; 5.E.236.230; 5.E.236.231; 5.E.236.236; 5.E.236.237; 5.E.236.238;
5.E.236.239; 5.E.236.154; 5.E.236.157; 5.E.236.166; 5.E.236.169; 5.E.236.172;
5.E.236.175; 5.E.236.240; 5.E.236.244; 5.E.237.228; 5.E.237.229; 5.E.237.230;
5.E.237.231; 5.E.237.236; 5.E.237.237; 5.E.237.238; 5.E.237.239; 5.E.237.154;
5.E.237.157; 5.E.237.166; 5.E.237.169; 5.E.237.172; 5.E.237.175; 5.E.237.240;
5.E.237.244; 5.E.238.228; 5.E.238.229; 5.E.238.230; 5.E.238.231; 5.E.238.236;
5.E.238.237; 5.E.238.238; 5.E.238.239; 5.E.238.154; 5.E.238.157; 5.E.238.166;

TABLE 100-continued

5.E.238.169; 5.E.238.172; 5.E.238.175; 5.E.238.240; 5.E.238.244; 5.E.239.228;
5.E.239.229; 5.E.239.230; 5.E.239.231; 5.E.239.236; 5.E.239.237; 5.E.239.238;
5.E.239.239; 5.E.239.154; 5.E.239.157; 5.E.239.166; 5.E.239.169; 5.E.239.172;
5.E.239.175; 5.E.239.240; 5.E.239.244; 5.E.154.228; 5.E.154.229; 5.E.154.230;
5.E.154.231; 5.E.154.236; 5.E.154.237; 5.E.154.238; 5.E.154.239; 5.E.154.154;
5.E.154.157; 5.E.154.166; 5.E.154.169; 5.E.154.172; 5.E.154.175; 5.E.154.240;
5.E.154.244; 5.E.157.228; 5.E.157.229; 5.E.157.230; 5.E.157.231; 5.E.157.236;
5.E.157.237; 5.E.157.238; 5.E.157.239; 5.E.157.154; 5.E.157.157; 5.E.157.166;
5.E.157.169; 5.E.157.172; 5.E.157.175; 5.E.157.240; 5.E.157.244; 5.E.166.228;
5.E.166.229; 5.E.166.230; 5.E.166.231; 5.E.166.236; 5.E.166.237; 5.E.166.238;
5.E.166.239; 5.E.166.154; 5.E.166.157; 5.E.166.166; 5.E.166.169; 5.E.166.172;
5.E.166.175; 5.E.166.240; 5.E.166.244; 5.E.169.228; 5.E.169.229; 5.E.169.230;
5.E.169.231; 5.E.169.236; 5.E.169.237; 5.E.169.238; 5.E.169.239; 5.E.169.154;
5.E.169.157; 5.E.169.166; 5.E.169.169; 5.E.169.172; 5.E.169.175; 5.E.169.240;
5.E.169.244; 5.E.172.228; 5.E.172.229; 5.E.172.230; 5.E.172.231; 5.E.172.236;
5.E.172.237; 5.E.172.238; 5.E.172.239; 5.E.172.154; 5.E.172.157; 5.E.172.166;
5.E.172.169; 5.E.172.172; 5.E.172.175; 5.E.172.240; 5.E.172.244; 5.E.175.228;
5.E.175.229; 5.E.175.230; 5.E.175.231; 5.E.175.236; 5.E.175.237; 5.E.175.238;
5.E.175.239; 5.E.175.154; 5.E.175.157; 5.E.175.166; 5.E.175.169; 5.E.175.172;
5.E.175.175; 5.E.175.240; 5.E.175.244; 5.E.240.228; 5.E.240.229; 5.E.240.230;
5.E.240.231; 5.E.240.236; 5.E.240.237; 5.E.240.238; 5.E.240.239; 5.E.240.154;
5.E.240.157; 5.E.240.166; 5.E.240.169; 5.E.240.172; 5.E.240.175; 5.E.240.240;
5.E.240.244; 5.E.244.228; 5.E.244.229; 5.E.244.230; 5.E.244.231; 5.E.244.236;
5.E.244.237; 5.E.244.238; 5.E.244.239; 5.E.244.154; 5.E.244.157; 5.E.244.166;
5.E.244.169; 5.E.244.172; 5.E.244.175; 5.E.244.240; 5.E.244.244;

Prodrugs of 5.G

5.G.228.228; 5.G.228.229; 5.G.228.230; 5.G.228.231; 5.G.228.236;
5.G.228.237; 5.G.228.238; 5.G.228.239; 5.G.228.154; 5.G.228.157;
5.G.228.166; 5.G.228.169; 5.G.228.172; 5.G.228.175; 5.G.228.240;
5.G.228.244; 5.G.229.228; 5.G.229.229; 5.G.229.230; 5.G.229.231;
5.G.229.236; 5.G.229.237; 5.G.229.238; 5.G.229.239; 5.G.229.154;
5.G.229.157; 5.G.229.166; 5.G.229.169; 5.G.229.172; 5.G.229.175;
5.G.229.240; 5.G.229.244; 5.G.230.228; 5.G.230.229; 5.G.230.230;
5.G.230.231; 5.G.230.236; 5.G.230.237; 5.G.230.238; 5.G.230.239;
5.G.230.154; 5.G.230.157; 5.G.230.166; 5.G.230.169; 5.G.230.172;
5.G.230.175; 5.G.230.240; 5.G.230.244; 5.G.231.228; 5.G.231.229;
5.G.231.230; 5.G.231.231; 5.G.231.236; 5.G.231.237; 5.G.231.238;
5.G.231.239; 5.G.231.154; 5.G.231.157; 5.G.231.166; 5.G.231.169;
5.G.231.172; 5.G.231.175; 5.G.231.240; 5.G.231.244; 5.G.236.228;
5.G.236.229; 5.G.236.230; 5.G.236.231; 5.G.236.236; 5.G.236.237;
5.G.236.238; 5.G.236.239; 5.G.236.154; 5.G.236.157; 5.G.236.166;
5.G.236.169; 5.G.236.172; 5.G.236.175; 5.G.236.240; 5.G.236.244;
5.G.237.228; 5.G.237.229; 5.G.237.230; 5.G.237.231; 5.G.237.236;
5.G.237.237; 5.G.237.238; 5.G.237.239; 5.G.237.154; 5.G.237.157;
5.G.237.166; 5.G.237.169; 5.G.237.172; 5.G.237.175; 5.G.237.240;
5.G.237.244; 5.G.238.228; 5.G.238.229; 5.G.238.230; 5.G.238.231;
5.G.238.236; 5.G.238.237; 5.G.238.238; 5.G.238.239; 5.G.238.154;
5.G.238.157; 5.G.238.166; 5.G.238.169; 5.G.238.172; 5.G.238.175;
5.G.238.240; 5.G.238.244; 5.G.239.228; 5.G.239.229; 5.G.239.230;
5.G.239.231; 5.G.239.236; 5.G.239.237; 5.G.239.238; 5.G.239.239;
5.G.239.154; 5.G.239.157; 5.G.239.166; 5.G.239.169; 5.G.239.172;
5.G.239.175; 5.G.239.240; 5.G.239.244; 5.G.154.228; 5.G.154.229;
5.G.154.230; 5.G.154.231; 5.G.154.236; 5.G.154.237; 5.G.154.238;
5.G.154.239; 5.G.154.154; 5.G.154.157; 5.G.154.166; 5.G.154.169;
5.G.154.172; 5.G.154.175; 5.G.154.240; 5.G.154.244; 5.G.157.228;
5.G.157.229; 5.G.157.230; 5.G.157.231; 5.G.157.236; 5.G.157.237;
5.G.157.238; 5.G.157.239; 5.G.157.154; 5.G.157.157; 5.G.157.166;
5.G.157.169; 5.G.157.172; 5.G.157.175; 5.G.157.240; 5.G.157.244;
5.G.166.228; 5.G.166.229; 5.G.166.230; 5.G.166.231; 5.G.166.236;
5.G.166.237; 5.G.166.238; 5.G.166.239; 5.G.166.154; 5.G.166.157;
5.G.166.166; 5.G.166.169; 5.G.166.172; 5.G.166.175; 5.G.166.240;
5.G.166.244; 5.G.169.228; 5.G.169.229; 5.G.169.230; 5.G.169.231;
5.G.169.236; 5.G.169.237; 5.G.169.238; 5.G.169.239; 5.G.169.154;
5.G.169.157; 5.G.169.166; 5.G.169.169; 5.G.169.172; 5.G.169.175;
5.G.169.240; 5.G.169.244; 5.G.172.228; 5.G.172.229; 5.G.172.230;
5.G.172.231; 5.G.172.236; 5.G.172.237; 5.G.172.238; 5.G.172.239;
5.G.172.154; 5.G.172.157; 5.G.172.166; 5.G.172.169; 5.G.172.172;
5.G.172.175; 5.G.172.240; 5.G.172.244; 5.G.175.228; 5.G.175.229;
5.G.175.230; 5.G.175.231; 5.G.175.236; 5.G.175.237; 5.G.175.238;
5.G.175.239; 5.G.175.154; 5.G.175.157; 5.G.175.166; 5.G.175.169;
5.G.175.172; 5.G.175.175; 5.G.175.240; 5.G.175.244; 5.G.240.228;
5.G.240.229; 5.G.240.230; 5.G.240.231; 5.G.240.236; 5.G.240.237;
5.G.240.238; 5.G.240.239; 5.G.240.154; 5.G.240.157; 5.G.240.166;
5.G.240.169; 5.G.240.172; 5.G.240.175; 5.G.240.240; 5.G.240.244;
5.G.244.228; 5.G.244.229; 5.G.244.230; 5.G.244.231; 5.G.244.236;
5.G.244.237; 5.G.244.238; 5.G.244.239; 5.G.244.154; 5.G.244.157;
5.G.244.166; 5.G.244.169; 5.G.244.172; 5.G.244.175; 5.G.244.240;
5.G.244.244;

TABLE 100-continued

Prodrugs of 5.I

5.I.228.228; 5.I.228.229; 5.I.228.230; 5.I.228.231; 5.I.228.236; 5.I.228.237;
5.I.228.238; 5.I.228.239; 5.I.228.154; 5.I.228.157; 5.I.228.166; 5.I.228.169;
5.I.228.172; 5.I.228.175; 5.I.228.240; 5.I.228.244; 5.I.229.228; 5.I.229.229;
5.I.229.230; 5.I.229.231; 5.I.229.236; 5.I.229.237; 5.I.229.238; 5.I.229.239;
5.I.229.154; 5.I.229.157; 5.I.229.166; 5.I.229.169; 5.I.229.172; 5.I.229.175;
5.I.229.240; 5.I.229.244; 5.I.230.228; 5.I.230.229; 5.I.230.230; 5.I.230.231;
5.I.230.236; 5.I.230.237; 5.I.230.238; 5.I.230.239; 5.I.230.154; 5.I.230.157;
5.I.230.166; 5.I.230.169; 5.I.230.172; 5.I.230.175; 5.I.230.240; 5.I.230.244;
5.I.231.228; 5.I.231.229; 5.I.231.230; 5.I.231.231; 5.I.231.236; 5.I.231.237;
5.I.231.238; 5.I.231.239; 5.I.231.154; 5.I.231.157; 5.I.231.166; 5.I.231.169;
5.I.231.172; 5.I.231.175; 5.I.231.240; 5.I.231.244; 5.I.236.228; 5.I.236.229;
5.I.236.230; 5.I.236.231; 5.I.236.236; 5.I.236.237; 5.I.236.238; 5.I.236.239;
5.I.236.154; 5.I.236.157; 5.I.236.166; 5.I.236.169; 5.I.236.172; 5.I.236.175;
5.I.236.240; 5.I.236.244; 5.I.237.228; 5.I.237.229; 5.I.237.230; 5.I.237.231;
5.I.237.236; 5.I.237.237; 5.I.237.238; 5.I.237.239; 5.I.237.154; 5.I.237.157;
5.I.237.166; 5.I.237.169; 5.I.237.172; 5.I.237.175; 5.I.237.240; 5.I.237.244;
5.I.238.228; 5.I.238.229; 5.I.238.230; 5.I.238.231; 5.I.238.236; 5.I.238.237;
5.I.238.238; 5.I.238.239; 5.I.238.154; 5.I.238.157; 5.I.238.166; 5.I.238.169;
5.I.238.172; 5.I.238.175; 5.I.238.240; 5.I.238.244; 5.I.239.228; 5.I.239.229;
5.I.239.230; 5.I.239.231; 5.I.239.236; 5.I.239.237; 5.I.239.238; 5.I.239.239;
5.I.239.154; 5.I.239.157; 5.I.239.166; 5.I.239.169; 5.I.239.172; 5.I.239.175;
5.I.239.240; 5.I.239.244; 5.I.154.228; 5.I.154.229; 5.I.154.230; 5.I.154.231;
5.I.154.236; 5.I.154.237; 5.I.154.238; 5.I.154.239; 5.I.154.154; 5.I.154.157;
5.I.154.166; 5.I.154.169; 5.I.154.172; 5.I.154.175; 5.I.154.240; 5.I.154.244;
5.I.157.228; 5.I.157.229; 5.I.157.230; 5.I.157.231; 5.I.157.236; 5.I.157.237;
5.I.157.238; 5.I.157.239; 5.I.157.154; 5.I.157.157; 5.I.157.166; 5.I.157.169;
5.I.157.172; 5.I.157.175; 5.I.157.240; 5.I.157.244; 5.I.166.228; 5.I.166.229;
5.I.166.230; 5.I.166.231; 5.I.166.236; 5.I.166.237; 5.I.166.238; 5.I.166.239;
5.I.166.154; 5.I.166.157; 5.I.166.166; 5.I.166.169; 5.I.166.172; 5.I.166.175;
5.I.166.240; 5.I.166.244; 5.I.169.228; 5.I.169.229; 5.I.169.230; 5.I.169.231;
5.I.169.236; 5.I.169.237; 5.I.169.238; 5.I.169.239; 5.I.169.154; 5.I.169.157;
5.I.169.166; 5.I.169.169; 5.I.169.172; 5.I.169.175; 5.I.169.240; 5.I.169.244;
5.I.172.228; 5.I.172.229; 5.I.172.230; 5.I.172.231; 5.I.172.236; 5.I.172.237;
5.I.172.238; 5.I.172.239; 5.I.172.154; 5.I.172.157; 5.I.172.166; 5.I.172.169;
5.I.172.172; 5.I.172.175; 5.I.172.240; 5.I.172.244; 5.I.175.228; 5.I.175.229;
5.I.175.230; 5.I.175.231; 5.I.175.236; 5.I.175.237; 5.I.175.238; 5.I.175.239;
5.I.175.154; 5.I.175.157; 5.I.175.166; 5.I.175.169; 5.I.175.172; 5.I.175.175;
5.I.175.240; 5.I.175.244; 5.I.240.228; 5.I.240.229; 5.I.240.230; 5.I.240.231;
5.I.240.236; 5.I.240.237; 5.I.240.238; 5.I.240.239; 5.I.240.154; 5.I.240.157;
5.I.240.166; 5.I.240.169; 5.I.240.172; 5.I.240.175; 5.I.240.240; 5.I.240.244;
5.I.244.228; 5.I.244.229; 5.I.244.230; 5.I.244.231; 5.I.244.236; 5.I.244.237;
5.I.244.238; 5.I.244.239; 5.I.244.154; 5.I.244.157; 5.I.244.166; 5.I.244.169;
5.I.244.172; 5.I.244.175; 5.I.244.240; 5.I.244.244;

Prodrugs of 5.J

5.J.228.228; 5.J.228.229; 5.J.228.230; 5.J.228.231; 5.J.228.236; 5.J.228.237;
5.J.228.238; 5.J.228.239; 5.J.228.154; 5.J.228.157; 5.J.228.166; 5.J.228.169;
5.J.228.172; 5.J.228.175; 5.J.228.240; 5.J.228.244; 5.J.229.228; 5.J.229.229;
5.J.229.230; 5.J.229.231; 5.J.229.236; 5.J.229.237; 5.J.229.238; 5.J.229.239;
5.J.229.154; 5.J.229.157; 5.J.229.166; 5.J.229.169; 5.J.229.172; 5.J.229.175;
5.J.229.240; 5.J.229.244; 5.J.230.228; 5.J.230.229; 5.J.230.230; 5.J.230.231;
5.J.230.236; 5.J.230.237; 5.J.230.238; 5.J.230.239; 5.J.230.154; 5.J.230.157;
5.J.230.166; 5.J.230.169; 5.J.230.172; 5.J.230.175; 5.J.230.240; 5.J.230.244;
5.J.231.228; 5.J.231.229; 5.J.231.230; 5.J.231.231; 5.J.231.236; 5.J.231.237;
5.J.231.238; 5.J.231.239; 5.J.231.154; 5.J.231.157; 5.J.231.166; 5.J.231.169;
5.J.231.172; 5.J.231.175; 5.J.231.240; 5.J.231.244; 5.J.236.228; 5.J.236.229;
5.J.236.230; 5.J.236.231; 5.J.236.236; 5.J.236.237; 5.J.236.238; 5.J.236.239;
5.J.236.154; 5.J.236.157; 5.J.236.166; 5.J.236.169; 5.J.236.172; 5.J.236.175;
5.J.236.240; 5.J.236.244; 5.J.237.228; 5.J.237.229; 5.J.237.230; 5.J.237.231;
5.J.237.236; 5.J.237.237; 5.J.237.238; 5.J.237.239; 5.J.237.154; 5.J.237.157;
5.J.237.166; 5.J.237.169; 5.J.237.172; 5.J.237.175; 5.J.237.240; 5.J.237.244;
5.J.238.228; 5.J.238.229; 5.J.238.230; 5.J.238.231; 5.J.238.236; 5.J.238.237;
5.J.238.238; 5.J.238.239; 5.J.238.154; 5.J.238.157; 5.J.238.166; 5.J.238.169;
5.J.238.172; 5.J.238.175; 5.J.238.240; 5.J.238.244; 5.J.239.228; 5.J.239.229;
5.J.239.230; 5.J.239.231; 5.J.239.236; 5.J.239.237; 5.J.239.238; 5.J.239.239;
5.J.239.154; 5.J.239.157; 5.J.239.166; 5.J.239.169; 5.J.239.172; 5.J.239.175;
5.J.239.240; 5.J.239.244; 5.J.154.228; 5.J.154.229; 5.J.154.230; 5.J.154.231;
5.J.154.236; 5.J.154.237; 5.J.154.238; 5.J.154.239; 5.J.154.154; 5.J.154.157;
5.J.154.166; 5.J.154.169; 5.J.154.172; 5.J.154.175; 5.J.154.240; 5.J.154.244;
5.J.157.228; 5.J.157.229; 5.J.157.230; 5.J.157.231; 5.J.157.236; 5.J.157.237;
5.J.157.238; 5.J.157.239; 5.J.157.154; 5.J.157.157; 5.J.157.166; 5.J.157.169;
5.J.157.172; 5.J.157.175; 5.J.157.240; 5.J.157.244; 5.J.166.228; 5.J.166.229;
5.J.166.230; 5.J.166.231; 5.J.166.236; 5.J.166.237; 5.J.166.238; 5.J.166.239;
5.J.166.154; 5.J.166.157; 5.J.166.166; 5.J.166.169; 5.J.166.172; 5.J.166.175;
5.J.166.240; 5.J.166.244; 5.J.169.228; 5.J.169.229; 5.J.169.230; 5.J.169.231;
5.J.169.236; 5.J.169.237; 5.J.169.238; 5.J.169.239; 5.J.169.154; 5.J.169.157;
5.J.169.166; 5.J.169.169; 5.J.169.172; 5.J.169.175; 5.J.169.240; 5.J.169.244;

TABLE 100-continued

5.J.172.228; 5.J.172.229; 5.J.172.230; 5.J.172.231; 5.J.172.236; 5.J.172.237;
5.J.172.238; 5.J.172.239; 5.J.172.154; 5.J.172.157; 5.J.172.166; 5.J.172.169;
5.J.172.172; 5.J.172.175; 5.J.172.240; 5.J.172.244; 5.J.175.228; 5.J.175.229;
5.J.175.230; 5.J.175.231; 5.J.175.236; 5.J.175.237; 5.J.175.238; 5.J.175.239;
5.J.175.154; 5.J.175.157; 5.J.175.166; 5.J.175.169; 5.J.175.172; 5.J.175.175;
5.J.175.240; 5.J.175.244; 5.J.240.228; 5.J.240.229; 5.J.240.230; 5.J.240.231;
5.J.240.236; 5.J.240.237; 5.J.240.238; 5.J.240.239; 5.J.240.154; 5.J.240.157;
5.J.240.166; 5.J.240.169; 5.J.240.172; 5.J.240.175; 5.J.240.240; 5.J.240.244;
5.J.244.228; 5.J.244.229; 5.J.244.230; 5.J.244.231; 5.J.244.236; 5.J.244.237;
5.J.244.238; 5.J.244.239; 5.J.244.154; 5.J.244.157; 5.J.244.166; 5.J.244.169;
5.J.244.172; 5.J.244.175; 5.J.244.240; 5.J.244.244;
Prodrugs of 5.L 5.L.228.228; 5.L.228.229; 5.L.228.230; 5.L.228.231; 5.L.228.236;
5.L.228.237; 5.L.228.238; 5.L.228.239; 5.L.228.154; 5.L.228.157; 5.L.228.166;
5.L.228.169; 5.L.228.172; 5.L.228.175; 5.L.228.240; 5.L.228.244; 5.L.229.228;
5.L.229.229; 5.L.229.230; 5.L.229.231; 5.L.229.236; 5.L.229.237; 5.L.229.238;
5.L.229.239; 5.L.229.154; 5.L.229.157; 5.L.229.166; 5.L.229.169; 5.L.229.172;
5.L.229.175; 5.L.229.240; 5.L.229.244; 5.L.230.228; 5.L.230.229; 5.L.230.230;
5.L.230.231; 5.L.230.236; 5.L.230.237; 5.L.230.238; 5.L.230.239; 5.L.230.154;
5.L.230.157; 5.L.230.166; 5.L.230.169; 5.L.230.172; 5.L.230.175; 5.L.230.240;
5.L.230.244; 5.L.231.228; 5.L.231.229; 5.L.231.230; 5.L.231.231; 5.L.231.236;
5.L.231.237; 5.L.231.238; 5.L.231.239; 5.L.231.154; 5.L.231.157; 5.L.231.166;
5.L.231.169; 5.L.231.172; 5.L.231.175; 5.L.231.240; 5.L.231.244; 5.L.236.228;
5.L.236.229; 5.L.236.230; 5.L.236.231; 5.L.236.236; 5.L.236.237; 5.L.236.238;
5.L.236.239; 5.L.236.154; 5.L.236.157; 5.L.236.166; 5.L.236.169; 5.L.236.172;
5.L.236.175; 5.L.236.240; 5.L.236.244; 5.L.237.228; 5.L.237.229; 5.L.237.230;
5.L.237.231; 5.L.237.236; 5.L.237.237; 5.L.237.238; 5.L.237.239; 5.L.237.154;
5.L.237.157; 5.L.237.166; 5.L.237.169; 5.L.237.172; 5.L.237.175; 5.L.237.240;
5.L.237.244; 5.L.238.228; 5.L.238.229; 5.L.238.230; 5.L.238.231; 5.L.238.236;
5.L.238.237; 5.L.238.238; 5.L.238.239; 5.L.238.154; 5.L.238.157; 5.L.238.166;
5.L.238.169; 5.L.238.172; 5.L.238.175; 5.L.238.240; 5.L.238.244; 5.L.239.228;
5.L.239.229; 5.L.239.230; 5.L.239.231; 5.L.239.236; 5.L.239.237; 5.L.239.238;
5.L.239.239; 5.L.239.154; 5.L.239.157; 5.L.239.166; 5.L.239.169; 5.L.239.172;
5.L.239.175; 5.L.239.240; 5.L.239.244; 5.L.154.228; 5.L.154.229; 5.L.154.230;
5.L.154.231; 5.L.154.236; 5.L.154.237; 5.L.154.238; 5.L.154.239; 5.L.154.154;
5.L.154.157; 5.L.154.166; 5.L.154.169; 5.L.154.172; 5.L.154.175; 5.L.154.240;
5.L.154.244; 5.L.157.228; 5.L.157.229; 5.L.157.230; 5.L.157.231; 5.L.157.236;
5.L.157.237; 5.L.157.238; 5.L.157.239; 5.L.157.154; 5.L.157.157; 5.L.157.166;
5.L.157.169; 5.L.157.172; 5.L.157.175; 5.L.157.240; 5.L.157.244; 5.L.166.228;
5.L.166.229; 5.L.166.230; 5.L.166.231; 5.L.166.236; 5.L.166.237; 5.L.166.238;
5.L.166.239; 5.L.166.154; 5.L.166.157; 5.L.166.166; 5.L.166.169; 5.L.166.172;
5.L.166.175; 5.L.166.240; 5.L.166.244; 5.L.169.228; 5.L.169.229; 5.L.169.230;
5.L.169.231; 5.L.169.236; 5.L.169.237; 5.L.169.238; 5.L.169.239; 5.L.169.154;
5.L.169.157; 5.L.169.166; 5.L.169.169; 5.L.169.172; 5.L.169.175; 5.L.169.240;
5.L.169.244; 5.L.172.228; 5.L.172.229; 5.L.172.230; 5.L.172.231; 5.L.172.236;
5.L.172.237; 5.L.172.238; 5.L.172.239; 5.L.172.154; 5.L.172.157; 5.L.172.166;
5.L.172.169; 5.L.172.172; 5.L.172.175; 5.L.172.240; 5.L.172.244; 5.L.175.228;
5.L.175.229; 5.L.175.230; 5.L.175.231; 5.L.175.236; 5.L.175.237; 5.L.175.238;
5.L.175.239; 5.L.175.154; 5.L.175.157; 5.L.175.166; 5.L.175.169; 5.L.175.172;
5.L.175.175; 5.L.175.240; 5.L.175.244; 5.L.240.228; 5.L.240.229; 5.L.240.230;
5.L.240.231; 5.L.240.236; 5.L.240.237; 5.L.240.238; 5.L.240.239; 5.L.240.154;
5.L.240.157; 5.L.240.166; 5.L.240.169; 5.L.240.172; 5.L.240.175; 5.L.240.240;
5.L.240.244; 5.L.244.228; 5.L.244.229; 5.L.244.230; 5.L.244.231; 5.L.244.236;
5.L.244.237; 5.L.244.238; 5.L.244.239; 5.L.244.154; 5.L.244.157; 5.L.244.166;
5.L.244.169; 5.L.244.172; 5.L.244.175; 5.L.244.240; 5.L.244.244;
Prodrugs of 5.O 5.O.228.228; 5.O.228.229; 5.O.228.230; 5.O.228.231; 5.O.228.236;
5.O.228.237; 5.O.228.238; 5.O.228.239; 5.O.228.154; 5.O.228.157;
5.O.228.166; 5.O.228.169; 5.O.228.172; 5.O.228.175; 5.O.228.240;
5.O.228.244; 5.O.229.228; 5.O.229.229; 5.O.229.230; 5.O.229.231;
5.O.229.236; 5.O.229.237; 5.O.229.238; 5.O.229.239; 5.O.229.154;
5.O.229.157; 5.O.229.166; 5.O.229.169; 5.O.229.172; 5.O.229.175;
5.O.229.240; 5.O.229.244; 5.O.230.228; 5.O.230.229; 5.O.230.230;
5.O.230.231; 5.O.230.236; 5.O.230.237; 5.O.230.238; 5.O.230.239;
5.O.230.154; 5.O.230.157; 5.O.230.166; 5.O.230.169; 5.O.230.172;
5.O.230.175; 5.O.230.240; 5.O.230.244; 5.O.231.228; 5.O.231.229;
5.O.231.230; 5.O.231.231; 5.O.231.236; 5.O.231.237; 5.O.231.238;
5.O.231.239; 5.O.231.154; 5.O.231.157; 5.O.231.166; 5.O.231.169;
5.O.231.172; 5.O.231.175; 5.O.231.240; 5.O.231.244; 5.O.236.228;
5.O.236.229; 5.O.236.230; 5.O.236.231; 5.O.236.236; 5.O.236.237;
5.O.236.238; 5.O.236.239; 5.O.236.154; 5.O.236.157; 5.O.236.166;
5.O.236.169; 5.O.236.172; 5.O.236.175; 5.O.236.240; 5.O.236.244;
5.O.237.228; 5.O.237.229; 5.O.237.230; 5.O.237.231; 5.O.237.236;
5.O.237.237; 5.O.237.238; 5.O.237.239; 5.O.237.154; 5.O.237.157;
5.O.237.166; 5.O.237.169; 5.O.237.172; 5.O.237.175; 5.O.237.240;
5.O.237.244; 5.O.238.228; 5.O.238.229; 5.O.238.230; 5.O.238.231;
5.O.238.236; 5.O.238.237; 5.O.238.238; 5.O.238.239; 5.O.238.154;

TABLE 100-continued

5.O.238.157; 5.O.238.166; 5.O.238.169; 5.O.238.172; 5.O.238.175;
5.O.238.240; 5.O.238.244; 5.O.239.228; 5.O.239.229; 5.O.239.230;
5.O.239.231; 5.O.239.236; 5.O.239.237; 5.O.239.238; 5.O.239.239;
5.O.239.154; 5.O.239.157; 5.O.239.166; 5.O.239.169; 5.O.239.172;
5.O.239.175; 5.O.239.240; 5.O.239.244; 5.O.154.228; 5.O.154.229;
5.O.154.230; 5.O.154.231; 5.O.154.236; 5.O.154.237; 5.O.154.238;
5.O.154.239; 5.O.154.154; 5.O.154.157; 5.O.154.166; 5.O.154.169;
5.O.154.172; 5.O.154.175; 5.O.154.240; 5.O.154.244; 5.O.157.228;
5.O.157.229; 5.O.157.230; 5.O.157.231; 5.O.157.236; 5.O.157.237;
5.O.157.238; 5.O.157.239; 5.O.157.154; 5.O.157.157; 5.O.157.166;
5.O.157.169; 5.O.157.172; 5.O.157.175; 5.O.157.240; 5.O.157.244;
5.O.166.228; 5.O.166.229; 5.O.166.230; 5.O.166.231; 5.O.166.236;
5.O.166.237; 5.O.166.238; 5.O.166.239; 5.O.166.154; 5.O.166.157;
5.O.166.166; 5.O.166.169; 5.O.166.172; 5.O.166.175; 5.O.166.240;
5.O.166.244; 5.O.169.228; 5.O.169.229; 5.O.169.230; 5.O.169.231;
5.O.169.236; 5.O.169.237; 5.O.169.238; 5.O.169.239; 5.O.169.154;
5.O.169.157; 5.O.169.166; 5.O.169.169; 5.O.169.172; 5.O.169.175;
5.O.169.240; 5.O.169.244; 5.O.172.228; 5.O.172.229; 5.O.172.230;
5.O.172.231; 5.O.172.236; 5.O.172.237; 5.O.172.238; 5.O.172.239;
5.O.172.154; 5.O.172.157; 5.O.172.166; 5.O.172.169; 5.O.172.172;
5.O.172.175; 5.O.172.240; 5.O.172.244; 5.O.175.228; 5.O.175.229;
5.O.175.230; 5.O.175.231; 5.O.175.236; 5.O.175.237; 5.O.175.238;
5.O.175.239; 5.O.175.154; 5.O.175.157; 5.O.175.166; 5.O.175.169;
5.O.175.172; 5.O.175.175; 5.O.175.240; 5.O.175.244; 5.O.240.228;
5.O.240.229; 5.O.240.230; 5.O.240.231; 5.O.240.236; 5.O.240.237;
5.O.240.238; 5.O.240.239; 5.O.240.154; 5.O.240.157; 5.O.240.166;
5.O.240.169; 5.O.240.172; 5.O.240.175; 5.O.240.240; 5.O.240.244;
5.O.244.228; 5.O.244.229; 5.O.244.230; 5.O.244.231; 5.O.244.236;
5.O.244.237; 5.O.244.238; 5.O.244.239; 5.O.244.154; 5.O.244.157;
5.O.244.166; 5.O.244.169; 5.O.244.172; 5.O.244.175; 5.O.244.240;
5.O.244.244;
Prodrugs of 5.P 5.P.228.228; 5.P.228.229; 5.P.228.230; 5.P.228.231; 5.P.228.236;
5.P.228.237; 5.P.228.238; 5.P.228.239; 5.P.228.154; 5.P.228.157; 5.P.228.166;
5.P.228.169; 5.P.228.172; 5.P.228.175; 5.P.228.240; 5.P.228.244; 5.P.229.228;
5.P.229.229; 5.P.229.230; 5.P.229.231; 5.P.229.236; 5.P.229.237; 5.P.229.238;
5.P.229.239; 5.P.229.154; 5.P.229.157; 5.P.229.166; 5.P.229.169; 5.P.229.172;
5.P.229.175; 5.P.229.240; 5.P.229.244; 5.P.230.228; 5.P.230.229; 5.P.230.230;
5.P.230.231; 5.P.230.236; 5.P.230.237; 5.P.230.238; 5.P.230.239; 5.P.230.154;
5.P.230.157; 5.P.230.166; 5.P.230.169; 5.P.230.172; 5.P.230.175; 5.P.230.240;
5.P.230.244; 5.P.231.228; 5.P.231.229; 5.P.231.230; 5.P.231.231; 5.P.231.236;
5.P.231.237; 5.P.231.238; 5.P.231.239; 5.P.231.154; 5.P.231.157; 5.P.231.166;
5.P.231.169; 5.P.231.172; 5.P.231.175; 5.P.231.240; 5.P.231.244; 5.P.236.228;
5.P.236.229; 5.P.236.230; 5.P.236.231; 5.P.236.236; 5.P.236.237; 5.P.236.238;
5.P.236.239; 5.P.236.154; 5.P.236.157; 5.P.236.166; 5.P.236.169; 5.P.236.172;
5.P.236.175; 5.P.236.240; 5.P.236.244; 5.P.237.228; 5.P.237.229; 5.P.237.230;
5.P.237.231; 5.P.237.236; 5.P.237.237; 5.P.237.238; 5.P.237.239; 5.P.237.154;
5.P.237.157; 5.P.237.166; 5.P.237.169; 5.P.237.172; 5.P.237.175; 5.P.237.240;
5.P.237.244; 5.P.238.228; 5.P.238.229; 5.P.238.230; 5.P.238.231; 5.P.238.236;
5.P.238.237; 5.P.238.238; 5.P.238.229; 5.P.238.154; 5.P.238.157; 5.P.238.166;
5.P.238.169; 5.P.238.172; 5.P.238.175; 5.P.238.240; 5.P.238.244; 5.P.239.228;
5.P.239.229; 5.P.239.230; 5.P.239.231; 5.P.239.236; 5.P.239.237; 5.P.239.238;
5.P.239.239; 5.P.239.154; 5.P.239.157; 5.P.239.166; 5.P.239.169; 5.P.239.172;
5.P.239.175; 5.P.239.240; 5.P.239.244; 5.P.154.228; 5.P.154.229; 5.P.154.230;
5.P.154.231; 5.P.154.236; 5.P.154.237; 5.P.154.238; 5.P.154.239; 5.P.154.154;
5.P.154.157; 5.P.154.166; 5.P.154.169; 5.P.154.172; 5.P.154.175; 5.P.154.240;
5.P.154.244; 5.P.157.228; 5.P.157.229; 5.P.157.230; 5.P.157.231; 5.P.157.236;
5.P.157.237; 5.P.157.238; 5.P.157.239; 5.P.157.154; 5.P.157.157; 5.P.157.166;
5.P.157.169; 5.P.157.172; 5.P.157.175; 5.P.157.240; 5.P.157.244; 5.P.166.228;
5.P.166.229; 5.P.166.230; 5.P.166.231; 5.P.166.236; 5.P.166.237; 5.P.166.238;
5.P.166.239; 5.P.166.154; 5.P.166.157; 5.P.166.166; 5.P.166.169; 5.P.166.172;
5.P.166.175; 5.P.166.240; 5.P.166.244; 5.P.169.228; 5.P.169.229; 5.P.169.230;
5.P.169.231; 5.P.169.236; 5.P.169.237; 5.P.169.238; 5.P.169.239; 5.P.169.154;
5.P.169.157; 5.P.169.166; 5.P.169.169; 5.P.169.172; 5.P.169.175; 5.P.169.240;
5.P.169.244; 5.P.172.228; 5.P.172.229; 5.P.172.230; 5.P.172.231; 5.P.172.236;
5.P.172.237; 5.P.172.238; 5.P.172.239; 5.P.172.154; 5.P.172.157; 5.P.172.166;
5.P.172.169; 5.P.172.172; 5.P.172.175; 5.P.172.240; 5.P.172.244; 5.P.175.228;
5.P.175.229; 5.P.175.230; 5.P.175.231; 5.P.175.236; 5.P.175.237; 5.P.175.238;
5.P.175.239; 5.P.175.154; 5.P.175.157; 5.P.175.166; 5.P.175.169; 5.P.175.172;
5.P.175.175; 5.P.175.240; 5.P.175.244; 5.P.240.228; 5.P.240.229; 5.P.240.230;
5.P.240.231; 5.P.240.236; 5.P.240.237; 5.P.240.238; 5.P.240.239; 5.P.240.154;
5.P.240.157; 5.P.240.166; 5.P.240.169; 5.P.240.172; 5.P.240.175; 5.P.240.240;
5.P.240.244; 5.P.244.228; 5.P.244.229; 5.P.244.230; 5.P.244.231; 5.P.244.236;
5.P.244.237; 5.P.244.238; 5.P.244.239; 5.P.244.154; 5.P.244.157; 5.P.244.166;
5.P.244.169; 5.P.244.172; 5.P.244.175; 5.P.244.240; 5.P.244.244;

TABLE 100-continued

Prodrugs of 5.U

5.U.228.228; 5.U.228.229; 5.U.228.230; 5.U.228.231; 5.U.228.236;
5.U.228.237; 5.U.228.238; 5.U.228.239; 5.U.228.154; 5.U.228.157;
5.U.228.166; 5.U.228.169; 5.U.228.172; 5.U.228.175; 5.U.228.240;
5.U.228.244; 5.U.229.228; 5.U.229.229; 5.U.229.230; 5.U.229.231;
5.U.229.236; 5.U.229.237; 5.U.229.238; 5.U.229.239; 5.U.229.154;
5.U.229.157; 5.U.229.166; 5.U.229.169; 5.U.229.172; 5.U.229.175;
5.U.229.240; 5.U.229.244; 5.U.230.228; 5.U.230.229; 5.U.230.230;
5.U.230.231; 5.U.230.236; 5.U.230.237; 5.U.230.238; 5.U.230.239;
5.U.230.154; 5.U.230.157; 5.U.230.166; 5.U.230.169; 5.U.230.172;
5.U.230.175; 5.U.230.240; 5.U.230.244; 5.U.231.228; 5.U.231.229;
5.U.231.230; 5.U.231.231; 5.U.231.236; 5.U.231.237; 5.U.231.238;
5.U.231.239; 5.U.231.154; 5.U.231.157; 5.U.231.166; 5.U.231.169;
5.U.231.172; 5.U.231.175; 5.U.231.240; 5.U.231.244; 5.U.236.228;
5.U.236.229; 5.U.236.230; 5.U.236.231; 5.U.236.236; 5.U.236.237;
5.U.236.238; 5.U.236.239; 5.U.236.154; 5.U.236.157; 5.U.236.166;
5.U.236.169; 5.U.236.172; 5.U.236.175; 5.U.236.240; 5.U.236.244;
5.U.237.228; 5.U.237.229; 5.U.237.230; 5.U.237.231; 5.U.237.236;
5.U.237.237; 5.U.237.238; 5.U.237.239; 5.U.237.154; 5.U.237.157;
5.U.237.166; 5.U.237.169; 5.U.237.172; 5.U.237.175; 5.U.237.240;
5.U.237.244; 5.U.238.228; 5.U.238.229; 5.U.238.230; 5.U.238.231;
5.U.238.236; 5.U.238.237; 5.U.238.238; 5.U.238.239; 5.U.238.154;
5.U.238.157; 5.U.238.166; 5.U.238.169; 5.U.238.172; 5.U.238.175;
5.U.238.240; 5.U.238.244; 5.U.239.228; 5.U.239.229; 5.U.239.230;
5.U.239.231; 5.U.239.236; 5.U.239.237; 5.U.239.238; 5.U.239.239;
5.U.239.154; 5.U.239.157; 5.U.239.166; 5.U.239.169; 5.U.239.172;
5.U.239.175; 5.U.239.240; 5.U.239.244; 5.U.154.228; 5.U.154.229;
5.U.154.230; 5.U.154.231; 5.U.154.236; 5.U.154.237; 5.U.154.238;
5.U.154.239; 5.U.154.154; 5.U.154.157; 5.U.154.166; 5.U.154.169;
5.U.154.172; 5.U.154.175; 5.U.154.240; 5.U.154.244; 5.U.157.228;
5.U.157.229; 5.U.157.230; 5.U.157.231; 5.U.157.236; 5.U.157.237;
5.U.157.238; 5.U.157.239; 5.U.157.154; 5.U.157.157; 5.U.157.166;
5.U.157.169; 5.U.157.172; 5.U.157.175; 5.U.157.240; 5.U.157.244;
5.U.166.228; 5.U.166.229; 5.U.166.230; 5.U.166.231; 5.U.166.236;
5.U.166.237; 5.U.166.238; 5.U.166.239; 5.U.166.154; 5.U.166.157;
5.U.166.166; 5.U.166.169; 5.U.166.172; 5.U.166.175; 5.U.166.240;
5.U.166.244; 5.U.169.228; 5.U.169.229; 5.U.169.230; 5.U.169.231;
5.U.169.236; 5.U.169.237; 5.U.169.238; 5.U.169.239; 5.U.169.154;
5.U.169.157; 5.U.169.166; 5.U.169.169; 5.U.169.172; 5.U.169.175;
5.U.169.240; 5.U.169.244; 5.U.172.228; 5.U.172.229; 5.U.172.230;
5.U.172.231; 5.U.172.236; 5.U.172.237; 5.U.172.238; 5.U.172.239;
5.U.172.154; 5.U.172.157; 5.U.172.166; 5.U.172.169; 5.U.172.172;
5.U.172.175; 5.U.172.240; 5.U.172.244; 5.U.175.228; 5.U.175.229;
5.U.175.230; 5.U.175.231; 5.U.175.236; 5.U.175.237; 5.U.175.238;
5.U.175.239; 5.U.175.154; 5.U.175.157; 5.U.175.166; 5.U.175.169;
5.U.175.172; 5.U.175.175; 5.U.175.240; 5.U.175.244; 5.U.240.228;
5.U.240.229; 5.U.240.230; 5.U.240.231; 5.U.240.236; 5.U.240.237;
5.U.240.238; 5.U.240.239; 5.U.240.154; 5.U.240.157; 5.U.240.166;
5.U.240.169; 5.U.240.172; 5.U.240.175; 5.U.240.240; 5.U.240.244;
5.U.244.228; 5.U.244.229; 5.U.244.230; 5.U.244.231; 5.U.244.236;
5.U.244.237; 5.U.244.238; 5.U.244.239; 5.U.244.154; 5.U.244.157;
5.U.244.166; 5.U.244.169; 5.U.244.172; 5.U.244.175; 5.U.244.240;
5.U.244.244;

Prodrugs of 5.W

5.W.228.228; 5.W.228.229; 5.W.228.230; 5.W.228.231; 5.W.228.236;
5.W.228.237; 5.W.228.238; 5.W.228.239; 5.W.228.154; 5.W.228.157;
5.W.228.166; 5.W.228.169; 5.W.228.172; 5.W.228.175; 5.W.228.240;
5.W.228.244; 5.W.229.228; 5.W.229.229; 5.W.229.230; 5.W.229.231;
5.W.229.236; 5.W.229.237; 5.W.229.238; 5.W.229.239; 5.W.229.154;
5.W.229.157; 5.W.229.166; 5.W.229.169; 5.W.229.172; 5.W.229.175;
5.W.229.240; 5.W.229.244; 5.W.230.228; 5.W.230.229; 5.W.230.230;
5.W.230.231; 5.W.230.236; 5.W.230.237; 5.W.230.238; 5.W.230.239;
5.W.230.154; 5.W.230.157; 5.W.230.166; 5.W.230.169; 5.W.230.172;
5.W.230.175; 5.W.230.240; 5.W.230.244; 5.W.231.228; 5.W.231.229;
5.W.231.230; 5.W.231.231; 5.W.231.236; 5.W.231.237; 5.W.231.238;
5.W.231.239; 5.W.231.154; 5.W.231.157; 5.W.231.166; 5.W.231.169;
5.W.231.172; 5.W.231.175; 5.W.231.240; 5.W.231.244; 5.W.236.228;
5.W.236.229; 5.W.236.230; 5.W.236.231; 5.W.236.236; 5.W.236.237;
5.W.236.238; 5.W.236.239; 5.W.236.154; 5.W.236.157; 5.W.236.166;
5.W.236.169; 5.W.236.172; 5.W.236.175; 5.W.236.240; 5.W.236.244;
5.W.237.228; 5.W.237.229; 5.W.237.230; 5.W.237.231; 5.W.237.236;
5.W.237.237; 5.W.237.238; 5.W.237.239; 5.W.237.154; 5.W.237.157;
5.W.237.166; 5.W.237.169; 5.W.237.172; 5.W.237.175; 5.W.237.240;
5.W.237.244; 5.W.238.228; 5.W.238.229; 5.W.238.230; 5.W.238.231;
5.W.238.236; 5.W.238.237; 5.W.238.238; 5.W.238.239; 5.W.238.154;
5.W.238.157; 5.W.238.166; 5.W.238.169; 5.W.238.172; 5.W.238.175;
5.W.238.240; 5.W.238.244; 5.W.239.228; 5.W.239.229; 5.W.239.230;

TABLE 100-continued

5.W.239.231; 5.W.239.236; 5.W.239.237; 5.W.239.238; 5.W.239.239;
5.W.239.154; 5.W.239.157; 5.W.239.166; 5.W.239.169; 5.W.239.172;
5.W.239.175; 5.W.239.240; 5.W.239.244; 5.W.154.228; 5.W.154.229;
5.W.154.230; 5.W.154.231; 5.W.154.236; 5.W.154.237; 5.W.154.238;
5.W.154.239; 5.W.154.154; 5.W.154.157; 5.W.154.166; 5.W.154.169;
5.W.154.172; 5.W.154.175; 5.W.154.240; 5.W.154.244; 5.W.157.228;
5.W.157.229; 5.W.157.230; 5.W.157.231; 5.W.157.236; 5.W.157.237;
5.W.157.238; 5.W.157.239; 5.W.157.154; 5.W.157.157; 5.W.157.166;
5.W.157.169; 5.W.157.172; 5.W.157.175; 5.W.157.240; 5.W.157.244;
5.W.166.228; 5.W.166.229; 5.W.166.230; 5.W.166.231; 5.W.166.236;
5.W.166.237; 5.W.166.238; 5.W.166.239; 5.W.166.154; 5.W.166.157;
5.W.166.166; 5.W.166.169; 5.W.166.172; 5.W.166.175; 5.W.166.240;
5.W.166.244; 5.W.169.228; 5.W.169.229; 5.W.169.230; 5.W.169.231;
5.W.169.236; 5.W.169.237; 5.W.169.238; 5.W.169.239; 5.W.169.154;
5.W.169.157; 5.W.169.166; 5.W.169.169; 5.W.169.172; 5.W.169.175;
5.W.169.240; 5.W.169.244; 5.W.172.228; 5.W.172.229; 5.W.172.230;
5.W.172.231; 5.W.172.236; 5.W.172.237; 5.W.172.238; 5.W.172.239;
5.W.172.154; 5.W.172.157; 5.W.172.166; 5.W.172.169; 5.W.172.172;
5.W.172.175; 5.W.172.240; 5.W.172.244; 5.W.175.228; 5.W.175.229;
5.W.175.230; 5.W.175.231; 5.W.175.236; 5.W.175.237; 5.W.175.238;
5.W.175.239; 5.W.175.154; 5.W.175.157; 5.W.175.166; 5.W.175.169;
5.W.175.172; 5.W.175.175; 5.W.175.240; 5.W.175.244; 5.W.240.228;
5.W.240.229; 5.W.240.230; 5.W.240.231; 5.W.240.236; 5.W.240.237;
5.W.240.238; 5.W.240.239; 5.W.240.154; 5.W.240.157; 5.W.240.166;
5.W.240.169; 5.W.240.172; 5.W.240.175; 5.W.240.240; 5.W.240.244;
5.W.244.228; 5.W.244.229; 5.W.244.230; 5.W.244.231; 5.W.244.236;
5.W.244.237; 5.W.244.238; 5.W.244.239; 5.W.244.154; 5.W.244.157;
5.W.244.166; 5.W.244.169; 5.W.244.172; 5.W.244.175; 5.W.244.240; 5.W.244.244;
Prodrugs of 5.Y 5.Y.228.228; 5.Y.228.229; 5.Y.228.230; 5.Y.228.231; 5.Y.228.236;
5.Y.228.237; 5.Y.228.238; 5.Y.228.239; 5.Y.228.154; 5.Y.228.157; 5.Y.228.166;
5.Y.228.169; 5.Y.228.172; 5.Y.228.175; 5.Y.228.240; 5.Y.228.244; 5.Y.229.228;
5.Y.229.229; 5.Y.229.230; 5.Y.229.231; 5.Y.229.236; 5.Y.229.237; 5.Y.229.238;
5.Y.229.239; 5.Y.229.154; 5.Y.229.157; 5.Y.229.166; 5.Y.229.169; 5.Y.229.172;
5.Y.229.175; 5.Y.229.240; 5.Y.229.244; 5.Y.230.228; 5.Y.230.229; 5.Y.230.230;
5.Y.230.231; 5.Y.230.236; 5.Y.230.237; 5.Y.230.238; 5.Y.230.154;
5.Y.230.157; 5.Y.230.166; 5.Y.230.169; 5.Y.230.172; 5.Y.230.175; 5.Y.230.240;
5.Y.230.244; 5.Y.231.228; 5.Y.231.229; 5.Y.231.230; 5.Y.231.231; 5.Y.231.236;
5.Y.231.237; 5.Y.231.238; 5.Y.231.239; 5.Y.231.154; 5.Y.231.157; 5.Y.231.166;
5.Y.231.169; 5.Y.231.172; 5.Y.231.175; 5.Y.231.240; 5.Y.231.244; 5.Y.236.228;
5.Y.236.229; 5.Y.236.230; 5.Y.236.231; 5.Y.236.236; 5.Y.236.237; 5.Y.236.238;
5.Y.236.239; 5.Y.236.154; 5.Y.236.157; 5.Y.236.166; 5.Y.236.169; 5.Y.236.172;
5.Y.236.175; 5.Y.236.240; 5.Y.236.244; 5.Y.237.228; 5.Y.237.229; 5.Y.237.230;
5.Y.237.231; 5.Y.237.236; 5.Y.237.237; 5.Y.237.238; 5.Y.237.239; 5.Y.237.154;
5.Y.237.157; 5.Y.237.166; 5.Y.237.169; 5.Y.237.172; 5.Y.237.175; 5.Y.237.240;
5.Y.237.244; 5.Y.238.228; 5.Y.238.229; 5.Y.238.230; 5.Y.238.231; 5.Y.238.236;
5.Y.238.237; 5.Y.238.238; 5.Y.238.239; 5.Y.238.154; 5.Y.238.157; 5.Y.238.166;
5.Y.238.169; 5.Y.238.172; 5.Y.238.175; 5.Y.238.240; 5.Y.238.244; 5.Y.239.228;
5.Y.239.229; 5.Y.239.230; 5.Y.239.231; 5.Y.239.236; 5.Y.239.237; 5.Y.239.238;
5.Y.239.239; 5.Y.239.154; 5.Y.239.157; 5.Y.239.166; 5.Y.239.169; 5.Y.239.172;
5.Y.239.175; 5.Y.239.240; 5.Y.239.244; 5.Y.154.228; 5.Y.154.229; 5.Y.154.230;
5.Y.154.231; 5.Y.154.236; 5.Y.154.237; 5.Y.154.238; 5.Y.154.239; 5.Y.154.154;
5.Y.154.157; 5.Y.154.166; 5.Y.154.169; 5.Y.154.172; 5.Y.154.175; 5.Y.154.240;
5.Y.154.244; 5.Y.157.228; 5.Y.157.229; 5.Y.157.230; 5.Y.157.231; 5.Y.157.236;
5.Y.157.237; 5.Y.157.238; 5.Y.157.239; 5.Y.157.154; 5.Y.157.157; 5.Y.157.166;
5.Y.157.169; 5.Y.157.172; 5.Y.157.175; 5.Y.157.240; 5.Y.157.244; 5.Y.166.228;
5.Y.166.229; 5.Y.166.230; 5.Y.166.231; 5.Y.166.236; 5.Y.166.237; 5.Y.166.238;
5.Y.166.239; 5.Y.166.154; 5.Y.166.157; 5.Y.166.166; 5.Y.166.169; 5.Y.166.172;
5.Y.166.175; 5.Y.166.240; 5.Y.166.244; 5.Y.169.228; 5.Y.169.229; 5.Y.169.230;
5.Y.169.231; 5.Y.169.236; 5.Y.169.237; 5.Y.169.238; 5.Y.169.239; 5.Y.169.154;
5.Y.169.157; 5.Y.169.166; 5.Y.169.169; 5.Y.169.172; 5.Y.169.175; 5.Y.169.240;
5.Y.169.244; 5.Y.172.228; 5.Y.172.229; 5.Y.172.230; 5.Y.172.231; 5.Y.172.236;
5.Y.172.237; 5.Y.172.238; 5.Y.172.239; 5.Y.172.154; 5.Y.172.157; 5.Y.172.166;
5.Y.172.169; 5.Y.172.172; 5.Y.172.175; 5.Y.172.240; 5.Y.172.244; 5.Y.175.228;
5.Y.175.229; 5.Y.175.230; 5.Y.175.231; 5.Y.175.236; 5.Y.175.237; 5.Y.175.238;
5.Y.175.239; 5.Y.175.154; 5.Y.175.157; 5.Y.175.166; 5.Y.175.169; 5.Y.175.172;
5.Y.175.175; 5.Y.175.240; 5.Y.175.244; 5.Y.240.228; 5.Y.240.229; 5.Y.240.230;
5.Y.240.231; 5.Y.240.236; 5.Y.240.237; 5.Y.240.238; 5.Y.240.239; 5.Y.240.154;
5.Y.240.157; 5.Y.240.166; 5.Y.240.169; 5.Y.240.172; 5.Y.240.175; 5.Y.240.240;
5.Y.240.244; 5.Y.244.228; 5.Y.244.229; 5.Y.244.230; 5.Y.244.231; 5.Y.244.236;
5.Y.244.237; 5.Y.244.238; 5.Y.244.239; 5.Y.244.154; 5.Y.244.157; 5.Y.244.166;
5.Y.244.169; 5.Y.244.172; 5.Y.244.175; 5.Y.244.240; 5.Y.244.244;
Prodrugs of 6.B 6.B.228.228; 6.B.228.229; 6.B.228.230; 6.B.228.231; 6.B.228.236;
6.B.228.237; 6.B.228.238; 6.B.228.239; 6.B.228.154; 6.B.228.157; 6.B.228.166;
6.B.228.169; 6.B.228.172; 6.B.228.175; 6.B.228.240; 6.B.228.244; 6.B.229.228;
6.B.229.229; 6.B.229.230; 6.B.229.231; 6.B.229.236; 6.B.229.237; 6.B.229.238;

TABLE 100-continued

6.B.229.239; 6.B.229.154; 6.B.229.157; 6.B.229.166; 6.B.229.169; 6.B.229.172; 6.B.229.175; 6.B.229.240; 6.B.229.244; 6.B.230.228; 6.B.230.229; 6.B.230.230; 6.B.230.231; 6.B.230.236; 6.B.230.237; 6.B.230.238; 6.B.230.239; 6.B.230.154; 6.B.230.157; 6.B.230.166; 6.B.230.169; 6.B.230.172; 6.B.230.175; 6.B.230.240; 6.B.230.244; 6.B.231.228; 6.B.231.229; 6.B.231.230; 6.B.231.231; 6.B.231.236; 6.B.231.237; 6.B.231.238; 6.B.231.239; 6.B.231.154; 6.B.231.157; 6.B.231.166; 6.B.231.169; 6.B.231.172; 6.B.231.175; 6.B.231.240; 6.B.231.244; 6.B.236.228; 6.B.236.229; 6.B.236.230; 6.B.236.231; 6.B.236.236; 6.B.236.237; 6.B.236.238; 6.B.236.239; 6.B.236.154; 6.B.236.157; 6.B.236.166; 6.B.236.169; 6.B.236.172; 6.B.236.175; 6.B.236.240; 6.B.236.244; 6.B.237.228; 6.B.237.229; 6.B.237.230; 6.B.237.231; 6.B.237.236; 6.B.237.237; 6.B.237.238; 6.B.237.239; 6.B.237.154; 6.B.237.157; 6.B.237.166; 6.B.237.169; 6.B.237.172; 6.B.237.175; 6.B.237.240; 6.B.237.244; 6.B.238.228; 6.B.238.229; 6.B.238.230; 6.B.238.231; 6.B.238.236; 6.B.238.237; 6.B.238.238; 6.B.238.239; 6.B.238.154; 6.B.238.157; 6.B.238.166; 6.B.238.169; 6.B.238.172; 6.B.238.175; 6.B.238.240; 6.B.238.244; 6.B.239.228; 6.B.239.229; 6.B.239.230; 6.B.239.231; 6.B.239.236; 6.B.239.237; 6.B.239.238; 6.B.239.239; 6.B.239.154; 6.B.239.157; 6.B.239.166; 6.B.239.169; 6.B.239.172; 6.B.239.175; 6.B.239.240; 6.B.239.244; 6.B.154.228; 6.B.154.229; 6.B.154.230; 6.B.154.231; 6.B.154.236; 6.B.154.237; 6.B.154.238; 6.B.154.239; 6.B.154.154; 6.B.154.157; 6.B.154.166; 6.B.154.169; 6.B.154.172; 6.B.154.175; 6.B.154.240; 6.B.154.244; 6.B.157.228; 6.B.157.229; 6.B.157.230; 6.B.157.231; 6.B.157.236; 6.B.157.237; 6.B.157.238; 6.B.157.239; 6.B.157.154; 6.B.157.157; 6.B.157.166; 6.B.157.169; 6.B.157.172; 6.B.157.175; 6.B.157.240; 6.B.157.244; 6.B.166.228; 6.B.166.229; 6.B.166.230; 6.B.166.231; 6.B.166.236; 6.B.166.237; 6.B.166.238; 6.B.166.239; 6.B.166.154; 6.B.166.157; 6.B.166.166; 6.B.166.169; 6.B.166.172; 6.B.166.175; 6.B.166.240; 6.B.166.244; 6.B.169.228; 6.B.169.229; 6.B.169.230; 6.B.169.231; 6.B.169.236; 6.B.169.237; 6.B.169.238; 6.B.169.239; 6.B.169.154; 6.B.169.157; 6.B.169.166; 6.B.169.169; 6.B.169.172; 6.B.169.175; 6.B.169.240; 6.B.169.244; 6.B.172.228; 6.B.172.229; 6.B.172.230; 6.B.172.231; 6.B.172.236; 6.B.172.237; 6.B.172.238; 6.B.172.239; 6.B.172.154; 6.B.172.157; 6.B.172.166; 6.B.172.169; 6.B.172.172; 6.B.172.175; 6.B.172.240; 6.B.172.244; 6.B.175.228; 6.B.175.229; 6.B.175.230; 6.B.175.231; 6.B.175.236; 6.B.175.237; 6.B.175.238; 6.B.175.239; 6.B.175.154; 6.B.175.157; 6.B.175.166; 6.B.175.169; 6.B.175.172; 6.B.175.175; 6.B.175.240; 6.B.175.244; 6.B.240.228; 6.B.240.229; 6.B.240.230; 6.B.240.231; 6.B.240.236; 6.B.240.237; 6.B.240.238; 6.B.240.239; 6.B.240.154; 6.B.240.157; 6.B.240.166; 6.B.240.169; 6.B.240.172; 6.B.240.175; 6.B.240.240; 6.B.240.244; 6.B.244.228; 6.B.244.229; 6.B.244.230; 6.B.244.231; 6.B.244.236; 6.B.244.237; 6.B.244.238; 6.B.244.239; 6.B.244.154; 6.B.244.157; 6.B.244.166; 6.B.244.169; 6.B.244.172; 6.B.244.175; 6.B.244.240; 6.B.244.244;
Prodrugs of 6.D 6.D.228.228; 6.D.228.229; 6.D.228.230; 6.D.228.231; 6.D.228.236; 6.D.228.237; 6.D.228.238; 6.D.228.239; 6.D.228.154; 6.D.228.157; 6.D.228.166; 6.D.228.169; 6.D.228.172; 6.D.228.175; 6.D.228.240; 6.D.228.244; 6.D.229.228; 6.D.229.229; 6.D.229.230; 6.D.229.231; 6.D.229.236; 6.D.229.237; 6.D.229.238; 6.D.229.239; 6.D.229.154; 6.D.229.157; 6.D.229.166; 6.D.229.169; 6.D.229.172; 6.D.229.175; 6.D.229.240; 6.D.229.244; 6.D.230.228; 6.D.230.229; 6.D.230.230; 6.D.230.231; 6.D.230.236; 6.D.230.237; 6.D.230.238; 6.D.230.239; 6.D.230.154; 6.D.230.157; 6.D.230.166; 6.D.230.169; 6.D.230.172; 6.D.230.175; 6.D.230.240; 6.D.230.244; 6.D.231.228; 6.D.231.229; 6.D.231.230; 6.D.231.231; 6.D.231.236; 6.D.231.237; 6.D.231.238; 6.D.231.239; 6.D.231.154; 6.D.231.157; 6.D.231.166; 6.D.231.169; 6.D.231.172; 6.D.231.175; 6.D.231.240; 6.D.231.244; 6.D.236.228; 6.D.236.229; 6.D.236.230; 6.D.236.231; 6.D.236.236; 6.D.236.237; 6.D.236.238; 6.D.236.239; 6.D.236.154; 6.D.236.157; 6.D.236.166; 6.D.236.169; 6.D.236.172; 6.D.236.175; 6.D.236.240; 6.D.236.244; 6.D.237.228; 6.D.237.229; 6.D.237.230; 6.D.237.231; 6.D.237.236; 6.D.237.237; 6.D.237.238; 6.D.237.239; 6.D.237.154; 6.D.237.157; 6.D.237.166; 6.D.237.169; 6.D.237.172; 6.D.237.175; 6.D.237.240; 6.D.237.244; 6.D.238.228; 6.D.238.229; 6.D.238.230; 6.D.238.231; 6.D.238.236; 6.D.238.237; 6.D.238.238; 6.D.238.239; 6.D.238.154; 6.D.238.157; 6.D.238.166; 6.D.238.169; 6.D.238.172; 6.D.238.175; 6.D.238.240; 6.D.238.244; 6.D.239.228; 6.D.239.229; 6.D.239.230; 6.D.239.231; 6.D.239.236; 6.D.239.237; 6.D.239.238; 6.D.239.239; 6.D.239.154; 6.D.239.157; 6.D.239.166; 6.D.239.169; 6.D.239.172; 6.D.239.175; 6.D.239.240; 6.D.239.244; 6.D.154.228; 6.D.154.229; 6.D.154.230; 6.D.154.231; 6.D.154.236; 6.D.154.237; 6.D.154.238; 6.D.154.239; 6.D.154.154; 6.D.154.157; 6.D.154.166; 6.D.154.169; 6.D.154.172; 6.D.154.175; 6.D.154.240; 6.D.154.244; 6.D.157.228; 6.D.157.229; 6.D.157.230; 6.D.157.231; 6.D.157.236; 6.D.157.237; 6.D.157.238; 6.D.157.239; 6.D.157.154; 6.D.157.157; 6.D.157.166; 6.D.157.169; 6.D.157.172; 6.D.157.175; 6.D.157.240; 6.D.157.244; 6.D.166.228; 6.D.166.229; 6.D.166.230; 6.D.166.231; 6.D.166.236; 6.D.166.237; 6.D.166.238; 6.D.166.239; 6.D.166.154; 6.D.166.157; 6.D.166.166; 6.D.166.169; 6.D.166.172; 6.D.166.175; 6.D.166.240; 6.D.166.244; 6.D.169.228; 6.D.169.229; 6.D.169.230; 6.D.169.231; 6.D.169.236; 6.D.169.237; 6.D.169.238; 6.D.169.239; 6.D.169.154; 6.D.169.157; 6.D.169.166; 6.D.169.169; 6.D.169.172; 6.D.169.175;

TABLE 100-continued

6.D.169.240; 6.D.169.244; 6.D.172.228; 6.D.172.229; 6.D.172.230;
6.D.172.231; 6.D.172.236; 6.D.172.237; 6.D.172.238; 6.D.172.239;
6.D.172.154; 6.D.172.157; 6.D.172.166; 6.D.172.169; 6.D.172.172;
6.D.172.175; 6.D.172.240; 6.D.172.244; 6.D.175.228; 6.D.175.229;
6.D.175.230; 6.D.175.231; 6.D.175.236; 6.D.175.237; 6.D.175.238;
6.D.175.239; 6.D.175.154; 6.D.175.157; 6.D.175.166; 6.D.175.169;
6.D.175.172; 6.D.175.175; 6.D.175.240; 6.D.175.244; 6.D.240.228;
6.D.240.229; 6.D.240.230; 6.D.240.231; 6.D.240.236; 6.D.240.237;
6.D.240.238; 6.D.240.239; 6.D.240.154; 6.D.240.157; 6.D.240.166;
6.D.240.169; 6.D.240.172; 6.D.240.175; 6.D.240.240; 6.D.240.244;
6.D.244.228; 6.D.244.229; 6.D.244.230; 6.D.244.231; 6.D.244.236;
6.D.244.237; 6.D.244.238; 6.D.244.239; 6.D.244.154; 6.D.244.157;
6.D.244.166; 6.D.244.169; 6.D.244.172; 6.D.244.175; 6.D.244.240;
6.D.244.244;

Prodrugs of 6.E

6.E.228.228; 6.E.228.229; 6.E.228.230; 6.E.228.231; 6.E.228.236;
6.E.228.237; 6.E.228.238; 6.E.228.239; 6.E.228.154; 6.E.228.157; 6.E.228.166;
6.E.228.169; 6.E.228.172; 6.E.228.175; 6.E.228.240; 6.E.228.244; 6.E.229.228;
6.E.229.229; 6.E.229.230; 6.E.229.231; 6.E.229.236; 6.E.229.237; 6.E.229.238;
6.E.229.239; 6.E.229.154; 6.E.229.157; 6.E.229.166; 6.E.229.169; 6.E.229.172;
6.E.229.175; 6.E.229.240; 6.E.229.244; 6.E.230.228; 6.E.230.229; 6.E.230.230;
6.E.230.231; 6.E.230.236; 6.E.230.237; 6.E.230.238; 6.E.230.239; 6.E.230.154;
6.E.230.157; 6.E.230.166; 6.E.230.169; 6.E.230.172; 6.E.230.175; 6.E.230.240;
6.E.230.244; 6.E.231.228; 6.E.231.229; 6.E.231.230; 6.E.231.231; 6.E.231.236;
6.E.231.237; 6.E.231.238; 6.E.231.239; 6.E.231.154; 6.E.231.157; 6.E.231.166;
6.E.231.169; 6.E.231.172; 6.E.231.175; 6.E.231.240; 6.E.231.244; 6.E.236.228;
6.E.236.229; 6.E.236.230; 6.E.236.231; 6.E.236.236; 6.E.236.237; 6.E.236.238;
6.E.236.239; 6.E.236.154; 6.E.236.157; 6.E.236.166; 6.E.236.169; 6.E.236.172;
6.E.236.175; 6.E.236.240; 6.E.236.244; 6.E.237.228; 6.E.237.229; 6.E.237.230;
6.E.237.231; 6.E.237.236; 6.E.237.237; 6.E.237.238; 6.E.237.239; 6.E.237.154;
6.E.237.157; 6.E.237.166; 6.E.237.169; 6.E.237.172; 6.E.237.175; 6.E.237.240;
6.E.237.244; 6.E.238.228; 6.E.238.229; 6.E.238.230; 6.E.238.231; 6.E.238.236;
6.E.238.237; 6.E.238.238; 6.E.238.239; 6.E.238.154; 6.E.238.157; 6.E.238.166;
6.E.238.169; 6.E.238.172; 6.E.238.175; 6.E.238.240; 6.E.238.244; 6.E.239.228;
6.E.239.229; 6.E.239.230; 6.E.239.231; 6.E.239.236; 6.E.239.237; 6.E.239.238;
6.E.239.239; 6.E.239.154; 6.E.239.157; 6.E.239.166; 6.E.239.169; 6.E.239.172;
6.E.239.175; 6.E.239.240; 6.E.239.244; 6.E.154.228; 6.E.154.229; 6.E.154.230;
6.E.154.231; 6.E.154.236; 6.E.154.237; 6.E.154.238; 6.E.154.239; 6.E.154.154;
6.E.154.157; 6.E.154.166; 6.E.154.169; 6.E.154.172; 6.E.154.175; 6.E.154.240;
6.E.154.244; 6.E.157.228; 6.E.157.229; 6.E.157.230; 6.E.157.231; 6.E.157.236;
6.E.157.237; 6.E.157.238; 6.E.157.239; 6.E.157.154; 6.E.157.157; 6.E.157.166;
6.E.157.169; 6.E.157.172; 6.E.157.175; 6.E.157.240; 6.E.157.244; 6.E.166.228;
6.E.166.229; 6.E.166.230; 6.E.166.231; 6.E.166.236; 6.E.166.237; 6.E.166.238;
6.E.166.239; 6.E.166.154; 6.E.166.157; 6.E.166.166; 6.E.166.169; 6.E.166.172;
6.E.166.175; 6.E.166.240; 6.E.166.244; 6.E.169.228; 6.E.169.229; 6.E.169.230;
6.E.169.231; 6.E.169.236; 6.E.169.237; 6.E.169.238; 6.E.169.239; 6.E.169.154;
6.E.169.157; 6.E.169.166; 6.E.169.169; 6.E.169.172; 6.E.169.175; 6.E.169.240;
6.E.169.244; 6.E.172.228; 6.E.172.229; 6.E.172.230; 6.E.172.231; 6.E.172.236;
6.E.172.237; 6.E.172.238; 6.E.172.239; 6.E.172.154; 6.E.172.157; 6.E.172.166;
6.E.172.169; 6.E.172.172; 6.E.172.175; 6.E.172.240; 6.E.172.244; 6.E.175.228;
6.E.175.229; 6.E.175.230; 6.E.175.231; 6.E.175.236; 6.E.175.237; 6.E.175.238;
6.E.175.239; 6.E.175.154; 6.E.175.157; 6.E.175.166; 6.E.175.169; 6.E.175.172;
6.E.175.175; 6.E.175.240; 6.E.175.244; 6.E.240.228; 6.E.240.229; 6.E.240.230;
6.E.240.231; 6.E.240.236; 6.E.240.237; 6.E.240.238; 6.E.240.239; 6.E.240.154;
6.E.240.157; 6.E.240.166; 6.E.240.169; 6.E.240.172; 6.E.240.175; 6.E.240.240;
6.E.240.244; 6.E.244.228; 6.E.244.229; 6.E.244.230; 6.E.244.231; 6.E.244.236;
6.E.244.237; 6.E.244.238; 6.E.244.239; 6.E.244.154; 6.E.244.157; 6.E.244.166;
6.E.244.169; 6.E.244.172; 6.E.244.175; 6.E.244.240; 6.E.244.244;

Prodrugs of 6.G

6.G.228.228; 6.G.228.229; 6.G.228.230; 6.G.228.231; 6.G.228.236;
6.G.228.237; 6.G.228.238; 6.G.228.239; 6.G.228.154; 6.G.228.157;
6.G.228.166; 6.G.228.169; 6.G.228.172; 6.G.228.175; 6.G.228.240;
6.G.228.244; 6.G.229.228; 6.G.229.229; 6.G.229.230; 6.G.229.231;
6.G.229.236; 6.G.229.237; 6.G.229.238; 6.G.229.239; 6.G.229.154;
6.G.229.157; 6.G.229.166; 6.G.229.169; 6.G.229.172; 6.G.229.175;
6.G.229.240; 6.G.229.244; 6.G.230.228; 6.G.230.229; 6.G.230.230;
6.G.230.231; 6.G.230.236; 6.G.230.237; 6.G.230.238; 6.G.230.239;
6.G.230.154; 6.G.230.157; 6.G.230.166; 6.G.230.169; 6.G.230.172;
6.G.230.175; 6.G.230.240; 6.G.230.244; 6.G.231.228; 6.G.231.229;
6.G.231.230; 6.G.231.231; 6.G.231.236; 6.G.231.237; 6.G.231.238;
6.G.231.239; 6.G.231.154; 6.G.231.157; 6.G.231.166; 6.G.231.169;
6.G.231.172; 6.G.231.175; 6.G.231.240; 6.G.231.244; 6.G.236.228;
6.G.236.229; 6.G.236.230; 6.G.236.231; 6.G.236.236; 6.G.236.237;
6.G.236.238; 6.G.236.239; 6.G.236.154; 6.G.236.157; 6.G.236.166;
6.G.236.169; 6.G.236.172; 6.G.236.175; 6.G.236.240; 6.G.236.244;
6.G.237.228; 6.G.237.229; 6.G.237.230; 6.G.237.231; 6.G.237.236;
6.G.237.237; 6.G.237.238; 6.G.237.239; 6.G.237.154; 6.G.237.157;

TABLE 100-continued

6.G.237.166; 6.G.237.169; 6.G.237.172; 6.G.237.175; 6.G.237.240;
6.G.237.244; 6.G.238.228; 6.G.238.229; 6.G.238.230; 6.G.238.231;
6.G.238.236; 6.G.238.237; 6.G.238.238; 6.G.238.239; 6.G.238.154;
6.G.238.157; 6.G.238.166; 6.G.238.169; 6.G.238.172; 6.G.238.175;
6.G.238.240; 6.G.238.244; 6.G.239.228; 6.G.239.229; 6.G.239.230;
6.G.239.231; 6.G.239.236; 6.G.239.237; 6.G.239.238; 6.G.239.239;
6.G.239.154; 6.G.239.157; 6.G.239.166; 6.G.239.169; 6.G.239.172;
6.G.239.175; 6.G.239.240; 6.G.239.244; 6.G.154.228; 6.G.154.229;
6.G.154.230; 6.G.154.231; 6.G.154.236; 6.G.154.237; 6.G.154.238;
6.G.154.239; 6.G.154.154; 6.G.154.157; 6.G.154.166; 6.G.154.169;
6.G.154.172; 6.G.154.175; 6.G.154.240; 6.G.154.244; 6.G.157.228;
6.G.157.229; 6.G.157.230; 6.G.157.231; 6.G.157.236; 6.G.157.237;
6.G.157.238; 6.G.157.239; 6.G.157.154; 6.G.157.157; 6.G.157.166;
6.G.157.169; 6.G.157.172; 6.G.157.175; 6.G.157.240; 6.G.157.244;
6.G.166.228; 6.G.166.229; 6.G.166.230; 6.G.166.231; 6.G.166.236;
6.G.166.237; 6.G.166.238; 6.G.166.239; 6.G.166.154; 6.G.166.157;
6.G.166.166; 6.G.166.169; 6.G.166.172; 6.G.166.175; 6.G.166.240;
6.G.166.244; 6.G.169.228; 6.G.169.229; 6.G.169.230; 6.G.169.231;
6.G.169.236; 6.G.169.237; 6.G.169.238; 6.G.169.239; 6.G.169.154;
6.G.169.157; 6.G.169.166; 6.G.169.169; 6.G.169.172; 6.G.169.175;
6.G.169.240; 6.G.169.244; 6.G.172.228; 6.G.172.229; 6.G.172.230;
6.G.172.231; 6.G.172.236; 6.G.172.237; 6.G.172.238; 6.G.172.239;
6.G.172.154; 6.G.172.157; 6.G.172.166; 6.G.172.169; 6.G.172.172;
6.G.172.175; 6.G.172.240; 6.G.172.244; 6.G.175.228; 6.G.175.229;
6.G.175.230; 6.G.175.231; 6.G.175.236; 6.G.175.237; 6.G.175.238;
6.G.175.239; 6.G.175.154; 6.G.175.157; 6.G.175.166; 6.G.175.169;
6.G.175.172; 6.G.175.175; 6.G.175.240; 6.G.175.244; 6.G.240.228;
6.G.240.229; 6.G.240.230; 6.G.240.231; 6.G.240.236; 6.G.240.237;
6.G.240.238; 6.G.240.239; 6.G.240.154; 6.G.240.157; 6.G.240.166;
6.G.240.169; 6.G.240.172; 6.G.240.175; 6.G.240.240; 6.G.240.244;
6.G.244.228; 6.G.244.229; 6.G.244.230; 6.G.244.231; 6.G.244.236;
6.G.244.237; 6.G.244.238; 6.G.244.239; 6.G.244.154; 6.G.244.157;
6.G.244.166; 6.G.244.169; 6.G.244.172; 6.G.244.175; 6.G.244.240;
6.G.244.244;

Prodrugs of 6.I

6.I.228.228; 6.I.228.229; 6.I.228.230; 6.I.228.231; 6.I.228.236; 6.I.228.237;
6.I.228.238; 6.I.228.239; 6.I.228.154; 6.I.228.157; 6.I.228.166; 6.I.228.169;
6.I.228.172; 6.I.228.175; 6.I.228.240; 6.I.228.244; 6.I.229.228; 6.I.229.229;
6.I.229.230; 6.I.229.231; 6.I.229.236; 6.I.229.237; 6.I.229.238; 6.I.229.239;
6.I.229.154; 6.I.229.157; 6.I.229.166; 6.I.229.169; 6.I.229.172; 6.I.229.175;
6.I.229.240; 6.I.229.244; 6.I.230.228; 6.I.230.229; 6.I.230.230; 6.I.230.231;
6.I.230.236; 6.I.230.237; 6.I.230.238; 6.I.230.239; 6.I.230.154; 6.I.230.157;
6.I.230.166; 6.I.230.169; 6.I.230.172; 6.I.230.175; 6.I.230.240; 6.I.230.244;
6.I.231.228; 6.I.231.229; 6.I.231.230; 6.I.231.231; 6.I.231.236; 6.I.231.237;
6.I.231.238; 6.I.231.239; 6.I.231.154; 6.I.231.157; 6.I.231.166; 6.I.231.169;
6.I.231.172; 6.I.231.175; 6.I.231.240; 6.I.231.244; 6.I.236.228; 6.I.236.229;
6.I.236.230; 6.I.236.231; 6.I.236.236; 6.I.236.237; 6.I.236.238; 6.I.236.239;
6.I.236.154; 6.I.236.157; 6.I.236.166; 6.I.236.169; 6.I.236.172; 6.I.236.175;
6.I.236.240; 6.I.236.244; 6.I.237.228; 6.I.237.229; 6.I.237.230; 6.I.237.231;
6.I.237.236; 6.I.237.237; 6.I.237.238; 6.I.237.239; 6.I.237.154; 6.I.237.157;
6.I.237.166; 6.I.237.169; 6.I.237.172; 6.I.237.175; 6.I.237.240; 6.I.237.244;
6.I.238.228; 6.I.238.229; 6.I.238.230; 6.I.238.231; 6.I.238.236; 6.I.238.237;
6.I.238.238; 6.I.238.239; 6.I.238.154; 6.I.238.157; 6.I.238.166; 6.I.238.169;
6.I.238.172; 6.I.238.175; 6.I.238.240; 6.I.238.244; 6.I.239.228; 6.I.239.229;
6.I.239.230; 6.I.239.231; 6.I.239.236; 6.I.239.237; 6.I.239.238; 6.I.239.239;
6.I.239.154; 6.I.239.157; 6.I.239.166; 6.I.239.169; 6.I.239.172; 6.I.239.175;
6.I.239.240; 6.I.239.244; 6.I.154.228; 6.I.154.229; 6.I.154.230; 6.I.154.231;
6.I.154.236; 6.I.154.237; 6.I.154.238; 6.I.154.239; 6.I.154.154; 6.I.154.157;
6.I.154.166; 6.I.154.169; 6.I.154.172; 6.I.154.175; 6.I.154.240; 6.I.154.244;
6.I.157.228; 6.I.157.229; 6.I.157.230; 6.I.157.231; 6.I.157.236; 6.I.157.237;
6.I.157.238; 6.I.157.239; 6.I.157.154; 6.I.157.157; 6.I.157.166; 6.I.157.169;
6.I.157.172; 6.I.157.175; 6.I.157.240; 6.I.157.244; 6.I.166.228; 6.I.166.229;
6.I.166.230; 6.I.166.231; 6.I.166.236; 6.I.166.237; 6.I.166.238; 6.I.166.239;
6.I.166.154; 6.I.166.157; 6.I.166.166; 6.I.166.169; 6.I.166.172; 6.I.166.175;
6.I.166.240; 6.I.166.244; 6.I.169.228; 6.I.169.229; 6.I.169.230; 6.I.169.231;
6.I.169.236; 6.I.169.237; 6.I.169.238; 6.I.169.239; 6.I.169.154; 6.I.169.157;
6.I.169.166; 6.I.169.169; 6.I.169.172; 6.I.169.175; 6.I.169.240; 6.I.169.244;
6.I.172.228; 6.I.172.229; 6.I.172.230; 6.I.172.231; 6.I.172.236; 6.I.172.237;
6.I.172.238; 6.I.172.239; 6.I.172.154; 6.I.172.157; 6.I.172.166; 6.I.172.169;
6.I.172.172; 6.I.172.175; 6.I.172.240; 6.I.172.244; 6.I.175.228; 6.I.175.229;
6.I.175.230; 6.I.175.231; 6.I.175.236; 6.I.175.237; 6.I.175.238; 6.I.175.239;
6.I.175.154; 6.I.175.157; 6.I.175.166; 6.I.175.169; 6.I.175.172; 6.I.175.175;
6.I.175.240; 6.I.175.244; 6.I.240.228; 6.I.240.229; 6.I.240.230; 6.I.240.231;
6.I.240.236; 6.I.240.237; 6.I.240.238; 6.I.240.239; 6.I.240.154; 6.I.240.157;
6.I.240.166; 6.I.240.169; 6.I.240.172; 6.I.240.175; 6.I.240.240; 6.I.240.244;
6.I.244.228; 6.I.244.229; 6.I.244.230; 6.I.244.231; 6.I.244.236; 6.I.244.237;
6.I.244.238; 6.I.244.239; 6.I.244.154; 6.I.244.157; 6.I.244.166; 6.I.244.169;
6.I.244.172; 6.I.244.175; 6.I.244.240; 6.I.244.244;

TABLE 100-continued

Prodrugs of 6.J

6.J.228.228; 6.J.228.229; 6.J.228.230; 6.J.228.231; 6.J.228.236; 6.J.228.237;
6.J.228.238; 6.J.228.239; 6.J.228.154; 6.J.228.157; 6.J.228.166; 6.J.228.169;
6.J.228.172; 6.J.228.175; 6.J.228.240; 6.J.228.244; 6.J.229.228; 6.J.229.229;
6.J.229.230; 6.J.229.231; 6.J.229.236; 6.J.229.237; 6.J.229.238; 6.J.229.239;
6.J.229.154; 6.J.229.157; 6.J.229.166; 6.J.229.169; 6.J.229.172; 6.J.229.175;
6.J.229.240; 6.J.229.244; 6.J.230.228; 6.J.230.229; 6.J.230.230; 6.J.230.231;
6.J.230.236; 6.J.230.237; 6.J.230.238; 6.J.230.239; 6.J.230.154; 6.J.230.157;
6.J.230.166; 6.J.230.169; 6.J.230.172; 6.J.230.175; 6.J.230.240; 6.J.230.244;
6.J.231.228; 6.J.231.229; 6.J.231.230; 6.J.231.231; 6.J.231.236; 6.J.231.237;
6.J.231.238; 6.J.231.239; 6.J.231.154; 6.J.231.157; 6.J.231.166; 6.J.231.169;
6.J.231.172; 6.J.231.175; 6.J.231.240; 6.J.231.244; 6.J.236.228; 6.J.236.229;
6.J.236.230; 6.J.236.231; 6.J.236.236; 6.J.236.237; 6.J.236.238; 6.J.236.239;
6.J.236.154; 6.J.236.157; 6.J.236.166; 6.J.236.169; 6.J.236.172; 6.J.236.175;
6.J.236.240; 6.J.236.244; 6.J.237.228; 6.J.237.229; 6.J.237.230; 6.J.237.231;
6.J.237.236; 6.J.237.237; 6.J.237.238; 6.J.237.239; 6.J.237.154; 6.J.237.157;
6.J.237.166; 6.J.237.169; 6.J.237.172; 6.J.237.175; 6.J.237.240; 6.J.237.244;
6.J.238.228; 6.J.238.229; 6.J.238.230; 6.J.238.231; 6.J.238.236; 6.J.238.237;
6.J.238.238; 6.J.238.239; 6.J.238.154; 6.J.238.157; 6.J.238.166; 6.J.238.169;
6.J.238.172; 6.J.238.175; 6.J.238.240; 6.J.238.244; 6.J.239.228; 6.J.239.229;
6.J.239.230; 6.J.239.231; 6.J.239.236; 6.J.239.237; 6.J.239.238; 6.J.239.239;
6.J.239.154; 6.J.239.157; 6.J.239.166; 6.J.239.169; 6.J.239.172; 6.J.239.175;
6.J.239.240; 6.J.239.244; 6.J.154.228; 6.J.154.229; 6.J.154.230; 6.J.154.231;
6.J.154.236; 6.J.154.237; 6.J.154.238; 6.J.154.239; 6.J.154.154; 6.J.154.157;
6.J.154.166; 6.J.154.169; 6.J.154.172; 6.J.154.175; 6.J.154.240; 6.J.154.244;
6.J.157.228; 6.J.157.229; 6.J.157.230; 6.J.157.231; 6.J.157.236; 6.J.157.237;
6.J.157.238; 6.J.157.239; 6.J.157.154; 6.J.157.157; 6.J.157.166; 6.J.157.169;
6.J.157.172; 6.J.157.175; 6.J.157.240; 6.J.157.244; 6.J.166.228; 6.J.166.229;
6.J.166.230; 6.J.166.231; 6.J.166.236; 6.J.166.237; 6.J.166.238; 6.J.166.239;
6.J.166.154; 6.J.166.157; 6.J.166.166; 6.J.166.169; 6.J.166.172; 6.J.166.175;
6.J.166.240; 6.J.166.244; 6.J.169.228; 6.J.169.229; 6.J.169.230; 6.J.169.231;
6.J.169.236; 6.J.169.237; 6.J.169.238; 6.J.169.239; 6.J.169.154; 6.J.169.157;
6.J.169.166; 6.J.169.169; 6.J.169.172; 6.J.169.175; 6.J.169.240; 6.J.169.244;
6.J.172.228; 6.J.172.229; 6.J.172.230; 6.J.172.231; 6.J.172.236; 6.J.172.237;
6.J.172.238; 6.J.172.239; 6.J.172.154; 6.J.172.157; 6.J.172.166; 6.J.172.169;
6.J.172.172; 6.J.172.175; 6.J.172.240; 6.J.172.244; 6.J.175.228; 6.J.175.229;
6.J.175.230; 6.J.175.231; 6.J.175.236; 6.J.175.237; 6.J.175.238; 6.J.175.239;
6.J.175.154; 6.J.175.157; 6.J.175.166; 6.J.175.169; 6.J.175.172; 6.J.175.175;
6.J.175.240; 6.J.175.244; 6.J.240.228; 6.J.240.229; 6.J.240.230; 6.J.240.231;
6.J.240.236; 6.J.240.237; 6.J.240.238; 6.J.240.239; 6.J.240.154; 6.J.240.157;
6.J.240.166; 6.J.240.169; 6.J.240.172; 6.J.240.175; 6.J.240.240; 6.J.240.244;
6.J.244.228; 6.J.244.229; 6.J.244.230; 6.J.244.231; 6.J.244.236; 6.J.244.237;
6.J.244.238; 6.J.244.239; 6.J.244.154; 6.J.244.157; 6.J.244.166; 6.J.244.169;
6.J.244.172; 6.J.244.175; 6.J.244.240; 6.J.244.244;

Prodrugs of 6.L

6.L.228.228; 6.L.228.229; 6.L.228.230; 6.L.228.231; 6.L.228.236;
6.L.228.237; 6.L.228.238; 6.L.228.239; 6.L.228.154; 6.L.228.157; 6.L.228.166;
6.L.228.169; 6.L.228.172; 6.L.228.175; 6.L.228.240; 6.L.228.244; 6.L.229.228;
6.L.229.229; 6.L.229.230; 6.L.229.231; 6.L.229.236; 6.L.229.237; 6.L.229.238;
6.L.229.239; 6.L.229.154; 6.L.229.157; 6.L.229.166; 6.L.229.169; 6.L.229.172;
6.L.229.175; 6.L.229.240; 6.L.229.244; 6.L.230.228; 6.L.230.229; 6.L.230.230;
6.L.230.231; 6.L.230.236; 6.L.230.237; 6.L.230.238; 6.L.230.239; 6.L.230.154;
6.L.230.157; 6.L.230.166; 6.L.230.169; 6.L.230.172; 6.L.230.175; 6.L.230.240;
6.L.230.244; 6.L.231.228; 6.L.231.229; 6.L.231.230; 6.L.231.231; 6.L.231.236;
6.L.231.237; 6.L.231.238; 6.L.231.239; 6.L.231.154; 6.L.231.157; 6.L.231.166;
6.L.231.169; 6.L.231.172; 6.L.231.175; 6.L.231.240; 6.L.231.244; 6.L.236.228;
6.L.236.229; 6.L.236.230; 6.L.236.231; 6.L.236.236; 6.L.236.237; 6.L.236.238;
6.L.236.239; 6.L.236.154; 6.L.236.157; 6.L.236.166; 6.L.236.169; 6.L.236.172;
6.L.236.175; 6.L.236.240; 6.L.236.244; 6.L.237.228; 6.L.237.229; 6.L.237.230;
6.L.237.231; 6.L.237.236; 6.L.237.237; 6.L.237.238; 6.L.237.239; 6.L.237.154;
6.L.237.157; 6.L.237.166; 6.L.237.169; 6.L.237.172; 6.L.237.175; 6.L.237.240;
6.L.237.244; 6.L.238.228; 6.L.238.229; 6.L.238.230; 6.L.238.231; 6.L.238.236;
6.L.238.237; 6.L.238.238; 6.L.238.239; 6.L.238.154; 6.L.238.157; 6.L.238.166;
6.L.238.169; 6.L.238.172; 6.L.238.175; 6.L.238.240; 6.L.238.244; 6.L.239.228;
6.L.239.229; 6.L.239.230; 6.L.239.231; 6.L.239.236; 6.L.239.237; 6.L.239.238;
6.L.239.239; 6.L.239.154; 6.L.239.157; 6.L.239.166; 6.L.239.169; 6.L.239.172;
6.L.239.175; 6.L.239.240; 6.L.239.244; 6.L.154.228; 6.L.154.229; 6.L.154.230;
6.L.154.231; 6.L.154.236; 6.L.154.237; 6.L.154.238; 6.L.154.239; 6.L.154.154;
6.L.154.157; 6.L.154.166; 6.L.154.169; 6.L.154.172; 6.L.154.175; 6.L.154.240;
6.L.154.244; 6.L.157.228; 6.L.157.229; 6.L.157.230; 6.L.157.231; 6.L.157.236;
6.L.157.237; 6.L.157.238; 6.L.157.239; 6.L.157.154; 6.L.157.157; 6.L.157.166;
6.L.157.169; 6.L.157.172; 6.L.157.175; 6.L.157.240; 6.L.157.244; 6.L.166.228;
6.L.166.229; 6.L.166.230; 6.L.166.231; 6.L.166.236; 6.L.166.237; 6.L.166.238;
6.L.166.239; 6.L.166.154; 6.L.166.157; 6.L.166.166; 6.L.166.169; 6.L.166.172;
6.L.166.175; 6.L.166.240; 6.L.166.244; 6.L.169.228; 6.L.169.229; 6.L.169.230;
6.L.169.231; 6.L.169.236; 6.L.169.237; 6.L.169.238; 6.L.169.239; 6.L.169.154;
6.L.169.157; 6.L.169.166; 6.L.169.169; 6.L.169.172; 6.L.169.175; 6.L.169.240;

TABLE 100-continued

6.L.169.244; 6.L.172.228; 6.L.172.229; 6.L.172.230; 6.L.172.231; 6.L.172.236;
6.L.172.237; 6.L.172.238; 6.L.172.239; 6.L.172.154; 6.L.172.157; 6.L.172.166;
6.L.172.169; 6.L.172.172; 6.L.172.175; 6.L.172.240; 6.L.172.244; 6.L.175.228;
6.L.175.229; 6.L.175.230; 6.L.175.231; 6.L.175.236; 6.L.175.237; 6.L.175.238;
6.L.175.239; 6.L.175.154; 6.L.175.157; 6.L.175.166; 6.L.175.169; 6.L.175.172;
6.L.175.175; 6.L.175.240; 6.L.175.244; 6.L.240.228; 6.L.240.229; 6.L.240.230;
6.L.240.231; 6.L.240.236; 6.L.240.237; 6.L.240.238; 6.L.240.239; 6.L.240.154;
6.L.240.157; 6.L.240.166; 6.L.240.169; 6.L.240.172; 6.L.240.175; 6.L.240.240;
6.L.240.244; 6.L.244.228; 6.L.244.229; 6.L.244.230; 6.L.244.231; 6.L.244.236;
6.L.244.237; 6.L.244.238; 6.L.244.239; 6.L.244.154; 6.L.244.157; 6.L.244.166;
6.L.244.169; 6.L.244.172; 6.L.244.175; 6.L.244.240; 6.L.244.244;
Prodrugs of 6.O 6.O.228.228; 6.O.228.229; 6.O.228.230; 6.O.228.231; 6.O.228.236;
6.O.228.237; 6.O.228.238; 6.O.228.239; 6.O.228.154; 6.O.228.157;
6.O.228.166; 6.O.228.169; 6.O.228.172; 6.O.228.175; 6.O.228.240;
6.O.228.244; 6.O.229.228; 6.O.229.229; 6.O.229.230; 6.O.229.231;
6.O.229.236; 6.O.229.237; 6.O.229.238; 6.O.229.239; 6.O.229.154;
6.O.229.157; 6.O.229.166; 6.O.229.169; 6.O.229.172; 6.O.229.175;
6.O.229.240; 6.O.229.244; 6.O.230.228; 6.O.230.229; 6.O.230.230;
6.O.230.231; 6.O.230.236; 6.O.230.237; 6.O.230.238; 6.O.230.239;
6.O.230.154; 6.O.230.157; 6.O.230.166; 6.O.230.169; 6.O.230.172;
6.O.230.175; 6.O.230.240; 6.O.230.244; 6.O.231.228; 6.O.231.229;
6.O.231.230; 6.O.231.231; 6.O.231.236; 6.O.231.237; 6.O.231.238;
6.O.231.239; 6.O.231.154; 6.O.231.157; 6.O.231.166; 6.O.231.169;
6.O.231.172; 6.O.231.175; 6.O.231.240; 6.O.231.244; 6.O.236.228;
6.O.236.229; 6.O.236.230; 6.O.236.231; 6.O.236.236; 6.O.236.237;
6.O.236.238; 6.O.236.239; 6.O.236.154; 6.O.236.157; 6.O.236.166;
6.O.236.169; 6.O.236.172; 6.O.236.175; 6.O.236.240; 6.O.236.244;
6.O.237.228; 6.O.237.229; 6.O.237.230; 6.O.237.231; 6.O.237.236;
6.O.237.237; 6.O.237.238; 6.O.237.239; 6.O.237.154; 6.O.237.157;
6.O.237.166; 6.O.237.169; 6.O.237.172; 6.O.237.175; 6.O.237.240;
6.O.237.244; 6.O.238.228; 6.O.238.229; 6.O.238.230; 6.O.238.231;
6.O.238.236; 6.O.238.237; 6.O.238.238; 6.O.238.239; 6.O.238.154;
6.O.238.157; 6.O.238.166; 6.O.238.169; 6.O.238.172; 6.O.238.175;
6.O.238.240; 6.O.238.244; 6.O.239.228; 6.O.239.229; 6.O.239.230;
6.O.239.231; 6.O.239.236; 6.O.239.237; 6.O.239.238; 6.O.239.239;
6.O.239.154; 6.O.239.157; 6.O.239.166; 6.O.239.169; 6.O.239.172;
6.O.239.175; 6.O.239.240; 6.O.239.244; 6.O.154.228; 6.O.154.229;
6.O.154.230; 6.O.154.231; 6.O.154.236; 6.O.154.237; 6.O.154.238;
6.O.154.239; 6.O.154.154; 6.O.154.157; 6.O.154.166; 6.O.154.169;
6.O.154.172; 6.O.154.175; 6.O.154.240; 6.O.154.244; 6.O.157.228;
6.O.157.229; 6.O.157.230; 6.O.157.231; 6.O.157.236; 6.O.157.237;
6.O.157.238; 6.O.157.239; 6.O.157.154; 6.O.157.157; 6.O.157.166;
6.O.157.169; 6.O.157.172; 6.O.157.175; 6.O.157.240; 6.O.157.244;
6.O.166.228; 6.O.166.229; 6.O.166.230; 6.O.166.231; 6.O.166.236;
6.O.166.237; 6.O.166.238; 6.O.166.239; 6.O.166.154; 6.O.166.157;
6.O.166.166; 6.O.166.169; 6.O.166.172; 6.O.166.175; 6.O.166.240;
6.O.166.244; 6.O.169.228; 6.O.169.229; 6.O.169.230; 6.O.169.231;
6.O.169.236; 6.O.169.237; 6.O.169.238; 6.O.169.239; 6.O.169.154;
6.O.169.157; 6.O.169.166; 6.O.169.169; 6.O.169.172; 6.O.169.175;
6.O.169.240; 6.O.169.244; 6.O.172.228; 6.O.172.229; 6.O.172.230;
6.O.172.231; 6.O.172.236; 6.O.172.237; 6.O.172.238; 6.O.172.239;
6.O.172.154; 6.O.172.157; 6.O.172.166; 6.O.172.169; 6.O.172.172;
6.O.172.175; 6.O.172.240; 6.O.172.244; 6.O.175.228; 6.O.175.229;
6.O.175.230; 6.O.175.231; 6.O.175.236; 6.O.175.237; 6.O.175.238;
6.O.175.239; 6.O.175.154; 6.O.175.157; 6.O.175.166; 6.O.175.169;
6.O.175.172; 6.O.175.175; 6.O.175.240; 6.O.175.244; 6.O.240.228;
6.O.240.229; 6.O.240.230; 6.O.240.231; 6.O.240.236; 6.O.240.237;
6.O.240.238; 6.O.240.239; 6.O.240.154; 6.O.240.157; 6.O.240.166;
6.O.240.169; 6.O.240.172; 6.O.240.175; 6.O.240.240; 6.O.240.244;
6.O.244.228; 6.O.244.229; 6.O.244.230; 6.O.244.231; 6.O.244.236;
6.O.244.237; 6.O.244.238; 6.O.244.239; 6.O.244.154; 6.O.244.157;
6.O.244.166; 6.O.244.169; 6.O.244.172; 6.O.244.175; 6.O.244.240;
6.O.244.244;
Prodrugs of 6.P 6.P.228.228; 6.P.228.229; 6.P.228.230; 6.P.228.231; 6.P.228.236;
6.P.228.237; 6.P.228.238; 6.P.228.239; 6.P.228.154; 6.P.228.157; 6.P.228.166;
6.P.228.169; 6.P.228.172; 6.P.228.175; 6.P.228.240; 6.P.228.244; 6.P.229.228;
6.P.229.229; 6.P.229.230; 6.P.229.231; 6.P.229.236; 6.P.229.237; 6.P.229.238;
6.P.229.239; 6.P.229.154; 6.P.229.157; 6.P.229.166; 6.P.229.169; 6.P.229.172;
6.P.229.175; 6.P.229.240; 6.P.229.244; 6.P.230.228; 6.P.230.229; 6.P.230.230;
6.P.230.231; 6.P.230.236; 6.P.230.237; 6.P.230.238; 6.P.230.239; 6.P.230.154;
6.P.230.157; 6.P.230.166; 6.P.230.169; 6.P.230.172; 6.P.230.175; 6.P.230.240;
6.P.230.244; 6.P.231.228; 6.P.231.229; 6.P.231.230; 6.P.231.231; 6.P.231.236;
6.P.231.237; 6.P.231.238; 6.P.231.239; 6.P.231.154; 6.P.231.157; 6.P.231.166;
6.P.231.169; 6.P.231.172; 6.P.231.175; 6.P.231.240; 6.P.231.244; 6.P.236.228;
6.P.236.229; 6.P.236.230; 6.P.236.231; 6.P.236.236; 6.P.236.237; 6.P.236.238;

TABLE 100-continued

6.P.236.239; 6.P.236.154; 6.P.236.157; 6.P.236.166; 6.P.236.169; 6.P.236.172;
6.P.236.175; 6.P.236.240; 6.P.236.244; 6.P.237.228; 6.P.237.229; 6.P.237.230;
6.P.237.231; 6.P.237.236; 6.P.237.237; 6.P.237.238; 6.P.237.239; 6.P.237.154;
6.P.237.157; 6.P.237.166; 6.P.237.169; 6.P.237.172; 6.P.237.175; 6.P.237.240;
6.P.237.244; 6.P.238.228; 6.P.238.229; 6.P.238.230; 6.P.238.231; 6.P.238.236;
6.P.238.237; 6.P.238.238; 6.P.238.239; 6.P.238.154; 6.P.238.157; 6.P.238.166;
6.P.238.169; 6.P.238.172; 6.P.238.175; 6.P.238.240; 6.P.238.244; 6.P.239.228;
6.P.239.229; 6.P.239.230; 6.P.239.231; 6.P.239.236; 6.P.239.237; 6.P.239.238;
6.P.239.239; 6.P.239.154; 6.P.239.157; 6.P.239.166; 6.P.239.169; 6.P.239.172;
6.P.239.175; 6.P.239.240; 6.P.239.244; 6.P.154.228; 6.P.154.229; 6.P.154.230;
6.P.154.231; 6.P.154.236; 6.P.154.237; 6.P.154.238; 6.P.154.239; 6.P.154.154;
6.P.154.157; 6.P.154.166; 6.P.154.169; 6.P.154.172; 6.P.154.175; 6.P.154.240;
6.P.154.244; 6.P.157.228; 6.P.157.229; 6.P.157.230; 6.P.157.231; 6.P.157.236;
6.P.157.237; 6.P.157.238; 6.P.157.239; 6.P.157.154; 6.P.157.157; 6.P.157.166;
6.P.157.169; 6.P.157.172; 6.P.157.175; 6.P.157.240; 6.P.157.244; 6.P.166.228;
6.P.166.229; 6.P.166.230; 6.P.166.231; 6.P.166.236; 6.P.166.237; 6.P.166.238;
6.P.166.239; 6.P.166.154; 6.P.166.157; 6.P.166.166; 6.P.166.169; 6.P.166.172;
6.P.166.175; 6.P.166.240; 6.P.166.244; 6.P.169.228; 6.P.169.229; 6.P.169.230;
6.P.169.231; 6.P.169.236; 6.P.169.237; 6.P.169.238; 6.P.169.239; 6.P.169.154;
6.P.169.157; 6.P.169.166; 6.P.169.169; 6.P.169.172; 6.P.169.175; 6.P.169.240;
6.P.169.244; 6.P.172.228; 6.P.172.229; 6.P.172.230; 6.P.172.231; 6.P.172.236;
6.P.172.237; 6.P.172.238; 6.P.172.239; 6.P.172.154; 6.P.172.157; 6.P.172.166;
6.P.172.169; 6.P.172.172; 6.P.172.175; 6.P.172.240; 6.P.172.244; 6.P.175.228;
6.P.175.229; 6.P.175.230; 6.P.175.231; 6.P.175.236; 6.P.175.237; 6.P.175.238;
6.P.175.239; 6.P.175.154; 6.P.175.157; 6.P.175.166; 6.P.175.169; 6.P.175.172;
6.P.175.175; 6.P.175.240; 6.P.175.244; 6.P.240.228; 6.P.240.229; 6.P.240.230;
6.P.240.231; 6.P.240.236; 6.P.240.237; 6.P.240.238; 6.P.240.239; 6.P.240.154;
6.P.240.157; 6.P.240.166; 6.P.240.169; 6.P.240.172; 6.P.240.175; 6.P.240.240;
6.P.240.244; 6.P.244.228; 6.P.244.229; 6.P.244.230; 6.P.244.231; 6.P.244.236;
6.P.244.237; 6.P.244.238; 6.P.244.239; 6.P.244.154; 6.P.244.157; 6.P.244.166;
6.P.244.169; 6.P.244.172; 6.P.244.175; 6.P.244.240; 6.P.244.244;
Prodrugs of 6.U 6.U.228.228; 6.U.228.229; 6.U.228.230; 6.U.228.231; 6.U.228.236;
6.U.228.237; 6.U.228.238; 6.U.228.239; 6.U.228.154; 6.U.228.157;
6.U.228.166; 6.U.228.169; 6.U.228.172; 6.U.228.175; 6.U.228.240;
6.U.228.244; 6.U.229.228; 6.U.229.229; 6.U.229.230; 6.U.229.231;
6.U.229.236; 6.U.229.237; 6.U.229.238; 6.U.229.239; 6.U.229.154;
6.U.229.157; 6.U.229.166; 6.U.229.169; 6.U.229.172; 6.U.229.175;
6.U.229.240; 6.U.229.244; 6.U.230.228; 6.U.230.229; 6.U.230.230;
6.U.230.231; 6.U.230.236; 6.U.230.237; 6.U.230.238; 6.U.230.239;
6.U.230.154; 6.U.230.157; 6.U.230.166; 6.U.230.169; 6.U.230.172;
6.U.230.175; 6.U.230.240; 6.U.230.244; 6.U.231.228; 6.U.231.229;
6.U.231.230; 6.U.231.231; 6.U.231.236; 6.U.231.237; 6.U.231.238;
6.U.231.239; 6.U.231.154; 6.U.231.157; 6.U.231.166; 6.U.231.169;
6.U.231.172; 6.U.231.175; 6.U.231.240; 6.U.231.244; 6.U.236.228;
6.U.236.229; 6.U.236.230; 6.U.236.231; 6.U.236.236; 6.U.236.237;
6.U.236.238; 6.U.236.239; 6.U.236.154; 6.U.236.157; 6.U.236.166;
6.U.236.169; 6.U.236.172; 6.U.236.175; 6.U.236.240; 6.U.236.244;
6.U.237.228; 6.U.237.229; 6.U.237.230; 6.U.237.231; 6.U.237.236;
6.U.237.237; 6.U.237.238; 6.U.237.239; 6.U.237.154; 6.U.237.157;
6.U.237.166; 6.U.237.169; 6.U.237.172; 6.U.237.175; 6.U.237.240;
6.U.237.244; 6.U.238.228; 6.U.238.229; 6.U.238.230; 6.U.238.231;
6.U.238.236; 6.U.238.237; 6.U.238.238; 6.U.238.239; 6.U.238.154;
6.U.238.157; 6.U.238.166; 6.U.238.169; 6.U.238.172; 6.U.238.175;
6.U.238.240; 6.U.238.244; 6.U.239.228; 6.U.239.229; 6.U.239.230;
6.U.239.231; 6.U.239.236; 6.U.239.237; 6.U.239.238; 6.U.239.239;
6.U.239.154; 6.U.239.157; 6.U.239.166; 6.U.239.169; 6.U.239.172;
6.U.239.175; 6.U.239.240; 6.U.239.244; 6.U.154.228; 6.U.154.229;
6.U.154.230; 6.U.154.231; 6.U.154.236; 6.U.154.237; 6.U.154.238;
6.U.154.239; 6.U.154.154; 6.U.154.157; 6.U.154.166; 6.U.154.169;
6.U.154.172; 6.U.154.175; 6.U.154.240; 6.U.154.244; 6.U.157.228;
6.U.157.229; 6.U.157.230; 6.U.157.231; 6.U.157.236; 6.U.157.237;
6.U.157.238; 6.U.157.239; 6.U.157.154; 6.U.157.157; 6.U.157.166;
6.U.157.169; 6.U.157.172; 6.U.157.175; 6.U.157.240; 6.U.157.244;
6.U.166.228; 6.U.166.229; 6.U.166.230; 6.U.166.231; 6.U.166.236;
6.U.166.237; 6.U.166.238; 6.U.166.239; 6.U.166.154; 6.U.166.157;
6.U.166.166; 6.U.166.169; 6.U.166.172; 6.U.166.175; 6.U.166.240;
6.U.166.244; 6.U.169.228; 6.U.169.229; 6.U.169.230; 6.U.169.231;
6.U.169.236; 6.U.169.237; 6.U.169.238; 6.U.169.239; 6.U.169.154;
6.U.169.157; 6.U.169.166; 6.U.169.169; 6.U.169.172; 6.U.169.175;
6.U.169.240; 6.U.169.244; 6.U.172.228; 6.U.172.229; 6.U.172.230;
6.U.172.231; 6.U.172.236; 6.U.172.237; 6.U.172.238; 6.U.172.239;
6.U.172.154; 6.U.172.157; 6.U.172.166; 6.U.172.169; 6.U.172.172;
6.U.172.175; 6.U.172.240; 6.U.172.244; 6.U.175.228; 6.U.175.229;
6.U.175.230; 6.U.175.231; 6.U.175.236; 6.U.175.237; 6.U.175.238;
6.U.175.239; 6.U.175.154; 6.U.175.157; 6.U.175.166; 6.U.175.169;
6.U.175.172; 6.U.175.175; 6.U.175.240; 6.U.175.244; 6.U.240.228;
6.U.240.229; 6.U.240.230; 6.U.240.231; 6.U.240.236; 6.U.240.237;

TABLE 100-continued

6.U.240.238; 6.U.240.239; 6.U.240.154; 6.U.240.157; 6.U.240.166;
6.U.240.169; 6.U.240.172; 6.U.240.175; 6.U.240.240; 6.U.240.244;
6.U.244.228; 6.U.244.229; 6.U.244.230; 6.U.244.231; 6.U.244.236;
6.U.244.237; 6.U.244.238; 6.U.244.239; 6.U.244.154; 6.U.244.157;
6.U.244.166; 6.U.244.169; 6.U.244.172; 6.U.244.175; 6.U.244.240;
6.U.244.244;
Prodrugs of 6.W 6.W.228.228; 6.W.228.229; 6.W.228.230; 6.W.228.231; 6.W.228.236;
6.W.228.237; 6.W.228.238; 6.W.228.239; 6.W.228.154; 6.W.228.157;
6.W.228.166; 6.W.228.169; 6.W.228.172; 6.W.228.175; 6.W.228.240;
6.W.228.244; 6.W.229.228; 6.W.229.229; 6.W.229.230; 6.W.229.231;
6.W.229.236; 6.W.229.237; 6.W.229.238; 6.W.229.239; 6.W.229.154;
6.W.229.157; 6.W.229.166; 6.W.229.169; 6.W.229.172; 6.W.229.175;
6.W.229.240; 6.W.229.244; 6.W.230.228; 6.W.230.229; 6.W.230.230;
6.W.230.231; 6.W.230.236; 6.W.230.237; 6.W.230.238; 6.W.230.239;
6.W.230.154; 6.W.230.157; 6.W.230.166; 6.W.230.169; 6.W.230.172;
6.W.230.175; 6.W.230.240; 6.W.230.244; 6.W.231.228; 6.W.231.229;
6.W.231.230; 6.W.231.231; 6.W.231.236; 6.W.231.237; 6.W.231.238;
6.W.231.239; 6.W.231.154; 6.W.231.157; 6.W.231.166; 6.W.231.169;
6.W.231.172; 6.W.231.175; 6.W.231.240; 6.W.231.244; 6.W.236.228;
6.W.236.229; 6.W.236.230; 6.W.236.231; 6.W.236.236; 6.W.236.237;
6.W.236.238; 6.W.236.239; 6.W.236.154; 6.W.236.157; 6.W.236.166;
6.W.236.169; 6.W.236.172; 6.W.236.175; 6.W.236.240; 6.W.236.244;
6.W.237.228; 6.W.237.229; 6.W.237.230; 6.W.237.231; 6.W.237.236;
6.W.237.237; 6.W.237.238; 6.W.237.239; 6.W.237.154; 6.W.237.157;
6.W.237.166; 6.W.237.169; 6.W.237.172; 6.W.237.175; 6.W.237.240;
6.W.237.244; 6.W.238.228; 6.W.238.229; 6.W.238.230; 6.W.238.231;
6.W.238.236; 6.W.238.237; 6.W.238.238; 6.W.238.239; 6.W.238.154;
6.W.238.157; 6.W.238.166; 6.W.238.169; 6.W.238.172; 6.W.238.175;
6.W.238.240; 6.W.238.244; 6.W.239.228; 6.W.239.229; 6.W.239.230;
6.W.239.231; 6.W.239.236; 6.W.239.237; 6.W.239.238; 6.W.239.239;
6.W.239.154; 6.W.239.157; 6.W.239.166; 6.W.239.169; 6.W.239.172;
6.W.239.175; 6.W.239.240; 6.W.239.244; 6.W.154.228; 6.W.154.229;
6.W.154.230; 6.W.154.231; 6.W.154.236; 6.W.154.237; 6.W.154.238;
6.W.154.239; 6.W.154.154; 6.W.154.157; 6.W.154.166; 6.W.154.169;
6.W.154.172; 6.W.154.175; 6.W.154.240; 6.W.154.244; 6.W.157.228;
6.W.157.229; 6.W.157.230; 6.W.157.231; 6.W.157.236; 6.W.157.237;
6.W.157.238; 6.W.157.239; 6.W.157.154; 6.W.157.157; 6.W.157.166;
6.W.157.169; 6.W.157.172; 6.W.157.175; 6.W.157.240; 6.W.157.244;
6.W.166.228; 6.W.166.229; 6.W.166.230; 6.W.166.231; 6.W.166.236;
6.W.166.237; 6.W.166.238; 6.W.166.239; 6.W.166.154; 6.W.166.157;
6.W.166.166; 6.W.166.169; 6.W.166.172; 6.W.166.175; 6.W.166.240;
6.W.166.244; 6.W.169.228; 6.W.169.229; 6.W.169.230; 6.W.169.231;
6.W.169.236; 6.W.169.237; 6.W.169.238; 6.W.169.239; 6.W.169.154;
6.W.169.157; 6.W.169.166; 6.W.169.169; 6.W.169.172; 6.W.169.175;
6.W.169.240; 6.W.169.244; 6.W.172.228; 6.W.172.229; 6.W.172.230;
6.W.172.231; 6.W.172.236; 6.W.172.237; 6.W.172.238; 6.W.172.239;
6.W.172.154; 6.W.172.157; 6.W.172.166; 6.W.172.169; 6.W.172.172;
6.W.172.175; 6.W.172.240; 6.W.172.244; 6.W.175.228; 6.W.175.229;
6.W.175.230; 6.W.175.231; 6.W.175.236; 6.W.175.237; 6.W.175.238;
6.W.175.239; 6.W.175.154; 6.W.175.157; 6.W.175.166; 6.W.175.169;
6.W.175.172; 6.W.175.175; 6.W.175.240; 6.W.175.244; 6.W.240.228;
6.W.240.229; 6.W.240.230; 6.W.240.231; 6.W.240.236; 6.W.240.237;
6.W.240.238; 6.W.240.239; 6.W.240.154; 6.W.240.157; 6.W.240.166;
6.W.240.169; 6.W.240.172; 6.W.240.175; 6.W.240.240; 6.W.240.244;
6.W.244.228; 6.W.244.229; 6.W.244.230; 6.W.244.231; 6.W.244.236;
6.W.244.237; 6.W.244.238; 6.W.244.239; 6.W.244.154; 6.W.244.157;
6.W.244.166; 6.W.244.169; 6.W.244.172; 6.W.244.175; 6.W.244.240; 6.W.244.244;
Prodrugs of 6.Y 6.Y.228.228; 6.Y.228.229; 6.Y.228.230; 6.Y.228.231; 6.Y.228.236;
6.Y.228.237; 6.Y.228.238; 6.Y.228.239; 6.Y.228.154; 6.Y.228.157;
6.Y.228.166; 6.Y.228.169; 6.Y.228.172; 6.Y.228.175; 6.Y.228.240;
6.Y.228.244; 6.Y.229.228; 6.Y.229.229; 6.Y.229.230; 6.Y.229.231;
6.Y.229.236; 6.Y.229.237; 6.Y.229.238; 6.Y.229.239; 6.Y.229.154;
6.Y.229.157; 6.Y.229.166; 6.Y.229.169; 6.Y.229.172; 6.Y.229.175;
6.Y.229.240; 6.Y.229.244; 6.Y.230.228; 6.Y.230.229; 6.Y.230.230;
6.Y.230.231; 6.Y.230.236; 6.Y.230.237; 6.Y.230.238; 6.Y.230.239;
6.Y.230.154; 6.Y.230.157; 6.Y.230.166; 6.Y.230.169; 6.Y.230.172;
6.Y.230.175; 6.Y.230.240; 6.Y.230.244; 6.Y.231.228; 6.Y.231.229;
6.Y.231.230; 6.Y.231.231; 6.Y.231.236; 6.Y.231.237; 6.Y.231.238;
6.Y.231.239; 6.Y.231.154; 6.Y.231.157; 6.Y.231.166; 6.Y.231.169;
6.Y.231.172; 6.Y.231.175; 6.Y.231.240; 6.Y.231.244; 6.Y.236.228;
6.Y.236.229; 6.Y.236.230; 6.Y.236.231; 6.Y.236.236; 6.Y.236.237;
6.Y.236.238; 6.Y.236.239; 6.Y.236.154; 6.Y.236.157; 6.Y.236.166;
6.Y.236.169; 6.Y.236.172; 6.Y.236.175; 6.Y.236.240; 6.Y.236.244;
6.Y.237.228; 6.Y.237.229; 6.Y.237.230; 6.Y.237.231; 6.Y.237.236;
6.Y.237.237; 6.Y.237.238; 6.Y.237.239; 6.Y.237.154; 6.Y.237.157;

TABLE 100-continued

6.Y.237.166; 6.Y.237.169; 6.Y.237.172; 6.Y.237.175; 6.Y.237.240;
6.Y.237.244; 6.Y.238.228; 6.Y.238.229; 6.Y.238.230; 6.Y.238.231;
6.Y.238.236; 6.Y.238.237; 6.Y.238.238; 6.Y.238.239; 6.Y.238.154;
6.Y.238.157; 6.Y.238.166; 6.Y.238.169; 6.Y.238.172; 6.Y.238.175;
6.Y.238.240; 6.Y.238.244; 6.Y.239.228; 6.Y.239.229; 6.Y.239.230;
6.Y.239.231; 6.Y.239.236; 6.Y.239.237; 6.Y.239.238; 6.Y.239.239;
6.Y.239.154; 6.Y.239.157; 6.Y.239.166; 6.Y.239.169; 6.Y.239.172;
6.Y.239.175; 6.Y.239.240; 6.Y.239.244; 6.Y.154.228; 6.Y.154.229;
6.Y.154.230; 6.Y.154.231; 6.Y.154.236; 6.Y.154.237; 6.Y.154.238;
6.Y.154.239; 6.Y.154.154; 6.Y.154.157; 6.Y.154.166; 6.Y.154.169;
6.Y.154.172; 6.Y.154.175; 6.Y.154.240; 6.Y.154.244; 6.Y.157.228;
6.Y.157.229; 6.Y.157.230; 6.Y.157.231; 6.Y.157.236; 6.Y.157.237;
6.Y.157.238; 6.Y.157.239; 6.Y.157.154; 6.Y.157.157; 6.Y.157.166;
6.Y.157.169; 6.Y.157.172; 6.Y.157.175; 6.Y.157.240; 6.Y.157.244;
6.Y.166.228; 6.Y.166.229; 6.Y.166.230; 6.Y.166.231; 6.Y.166.236;
6.Y.166.237; 6.Y.166.238; 6.Y.166.239; 6.Y.166.154; 6.Y.166.157;
6.Y.166.166; 6.Y.166.169; 6.Y.166.172; 6.Y.166.175; 6.Y.166.240;
6.Y.166.244; 6.Y.169.228; 6.Y.169.229; 6.Y.169.230; 6.Y.169.231;
6.Y.169.236; 6.Y.169.237; 6.Y.169.238; 6.Y.169.239; 6.Y.169.154;
6.Y.169.157; 6.Y.169.166; 6.Y.169.169; 6.Y.169.172; 6.Y.169.175;
6.Y.169.240; 6.Y.169.244; 6.Y.172.228; 6.Y.172.229; 6.Y.172.230;
6.Y.172.231; 6.Y.172.236; 6.Y.172.237; 6.Y.172.238; 6.Y.172.239;
6.Y.172.154; 6.Y.172.157; 6.Y.172.166; 6.Y.172.169; 6.Y.172.172;
6.Y.172.175; 6.Y.172.240; 6.Y.172.244; 6.Y.175.228; 6.Y.175.229;
6.Y.175.230; 6.Y.175.231; 6.Y.175.236; 6.Y.175.237; 6.Y.175.238;
6.Y.175.239; 6.Y.175.154; 6.Y.175.157; 6.Y.175.166; 6.Y.175.169;
6.Y.175.172; 6.Y.175.175; 6.Y.175.240; 6.Y.175.244; 6.Y.240.228;
6.Y.240.229; 6.Y.240.230; 6.Y.240.231; 6.Y.240.236; 6.Y.240.237;
6.Y.240.238; 6.Y.240.239; 6.Y.240.154; 6.Y.240.157; 6.Y.240.166;
6.Y.240.169; 6.Y.240.172; 6.Y.240.175; 6.Y.240.240; 6.Y.240.244;
6.Y.244.228; 6.Y.244.229; 6.Y.244.230; 6.Y.244.231; 6.Y.244.236;
6.Y.244.237; 6.Y.244.238; 6.Y.244.239; 6.Y.244.154; 6.Y.244.157;
6.Y.244.166; 6.Y.244.169; 6.Y.244.172; 6.Y.244.175; 6.Y.244.240;
6.Y.244.244;

Prodrugs of 7.AH

7.AH.4.157; 7.AH.4.158; 7.AH.4.196; 7.AH.4.223; 7.AH.4.240; 7.AH.4.244;
7.AH.4.243; 7.AH.4.247; 7.AH.5.157; 7.AH.5.158; 7.AH.5.196; 7.AH.5.223;
7.AH.5.240; 7.AH.5.244; 7.AH.5.243; 7.AH.5.247; 7.AH.7.157; 7.AH.7.158;
7.AH.7.196; 7.AH.7.223; 7.AH.7.240; 7.AH.7.244; 7.AH.7.243; 7.AH.7.247;
7.AH.15.157; 7.AH.15.158; 7.AH.15.196; 7.AH.15.223; 7.AH.15.240;
7.AH.15.244; 7.AH.15.243; 7.AH.15.247; 7.AH.16.157; 7.AH.16.158;
7.AH.16.196; 7.AH.16.223; 7.AH.16.240; 7.AH.16.244; 7.AH.16.243;
7.AH.16.247; 7.AH.18.157; 7.AH.18.158; 7.AH.18.196; 7.AH.18.223;
7.AH.18.240; 7.AH.18.244; 7.AH.18.243; 7.AH.18.247; 7.AH.26.157;
7.AH.26.158; 7.AH.26.196; 7.AH.26.223; 7.AH.26.240; 7.AH.26.244;
7.AH.26.243; 7.AH.26.247; 7.AH.27.157; 7.AH.27.158; 7.AH.27.196;
7.AH.27.223; 7.AH.27.240; 7.AH.27.244; 7.AH.27.243; 7.AH.27.247;
7.AH.29.157; 7.AH.29.158; 7.AH.29.196; 7.AH.29.223; 7.AH.29.240;
7.AH.29.244; 7.AH.29.243; 7.AH.29.247; 7.AH.54.157; 7.AH.54.158;
7.AH.54.196; 7.AH.54.223; 7.AH.54.240; 7.AH.54.244; 7.AH.54.243;
7.AH.54.247; 7.AH.55.157; 7.AH.55.158; 7.AH.55.196; 7.AH.55.223;
7.AH.55.240; 7.AH.55.244; 7.AH.55.243; 7.AH.55.247; 7.AH.56.157;
7.AH.56.158; 7.AH.56.196; 7.AH.56.223; 7.AH.56.240; 7.AH.56.244;
7.AH.56.243; 7.AH.56.247; 7.AH.157.157; 7.AH.157.158; 7.AH.157.196;
7.AH.157.223; 7.AH.157.240; 7.AH.157.244; 7.AH.157.243; 7.AH.157.247;
7.AH.196.157; 7.AH.196.158; 7.AH.196.196; 7.AH.196.223; 7.AH.196.240;
7.AH.196.244; 7.AH.196.243; 7.AH.196.247; 7.AH.223.157; 7.AH.223.158;
7.AH.223.196; 7.AH.223.223; 7.AH.223.240; 7.AH.223.244; 7.AH.223.243;
7.AH.223.247; 7.AH.240.157; 7.AH.240.158; 7.AH.240.196; 7.AH.240.223;
7.AH.240.240; 7.AH.240.244; 7.AH.240.243; 7.AH.240.247; 7.AH.244.157;
7.AH.244.158; 7.AH.244.196; 7.AH.244.223; 7.AH.244.240; 7.AH.244.244;
7.AH.244.243; 7.AH.244.247; 7.AH.247.157; 7.AH.247.158; 7.AH.247.196;
7.AH.247.223; 7.AH.247.240; 7.AH.247.244; 7.AH.247.243; 7.AH.247.247;

Prodrugs of 7.AJ

7.AJ.4.157; 7.AJ.4.158; 7.AJ.4.196; 7.AJ.4.223; 7.AJ.4.240; 7.AJ.4.244;
7.AJ.4.243; 7.AJ.4.247; 7.AJ.5.157; 7.AJ.5.158; 7.AJ.5.196; 7.AJ.5.223;
7.AJ.5.240; 7.AJ.5.244; 7.AJ.5.243; 7.AJ.5.247; 7.AJ.7.157; 7.AJ.7.158;
7.AJ.7.196; 7.AJ.7.223; 7.AJ.7.240; 7.AJ.7.244; 7.AJ.7.243; 7.AJ.7.247;
7.AJ.15.157; 7.AJ.15.158; 7.AJ.15.196; 7.AJ.15.223; 7.AJ.15.240; 7.AJ.15.244;
7.AJ.15.243; 7.AJ.15.247; 7.AJ.16.157; 7.AJ.16.158; 7.AJ.16.196; 7.AJ.16.223;
7.AJ.16.240; 7.AJ.16.244; 7.AJ.16.243; 7.AJ.16.247; 7.AJ.18.157; 7.AJ.18.158;
7.AJ.18.196; 7.AJ.18.223; 7.AJ.18.240; 7.AJ.18.244; 7.AJ.18.243; 7.AJ.18.247;
7.AJ.26.157; 7.AJ.26.158; 7.AJ.26.196; 7.AJ.26.223; 7.AJ.26.240; 7.AJ.26.244;
7.AJ.26.243; 7.AJ.26.247; 7.AJ.27.157; 7.AJ.27.158; 7.AJ.27.196; 7.AJ.27.223;
7.AJ.27.240; 7.AJ.27.244; 7.AJ.27.243; 7.AJ.27.247; 7.AJ.29.157; 7.AJ.29.158;
7.AJ.29.196; 7.AJ.29.223; 7.AJ.29.240; 7.AJ.29.244; 7.AJ.29.243; 7.AJ.29.247;
7.AJ.54.157; 7.AJ.54.158; 7.AJ.54.196; 7.AJ.54.223; 7.AJ.54.240; 7.AJ.54.244;

TABLE 100-continued

7.AJ.54.243; 7.AJ.54.247; 7.AJ.55.157; 7.AJ.55.158; 7.AJ.55.196; 7.AJ.55.223;
7.AJ.55.240; 7.AJ.55.244; 7.AJ.55.243; 7.AJ.55.247; 7.AJ.56.157; 7.AJ.56.158;
7.AJ.56.196; 7.AJ.56.223; 7.AJ.56.240; 7.AJ.56.244; 7.AJ.56.243; 7.AJ.56.247;
7.AJ.157.157; 7.AJ.157.158; 7.AJ.157.196; 7.AJ.157.223; 7.AJ.157.240;
7.AJ.157.244; 7.AJ.157.243; 7.AJ.157.247; 7.AJ.196.157; 7.AJ.196.158;
7.AJ.196.196; 7.AJ.196.223; 7.AJ.196.240; 7.AJ.196.244; 7.AJ.196.243;
7.AJ.196.247; 7.AJ.223.157; 7.AJ.223.158; 7.AJ.223.196; 7.AJ.223.223;
7.AJ.223.240; 7.AJ.223.244; 7.AJ.223.243; 7.AJ.223.247; 7.AJ.240.157;
7.AJ.240.158; 7.AJ.240.196; 7.AJ.240.223; 7.AJ.240.240; 7.AJ.240.244;
7.AJ.240.243; 7.AJ.240.247; 7.AJ.244.157; 7.AJ.244.158; 7.AJ.244.196;
7.AJ.244.223; 7.AJ.244.240; 7.AJ.244.244; 7.AJ.244.243; 7.AJ.244.247;
7.AJ.247.157; 7.AJ.247.158; 7.AJ.247.196; 7.AJ.247.223; 7.AJ.247.240;
7.AJ.247.244; 7.AJ.247.243; 7.AJ.247.247;
Prodrugs of 7.AN 7.AN.4.157; 7.AN.4.158; 7.AN.4.196; 7.AN.4.223; 7.AN.4.240; 7.AN.4.244;
7.AN.4.243; 7.AN.4.247; 7.AN.5.157; 7.AN.5.158; 7.AN.5.196; 7.AN.5.223;
7.AN.5.240; 7.AN.5.244; 7.AN.5.243; 7.AN.5.247; 7.AN.7.157; 7.AN.7.158;
7.AN.7.196; 7.AN.7.223; 7.AN.7.240; 7.AN.7.244; 7.AN.7.243; 7.AN.7.247;
7.AN.15.157; 7.AN.15.158; 7.AN.15.196; 7.AN.15.223; 7.AN.15.240;
7.AN.15.244; 7.AN.15.243; 7.AN.15.247; 7.AN.16.157; 7.AN.16.158;
7.AN.16.196; 7.AN.16.223; 7.AN.16.240; 7.AN.16.244; 7.AN.16.243;
7.AN.16.247; 7.AN.18.157; 7.AN.18.158; 7.AN.18.196; 7.AN.18.223;
7.AN.18.240; 7.AN.18.244; 7.AN.18.243; 7.AN.18.247; 7.AN.26.157;
7.AN.26.158; 7.AN.26.196; 7.AN.26.223; 7.AN.26.240; 7.AN.26.244;
7.AN.26.243; 7.AN.26.247; 7.AN.27.157; 7.AN.27.158; 7.AN.27.196;
7.AN.27.223; 7.AN.27.240; 7.AN.27.244; 7.AN.27.243; 7.AN.27.247;
7.AN.29.157; 7.AN.29.158; 7.AN.29.196; 7.AN.29.223; 7.AN.29.240;
7.AN.29.244; 7.AN.29.243; 7.AN.29.247; 7.AN.54.157; 7.AN.54.158;
7.AN.54.196; 7.AN.54.223; 7.AN.54.240; 7.AN.54.244; 7.AN.54.243;
7.AN.54.247; 7.AN.55.157; 7.AN.55.158; 7.AN.55.196; 7.AN.55.223;
7.AN.55.240; 7.AN.55.244; 7.AN.55.243; 7.AN.55.247; 7.AN.56.157;
7.AN.56.158; 7.AN.56.196; 7.AN.56.223; 7.AN.56.240; 7.AN.56.244;
7.AN.56.243; 7.AN.56.247; 7.AN.157.157; 7.AN.157.158; 7.AN.157.196;
7.AN.157.223; 7.AN.157.240; 7.AN.157.244; 7.AN.157.243; 7.AN.157.247;
7.AN.196.157; 7.AN.196.158; 7.AN.196.196; 7.AN.196.223; 7.AN.196.240;
7.AN.196.244; 7.AN.196.243; 7.AN.196.247; 7.AN.223.157; 7.AN.223.158;
7.AN.223.196; 7.AN.223.223; 7.AN.223.240; 7.AN.223.244; 7.AN.223.243;
7.AN.223.247; 7.AN.240.157; 7.AN.240.158; 7.AN.240.196; 7.AN.240.223;
7.AN.240.240; 7.AN.240.244; 7.AN.240.243; 7.AN.240.247; 7.AN.244.157;
7.AN.244.158; 7.AN.244.196; 7.AN.244.223; 7.AN.244.240; 7.AN.244.244;
7.AN.244.243; 7.AN.244.247; 7.AN.247.157; 7.AN.247.158; 7.AN.247.196;
7.AN.247.223; 7.AN.247.240; 7.AN.247.244; 7.AN.247.243; 7.AN.247.247;
Prodrugs of 7.AP 7.AP.4.157; 7.AP.4.158; 7.AP.4.196; 7.AP.4.223; 7.AP.4.240; 7.AP.4.244;
7.AP.4.243; 7.AP.4.247; 7.AP.5.157; 7.AP.5.158; 7.AP.5.196; 7.AP.5.223;
7.AP.5.240; 7.AP.5.244; 7.AP.5.243; 7.AP.5.247; 7.AP.7.157; 7.AP.7.158;
7.AP.7.196; 7.AP.7.223; 7.AP.7.240; 7.AP.7.244; 7.AP.7.243; 7.AP.7.247;
7.AP.15.157; 7.AP.15.158; 7.AP.15.196; 7.AP.15.223; 7.AP.15.240;
7.AP.15.244; 7.AP.15.243; 7.AP.15.247; 7.AP.16.157; 7.AP.16.158;
7.AP.16.196; 7.AP.16.223; 7.AP.16.240; 7.AP.16.244; 7.AP.16.243;
7.AP.16.247; 7.AP.18.157; 7.AP.18.158; 7.AP.18.196; 7.AP.18.223;
7.AP.18.240; 7.AP.18.244; 7.AP.18.243; 7.AP.18.247; 7.AP.26.157;
7.AP.26.158; 7.AP.26.196; 7.AP.26.223; 7.AP.26.240; 7.AP.26.244;
7.AP.26.243; 7.AP.26.247; 7.AP.27.157; 7.AP.27.158; 7.AP.27.196;
7.AP.27.223; 7.AP.27.240; 7.AP.27.244; 7.AP.27.243; 7.AP.27.247;
7.AP.29.157; 7.AP.29.158; 7.AP.29.196; 7.AP.29.223; 7.AP.29.240;
7.AP.29.244; 7.AP.29.243; 7.AP.29.247; 7.AP.54.157; 7.AP.54.158;
7.AP.54.196; 7.AP.54.223; 7.AP.54.240; 7.AP.54.244; 7.AP.54.243;
7.AP.54.247; 7.AP.55.157; 7.AP.55.158; 7.AP.55.196; 7.AP.55.223;
7.AP.55.240; 7.AP.55.244; 7.AP.55.243; 7.AP.55.247; 7.AP.56.157;
7.AP.56.158; 7.AP.56.196; 7.AP.56.223; 7.AP.56.240; 7.AP.56.244;
7.AP.56.243; 7.AP.56.247; 7.AP.157.157; 7.AP.157.158; 7.AP.157.196;
7.AP.157.223; 7.AP.157.240; 7.AP.157.244; 7.AP.157.243; 7.AP.157.247;
7.AP.196.157; 7.AP.196.158; 7.AP.196.196; 7.AP.196.223; 7.AP.196.240;
7.AP.196.244; 7.AP.196.243; 7.AP.196.247; 7.AP.223.157; 7.AP.223.158;
7.AP.223.196; 7.AP.223.223; 7.AP.223.240; 7.AP.223.244; 7.AP.223.243;
7.AP.223.247; 7.AP.240.157; 7.AP.240.158; 7.AP.240.196; 7.AP.240.223;
7.AP.240.240; 7.AP.240.244; 7.AP.240.243; 7.AP.240.247; 7.AP.244.157;
7.AP.244.158; 7.AP.244.196; 7.AP.244.223; 7.AP.244.240; 7.AP.244.244;
7.AP.244.243; 7.AP.244.247; 7.AP.247.157; 7.AP.247.158; 7.AP.247.196;
7.AP.247.223; 7.AP.247.240; 7.AP.247.244; 7.AP.247.243; 7.AP.247.247;
Prodrugs of 7.AZ 7.AZ.4.157; 7.AZ.4.158; 7.AZ.4.196; 7.AZ.4.223; 7.AZ.4.240; 7.AZ.4.244;
7.AZ.4.243; 7.AZ.4.247; 7.AZ.5.157; 7.AZ.5.158; 7.AZ.5.196; 7.AZ.5.223;
7.AZ.5.240; 7.AZ.5.244; 7.AZ.5.243; 7.AZ.5.247; 7.AZ.7.157; 7.AZ.7.158;
7.AZ.7.196; 7.AZ.7.223; 7.AZ.7.240; 7.AZ.7.244; 7.AZ.7.243; 7.AZ.7.247;

TABLE 100-continued

7.AZ.15.157; 7.AZ.15.158; 7.AZ.15.196; 7.AZ.15.223; 7.AZ.15.240;
7.AZ.15.244; 7.AZ.15.243; 7.AZ.15.247; 7.AZ.16.157; 7.AZ.16.158;
7.AZ.16.196; 7.AZ.16.223; 7.AZ.16.240; 7.AZ.16.244; 7.AZ.16.243;
7.AZ.16.247; 7.AZ.18.157; 7.AZ.18.158; 7.AZ.18.196; 7.AZ.18.223;
7.AZ.18.240; 7.AZ.18.244; 7.AZ.18.243; 7.AZ.18.247; 7.AZ.26.157;
7.AZ.26.158; 7.AZ.26.196; 7.AZ.26.223; 7.AZ.26.240; 7.AZ.26.244;
7.AZ.26.243; 7.AZ.26.247; 7.AZ.27.157; 7.AZ.27.158; 7.AZ.27.196;
7.AZ.27.223; 7.AZ.27.240; 7.AZ.27.244; 7.AZ.27.243; 7.AZ.27.247;
7.AZ.29.157; 7.AZ.29.158; 7.AZ.29.196; 7.AZ.29.223; 7.AZ.29.240;
7.AZ.29.244; 7.AZ.29.243; 7.AZ.29.247; 7.AZ.54.157; 7.AZ.54.158;
7.AZ.54.196; 7.AZ.54.223; 7.AZ.54.240; 7.AZ.54.244; 7.AZ.54.243;
7.AZ.54.247; 7.AZ.55.157; 7.AZ.55.158; 7.AZ.55.196; 7.AZ.55.223;
7.AZ.55.240; 7.AZ.55.244; 7.AZ.55.243; 7.AZ.55.247; 7.AZ.56.157;
7.AZ.56.158; 7.AZ.56.196; 7.AZ.56.223; 7.AZ.56.240; 7.AZ.56.244;
7.AZ.56.243; 7.AZ.56.247; 7.AZ.157.157; 7.AZ.157.158; 7.AZ.157.196;
7.AZ.157.223; 7.AZ.157.240; 7.AZ.157.244; 7.AZ.157.243; 7.AZ.157.247;
7.AZ.196.157; 7.AZ.196.158; 7.AZ.196.196; 7.AZ.196.223; 7.AZ.196.240;
7.AZ.196.244; 7.AZ.196.243; 7.AZ.196.247; 7.AZ.223.157; 7.AZ.223.158;
7.AZ.223.196; 7.AZ.223.223; 7.AZ.223.240; 7.AZ.223.244; 7.AZ.223.243;
7.AZ.223.247; 7.AZ.240.157; 7.AZ.240.158; 7.AZ.240.196; 7.AZ.240.223;
7.AZ.240.240; 7.AZ.240.244; 7.AZ.240.243; 7.AZ.240.247; 7.AZ.244.157;
7.AZ.244.158; 7.AZ.244.196; 7.AZ.244.223; 7.AZ.244.240; 7.AZ.244.244;
7.AZ.244.243; 7.AZ.244.247; 7.AZ.247.157; 7.AZ.247.158; 7.AZ.247.196;
7.AZ.247.223; 7.AZ.247.240; 7.AZ.247.244; 7.AZ.247.243; 7.AZ.247.247;
Prodrugs of 7.BF 7.BF.4.157; 7.BF.4.158; 7.BF.4.196; 7.BF.4.223; 7.BF.4.240; 7.BF.4.244;
7.BF.4.243; 7.BF.4.247; 7.BF.5.157; 7.BF.5.158; 7.BF.5.196; 7.BF.5.223;
7.BF.5.240; 7.BF.5.244; 7.BF.5.243; 7.BF.5.247; 7.BF.7.157; 7.BF.7.158;
7.BF.7.196; 7.BF.7.223; 7.BF.7.240; 7.BF.7.244; 7.BF.7.243; 7.BF.7.247;
7.BF.15.157; 7.BF.15.158; 7.BF.15.196; 7.BF.15.223; 7.BF.15.240;
7.BF.15.244; 7.BF.15.243; 7.BF.15.247; 7.BF.16.157; 7.BF.16.158;
7.BF.16.196; 7.BF.16.223; 7.BF.16.240; 7.BF.16.244; 7.BF.16.243;
7.BF.16.247; 7.BF.18.157; 7.BF.18.158; 7.BF.18.196; 7.BF.18.223;
7.BF.18.240; 7.BF.18.244; 7.BF.18.243; 7.BF.18.247; 7.BF.26.157;
7.BF.26.158; 7.BF.26.196; 7.BF.26.223; 7.BF.26.240; 7.BF.26.244;
7.BF.26.243; 7.BF.26.247; 7.BF.27.157; 7.BF.27.158; 7.BF.27.196;
7.BF.27.223; 7.BF.27.240; 7.BF.27.244; 7.BF.27.243; 7.BF.27.247;
7.BF.29.157; 7.BF.29.158; 7.BF.29.196; 7.BF.29.223; 7.BF.29.240;
7.BF.29.244; 7.BF.29.243; 7.BF.29.247; 7.BF.54.157; 7.BF.54.158;
7.BF.54.196; 7.BF.54.223; 7.BF.54.240; 7.BF.54.244; 7.BF.54.243;
7.BF.54.247; 7.BF.55.157; 7.BF.55.158; 7.BF.55.196; 7.BF.55.223;
7.BF.55.240; 7.BF.55.244; 7.BF.55.243; 7.BF.55.247; 7.BF.56.157;
7.BF.56.158; 7.BF.56.196; 7.BF.56.223; 7.BF.56.240; 7.BF.56.244;
7.BF.56.243; 7.BF.56.247; 7.BF.157.157; 7.BF.157.158; 7.BF.157.196;
7.BF.157.223; 7.BF.157.240; 7.BF.157.244; 7.BF.157.243; 7.BF.157.247;
7.BF.196.157; 7.BF.196.158; 7.BF.196.196; 7.BF.196.223; 7.BF.196.240;
7.BF.196.244; 7.BF.196.243; 7.BF.196.247; 7.BF.223.157; 7.BF.223.158;
7.BF.223.196; 7.BF.223.223; 7.BF.223.240; 7.BF.223.244; 7.BF.223.243;
7.BF.223.247; 7.BF.240.157; 7.BF.240.158; 7.BF.240.196; 7.BF.240.223;
7.BF.240.240; 7.BF.240.244; 7.BF.240.243; 7.BF.240.247; 7.BF.244.157;
7.BF.244.158; 7.BF.244.196; 7.BF.244.223; 7.BF.244.240; 7.BF.244.244;
7.BF.244.243; 7.BF.244.247; 7.BF.247.157; 7.BF.247.158; 7.BF.247.196;
7.BF.247.223; 7.BF.247.240; 7.BF.247.244; 7.BF.247.243; 7.BF.247.247;
Prodrugs of 7.CI 7.CI.4.157; 7.CI.4.158; 7.CI.4.196; 7.CI.4.223; 7.CI.4.240; 7.CI.4.244;
7.CI.4.243; 7.CI.4.247; 7.CI.5.157; 7.CI.5.158; 7.CI.5.196; 7.CI.5.223;
7.CI.5.240; 7.CI.5.244; 7.CI.5.243; 7.CI.5.247; 7.CI.7.157; 7.CI.7.158;
7.CI.7.196; 7.CI.7.223; 7.CI.7.240; 7.CI.7.244; 7.CI.7.243; 7.CI.7.247;
7.CI.15.157; 7.CI.15.158; 7.CI.15.196; 7.CI.15.223; 7.CI.15.240; 7.CI.15.244;
7.CI.15.243; 7.CI.15.247; 7.CI.16.157; 7.CI.16.158; 7.CI.16.196; 7.CI.16.223;
7.CI.16.240; 7.CI.16.244; 7.CI.16.243; 7.CI.16.247; 7.CI.18.157; 7.CI.18.158;
7.CI.18.196; 7.CI.18.223; 7.CI.18.240; 7.CI.18.244; 7.CI.18.243; 7.CI.18.247;
7.CI.26.157; 7.CI.26.158; 7.CI.26.196; 7.CI.26.223; 7.CI.26.240; 7.CI.26.244;
7.CI.26.243; 7.CI.26.247; 7.CI.27.157; 7.CI.27.158; 7.CI.27.196; 7.CI.27.223;
7.CI.27.240; 7.CI.27.244; 7.CI.27.243; 7.CI.27.247; 7.CI.29.157; 7.CI.29.158;
7.CI.29.196; 7.CI.29.223; 7.CI.29.240; 7.CI.29.244; 7.CI.29.243; 7.CI.29.247;
7.CI.54.157; 7.CI.54.158; 7.CI.54.196; 7.CI.54.223; 7.CI.54.240; 7.CI.54.244;
7.CI.54.243; 7.CI.54.247; 7.CI.55.157; 7.CI.55.158; 7.CI.55.196; 7.CI.55.223;
7.CI.55.240; 7.CI.55.244; 7.CI.55.243; 7.CI.55.247; 7.CI.56.157; 7.CI.56.158;
7.CI.56.196; 7.CI.56.223; 7.CI.56.240; 7.CI.56.244; 7.CI.56.243; 7.CI.56.247;
7.CI.157.157; 7.CI.157.158; 7.CI.157.196; 7.CI.157.223; 7.CI.157.240;
7.CI.157.244; 7.CI.157.243; 7.CI.157.247; 7.CI.196.157; 7.CI.196.158;
7.CI.196.196; 7.CI.196.223; 7.CI.196.240; 7.CI.196.244; 7.CI.196.243;
7.CI.196.247; 7.CI.223.157; 7.CI.223.158; 7.CI.223.196; 7.CI.223.223;
7.CI.223.240; 7.CI.223.244; 7.CI.223.243; 7.CI.223.247; 7.CI.240.157;
7.CI.240.158; 7.CI.240.196; 7.CI.240.223; 7.CI.240.240; 7.CI.240.244;
7.CI.240.243; 7.CI.240.247; 7.CI.244.157; 7.CI.244.158; 7.CI.244.196;

TABLE 100-continued

7.CI.244.223; 7.CI.244.240; 7.CI.244.244; 7.CI.244.243; 7.CI.244.247;
7.CI.247.157; 7.CI.247.158; 7.CI.247.196; 7.CI.247.223; 7.CI.247.240;
7.CI.247.244; 7.CI.247.243; 7.CI.247.247;
Prodrugs of 7.CO 7.CO.4.157; 7.CO.4.158; 7.CO.4.196; 7.CO.4.223; 7.CO.4.240; 7.CO.4.244;
7.CO.4.243; 7.CO.4.247; 7.CO.5.157; 7.CO.5.158; 7.CO.5.196; 7.CO.5.223;
7.CO.5.240; 7.CO.5.244; 7.CO.5.243; 7.CO.5.247; 7.CO.7.157; 7.CO.7.158;
7.CO.7.196; 7.CO.7.223; 7.CO.7.240; 7.CO.7.244; 7.CO.7.243; 7.CO.7.247;
7.CO.15.157; 7.CO.15.158; 7.CO.15.196; 7.CO.15.223; 7.CO.15.240;
7.CO.15.244; 7.CO.15.243; 7.CO.15.247; 7.CO.16.157; 7.CO.16.158;
7.CO.16.196; 7.CO.16.223; 7.CO.16.240; 7.CO.16.244; 7.CO.16.243;
7.CO.16.247; 7.CO.18.157; 7.CO.18.158; 7.CO.18.196; 7.CO.18.223;
7.CO.18.240; 7.CO.18.244; 7.CO.18.243; 7.CO.18.247; 7.CO.26.157;
7.CO.26.158; 7.CO.26.196; 7.CO.26.223; 7.CO.26.240; 7.CO.26.244;
7.CO.26.243; 7.CO.26.247; 7.CO.27.157; 7.CO.27.158; 7.CO.27.196;
7.CO.27.223; 7.CO.27.240; 7.CO.27.244; 7.CO.27.243; 7.CO.27.247;
7.CO.29.157; 7.CO.29.158; 7.CO.29.196; 7.CO.29.223; 7.CO.29.240;
7.CO.29.244; 7.CO.29.243; 7.CO.29.247; 7.CO.54.157; 7.CO.54.158;
7.CO.54.196; 7.CO.54.223; 7.CO.54.240; 7.CO.54.244; 7.CO.54.243;
7.CO.54.247; 7.CO.55.157; 7.CO.55.158; 7.CO.55.196; 7.CO.55.223;
7.CO.55.240; 7.CO.55.244; 7.CO.55.243; 7.CO.55.247; 7.CO.56.157;
7.CO.56.158; 7.CO.56.196; 7.CO.56.223; 7.CO.56.240; 7.CO.56.244;
7.CO.56.243; 7.CO.56.247; 7.CO.157.157; 7.CO.157.158; 7.CO.157.196;
7.CO.157.223; 7.CO.157.240; 7.CO.157.244; 7.CO.157.243; 7.CO.157.247;
7.CO.196.157; 7.CO.196.158; 7.CO.196.196; 7.CO.196.223; 7.CO.196.240;
7.CO.196.244; 7.CO.196.243; 7.CO.196.247; 7.CO.223.157; 7.CO.223.158;
7.CO.223.196; 7.CO.223.223; 7.CO.223.240; 7.CO.223.244; 7.CO.223.243;
7.CO.223.247; 7.CO.240.157; 7.CO.240.158; 7.CO.240.196; 7.CO.240.223;
7.CO.240.240; 7.CO.240.244; 7.CO.240.243; 7.CO.240.247; 7.CO.244.157;
7.CO.244.158; 7.CO.244.196; 7.CO.244.223; 7.CO.244.240; 7.CO.244.244;
7.CO.244.243; 7.CO.244.247; 7.CO.4.157; 7.CO.4.158; 7.CO.4.196;
7.CO.4.223; 7.CO.4.240; 7.CO.4.244; 7.CO.4.243; 7.CO.4.247;
Prodrugs of 8.AH 8.AH.4.157; 8.AH.4.158; 8.AH.4.196; 8.AH.4.223; 8.AH.4.240; 8.AH.4.244;
8.AH.4.243; 8.AH.4.247; 8.AH.5.157; 8.AH.5.158; 8.AH.5.196; 8.AH.5.223;
8.AH.5.240; 8.AH.5.244; 8.AH.5.243; 8.AH.5.247; 8.AH.7.157; 8.AH.7.158;
8.AH.7.196; 8.AH.7.223; 8.AH.7.240; 8.AH.7.244; 8.AH.7.243; 8.AH.7.247;
8.AH.15.157; 8.AH.15.158; 8.AH.15.196; 8.AH.15.223; 8.AH.15.240;
8.AH.15.244; 8.AH.15.243; 8.AH.15.247; 8.AH.16.157; 8.AH.16.158;
8.AH.16.196; 8.AH.16.223; 8.AH.16.240; 8.AH.16.244; 8.AH.16.243;
8.AH.16.247; 8.AH.18.157; 8.AH.18.158; 8.AH.18.196; 8.AH.18.223;
8.AH.18.240; 8.AH.18.244; 8.AH.18.243; 8.AH.18.247; 8.AH.26.157;
8.AH.26.158; 8.AH.26.196; 8.AH.26.223; 8.AH.26.240; 8.AH.26.244;
8.AH.26.243; 8.AH.26.247; 8.AH.27.157; 8.AH.27.158; 8.AH.27.196;
8.AH.27.223; 8.AH.27.240; 8.AH.27.244; 8.AH.27.243; 8.AH.27.247;
8.AH.29.157; 8.AH.29.158; 8.AH.29.196; 8.AH.29.223; 8.AH.29.240;
8.AH.29.244; 8.AH.29.243; 8.AH.29.247; 8.AH.54.157; 8.AH.54.158;
8.AH.54.196; 8.AH.54.223; 8.AH.54.240; 8.AH.54.244; 8.AH.54.243;
8.AH.54.247; 8.AH.55.157; 8.AH.55.158; 8.AH.55.196; 8.AH.55.223;
8.AH.55.240; 8.AH.55.244; 8.AH.55.243; 8.AH.55.247; 8.AH.56.157;
8.AH.56.158; 8.AH.56.196; 8.AH.56.223; 8.AH.56.240; 8.AH.56.244;
8.AH.56.243; 8.AH.56.247; 8.AH.157.157; 8.AH.157.158; 8.AH.157.196;
8.AH.157.223; 8.AH.157.240; 8.AH.157.244; 8.AH.157.243; 8.AH.157.247;
8.AH.196.157; 8.AH.196.158; 8.AH.196.196; 8.AH.196.223; 8.AH.196.240;
8.AH.196.244; 8.AH.196.243; 8.AH.196.247; 8.AH.223.157; 8.AH.223.158;
8.AH.223.196; 8.AH.223.223; 8.AH.223.240; 8.AH.223.244; 8.AH.223.243;
8.AH.223.247; 8.AH.240.157; 8.AH.240.158; 8.AH.240.196; 8.AH.240.223;
8.AH.240.240; 8.AH.240.244; 8.AH.240.243; 8.AH.240.247; 8.AH.244.157;
8.AH.244.158; 8.AH.244.196; 8.AH.244.223; 8.AH.244.240; 8.AH.244.244;
8.AH.244.243; 8.AH.244.247; 8.AH.247.157; 8.AH.247.158; 8.AH.247.196;
8.AH.247.223; 8.AH.247.240; 8.AH.247.244; 8.AH.247.243; 8.AH.247.247;
Prodrugs of 8.AJ 8.AJ.4.157; 8.AJ.4.158; 8.AJ.4.196; 8.AJ.4.223; 8.AJ.4.240; 8.AJ.4.244;
8.AJ.4.243; 8.AJ.4.247; 8.AJ.5.157; 8.AJ.5.158; 8.AJ.5.196; 8.AJ.5.223;
8.AJ.5.240; 8.AJ.5.244; 8.AJ.5.243; 8.AJ.5.247; 8.AJ.7.157; 8.AJ.7.158;
8.AJ.7.196; 8.AJ.7.223; 8.AJ.7.240; 8.AJ.7.244; 8.AJ.7.243; 8.AJ.7.247;
8.AJ.15.157; 8.AJ.15.158; 8.AJ.15.196; 8.AJ.15.223; 8.AJ.15.240; 8.AJ.15.244;
8.AJ.15.243; 8.AJ.15.247; 8.AJ.16.157; 8.AJ.16.158; 8.AJ.16.196; 8.AJ.16.223;
8.AJ.16.240; 8.AJ.16.244; 8.AJ.16.243; 8.AJ.16.247; 8.AJ.18.157; 8.AJ.18.158;
8.AJ.18.196; 8.AJ.18.223; 8.AJ.18.240; 8.AJ.18.244; 8.AJ.18.243; 8.AJ.18.247;
8.AJ.26.157; 8.AJ.26.158; 8.AJ.26.196; 8.AJ.26.223; 8.AJ.26.240; 8.AJ.26.244;
8.AJ.26.243; 8.AJ.26.247; 8.AJ.27.157; 8.AJ.27.158; 8.AJ.27.196; 8.AJ.27.223;
8.AJ.27.240; 8.AJ.27.244; 8.AJ.27.243; 8.AJ.27.247; 8.AJ.29.157; 8.AJ.29.158;
8.AJ.29.196; 8.AJ.29.223; 8.AJ.29.240; 8.AJ.29.244; 8.AJ.29.243; 8.AJ.29.247;
8.AJ.54.157; 8.AJ.54.158; 8.AJ.54.196; 8.AJ.54.223; 8.AJ.54.240; 8.AJ.54.244;
8.AJ.54.243; 8.AJ.54.247; 8.AJ.55.157; 8.AJ.55.158; 8.AJ.55.196; 8.AJ.55.223;

TABLE 100-continued

8.AJ.55.240; 8.AJ.55.244; 8.AJ.55.243; 8.AJ.55.247; 8.AJ.56.157; 8.AJ.56.158;
8.AJ.56.196; 8.AJ.56.223; 8.AJ.56.240; 8.AJ.56.244; 8.AJ.56.243; 8.AJ.56.247;
8.AJ.157.157; 8.AJ.157.158; 8.AJ.157.196; 8.AJ.157.223; 8.AJ.157.240;
8.AJ.157.244; 8.AJ.157.243; 8.AJ.157.247; 8.AJ.196.157; 8.AJ.196.158;
8.AJ.196.196; 8.AJ.196.223; 8.AJ.196.240; 8.AJ.196.244; 8.AJ.196.243;
8.AJ.196.247; 8.AJ.223.157; 8.AJ.223.158; 8.AJ.223.196; 8.AJ.223.223;
8.AJ.223.240; 8.AJ.223.244; 8.AJ.223.243; 8.AJ.223.247; 8.AJ.240.157;
8.AJ.240.158; 8.AJ.240.196; 8.AJ.240.223; 8.AJ.240.240; 8.AJ.240.244;
8.AJ.240.243; 8.AJ.240.247; 8.AJ.244.157; 8.AJ.244.158; 8.AJ.244.196;
8.AJ.244.223; 8.AJ.244.240; 8.AJ.244.244; 8.AJ.244.243; 8.AJ.244.247;
8.AJ.247.157; 8.AJ.247.158; 8.AJ.247.196; 8.AJ.247.223; 8.AJ.247.240;
8.AJ.247.244; 8.AJ.247.243; 8.AJ.247.247;

Prodrugs of 8.AN

8.AN.4.157; 8.AN.4.158; 8.AN.4.196; 8.AN.4.223; 8.AN.4.240; 8.AN.4.244;
8.AN.4.243; 8.AN.4.247; 8.AN.5.157; 8.AN.5.158; 8.AN.5.196; 8.AN.5.223;
8.AN.5.240; 8.AN.5.244; 8.AN.5.243; 8.AN.5.247; 8.AN.7.157; 8.AN.7.158;
8.AN.7.196; 8.AN.7.223; 8.AN.7.240; 8.AN.7.244; 8.AN.7.243; 8.AN.7.247;
8.AN.15.157; 8.AN.15.158; 8.AN.15.196; 8.AN.15.223; 8.AN.15.240;
8.AN.15.244; 8.AN.15.243; 8.AN.15.247; 8.AN.16.157; 8.AN.16.158;
8.AN.16.196; 8.AN.16.223; 8.AN.16.240; 8.AN.16.244; 8.AN.16.243;
8.AN.16.247; 8.AN.18.157; 8.AN.18.158; 8.AN.18.196; 8.AN.18.223;
8.AN.18.240; 8.AN.18.244; 8.AN.18.243; 8.AN.18.247; 8.AN.26.157;
8.AN.26.158; 8.AN.26.196; 8.AN.26.223; 8.AN.26.240; 8.AN.26.244;
8.AN.26.243; 8.AN.26.247; 8.AN.27.157; 8.AN.27.158; 8.AN.27.196;
8.AN.27.223; 8.AN.27.240; 8.AN.27.244; 8.AN.27.243; 8.AN.27.247;
8.AN.29.157; 8.AN.29.158; 8.AN.29.196; 8.AN.29.223; 8.AN.29.240;
8.AN.29.244; 8.AN.29.243; 8.AN.29.247; 8.AN.54.157; 8.AN.54.158;
8.AN.54.196; 8.AN.54.223; 8.AN.54.240; 8.AN.54.244; 8.AN.54.243;
8.AN.54.247; 8.AN.55.157; 8.AN.55.158; 8.AN.55.196; 8.AN.55.223;
8.AN.55.240; 8.AN.55.244; 8.AN.55.243; 8.AN.55.247; 8.AN.56.157;
8.AN.56.158; 8.AN.56.196; 8.AN.56.223; 8.AN.56.240; 8.AN.56.244;
8.AN.56.243; 8.AN.56.247; 8.AN.157.157; 8.AN.157.158; 8.AN.157.196;
8.AN.157.223; 8.AN.157.240; 8.AN.157.244; 8.AN.157.243; 8.AN.157.247;
8.AN.196.157; 8.AN.196.158; 8.AN.196.196; 8.AN.196.223; 8.AN.196.240;
8.AN.196.244; 8.AN.196.243; 8.AN.196.247; 8.AN.223.157; 8.AN.223.158;
8.AN.223.196; 8.AN.223.223; 8.AN.223.240; 8.AN.223.244; 8.AN.223.243;
8.AN.223.247; 8.AN.240.157; 8.AN.240.158; 8.AN.240.196; 8.AN.240.223;
8.AN.240.240; 8.AN.240.244; 8.AN.240.243; 8.AN.240.247; 8.AN.244.157;
8.AN.244.158; 8.AN.244.196; 8.AN.244.223; 8.AN.244.240; 8.AN.244.244;
8.AN.244.243; 8.AN.244.247; 8.AN.247.157; 8.AN.247.158; 8.AN.247.196;
8.AN.247.223; 8.AN.247.240; 8.AN.247.244; 8.AN.247.243; 8.AN.247.247;

Prodrugs of 8.AP

8.AP.4.157; 8.AP.4.158; 8.AP.4.196; 8.AP.4.223; 8.AP.4.240; 8.AP.4.244;
8.AP.4.243; 8.AP.4.247; 8.AP.5.157; 8.AP.5.158; 8.AP.5.196; 8.AP.5.223;
8.AP.5.240; 8.AP.5.244; 8.AP.5.243; 8.AP.5.247; 8.AP.7.157; 8.AP.7.158;
8.AP.7.196; 8.AP.7.223; 8.AP.7.240; 8.AP.7.244; 8.AP.7.243; 8.AP.7.247;
8.AP.15.157; 8.AP.15.158; 8.AP.15.196; 8.AP.15.223; 8.AP.15.240;
8.AP.15.244; 8.AP.15.243; 8.AP.15.247; 8.AP.16.157; 8.AP.16.158;
8.AP.16.196; 8.AP.16.223; 8.AP.16.240; 8.AP.16.244; 8.AP.16.243;
8.AP.16.247; 8.AP.18.157; 8.AP.18.158; 8.AP.18.196; 8.AP.18.223;
8.AP.18.240; 8.AP.18.244; 8.AP.18.243; 8.AP.18.247; 8.AP.26.157;
8.AP.26.158; 8.AP.26.196; 8.AP.26.223; 8.AP.26.240; 8.AP.26.244;
8.AP.26.243; 8.AP.26.247; 8.AP.27.157; 8.AP.27.158; 8.AP.27.196;
8.AP.27.223; 8.AP.27.240; 8.AP.27.244; 8.AP.27.243; 8.AP.27.247;
8.AP.29.157; 8.AP.29.158; 8.AP.29.196; 8.AP.29.223; 8.AP.29.240;
8.AP.29.244; 8.AP.29.243; 8.AP.29.247; 8.AP.54.157; 8.AP.54.158;
8.AP.54.196; 8.AP.54.223; 8.AP.54.240; 8.AP.54.244; 8.AP.54.243;
8.AP.54.247; 8.AP.55.157; 8.AP.55.158; 8.AP.55.196; 8.AP.55.223;
8.AP.55.240; 8.AP.55.244; 8.AP.55.243; 8.AP.55.247; 8.AP.56.157;
8.AP.56.158; 8.AP.56.196; 8.AP.56.223; 8.AP.56.240; 8.AP.56.244;
8.AP.56.243; 8.AP.56.247; 8.AP.157.157; 8.AP.157.158; 8.AP.157.196;
8.AP.157.223; 8.AP.157.240; 8.AP.157.244; 8.AP.157.243; 8.AP.157.247;
8.AP.196.157; 8.AP.196.158; 8.AP.196.196; 8.AP.196.223; 8.AP.196.240;
8.AP.196.244; 8.AP.196.243; 8.AP.196.247; 8.AP.223.157; 8.AP.223.158;
8.AP.223.196; 8.AP.223.223; 8.AP.223.240; 8.AP.223.244; 8.AP.223.243;
8.AP.223.247; 8.AP.240.157; 8.AP.240.158; 8.AP.240.196; 8.AP.240.223;
8.AP.240.240; 8.AP.240.244; 8.AP.240.243; 8.AP.240.247; 8.AP.244.157;
8.AP.244.158; 8.AP.244.196; 8.AP.244.223; 8.AP.244.240; 8.AP.244.244;
8.AP.244.243; 8.AP.244.247; 8.AP.247.157; 8.AP.247.158; 8.AP.247.196;
8.AP.247.223; 8.AP.247.240; 8.AP.247.244; 8.AP.247.243; 8.AP.247.247;

Prodrugs of 8.AZ

8.AZ.4.157; 8.AZ.4.158; 8.AZ.4.196; 8.AZ.4.223; 8.AZ.4.240; 8.AZ.4.244;
8.AZ.4.243; 8.AZ.4.247; 8.AZ.5.157; 8.AZ.5.158; 8.AZ.5.196; 8.AZ.5.223;
8.AZ.5.240; 8.AZ.5.244; 8.AZ.5.243; 8.AZ.5.247; 8.AZ.7.157; 8.AZ.7.158;
8.AZ.7.196; 8.AZ.7.223; 8.AZ.7.240; 8.AZ.7.244; 8.AZ.7.243; 8.AZ.7.247;
8.AZ.15.157; 8.AZ.15.158; 8.AZ.15.196; 8.AZ.15.223; 8.AZ.15.240;

TABLE 100-continued

8.AZ.15.244; 8.AZ.15.243; 8.AZ.15.247; 8.AZ.16.157; 8.AZ.16.158;
8.AZ.16.196; 8.AZ.16.223; 8.AZ.16.240; 8.AZ.16.244; 8.AZ.16.243;
8.AZ.16.247; 8.AZ.18.157; 8.AZ.18.158; 8.AZ.18.196; 8.AZ.18.223;
8.AZ.18.240; 8.AZ.18.244; 8.AZ.18.243; 8.AZ.18.247; 8.AZ.26.157;
8.AZ.26.158; 8.AZ.26.196; 8.AZ.26.223; 8.AZ.26.240; 8.AZ.26.244;
8.AZ.26.243; 8.AZ.26.247; 8.AZ.27.157; 8.AZ.27.158; 8.AZ.27.196;
8.AZ.27.223; 8.AZ.27.240; 8.AZ.27.244; 8.AZ.27.243; 8.AZ.27.247;
8.AZ.29.157; 8.AZ.29.158; 8.AZ.29.196; 8.AZ.29.223; 8.AZ.29.240;
8.AZ.29.244; 8.AZ.29.243; 8.AZ.29.247; 8.AZ.54.157; 8.AZ.54.158;
8.AZ.54.196; 8.AZ.54.223; 8.AZ.54.240; 8.AZ.54.244; 8.AZ.54.243;
8.AZ.54.247; 8.AZ.55.157; 8.AZ.55.158; 8.AZ.55.196; 8.AZ.55.223;
8.AZ.55.240; 8.AZ.55.244; 8.AZ.55.243; 8.AZ.55.247; 8.AZ.56.157;
8.AZ.56.158; 8.AZ.56.196; 8.AZ.56.223; 8.AZ.56.240; 8.AZ.56.244;
8.AZ.56.243; 8.AZ.56.247; 8.AZ.157.157; 8.AZ.157.158; 8.AZ.157.196;
8.AZ.157.223; 8.AZ.157.240; 8.AZ.157.244; 8.AZ.157.243; 8.AZ.157.247;
8.AZ.196.157; 8.AZ.196.158; 8.AZ.196.196; 8.AZ.196.223; 8.AZ.196.240;
8.AZ.196.244; 8.AZ.196.243; 8.AZ.196.247; 8.AZ.223.157; 8.AZ.223.158;
8.AZ.223.196; 8.AZ.223.223; 8.AZ.223.240; 8.AZ.223.244; 8.AZ.223.243;
8.AZ.223.247; 8.AZ.240.157; 8.AZ.240.158; 8.AZ.240.196; 8.AZ.240.223;
8.AZ.240.240; 8.AZ.240.244; 8.AZ.240.243; 8.AZ.240.247; 8.AZ.244.157;
8.AZ.244.158; 8.AZ.244.196; 8.AZ.244.223; 8.AZ.244.240; 8.AZ.244.244;
8.AZ.244.243; 8.AZ.244.247; 8.AZ.247.157; 8.AZ.247.158; 8.AZ.247.196;
8.AZ.247.223; 8.AZ.247.240; 8.AZ.247.244; 8.AZ.247.243; 8.AZ.247.247;

Prodrugs of 8.BF

8.BF.4.157; 8.BF.4.158; 8.BF.4.196; 8.BF.4.223; 8.BF.4.240; 8.BF.4.244;
8.BF.4.243; 8.BF.4.247; 8.BF.5.157; 8.BF.5.158; 8.BF.5.196; 8.BF.5.223;
8.BF.5.240; 8.BF.5.244; 8.BF.5.243; 8.BF.5.247; 8.BF.7.157; 8.BF.7.158;
8.BF.7.196; 8.BF.7.223; 8.BF.7.240; 8.BF.7.244; 8.BF.7.243; 8.BF.7.247;
8.BF.15.157; 8.BF.15.158; 8.BF.15.196; 8.BF.15.223; 8.BF.15.240;
8.BF.15.244; 8.BF.15.243; 8.BF.15.247; 8.BF.16.157; 8.BF.16.158;
8.BF.16.196; 8.BF.16.223; 8.BF.16.240; 8.BF.16.244; 8.BF.16.243;
8.BF.16.247; 8.BF.18.157; 8.BF.18.158; 8.BF.18.196; 8.BF.18.223;
8.BF.18.240; 8.BF.18.244; 8.BF.18.243; 8.BF.18.247; 8.BF.26.157;
8.BF.26.158; 8.BF.26.196; 8.BF.26.223; 8.BF.26.240; 8.BF.26.244;
8.BF.26.243; 8.BF.26.247; 8.BF.27.157; 8.BF.27.158; 8.BF.27.196;
8.BF.27.223; 8.BF.27.240; 8.BF.27.244; 8.BF.27.243; 8.BF.27.247;
8.BF.29.157; 8.BF.29.158; 8.BF.29.196; 8.BF.29.223; 8.BF.29.240;
8.BF.29.244; 8.BF.29.243; 8.BF.29.247; 8.BF.54.157; 8.BF.54.158;
8.BF.54.196; 8.BF.54.223; 8.BF.54.240; 8.BF.54.244; 8.BF.54.243;
8.BF.54.247; 8.BF.55.157; 8.BF.55.158; 8.BF.55.196; 8.BF.55.223;
8.BF.55.240; 8.BF.55.244; 8.BF.55.243; 8.BF.55.247; 8.BF.56.157;
8.BF.56.158; 8.BF.56.196; 8.BF.56.223; 8.BF.56.240; 8.BF.56.244;
8.BF.56.243; 8.BF.56.247; 8.BF.157.157; 8.BF.157.158; 8.BF.157.196;
8.BF.157.223; 8.BF.157.240; 8.BF.157.244; 8.BF.157.243; 8.BF.157.247;
8.BF.196.157; 8.BF.196.158; 8.BF.196.196; 8.BF.196.223; 8.BF.196.240;
8.BF.196.244; 8.BF.196.243; 8.BF.196.247; 8.BF.223.157; 8.BF.223.158;
8.BF.223.196; 8.BF.223.223; 8.BF.223.240; 8.BF.223.244; 8.BF.223.243;
8.BF.223.247; 8.BF.240.157; 8.BF.240.158; 8.BF.240.196; 8.BF.240.223;
8.BF.240.240; 8.BF.240.244; 8.BF.240.243; 8.BF.240.247; 8.BF.244.157;
8.BF.244.158; 8.BF.244.196; 8.BF.244.223; 8.BF.244.240; 8.BF.244.244;
8.BF.244.243; 8.BF.244.247; 8.BF.247.157; 8.BF.247.158; 8.BF.247.196;
8.BF.247.223; 8.BF.247.240; 8.BF.247.244; 8.BF.247.243; 8.BF.247.247;

Prodrugs of 8.CI

8.CI.4.157; 8.CI.4.158; 8.CI.4.196; 8.CI.4.223; 8.CI.4.240; 8.CI.4.244;
8.CI.4.243; 8.CI.4.247; 8.CI.5.157; 8.CI.5.158; 8.CI.5.196; 8.CI.5.223;
8.CI.5.240; 8.CI.5.244; 8.CI.5.243; 8.CI.5.247; 8.CI.7.157; 8.CI.7.158;
8.CI.7.196; 8.CI.7.223; 8.CI.7.240; 8.CI.7.244; 8.CI.7.243; 8.CI.7.247;
8.CI.15.157; 8.CI.15.158; 8.CI.15.196; 8.CI.15.223; 8.CI.15.240; 8.CI.15.244;
8.CI.15.243; 8.CI.15.247; 8.CI.16.157; 8.CI.16.158; 8.CI.16.196; 8.CI.16.223;
8.CI.16.240; 8.CI.16.244; 8.CI.16.243; 8.CI.16.247; 8.CI.18.157; 8.CI.18.158;
8.CI.18.196; 8.CI.18.223; 8.CI.18.240; 8.CI.18.244; 8.CI.18.243; 8.CI.18.247;
8.CI.26.157; 8.CI.26.158; 8.CI.26.196; 8.CI.26.223; 8.CI.26.240; 8.CI.26.244;
8.CI.26.243; 8.CI.26.247; 8.CI.27.157; 8.CI.27.158; 8.CI.27.196; 8.CI.27.223;
8.CI.27.240; 8.CI.27.244; 8.CI.27.243; 8.CI.27.247; 8.CI.29.157; 8.CI.29.158;
8.CI.29.196; 8.CI.29.223; 8.CI.29.240; 8.CI.29.244; 8.CI.29.243; 8.CI.29.247;
8.CI.54.157; 8.CI.54.158; 8.CI.54.196; 8.CI.54.223; 8.CI.54.240; 8.CI.54.244;
8.CI.54.243; 8.CI.54.247; 8.CI.55.157; 8.CI.55.158; 8.CI.55.196; 8.CI.55.223;
8.CI.55.240; 8.CI.55.244; 8.CI.55.243; 8.CI.55.247; 8.CI.56.157; 8.CI.56.158;
8.CI.56.196; 8.CI.56.223; 8.CI.56.240; 8.CI.56.244; 8.CI.56.243; 8.CI.56.247;
8.CI.157.157; 8.CI.157.158; 8.CI.157.196; 8.CI.157.223; 8.CI.157.240;
8.CI.157.244; 8.CI.157.243; 8.CI.157.247; 8.CI.196.157; 8.CI.196.158;
8.CI.196.196; 8.CI.196.223; 8.CI.196.240; 8.CI.196.244; 8.CI.196.243;
8.CI.196.247; 8.CI.223.157; 8.CI.223.158; 8.CI.223.196; 8.CI.223.223;
8.CI.223.240; 8.CI.223.244; 8.CI.223.243; 8.CI.223.247; 8.CI.240.157;
8.CI.240.158; 8.CI.240.196; 8.CI.240.223; 8.CI.240.240; 8.CI.240.244;
8.CI.240.243; 8.CI.240.247; 8.CI.244.157; 8.CI.244.158; 8.CI.244.196;
8.CI.244.223; 8.CI.244.240; 8.CI.244.244; 8.CI.244.243; 8.CI.244.247;

TABLE 100-continued

8.CI.247.157; 8.CI.247.158; 8.CI.247.196; 8.CI.247.223; 8.CI.247.240;
8.CI.247.244; 8.CI.247.243; 8.CI.247.247;
Prodrugs of 8.CO 8.CO.4.157; 8.CO.4.158; 8.CO.4.196; 8.CO.4.223; 8.CO.4.240; 8.CO.4.244;
8.CO.4.243; 8.CO.4.247; 8.CO.5.157; 8.CO.5.158; 8.CO.5.196; 8.CO.5.223;
8.CO.5.240; 8.CO.5.244; 8.CO.5.243; 8.CO.5.247; 8.CO.7.157; 8.CO.7.158;
8.CO.7.196; 8.CO.7.223; 8.CO.7.240; 8.CO.7.244; 8.CO.7.243; 8.CO.7.247;
8.CO.15.157; 8.CO.15.158; 8.CO.15.196; 8.CO.15.223; 8.CO.15.240;
8.CO.15.244; 8.CO.15.243; 8.CO.15.247; 8.CO.16.157; 8.CO.16.158;
8.CO.16.196; 8.CO.16.223; 8.CO.16.240; 8.CO.16.244; 8.CO.16.243;
8.CO.16.247; 8.CO.18.157; 8.CO.18.158; 8.CO.18.196; 8.CO.18.223;
8.CO.18.240; 8.CO.18.244; 8.CO.18.243; 8.CO.18.247; 8.CO.26.157;
8.CO.26.158; 8.CO.26.196; 8.CO.26.223; 8.CO.26.240; 8.CO.26.244;
8.CO.26.243; 8.CO.26.247; 8.CO.27.157; 8.CO.27.158; 8.CO.27.196;
8.CO.27.223; 8.CO.27.240; 8.CO.27.244; 8.CO.27.243; 8.CO.27.247;
8.CO.29.157; 8.CO.29.158; 8.CO.29.196; 8.CO.29.223; 8.CO.29.240;
8.CO.29.244; 8.CO.29.243; 8.CO.29.247; 8.CO.54.157; 8.CO.54.158;
8.CO.54.196; 8.CO.54.223; 8.CO.54.240; 8.CO.54.244; 8.CO.54.243;
8.CO.54.247; 8.CO.55.157; 8.CO.55.158; 8.CO.55.196; 8.CO.55.223;
8.CO.55.240; 8.CO.55.244; 8.CO.55.243; 8.CO.55.247; 8.CO.56.157;
8.CO.56.158; 8.CO.56.196; 8.CO.56.223; 8.CO.56.240; 8.CO.56.244;
8.CO.56.243; 8.CO.56.247; 8.CO.157.157; 8.CO.157.158; 8.CO.157.196;
8.CO.157.223; 8.CO.157.240; 8.CO.157.244; 8.CO.157.243; 8.CO.157.247;
8.CO.196.157; 8.CO.196.158; 8.CO.196.196; 8.CO.196.223; 8.CO.196.240;
8.CO.196.244; 8.CO.196.243; 8.CO.196.247; 8.CO.223.157; 8.CO.223.158;
8.CO.223.196; 8.CO.223.223; 8.CO.223.240; 8.CO.223.244; 8.CO.223.243;
8.CO.223.247; 8.CO.240.157; 8.CO.240.158; 8.CO.240.196; 8.CO.240.223;
8.CO.240.240; 8.CO.240.244; 8.CO.240.243; 8.CO.240.247; 8.CO.244.157;
8.CO.244.158; 8.CO.244.196; 8.CO.244.223; 8.CO.244.240; 8.CO.244.244;
8.CO.244.243; 8.CO.244.247; 8.CO.247.157; 8.CO.247.158; 8.CO.247.196;
8.CO.247.223; 8.CO.247.240; 8.CO.247.244; 8.CO.247.243; 8.CO.247.247;
Prodrugs of 9.AH 9.AH.4.157; 9.AH.4.158; 9.AH.4.196; 9.AH.4.223; 9.AH.4.240; 9.AH.4.244;
9.AH.4.243; 9.AH.4.247; 9.AH.5.157; 9.AH.5.158; 9.AH.5.196; 9.AH.5.223;
9.AH.5.240; 9.AH.5.244; 9.AH.5.243; 9.AH.5.247; 9.AH.7.157; 9.AH.7.158;
9.AH.7.196; 9.AH.7.223; 9.AH.7.240; 9.AH.7.244; 9.AH.7.243; 9.AH.7.247;
9.AH.15.157; 9.AH.15.158; 9.AH.15.196; 9.AH.15.223; 9.AH.15.240;
9.AH.15.244; 9.AH.15.243; 9.AH.15.247; 9.AH.16.157; 9.AH.16.158;
9.AH.16.196; 9.AH.16.223; 9.AH.16.240; 9.AH.16.244; 9.AH.16.243;
9.AH.16.247; 9.AH.18.157; 9.AH.18.158; 9.AH.18.196; 9.AH.18.223;
9.AH.18.240; 9.AH.18.244; 9.AH.18.243; 9.AH.18.247; 9.AH.26.157;
9.AH.26.158; 9.AH.26.196; 9.AH.26.223; 9.AH.26.240; 9.AH.26.244;
9.AH.26.243; 9.AH.26.247; 9.AH.27.157; 9.AH.27.158; 9.AH.27.196;
9.AH.27.223; 9.AH.27.240; 9.AH.27.244; 9.AH.27.243; 9.AH.27.247;
9.AH.29.157; 9.AH.29.158; 9.AH.29.196; 9.AH.29.223; 9.AH.29.240;
9.AH.29.244; 9.AH.29.243; 9.AH.29.247; 9.AH.54.157; 9.AH.54.158;
9.AH.54.196; 9.AH.54.223; 9.AH.54.240; 9.AH.54.244; 9.AH.54.243;
9.AH.54.247; 9.AH.55.157; 9.AH.55.158; 9.AH.55.196; 9.AH.55.223;
9.AH.55.240; 9.AH.55.244; 9.AH.55.243; 9.AH.55.247; 9.AH.56.157;
9.AH.56.158; 9.AH.56.196; 9.AH.56.223; 9.AH.56.240; 9.AH.56.244;
9.AH.56.243; 9.AH.56.247; 9.AH.157.157; 9.AH.157.158; 9.AH.157.196;
9.AH.157.223; 9.AH.157.240; 9.AH.157.244; 9.AH.157.243; 9.AH.157.247;
9.AH.196.157; 9.AH.196.158; 9.AH.196.196; 9.AH.196.223; 9.AH.196.240;
9.AH.196.244; 9.AH.196.243; 9.AH.196.247; 9.AH.223.157; 9.AH.223.158;
9.AH.223.196; 9.AH.223.223; 9.AH.223.240; 9.AH.223.244; 9.AH.223.243;
9.AH.223.247; 9.AH.240.157; 9.AH.240.158; 9.AH.240.196; 9.AH.240.223;
9.AH.240.240; 9.AH.240.244; 9.AH.240.243; 9.AH.240.247; 9.AH.244.157;
9.AH.244.158; 9.AH.244.196; 9.AH.244.223; 9.AH.244.240; 9.AH.244.244;
9.AH.244.243; 9.AH.244.247; 9.AH.247.157; 9.AH.247.158; 9.AH.247.196;
9.AH.247.223; 9.AH.247.240; 9.AH.247.244; 9.AH.247.243; 9.AH.247.247;
Prodrugs of 9.AJ 9.AJ.4.157; 9.AJ.4.158; 9.AJ.4.196; 9.AJ.4.223; 9.AJ.4.240; 9.AJ.4.244;
9.AJ.4.243; 9.AJ.4.247; 9.AJ.5.157; 9.AJ.5.158; 9.AJ.5.196; 9.AJ.5.223;
9.AJ.5.240; 9.AJ.5.244; 9.AJ.5.243; 9.AJ.5.247; 9.AJ.7.157; 9.AJ.7.158;
9.AJ.7.196; 9.AJ.7.223; 9.AJ.7.240; 9.AJ.7.244; 9.AJ.7.243; 9.AJ.7.247;
9.AJ.15.157; 9.AJ.15.158; 9.AJ.15.196; 9.AJ.15.223; 9.AJ.15.240; 9.AJ.15.244;
9.AJ.15.243; 9.AJ.15.247; 9.AJ.16.157; 9.AJ.16.158; 9.AJ.16.196; 9.AJ.16.223;
9.AJ.16.240; 9.AJ.16.244; 9.AJ.16.243; 9.AJ.16.247; 9.AJ.18.157; 9.AJ.18.158;
9.AJ.18.196; 9.AJ.18.223; 9.AJ.18.240; 9.AJ.18.244; 9.AJ.18.243; 9.AJ.18.247;
9.AJ.26.157; 9.AJ.26.158; 9.AJ.26.196; 9.AJ.26.223; 9.AJ.26.240; 9.AJ.26.244;
9.AJ.26.243; 9.AJ.26.247; 9.AJ.27.157; 9.AJ.27.158; 9.AJ.27.196; 9.AJ.27.223;
9.AJ.27.240; 9.AJ.27.244; 9.AJ.27.243; 9.AJ.27.247; 9.AJ.29.157; 9.AJ.29.158;
9.AJ.29.196; 9.AJ.29.223; 9.AJ.29.240; 9.AJ.29.244; 9.AJ.29.243; 9.AJ.29.247;
9.AJ.54.157; 9.AJ.54.158; 9.AJ.54.196; 9.AJ.54.223; 9.AJ.54.240; 9.AJ.54.244;
9.AJ.54.243; 9.AJ.54.247; 9.AJ.55.157; 9.AJ.55.158; 9.AJ.55.196; 9.AJ.55.223;
9.AJ.55.240; 9.AJ.55.244; 9.AJ.55.243; 9.AJ.55.247; 9.AJ.56.157; 9.AJ.56.158;

TABLE 100-continued

9.AJ.56.196; 9.AJ.56.223; 9.AJ.56.240; 9.AJ.56.244; 9.AJ.56.243; 9.AJ.56.247;
9.AJ.157.157; 9.AJ.157.158; 9.AJ.157.196; 9.AJ.157.223; 9.AJ.157.240;
9.AJ.157.244; 9.AJ.157.243; 9.AJ.157.247; 9.AJ.196.157; 9.AJ.196.158;
9.AJ.196.196; 9.AJ.196.223; 9.AJ.196.240; 9.AJ.196.244; 9.AJ.196.243;
9.AJ.196.247; 9.AJ.223.157; 9.AJ.223.158; 9.AJ.223.196; 9.AJ.223.223;
9.AJ.223.240; 9.AJ.223.244; 9.AJ.223.243; 9.AJ.223.247; 9.AJ.240.157;
9.AJ.240.158; 9.AJ.240.196; 9.AJ.240.223; 9.AJ.240.240; 9.AJ.240.244;
9.AJ.240.243; 9.AJ.240.247; 9.AJ.244.157; 9.AJ.244.158; 9.AJ.244.196;
9.AJ.244.223; 9.AJ.244.240; 9.AJ.244.244; 9.AJ.244.243; 9.AJ.244.247;
9.AJ.247.157; 9.AJ.247.158; 9.AJ.247.196; 9.AJ.247.223; 9.AJ.247.240;
9.AJ.247.244; 9.AJ.247.243; 9.AJ.247.247;
Prodrugs of 9.AN 9.AN.4.157; 9.AN.4.158; 9.AN.4.196; 9.AN.4.223; 9.AN.4.240; 9.AN.4.244;
9.AN.4.243; 9.AN.4.247; 9.AN.5.157; 9.AN.5.158; 9.AN.5.196; 9.AN.5.223;
9.AN.5.240; 9.AN.5.244; 9.AN.5.243; 9.AN.5.247; 9.AN.7.157; 9.AN.7.158;
9.AN.7.196; 9.AN.7.223; 9.AN.7.240; 9.AN.7.244; 9.AN.7.243; 9.AN.7.247;
9.AN.15.157; 9.AN.15.158; 9.AN.15.196; 9.AN.15.223; 9.AN.15.240;
9.AN.15.244; 9.AN.15.243; 9.AN.15.247; 9.AN.16.157; 9.AN.16.158;
9.AN.16.196; 9.AN.16.223; 9.AN.16.240; 9.AN.16.244; 9.AN.16.243;
9.AN.16.247; 9.AN.18.157; 9.AN.18.158; 9.AN.18.196; 9.AN.18.223;
9.AN.18.240; 9.AN.18.244; 9.AN.18.243; 9.AN.18.247; 9.AN.26.157;
9.AN.26.158; 9.AN.26.196; 9.AN.26.223; 9.AN.26.240; 9.AN.26.244;
9.AN.26.243; 9.AN.26.247; 9.AN.27.157; 9.AN.27.158; 9.AN.27.196;
9.AN.27.223; 9.AN.27.240; 9.AN.27.244; 9.AN.27.243; 9.AN.27.247;
9.AN.29.157; 9.AN.29.158; 9.AN.29.196; 9.AN.29.223; 9.AN.29.240;
9.AN.29.244; 9.AN.29.243; 9.AN.29.247; 9.AN.54.157; 9.AN.54.158;
9.AN.54.196; 9.AN.54.223; 9.AN.54.240; 9.AN.54.244; 9.AN.54.243;
9.AN.54.247; 9.AN.55.157; 9.AN.55.158; 9.AN.55.196; 9.AN.55.223;
9.AN.55.240; 9.AN.55.244; 9.AN.55.243; 9.AN.55.247; 9.AN.56.157;
9.AN.56.158; 9.AN.56.196; 9.AN.56.223; 9.AN.56.240; 9.AN.56.244;
9.AN.56.243; 9.AN.56.247; 9.AN.157.157; 9.AN.157.158; 9.AN.157.196;
9.AN.157.223; 9.AN.157.240; 9.AN.157.244; 9.AN.157.243; 9.AN.157.247;
9.AN.196.157; 9.AN.196.158; 9.AN.196.196; 9.AN.196.223; 9.AN.196.240;
9.AN.196.244; 9.AN.196.243; 9.AN.196.247; 9.AN.223.157; 9.AN.223.158;
9.AN.223.196; 9.AN.223.223; 9.AN.223.240; 9.AN.223.244; 9.AN.223.243;
9.AN.223.247; 9.AN.240.157; 9.AN.240.158; 9.AN.240.196; 9.AN.240.223;
9.AN.240.240; 9.AN.240.244; 9.AN.240.243; 9.AN.240.247; 9.AN.244.157;
9.AN.244.158; 9.AN.244.196; 9.AN.244.223; 9.AN.244.240; 9.AN.244.244;
9.AN.244.243; 9.AN.244.247; 9.AN.247.157; 9.AN.247.158; 9.AN.247.196;
9.AN.247.223; 9.AN.247.240; 9.AN.247.244; 9.AN.247.243; 9.AN.247.247;
Prodrugs of 9.AP 9.AP.4.157; 9.AP.4.158; 9.AP.4.196; 9.AP.4.223; 9.AP.4.240; 9.AP.4.244;
9.AP.4.243; 9.AP.4.247; 9.AP.5.157; 9.AP.5.158; 9.AP.5.196; 9.AP.5.223;
9.AP.5.240; 9.AP.5.244; 9.AP.5.243; 9.AP.5.247; 9.AP.7.157; 9.AP.7.158;
9.AP.7.196; 9.AP.7.223; 9.AP.7.240; 9.AP.7.244; 9.AP.7.243; 9.AP.7.247;
9.AP.15.157; 9.AP.15.158; 9.AP.15.196; 9.AP.15.223; 9.AP.15.240;
9.AP.15.244; 9.AP.15.243; 9.AP.15.247; 9.AP.16.157; 9.AP.16.158;
9.AP.16.196; 9.AP.16.223; 9.AP.16.240; 9.AP.16.244; 9.AP.16.243;
9.AP.16.247; 9.AP.18.157; 9.AP.18.158; 9.AP.18.196; 9.AP.18.223;
9.AP.18.240; 9.AP.18.244; 9.AP.18.243; 9.AP.18.247; 9.AP.26.157;
9.AP.26.158; 9.AP.26.196; 9.AP.26.223; 9.AP.26.240; 9.AP.26.244;
9.AP.26.243; 9.AP.26.247; 9.AP.27.157; 9.AP.27.158; 9.AP.27.196;
9.AP.27.223; 9.AP.27.240; 9.AP.27.244; 9.AP.27.243; 9.AP.27.247;
9.AP.29.157; 9.AP.29.158; 9.AP.29.196; 9.AP.29.223; 9.AP.29.240;
9.AP.29.244; 9.AP.29.243; 9.AP.29.247; 9.AP.54.157; 9.AP.54.158;
9.AP.54.196; 9.AP.54.223; 9.AP.54.240; 9.AP.54.244; 9.AP.54.243;
9.AP.54.247; 9.AP.55.157; 9.AP.55.158; 9.AP.55.196; 9.AP.55.223;
9.AP.55.240; 9.AP.55.244; 9.AP.55.243; 9.AP.55.247; 9.AP.56.157;
9.AP.56.158; 9.AP.56.196; 9.AP.56.223; 9.AP.56.240; 9.AP.56.244;
9.AP.56.243; 9.AP.56.247; 9.AP.157.157; 9.AP.157.158; 9.AP.157.196;
9.AP.157.223; 9.AP.157.240; 9.AP.157.244; 9.AP.157.243; 9.AP.157.247;
9.AP.196.157; 9.AP.196.158; 9.AP.196.196; 9.AP.196.223; 9.AP.196.240;
9.AP.196.244; 9.AP.196.243; 9.AP.196.247; 9.AP.223.157; 9.AP.223.158;
9.AP.223.196; 9.AP.223.223; 9.AP.223.240; 9.AP.223.244; 9.AP.223.243;
9.AP.223.247; 9.AP.240.157; 9.AP.240.158; 9.AP.240.196; 9.AP.240.223;
9.AP.240.240; 9.AP.240.244; 9.AP.240.243; 9.AP.240.247; 9.AP.244.157;
9.AP.244.158; 9.AP.244.196; 9.AP.244.223; 9.AP.244.240; 9.AP.244.244;
9.AP.244.243; 9.AP.244.247; 9.AP.247.157; 9.AP.247.158; 9.AP.247.196;
9.AP.247.223; 9.AP.247.240; 9.AP.247.244; 9.AP.247.243; 9.AP.247.247;
Prodrugs of 9.AZ 9.AZ.4.157; 9.AZ.4.158; 9.AZ.4.196; 9.AZ.4.223; 9.AZ.4.240; 9.AZ.4.244;
9.AZ.4.243; 9.AZ.4.247; 9.AZ.5.157; 9.AZ.5.158; 9.AZ.5.196; 9.AZ.5.223;
9.AZ.5.240; 9.AZ.5.244; 9.AZ.5.243; 9.AZ.5.247; 9.AZ.7.157; 9.AZ.7.158;
9.AZ.7.196; 9.AZ.7.223; 9.AZ.7.240; 9.AZ.7.244; 9.AZ.7.243; 9.AZ.7.247;
9.AZ.15.157; 9.AZ.15.158; 9.AZ.15.196; 9.AZ.15.223; 9.AZ.15.240;
9.AZ.15.244; 9.AZ.15.243; 9.AZ.15.247; 9.AZ.16.157; 9.AZ.16.158;

TABLE 100-continued

9.AZ.16.196; 9.AZ.16.223; 9.AZ.16.240; 9.AZ.16.244; 9.AZ.16.243;
9.AZ.16.247; 9.AZ.18.157; 9.AZ.18.158; 9.AZ.18.196; 9.AZ.18.223;
9.AZ.18.240; 9.AZ.18.244; 9.AZ.18.243; 9.AZ.18.247; 9.AZ.26.157;
9.AZ.26.158; 9.AZ.26.196; 9.AZ.26.223; 9.AZ.26.240; 9.AZ.26.244;
9.AZ.26.243; 9.AZ.26.247; 9.AZ.27.157; 9.AZ.27.158; 9.AZ.27.196;
9.AZ.27.223; 9.AZ.27.240; 9.AZ.27.244; 9.AZ.27.243; 9.AZ.27.247;
9.AZ.29.157; 9.AZ.29.158; 9.AZ.29.196; 9.AZ.29.223; 9.AZ.29.240;
9.AZ.29.244; 9.AZ.29.243; 9.AZ.29.247; 9.AZ.54.157; 9.AZ.54.158;
9.AZ.54.196; 9.AZ.54.223; 9.AZ.54.240; 9.AZ.54.244; 9.AZ.54.243;
9.AZ.54.247; 9.AZ.55.157; 9.AZ.55.158; 9.AZ.55.196; 9.AZ.55.223;
9.AZ.55.240; 9.AZ.55.244; 9.AZ.55.243; 9.AZ.55.247; 9.AZ.56.157;
9.AZ.56.158; 9.AZ.56.196; 9.AZ.56.223; 9.AZ.56.240; 9.AZ.56.244;
9.AZ.56.243; 9.AZ.56.247; 9.AZ.157.157; 9.AZ.157.158; 9.AZ.157.196;
9.AZ.157.223; 9.AZ.157.240; 9.AZ.157.244; 9.AZ.157.243; 9.AZ.157.247;
9.AZ.196.157; 9.AZ.196.158; 9.AZ.196.196; 9.AZ.196.223; 9.AZ.196.240;
9.AZ.196.244; 9.AZ.196.243; 9.AZ.196.247; 9.AZ.223.157; 9.AZ.223.158;
9.AZ.223.196; 9.AZ.223.223; 9.AZ.223.240; 9.AZ.223.244; 9.AZ.223.243;
9.AZ.223.247; 9.AZ.240.157; 9.AZ.240.158; 9.AZ.240.196; 9.AZ.240.223;
9.AZ.240.240; 9.AZ.240.244; 9.AZ.240.243; 9.AZ.240.247; 9.AZ.244.157;
9.AZ.244.158; 9.AZ.244.196; 9.AZ.244.223; 9.AZ.244.240; 9.AZ.244.244;
9.AZ.244.243; 9.AZ.244.247; 9.AZ.247.157; 9.AZ.247.158; 9.AZ.247.196;
9.AZ.247.223; 9.AZ.247.240; 9.AZ.247.244; 9.AZ.247.243; 9.AZ.247.247;
Prodrugs of 9.BF 9.BF.4.157; 9.BF.4.158; 9.BF.4.196; 9.BF.4.223; 9.BF.4.240; 9.BF.4.244;
9.BF.4.243; 9.BF.4.247; 9.BF.5.157; 9.BF.5.158; 9.BF.5.196; 9.BF.5.223;
9.BF.5.240; 9.BF.5.244; 9.BF.5.243; 9.BF.5.247; 9.BF.7.157; 9.BF.7.158;
9.BF.7.196; 9.BF.7.223; 9.BF.7.240; 9.BF.7.244; 9.BF.7.243; 9.BF.7.247;
9.BF.15.157; 9.BF.15.158; 9.BF.15.196; 9.BF.15.223; 9.BF.15.240;
9.BF.15.244; 9.BF.15.243; 9.BF.15.247; 9.BF.16.157; 9.BF.16.158;
9.BF.16.196; 9.BF.16.223; 9.BF.16.240; 9.BF.16.244; 9.BF.16.243;
9.BF.16.247; 9.BF.18.157; 9.BF.18.158; 9.BF.18.196; 9.BF.18.223;
9.BF.18.240; 9.BF.18.244; 9.BF.18.243; 9.BF.18.247; 9.BF.26.157;
9.BF.26.158; 9.BF.26.196; 9.BF.26.223; 9.BF.26.240; 9.BF.26.244;
9.BF.26.243; 9.BF.26.247; 9.BF.27.157; 9.BF.27.158; 9.BF.27.196;
9.BF.27.223; 9.BF.27.240; 9.BF.27.244; 9.BF.27.243; 9.BF.27.247;
9.BF.29.157; 9.BF.29.158; 9.BF.29.196; 9.BF.29.223; 9.BF.29.240;
9.BF.29.244; 9.BF.29.243; 9.BF.29.247; 9.BF.54.157; 9.BF.54.158;
9.BF.54.196; 9.BF.54.223; 9.BF.54.240; 9.BF.54.244; 9.BF.54.243;
9.BF.54.247; 9.BF.55.157; 9.BF.55.158; 9.BF.55.196; 9.BF.55.223;
9.BF.55.240; 9.BF.55.244; 9.BF.55.243; 9.BF.55.247; 9.BF.56.157;
9.BF.56.158; 9.BF.56.196; 9.BF.56.223; 9.BF.56.240; 9.BF.56.244;
9.BF.56.243; 9.BF.56.247; 9.BF.157.157; 9.BF.157.158; 9.BF.157.196;
9.BF.157.223; 9.BF.157.240; 9.BF.157.244; 9.BF.157.243; 9.BF.157.247;
9.BF.196.157; 9.BF.196.158; 9.BF.196.196; 9.BF.196.223; 9.BF.196.240;
9.BF.196.244; 9.BF.196.243; 9.BF.196.247; 9.BF.223.157; 9.BF.223.158;
9.BF.223.196; 9.BF.223.223; 9.BF.223.240; 9.BF.223.244; 9.BF.223.243;
9.BF.223.247; 9.BF.240.157; 9.BF.240.158; 9.BF.240.196; 9.BF.240.223;
9.BF.240.240; 9.BF.240.244; 9.BF.240.243; 9.BF.240.247; 9.BF.244.157;
9.BF.244.158; 9.BF.244.196; 9.BF.244.223; 9.BF.244.240; 9.BF.244.244;
9.BF.244.243; 9.BF.244.247; 9.BF.247.157; 9.BF.247.158; 9.BF.247.196;
9.BF.247.223; 9.BF.247.240; 9.BF.247.244; 9.BF.247.243; 9.BF.247.247;
Prodrugs of 9.CI 9.CI.4.157; 9.CI.4.158; 9.CI.4.196; 9.CI.4.223; 9.CI.4.240; 9.CI.4.244;
9.CI.4.243; 9.CI.4.247; 9.CI.5.157; 9.CI.5.158; 9.CI.5.196; 9.CI.5.223;
9.CI.5.240; 9.CI.5.244; 9.CI.5.243; 9.CI.5.247; 9.CI.7.157; 9.CI.7.158;
9.CI.7.196; 9.CI.7.223; 9.CI.7.240; 9.CI.7.244; 9.CI.7.243; 9.CI.7.247;
9.CI.15.157; 9.CI.15.158; 9.CI.15.196; 9.CI.15.223; 9.CI.15.240; 9.CI.15.244;
9.CI.15.243; 9.CI.15.247; 9.CI.16.157; 9.CI.16.158; 9.CI.16.196; 9.CI.16.223;
9.CI.16.240; 9.CI.16.244; 9.CI.16.243; 9.CI.16.247; 9.CI.18.157; 9.CI.18.158;
9.CI.18.196; 9.CI.18.223; 9.CI.18.240; 9.CI.18.244; 9.CI.18.243; 9.CI.18.247;
9.CI.26.157; 9.CI.26.158; 9.CI.26.196; 9.CI.26.223; 9.CI.26.240; 9.CI.26.244;
9.CI.26.243; 9.CI.26.247; 9.CI.27.157; 9.CI.27.158; 9.CI.27.196; 9.CI.27.223;
9.CI.27.240; 9.CI.27.244; 9.CI.27.243; 9.CI.27.247; 9.CI.29.157; 9.CI.29.158;
9.CI.29.196; 9.CI.29.223; 9.CI.29.240; 9.CI.29.244; 9.CI.29.243; 9.CI.29.247;
9.CI.54.157; 9.CI.54.158; 9.CI.54.196; 9.CI.54.223; 9.CI.54.240; 9.CI.54.244;
9.CI.54.243; 9.CI.54.247; 9.CI.55.157; 9.CI.55.158; 9.CI.55.196; 9.CI.55.223;
9.CI.55.240; 9.CI.55.244; 9.CI.55.243; 9.CI.55.247; 9.CI.56.157; 9.CI.56.158;
9.CI.56.196; 9.CI.56.223; 9.CI.56.240; 9.CI.56.244; 9.CI.56.243; 9.CI.56.247;
9.CI.157.157; 9.CI.157.158; 9.CI.157.196; 9.CI.157.223; 9.CI.157.240;
9.CI.157.244; 9.CI.157.243; 9.CI.157.247; 9.CI.196.157; 9.CI.196.158;
9.CI.196.196; 9.CI.196.223; 9.CI.196.240; 9.CI.196.244; 9.CI.196.243;
9.CI.196.247; 9.CI.223.157; 9.CI.223.158; 9.CI.223.196; 9.CI.223.223;
9.CI.223.240; 9.CI.223.244; 9.CI.223.243; 9.CI.223.247; 9.CI.240.157;
9.CI.240.158; 9.CI.240.196; 9.CI.240.223; 9.CI.240.240; 9.CI.240.244;
9.CI.240.243; 9.CI.240.247; 9.CI.244.157; 9.CI.244.158; 9.CI.244.196;

TABLE 100-continued

9.CI.244.223; 9.CI.244.240; 9.CI.244.244; 9.CI.244.243; 9.CI.244.247;
9.CI.247.157; 9.CI.247.158; 9.CI.247.196; 9.CI.247.223; 9.CI.247.240;
9.CI.247.244; 9.CI.247.243; 9.CI.247.247;
Prodrugs of 9.CO 9.CO.4.157; 9.CO.4.158; 9.CO.4.196; 9.CO.4.223; 9.CO.4.240; 9.CO.4.244;
9.CO.4.243; 9.CO.4.247; 9.CO.5.157; 9.CO.5.158; 9.CO.5.196; 9.CO.5.223;
9.CO.5.240; 9.CO.5.244; 9.CO.5.243; 9.CO.5.247; 9.CO.7.157; 9.CO.7.158;
9.CO.7.196; 9.CO.7.223; 9.CO.7.240; 9.CO.7.244; 9.CO.7.243; 9.CO.7.247;
9.CO.15.157; 9.CO.15.158; 9.CO.15.196; 9.CO.15.223; 9.CO.15.240;
9.CO.15.244; 9.CO.15.243; 9.CO.15.247; 9.CO.16.157; 9.CO.16.158;
9.CO.16.196; 9.CO.16.223; 9.CO.16.240; 9.CO.16.244; 9.CO.16.243;
9.CO.16.247; 9.CO.18.157; 9.CO.18.158; 9.CO.18.196; 9.CO.18.223;
9.CO.18.240; 9.CO.18.244; 9.CO.18.243; 9.CO.18.247; 9.CO.26.157;
9.CO.26.158; 9.CO.26.196; 9.CO.26.223; 9.CO.26.240; 9.CO.26.244;
9.CO.26.243; 9.CO.26.247; 9.CO.27.157; 9.CO.27.158; 9.CO.27.196;
9.CO.27.223; 9.CO.27.240; 9.CO.27.244; 9.CO.27.243; 9.CO.27.247;
9.CO.29.157; 9.CO.29.158; 9.CO.29.196; 9.CO.29.223; 9.CO.29.240;
9.CO.29.244; 9.CO.29.243; 9.CO.29.247; 9.CO.54.157; 9.CO.54.158;
9.CO.54.196; 9.CO.54.223; 9.CO.54.240; 9.CO.54.244; 9.CO.54.243;
9.CO.54.247; 9.CO.55.157; 9.CO.55.158; 9.CO.55.196; 9.CO.55.223;
9.CO.55.240; 9.CO.55.244; 9.CO.55.243; 9.CO.55.247; 9.CO.56.157;
9.CO.56.158; 9.CO.56.196; 9.CO.56.223; 9.CO.56.240; 9.CO.56.244;
9.CO.56.243; 9.CO.56.247; 9.CO.157.157; 9.CO.157.158; 9.CO.157.196;
9.CO.157.223; 9.CO.157.240; 9.CO.157.244; 9.CO.157.243; 9.CO.157.247;
9.CO.196.157; 9.CO.196.158; 9.CO.196.196; 9.CO.196.223; 9.CO.196.240;
9.CO.196.244; 9.CO.196.243; 9.CO.196.247; 9.CO.223.157; 9.CO.223.158;
9.CO.223.196; 9.CO.223.223; 9.CO.223.240; 9.CO.223.244; 9.CO.223.243;
9.CO.223.247; 9.CO.240.157; 9.CO.240.158; 9.CO.240.196; 9.CO.240.223;
9.CO.240.240; 9.CO.240.244; 9.CO.240.243; 9.CO.240.247; 9.CO.244.157;
9.CO.244.158; 9.CO.244.196; 9.CO.244.223; 9.CO.244.240; 9.CO.244.244;
9.CO.244.243; 9.CO.244.247; 9.CO.247.157; 9.CO.247.158; 9.CO.247.196;
9.CO.247.223; 9.CO.247.240; 9.CO.247.244; 9.CO.247.243; 9.CO.247.247;
Prodrugs of 10.AH 10.AH.4.157; 10.AH.4.158; 10.AH.4.196; 10.AH.4.223; 10.AH.4.240;
10.AH.4.244; 10.AH.4.243; 10.AH.4.247; 10.AH.5.157; 10.AH.5.158;
10.AH.5.196; 10.AH.5.223; 10.AH.5.240; 10.AH.5.244; 10.AH.5.243;
10.AH.5.247; 10.AH.7.157; 10.AH.7.158; 10.AH.7.196; 10.AH.7.223;
10.AH.7.240; 10.AH.7.244; 10.AH.7.243; 10.AH.7.247; 10.AH.15.157;
10.AH.15.158; 10.AH.15.196; 10.AH.15.223; 10.AH.15.240; 10.AH.15.244;
10.AH.15.243; 10.AH.15.247; 10.AH.16.157; 10.AH.16.158; 10.AH.16.196;
10.AH.16.223; 10.AH.16.240; 10.AH.16.244; 10.AH.16.243; 10.AH.16.247;
10.AH.18.157; 10.AH.18.158; 10.AH.18.196; 10.AH.18.223; 10.AH.18.240;
10.AH.18.244; 10.AH.18.243; 10.AH.18.247; 10.AH.26.157; 10.AH.26.158;
10.AH.26.196; 10.AH.26.223; 10.AH.26.240; 10.AH.26.244; 10.AH.26.243;
10.AH.26.247; 10.AH.27.157; 10.AH.27.158; 10.AH.27.196; 10.AH.27.223;
10.AH.27.240; 10.AH.27.244; 10.AH.27.243; 10.AH.27.247; 10.AH.29.157;
10.AH.29.158; 10.AH.29.196; 10.AH.29.223; 10.AH.29.240; 10.AH.29.244;
10.AH.29.243; 10.AH.29.247; 10.AH.54.157; 10.AH.54.158; 10.AH.54.196;
10.AH.54.223; 10.AH.54.240; 10.AH.54.244; 10.AH.54.243; 10.AH.54.247;
10.AH.55.157; 10.AH.55.158; 10.AH.55.196; 10.AH.55.223; 10.AH.55.240;
10.AH.55.244; 10.AH.55.243; 10.AH.55.247; 10.AH.56.157; 10.AH.56.158;
10.AH.56.196; 10.AH.56.223; 10.AH.56.240; 10.AH.56.244; 10.AH.56.243;
10.AH.56.247; 10.AH.157.157; 10.AH.157.158; 10.AH.157.196;
10.AH.157.223; 10.AH.157.240; 10.AH.157.244; 10.AH.157.243;
10.AH.157.247; 10.AH.196.157; 10.AH.196.158; 10.AH.196.196;
10.AH.196.223; 10.AH.196.240; 10.AH.196.244; 10.AH.196.243;
10.AH.196.247; 10.AH.223.157; 10.AH.223.158; 10.AH.223.196;
10.AH.223.223; 10.AH.223.240; 10.AH.223.244; 10.AH.223.243;
10.AH.223.247; 10.AH.240.157; 10.AH.240.158; 10.AH.240.196;
10.AH.240.223; 10.AH.240.240; 10.AH.240.244; 10.AH.240.243;
10.AH.240.247; 10.AH.244.157; 10.AH.244.158; 10.AH.244.196;
10.AH.244.223; 10.AH.244.240; 10.AH.244.244; 10.AH.244.243;
10.AH.244.247; 10.AH.247.157; 10.AH.247.158; 10.AH.247.196;
10.AH.247.223; 10.AH.247.240; 10.AH.247.244; 10.AH.247.243;
10.AH.247.247;
Prodrugs of 10.AJ 10.AJ.4.157; 10.AJ.4.158; 10.AJ.4.196; 10.AJ.4.223; 10.AJ.4.240;
10.AJ.4.244; 10.AJ.4.243; 10.AJ.4.247; 10.AJ.5.157; 10.AJ.5.158; 10.AJ.5.196;
10.AJ.5.223; 10.AJ.5.240; 10.AJ.5.244; 10.AJ.5.243; 10.AJ.5.247; 10.AJ.7.157;
10.AJ.7.158; 10.AJ.7.196; 10.AJ.7.223; 10.AJ.7.240; 10.AJ.7.244; 10.AJ.7.243;
10.AJ.7.247; 10.AJ.15.157; 10.AJ.15.158; 10.AJ.15.196; 10.AJ.15.223;
10.AJ.15.240; 10.AJ.15.244; 10.AJ.15.243; 10.AJ.15.247; 10.AJ.16.157;
10.AJ.16.158; 10.AJ.16.196; 10.AJ.16.223; 10.AJ.16.240; 10.AJ.16.244;
10.AJ.16.243; 10.AJ.16.247; 10.AJ.18.157; 10.AJ.18.158; 10.AJ.18.196;
10.AJ.18.223; 10.AJ.18.240; 10.AJ.18.244; 10.AJ.18.243; 10.AJ.18.247;
10.AJ.26.157; 10.AJ.26.158; 10.AJ.26.196; 10.AJ.26.223; 10.AJ.26.240;

TABLE 100-continued

10.AJ.26.244; 10.AJ.26.243; 10.AJ.26.247; 10.AJ.27.157; 10.AJ.27.158;
10.AJ.27.196; 10.AJ.27.223; 10.AJ.27.240; 10.AJ.27.244; 10.AJ.27.243;
10.AJ.27.247; 10.AJ.29.157; 10.AJ.29.158; 10.AJ.29.196; 10.AJ.29.223;
10.AJ.29.240; 10.AJ.29.244; 10.AJ.29.243; 10.AJ.29.247; 10.AJ.54.157;
10.AJ.54.158; 10.AJ.54.196; 10.AJ.54.223; 10.AJ.54.240; 10.AJ.54.244;
10.AJ.54.243; 10.AJ.54.247; 10.AJ.55.157; 10.AJ.55.158; 10.AJ.55.196;
10.AJ.55.223; 10.AJ.55.240; 10.AJ.55.244; 10.AJ.55.243; 10.AJ.55.247;
10.AJ.56.157; 10.AJ.56.158; 10.AJ.56.196; 10.AJ.56.223; 10.AJ.56.240;
10.AJ.56.244; 10.AJ.56.243; 10.AJ.56.247; 10.AJ.157.157; 10.AJ.157.158;
10.AJ.157.196; 10.AJ.157.223; 10.AJ.157.240; 10.AJ.157.244; 10.AJ.157.243;
10.AJ.157.247; 10.AJ.196.157; 10.AJ.196.158; 10.AJ.196.196; 10.AJ.196.223;
10.AJ.196.240; 10.AJ.196.244; 10.AJ.196.243; 10.AJ.196.247; 10.AJ.223.157;
10.AJ.223.158; 10.AJ.223.196; 10.AJ.223.223; 10.AJ.223.240; 10.AJ.223.244;
10.AJ.223.243; 10.AJ.223.247; 10.AJ.240.157; 10.AJ.240.158; 10.AJ.240.196;
10.AJ.240.223; 10.AJ.240.240; 10.AJ.240.244; 10.AJ.240.243; 10.AJ.240.247;
10.AJ.244.157; 10.AJ.244.158; 10.AJ.244.196; 10.AJ.244.223; 10.AJ.244.240;
10.AJ.244.244; 10.AJ.244.243; 10.AJ.244.247; 10.AJ.247.157; 10.AJ.247.158;
10.AJ.247.196; 10.AJ.247.223; 10.AJ.247.240; 10.AJ.247.244; 10.AJ.247.243;
10.AJ.247.247;
Prodrugs of 10.AN 10.AN.4.157; 10.AN.4.158; 10.AN.4.196; 10.AN.4.223; 10.AN.4.240;
10.AN.4.244; 10.AN.4.243; 10.AN.4.247; 10.AN.5.157; 10.AN.5.158;
10.AN.5.196; 10.AN.5.223; 10.AN.5.240; 10.AN.5.244; 10.AN.5.243;
10.AN.5.247; 10.AN.7.157; 10.AN.7.158; 10.AN.7.196; 10.AN.7.223;
10.AN.7.240; 10.AN.7.244; 10.AN.7.243; 10.AN.7.247; 10.AN.15.157;
10.AN.15.158; 10.AN.15.196; 10.AN.15.223; 10.AN.15.240; 10.AN.15.244;
10.AN.15.243; 10.AN.15.247; 10.AN.16.157; 10.AN.16.158; 10.AN.16.196;
10.AN.16.223; 10.AN.16.240; 10.AN.16.244; 10.AN.16.243; 10.AN.16.247;
10.AN.18.157; 10.AN.18.158; 10.AN.18.196; 10.AN.18.223; 10.AN.18.240;
10.AN.18.244; 10.AN.18.243; 10.AN.18.247; 10.AN.26.157; 10.AN.26.158;
10.AN.26.196; 10.AN.26.223; 10.AN.26.240; 10.AN.26.244; 10.AN.26.243;
10.AN.26.247; 10.AN.27.157; 10.AN.27.158; 10.AN.27.196; 10.AN.27.223;
10.AN.27.240; 10.AN.27.244; 10.AN.27.243; 10.AN.27.247; 10.AN.29.157;
10.AN.29.158; 10.AN.29.196; 10.AN.29.223; 10.AN.29.240; 10.AN.29.244;
10.AN.29.243; 10.AN.29.247; 10.AN.54.157; 10.AN.54.158; 10.AN.54.196;
10.AN.54.223; 10.AN.54.240; 10.AN.54.244; 10.AN.54.243; 10.AN.54.247;
10.AN.55.157; 10.AN.55.158; 10.AN.55.196; 10.AN.55.223; 10.AN.55.240;
10.AN.55.244; 10.AN.55.243; 10.AN.55.247; 10.AN.56.157; 10.AN.56.158;
10.AN.56.196; 10.AN.56.223; 10.AN.56.240; 10.AN.56.244; 10.AN.56.243;
10.AN.56.247; 10.AN.157.157; 10.AN.157.158; 10.AN.157.196;
10.AN.157.223; 10.AN.157.240; 10.AN.157.244; 10.AN.157.243;
10.AN.157.247; 10.AN.196.157; 10.AN.196.158; 10.AN.196.196;
10.AN.196.223; 10.AN.196.240; 10.AN.196.244; 10.AN.196.243;
10.AN.196.247; 10.AN.223.157; 10.AN.223.158; 10.AN.223.196;
10.AN.223.223; 10.AN.223.240; 10.AN.223.244; 10.AN.223.243;
10.AN.223.247; 10.AN.240.157; 10.AN.240.158; 10.AN.240.196;
10.AN.240.223; 10.AN.240.240; 10.AN.240.244; 10.AN.240.243;
10.AN.240.247; 10.AN.244.157; 10.AN.244.158; 10.AN.244.196;
10.AN.244.223; 10.AN.244.240; 10.AN.244.244; 10.AN.244.243;
10.AN.244.247; 10.AN.247.157; 10.AN.247.158; 10.AN.247.196;
10.AN.247.223; 10.AN.247.240; 10.AN.247.244; 10.AN.247.243;
10.AN.247.247;
Prodrugs of 10.AP 10.AP.4.157; 10.AP.4.158; 10.AP.4.196; 10.AP.4.223; 10.AP.4.240;
10.AP.4.244; 10.AP.4.243; 10.AP.4.247; 10.AP.5.157; 10.AP.5.158;
10.AP.5.196; 10.AP.5.223; 10.AP.5.240; 10.AP.5.244; 10.AP.5.243;
10.AP.5.247; 10.AP.7.157; 10.AP.7.158; 10.AP.7.196; 10.AP.7.223;
10.AP.7.240; 10.AP.7.244; 10.AP.7.243; 10.AP.7.247; 10.AP.15.157;
10.AP.15.158; 10.AP.15.196; 10.AP.15.223; 10.AP.15.240; 10.AP.15.244;
10.AP.15.243; 10.AP.15.247; 10.AP.16.157; 10.AP.16.158; 10.AP.16.196;
10.AP.16.223; 10.AP.16.240; 10.AP.16.244; 10.AP.16.243; 10.AP.16.247;
10.AP.18.157; 10.AP.18.158; 10.AP.18.196; 10.AP.18.223; 10.AP.18.240;
10.AP.18.244; 10.AP.18.243; 10.AP.18.247; 10.AP.26.157; 10.AP.26.158;
10.AP.26.196; 10.AP.26.223; 10.AP.26.240; 10.AP.26.244; 10.AP.26.243;
10.AP.26.247; 10.AP.27.157; 10.AP.27.158; 10.AP.27.196; 10.AP.27.223;
10.AP.27.240; 10.AP.27.244; 10.AP.27.243; 10.AP.27.247; 10.AP.29.157;
10.AP.29.158; 10.AP.29.196; 10.AP.29.223; 10.AP.29.240; 10.AP.29.244;
10.AP.29.243; 10.AP.29.247; 10.AP.54.157; 10.AP.54.158; 10.AP.54.196;
10.AP.54.223; 10.AP.54.240; 10.AP.54.244; 10.AP.54.243; 10.AP.54.247;
10.AP.55.157; 10.AP.55.158; 10.AP.55.196; 10.AP.55.223; 10.AP.55.240;
10.AP.55.244; 10.AP.55.243; 10.AP.55.247; 10.AP.56.157; 10.AP.56.158;
10.AP.56.196; 10.AP.56.223; 10.AP.56.240; 10.AP.56.244; 10.AP.56.243;
10.AP.56.247; 10.AP.157.157; 10.AP.157.158; 10.AP.157.196; 10.AP.157.223;
10.AP.157.240; 10.AP.157.244; 10.AP.157.243; 10.AP.157.247;
10.AP.196.157; 10.AP.196.158; 10.AP.196.196; 10.AP.196.223;
10.AP.196.240; 10.AP.196.244; 10.AP.196.243; 10.AP.196.247;
10.AP.223.157; 10.AP.223.158; 10.AP.223.196; 10.AP.223.223;

TABLE 100-continued

10.AP.223.240; 10.AP.223.244; 10.AP.223.243; 10.AP.223.247;
10.AP.240.157; 10.AP.240.158; 10.AP.240.196; 10.AP.240.223;
10.AP.240.240; 10.AP.240.244; 10.AP.240.243; 10.AP.240.247;
10.AP.244.157; 10.AP.244.158; 10.AP.244.196; 10.AP.244.223;
10.AP.244.240; 10.AP.244.244; 10.AP.244.243; 10.AP.244.247;
10.AP.247.157; 10.AP.247.158; 10.AP.247.196; 10.AP.247.223;
10.AP.247.240; 10.AP.247.244; 10.AP.247.243; 10.AP.247.247;
Prodrugs of 10.AZ 10.AZ.4.157; 10.AZ.4.158; 10.AZ.4.196; 10.AZ.4.223; 10.AZ.4.240;
10.AZ.4.244; 10.AZ.4.243; 10.AZ.4.247; 10.AZ.5.157; 10.AZ.5.158;
10.AZ.5.196; 10.AZ.5.223; 10.AZ.5.240; 10.AZ.5.244; 10.AZ.5.243;
10.AZ.5.247; 10.AZ.7.157; 10.AZ.7.158; 10.AZ.7.196; 10.AZ.7.223;
10.AZ.7.240; 10.AZ.7.244; 10.AZ.7.243; 10.AZ.7.247; 10.AZ.15.157;
10.AZ.15.158; 10.AZ.15.196; 10.AZ.15.223; 10.AZ.15.240; 10.AZ.15.244;
10.AZ.15.243; 10.AZ.15.247; 10.AZ.16.157; 10.AZ.16.158; 10.AZ.16.196;
10.AZ.16.223; 10.AZ.16.240; 10.AZ.16.244; 10.AZ.16.243; 10.AZ.16.247;
10.AZ.18.157; 10.AZ.18.158; 10.AZ.18.196; 10.AZ.18.223; 10.AZ.18.240;
10.AZ.18.244; 10.AZ.18.243; 10.AZ.18.247; 10.AZ.26.157; 10.AZ.26.158;
10.AZ.26.196; 10.AZ.26.223; 10.AZ.26.240; 10.AZ.26.244; 10.AZ.26.243;
10.AZ.26.247; 10.AZ.27.157; 10.AZ.27.158; 10.AZ.27.196; 10.AZ.27.223;
10.AZ.27.240; 10.AZ.27.244; 10.AZ.27.243; 10.AZ.27.247; 10.AZ.29.157;
10.AZ.29.158; 10.AZ.29.196; 10.AZ.29.223; 10.AZ.29.240; 10.AZ.29.244;
10.AZ.29.243; 10.AZ.29.247; 10.AZ.54.157; 10.AZ.54.158; 10.AZ.54.196;
10.AZ.54.223; 10.AZ.54.240; 10.AZ.54.244; 10.AZ.54.243; 10.AZ.54.247;
10.AZ.55.157; 10.AZ.55.158; 10.AZ.55.196; 10.AZ.55.223; 10.AZ.55.240;
10.AZ.55.244; 10.AZ.55.243; 10.AZ.55.247; 10.AZ.56.157; 10.AZ.56.158;
10.AZ.56.196; 10.AZ.56.223; 10.AZ.56.240; 10.AZ.56.244; 10.AZ.56.243;
10.AZ.56.247; 10.AZ.157.157; 10.AZ.157.158; 10.AZ.157.196; 10.AZ.157.223;
10.AZ.157.240; 10.AZ.157.244; 10.AZ.157.243; 10.AZ.157.247;
10.AZ.196.157; 10.AZ.196.158; 10.AZ.196.196; 10.AZ.196.223;
10.AZ.196.240; 10.AZ.196.244; 10.AZ.196.243; 10.AZ.196.247;
10.AZ.223.157; 10.AZ.223.158; 10.AZ.223.196; 10.AZ.223.223;
10.AZ.223.240; 10.AZ.223.244; 10.AZ.223.243; 10.AZ.223.247;
10.AZ.240.157; 10.AZ.240.158; 10.AZ.240.196; 10.AZ.240.223;
10.AZ.240.240; 10.AZ.240.244; 10.AZ.240.243; 10.AZ.240.247;
10.AZ.244.157; 10.AZ.244.158; 10.AZ.244.196; 10.AZ.244.223;
10.AZ.244.240; 10.AZ.244.244; 10.AZ.244.243; 10.AZ.244.247;
10.AZ.247.157; 10.AZ.247.158; 10.AZ.247.196; 10.AZ.247.223;
10.AZ.247.240; 10.AZ.247.244; 10.AZ.247.243; 10.AZ.247.247;
Prodrugs of 10.BF 10.BF.4.157; 10.BF.4.158; 10.BF.4.196; 10.BF.4.223; 10.BF.4.240;
10.BF.4.244; 10.BF.4.243; 10.BF.4.247; 10.BF.5.157; 10.BF.5.158;
10.BF.5.196; 10.BF.5.223; 10.BF.5.240; 10.BF.5.244; 10.BF.5.243;
10.BF.5.247; 10.BF.7.157; 10.BF.7.158; 10.BF.7.196; 10.BF.7.223;
10.BF.7.240; 10.BF.7.244; 10.BF.7.243; 10.BF.7.247; 10.BF.15.157;
10.BF.15.158; 10.BF.15.196; 10.BF.15.223; 10.BF.15.240; 10.BF.15.244;
10.BF.15.243; 10.BF.15.247; 10.BF.16.157; 10.BF.16.158; 10.BF.16.196;
10.BF.16.223; 10.BF.16.240; 10.BF.16.244; 10.BF.16.243; 10.BF.16.247;
10.BF.18.157; 10.BF.18.158; 10.BF.18.196; 10.BF.18.223; 10.BF.18.240;
10.BF.18.244; 10.BF.18.243; 10.BF.18.247; 10.BF.26.157; 10.BF.26.158;
10.BF.26.196; 10.BF.26.223; 10.BF.26.240; 10.BF.26.244; 10.BF.26.243;
10.BF.26.247; 10.BF.27.157; 10.BF.27.158; 10.BF.27.196; 10.BF.27.223;
10.BF.27.240; 10.BF.27.244; 10.BF.27.243; 10.BF.27.247; 10.BF.29.157;
10.BF.29.158; 10.BF.29.196; 10.BF.29.223; 10.BF.29.240; 10.BF.29.244;
10.BF.29.243; 10.BF.29.247; 10.BF.54.157; 10.BF.54.158; 10.BF.54.196;
10.BF.54.223; 10.BF.54.240; 10.BF.54.244; 10.BF.54.243; 10.BF.54.247;
10.BF.55.157; 10.BF.55.158; 10.BF.55.196; 10.BF.55.223; 10.BF.55.240;
10.BF.55.244; 10.BF.55.243; 10.BF.55.247; 10.BF.56.157; 10.BF.56.158;
10.BF.56.196; 10.BF.56.223; 10.BF.56.240; 10.BF.56.244; 10.BF.56.243;
10.BF.56.247; 10.BF.157.157; 10.BF.157.158; 10.BF.157.196; 10.BF.157.223;
10.BF.157.240; 10.BF.157.244; 10.BF.157.243; 10.BF.157.247; 10.BF.196.157;
10.BF.196.158; 10.BF.196.196; 10.BF.196.223; 10.BF.196.240; 10.BF.196.244;
10.BF.196.243; 10.BF.196.247; 10.BF.223.157; 10.BF.223.158; 10.BF.223.196;
10.BF.223.223; 10.BF.223.240; 10.BF.223.244; 10.BF.223.243; 10.BF.223.247;
10.BF.240.157; 10.BF.240.158; 10.BF.240.196; 10.BF.240.223; 10.BF.240.240;
10.BF.240.244; 10.BF.240.243; 10.BF.240.247; 10.BF.244.157; 10.BF.244.158;
10.BF.244.196; 10.BF.244.223; 10.BF.244.240; 10.BF.244.244; 10.BF.244.243;
10.BF.244.247; 10.BF.247.157; 10.BF.247.158; 10.BF.247.196; 10.BF.247.223;
10.BF.247.240; 10.BF.247.244; 10.BF.247.243; 10.BF.247.247;
Prodrugs of 10.CI 10.CI.4.157; 10.CI.4.158; 10.CI.4.196; 10.CI.4.223; 10.CI.4.240;
10.CI.4.244; 10.CI.4.243; 10.CI.4.247; 10.CI.5.157; 10.CI.5.158; 10.CI.5.196;
10.CI.5.223; 10.CI.5.240; 10.CI.5.244; 10.CI.5.243; 10.CI.5.247; 10.CI.7.157;
10.CI.7.158; 10.CI.7.196; 10.CI.7.223; 10.CI.7.240; 10.CI.7.244; 10.CI.7.243;
10.CI.7.247; 10.CI.15.157; 10.CI.15.158; 10.CI.15.196; 10.CI.15.223;
10.CI.15.240; 10.CI.15.244; 10.CI.15.243; 10.CI.15.247; 10.CI.16.157;

TABLE 100-continued

10.CI.16.158; 10.CI.16.196; 10.CI.16.223; 10.CI.16.240; 10.CI.16.244;
10.CI.16.243; 10.CI.16.247; 10.CI.18.157; 10.CI.18.158; 10.CI.18.196;
10.CI.18.223; 10.CI.18.240; 10.CI.18.244; 10.CI.18.243; 10.CI.18.247;
10.CI.26.157; 10.CI.26.158; 10.CI.26.196; 10.CI.26.223; 10.CI.26.240;
10.CI.26.244; 10.CI.26.243; 10.CI.26.247; 10.CI.27.157; 10.CI.27.158;
10.CI.27.196; 10.CI.27.223; 10.CI.27.240; 10.CI.27.244; 10.CI.27.243;
10.CI.27.247; 10.CI.29.157; 10.CI.29.158; 10.CI.29.196; 10.CI.29.223;
10.CI.29.240; 10.CI.29.244; 10.CI.29.243; 10.CI.29.247; 10.CI.54.157;
10.CI.54.158; 10.CI.54.196; 10.CI.54.223; 10.CI.54.240; 10.CI.54.244;
10.CI.54.243; 10.CI.54.247; 10.CI.55.157; 10.CI.55.158; 10.CI.55.196;
10.CI.55.223; 10.CI.55.240; 10.CI.55.244; 10.CI.55.243; 10.CI.55.247;
10.CI.56.157; 10.CI.56.158; 10.CI.56.196; 10.CI.56.223; 10.CI.56.240;
10.CI.56.244; 10.CI.56.243; 10.CI.56.247; 10.CI.157.157; 10.CI.157.158;
10.CI.157.196; 10.CI.157.223; 10.CI.157.240; 10.CI.157.244; 10.CI.157.243;
10.CI.157.247; 10.CI.196.157; 10.CI.196.158; 10.CI.196.196; 10.CI.196.223;
10.CI.196.240; 10.CI.196.244; 10.CI.196.243; 10.CI.196.247; 10.CI.223.157;
10.CI.223.158; 10.CI.223.196; 10.CI.223.223; 10.CI.223.240; 10.CI.223.244;
10.CI.223.243; 10.CI.223.247; 10.CI.240.157; 10.CI.240.158; 10.CI.240.196;
10.CI.240.223; 10.CI.240.240; 10.CI.240.244; 10.CI.240.243; 10.CI.240.247;
10.CI.244.157; 10.CI.244.158; 10.CI.244.196; 10.CI.244.223; 10.CI.244.240;
10.CI.244.244; 10.CI.244.243; 10.CI.244.247; 10.CI.247.157; 10.CI.247.158;
10.CI.247.196; 10.CI.247.223; 10.CI.247.240; 10.CI.247.244; 10.CI.247.243;
10.CI.247.247;
Prodrugs of 10.CO 10.CO.4.157; 10.CO.4.158; 10.CO.4.196; 10.CO.4.223; 10.CO.4.240;
10.CO.4.244; 10.CO.4.243; 10.CO.4.247; 10.CO.5.157; 10.CO.5.158;
10.CO.5.196; 10.CO.5.223; 10.CO.5.240; 10.CO.5.244; 10.CO.5.243;
10.CO.5.247; 10.CO.7.157; 10.CO.7.158; 10.CO.7.196; 10.CO.7.223;
10.CO.7.240; 10.CO.7.244; 10.CO.7.243; 10.CO.7.247; 10.CO.15.157;
10.CO.15.158; 10.CO.15.196; 10.CO.15.223; 10.CO.15.240; 10.CO.15.244;
10.CO.15.243; 10.CO.15.247; 10.CO.16.157; 10.CO.16.158; 10.CO.16.196;
10.CO.16.223; 10.CO.16.240; 10.CO.16.244; 10.CO.16.243; 10.CO.16.247;
10.CO.18.157; 10.CO.18.158; 10.CO.18.196; 10.CO.18.223; 10.CO.18.240;
10.CO.18.244; 10.CO.18.243; 10.CO.18.247; 10.CO.26.157; 10.CO.26.158;
10.CO.26.196; 10.CO.26.223; 10.CO.26.240; 10.CO.26.244; 10.CO.26.243;
10.CO.26.247; 10.CO.27.157; 10.CO.27.158; 10.CO.27.196; 10.CO.27.223;
10.CO.27.240; 10.CO.27.244; 10.CO.27.243; 10.CO.27.247; 10.CO.29.157;
10.CO.29.158; 10.CO.29.196; 10.CO.29.223; 10.CO.29.240; 10.CO.29.244;
10.CO.29.243; 10.CO.29.247; 10.CO.54.157; 10.CO.54.158; 10.CO.54.196;
10.CO.54.223; 10.CO.54.240; 10.CO.54.244; 10.CO.54.243; 10.CO.54.247;
10.CO.55.157; 10.CO.55.158; 10.CO.55.196; 10.CO.55.223; 10.CO.55.240;
10.CO.55.244; 10.CO.55.243; 10.CO.55.247; 10.CO.56.157; 10.CO.56.158;
10.CO.56.196; 10.CO.56.223; 10.CO.56.240; 10.CO.56.244; 10.CO.56.243;
10.CO.56.247; 10.CO.157.157; 10.CO.157.158; 10.CO.157.196;
10.CO.157.223; 10.CO.157.240; 10.CO.157.244; 10.CO.157.243;
10.CO.157.247; 10.CO.196.157; 10.CO.196.158; 10.CO.196.196;
10.CO.196.223; 10.CO.196.240; 10.CO.196.244; 10.CO.196.243;
10.CO.196.247; 10.CO.223.157; 10.CO.223.158; 10.CO.223.196;
10.CO.223.223; 10.CO.223.240; 10.CO.223.244; 10.CO.223.243;
10.CO.223.247; 10.CO.240.157; 10.CO.240.158; 10.CO.240.196;
10.CO.240.223; 10.CO.240.240; 10.CO.240.244; 10.CO.240.243;
10.CO.240.247; 10.CO.244.157; 10.CO.244.158; 10.CO.244.196;
10.CO.244.223; 10.CO.244.240; 10.CO.244.244; 10.CO.244.243;
10.CO.244.247; 10.CO.247.157; 10.CO.247.158; 10.CO.247.196;
10.CO.247.223; 10.CO.247.240; 10.CO.247.244; 10.CO.247.243;
10.CO.247.247;
Prodrugs of 11.AH 11.AH.4.157; 11.AH.4.158; 11.AH.4.196; 11.AH.4.223; 11.AH.4.240;
11.AH.4.244; 11.AH.4.243; 11.AH.4.247; 11.AH.5.157; 11.AH.5.158;
11.AH.5.196; 11.AH.5.223; 11.AH.5.240; 11.AH.5.244; 11.AH.5.243;
11.AH.5.247; 11.AH.7.157; 11.AH.7.158; 11.AH.7.196; 11.AH.7.223;
11.AH.7.240; 11.AH.7.244; 11.AH.7.243; 11.AH.7.247; 11.AH.15.157;
11.AH.15.158; 11.AH.15.196; 11.AH.15.223; 11.AH.15.240; 11.AH.15.244;
11.AH.15.243; 11.AH.15.247; 11.AH.16.157; 11.AH.16.158; 11.AH.16.196;
11.AH.16.223; 11.AH.16.240; 11.AH.16.244; 11.AH.16.243; 11.AH.16.247;
11.AH.18.157; 11.AH.18.158; 11.AH.18.196; 11.AH.18.223; 11.AH.18.240;
11.AH.18.244; 11.AH.18.243; 11.AH.18.247; 11.AH.26.157; 11.AH.26.158;
11.AH.26.196; 11.AH.26.223; 11.AH.26.240; 11.AH.26.244; 11.AH.26.243;
11.AH.26.247; 11.AH.27.157; 11.AH.27.158; 11.AH.27.196; 11.AH.27.223;
11.AH.27.240; 11.AH.27.244; 11.AH.27.243; 11.AH.27.247; 11.AH.29.157;
11.AH.29.158; 11.AH.29.196; 11.AH.29.223; 11.AH.29.240; 11.AH.29.244;
11.AH.29.243; 11.AH.29.247; 11.AH.54.157; 11.AH.54.158; 11.AH.54.196;
11.AH.54.223; 11.AH.54.240; 11.AH.54.244; 11.AH.54.243; 11.AH.54.247;
11.AH.55.157; 11.AH.55.158; 11.AH.55.196; 11.AH.55.223; 11.AH.55.240;
11.AH.55.244; 11.AH.55.243; 11.AH.55.247; 11.AH.56.157; 11.AH.56.158;
11.AH.56.196; 11.AH.56.223; 11.AH.56.240; 11.AH.56.244; 11.AH.56.243;
11.AH.56.247; 11.AH.157.157; 11.AH.157.158; 11.AH.157.196;

TABLE 100-continued

11.AH.157.223; 11.AH.157.240; 11.AH.157.244; 11.AH.157.243;
11.AH.157.247; 11.AH.196.157; 11.AH.196.158; 11.AH.196.196;
11.AH.196.223; 11.AH.196.240; 11.AH.196.244; 11.AH.196.243;
11.AH.196.247; 11.AH.223.157; 11.AH.223.158; 11.AH.223.196;
11.AH.223.223; 11.AH.223.240; 11.AH.223.244; 11.AH.223.243;
11.AH.223.247; 11.AH.240.157; 11.AH.240.158; 11.AH.240.196;
11.AH.240.223; 11.AH.240.240; 11.AH.240.244; 11.AH.240.243;
11.AH.240.247; 11.AH.244.157; 11.AH.244.158; 11.AH.244.196;
11.AH.244.223; 11.AH.244.240; 11.AH.244.244; 11.AH.244.243;
11.AH.244.247; 11.AH.247.157; 11.AH.247.158; 11.AH.247.196;
11.AH.247.223; 11.AH.247.240; 11.AH.247.244; 11.AH.247.243;
11.AH.247.247;
Prodrugs of 11.AJ 11.AJ.4.157; 11.AJ.4.158; 11.AJ.4.196; 11.AJ.4.223; 11.AJ.4.240;
11.AJ.4.244; 11.AJ.4.243; 11.AJ.4.247; 11.AJ.5.157; 11.AJ.5.158; 11.AJ.5.196;
11.AJ.5.223; 11.AJ.5.240; 11.AJ.5.244; 11.AJ.5.243; 11.AJ.5.247; 11.AJ.7.157;
11.AJ.7.158; 11.AJ.7.196; 11.AJ.7.223; 11.AJ.7.240; 11.AJ.7.244; 11.AJ.7.243;
11.AJ.7.247; 11.AJ.15.157; 11.AJ.15.158; 11.AJ.15.196; 11.AJ.15.223;
11.AJ.15.240; 11.AJ.15.244; 11.AJ.15.243; 11.AJ.15.247; 11.AJ.16.157;
11.AJ.16.158; 11.AJ.16.196; 11.AJ.16.223; 11.AJ.16.240; 11.AJ.16.244;
11.AJ.16.243; 11.AJ.16.247; 11.AJ.18.157; 11.AJ.18.158; 11.AJ.18.196;
11.AJ.18.223; 11.AJ.18.240; 11.AJ.18.244; 11.AJ.18.243; 11.AJ.18.247;
11.AJ.26.157; 11.AJ.26.158; 11.AJ.26.196; 11.AJ.26.223; 11.AJ.26.240;
11.AJ.26.244; 11.AJ.26.243; 11.AJ.26.247; 11.AJ.27.157; 11.AJ.27.158;
11.AJ.27.196; 11.AJ.27.223; 11.AJ.27.240; 11.AJ.27.244; 11.AJ.27.243;
11.AJ.27.247; 11.AJ.29.157; 11.AJ.29.158; 11.AJ.29.196; 11.AJ.29.223;
11.AJ.29.240; 11.AJ.29.244; 11.AJ.29.243; 11.AJ.29.247; 11.AJ.54.157;
11.AJ.54.158; 11.AJ.54.196; 11.AJ.54.223; 11.AJ.54.240; 11.AJ.54.244;
11.AJ.54.243; 11.AJ.54.247; 11.AJ.55.157; 11.AJ.55.158; 11.AJ.55.196;
11.AJ.55.223; 11.AJ.55.240; 11.AJ.55.244; 11.AJ.55.243; 11.AJ.55.247;
11.AJ.56.157; 11.AJ.56.158; 11.AJ.56.196; 11.AJ.56.223; 11.AJ.56.240;
11.AJ.56.244; 11.AJ.56.243; 11.AJ.56.247; 11.AJ.157.157; 11.AJ.157.158;
11.AJ.157.196; 11.AJ.157.223; 11.AJ.157.240; 11.AJ.157.244; 11.AJ.157.243;
11.AJ.157.247; 11.AJ.196.157; 11.AJ.196.158; 11.AJ.196.196; 11.AJ.196.223;
11.AJ.196.240; 11.AJ.196.244; 11.AJ.196.243; 11.AJ.196.247; 11.AJ.223.157;
11.AJ.223.158; 11.AJ.223.196; 11.AJ.223.223; 11.AJ.223.240; 11.AJ.223.244;
11.AJ.223.243; 11.AJ.223.247; 11.AJ.240.157; 11.AJ.240.158; 11.AJ.240.196;
11.AJ.240.223; 11.AJ.240.240; 11.AJ.240.244; 11.AJ.240.243; 11.AJ.240.247;
11.AJ.244.157; 11.AJ.244.158; 11.AJ.244.196; 11.AJ.244.223; 11.AJ.244.240;
11.AJ.244.244; 11.AJ.244.243; 11.AJ.244.247; 11.AJ.247.157; 11.AJ.247.158;
11.AJ.247.196; 11.AJ.247.223; 11.AJ.247.240; 11.AJ.247.244; 11.AJ.247.243;
11.AJ.247.247;
Prodrugs of 11.AN 11.AN.4.157; 11.AN.4.158; 11.AN.4.196; 11.AN.4.223; 11.AN.4.240;
11.AN.4.244; 11.AN.4.243; 11.AN.4.247; 11.AN.5.157; 11.AN.5.158;
11.AN.5.196; 11.AN.5.223; 11.AN.5.240; 11.AN.5.244; 11.AN.5.243;
11.AN.5.247; 11.AN.7.157; 11.AN.7.158; 11.AN.7.196; 11.AN.7.223;
11.AN.7.240; 11.AN.7.244; 11.AN.7.243; 11.AN.7.247; 11.AN.15.157;
11.AN.15.158; 11.AN.15.196; 11.AN.15.223; 11.AN.15.240; 11.AN.15.244;
11.AN.15.243; 11.AN.15.247; 11.AN.16.157; 11.AN.16.158; 11.AN.16.196;
11.AN.16.223; 11.AN.16.240; 11.AN.16.244; 11.AN.16.243; 11.AN.16.247;
11.AN.18.157; 11.AN.18.158; 11.AN.18.196; 11.AN.18.223; 11.AN.18.240;
11.AN.18.244; 11.AN.18.243; 11.AN.18.247; 11.AN.26.157; 11.AN.26.158;
11.AN.26.196; 11.AN.26.223; 11.AN.26.240; 11.AN.26.244; 11.AN.26.243;
11.AN.26.247; 11.AN.27.157; 11.AN.27.158; 11.AN.27.196; 11.AN.27.223;
11.AN.27.240; 11.AN.27.244; 11.AN.27.243; 11.AN.27.247; 11.AN.29.157;
11.AN.29.158; 11.AN.29.196; 11.AN.29.223; 11.AN.29.240; 11.AN.29.244;
11.AN.29.243; 11.AN.29.247; 11.AN.54.157; 11.AN.54.158; 11.AN.54.196;
11.AN.54.223; 11.AN.54.240; 11.AN.54.244; 11.AN.54.243; 11.AN.54.247;
11.AN.55.157; 11.AN.55.158; 11.AN.55.196; 11.AN.55.223; 11.AN.55.240;
11.AN.55.244; 11.AN.55.243; 11.AN.55.247; 11.AN.56.157; 11.AN.56.158;
11.AN.56.196; 11.AN.56.223; 11.AN.56.240; 11.AN.56.244; 11.AN.56.243;
11.AN.56.247; 11.AN.157.157; 11.AN.157.158; 11.AN.157.196;
11.AN.157.223; 11.AN.157.240; 11.AN.157.244; 11.AN.157.243;
11.AN.157.247; 11.AN.196.157; 11.AN.196.158; 11.AN.196.196;
11.AN.196.223; 11.AN.196.240; 11.AN.196.244; 11.AN.196.243;
11.AN.196.247; 11.AN.223.157; 11.AN.223.158; 11.AN.223.196;
11.AN.223.223; 11.AN.223.240; 11.AN.223.244; 11.AN.223.243;
11.AN.223.247; 11.AN.240.157; 11.AN.240.158; 11.AN.240.196;
11.AN.240.223; 11.AN.240.240; 11.AN.240.244; 11.AN.240.243;
11.AN.240.247; 11.AN.244.157; 11.AN.244.158; 11.AN.244.196;
11.AN.244.223; 11.AN.244.240; 11.AN.244.244; 11.AN.244.243;
11.AN.244.247; 11.AN.247.157; 11.AN.247.158; 11.AN.247.196;
11.AN.247.223; 11.AN.247.240; 11.AN.247.244; 11.AN.247.243;
11.AN.247.247;

TABLE 100-continued

Prodrugs of 11.AP

11.AP.4.157; 11.AP.4.158; 11.AP.4.196; 11.AP.4.223; 11.AP.4.240;
11.AP.4.244; 11.AP.4.243; 11.AP.4.247; 11.AP.5.157; 11.AP.5.158;
11.AP.5.196; 11.AP.5.223; 11.AP.5.240; 11.AP.5.244; 11.AP.5.243;
11.AP.5.247; 11.AP.7.157; 11.AP.7.158; 11.AP.7.196; 11.AP.7.223;
11.AP.7.240; 11.AP.7.244; 11.AP.7.243; 11.AP.7.247; 11.AP.15.157;
11.AP.15.158; 11.AP.15.196; 11.AP.15.223; 11.AP.15.240; 11.AP.15.244;
11.AP.15.243; 11.AP.15.247; 11.AP.16.157; 11.AP.16.158; 11.AP.16.196;
11.AP.16.223; 11.AP.16.240; 11.AP.16.244; 11.AP.16.243; 11.AP.16.247;
11.AP.18.157; 11.AP.18.158; 11.AP.18.196; 11.AP.18.223; 11.AP.18.240;
11.AP.18.244; 11.AP.18.243; 11.AP.18.247; 11.AP.26.157; 11.AP.26.158;
11.AP.26.196; 11.AP.26.223; 11.AP.26.240; 11.AP.26.244; 11.AP.26.243;
11.AP.26.247; 11.AP.27.157; 11.AP.27.158; 11.AP.27.196; 11.AP.27.223;
11.AP.27.240; 11.AP.27.244; 11.AP.27.243; 11.AP.27.247; 11.AP.29.157;
11.AP.29.158; 11.AP.29.196; 11.AP.29.223; 11.AP.29.240; 11.AP.29.244;
11.AP.29.243; 11.AP.29.247; 11.AP.54.157; 11.AP.54.158; 11.AP.54.196;
11.AP.54.223; 11.AP.54.240; 11.AP.54.244; 11.AP.54.243; 11.AP.54.247;
11.AP.55.157; 11.AP.55.158; 11.AP.55.196; 11.AP.55.223; 11.AP.55.240;
11.AP.55.244; 11.AP.55.243; 11.AP.55.247; 11.AP.56.157; 11.AP.56.158;
11.AP.56.196; 11.AP.56.223; 11.AP.56.240; 11.AP.56.244; 11.AP.56.243;
11.AP.56.247; 11.AP.157.157; 11.AP.157.158; 11.AP.157.196; 11.AP.157.223;
11.AP.157.240; 11.AP.157.244; 11.AP.157.243; 11.AP.157.247;
11.AP.196.157; 11.AP.196.158; 11.AP.196.196; 11.AP.196.223;
11.AP.196.240; 11.AP.196.244; 11.AP.196.243; 11.AP.196.247;
11.AP.223.157; 11.AP.223.158; 11.AP.223.196; 11.AP.223.223;
11.AP.223.240; 11.AP.223.244; 11.AP.223.243; 11.AP.223.247;
11.AP.240.157; 11.AP.240.158; 11.AP.240.196; 11.AP.240.223;
11.AP.240.240; 11.AP.240.244; 11.AP.240.243; 11.AP.240.247;
11.AP.244.157; 11.AP.244.158; 11.AP.244.196; 11.AP.244.223;
11.AP.244.240; 11.AP.244.244; 11.AP.244.243; 11.AP.244.247;
11.AP.247.157; 11.AP.247.158; 11.AP.247.196; 11.AP.247.223;
11.AP.247.240; 11.AP.247.244; 11.AP.247.243; 11.AP.247.247;

Prodrugs of 11.AZ

11.AZ.4.157; 11.AZ.4.158; 11.AZ.4.196; 11.AZ.4.223; 11.AZ.4.240;
11.AZ.4.244; 11.AZ.4.243; 11.AZ.4.247; 11.AZ.5.157; 11.AZ.5.158;
11.AZ.5.196; 11.AZ.5.223; 11.AZ.5.240; 11.AZ.5.244; 11.AZ.5.243;
11.AZ.5.247; 11.AZ.7.157; 11.AZ.7.158; 11.AZ.7.196; 11.AZ.7.223;
11.AZ.7.240; 11.AZ.7.244; 11.AZ.7.243; 11.AZ.7.247; 11.AZ.15.157;
11.AZ.15.158; 11.AZ.15.196; 11.AZ.15.223; 11.AZ.15.240; 11.AZ.15.244;
11.AZ.15.243; 11.AZ.15.247; 11.AZ.16.157; 11.AZ.16.158; 11.AZ.16.196;
11.AZ.16.223; 11.AZ.16.240; 11.AZ.16.244; 11.AZ.16.243; 11.AZ.16.247;
11.AZ.18.157; 11.AZ.18.158; 11.AZ.18.196; 11.AZ.18.223; 11.AZ.18.240;
11.AZ.18.244; 11.AZ.18.243; 11.AZ.18.247; 11.AZ.26.157; 11.AZ.26.158;
11.AZ.26.196; 11.AZ.26.223; 11.AZ.26.240; 11.AZ.26.244; 11.AZ.26.243;
11.AZ.26.247; 11.AZ.27.157; 11.AZ.27.158; 11.AZ.27.196; 11.AZ.27.223;
11.AZ.27.240; 11.AZ.27.244; 11.AZ.27.243; 11.AZ.27.247; 11.AZ.29.157;
11.AZ.29.158; 11.AZ.29.196; 11.AZ.29.223; 11.AZ.29.240; 11.AZ.29.244;
11.AZ.29.243; 11.AZ.29.247; 11.AZ.54.157; 11.AZ.54.158; 11.AZ.54.196;
11.AZ.54.223; 11.AZ.54.240; 11.AZ.54.244; 11.AZ.54.243; 11.AZ.54.247;
11.AZ.55.157; 11.AZ.55.158; 11.AZ.55.196; 11.AZ.55.223; 11.AZ.55.240;
11.AZ.55.244; 11.AZ.55.243; 11.AZ.55.247; 11.AZ.56.157; 11.AZ.56.158;
11.AZ.56.196; 11.AZ.56.223; 11.AZ.56.240; 11.AZ.56.244; 11.AZ.56.243;
11.AZ.56.247; 11.AZ.157.157; 11.AZ.157.158; 11.AZ.157.196; 11.AZ.157.223;
11.AZ.157.240; 11.AZ.157.244; 11.AZ.157.243; 11.AZ.157.247;
11.AZ.196.157; 11.AZ.196.158; 11.AZ.196.196; 11.AZ.196.223;
11.AZ.196.240; 11.AZ.196.244; 11.AZ.196.243; 11.AZ.196.247;
11.AZ.223.157; 11.AZ.223.158; 11.AZ.223.196; 11.AZ.223.223;
11.AZ.223.240; 11.AZ.223.244; 11.AZ.223.243; 11.AZ.223.247;
11.AZ.240.157; 11.AZ.240.158; 11.AZ.240.196; 11.AZ.240.223;
11.AZ.240.240; 11.AZ.240.244; 11.AZ.240.243; 11.AZ.240.247;
11.AZ.244.157; 11.AZ.244.158; 11.AZ.244.196; 11.AZ.244.223;
11.AZ.244.240; 11.AZ.244.244; 11.AZ.244.243; 11.AZ.244.247;
11.AZ.247.157; 11.AZ.247.158; 11.AZ.247.196; 11.AZ.247.223;
11.AZ.247.240; 11.AZ.247.244; 11.AZ.247.243; 11.AZ.247.247;

Prodrugs of 11.BF

11.BF.4.157; 11.BF.4.158; 11.BF.4.196; 11.BF.4.223; 11.BF.4.240;
11.BF.4.244; 11.BF.4.243; 11.BF.4.247; 11.BF.5.157; 11.BF.5.158;
11.BF.5.196; 11.BF.5.223; 11.BF.5.240; 11.BF.5.244; 11.BF.5.243;
11.BF.5.247; 11.BF.7.157; 11.BF.7.158; 11.BF.7.196; 11.BF.7.223;
11.BF.7.240; 11.BF.7.244; 11.BF.7.243; 11.BF.7.247; 11.BF.15.157;
11.BF.15.158; 11.BF.15.196; 11.BF.15.223; 11.BF.15.240; 11.BF.15.244;
11.BF.15.243; 11.BF.15.247; 11.BF.16.157; 11.BF.16.158; 11.BF.16.196;
11.BF.16.223; 11.BF.16.240; 11.BF.16.244; 11.BF.16.243; 11.BF.16.247;
11.BF.18.157; 11.BF.18.158; 11.BF.18.196; 11.BF.18.223; 11.BF.18.240;
11.BF.18.244; 11.BF.18.243; 11.BF.18.247; 11.BF.26.157; 11.BF.26.158;
11.BF.26.196; 11.BF.26.223; 11.BF.26.240; 11.BF.26.244; 11.BF.26.243;

TABLE 100-continued

11.BF.26.247; 11.BF.27.157; 11.BF.27.158; 11.BF.27.196; 11.BF.27.223;
11.BF.27.240; 11.BF.27.244; 11.BF.27.243; 11.BF.27.247; 11.BF.29.157;
11.BF.29.158; 11.BF.29.196; 11.BF.29.223; 11.BF.29.240; 11.BF.29.244;
11.BF.29.243; 11.BF.29.247; 11.BF.54.157; 11.BF.54.158; 11.BF.54.196;
11.BF.54.223; 11.BF.54.240; 11.BF.54.244; 11.BF.54.243; 11.BF.54.247;
11.BF.55.157; 11.BF.55.158; 11.BF.55.196; 11.BF.55.223; 11.BF.55.240;
11.BF.55.244; 11.BF.55.243; 11.BF.55.247; 11.BF.56.157; 11.BF.56.158;
11.BF.56.196; 11.BF.56.223; 11.BF.56.240; 11.BF.56.244; 11.BF.56.243;
11.BF.56.247; 11.BF.157.157; 11.BF.157.158; 11.BF.157.196; 11.BF.157.223;
11.BF.157.240; 11.BF.157.244; 11.BF.157.243; 11.BF.157.247; 11.BF.196.157;
11.BF.196.158; 11.BF.196.196; 11.BF.196.223; 11.BF.196.240; 11.BF.196.244;
11.BF.196.243; 11.BF.196.247; 11.BF.223.157; 11.BF.223.158; 11.BF.223.196;
11.BF.223.223; 11.BF.223.240; 11.BF.223.244; 11.BF.223.243; 11.BF.223.247;
11.BF.240.157; 11.BF.240.158; 11.BF.240.196; 11.BF.240.223; 11.BF.240.240;
11.BF.240.244; 11.BF.240.243; 11.BF.240.247; 11.BF.244.157; 11.BF.244.158;
11.BF.244.196; 11.BF.244.223; 11.BF.244.240; 11.BF.244.244; 11.BF.244.243;
11.BF.244.247; 11.BF.247.157; 11.BF.247.158; 11.BF.247.196; 11.BF.247.223;
11.BF.247.240; 11.BF.247.244; 11.BF.247.243; 11.BF.247.247;
Prodrugs of 11.CI 11.CI.4.157; 11.CI.4.158; 11.CI.4.196; 11.CI.4.223; 11.CI.4.240;
11.CI.4.244; 11.CI.4.243; 11.CI.4.247; 11.CI.5.157; 11.CI.5.158; 11.CI.5.196;
11.CI.5.223; 11.CI.5.240; 11.CI.5.244; 11.CI.5.243; 11.CI.5.247; 11.CI.7.157;
11.CI.7.158; 11.CI.7.196; 11.CI.7.223; 11.CI.7.240; 11.CI.7.244; 11.CI.7.243;
11.CI.7.247; 11.CI.15.157; 11.CI.15.158; 11.CI.15.196; 11.CI.15.223;
11.CI.15.240; 11.CI.15.244; 11.CI.15.243; 11.CI.15.247; 11.CI.16.157;
11.CI.16.158; 11.CI.16.196; 11.CI.16.223; 11.CI.16.240; 11.CI.16.244;
11.CI.16.243; 11.CI.16.247; 11.CI.18.157; 11.CI.18.158; 11.CI.18.196;
11.CI.18.223; 11.CI.18.240; 11.CI.18.244; 11.CI.18.243; 11.CI.18.247;
11.CI.26.157; 11.CI.26.158; 11.CI.26.196; 11.CI.26.223; 11.CI.26.240;
11.CI.26.244; 11.CI.26.243; 11.CI.26.247; 11.CI.27.157; 11.CI.27.158;
11.CI.27.196; 11.CI.27.223; 11.CI.27.240; 11.CI.27.244; 11.CI.27.243;
11.CI.27.247; 11.CI.29.157; 11.CI.29.158; 11.CI.29.196; 11.CI.29.223;
11.CI.29.240; 11.CI.29.244; 11.CI.29.243; 11.CI.29.247; 11.CI.54.157;
11.CI.54.158; 11.CI.54.196; 11.CI.54.223; 11.CI.54.240; 11.CI.54.244;
11.CI.54.243; 11.CI.54.247; 11.CI.55.157; 11.CI.55.158; 11.CI.55.196;
11.CI.55.223; 11.CI.55.240; 11.CI.55.244; 11.CI.55.243; 11.CI.55.247;
11.CI.56.157; 11.CI.56.158; 11.CI.56.196; 11.CI.56.223; 11.CI.56.240;
11.CI.56.244; 11.CI.56.243; 11.CI.56.247; 11.CI.157.157; 11.CI.157.158;
11.CI.157.196; 11.CI.157.223; 11.CI.157.240; 11.CI.157.244; 11.CI.157.243;
11.CI.157.247; 11.CI.196.157; 11.CI.196.158; 11.CI.196.196; 11.CI.196.223;
11.CI.196.240; 11.CI.196.244; 11.CI.196.243; 11.CI.196.247; 11.CI.223.157;
11.CI.223.158; 11.CI.223.196; 11.CI.223.223; 11.CI.223.240; 11.CI.223.244;
11.CI.223.243; 11.CI.223.247; 11.CI.240.157; 11.CI.240.158; 11.CI.240.196;
11.CI.240.223; 11.CI.240.240; 11.CI.240.244; 11.CI.240.243; 11.CI.240.247;
11.CI.244.157; 11.CI.244.158; 11.CI.244.196; 11.CI.244.223; 11.CI.244.240;
11.CI.244.244; 11.CI.244.243; 11.CI.244.247; 11.CI.247.157; 11.CI.247.158;
11.CI.247.196; 11.CI.247.223; 11.CI.247.240; 11.CI.247.244; 11.CI.247.243;
11.CI.247.247;
Prodrugs of 11.CO 11.CO.4.157; 11.CO.4.158; 11.CO.4.196; 11.CO.4.223; 11.CO.4.240;
11.CO.4.244; 11.CO.4.243; 11.CO.4.247; 11.CO.5.157; 11.CO.5.158;
11.CO.5.196; 11.CO.5.223; 11.CO.5.240; 11.CO.5.244; 11.CO.5.243;
11.CO.5.247; 11.CO.7.157; 11.CO.7.158; 11.CO.7.196; 11.CO.7.223;
11.CO.7.240; 11.CO.7.244; 11.CO.7.243; 11.CO.7.247; 11.CO.15.157;
11.CO.15.158; 11.CO.15.196; 11.CO.15.223; 11.CO.15.240; 11.CO.15.244;
11.CO.15.243; 11.CO.15.247; 11.CO.16.157; 11.CO.16.158; 11.CO.16.196;
11.CO.16.223; 11.CO.16.240; 11.CO.16.244; 11.CO.16.243; 11.CO.16.247;
11.CO.18.157; 11.CO.18.158; 11.CO.18.196; 11.CO.18.223; 11.CO.18.240;
11.CO.18.244; 11.CO.18.243; 11.CO.18.247; 11.CO.26.157; 11.CO.26.158;
11.CO.26.196; 11.CO.26.223; 11.CO.26.240; 11.CO.26.244; 11.CO.26.243;
11.CO.26.247; 11.CO.27.157; 11.CO.27.158; 11.CO.27.196; 11.CO.27.223;
11.CO.27.240; 11.CO.27.244; 11.CO.27.243; 11.CO.27.247; 11.CO.29.157;
11.CO.29.158; 11.CO.29.196; 11.CO.29.223; 11.CO.29.240; 11.CO.29.244;
11.CO.29.243; 11.CO.29.247; 11.CO.54.157; 11.CO.54.158; 11.CO.54.196;
11.CO.54.223; 11.CO.54.240; 11.CO.54.244; 11.CO.54.243; 11.CO.54.247;
11.CO.55.157; 11.CO.55.158; 11.CO.55.196; 11.CO.55.223; 11.CO.55.240;
11.CO.55.244; 11.CO.55.243; 11.CO.55.247; 11.CO.56.157; 11.CO.56.158;
11.CO.56.196; 11.CO.56.223; 11.CO.56.240; 11.CO.56.244; 11.CO.56.243;
11.CO.56.247; 11.CO.157.157; 11.CO.157.158; 11.CO.157.196;
11.CO.157.223; 11.CO.157.240; 11.CO.157.244; 11.CO.157.243;
11.CO.157.247; 11.CO.196.157; 11.CO.196.158; 11.CO.196.196;
11.CO.196.223; 11.CO.196.240; 11.CO.196.244; 11.CO.196.243;
11.CO.196.247; 11.CO.223.157; 11.CO.223.158; 11.CO.223.196;
11.CO.223.223; 11.CO.223.240; 11.CO.223.244; 11.CO.223.243;
11.CO.223.247; 11.CO.240.157; 11.CO.240.158; 11.CO.240.196;
11.CO.240.223; 11.CO.240.240; 11.CO.240.244; 11.CO.240.243;
11.CO.240.247; 11.CO.244.157; 11.CO.244.158; 11.CO.244.196;

TABLE 100-continued

11.CO.244.223; 11.CO.244.240; 11.CO.244.244; 11.CO.244.243;
11.CO.244.247; 11.CO.247.157; 11.CO.247.158; 11.CO.247.196;
11.CO.247.223; 11.CO.247.240; 11.CO.247.244; 11.CO.247.243;
11.CO.247.247;
Prodrugs of 12.AH 12.AH.4.157; 12.AH.4.158; 12.AH.4.196; 12.AH.4.223; 12.AH.4.240;
12.AH.4.244; 12.AH.4.243; 12.AH.4.247; 12.AH.5.157; 12.AH.5.158;
12.AH.5.196; 12.AH.5.223; 12.AH.5.240; 12.AH.5.244; 12.AH.5.243;
12.AH.5.247; 12.AH.7.157; 12.AH.7.158; 12.AH.7.196; 12.AH.7.223;
12.AH.7.240; 12.AH.7.244; 12.AH.7.243; 12.AH.7.247; 12.AH.15.157;
12.AH.15.158; 12.AH.15.196; 12.AH.15.223; 12.AH.15.240; 12.AH.15.244;
12.AH.15.243; 12.AH.15.247; 12.AH.16.157; 12.AH.16.158; 12.AH.16.196;
12.AH.16.223; 12.AH.16.240; 12.AH.16.244; 12.AH.16.243; 12.AH.16.247;
12.AH.18.157; 12.AH.18.158; 12.AH.18.196; 12.AH.18.223; 12.AH.18.240;
12.AH.18.244; 12.AH.18.243; 12.AH.18.247; 12.AH.26.157; 12.AH.26.158;
12.AH.26.196; 12.AH.26.223; 12.AH.26.240; 12.AH.26.244; 12.AH.26.243;
12.AH.26.247; 12.AH.27.157; 12.AH.27.158; 12.AH.27.196; 12.AH.27.223;
12.AH.27.240; 12.AH.27.244; 12.AH.27.243; 12.AH.27.247; 12.AH.29.157;
12.AH.29.158; 12.AH.29.196; 12.AH.29.223; 12.AH.29.240; 12.AH.29.244;
12.AH.29.243; 12.AH.29.247; 12.AH.54.157; 12.AH.54.158; 12.AH.54.196;
12.AH.54.223; 12.AH.54.240; 12.AH.54.244; 12.AH.54.243; 12.AH.54.247;
12.AH.55.157; 12.AH.55.158; 12.AH.55.196; 12.AH.55.223; 12.AH.55.240;
12.AH.55.244; 12.AH.55.243; 12.AH.55.247; 12.AH.56.157; 12.AH.56.158;
12.AH.56.196; 12.AH.56.223; 12.AH.56.240; 12.AH.56.244; 12.AH.56.243;
12.AH.56.247; 12.AH.157.157; 12.AH.157.158; 12.AH.157.196;
12.AH.157.223; 12.AH.157.240; 12.AH.157.244; 12.AH.157.243;
12.AH.157.247; 12.AH.196.157; 12.AH.196.158; 12.AH.196.196;
12.AH.196.223; 12.AH.196.240; 12.AH.196.244; 12.AH.196.243;
12.AH.196.247; 12.AH.223.157; 12.AH.223.158; 12.AH.223.196;
12.AH.223.223; 12.AH.223.240; 12.AH.223.244; 12.AH.223.243;
12.AH.223.247; 12.AH.240.157; 12.AH.240.158; 12.AH.240.196;
12.AH.240.223; 12.AH.240.240; 12.AH.240.244; 12.AH.240.243;
12.AH.240.247; 12.AH.244.157; 12.AH.244.158; 12.AH.244.196;
12.AH.244.223; 12.AH.244.240; 12.AH.244.244; 12.AH.244.243;
12.AH.244.247; 12.AH.247.157; 12.AH.247.158; 12.AH.247.196;
12.AH.247.223; 12.AH.247.240; 12.AH.247.244; 12.AH.247.243;
12.AH.247.247;
Prodrugs of 12.AJ 12.AJ.4.157; 12.AJ.4.158; 12.AJ.4.196; 12.AJ.4.223; 12.AJ.4.240;
12.AJ.4.244; 12.AJ.4.243; 12.AJ.4.247; 12.AJ.5.157; 12.AJ.5.158; 12.AJ.5.196;
12.AJ.5.223; 12.AJ.5.240; 12.AJ.5.244; 12.AJ.5.243; 12.AJ.5.247; 12.AJ.7.157;
12.AJ.7.158; 12.AJ.7.196; 12.AJ.7.223; 12.AJ.7.240; 12.AJ.7.244; 12.AJ.7.243;
12.AJ.7.247; 12.AJ.15.157; 12.AJ.15.158; 12.AJ.15.196; 12.AJ.15.223;
12.AJ.15.240; 12.AJ.15.244; 12.AJ.15.243; 12.AJ.15.247; 12.AJ.16.157;
12.AJ.16.158; 12.AJ.16.196; 12.AJ.16.223; 12.AJ.16.240; 12.AJ.16.244;
12.AJ.16.243; 12.AJ.16.247; 12.AJ.18.157; 12.AJ.18.158; 12.AJ.18.196;
12.AJ.18.223; 12.AJ.18.240; 12.AJ.18.244; 12.AJ.18.243; 12.AJ.18.247;
12.AJ.26.157; 12.AJ.26.158; 12.AJ.26.196; 12.AJ.26.223; 12.AJ.26.240;
12.AJ.26.244; 12.AJ.26.243; 12.AJ.26.247; 12.AJ.27.157; 12.AJ.27.158;
12.AJ.27.196; 12.AJ.27.223; 12.AJ.27.240; 12.AJ.27.244; 12.AJ.27.243;
12.AJ.27.247; 12.AJ.29.157; 12.AJ.29.158; 12.AJ.29.196; 12.AJ.29.223;
12.AJ.29.240; 12.AJ.29.244; 12.AJ.29.243; 12.AJ.29.247; 12.AJ.54.157;
12.AJ.54.158; 12.AJ.54.196; 12.AJ.54.223; 12.AJ.54.240; 12.AJ.54.244;
12.AJ.54.243; 12.AJ.54.247; 12.AJ.55.157; 12.AJ.55.158; 12.AJ.55.196;
12.AJ.55.223; 12.AJ.55.240; 12.AJ.55.244; 12.AJ.55.243; 12.AJ.55.247;
12.AJ.56.157; 12.AJ.56.158; 12.AJ.56.196; 12.AJ.56.223; 12.AJ.56.240;
12.AJ.56.244; 12.AJ.56.243; 12.AJ.56.247; 12.AJ.157.157; 12.AJ.157.158;
12.AJ.157.196; 12.AJ.157.223; 12.AJ.157.240; 12.AJ.157.244; 12.AJ.157.243;
12.AJ.157.247; 12.AJ.196.157; 12.AJ.196.158; 12.AJ.196.196; 12.AJ.196.223;
12.AJ.196.240; 12.AJ.196.244; 12.AJ.196.243; 12.AJ.196.247; 12.AJ.223.157;
12.AJ.223.158; 12.AJ.223.196; 12.AJ.223.223; 12.AJ.223.240; 12.AJ.223.244;
12.AJ.223.243; 12.AJ.223.247; 12.AJ.240.157; 12.AJ.240.158; 12.AJ.240.196;
12.AJ.240.223; 12.AJ.240.240; 12.AJ.240.244; 12.AJ.240.243; 12.AJ.240.247;
12.AJ.244.157; 12.AJ.244.158; 12.AJ.244.196; 12.AJ.244.223; 12.AJ.244.240;
12.AJ.244.244; 12.AJ.244.243; 12.AJ.244.247; 12.AJ.247.157; 12.AJ.247.158;
12.AJ.247.196; 12.AJ.247.223; 12.AJ.247.240; 12.AJ.247.244; 12.AJ.247.243;
12.AJ.247.247;
Prodrugs of 12.AN 12.AN.4.157; 12.AN.4.158; 12.AN.4.196; 12.AN.4.223; 12.AN.4.240;
12.AN.4.244; 12.AN.4.243; 12.AN.4.247; 12.AN.5.157; 12.AN.5.158;
12.AN.5.196; 12.AN.5.223; 12.AN.5.240; 12.AN.5.244; 12.AN.5.243;
12.AN.5.247; 12.AN.7.157; 12.AN.7.158; 12.AN.7.196; 12.AN.7.223;
12.AN.7.240; 12.AN.7.244; 12.AN.7.243; 12.AN.7.247; 12.AN.15.157;
12.AN.15.158; 12.AN.15.196; 12.AN.15.223; 12.AN.15.240; 12.AN.15.244;
12.AN.15.243; 12.AN.15.247; 12.AN.16.157; 12.AN.16.158; 12.AN.16.196;
12.AN.16.223; 12.AN.16.240; 12.AN.16.244; 12.AN.16.243; 12.AN.16.247;

TABLE 100-continued

12.AN.18.157; 12.AN.18.158; 12.AN.18.196; 12.AN.18.223; 12.AN.18.240;
12.AN.18.244; 12.AN.18.243; 12.AN.18.247; 12.AN.26.157; 12.AN.26.158;
12.AN.26.196; 12.AN.26.223; 12.AN.26.240; 12.AN.26.244; 12.AN.26.243;
12.AN.26.247; 12.AN.27.157; 12.AN.27.158; 12.AN.27.196; 12.AN.27.223;
12.AN.27.240; 12.AN.27.244; 12.AN.27.243; 12.AN.27.247; 12.AN.29.157;
12.AN.29.158; 12.AN.29.196; 12.AN.29.223; 12.AN.29.240; 12.AN.29.244;
12.AN.29.243; 12.AN.29.247; 12.AN.54.157; 12.AN.54.158; 12.AN.54.196;
12.AN.54.223; 12.AN.54.240; 12.AN.54.244; 12.AN.54.243; 12.AN.54.247;
12.AN.55.157; 12.AN.55.158; 12.AN.55.196; 12.AN.55.223; 12.AN.55.240;
12.AN.55.244; 12.AN.55.243; 12.AN.55.247; 12.AN.56.157; 12.AN.56.158;
12.AN.56.196; 12.AN.56.223; 12.AN.56.240; 12.AN.56.244; 12.AN.56.243;
12.AN.56.247; 12.AN.157.157; 12.AN.157.158; 12.AN.157.196;
12.AN.157.223; 12.AN.157.240; 12.AN.157.244; 12.AN.157.243;
12.AN.157.247; 12.AN.196.157; 12.AN.196.158; 12.AN.196.196;
12.AN.196.223; 12.AN.196.240; 12.AN.196.244; 12.AN.196.243;
12.AN.196.247; 12.AN.223.157; 12.AN.223.158; 12.AN.223.196;
12.AN.223.223; 12.AN.223.240; 12.AN.223.244; 12.AN.223.243;
12.AN.223.247; 12.AN.240.157; 12.AN.240.158; 12.AN.240.196;
12.AN.240.223; 12.AN.240.240; 12.AN.240.244; 12.AN.240.243;
12.AN.240.247; 12.AN.244.157; 12.AN.244.158; 12.AN.244.196;
12.AN.244.223; 12.AN.244.240; 12.AN.244.244; 12.AN.244.243;
12.AN.244.247; 12.AN.247.157; 12.AN.247.158; 12.AN.247.196;
12.AN.247.223; 12.AN.247.240; 12.AN.247.244; 12.AN.247.243;
12.AN.247.247;
Prodrugs of 12.AP 12.AP.4.157; 12.AP.4.158; 12.AP.4.196; 12.AP.4.223; 12.AP.4.240;
12.AP.4.244; 12.AP.4.243; 12.AP.4.247; 12.AP.5.157; 12.AP.5.158;
12.AP.5.196; 12.AP.5.223; 12.AP.5.240; 12.AP.5.244; 12.AP.5.243;
12.AP.5.247; 12.AP.7.157; 12.AP.7.158; 12.AP.7.196; 12.AP.7.223;
12.AP.7.240; 12.AP.7.244; 12.AP.7.243; 12.AP.7.247; 12.AP.15.157;
12.AP.15.158; 12.AP.15.196; 12.AP.15.223; 12.AP.15.240; 12.AP.15.244;
12.AP.15.243; 12.AP.15.247; 12.AP.16.157; 12.AP.16.158; 12.AP.16.196;
12.AP.16.223; 12.AP.16.240; 12.AP.16.244; 12.AP.16.243; 12.AP.16.247;
12.AP.18.157; 12.AP.18.158; 12.AP.18.196; 12.AP.18.223; 12.AP.18.240;
12.AP.18.244; 12.AP.18.243; 12.AP.18.247; 12.AP.26.157; 12.AP.26.158;
12.AP.26.196; 12.AP.26.223; 12.AP.26.240; 12.AP.26.244; 12.AP.26.243;
12.AP.26.247; 12.AP.27.157; 12.AP.27.158; 12.AP.27.196; 12.AP.27.223;
12.AP.27.240; 12.AP.27.244; 12.AP.27.243; 12.AP.27.247; 12.AP.29.157;
12.AP.29.158; 12.AP.29.196; 12.AP.29.223; 12.AP.29.240; 12.AP.29.244;
12.AP.29.243; 12.AP.29.247; 12.AP.54.157; 12.AP.54.158; 12.AP.54.196;
12.AP.54.223; 12.AP.54.240; 12.AP.54.244; 12.AP.54.243; 12.AP.54.247;
12.AP.55.157; 12.AP.55.158; 12.AP.55.196; 12.AP.55.223; 12.AP.55.240;
12.AP.55.244; 12.AP.55.243; 12.AP.55.247; 12.AP.56.157; 12.AP.56.158;
12.AP.56.196; 12.AP.56.223; 12.AP.56.240; 12.AP.56.244; 12.AP.56.243;
12.AP.56.247; 12.AP.157.157; 12.AP.157.158; 12.AP.157.196; 12.AP.157.223;
12.AP.157.240; 12.AP.157.244; 12.AP.157.243; 12.AP.157.247;
12.AP.196.157; 12.AP.196.158; 12.AP.196.196; 12.AP.196.223;
12.AP.196.240; 12.AP.196.244; 12.AP.196.243; 12.AP.196.247;
12.AP.223.157; 12.AP.223.158; 12.AP.223.196; 12.AP.223.223;
12.AP.223.240; 12.AP.223.244; 12.AP.223.243; 12.AP.223.247;
12.AP.240.157; 12.AP.240.158; 12.AP.240.196; 12.AP.240.223;
12.AP.240.240; 12.AP.240.244; 12.AP.240.243; 12.AP.240.247;
12.AP.244.157; 12.AP.244.158; 12.AP.244.196; 12.AP.244.223;
12.AP.244.240; 12.AP.244.244; 12.AP.244.243; 12.AP.244.247;
12.AP.247.157; 12.AP.247.158; 12.AP.247.196; 12.AP.247.223;
12.AP.247.240; 12.AP.247.244; 12.AP.247.243; 12.AP.247.247;
Prodrugs of 12.AZ 12.AZ.4.157; 12.AZ.4.158; 12.AZ.4.196; 12.AZ.4.223; 12.AZ.4.240;
12.AZ.4.244; 12.AZ.4.243; 12.AZ.4.247; 12.AZ.5.157; 12.AZ.5.158;
12.AZ.5.196; 12.AZ.5.223; 12.AZ.5.240; 12.AZ.5.244; 12.AZ.5.243;
12.AZ.5.247; 12.AZ.7.157; 12.AZ.7.158; 12.AZ.7.196; 12.AZ.7.223;
12.AZ.7.240; 12.AZ.7.244; 12.AZ.7.243; 12.AZ.7.247; 12.AZ.15.157;
12.AZ.15.158; 12.AZ.15.196; 12.AZ.15.223; 12.AZ.15.240; 12.AZ.15.244;
12.AZ.15.243; 12.AZ.15.247; 12.AZ.16.157; 12.AZ.16.158; 12.AZ.16.196;
12.AZ.16.223; 12.AZ.16.240; 12.AZ.16.244; 12.AZ.16.243; 12.AZ.16.247;
12.AZ.18.157; 12.AZ.18.158; 12.AZ.18.196; 12.AZ.18.223; 12.AZ.18.240;
12.AZ.18.244; 12.AZ.18.243; 12.AZ.18.247; 12.AZ.26.157; 12.AZ.26.158;
12.AZ.26.196; 12.AZ.26.223; 12.AZ.26.240; 12.AZ.26.244; 12.AZ.26.243;
12.AZ.26.247; 12.AZ.27.157; 12.AZ.27.158; 12.AZ.27.196; 12.AZ.27.223;
12.AZ.27.240; 12.AZ.27.244; 12.AZ.27.243; 12.AZ.27.247; 12.AZ.29.157;
12.AZ.29.158; 12.AZ.29.196; 12.AZ.29.223; 12.AZ.29.240; 12.AZ.29.244;
12.AZ.29.243; 12.AZ.29.247; 12.AZ.54.157; 12.AZ.54.158; 12.AZ.54.196;
12.AZ.54.223; 12.AZ.54.240; 12.AZ.54.244; 12.AZ.54.243; 12.AZ.54.247;
12.AZ.55.157; 12.AZ.55.158; 12.AZ.55.196; 12.AZ.55.223; 12.AZ.55.240;
12.AZ.55.244; 12.AZ.55.243; 12.AZ.55.247; 12.AZ.56.157; 12.AZ.56.158;
12.AZ.56.196; 12.AZ.56.223; 12.AZ.56.240; 12.AZ.56.244; 12.AZ.56.243;
12.AZ.56.247; 12.AZ.157.157; 12.AZ.157.158; 12.AZ.157.196; 12.AZ.157.223;

TABLE 100-continued

12.AZ.157.240; 12.AZ.157.244; 12.AZ.157.243; 12.AZ.157.247;
12.AZ.196.157; 12.AZ.196.158; 12.AZ.196.196; 12.AZ.196.223;
12.AZ.196.240; 12.AZ.196.244; 12.AZ.196.243; 12.AZ.196.247;
12.AZ.223.157; 12.AZ.223.158; 12.AZ.223.196; 12.AZ.223.223;
12.AZ.223.240; 12.AZ.223.244; 12.AZ.223.243; 12.AZ.223.247;
12.AZ.240.157; 12.AZ.240.158; 12.AZ.240.196; 12.AZ.240.223;
12.AZ.240.240; 12.AZ.240.244; 12.AZ.240.243; 12.AZ.240.247;
12.AZ.244.157; 12.AZ.244.158; 12.AZ.244.196; 12.AZ.244.223;
12.AZ.244.240; 12.AZ.244.244; 12.AZ.244.243; 12.AZ.244.247;
12.AZ.247.157; 12.AZ.247.158; 12.AZ.247.196; 12.AZ.247.223;
12.AZ.247.240; 12.AZ.247.244; 12.AZ.247.243; 12.AZ.247.247;
Prodrugs of 12.BF 12.BF.4.157; 12.BF.4.158; 12.BF.4.196; 12.BF.4.223; 12.BF.4.240;
12.BF.4.244; 12.BF.4.243; 12.BF.4.247; 12.BF.5.157; 12.BF.5.158;
12.BF.5.196; 12.BF.5.223; 12.BF.5.240; 12.BF.5.244; 12.BF.5.243;
12.BF.5.247; 12.BF.7.157; 12.BF.7.158; 12.BF.7.196; 12.BF.7.223;
12.BF.7.240; 12.BF.7.244; 12.BF.7.243; 12.BF.7.247; 12.BF.15.157;
12.BF.15.158; 12.BF.15.196; 12.BF.15.223; 12.BF.15.240; 12.BF.15.244;
12.BF.15.243; 12.BF.15.247; 12.BF.16.157; 12.BF.16.158; 12.BF.16.196;
12.BF.16.223; 12.BF.16.240; 12.BF.16.244; 12.BF.16.243; 12.BF.16.247;
12.BF.18.157; 12.BF.18.158; 12.BF.18.196; 12.BF.18.223; 12.BF.18.240;
12.BF.18.244; 12.BF.18.243; 12.BF.18.247; 12.BF.26.157; 12.BF.26.158;
12.BF.26.196; 12.BF.26.223; 12.BF.26.240; 12.BF.26.244; 12.BF.26.243;
12.BF.26.247; 12.BF.27.157; 12.BF.27.158; 12.BF.27.196; 12.BF.27.223;
12.BF.27.240; 12.BF.27.244; 12.BF.27.243; 12.BF.27.247; 12.BF.29.157;
12.BF.29.158; 12.BF.29.196; 12.BF.29.223; 12.BF.29.240; 12.BF.29.244;
12.BF.29.243; 12.BF.29.247; 12.BF.54.157; 12.BF.54.158; 12.BF.54.196;
12.BF.54.223; 12.BF.54.240; 12.BF.54.244; 12.BF.54.243; 12.BF.54.247;
12.BF.55.157; 12.BF.55.158; 12.BF.55.196; 12.BF.55.223; 12.BF.55.240;
12.BF.55.244; 12.BF.55.243; 12.BF.55.247; 12.BF.56.157; 12.BF.56.158;
12.BF.56.196; 12.BF.56.223; 12.BF.56.240; 12.BF.56.244; 12.BF.56.243;
12.BF.56.247; 12.BF.157.157; 12.BF.157.158; 12.BF.157.196; 12.BF.157.223;
12.BF.157.240; 12.BF.157.244; 12.BF.157.243; 12.BF.157.247; 12.BF.196.157;
12.BF.196.158; 12.BF.196.196; 12.BF.196.223; 12.BF.196.240; 12.BF.196.244;
12.BF.196.243; 12.BF.196.247; 12.BF.223.157; 12.BF.223.158; 12.BF.223.196;
12.BF.223.223; 12.BF.223.240; 12.BF.223.244; 12.BF.223.243; 12.BF.223.247;
12.BF.240.157; 12.BF.240.158; 12.BF.240.196; 12.BF.240.223; 12.BF.240.240;
12.BF.240.244; 12.BF.240.243; 12.BF.240.247; 12.BF.244.157; 12.BF.244.158;
12.BF.244.196; 12.BF.244.223; 12.BF.244.240; 12.BF.244.244; 12.BF.244.243;
12.BF.244.247; 12.BF.247.157; 12.BF.247.158; 12.BF.247.196; 12.BF.247.223;
12.BF.247.240; 12.BF.247.244; 12.BF.247.243; 12.BF.247.247;
Prodrugs of 12.CI 12.CI.4.157; 12.CI.4.158; 12.CI.4.196; 12.CI.4.223; 12.CI.4.240;
12.CI.4.244; 12.CI.4.243; 12.CI.4.247; 12.CI.5.157; 12.CI.5.158; 12.CI.5.196;
12.CI.5.223; 12.CI.5.240; 12.CI.5.244; 12.CI.5.243; 12.CI.5.247; 12.CI.7.157;
12.CI.7.158; 12.CI.7.196; 12.CI.7.223; 12.CI.7.240; 12.CI.7.244; 12.CI.7.243;
12.CI.7.247; 12.CI.15.157; 12.CI.15.158; 12.CI.15.196; 12.CI.15.223;
12.CI.15.240; 12.CI.15.244; 12.CI.15.243; 12.CI.15.247; 12.CI.16.157;
12.CI.16.158; 12.CI.16.196; 12.CI.16.223; 12.CI.16.240; 12.CI.16.244;
12.CI.16.243; 12.CI.16.247; 12.CI.18.157; 12.CI.18.158; 12.CI.18.196;
12.CI.18.223; 12.CI.18.240; 12.CI.18.244; 12.CI.18.243; 12.CI.18.247;
12.CI.26.157; 12.CI.26.158; 12.CI.26.196; 12.CI.26.223; 12.CI.26.240;
12.CI.26.244; 12.CI.26.243; 12.CI.26.247; 12.CI.27.157; 12.CI.27.158;
12.CI.27.196; 12.CI.27.223; 12.CI.27.240; 12.CI.27.244; 12.CI.27.243;
12.CI.27.247; 12.CI.29.157; 12.CI.29.158; 12.CI.29.196; 12.CI.29.223;
12.CI.29.240; 12.CI.29.244; 12.CI.29.243; 12.CI.29.247; 12.CI.54.157;
12.CI.54.158; 12.CI.54.196; 12.CI.54.223; 12.CI.54.240; 12.CI.54.244;
12.CI.54.243; 12.CI.54.247; 12.CI.55.157; 12.CI.55.158; 12.CI.55.196;
12.CI.55.223; 12.CI.55.240; 12.CI.55.244; 12.CI.55.243; 12.CI.55.247;
12.CI.56.157; 12.CI.56.158; 12.CI.56.196; 12.CI.56.223; 12.CI.56.240;
12.CI.56.244; 12.CI.56.243; 12.CI.56.247; 12.CI.157.157; 12.CI.157.158;
12.CI.157.196; 12.CI.157.223; 12.CI.157.240; 12.CI.157.244; 12.CI.157.243;
12.CI.157.247; 12.CI.196.157; 12.CI.196.158; 12.CI.196.196; 12.CI.196.223;
12.CI.196.240; 12.CI.196.244; 12.CI.196.243; 12.CI.196.247; 12.CI.223.157;
12.CI.223.158; 12.CI.223.196; 12.CI.223.223; 12.CI.223.240; 12.CI.223.244;
12.CI.223.243; 12.CI.223.247; 12.CI.240.157; 12.CI.240.158; 12.CI.240.196;
12.CI.240.223; 12.CI.240.240; 12.CI.240.244; 12.CI.240.243; 12.CI.240.247;
12.CI.244.157; 12.CI.244.158; 12.CI.244.196; 12.CI.244.223; 12.CI.244.240;
12.CI.244.244; 12.CI.244.243; 12.CI.244.247; 12.CI.247.157; 12.CI.247.158;
12.CI.247.196; 12.CI.247.223; 12.CI.247.240; 12.CI.247.244; 12.CI.247.243;
12.CI.247.247;
Prodrugs of 12.CO 12.CO.4.157; 12.CO.4.158; 12.CO.4.196; 12.CO.4.223; 12.CO.4.240;
12.CO.4.244; 12.CO.4.243; 12.CO.4.247; 12.CO.5.157; 12.CO.5.158;
12.CO.5.196; 12.CO.5.223; 12.CO.5.240; 12.CO.5.244; 12.CO.5.243;
12.CO.5.247; 12.CO.7.157; 12.CO.7.158; 12.CO.7.196; 12.CO.7.223;

TABLE 100-continued

12.CO.7.240; 12.CO.7.244; 12.CO.7.243; 12.CO.7.247; 12.CO.15.157;
12.CO.15.158; 12.CO.15.196; 12.CO.15.223; 12.CO.15.240; 12.CO.15.244;
12.CO.15.243; 12.CO.15.247; 12.CO.16.157; 12.CO.16.158; 12.CO.16.196;
12.CO.16.223; 12.CO.16.240; 12.CO.16.244; 12.CO.16.243; 12.CO.16.247;
12.CO.18.157; 12.CO.18.158; 12.CO.18.196; 12.CO.18.223; 12.CO.18.240;
12.CO.18.244; 12.CO.18.243; 12.CO.18.247; 12.CO.26.157; 12.CO.26.158;
12.CO.26.196; 12.CO.26.223; 12.CO.26.240; 12.CO.26.244; 12.CO.26.243;
12.CO.26.247; 12.CO.27.157; 12.CO.27.158; 12.CO.27.196; 12.CO.27.223;
12.CO.27.240; 12.CO.27.244; 12.CO.27.243; 12.CO.27.247; 12.CO.29.157;
12.CO.29.158; 12.CO.29.196; 12.CO.29.223; 12.CO.29.240; 12.CO.29.244;
12.CO.29.243; 12.CO.29.247; 12.CO.54.157; 12.CO.54.158; 12.CO.54.196;
12.CO.54.223; 12.CO.54.240; 12.CO.54.244; 12.CO.54.243; 12.CO.54.247;
12.CO.55.157; 12.CO.55.158; 12.CO.55.196; 12.CO.55.223; 12.CO.55.240;
12.CO.55.244; 12.CO.55.243; 12.CO.55.247; 12.CO.56.157; 12.CO.56.158;
12.CO.56.196; 12.CO.56.223; 12.CO.56.240; 12.CO.56.244; 12.CO.56.243;
12.CO.56.247; 12.CO.157.157; 12.CO.157.158; 12.CO.157.196;
12.CO.157.223; 12.CO.157.240; 12.CO.157.244; 12.CO.157.243;
12.CO.157.247; 12.CO.196.157; 12.CO.196.158; 12.CO.196.196;
12.CO.196.223; 12.CO.196.240; 12.CO.196.244; 12.CO.196.243;
12.CO.196.247; 12.CO.223.157; 12.CO.223.158; 12.CO.223.196;
12.CO.223.223; 12.CO.223.240; 12.CO.223.244; 12.CO.223.243;
12.CO.223.247; 12.CO.240.157; 12.CO.240.158; 12.CO.240.196;
12.CO.240.223; 12.CO.240.240; 12.CO.240.244; 12.CO.240.243;
12.CO.240.247; 12.CO.244.157; 12.CO.244.158; 12.CO.244.196;
12.CO.244.223; 12.CO.244.240; 12.CO.244.244; 12.CO.244.243;
12.CO.244.247; 12.CO.247.157; 12.CO.247.158; 12.CO.247.196;
12.CO.247.223; 12.CO.247.240; 12.CO.247.244; 12.CO.247.243;
12.CO.247.247.
Prodrugs of 13.B 13.B.228.228; 13.B.228.229; 13.B.228.230; 13.B.228.231; 13.B.228.236;
13.B.228.237; 13.B.228.238; 13.B.228.239; 13.B.228.154; 13.B.228.157;
13.B.228.166; 13.B.228.169; 13.B.228.172; 13.B.228.175; 13.B.228.240;
13.B.228.244; 13.B.229.228; 13.B.229.229; 13.B.229.230; 13.B.229.231;
13.B.229.236; 13.B.229.237; 13.B.229.238; 13.B.229.239; 13.B.229.154;
13.B.229.157; 13.B.229.166; 13.B.229.169; 13.B.229.172; 13.B.229.175;
13.B.229.240; 13.B.229.244; 13.B.230.228; 13.B.230.229; 13.B.230.230;
13.B.230.231; 13.B.230.236; 13.B.230.237; 13.B.230.238; 13.B.230.239;
13.B.230.154; 13.B.230.157; 13.B.230.166; 13.B.230.169; 13.B.230.172;
13.B.230.175; 13.B.230.240; 13.B.230.244; 13.B.231.228; 13.B.231.229;
13.B.231.230; 13.B.231.231; 13.B.231.236; 13.B.231.237; 13.B.231.238;
13.B.231.239; 13.B.231.154; 13.B.231.157; 13.B.231.166; 13.B.231.169;
13.B.231.172; 13.B.231.175; 13.B.231.240; 13.B.231.244; 13.B.236.228;
13.B.236.229; 13.B.236.230; 13.B.236.231; 13.B.236.236; 13.B.236.237;
13.B.236.238; 13.B.236.239; 13.B.236.154; 13.B.236.157; 13.B.236.166;
13.B.236.169; 13.B.236.172; 13.B.236.175; 13.B.236.240; 13.B.236.244;
13.B.237.228; 13.B.237.229; 13.B.237.230; 13.B.237.231; 13.B.237.236;
13.B.237.237; 13.B.237.238; 13.B.237.239; 13.B.237.154; 13.B.237.157;
13.B.237.166; 13.B.237.169; 13.B.237.172; 13.B.237.175; 13.B.237.240;
13.B.237.244; 13.B.238.228; 13.B.238.229; 13.B.238.230; 13.B.238.231;
13.B.238.236; 13.B.238.237; 13.B.238.238; 13.B.238.239; 13.B.238.154;
13.B.238.157; 13.B.238.166; 13.B.238.169; 13.B.238.172; 13.B.238.175;
13.B.238.240; 13.B.238.244; 13.B.239.228; 13.B.239.229; 13.B.239.230;
13.B.239.231; 13.B.239.236; 13.B.239.237; 13.B.239.238; 13.B.239.239;
13.B.239.154; 13.B.239.157; 13.B.239.166; 13.B.239.169; 13.B.239.172;
13.B.239.175; 13.B.239.240; 13.B.239.244; 13.B.154.228; 13.B.154.229;
13.B.154.230; 13.B.154.231; 13.B.154.236; 13.B.154.237; 13.B.154.238;
13.B.154.239; 13.B.154.154; 13.B.154.157; 13.B.154.166; 13.B.154.169;
13.B.154.172; 13.B.154.175; 13.B.154.240; 13.B.154.244; 13.B.157.228;
13.B.157.229; 13.B.157.230; 13.B.157.231; 13.B.157.236; 13.B.157.237;
13.B.157.238; 13.B.157.239; 13.B.157.154; 13.B.157.157; 13.B.157.166;
13.B.157.169; 13.B.157.172; 13.B.157.175; 13.B.157.240; 13.B.157.244;
13.B.166.228; 13.B.166.229; 13.B.166.230; 13.B.166.231; 13.B.166.236;
13.B.166.237; 13.B.166.238; 13.B.166.239; 13.B.166.154; 13.B.166.157;
13.B.166.166; 13.B.166.169; 13.B.166.172; 13.B.166.175; 13.B.166.240;
13.B.166.244; 13.B.169.228; 13.B.169.229; 13.B.169.230; 13.B.169.231;
13.B.169.236; 13.B.169.237; 13.B.169.238; 13.B.169.239; 13.B.169.154;
13.B.169.157; 13.B.169.166; 13.B.169.169; 13.B.169.172; 13.B.169.175;
13.B.169.240; 13.B.169.244; 13.B.172.228; 13.B.172.229; 13.B.172.230;
13.B.172.231; 13.B.172.236; 13.B.172.237; 13.B.172.238; 13.B.172.239;
13.B.172.154; 13.B.172.157; 13.B.172.166; 13.B.172.169; 13.B.172.172;
13.B.172.175; 13.B.172.240; 13.B.172.244; 13.B.175.228; 13.B.175.229;
13.B.175.230; 13.B.175.231; 13.B.175.236; 13.B.175.237; 13.B.175.238;
13.B.175.239; 13.B.175.154; 13.B.175.157; 13.B.175.166; 13.B.175.169;
13.B.175.172; 13.B.175.175; 13.B.175.240; 13.B.175.244; 13.B.240.228;
13.B.240.229; 13.B.240.230; 13.B.240.231; 13.B.240.236; 13.B.240.237;
13.B.240.238; 13.B.240.239; 13.B.240.154; 13.B.240.157; 13.B.240.166;
13.B.240.169; 13.B.240.172; 13.B.240.175; 13.B.240.240; 13.B.240.244;
13.B.244.228; 13.B.244.229; 13.B.244.230; 13.B.244.231; 13.B.244.236;

TABLE 100-continued

13.B.244.237; 13.B.244.238; 13.B.244.239; 13.B.244.154; 13.B.244.157;
13.B.244.166; 13.B.244.169; 13.B.244.172; 13.B.244.175; 13.B.244.240;
13.B.244.244;

Prodrugs of 13.D

13.D.228.228; 13.D.228.229; 13.D.228.230; 13.D.228.231; 13.D.228.236;
13.D.228.237; 13.D.228.238; 13.D.228.239; 13.D.228.154; 13.D.228.157;
13.D.228.166; 13.D.228.169; 13.D.228.172; 13.D.228.175; 13.D.228.240;
13.D.228.244; 13.D.229.228; 13.D.229.229; 13.D.229.230; 13.D.229.231;
13.D.229.236; 13.D.229.237; 13.D.229.238; 13.D.229.239; 13.D.229.154;
13.D.229.157; 13.D.229.166; 13.D.229.169; 13.D.229.172; 13.D.229.175;
13.D.229.240; 13.D.229.244; 13.D.230.228; 13.D.230.229; 13.D.230.230;
13.D.230.231; 13.D.230.236; 13.D.230.237; 13.D.230.238; 13.D.230.239;
13.D.230.154; 13.D.230.157; 13.D.230.166; 13.D.230.169; 13.D.230.172;
13.D.230.175; 13.D.230.240; 13.D.230.244; 13.D.231.228; 13.D.231.229;
13.D.231.230; 13.D.231.231; 13.D.231.236; 13.D.231.237; 13.D.231.238;
13.D.231.239; 13.D.231.154; 13.D.231.157; 13.D.231.166; 13.D.231.169;
13.D.231.172; 13.D.231.175; 13.D.231.240; 13.D.231.244; 13.D.236.228;
13.D.236.229; 13.D.236.230; 13.D.236.231; 13.D.236.236; 13.D.236.237;
13.D.236.238; 13.D.236.239; 13.D.236.154; 13.D.236.157; 13.D.236.166;
13.D.236.169; 13.D.236.172; 13.D.236.175; 13.D.236.240; 13.D.236.244;
13.D.237.228; 13.D.237.229; 13.D.237.230; 13.D.237.231; 13.D.237.236;
13.D.237.237; 13.D.237.238; 13.D.237.239; 13.D.237.154; 13.D.237.157;
13.D.237.166; 13.D.237.169; 13.D.237.172; 13.D.237.175; 13.D.237.240;
13.D.237.244; 13.D.238.228; 13.D.238.229; 13.D.238.230; 13.D.238.231;
13.D.238.236; 13.D.238.237; 13.D.238.238; 13.D.238.239; 13.D.238.154;
13.D.238.157; 13.D.238.166; 13.D.238.169; 13.D.238.172; 13.D.238.175;
13.D.238.240; 13.D.238.244; 13.D.239.228; 13.D.239.229; 13.D.239.230;
13.D.239.231; 13.D.239.236; 13.D.239.237; 13.D.239.238; 13.D.239.239;
13.D.239.154; 13.D.239.157; 13.D.239.166; 13.D.239.169; 13.D.239.172;
13.D.239.175; 13.D.239.240; 13.D.239.244; 13.D.154.228; 13.D.154.229;
13.D.154.230; 13.D.154.231; 13.D.154.236; 13.D.154.237; 13.D.154.238;
13.D.154.239; 13.D.154.154; 13.D.154.157; 13.D.154.166; 13.D.154.169;
13.D.154.172; 13.D.154.175; 13.D.154.240; 13.D.154.244; 13.D.157.228;
13.D.157.229; 13.D.157.230; 13.D.157.231; 13.D.157.236; 13.D.157.237;
13.D.157.238; 13.D.157.239; 13.D.157.154; 13.D.157.157; 13.D.157.166;
13.D.157.169; 13.D.157.172; 13.D.157.175; 13.D.157.240; 13.D.157.244;
13.D.166.228; 13.D.166.229; 13.D.166.230; 13.D.166.231; 13.D.166.236;
13.D.166.237; 13.D.166.238; 13.D.166.239; 13.D.166.154; 13.D.166.157;
13.D.166.166; 13.D.166.169; 13.D.166.172; 13.D.166.175; 13.D.166.240;
13.D.166.244; 13.D.169.228; 13.D.169.229; 13.D.169.230; 13.D.169.231;
13.D.169.236; 13.D.169.237; 13.D.169.238; 13.D.169.239; 13.D.169.154;
13.D.169.157; 13.D.169.166; 13.D.169.169; 13.D.169.172; 13.D.169.175;
13.D.169.240; 13.D.169.244; 13.D.172.228; 13.D.172.229; 13.D.172.230;
13.D.172.231; 13.D.172.236; 13.D.172.237; 13.D.172.238; 13.D.172.239;
13.D.172.154; 13.D.172.157; 13.D.172.166; 13.D.172.169; 13.D.172.172;
13.D.172.175; 13.D.172.240; 13.D.172.244; 13.D.175.228; 13.D.175.229;
13.D.175.230; 13.D.175.231; 13.D.175.236; 13.D.175.237; 13.D.175.238;
13.D.175.239; 13.D.175.154; 13.D.175.157; 13.D.175.166; 13.D.175.169;
13.D.175.172; 13.D.175.175; 13.D.175.240; 13.D.175.244; 13.D.240.228;
13.D.240.229; 13.D.240.230; 13.D.240.231; 13.D.240.236; 13.D.240.237;
13.D.240.238; 13.D.240.239; 13.D.240.154; 13.D.240.157; 13.D.240.166;
13.D.240.169; 13.D.240.172; 13.D.240.175; 13.D.240.240; 13.D.240.244;
13.D.244.228; 13.D.244.229; 13.D.244.230; 13.D.244.231; 13.D.244.236;
13.D.244.237; 13.D.244.238; 13.D.244.239; 13.D.244.154; 13.D.244.157;
13.D.244.166; 13.D.244.169; 13.D.244.172; 13.D.244.175; 13.D.244.240;
13.D.244.244;

Prodrugs of 13.E

13.E.228.228; 13.E.228.229; 13.E.228.230; 13.E.228.231; 13.E.228.236;
13.E.228.237; 13.E.228.238; 13.E.228.239; 13.E.228.154; 13.E.228.157;
13.E.228.166; 13.E.228.169; 13.E.228.172; 13.E.228.175; 13.E.228.240;
13.E.228.244; 13.E.229.228; 13.E.229.229; 13.E.229.230; 13.E.229.231;
13.E.229.236; 13.E.229.237; 13.E.229.238; 13.E.229.239; 13.E.229.154;
13.E.229.157; 13.E.229.166; 13.E.229.169; 13.E.229.172; 13.E.229.175;
13.E.229.240; 13.E.229.244; 13.E.230.228; 13.E.230.229; 13.E.230.230;
13.E.230.231; 13.E.230.236; 13.E.230.237; 13.E.230.238; 13.E.230.239;
13.E.230.154; 13.E.230.157; 13.E.230.166; 13.E.230.169; 13.E.230.172;
13.E.230.175; 13.E.230.240; 13.E.230.244; 13.E.231.228; 13.E.231.229;
13.E.231.230; 13.E.231.231; 13.E.231.236; 13.E.231.237; 13.E.231.238;
13.E.231.239; 13.E.231.154; 13.E.231.157; 13.E.231.166; 13.E.231.169;
13.E.231.172; 13.E.231.175; 13.E.231.240; 13.E.231.244; 13.E.236.228;
13.E.236.229; 13.E.236.230; 13.E.236.231; 13.E.236.236; 13.E.236.237;
13.E.236.238; 13.E.236.239; 13.E.236.154; 13.E.236.157; 13.E.236.166;
13.E.236.169; 13.E.236.172; 13.E.236.175; 13.E.236.240; 13.E.236.244;
13.E.237.228; 13.E.237.229; 13.E.237.230; 13.E.237.231; 13.E.237.236;
13.E.237.237; 13.E.237.238; 13.E.237.239; 13.E.237.154; 13.E.237.157;
13.E.237.166; 13.E.237.169; 13.E.237.172; 13.E.237.175; 13.E.237.240;
13.E.237.244; 13.E.238.228; 13.E.238.229; 13.E.238.230; 13.E.238.231;

TABLE 100-continued

13.E.238.236; 13.E.238.237; 13.E.238.238; 13.E.238.239; 13.E.238.154;
13.E.238.157; 13.E.238.166; 13.E.238.169; 13.E.238.172; 13.E.238.175;
13.E.238.240; 13.E.238.244; 13.E.239.228; 13.E.239.229; 13.E.239.230;
13.E.239.231; 13.E.239.236; 13.E.239.237; 13.E.239.238; 13.E.239.239;
13.E.239.154; 13.E.239.157; 13.E.239.166; 13.E.239.169; 13.E.239.172;
13.E.239.175; 13.E.239.240; 13.E.239.244; 13.E.154.228; 13.E.154.229;
13.E.154.230; 13.E.154.231; 13.E.154.236; 13.E.154.237; 13.E.154.238;
13.E.154.239; 13.E.154.154; 13.E.154.157; 13.E.154.166; 13.E.154.169;
13.E.154.172; 13.E.154.175; 13.E.154.240; 13.E.154.244; 13.E.157.228;
13.E.157.229; 13.E.157.230; 13.E.157.231; 13.E.157.236; 13.E.157.237;
13.E.157.238; 13.E.157.239; 13.E.157.154; 13.E.157.157; 13.E.157.166;
13.E.157.169; 13.E.157.172; 13.E.157.175; 13.E.157.240; 13.E.157.244;
13.E.166.228; 13.E.166.229; 13.E.166.230; 13.E.166.231; 13.E.166.236;
13.E.166.237; 13.E.166.238; 13.E.166.239; 13.E.166.154; 13.E.166.157;
13.E.166.166; 13.E.166.169; 13.E.166.172; 13.E.166.175; 13.E.166.240;
13.E.166.244; 13.E.169.228; 13.E.169.229; 13.E.169.230; 13.E.169.231;
13.E.169.236; 13.E.169.237; 13.E.169.238; 13.E.169.239; 13.E.169.154;
13.E.169.157; 13.E.169.166; 13.E.169.169; 13.E.169.172; 13.E.169.175;
13.E.169.240; 13.E.169.244; 13.E.172.228; 13.E.172.229; 13.E.172.230;
13.E.172.231; 13.E.172.236; 13.E.172.237; 13.E.172.238; 13.E.172.239;
13.E.172.154; 13.E.172.157; 13.E.172.166; 13.E.172.169; 13.E.172.172;
13.E.172.175; 13.E.172.240; 13.E.172.244; 13.E.175.228; 13.E.175.229;
13.E.175.230; 13.E.175.231; 13.E.175.236; 13.E.175.237; 13.E.175.238;
13.E.175.239; 13.E.175.154; 13.E.175.157; 13.E.175.166; 13.E.175.169;
13.E.175.172; 13.E.175.175; 13.E.175.240; 13.E.175.244; 13.E.240.228;
13.E.240.229; 13.E.240.230; 13.E.240.231; 13.E.240.236; 13.E.240.237;
13.E.240.238; 13.E.240.239; 13.E.240.154; 13.E.240.157; 13.E.240.166;
13.E.240.169; 13.E.240.172; 13.E.240.175; 13.E.240.240; 13.E.240.244;
13.E.244.228; 13.E.244.229; 13.E.244.230; 13.E.244.231; 13.E.244.236;
13.E.244.237; 13.E.244.238; 13.E.244.239; 13.E.244.154; 13.E.244.157;
13.E.244.166; 13.E.244.169; 13.E.244.172; 13.E.244.175; 13.E.244.240;
13.E.244.244;

Prodrugs of 13.G

13.G.228.228; 13.G.228.229; 13.G.228.230; 13.G.228.231; 13.G.228.236;
13.G.228.237; 13.G.228.238; 13.G.228.239; 13.G.228.154; 13.G.228.157;
13.G.228.166; 13.G.228.169; 13.G.228.172; 13.G.228.175; 13.G.228.240;
13.G.228.244; 13.G.229.228; 13.G.229.229; 13.G.229.230; 13.G.229.231;
13.G.229.236; 13.G.229.237; 13.G.229.238; 13.G.229.239; 13.G.229.154;
13.G.229.157; 13.G.229.166; 13.G.229.169; 13.G.229.172; 13.G.229.175;
13.G.229.240; 13.G.229.244; 13.G.230.228; 13.G.230.229; 13.G.230.230;
13.G.230.231; 13.G.230.236; 13.G.230.237; 13.G.230.238; 13.G.230.239;
13.G.230.154; 13.G.230.157; 13.G.230.166; 13.G.230.169; 13.G.230.172;
13.G.230.175; 13.G.230.240; 13.G.230.244; 13.G.231.228; 13.G.231.229;
13.G.231.230; 13.G.231.231; 13.G.231.236; 13.G.231.237; 13.G.231.238;
13.G.231.239; 13.G.231.154; 13.G.231.157; 13.G.231.166; 13.G.231.169;
13.G.231.172; 13.G.231.175; 13.G.231.240; 13.G.231.244; 13.G.236.228;
13.G.236.229; 13.G.236.230; 13.G.236.231; 13.G.236.236; 13.G.236.237;
13.G.236.238; 13.G.236.239; 13.G.236.154; 13.G.236.157; 13.G.236.166;
13.G.236.169; 13.G.236.172; 13.G.236.175; 13.G.236.240; 13.G.236.244;
13.G.237.228; 13.G.237.229; 13.G.237.230; 13.G.237.231; 13.G.237.236;
13.G.237.237; 13.G.237.238; 13.G.237.239; 13.G.237.154; 13.G.237.157;
13.G.237.166; 13.G.237.169; 13.G.237.172; 13.G.237.175; 13.G.237.240;
13.G.237.244; 13.G.238.228; 13.G.238.229; 13.G.238.230; 13.G.238.231;
13.G.238.236; 13.G.238.237; 13.G.238.238; 13.G.238.239; 13.G.238.154;
13.G.238.157; 13.G.238.166; 13.G.238.169; 13.G.238.172; 13.G.238.175;
13.G.238.240; 13.G.238.244; 13.G.239.228; 13.G.239.229; 13.G.239.230;
13.G.239.231; 13.G.239.236; 13.G.239.237; 13.G.239.238; 13.G.239.239;
13.G.239.154; 13.G.239.157; 13.G.239.166; 13.G.239.169; 13.G.239.172;
13.G.239.175; 13.G.239.240; 13.G.239.244; 13.G.154.228; 13.G.154.229;
13.G.154.230; 13.G.154.231; 13.G.154.236; 13.G.154.237; 13.G.154.238;
13.G.154.239; 13.G.154.154; 13.G.154.157; 13.G.154.166; 13.G.154.169;
13.G.154.172; 13.G.154.175; 13.G.154.240; 13.G.154.244; 13.G.157.228;
13.G.157.229; 13.G.157.230; 13.G.157.231; 13.G.157.236; 13.G.157.237;
13.G.157.238; 13.G.157.239; 13.G.157.154; 13.G.157.157; 13.G.157.166;
13.G.157.169; 13.G.157.172; 13.G.157.175; 13.G.157.240; 13.G.157.244;
13.G.166.228; 13.G.166.229; 13.G.166.230; 13.G.166.231; 13.G.166.236;
13.G.166.237; 13.G.166.238; 13.G.166.239; 13.G.166.154; 13.G.166.157;
13.G.166.166; 13.G.166.169; 13.G.166.172; 13.G.166.175; 13.G.166.240;
13.G.166.244; 13.G.169.228; 13.G.169.229; 13.G.169.230; 13.G.169.231;
13.G.169.236; 13.G.169.237; 13.G.169.238; 13.G.169.239; 13.G.169.154;
13.G.169.157; 13.G.169.166; 13.G.169.169; 13.G.169.172; 13.G.169.175;
13.G.169.240; 13.G.169.244; 13.G.172.228; 13.G.172.229; 13.G.172.230;
13.G.172.231; 13.G.172.236; 13.G.172.237; 13.G.172.238; 13.G.172.239;
13.G.172.154; 13.G.172.157; 13.G.172.166; 13.G.172.169; 13.G.172.172;
13.G.172.175; 13.G.172.240; 13.G.172.244; 13.G.175.228; 13.G.175.229;
13.G.175.230; 13.G.175.231; 13.G.175.236; 13.G.175.237; 13.G.175.238;
13.G.175.239; 13.G.175.154; 13.G.175.157; 13.G.175.166; 13.G.175.169;
13.G.175.172; 13.G.175.175; 13.G.175.240; 13.G.175.244; 13.G.240.228;

TABLE 100-continued

13.G.240.229; 13.G.240.230; 13.G.240.231; 13.G.240.236; 13.G.240.237;
13.G.240.238; 13.G.240.239; 13.G.240.154; 13.G.240.157; 13.G.240.166;
13.G.240.169; 13.G.240.172; 13.G.240.175; 13.G.240.240; 13.G.240.244;
13.G.244.228; 13.G.244.229; 13.G.244.230; 13.G.244.231; 13.G.244.236;
13.G.244.237; 13.G.244.238; 13.G.244.239; 13.G.244.154; 13.G.244.157;
13.G.244.166; 13.G.244.169; 13.G.244.172; 13.G.244.175; 13.G.244.240;
13.G.244.244;
Prodrugs of 13.I 13.I.228.228; 13.I.228.229; 13.I.228.230; 13.I.228.231; 13.I.228.236;
13.I.228.237; 13.I.228.238; 13.I.228.239; 13.I.228.154; 13.I.228.157;
13.I.228.166; 13.I.228.169; 13.I.228.172; 13.I.228.175; 13.I.228.240;
13.I.228.244; 13.I.229.228; 13.I.229.229; 13.I.229.230; 13.I.229.231;
13.I.229.236; 13.I.229.237; 13.I.229.238; 13.I.229.239; 13.I.229.154;
13.I.229.157; 13.I.229.166; 13.I.229.169; 13.I.229.172; 13.I.229.175;
13.I.229.240; 13.I.229.244; 13.I.230.228; 13.I.230.229; 13.I.230.230;
13.I.230.231; 13.I.230.236; 13.I.230.237; 13.I.230.238; 13.I.230.239;
13.I.230.154; 13.I.230.157; 13.I.230.166; 13.I.230.169; 13.I.230.172;
13.I.230.175; 13.I.230.240; 13.I.230.244; 13.I.231.228; 13.I.231.229;
13.I.231.230; 13.I.231.231; 13.I.231.236; 13.I.231.237; 13.I.231.238;
13.I.231.239; 13.I.231.154; 13.I.231.157; 13.I.231.166; 13.I.231.169;
13.I.231.172; 13.I.231.175; 13.I.231.240; 13.I.231.244; 13.I.236.228;
13.I.236.229; 13.I.236.230; 13.I.236.231; 13.I.236.236; 13.I.236.237;
13.I.236.238; 13.I.236.239; 13.I.236.154; 13.I.236.157; 13.I.236.166;
13.I.236.169; 13.I.236.172; 13.I.236.175; 13.I.236.240; 13.I.236.244;
13.I.237.228; 13.I.237.229; 13.I.237.230; 13.I.237.231; 13.I.237.236;
13.I.237.237; 13.I.237.238; 13.I.237.239; 13.I.237.154; 13.I.237.157;
13.I.237.166; 13.I.237.169; 13.I.237.172; 13.I.237.175; 13.I.237.240;
13.I.237.244; 13.I.238.228; 13.I.238.229; 13.I.238.230; 13.I.238.231;
13.I.238.236; 13.I.238.237; 13.I.238.238; 13.I.238.239; 13.I.238.154;
13.I.238.157; 13.I.238.166; 13.I.238.169; 13.I.238.172; 13.I.238.175;
13.I.238.240; 13.I.238.244; 13.I.239.228; 13.I.239.229; 13.I.239.230;
13.I.239.231; 13.I.239.236; 13.I.239.237; 13.I.239.238; 13.I.239.239;
13.I.239.154; 13.I.239.157; 13.I.239.166; 13.I.239.169; 13.I.239.172;
13.I.239.175; 13.I.239.240; 13.I.239.244; 13.I.154.228; 13.I.154.229;
13.I.154.230; 13.I.154.231; 13.I.154.236; 13.I.154.237; 13.I.154.238;
13.I.154.239; 13.I.154.154; 13.I.154.157; 13.I.154.166; 13.I.154.169;
13.I.154.172; 13.I.154.175; 13.I.154.240; 13.I.154.244; 13.I.157.228;
13.I.157.229; 13.I.157.230; 13.I.157.231; 13.I.157.236; 13.I.157.237;
13.I.157.238; 13.I.157.239; 13.I.157.154; 13.I.157.157; 13.I.157.166;
13.I.157.169; 13.I.157.172; 13.I.157.175; 13.I.157.240; 13.I.157.244;
13.I.166.228; 13.I.166.229; 13.I.166.230; 13.I.166.231; 13.I.166.236;
13.I.166.237; 13.I.166.238; 13.I.166.239; 13.I.166.154; 13.I.166.157;
13.I.166.166; 13.I.166.169; 13.I.166.172; 13.I.166.175; 13.I.166.240;
13.I.166.244; 13.I.169.228; 13.I.169.229; 13.I.169.230; 13.I.169.231;
13.I.169.236; 13.I.169.237; 13.I.169.238; 13.I.169.239; 13.I.169.154;
13.I.169.157; 13.I.169.166; 13.I.169.169; 13.I.169.172; 13.I.169.175;
13.I.169.240; 13.I.169.244; 13.I.172.228; 13.I.172.229; 13.I.172.230;
13.I.172.231; 13.I.172.236; 13.I.172.237; 13.I.172.238; 13.I.172.239;
13.I.172.154; 13.I.172.157; 13.I.172.166; 13.I.172.169; 13.I.172.172;
13.I.172.175; 13.I.172.240; 13.I.172.244; 13.I.175.228; 13.I.175.229;
13.I.175.230; 13.I.175.231; 13.I.175.236; 13.I.175.237; 13.I.175.238;
13.I.175.239; 13.I.175.154; 13.I.175.157; 13.I.175.166; 13.I.175.169;
13.I.175.172; 13.I.175.175; 13.I.175.240; 13.I.175.244; 13.I.240.228;
13.I.240.229; 13.I.240.230; 13.I.240.231; 13.I.240.236; 13.I.240.237;
13.I.240.238; 13.I.240.239; 13.I.240.154; 13.I.240.157; 13.I.240.166;
13.I.240.169; 13.I.240.172; 13.I.240.175; 13.I.240.240; 13.I.240.244;
13.I.244.228; 13.I.244.229; 13.I.244.230; 13.I.244.231; 13.I.244.236;
13.I.244.237; 13.I.244.238; 13.I.244.239; 13.I.244.154; 13.I.244.157;
13.I.244.166; 13.I.244.169; 13.I.244.172; 13.I.244.175; 13.I.244.240;
13.I.244.244;
Prodrugs of 13.J 13.J.228.228; 13.J.228.229; 13.J.228.230; 13.J.228.231; 13.J.228.236;
13.J.228.237; 13.J.228.238; 13.J.228.239; 13.J.228.154; 13.J.228.157;
13.J.228.166; 13.J.228.169; 13.J.228.172; 13.J.228.175; 13.J.228.240;
13.J.228.244; 13.J.229.228; 13.J.229.229; 13.J.229.230; 13.J.229.231;
13.J.229.236; 13.J.229.237; 13.J.229.238; 13.J.229.239; 13.J.229.154;
13.J.229.157; 13.J.229.166; 13.J.229.169; 13.J.229.172; 13.J.229.175;
13.J.229.240; 13.J.229.244; 13.J.230.228; 13.J.230.229; 13.J.230.230;
13.J.230.231; 13.J.230.236; 13.J.230.237; 13.J.230.238; 13.J.230.239;
13.J.230.154; 13.J.230.157; 13.J.230.166; 13.J.230.169; 13.J.230.172;
13.J.230.175; 13.J.230.240; 13.J.230.244; 13.J.231.228; 13.J.231.229;
13.J.231.230; 13.J.231.231; 13.J.231.236; 13.J.231.237; 13.J.231.238;
13.J.231.239; 13.J.231.154; 13.J.231.157; 13.J.231.166; 13.J.231.169;
13.J.231.172; 13.J.231.175; 13.J.231.240; 13.J.231.244; 13.J.236.228;
13.J.236.229; 13.J.236.230; 13.J.236.231; 13.J.236.236; 13.J.236.237;
13.J.236.238; 13.J.236.239; 13.J.236.154; 13.J.236.157; 13.J.236.166;
13.J.236.169; 13.J.236.172; 13.J.236.175; 13.J.236.240; 13.J.236.244;

TABLE 100-continued

13.J.237.228; 13.J.237.229; 13.J.237.230; 13.J.237.231; 13.J.237.236;
13.J.237.237; 13.J.237.238; 13.J.237.239; 13.J.237.154; 13.J.237.157;
13.J.237.166; 13.J.237.169; 13.J.237.172; 13.J.237.175; 13.J.237.240;
13.J.237.244; 13.J.238.228; 13.J.238.229; 13.J.238.230; 13.J.238.231;
13.J.238.236; 13.J.238.237; 13.J.238.238; 13.J.238.239; 13.J.238.154;
13.J.238.157; 13.J.238.166; 13.J.238.169; 13.J.238.172; 13.J.238.175;
13.J.238.240; 13.J.238.244; 13.J.239.228; 13.J.239.229; 13.J.239.230;
13.J.239.231; 13.J.239.236; 13.J.239.237; 13.J.239.238; 13.J.239.239;
13.J.239.154; 13.J.239.157; 13.J.239.166; 13.J.239.169; 13.J.239.172;
13.J.239.175; 13.J.239.240; 13.J.239.244; 13.J.154.228; 13.J.154.229;
13.J.154.230; 13.J.154.231; 13.J.154.236; 13.J.154.237; 13.J.154.238;
13.J.154.239; 13.J.154.154; 13.J.154.157; 13.J.154.166; 13.J.154.169;
13.J.154.172; 13.J.154.175; 13.J.154.240; 13.J.154.244; 13.J.157.228;
13.J.157.229; 13.J.157.230; 13.J.157.231; 13.J.157.236; 13.J.157.237;
13.J.157.238; 13.J.157.239; 13.J.157.154; 13.J.157.157; 13.J.157.166;
13.J.157.169; 13.J.157.172; 13.J.157.175; 13.J.157.240; 13.J.157.244;
13.J.166.228; 13.J.166.229; 13.J.166.230; 13.J.166.231; 13.J.166.236;
13.J.166.237; 13.J.166.238; 13.J.166.239; 13.J.166.154; 13.J.166.157;
13.J.166.166; 13.J.166.169; 13.J.166.172; 13.J.166.175; 13.J.166.240;
13.J.166.244; 13.J.169.228; 13.J.169.229; 13.J.169.230; 13.J.169.231;
13.J.169.236; 13.J.169.237; 13.J.169.238; 13.J.169.239; 13.J.169.154;
13.J.169.157; 13.J.169.166; 13.J.169.169; 13.J.169.172; 13.J.169.175;
13.J.169.240; 13.J.169.244; 13.J.172.228; 13.J.172.229; 13.J.172.230;
13.J.172.231; 13.J.172.236; 13.J.172.237; 13.J.172.238; 13.J.172.239;
13.J.172.154; 13.J.172.157; 13.J.172.166; 13.J.172.169; 13.J.172.172;
13.J.172.175; 13.J.172.240; 13.J.172.244; 13.J.175.228; 13.J.175.229;
13.J.175.230; 13.J.175.231; 13.J.175.236; 13.J.175.237; 13.J.175.238;
13.J.175.239; 13.J.175.154; 13.J.175.157; 13.J.175.166; 13.J.175.169;
13.J.175.172; 13.J.175.175; 13.J.175.240; 13.J.175.244; 13.J.240.228;
13.J.240.229; 13.J.240.230; 13.J.240.231; 13.J.240.236; 13.J.240.237;
13.J.240.238; 13.J.240.239; 13.J.240.154; 13.J.240.157; 13.J.240.166;
13.J.240.169; 13.J.240.172; 13.J.240.175; 13.J.240.240; 13.J.240.244;
13.J.244.228; 13.J.244.229; 13.J.244.230; 13.J.244.231; 13.J.244.236;
13.J.244.237; 13.J.244.238; 13.J.244.239; 13.J.244.154; 13.J.244.157;
13.J.244.166; 13.J.244.169; 13.J.244.172; 13.J.244.175; 13.J.244.240;
13.J.244.244;
Prodrugs of 13.L 13.L.228.228; 13.L.228.229; 13.L.228.230; 13.L.228.231; 13.L.228.236;
13.L.228.237; 13.L.228.238; 13.L.228.239; 13.L.228.154; 13.L.228.157;
13.L.228.166; 13.L.228.169; 13.L.228.172; 13.L.228.175; 13.L.228.240;
13.L.228.244; 13.L.229.228; 13.L.229.229; 13.L.229.230; 13.L.229.231;
13.L.229.236; 13.L.229.237; 13.L.229.238; 13.L.229.239; 13.L.229.154;
13.L.229.157; 13.L.229.166; 13.L.229.169; 13.L.229.172; 13.L.229.175;
13.L.229.240; 13.L.229.244; 13.L.230.228; 13.L.230.229; 13.L.230.230;
13.L.230.231; 13.L.230.236; 13.L.230.237; 13.L.230.238; 13.L.230.239;
13.L.230.154; 13.L.230.157; 13.L.230.166; 13.L.230.169; 13.L.230.172;
13.L.230.175; 13.L.230.240; 13.L.230.244; 13.L.231.228; 13.L.231.229;
13.L.231.230; 13.L.231.231; 13.L.231.236; 13.L.231.237; 13.L.231.238;
13.L.231.239; 13.L.231.154; 13.L.231.157; 13.L.231.166; 13.L.231.169;
13.L.231.172; 13.L.231.175; 13.L.231.240; 13.L.231.244; 13.L.236.228;
13.L.236.229; 13.L.236.230; 13.L.236.231; 13.L.236.236; 13.L.236.237;
13.L.236.238; 13.L.236.239; 13.L.236.154; 13.L.236.157; 13.L.236.166;
13.L.236.169; 13.L.236.172; 13.L.236.175; 13.L.236.240; 13.L.236.244;
13.L.237.228; 13.L.237.229; 13.L.237.230; 13.L.237.231; 13.L.237.236;
13.L.237.237; 13.L.237.238; 13.L.237.239; 13.L.237.154; 13.L.237.157;
13.L.237.166; 13.L.237.169; 13.L.237.172; 13.L.237.175; 13.L.237.240;
13.L.237.244; 13.L.238.228; 13.L.238.229; 13.L.238.230; 13.L.238.231;
13.L.238.236; 13.L.238.237; 13.L.238.238; 13.L.238.239; 13.L.238.154;
13.L.238.157; 13.L.238.166; 13.L.238.169; 13.L.238.172; 13.L.238.175;
13.L.238.240; 13.L.238.244; 13.L.239.228; 13.L.239.229; 13.L.239.230;
13.L.239.231; 13.L.239.236; 13.L.239.237; 13.L.239.238; 13.L.239.239;
13.L.239.154; 13.L.239.157; 13.L.239.166; 13.L.239.169; 13.L.239.172;
13.L.239.175; 13.L.239.240; 13.L.239.244; 13.L.154.228; 13.L.154.229;
13.L.154.230; 13.L.154.231; 13.L.154.236; 13.L.154.237; 13.L.154.238;
13.L.154.239; 13.L.154.154; 13.L.154.157; 13.L.154.166; 13.L.154.169;
13.L.154.172; 13.L.154.175; 13.L.154.240; 13.L.154.244; 13.L.157.228;
13.L.157.229; 13.L.157.230; 13.L.157.231; 13.L.157.236; 13.L.157.237;
13.L.157.238; 13.L.157.239; 13.L.157.154; 13.L.157.157; 13.L.157.166;
13.L.157.169; 13.L.157.172; 13.L.157.175; 13.L.157.240; 13.L.157.244;
13.L.166.228; 13.L.166.229; 13.L.166.230; 13.L.166.231; 13.L.166.236;
13.L.166.237; 13.L.166.238; 13.L.166.239; 13.L.166.154; 13.L.166.157;
13.L.166.166; 13.L.166.169; 13.L.166.172; 13.L.166.175; 13.L.166.240;
13.L.166.244; 13.L.169.228; 13.L.169.229; 13.L.169.230; 13.L.169.231;
13.L.169.236; 13.L.169.237; 13.L.169.238; 13.L.169.239; 13.L.169.154;
13.L.169.157; 13.L.169.166; 13.L.169.169; 13.L.169.172; 13.L.169.175;
13.L.169.240; 13.L.169.244; 13.L.172.228; 13.L.172.229; 13.L.172.230;
13.L.172.231; 13.L.172.236; 13.L.172.237; 13.L.172.238; 13.L.172.239;
13.L.172.154; 13.L.172.157; 13.L.172.166; 13.L.172.169; 13.L.172.172;

TABLE 100-continued

13.L.172.175; 13.L.172.240; 13.L.172.244; 13.L.175.228; 13.L.175.229;
13.L.175.230; 13.L.175.231; 13.L.175.236; 13.L.175.237; 13.L.175.238;
13.L.175.239; 13.L.175.154; 13.L.175.157; 13.L.175.166; 13.L.175.169;
13.L.175.172; 13.L.175.175; 13.L.175.240; 13.L.175.244; 13.L.240.228;
13.L.240.229; 13.L.240.230; 13.L.240.231; 13.L.240.236; 13.L.240.237;
13.L.240.238; 13.L.240.239; 13.L.240.154; 13.L.240.157; 13.L.240.166;
13.L.240.169; 13.L.240.172; 13.L.240.175; 13.L.240.240; 13.L.240.244;
13.L.244.228; 13.L.244.229; 13.L.244.230; 13.L.244.231; 13.L.244.236;
13.L.244.237; 13.L.244.238; 13.L.244.239; 13.L.244.154; 13.L.244.157;
13.L.244.166; 13.L.244.169; 13.L.244.172; 13.L.244.175; 13.L.244.240;
13.L.244.244;
Prodrugs of 13.O 13.O.228.228; 13.O.228.229; 13.O.228.230; 13.O.228.231; 13.O.228.236;
13.O.228.237; 13.O.228.238; 13.O.228.239; 13.O.228.154; 13.O.228.157;
13.O.228.166; 13.O.228.169; 13.O.228.172; 13.O.228.175; 13.O.228.240;
13.O.228.244; 13.O.229.228; 13.O.229.229; 13.O.229.230; 13.O.229.231;
13.O.229.236; 13.O.229.237; 13.O.229.238; 13.O.229.239; 13.O.229.154;
13.O.229.157; 13.O.229.166; 13.O.229.169; 13.O.229.172; 13.O.229.175;
13.O.229.240; 13.O.229.244; 13.O.230.228; 13.O.230.229; 13.O.230.230;
13.O.230.231; 13.O.230.236; 13.O.230.237; 13.O.230.238; 13.O.230.239;
13.O.230.154; 13.O.230.157; 13.O.230.166; 13.O.230.169; 13.O.230.172;
13.O.230.175; 13.O.230.240; 13.O.230.244; 13.O.231.228; 13.O.231.229;
13.O.231.230; 13.O.231.231; 13.O.231.236; 13.O.231.237; 13.O.231.238;
13.O.231.239; 13.O.231.154; 13.O.231.157; 13.O.231.166; 13.O.231.169;
13.O.231.172; 13.O.231.175; 13.O.231.240; 13.O.231.244; 13.O.236.228;
13.O.236.229; 13.O.236.230; 13.O.236.231; 13.O.236.236; 13.O.236.237;
13.O.236.238; 13.O.236.239; 13.O.236.154; 13.O.236.157; 13.O.236.166;
13.O.236.169; 13.O.236.172; 13.O.236.175; 13.O.236.240; 13.O.236.244;
13.O.237.228; 13.O.237.229; 13.O.237.230; 13.O.237.231; 13.O.237.236;
13.O.237.237; 13.O.237.238; 13.O.237.239; 13.O.237.154; 13.O.237.157;
13.O.237.166; 13.O.237.169; 13.O.237.172; 13.O.237.175; 13.O.237.240;
13.O.237.244; 13.O.238.228; 13.O.238.229; 13.O.238.230; 13.O.238.231;
13.O.238.236; 13.O.238.237; 13.O.238.238; 13.O.238.239; 13.O.238.154;
13.O.238.157; 13.O.238.166; 13.O.238.169; 13.O.238.172; 13.O.238.175;
13.O.238.240; 13.O.238.244; 13.O.239.228; 13.O.239.229; 13.O.239.230;
13.O.239.231; 13.O.239.236; 13.O.239.237; 13.O.239.238; 13.O.239.239;
13.O.239.154; 13.O.239.157; 13.O.239.166; 13.O.239.169; 13.O.239.172;
13.O.239.175; 13.O.239.240; 13.O.239.244; 13.O.154.228; 13.O.154.229;
13.O.154.230; 13.O.154.231; 13.O.154.236; 13.O.154.237; 13.O.154.238;
13.O.154.239; 13.O.154.154; 13.O.154.157; 13.O.154.166; 13.O.154.169;
13.O.154.172; 13.O.154.175; 13.O.154.240; 13.O.154.244; 13.O.157.228;
13.O.157.229; 13.O.157.230; 13.O.157.231; 13.O.157.236; 13.O.157.237;
13.O.157.238; 13.O.157.239; 13.O.157.154; 13.O.157.157; 13.O.157.166;
13.O.157.169; 13.O.157.172; 13.O.157.175; 13.O.157.240; 13.O.157.244;
13.O.166.228; 13.O.166.229; 13.O.166.230; 13.O.166.231; 13.O.166.236;
13.O.166.237; 13.O.166.238; 13.O.166.239; 13.O.166.154; 13.O.166.157;
13.O.166.166; 13.O.166.169; 13.O.166.172; 13.O.166.175; 13.O.166.240;
13.O.166.244; 13.O.169.228; 13.O.169.229; 13.O.169.230; 13.O.169.231;
13.O.169.236; 13.O.169.237; 13.O.169.238; 13.O.169.239; 13.O.169.154;
13.O.169.157; 13.O.169.166; 13.O.169.169; 13.O.169.172; 13.O.169.175;
13.O.169.240; 13.O.169.244; 13.O.172.228; 13.O.172.229; 13.O.172.230;
13.O.172.231; 13.O.172.236; 13.O.172.237; 13.O.172.238; 13.O.172.239;
13.O.172.154; 13.O.172.157; 13.O.172.166; 13.O.172.169; 13.O.172.172;
13.O.172.175; 13.O.172.240; 13.O.172.244; 13.O.175.228; 13.O.175.229;
13.O.175.230; 13.O.175.231; 13.O.175.236; 13.O.175.237; 13.O.175.238;
13.O.175.239; 13.O.175.154; 13.O.175.157; 13.O.175.166; 13.O.175.169;
13.O.175.172; 13.O.175.175; 13.O.175.240; 13.O.175.244; 13.O.240.228;
13.O.240.229; 13.O.240.230; 13.O.240.231; 13.O.240.236; 13.O.240.237;
13.O.240.238; 13.O.240.239; 13.O.240.154; 13.O.240.157; 13.O.240.166;
13.O.240.169; 13.O.240.172; 13.O.240.175; 13.O.240.240; 13.O.240.244;
13.O.244.228; 13.O.244.229; 13.O.244.230; 13.O.244.231; 13.O.244.236;
13.O.244.237; 13.O.244.238; 13.O.244.239; 13.O.244.154; 13.O.244.157;
13.O.244.166; 13.O.244.169; 13.O.244.172; 13.O.244.175; 13.O.244.240;
13.O.244.244;
Prodrugs of 13.P 13.P.228.228; 13.P.228.229; 13.P.228.230; 13.P.228.231; 13.P.228.236;
13.P.228.237; 13.P.228.238; 13.P.228.239; 13.P.228.154; 13.P.228.157;
13.P.228.166; 13.P.228.169; 13.P.228.172; 13.P.228.175; 13.P.228.240;
13.P.228.244; 13.P.229.228; 13.P.229.229; 13.P.229.230; 13.P.229.231;
13.P.229.236; 13.P.229.237; 13.P.229.238; 13.P.229.239; 13.P.229.154;
13.P.229.157; 13.P.229.166; 13.P.229.169; 13.P.229.172; 13.P.229.175;
13.P.229.240; 13.P.229.244; 13.P.230.228; 13.P.230.229; 13.P.230.230;
13.P.230.231; 13.P.230.236; 13.P.230.237; 13.P.230.238; 13.P.230.239;
13.P.230.154; 13.P.230.157; 13.P.230.166; 13.P.230.169; 13.P.230.172;
13.P.230.175; 13.P.230.240; 13.P.230.244; 13.P.231.228; 13.P.231.229;
13.P.231.230; 13.P.231.231; 13.P.231.236; 13.P.231.237; 13.P.231.238;
13.P.231.239; 13.P.231.154; 13.P.231.157; 13.P.231.166; 13.P.231.169;

TABLE 100-continued

13.P.231.172; 13.P.231.175; 13.P.231.240; 13.P.231.244; 13.P.236.228;
13.P.236.229; 13.P.236.230; 13.P.236.231; 13.P.236.236; 13.P.236.237;
13.P.236.238; 13.P.236.239; 13.P.236.154; 13.P.236.157; 13.P.236.166;
13.P.236.169; 13.P.236.172; 13.P.236.175; 13.P.236.240; 13.P.236.244;
13.P.237.228; 13.P.237.229; 13.P.237.230; 13.P.237.231; 13.P.237.236;
13.P.237.237; 13.P.237.238; 13.P.237.239; 13.P.237.154; 13.P.237.157;
13.P.237.166; 13.P.237.169; 13.P.237.172; 13.P.237.175; 13.P.237.240;
13.P.237.244; 13.P.238.228; 13.P.238.229; 13.P.238.230; 13.P.238.231;
13.P.238.236; 13.P.238.237; 13.P.238.238; 13.P.238.239; 13.P.238.154;
13.P.238.157; 13.P.238.166; 13.P.238.169; 13.P.238.172; 13.P.238.175;
13.P.238.240; 13.P.238.244; 13.P.239.228; 13.P.239.229; 13.P.239.230;
13.P.239.231; 13.P.239.236; 13.P.239.237; 13.P.239.238; 13.P.239.239;
13.P.239.154; 13.P.239.157; 13.P.239.166; 13.P.239.169; 13.P.239.172;
13.P.239.175; 13.P.239.240; 13.P.239.244; 13.P.154.228; 13.P.154.229;
13.P.154.230; 13.P.154.231; 13.P.154.236; 13.P.154.237; 13.P.154.238;
13.P.154.239; 13.P.154.154; 13.P.154.157; 13.P.154.166; 13.P.154.169;
13.P.154.172; 13.P.154.175; 13.P.154.240; 13.P.154.244; 13.P.157.228;
13.P.157.229; 13.P.157.230; 13.P.157.231; 13.P.157.236; 13.P.157.237;
13.P.157.238; 13.P.157.239; 13.P.157.154; 13.P.157.157; 13.P.157.166;
13.P.157.169; 13.P.157.172; 13.P.157.175; 13.P.157.240; 13.P.157.244;
13.P.166.228; 13.P.166.229; 13.P.166.230; 13.P.166.231; 13.P.166.236;
13.P.166.237; 13.P.166.238; 13.P.166.239; 13.P.166.154; 13.P.166.157;
13.P.166.166; 13.P.166.169; 13.P.166.172; 13.P.166.175; 13.P.166.240;
13.P.166.244; 13.P.169.228; 13.P.169.229; 13.P.169.230; 13.P.169.231;
13.P.169.236; 13.P.169.237; 13.P.169.238; 13.P.169.239; 13.P.169.154;
13.P.169.157; 13.P.169.166; 13.P.169.169; 13.P.169.172; 13.P.169.175;
13.P.169.240; 13.P.169.244; 13.P.172.228; 13.P.172.229; 13.P.172.230;
13.P.172.231; 13.P.172.236; 13.P.172.237; 13.P.172.238; 13.P.172.239;
13.P.172.154; 13.P.172.157; 13.P.172.166; 13.P.172.169; 13.P.172.172;
13.P.172.175; 13.P.172.240; 13.P.172.244; 13.P.175.228; 13.P.175.229;
13.P.175.230; 13.P.175.231; 13.P.175.236; 13.P.175.237; 13.P.175.238;
13.P.175.239; 13.P.175.154; 13.P.175.157; 13.P.175.166; 13.P.175.169;
13.P.175.172; 13.P.175.175; 13.P.175.240; 13.P.175.244; 13.P.240.228;
13.P.240.229; 13.P.240.230; 13.P.240.231; 13.P.240.236; 13.P.240.237;
13.P.240.238; 13.P.240.239; 13.P.240.154; 13.P.240.157; 13.P.240.166;
13.P.240.169; 13.P.240.172; 13.P.240.175; 13.P.240.240; 13.P.240.244;
13.P.244.228; 13.P.244.229; 13.P.244.230; 13.P.244.231; 13.P.244.236;
13.P.244.237; 13.P.244.238; 13.P.244.239; 13.P.244.154; 13.P.244.157;
13.P.244.166; 13.P.244.169; 13.P.244.172; 13.P.244.175; 13.P.244.240;
13.P.244.244;

Prodrugs of 13.U

13.U.228.228; 13.U.228.229; 13.U.228.230; 13.U.228.231; 13.U.228.236;
13.U.228.237; 13.U.228.238; 13.U.228.239; 13.U.228.154; 13.U.228.157;
13.U.228.166; 13.U.228.169; 13.U.228.172; 13.U.228.175; 13.U.228.240;
13.U.228.244; 13.U.229.228; 13.U.229.229; 13.U.229.230; 13.U.229.231;
13.U.229.236; 13.U.229.237; 13.U.229.238; 13.U.229.239; 13.U.229.154;
13.U.229.157; 13.U.229.166; 13.U.229.169; 13.U.229.172; 13.U.229.175;
13.U.229.240; 13.U.229.244; 13.U.230.228; 13.U.230.229; 13.U.230.230;
13.U.230.231; 13.U.230.236; 13.U.230.237; 13.U.230.238; 13.U.230.239;
13.U.230.154; 13.U.230.157; 13.U.230.166; 13.U.230.169; 13.U.230.172;
13.U.230.175; 13.U.230.240; 13.U.230.244; 13.U.231.228; 13.U.231.229;
13.U.231.230; 13.U.231.231; 13.U.231.236; 13.U.231.237; 13.U.231.238;
13.U.231.239; 13.U.231.154; 13.U.231.157; 13.U.231.166; 13.U.231.169;
13.U.231.172; 13.U.231.175; 13.U.231.240; 13.U.231.244; 13.U.236.228;
13.U.236.229; 13.U.236.230; 13.U.236.231; 13.U.236.236; 13.U.236.237;
13.U.236.238; 13.U.236.239; 13.U.236.154; 13.U.236.157; 13.U.236.166;
13.U.236.169; 13.U.236.172; 13.U.236.175; 13.U.236.240; 13.U.236.244;
13.U.237.228; 13.U.237.229; 13.U.237.230; 13.U.237.231; 13.U.237.236;
13.U.237.237; 13.U.237.238; 13.U.237.239; 13.U.237.154; 13.U.237.157;
13.U.237.166; 13.U.237.169; 13.U.237.172; 13.U.237.175; 13.U.237.240;
13.U.237.244; 13.U.238.228; 13.U.238.229; 13.U.238.230; 13.U.238.231;
13.U.238.236; 13.U.238.237; 13.U.238.238; 13.U.238.239; 13.U.238.154;
13.U.238.157; 13.U.238.166; 13.U.238.169; 13.U.238.172; 13.U.238.175;
13.U.238.240; 13.U.238.244; 13.U.239.228; 13.U.239.229; 13.U.239.230;
13.U.239.231; 13.U.239.236; 13.U.239.237; 13.U.239.238; 13.U.239.239;
13.U.239.154; 13.U.239.157; 13.U.239.166; 13.U.239.169; 13.U.239.172;
13.U.239.175; 13.U.239.240; 13.U.239.244; 13.U.154.228; 13.U.154.229;
13.U.154.230; 13.U.154.231; 13.U.154.236; 13.U.154.237; 13.U.154.238;
13.U.154.239; 13.U.154.154; 13.U.154.157; 13.U.154.166; 13.U.154.169;
13.U.154.172; 13.U.154.175; 13.U.154.240; 13.U.154.244; 13.U.157.228;
13.U.157.229; 13.U.157.230; 13.U.157.231; 13.U.157.236; 13.U.157.237;
13.U.157.238; 13.U.157.239; 13.U.157.154; 13.U.157.157; 13.U.157.166;
13.U.157.169; 13.U.157.172; 13.U.157.175; 13.U.157.240; 13.U.157.244;
13.U.166.228; 13.U.166.229; 13.U.166.230; 13.U.166.231; 13.U.166.236;
13.U.166.237; 13.U.166.238; 13.U.166.239; 13.U.166.154; 13.U.166.157;
13.U.166.166; 13.U.166.169; 13.U.166.172; 13.U.166.175; 13.U.166.240;
13.U.166.244; 13.U.169.228; 13.U.169.229; 13.U.169.230; 13.U.169.231;
13.U.169.236; 13.U.169.237; 13.U.169.238; 13.U.169.239; 13.U.169.154;

TABLE 100-continued

13.U.169.157; 13.U.169.166; 13.U.169.169; 13.U.169.172; 13.U.169.175;
13.U.169.240; 13.U.169.244; 13.U.172.228; 13.U.172.229; 13.U.172.230;
13.U.172.231; 13.U.172.236; 13.U.172.237; 13.U.172.238; 13.U.172.239;
13.U.172.154; 13.U.172.157; 13.U.172.166; 13.U.172.169; 13.U.172.172;
13.U.172.175; 13.U.172.240; 13.U.172.244; 13.U.175.228; 13.U.175.229;
13.U.175.230; 13.U.175.231; 13.U.175.236; 13.U.175.237; 13.U.175.238;
13.U.175.239; 13.U.175.154; 13.U.175.157; 13.U.175.166; 13.U.175.169;
13.U.175.172; 13.U.175.175; 13.U.175.240; 13.U.175.244; 13.U.240.228;
13.U.240.229; 13.U.240.230; 13.U.240.231; 13.U.240.236; 13.U.240.237;
13.U.240.238; 13.U.240.239; 13.U.240.154; 13.U.240.157; 13.U.240.166;
13.U.240.169; 13.U.240.172; 13.U.240.175; 13.U.240.240; 13.U.240.244;
13.U.244.228; 13.U.244.229; 13.U.244.230; 13.U.244.231; 13.U.244.236;
13.U.244.237; 13.U.244.238; 13.U.244.239; 13.U.244.154; 13.U.244.157;
13.U.244.166; 13.U.244.169; 13.U.244.172; 13.U.244.175; 13.U.244.240;
13.U.244.244;
Prodrugs of 13.W 13.W.228.228; 13.W.228.229; 13.W.228.230; 13.W.228.231; 13.W.228.236;
13.W.228.237; 13.W.228.238; 13.W.228.239; 13.W.228.154; 13.W.228.157;
13.W.228.166; 13.W.228.169; 13.W.228.172; 13.W.228.175; 13.W.228.240;
13.W.228.244; 13.W.229.228; 13.W.229.229; 13.W.229.230; 13.W.229.231;
13.W.229.236; 13.W.229.237; 13.W.229.238; 13.W.229.239; 13.W.229.154;
13.W.229.157; 13.W.229.166; 13.W.229.169; 13.W.229.172; 13.W.229.175;
13.W.229.240; 13.W.229.244; 13.W.230.228; 13.W.230.229; 13.W.230.230;
13.W.230.231; 13.W.230.236; 13.W.230.237; 13.W.230.238; 13.W.230.239;
13.W.230.154; 13.W.230.157; 13.W.230.166; 13.W.230.169; 13.W.230.172;
13.W.230.175; 13.W.230.240; 13.W.230.244; 13.W.231.228; 13.W.231.229;
13.W.231.230; 13.W.231.231; 13.W.231.236; 13.W.231.237; 13.W.231.238;
13.W.231.239; 13.W.231.154; 13.W.231.157; 13.W.231.166; 13.W.231.169;
13.W.231.172; 13.W.231.175; 13.W.231.240; 13.W.231.244; 13.W.236.228;
13.W.236.229; 13.W.236.230; 13.W.236.231; 13.W.236.236; 13.W.236.237;
13.W.236.238; 13.W.236.239; 13.W.236.154; 13.W.236.157; 13.W.236.166;
13.W.236.169; 13.W.236.172; 13.W.236.175; 13.W.236.240; 13.W.236.244;
13.W.237.228; 13.W.237.229; 13.W.237.230; 13.W.237.231; 13.W.237.236;
13.W.237.237; 13.W.237.238; 13.W.237.239; 13.W.237.154; 13.W.237.157;
13.W.237.166; 13.W.237.169; 13.W.237.172; 13.W.237.175; 13.W.237.240;
13.W.237.244; 13.W.238.228; 13.W.238.229; 13.W.238.230; 13.W.238.231;
13.W.238.236; 13.W.238.237; 13.W.238.238; 13.W.238.239; 13.W.238.154;
13.W.238.157; 13.W.238.166; 13.W.238.169; 13.W.238.172; 13.W.238.175;
13.W.238.240; 13.W.238.244; 13.W.239.228; 13.W.239.229; 13.W.239.230;
13.W.239.231; 13.W.239.236; 13.W.239.237; 13.W.239.238; 13.W.239.239;
13.W.239.154; 13.W.239.157; 13.W.239.166; 13.W.239.169; 13.W.239.172;
13.W.239.175; 13.W.239.240; 13.W.239.244; 13.W.154.228; 13.W.154.229;
13.W.154.230; 13.W.154.231; 13.W.154.236; 13.W.154.237; 13.W.154.238;
13.W.154.239; 13.W.154.154; 13.W.154.157; 13.W.154.166; 13.W.154.169;
13.W.154.172; 13.W.154.175; 13.W.154.240; 13.W.154.244; 13.W.157.228;
13.W.157.229; 13.W.157.230; 13.W.157.231; 13.W.157.236; 13.W.157.237;
13.W.157.238; 13.W.157.239; 13.W.157.154; 13.W.157.157; 13.W.157.166;
13.W.157.169; 13.W.157.172; 13.W.157.175; 13.W.157.240; 13.W.157.244;
13.W.166.228; 13.W.166.229; 13.W.166.230; 13.W.166.231; 13.W.166.236;
13.W.166.237; 13.W.166.238; 13.W.166.239; 13.W.166.154; 13.W.166.157;
13.W.166.166; 13.W.166.169; 13.W.166.172; 13.W.166.175; 13.W.166.240;
13.W.166.244; 13.W.169.228; 13.W.169.229; 13.W.169.230; 13.W.169.231;
13.W.169.236; 13.W.169.237; 13.W.169.238; 13.W.169.239; 13.W.169.154;
13.W.169.157; 13.W.169.166; 13.W.169.169; 13.W.169.172; 13.W.169.175;
13.W.169.240; 13.W.169.244; 13.W.172.228; 13.W.172.229; 13.W.172.230;
13.W.172.231; 13.W.172.236; 13.W.172.237; 13.W.172.238; 13.W.172.239;
13.W.172.154; 13.W.172.157; 13.W.172.166; 13.W.172.169; 13.W.172.172;
13.W.172.175; 13.W.172.240; 13.W.172.244; 13.W.175.228; 13.W.175.229;
13.W.175.230; 13.W.175.231; 13.W.175.236; 13.W.175.237; 13.W.175.238;
13.W.175.239; 13.W.175.154; 13.W.175.157; 13.W.175.166; 13.W.175.169;
13.W.175.172; 13.W.175.175; 13.W.175.240; 13.W.175.244; 13.W.240.228;
13.W.240.229; 13.W.240.230; 13.W.240.231; 13.W.240.236; 13.W.240.237;
13.W.240.238; 13.W.240.239; 13.W.240.154; 13.W.240.157; 13.W.240.166;
13.W.240.169; 13.W.240.172; 13.W.240.175; 13.W.240.240; 13.W.240.244;
13.W.244.228; 13.W.244.229; 13.W.244.230; 13.W.244.231; 13.W.244.236;
13.W.244.237; 13.W.244.238; 13.W.244.239; 13.W.244.154; 13.W.244.157;
13.W.244.166; 13.W.244.169; 13.W.244.172; 13.W.244.175; 13.W.244.240; 13.W.244.244;
Prodrugs of 13.Y 13.Y.228.228; 13.Y.228.229; 13.Y.228.230; 13.Y.228.231; 13.Y.228.236;
13.Y.228.237; 13.Y.228.238; 13.Y.228.239; 13.Y.228.154; 13.Y.228.157;
13.Y.228.166; 13.Y.228.169; 13.Y.228.172; 13.Y.228.175; 13.Y.228.240;
13.Y.228.244; 13.Y.229.228; 13.Y.229.229; 13.Y.229.230; 13.Y.229.231;
13.Y.229.236; 13.Y.229.237; 13.Y.229.238; 13.Y.229.239; 13.Y.229.154;
13.Y.229.157; 13.Y.229.166; 13.Y.229.169; 13.Y.229.172; 13.Y.229.175;
13.Y.229.240; 13.Y.229.244; 13.Y.230.228; 13.Y.230.229; 13.Y.230.230;
13.Y.230.231; 13.Y.230.236; 13.Y.230.237; 13.Y.230.238; 13.Y.230.239;
13.Y.230.154; 13.Y.230.157; 13.Y.230.166; 13.Y.230.169; 13.Y.230.172;

TABLE 100-continued

13.Y.230.175; 13.Y.230.240; 13.Y.230.244; 13.Y.231.228; 13.Y.231.229;
13.Y.231.230; 13.Y.231.231; 13.Y.231.236; 13.Y.231.237; 13.Y.231.238;
13.Y.231.239; 13.Y.231.154; 13.Y.231.157; 13.Y.231.166; 13.Y.231.169;
13.Y.231.172; 13.Y.231.175; 13.Y.231.240; 13.Y.231.244; 13.Y.236.228;
13.Y.236.229; 13.Y.236.230; 13.Y.236.231; 13.Y.236.236; 13.Y.236.237;
13.Y.236.238; 13.Y.236.239; 13.Y.236.154; 13.Y.236.157; 13.Y.236.166;
13.Y.236.169; 13.Y.236.172; 13.Y.236.175; 13.Y.236.240; 13.Y.236.244;
13.Y.237.228; 13.Y.237.229; 13.Y.237.230; 13.Y.237.231; 13.Y.237.236;
13.Y.237.237; 13.Y.237.238; 13.Y.237.239; 13.Y.237.154; 13.Y.237.157;
13.Y.237.166; 13.Y.237.169; 13.Y.237.172; 13.Y.237.175; 13.Y.237.240;
13.Y.237.244; 13.Y.238.228; 13.Y.238.229; 13.Y.238.230; 13.Y.238.231;
13.Y.238.236; 13.Y.238.237; 13.Y.238.238; 13.Y.238.239; 13.Y.238.154;
13.Y.238.157; 13.Y.238.166; 13.Y.238.169; 13.Y.238.172; 13.Y.238.175;
13.Y.238.240; 13.Y.238.244; 13.Y.239.228; 13.Y.239.229; 13.Y.239.230;
13.Y.239.231; 13.Y.239.236; 13.Y.239.237; 13.Y.239.238; 13.Y.239.239;
13.Y.239.154; 13.Y.239.157; 13.Y.239.166; 13.Y.239.169; 13.Y.239.172;
13.Y.239.175; 13.Y.239.240; 13.Y.239.244; 13.Y.154.228; 13.Y.154.229;
13.Y.154.230; 13.Y.154.231; 13.Y.154.236; 13.Y.154.237; 13.Y.154.238;
13.Y.154.239; 13.Y.154.154; 13.Y.154.157; 13.Y.154.166; 13.Y.154.169;
13.Y.154.172; 13.Y.154.175; 13.Y.154.240; 13.Y.154.244; 13.Y.157.228;
13.Y.157.229; 13.Y.157.230; 13.Y.157.231; 13.Y.157.236; 13.Y.157.237;
13.Y.157.238; 13.Y.157.239; 13.Y.157.154; 13.Y.157.157; 13.Y.157.166;
13.Y.157.169; 13.Y.157.172; 13.Y.157.175; 13.Y.157.240; 13.Y.157.244;
13.Y.166.228; 13.Y.166.229; 13.Y.166.230; 13.Y.166.231; 13.Y.166.236;
13.Y.166.237; 13.Y.166.238; 13.Y.166.239; 13.Y.166.154; 13.Y.166.157;
13.Y.166.166; 13.Y.166.169; 13.Y.166.172; 13.Y.166.175; 13.Y.166.240;
13.Y.166.244; 13.Y.169.228; 13.Y.169.229; 13.Y.169.230; 13.Y.169.231;
13.Y.169.236; 13.Y.169.237; 13.Y.169.238; 13.Y.169.239; 13.Y.169.154;
13.Y.169.157; 13.Y.169.166; 13.Y.169.169; 13.Y.169.172; 13.Y.169.175;
13.Y.169.240; 13.Y.169.244; 13.Y.172.228; 13.Y.172.229; 13.Y.172.230;
13.Y.172.231; 13.Y.172.236; 13.Y.172.237; 13.Y.172.238; 13.Y.172.239;
13.Y.172.154; 13.Y.172.157; 13.Y.172.166; 13.Y.172.169; 13.Y.172.172;
13.Y.172.175; 13.Y.172.240; 13.Y.172.244; 13.Y.175.228; 13.Y.175.229;
13.Y.175.230; 13.Y.175.231; 13.Y.175.236; 13.Y.175.237; 13.Y.175.238;
13.Y.175.239; 13.Y.175.154; 13.Y.175.157; 13.Y.175.166; 13.Y.175.169;
13.Y.175.172; 13.Y.175.175; 13.Y.175.240; 13.Y.175.244; 13.Y.240.228;
13.Y.240.229; 13.Y.240.230; 13.Y.240.231; 13.Y.240.236; 13.Y.240.237;
13.Y.240.238; 13.Y.240.239; 13.Y.240.154; 13.Y.240.157; 13.Y.240.166;
13.Y.240.169; 13.Y.240.172; 13.Y.240.175; 13.Y.240.240; 13.Y.240.244;
13.Y.244.228; 13.Y.244.229; 13.Y.244.230; 13.Y.244.231; 13.Y.244.236;
13.Y.244.237; 13.Y.244.238; 13.Y.244.239; 13.Y.244.154; 13.Y.244.157;
13.Y.244.166; 13.Y.244.169; 13.Y.244.172; 13.Y.244.175; 13.Y.244.240;
13.Y.244.244;

Prodrugs of 14.AH

14.AH.4.157; 14.AH.4.158; 14.AH.4.196; 14.AH.4.223; 14.AH.4.240;
14.AH.4.244; 14.AH.4.243; 14.AH.4.247; 14.AH.5.157; 14.AH.5.158;
14.AH.5.196; 14.AH.5.223; 14.AH.5.240; 14.AH.5.244; 14.AH.5.243;
14.AH.5.247; 14.AH.7.157; 14.AH.7.158; 14.AH.7.196; 14.AH.7.223;
14.AH.7.240; 14.AH.7.244; 14.AH.7.243; 14.AH.7.247; 14.AH.15.157;
14.AH.15.158; 14.AH.15.196; 14.AH.15.223; 14.AH.15.240; 14.AH.15.244;
14.AH.15.243; 14.AH.15.247; 14.AH.16.157; 14.AH.16.158; 14.AH.16.196;
14.AH.16.223; 14.AH.16.240; 14.AH.16.244; 14.AH.16.243; 14.AH.16.247;
14.AH.18.157; 14.AH.18.158; 14.AH.18.196; 14.AH.18.223; 14.AH.18.240;
14.AH.18.244; 14.AH.18.243; 14.AH.18.247; 14.AH.26.157; 14.AH.26.158;
14.AH.26.196; 14.AH.26.223; 14.AH.26.240; 14.AH.26.244; 14.AH.26.243;
14.AH.26.247; 14.AH.27.157; 14.AH.27.158; 14.AH.27.196; 14.AH.27.223;
14.AH.27.240; 14.AH.27.244; 14.AH.27.243; 14.AH.27.247; 14.AH.29.157;
14.AH.29.158; 14.AH.29.196; 14.AH.29.223; 14.AH.29.240; 14.AH.29.244;
14.AH.29.243; 14.AH.29.247; 14.AH.54.157; 14.AH.54.158; 14.AH.54.196;
14.AH.54.223; 14.AH.54.240; 14.AH.54.244; 14.AH.54.243; 14.AH.54.247;
14.AH.55.157; 14.AH.55.158; 14.AH.55.196; 14.AH.55.223; 14.AH.55.240;
14.AH.55.244; 14.AH.55.243; 14.AH.55.247; 14.AH.56.157; 14.AH.56.158;
14.AH.56.196; 14.AH.56.223; 14.AH.56.240; 14.AH.56.244; 14.AH.56.243;
14.AH.56.247; 14.AH.157.157; 14.AH.157.158; 14.AH.157.196;
14.AH.157.223; 14.AH.157.240; 14.AH.157.244; 14.AH.157.243;
14.AH.157.247; 14.AH.196.157; 14.AH.196.158; 14.AH.196.196;
14.AH.196.223; 14.AH.196.240; 14.AH.196.244; 14.AH.196.243;
14.AH.196.247; 14.AH.223.157; 14.AH.223.158; 14.AH.223.196;
14.AH.223.223; 14.AH.223.240; 14.AH.223.244; 14.AH.223.243;
14.AH.223.247; 14.AH.240.157; 14.AH.240.158; 14.AH.240.196;
14.AH.240.223; 14.AH.240.240; 14.AH.240.244; 14.AH.240.243;
14.AH.240.247; 14.AH.244.157; 14.AH.244.158; 14.AH.244.196;
14.AH.244.223; 14.AH.244.240; 14.AH.244.244; 14.AH.244.243;
14.AH.244.247; 14.AH.247.157; 14.AH.247.158; 14.AH.247.196;
14.AH.247.223; 14.AH.247.240; 14.AH.247.244; 14.AH.247.243;
14.AH.247.247;

TABLE 100-continued

Prodrugs of 14.AJ

14.AJ.4.157; 14.AJ.4.158; 14.AJ.4.196; 14.AJ.4.223; 14.AJ.4.240;
14.AJ.4.244; 14.AJ.4.243; 14.AJ.4.247; 14.AJ.5.157; 14.AJ.5.158; 14.AJ.5.196;
14.AJ.5.223; 14.AJ.5.240; 14.AJ.5.244; 14.AJ.5.243; 14.AJ.5.247; 14.AJ.7.157;
14.AJ.7.158; 14.AJ.7.196; 14.AJ.7.223; 14.AJ.7.240; 14.AJ.7.244; 14.AJ.7.243;
14.AJ.7.247; 14.AJ.15.157; 14.AJ.15.158; 14.AJ.15.196; 14.AJ.15.223;
14.AJ.15.240; 14.AJ.15.244; 14.AJ.15.243; 14.AJ.15.247; 14.AJ.16.157;
14.AJ.16.158; 14.AJ.16.196; 14.AJ.16.223; 14.AJ.16.240; 14.AJ.16.244;
14.AJ.16.243; 14.AJ.16.247; 14.AJ.18.157; 14.AJ.18.158; 14.AJ.18.196;
14.AJ.18.223; 14.AJ.18.240; 14.AJ.18.244; 14.AJ.18.243; 14.AJ.18.247;
14.AJ.26.157; 14.AJ.26.158; 14.AJ.26.196; 14.AJ.26.223; 14.AJ.26.240;
14.AJ.26.244; 14.AJ.26.243; 14.AJ.26.247; 14.AJ.27.157; 14.AJ.27.158;
14.AJ.27.196; 14.AJ.27.223; 14.AJ.27.240; 14.AJ.27.244; 14.AJ.27.243;
14.AJ.27.247; 14.AJ.29.157; 14.AJ.29.158; 14.AJ.29.196; 14.AJ.29.223;
14.AJ.29.240; 14.AJ.29.244; 14.AJ.29.243; 14.AJ.29.247; 14.AJ.54.157;
14.AJ.54.158; 14.AJ.54.196; 14.AJ.54.223; 14.AJ.54.240; 14.AJ.54.244;
14.AJ.54.243; 14.AJ.54.247; 14.AJ.55.157; 14.AJ.55.158; 14.AJ.55.196;
14.AJ.55.223; 14.AJ.55.240; 14.AJ.55.244; 14.AJ.55.243; 14.AJ.55.247;
14.AJ.56.157; 14.AJ.56.158; 14.AJ.56.196; 14.AJ.56.223; 14.AJ.56.240;
14.AJ.56.244; 14.AJ.56.243; 14.AJ.56.247; 14.AJ.157.157; 14.AJ.157.158;
14.AJ.157.196; 14.AJ.157.223; 14.AJ.157.240; 14.AJ.157.244; 14.AJ.157.243;
14.AJ.157.247; 14.AJ.196.157; 14.AJ.196.158; 14.AJ.196.196; 14.AJ.196.223;
14.AJ.196.240; 14.AJ.196.244; 14.AJ.196.243; 14.AJ.196.247; 14.AJ.223.157;
14.AJ.223.158; 14.AJ.223.196; 14.AJ.223.223; 14.AJ.223.240; 14.AJ.223.244;
14.AJ.223.243; 14.AJ.223.247; 14.AJ.240.157; 14.AJ.240.158; 14.AJ.240.196;
14.AJ.240.223; 14.AJ.240.240; 14.AJ.240.244; 14.AJ.240.243; 14.AJ.240.247;
14.AJ.244.157; 14.AJ.244.158; 14.AJ.244.196; 14.AJ.244.223; 14.AJ.244.240;
14.AJ.244.244; 14.AJ.244.243; 14.AJ.244.247; 14.AJ.247.157; 14.AJ.247.158;
14.AJ.247.196; 14.AJ.247.223; 14.AJ.247.240; 14.AJ.247.244; 14.AJ.247.243;
14.AJ.247.247;

Prodrugs of 14.AN

14.AN.4.157; 14.AN.4.158; 14.AN.4.196; 14.AN.4.223; 14.AN.4.240;
14.AN.4.244; 14.AN.4.243; 14.AN.4.247; 14.AN.5.157; 14.AN.5.158;
14.AN.5.196; 14.AN.5.223; 14.AN.5.240; 14.AN.5.244; 14.AN.5.243;
14.AN.5.247; 14.AN.7.157; 14.AN.7.158; 14.AN.7.196; 14.AN.7.223;
14.AN.7.240; 14.AN.7.244; 14.AN.7.243; 14.AN.7.247; 14.AN.15.157;
14.AN.15.158; 14.AN.15.196; 14.AN.15.223; 14.AN.15.240; 14.AN.15.244;
14.AN.15.243; 14.AN.15.247; 14.AN.16.157; 14.AN.16.158; 14.AN.16.196;
14.AN.16.223; 14.AN.16.240; 14.AN.16.244; 14.AN.16.243; 14.AN.16.247;
14.AN.18.157; 14.AN.18.158; 14.AN.18.196; 14.AN.18.223; 14.AN.18.240;
14.AN.18.244; 14.AN.18.243; 14.AN.18.247; 14.AN.26.157; 14.AN.26.158;
14.AN.26.196; 14.AN.26.223; 14.AN.26.240; 14.AN.26.244; 14.AN.26.243;
14.AN.26.247; 14.AN.27.157; 14.AN.27.158; 14.AN.27.196; 14.AN.27.223;
14.AN.27.240; 14.AN.27.244; 14.AN.27.243; 14.AN.27.247; 14.AN.29.157;
14.AN.29.158; 14.AN.29.196; 14.AN.29.223; 14.AN.29.240; 14.AN.29.244;
14.AN.29.243; 14.AN.29.247; 14.AN.54.157; 14.AN.54.158; 14.AN.54.196;
14.AN.54.223; 14.AN.54.240; 14.AN.54.244; 14.AN.54.243; 14.AN.54.247;
14.AN.55.157; 14.AN.55.158; 14.AN.55.196; 14.AN.55.223; 14.AN.55.240;
14.AN.55.244; 14.AN.55.243; 14.AN.55.247; 14.AN.56.157; 14.AN.56.158;
14.AN.56.196; 14.AN.56.223; 14.AN.56.240; 14.AN.56.244; 14.AN.56.243;
14.AN.56.247; 14.AN.157.157; 14.AN.157.158; 14.AN.157.196;
14.AN.157.223; 14.AN.157.240; 14.AN.157.244; 14.AN.157.243;
14.AN.157.247; 14.AN.196.157; 14.AN.196.158; 14.AN.196.196;
14.AN.196.223; 14.AN.196.240; 14.AN.196.244; 14.AN.196.243;
14.AN.196.247; 14.AN.223.157; 14.AN.223.158; 14.AN.223.196;
14.AN.223.223; 14.AN.223.240; 14.AN.223.244; 14.AN.223.243;
14.AN.223.247; 14.AN.240.157; 14.AN.240.158; 14.AN.240.196;
14.AN.240.223; 14.AN.240.240; 14.AN.240.244; 14.AN.240.243;
14.AN.240.247; 14.AN.244.157; 14.AN.244.158; 14.AN.244.196;
14.AN.244.223; 14.AN.244.240; 14.AN.244.244; 14.AN.244.243;
14.AN.244.247; 14.AN.247.157; 14.AN.247.158; 14.AN.247.196;
14.AN.247.223; 14.AN.247.240; 14.AN.247.244; 14.AN.247.243;
14.AN.247.247;

Prodrugs of 14.AP

14.AP.4.157; 14.AP.4.158; 14.AP.4.196; 14.AP.4.223; 14.AP.4.240;
14.AP.4.244; 14.AP.4.243; 14.AP.4.247; 14.AP.5.157; 14.AP.5.158;
14.AP.5.196; 14.AP.5.223; 14.AP.5.240; 14.AP.5.244; 14.AP.5.243;
14.AP.5.247; 14.AP.7.157; 14.AP.7.158; 14.AP.7.196; 14.AP.7.223;
14.AP.7.240; 14.AP.7.244; 14.AP.7.243; 14.AP.7.247; 14.AP.15.157;
14.AP.15.158; 14.AP.15.196; 14.AP.15.223; 14.AP.15.240; 14.AP.15.244;
14.AP.15.243; 14.AP.15.247; 14.AP.16.157; 14.AP.16.158; 14.AP.16.196;
14.AP.16.223; 14.AP.16.240; 14.AP.16.244; 14.AP.16.243; 14.AP.16.247;
14.AP.18.157; 14.AP.18.158; 14.AP.18.196; 14.AP.18.223; 14.AP.18.240;
14.AP.18.244; 14.AP.18.243; 14.AP.18.247; 14.AP.26.157; 14.AP.26.158;
14.AP.26.196; 14.AP.26.223; 14.AP.26.240; 14.AP.26.244; 14.AP.26.243;
14.AP.26.247; 14.AP.27.157; 14.AP.27.158; 14.AP.27.196; 14.AP.27.223;

TABLE 100-continued

14.AP.27.240; 14.AP.27.244; 14.AP.27.243; 14.AP.27.247; 14.AP.29.157;
14.AP.29.158; 14.AP.29.196; 14.AP.29.223; 14.AP.29.240; 14.AP.29.244;
14.AP.29.243; 14.AP.29.247; 14.AP.54.157; 14.AP.54.158; 14.AP.54.196;
14.AP.54.223; 14.AP.54.240; 14.AP.54.244; 14.AP.54.243; 14.AP.54.247;
14.AP.55.157; 14.AP.55.158; 14.AP.55.196; 14.AP.55.223; 14.AP.55.240;
14.AP.55.244; 14.AP.55.243; 14.AP.55.247; 14.AP.56.157; 14.AP.56.158;
14.AP.56.196; 14.AP.56.223; 14.AP.56.240; 14.AP.56.244; 14.AP.56.243;
14.AP.56.247; 14.AP.157.157; 14.AP.157.158; 14.AP.157.196; 14.AP.157.223;
14.AP.157.240; 14.AP.157.244; 14.AP.157.243; 14.AP.157.247;
14.AP.196.157; 14.AP.196.158; 14.AP.196.196; 14.AP.196.223;
14.AP.196.240; 14.AP.196.244; 14.AP.196.243; 14.AP.196.247;
14.AP.223.157; 14.AP.223.158; 14.AP.223.196; 14.AP.223.223;
14.AP.223.240; 14.AP.223.244; 14.AP.223.243; 14.AP.223.247;
14.AP.240.157; 14.AP.240.158; 14.AP.240.196; 14.AP.240.223;
14.AP.240.240; 14.AP.240.244; 14.AP.240.243; 14.AP.240.247;
14.AP.244.157; 14.AP.244.158; 14.AP.244.196; 14.AP.244.223;
14.AP.244.240; 14.AP.244.244; 14.AP.244.243; 14.AP.244.247;
14.AP.247.157; 14.AP.247.158; 14.AP.247.196; 14.AP.247.223;
14.AP.247.240; 14.AP.247.244; 14.AP.247.243; 14.AP.247.247;
Prodrugs of 14.AZ 14.AZ.4.157; 14.AZ.4.158; 14.AZ.4.196; 14.AZ.4.223; 14.AZ.4.240;
14.AZ.4.244; 14.AZ.4.243; 14.AZ.4.247; 14.AZ.5.157; 14.AZ.5.158;
14.AZ.5.196; 14.AZ.5.223; 14.AZ.5.240; 14.AZ.5.244; 14.AZ.5.243;
14.AZ.5.247; 14.AZ.7.157; 14.AZ.7.158; 14.AZ.7.196; 14.AZ.7.223;
14.AZ.7.240; 14.AZ.7.244; 14.AZ.7.243; 14.AZ.7.247; 14.AZ.15.157;
14.AZ.15.158; 14.AZ.15.196; 14.AZ.15.223; 14.AZ.15.240; 14.AZ.15.244;
14.AZ.15.243; 14.AZ.15.247; 14.AZ.16.157; 14.AZ.16.158; 14.AZ.16.196;
14.AZ.16.223; 14.AZ.16.240; 14.AZ.16.244; 14.AZ.16.243; 14.AZ.16.247;
14.AZ.18.157; 14.AZ.18.158; 14.AZ.18.196; 14.AZ.18.223; 14.AZ.18.240;
14.AZ.18.244; 14.AZ.18.243; 14.AZ.18.247; 14.AZ.26.157; 14.AZ.26.158;
14.AZ.26.196; 14.AZ.26.223; 14.AZ.26.240; 14.AZ.26.244; 14.AZ.26.243;
14.AZ.26.247; 14.AZ.27.157; 14.AZ.27.158; 14.AZ.27.196; 14.AZ.27.223;
14.AZ.27.240; 14.AZ.27.244; 14.AZ.27.243; 14.AZ.27.247; 14.AZ.29.157;
14.AZ.29.158; 14.AZ.29.196; 14.AZ.29.223; 14.AZ.29.240; 14.AZ.29.244;
14.AZ.29.243; 14.AZ.29.247; 14.AZ.54.157; 14.AZ.54.158; 14.AZ.54.196;
14.AZ.54.223; 14.AZ.54.240; 14.AZ.54.244; 14.AZ.54.243; 14.AZ.54.247;
14.AZ.55.157; 14.AZ.55.158; 14.AZ.55.196; 14.AZ.55.223; 14.AZ.55.240;
14.AZ.55.244; 14.AZ.55.243; 14.AZ.55.247; 14.AZ.56.157; 14.AZ.56.158;
14.AZ.56.196; 14.AZ.56.223; 14.AZ.56.240; 14.AZ.56.244; 14.AZ.56.243;
14.AZ.56.247; 14.AZ.157.157; 14.AZ.157.158; 14.AZ.157.196; 14.AZ.157.223;
14.AZ.157.240; 14.AZ.157.244; 14.AZ.157.243; 14.AZ.157.247;
14.AZ.196.157; 14.AZ.196.158; 14.AZ.196.196; 14.AZ.196.223;
14.AZ.196.240; 14.AZ.196.244; 14.AZ.196.243; 14.AZ.196.247;
14.AZ.223.157; 14.AZ.223.158; 14.AZ.223.196; 14.AZ.223.223;
14.AZ.223.240; 14.AZ.223.244; 14.AZ.223.243; 14.AZ.223.247;
14.AZ.240.157; 14.AZ.240.158; 14.AZ.240.196; 14.AZ.240.223;
14.AZ.240.240; 14.AZ.240.244; 14.AZ.240.243; 14.AZ.240.247;
14.AZ.244.157; 14.AZ.244.158; 14.AZ.244.196; 14.AZ.244.223;
14.AZ.244.240; 14.AZ.244.244; 14.AZ.244.243; 14.AZ.244.247;
14.AZ.247.157; 14.AZ.247.158; 14.AZ.247.196; 14.AZ.247.223;
14.AZ.247.240; 14.AZ.247.244; 14.AZ.247.243; 14.AZ.247.247;
Prodrugs of 14.BF 14.BF.4.157; 14.BF.4.158; 14.BF.4.196; 14.BF.4.223; 14.BF.4.240;
14.BF.4.244; 14.BF.4.243; 14.BF.4.247; 14.BF.5.157; 14.BF.5.158;
14.BF.5.196; 14.BF.5.223; 14.BF.5.240; 14.BF.5.244; 14.BF.5.243;
14.BF.5.247; 14.BF.7.157; 14.BF.7.158; 14.BF.7.196; 14.BF.7.223;
14.BF.7.240; 14.BF.7.244; 14.BF.7.243; 14.BF.7.247; 14.BF.15.157;
14.BF.15.158; 14.BF.15.196; 14.BF.15.223; 14.BF.15.240; 14.BF.15.244;
14.BF.15.243; 14.BF.15.247; 14.BF.16.157; 14.BF.16.158; 14.BF.16.196;
14.BF.16.223; 14.BF.16.240; 14.BF.16.244; 14.BF.16.243; 14.BF.16.247;
14.BF.18.157; 14.BF.18.158; 14.BF.18.196; 14.BF.18.223; 14.BF.18.240;
14.BF.18.244; 14.BF.18.243; 14.BF.18.247; 14.BF.26.157; 14.BF.26.158;
14.BF.26.196; 14.BF.26.223; 14.BF.26.240; 14.BF.26.244; 14.BF.26.243;
14.BF.26.247; 14.BF.27.157; 14.BF.27.158; 14.BF.27.196; 14.BF.27.223;
14.BF.27.240; 14.BF.27.244; 14.BF.27.243; 14.BF.27.247; 14.BF.29.157;
14.BF.29.158; 14.BF.29.196; 14.BF.29.223; 14.BF.29.240; 14.BF.29.244;
14.BF.29.243; 14.BF.29.247; 14.BF.54.157; 14.BF.54.158; 14.BF.54.196;
14.BF.54.223; 14.BF.54.240; 14.BF.54.244; 14.BF.54.243; 14.BF.54.247;
14.BF.55.157; 14.BF.55.158; 14.BF.55.196; 14.BF.55.223; 14.BF.55.240;
14.BF.55.244; 14.BF.55.243; 14.BF.55.247; 14.BF.56.157; 14.BF.56.158;
14.BF.56.196; 14.BF.56.223; 14.BF.56.240; 14.BF.56.244; 14.BF.56.243;
14.BF.56.247; 14.BF.157.157; 14.BF.157.158; 14.BF.157.196; 14.BF.157.223;
14.BF.157.240; 14.BF.157.244; 14.BF.157.243; 14.BF.157.247; 14.BF.196.157;
14.BF.196.158; 14.BF.196.196; 14.BF.196.223; 14.BF.196.240; 14.BF.196.244;
14.BF.196.243; 14.BF.196.247; 14.BF.223.157; 14.BF.223.158; 14.BF.223.196;
14.BF.223.223; 14.BF.223.240; 14.BF.223.244; 14.BF.223.243; 14.BF.223.247;
14.BF.240.157; 14.BF.240.158; 14.BF.240.196; 14.BF.240.223; 14.BF.240.240;

TABLE 100-continued

14.BF.240.244; 14.BF.240.243; 14.BF.240.247; 14.BF.244.157; 14.BF.244.158;
14.BF.244.196; 14.BF.244.223; 14.BF.244.240; 14.BF.244.244; 14.BF.244.243;
14.BF.244.247; 14.BF.247.157; 14.BF.247.158; 14.BF.247.196; 14.BF.247.223;
14.BF.247.240; 14.BF.247.244; 14.BF.247.243; 14.BF.247.247;

Prodrugs of 14.CI

14.CI.4.157; 14.CI.4.158; 14.CI.4.196; 14.CI.4.223; 14.CI.4.240;
14.CI.4.244; 14.CI.4.243; 14.CI.4.247; 14.CI.5.157; 14.CI.5.158; 14.CI.5.196;
14.CI.5.223; 14.CI.5.240; 14.CI.5.244; 14.CI.5.243; 14.CI.5.247; 14.CI.7.157;
14.CI.7.158; 14.CI.7.196; 14.CI.7.223; 14.CI.7.240; 14.CI.7.244; 14.CI.7.243;
14.CI.7.247; 14.CI.15.157; 14.CI.15.158; 14.CI.15.196; 14.CI.15.223;
14.CI.15.240; 14.CI.15.244; 14.CI.15.243; 14.CI.15.247; 14.CI.16.157;
14.CI.16.158; 14.CI.16.196; 14.CI.16.223; 14.CI.16.240; 14.CI.16.244;
14.CI.16.243; 14.CI.16.247; 14.CI.18.157; 14.CI.18.158; 14.CI.18.196;
14.CI.18.223; 14.CI.18.240; 14.CI.18.244; 14.CI.18.243; 14.CI.18.247;
14.CI.26.157; 14.CI.26.158; 14.CI.26.196; 14.CI.26.223; 14.CI.26.240;
14.CI.26.244; 14.CI.26.243; 14.CI.26.247; 14.CI.27.157; 14.CI.27.158;
14.CI.27.196; 14.CI.27.223; 14.CI.27.240; 14.CI.27.244; 14.CI.27.243;
14.CI.27.247; 14.CI.29.157; 14.CI.29.158; 14.CI.29.196; 14.CI.29.223;
14.CI.29.240; 14.CI.29.244; 14.CI.29.243; 14.CI.29.247; 14.CI.54.157;
14.CI.54.158; 14.CI.54.196; 14.CI.54.223; 14.CI.54.240; 14.CI.54.244;
14.CI.54.243; 14.CI.54.247; 14.CI.55.157; 14.CI.55.158; 14.CI.55.196;
14.CI.55.223; 14.CI.55.240; 14.CI.55.244; 14.CI.55.243; 14.CI.55.247;
14.CI.56.157; 14.CI.56.158; 14.CI.56.196; 14.CI.56.223; 14.CI.56.240;
14.CI.56.244; 14.CI.56.243; 14.CI.56.247; 14.CI.157.157; 14.CI.157.158;
14.CI.157.196; 14.CI.157.223; 14.CI.157.240; 14.CI.157.244; 14.CI.157.243;
14.CI.157.247; 14.CI.196.157; 14.CI.196.158; 14.CI.196.196; 14.CI.196.223;
14.CI.196.240; 14.CI.196.244; 14.CI.196.243; 14.CI.196.247; 14.CI.223.157;
14.CI.223.158; 14.CI.223.196; 14.CI.223.223; 14.CI.223.240; 14.CI.223.244;
14.CI.223.243; 14.CI.223.247; 14.CI.240.157; 14.CI.240.158; 14.CI.240.196;
14.CI.240.223; 14.CI.240.240; 14.CI.240.244; 14.CI.240.243; 14.CI.240.247;
14.CI.244.157; 14.CI.244.158; 14.CI.244.196; 14.CI.244.223; 14.CI.244.240;
14.CI.244.244; 14.CI.244.243; 14.CI.244.247; 14.CI.247.157; 14.CI.247.158;
14.CI.247.196; 14.CI.247.223; 14.CI.247.240; 14.CI.247.244; 14.CI.247.243;
14.CI.247.247;

Prodrugs of 14.CO

14.CO.4.157; 14.CO.4.158; 14.CO.4.196; 14.CO.4.223; 14.CO.4.240;
14.CO.4.244; 14.CO.4.243; 14.CO.4.247; 14.CO.5.157; 14.CO.5.158;
14.CO.5.196; 14.CO.5.223; 14.CO.5.240; 14.CO.5.244; 14.CO.5.243;
14.CO.5.247; 14.CO.7.157; 14.CO.7.158; 14.CO.7.196; 14.CO.7.223;
14.CO.7.240; 14.CO.7.244; 14.CO.7.243; 14.CO.7.247; 14.CO.15.157;
14.CO.15.158; 14.CO.15.196; 14.CO.15.223; 14.CO.15.240; 14.CO.15.244;
14.CO.15.243; 14.CO.15.247; 14.CO.16.157; 14.CO.16.158; 14.CO.16.196;
14.CO.16.223; 14.CO.16.240; 14.CO.16.244; 14.CO.16.243; 14.CO.16.247;
14.CO.18.157; 14.CO.18.158; 14.CO.18.196; 14.CO.18.223; 14.CO.18.240;
14.CO.18.244; 14.CO.18.243; 14.CO.18.247; 14.CO.26.157; 14.CO.26.158;
14.CO.26.196; 14.CO.26.223; 14.CO.26.240; 14.CO.26.244; 14.CO.26.243;
14.CO.26.247; 14.CO.27.157; 14.CO.27.158; 14.CO.27.196; 14.CO.27.223;
14.CO.27.240; 14.CO.27.244; 14.CO.27.243; 14.CO.27.247; 14.CO.29.157;
14.CO.29.158; 14.CO.29.196; 14.CO.29.223; 14.CO.29.240; 14.CO.29.244;
14.CO.29.243; 14.CO.29.247; 14.CO.54.157; 14.CO.54.158; 14.CO.54.196;
14.CO.54.223; 14.CO.54.240; 14.CO.54.244; 14.CO.54.243; 14.CO.54.247;
14.CO.55.157; 14.CO.55.158; 14.CO.55.196; 14.CO.55.223; 14.CO.55.240;
14.CO.55.244; 14.CO.55.243; 14.CO.55.247; 14.CO.56.157; 14.CO.56.158;
14.CO.56.196; 14.CO.56.223; 14.CO.56.240; 14.CO.56.244; 14.CO.56.243;
14.CO.56.247; 14.CO.157.157; 14.CO.157.158; 14.CO.157.196;
14.CO.157.223; 14.CO.157.240; 14.CO.157.244; 14.CO.157.243;
14.CO.157.247; 14.CO.196.157; 14.CO.196.158; 14.CO.196.196;
14.CO.196.223; 14.CO.196.240; 14.CO.196.244; 14.CO.196.243;
14.CO.196.247; 14.CO.223.157; 14.CO.223.158; 14.CO.223.196;
14.CO.223.223; 14.CO.223.240; 14.CO.223.244; 14.CO.223.243;
14.CO.223.247; 14.CO.240.157; 14.CO.240.158; 14.CO.240.196;
14.CO.240.223; 14.CO.240.240; 14.CO.240.244; 14.CO.240.243;
14.CO.240.247; 14.CO.244.157; 14.CO.244.158; 14.CO.244.196;
14.CO.244.223; 14.CO.244.240; 14.CO.244.244; 14.CO.244.243;
14.CO.244.247; 14.CO.4.157; 14.CO.4.158; 14.CO.4.196; 14.CO.4.223;
14.CO.4.240; 14.CO.4.244; 14.CO.4.243; 14.CO.4.247;

All literature and patent citations herein are hereby expressly incorporated by reference at the locations of their citation. Specifically cited sections or pages of the above cited works are incorporated by reference with specificity. The invention has been described in detail sufficient to allow one of ordinary skill in the art to make and use the subject matter of the following claims. It is apparent that certain modifications of the methods and compositions of the following claims can be made within the scope and spirit of the invention.

In the claims hereinbelow, the subscript and superscripts of a given variable are distinct. For example, $R_1$ is distinct from $R^1$.

We claim:
1. A method for inhibiting inflammatory activity in vitro comprising contacting a sample in need of such treatment with a conjugate or a pharmaceutically acceptable salt or solvate thereof wherein the conjugate is a compound of the formula:

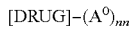

wherein:
DRUG is a compound of formula 556:

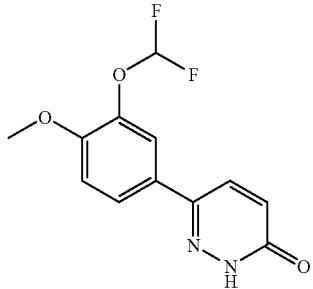

wherein:
nn is 1, 2, or 3;
$A^0$ is $A^1$, $A^2$ or $W^3$ with the proviso that the conjugate includes at least one $A^1$;

$A^1$ is:

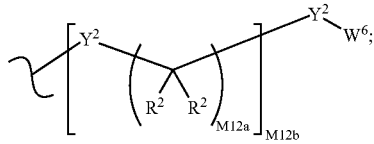

$A^2$ is:

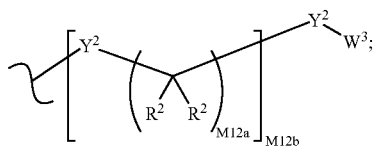

$A^3$ is:

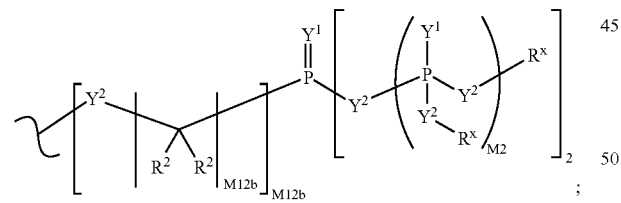

$Y^1$ is independently O, S, $N(R^x)$, $N(O)(R^x)$, $N(OR^x)$, $N(O)(OR^x)$, or $N(N(R^x)(R^x))$;
$Y^2$ is independently a bond, O, $N(R^x)$, $N(O)(R^x)$, $N(OR^x)$, $N(O)(OR^x)$, $N(N(R^x)(R^x))$, —$S(O)_{M2}$—, or —$S(O)_{M2}$—$S(O)_{M2}$—; and when $Y^2$ joins two phosphorous atoms $Y^2$ can also be $C(R^2)(R^2)$;
$R^x$ is independently H, $R^1$, $R^2$, $W^3$, a protecting group, or the formula:

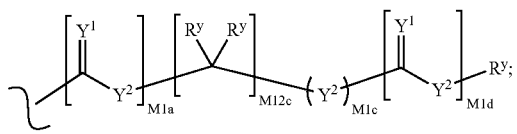

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;
$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;
$R^{3a}$ is F, Cl, Br, I, —CN, $N_3$ or —$NO_2$;
$R^{3b}$ is $Y^1$;
$R^{3c}$ is —$R^x$, —$N(R^x)(R^x)$, —$SR^x$, —$S(O)R^x$, —$S(O)_2R^x$, —$S(O)(OR^x)$, —$S(O)_2(OR^x)$, —$OC(Y^1)R^x$, —$OC(Y^1)OR^x$, —$OC(Y^1)(N(R^x)(R^x))$, —$SC(Y^1)R^x$, —$SC(Y^1)OR^x$, —$SC(Y^1)(N(R^x)(R^x))$, —$N(R^x)C(Y^1)R^x$, —$N(R^x)C(Y^1)OR^x$, or —$N(R^x)C(Y^1)(N(R^x)(R^x))$;
$R^{3d}$ is —$C(Y^1)R^x$, —$C(Y^1)OR^x$ or —$C(Y^1)(N(R^x)(R^x))$;
$R^4$ is an alkyl of 1 to 18 carbon atoms, alkenyl of 2 to 18 carbon atoms, or alkynyl of 2 to 18 carbon atoms;
$R^5$ is $R^4$ wherein each $R^4$ is substituted with 0 to 3 $R^3$ groups;
$W^3$ is $W^4$ or $W^5$;
$W^4$ is $R^5$, —$C(Y^1)R^5$, —$C(Y^1)W^5$, —$SO_{M2}R^5$, or —$SO_{M2}W^5$;
$W^5$ is carbocycle wherein $W^5$ is independently substituted with 0 to 3 $R^2$ groups;
$W^6$ is $W^3$ independently substituted with 1, 2, or 3 $A^3$ groups;
M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1; and
M12c is 0, 1, 2, 3, 4, 5, 6, 7, 8, 9, 10, 11 or 12.

2. A method of treating inflammation in a mammal, comprising administering a conjugate or a pharmaceutically acceptable salt or solvate thereof, to the mammal, wherein the conjugate is a compound of formula:

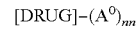

wherein:
DRUG is a compound of formula 556:

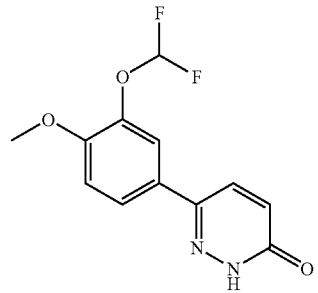

wherein:
nn is 1, 2 or 3;
$A^0$ is $A^1$, $A^2$ or $W^3$ with the proviso that the conjugate includes at least one $A^1$;

$A^1$ is:

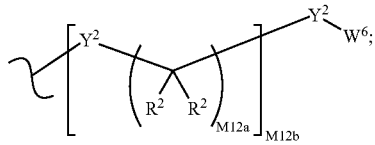

$A^2$ is:

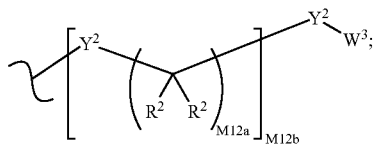

$A^3$ is:

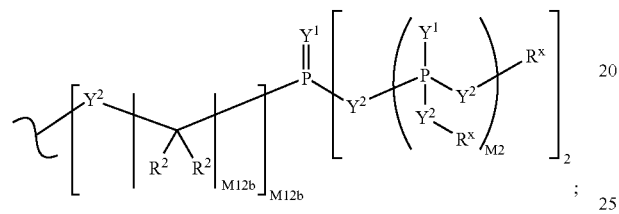

$Y^1$ is independently O, S, $N(R^x)$, $N(O)(R^x)$, $N(OR^x)$, $N(O)(OR^x)$, or $N(N(R^x)(R^x))$;

$Y^2$ is independently a bond, O, $N(R^x)$, $N(O)(R^x)$, $N(OR^x)$, $N(O)(OR^x)$, $N(N(R^x)(R^x))$, $-S(O)_{M2}-$, or $-S(O)_{M2}-S(O)_{M2}-$; and when $Y^2$ joins two phosphorous atoms $Y^2$ can also be $C(R^2)(R^2)$;

$R^x$ is independently H, $R^1$, $R^2$, $W^3$, a protecting group, or the formula:

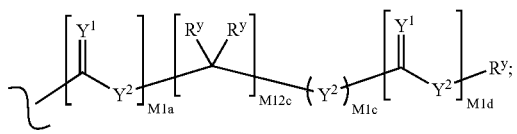

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, $-CN$, $N_3$ or $-NO_2$;

$R^{3b}$ is $Y^1$;

$R^{3c}$ is $-R^x$, $-N(R^x)(R^x)$, $-SR^x$, $-S(O)R^x$, $-S(O)_2R^x$, $-S(O)(OR^x)$, $-S(O)_2(OR^x)$, $-OC(Y^1)R^x$, $-OC(Y^1)OR^x$, $-OC(Y^1)(N(R^x)(R^x))$, $-SC(Y^1)R^x$, $-SC(Y^1)OR^x$, $-SC(Y^1)(N(R^x)(R^x))$, $-N(R^x)C(Y^1)R^x$, $-N(R^x)C(Y^1)OR^x$, or $-N(R^x)C(Y^1)(N(R^x)(R^x))$;

$R^{3d}$ is $-C(Y^1)R^x$, $-C(Y^1)OR^x$ or $-C(Y^1)(N(R^x)(R^x))$;

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, $-C(Y^1)R^5$, $-C(Y^1)W^5$, $-SO_{M2}R^5$, or $-SO_{M2}W^5$;

$W^5$ is carbocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

3. The method of claim 1 wherein the conjugate is a compound of formula 103:

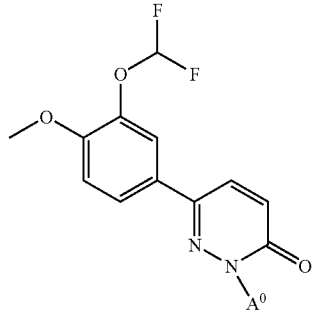

wherein $A^0$ is $A^1$.

4. The method of claim 1 wherein each $A^3$ is of the formula:

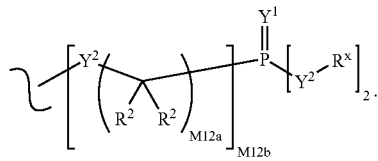

5. The method of claim 1 wherein each $A^3$ is of the formula:

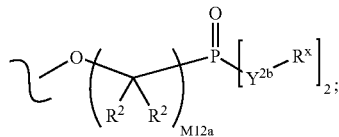

wherein $Y^{2b}$ is O or $N(R^x)$.

6. The method of claim 1 wherein each $A^3$ is of the formula:

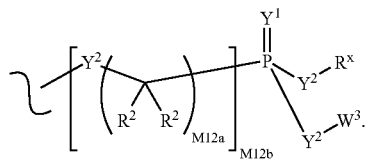

7. The method of claim 1 wherein each $A^3$ is of the formula:

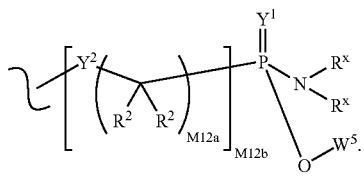

8. The method of claim 1 wherein each $A^3$ is of the formula:

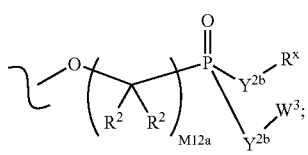

wherein $Y^{2b}$ is O or N($R^x$).

9. The method of claim 1 wherein each $A^3$ is of the formula:

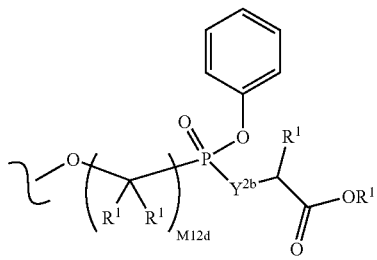

wherein the phenyl carbocycle is substituted with 0, 1, 2, or 3 $R^2$ groups.

10. The method of claim 1 wherein each $A^3$ is of the formula:

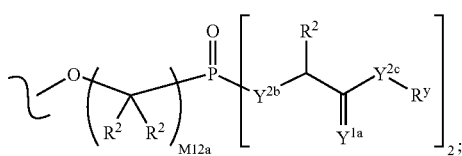

wherein:
$Y^{1a}$ is O or S;
$Y^{2b}$ is O or N($R^2$); and
$Y^{2c}$ is O, N($R^y$) or S.

11. The method of claim 1 wherein $A^0$ is of the formula:

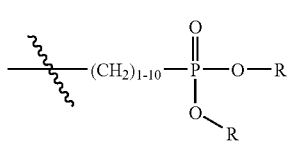

wherein each R is independently alkyl.

12. The method of claim 2 wherein the conjugate is of formula 103:

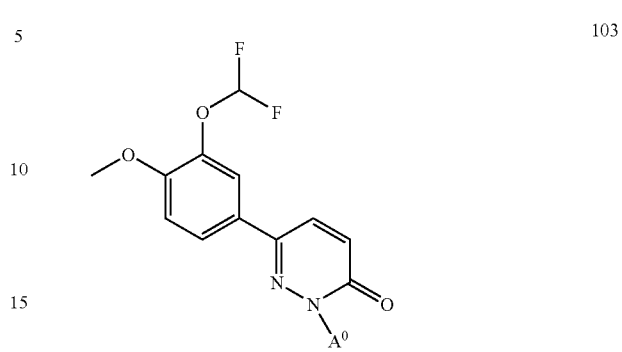

wherein:
$A^0$ is $A^1$.

13. The method of claim 2 wherein each $A^3$ is of the formula:

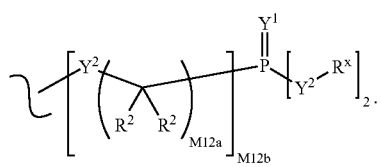

14. The method of claim 2 wherein each $A^3$ is of the formula:

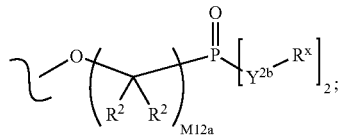

wherein $Y^{2b}$ is O or N($R^x$).

15. The method of claim 2 wherein each $A^3$ is of the formula:

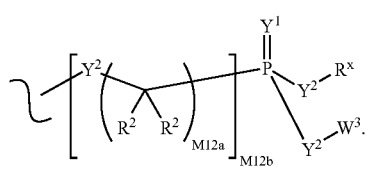

16. The method of claim 2 wherein each $A^3$ is of the formula:

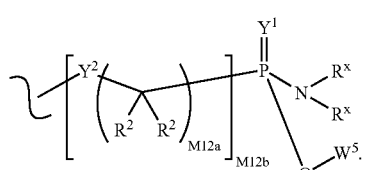

17. The method of claim 2 wherein each $A^3$ is of the formula:

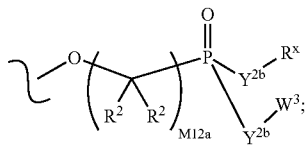

wherein $Y^{2b}$ is O or $N(R^x)$.

18. The method of claim 2 wherein each $A^3$ is of the formula:

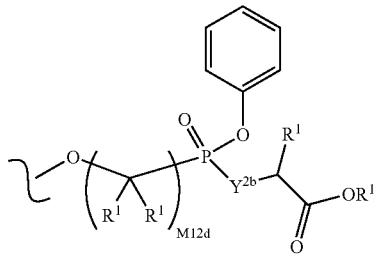

wherein the phenyl carbocycle is substituted with 0, 1, 2, or 3 $R^2$ groups.

19. The method of claim 2 wherein each $A^3$ is of the formula:

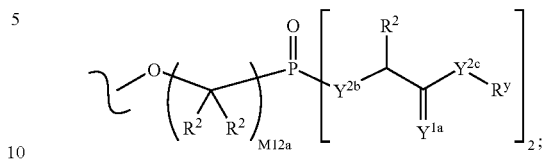

wherein:
$Y^{1a}$ is O or S;
$Y^{2b}$ is O or $N(R^2)$; and
$Y^{2c}$ is O, $N(R^y)$ or S.

20. The method of claim 2 wherein $A^0$ is of the formula:

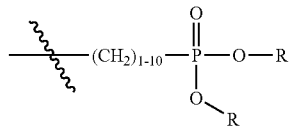

wherein each R is independently alkyl.

* * * * *